United States Patent
Baldwin et al.

(10) Patent No.: US 7,754,737 B2
(45) Date of Patent: Jul. 13, 2010

(54) DIAMINOALKANE ASPARTIC PROTEASE INHIBITORS

(75) Inventors: John J. Baldwin, Gwynedd, PA (US); David A. Claremon, Maple Glen, PA (US); Colin M. Tice, Maple Glen, PA (US); Salvacion Cacatian, Philadelphia, PA (US); Lawrence W. Dillard, Yardley, PA (US); Alexey V. Ishchenko, Elkins Park, PA (US); Jing Yuan, Lansdale, PA (US); Zhenrong Xu, Horsham, PA (US); Gerard McGeehan, Garnet Valley, PA (US); Wei Zhao, Eagleville, PA (US); Robert D. Simpson, Wilmington, DE (US); Suresh B. Singh, Kendall Park, NJ (US); Patrick T. Flaherty, Pittsburgh, PA (US); Jean-Pierre Wery, Indianapolis, IN (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 61 days.

(21) Appl. No.: 11/664,558

(22) PCT Filed: Oct. 7, 2005

(86) PCT No.: PCT/US2005/036230

§ 371 (c)(1),
(2), (4) Date: Jan. 23, 2008

(87) PCT Pub. No.: WO2006/042150

PCT Pub. Date: Apr. 20, 2006

(65) Prior Publication Data

US 2009/0018103 A1  Jan. 15, 2009

Related U.S. Application Data

(60) Provisional application No. 60/616,770, filed on Oct. 7, 2004.

(51) Int. Cl.
*C07D 417/04* (2006.01)
*C07D 409/06* (2006.01)
*C07D 405/06* (2006.01)
*C07D 401/06* (2006.01)
*C07D 417/06* (2006.01)
*C07D 265/30* (2006.01)
*C07D 211/22* (2006.01)
*C07D 211/26* (2006.01)
*A61K 31/5377* (2006.01)
*A61K 31/5375* (2006.01)
*A61K 31/445* (2006.01)
*A61K 31/4525* (2006.01)
*A61K 31/453* (2006.01)
*A61K 31/4535* (2006.01)
*A61K 31/454* (2006.01)
*A61K 31/4545* (2006.01)

(52) U.S. Cl. .............. 514/330; 514/331; 514/316; 514/326; 514/320; 514/323; 514/318; 514/210.2; 546/226; 546/232; 546/235; 546/189; 546/209; 546/212; 546/205; 546/194; 546/210; 546/200; 546/199; 544/169

(58) Field of Classification Search ............. 546/226
See application file for complete search history.

(56) References Cited

U.S. PATENT DOCUMENTS

| 3,071,618 | A | 1/1963 | Pinson et al. |
| 4,908,372 | A | 3/1990 | Carr et al. |
| 5,218,002 | A | 6/1993 | Stroech et al. |
| 5,371,093 | A | 12/1994 | Carr et al. |
| 5,380,731 | A | 1/1995 | Carr et al. |
| 5,767,144 | A | 6/1998 | Winn et al. |
| 6,162,927 | A | 12/2000 | Winn et al. |
| 6,900,329 | B2 | 5/2005 | Clader et al. |
| 6,946,481 | B1 | 9/2005 | Winn et al. |
| 2007/0093492 | A1 | 4/2007 | Jiaang et al. |

FOREIGN PATENT DOCUMENTS

| EP | 1 882 684 A1 | 1/2008 |
| GB | 1351761 A | 5/1974 |

(Continued)

OTHER PUBLICATIONS

Shabat, D.; Sinha, S.; Reymond, J.; Keinan, E. Angew. Chem. 1996, 108, 2800-2802.*

(Continued)

*Primary Examiner*—Rebecca L Anderson
*Assistant Examiner*—Matthew P Coughlin
(74) *Attorney, Agent, or Firm*—Hamilton, Brook, Smith & Reynolds, P.C.

(57) ABSTRACT

Diaminoalkanes of Formula I have now been found which are orally active and bind to aspartic proteases to inhibit their activity. They are useful in the treatment or amelioration of diseases associated with elevated levels of aspartic protease activity. The invention also relates to a method for the use of the compounds of Formula I in ameliorating or treating aspartic protease related disorders in a subject in need thereof comprising administering to said subject an effective amount of a compound of Formula I.

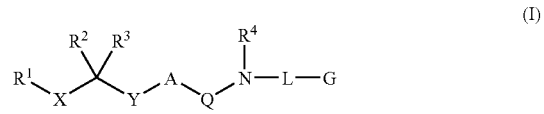

(I)

10 Claims, No Drawings

FOREIGN PATENT DOCUMENTS

| WO | WO 98/54179 A1 | 12/1998 |
| WO | WO 99/54321 | 10/1999 |
| WO | WO 00/40558 | 7/2000 |
| WO | WO 00/63172 | 10/2000 |
| WO | WO 2004/002483 | 1/2004 |
| WO | WO 2006/023844 | 3/2006 |
| WO | WO 2007/070201 A1 | 6/2007 |
| WO | WO 2008/036216 A1 | 3/2008 |
| WO | WO 2008/036247 A1 | 3/2008 |

OTHER PUBLICATIONS

Jordan, V. C. Nature Reviews: Drug Discovery, 2, 2003, pp. 205-213.*

Dörwald, F. Zaragoza. Side Reactions in Organic Synthesis: A Guide to Successful Synthesis Design, Weinheim: Wiley-VCH Verlag GmbH & Co. KGaA, 2005, Preface.*

Maibaum, J., et al., "Renin Inhibitors as Novel Treatments for Cardiovascular Disease," *Expert Opinion on Therapeutic Patents,* vol. 13, No. 5, pp. 589-603 (2003).

Moffett, R.B., "New Compounds with Possible Pharmacological Activity," *Journal of Chemical and Engineering Data,* vol. 25, No. 2, pp. 176-183 (1980).

Whitehead, C.W., "The Synthesis of 5-Carbethoxyuracils," *Journal of the American Chemical Society,* vol. 74, pp. 4267-4271 (1952).

Garrigues, B., et al., "Synthèse de 2-tert-butylthiophènes substitùes en position 5," *Bulletin De La Societe Chimique De France,* vol. 130, No. 1, pp. 58-63 (1993).

Schultz O.E., et al., "Pyridine and quinoline analogues of procaine and procainamide," *Arzneimittel-Forschung,* vol. 22, No. 7, pp. 1117-1120 (1972).

Praly-Deprez, I., et al., "Synthesis of 11-amino-substituted-5,6-dimethyl-5H-pyrido[3',4':4,5]pyrrolo-[2,3-g]isoquinolines as New Ellipticine Analogues," *Journal of the Chemical Society,* Perkin Transactions 1., No. 12, pp. 3173-3175 (1991).

Database Beilstein XP002366304, Database Accession No. 7588231, 4-(2,2-dimethoxypropyl)-N-(2-hydroxyethyl) benzamide, vol. 108, No. 22, pp. 2800-2802 (1996).

International Search Report, International Application No. PCT/US2006/043920 (Mar. 20, 2007).

Written Opinion of the International Searching Authority, International Application No. PCT/US2006/043920 (Mar. 20, 2007).

International Search Report, International Application No. PCT/US2005/036230 (Feb. 20, 2006).

Written Opinion of the International Searching Authority, International Application No. PCT/US2005/036230 (Feb. 20, 2006).

International Search Report, International Application No. PCT/US2007/020164 (Dec. 28, 2007).

Written Opinion of the International Searching Authority, International Application No. PCT/US2007/020164 (Dec. 28, 2007).

International Search Report, International Application No. PCT/US2007/020086 (Feb. 5, 2008).

Written Opinion of the International Searching Authority, International Application No. PCT/US2007/020086 (Feb. 5, 2008).

Notification Concerning Transmittal of International Preliminary Report on Patentability, International Application No. PCT/US2007/020164, Date of Mailing Apr. 2, 2009.

Notification Concerning Transmittal of International Preliminary Report on Patentability, International Application No. PCT/US2007/020086, Date of Mailing Apr. 2, 2009.

Written Opinion of the International Searching Authority, International Application No. PCT/US08/67650, Date of Mailing Jun. 22, 2009.

International Search Report, International Application No. PCT/US08/67650, Date of Mailing Jun. 22, 2009.

English Translation of Notification of the First Office Action, Chinese Patent Application No. 200580042064.7, Date of Notification May 8, 2009.

* cited by examiner

DIAMINOALKANE ASPARTIC PROTEASE INHIBITORS

RELATED APPLICATION

This application is the U.S. National Stage of International Application No. PCT/US2005/036230, filed Oct. 7, 2005, published in English, and claims priority under 35 U.S.C. §119 or §365 to U.S. Provisional Patent Application No. 60/616,770, filed Oct. 7, 2004, entire teachings of which are incorporated herein by reference.

BACKGROUND

Aspartic proteases, including renin, β-secretase (BACE), HIV protease, HTLV protease and plasmepsins I and II, are implicated in a number of disease states. In hypertension elevated levels of angiotensin I, the product of renin catalyzed cleavage of angioteninogen are present. Elevated levels of β amyloid, the product of BACE activity on amyloid precursor protein, are widely believed to be responsible for the amyloid plaques present In the brains of Alzheimer's disease patients. The viruses HIV and HTLV depend on their respective aspartic proteases for viral maturation. *Plasmodium falciparum* uses plasmepsins I and II to degrade hemoglobin.

In the renin-angiotensin-aldosterone system (RAAS) the biologically active peptide angiotensin II (Ang II) is generated by a two-step mechanism. The highly specific aspartic protease renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAAS represents a major advance in the treatment of cardiovascular diseases (Zaman, M. A. et al *Nature Reviews Drug Discovery* 2002, 1, 621-636). ACE inhibitors and $AT_1$ blockers have been accepted as treatments of hypertension (Waeber B. et al., "The renin-angiotensin system: role in experimental and human hypertension", in Berkenhager W. H., Reid J. L. (eds): *Hypertension*, Amsterdam, Elsevier Science Publishing Co, 1996, 489-519; Weber M. A., *Am. J. Hypertens.*, 1992, 5, 247S). In addition, ACE inhibitors are used for renal protection (Rosenberg M. E. et al., *Kidney International*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (*Suppl.* 3*A*), 83) and myocardial infarction (Pfeffer M. A. et al., *N Engl. J: Med*, 1992, 327, 669).

Interest in the development of renin inhibitors stems from the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be bypassed by chymase, a serine protease (Husain A., *J. Hypertens.*, 1993, 11, 1155). In patients, inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). Chymase is not inhibited by ACE inhibitors. Therefore, the formation of Ang II is still possible in patients treated with ACE inhibitors. Blockade of the AT1 receptor (e.g., by losartan) on the other hand overexposes other AT-receptor subtypes to Ang II, whose concentration is dramatically increased by the blockade of AT1 receptors. In summary, renin inhibitors are not only expected to be superior to ACE inhibitors and $AT_1$ blockers with regard to safety, but more importantly also with regard to their efficacy in blocking the RAAS.

Only limited clinical experience (Azizi M. et al., *J. Hypertens.*, 1994, 12, 419; Neutel J. M. et al., *Am. Heart*, 1991, 122, 1094) has been generated with renin inhibitors because their peptidomimetic character imparts insufficient oral activity (Kleinert H. D., *Cardiovasc. Drugs*, 1995, 9, 645). The clinical development of several compounds has been stopped because of this problem together with the high cost of goods. It appears as though only one compound has entered clinical trials (Rahuel J. et al., *Chem. Biol.*, 2000, 7, 493; Mealy N. E., *Drugs of the Future*, 2001, 26, 1139). Thus, metabolically stable, orally bioavailable and sufficiently soluble renin inhibitors that can be prepared on a large scale are not available. Recently, the first non-peptide renin inhibitors were described which show high in vitro activity (Oefner C. et al., *Chem. Biol.*, 1999, 6, 127; Patent Application WO 97/09311; Maerki H. P. et al., *II Farmaco*, 2001, 56, 21). The present invention relates to the unexpected identification of renin inhibitors of a non-peptidic nature and of low molecular weight. Orally active renin inhibitors which are active in indications beyond blood pressure regulation where the tissular renin-chymase system may be activated leading to pathophysiologically altered local functions such as renal, cardiac and vascular remodeling, atherosclerosis, and restenosis, are described.

All documents cited herein are incorporated by reference.

SUMMARY OF THE INVENTION

Diaminoalkanes of Formula I have now been found which are orally active and bind to aspartic proteases to inhibit their activity. They are useful in the treatment or amelioration of diseases associated with aspartic protease activity.

The invention also relates to a method for the use of the compounds of Formula I in ameliorating or treating aspartic protease related disorders in a subject in need thereof comprising administering to said subject an effective amount of a compound of Formula I.

DETAILED DESCRIPTION OF THE INVENTION

In a first embodiment, the invention provides compounds of Formula I

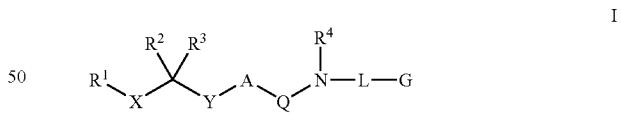

wherein $R^1$ is a) $(C_1-C_{12})$alkyl, $(C_3-C_7)$cycloalkyl, $(C_4-C_{12})$cycloalkylalkyl, halo$(C_1-C_{12})$alkyl, halo$(C_3-C_7)$-cycloalkyl, halo$(C_4-C_{12})$cycloalkylalkyl, saturated heterocyclyl optionally substituted with 1 to 5 groups independently selected from: halogen, $(C_1-C_6)$alkyl, halo$(C_1-C_6)$alkyl, and oxo; or b) phenyl, napthyl, heteroaryl, or bicyclic heteroaryl each optionally substituted with 1 to 5 groups independently selected from:

1) fluorine, chlorine, bromine, iodine, cyano, nitro, amino, hydroxy, carboxy, $(C_1-C_8)$alkyl, $(C_3-C_8)$cycloalkyl, $(C_1-C_3)$alkyl$(C_3-C_8)$cycloalkyl, di$(C_1-C_3)$alkyl$(C_3-C_8)$cycloalkyl, $(C_4-C_8)$cycloalkylalkyl, $(C_2-C_6)$alkenyl, $(C_5-C_8)$cycloalkenyl, (C₅-C₈)cyclo-alkylalkenyl, (C₂-C₈)alkynyl, (C₃-C₈)cycloalkyl(C₂-C₄)alkynyl, halo(C₁-C₈)alkyl, halo(C₃-C₆)cycloalkyl, halo(C₄-C₈)cycloalkylalkyl, (C₁-C₃)alkyl(C₄-C₈)cycloalkylalkyl, di(C₁-C₃)alkyl(C₄-C₈)cycloalkylalkyl, halo(C₂-C₈)alkenyl, halo(C₅-C₈)cycloalkenyl, halo(C₆-C₈)cycloalkenylalkyl, halo(C₃-C₈)alkynyl, halo(C₅-C₈)cycloalkylalkynyl, (C₁-C₈)alkoxy, (C₃-C₈)cycloalkoxy, (C₄-C₈)cycloalkylalkoxy, (C₁-C₃)alkyl(C₃-C₈)cycloalkoxy, (C₁-C₃)alkyl(C₄-C₈)cycloalkylalkoxy, di(C₁-C₃)alkyl(C₃-C₈)cycloalkoxy, di(C₁-C₃)alkyl(C₄-C₈)cycloalkylalkoxy, halo(C₁-C₆)alkoxy, halo(C₃-C₆)cycloalkoxy, halo(C₄-C₈)cycloalkylalkoxy, (C₁-C₈)alkylthio, (C₃-C₈)cycloalkylthio, (C₄-C₈)cycloalkylalkylthio, (C₁-C₃)alkyl(C₃-C₈)cycloalkylthio, C₃)alkyl(C₄-C₈)cycloalkylalkylthio, halo(C₁-C₃)alkylthio, halo(C₃-C₈)cycloalkylthio, halo(C₄-C₈)-cycloalkylalkylthio, (C₁-C₈)alkanesulfinyl, (C₃-C₈)cycloalkanesulfinyl, (C₄-C₈)cycloalkyl-alkanesulfinyl, (C₁-C₃)alkyl(C₃-C₈)cycloalkane-sulfinyl, (C₁-C₃)alkyl(C₄-C₈)cycloalkyl-alkanesulfinyl, di(C₁-C₃)alkyl(C₃-C₈)cycloalkane-sulfinyl, di(C₁-C₃)alkyl(C₄-C₈)cycloalkyl-alkanesulfinyl, halo(C₁-C₈)alkanesulfinyl, halo(C₃-C₈)cycloalkanesulfinyl, halo(C₄-C₈)cycloalkylalkanesulfinyl, (C₁-C₈)alkane-sulfonyl, (C₃-C₈)cycloalkanesulfonyl, (C₄-C₈)cycloalkylalkanesulfonyl, (C₁-C₃)alkyl(C₃-C₈)cycloalkanesulfonyl, (C₁-C₃)alkyl(C₄-C₈)cycloalkyl-alkanesulfonyl, di(C₁-C₃)alkyl(C₃-C₈)cycloalkanesulfonyl, di(C₁-C₃)alkyl(C₄-C₈)cycloalkyl-alkanesulfonyl, halo(C₁-C₈)alkanesulfonyl, halo(C₃-C₈)cycloalkanesulfonyl, halo(C₄-C₈)cycloalkylalkane-sulfonyl, (C₁-C₈)alkylamino, di(C₁-C₈)alkylamino, (C₁-C₆)alkoxy(C₁-C₆)alkoxy, halo(C₁-C₆)alkoxy(C₁-C₆)alkoxy, (C₁-C₈)alkoxycarbonyl, aminocarbonyl, (C₁-C₈)alkylamino-carbonyl, di(C₁-C₈)alkylaminocarbonyl, piperidino, pyrrolidino, cyano(C₁-C₆)alkyl, hydroxy(C₁-C₆)alkyl, carboxy(C₁-C₆)alkyl, (C₁-C₈)alkoxy(C₁-C₆)alkyl, (C₃-C₈)cycloalkoxy(C₁-C₆)alkyl, (C₄-C₈)cycloalkylalkoxy(C₁-C₆)alkyl, halo(C₁-C₆)alkoxy(C₁-C₆)alkyl, halo(C₃-C₆)cycloalkoxy(C₁-C₆)alkyl, halo(C₄-C₈)-cycloalkylalkoxy(C₁-C₆)alkyl, (C₁-C₈)alkylthio(C₁-C₆)alkyl, (C₃-C₈)cycloalkylthio(C₁-C₆)alkyl, (C₄-C₈)cycloalkylalkylthio(C₁-C₆)alkyl, halo(C₁-C₈)alkylthio(C₁-C₆)alkyl, halo(C₃-C₈)cycloalkylthio(C₁-C₆)alkyl, halo(C₄-C₈)-cycloalkylalkylthio(C₁-C₆)alkyl, (C₁-C₈)alkanesulfinyl(C₁-C₆)alkyl, (C₃-C₈)-cycloalkanesulfinyl(C₁-C₆)alkyl, (C₄-C₈)cycloalkyl-alkanesulfinyl(C₁-C₆)alkyl, halo(C₁-C₈)alkanesulfinyl(C₁-C₆)alkyl, halo(C₃-C₈)cycloalkanesulfinyl(C₁-C₆)alkyl, halo(C₄-C₈)cycloalkylalkanesulfinyl(C₁-C₆)alkyl, (C₁-C₈)alkane-sulfonyl(C₁-C₆)alkyl, (C₃-C₈)cycloalkanesulfonyl(C₁-C₆)alkyl, (C₄-C₈)cycloalkylalkanesulfonyl(C₁-C₆)alkyl, halo(C₁-C₈)alkanesulfonyl(C₁-C₆)alkyl, halo(C₃-C₈)cycloalkanesulfonyl(C₁-C₆)alkyl, halo(C₄-C₈)cycloalkylalkanesulfonyl(C₁-C₆)alkyl, (C₁-C₈)alkylamino(C₁-C₆)alkyl, di(C₁-C₈)alkylamino(C₁-C₆)alkyl, (C₁-C₈)alkoxycarbonyl(C₁-C₆)alkyl, (C₁-C₈)acyloxy(C₁-C₆)alkyl, (C₁-C₈)alkylamino-carbonyl(C₁-C₆)alkyl, di(C₁-C₈)alkylaminocarbonyl(C₁-C₆)alkyl, (C₁-C₈)acylamino(C₁-C₆)alkyl, piperidino(C₁-C₆)alkyl and pyrrolidino(C₁-C₆)alkyl, (C₁-C₈)alkoxycarbonylamino, (C₁-C₈)alkoxycarbonylamino(C₁-C₆)alkyl, aminocarboxy(C₁-C₆)alkyl, (C₁-C₈)alkylaminocarboxy(C₁-C₆)alkyl and di(C₁-C₈)alkylaminocarboxy(C₁-C₆)alkyl; or 2) phenyl, napthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl(C₁-C₃)alkyl, naphthyl(C₁-C₃)alkyl, heteroaryl(C₁-C₃)alkyl, bicyclic heteroaryl(C₁-C₃)alkyl, phenyl(C₁-C₃)alkoxy, naphthyl(C₁-C₃)alkoxy, heteroaryl(C₁-C₃)alkoxy, and bicyclic heteroaryl(C₁-C₃)alkoxy, each optionally substituted with 1 to 5 groups independently selected from: fluorine, chlorine, cyano, (C₁-C₆)alkyl, halo(C₁-C₆)alkyl, (C₁-C₆)alkoxy, halo(C₁-C₆)alkoxy, (C₁-C₆)alkanesulfonyl, (C₁-C₆)alkoxy-carbonyl, and aminocarbonyl;

X and Y is each independently CH₂ or a single bond;

$R^2$ is substituted or unsubstituted (C₁-C₁₂)alkyl, (C₂-C₁₂)alkenyl, (C₂-C₁₂)alkynyl, (C₁-C₁₂)alkoxy, (C₂-C₁₂)alkenyloxy, (C₁-C₁₂)alkylthio, (C₁-C₆)alkoxy(C₁-C₆)alkyl, (C₁-C₆)alkylthio(C₁-C₆)alkyl, (C₁-C₆)alkoxy(C₁-C₆)alkoxy, (C₁-C₆)alkoxy(C₁-C₆)alkylthio, (C₁-C₆)alkylthio(C₁-C₆)alkoxy, (C₁-C₆)alkylthio(C₁-C₆)alkylthio, (C₁-C₄)alkoxy(C₁-C₄)alkoxy(C₁-C₄)alkyl, aminocarbonylamino(C₁-C₁₂)alkyl, aminocarbonylamino(C₁-C₁₂)alkoxy, aminocarbonylamino(C₁-C₁₂)alkylthio, (C₁-C₆)-alkanoylamino(C₁-C₆)alkyl, (C₁-C₆)alkanoylamino(C₁-C₆)alkoxy, (C₁-C₆)alkanoylamino(C₁-C₆)alkylthio, (C₃-C₄)cycloalkanecarbonylamino(C₁-C₆)alkyl, (C₃-C₄)cycloalkanecarbonylamino(C₁-C₆)alkoxy, (C₃-C₄)cycloalkanecarbonylamino(C₁-C₆)alkylthio, aminosulfonylamino(C₁-C₁₂)alkyl, aminosulfonylamino(C₁-C₁₂)alkoxy, aminosulfonylamino(C₁-C₁₂)alkylthio, (C₁-C₆)alkanesulfonylamino(C₁-C₆)alkyl, (C₁-C₆)alkanesulfonylamino(C₁-C₆)alkoxy, (C₁-C₆)alkanesulfonylamino(C₁-C₆)alkylthio, (C₁-C₆)alkylaminocarbonylamino(C₁-C₆)alkyl, (C₁-C₆)alkylaminocarbonylamino(C₁-C₆)alkoxy, (C₁-C₆)alkylaminocarbonyl-amino(C₁-C₆)alkylthio, di(C₁-C₆)alkylaminocarbonylamino(C₁-C₆)alkyl, di(C₁-C₆)alkylaminocarbonylamino(C₁-C₆)alkoxy or di(C₁-C₆)alkylaminocarbonyl-amino(C₁-C₆)alkylthio, wherein the substituted (C₁-C₁₂)alkyl, (C₂-C₁₂)alkenyl, (C₂-C₁₂)alkynyl, (C₁-C₁₂)alkoxy, (C₁-C₁₂)alkylthio, (C₁-C₆)alkoxy(C₁-C₆)alkyl, (C₁-C₆)alkylthio(C₁-C₆)alkyl, (C₁-C₆)alkoxy(C₁-C₆)alkoxy, (C₁-C₆)alkoxy(C₁-C₆)alkylthio, (C₁-C₆)alkylthio(C₁-C₆)alkoxy, (C₁-C₆)alkylthio(C₁-C₆)alkylthio, (C₁-C₄)alkoxy(C₁-C₄)alkoxy(C₁-C₄)alkyl, aminocarbonylamino(C₁-C₁₂)alkyl, aminocarbonylamino(C₁-C₁₂)alkoxy, aminocarbonylamino(C₁-C₁₂)alkylthio, (C₁-C₆)-alkanoylamino(C₁-C₆)alkyl, (C₁-C₆)alkanoylamino(C₁-C₆)alkoxy, (C₁-C₆)alkanoylamino(C₁-C₆)alkylthio, (C₃-C₄)cycloalkanecarbonylamino(C₁-C₆)alkyl, (C₃-C₄)cycloalkanecarbonylamino(C₁-C₆)alkoxy, (C₃-C₄)cycloalkanecarbonylamino(C₁-C₆)alkylthio, aminosulfonylamino(C₁-C₁₂)alkyl, aminosulfonylamino(C₁-C₁₂)alkoxy, aminosulfonylamino(C₁-C₁₂)alkylthio, C₁-C₆)alkanesulfonylamino(C₁-C₆)alkyl, (C₁-C₆)alkanesulfonylamino(C₁-C₆)alkoxy, (C₁-C₆)alkanesulfonylamino(C₁-C₆)alkylthio, (C₁-C₆)alkylaminocarbonylamino(C₁-C₆)alkyl, (C₁-C₆)alkylaminocarbonylamino(C₁-C₆)alkoxy, (C₁-C₆)alkylaminocarbonyl-amino(C₁-C₆)alkylthio, di(C₁-C₆)alkylaminocarbonylamino(C₁-C₆)alkyl, di(C₁-C₆)alkylaminocarbonylamino(C₁-C₆)alkoxy and di(C₁-C₆)alkylaminocarbonyl-amino(C₁-C₆)alkylthio represented by $R^2$ is substituted by at least one of:

a) one or more halogen atoms, and b) one substituent selected from cyano, hydroxyl, (C₁-C₃)alkoxy, (C₃-C₆)cycloalkyl, (C₃-C₆)cycloalkoxy, halo(C₁-C₃)alkoxy, halo(C₃-C₆)cycloalkyl, and halo(C₃-C₆)cycloalkoxy, and wherein the thio-moiety of said unsubstituted or substituted (C₁-C₁₂)alkylthio, (C₁-C₆)alkylthio(C₁-C₆)alkyl, (C₁-C₆)alkoxy(C₁-C₆)alkylthio, (C₁-C₆)alkylthio(C₁-C₆)alkoxy, (C₁-C₆)alkylthio(C₁-C₆)alkylthio, aminocarbonylamino(C₁-C₁₂)alkylthio, (C₁-C₆)alkanoylamino(C₁-C₆)alkylthio, (C₃-

$C_4$)cycloalkanecarbonylamino($C_1$-$C_6$)alkylthio, aminosulfonylamino($C_1$-$C_{12}$)alkylthio, ($C_1$-$C_6$)alkanesulfonylamino($C_1$-$C_6$)alkylthio, ($C_1$-$C_6$)alkylaminocarbonyl-amino($C_1$-$C_6$)alkylthio and di($C_1$-$C_6$)alkylaminocarbonyl-amino($C_1$-$C_6$)alkylthio, is optionally replaced by a sulfinyl (sulfoxide, i.e., —S(O)—) or a sulfonyl (sulfone, i.e., —S(O)$_2$—) moiety, and wherein the carbonyl moiety of said unsubstituted or substituted aminocarbonylamino($C_1$-$C_{12}$)alkyl, aminocarbonylamino($C_1$-$C_{12}$)alkoxy, aminocarbonylamino($C_1$-$C_{12}$)alkylthio, ($C_1$-$C_6$)-alkanoylamino($C_1$-$C_6$)alkyl, ($C_1$-$C_6$)alkanoylamino($C_1$-$C_6$)alkoxy, ($C_1$-$C_6$)alkanoylamino($C_1$-$C_6$)alkylthio, ($C_3$-$C_4$)cycloalkanecarbonylamino($C_1$-$C_6$)alkyl, ($C_3$-$C_4$)cycloalkanecarbonylamino($C_1$-$C_6$)alkoxy, ($C_3$-$C_4$)cycloalkanecarbonylamino($C_1$-$C_6$)alkylthio($C_1$-$C_6$)alkylaminocarbonylamino($C_1$-$C_6$)alkyl, ($C_1$-$C_6$)alkylaminocarbonylamino($C_1$-$C_6$)alkoxy, ($C_1$-$C_6$)alkylaminocarbonyl-amino($C_1$-$C_6$)alkylthio, di($C_1$-$C_6$)alkylaminocarbonylamino($C_1$-$C_6$)alkyl, di($C_1$-$C_6$)alkylaminocarbonylamino($C_1$-$C_6$)alkoxy and di($C_1$-$C_6$)alkylaminocarbonyl-amino($C_1$-$C_6$)alkylthio is optionally replaced by a thiocarbonyl moiety, $R^3$ is 1) H, halogen, ($C_1$-$C_6$)alkyl, ($C_1$-$C_6$)alkoxy, hydroxyl, hydroxy($C_1$-$C_6$)alkyl, hydroxy($C_1$-$C_6$)alkoxy, ($C_1$-$C_6$)alkanoylamino, ($C_1$-$C_6$)-alkoxycarbonylamino, ($C_1$-$C_6$)alkylamino-carbonylamino, di($C_1$-$C_6$)alkylaminocarbonylamino, ($C_1$-$C_6$)alkanesulfonylamino, ($C_1$-$C_6$)alkylaminosulfonylamino, or di($C_1$-$C_6$)alkylaminosulfonylamino, or 2) phenylamino or heteroarylamino in which each phenylamino and heteroarylamino group is optionally substituted with 1 to 5 groups independently selected from:

fluorine, chlorine, bromine, iodine, cyano, nitro, amino, hydroxy, carboxy, ($C_1$-$C_6$)alkyl, ($C_3$-$C_6$)cycloalkyl, ($C_4$-$C_7$)cycloalkylalkyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, amino-carbonyl, ($C_1$-$C_6$)alkylaminocarbonyl, and di($C_1$-$C_6$)alkylaminocarbonyl, cyano($C_1$-$C_6$)alkyl, hydroxy($C_1$-$C_6$)alkyl, carboxy($C_1$-$C_6$)alkyl, ($C_1$-$C_6$)alkoxy($C_1$-$C_6$)alkyl, ($C_3$-$C_8$)cycloalkoxy($C_1$-$C_6$)alkyl, ($C_4$-$C_8$)cycloalkylalkoxy($C_1$-$C_6$)alkyl, halo($C_1$-$C_6$)alkoxy($C_1$-$C_6$)alkyl, halo($C_3$-$C_6$)cycloalkoxy($C_1$-$C_6$)alkyl, halo($C_4$-$C_8$)cycloalkylalkoxy($C_1$-$C_6$)alkyl, ($C_1$-$C_8$)alkylthio($C_1$-$C_6$)alkyl, ($C_3$-$C_8$)cycloalkylthio($C_1$-$C_6$)alkyl, ($C_4$-$C_8$)cycloalkylalkylthio($C_1$-$C_6$)alkyl, halo($C_1$-$C_8$)alkylthio($C_1$-$C_6$)alkyl, halo($C_3$-$C_8$)cycloalkylthio($C_1$-$C_6$)alkyl, halo($C_4$-$C_8$)-cycloalkylalkylthio($C_1$-$C_6$)alkyl, ($C_1$-$C_8$)alkanesulfinyl($C_1$-$C_6$)alkyl, ($C_3$-$C_8$)-cycloalkanesulfinyl($C_1$-$C_8$)alkyl, ($C_4$-$C_8$)cycloalkyl-alkanesulfinyl($C_1$-$C_6$)alkyl, halo($C_1$-$C_8$)alkanesulfinyl($C_1$-$C_6$)alkyl, halo($C_3$-$C_8$)cycloalkanesulfinyl($C_1$-$C_6$)alkyl, halo($C_4$-$C_8$)cycloalkylalkanesulfinyl($C_1$-$C_6$)alkyl, ($C_1$-$C_8$)alkane-sulfonyl($C_1$-$C_6$)alkyl, ($C_3$-$C_8$)cycloalkanesulfonyl($C_1$-$C_6$)alkyl, ($C_4$-$C_8$)cycloalkylalkanesulfonyl($C_1$-$C_6$)alkyl, halo($C_1$-$C_8$)alkanesulfonyl($C_1$-$C_6$)alkyl, halo($C_3$-$C_8$)cycloalkanesulfonyl($C_1$-$C_6$)alkyl, halo($C_4$-$C_8$)cycloalkylalkanesulfonyl($C_1$-$C_6$)alkyl, ($C_1$-$C_8$)alkylamino($C_1$-$C_6$)alkyl, di($C_1$-$C_8$)alkylamino($C_1$-$C_6$)alkyl, ($C_1$-$C_8$)alkoxycarbonyl($C_1$-$C_6$)alkyl, ($C_1$-$C_8$)acyloxy($C_1$-$C_6$)alkyl, aminocarbonyl($C_1$-$C_6$)alkyl, ($C_1$-$C_8$)alkylaminocarbonyl($C_1$-$C_6$)alkyl, di($C_1$-$C_8$)alkylaminocarbonyl($C_1$-$C_6$)alkyl($C_1$-$C_8$)acylamino($C_1$-$C_6$)alkyl, ($C_1$-$C_8$)alkoxycarbonylamino, ($C_1$-$C_8$)alkoxycarbonylamino($C_1$-$C_6$)alkyl, aminocarboxy($C_1$-$C_6$)alkyl, ($C_1$-$C_8$)alkylaminocarboxy($C_1$-$C_6$)alkyl and di($C_1$-$C_8$)alkylaminocarboxy($C_1$-$C_6$)alkyl;

provided that when $R^3$ is hydroxyl, halogen or optionally substituted phenylamino or heteroarylamino, then $R^2$ is not a substituted or unsubstituted ($C_1$-$C_{12}$)alkoxy, ($C_2$-$C_{12}$)alkenyloxy, ($C_1$-$C_{12}$)alkylthio, ($C_1$-$C_6$)alkoxy($C_1$-$C_6$)alkoxy, ($C_1$-$C_6$)alkoxy($C_1$-$C_6$)alkylthio, ($C_1$-$C_6$)alkylthio($C_1$-$C_6$)alkoxy, ($C_1$-$C_6$)-alkylthio($C_1$-$C_6$)alkylthio, aminocarbonylamino($C_1$-$C_{12}$)alkoxy, aminocarbonyl-amino($C_1$-$C_{12}$)alkylthio, ($C_1$-$C_6$)alkanoylamino($C_1$-$C_6$)alkoxy, ($C_1$-$C_6$)alkanoylamino($C_1$-$C_6$)alkylthio, $C_3$-$C_4$)cycloalkanecarbonylamino($C_1$-$C_6$)alkoxy, ($C_3$-$C_4$)cycloalkanecarbonylamino($C_1$-$C_6$)alkylthio, aminosulfonylamino($C_1$-$C_{12}$)alkoxy, aminosulfonylamino($C_1$-$C_{12}$)alkylthio, ($C_1$-$C_6$)alkanesulfonylamino($C_1$-$C_6$)alkoxy, ($C_1$-$C_6$)alkanesulfonylamino($C_1$-$C_6$)alkylthio, ($C_1$-$C_6$)alkylaminocarbonyl-amino($C_1$-$C_6$)alkoxy, ($C_1$-$C_6$)alkylaminocarbonylamino($C_1$-$C_6$)alkylthio, di($C_1$-$C_6$)alkylaminocarbonyl-amino($C_1$-$C_6$)alkoxy or di($C_1$-$C_6$)alkylaminocarbonylamino($C_1$-$C_6$)alkylthio, provided further that when $R^3$ is hydroxyl, halogen or optionally substituted phenylamino or heteroarylamino, then $R^2$ is not a unsubstituted or substituted ($C_1$-$C_{12}$)alkylthio, ($C_1$-$C_6$)alkoxy($C_1$-$C_6$)alkylthio, ($C_1$-$C_6$)alkylthio($C_1$-$C_6$)alkylthio, aminocarbonylamino($C_1$-$C_{12}$)alkylthio, ($C_1$-$C_6$)alkanoylamino($C_1$-$C_6$)alkylthio, ($C_3$-$C_4$)cycloalkanecarbonylamino($C_1$-$C_6$)alkylthio, aminosulfonylamino($C_1$-$C_{12}$)alkylthio, ($C_1$-$C_6$)alkanesulfonylamino($C_1$-$C_6$)alkylthio, ($C_1$-$C_6$)alkylaminocarbonylamino($C_1$-$C_6$)alkylthio and di($C_1$-$C_6$)alkylaminocarbonylamino($C_1$-$C_6$)alkylthio wherein the thiomoiety moiety is replaced by a sulfinyl (sulfoxide, i.e., —S(O)—) or a sulfonyl (sulfone, i.e., —S(O)$_2$—) moiety, and provided further that when $R^3$ is hydroxyl, halogen or optionally substituted phenylamino or heteroarylamino, then $R^2$ is not a unsubstituted or substituted aminocarbonylamino($C_1$-$C_{12}$)alkoxy, aminocarbonylamino($C_1$-$C_{12}$)alkylthio, ($C_1$-$C_6$)alkanoylamino($C_1$-$C_6$)alkoxy, $C_3$-$C_4$)cycloalkanecarbonylamino($C_1$-$C_6$)alkoxy, ($C_3$-$C_4$)cycloalkanecarbonylamino($C_1$-$C_6$)alkylthio, ($C_1$-$C_6$)alkanoylamino($C_1$-$C_6$)alkylthio, ($C_1$-$C_6$)alkylaminocarbonyl-amino($C_1$-$C_6$)alkoxy, ($C_1$-$C_6$)alkylaminocarbonylamino($C_1$-$C_6$)alkylthio, di($C_1$-$C_6$)alkylaminocarbonyl-amino($C_1$-$C_6$)alkoxy or di($C_1$-$C_6$)alkylaminocarbonylamino($C_1$-$C_6$)alkylthio, wherein the carbonyl moiety is replaced by a thiocarbonyl moiety, A is a saturated or unsaturated 4-, 5-, 6-, or 7-membered ring which is optionally bridged by $(CH_2)_m$ via bonds to two members of said ring, wherein said ring is composed of carbon atoms, and 0-2 hetero atoms selected from 0, 1, or 2 nitrogen atoms, 0 or 1 oxygen atoms, and 0 or 1 sulfur atoms, said ring atoms being substituted with the appropriate number of hydrogen atoms, said ring being optionally substituted with up to four independently selected halogen atoms, ($C_1$-$C_6$)alkyl groups, halo($C_1$-$C_6$)alkyl groups or oxo groups, and wherein m is 1 to 3;

Q and Y are attached to carbon or nitrogen atoms in ring A in a 1,2 or 1,3 or 1,4 relationship;

Q is a divalent radical selected from

Q1: C(=O) (carbonyl)

Q2: C(=S) (thiocarbonyl)

Q3: S(=O)₂ (sulfonyl)

Q4: C=CH-NO₂

Q5: C=N-CN

Q6: C(=O)-C(=O)

Q7: CH₂-C(=O)-CH₂ (or similar β-keto)

Q8: C(=O)-CH₂-C(=O)

Q9: squarate (cyclobutenedione)

Q10: 1,2,5-thiadiazole

Q11: 1,2,5-thiadiazole 1-oxide

Q12: 1,2,5-thiadiazole 1,1-dioxide

Q13: N-methyl-1,2,4,6-thiatriazine 1,1-dioxide wherein A and N are attached to the truncated bonds $R^4$ is H, $(C_1-C_6)$alkyl, halo$(C_1-C_6)$alkyl; $(C_1-C_3)$alkoxy$(C_1-C_3)$alkyl, or cyano$(C_1-C_6)$alkyl;

L is 1) a linear $(C_2-C_4)$alkyl chain when G is OH, OR$^9$, NH$_2$, NHR$^9$, NR$^9$R$^{10}$, NHC(=NH)NH$_2$, or NHC(=NH)NHR$^9$, or 2) a linear $(C_1-C_3)$alkyl chain when G is C(=NH)NH$_2$ or C(=NH)NHR$^9$;

L is optionally substituted by 1-4 groups independently selected from $R^5$, $R^6$, $R^7$, and $R^8$;

one or more of the carbon atoms of L may be part of a 3-, 4-, 5-, 6-, or 7-membered saturated ring composed of carbon atoms, and 0-2 hetero atoms selected from 0 or 1 nitrogen atoms, 0 or 1 oxygen atoms, and 0 or 1 sulfur atoms; said saturated ring being optionally substituted with up to four groups selected from halogen, $(C_1-C_6)$alkyl, halo$(C_1-C_6)$alkyl, $(C_3-C_6)$cycloalkyl, halo$(C_3-C_6)$cycloalkyl, $(C_4-C_7)$cycloalkylalkyl, halo$(C_4-C_7)$cycloalkylalkyl, and oxo;

$R^5$, $R^6$, $R^7$, and $R^8$ is each independently selected from 1) $(C_1-C_{12})$alkyl, $(C_3-C_8)$cycloalkyl, $(C_3-C_8)$cycloalkyl$(C_1-C_3)$alkyl, $(C_2-C_{12})$alkenyl, $(C_5-C_8)$cycloalkyl$(C_1-C_3)$alkenyl, $(C_2-C_{12})$alkynyl, $(C_3-C_8)$cycloalkyl$(C_1-C_3)$alkynyl, $(C_4-C_{12})$bicycloalkyl$(C_1-C_3)$alkyl, $(C_8-C_{14})$tricycloalkyl$(C_1-C_3)$alkyl, $(C_1-C_6)$alkoxy$(C_1-C_6)$alkyl, $(C_3-C_8)$cycloalkoxy$(C_1-C_3)$alkyl, $(C_1-C_6)$alkylthio$(C_1-C_6)$alkyl, $(C_3-C_8)$cycloalkylthio$(C_1-C_3)$alkyl, saturated heterocyclyl, and saturated heterocyclyl$(C_1-C_3)$alkyl wherein (a) hydrogen atoms in these groups are optionally substituted by 1 to 6 groups independently selected from halogen, cyano, hydroxyl, $(C_1-C_3)$alkyl, $(C_1-C_3)$alkoxy, $(C_3-C_6)$cycloalkyl, $(C_3-C_6)$cycloalkoxy, halo$(C_1-C_3)$alkyl, halo$(C_1-C_3)$alkoxy, halo$(C_3-C_6)$cycloalkyl, halo$(C_3-C_6)$cycloalkoxy and wherein (b) divalent sulfur atoms are optionally oxidized to sulfoxide or sulfone; or 2) phenyl, naphthyl, heteroaryl, phenyl$(C_1-C_3)$alkyl, naphthyl$(C_1-C_3)$alkyl, and heteroaryl$(C_1-C_3)$alkyl, each optionally substituted with 1 to 3 groups independently selected from:

fluorine, chlorine, bromine, iodine, cyano, nitro, amino, hydroxy, carboxy, $(C_1-C_6)$alkyl, $(C_3-C_6)$cycloalkyl, $(C_4-C_7)$cycloalkylalkyl, $(C_2-C_6)$alkynyl, $(C_3-C_6)$cycloalkyl-$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cyclo-alkylthio, $(C_4-C_7)$cycloalkylalkylthio, halo$(C_1-C_6)$alkylthio, halo$(C_3-C_6)$cycloalkylthio, halo($C_4$-

$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, aminocarbonyl, ($C_1$-$C_6$)alkylaminocarbonyl, di($C_1$-$C_6$)alkylaminocarbonyl, cyano($C_1$-$C_6$)alkyl, hydroxy($C_1$-$C_6$)alkyl, carboxy($C_1$-$C_6$)alkyl, ($C_1$-$C_6$)alkoxy($C_1$-$C_6$)alkyl, ($C_3$-$C_8$)cycloalkoxy($C_1$-$C_6$)alkyl, ($C_4$-$C_8$)cycloalkylalkoxy($C_1$-$C_6$)alkyl, halo($C_1$-$C_8$)alkoxy($C_1$-$C_6$)alkyl, halo($C_3$-$C_6$)cycloalkoxy($C_1$-$C_6$)alkyl, halo($C_4$-$C_8$)cycloalkylalkoxy($C_1$-$C_6$)alkyl, ($C_1$-$C_8$)alkylthio($C_1$-$C_6$)alkyl, ($C_3$-$C_8$)cycloalkylthio($C_1$-$C_6$)alkyl, ($C_4$-$C_8$)cycloalkylalkylthio($C_1$-$C_6$)alkyl, halo($C_1$-$C_8$)alkylthio($C_1$-$C_6$)alkyl, halo($C_3$-$C_8$)cycloalkylthio($C_1$-$C_6$)alkyl, halo($C_4$-$C_8$)cycloalkylalkylthio($C_1$-$C_6$)alkyl, ($C_1$-$C_8$)alkanesulfinyl($C_1$-$C_6$)alkyl, ($C_3$-$C_8$)-cycloalkanesulfinyl($C_1$-$C_6$)alkyl, ($C_4$-$C_8$)cycloalkyl-alkanesulfinyl($C_1$-$C_6$)alkyl, halo($C_1$-$C_8$)alkanesulfinyl($C_1$-$C_6$)alkyl, halo($C_3$-$C_8$)cycloalkanesulfinyl($C_1$-$C_6$)alkyl, halo($C_4$-$C_8$)cycloalkylalkanesulfinyl($C_1$-$C_6$)alkyl, ($C_1$-$C_8$)alkane-sulfonyl($C_1$-$C_6$)alkyl, ($C_3$-$C_8$)cycloalkanesulfonyl($C_1$-$C_6$)alkyl, ($C_4$-$C_8$)cycloalkylalkanesulfonyl($C_1$-$C_6$)alkyl, halo($C_1$-$C_8$)alkanesulfonyl($C_1$-$C_6$)alkyl, halo($C_3$-$C_8$)cycloalkanesulfonyl($C_1$-$C_6$)alkyl, halo($C_4$-$C_8$)cycloalkylalkanesulfonyl($C_1$-$C_6$)alkyl, ($C_1$-$C_8$)alkylamino($C_1$-$C_6$)alkyl, di($C_1$-$C_8$)alkylamino($C_1$-$C_6$)alkyl, ($C_1$-$C_8$)alkoxycarbonyl($C_1$-$C_6$)alkyl, ($C_1$-$C_8$)acyloxy($C_1$-$C_6$)alkyl, aminocarbonyl($C_1$-$C_6$)alkyl, ($C_1$-$C_8$)alkylamino-carbonyl($C_1$-$C_6$)alkyl, di($C_1$-$C_8$)alkylaminocarbonyl($C_1$-$C_6$)alkyl ($C_1$-$C_8$)acylamino($C_1$-$C_6$)alkyl, ($C_1$-$C_8$)alkoxycarbonylamino, ($C_1$-$C_8$)alkoxycarbonylamino($C_1$-$C_6$)alkyl, aminocarboxy($C_1$-$C_6$)alkyl, ($C_1$-$C_8$)alkylamino-carboxy($C_1$-$C_6$)alkyl and di($C_1$-$C_8$)alkylaminocarboxy($C_1$-$C_6$)alkyl, phenyl, napthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl($C_1$-$C_3$)alkyl, napthyl($C_1$-$C_3$)alkyl, heteroaryl($C_1$-$C_3$)alkyl, and bicyclic heteroaryl($C_1$-$C_3$)alkyl, wherein the aromatic and heteroaromatic groups are optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, halo($C_1$-$C_3$)-alkoxy, ($C_1$-$C_3$)alkanesulfonyl, and ($C_1$-$C_3$)alkoxycarbonyl;

G is OH, $OR^9$, $NH_2$, $NHR^9$, $NR^9R^{10}$, $C(=NH)NH_2$, $C(=NH)NHR^9$, $NHC(=NH)NH_2$, or $NHC(=NH)NHR^9$;

$R^9$ is a) ($C_1$-$C_{12}$)alkyl, ($C_4$-$C_{12}$)cycloalkylalkyl, halo($C_1$-$C_{12}$)alkyl, halo($C_4$-$C_{12}$)cycloalkylalkyl, ($C_2$-$C_{12}$)alkenyl, ($C_5$-$C_{12}$)cycloalkylalkenyl, halo($C_2$-$C_{12}$)alkenyl, halo($C_5$-$C_{12}$)cycloalkylalkenyl, ($C_2$-$C_{12}$)alkynyl, ($C_5$-$C_{12}$)cycloalkylalkynyl, halo($C_2$-$C_{12}$)alkynyl, halo($C_5$-$C_{12}$)cycloalkylalkynyl, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio($C_1$-$C_6$)alkyl, halo($C_1$-$C_6$)alkylthio($C_1$-$C_6$)alkyl, ($C_1$-$C_6$)alkanesulfinyl($C_1$-$C_6$)alkyl, halo($C_1$-$C_6$)alkane-sulfinyl($C_1$-$C_6$)alkyl, ($C_1$-$C_6$)alkanesulfonyl($C_1$-$C_6$)alkyl, halo($C_1$-$C_6$)alkanesulfonyl($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylamino-carbonyl($C_1$-$C_6$)alkyl, cyano($C_1$-$C_6$)alkyl, carboxy($C_1$-$C_6$)alkyl, ($C_1$-$C_6$)alkoxycarbonyl($C_1$-$C_6$)alkyl, saturated heterocyclyl, or saturated heterocyclyl($C_1$-$C_6$)alkyl orb) phenyl, naphthyl, heteroaryl, phenyl($C_1$-$C_3$)alkyl, naphthyl($C_1$-$C_3$)alkyl, or heteroaryl($C_1$-$C_3$) alkyl, each optionally substituted by 1 to 3 groups independently selected from:

1) fluorine, chlorine, bromine, iodine, cyano, nitro, amino, hydroxy, carboxy, ($C_1$-$C_6$)alkyl, ($C_3$-$C_6$)cycloalkyl, ($C_4$-$C_7$)cycloalkylalkyl, ($C_2$-$C_6$)alkynyl, ($C_3$-$C_6$)cycloalkyl-($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkane-sulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, aminocarbonyl, ($C_1$-$C_6$)alkylaminocarbonyl and di($C_1$-$C_6$)alkylaminocarbonyl, cyano($C_1$-$C_6$)alkyl, hydroxy($C_1$-$C_6$)alkyl, carboxy($C_1$-$C_6$)alkyl, ($C_1$-$C_6$)alkoxy($C_1$-$C_6$)alkyl, ($C_3$-$C_8$)cycloalkoxy($C_1$-$C_6$)alkyl, ($C_4$-$C_8$)cycloalkylalkoxy($C_1$-$C_6$)alkyl, halo($C_1$-$C_6$)alkoxy($C_1$-$C_6$)alkyl, halo($C_3$-$C_8$)cycloalkoxy($C_1$-$C_6$)alkyl, halo($C_4$-$C_8$)cycloalkylalkoxy($C_1$-$C_6$)alkyl, ($C_1$-$C_8$)alkylthio($C_1$-$C_6$)alkyl, ($C_3$-$C_8$)cycloalkylthio($C_1$-$C_6$)alkyl, ($C_4$-$C_8$)cycloalkylalkylthio($C_1$-$C_6$)alkyl, halo($C_1$-$C_8$)alkylthio($C_1$-$C_6$)alkyl, halo($C_3$-$C_8$)cycloalkylthio($C_1$-$C_6$)alkyl, halo($C_4$-$C_8$)-cycloalkylalkylthio($C_1$-$C_6$)alkyl, ($C_1$-$C_8$)alkanesulfinyl($C_1$-$C_6$)alkyl, ($C_3$-$C_8$)-cycloalkanesulfinyl($C_1$-$C_6$)alkyl, ($C_4$-$C_8$)cycloalkyl-alkanesulfinyl($C_1$-$C_6$)alkyl, halo($C_1$-$C_8$)alkanesulfinyl($C_1$-$C_6$)alkyl, halo($C_3$-$C_8$)cycloalkanesulfinyl($C_1$-$C_6$)alkyl, halo($C_4$-$C_8$)cycloalkylalkanesulfinyl($C_1$-$C_6$)alkyl, ($C_1$-$C_8$)alkane-sulfonyl($C_1$-$C_6$)alkyl, ($C_3$-$C_8$)cycloalkanesulfonyl($C_1$-$C_6$)alkyl, ($C_4$-$C_8$)cycloalkylalkanesulfonyl($C_1$-$C_6$)alkyl, halo($C_1$-$C_5$)alkanesulfonyl ($C_1$-$C_6$)alkyl, halo($C_3$-$C_8$)cycloalkanesulfonyl($C_1$-$C_6$)alkyl, halo($C_4$-$C_8$)cycloalkylalkanesulfonyl($C_1$-$C_6$)alkyl, ($C_1$-$C_8$)alkylamino($C_1$-$C_6$)alkyl, di($C_1$-$C_8$)alkylamino($C_1$-$C_6$)alkyl, ($C_1$-$C_8$)alkoxycarbonyl($C_1$-$C_6$)alkyl, ($C_1$-$C_8$)acyloxy($C_1$-$C_6$)alkyl, aminocarbonyl($C_1$-$C_6$)alkyl, ($C_1$-$C_8$)alkylaminocarbonyl($C_1$-$C_6$)alkyl, di($C_1$-$C_8$)alkylaminocarbonyl($C_1$-$C_6$)alkyl($C_1$-$C_8$)acylamino($C_1$-$C_6$)alkyl, ($C_1$-$C_8$)alkoxycarbonylamino, ($C_1$-$C_8$)alkoxycarbonylamino($C_1$-$C_6$)alkyl, aminocarboxy($C_1$-$C_6$)alkyl, ($C_1$-$C_8$)alkylaminocarboxy($C_1$-$C_6$)alkyl and di($C_1$-$C_8$)alkylaminocarboxy($C_1$-$C_6$)alkyl; or 2) phenyl, napthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl($C_1$-$C_3$)alkyl, napthyl($C_1$-$C_3$)alkyl, heteroaryl($C_1$-$C_3$)alkyl, and bicyclic heteroaryl($C_1$-$C_3$)alkyl, each optionally substituted with 1 to 3 groups independently selected from fluorine, chlorine, cyano, ($C_1$-$C_3$)alkyl, halo ($C_1$-$C_3$)alkyl, ($C_1$-$C_3$)alkoxy, halo($C_1$-$C_3$)alkoxy, ($C_1$-$C_3$)alkanesulfonyl, and ($C_1$-$C_3$)-alkoxycarbonyl; or b) $R^9$ is a saturated divalent radical composed of carbon atoms, and 0, 1 or 2 hetero atoms selected from 0 or 1 nitrogen atoms, 0 or 1 oxygen atoms, and 0 or 1 sulfur atoms that is attached to any core carbon atom on L to form a saturated 3-, 4-, 5-, 6-, or 7-membered L-G ring; said L-G ring being optionally substituted with 1 to 4 groups selected from halogen, fluorine, $(C_1-C_8)$alkyl, halo$(C_1-C_8)$alkyl, $(C_3-C_8)$cycloalkyl, halo$(C_3-C_8)$cycloalkyl, hydroxy$(C_3-C_8)$cycloalkyl, $(C_3-C_8)$cycloalkyl$(C_1-C_3)$alkyl, halo$(C_3-C_8)$cycloalkyl$(C_1-C_3)$alkyl, hydroxylated $(C_3-C_8)$cycloalkyl$(C_1-C_3)$alkyl, $(C_1-C_8)$alkoxy, halo$(C_1-C_8)$alkoxy, $(C_3-C_8)$cycloalkoxy, halo$(C_3-C_8)$cycloalkoxy, hydroxy$(C_3-C_8)$cycloalkoxy, $(C_1-C_8)$alkoxy$(C_1-C_3)$alkyl, halo$(C_1-C_8)$alkoxy$(C_1-C_3)$alkyl, $(C_3-C_8)$cycloalkoxy$(C_1-C_3)$alkyl, halo$(C_3-C_8)$cycloalkoxy$(C_1-C_3)$alkyl, hydroxy$(C_3-C_8)$cycloalkoxy$(C_1-C_3)$alkyl, $(C_3-C_8)$cycloalkyl$(C_1-C_3)$alkoxy$(C_1-C_3)$alkyl, halo$(C_3-C_8)$cycloalkyl$(C_1-C_3)$alkoxy$(C_1-C_3)$alkyl, hydroxylated$(C_3-C_8)$cycloalkyl$(C_1-C_3)$alkoxy$(C_1-C_3)$alkyl, $(C_1-C_8)$alkylthio, halo$(C_1-C_8)$alkylthio, $(C_3-C_8)$cycloalkylthio, halo$(C_3-C_8)$cycloalkylthio, hydroxy$(C_3-C_8)$cycloalkylthio, $(C_3-C_8)$cycloalkyl$(C_1-C_3)$alkylthio, halo$(C_3-C_8)$cycloalkyl$(C_1-C_3)$alkylthio, hydroxylated$(C_3-C_8)$cycloalkyl$(C_1-C_3)$alkylthio, $(C_1-C_8)$alkylthio$(C_1-C_3)$alkyl, halo$(C_1-C_8)$alkylthio$(C_1-C_3)$alkyl, $(C_3-C_8)$cycloalkylthio$(C_1-C_3)$alkyl, halo$(C_3-C_8)$cycloalkylthio$(C_1-C_3)$alkyl, hydroxy$(C_3-C_8)$cycloalkylthio$(C_1-C_3)$alkyl, $(C_3-C_8)$cycloalkyl$(C_1-C_3)$alkylthio$(C_1-C_3)$alkyl, halo$(C_3-C_8)$cycloalkyl$(C_1-C_3)$alkylthio$(C_1-C_3)$alkyl, hydroxylated$(C_3-C_8)$cycloalkyl$(C_1-C_3)$alkylthio$(C_1-C_3)$alkyl and oxo;

$R^{10}$ is $(C_1-C_6)$alkyl or halo$(C_1-C_6)$alkyl;

provided that when $R^2$ is $(C_1-C_{12})$alkyl and $R^3$ is OH, only a single substituent $R^5$ is allowed on L;

and the enantiomers, diastereomers, and salts thereof.

A second embodiment of the invention is a compound of Formula I wherein:

$R^1$ is a) $(C_1-C_9)$alkyl, $(C_3-C_7)$cycloalkyl, $(C_4-C_9)$cycloalkylalkyl, halo$(C_1-C_9)$alkyl, halo$(C_3-C_7)$cycloalkyl, halo$(C_4-C_9)$cycloalkylalkyl, saturated heterocyclyl optionally substituted with 1 to 3 groups independently selected from fluorine, $(C_1-C_3)$alkyl, halo$(C_1-C_3)$alkyl, and oxo;

or b) phenyl, napthyl, heteroaryl, or bicyclic heteroaryl each optionally substituted with 1 to 3 groups independently selected from:

1) fluorine, chlorine, bromine, cyano, nitro, $(C_1-C_6)$alkyl, $(C_3-C_6)$cycloalkyl, $(C_1-C_2)$alkyl$(C_3-C_6)$cycloalkyl, di$(C_1-C_2)$alkyl$(C_3-C_6)$cycloalkyl, $(C_4-C_7)$cycloalkylalkyl, $(C_2-C_6)$alkenyl, $(C_5-C_7)$cycloalkenyl, $(C_5-C_8)$cycloalkylalkenyl, $(C_3-C_6)$cycloalkyl-ethynyl, halo$(C_1-C_6)$alkyl, halo$(C_3-C_6)$cycloalkyl, halo$(C_4-C_7)$cycloalkylalkyl, $(C_1-C_2)$alkyl$(C_4-C_7)$cycloalkylalkyl, di$(C_1-C_2)$alkyl$(C_4-C_7)$cycloalkylalkyl, halo$(C_5-C_7)$cycloalkylethynyl, $(C_1-C_6)$alkoxy, $(C_3-C_6)$cycloalkoxy, $(C_4-C_7)$cycloalkylalkoxy, $(C_1-C_2)$alkyl$(C_3-C_7)$cycloalkoxy, $(C_1-C_2)$alkyl$(C_4-C_7)$cycloalkylalkoxy, di$(C_1-C_2)$-alkyl$(C_3-C_7)$cycloalkoxy, di$(C_1-C_2)$alkyl$(C_4-C_7)$cycloalkylalkoxy, halo$(C_1-C_6)$alkoxy, halo$(C_2-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$-cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$-alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, piperidino, and pyrrolidino; or 2) phenyl, napthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl$(C_1-C_3)$alkyl, napthyl$(C_1-C_3)$alkyl, heteroaryl$(C_1-C_3)$alkyl, or, bicyclic heteroaryl$(C_1-C_3)$alkyl, phenyl$(C_1-C_3)$alkoxy, naphthyl$(C_1-C_3)$alkoxy, heteroaryl$(C_1-C_3)$alkoxy, and bicyclic heteroaryl$(C_1-C_3)$alkoxy, each optionally substituted with 1 to 3 groups independently selected from:

fluorine, chlorine, cyano, $(C_1-C_3)$alkyl, halo$(C_1-C_3)$alkyl, $(C_1-C_3)$alkoxy, halo$(C_1-C_3)$alkoxy, $(C_1-C_3)$alkanesulfonyl, $(C_1-C_3)$-alkoxycarbonyl, and aminocarbonyl;

X and Y is each a single bond;

$R^2$ is a substituted or unsubstituted $(C_1-C_{10})$alkyl, $(C_2-C_{10})$alkenyl, $(C_2-C_{10})$alkynyl, $(C_1-C_{10})$alkoxy, $(C_2-C_{12})$alkenyloxy, $(C_1-C_{10})$alkylthio, $(C_1-C_5)$alkoxy$(C_1-C_5)$alkyl, $(C_1-C_5)$alkylthio$(C_1-C_5)$alkyl, $(C_1-C_5)$alkoxy$(C_1-C_5)$alkoxy, $(C_1-C_5)$alkoxy$(C_1-C_5)$alkylthio, $(C_1-C_5)$alkylthio$(C_1-C_5)$alkoxy, $(C_1-C_5)$alkylthio$(C_1-C_5)$alkylthio, $(C_1-C_3)$alkoxy$(C_1-C_3)$alkoxy$(C_1-C_3)$alkyl, aminocarbonylamino$(C_1-C_{10})$alkyl, aminocarbonylamino$(C_1-C_{10})$alkoxy, aminocarbonylamino$(C_1-C_{10})$alkylthio, $(C_1-C_8)$alkanoylamino$(C_1-C_5)$alkyl, $(C_1-C_5)$alkanoylamino$(C_1-C_5)$alkoxy, $(C_1-C_5)$alkanoylamino$(C_1-C_5)$alkylthio, aminosulfonylamino$(C_1-C_{10})$alkyl, aminosulfonylamino$(C_1-C_{10})$alkoxy, aminosulfonylamino$(C_1-C_{10})$alkylthio, $(C_1-C_5)$alkane-sulfonylamino$(C_1-C_5)$alkyl, $(C_1-C_5)$alkanesulfonylamino$(C_1-C_5)$alkoxy, $(C_1-C_5)$alkanesulfonyl-amino$(C_1-C_5)$alkylthio, $(C_1-C_5)$alkyl-aminocarbonylamino$(C_1-C_5)$alkyl, $(C_1-C_5)$alkylaminocarbonylamino$(C_1-C_5)$alkoxy, $(C_1-C_5)$alkylaminocarbonylamino$(C_1-C_5)$alkylthio, $(C_3-C_4)$cycloalkanecarbonylamino$(C_1-C_5)$alkyl, $(C_3-C_4)$cycloalkanecarbonylamino$(C_1-C_5)$alkoxy, $(C_3-C_4)$cycloalkanecarbonylamino$(C_1-C_5)$alkylthio, di$(C_1-C_5)$alkylaminocarbonylamino$(C_1-C_5)$alkyl, di$(C_1-C_5)$alkylaminocarbonylamino$(C_1-C_5)$alkoxy, di$(C_1-C_5)$-alkylaminocarbonylamino$(C_1-C_5)$alkylthio, wherein the substituted $(C_1-C_{10})$alkyl, $(C_2-C_{10})$alkenyl, $(C_2-C_{10})$alkynyl, $(C_1-C_{10})$alkoxy, $(C_1-C_{10})$alkylthio, $(C_1-C_5)$alkoxy$(C_1-C_5)$alkyl, $(C_1-C_5)$alkylthio$(C_1-C_5)$alkyl, $(C_1-C_5)$alkoxy$(C_1-C_5)$alkoxy, $(C_1-C_5)$alkoxy$(C_1-C_5)$alkylthio, $(C_1-C_5)$alkylthio$(C_1-C_5)$alkoxy, $(C_1-C_5)$alkylthio$(C_1-C_5)$alkylthio, $(C_1-C_3)$alkoxy$(C_1-C_3)$alkoxy$(C_1-C_3)$alkyl, aminocarbonylamino$(C_1-C_{10})$alkyl, aminocarbonylamino$(C_1-C_{10})$alkoxy, aminocarbonylamino$(C_1-C_{10})$alkylthio, $(C_1-C_5)$alkanoylamino$(C_1-C_5)$alkyl, $(C_1-C_5)$alkanoylamino$(C_1-C_5)$alkoxy, $(C_1-C_5)$alkanoylamino$(C_1-C_5)$alkylthio, $(C_3-C_4)$cycloalkanecarbonylamino$(C_1-C_5)$alkyl, $(C_3-C_4)$cycloalkanecarbonylamino$(C_1-C_5)$alkoxy, $(C_3-C_4)$cycloalkanecarbonylamino$(C_1-C_5)$alkylthio, aminosulfonylamino$(C_1-C_{10})$alkyl, aminosulfonylamino$(C_1-C_{10})$alkoxy, aminosulfonylamino$(C_1-C_{10})$alkylthio, $(C_1-C_5)$alkane-sulfonylamino$(C_1-C_5)$alkyl, $(C_1-C_5)$alkanesulfonylamino$(C_1-C_5)$alkoxy, $(C_1-C_5)$alkanesulfonyl-amino$(C_1-C_5)$alkylthio, $(C_1-C_5)$alkyl-aminocarbonylamino$(C_1-C_5)$alkyl, $(C_1-C_5)$alkylaminocarbonylamino$(C_1-C_5)$alkoxy, $(C_1-C_5)$alkylaminocarbonylamino$(C_1-C_5)$alkylthio, di$(C_1-C_5)$alkylaminocarbonylamino$(C_1-C_5)$alkyl, di$(C_1-C_5)$alkylaminocarbonylamino$(C_1-C_5)$alkoxy, di$(C_1-C_5)$alkylaminocarbonylamino$(C_1-C_5)$alkylthio represented by $R^2$ is substituted by at least one of: (a) 1 to 5 fluorine atoms and (b) by one group selected from cyano, hydroxyl, $(C_1-C_3)$ alkoxy, $(C_3-C_4)$cycloalkyl, $(C_3-C_4)$cycloalkoxy, halo$(C_1-C_3)$alkoxy, halo$(C_3-C_4)$cycloalkyl, and halo$(C_3-C_4)$cycloalkoxy, and wherein the thio-moiety of the unsubstituted or substituted $(C_1-C_{10})$alkylthio, $(C_1-C_5)$alkylthio$(C_1-C_5)$alkyl, $(C_1-C_5)$alkoxy$(C_1-C_5)$alkylthio, $(C_1-C_5)$alkylthio$(C_1-C_5)$alkoxy, $(C_1-C_5)$alkylthio$(C_1-C_5)$alkylthio, aminocarbonylamino$(C_1-C_{10})$alkylthio, $(C_1-C_5)$alkanoylamino$(C_1-C_5)$alkylthio, $(C_3-C_4)$cycloalkanecarbonylamino$(C_1-C_5)$alkylthio, aminosulfonylamino$(C_1-C_{10})$alkylthio, $(C_1-C_5)$alkanesulfonyl-amino $(C_1-C_5)$alkylthio, $(C_1-C_5)$-alkylaminocarbonylamino$(C_1-C_5)$alkylthio or di$(C_1-C_5)$alkylaminocarbonylamino$(C_1-C_5)$alkylthio represented by $R^2$ is optionally replaced by a sulfinyl (sulfoxide, i.e., —S(O)—) or a sulfonyl (sulfone, i.e., —S(O)$_2$—) moiety, and wherein the carbonyl moiety of the unsubstituted or substituted aminocarbonylamino$(C_1-C_{10})$alkyl, aminocarbonylamino$(C_1-C_{10})$alkoxy, aminocarbonylamino$(C_1-C_{10})$alkylthio, $(C_1-C_5)$alkanoylamino$(C_1-C_5)$alkyl, $(C_1-C_5)$alkanoylamino$(C_1-C_5)$alkoxy, $(C_1-C_5)$alkanoylamino$(C_1-C_5)$alkylthio, $(C_3-C_4)$cycloalkanecarbonylamino$(C_1-C_5)$alkyl, $(C_3-C_4)$cycloalkanecarbonylamino$(C_1-C_5)$alkoxy, $(C_3-C_4)$cycloalkanecarbonylamino$(C_1-C_5)$alkylthio, $(C_1-C_5)$alkylaminocarbonylamino$(C_1-C_5)$alkyl, $(C_1-C_5)$alkylaminocarbonylamino$(C_1-C_5)$alkoxy, $(C_1-C_5)$-alkylaminocarbonylamino$(C_1-C_5)$alkylthio, di$(C_1-C_5)$alkylaminocarbonylamino$(C_1-C_5)$alkyl, di$(C_1-C_5)$alkylaminocarbonylamino$(C_1-C_5)$alkoxy and di$(C_1-C_5)$-alkylaminocarbonylamino$(C_1-C_5)$alkylthio represented by $R^2$ is optionally replaced with a thiocarbonyl, $R^3$ is H, halogen, $(C_1-C_3)$alkyl, $(C_1-C_3)$alkoxy, hydroxyl, hydroxy$(C_1-C_3)$alkyl, hydroxy$(C_1-C_3)$alkoxy, $(C_1-C_4)$alkanoylamino, $(C_1-C_3)$alkoxycarbonylamino, $(C_1-C_3)$alkylamino-carbonylamino, di$(C_1-C_3)$alkylaminocarbonylamino, $(C_1-C_3)$alkanesulfonylamino, $(C_1-C_3)$alkylaminosulfonylamino di$(C_1-C_3)$alkylaminosulfonylamino, phenylamino, or heteroarylamino in which each phenylamino and heteroarylamino group is optionally substituted with 1 to 3 groups independently selected from:

fluorine, chlorine, cyano, $(C_1-C_3)$alkyl, halo$(C_1-C_3)$alkyl, $(C_1-C_3)$alkoxy, halo$(C_1-C_3)$alkoxy, $(C_1-C_3)$alkanesulfonyl, and $(C_1-C_3)$alkoxycarbonyl;

provided that when $R^3$ is hydroxyl, halogen, or optionally substituted phenylamino or heteroarylamino, then $R^2$ is not a substituted or unsubstituted $(C_1-C_{10})$alkoxy, $(C_2-C_{12})$alkenyloxy, $(C_1-C_{10})$alkylthio, $(C_1-C_5)$alkoxy$(C_1-C_5)$alkoxy, $(C_1-C_5)$alkoxy$(C_1-C_5)$alkylthio, $(C_1-C_5)$alkylthio$(C_1-C_5)$alkoxy, $(C_1-C_5)$alkylthio$(C_1-C_5)$alkylthio, aminocarbonylamino$(C_1-C_{10})$alkoxy, aminocarbonylamino$(C_1-C_{10})$alkylthio, $(C_1-C_5)$alkanoylamino$(C_1-C_5)$alkoxy, $(C_1-C_5)$alkanoylamino$(C_1-C_5)$alkylthio, $(C_3-C_4)$cycloalkanecarbonylamino$(C_1-C_5)$alkoxy, $(C_3-C_4)$cycloalkanecarbonylamino$(C_1-C_5)$alkylthio, aminosulfonylamino$(C_1-C_{10})$alkoxy, aminosulfonylamino$(C_1-C_{10})$alkylthio, $(C_1-C_5)$alkane-sulfonylamino$(C_1-C_5)$alkoxy, $(C_1-C_5)$alkanesulfonylamino$(C_1-C_5)$alkylthio, $(C_1-C_5)$alkyl-aminocarbonylamino$(C_1-C_5)$alkoxy, $(C_1-C_5)$alkylaminocarbonylamino$(C_1-C_5)$alkylthio, di$(C_1-C_5)$alkylaminocarbonylamino$(C_1-C_5)$alkoxy or di$(C_1-C_5)$ alkylaminocarbonylamino$(C_1-C_5)$alkylthio, provided further that when $R^3$ is hydroxyl, halogen, or optionally substituted phenylamino or heteroarylamino, then $R^2$ is not a unsubstituted or substituted $(C_1-C_{10})$alkylthio, $(C_1-C_5)$alkoxy$(C_1-C_5)$alkylthio, $(C_1-C_5)$alkylthio$(C_1-C_5)$alkylthio, aminocarbonylamino$(C_1-C_{10})$alkylthio, $(C_1-C_5)$alkanoylamino$(C_1-C_5)$alkylthio, $(C_3-C_4)$cycloalkanecarbonylamino$(C_1-C_5)$alkylthio, aminosulfonylamino$(C_1-C_{10})$alkylthio, $(C_1-C_5)$alkanesulfonyl-amino$(C_1-C_5)$alkylthio, $(C_1-C_5)$-alkylaminocarbonylamino$(C_1-C_5)$alkylthio, di$(C_1-C_5)$-alkylaminocarbonylamino$(C_1-C_5)$alkylthio wherein the thio moiety is replaced by a sulfinyl (sulfoxide, i.e., —S(O)—) or a sulfonyl (sulfone, i.e., —S(O)$_2$—) moiety, and provided further that when $R^3$ is hydroxyl, halogen, or optionally substituted phenylamino or heteroarylamino, then $R^2$ is not a unsubstituted or substituted aminocarbonylamino$(C_1-C_{10})$alkoxy, aminocarbonylamino$(C_1-C_{10})$alkylthio, $(C_1-C_5)$alkanoylamino$(C_1-C_5)$alkoxy, $(C_1-C_5)$alkanoylamino$(C_1-C_5)$alkylthio, $(C_3-C_4)$cycloalkanecarbonylamino $(C_1-C_5)$alkoxy, $(C_3-C_4)$cycloalkanecarbonylamino$(C_1-C_5)$alkylthio, $(C_1-C_5)$alkylaminocarbonylamino$(C_1-C_5)$alkoxy, $(C_1-C_5)$alkylaminocarbonylamino$(C_1-C_5)$alkylthio, di$(C_1-C_5)$alkylaminocarbonylamino$(C_1-C_5)$alkoxy and di$(C_1-C_5)$-alkylaminocarbonylamino$(C_1-C_5)$alkylthio, wherein the carbonyl moiety is replaced with a thiocarbonyl moiety A is a saturated or unsaturated 4-, 5-, 6- or 7-membered ring wherein said ring is composed of carbon atoms, and 0-2 hetero atoms selected from 0, 1 or 2 nitrogen atoms, 0 or 1 oxygen atoms, and 0 or 1 sulfur atoms, said ring atoms being substituted with the appropriate number of hydrogen atoms; said ring being optionally substituted with up to four independently selected halogen atoms, $(C_1-C_6)$alkyl groups, halo $(C_1-C_6)$alkyl groups, and oxo groups;

Q and Y are attached to carbon or nitrogen atoms in ring A in a 1,3 relationship;

Q is a divalent radical selected from:

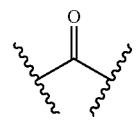
Q1

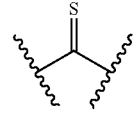
Q2

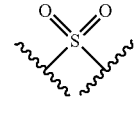
Q3

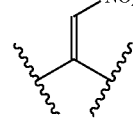
Q4

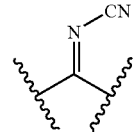
Q5

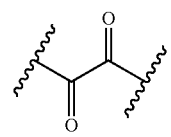
Q6

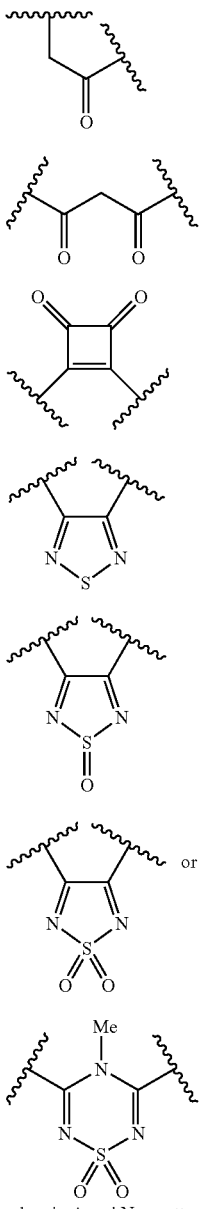

wherein A and N are attached to the truncated bonds $R^4$ is H, $(C_1-C_3)$alkyl, halo$(C_1-C_3)$alkyl; $(C_1-C_2)$alkoxy$(C_1-C_2)$alkyl, or cyano$(C_1-C_3)$alkyl;

L is 1) a linear $(C_2-C_3)$alkyl chain when G is OH, $OR^9$, $NH_2$, $NHR^9$, NHC(=NH)$NH_2$, or NHC(=NH)$NHR^9$ or 2) a linear $(C_1-C_2)$alkyl chain when G is C(=NH)$NH_2$ or C(=NH)$NHR^9$;

L is optionally substituted by 1-4 groups independently selected from $R^5$, $R^6$, $R^7$, and $R^8$;

one or more of the carbon atoms of L may be part of a 3-, 4-, 5-, 6- or 7-membered saturated ring composed of carbon atoms, and 0-2 heteroatoms selected from 0 or 1 nitrogen atoms, 0 or 1 oxygen atoms, and 0 or 1 sulfur atoms; said saturated ring being optionally substituted with up to four groups selected from fluorine, $(C_1-C_3)$alkyl, halo$(C_1-C_3)$alkyl, $(C_3-C_6)$cycloalkyl, halo$(C_3-C_6)$cycloalkyl, $(C_4-C_7)$cycloalkylalkyl, halo$(C_4-C_7)$cycloalkylalkyl, and oxo;

$R^5$, $R^6$, $R^7$, and $R^8$ is each independently 1) $(C_1-C_{10})$alkyl, $(C_3-C_7)$cycloalkyl, $(C_3-C_7)$cycloalkyl$(C_1-C_3)$alkyl, $(C_2-C_{10})$alkenyl, $(C_5-C_7)$cycloalkyl$(C_1-C_3)$alkenyl, $(C_2-C_{10})$alkynyl, $(C_3-C_7)$cycloalkyl$(C_1-C_3)$alkynyl, $(C_4-C_{10})$bicycloalkyl$(C_1-C_3)$alkyl, $(C_8-C_{12})$tricycloalkyl$(C_1-C_3)$alkyl, $(C_1-C_6)$alkoxy$(C_1-C_6)$alkyl, $(C_3-C_7)$cycloalkoxy$(C_1-C_3)$alkyl, $(C_1-C_6)$alkylthio$(C_1-C_6)$alkyl, $(C_3-C_7)$cycloalkylthio$(C_1-C_3)$alkyl, saturated heterocyclyl, or saturated heterocyclyl$(C_1-C_3)$alkyl wherein (a) hydrogen atoms in these groups are optionally substituted by 1 to 6 groups independently selected from fluorine, cyano, hydroxyl, $(C_1-C_3)$alkyl, $(C_1-C_3)$alkoxy, halo$(C_1-C_3)$alkyl, halo$(C_1-C_3)$alkoxy and wherein (b) divalent sulfur atoms are optionally oxidized to sulfoxide or sulfone; or 2) phenyl, naphthyl, heteroaryl, phenyl$(C_1-C_3)$alkyl, naphthyl$(C_1-C_3)$alkyl, or heteroaryl$(C_1-C_3)$alkyl each optionally substituted with 1 to 3 groups independently selected from:

fluorine, chlorine, cyano, $(C_1-C_3)$alkyl, halo$(C_1-C_3)$alkyl, $(C_1-C_3)$alkoxy, halo$(C_1-C_3)$alkoxy, $(C_1-C_3)$alkanesulfonyl, and $(C_1-C_3)$alkoxycarbonyl;

G is OH, $OR^9$, $NH_2$, $NHR^9$, $NR^9R^{10}$, C(=NH)$NH_2$, C(=NH)$NHR^9$, NHC(=NH)$NH_2$, or NHC(=NH)$NHR^9$;

$R^9$ is a) $(C_1-C_{10})$alkyl, $(C_4-C_{10})$cycloalkylalkyl, halo$(C_1-C_{10})$alkyl, halo$(C_4-C_{10})$cycloalkylalkyl, $(C_2-C_{10})$alkenyl, $(C_5-C_{10})$cycloalkylalkenyl, halo$(C_2-C_{10})$alkenyl, halo$(C_5-C_{10})$cycloalkylalkenyl, $(C_2-C_{10})$alkynyl, $(C_5-C_{10})$cycloalkylalkynyl, halo$(C_2-C_{10})$alkynyl, halo$(C_5-C_{10})$cycloalkylalkynyl, $(C_1-C_5)$alkoxy$(C_1-C_5)$alkyl, halo$(C_1-C_5)$alkoxy$(C_1-C_5)$alkyl, $(C_1-C_5)$alkylthio$(C_1-C_5)$alkyl, halo$(C_1-C_5)$-alkylthio$(C_1-C_5)$alkyl, $(C_1-C_5)$alkanesulfinyl$(C_1-C_5)$alkyl, halo$(C_1-C_5)$alkanesulfinyl$(C_1-C_5)$alkyl, $(C_1-C_5)$alkanesulfonyl$(C_1-C_5)$alkyl, halo$(C_1-C_6)$alkanesulfonyl$(C_1-C_5)$alkyl, aminocarbonyl$(C_1-C_5)$alkyl, $(C_1-C_6)$alkylaminocarbonyl$(C_1-C_6)$alkyl, di$(C_1-C_6)$alkylaminocarbonyl$(C_1-C_6)$alkyl cyano$(C_1-C_5)$alkyl, saturated heterocyclyl, saturated heterocyclyl$(C_1-C_3)$alkyl or b) phenyl, naphthyl, heteroaryl, phenyl$(C_1-C_3)$alkyl, naphthyl$(C_1-C_3)$alkyl, or heteroaryl$(C_1-C_3)$alkyl each optionally substituted by 1 to 3 groups independently selected from:

fluorine, chlorine, cyano, $(C_1-C_3)$alkyl, halo$(C_1-C_3)$alkyl, $(C_1-C_3)$alkoxy, halo$(C_1-C_3)$alkoxy, $(C_1-C_3)$alkanesulfonyl, and $(C_1-C_3)$alkoxycarbonyl; or b) $R^9$ is a saturated divalent radical composed of carbon atoms, 0 or 1 nitrogen atom, 0 or 1 oxygen atoms, and 0, or 1 sulfur atoms that is attached to any core carbon atom on the chain L to form a saturated 3-, 4-, 5-, 6- or 7-membered ring; said ring being optionally substituted with 1-4 groups selected from fluorine, $(C_1-C_8)$alkyl, halo$(C_1-C_8)$alkyl, $(C_3-C_8)$cycloalkyl, halo$(C_3-C_8)$cycloalkyl, hydroxy$(C_3-C_8)$cycloalkyl, $(C_3-C_8)$cycloalkyl$(C_1-C_3)$alkyl, halo$(C_3-C_8)$cycloalkyl$(C_1-C_3)$alkyl, hydroxylated $(C_3-C_8)$cycloalkyl$(C_1-C_3)$alkyl, $(C_1-C_8)$alkoxy, halo$(C_1-C_8)$alkoxy, $(C_3-C_8)$cycloalkoxy, halo$(C_3-C_8)$cycloalkoxy, hydroxy$(C_3-C_8)$cycloalkoxy, $(C_1-C_8)$alkoxy$(C_1-C_3)$alkyl, halo$(C_1-C_8)$alkoxy$(C_1-C_3)$alkyl, $(C_3-C_8)$cycloalkoxy$(C_1-C_3)$alkyl, halo$(C_3-C_8)$cycloalkoxy$(C_1-C_3)$alkyl, hydroxy$(C_3-C_8)$cycloalkoxy$(C_1-C_3)$alkyl, $(C_3-C_8)$cycloalkyl$(C_1-C_3)$alkoxy$(C_1-C_3)$alkyl, halo$(C_3-C_8)$cycloalkyl$(C_1-C_3)$alkoxy$(C_1-C_3)$alkyl, hydroxylated$(C_3-C_8)$cycloalkyl$(C_1-C_3)$alkoxy$(C_1-C_3)$alkyl, $(C_1-C_8)$alkylthio, halo$(C_1-C_8)$alkylthio, $(C_3-C_8)$cycloalkylthio, halo$(C_3-C_8)$cycloalkylthio, hydroxy$(C_3-C_8)$cycloalkylthio, $(C_3-C_8)$cycloalkyl$(C_1-C_3)$alkylthio, halo$(C_3-C_8)$cycloalkyl$(C_1-C_3)$alkylthio, hydroxylated$(C_3-C_8)$ cycloalkyl($C_1$-$C_3$)alkylthio, ($C_1$-$C_8$)alkylthio($C_1$-$C_3$)alkyl, halo($C_1$-$C_8$)alkylthio($C_1$-$C_3$)alkyl, ($C_3$-$C_8$)cycloalkylthio ($C_1$-$C_3$)alkyl, halo($C_3$-$C_8$)cycloalkylthio($C_1$-$C_3$)alkyl, hydroxy($C_3$-$C_8$)cycloalkylthio($C_1$-$C_3$)alkyl, ($C_3$-$C_8$)cycloalkyl($C_1$-$C_3$)alkylthio($C_1$-$C_3$)alkyl, halo($C_3$-$C_8$)cycloalkyl($C_1$-$C_3$)alkylthio($C_1$-$C_3$)alkyl, hydroxylated($C_3$-$C_8$) cycloalkyl($C_1$-$C_3$)alkylthio($C_1$-$C_3$)alkyl and oxo;

$R^{10}$ is ($C_1$-$C_6$)alkyl or halo($C_1$-$C_6$)alkyl;

provided that when $R^2$ is ($C_1$-$C_{10}$)alkyl and $R^3$ is OH, only a single substituent $R^5$ is allowed on L;

and the enantiomers, diastereomers and salts thereof.

A third embodiment of the invention is a compound of Formula I, wherein $R^1$ is a) ($C_3$-$C_7$)cycloalkyl; or b) phenyl, heteroaryl, or bicyclic heteroaryl optionally substituted with 1 to 3 groups independently selected from:

1) fluorine, chlorine, bromine, cyano, nitro, ($C_1$-$C_6$)alkyl, ($C_3$-$C_6$)cycloalkyl, ($C_4$-$C_7$)cycloalkylalkyl, ($C_2$-$C_6$)alkenyl, ($C_5$-$C_6$)cycloalkenyl, ($C_5$-$C_8$)cycloalkylalkenyl, ($C_2$-$C_6$) alkynyl, ($C_3$-$C_6$)cycloalkylethynyl, halo($C_1$-$C_6$)alkyl, halo ($C_3$-$C_6$)cycloalkyl, halo($C_4$-$C_7$)-cycloalkylalkyl, halo($C_2$-$C_6$)alkenyl, halo($C_3$-$C_6$)alkynyl, halo($C_3$-$C_6$) cycloalkylethynyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$) cycloalkoxy, halo($C_4$-$C_7$)cycloalkylalkoxy, ($C_3$-$C_6$) alkenyloxy and ($C_1$-$C_6$)alkanesulfonyl; or 2) phenyl, heteroaryl, phenoxy, heteroaryloxy, phenylthio, heteroarylthio, benzyl, heteroarylmethyl, benzyloxy and heteroaryloxy, each optionally substituted with 1 to 3 groups independently selected from:

fluorine, chlorine, cyano, ($C_1$-$C_3$)alkyl, halo($C_1$-$C_3$)alkyl, ($C_1$-$C_3$)-alkoxy, halo($C_1$-$C_3$)alkoxy, and aminocarbonyl;

X and Y is each a single bond;

$R^2$ is ($C_1$-$C_8$)alkyl, ($C_4$-$C_8$)cycloalkylalkyl, fluoro($C_1$-$C_8$) alkyl, fluoro($C_4$-$C_8$)cycloalkylalkyl, ($C_1$-$C_8$)alkoxy, ($C_2$-$C_8$) alkenyloxy, ($C_4$-$C_8$)cycloalkylalkoxy, fluoro($C_1$-$C_8$)alkoxy, hydroxy($C_1$-$C_8$)alkyl, ($C_1$-$C_5$)alkoxy($C_1$-$C_5$)alkyl, ($C_1$-$C_5$) alkoxy($C_1$-$C_5$)hydroxyalkyl, ($C_3$-$C_4$)cycloalkoxy($C_1$-$C_5$) alkyl, fluoro($C_1$-$C_5$)alkoxy($C_1$-$C_5$)alkyl, fluoro($C_3$-$C_4$)cycloalkoxy($C_1$-$C_5$)alkyl, ($C_1$-$C_5$)alkylthio($C_1$-$C_5$)alkyl, ($C_1$-$C_5$)alkoxy($C_1$-$C_5$)alkoxy, hydroxy($C_1$-$C_8$)alkoxy, ($C_3$-$C_4$) cycloalkoxy($C_1$-$C_5$)alkoxy, fluoro($C_1$-$C_5$)alkoxy($C_1$-$C_5$) alkoxy, fluoro($C_3$-$C_4$)cycloalkoxy($C_1$-$C_5$)alkoxy, ($C_1$-$C_3$) alkoxy($C_1$-$C_3$)alkoxy($C_1$-$C_3$)alkyl, fluoro($C_1$-$C_3$)alkoxy ($C_1$-$C_3$)alkoxy($C_1$-$C_3$)alkyl, aminocarbonylamino($C_1$-$C_8$) alkyl, aminocarbonylamino($C_1$-$C_8$)alkoxy, ($C_1$-$C_5$) alkanoylamino($C_1$-$C_5$)alkyl, ($C_1$-$C_5$)alkanoylamino($C_1$-$C_5$) alkoxy, fluoro($C_1$-$C_5$)alkanoylamino($C_1$-$C_5$)alkyl, fluoro ($C_1$-$C_5$)alkanoylamino($C_1$-$C_5$)alkoxy, ($C_3$-$C_4$) cycloalkanecarbonylamino($C_1$-$C_6$)alkyl, ($C_3$-$C_4$) cycloalkanecarbonylamino($C_1$-$C_6$)alkoxy, ($C_1$-$C_3$)alkoxy ($C_1$-$C_5$)alkanoylamino($C_1$-$C_5$)alkyl, ($C_1$-$C_3$)alkoxy($C_1$-$C_5$) alkanoylamino($C_1$-$C_5$)alkoxy, ($C_3$-$C_4$) cycloalkanecarbonyllamino($C_1$-$C_5$)alkyl, ($C_3$-$C_4$) cycloalkanecarbonyllamino($C_1$-$C_5$)alkoxy, aminosulfonylamino($C_1$-$C_8$)alkyl, aminosulfonylamino($C_1$-$C_8$)alkoxy, ($C_1$-$C_5$)alkanesulfonyl-amino($C_1$-$C_5$)alkyl, ($C_1$-$C_5$)alkanesulfonylamino($C_1$-$C_5$)alkoxy, ($C_1$-$C_5$)alkylaminocarbonylamino($C_1$-$C_5$)alkyl, di($C_1$-$C_5$) alkylaminocarbonylamino($C_1$-$C_5$)alkyl, ($C_1$-$C_5$) alkylaminocarbonylamino($C_1$-$C_5$)alkoxy, di($C_1$-$C_5$) alkylaminocarbonylamino($C_1$-$C_5$)alkoxy, $R^3$ is H, halogen, OH, ($C_1$-$C_4$)alkanoylamino, or ($C_1$-$C_3$) alkoxy;

provided that when $R^3$ is OH or halogen, then $R^2$ is not ($C_1$-$C_8$)alkoxy, ($C_4$-$C_8$)cycloalkylalkoxy, fluoro($C_1$-$C_8$) alkoxy, ($C_2$-$C_8$)alkenyloxy, ($C_1$-$C_5$)alkoxy($C_1$-$C_5$)alkoxy, hydroxy($C_1$-$C_8$)alkoxy, ($C_3$-$C_4$)cycloalkoxy($C_1$-$C_5$)alkoxy, fluoro($C_1$-$C_5$)alkoxy($C_1$-$C_5$)alkoxy, fluoro($C_3$-$C_4$)cycloalkoxy($C_1$-$C_5$)alkoxy, aminocarbonylamino($C_1$-$C_8$) alkoxy, ($C_1$-$C_5$)alkanoyl-amino($C_1$-$C_5$)alkoxy, fluoro($C_1$-$C_5$)alkanoylamino($C_1$-$C_5$)alkoxy, ($C_3$-$C_4$) cycloalkanecarbonylamino($C_1$-$C_6$)alkoxy, ($C_1$-$C_3$)alkoxy ($C_1$-$C_5$)alkanoyl-amino($C_1$-$C_5$)alkoxy, ($C_3$-$C_4$) cycloalkanecarbonylamino($C_1$-$C_5$)alkoxy, aminosulfonylamino($C_1$-$C_8$)alkoxy, ($C_1$-$C_5$)alkanesulfonylamino($C_1$-$C_5$)alkoxy($C_1$-$C_5$)alkylaminocarbonylamino($C_1$-$C_5$)alkoxy, di($C_1$-$C_5$)alkylaminocarbonylamino($C_1$-$C_5$) alkoxy, A is a saturated 5-, 6-, or 7-membered ring wherein said ring is composed of carbon atoms and 0-2 heteroatoms selected from 0 or 1 nitrogen atoms, 0 or 1 oxygen atoms, and 0 or 1 sulfur atoms; said ring atoms being substituted with the appropriate number of hydrogen atoms; said ring being optionally substituted with up to four independently selected fluorine atoms, ($C_1$-$C_3$)alkyl groups, halo($C_1$-$C_3$)alkyl groups, or oxo groups;

the substituents Q and Y are attached in a 1,3 relationship;

Q is Q1, Q2, Q4, Q5, Q9, or Q10

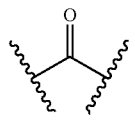

Q1

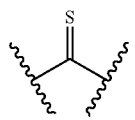

Q2

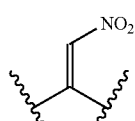

Q4

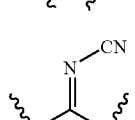

Q5

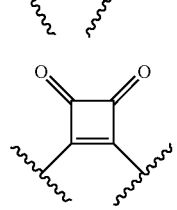

Q9

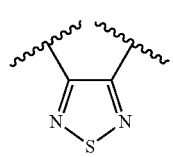

Q10 wherein A and N are attached to the truncated bonds $R^4$ is H or $(C_1-C_3)$alkyl;

L is $C_2$ alkyl in which one hydrogen atom is optionally replaced with $R^5$ and a second hydrogen atom is optionally replaced with $R^6$;

$R^5$ is a) $(C_1-C_{10})$alkyl, $(C_3-C_7)$cycloalkyl$(C_1-C_2)$alkyl, fluoro$(C_1-C_{10})$alkyl, hydroxy$(C_1-C_{10})$alkyl, fluoro$(C_3-C_7)$cycloalkyl$(C_1-C_2)$alkyl, hydroxylated fluoro$(C_3-C_7)$cycloalkyl$(C_1-C_2)$alkyl, hydroxylated $(C_3-C_7)$cycloalkyl$(C_1-C_2)$alkyl, $(C_1-C_2)$alkyl$(C_3-C_7)$cycloalkyl$(C_1-C_2)$alkyl, di$(C_1-C_2)$alkyl$(C_3-C_7)$cycloalkyl$(C_1-C_2)$alkyl, hydroxylated $(C_1-C_2)$alkyl$(C_3-C_7)$cycloalkyl$(C_1-C_2)$alkyl, hydroxylated di$(C_1-C_2)$alkyl$(C_3-C_7)$cycloalkyl$(C_1-C_2)$alkyl, $(C_4-C_{10})$bicycloalkyl$(C_1-C_2)$alkyl, $(C_8-C_{12})$tricycloalkyl$(C_1-C_2)$alkyl, $(C_1-C_6)$alkoxy$(C_1-C_6)$alkyl, halo$(C_1-C_6)$alkoxy$(C_1-C_6)$alkyl, $(C_3-C_7)$cycloalkoxy$(C_1-C_3)$alkyl, $(C_1-C_5)$alkylthio$(C_1-C_5)$alkyl, halo$(C_1-C_5)$alkylthio$(C_1-C_5)$alkyl, or saturated heterocyclyl$(C_1-C_3)$alkyl; or b) phenyl$(C_1-C_2)$alkyl or heteroaryl$(C_1-C_2)$alkyl each optionally substituted with 1 to 3 groups independently selected from fluorine, chlorine, cyano, $(C_1-C_3)$alkyl, halo$(C_1-C_3)$alkyl, $(C_1-C_3)$alkoxy, and halo$(C_1-C_3)$alkoxy;

$R^6$ is absent or is $(C_1-C_6)$alkyl, hydroxy$(C_1-C_6)$alkyl, or $(C_1-C_3)$alkoxy$(C_1-C_3)$alkyl;

$R^7$ and $R^8$ are absent;

G is OH, $NH_2$, $NHR^9$, or $NR^9R^{10}$;

$R^9$ is a) $(C_1-C_6)$alkyl, halo$(C_1-C_6)$alkyl, $(C_4-C_{10})$cycloalkylalkyl, $(C_1-C_5)$alkoxy$(C_1-C_5)$alkyl, aminocarbonyl$(C_1-C_5)$alkyl, $(C_1-C_6)$alkylaminocarbonyl$(C_1-C_6)$alkyl, or di$(C_1-C_6)$alkyl-aminocarbonyl$(C_1-C_6)$alkyl; or b) phenyl$(C_1-C_2)$alkyl optionally substituted with 1 to 3 groups independently selected from:

fluorine, chlorine, cyano, $(C_1-C_3)$alkyl, halo$(C_1-C_3)$alkyl, $(C_1-C_3)$alkoxy, and halo$(C_1-C_3)$alkoxy;

or c) is attached to L and is —$(CH_2)_2$—, —$(CH_2)_3$—, or —$(CH_2)_4$— optionally substituted with 1 or 2 groups independently selected from fluorine, $(C_1-C_8)$alkyl, halo$(C_1-C_8)$alkyl, $(C_3-C_8)$cycloalkyl, halo$(C_3-C_8)$cycloalkyl, hydroxy$(C_3-C_8)$Cycloalkyl, $(C_3-C_8)$cycloalkyl$(C_1-C_3)$alkyl, halo$(C_3-C_8)$cycloalkyl$(C_1-C_3)$alkyl, and hydroxylated $(C_3-C_8)$cycloalkyl$(C_1-C_3)$alkyl, $(C_1-C_8)$alkoxy, halo$(C_1-C_8)$alkoxy, $(C_3-C_8)$cycloalkoxy, halo$(C_3-C_8)$cycloalkoxy, hydroxy$(C_3-C_8)$cycloalkoxy, $(C_1-C_8)$alkoxy$(C_1-C_3)$alkyl, halo$(C_1-C_8)$alkoxy$(C_1-C_3)$alkyl, $(C_3-C_8)$cycloalkoxy$(C_1-C_3)$alkyl, halo$(C_3-C_8)$cycloalkoxy$(C_1-C_3)$alkyl, hydroxy$(C_3-C_8)$cycloalkoxy$(C_1-C_3)$alkyl, $(C_3-C_8)$cycloalkyl$(C_1-C_3)$alkoxy$(C_1-C_3)$alkyl, halo$(C_3-C_8)$cycloalkyl$(C_1-C_3)$alkoxy$(C_1-C_3)$alkyl, hydroxylated$(C_3-C_8)$cycloalkyl$(C_1-C_3)$alkoxy$(C_1-C_3)$alkyl, $(C_1-C_8)$alkylthio, halo$(C_1-C_8)$alkylthio, $(C_3-C_8)$cycloalkylthio, halo$(C_3-C_8)$cycloalkylthio, hydroxy$(C_3-C_8)$cycloalkylthio, $(C_3-C_8)$cycloalkyl$(C_1-C_3)$alkylthio, halo$(C_3-C_8)$cycloalkyl$(C_1-C_3)$alkylthio, hydroxylated$(C_3-C_8)$cycloalkyl$(C_1-C_3)$alkylthio, $(C_1-C_8)$alkylthio$(C_1-C_3)$alkyl, halo$(C_1-C_8)$alkylthio$(C_1-C_3)$alkyl, $(C_3-C_8)$cycloalkylthio$(C_1-C_3)$alkyl, halo$(C_3-C_8)$cycloalkylthio$(C_1-C_3)$alkyl, hydroxy$(C_3-C_8)$cycloalkylthio$(C_1-C_3)$alkyl, $(C_3-C_8)$cycloalkyl$(C_1-C_3)$alkylthio$(C_1-C_3)$alkyl, halo$(C_3-C_8)$cycloalkyl$(C_1-C_3)$alkylthio$(C_1-C_3)$alkyl, and hydroxylated$(C_3-C_8)$cycloalkyl$(C_1-C_3)$alkylthio$(C_1-C_3)$alkyl;

$R^{10}$ is $(C_1-C_3)$alkyl or halo$(C_1-C_3)$alkyl;

provided that when $R^2$ is $(C_1-C_8)$alkyl and $R^3$ is OH, only a single substituent $R^5$ is allowed on L;

and the enantiomers, diastereomers and salts thereof.

A fourth embodiment of the invention is a compound of Formula I, wherein $R^1$ is a) cyclohexyl or trifluoromethyl; or b) phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl optionally substituted with 1 to 3 substituents independently selected from:

fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, ethyl, trifluoromethyl, and aminocarbonyl;

X and Y is each a single bond;

$R^2$ is methyl, ethyl, propyl, butyl, pentyl, hexyl, 5-pentenyloxy, 3,3,3-trifluoropropyl, 4,4-difluoropentyl, 3-(cyclopropyl)propyl, 4-(cyclopropyl)butyl, 3-hydroxypropyl, 4-hydroxybutyl, 4-hydroxypentyl, 4-hydroxyhexyl, 5-hydroxyhexyl, 2-hydroxyethoxy, 3-methoxypropyl, 3-ethoxypropyl, 4-methoxybutyl, 4-ethoxybutyl, 2-(ethoxy)ethoxy, 3-methoxypropoxy, 3-ethoxypropoxy, 3-propoxypropoxy, 2-cyclopropylethoxy, (2-(methoxy)ethoxy)methyl, 3-(acetylamino)propyl, 3-(propionylamino)propyl, 3-(butanoylamino)propyl, 3-((2-methoxypropionyl)amino)propyl, 3-(cyclopropanecarbonylamino)propyl, 3-(trifluoroacetylamino)propyl, 3-(methylaminocarbonylamino)propyl, 3-(dimethylaminocarbonylamino)propyl, 2-(acetylamino)ethoxy, 2-(propionylamino)ethoxy, methoxymethylcarbonylaminomethyl, 3-(aminosulfonylamino)propyl or 3-(methanesulfonylamino)propyl;

$R^3$ is H, F, OH, methoxy, ethoxy, 3-hydroxypropoxy, acetylamino, propionylamino, (2-methylpropionyl)amino, or butanoylamino, provided that when $R^3$ is F or OH, $R^2$ is not 2-(ethoxy)ethoxy, 3-methoxypropoxy, 3-ethoxypropoxy, 3-propoxypropoxy, 2-cyclopropylethoxy, 2-(acetylamino)ethoxy or 2-(propionylamino)ethoxy;

A is 2,4-disubstituted morpholine with $R^1XCR^2R^3Y$ attached at the 2-position and Q attached at the 4-position, 1,3-disubstituted piperidine with $R^1XCR^2R^3Y$ attached at the 3-position and Q attached at the 1-position, 1,3-disubstituted-3-methylpiperidine with $R^1XCR^2R^3Y$ attached at the 3-position and Q attached at the 1-position, 1,3-disubstituted benzene, or 1,3-disubstituted cyclohexane;

Q is Q1, Q2, Q4, Q5, Q9, or Q10

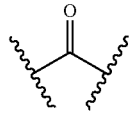

Q1

-continued

Q2

Q4

Q5

Q9

Q10 wherein A and N are attached to the truncated bonds $R^4$ is H or methyl;

L is a $C_2$ alkyl chain in which one hydrogen atom is optionally replaced with a group selected from $R^5$;

$R^5$ is methyl, isobutyl, t-butylmethyl, 2,2,2-trifluoroethyl, 2-(trifluoromethyl)propyl, cyclopropylmethyl, cyclopentylmethyl, cyclohexylmethyl, 2-(cyclohexyl)ethyl, (3-noradamantyl)methyl, (3,3-difluorocyclobutyl)methyl, (3,4-difluorocyclopentyl)methyl, 4,4-difluorocyclohexylmethyl, (4-methylcyclohexyl)methyl, tert-butoxymethyl, (2-tetrahydrofuranyl)methyl, (2-tetrahydropyranyl)methyl, (4-tetrahydropyranyl)methyl, (3-methoxycyclobutyl)methyl, (4-methoxycyclohexyl)methyl, benzyl, phenethyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (4-fluorocyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, (3-noradamantyl)(hydroxy)methyl, 2-methoxy-2-methylpropyl, or 2,2-dimethyl-3-methoxypropyl;

$R^6$ is absent or is methyl or hydroxymethyl;

$R^7$ and $R^8$ are absent;

G is $NH_2$, $NHR^9$, or $NR^9R^{10}$;

$R^9$ is methyl, ethyl, propyl, butyl, isobutyl, pentyl, isopentyl, aminocarbonylmethyl, —$(CH_2)_3$—, —$(CH_2)_4$—, —$(CH_2)_2CH$(c-hex)-, or —$(CH_2)_2CH(OCH(C_2H_5)_2)$—;

$R^{10}$ is methyl;

provided that when $R^2$ is methyl, ethyl, propyl, butyl, pentyl or hexyl and $R^3$ is OH, $R^6$ is absent;

and the enantiomers, diastereomers, and salts thereof.

A fifth embodiment of the invention is a compound of Formula II:

II wherein

Z is $CH_2$ or O;

$R^1$ is a) ($C_3$-$C_7$)cycloalkyl; or b) phenyl, heteroaryl, or bicyclic heteroaryl optionally substituted with 1 to 3 groups independently selected from:

1) fluorine, chlorine, bromine, cyano, nitro, ($C_1$-$C_6$)alkyl, ($C_3$-$C_6$)cycloalkyl, ($C_4$-$C_7$)cycloalkylalkyl, ($C_2$-$C_6$)alkenyl, ($C_5$-$C_7$)cycloalkylalkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, halo($C_2$-$C_6$)alkenyl, halo($C_3$-$C_6$)alkynyl, halo($C_5$-$C_7$)cycloalkylalkynyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy and ($C_1$-$C_6$)alkanesulfonyl; or 2) phenyl, heteroaryl, phenoxy, heteroaryloxy, phenylthio, heteroarylthio, benzyl, heteroarylmethyl, benzyloxy and heteroaryloxy, each optionally substituted with 1 to 3 groups independently selected from:

fluorine, chlorine, cyano, ($C_1$-$C_3$)alkyl, halo($C_1$-$C_3$)alkyl, ($C_1$-$C_3$)-alkoxy, and halo($C_1$-$C_3$)alkoxy, and aminocarbonyl;

$R^2$ is ($C_1$-$C_{10}$)alkyl, ($C_4$-$C_{10}$)cycloalkylalkyl, halo($C_1$-$C_{10}$)alkyl, halo($C_4$-$C_{10}$)cycloalkylalkyl, ($C_1$-$C_{10}$)alkoxy, ($C_4$-$C_{10}$)cycloalkylalkoxy, halo($C_1$-$C_{10}$)alkoxy, ($C_1$-$C_{10}$)alkylthio, halo($C_1$-$C_{10}$)alkylthio, hydroxy($C_1$-$C_{10}$)alkyl, ($C_1$-$C_5$)alkoxy($C_1$-$C_5$)alkyl, ($C_1$-$C_5$)alkoxy($C_1$-$C_5$)hydroxyalkyl, ($C_3$-$C_6$)cycloalkoxy($C_1$-$C_6$)alkyl, halo($C_1$-$C_5$)alkoxy($C_1$-$C_5$)alkyl, halo($C_3$-$C_6$)cycloalkoxy($C_1$-$C_5$)alkyl, ($C_1$-$C_5$)alkylthio($C_1$-$C_5$)alkyl, halo($C_1$-$C_5$)alkylthio($C_1$-$C_5$)alkyl, ($C_1$-$C_5$)alkoxy($C_1$-$C_5$)alkoxy, hydroxy($C_1$-$C_{10}$)alkoxy, ($C_3$-$C_6$)cycloalkoxy($C_1$-$C_5$)alkoxy, halo($C_1$-$C_5$)alkoxy($C_1$-$C_5$)alkoxy, halo($C_3$-$C_6$)cycloalkoxy($C_1$-$C_5$)alkoxy, hydroxy($C_1$-$C_{10}$)alkylthio, ($C_2$-$C_5$)alkoxy($C_1$-$C_5$)alkylthio, ($C_1$-$C_5$)alkylthio($C_1$-$C_5$)alkoxy, ($C_1$-$C_5$)alkylthio($C_1$-$C_5$)alkylthio, ($C_3$-$C_4$)-cycloalkanecarbonylamino($C_1$-$C_5$)alkyl, ($C_3$-$C_4$)cycloalkanecarbonylamino($C_1$-$C_5$)alkoxy, ($C_3$-$C_4$)cycloalkanecarbonylamino($C_1$-$C_5$)alkylthio, ($C_1$-$C_5$)alkylaminocarbonylamino($C_1$-$C_5$)alkyl, ($C_1$-$C_5$)alkylaminocarbonylamino($C_1$-$C_5$)alkoxy, ($C_1$-$C_5$)alkylaminocarbonylamino($C_1$-$C_5$)alkylthio, di($C_1$-$C_5$)alkylaminocarbonylamino($C_1$-$C_5$)alkyl, di($C_1$-$C_5$)alkylaminocarbonylamino($C_1$-$C_5$)alkoxy, di($C_1$-$C_5$)alkylaminocarbonylamino($C_1$-$C_5$)alkylthio, $R^3$ is H, F, OH, ($C_1$-$C_4$)alkanoylamino, or ($C_1$-$C_3$)alkoxy;

provided that when $R^3$ is OH or F, $R^2$ is not ($C_2$-$C_{10}$)alkoxy, ($C_4$-$C_{10}$)cycloalkylalkoxy, halo($C_2$-$C_{10}$)alkoxy, ($C_2$-$C_{10}$)alkylthio, halo($C_2$-$C_{10}$)alkylthio, ($C_1$-$C_5$)alkoxy($C_1$-$C_5$)alkoxy, hydroxy($C_2$-$C_{10}$)alkoxy, ($C_3$-$C_6$)cycloalkoxy($C_1$-$C_5$)alkoxy, halo($C_1$-$C_5$)alkoxy($C_1$-$C_5$)alkoxy, halo($C_3$-$C_6$)- cycloalkoxy($C_1$-$C_5$)alkoxy, hydroxy($C_2$-$C_{10}$)alkylthio, ($C_2$-$C_5$)alkoxy($C_1$-$C_5$)alkylthio, ($C_1$-$C_5$)alkyl-thio($C_1$-$C_5$)alkoxy, ($C_1$-$C_5$)alkylthio($C_1$-$C_5$)alkylthio, ($C_3$-$C_4$)cycloalkane-carbonylamino($C_1$-$C_5$)alkoxy, ($C_3$-$C_4$)cycloalkanecarbonylamino($C_1$-$C_5$)alkylthio, ($C_1$-$C_5$)-alkylaminocarbonylamino($C_1$-$C_5$)alkoxy, ($C_1$-$C_5$)alkylaminocarbonylamino($C_1$-$C_5$)alkylthio, di($C_1$-$C_5$)alkylaminocarbonylamino($C_1$-$C_5$)alkoxy or di($C_1$-$C_5$)alkylaminocarbonylamino($C_1$-$C_5$)alkylthio, Q is Q1, Q2, Q4, Q5, Q9, or Q10

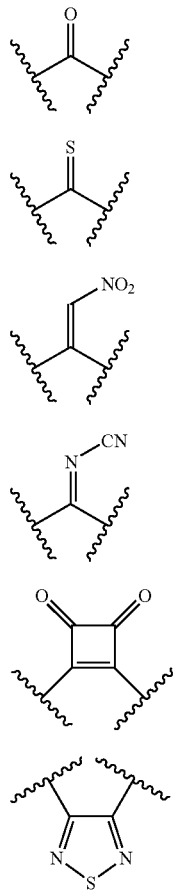

wherein N and N are attached to the truncated bonds $R^4$ is H or ($C_1$-$C_3$)alkyl;

$R^5$ is a) ($C_1$-$C_{10}$)alkyl, ($C_4$-$C_{10}$)cycloalkylalkyl, halo($C_1$-$C_{10}$)alkyl, hydroxy($C_1$-$C_{10}$)alkyl, halo($C_4$-$C_{10}$)cycloalkylalkyl, hydroxylated ($C_4$-$C_{10}$)cycloalkylalkyl, ($C_1$-$C_2$)alkyl($C_4$-$C_{10}$)cycloalkylalkyl, di($C_1$-$C_2$)alkyl($C_4$-$C_{10}$)cycloalkylalkyl, hydroxylated ($C_1$-$C_2$)alkyl($C_4$-$C_{10}$)cycloalkylalkyl, hydroxylated di($C_1$-$C_2$)alkyl($C_4$-$C_{10}$)cycloalkylalkyl, ($C_4$-$C_{10}$)bicycloalkyl($C_1$-$C_3$)alkyl, ($C_8$-$C_{12}$)tricycloalkyl($C_1$-$C_3$)alkyl, ($C_1$-$C_5$)alkoxy($C_1$-$C_5$)alkyl, halo($C_1$-$C_5$)alkoxy($C_1$-$C_5$)alkyl, ($C_1$-$C_5$)alkylthio($C_1$-$C_5$)alkyl, halo($C_1$-$C_5$)alkylthio($C_1$-$C_5$)alkyl, or saturated heterocyclyl($C_1$-$C_3$)alkyl; or b) phenyl($C_1$-$C_2$)alkyl or heteroaryl($C_1$-$C_2$)alkyl each optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, and halo($C_1$-$C_3$)alkoxy;

$R^6$ is absent or is ($C_1$-$C_6$)alkyl, hydroxy($C_1$-$C_6$)alkyl, or ($C_1$-$C_3$)alkoxy($C_1$-$C_3$)alkyl;

G is OH, $NH_2$, $NHR^9$, or $NR^9R^{10}$;

$R^9$ is a) ($C_1$-$C_6$)alkyl, halo($C_1$-$C_6$)alkyl, ($C_4$-$C_{10}$)cycloalkylalkyl, ($C_1$-$C_5$)alkoxy($C_1$-$C_5$)alkyl, or aminocarbonyl($C_1$-$C_6$)alkyl or b) phenyl($C_1$-$C_2$)alkyl optionally substituted with 1 to 3 groups independently selected from:

fluorine, chlorine, cyano, ($C_1$-$C_3$)alkyl, halo($C_1$-$C_3$)alkyl, ($C_1$-$C_3$)alkoxy, and halo($C_1$-$C_3$)alkoxy; or c) $R^5$ and $R^9$ together are —$CH_2$—, —$(CH_2)_2$—, —$(CH_2)_3$—, or —$(CH_2)_4$—, optionally substituted with 1 or 2 groups independently selected from fluorine, ($C_1$-$C_3$)alkyl, halo($C_1$-$C_3$)alkyl, ($C_3$-$C_6$)cycloalkyl, halo($C_3$-$C_6$)cycloalkyl, hydroxy($C_3$-$C_6$)cycloalkyl, ($C_3$-$C_6$)cycloalkyl($C_1$-$C_2$)alkyl, halo($C_3$-$C_6$)cycloalkyl($C_1$-$C_2$)alkyl, and hydroxylated($C_3$-$C_6$)cycloalkyl($C_1$-$C_2$)alkyl, and form a 4-, 5-, 6-, or 7-membered ring with the atoms through which they are connected;

$R^{10}$ is ($C_1$-$C_3$)alkyl or halo($C_1$-$C_3$)alkyl; and provided that when $R^2$ is ($C_1$-$C_{10}$)alkyl and $R^3$ is OH, $R^6$ is not ($C_1$-$C_3$)alkoxy($C_1$-$C_3$)alkyl:

the enantiomers, diastereomers and salts thereof.

A sixth embodiment of the invention is a compound of Formula IIa with the stereochemical configuration shown:

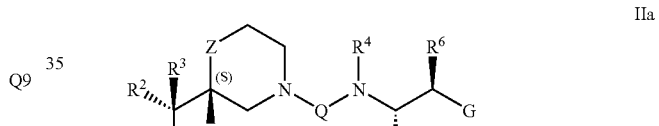

IIa wherein

Z is $CH_2$ or O;

$R^1$ is a) ($C_3$-$C_7$)cycloalkyl; or b) phenyl, heteroaryl, or bicyclic heteroaryl optionally substituted with 1 to 3 groups independently selected from:

1) fluorine, chlorine, bromine, cyano, nitro, ($C_1$-$C_6$)alkyl, ($C_3$-$C_6$)cycloalkyl, ($C_4$-$C_7$)cycloalkylalkyl, ($C_2$-$C_6$)alkenyl, ($C_5$-$C_7$)cycloalkylalkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, halo($C_2$-$C_6$)alkenyl, halo($C_3$-$C_6$)alkynyl, halo($C_5$-$C_7$)cycloalkylalkynyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy and ($C_1$-$C_6$)alkanesulfonyl; or 2) phenyl, heteroaryl, phenoxy, heteroaryloxy, phenylthio, heteroarylthio, benzyl, heteroarylmethyl, benzyloxy, and heteroaryloxy, each optionally substituted with 1 to 3 groups independently selected from:

fluorine, chlorine, cyano, ($C_1$-$C_3$)alkyl, halo($C_1$-$C_3$)alkyl, ($C_1$-$C_3$)-alkoxy, halo($C_1$-$C_3$)alkoxy, and aminocarbonyl;

$R^2$ is ($C_1$-$C_8$)alkyl, ($C_4$-$C_8$)cycloalkylalkyl, fluoro($C_1$-$C_8$)alkyl, fluoro($C_4$-$C_8$)cycloalkylalkyl, ($C_1$-$C_8$)alkoxy, ($C_4$-$C_8$)cycloalkylalkoxy, fluoro($C_1$-$C_8$)alkoxy, hydroxy($C_1$-$C_8$)alkyl, ($C_1$-$C_5$)alkoxy($C_1$-$C_5$)alkyl, ($C_1$-$C_5$)alkoxy($C_1$-$C_5$)

hydroxyalkyl, $(C_3-C_4)$cycloalkoxy$(C_1-C_5)$alkyl, fluoro$(C_1-C_5)$alkoxy$(C_1-C_5)$alkyl, fluoro$(C_3-C_4)$cycloalkoxy$(C_1-C_5)$alkyl, $(C_1-C_5)$alkylthio$(C_1-C_5)$alkyl, $(C_1-C_5)$alkoxy$(C_1-C_5)$alkoxy, hydroxy$(C_1-C_8)$alkoxy, $(C_3-C_4)$cycloalkoxy$(C_1-C_5)$alkoxy, fluoro$(C_1-C_5)$alkoxy$(C_1-C_5)$alkoxy, fluoro$(C_3-C_4)$cycloalkoxy$(C_1-C_8)$alkoxy, $(C_1-C_3)$alkoxy$(C_1-C_3)$alkoxy$(C_1-C_3)$alkyl, fluoro$(C_1-C_3)$alkoxy$(C_1-C_3)$alkoxy$(C_1-C_3)$alkyl, aminocarbonylamino$(C_1-C_8)$alkyl, aminocarbonylamino$(C_1-C_8)$alkoxy, $(C_1-C_5)$alkanoylamino$(C_1-C_5)$alkyl, $(C_1-C_5)$alkanoylamino$(C_1-C_5)$alkoxy, fluoro$(C_1-C_5)$alkanoylamino$(C_1-C_5)$alkyl, fluoro$(C_1-C_5)$alkanoylamino$(C_1-C_5)$alkoxy, $(C_1-C_3)$alkoxy$(C_1-C_5)$alkanoylamino$(C_1-C_5)$alkyl, $(C_1-C_3)$alkoxy$(C_1-C_5)$alkanoylamino$(C_1-C_5)$alkoxy, $(C_3-C_4)$cycloalkanecarbonylamino$(C_1-C_5)$alkyl, $(C_3-C_4)$cycloalkanecarbonylamino$(C_1-C_5)$alkoxy, aminosulfonylamino$(C_1-C_8)$alkyl, aminosulfonylamino$(C_1-C_8)$alkoxy, $(C_1-C_5)$alkanesulfonyl-amino$(C_1-C_5)$alkyl, $(C_1-C_5)$alkanesulfonylamino$(C_1-C_5)$alkoxy, $(C_1-C_5)$alkylaminocarbonylamino$(C_1-C_5)$alkyl, di$(C_1-C_5)$alkylaminocarbonylamino$(C_1-C_5)$alkyl, $(C_1-C_5)$alkylaminocarbonylamino$(C_1-C_8)$alkoxy, di$(C_1-C_5)$alkylaminocarbonylamino$(C_1-C_5)$alkoxy, $R^3$ is H, F, OH, $(C_1-C_4)$alkanoylamino, or $(C_1-C_3)$alkoxy;

provided that when $R^3$ is OH or F, $R^2$ is not $(C_2-C_{10})$alkoxy, $(C_4-C_{10})$cycloalkylalkoxy, halo$(C_2-C_{10})$alkoxy, $(C_2-C_{10})$alkylthio, halo$(C_2-C_{10})$alkylthio, $(C_1-C_5)$alkoxy$(C_1-C_5)$alkoxy, hydroxy$(C_2-C_{10})$alkoxy, $(C_3-C_6)$cycloalkoxy$(C_1-C_5)$alkoxy, halo$(C_1-C_5)$alkoxy$(C_1-C_8)$alkoxy, halo$(C_3-C_6)$cycloalkoxy$(C_1-C_5)$alkoxy, hydroxy$(C_2-C_{10})$alkylthio, $(C_2-C_5)$alkoxy$(C_1-C_5)$alkylthio, $(C_1-C_5)$alkyl-thio$(C_1-C_5)$alkoxy, or $(C_1-C_5)$alkylthio$(C_1-C_5)$alkylthio, $(C_3-C_4)$cycloalkane-carbonylamino$(C_1-C_5)$alkoxy, $(C_3-C_4)$cycloalkanecarbonylamino$(C_1-C_5)$alkylthio, $(C_1-C_5)$-alkylaminocarbonylamino$(C_1-C_5)$alkoxy, $(C_1-C_5)$alkylaminocarbonylamino$(C_1-C_5)$alkylthio, di$(C_1-C_5)$alkylaminocarbonylamino$(C_1-C_5)$alkoxy or di$(C_1-C_5)$alkylaminocarbonylamino$(C_1-C_5)$alkylthio, Q is Q1, Q2, Q4, Q5, Q9, or Q10

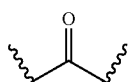
Q1

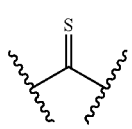
Q2

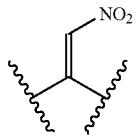
Q4

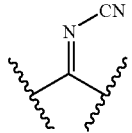
Q5

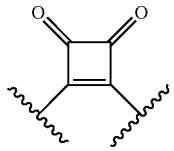
Q9

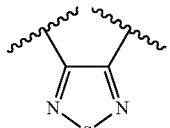
Q10 wherein N and N are attached to the truncated bonds $R^4$ is H or $(C_1-C_3)$alkyl;

$R^5$ is a) $(C_1-C_{10})$alkyl, $(C_4-C_{10})$cycloalkylalkyl, halo$(C_1-C_{10})$alkyl, hydroxy$(C_1-C_{10})$alkyl, halo$(C_4-C_{10})$cycloalkylalkyl, hydroxylated $(C_4-C_{10})$cycloalkylalkyl, $(C_1-C_2)$alkyl$(C_4-C_{10})$cycloalkylalkyl, di$(C_1-C_2)$alkyl$(C_4-C_{10})$cycloalkylalkyl, hydroxylated $(C_1-C_2)$alkyl$(C_4-C_{10})$cycloalkylalkyl, hydroxylated di$(C_1-C_2)$alkyl$(C_4-C_{10})$cycloalkylalkyl, $(C_4-C_{10})$bicycloalkyl$(C_1-C_2)$alkyl, $(C_8-C_{12})$tricycloalkyl$(C_1-C_2)$alkyl, $(C_1-C_5)$alkoxy$(C_1-C_5)$alkyl, halo$(C_1-C_5)$alkoxy$(C_1-C_5)$alkyl, $(C_1-C_5)$alkylthio$(C_1-C_5)$alkyl, halo$(C_1-C_5)$alkylthio$(C_1-C_5)$alkyl, or saturated heterocyclyl$(C_1-C_3)$alkyl; or b) phenyl$(C_1-C_2)$alkyl or heteroaryl$(C_1-C_2)$alkyl each optionally substituted with 1 to 3 groups independently selected from fluorine, chlorine, cyano, $(C_1-C_3)$alkyl, halo$(C_1-C_3)$alkyl, $(C_1-C_3)$alkoxy, and halo$(C_1-C_3)$alkoxy;

G is OH, $NH_2$, $NHR^9$, or $NR^9R^{10}$;

$R^6$ is absent or is $(C_1-C_6)$alkyl, hydroxy$(C_1-C_6)$alkyl, or $(C_1-C_3)$alkoxy$(C_1-C_3)$alkyl;

$R^9$ is a) $(C_1-C_6)$alkyl, halo$(C_1-C_6)$alkyl, $(C_4-C_{10})$cycloalkylalkyl, $(C_1-C_5)$alkoxy$(C_1-C_5)$alkyl, or aminocarbonyl$(C_1-C_6)$alkyl; or b) phenyl$(C_1-C_2)$alkyl optionally substituted with 1 to 3 groups independently selected from:

fluorine, chlorine, cyano, $(C_1-C_3)$alkyl, halo$(C_1-C_3)$alkyl, $(C_1-C_3)$alkoxy, and halo$(C_1-C_3)$alkoxy; or c) $R^5$ and $R^9$ together are $—(CH_2)_2—$, $—(CH_2)_3—$, or $—(CH_2)_4—$ and form a 4-, 5-, 6-, or 7-membered ring with the atoms through which they are connected that is optionally substituted with 1 or 2 groups independently selected from fluorine, $(C_1-C_8)$alkyl, halo$(C_1-C_8)$alkyl, $(C_3-C_8)$cycloalkyl, halo$(C_3-C_8)$cycloalkyl, hydroxy$(C_3-C_8)$cycloalkyl, $(C_3-C_8)$cycloalkyl$(C_1-C_3)$alkyl, halo$(C_3-C_8)$cycloalkyl$(C_1-C_3)$alkyl, and hydroxylated $(C_3-C_8)$cycloalkyl$(C_1-C_3)$alkyl, $(C_1-C_8)$alkoxy, halo$(C_1-C_8)$alkoxy, $(C_3-C_8)$cycloalkoxy, halo$(C_3-C_8)$cycloalkoxy, hydroxy$(C_3-C_8)$cycloalkoxy, $(C_1-C_8)$alkoxy$(C_1-C_3)$alkyl, halo$(C_1-C_8)$alkoxy$(C_1-C_3)$alkyl, $(C_3-C_8)$cycloalkoxy$(C_1-C_3)$alkyl, halo$(C_3-C_8)$cycloalkoxy$(C_1-C_3)$alkyl, hydroxy$(C_3-C_8)$cycloalkoxy$(C_1-C_3)$alkyl, $(C_3-C_8)$cycloalkyl$(C_1-C_3)$alkoxy$(C_1-C_3)$alkyl, halo$(C_3-C_8)$cycloalkyl$(C_1-C_3)$alkoxy$(C_1-C_3)$alkyl, hydroxylated$(C_3-C_8)$cycloalkyl$(C_1-C_3)$alkoxy$(C_1-C_3)$alkyl, $(C_1-C_8)$alkylthio, halo$(C_1-C_8)$alkylthio, $(C_3-C_8)$cycloalkylthio, halo$(C_3-C_8)$cycloalkylthio, hydroxy$(C_3-C_8)$cycloalkylthio, $(C_3-C_8)$cycloalkyl$(C_1-C_3)$alkylthio, halo$(C_3-C_8)$cycloalkyl$(C_1-C_3)$ alkylthio, hydroxylated($C_3$-$C_8$)cycloalkyl($C_1$-$C_3$)alkylthio, ($C_1$-$C_8$)alkylthio($C_1$-$C_3$)alkyl, halo($C_1$-$C_8$)alkylthio($C_1$-$C_3$)alkyl, ($C_3$-$C_8$)cycloalkylthio($C_1$-$C_3$)alkyl, halo($C_3$-$C_8$)cycloalkylthio($C_1$-$C_3$)alkyl, hydroxy($C_3$-$C_8$)cycloalkylthio($C_1$-$C_3$)alkyl, ($C_3$-$C_8$)cycloalkyl($C_1$-$C_3$)alkylthio($C_1$-$C_3$)alkyl, halo($C_3$-$C_8$)cycloalkyl($C_1$-$C_3$)alkylthio($C_1$-$C_3$)alkyl, and hydroxylated($C_3$-$C_8$)cycloalkyl($C_1$-$C_3$)alkylthio($C_1$-$C_3$)alkyl;

$R^{10}$ is ($C_1$-$C_3$)alkyl or halo($C_1$-$C_3$)alkyl; and provided that when $R^2$ is ($C_1$-$C_{10}$)alkyl and $R^3$ is OH, $R^6$ is not ($C_1$-$C_3$)alkoxy($C_1$-$C_3$)alkyl:

the salts thereof.

A seventh embodiment of the invention is a compound of Formula IIa, wherein:

$R^1$ is a) cyclohexyl or trifluoromethyl; or b) phenyl, 2-thienyl, 3-thienyl, 2-pyridyl, 2-imidazolyl, or 2-thiazolyl, optionally substituted with 1 to 3 substituents independently selected from:

fluorine, chlorine, bromine, cyano, methyl, ethyl, isopropyl, trifluoromethyl, allyl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and 3-pyridyloxy, wherein the phenyl and phenoxy, benzyloxy and pyridyloxy groups are optionally substituted with 1 to 3 substituents independently selected from fluorine, chlorine, cyano, methyl, ethyl, and trifluoromethyl;

or c) 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl, optionally substituted with 1 to 3 substituents independently selected from fluorine, methyl, isobutyl, and t-butyl;

$R^2$ is hydrogen, methyl, ethyl, propyl, butyl, hexyl, 5-pentenyl, 3,3,3-trifluoropropyl, 4,4-difluoropentyl, 3-(cyclopropyl)propyl, 4-(cyclopropyl)butyl, 3-hydroxypropyl, 4-hydroxybutyl, 4-hydroxypentyl, 4-hydroxyhexyl, 5-hydroxyhexyl, 2-hydroxyethoxy, 3-ethoxypropyl, 4-methoxybutyl, 4-ethoxybutyl, 2-(ethoxy)-ethoxy, 3-methoxypropoxy, 3-ethoxypropoxy, 3-propoxypropoxy, 2-cyclopropylethoxy, (2-(methoxy)ethoxy)methyl, 3-(acetylamino)propyl, 3-(propionylamino)propyl, 3-(butanoylamino)propyl, 3-((2-methoxypropionyl)amino)propyl, 3-(cyclopropanecarbonylamino)propyl, 3-(trifluoroacetylamino)propyl, 3-(methylaminocarbonylamino)propyl, 3-(dimethylaminocarbonylamino)propyl, methoxymethylcarbonylaminomethyl, or 3-(aminosulfonylamino)propyl $R^3$ is H, F, OH, methoxy, 3-hydroxypropoxy, acetylamino, propionylamino, (2-methylpropionyl)amino, or butanoylamino;

provided that when $R^3$ is F or OH, $R^2$ is not 3-methoxypropoxy, 3-ethoxypropoxy, 3-propoxypropoxy, or 2-cyclopropylethoxy;

Q is Q1, Q2, Q4, Q5, Q9, or Q10

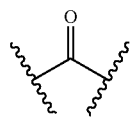
Q1

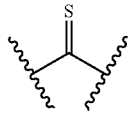
Q2

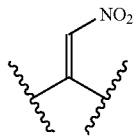
Q4

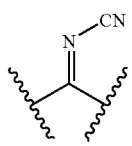
Q5

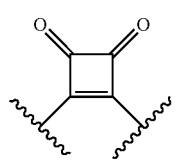
Q9

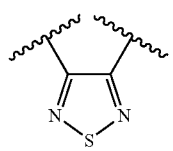
Q10 wherein N and N are attached to the truncated bonds $R^4$ is H or methyl;

$R^5$ is methyl, isobutyl, t-butylmethyl, 2,2,2-trifluoroethyl, 2-(trifluoromethyl)propyl, cyclopropylmethyl, cyclopentylmethyl, cyclohexylmethyl, 2-(cyclohexyl)ethyl, (3-noradamantyl)methyl, (3,3-difluorocyclobutyl)methyl, (3,4-difluorocyclopentyl)methyl, (4,4-difluorocyclohexyl)methyl, (4-methylcyclohexyl)methyl, tert-butoxymethyl, (2-tetrahydrofuranyl)methyl, (2-tetrahydropyranyl)methyl, (4-tetrahydro-pyranyl)methyl, (3-methoxycyclobutyl)methyl, (4-methoxycyclohexyl)methyl, benzyl, phenethyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (4-fluorocyclohexyl)(hydroxy)methyl, (cycloheptyl)(hydroxy)methyl, (1-hydroxycyclohexyl)methyl, (4-hydroxycyclohexyl)methyl, (3-noradamantyl)(hydroxy)methyl, or 2-methoxy-2-methylpropyl;

$R^6$ is absent or is methyl or hydroxymethyl;

G is $NH_2$, $NHR^9$, or $NR^9R^{10}$;

$R^9$ is methyl, ethyl, propyl, butyl, isobutyl, pentyl or isopentyl, 2,2,2-trifluoroethyl, 2-methoxyethyl, or aminocarbonylmethyl; or $R^9$ together with $R^5$ is —$(CH_2)_3$—, —$(CH_2)_4$—$(CH_2)_2CH$(c-hex)-, or —$(CH_2)_2CH(OCH(C_2H_5)_2)$—;

$R^{10}$ is methyl;

and the salts thereof.

An eighth embodiment of the invention is a compound of Formula II:

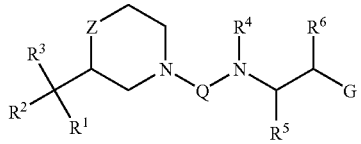

wherein

Z is CH$_2$ or O;

R$^1$ is a) (C$_3$-C$_7$)cycloalkyl; or b) phenyl, heteroaryl, or bicyclic heteroaryl optionally substituted with 1 to 3 groups independently selected from:

1) fluorine, chlorine, bromine, cyano, nitro, (C$_1$-C$_6$)alkyl, (C$_3$-C$_6$)cycloalkyl, (C$_4$-C$_7$)cycloalkylalkyl, (C$_2$-C$_6$)alkenyl, (C$_5$-C$_7$)cycloalkylalkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, halo(C$_2$-C$_6$)alkenyl, halo(C$_3$-C$_6$)alkynyl, halo(C$_5$-C$_7$)cycloalkylalkynyl, (C$_1$-C$_6$) alkoxy, (C$_3$-C$_6$)cycloalkoxy, (C$_4$-C$_7$)cycloalkylalkoxy, halo (C$_1$-C$_6$)alkoxy, halo(C$_3$-C$_6$)cycloalkoxy, halo(C$_4$-C$_7$)cycloalkylalkoxy and (C$_1$-C$_6$)alkanesulfonyl; or 2) phenyl, heteroaryl, phenoxy, heteroaryloxy, phenylthio, heteroarylthio, benzyl, heteroarylmethyl, benzyloxy and heteroaryloxy, each optionally substituted with 1 to 3 groups independently selected from:

fluorine, chlorine, cyano, (C$_1$-C$_3$)alkyl, halo(C$_1$-C$_3$)alkyl, (C$_1$-C$_3$)-alkoxy, and halo(C$_1$-C$_3$)alkoxy, and aminocarbonyl;

R$^2$ is (C$_1$-C$_{10}$)alkyl, (C$_4$-C$_{10}$)cycloalkylalkyl, halo(C$_1$-C$_{10}$)alkyl, halo(C$_4$-C$_{10}$)cycloalkylalkyl, (C$_1$-C$_{10}$)alkoxy, (C$_4$-C$_{10}$)cycloalkylalkoxy, halo(C$_1$-C$_{10}$)alkoxy, (C$_1$-C$_{10}$)alkylthio, halo(C$_1$-C$_{10}$)alkylthio, hydroxy(C$_1$-C$_{10}$)alkyl, (C$_1$-C$_5$)alkoxy(C$_1$-C$_5$)alkyl, (C$_1$-C$_5$)alkoxy(C$_1$-C$_5$)hydroxyalkyl, (C$_3$-C$_6$)cycloalkoxy(C$_1$-C$_6$)alkyl, halo(C$_1$-C$_5$)alkoxy(C$_1$-C$_5$)alkyl, halo(C$_3$-C$_6$)cycloalkoxy(C$_1$-C$_5$)alkyl, (C$_1$-C$_5$) alkylthio(C$_1$-C$_5$)alkyl, halo(C$_1$-C$_5$)alkylthio(C$_1$-C$_5$)alkyl, (C$_1$-C$_5$)alkoxy(C$_1$-C$_5$)alkoxy, hydroxy(C$_1$-C$_{10}$)alkoxy, (C$_3$-C$_6$)cycloalkoxy(C$_1$-C$_5$)alkoxy, halo(C$_1$-C$_5$)alkoxy(C$_1$-C$_5$)alkoxy, halo(C$_3$-C$_6$)cycloalkoxy(C$_1$-C$_5$)alkoxy, hydroxy(C$_1$-C$_{10}$)-alkylthio, (C$_2$-C$_5$)alkoxy(C$_1$-C$_5$)alkylthio, (C$_1$-C$_5$) alkylthio(C$_1$-C$_5$)alkoxy, (C$_1$-C$_5$)alkylthio(C$_1$-C$_5$)alkylthio, (C$_3$-C$_4$)cycloalkanecarbonylamino(C$_1$-C$_8$)alkyl, (C$_3$-C$_4$)cycloalkanecarbonylamino(C$_1$-C$_5$)alkoxy, (C$_3$-C$_4$)cycloalkanecarbonylamino(C$_1$-C$_5$)alkylthio, (C$_1$-C$_5$)alkylaminocarbonylamino(C$_1$-C$_5$)alkyl, (C$_1$-C$_5$)alkylaminocarbonylamino (C$_1$-C$_5$)alkoxy, (C$_1$-C$_5$)alkylaminocarbonylamino(C$_1$-C$_5$) alkylthio, di(C$_1$-C$_5$)alkylaminocarbonylamino(C$_1$-C$_5$)alkyl, di(C$_1$-C$_5$)alkylaminocarbonylamino(C$_1$-C$_5$)alkoxy, di(C$_1$-C$_5$)alkylaminocarbonylamino(C$_1$-C$_5$)alkylthio, R$^3$ is H, F, OH, (C$_1$-C$_4$)alkanoylamino, (C$_1$-C$_3$)alkoxy;

provided that when R$^3$ is OH or F, R$^2$ is not (C$_2$-C$_{10}$)alkoxy, (C$_4$-C$_{10}$)cycloalkylalkoxy, halo(C$_2$-C$_{10}$)alkoxy, (C$_2$-C$_{10}$) alkylthio, halo(C$_2$-C$_{10}$)alkylthio, (C$_1$-C$_5$)alkoxy(C$_1$-C$_5$) alkoxy, hydroxy(C$_2$-C$_{10}$)alkoxy, (C$_3$-C$_6$)cycloalkoxy(C$_1$-C$_5$)alkoxy, halo(C$_1$-C$_5$)alkoxy(C$_1$-C$_5$)alkoxy, halo(C$_3$-C$_6$)-cycloalkoxy(C$_1$-C$_5$)alkoxy, hydroxy(C$_2$-C$_{10}$)alkylthio, (C$_2$-C$_5$)alkoxy(C$_1$-C$_5$)alkylthio, (C$_1$-C$_5$)alkyl-thio(C$_1$-C$_5$) alkoxy, or (C$_1$-C$_5$)alkylthio(C$_1$-C$_5$)alkylthio, (C$_3$-C$_4$) cycloalkane-carbonylamino(C$_1$-C$_5$)alkoxy, (C$_3$-C$_4$) cycloalkanecarbonylamino(C$_1$-C$_8$)alkylthio, (C$_1$-C$_5$)-alkylaminocarbonylamino(C$_1$-C$_5$)alkoxy, (C$_1$-C$_5$) alkylaminocarbonylamino(C$_1$-C$_5$)alkylthio, di(C$_1$-C$_5$)alkylaminocarbonylamino(C$_1$-C$_5$)alkoxy or di(C$_1$-C$_5$) alkylaminocarbonylamino(C$_1$-C$_5$)alkylthio;

Q is Q1, Q2, Q4, Q5, Q9, or Q10

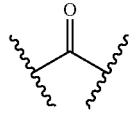

Q1

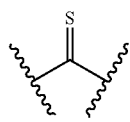

Q2

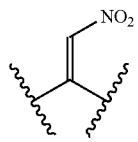

Q4

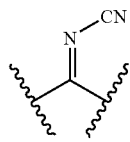

Q5

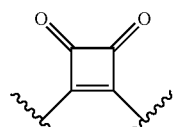

Q9

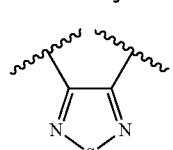

Q10 wherein N and N are attached to the truncated bonds

R$^4$ is H or (C$_1$-C$_3$)alkyl;

R$^5$ is absent or is (C$_1$-C$_6$)alkyl, hydroxy(C$_1$-C$_6$)alkyl, or (C$_1$-C$_3$)alkoxy(C$_1$-C$_3$)alkyl;

R$^6$ is a) (C$_1$-C$_{10}$)alkyl, (C$_4$-C$_{10}$)cycloalkylalkyl, halo(C$_1$-C$_{10}$)alkyl, hydroxy(C$_1$-C$_{10}$)alkyl, halo(C$_4$-C$_{10}$)cycloalkylalkyl, hydroxylated (C$_4$-C$_{10}$)cycloalkylalkyl, (C$_1$-C$_2$)alkyl (C$_4$-C$_{10}$)cycloalkylalkyl, di(C$_1$-C$_2$)alkyl(C$_4$-C$_{10}$) cycloalkylalkyl, hydroxylated (C$_1$-C$_2$)alkyl(C$_4$-C$_{10}$) cycloalkylalkyl, hydroxylated di(C$_1$-C$_2$)alkyl(C$_4$-C$_{10}$) cycloalkylalkyl, (C$_4$-C$_{10}$)bicycloalkyl(C$_1$-C$_3$)alkyl, (C$_8$-C$_{12}$) tricycloalkyl(C$_1$-C$_3$)alkyl, (C$_1$-C$_5$)alkoxy(C$_1$-C$_5$)alkyl, halo (C$_1$-C$_5$)alkoxy(C$_1$-C$_5$)alkyl, (C$_1$-C$_5$)alkylthio(C$_1$-C$_5$)alkyl, halo(C$_1$-C$_5$)alkylthio(C$_1$-C$_5$)alkyl, or saturated heterocyclyl (C$_1$-C$_3$)alkyl; or b) phenyl(C$_1$-C$_2$)alkyl or heteroaryl(C$_1$-C$_2$)alkyl, each optionally substituted with 1 to 3 groups independently selected from fluorine, chlorine, cyano, (C$_1$-C$_3$)alkyl, halo(C$_1$-C$_3$)alkyl, (C$_1$-C$_3$)alkoxy, and halo(C$_1$-C$_3$)alkoxy;

G is OH, NH$_2$, NHR$^9$, or NR$^9$R$^{10}$;

R⁹ is a) $(C_1-C_6)$alkyl, halo$(C_1-C_6)$alkyl, $(C_4-C_{10})$cycloalkylalkyl, $(C_1-C_5)$alkoxy$(C_1-C_5)$alkyl, or aminocarbonyl$(C_1-C_6)$alkyl; or b) phenyl$(C_1-C_2)$alkyl optionally substituted with 1 to 3 groups independently selected from:

fluorine, chlorine, cyano, $(C_1-C_3)$alkyl, halo$(C_1-C_3)$alkyl, $(C_1-C_3)$alkoxy, and halo$(C_1-C_3)$alkoxy; or c) R⁶ and R⁹ together are —CH₂—, —(CH₂)₂—, —(CH₂)₃—, or —(CH₂)₄—, optionally substituted with 1 or 2 groups independently selected from fluorine, $(C_1-C_3)$alkyl, halo$(C_1-C_3)$alkyl, $(C_3-C_6)$cycloalkyl, halo$(C_3-C_6)$cycloalkyl, hydroxy$(C_3-C_6)$cycloalkyl, $(C_3-C_6)$cycloalkyl$(C_1-C_2)$alkyl, halo$(C_3-C_6)$cycloalkyl$(C_1-C_2)$alkyl, and hydroxylated$(C_3-C_6)$cycloalkyl$(C_1-C_2)$alkyl, and form a 4-, 5-, 6-, or 7-membered ring with the atoms through which they are connected;

R¹⁰ is $(C_1-C_3)$alkyl or halo$(C_1-C_3)$alkyl; and provided that when R² is $(C_1-C_{10})$alkyl and R³ is OH, R⁶ is not $(C_1-C_5)$alkoxy$(C_1-C_5)$alkyl, halo$(C_1-C_5)$alkoxy$(C_1-C_5)$alkyl, $(C_1-C_5)$alkylthio$(C_1-C_5)$alkyl, halo$(C_1-C_5)$alkylthio$(C_1-C_5)$alkyl;

the enantiomers, diastereomers, and salts thereof.

A ninth embodiment of the invention is a compound of Formula IIb with the stereochemical configuration shown:

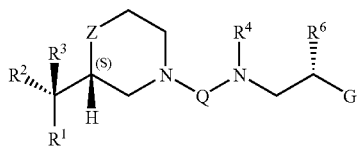

IIIb wherein

Z is CH₂ or O;

R¹ is a) $(C_3-C_7)$cycloalkyl; or b) phenyl, heteroaryl, or bicyclic heteroaryl, optionally substituted with 1 to 3 groups independently selected from:

1) fluorine, chlorine, bromine, cyano, nitro, $(C_1-C_6)$alkyl, $(C_3-C_6)$cycloalkyl, $(C_4-C_7)$cycloalkylalkyl, $(C_2-C_6)$alkenyl, $(C_5-C_7)$cycloalkylalkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, halo$(C_2-C_6)$alkenyl, halo$(C_3-C_6)$alkynyl, halo$(C_5-C_7)$cycloalkylalkynyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy and $(C_1-C_6)$alkanesulfonyl; or 2) phenyl, heteroaryl, phenoxy, heteroaryloxy, phenylthio, heteroarylthio, benzyl, heteroarylmethyl, benzyloxy and heteroaryloxy, each optionally substituted with 1 to 3 groups independently selected from:

fluorine, chlorine, cyano, $(C_1-C_3)$alkyl, halo$(C_1-C_3)$alkyl, $(C_1-C_3)$-alkoxy, and halo$(C_1-C_3)$alkoxy, and aminocarbonyl;

R² is $(C_1-C_8)$alkyl, $(C_4-C_8)$cycloalkylalkyl, fluoro$(C_1-C_8)$alkyl, fluoro$(C_4-C_8)$cycloalkylalkyl, $(C_1-C_8)$alkoxy, $(C_4-C_8)$cycloalkylalkoxy, fluoro$(C_1-C_8)$alkoxy, hydroxy$(C_1-C_8)$alkyl, $(C_1-C_5)$alkoxy$(C_1-C_5)$alkyl, $(C_1-C_5)$alkoxy$(C_1-C_5)$hydroxyalkyl, $(C_3-C_4)$cycloalkoxy$(C_1-C_5)$alkyl, fluoro$(C_1-C_5)$alkoxy$(C_1-C_5)$alkyl, fluoro$(C_3-C_4)$cycloalkoxy$(C_1-C_5)$alkyl, $(C_1-C_5)$alkylthio$(C_1-C_5)$alkyl, $(C_1-C_5)$alkoxy$(C_1-C_5)$alkoxy, hydroxy$(C_1-C_5)$alkoxy, $(C_3-C_4)$cycloalkoxy$(C_1-C_5)$alkoxy, fluoro$(C_1-C_5)$alkoxy$(C_1-C_5)$alkoxy, fluoro$(C_3-C_4)$cycloalkoxy$(C_1-C_5)$alkoxy, $(C_1-C_3)$alkoxy$(C_1-C_3)$alkoxy$(C_1-C_3)$alkyl, fluoro$(C_1-C_3)$alkoxy$(C_1-C_3)$alkoxy$(C_1-C_3)$alkyl, aminocarbonylamino$(C_1-C_8)$alkyl, aminocarbonylamino$(C_1-C_8)$alkoxy, $(C_1-C_5)$alkanoylamino$(C_1-C_5)$alkyl, $(C_1-C_5)$alkanoylamino$(C_1-C_5)$alkoxy, fluoro$(C_1-C_5)$alkanoylamino$(C_1-C_5)$alkyl, fluoro$(C_1-C_5)$alkanoylamino$(C_1-C_5)$alkoxy, $(C_1-C_3)$alkoxy$(C_1-C_5)$alkanoylamino$(C_1-C_5)$alkyl, $(C_1-C_3)$alkoxy$(C_1-C_5)$alkanoylamino$(C_1-C_5)$alkoxy, $(C_3-C_4)$cycloalkanecarbonylamino$(C_1-C_5)$alkyl, $(C_3-C_4)$cycloalkanecarbonyllamino$(C_1-C_5)$alkoxy, aminosulfonylamino$(C_1-C_8)$alkyl, aminosulfonylamino$(C_1-C_8)$alkoxy, $(C_1-C_5)$alkanesulfonyl-amino$(C_1-C_5)$alkyl, $(C_1-C_5)$alkanesulfonylamino$(C_1-C_5)$alkoxy, $(C_1-C_5)$alkylaminocarbonylamino$(C_1-C_5)$alkyl, di$(C_1-C_5)$alkylaminocarbonylamino$(C_1-C_5)$alkyl, $(C_1-C_5)$alkylaminocarbonylamino$(C_1-C_5)$alkoxy, di$(C_1-C_5)$alkylaminocarbonylamino$(C_1-C_5)$alkoxy, R³ is H, F, OH, $(C_1-C_4)$alkanoylamino, or $(C_1-C_3)$alkoxy;

provided that when R³ is OH or F, R² is not $(C_2-C_{10})$alkoxy, $(C_4-C_{10})$cycloalkylalkoxy, halo$(C_2-C_{10})$alkoxy, $(C_2-C_{10})$alkylthio, halo$(C_2-C_{10})$alkylthio, $(C_1-C_5)$alkoxy$(C_1-C_5)$alkoxy, hydroxy$(C_2-C_{10})$alkoxy, $(C_3-C_6)$cycloalkoxy$(C_1-C_5)$alkoxy, halo$(C_1-C_5)$alkoxy$(C_1-C_5)$alkoxy, halo$(C_3-C_6)$cycloalkoxy$(C_1-C_5)$alkoxy, hydroxy$(C_2-C_{10})$alkylthio, $(C_2-C_5)$alkoxy$(C_1-C_5)$alkylthio, $(C_1-C_5)$alkyl-thio$(C_1-C_5)$alkoxy, or $(C_1-C_5)$alkylthio$(C_1-C_5)$alkylthio, $(C_3-C_4)$cycloalkane-carbonylamino$(C_1-C_5)$alkoxy, $(C_3-C_4)$cycloalkanecarbonylamino$(C_1-C_5)$alkylthio, $(C_1-C_5)$alkyl-aminocarbonylamino$(C_1-C_5)$alkoxy, $(C_1-C_5)$alkylaminocarbonylamino$(C_1-C_5)$alkylthio, di$(C_1-C_5)$alkylaminocarbonylamino$(C_1-C_5)$alkoxy or di$(C_1-C_5)$alkylaminocarbonylamino$(C_1-C_5)$alkylthio;

Q is Q1, Q2, Q4, Q5, Q9, or Q10

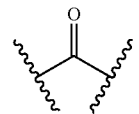

Q1

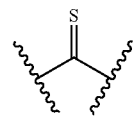

Q2

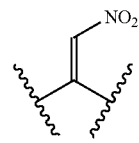

Q4

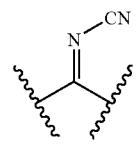

Q5

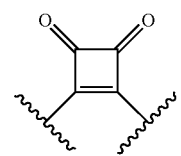

Q9

-continued

Q10

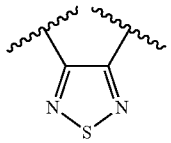

wherein N and N are attached to the truncated bonds $R^4$ is H or $(C_1-C_3)$alkyl;

$R^5$ is absent or is $(C_1-C_3)$alkyl or hydroxy$(C_1-C_3)$alkyl;

$R^6$ is a) $(C_1-C_{10})$alkyl, $(C_4-C_{10})$cycloalkylalkyl, halo$(C_1-C_{10})$alkyl, hydroxy$(C_1-C_{10})$alkyl, halo$(C_4-C_{10})$cycloalkylalkyl, hydroxylated $(C_4-C_{10})$cycloalkylalkyl, $(C_1-C_2)$alkyl$(C_4-C_{10})$cycloalkylalkyl, di$(C_1-C_2)$alkyl$(C_4-C_{10})$cycloalkylalkyl, hydroxylated $(C_1-C_2)$alkyl$(C_4-C_{10})$cycloalkylalkyl, hydroxylated di$(C_1-C_2)$alkyl$(C_4-C_{10})$cycloalkylalkyl, $(C_4-C_{10})$bicycloalkyl$(C_1-C_2)$alkyl, $(C_8-C_{12})$tricycloalkyl$(C_1-C_2)$alkyl, $(C_1-C_5)$alkoxy$(C_1-C_5)$alkyl, halo$(C_1-C_5)$alkoxy$(C_1-C_5)$alkyl, $(C_1-C_5)$alkylthio$(C_1-C_5)$alkyl, halo$(C_1-C_5)$alkylthio$(C_1-C_5)$alkyl, or saturated heterocyclyl$(C_1-C_3)$alkyl; or b) phenyl$(C_1-C_2)$alkyl or heteroaryl$(C_1-C_2)$alkyl, each optionally substituted with 1 to 3 groups independently selected from fluorine, chlorine, cyano, $(C_1-C_3)$alkyl, halo$(C_1-C_3)$alkyl, $(C_1-C_3)$alkoxy, and halo$(C_1-C_3)$alkoxy;

G is OH, $NH_2$, $NHR^9$, or $NR^9R^{10}$;

$R^9$ is a) $(C_1-C_6)$alkyl, halo$(C_1-C_6)$alkyl, $(C_4-C_{10})$cycloalkylalkyl, $(C_1-C_5)$alkoxy$(C_1-C_5)$alkyl, or aminocarbonyl$(C_1-C_6)$alkyl; or b) phenyl$(C_1-C_2)$alkyl optionally substituted with 1 to 3 groups independently selected from:

fluorine, chlorine, cyano, $(C_1-C_3)$alkyl, halo$(C_1-C_3)$alkyl, $(C_1-C_3)$alkoxy, and halo$(C_1-C_3)$alkoxy; or c) $R^6$ and $R^9$ together are $-(CH_2)_2-$, $-(CH_2)_3-$, or $-(CH_2)_4-$ and form a 4-, 5-, 6-, or 7-membered ring with the atoms through which they are connected that is optionally substituted with 1 or 2 groups independently selected from fluorine, $(C_1-C_8)$alkyl, halo$(C_1-C_8)$alkyl, $(C_3-C_8)$cycloalkyl, halo$(C_3-C_8)$cycloalkyl, hydroxy$(C_3-C_8)$cycloalkyl, $(C_3-C_8)$cycloalkyl$(C_1-C_3)$alkyl, halo$(C_3-C_8)$cycloalkyl$(C_1-C_3)$alkyl, and hydroxylated $(C_3-C_8)$cycloalkyl$(C_1-C_3)$alkyl, $(C_1-C_8)$alkoxy, halo$(C_1-C_8)$alkoxy, $(C_3-C_8)$cycloalkoxy, halo$(C_3-C_8)$cycloalkoxy, hydroxy$(C_3-C_8)$cycloalkoxy, $(C_1-C_8)$alkoxy$(C_1-C_3)$alkyl, halo$(C_1-C_8)$alkoxy$(C_1-C_3)$alkyl, $(C_3-C_8)$cycloalkoxy$(C_1-C_3)$alkyl, halo$(C_3-C_8)$cycloalkoxy$(C_1-C_3)$alkyl, hydroxy$(C_3-C_8)$cycloalkoxy$(C_1-C_3)$alkyl, $(C_3-C_8)$cycloalkyl$(C_1-C_3)$alkoxy$(C_1-C_3)$alkyl, halo$(C_3-C_8)$cycloalkyl$(C_1-C_3)$alkoxy$(C_1-C_3)$alkyl, hydroxylated$(C_3-C_8)$cycloalkyl$(C_1-C_3)$alkoxy$(C_1-C_3)$alkyl, $(C_1-C_8)$alkylthio, halo$(C_1-C_8)$alkylthio, $(C_3-C_8)$cycloalkylthio, halo$(C_3-C_8)$cycloalkylthio, hydroxy$(C_3-C_8)$cycloalkylthio, $(C_3-C_8)$cycloalkyl$(C_1-C_3)$alkylthio, halo$(C_3-C_8)$cycloalkyl$(C_1-C_3)$alkylthio, hydroxylated$(C_3-C_8)$cycloalkyl$(C_1-C_3)$alkylthio, $(C_1-C_8)$alkylthio$(C_1-C_3)$alkyl, halo$(C_1-C_8)$alkylthio$(C_1-C_3)$alkyl, $(C_3-C_8)$cycloalkylthio$(C_1-C_3)$alkyl, halo$(C_3-C_8)$cycloalkylthio$(C_1-C_3)$alkyl, hydroxy$(C_3-C_8)$cycloalkylthio$(C_1-C_3)$alkyl, $(C_3-C_8)$cycloalkyl$(C_1-C_3)$alkylthio$(C_1-C_3)$alkyl, halo$(C_3-C_8)$cycloalkyl$(C_1-C_3)$alkylthio$(C_1-C_3)$alkyl, and hydroxylated$(C_3-C_8)$cycloalkyl$(C_1-C_3)$alkylthio$(C_1-C_3)$alkyl;

$R^{10}$ is $(C_1-C_3)$alkyl or halo$(C_1-C_3)$alkyl; and the salts thereof.

A tenth embodiment of the invention is a compound of Formula II:

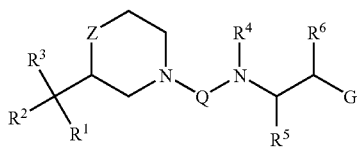

II wherein

Z is $CH_2$ or O;

$R^1$ is a) $(C_3-C_7)$cycloalkyl; or b) phenyl, heteroaryl, or bicyclic heteroaryl optionally substituted with 1 to 3 groups independently selected from:

1) fluorine, chlorine, bromine, cyano, nitro, $(C_1-C_6)$alkyl, $(C_3-C_6)$cycloalkyl, $(C_4-C_7)$cycloalkylalkyl, $(C_2-C_6)$alkenyl, $(C_5-C_7)$cycloalkylalkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, halo$(C_2-C_6)$alkenyl, halo$(C_3-C_6)$alkynyl, halo$(C_5-C_7)$cycloalkylalkynyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy and $(C_1-C_6)$alkanesulfonyl; or 2) phenyl, heteroaryl, phenoxy, heteroaryloxy, phenylthio, heteroarylthio, benzyl, heteroarylmethyl, benzyloxy and heteroaryloxy, each optionally substituted with 1 to 3 groups independently selected from:

fluorine, chlorine, cyano, $(C_1-C_3)$alkyl, halo$(C_1-C_3)$alkyl, $(C_1-C_3)$-alkoxy, and halo$(C_1-C_3)$alkoxy, and aminocarbonyl;

$R^2$ is $(C_1-C_{10})$alkyl, $(C_4-C_{10})$cycloalkylalkyl, halo$(C_1-C_{10})$alkyl, halo$(C_4-C_{10})$cycloalkylalkyl, $(C_1-C_{10})$alkoxy, $(C_4-C_{10})$cycloalkylalkoxy, halo$(C_1-C_{10})$alkoxy, $(C_1-C_{10})$alkylthio, halo$(C_1-C_{10})$alkylthio, hydroxy$(C_1-C_{10})$alkyl, $(C_1-C_5)$alkoxy$(C_1-C_5)$alkyl, $(C_1-C_5)$alkoxy$(C_1-C_5)$hydroxyalkyl, $(C_3-C_6)$cycloalkoxy$(C_1-C_6)$alkyl, halo$(C_1-C_5)$alkoxy$(C_1-C_5)$alkyl, halo$(C_3-C_6)$cycloalkoxy$(C_1-C_5)$alkyl, $(C_1-C_5)$alkylthio$(C_1-C_5)$alkyl, halo$(C_1-C_5)$alkylthio$(C_1-C_5)$alkyl, $(C_1-C_5)$alkoxy$(C_1-C_5)$alkoxy, hydroxy$(C_1-C_{10})$alkoxy, $(C_3-C_6)$cycloalkoxy$(C_1-C_5)$alkoxy, halo$(C_1-C_5)$alkoxy$(C_1-C_5)$alkoxy, halo$(C_3-C_6)$cycloalkoxy$(C_1-C_5)$alkoxy, hydroxy$(C_1-C_{10})$-alkylthio, $(C_2-C_5)$alkoxy$(C_1-C_5)$alkylthio, $(C_1-C_5)$alkylthio$(C_1-C_5)$alkoxy, $(C_1-C_5)$alkylthio$(C_1-C_5)$alkylthio, $(C_3-C_4)$cycloalkanecarbonylamino$(C_1-C_5)$alkyl, $(C_3-C_4)$cycloalkanecarbonylamino$(C_1-C_5)$alkoxy, $(C_3-C_4)$cycloalkanecarbonylamino$(C_1-C_5)$alkylthio, $(C_1-C_5)$alkylaminocarbonylamino$(C_1-C_5)$alkyl, $(C_1-C_5)$alkylaminocarbonylamino$(C_1-C_5)$alkoxy, $(C_1-C_5)$alkylaminocarbonylamino$(C_1-C_5)$alkylthio, di$(C_1-C_5)$alkylaminocarbonylamino$(C_1-C_5)$alkyl, di$(C_1-C_5)$alkylaminocarbonylamino$(C_1-C_5)$alkoxy, di$(C_1-C_5)$alkylaminocarbonylamino$(C_1-C_5)$alkylthio, $R^3$ is H, F, OH, $(C_1-C_4)$alkanoylamino, $(C_1-C_3)$alkoxy;

provided that when $R^3$ is OH or F, $R^2$ is not $(C_2-C_{10})$alkoxy, $(C_4-C_{10})$cycloalkylalkoxy, halo$(C_2-C_{10})$alkoxy, $(C_2-C_{10})$alkylthio, halo$(C_2-C_{10})$alkylthio, $(C_1-C_5)$alkoxy$(C_1-C_5)$ alkoxy, hydroxy($C_2$-$C_{10}$)alkoxy, ($C_3$-$C_6$)cycloalkoxy($C_1$-$C_5$)alkoxy, halo($C_1$-$C_5$)alkoxy($C_1$-$C_5$)alkoxy, halo($C_3$-$C_6$)cycloalkoxy($C_1$-$C_5$)alkoxy, hydroxy($C_2$-$C_{10}$)alkylthio, ($C_2$-$C_5$)alkoxy($C_1$-$C_5$)alkylthio, ($C_1$-$C_5$)alkyl-thio($C_1$-$C_5$)alkoxy, or ($C_1$-$C_5$)alkylthio($C_1$-$C_5$)alkylthio, ($C_3$-$C_4$)cycloalkane-carbonylamino($C_1$-$C_5$)alkoxy, ($C_3$-$C_4$)cycloalkanecarbonylamino($C_1$-$C_5$)alkylthio, ($C_1$-$C_5$)alkylaminocarbonylamino($C_1$-$C_5$)alkoxy, ($C_1$-$C_5$)alkylaminocarbonylamino($C_1$-$C_5$)alkylthio, di($C_1$-$C_5$)alkylaminocarbonylamino($C_1$-$C_5$)alkoxy or di($C_1$-$C_5$)alkylaminocarbonylamino($C_1$-$C_5$)alkylthio;

Q is Q1, Q2, Q4, Q5, Q9, or Q10

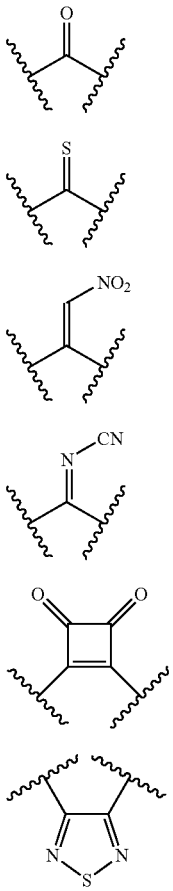

wherein N and N are attached to the truncated bonds $R^4$ is H or ($C_1$-$C_3$)alkyl;

$R^6$ is H

G is $NHR^9$;

$R^5$ and $R^9$ together are —$(CH_2)_3$—, optionally substituted with 1 or 2 groups independently selected from the group consisting of fluorine, ($C_1$-$C_8$)alkyl, halo($C_1$-$C_8$)alkyl, ($C_3$-$C_8$)cycloalkyl, halo($C_3$-$C_8$)cycloalkyl, hydroxy($C_3$-$C_8$)cycloalkyl, ($C_3$-$C_8$)cycloalkyl($C_1$-$C_3$)alkyl, halo($C_3$-$C_8$)cycloalkyl($C_1$-$C_3$)alkyl, and hydroxylated ($C_3$-$C_8$)cycloalkyl ($C_1$-$C_3$)alkyl, ($C_1$-$C_8$)alkoxy, halo($C_1$-$C_8$)alkoxy, ($C_3$-$C_8$)cycloalkoxy, halo($C_3$-$C_8$)cycloalkoxy, hydroxy($C_3$-$C_8$)cycloalkoxy, ($C_1$-$C_8$)alkoxy($C_1$-$C_3$)alkyl, halo($C_1$-$C_8$)alkoxy($C_1$-$C_3$)alkyl, ($C_3$-$C_8$)cycloalkoxy($C_1$-$C_3$)alkyl, halo ($C_3$-$C_8$)cycloalkoxy($C_1$-$C_3$)alkyl, hydroxy($C_3$-$C_8$)cycloalkoxy($C_1$-$C_3$)alkyl, ($C_3$-$C_8$)cycloalkyl($C_1$-$C_3$)alkoxy ($C_1$-$C_3$)alkyl, halo($C_3$-$C_8$)cycloalkyl($C_1$-$C_3$)alkoxy($C_1$-$C_3$)alkyl, hydroxylated($C_3$-$C_8$)cycloalkyl($C_1$-$C_3$)alkoxy($C_1$-$C_3$)alkyl, ($C_1$-$C_8$)alkylthio, halo($C_1$-$C_8$)alkylthio, ($C_3$-$C_8$)cycloalkylthio, halo($C_3$-$C_8$)cycloalkylthio, hydroxy($C_3$-$C_8$)cycloalkylthio, ($C_3$-$C_8$)cycloalkyl($C_1$-$C_3$)alkylthio, halo($C_3$-$C_8$)cycloalkyl($C_1$-$C_3$)alkylthio, hydroxylated($C_3$-$C_8$)cycloalkyl($C_1$-$C_3$)alkylthio, ($C_1$-$C_8$)alkylthio($C_1$-$C_3$)alkyl, halo($C_1$-$C_8$)alkylthio($C_1$-$C_3$)alkyl, ($C_3$-$C_8$)cycloalkylthio($C_1$-$C_3$)alkyl, halo($C_3$-$C_8$)cycloalkylthio($C_1$-$C_3$)alkyl, hydroxy($C_3$-$C_8$)cycloalkylthio($C_1$-$C_3$)alkyl, ($C_3$-$C_8$)cycloalkyl($C_1$-$C_3$)alkylthio($C_1$-$C_3$)alkyl, halo($C_3$-$C_8$)cycloalkyl($C_1$-$C_3$)alkylthio($C_1$-$C_3$)alkyl, and hydroxylated($C_3$-$C_8$)cycloalkyl($C_1$-$C_3$)alkylthio($C_1$-$C_3$)alkyl;

the enantiomers, diastereomers, and salts thereof.

An eleventh embodiment of the invention is a compound of Formula IIc with the stereochemical configuration shown:

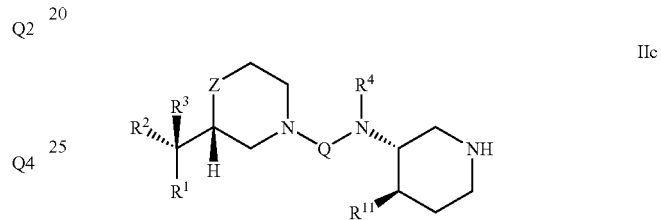

IIc wherein

Z is $CH_2$ or O;

$R^1$ is a) ($C_3$-$C_7$)cycloalkyl; or b) phenyl, heteroaryl, or bicyclic heteroaryl; optionally substituted with 1 to 3 groups independently selected from:

1) fluorine, chlorine, bromine, cyano, nitro, ($C_1$-$C_6$)alkyl, ($C_3$-$C_6$)cycloalkyl, ($C_4$-$C_7$)cycloalkylalkyl, ($C_2$-$C_6$)alkenyl, ($C_5$-$C_7$)cycloalkylalkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, halo($C_2$-$C_6$)alkenyl, halo($C_3$-$C_6$)alkynyl, halo($C_5$-$C_7$)cycloalkylalkynyl, ($C_1$-$C_6$) alkoxy, ($C_3$-$C_6$)cycloalkoxy, ($C_4$-$C_7$)cycloalkylalkoxy, halo ($C_1$-$C_6$)alkoxy, halo($C_3$-$C_6$)cycloalkoxy, halo($C_4$-$C_7$)cycloalkylalkoxy and ($C_1$-$C_6$)alkanesulfonyl; or 2) phenyl, heteroaryl, phenoxy, heteroaryloxy, phenylthio, heteroarylthio, benzyl, heteroarylmethyl, benzyloxy and heteroaryloxy, each optionally substituted with 1 to 3 groups independently selected from:

fluorine, chlorine, cyano, ($C_1$-$C_3$)alkyl, halo($C_1$-$C_3$)alkyl, ($C_1$-$C_3$)-alkoxy, and halo($C_1$-$C_3$)alkoxy, and aminocarbonyl;

$R^2$ is ($C_1$-$C_{10}$)alkyl, ($C_4$-$C_{10}$)cycloalkylalkyl, halo($C_1$-$C_{10}$)alkyl, halo($C_4$-$C_{10}$)cycloalkylalkyl, ($C_1$-$C_{10}$)alkoxy, ($C_4$-$C_{10}$)cycloalkylalkoxy, halo($C_1$-$C_{10}$)alkoxy, ($C_1$-$C_{10}$)alkylthio, halo($C_1$-$C_{10}$)alkylthio, hydroxy($C_1$-$C_{10}$)alkyl, ($C_1$-$C_5$)alkoxy($C_1$-$C_5$)alkyl, ($C_1$-$C_5$)alkoxy($C_1$-$C_5$)hydroxyalkyl, ($C_3$-$C_6$)cycloalkoxy($C_1$-$C_6$)alkyl, halo($C_1$-$C_5$)alkoxy($C_1$-$C_5$)alkyl, halo($C_3$-$C_6$)cycloalkoxy($C_1$-$C_5$)alkyl, ($C_1$-$C_5$) alkylthio($C_1$-$C_5$)alkyl, halo($C_1$-$C_5$)alkylthio($C_1$-$C_5$)alkyl, ($C_1$-$C_5$)alkoxy($C_1$-$C_5$)alkoxy, hydroxy($C_1$-$C_{10}$)alkoxy, ($C_3$-$C_6$)cycloalkoxy($C_1$-$C_5$)alkoxy, halo($C_1$-$C_5$)alkoxy($C_1$-$C_5$) alkoxy, halo($C_3$-$C_6$)cycloalkoxy($C_1$-$C_5$)alkoxy, hydroxy($C_1$-$C_{10}$)alkylthio, ($C_2$-$C_5$)alkoxy($C_1$-$C_5$)alkylthio, ($C_1$-$C_5$) alkylthio($C_1$-$C_5$)alkoxy, ($C_1$-$C_5$)alkylthio($C_1$-$C_5$)alkylthio, ($C_3$-$C_4$)cycloalkane-carbonylamino($C_1$-$C_5$)alkyl, ($C_3$-$C_4$) cycloalkanecarbonylamino($C_1$-$C_5$)alkoxy, ($C_3$-$C_4$)cycloalkane-carbonylamino($C_1$-$C_5$)alkylthio, ($C_1$-$C_5$)alkylaminocarbonylamino($C_1$-$C_5$)alkyl, ($C_1$-$C_5$)alkylaminocarbonylamino($C_1$-$C_5$)alkoxy, ($C_1$-$C_5$) alkylaminocarbonylamino($C_1$-$C_5$)alkylthio, di($C_1$-$C_5$) alkylaminocarbonylamino($C_1$-$C_5$)alkyl, di($C_1$-$C_5$) alkylaminocarbonylamino($C_1$-$C_5$)alkoxy, di($C_1$-$C_5$) alkylaminocarbonylamino($C_1$-$C_5$)alkylthio, $R^3$ is H, F, OH, ($C_1$-$C_4$)alkanoylamino, or ($C_1$-$C_3$)alkoxy;

provided that when $R^3$ is OH or F, $R^2$ is not ($C_2$-$C_{10}$)alkoxy, ($C_4$-$C_{10}$)cycloalkylalkoxy, halo($C_2$-$C_{10}$)alkoxy, ($C_2$-$C_{10}$)alkylthio, halo($C_2$-$C_{10}$)alkylthio, ($C_1$-$C_5$)alkoxy($C_1$-$C_5$)alkoxy, hydroxy($C_2$-$C_{10}$)alkoxy, ($C_3$-$C_6$)cycloalkoxy($C_1$-$C_5$)alkoxy, halo($C_1$-$C_5$)alkoxy($C_1$-$C_5$)alkoxy, halo($C_3$-$C_6$)cycloalkoxy($C_1$-$C_5$)alkoxy, hydroxy($C_2$-$C_{10}$)alkylthio, ($C_2$-$C_5$)alkoxy($C_1$-$C_5$)alkylthio, ($C_1$-$C_5$)alkyl-thio($C_1$-$C_5$)alkoxy, or ($C_1$-$C_5$)alkylthio($C_1$-$C_5$)alkylthio, ($C_3$-$C_4$)cycloalkane-carbonylamino($C_1$-$C_5$)alkoxy, ($C_3$-$C_4$)cycloalkanecarbonylamino($C_1$-$C_5$)alkylthio, ($C_1$-$C_5$)alkylaminocarbonylamino($C_1$-$C_5$)alkoxy, ($C_1$-$C_5$) alkylaminocarbonylamino($C_1$-$C_5$)alkylthio, di($C_1$-$C_5$) alkylaminocarbonylamino($C_1$-$C_5$)alkoxy or di($C_1$-$C_5$) alkylaminocarbonylamino($C_1$-$C_5$)alkylthio;

Q is Q1, Q2, Q4, Q5, Q9, or Q10

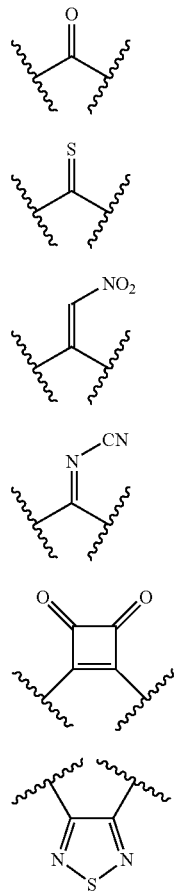

wherein N and N are attached to the truncated bonds $R^4$ is H or ($C_1$-$C_3$)alkyl;

$R^{11}$ is fluorine, ($C_1$-$C_8$)alkyl, halo($C_1$-$C_8$)alkyl, ($C_3$-$C_8$)cycloalkyl, halo($C_3$-$C_8$)cycloalkyl, hydroxy($C_3$-$C_8$)cycloalkyl, ($C_3$-$C_8$)cycloalkyl($C_1$-$C_3$)alkyl, halo($C_3$-$C_8$)cycloalkyl($C_1$-$C_3$)alkyl, hydroxylated ($C_3$-$C_8$)cycloalkyl($C_1$-$C_3$)alkyl, ($C_1$-$C_8$)alkoxy, halo($C_1$-$C_8$)alkoxy, ($C_3$-$C_8$)cycloalkoxy, halo($C_3$-$C_8$)cycloalkoxy, hydroxy($C_3$-$C_8$)cycloalkoxy, ($C_1$-$C_8$)alkoxy($C_1$-$C_3$)alkyl, halo($C_1$-$C_8$)alkoxy($C_1$-$C_3$)alkyl, ($C_3$-$C_8$)cycloalkoxy($C_1$-$C_3$)alkyl, halo($C_3$-$C_8$)cycloalkoxy($C_1$-$C_3$)alkyl, hydroxy($C_3$-$C_8$)cycloalkoxy($C_1$-$C_3$)alkyl, ($C_3$-$C_8$)cycloalkyl($C_1$-$C_3$)alkoxy($C_1$-$C_3$)alkyl, halo($C_3$-$C_8$)cycloalkyl($C_1$-$C_3$)alkoxy($C_1$-$C_3$)alkyl, hydroxylated($C_3$-$C_8$)cycloalkyl($C_1$-$C_3$)alkoxy($C_1$-$C_3$)alkyl, ($C_1$-$C_8$)alkylthio, halo($C_1$-$C_8$)alkylthio, ($C_3$-$C_8$)cycloalkylthio, halo($C_3$-$C_8$)cycloalkylthio, hydroxy($C_3$-$C_8$)cycloalkylthio, ($C_3$-$C_8$)cycloalkyl($C_1$-$C_3$)alkylthio, halo($C_3$-$C_8$)cycloalkyl($C_1$-$C_3$)alkylthio, hydroxylated($C_3$-$C_8$)cycloalkyl($C_1$-$C_3$)alkylthio, ($C_1$-$C_8$)alkylthio($C_1$-$C_3$)alkyl, halo($C_1$-$C_8$)alkylthio($C_1$-$C_3$)alkyl, ($C_3$-$C_8$)cycloalkylthio($C_1$-$C_3$)alkyl, halo($C_3$-$C_8$)cycloalkylthio($C_1$-$C_3$)alkyl, hydroxy($C_3$-$C_8$)cycloalkylthio($C_1$-$C_3$)alkyl, ($C_3$-$C_8$)cycloalkyl($C_1$-$C_3$)alkylthio($C_1$-$C_3$) alkyl, halo($C_3$-$C_8$)cycloalkyl($C_1$-$C_3$)alkylthio($C_1$-$C_3$)alkyl, and hydroxylated($C_3$-$C_8$)cycloalkyl($C_1$-$C_3$)alkylthio($C_1$-$C_3$) alkyl;

and the salts thereof.

Another embodiment of the invention provides compounds of Formula Ia

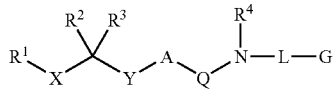

Ia wherein $R^1$ is a) ($C_1$-$C_{12}$)alkyl, ($C_3$-$C_7$)cycloalkyl, ($C_4$-$C_{12}$)cycloalkylalkyl, halo($C_1$-$C_{12}$)alkyl, halo($C_3$-$C_7$)-cycloalkyl, halo($C_4$-$C_{12}$)cycloalkylalkyl, saturated heterocyclyl optionally substituted with 1 to 5 groups independently selected from: fluorine, ($C_1$-$C_6$)alkyl, halo($C_1$-$C_6$)alkyl and oxo);

or b) phenyl, napthyl, heteroaryl or bicyclic heteroaryl each optionally substituted with 1 to 5 groups independently selected from:

1) fluorine, chlorine, bromine, iodine, cyano, nitro, amino, hydroxy, carboxy, ($C_1$-$C_6$)alkyl, ($C_3$-$C_6$)cycloalkyl, ($C_4$-$C_7$) cycloalkylalkyl, ($C_2$-$C_6$)alkenyl, ($C_5$-$C_7$)cycloalkylalkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, halo($C_2$-$C_6$)alkenyl, halo($C_5$-$C_6$)cycloalkenyl, halo($C_6$-$C_7$)cycloalkenylalkyl, halo($C_3$-$C_6$)alkynyl, halo($C_5$-$C_7$) cycloalkylalkynyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo($C_4$-$C_7$)-cycloalkylalkylthio, ($C_1$-$C_6$)alkanesulfinyl, ($C_3$-$C_6$)cycloalkanesulfinyl, ($C_4$-$C_7$)cycloalkyl-alkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$) cycloalkanesulfonyl, ($C_4$-$C_7$)-cycloalkylalkanesulfonyl, halo ($C_1$-$C_6$)alkanesulfonyl, halo($C_3$-$C_6$)cycloalkanesulfonyl, halo($C_4$-$C_7$)cycloalkylalkane-sulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, aminocarbonyl, ($C_1$-$C_6$)alkylamino-carbonyl, and di($C_1$-$C_6$)alkylaminocarbonyl; or 2) phenyl, napthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl($C_1$-$C_3$)alkyl, napthyl($C_1$-$C_3$)alkyl, heteroaryl($C_1$-$C_3$)alkyl, bicyclic heteroaryl($C_1$-$C_3$)alkyl, each optionally substituted with 1 to 5 groups independently selected from: fluorine, chlorine, cyano, ($C_1$-$C_3$)alkyl, halo($C_1$-$C_3$)alkyl, ($C_1$-$C_3$)alkoxy, halo($C_1$-$C_3$)alkoxy, ($C_1$-$C_3$)alkanesulfonyl, and ($C_1$-$C_3$)alkoxycarbonyl;

X and Y is each independently $CH_2$ or a single bond;

$R^2$ is ($C_1$-$C_{12}$)alkyl, ($C_4$-$C_{12}$)cycloalkylalkyl, halo($C_1$-$C_{12}$)alkyl, halo($C_4$-$C_{12}$)cycloalkylalkyl, ($C_2$-$C_{12}$)alkenyl, ($C_5$-$C_{12}$)cycloalkylalkenyl, halo($C_2$-$C_{12}$)alkenyl, halo($C_5$-$C_{12}$)cycloalkylalkenyl, ($C_2$-$C_{12}$)alkynyl, ($C_5$-$C_{12}$)cycloalkylalkynyl, halo($C_3$-$C_{12}$)alkynyl, halo($C_5$-$C_{12}$)cycloalkylalkynyl, ($C_1$-$C_{12}$)alkoxy, ($C_4$-$C_{12}$)cycloalkylalkoxy, halo($C_1$-$C_{12}$)alkoxy, ($C_1$-$C_{12}$)alkylthio, halo($C_1$-$C_{12}$)alkylthio, ($C_1$-$C_{12}$)alkanesulfinyl, halo($C_1$-$C_{12}$)alksulfinyl, ($C_1$-$C_{12}$)alkanesulfonyl, halo($C_1$-$C_{12}$)alksulfonyl, hydroxy($C_1$-$C_{12}$)alkyl, ($C_1$-$C_6$)alkoxy($C_1$-$C_6$)alkyl, ($C_1$-$C_6$)cycloalkoxy($C_1$-$C_6$)alkyl, halo($C_1$-$C_6$)alkoxy($C_1$-$C_6$)alkyl, halo($C_1$-$C_6$)cycloalkoxy($C_1$-$C_6$)alkyl, ($C_1$-$C_6$)alkylthio($C_1$-$C_6$)alkyl, halo($C_1$-$C_6$)alkylthio($C_1$-$C_6$)alkyl, ($C_1$-$C_6$)alkanesulfinyl($C_1$-$C_6$)alkyl, halo($C_1$-$C_6$)alkanesulfinyl($C_1$-$C_6$)alkyl, ($C_1$-$C_6$)alkanesulfonyl($C_1$-$C_6$)alkyl, halo($C_1$-$C_6$)alkanesulfonyl($C_1$-$C_6$)alkyl, ($C_1$-$C_6$)alkoxy($C_1$-$C_6$)alkoxy, hydroxy($C_1$-$C_6$)alkoxy, ($C_1$-$C_6$)cycloalkoxy($C_1$-$C_6$)alkoxy, halo($C_1$-$C_6$)alkoxy($C_1$-$C_6$)-alkoxy, halo($C_1$-$C_6$)cycloalkoxy($C_1$-$C_6$)alkoxy, hydroxy($C_1$-$C_{12}$)alkylthio, ($C_1$-$C_6$)alkoxy($C_1$-$C_6$)alkylthio, ($C_1$-$C_6$)alkylthio($C_1$-$C_6$)alkoxy, ($C_1$-$C_6$)alkylthio($C_1$-$C_6$)alkylthio, ($C_1$-$C_6$)alkoxy($C_1$-$C_6$)-alkylsulfinyl, ($C_1$-$C_6$)alkylsulfinyl($C_1$-$C_6$)alkoxy, ($C_1$-$C_6$)alkylsulfinyl($C_1$-$C_6$)alkylsulfinyl, ($C_1$-$C_6$)-alkoxy($C_1$-$C_6$)alkylsulfonyl, ($C_1$-$C_6$)alkylsulfonyl($C_1$-$C_6$)alkoxy, ($C_1$-$C_6$)alkylsulfonyl($C_1$-$C_6$)alkyl-sulfonyl, ($C_1$-$C_4$)alkoxy($C_1$-$C_4$)alkoxy($C_1$-$C_4$)alkyl, halo($C_1$-$C_4$)alkoxy($C_1$-$C_4$)alkoxy($C_1$-$C_4$)alkyl, cyano($C_1$-$C_{12}$)alkyl, cyano($C_1$-$C_{12}$)alkoxy, cyano($C_1$-$C_6$)alkoxy($C_1$-$C_6$)alkyl, cyano($C_1$-$C_6$)alkoxy-($C_1$-$C_6$)alkoxy, cyano($C_1$-$C_6$)alkoxy($C_1$-$C_6$)alkylthio, aminocarbonylamino($C_1$-$C_{12}$)alkyl, aminocarbonylamino($C_1$-$C_{12}$)alkoxy, aminocarbonylamino($C_1$-$C_{12}$)alkylthio, ($C_1$-$C_6$)alkanoyl-amino($C_1$-$C_6$)alkyl, ($C_1$-$C_6$)alkanoylamino($C_1$-$C_6$)alkoxy, ($C_1$-$C_6$)alkanoylamino($C_1$-$C_6$)alkylthio, aminosulfonylamino($C_1$-$C_{12}$)alkyl, aminosulfonylamino($C_1$-$C_{12}$)alkoxy, aminosulfonylamino($C_1$-$C_{12}$)alkylthio, ($C_1$-$C_6$)alkanesulfonylamino($C_1$-$C_6$)alkyl, ($C_1$-$C_6$)alkanesulfonylamino($C_1$-$C_6$)alkoxy, or ($C_1$-$C_6$)alkanesulfonylamino($C_1$-$C_6$)alkylthio;

$R^3$ is H, halogen, ($C_1$-$C_6$)alkyl, hydroxyl, hydroxy($C_1$-$C_6$)alkyl, ($C_1$-$C_6$)alkanoylamino, ($C_1$-$C_6$)-alkoxycarbonylamino, ($C_1$-$C_6$)alkylaminocarbonylamino, di($C_1$-$C_6$)alkylaminocarbonylamino, ($C_1$-$C_6$)alkanesulfonylamino, ($C_1$-$C_6$)alkylaminosulfonylamino, di($C_1$-$C_6$)alkylaminosulfonyl-amino, or phenylamino or heteroarylamino in which each phenylamino and heteroarylamino group is optionally substituted with 1 to 5 groups independently selected from:

fluorine, chlorine, bromine, iodine, cyano, nitro, amino, hydroxy, carboxy, ($C_1$-$C_6$)alkyl, ($C_3$-$C_6$)cycloalkyl, ($C_4$-$C_7$)cycloalkylalkyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, amino-carbonyl, ($C_1$-$C_6$)alkylaminocarbonyl, and di($C_1$-$C_6$)alkylaminocarbonyl;

provided that when $R^3$ is hydroxyl, halogen or optionally substituted phenylamino or heteroarylamino, $R^2$ is not ($C_1$-$C_{12}$)alkoxy, ($C_4$-$C_{12}$)cycloalkylalkoxy, halo($C_1$-$C_{12}$)alkoxy, ($C_1$-$C_{12}$)alkylthio, halo($C_1$-$C_{12}$)alkylthio, ($C_1$-$C_{12}$)alkanesulfinyl, halo($C_1$-$C_{12}$)alksulfinyl, ($C_1$-$C_{12}$)-alkanesulfonyl, halo($C_1$-$C_{12}$)alksulfonyl, ($C_1$-$C_6$)alkoxy($C_1$-$C_6$)alkoxy, hydroxy($C_1$-$C_6$)alkoxy, ($C_1$-$C_6$)cycloalkoxy($C_1$-$C_6$)alkoxy, halo($C_1$-$C_6$)alkoxy($C_1$-$C_6$)alkoxy, halo($C_1$-$C_6$)cycloalkoxy($C_1$-$C_6$)alkoxy, hydroxy($C_1$-$C_6$)alkylthio, ($C_1$-$C_6$)alkoxy($C_1$-$C_6$)alkylthio, ($C_1$-$C_6$)alkylthio($C_1$-$C_6$)alkoxy, ($C_1$-$C_6$)alkylthio($C_1$-$C_6$)alkylthio, ($C_1$-$C_6$)alkoxy($C_1$-$C_6$)alkylsulfinyl, ($C_1$-$C_6$)alkylsulfinyl($C_1$-$C_6$)alkoxy, ($C_1$-$C_6$)alkylsulfinyl($C_1$-$C_6$)alkylsulfinyl, ($C_1$-$C_6$)alkoxy($C_1$-$C_6$)alkylsulfonyl, ($C_1$-$C_6$)-alkylsulfonyl($C_1$-$C_6$)alkoxy, ($C_1$-$C_6$)alkylsulfonyl($C_1$-$C_6$)alkylsulfonyl, cyano($C_1$-$C_{12}$)alkoxy, cyano($C_1$-$C_6$)alkoxy($C_1$-$C_6$)alkoxy, cyano($C_1$-$C_6$)alkoxy($C_1$-$C_6$)alkylthio, aminocarbonylamino($C_1$-$C_6$)alkoxy, aminocarbonylamino($C_1$-$C_6$)alkylthio, ($C_1$-$C_6$)alkanoylamino($C_1$-$C_6$)alkoxy, ($C_1$-$C_6$)-alkanoylamino($C_1$-$C_6$)alkylthio, aminosulfonylamino($C_1$-$C_6$)alkoxy, aminosulfonylamino($C_1$-$C_6$)-alkylthio, ($C_1$-$C_6$)alkanesulfonylamino($C_1$-$C_6$)alkoxy, or ($C_1$-$C_6$)alkanesulfonylamino($C_1$-$C_6$)alkylthio;

A is a saturated or unsaturated 4-, 5-, 6-, or 7-membered ring which is optionally bridged by $(CH_2)_m$ wherein said ring is composed of carbon atoms, and 0-2 hetero atoms selected from 0, 1 or 2 nitrogen atoms, 0 or 1 oxygen atoms, and 0 or 1 sulfur atoms, said ring atoms being substituted with the appropriate number of hydrogen atoms, said ring being optionally substituted with up to four independently selected halogen atoms, ($C_1$-$C_6$)alkyl groups, halo($C_1$-$C_6$)alkyl groups or oxo groups;

Q and Y are attached to carbon or nitrogen atoms in ring A in a 1,2 or 1,3 or 1,4 relationship;

m is 1 to 3;

Q is a divalent radical selected from

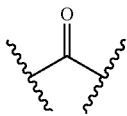

Q1

-continued

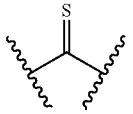
Q2

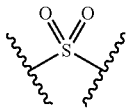
Q3

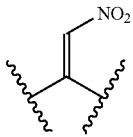
Q4

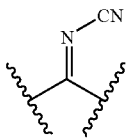
Q5

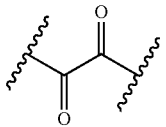
Q6

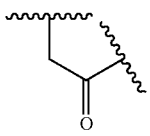
Q7

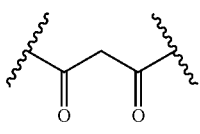
Q8

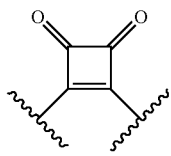
Q9

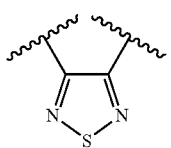
Q10

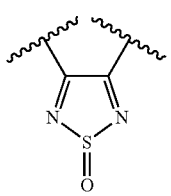
Q11

-continued

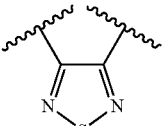
Q12 or

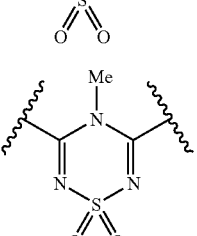
Q13 wherein A and N are attached to the truncated bonds $R^4$ is H, $(C_1-C_6)$alkyl, halo$(C_1-C_6)$alkyl; $(C_1-C_3)$alkoxy$(C_1-C_3)$alkyl, or cyano$(C_1-C_6)$alkyl;

L is 1) a linear $(C_2-C_4)$alkyl chain when G is OH, $OR^9$, $NH_2$, $NHR^9$, $NR^9R^{10}$, NHC(=NH)$NH_2$ or NHC(=NH)$NHR^9$, or 2) a linear $(C_1-C_3)$alkyl chain when G is C(=NH)$NH_2$ or C(=NH)$NHR^9$;

L is optionally substituted by 1-4 groups independently selected from $R^5$, $R^6$, $R^7$, and $R^8$;

one or more of the carbon atoms of L may be part of a 3-, 4-, 5-, 6-, or 7-membered saturated ring composed of carbon atoms, and 0-2 hetero atoms selected from 0 or 1 nitrogen atoms, 0 or 1 oxygen atoms, and 0 or 1 sulfur atoms; said ring being optionally substituted with up to four groups selected from halogen, $(C_1-C_6)$alkyl, halo$(C_1-C_6)$alkyl, $(C_3-C_6)$cycloalkyl, halo$(C_3-C_6)$cycloalkyl, $(C_4-C_7)$cycloalkylalkyl, halo$(C_4-C_7)$cycloalkylalkyl, and oxo);

$R^5$, $R^6$, $R^7$, and $R^8$ is each independently selected from 1) $(C_1-C_{12})$alkyl, $(C_4-C_{12})$cycloalkylalkyl, halo$(C_1-C_{12})$alkyl, halo$(C_4-C_{12})$cycloalkylalkyl, $(C_2-C_{12})$alkenyl, $(C_5-C_{12})$cycloalkylalkenyl, halo$(C_2-C_{12})$alkenyl, halo$(C_5-C_{12})$cycloalkylalkenyl, $(C_2-C_{12})$alkynyl, $(C_5-C_{12})$cycloalkylalkynyl, halo$(C_2-C_{12})$alkynyl, halo$(C_5-C_{12})$cycloalkylalkynyl, $(C_1-C_6)$alkoxy$(C_1-C_6)$alkyl, halo$(C_1-C_6)$alkoxy$(C_1-C_6)$alkyl, $(C_1-C_6)$alkylthio$(C_1-C_6)$alkyl, halo$(C_1-C_6)$alkylthio$(C_1-C_6)$alkyl, $(C_1-C_6)$alkanesulfinyl$(C_1-C_6)$alkyl, halo$(C_1-C_6)$alkanesulfinyl$(C_1-C_6)$alkyl, $(C_1-C_6)$alkane-sulfonyl$(C_1-C_6)$alkyl, halo$(C_1-C_6)$alkanesulfonyl$(C_1-C_6)$alkyl, aminocarbonyl$(C_1-C_6)$alkyl, cyano$(C_1-C_6)$alkyl, saturated heterocyclyl, or saturated heterocyclyl$(C_1-C_6)$alkyl, or 2) phenyl, naphthyl, heteroaryl, phenyl$(C_1-C_3)$alkyl, naphthyl$(C_1-C_3)$alkyl, or heteroaryl$(C_1-C_3)$alkyl, each optionally substituted with 1 to 3 groups independently selected from:

fluorine, chlorine, bromine, iodine, cyano, nitro, amino, hydroxy, carboxy, $(C_1-C_6)$alkyl, $(C_3-C_6)$cycloalkyl, $(C_4-C_7)$cycloalkylalkyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-$ $C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, aminocarbonyl, ($C_1$-$C_6$)alkylaminocarbonyl, di($C_1$-$C_6$)alkylaminocarbonyl, phenyl, napthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl($C_1$-$C_3$)alkyl, napthyl($C_1$-$C_3$)alkyl, heteroaryl($C_1$-$C_3$)alkyl, or bicyclic heteroaryl($C_1$-$C_3$)alkyl, wherein the aromatic and heteroaromatic groups are optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, halo($C_1$-$C_3$)alkoxy, ($C_1$-$C_3$)alkanesulfonyl, and ($C_1$-$C_3$)alkoxycarbonyl;

G is OH, $OR^9$, $NH_2$, $NHR^9$, $NR^9R^{10}$, C(=NH)$NH_2$, C(=NH)$NHR^9$, NHC(=NH)$NH_2$, or NHC(=NH)$NHR^9$;

$R^9$ is a) ($C_1$-$C_{12}$)alkyl, ($C_4$-$C_{12}$)cycloalkylalkyl, halo($C_1$-$C_{12}$)alkyl, halo($C_4$-$C_{12}$)cycloalkylalkyl, ($C_2$-$C_{12}$)alkenyl, ($C_5$-$C_{12}$)cycloalkylalkenyl, halo($C_2$-$C_{12}$)alkenyl, halo($C_5$-$C_{12}$)cycloalkylalkenyl, ($C_2$-$C_{12}$)alkynyl, ($C_5$-$C_{12}$)cycloalkylalkynyl, halo($C_2$-$C_{12}$)alkynyl, halo($C_5$-$C_{12}$)cycloalkylalkynyl, ($C_1$-$C_6$)alkoxy($C_1$-$C_6$)alkyl, halo($C_1$-$C_6$)alkoxy($C_1$-$C_8$)alkyl, ($C_1$-$C_6$)alkylthio($C_1$-$C_6$)alkyl, halo($C_1$-$C_6$)alkylthio($C_1$-$C_6$)alkyl, ($C_1$-$C_6$)alkanesulfinyl($C_1$-$C_6$)alkyl, halo($C_1$-$C_6$)alkanesulfinyl($C_1$-$C_6$)alkyl, ($C_1$-$C_6$)alkanesulfonyl($C_1$-$C_6$)alkyl, halo($C_1$-$C_6$)alkanesulfonyl($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylamino-carbonyl($C_1$-$C_6$)alkyl, cyano($C_1$-$C_6$)alkyl, carboxy($C_1$-$C_6$)alkyl, ($C_1$-$C_6$)alkoxycarbonyl($C_1$-$C_6$)alkyl, saturated heterocyclyl, or saturated heterocyclyl($C_1$-$C_6$)alkyl or b) phenyl, naphthyl, heteroaryl, phenyl($C_1$-$C_3$)alkyl, naphthyl($C_1$-$C_3$)alkyl, or heteroaryl($C_1$-$C_3$)alkyl, each optionally substituted by 1 to 3 groups independently selected from:

1) fluorine, chlorine, bromine, iodine, cyano, nitro, amino, hydroxy, carboxy, ($C_1$-$C_6$)alkyl, ($C_3$-$C_6$)cycloalkyl, ($C_4$-$C_7$)cycloalkylalkyl, ($C_2$-$C_6$)alkenyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkylalkylthio, halo($C_1$-$C_6$)alkylthio, halo($C_3$-$C_6$)cycloalkylthio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, aminocarbonyl, ($C_1$-$C_6$)alkylaminocarbonyl and di($C_1$-$C_6$)alkylaminocarbonyl; or 2) phenyl, napthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl($C_1$-$C_3$)alkyl, napthyl($C_1$-$C_3$)alkyl, heteroaryl($C_1$-$C_3$)alkyl, and bicyclic heteroaryl($C_1$-$C_3$)alkyl, each optionally substituted with 1 to 3 groups independently selected from fluorine, chlorine, cyano, ($C_1$-$C_3$)alkyl, halo ($C_1$-$C_3$)alkyl, ($C_1$-$C_3$)alkoxy, halo($C_1$-$C_3$)alkoxy, ($C_1$-$C_3$)alkanesulfonyl, and ($C_1$-$C_3$)alkoxycarbonyl; or b) $R^9$ is a saturated divalent radical composed of carbon atoms, and 0, 1 or 2 hetero atoms selected from 0 or 1 nitrogen atoms, 0 or 1 oxygen atoms, and 0 or 1 sulfur atoms that is attached to any core carbon atom on the chain L to form a saturated 3-, 4-, 5-, 6-, or 7-membered ring; said ring being optionally substituted with 1-4 groups selected from halogen, ($C_1$-$C_6$)alkyl, halo($C_1$-$C_6$)alkyl, ($C_1$-$C_6$)cycloalkyl, halo($C_1$-$C_6$)cycloalkyl, ($C_1$-$C_6$)cycloalkyl($C_1$-$C_2$)alkyl, halo($C_1$-$C_6$)cycloalkyl($C_1$-$C_2$)alkyl, and oxo);

$R^{10}$ is ($C_1$-$C_6$)alkyl or halo($C_1$-$C_6$)alkyl;

and the enantiomers, diastereomers, and salts thereof.

An embodiment of the invention is a compound of Formula Ia wherein:

$R^1$ is a) ($C_1$-$C_9$)alkyl, ($C_3$-$C_7$)cycloalkyl, ($C_4$-$C_9$)cycloalkylalkyl, halo($C_1$-$C_9$)alkyl, halo($C_3$-$C_7$)cycloalkyl, halo($C_4$-$C_9$)cycloalkylalkyl, saturated heterocyclyl optionally substituted with 1 to 3 groups independently selected from fluorine, ($C_1$-$C_3$)alkyl, halo($C_1$-$C_3$)alkyl and oxo;

or b) phenyl, napthyl, heteroaryl, or bicyclic heteroaryl each optionally substituted with 1 to 3 groups independently selected from:

1) fluorine, chlorine, bromine, cyano, nitro, ($C_1$-$C_3$)alkyl, ($C_3$-$C_6$)cycloalkyl, ($C_4$-$C_7$)cycloalkylalkyl, ($C_3$-$C_6$)cycloalkylethynyl, halo($C_1$-$C_3$)alkyl, halo($C_3$-$C_6$)-cycloalkyl, halo($C_4$-$C_7$)cycloalkylalkyl, halo($C_5$-$C_7$)cycloalkylethynyl, ($C_1$-$C_3$)alkoxy, ($C_3$-$C_6$)cycloalkoxy, ($C_4$-$C_7$)cycloalkylalkoxy, halo($C_1$-$C_3$)alkoxy, halo($C_3$-$C_6$)cycloalkoxy, halo($C_4$-$C_7$)cycloalkylalkoxy, ($C_1$-$C_3$)alkylthio, ($C_3$-$C_6$)cycloalkylthio, ($C_4$-$C_7$)cycloalkylalkylthio, halo($C_1$-$C_3$)alkylthio, halo($C_3$-$C_6$)cycloalkylthio, halo($C_4$-$C_7$)cycloalkylalkylthio, ($C_1$-$C_3$)alkanesulfinyl, ($C_3$-$C_6$)cycloalkanesulfinyl, ($C_4$-$C_7$)cycloalkylalkanesulfinyl, halo($C_1$-$C_3$)alkanesulfinyl, halo ($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl and ($C_1$-$C_6$)alkylamino; or 2) phenyl, napthyl, heteroaryl, bicyclic heteroaryl, phenoxy, naphthyloxy, heteroaryloxy, bicyclic heteroaryloxy, phenylthio, naphthylthio, heteroarylthio, bicyclic heteroarylthio, phenylsulfinyl, naphthylsulfinyl, heteroarylsulfinyl, bicyclic heteroarylsulfinyl, phenylsulfonyl, naphthylsulfonyl, heteroarylsulfonyl, bicyclic heteroarylsulfonyl, phenyl($C_1$-$C_3$)alkyl, napthyl($C_1$-$C_3$)alkyl, heteroaryl($C_1$-$C_3$)alkyl, or, bicyclic heteroaryl($C_1$-$C_3$)alkyl, each optionally substituted with 1 to 3 groups independently selected from:

fluorine, chlorine, cyano, ($C_1$-$C_3$)alkyl, halo($C_1$-$C_3$)alkyl, ($C_1$-$C_3$)alkoxy, halo($C_1$-$C_3$)alkoxy, ($C_1$-$C_3$)alkanesulfonyl, and ($C_1$-$C_3$)alkoxycarbonyl;

X and Y is each a single bond;

$R^2$ is ($C_2$-$C_{10}$)alkyl, ($C_4$-$C_{10}$)cycloalkylalkyl, halo($C_2$-$C_{10}$)alkyl, halo($C_4$-$C_{10}$)cycloalkylalkyl, ($C_2$-$C_{10}$)alkenyl, ($C_5$-$C_{10}$)cycloalkylalkenyl, halo($C_2$-$C_{10}$)alkenyl, halo($C_5$-$C_{10}$)cycloalkylalkenyl, ($C_2$-$C_{10}$)alkynyl, ($C_5$-$C_{10}$)cycloalkylalkynyl, halo($C_3$-$C_{10}$)alkynyl, halo($C_5$-$C_{10}$)

cycloalkylalkynyl, $(C_2-C_{10})$alkoxy, $(C_4-C_{10})$ cycloalkylalkoxy, halo$(C_2-C_{10})$alkoxy, $(C_2-C_{10})$alkylthio, halo$(C_2-C_{10})$alkylthio, $(C_2-C_{10})$alkanesulfinyl, halo$(C_2-C_{10})$ alksulfinyl, $(C_2-C_{10})$alkanesulfonyl, halo$(C_2-C_{10})$alksulfonyl, hydroxy$(C_2-C_{10})$alkyl, $(C_1-C_5)$alkoxy$(C_1-C_5)$alkyl, $(C_1-C_5)$cycloalkoxy$(C_1-C_5)$alkyl, halo$(C_1-C_5)$alkoxy$(C_1-C_5)$ alkyl, halo$(C_1-C_5)$cycloalkoxy$(C_1-C_5)$alkyl, $(C_1-C_5)$ alkylthio$(C_1-C_5)$alkyl, halo$(C_1-C_5)$alkylthio$(C_1-C_5)$alkyl, $(C_1-C_5)$alkanesulfinyl$(C_1-C_5)$alkyl, halo$(C_1-C_5)$alkanesulfinyl$(C_1-C_5)$alkyl, $(C_1-C_5)$alkanesulfonyl$(C_1-C_5)$alkyl, halo $(C_1-C_5)$alkanesulfonyl$(C_1-C_5)$alkyl, $(C_1-C_5)$alkoxy$(C_1-C_5)$-alkoxy, hydroxy$(C_2-C_{10})$alkoxy, $(C_1-C_5)$cycloalkoxy$(C_1-C_5)$alkoxy, halo$(C_1-C_5)$alkoxy$(C_1-C_5)$-alkoxy, halo$(C_1-C_5)$ cycloalkoxy$(C_1-C_5)$alkoxy, hydroxy$(C_2-C_{10})$alkylthio, $(C_1-C_5)$alkoxy$(C_1-C_5)$alkylthio, $(C_1-C_5)$alkylthio$(C_1-C_5)$alkoxy, $(C_1-C_5)$alkylthio$(C_1-C_5)$alkylthio, $(C_1-C_5)$alkoxy$(C_1-C_5)$ alkylsulfinyl, $(C_1-C_5)$alkylsulfinyl$(C_1-C_5)$alkoxy, $(C_1-C_5)$ alkylsulfinyl$(C_1-C_5)$-alkylsulfinyl, $(C_1-C_5)$alkoxy$(C_1-C_5)$ alkylsulfonyl, $(C_1-C_5)$alkylsulfonyl$(C_1-C_5)$alkoxy, $(C_1-C_5)$ alkylsulfonyl$(C_1-C_5)$alkyl-sulfonyl, $(C_1-C_3)$alkoxy$(C_1-C_3)$ alkoxy$(C_1-C_3)$alkyl, halo$(C_1-C_3)$alkoxy$(C_1-C_3)$alkoxy$(C_1-C_3)$alkyl, cyano$(C_2-C_{10})$alkyl, cyano$(C_2-C_{10})$alkoxy, cyano $(C_1-C_5)$alkoxy$(C_1-C_5)$alkyl, cyano$(C_1-C_5)$alkoxy-$(C_1-C_5)$ alkoxy, cyano$(C_1-C_5)$alkoxy$(C_1-C_5)$alkylthio, aminocarbonylamino$(C_2-C_{10})$alkyl, aminocarbonylamino $(C_2-C_{10})$alkoxy, aminocarbonyl-amino$(C_2-C_{10})$alkylthio, $(C_1-C_5)$alkanoyl-amino$(C_1-C_5)$alkyl, $(C_1-C_5)$alkanoylamino $(C_1-C_5)$alkoxy, $(C_1-C_5)$alkanoylamino$(C_1-C_5)$alkylthio, aminosulfonylamino$(C_2-C_{10})$alkyl, aminosulfonyl-amino $(C_2-C_{10})$alkoxy, aminosulfonylamino$(C_2-C_{10})$alkylthio, $(C_1-C_5)$alkanesulfonylamino$(C_1-C_5)$alkyl, $(C_1-C_5)$alkanesulfonylamino$(C_1-C_5)$alkoxy, or $(C_1-C_5)$alkanesulfonylamino $(C_1-C_5)$alkylthio.

$R^3$ is H, halogen, $(C_1-C_3)$alkyl, hydroxyl, hydroxy$(C_1-C_3)$ alkyl, $(C_1-C_3)$alkanoylamino, $(C_1-C_3)$-alkoxy-carbonylamino, $(C_1-C_3)$alkylaminocarbonylamino, di$(C_1-C_3)$alkylaminocarbonylamino, $(C_1-C_3)$alkanesulfonylamino, $(C_1-C_3)$alkylaminosulfonylamino di$(C_1-C_3)$ alkylaminosulfonylamino, phenylamino, or heteroarylamino in which each phenylamino and heteroarylamino group is optionally substituted with 1 to 3 groups independently selected from:

fluorine, chlorine, cyano, $(C_1-C_3)$alkyl, halo$(C_1-C_3)$alkyl, $(C_1-C_3)$alkoxy, halo$(C_1-C_3)$alkoxy, $(C_1-C_3)$alkanesulfonyl, and $(C_1-C_3)$alkoxycarbonyl;

provided that when $R^3$ is hydroxyl, halogen, or optionally substituted phenylamino or heteroarylamino, $R^2$ is not $(C_2-C_{10})$alkoxy, $(C_4-C_{10})$cycloalkylalkoxy, halo$(C_2-C_{10})$alkoxy, $(C_2-C_{10})$alkylthio, halo$(C_2-C_{10})$alkylthio, $(C_2-C_{10})$alkanesulfinyl, halo$(C_2-C_{10})$alksulfinyl, $(C_2-C_{10})$alkanesulfonyl, halo$(C_2-C_{10})$-alksulfonyl, $(C_1-C_5)$alkoxy$(C_1-C_5)$alkoxy, hydroxy$(C_1-C_5)$alkoxy, $(C_1-C_5)$cycloalkoxy$(C_1-C_5)$alkoxy, halo$(C_1-C_5)$alkoxy$(C_1-C_5)$alkoxy, halo$(C_1-C_5)$cycloalkoxy $(C_1-C_5)$alkoxy, hydroxy$(C_1-C_5)$alkylthio, $(C_1-C_5)$alkoxy $(C_1-C_5)$alkylthio, $(C_1-C_5)$alkylthio$(C_1-C_5)$alkoxy, $(C_1-C_5)$ alkylthio$(C_1-C_5)$alkylthio, $(C_1-C_5)$alkoxy$(C_1-C_5)$ alkylsulfinyl, $(C_1-C_5)$alkylsulfinyl$(C_1-C_5)$alkoxy, $(C_1-C_5)$ alkylsulfinyl$(C_1-C_5)$alkyl-sulfinyl, $(C_1-C_5)$alkoxy$(C_1-C_5)$ alkylsulfonyl, $(C_1-C_5)$alkylsulfonyl$(C_1-C_5)$alkoxy, $(C_1-C_5)$ alkyl-sulfonyl$(C_1-C_5)$alkylsulfonyl, cyano$(C_2-C_{10})$alkoxy, cyano$(C_1-C_5)$alkoxy$(C_1-C_5)$alkoxy, cyano$(C_1-C_5)$alkoxy $(C_1-C_5)$alkylthio, aminocarbonylamino$(C_1-C_5)$alkoxy, aminocarbonylamino$(C_1-C_5)$alkylthio, $(C_1-C_5)$alkanoylamino $(C_1-C_5)$alkoxy, $(C_1-C_5)$alkanoylamino$(C_1-C_5)$alkylthio, aminosulfonylamino$(C_1-C_5)$alkoxy, aminosulfonylamino $(C_1-C_5)$alkylthio, $(C_1-C_5)$alkanesulfonyl-amino$(C_1-C_5)$ alkoxy, or $(C_1-C_5)$alkanesulfonylamino$(C_1-C_5)$alkylthio;

A is a saturated or unsaturated 4-, 5-, 6- or 7-membered ring wherein said ring is composed of carbon atoms, and 0-2 hetero atoms selected from 0, 1 or 2 nitrogen atoms, 0 or 1 oxygen atoms, and 0 or 1 sulfur atoms, said ring atoms being substituted with the appropriate number of hydrogen atoms; said ring being optionally substituted with up to four independently selected halogen atoms, $(C_1-C_6)$alkyl groups, halo $(C_1-C_6)$alkyl groups, and oxo groups;

Q and Y are attached to carbon or nitrogen atoms in ring A in a 1,3 relationship;

Q is a divalent radical selected from:

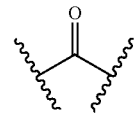

Q1

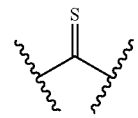

Q2

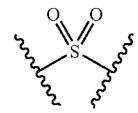

Q3

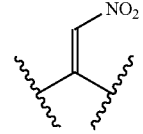

Q4

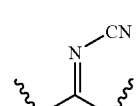

Q5

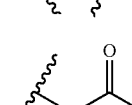

Q6

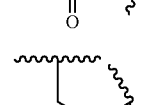

Q7

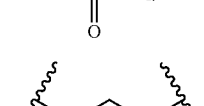

Q8

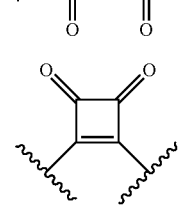

Q9

-continued

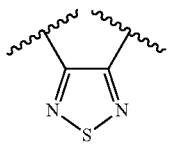
Q10

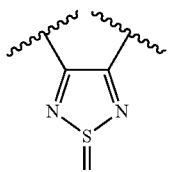
Q11

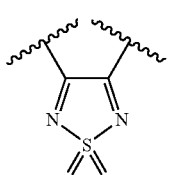
Q12 or

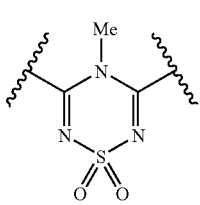
Q13 wherein A and N are attached to the truncated bonds $R^4$ is H, $(C_1-C_3)$alkyl, halo$(C_1-C_3)$alkyl; $(C_1-C_2)$alkoxy$(C_1-C_2)$alkyl, or cyano$(C_1-C_3)$alkyl;

L is 1) a linear $(C_2-C_3)$alkyl chain when G is OH, OR$^9$, NH$_2$, NHR$^9$, NHC(=NH)NH$_2$, or NHC(=NH)NHR$^9$ or 2) a linear $(C_1-C_2)$alkyl chain when G is C(=NH)NH$_2$ or C(=NH)NHR$^9$;

L is optionally substituted by 1-4 groups independently selected from $R^5$, $R^6$, $R^7$, and $R^8$;

one or more of the carbon atoms of L may be part of a 3-, 4-, 5-, 6- or 7-membered saturated ring composed of carbon atoms, and 0-2 heteroatoms selected from 0 or 1 nitrogen atoms, 0 or 1 oxygen atoms, and 0 or 1 sulfur atoms; said ring being optionally substituted with up to four groups selected from fluorine, $(C_1-C_3)$alkyl, halo$(C_1-C_3)$alkyl, $(C_3-C_6)$cycloalkyl, halo$(C_3-C_6)$cycloalkyl, $(C_4-C_7)$cycloalkylalkyl, halo$(C_4-C_7)$cycloalkylalkyl, and oxo;

$R^5$, $R^6$, $R^7$, and $R^8$ is each independently a) $(C_1-C_{10})$alkyl, $(C_4-C_{10})$cycloalkylalkyl, halo$(C_1-C_{10})$alkyl, halo$(C_4-C_{10})$cycloalkylalkyl, $(C_2-C_{10})$alkenyl, $(C_5-C_{10})$cycloalkylalkenyl, halo$(C_2-C_{10})$alkenyl, halo$(C_5-C_{10})$cycloalkylalkenyl, $(C_2-C_{10})$alkynyl, $(C_5-C_{10})$cycloalkylalkynyl, halo$(C_2-C_{10})$alkynyl, halo$(C_5-C_{10})$cycloalkylalkynyl, $(C_1-C_5)$alkoxy$(C_1-C_5)$alkyl, halo$(C_1-C_5)$alkoxy$(C_1-C_5)$alkyl, $(C_1-C_5)$alkylthio$(C_1-C_5)$alkyl, halo$(C_1-C_5)$alkylthio$(C_1-C_5)$alkyl, $(C_1-C_5)$alkanesulfinyl$(C_1-C_5)$alkyl, halo$(C_1-C_5)$alkanesulfinyl$(C_1-C_5)$alkyl, $(C_1-C_5)$alkanesulfonyl$(C_1-C_5)$alkyl, halo$(C_1-C_5)$alkanesulfonyl$(C_1-C_5)$alkyl, aminocarbonyl$(C_1-C_5)$alkyl, cyano$(C_1-C_5)$alkyl, saturated heterocyclyl, or saturated heterocyclyl$(C_1-C_3)$alkyl, or b) phenyl, naphthyl, heteroaryl, phenyl$(C_1-C_3)$alkyl, naphthyl$(C_1-C_3)$alkyl, or heteroaryl$(C_1-C_3)$alkyl each optionally substituted with 1 to 3 groups independently selected from:

fluorine, chlorine, cyano, $(C_1-C_3)$alkyl, halo$(C_1-C_3)$alkyl, $(C_1-C_3)$alkoxy, halo$(C_1-C_3)$alkoxy, $(C_1-C_3)$alkanesulfonyl, and $(C_1-C_3)$alkoxycarbonyl;

G is OH, OR$^9$, NH$_2$, NHR$^9$, NR$^9$R$^{10}$, C(=NH)NH$_2$, C(=NH)NHR$^9$, NHC(=NH)NH$_2$, or NHC(=NH)NHR$^9$;

$R^9$ is a) $(C_1-C_{10})$alkyl, $(C_4-C_{10})$cycloalkylalkyl, halo$(C_1-C_{10})$alkyl, halo$(C_4-C_{10})$cycloalkylalkyl, $(C_2-C_{10})$alkenyl, $(C_5-C_{10})$cycloalkylalkenyl, halo$(C_2-C_{10})$alkenyl, halo$(C_5-C_{10})$cycloalkylalkenyl, $(C_2-C_{10})$alkynyl, $(C_5-C_{10})$cycloalkylalkynyl, halo$(C_2-C_{10})$alkynyl, halo$(C_5-C_{10})$cycloalkylalkynyl, $(C_1-C_5)$alkoxy$(C_1-C_5)$alkyl, halo$(C_1-C_5)$alkoxy$(C_1-C_5)$alkyl, $(C_1-C_5)$alkylthio$(C_1-C_5)$alkyl, halo$(C_1-C_5)$-alkylthio$(C_1-C_5)$alkyl, $(C_1-C_5)$alkanesulfinyl$(C_1-C_5)$alkyl, halo$(C_1-C_5)$alkanesulfinyl$(C_1-C_5)$alkyl, $(C_1-C_5)$alkanesulfonyl$(C_1-C_5)$alkyl, halo$(C_1-C_5)$alkanesulfonyl$(C_1-C_5)$alkyl, aminocarbonyl$(C_1-C_5)$alkyl, $(C_1-C_6)$alkylaminocarbonyl$(C_1-C_6)$alkyl, di$(C_1-C_6)$alkylaminocarbonyl$(C_1-C_6)$alkyl cyano$(C_1-C_5)$alkyl, saturated heterocyclyl, saturated heterocyclyl$(C_1-C_3)$alkyl or b) phenyl, naphthyl, heteroaryl, phenyl$(C_1-C_3)$alkyl, naphthyl$(C_1-C_3)$alkyl, or heteroaryl$(C_1-C_3)$alkyl each optionally substituted by 1 to 3 groups independently selected from:

fluorine, chlorine, cyano, $(C_1-C_3)$alkyl, halo$(C_1-C_3)$alkyl, $(C_1-C_3)$alkoxy, halo$(C_1-C_3)$alkoxy, $(C_1-C_3)$alkanesulfonyl, and $(C_1-C_3)$alkoxycarbonyl; or b) $R^9$ is a saturated divalent radical composed of carbon atoms, 0 or 1 nitrogen atom, 0 or 1 oxygen atoms, and 0, or 1 sulfur atoms that is attached to any core carbon atom on the chain L to form a saturated 3-, 4-, 5-, 6- or 7-membered ring; said ring being optionally substituted with 1-4 groups selected from fluorine, $(C_1-C_3)$alkyl, halo$(C_1-C_3)$alkyl, $(C_3-C_6)$cycloalkyl, halo$(C_3-C_6)$cycloalkyl, $(C_4-C_7)$cycloalkylalkyl, halo$(C_4-C_7)$cycloalkylalkyl, and oxo;

$R^{10}$ is $(C_1-C_6)$alkyl or halo$(C_1-C_6)$alkyl;

and the enantiomers, diastereomers and salts thereof.

Another embodiment of the invention is a compound of Formula Ia, wherein $R^1$ is a) $(C_3-C_7)$cycloalkyl; or b) phenyl optionally substituted with 1 to 3 groups independently selected from:

1) fluorine, chlorine, bromine, cyano, nitro, $(C_1-C_6)$alkyl, $(C_3-C_6)$cycloalkyl, $(C_4-C_7)$cycloalkylalkyl, $(C_2-C_6)$alkenyl, $(C_5-C_7)$cycloalkylalkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, halo$(C_2-C_6)$alkenyl, halo$(C_3-C_6)$alkynyl, halo$(C_5-C_7)$cycloalkyl-lalkynyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, and $(C_1-C_6)$-alkanesulfonyl; or 2) phenyl, heteroaryl, phenoxy, heteroaryloxy, phenylthio, heteroarylthio, benzyl and heteroarylmethyl, each optionally substituted with 1 to 3 groups independently selected from:

fluorine, chlorine, cyano, $(C_1-C_3)$alkyl, halo$(C_1-C_3)$alkyl, $(C_1-C_3)$-alkoxy, and halo$(C_1-C_3)$alkoxy;

X and Y is each a single bond;

$R^2$ is $(C_2-C_{10})$alkyl, $(C_4-C_{10})$cycloalkylalkyl, halo$(C_2-C_{10})$alkyl, halo$(C_4-C_{10})$cycloalkylalkyl, $(C_2-C_{10})$alkoxy, $(C_4-C_{10})$cycloalkylalkoxy, halo$(C_2-C_{10})$alkoxy, $(C_2-C_{10})$alkylthio, halo($C_2$-$C_{10}$)alkylthio, hydroxy($C_2$-$C_{10}$)alkyl, ($C_1$-$C_5$)alkoxy($C_1$-$C_5$)alkyl, ($C_3$-$C_6$)cycloalkoxy($C_1$-$C_6$)alkyl, halo($C_1$-$C_5$)-alkoxy($C_1$-$C_5$)alkyl, halo($C_3$-$C_6$)cycloalkoxy($C_1$-$C_5$)alkyl, ($C_1$-$C_5$)alkylthio($C_1$-$C_5$)alkyl, halo($C_1$-$C_5$)alkylthio($C_1$-$C_5$)alkyl, ($C_1$-$C_5$)alkoxy($C_1$-$C_5$)alkoxy, hydroxy($C_2$-$C_{10}$)alkoxy, ($C_3$-$C_6$)cyclo-alkoxy($C_1$-$C_5$)alkoxy, halo($C_1$-$C_5$)alkoxy($C_1$-$C_5$)alkoxy, halo($C_3$-$C_6$)cycloalkoxy($C_1$-$C_5$)alkoxy, hydroxy($C_2$-$C_{10}$)alkylthio, ($C_2$-$C_5$)alkoxy($C_1$-$C_5$)alkylthio, ($C_1$-$C_5$)alkylthio($C_1$-$C_5$)alkoxy, ($C_1$-$C_5$)-alkylthio($C_1$-$C_5$)alkylthio;

$R^3$ is H, halogen, or OH;

provided that when $R^3$ is OH or halogen, $R^2$ is not ($C_2$-$C_{10}$)alkoxy, ($C_4$-$C_{10}$)cycloalkylalkoxy, halo($C_2$-$C_{10}$)alkoxy, ($C_2$-$C_{10}$)alkylthio, halo($C_2$-$C_{10}$)alkylthio, ($C_1$-$C_5$)alkoxy($C_1$-$C_5$)alkyl, hydroxy($C_2$-$C_{10}$)alkoxy, ($C_3$-$C_6$)cycloalkoxy($C_1$-$C_5$)alkoxy, halo($C_1$-$C_5$)alkoxy($C_1$-$C_5$)alkoxy, halo($C_3$-$C_6$)cycloalkoxy($C_1$-$C_5$)alkoxy, hydroxy($C_2$-$C_{10}$)alkylthio, ($C_2$-$C_5$)alkoxy($C_1$-$C_5$)alkylthio, ($C_1$-$C_5$)alkylthio($C_1$-$C_5$)alkoxy, or ($C_1$-$C_5$)alkylthio($C_1$-$C_5$)alkylthio;

A is a saturated 5-, 6-, or 7-membered ring wherein said ring is composed of carbon atoms and 0-2 heteroatoms selected from 0 or 1 nitrogen atoms, 0 or 1 oxygen atoms, and 0 or 1 sulfur atoms; said ring atoms being substituted with the appropriate number of hydrogen atoms; said ring being optionally substituted with up to four independently selected fluorine atoms, ($C_1$-$C_3$)alkyl groups, halo($C_1$-$C_3$)alkyl groups, or oxo groups;

the substituents Q and Y are attached in a 1,3 relationship;

Q is Q1, Q2, Q4, Q5, Q9, or Q10

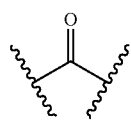
Q1

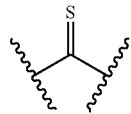
Q2

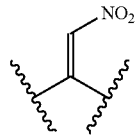
Q4

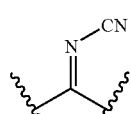
Q5

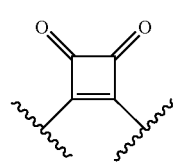
Q9

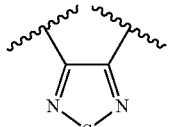
Q10 wherein A and N are attached to the truncated bonds $R^4$ is H or ($C_1$-$C_3$)alkyl;

L is a $C_2$ alkyl chain in which one hydrogen atom is optionally replaced with a group selected from $R^5$ and a second hydrogen atom is optionally replaced with a group selected from $R^6$;

$R^5$ is a) ($C_1$-$C_{10}$)alkyl, ($C_4$-$C_{10}$)cycloalkylalkyl, halo($C_1$-$C_{10}$)alkyl, halo($C_4$-$C_{10}$)cycloalkylalkyl, ($C_1$-$C_5$)alkoxy($C_1$-$C_5$)alkyl, halo($C_1$-$C_5$)alkoxy($C_1$-$C_5$)alkyl, ($C_1$-$C_5$)alkylthio($C_1$-$C_5$)alkyl, halo($C_1$-$C_5$)alkylthio($C_1$-$C_5$)alkyl, or saturated heterocyclyl($C_1$-$C_3$)alkyl; or b) phenyl($C_1$-$C_2$)alkyl or heteroaryl($C_1$-$C_2$)alkyl each optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, and halo($C_1$-$C_3$)alkoxy;

$R^6$ is absent or is ($C_1$-$C_6$)alkyl or ($C_1$-$C_3$)alkoxy($C_1$-$C_3$)alkyl;

$R^7$ and $R^8$ are absent;

G is OH, $NH_2$, $NHR^9$, or $NR^9R^{10}$;

$R^9$ is a) ($C_1$-$C_6$)alkyl, halo($C_1$-$C_6$)alkyl, ($C_4$-$C_{10}$)cycloalkylalkyl, ($C_1$-$C_5$)alkoxy($C_1$-$C_5$)alkyl, aminocarbonyl($C_1$-$C_5$)alkyl, ($C_1$-$C_6$)alkylaminocarbonyl($C_1$-$C_6$)alkyl, or di($C_1$-$C_6$)alkyl-aminocarbonyl($C_1$-$C_6$)alkyl; or b) phenyl($C_1$-$C_2$)alkyl optionally substituted with 1 to 3 groups independently selected from:

fluorine, chlorine, cyano, ($C_1$-$C_3$)alkyl, halo($C_1$-$C_3$)alkyl, ($C_1$-$C_3$)alkoxy, and halo($C_1$-$C_3$)alkoxy;

or c) is attached to L and is —$(CH_2)_2$—, —$(CH_2)_3$—, or —$(CH_2)_4$— optionally substituted with 1 or 2 groups independently selected from fluorine, ($C_1$-$C_3$)alkyl, and halo($C_1$-$C_3$)alkyl;

$R^{10}$ is ($C_1$-$C_3$)alkyl or halo($C_1$-$C_3$)alkyl;

and the enantiomers, diastereomers and salts thereof.

Another embodiment of the invention is a compound of Formula Ia, wherein $R^1$ is a) cyclohexyl; or b) phenyl optionally substituted with 1 to 3 substituents independently selected from:

fluorine, chlorine, cyano, methyl, ethyl, isopropyl, trifluoromethyl, allyl, cyclopropylethynyl, phenyl and phenoxy, wherein the phenyl and phenoxy groups are optionally substituted with 1 to 3 substituents independently selected from fluorine, chlorine, cyano, methyl, and trifluoromethyl;

X and Y is each a single bond;

$R^2$ is butyl, hexyl, 3,3,3-trifluoropropyl, 3-(cyclopropyl)propyl, 4-(cyclopropyl)butyl, 3-ethoxypropyl, 4-methoxybutyl, 4-ethoxybutyl, 3-methoxypropoxy, 3-ethoxypropoxy, 3-propoxypropoxy, or 2-cyclopropylethoxy;

$R^3$ is H, F, or OH;

provided that when $R^3$ is F or OH, $R^2$ is not 3-methoxypropoxy, 3-ethoxypropoxy, 3-propoxypropoxy, or 2-cyclopropylethoxy;

A is 2,4-disubstituted morpholine with $R^1XCR^2R^3Y$ attached at the 2-position and Q attached at the 4-position, 1,3-disubstituted piperidine with $R^1XCR^2R^3Y$ attached at the 3-position and Q attached at the 1-position, 1,3-disubstituted-3-methylpiperidine with $R^1XCR^2R^3Y$ attached at the 3-position and Q attached at the 1-position, 1,3-disubstituted benzene, or 1,3-disubstituted cyclohexane;

Q is Q1, Q4, Q9, or Q10

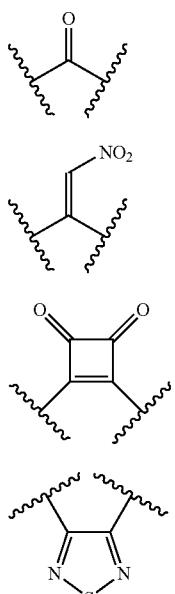

wherein A and N are attached to the truncated bonds $R^4$ is H or methyl;

L is a $C_2$ alkyl chain in which one hydrogen atom is optionally replaced with a group selected from $R^5$;

$R^5$ is methyl, isobutyl, 2-(trifluoromethyl)propyl, cyclopentylmethyl, cyclohexylmethyl, 4,4-difluorocyclohexylmethyl, tert-butoxymethyl, or benzyl;

$R^6$ is absent or is methyl;

$R^7$ and $R^8$ are absent;

G is $NH_2$, $NHR^9$, or $NR^9R^{10}$;

$R^9$ is methyl, ethyl, propyl, butyl, isobutyl, pentyl, isopentyl, aminocarbonylmethyl, or —$(CH_2)_3$—;

$R^{10}$ is methyl;

and the enantiomers, diastereomers, and salts thereof.

Another embodiment of the invention is a compound of Formula IId:

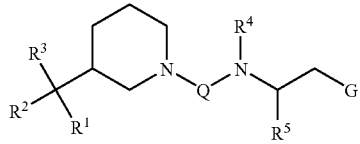

wherein $R^1$ is a) $(C_3\text{-}C_7)$cycloalkyl; or b) phenyl optionally substituted with 1 to 3 groups independently selected from:

1) fluorine, chlorine, bromine, cyano, nitro, $(C_1\text{-}C_6)$alkyl, $(C_3\text{-}C_6)$cycloalkyl, $(C_4\text{-}C_7)$cycloalkylalkyl, $(C_2\text{-}C_6)$alkenyl, $(C_5\text{-}C_7)$cycloalkylalkenyl, $(C_2\text{-}C_6)$alkynyl, $(C_3\text{-}C_6)$cycloalkyl$(C_2\text{-}C_4)$alkynyl, halo$(C_1\text{-}C_6)$alkyl, halo$(C_3\text{-}C_6)$cycloalkyl, halo$(C_4\text{-}C_7)$cycloalkylalkyl, halo$(C_2\text{-}C_6)$alkenyl, halo$(C_3\text{-}C_6)$alkynyl, halo$(C_5\text{-}C_7)$cycloalkylalkynyl, $(C_1\text{-}C_6)$alkoxy, $(C_3\text{-}C_6)$cycloalkoxy, $(C_4\text{-}C_7)$cycloalkylalkoxy, halo$(C_1\text{-}C_6)$alkoxy, halo$(C_3\text{-}C_6)$cycloalkoxy, halo$(C_4\text{-}C_7)$cycloalkylalkoxy and $(C_1\text{-}C_6)$alkanesulfonyl; or 2) phenyl, heteroaryl, phenoxy, heteroaryloxy, phenylthio, heteroarylthio, benzyl, and heteroarylmethyl, each optionally substituted with 1 to 3 groups independently selected from:

fluorine, chlorine, cyano, $(C_1\text{-}C_3)$alkyl, halo$(C_1\text{-}C_3)$alkyl, $(C_1\text{-}C_3)$-alkoxy, and halo$(C_1\text{-}C_3)$alkoxy;

$R^2$ is $(C_2\text{-}C_{10})$alkyl, $(C_4\text{-}C_{10})$cycloalkylalkyl, halo$(C_2\text{-}C_{10})$alkyl, halo$(C_4\text{-}C_{10})$cycloalkylalkyl, $(C_2\text{-}C_{10})$alkoxy, $(C_4\text{-}C_{10})$cycloalkylalkoxy, halo$(C_2\text{-}C_{10})$alkoxy, $(C_2\text{-}C_{10})$alkylthio, halo$(C_2\text{-}C_{10})$alkylthio, hydroxy$(C_2\text{-}C_{10})$alkyl, $(C_1\text{-}C_5)$alkoxy$(C_1\text{-}C_5)$alkyl, $(C_3\text{-}C_6)$cycloalkoxy$(C_1\text{-}C_6)$alkyl, halo$(C_1\text{-}C_5)$alkoxy$(C_1\text{-}C_5)$alkyl, halo$(C_3\text{-}C_6)$cycloalkoxy$(C_1\text{-}C_5)$alkyl, $(C_1\text{-}C_5)$alkylthio$(C_1\text{-}C_5)$alkyl, halo$(C_1\text{-}C_5)$alkylthio$(C_1\text{-}C_5)$alkyl, $(C_1\text{-}C_5)$alkoxy$(C_1\text{-}C_5)$alkoxy, hydroxy$(C_2\text{-}C_{10})$alkoxy, $(C_3\text{-}C_6)$cycloalkoxy-$(C_1\text{-}C_5)$alkoxy, halo$(C_1\text{-}C_5)$alkoxy$(C_1\text{-}C_5)$alkoxy, halo$(C_3\text{-}C_6)$cycloalkoxy$(C_1\text{-}C_5)$alkoxy, hydroxy$(C_2\text{-}C_{10})$alkylthio, $(C_2\text{-}C_5)$alkoxy$(C_1\text{-}C_5)$alkylthio, $(C_1\text{-}C_5)$alkylthio$(C_1\text{-}C_5)$alkoxy, or $(C_1\text{-}C_5)$-alkylthio$(C_1\text{-}C_5)$alkylthio;

$R^3$ is H, F, or OH;

provided that when $R^3$ is OH or F, $R^2$ is not $(C_2\text{-}C_{10})$alkoxy, $(C_4\text{-}C_{10})$cycloalkylalkoxy, halo$(C_2\text{-}C_{10})$alkoxy, $(C_2\text{-}C_{10})$alkylthio, halo$(C_2\text{-}C_{10})$alkylthio, $(C_1\text{-}C_5)$alkoxy$(C_1\text{-}C_5)$alkoxy, hydroxy$(C_2\text{-}C_{10})$alkoxy, $(C_3\text{-}C_6)$cycloalkoxy$(C_1\text{-}C_5)$alkoxy, halo$(C_1\text{-}C_5)$alkoxy$(C_1\text{-}C_5)$alkoxy, halo$(C_3\text{-}C_6)$-cycloalkoxy$(C_1\text{-}C_5)$alkoxy, hydroxy$(C_2\text{-}C_{10})$alkylthio, $(C_2\text{-}C_5)$alkoxy$(C_1\text{-}C_5)$alkylthio, $(C_1\text{-}C_5)$alkyl-thio$(C_1\text{-}C_5)$alkoxy, or $(C_1\text{-}C_5)$alkylthio$(C_1\text{-}C_5)$alkylthio;

Q is Q1, Q2, Q4, Q5, Q9, or Q10

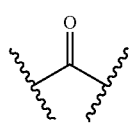

Q1

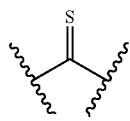

Q2

-continued

[Structure: NO2 group]

[Structure: CN group]

[Structure: cyclobutenedione]

[Structure: thiadiazole]
wherein N and N are attached to the truncated bonds

R⁴ is H or (C₁-C₃)alkyl;

R⁵ is a) (C₁-C₁₀)alkyl, (C₄-C₁₀)cycloalkylalkyl, halo(C₁-C₁₀)alkyl, halo(C₄-C₁₀)cycloalkylalkyl, (C₁-C₅)alkoxy(C₁-C₅)alkyl, halo(C₁-C₅)alkoxy(C₁-C₅)alkyl, (C₁-C₅)alkylthio(C₁-C₅)alkyl, halo(C₁-C₅)-alkylthio(C₁-C₅)alkyl; or b) phenyl(C₁-C₂)alkyl, or heteroaryl(C₁-C₂)alkyl each optionally substituted with 1 to 3 groups independently selected from fluorine, chlorine, cyano, (C₁-C₃)alkyl, halo(C₁-C₃)alkyl, (C₁-C₃)alkoxy, and halo(C₁-C₃)alkoxy;

G is OH, NH₂, NHR⁹, or NR⁹R¹⁰;

R⁹ is a) (C₁-C₆)alkyl, halo(C₁-C₆)alkyl, (C₄-C₁₀)cycloalkylalkyl, (C₁-C₅)alkoxy(C₁-C₅)alkyl, or aminocarbonyl(C₁-C₆)alkyl; b) phenyl(C₁-C₂)alkyl optionally substituted with 1 to 3 groups independently selected from:

fluorine, chlorine, cyano, (C₁-C₃)alkyl, halo(C₁-C₃)alkyl, (C₁-C₃)alkoxy, and halo(C₁-C₃)alkoxy; or c) R⁵ and R⁹ together are —CH₂—, —(CH₂)₂—, —(CH₂)₃— or —(CH₂)₄—, optionally substituted with 1 or 2 groups independently selected from fluorine, (C₁-C₃)alkyl and halo(C₁-C₃)alkyl, and form a 4-, 5-, 6-, or 7-membered ring with the atoms through which they are connected;

R¹⁰ is (C₁-C₃)alkyl or halo(C₁-C₃)alkyl; and salts thereof.

Another embodiment of the invention is a compound of Formula IIe with the stereochemical configuration shown:

[Structure IIe]

wherein

R¹ is a) (C₃-C₇)cycloalkyl; or b) phenyl optionally substituted with 1 to 3 groups independently selected from:

1) fluorine, chlorine, bromine, cyano, nitro, (C₁-C₆)alkyl, (C₃-C₆)cycloalkyl, (C₄-C₇)cycloalkylalkyl, (C₂-C₆)alkenyl, (C₅-C₇)cycloalkylalkenyl, (C₂-C₈)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, halo(C₂-C₆)alkenyl, halo(C₃-C₆)alkynyl, halo(C₅-C₇)cycloalkylalkynyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy and (C₁-C₆)alkanesulfonyl; or 2) phenyl, heteroaryl, phenoxy, heteroaryloxy, phenylthio, heteroarylthio, benzyl, and heteroarylmethyl, each optionally substituted with 1 to 3 groups independently selected from:

fluorine, chlorine, cyano, (C₁-C₃)alkyl, halo(C₁-C₃)alkyl, (C₁-C₃)-alkoxy, and halo(C₁-C₃)alkoxy;

R² is (C₂-C₁₀)alkyl, (C₄-C₁₀)cycloalkylalkyl, halo(C₂-C₁₀)alkyl, halo(C₄-C₁₀)cycloalkylalkyl, (C₂-C₁₀)alkoxy, (C₄-C₁₀)cycloalkylalkoxy, halo(C₂-C₁₀)alkoxy, (C₂-C₁₀)alkylthio, halo(C₂-C₁₀)alkylthio, hydroxy(C₂-C₁₀)alkyl, (C₁-C₅)alkoxy(C₁-C₅)alkyl, (C₃-C₆)cycloalkoxy(C₁-C₆)alkyl, halo(C₁-C₆)alkoxy(C₁-C₅)alkyl, halo(C₃-C₆)cycloalkoxy(C₁-C₅)alkyl, (C₁-C₅)alkylthio(C₁-C₅)alkyl, halo(C₁-C₅)alkylthio(C₁-C₅)alkyl, (C₁-C₅)alkoxy(C₁-C₅)alkoxy, hydroxy(C₂-C₁₀)alkoxy, (C₃-C₆)cycloalkoxy-(C₁-C₅)alkoxy, halo(C₁-C₅)alkoxy(C₁-C₅)alkoxy, halo(C₃-C₆)cycloalkoxy(C₁-C₅)alkoxy, hydroxy(C₂-C₁₀)alkylthio, (C₂-C₅)alkoxy(C₁-C₅)alkylthio, (C₁-C₅)alkylthio(C₁-C₅)alkoxy, or (C₁-C₅)-alkylthio(C₁-C₅)alkylthio;

R³ is H, F, or OH;

provided that when R³ is OH or F, R² is not (C₂-C₁₀)alkoxy, (C₄-C₁₀)cycloalkylalkoxy, halo(C₂-C₁₀)alkoxy, (C₂-C₁₀)alkylthio, halo(C₂-C₁₀)alkylthio, (C₁-C₅)alkoxy(C₁-C₅)alkoxy, hydroxy(C₂-C₁₀)alkoxy, (C₃-C₆)cycloalkoxy(C₁-C₅)alkoxy, halo(C₁-C₅)alkoxy(C₁-C₅)alkoxy, halo(C₃-C₆)-cycloalkoxy(C₁-C₅)alkoxy, hydroxy(C₂-C₁₀)alkylthio, (C₂-C₅)alkoxy(C₁-C₅)alkylthio, (C₁-C₅)alkyl-thio(C₁-C₅)alkoxy, or (C₁-C₅)alkylthio(C₁-C₅)alkylthio;

Q is Q1, Q2, Q4, Q5, Q9, or Q10

[Structure Q1: C=O]

[Structure Q2: C=S]

-continued

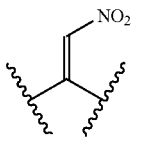
Q4

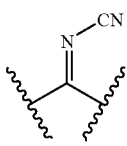
Q5

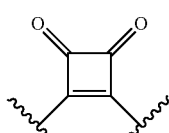
Q9

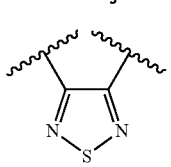
Q10 wherein N and N are attached to the truncated bonds $R^4$ is H or $(C_1-C_3)$alkyl;

$R^5$ is a) $(C_1-C_{10})$alkyl, $(C_4-C_{10})$cycloalkylalkyl, halo$(C_1-C_{10})$alkyl, halo$(C_4-C_{10})$cycloalkylalkyl, $(C_1-C_5)$alkoxy$(C_1-C_5)$alkyl, halo$(C_1-C_5)$alkoxy$(C_1-C_5)$alkyl, $(C_1-C_5)$alkylthio$(C_1-C_5)$alkyl, halo$(C_1-C_5)$-alkylthio$(C_1-C_5)$alkyl; or b) phenyl$(C_1-C_2)$alkyl, or heteroaryl$(C_1-C_2)$alkyl each optionally substituted with 1 to 3 groups independently selected from fluorine, chlorine, cyano, $(C_1-C_3)$alkyl, halo$(C_1-C_3)$alkyl, $(C_1-C_3)$alkoxy, and halo$(C_1-C_3)$alkoxy;

G is OH, $NH_2$, $NHR^9$, or $NR^9R^{10}$;

$R^9$ is a) $(C_1-C_6)$alkyl, halo$(C_1-C_6)$alkyl, $(C_4-C_{10})$cycloalkylalkyl, $(C_1-C_5)$alkoxy$(C_1-C_5)$alkyl, or aminocarbonyl$(C_1-C_6)$alkyl; b) phenyl$(C_1-C_2)$alkyl optionally substituted with 1 to 3 groups independently selected from:

fluorine, chlorine, cyano, $(C_1-C_3)$alkyl, halo$(C_1-C_3)$alkyl, $(C_1-C_3)$alkoxy, and halo$(C_1-C_3)$alkoxy; or c) $R^5$ and $R^9$ together are —$CH_2$—, —$(CH_2)_2$—, —$(CH_2)_3$— or —$(CH_2)_4$—, optionally substituted with 1 or 2 groups independently selected from fluorine, $(C_1-C_3)$alkyl and halo$(C_1-C_3)$alkyl, and form a 4-, 5-, 6-, or 7-membered ring with the atoms through which they are connected;

$R^{10}$ is $(C_1-C_3)$alkyl or halo$(C_1-C_3)$alkyl; and salts thereof.

Another embodiment of the invention is a compound of Formula IIe, wherein:

$R^1$ is a) cyclohexyl; or b) phenyl optionally substituted with 1 to 3 substituents independently selected from:

fluorine, chlorine, cyano, methyl, ethyl, isopropyl, trifluoromethyl, allyl, cyclopropylethynyl, phenyl, and phenoxy, wherein the phenyl and phenoxy groups are optionally substituted with 1 to 3 substituents independently selected from fluorine, chlorine, cyano, methyl, and trifluoromethyl;

$R^2$ is butyl, hexyl, 3,3,3-trifluoropropyl, 3-(cyclopropyl)propyl, 4-(cyclopropyl)butyl, 3-ethoxypropyl, 4-methoxybutyl, 4-ethoxybutyl, 3-methoxypropoxy, 3-ethoxypropoxy, 3-propoxypropoxy, or 2-cyclopropylethoxy;

$R^3$ is H, F, or OH;

provided that when $R^3$ is F or OH, $R^2$ is not 3-methoxypropoxy, 3-ethoxypropoxy, 3-propoxypropoxy, or 2-cyclopropylethoxy;

Q is Q1, Q4, Q9, or Q10

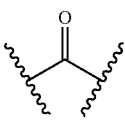
Q1

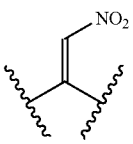
Q4

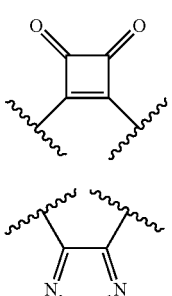
Q9

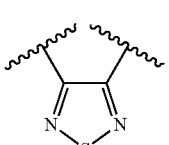
Q10 wherein N and N are attached to the truncated bonds $R^4$ is H or methyl;

$R^5$ is methyl, isobutyl, 2-(trifluoromethyl)propyl, cyclopentylmethyl, cyclohexylmethyl, 4,4-difluorocyclohexylmethyl, tert-butoxymethyl, or benzyl;

G is $NH_2$, $NHR^9$, or $NR^9R^{10}$;

$R^9$ is methyl, ethyl, propyl, butyl, isobutyl, pentyl or isopentyl, or aminocarbonylmethyl; or $R^9$ together with $R^5$ is —$(CH_2)_3$—;

$R^{10}$ is methyl;

and the salts thereof.

In a preferred embodiment, the compound is represented by Formula I; $R^1$ is as defined in the second embodiment, third or fourth embodiment and the remainder of the variables are as defined in the first embodiment.

In another preferred embodiment, the compound is represented by Formula I; $R^2$ is as defined in the second embodiment, third or fourth embodiment and the remainder of the variables are as defined in the first embodiment.

In another preferred embodiment, the compound is represented by Formula I; $R^3$ is as defined in the second embodiment, third or fourth embodiment and the remainder of the variables are as defined in the first embodiment.

In another preferred embodiment, the compound is represented by Formula I; $R^4$ is as defined in the second embodiment, third or fourth embodiment and the remainder of the variables are as defined in the first embodiment.

In another preferred embodiment, the compound is represented by Formula I; $R^5$ is as defined in the second embodiment, third or fourth embodiment and the remainder of the variables are as defined in the first embodiment.

In another preferred embodiment, the compound is represented by Formula I; $R^5$ is as defined in the second embodiment, third or fourth embodiment and the remainder of the variables are as defined in the first embodiment.

In another preferred embodiment, the compound is represented by Formula I; $R^6$ is as defined in the second embodiment, third or fourth embodiment and the remainder of the variables are as defined in the first embodiment.

In another preferred embodiment, the compound is represented by Formula I; $R^7$ and $R^8$ are as defined in the second embodiment, third or fourth embodiment and the remainder of the variables are as defined in the first embodiment.

In another preferred embodiment, the compound is represented by Formula I; $R^9$ is as defined in the second embodiment, third or fourth embodiment and the remainder of the variables are as defined in the first embodiment.

In another preferred embodiment, the compound is represented by Formula I; $R^{10}$ is as defined in the second embodiment, third or fourth embodiment and the remainder of the variables are as defined in the first embodiment.

In another preferred embodiment, the compound is represented by Formula I; A is as defined in the second embodiment, third or fourth embodiment and the remainder of the variables are as defined in the first embodiment.

In another preferred embodiment, the compound is represented by Formula I; X and Y are as defined in the second embodiment, third or fourth embodiment and the remainder of the variables are as defined in the first embodiment.

In another preferred embodiment, the compound is represented by Formula I; Q is as defined in the second embodiment, third or fourth embodiment and the remainder of the variables are as defined in the first embodiment.

In another preferred embodiment, the compound is represented by Formula II; $R^1$ is as defined in the fifth, sixth, seventh, eight, ninth or tenth embodiment and the remainder of the variables are as defined in the fifth embodiment.

In another preferred embodiment, the compound is represented by Formula II; $R^2$ is as defined in the fifth, sixth, seventh, eight, ninth or tenth embodiment and the remainder of the variables are as defined in the fifth embodiment.

In another preferred embodiment, the compound is represented by Formula II; G is as defined in the fifth, sixth, seventh, eight, ninth or tenth embodiment and the remainder of the variables are as defined in the fifth embodiment.

In a preferred embodiment, the compound is represented by Formula II; $R^1$ is as defined in the fifth, sixth, seventh, eight, ninth or tenth embodiment and the remainder of the variables are as defined in the fifth embodiment.

In another preferred embodiment, the compound is represented by Formula II; $R^2$ is as defined in the fifth, sixth, seventh, eight, ninth or tenth embodiment and the remainder of the variables are as defined in the fifth embodiment.

In another preferred embodiment, the compound is represented by Formula II; $R^3$ is as defined in the fifth, sixth, seventh, eight, ninth or tenth embodiment and the remainder of the variables are as defined in the fifth embodiment.

In another preferred embodiment, the compound is represented by Formula II; $R^4$ is as defined in the fifth, sixth, seventh, eight, ninth or tenth embodiment and the remainder of the variables are as defined in the fifth embodiment.

In another preferred embodiment, the compound is represented by Formula II; $R^5$ is as defined in the fifth, sixth, seventh, eight, ninth or tenth embodiment and the remainder of the variables are as defined in the fifth embodiment.

In another preferred embodiment, the compound is represented by Formula II; $R^5$ is as defined in the fifth, sixth, seventh, eight, ninth or tenth embodiment and the remainder of the variables are as defined in the fifth embodiment.

In another preferred embodiment, the compound is represented by Formula II; $R^6$ is as defined in the fifth, sixth, seventh, eight, ninth or tenth embodiment and the remainder of the variables are as defined in the fifth embodiment.

In another preferred embodiment, the compound is represented by Formula II; $R^7$ and $R^8$ are as defined in the fifth, sixth, seventh, eight, ninth or tenth embodiment and the remainder of the variables are as defined in the fifth embodiment.

In another preferred embodiment, the compound is represented by Formula II; $R^9$ is as defined in the fifth, sixth, seventh, eight, ninth or tenth embodiment and the remainder of the variables are as defined in the fifth embodiment.

In another preferred embodiment, the compound is represented by Formula II; $R^{10}$ is as defined in the fifth, sixth, seventh, eight, ninth or tenth embodiment and the remainder of the variables are as defined in the fifth embodiment.

In another preferred embodiment, the compound is represented by Formula II; A is as defined in the fifth, sixth, seventh, eight, ninth or tenth embodiment and the remainder of the variables are as defined in the fifth embodiment.

In another preferred embodiment, the compound is represented by Formula II; X and Y are as defined in the fifth, sixth, seventh, eight, ninth or tenth embodiment and the remainder of the variables are as defined in the fifth embodiment.

In another preferred embodiment, the compound is represented by Formula II; Q is as defined in the fifth, sixth, seventh, eight, ninth or tenth embodiment and the remainder of the variables are as defined in the fifth embodiment.

In another preferred embodiment, the compound is represented by Formula II; $R^2$ is as defined in the fifth, sixth, seventh, eight, ninth or tenth embodiment and the remainder of the variables are as defined in the fifth embodiment.

In another preferred embodiment, the compound is represented by Formula II; G is as defined in the fifth, sixth, seventh, eight, ninth or tenth embodiment and the remainder of the variables are as defined in the fifth embodiment.

In another preferred embodiment, the compound is represented by Formula II; $R^1$ is as defined in the fifth, sixth, seventh, eight, ninth or tenth embodiment and the remainder of the variables are as defined in the fifth embodiment.

In another preferred embodiment, the compound is represented by Formula II; $R^2$ is as defined in the fifth, sixth, seventh, eight, ninth or tenth embodiment and the remainder of the variables are as defined in the fifth embodiment.

In another preferred embodiment, the compound is represented by Formula II; G is as defined in the fifth, sixth, seventh, eight, ninth or tenth embodiment and the remainder of the variables are as defined in the fifth embodiment.

In a preferred embodiment, the compound is represented by Formula IIa; $R^1$ is as defined in the fifth, sixth, seventh, eight, ninth or tenth embodiment and the remainder of the variables are as defined in the sixth embodiment.

In another preferred embodiment, the compound is represented by Formula IIa; $R^2$ is as defined in the fifth, sixth, seventh, eight, ninth or tenth embodiment and the remainder of the variables are as defined in the sixth embodiment.

In another preferred embodiment, the compound is represented by Formula IIa; $R^3$ is as defined in the fifth, sixth, seventh, eight, ninth or tenth embodiment and the remainder of the variables are as defined in the sixth embodiment.

In another preferred embodiment, the compound is represented by Formula IIa; $R^4$ is as defined in the fifth, sixth, seventh, eight, ninth or tenth embodiment and the remainder of the variables are as defined in the sixth embodiment.

In another preferred embodiment, the compound is represented by Formula IIa; $R^5$ is as defined in the fifth, sixth, seventh, eight, ninth or tenth embodiment and the remainder of the variables are as defined in the sixth embodiment.

In another preferred embodiment, the compound is represented by Formula IIa; $R^5$ is as defined in the fifth, sixth, seventh, eight, ninth or tenth embodiment and the remainder of the variables are as defined in the sixth embodiment.

In another preferred embodiment, the compound is represented by Formula IIa; $R^6$ is as defined in the fifth, sixth, seventh, eight, ninth or tenth embodiment and the remainder of the variables are as defined in the sixth embodiment.

In another preferred embodiment, the compound is represented by Formula IIa; $R^7$ and $R^8$ are as defined in the fifth, sixth, seventh, eight, ninth or tenth embodiment and the remainder of the variables are as defined in the sixth embodiment.

In another preferred embodiment, the compound is represented by Formula IIa; $R^9$ is as defined in the fifth, sixth, seventh, eight, ninth or tenth embodiment and the remainder of the variables are as defined in the sixth embodiment.

In another preferred embodiment, the compound is represented by Formula IIa; $R^{10}$ is as defined in the fifth, sixth, seventh, eight, ninth or tenth embodiment and the remainder of the variables are as defined in the sixth embodiment.

In another preferred embodiment, the compound is represented by Formula IIa; A is as defined in the fifth, sixth, seventh, eight, ninth or tenth embodiment and the remainder of the variables are as defined in the sixth embodiment.

In another preferred embodiment, the compound is represented by Formula IIa; X and Y are as defined in the fifth, sixth, seventh, eight, ninth or tenth embodiment and the remainder of the variables are as defined in the sixth embodiment.

In another preferred embodiment, the compound is represented by Formula IIa; Q is as defined in the fifth, sixth, seventh, eight, ninth or tenth embodiment and the remainder of the variables are as defined in the sixth embodiment.

In another preferred embodiment, the compound is represented by Formula IIa; $R^2$ is as defined in the fifth, sixth, seventh, eight, ninth or tenth embodiment and the remainder of the variables are as defined in the sixth embodiment.

In another preferred embodiment, the compound is represented by Formula IIa; G is as defined in the fifth, sixth, seventh, eight, ninth or tenth embodiment and the remainder of the variables are as defined in the sixth embodiment.

In another preferred embodiment, the compound is represented by Formula IIb; $R^1$ is as defined in the fifth, sixth, seventh, eight, ninth or tenth embodiment and the remainder of the variables are as defined in the ninth embodiment.

In another preferred embodiment, the compound is represented by Formula IIb; $R^2$ is as defined in the fifth, sixth, seventh, eight, ninth or tenth embodiment and the remainder of the variables are as defined in the ninth embodiment.

In another preferred embodiment, the compound is represented by Formula IIb; G is as defined in the fifth, sixth, seventh, eight, ninth or tenth embodiment and the remainder of the variables are as defined in the ninth embodiment.

In a preferred embodiment, the compound is represented by Formula IIb; $R^1$ is as defined in the fifth, sixth, seventh, eight, ninth or tenth embodiment and the remainder of the variables are as defined in the ninth embodiment.

In another preferred embodiment, the compound is represented by Formula IIb; $R^2$ is as defined in the fifth, sixth, seventh, eight, ninth or tenth embodiment and the remainder of the variables are as defined in the ninth embodiment.

In another preferred embodiment, the compound is represented by Formula IIb; $R^3$ is as defined in the fifth, sixth, seventh, eight, ninth or tenth embodiment and the remainder of the variables are as defined in the ninth embodiment.

In another preferred embodiment, the compound is represented by Formula IIb; $R^4$ is as defined in the fifth, sixth, seventh, eight, ninth or tenth embodiment and the remainder of the variables are as defined in the ninth embodiment.

In another preferred embodiment, the compound is represented by Formula IIb; $R^5$ is as defined in the fifth, sixth, seventh, eight, ninth or tenth embodiment and the remainder of the variables are as defined in the ninth embodiment.

In another preferred embodiment, the compound is represented by Formula IIb; $R^5$ is as defined in the fifth, sixth, seventh, eight, ninth or tenth embodiment and the remainder of the variables are as defined in the ninth embodiment.

In another preferred embodiment, the compound is represented by Formula IIb; $R^6$ is as defined in the fifth, sixth, seventh, eight, ninth or tenth embodiment and the remainder of the variables are as defined in the ninth embodiment.

In another preferred embodiment, the compound is represented by Formula IIb; $R^7$ and $R^8$ are as defined in the fifth, sixth, seventh, eight, ninth or tenth embodiment and the remainder of the variables are as defined in the ninth embodiment.

In another preferred embodiment, the compound is represented by Formula IIb; $R^9$ is as defined in the fifth, sixth, seventh, eight, ninth or tenth embodiment and the remainder of the variables are as defined in the ninth embodiment.

In another preferred embodiment, the compound is represented by Formula IIb; $R^{10}$ is as defined in the fifth, sixth, seventh, eight, ninth or tenth embodiment and the remainder of the variables are as defined in the ninth embodiment.

In another preferred embodiment, the compound is represented by Formula IIb; A is as defined in the fifth, sixth, seventh, eight, ninth or tenth embodiment and the remainder of the variables are as defined in the ninth embodiment.

In another preferred embodiment, the compound is represented by Formula IIb; X and Y are as defined in the fifth, sixth, seventh, eight, ninth or tenth embodiment and the remainder of the variables are as defined in the ninth embodiment.

In another preferred embodiment, the compound is represented by Formula IIb; Q is as defined in the fifth, sixth, seventh, eight, ninth or tenth embodiment and the remainder of the variables are as defined in the ninth embodiment.

In another preferred embodiment, the compound is represented by Formula IIb; $R^2$ is as defined in the fifth, sixth, seventh, eight, ninth or tenth embodiment and the remainder of the variables are as defined in the ninth embodiment.

In another preferred embodiment, the compound is represented by Formula IIb; G is as defined in the fifth, sixth, seventh, eight, ninth or tenth embodiment and the remainder of the variables are as defined in the ninth embodiment.

Another embodiment of the invention is each of the following compounds and their enantiomers, diastereomers, and salts:

I-1 N-(1-amino-3-cyclohexylpropan-2-yl)-3-(1-hydroxy-1-phenylpentyl)piperidine-1-carboxamide
I-2 3-((3-methoxypropoxy)(phenyl)methyl)-N-(1-amino-3-cyclohexylpropan-2-yl)benzamide
I-3 3-((2-cyclopropylethoxy)(phenyl)methyl)-N-(1-amino-3-cyclohexylpropan-2-yl)piperidine-1-carboxamide
I-4 N-(1-amino-3-cyclohexylpropan-2-yl)-3-(5-methoxy-1-phenylpentyl)piperidine-1-carboxamide
I-5 3-((3-methoxypropoxy)(phenyl)methyl)-N-(1-amino-3-cyclohexylpropan-2-yl)piperidine-1-carboxamide
I-6 3-((3-methoxypropoxy)(phenyl)methyl)-N-(2-amino-3-cyclohexylpropyl)piperidine-1-carboxamide
I-7 N-(1-amino-3-cyclopentylpropan-2-yl)-3-(1-hydroxy-5-methoxy-1-phenylpentyl)piperidine-1-carboxamide
I-8 2-((3-methoxypropoxy)(phenyl)methyl)-N-(1-amino-3-cyclohexylpropan-2-yl)morpholine-4-carboxamide
I-9 N-(3-tert-butoxy-1-aminopropan-2-yl)-3-(1-hydroxy-5-methoxy-1-phenylpentyl)piperidine-1-carboxamide
I-10 3-(1-(3-fluorophenyl)-1-hydroxy-5-methoxypentyl)-N-(4-methyl-1-(methylamino)pentan-2-yl)piperidine-1-carboxamide
I-11 3-((3-methoxypropoxy)(phenyl)methyl)-N-(3-cyclohexyl-1-(methylamino)propan-2-yl)benzamide
I-12 N-(1-amino-3-phenylpropan-2-yl)-3-(1-hydroxy-5-methoxy-1-phenylpentyl)piperidine-1-carboxamide
I-13 N-(1-amino-3-cyclohexylpropan-2-yl)-3-(1-hydroxy-1-phenylheptyl)piperidine-1-carboxamide
I-14 N-(3-cyclohexyl-1-(methylamino)propan-2-yl)-3-(5-methoxy-1-phenylpentyl)piperidine-1-carboxamide
I-15 N-(1-amino-3-cyclohexylpropan-2-yl)-3-(5-ethoxy-1-phenylpentyl)piperidine-1-carboxamide
I-16 3-((3-methoxypropoxy)(phenyl)methyl)-N-(3-cyclohexyl-1-(methylamino)propan-2-yl)piperidine-1-carboxamide
I-17 3-((3-ethoxypropoxy)(phenyl)methyl)-N-(1-amino-3-cyclohexylpropan-2-yl)piperidine-1-carboxamide
I-18 3-((4-methoxybutoxy)(phenyl)methyl)-N-(1-amino-3-cyclohexylpropan-2-yl)piperidine-1-carboxamide
I-19 N-(1-amino-3-cyclohexylpropan-2-yl)-3-(1-hydroxy-5-methoxy-1-phenylpentyl)piperidine-1-carboxamide
I-20 3-((3-methoxypropoxy)(phenyl)methyl)-N-(1-amino-3-cyclohexylpropan-2-yl)-N-methylpiperidine-1-carboxamide
I-21 N-(3-cyclohexyl-1-(methylamino)propan-2-yl)-3-(1-hydroxy-4-methoxy-1-phenylbutyl)piperidine-1-carboxamide
I-22 3-((3-methoxypropoxy)(4-fluorophenyl)methyl)-N-(1-amino-3-cyclohexylpropan-2-yl)piperidine-1-carboxamide
I-23 3-((3-methoxypropoxy)(2-fluorophenyl)methyl)-N-(1-amino-3-cyclohexylpropan-2-yl)piperidine-1-carboxamide
I-24 N-(3-cyclohexyl-1-(methylamino)propan-2-yl)-3-(1-cyclohexyl-5-methoxypentyl)piperidine-1-carboxamide
I-25 N-(3-cyclohexyl-1-(methylamino)propan-2-yl)-3-(4-cyclopropyl-1-hydroxy-1-phenylbutyl)piperidine-1-carboxamide
I-26 3-((3-methoxypropoxy)(3-cyanophenyl)methyl)-N-(1-amino-3-cyclohexylpropan-2-yl)piperidine-1-carboxamide
I-27 N-(3-cyclohexyl-1-(methylamino)propan-2-yl)-3-(5-ethoxy-1-phenylpentyl)piperidine-1-carboxamide
I-28 N-(3-cyclohexyl-1-(methylamino)propan-2-yl)-3-(1-hydroxy-5-methoxy-1-phenylpentyl)cyclohexanecarboxamide
I-29 N-(1-amino-4-(trifluoromethyl)pentan-2-yl)-3-(1-hydroxy-5-methoxy-1-phenylpentyl)piperidine-1-carboxamide
I-30 3-((3-methoxypropoxy)(phenyl)methyl)-N-(3-cyclohexyl-1-(ethylamino)propan-2-yl)piperidine-1-carboxamide
I-31 N-(1-cyclohexyl-3-(methylamino)propan-2-yl)-3-((3-ethoxypropoxy)(phenyl)methyl)piperidine-1-carboxamide
I-32 N-(1-amino-3-cyclohexylpropan-2-yl)-3-(5-ethoxy-1-hydroxy-1-phenylpentyl)piperidine-1-carboxamide
I-33 N-(3-cyclohexyl-1-(methylamino)propan-2-yl)-3-(1-hydroxy-5-methoxy-1-phenylpentyl)piperidine-1-carboxamide
I-34 3-((3-ethoxypropoxy)(phenyl)methyl)-N-(1-amino-3-cyclohexylpropan-2-yl)-3-methylpiperidine-1-carboxamide
I-35 N-(3-cyclohexyl-1-(methylamino)propan-2-yl)-3-(4-ethoxy-1-hydroxy-1-phenylbutyl)piperidine-1-carboxamide
I-36 N-(2-amino-5-methoxy-4,4-dimethylpentyl)-3-(1-(3-chlorophenyl)-1-hydroxy-5-methoxypentyl)piperidine-1-carboxamide
I-37 N-(3-cyclohexyl-1-(methylamino)propan-2-yl)-3-(1-(3-fluorophenyl)-5-methoxypentyl)piperidine-1-carboxamide
I-38 N-(1-cyclohexyl-3-(methylamino)propan-2-yl)-3-(1-fluoro-5-methoxy-1-phenylpentyl)piperidine-1-carboxamide
I-39 3-((3-methoxypropoxy)(3-fluorophenyl)methyl)-N-(3-cyclohexyl-1-(methylamino)propan-2-yl)piperidine-1-carboxamide
I-40 N-(1-amino-3-cyclohexylpropan-2-yl)-3-(1-(3-fluorophenyl)-1-hydroxy-5-methoxypentyl)piperidine-1-carboxamide
I-41 N-(3-cyclohexyl-1-(methylamino)propan-2-yl)-3-(1-cyclohexyl-1-hydroxy-5-methoxypentyl)piperidine-1-carboxamide
I-42 3-((3-methoxypropoxy)(2,4-difluorophenyl)methyl)-N-(1-amino-3-cyclohexylpropan-2-yl)piperidine-1-carboxamide
I-43 3-((3-methoxypropoxy)(3,4-difluorophenyl)methyl)-N-(1-amino-3-cyclohexylpropan-2-yl)piperidine-1-carboxamide
I-44 3-(1-hydroxy-5-methoxy-1-(2-phenoxyphenyl)pentyl)-N-(1-(methylamino)propan-2-yl)piperidine-1-carboxamide
I-45 3-((3-methoxypropoxy)(3-cyanophenyl)methyl)-N-(3-cyclohexyl-1-(methylamino)propan-2-yl)piperidine-1-carboxamide
I-46 3-((3-methoxypropoxy)(2-allylphenyl)methyl)-N-(1-amino-3-cyclohexylpropan-2-yl)piperidine-1-carboxamide
I-47 3-((3-methoxypropoxy)(phenyl)methyl)-N-(3-cyclohexyl-1-(propylamino)propan-2-yl)piperidine-1-carboxamide
I-48 N-(3-cyclohexyl-1-(methylamino)propan-2-yl)-3-(5-ethoxy-1-hydroxy-1-phenylpentyl)piperidine-1-carboxamide
I-49 3-((3-propoxypropoxy)(phenyl)methyl)-N-(3-cyclohexyl-1-(methylamino)propan-2-yl)piperidine-1-carboxamide
I-50 N-(3-cyclohexyl-1-(methylamino)propan-2-yl)-3-(1-hydroxy-5-methoxy-1-m-tolylpentyl)piperidine-1-carboxamide I-51 N-(1-amino-5-methoxy-4,4-dimethylpentan-2-yl)-3-(1-(3-chlorophenyl)-1-hydroxy-5-methoxypentyl)piperidine-1-carboxamide I-52 N2-((Z)-1-(3-((3-methoxypropoxy)(phenyl)methyl)piperidin-1-yl)-2-nitrovinyl)-3-cyclohexylpropane-1,2-diamine I-53 N-(3-cyclohexyl-1-(methylamino)propan-2-yl)-3-(1-(3-fluorophenyl)-1-hydroxy-5-methoxypentyl)piperidine-1-carboxamide I-54 N-(2-amino-5-methoxy-4,4-dimethylpentyl)-3-(1-(2,3-difluorophenyl)-1-hydroxy-5-methoxypentyl)piperidine-1-carboxamide I-55 3-(1-amino-3-cyclohexylpropan-2-ylamino)-4-(3-((2-cyclopropylethoxy)(phenyl)methyl)piperidin-1-yl)cyclobut-3-ene-1,2-dione I-56 3-(1-hydroxy-5-methoxy-1-(2-phenoxyphenyl)pentyl)-N-(piperidin-3-yl)piperidine-1-carboxamide I-57 N-(3-cyclohexyl-1-(methylamino)propan-2-yl)-3-(4,4,4-trifluoro-1-hydroxy-1-m-tolylbutyl)piperidine-1-carboxamide I-58 3-(1-amino-3-cyclohexylpropan-2-ylamino)-4-(3-((3-methoxypropoxy)(phenyl)methyl)piperidin-1-yl)cyclobut-3-ene-1,2-dione I-59 3-(1-amino-3-cyclohexylpropan-2-ylamino)-4-(2-((3-methoxypropoxy)(phenyl)methyl)morpholino)cyclobut-3-ene-1,2-dione I-60 4-(3-((3-methoxypropoxy)(phenyl)methyl)piperidin-1-yl)-N-(1-amino-3-cyclohexylpropan-2-yl)-1,2,5-thiadiazol-3-amine I-61 3-((3-methoxypropoxy)(phenyl)methyl)-N-(1-(butylamino)-3-cyclohexylpropan-2-yl)piperidine-1-carboxamide I-62 3-((3-methoxypropoxy)(phenyl)methyl)-N-(3-cyclohexyl-1-(isobutylamino)propan-2-yl)piperidine-1-carboxamide I-63 N-(3-cyclohexyl-1-(dimethylamino)propan-2-yl)-3-(5-ethoxy-1-hydroxy-1-phenylpentyl)piperidine-1-carboxamide I-64 3-(1-(3-chlorophenyl)-1-hydroxy-5-methoxypentyl)-N-(3-cyclohexyl-1-(methylamino)propan-2-yl)piperidine-1-carboxamide I-65 3-((3-ethoxypropoxy)(3,4-difluorophenyl)methyl)-N-(3-cyclohexyl-1-(methylamino)propan-2-yl)piperidine-1-carboxamide I-66 N-(3-cyclohexyl-1-(methylamino)propan-2-yl)-3-(1-(2,5-difluorophenyl)-1-hydroxy-5-methoxypentyl)piperidine-1-carboxamide I-67 N-(3-(4,4-difluorocyclohexyl)-1-(methylamino)propan-2-yl)-3-(1-hydroxy-5-methoxy-1-phenylpentyl)piperidine-1-carboxamide I-68 N-(3-cyclohexyl-1-(methylamino)propan-2-yl)-3-(1-(3,4-difluorophenyl)-1-hydroxy-5-methoxypentyl)piperidine-1-carboxamide I-69 3-(1-amino-3-cyclohexylpropan-2-ylamino)-4-(3-(1-hydroxy-1-phenylheptyl)piperidin-1-yl)cyclobut-3-ene-1,2-dione I-70 3-(3-amino-1-cyclohexylbutan-2-ylamino)-4-(3-((3-methoxypropoxy)(phenyl)methyl)piperidin-1-yl)cyclobut-3-ene-1,2-dione I-71 3-(3-cyclohexyl-1-(methylamino)propan-2-ylamino)-4-(3-((3-methoxypropoxy)(phenyl)methyl)piperidin-1-yl)cyclobut-3-ene-1,2-dione I-72 3-(1-(2-(p-tolyloxy)-5-methylphenyl)-1-hydroxy-5-methoxypentyl)-N-(1-(methylamino)propan-2-yl)piperidine-1-carboxamide I-73 3-(3-((3-methoxypropoxy)(phenyl)methyl)piperidin-1-yl)-4-(N-(1-amino-3-cyclohexylpropan-2-yl)-N-methylamino)cyclobut-3-ene-1,2-dione I-74 3-((3-methoxypropoxy)(2-(trifluoromethyl)phenyl)methyl)-N-(1-amino-3-cyclohexylpropan-2-yl)piperidine-1-carboxamide I-75 3-(1-amino-3-cyclohexylpropan-2-ylamino)-4-(3-((3-methoxypropoxy)(4-fluorophenyl)methyl)piperidin-1-yl)cyclobut-3-ene-1,2-dione I-76 3-(1-amino-3-cyclohexylpropan-2-ylamino)-4-(3-((3-methoxypropoxy)(2-fluorophenyl)methyl)piperidin-1-yl)cyclobut-3-ene-1,2-dione I-77 3-((3-methoxypropoxy)(phenyl)methyl)-N-(3-cyclohexyl-1-(isopentylamino)propan-2-yl)piperidine-1-carboxamide I-78 3-((3-methoxypropoxy)(phenyl)methyl)-N-(3-cyclohexyl-1-(pentylamino)propan-2-yl)piperidine-1-carboxamide I-79 N-(3-cyclohexyl-1-(methylamino)propan-2-yl)-3-(1-hydroxy-1-(3-isopropylphenyl)-5-methoxypentyl)piperidine-1-carboxamide I-80 3-(1-(3-chlorophenyl)-4,4,4-trifluoro-1-hydroxybutyl)-N-(3-cyclohexyl-1-(methylamino)propan-2-yl)piperidine-1-carboxamide I-81 3-(1-(5-chloro-2-phenoxyphenyl)-1-hydroxy-5-methoxypentyl)-N-(1-(methylamino)propan-2-yl)piperidine-1-carboxamide I-82 3-(1-(3-chlorophenyl)-5-cyclopropyl-1-hydroxypentyl)-N-(3-cyclohexyl-1-(methylamino)propan-2-yl)piperidine-1-carboxamide I-83 3-((3-methoxypropoxy)(2-phenylphenyl)methyl)-N-(2-amino-3-cyclohexylpropyl)piperidine-1-carboxamide I-84 3-((3-methoxypropoxy)(2-(2-cyclopropylethynyl)phenyl)methyl)-N-(3-cyclohexyl-1-(methylamino)propan-2-yl)piperidine-1-carboxamide I-85 3-(3-cyclohexyl-1-(ethylamino)propan-2-ylamino)-4-(3-((3-methoxypropoxy)(phenyl)methyl)piperidin-1-yl)cyclobut-3-ene-1,2-dione I-86 3-(1-hydroxy-5-methoxy-1-(2-phenoxyphenyl)pentyl)-N-(4-methyl-1-(methylamino)pentan-2-yl)piperidine-1-carboxamide I-87 N-(1-amino-5-methoxy-4,4-dimethylpentan-2-yl)-3-(1-(2,3-difluorophenyl)-1-hydroxy-5-methoxypentyl)piperidine-1-carboxamide I-88 N-(3-(4,4-difluorocyclohexyl)-1-(methylamino)propan-2-yl)-3-(1-(3-fluorophenyl)-1-hydroxy-5-methoxypentyl)piperidine-1-carboxamide I-89 3-(1-amino-3-cyclohexylpropan-2-ylamino)-4-(3-((3-methoxypropoxy)(2,4-difluorophenyl)methyl)piperidin-1-yl)cyclobut-3-ene-1,2-dione I-90 3-(1-amino-3-cyclohexylpropan-2-ylamino)-4-(3-((3-methoxypropoxy)(3,4-difluorophenyl)methyl)piperidin-1-yl)cyclobut-3-ene-1,2-dione I-91 N-(1-(carbamoylmethylamino)-3-cyclohexylpropan-2-yl)-3-(1-(3-fluorophenyl)-1-hydroxy-5-methoxypentyl)piperidine-1-carboxamide I-92 3-(3-cyclohexyl-1-(propylamino)propan-2-ylamino)-4-(3-((3-methoxypropoxy)(phenyl)methyl)piperidin-1-yl)cyclobut-3-ene-1,2-dione I-93 N-(3-cyclohexyl-1-(methylamino)propan-2-yl)-3-(1-(3-(trifluoromethyl)phenyl)-1-hydroxy-5-methoxypentyl)piperidine-1-carboxamide I-94 3-(3-cyclohexyl-1-(isobutylamino)propan-2-ylamino)-4-(3-((3-methoxypropoxy)(phenyl)methyl)piperidin-1-yl)cyclobut-3-ene-1,2-dione I-95   3-(3-(butylamino)-1-cyclohexylpropan-2-ylamino)-4-(3-((3-methoxypropoxy)(phenyl)methyl)piperidin-1-yl)cyclobut-3-ene-1,2-dione
I-96   3-(1-(2-(p-tolyloxy)-5-methylphenyl)-1-hydroxy-5-methoxypentyl)-N-(4-methyl-1-(methylamino)pentan-2-yl)piperidine-1-carboxamide
I-97   3-(1-(5-chloro-2-phenoxyphenyl)-1-hydroxy-5-methoxypentyl)-N-(4-methyl-1-(methylamino)pentan-2-yl)piperidine-1-carboxamide
I-98   3-(3-cyclohexyl-1-(methylamino)propan-2-ylamino)-4-(3-((3-ethoxypropoxy)(3,4-difluorophenyl)methyl)piperidin-1-yl)cyclobut-3-ene-1,2-dione
I-99   3-(1-amino-3-cyclohexylpropan-2-ylamino)-4-(3-((3-methoxypropoxy)(2-(trifluoromethyl)phenyl)methyl)piperidin-1-yl)cyclobut-3-ene-1,2-dione
I-100   N-(3-cyclohexyl-1-(methylamino)propan-2-yl)-3-(1-hydroxy-5-methoxy-1-(2-phenoxyphenyl)pentyl)piperidine-1-carboxamide
I-101   3-(1-cyclohexyl-3-(pentylamino)propan-2-ylamino)-4-(3-((3-methoxypropoxy)(phenyl)methyl)piperidin-1-yl)cyclobut-3-ene-1,2-dione
I-102   3-(1-cyclohexyl-3-(isopentylamino)propan-2-ylamino)-4-(3-((3-methoxypropoxy)(phenyl)methyl)piperidin-1-yl)cyclobut-3-ene-1,2-dione
I-103   3-(1-(2-(p-tolyloxy)-5-methylphenyl)-1-hydroxy-5-methoxypentyl)-N-(3-cyclohexyl-1-(methylamino)propan-2-yl)piperidine-1-carboxamide
I-104   3-(1-(5-chloro-2-phenoxyphenyl)-1-hydroxy-5-methoxypentyl)-N-(3-cyclohexyl-1-(methylamino)propan-2-yl)piperidine-1-carboxamide
I-105   N-(3-cyclohexyl-1-(methylamino)propan-2-yl)-3-((pent-4-enyloxy)(phenyl)methyl)benzamide
I-106   N-(3-cyclohexyl-1-(methylamino)propan-2-yl)-3-(5-methoxy-1-phenylpentyl)benzamide
I-107   3-((2-ethoxyethoxy)(phenyl)methyl)-N-(3-cyclohexyl-1-(methylamino)propan-2-yl)benzamide
I-108   3-(1-(2-(cyclopropylmethoxy)phenyl)-1-hydroxy-5-methoxypentyl)-N-(1-(methylamino)propan-2-yl)piperidine-1-carboxamide
I-109   3-((S)-1-hydroxy-5-methoxy-1-m-tolylpentyl)-N-(4,4-dimethyl-1-(methylamino)pentan-2-yl)piperidine-1-carboxamide
I-110   N-(3-cyclohexyl-1-(methylamino)propan-2-yl)-3-(5-methoxy-1-(thiophen-2-yl)pentyl)piperidine-1-carboxamide
I-111   N-(3-cyclohexyl-1-(methylamino)propan-2-yl)-3-(1,1,1-trifluoro-2-hydroxy-6-methoxyhexan-2-yl)piperidine-1-carboxamide
I-112   3-((2-(acetylamino)ethoxy)(phenyl)methyl)-N-(3-cyclohexyl-1-(methylamino)propan-2-yl)benzamide
I-113   3-(1-(3-fluorophenyl)-1-hydroxy-5-methoxypentyl)-N-(4,4-dimethyl-1-(methylamino)pentan-2-yl)piperidine-1-carboxamide
I-114   N-(3-cyclohexyl-1-(methylamino)propan-2-yl)-3-(1-hydroxy-5-methoxy-1-phenylpentyl)benzamide
I-115   3-((3-ethoxypropoxy)(phenyl)methyl)-N-(3-cyclohexyl-1-(methylamino)propan-2-yl)benzamide
I-116   3-(1-(3-chlorophenyl)-1-hydroxy-5-methoxypentyl)-N-(4-methyl-1-(methylamino)pentan-2-yl)piperidine-1-carboxamide
I-117   3-(1-(2,3-difluorophenyl)-1-hydroxy-5-methoxypentyl)-N-(4-methyl-1-(methylamino)pentan-2-yl)piperidine-1-carboxamide
I-118   3-(1-(benzofuran-7-yl)-1-hydroxy-5-methoxypentyl)-N-(4-methyl-1-(methylamino)pentan-2-yl)piperidine-1-carboxamide
I-119   N-(3-cyclohexyl-1-(methylamino)propan-2-yl)-3-(1-hydroxy-5-methoxy-1-(pyridin-2-yl)pentyl)piperidine-1-carboxamide
I-120   3-(1-(2-(2-cyclopropylethoxy)phenyl)-1-hydroxy-5-methoxypentyl)-N-(1-(methylamino)propan-2-yl)piperidine-1-carboxamide
I-121   3-(1-(2-(cyclopentyloxy)phenyl)-1-hydroxy-5-methoxypentyl)-N-(1-(methylamino)propan-2-yl)piperidine-1-carboxamide
I-122   3-((3-methoxypropoxy)(phenyl)methyl)-N-(3-cyclohexyl-1-(methylamino)propan-2-yl)piperidine-1-carbothioamide
I-123   N-(1-amino-3-cyclohexylpropan-2-yl)-3-(1-(3-fluorophenyl)-1-hydroxy-5-methoxypentyl)piperidine-1-carboxamide
I-124   3-(1-hydroxy-5-methoxy-1-(2-(neopentyloxy)phenyl)pentyl)-N-(1-(methylamino)propan-2-yl)piperidine-1-carboxamide
I-125   N-(3-cyclohexyl-1-(methylamino)propan-2-yl)-3-(hydroxy-5-methoxy-1-(1-methyl-1H-imidazol-2-yl)pentyl)piperidine-1-carboxamide
I-126   N-(3-cyclohexyl-1-(methylamino)propan-2-yl)-3-(1-hydroxy-5-methoxy-1-(thiophen-2-yl)pentyl)piperidine-1-carboxamide
I-127   N-(3-cyclohexyl-1-(methylamino)propan-2-yl)-3-(1-hydroxy-5-methoxy-1-(thiophen-3-yl)pentyl)piperidine-1-carboxamide
I-128   N-(3-cyclohexyl-1-(methylamino)propan-2-yl)-3-(1-hydroxy-5-methoxy-1-m-tolylpentyl)benzamide
I-129   N-(3-cyclohexyl-1-(methylamino)propan-2-yl)-3-(1-hydroxy-5-methoxy-1-o-tolylpentyl)benzamide
I-130   N-(3-cyclohexyl-1-(methylamino)propan-2-yl)-3-(1-hydroxy-5-methoxy-1-(thiazol-2-yl)pentyl)piperidine-1-carboxamide
I-131   3-(1-(2-(3-methylphenyl)phenyl)-1-hydroxy-5-methoxypentyl)-N-(1-(methylamino)propan-2-yl)piperidine-1-carboxamide
I-132   3-(1-(2-(4-methylphenyl)phenyl)-1-hydroxy-5-methoxypentyl)-N-(1-(methylamino)propan-2-yl)piperidine-1-carboxamide
I-133   3-(1-(2-(2-methylphenyl)phenyl)-1-hydroxy-5-methoxypentyl)-N-(1-(methylamino)propan-2-yl)piperidine-1-carboxamide
I-134   3-(1-(3-chlorophenyl)-1-hydroxy-5-methoxypentyl)-N-(4,4-dimethyl-1-(methylamino)pentan-2-yl)piperidine-1-carboxamide
I-135   3-(1-(2,3-difluorophenyl)-1-hydroxy-5-methoxypentyl)-N-(4,4-dimethyl-1-(methylamino)pentan-2-yl)piperidine-1-carboxamide
I-136   3-(1-(2-(o-tolyloxy)phenyl)-1-hydroxy-5-methoxypentyl)-N-(2-aminoethyl)-N-methylpiperidine-1-carboxamide
I-137   N-(3-cyclohexyl-1-(methylamino)propan-2-yl)-3-(1-(3-fluorophenyl)-1-hydroxy-5-methoxypentyl)benzamide
I-138   N-(3-cyclohexyl-1-(methylamino)propan-2-yl)-3-(1-(4-fluorophenyl)-1-hydroxy-5-methoxypentyl)benzamide
I-139   3-(1-hydroxy-5-methoxy-1-(quinolin-8-yl)pentyl)-N-(4-methyl-1-(methylamino)pentan-2-yl)piperidine-1-carboxamide
I-140   3-(1-(2-(2-fluorophenyl)phenyl)-1-hydroxy-5-methoxypentyl)-N-(1-(methylamino)propan-2-yl)piperidine-1-carboxamide
I-141   3-(1-(2-phenyl-3-fluorophenyl)-1-hydroxy-5-methoxypentyl)-N-(1-(methylamino)propan-2-yl)piperidine-1-carboxamide I-142 3-(1-(2-(3-fluorophenyl)phenyl)-1-hydroxy-5-methoxypentyl)-N-(1-(methylamino)propan-2-yl)piperidine-1-carboxamide I-143 3-((S)-1-(2-(4-fluorophenyl)phenyl)-1-hydroxy-5-methoxypentyl)-N-(1-(methylamino)propan-2-yl)piperidine-1-carboxamide I-144 3-(1-hydroxy-5-methoxy-1-(2-methylbenzofuran-7-yl)pentyl)-N-(4-methyl-1-(methylamino)pentan-2-yl)piperidine-1-carboxamide I-145 3-(1-hydroxy-1-(2-isobutylbenzofuran-7-yl)-5-methoxypentyl)-N-(1-(methylamino)propan-2-yl)piperidine-1-carboxamide I-146 N-(3-cyclohexyl-1-(methylamino)propan-2-yl)-3-(1-hydroxy-5-methoxy-1-phenylpentyl)-3-methylpiperidine-1-carboxamide I-147 3-(1-(2-(cyclopentylmethoxy)phenyl)-1-hydroxy-5-methoxypentyl)-N-(1-(methylamino)propan-2-yl)piperidine-1-carboxamide I-148 N-(3-cyclohexyl-1-(methylamino)propan-2-yl)-3-(1-(2-fluoro-5-methylphenyl)-5-methoxypentyl)piperidine-1-carboxamide I-149 3-(1-(benzo[b]thiophen-7-yl)-1-hydroxy-5-methoxypentyl)-N-(4-methyl-1-(methylamino)pentan-2-yl)piperidine-1-carboxamide I-151 N-(3-cyclohexyl-1-(methylamino)propan-2-yl)-3-(1-(2-fluorophenyl)-1-hydroxy-5-methoxypentyl)piperidine-1-carboxamide I-152 3-((3-ethoxypropoxy)(3-fluorophenyl)methyl)-N-(3-cyclohexyl-1-(methylamino)propan-2-yl)piperidine-1-carboxamide I-153 N-(1-amino-3-cyclohexylpropan-2-yl)-3-(1-(3-chlorophenyl)-1-hydroxy-5-methoxypentyl)piperidine-1-carboxamide I-154 3-((3-ethoxypropoxy)(3-chlorophenyl)methyl)-N-(1-amino-3-cyclohexylpropan-2-yl)piperidine-1-carboxamide I-155 3-(1-(3-chlorophenyl)-1,5-dihydroxypentyl)-N-(3-cyclohexyl-1-(methylamino)propan-2-yl)piperidine-1-carboxamide I-156 3-(1-(3-chlorophenyl)-1-hydroxy-5-methoxypentyl)-N-(3-cyclopentyl-1-(methylamino)propan-2-yl)piperidine-1-carboxamide I-157 N-(3-cyclohexyl-1-(methylamino)propan-2-yl)-3-(1-hydroxy-5-methoxy-1-(5-methylthiazol-2-yl)pentyl)piperidine-1-carboxamide I-158 3-(1-(3-chlorophenyl)-1-hydroxy-5-methoxypentyl)-N-(3-cyclohexyl-1-hydroxypropan-2-yl)piperidine-1-carboxamide I-159 3-((3-methoxypropoxy)(4-chloropyridin-2-yl)methyl)-N-(3-cyclohexyl-1-(methylamino)propan-2-yl)piperidine-1-carboxamide I-160 3-(1-hydroxy-5-methoxy-1-(2-phenoxyphenyl)pentyl)-N-(2-methyl-1-(methylamino)propan-2-yl)piperidine-1-carboxamide I-161 3-(1-(2-(o-tolyloxy)phenyl)-1-hydroxy-5-methoxypentyl)-N-(1-(methylamino)propan-2-yl)piperidine-1-carboxamide I-162 3-(1-(2-(m-tolyloxy)phenyl)-1-hydroxy-5-methoxypentyl)-N-(1-(methylamino)propan-2-yl)piperidine-1-carboxamide I-163 N-(3-(3,3-difluorocyclobutyl)-1-(methylamino)propan-2-yl)-3-(1-(3-fluorophenyl)-1-hydroxy-5-methoxypentyl)piperidine-1-carboxamide I-165 3-((S)-1-(benzofuran-7-yl)-1-hydroxy-5-methoxypentyl)-N-(3-cyclopentyl-1-(methylamino)propan-2-yl)piperidine-1-carboxamide I-166 3-(1-(3-chloro-2-fluorophenyl)-1-hydroxy-5-methoxypentyl)-N-(4,4-dimethyl-1-(methylamino)pentan-2-yl)piperidine-1-carboxamide I-167 3-(1-(3-chlorophenyl)-1-hydroxy-5-methoxypentyl)-N-(3-cyclohexyl-1-(methylamino)propan-2-yl)benzamide I-168 3-(1-(2-(4-fluorophenoxy)phenyl)-1-hydroxy-5-methoxypentyl)-N-(1-(methylamino)propan-2-yl)piperidine-1-carboxamide I-169 3-(1-(5-fluoro-2-phenoxyphenyl)-1-hydroxy-5-methoxypentyl)-N-(1-(methylamino)propan-2-yl)piperidine-1-carboxamide I-170 3-(1-(2-(3-fluorophenoxy)phenyl)-1-hydroxy-5-methoxypentyl)-N-(1-(methylamino)propan-2-yl)piperidine-1-carboxamide I-171 3-(1-(2-(2-fluorophenoxy)phenyl)-1-hydroxy-5-methoxypentyl)-N-(1-(methylamino)propan-2-yl)piperidine-1-carboxamide I-172 N-(3-cyclopentyl-1-(methylamino)propan-2-yl)-3-((S)-1-(2,3-dihydrobenzofuran-7-yl)-1-hydroxy-5-methoxypentyl)piperidine-1-carboxamide I-173 N-(3-cyclohexyl-1-(methylamino)propan-2-yl)-3-(1-hydroxy-5-methoxy-1-(2,5-dimethylphenyl)pentyl)piperidine-1-carboxamide I-174 N-(3-cyclohexyl-1-(methylamino)propan-2-yl)-3-(1-(3-ethylphenyl)-1-hydroxy-5-methoxypentyl)piperidine-1-carboxamide I-175 N-(3-cyclohexyl-1-(methylamino)propan-2-yl)-3-(1-hydroxy-5-methoxy-1-(2,3-dimethylphenyl)pentyl)piperidine-1-carboxamide I-176 N-(3-cyclohexyl-1-(methylamino)propan-2-yl)-3-(1-hydroxy-5-methoxy-1-(3,5-dimethylphenyl)pentyl)piperidine-1-carboxamide I-177 3-(1-(2-(2-chlorophenyl)phenyl)-1-hydroxy-5-methoxypentyl)-N-(1-(methylamino)propan-2-yl)piperidine-1-carboxamide I-178 3-(1-(2-phenylphenyl)-1-hydroxy-5-methoxypentyl)-N-(1-(methylamino)propan-2-yl)piperidine-1-carboxamide I-179 N-(3-cyclohexyl-1-(methylamino)propan-2-yl)-3-(1-hydroxy-5-methoxy-1-(3-methoxyphenyl)pentyl)piperidine-1-carboxamide I-180 3-(1-(2-(cyclopropylmethoxy)phenyl)-1-hydroxy-5-methoxypentyl)-N-(4-methyl-1-(methylamino)pentan-2-yl)piperidine-1-carboxamide I-181 3-(1-(3-chlorophenyl)-4-cyclopropyl-1-hydroxybutyl)-N-(3-cyclohexyl-1-(methylamino)propan-2-yl)piperidine-1-carboxamide I-182 N-(3-cyclohexyl-1-(methylamino)propan-2-yl)-3-(1-(3-fluoro-5-methylphenyl)-1-hydroxy-5-methoxypentyl)piperidine-1-carboxamide I-183 N-(3-cyclohexyl-1-(methylamino)propan-2-yl)-3-((S)-1-(2-fluoro-5-methylphenyl)-1-hydroxy-5-methoxypentyl)piperidine-1-carboxamide I-184 N-(3-cyclohexyl-1-(methylamino)propan-2-yl)-3-(1-(5-fluoro-2-methylphenyl)-1-hydroxy-5-methoxypentyl)piperidine-1-carboxamide I-185 N-(3-cyclohexyl-1-(methylamino)propan-2-yl)-3-(1-(2-fluoro-3-methylphenyl)-1-hydroxy-5-methoxypentyl)piperidine-1-carboxamide I-186 N-(1-cyclohexyl-1-hydroxy-3-(methylamino)propan-2-yl)-3-(1-(3-fluorophenyl)-1-hydroxy-5-methoxypentyl)piperidine-1-carboxamide I-187 3-((S)-1-(3-fluorophenyl)-1-hydroxy-5-methoxypentyl)-N-(3-(1-hydroxycyclohexyl)-1-(methylamino)propan-2-yl)piperidine-1-carboxamide I-188 3-(1-(3-fluorophenyl)-1-hydroxy-5-methoxypentyl)-N-(3-(1-hydroxycyclohexyl)-2-(methylamino)propyl)piperidine-1-carboxamide I-190 3-((3-ethoxypropoxy)(3-chlorophenyl)methyl)-N-(3-cyclohexyl-1-(methylamino)propan-2-yl)piperidine-1-carboxamide I-191 3-(1-(3-chlorophenyl)-1,5-dihydroxyhexyl)-N-(3-cyclohexyl-1-(methylamino)propan-2-yl)piperidine-1-carboxamide I-192 3-(1-(2-chlorophenyl)-1-hydroxy-5-methoxypentyl)-N-(3-cyclohexyl-1-(methylamino)propan-2-yl)piperidine-1-carboxamide I-193 3-(1-(4-chloropyridin-2-yl)-1-hydroxy-5-methoxypentyl)-N-(3-cyclohexyl-1-(methylamino)propan-2-yl)piperidine-1-carboxamide I-194 3-((3-ethoxypropoxy)(phenyl)methyl)-N-(3-(4,4-difluorocyclohexyl)-1-(methylamino)propan-2-yl)piperidine-1-carboxamide I-195 N-(3-cyclohexyl-1-(methylamino)propan-2-yl)-3-(1-(3,5-difluorophenyl)-1-hydroxy-5-methoxypentyl)piperidine-1-carboxamide I-196 N-(3-cyclohexyl-1-(methylamino)propan-2-yl)-3-(1-(2,3-difluorophenyl)-1-hydroxy-5-methoxypentyl)piperidine-1-carboxamide I-197 N-(3-cyclopentyl-1-(methylamino)propan-2-yl)-3-(5-ethoxy-1-(2,3-difluorophenyl)-1-hydroxypentyl)piperidine-1-carboxamide I-198 N-(3-cyclohexyl-1-(methylamino)propan-2-yl)-3-(1-(2,3-difluorophenyl)-1-hydroxy-5-methoxypentyl)piperidine-1-carboxamide I-198 3-(1-(2-phenylphenyl)-1-hydroxy-5-methoxypentyl)-N-(4-methyl-1-(methylamino)pentan-2-yl)piperidine-1-carboxamide I-200 3-(1-(3-chlorophenyl)-1-hydroxy-5-methoxypentyl)-N-(3-(tetrahydro-2H-pyran-4-yl)-1-(methylamino)propan-2-yl)piperidine-1-carboxamide I-201 2-(1-(3-chlorophenyl)-1-hydroxy-5-methoxypentyl)-N-(3-cyclohexyl-1-(methylamino)propan-2-yl)morpholine-4-carboxamide I-202 N-(3-amino-1-cyclohexyl-1-hydroxypropan-2-yl)-3-(1-(3-chlorophenyl)-1-hydroxy-5-methoxypentyl)piperidine-1-carboxamide I-203 3-(1-(3-chlorophenyl)-1-hydroxy-5-methoxypentyl)-N-(1-cyclopentyl-1-hydroxy-3-(methylamino)propan-2-yl)piperidine-1-carboxamide I-204 3-(1-(2-(o-tolyloxy)phenyl)-1-hydroxy-5-methoxypentyl)-N-(2-methyl-1-(methylamino)propan-2-yl)piperidine-1-carboxamide I-205 3-(1-(2-(2-ethylphenoxy)phenyl)-1-hydroxy-5-methoxypentyl)-N-(1-(methylamino)propan-2-yl)piperidine-1-carboxamide I-206 3-(1-(3-chloro-2-fluorophenyl)-1-hydroxy-5-methoxypentyl)-N-(3-cyclopentyl-1-(methylamino)propan-2-yl)piperidine-1-carboxamide I-207 3-(1-(5-chloro-1-methyl-1H-imidazol-2-yl)-1-hydroxy-5-methoxypentyl)-N-(3-cyclohexyl-1-(methylamino)propan-2-yl)piperidine-1-carboxamide I-208 3-(1-(2,2-difluorobenzo[d][1,3]dioxol-4-yl)-1-hydroxy-5-methoxypentyl)-N-(4-methyl-1-(methylamino)pentan-2-yl)piperidine-1-carboxamide I-209 3-(1-(3-chlorophenyl)-1-hydroxyethyl)-N-(1-cyclohexyl-3-(methylamino)propan-2-yl)piperidine-1-carboxamide I-210 3-(1-(benzofuran-7-yl)-1-hydroxy-5-methoxypentyl)-N-(3-cyclohexyl-1-(methylamino)propan-2-yl)piperidine-1-carboxamide I-211 N-(3-cyclohexyl-1-(methylamino)propan-2-yl)-3-(1-hydroxy-1-(1H-indazol-7-yl)-5-methoxypentyl)piperidine-1-carboxamide I-212 N-(3-cyclohexyl-1-(methylamino)propan-2-yl)-3-(1-hydroxy-1-(1H-indazol-7-yl)-5-methoxypentyl)piperidine-1-carboxamide I-213 3-(1-(2-(4-fluorophenoxy)phenyl)-1-hydroxy-5-methoxypentyl)-N-(2-methyl-1-(methylamino)propan-2-yl)piperidine-1-carboxamide I-214 3-(1-(2-(3-fluorophenoxy)phenyl)-1-hydroxy-5-methoxypentyl)-N-(2-methyl-1-(methylamino)propan-2-yl)piperidine-1-carboxamide I-215 3-(1-(3-(o-tolyloxy)-2-fluorophenyl)-1-hydroxy-5-methoxypentyl)-N-(1-(methylamino)propan-2-yl)piperidine-1-carboxamide I-216 3-(1-(2-(o-tolyloxy)-3-fluorophenyl)-1-hydroxy-5-methoxypentyl)-N-(1-(methylamino)propan-2-yl)piperidine-1-carboxamide I-217 3-(1-(2-(5-fluoro-2-methylphenoxy)phenyl)-1-hydroxy-5-methoxypentyl)-N-(1-(methylamino)propan-2-yl)piperidine-1-carboxamide I-218 3-(1-(2-(4-fluoro-2-methylphenoxy)phenyl)-1-hydroxy-5-methoxypentyl)-N-(1-(methylamino)propan-2-yl)piperidine-1-carboxamide I-219 N-(3-cyclohexyl-1-(methylamino)propan-2-yl)-3-(1-(2,3-dihydrobenzofuran-7-yl)-1-hydroxy-5-methoxypentyl)piperidine-1-carboxamide I-220 3-(1-(3-chlorophenyl)-1-hydroxy-5-methoxypentyl)-N-(3-(3,3-difluorocyclobutyl)-1-(methylamino)propan-2-yl)piperidine-1-carboxamide I-221 N-(3-(3,3-difluorocyclobutyl)-1-(methylamino)propan-2-yl)-3-(1-(2,3-difluorophenyl)-1-hydroxy-5-methoxypentyl)piperidine-1-carboxamide I-222 3-(1-(2-(cyclopentyloxy)phenyl)-1-hydroxy-5-methoxypentyl)-N-(4-methyl-1-(methylamino)pentan-2-yl)piperidine-1-carboxamide I-223 3-(1-(2-(2-cyclopropylethoxy)phenyl)-1-hydroxy-5-methoxypentyl)-N-(4-methyl-1-(methylamino)pentan-2-yl)piperidine-1-carboxamide I-224 3-(1-(2-(2-chlorophenoxy)phenyl)-1-hydroxy-5-methoxypentyl)-N-(1-(methylamino)propan-2-yl)piperidine-1-carboxamide I-225 3-(1-hydroxy-5-methoxy-1-(2-(neopentyloxy)phenyl)pentyl)-N-(4-methyl-1-(methylamino)pentan-2-yl)piperidine-1-carboxamide I-226 N-(3-cyclohexyl-1-(methylamino)propan-2-yl)-3-(1-hydroxy-5-methoxy-1-(3-(methylthio)phenyl)pentyl)piperidine-1-carboxamide I-227 3-(4-(acetylamino)-1-(3-chlorophenyl)-1-hydroxybutyl)-N-(3-cyclohexyl-1-(methylamino)propan-2-yl)piperidine-1-carboxamide I-228 3-(1-(2-(allyloxy)-5-fluorophenyl)-5-ethoxy-1-hydroxypentyl)-N-(4-methyl-1-(methylamino)pentan-2-yl)piperidine-1-carboxamide I-229 N-(3-cyclohexyl-1-(methylamino)propan-2-yl)-3-(1-(5-fluoro-2-methoxyphenyl)-1-hydroxy-5-methoxypentyl)piperidine-1-carboxamide I-230 N-(3-cyclohexyl-1-(methylamino)propan-2-yl)-3-(1-(2-fluoro-6-methoxyphenyl)-1-hydroxy-5-methoxypentyl)piperidine-1-carboxamide I-231 3-(4-cyclopropyl-1-hydroxy-1-(2-phenoxyphenyl)butyl)-N-(4-methyl-1-(methylamino)pentan-2-yl)piperidine-1-carboxamide I-232 3-(1-(3-chlorophenyl)-1-hydroxy-5-methoxypentyl)-N-(5,5,5-trifluoro-4-methyl-1-(methylamino)pentan-2-yl)piperidine-1-carboxamide I-233 3-(1-(3-chlorophenyl)-1,5-dimethoxypentyl)-N-(3-cyclohexyl-1-(methylamino)propan-2-yl)piperidine-1-carboxamide I-234 3-(1-(3-chlorophenyl)-1-hydroxy-5-methoxypentyl)-N-(3-cyclohexyl-1-(ethylamino)propan-2-yl)piperidine-1-carboxamide I-235 3-(1-(3-chlorophenyl)-1,5-dihydroxyheptyl)-N-(3-cyclohexyl-1-(methylamino)propan-2-yl)piperidine-1-carboxamide I-236 3-(4-cyclopropyl-1-(3-fluorophenyl)-1-hydroxybutyl)-N-(3-(4,4-difluorocyclohexyl)-1-(methylamino)propan-2-yl)piperidine-1-carboxamide I-237 N-(3-(4,4-difluorocyclohexyl)-1-(methylamino)propan-2-yl)-3-(1-hydroxy-5-methoxy-1-m-tolylpentyl)piperidine-1-carboxamide I-238 3-((3-ethoxypropoxy)(m-tolyl)methyl)-N-(3-(4,4-difluorocyclohexyl)-1-(methylamino)propan-2-yl)piperidine-1-carboxamide I-239 N-(3-cyclohexyl-1-(methylamino)propan-2-yl)-3-(5-ethoxy-1-(2,3-difluorophenyl)-1-hydroxypentyl)piperidine-1-carboxamide I-240 3-(1-(2-fluoro-3-methylphenyl)-1-hydroxy-5-methoxypentyl)-N-(3-(4-fluorocyclohexyl)-1-(methylamino)propan-2-yl)piperidine-1-carboxamide I-241 N-(3-cyclopropyl-1-(methylamino)propan-2-yl)-3-(1-hydroxy-5-methoxy-1-(2-phenoxyphenyl)pentyl)piperidine-1-carboxamide I-242 3-(1-(2-(3-methylphenyl)phenyl)-1-hydroxy-5-methoxypentyl)-N-(4-methyl-1-(methylamino)pentan-2-yl)piperidine-1-carboxamide I-243 3-(1-(2-(4-methylphenyl)phenyl)-1-hydroxy-5-methoxypentyl)-N-(4-methyl-1-(methylamino)pentan-2-yl)piperidine-1-carboxamide I-244 3-(1-(3-chlorophenyl)-1-hydroxy-5-methoxypentyl)-N-(1-cyclohexyl-1-hydroxy-3-(methylamino)propan-2-yl)piperidine-1-carboxamide I-245 3-(1-(3-chlorophenyl)-1-hydroxy-5-methoxypentyl)-N-(3-(1-hydroxycyclohexyl)-1-(methylamino)propan-2-yl)piperidine-1-carboxamide I-246 3-(1-(3-chlorophenyl)-1-hydroxy-5-methoxypentyl)-N-(3-(1-hydroxycyclohexyl)-2-(methylamino)propyl)piperidine-1-carboxamide I-247 3-(1-(3-chlorophenyl)-1-hydroxy-5-methoxypentyl)-N-(3-cyclohexyl-1-(methylamino)propan-2-yl)piperidine-1-carbothioamide I-248 N-(3-cyclohexyl-1-(methylamino)propan-2-yl)-3-(1-hydroxy-5-methoxy-1-(quinolin-8-yl)pentyl)piperidine-1-carboxamide I-249 3-(1-(2-(p-tolyloxy)-5-methylphenyl)-1-hydroxy-5-methoxypentyl)-N-(2-methyl-1-(methylamino)propan-2-yl)piperidine-1-carboxamide I-250 3-(1-(3-chloro-5-fluorophenyl)-1-hydroxy-5-methoxypentyl)-N-(3-cyclohexyl-1-(methylamino)propan-2-yl)piperidine-1-carboxamide I-251 3-(1-(3-chloro-2-fluorophenyl)-1-hydroxy-5-methoxypentyl)-N-(3-cyclohexyl-1-(methylamino)propan-2-yl)piperidine-1-carboxamide I-252 3-(1-(3-chloro-2-fluorophenyl)-5-ethoxy-1-hydroxypentyl)-N-(3-cyclopentyl-1-(methylamino)propan-2-yl)piperidine-1-carboxamide I-253 3-(1-(3-chlorophenyl)-1-hydroxy-5-methoxypentyl)-N-(3-(4-fluorocyclohexyl)-1-(methylamino)propan-2-yl)piperidine-1-carboxamide I-254 3-(1-hydroxy-5-methoxy-1-(2-(pyridin-3-yloxy)phenyl)pentyl)-N-(4-methyl-1-(methylamino)pentan-2-yl)piperidine-1-carboxamide I-255 3-((3-ethoxypropoxy)(3-fluorophenyl)methyl)-N-(3-(4,4-difluorocyclohexyl)-1-(methylamino)propan-2-yl)piperidine-1-carboxamide I-256 N-(3-cyclohexyl-1-(methylamino)propan-2-yl)-3-(1-(2,3,5-trifluorophenyl)-1-hydroxy-5-methoxypentyl)piperidine-1-carboxamide I-257 N-(3-cyclopentyl-1-(methylamino)propan-2-yl)-3-(5-ethoxy-1-(2,3,5-trifluorophenyl)-1-hydroxypentyl)piperidine-1-carboxamide I-258 3-(1-(2-(2-ethylphenoxy)phenyl)-1-hydroxy-5-methoxypentyl)-N-(3-hydroxy-1-(methylamino)propan-2-yl)piperidine-1-carboxamide I-259 3-(1-(3-fluoro-2-phenylphenyl)-1-hydroxy-5-methoxypentyl)-N-(4-methyl-1-(methylamino)pentan-2-yl)piperidine-1-carboxamide I-260 3-(1-(2-(2-fluorophenyl)phenyl)-1-hydroxy-5-methoxypentyl)-N-(4-methyl-1-(methylamino)pentan-2-yl)piperidine-1-carboxamide I-261 3-(1-(2-(3-fluorophenyl)phenyl)-1-hydroxy-5-methoxypentyl)-N-(4-methyl-1-(methylamino)pentan-2-yl)piperidine-1-carboxamide I-262 3-(1-(2-(4-fluorophenyl)phenyl)-1-hydroxy-5-methoxypentyl)-N-(4-methyl-1-(methylamino)pentan-2-yl)piperidine-1-carboxamide I-263 3-(1-(3-chlorophenyl)-5,5-difluoro-1-hydroxyhexyl)-N-(3-cyclohexyl-1-(methylamino)propan-2-yl)piperidine-1-carboxamide I-264 3-((3-methoxypropoxy)(2,3-dichlorophenyl)methyl)-N-(3-cyclohexyl-1-(methylamino)propan-2-yl)piperidine-1-carboxamide I-265 3-(1-(2,3-dichlorophenyl)-1-hydroxy-5-methoxypentyl)-N-(3-cyclopentyl-1-(methylamino)propan-2-yl)piperidine-1-carboxamide I-266 3-((3-ethoxypropoxy)(2,3-dichlorophenyl)methyl)-N-(3-cyclopentyl-1-(methylamino)propan-2-yl)piperidine-1-carboxamide I-267 3-(1-(benzo[b]thiophen-7-yl)-1-hydroxy-5-methoxypentyl)-N-(3-cyclohexyl-1-(methylamino)propan-2-yl)piperidine-1-carboxamide I-268 3-(1-(benzo[b]thiophen-2-yl)-1-hydroxy-5-methoxypentyl)-N-(3-cyclohexyl-1-(methylamino)propan-2-yl)piperidine-1-carboxamide I-269 3-(1-hydroxy-5-methoxy-1-(3-(trifluoromethoxy)phenyl)pentyl)-N-(4,4-dimethyl-1-(methylamino)pentan-2-yl)piperidine-1-carboxamide I-270 N-(3-cyclohexyl-1-(methylamino)propan-2-yl)-3-(1-(5-fluorobenzofuran-7-yl)-1-hydroxy-5-methoxypentyl)piperidine-1-carboxamide I-271 3-(1-(3-chlorophenyl)-1-hydroxy-5-methoxypentyl)-N'-cyano-N-(3-cyclohexyl-1-(methylamino)propan-2-yl)piperidine-1-carboxamidine I-272 3-(1-acetamido-1-(3-fluorophenyl)-5-methoxypentyl)-N-(3-cyclohexyl-1-(methylamino)propan-2-yl)piperidine-1-carboxamide I-273 3-(1-(3-chloro-2-fluorophenyl)-1-hydroxy-5-methoxypentyl)-N-(3-(3,3-difluorocyclobutyl)-1-(methylamino)propan-2-yl)piperidine-1-carboxamide I-274 N-(3-cyclohexyl-1-(methylamino)propan-2-yl)-3-(1-(3-(trifluoromethyl)phenyl)-1-hydroxy-5-methoxypentyl)benzamide I-275 3-(1-(2-(o-tolyloxy)phenyl)-1-hydroxy-5-methoxypentyl)-N-(4-methyl-1-(methylamino)pentan-2-yl)piperidine-1-carboxamide I-276 3-(1-hydroxy-5-methoxy-1-(2-phenoxyphenyl)pentyl)-N-(4,4-dimethyl-1-(methylamino)pentan-2-yl)piperidine-1-carboxamide I-277 3-(1-(2-(benzyloxy)phenyl)-1-hydroxy-5-methoxypentyl)-N-(4-methyl-1-(methylamino)pentan-2-yl)piperidine-1-carboxamide I-278 3-(1-(2-(m-tolyloxy)phenyl)-1-hydroxy-5-methoxypentyl)-N-(4-methyl-1-(methylamino)pentan-2-yl)piperidine-1-carboxamide I-279 3-(1-(3-chloro-2-fluorophenyl)-5-ethoxy-1-hydroxypentyl)-N-(3-cyclohexyl-1-(methylamino)propan-2-yl)piperidine-1-carboxamide I-280 3-(1-(3-chloro-2-fluorophenyl)-1-hydroxy-5-methoxypentyl)-N-(1-(methylamino)-3-(4-methylcyclohexyl)propan-2-yl)piperidine-1-carboxamide I-281 N-(3-cyclohexyl-1-(methylamino)propan-2-yl)-3-(1-(2-(trifluoromethyl)phenyl)-1-hydroxy-5-methoxypentyl)piperidine-1-carboxamide I-282 N-(3-cyclohexyl-1-(methylamino)propan-2-yl)-3-(5-ethoxy-1-(2,3,5-trifluorophenyl)-1-hydroxypentyl)piperidine-1-carboxamide I-283 3-(1-(2-fluoro-3-methylphenyl)-1-hydroxy-5-methoxypentyl)-N-(3-(4,4-difluorocyclohexyl)-1-(methylamino)propan-2-yl)piperidine-1-carboxamide I-284 3-(1-(2,3-dichlorophenyl)-1-hydroxy-5-methoxypentyl)-N-(3-cyclohexyl-1-(methylamino)propan-2-yl)piperidine-1-carboxamide I-285 3-((3-ethoxypropoxy)(2,3-dichlorophenyl)methyl)-N-(3-cyclohexyl-1-(methylamino)propan-2-yl)piperidine-1-carboxamide I-286 3-(1-(2,3-dichlorophenyl)-5-ethoxy-1-hydroxypentyl)-N-(3-cyclopentyl-1-(methylamino)propan-2-yl)piperidine-1-carboxamide I-287 3-(1-(2-(4-fluorophenoxy)phenyl)-1-hydroxy-5-methoxypentyl)-N-(4-methyl-1-(methylamino)pentan-2-yl)piperidine-1-carboxamide I-288 3-(1-(5-fluoro-2-phenoxyphenyl)-1-hydroxy-5-methoxypentyl)-N-(4-methyl-1-(methylamino)pentan-2-yl)piperidine-1-carboxamide I-289 3-(1-(2-(3-fluorophenoxy)phenyl)-1-hydroxy-5-methoxypentyl)-N-(4-methyl-1-(methylamino)pentan-2-yl)piperidine-1-carboxamide I-290 3-(1-(2-(2-fluorophenoxy)phenyl)-1-hydroxy-5-methoxypentyl)-N-(4-methyl-1-(methylamino)pentan-2-yl)piperidine-1-carboxamide I-291 3-(1-(3-fluoro-2-phenoxyphenyl)-1-hydroxy-5-methoxypentyl)-N-(4-methyl-1-(methylamino)pentan-2-yl)piperidine-1-carboxamide I-292 3-(1-(3-(4-fluorophenoxy)phenyl)-1-hydroxy-5-methoxypentyl)-N-(4-methyl-1-(methylamino)pentan-2-yl)piperidine-1-carboxamide I-293 3-(1-(3-chlorophenyl)-1-hydroxy-5-methoxypentyl)-N-(3-(4,4-difluorocyclohexyl)-1-(methylamino)propan-2-yl)piperidine-1-carboxamide I-294 3-((3-ethoxypropoxy)(3-chlorophenyl)methyl)-N-(3-(4,4-difluorocyclohexyl)-1-(methylamino)propan-2-yl)piperidine-1-carboxamide I-295 3-(1-(3-chloro-2-fluorophenyl)-1-hydroxy-5-methoxypentyl)-N-(3-(4-fluorocyclohexyl)-1-(methylamino)propan-2-yl)piperidine-1-carboxamide I-296 3-(1-(2-(2-chlorophenyl)phenyl)-1-hydroxy-5-methoxypentyl)-N-(4-methyl-1-(methylamino)pentan-2-yl)piperidine-1-carboxamide I-297 3-(1-(2-(4-chlorophenyl)phenyl)-1-hydroxy-5-methoxypentyl)-N-(4-methyl-1-(methylamino)pentan-2-yl)piperidine-1-carboxamide I-298 3-(1-(2-(3-chlorophenyl)phenyl)-1-hydroxy-5-methoxypentyl)-N-(4-methyl-1-(methylamino)pentan-2-yl)piperidine-1-carboxamide I-299 N-(3-(4,4-difluorocyclohexyl)-1-(methylamino)propan-2-yl)-3-(1-(2,3-difluorophenyl)-1-hydroxy-5-methoxypentyl)piperidine-1-carboxamide I-300 2-(1-(3-chlorophenyl)-1-hydroxy-5-methoxypentyl)-N-(3-(4,4-difluorocyclohexyl)-1-(methylamino)propan-2-yl)morpholine-4-carboxamide I-301 3-(1-acetamido-1-(3-chlorophenyl)-5-methoxypentyl)-N-(3-cyclohexyl-1-(methylamino)propan-2-yl)piperidine-1-carboxamide I-302 3-(1-(benzofuran-7-yl)-1-hydroxy-5-methoxypentyl)-N-(3-(4,4-difluorocyclohexyl)-1-(methylamino)propan-2-yl)piperidine-1-carboxamide I-303 N-(4,4,4-trifluoro-1-(methylamino)butan-2-yl)-3-(1-hydroxy-5-methoxy-1-(2-phenoxyphenyl)pentyl)piperidine-1-carboxamide I-304 3-(1-(2-(2-(trifluoromethyl)phenoxy)phenyl)-1-hydroxy-5-methoxypentyl)-N-(1-(methylamino)propan-2-yl)piperidine-1-carboxamide I-305 N-(1-(2-methoxyethylamino)-3-cyclohexylpropan-2-yl)-3-(1-(3-chlorophenyl)-1-hydroxy-5-methoxypentyl)piperidine-1-carboxamide I-306 N-(3-cyclohexyl-1-(methylamino)propan-2-yl)-3-(1-(2,2-difluorobenzo[d][1,3]dioxol-4-yl)-1-hydroxy-5-methoxypentyl)piperidine-1-carboxamide I-307 3-(1-(2-(o-tolyloxy)-3-methylphenyl)-1-hydroxy-5-methoxypentyl)-N-(4-methyl-1-(methylamino)pentan-2-yl)piperidine-1-carboxamide I-308 3-(1-(2,3-dichlorophenyl)-5-ethoxy-1-hydroxypentyl)-N-(3-cyclohexyl-1-(methylamino)propan-2-yl)piperidine-1-carboxamide I-309 N-(3-cyclohexyl-1-(methylamino)propan-2-yl)-3-(1-hydroxy-5-methoxy-1-(3-(trifluoromethoxy)phenyl)pentyl)piperidine-1-carboxamide I-310 N-(3-cyclohexyl-1-(methylamino)propan-2-yl)-3-(1-hydroxy-5-methoxy-1-(2-(trifluoromethoxy)phenyl)pentyl)piperidine-1-carboxamide I-311 3-(1-(2-(p-tolyloxy)-3-fluorophenyl)-1-hydroxy-5-methoxypentyl)-N-(4-methyl-1-(methylamino)pentan-2-yl)piperidine-1-carboxamide I-312 3-(1-(2-(o-tolyloxy)-3-fluorophenyl)-1-hydroxy-5-methoxypentyl)-N-(4-methyl-1-(methylamino)pentan-2-yl)piperidine-1-carboxamide I-313 3-(1-(2-(5-fluoro-2-methylphenoxy)phenyl)-1-hydroxy-5-methoxypentyl)-N-(4-methyl-1-(methylamino)pentan-2-yl)piperidine-1-carboxamide I-314 3-(1-(2-(4-fluoro-2-methylphenoxy)phenyl)-1-hydroxy-5-methoxypentyl)-N-(4-methyl-1-(methylamino)pentan-2-yl)piperidine-1-carboxamide I-315 N-(3-cyclohexyl-1-(methylamino)propan-2-yl)-3-(1-(2-(cyclopentyloxy)phenyl)-1-hydroxy-5-methoxypentyl)piperidine-1-carboxamide I-316 3-(1-(2-(2-cyclopropylethoxy)phenyl)-1-hydroxy-5-methoxypentyl)-N-(3-cyclohexyl-1-(methylamino)propan-2-yl)piperidine-1-carboxamide I-317 3-(5-ethoxy-1-(2,3-difluorophenyl)-1-hydroxypentyl)-N-(3-(4,4-difluorocyclohexyl)-1-(methylamino)propan-2-yl)piperidine-1-carboxamide I-318 3-(1-(2-(4-fluorophenoxy)-5-fluorophenyl)-1-hydroxy-5-methoxypentyl)-N-(4-methyl-1-(methylamino)pentan-2-yl)piperidine-1-carboxamide I-319 3-(1-(3,5-difluoro-2-phenoxyphenyl)-1-hydroxy-5-methoxypentyl)-N-(4-methyl-1-(methylamino)pentan-2-yl)piperidine-1-carboxamide I-320 3-(1-(3-chloro-2-fluorophenyl)-1-hydroxy-5-methoxypentyl)-N-(3-(4,4-difluorocyclohexyl)-1-(methylamino)propan-2-yl)piperidine-1-carboxamide I-321 3-((3-ethoxypropoxy)(3-chloro-2-fluorophenyl)methyl)-N-(3-(4,4-difluorocyclohexyl)-1-(methylamino)propan-2-yl)piperidine-1-carboxamide I-322 3-(1-(3-chlorophenyl)-5-methoxy-1-(propionamido)pentyl)-N-(3-cyclohexyl-1-(methylamino)propan-2-yl)piperidine-1-carboxamide I-323 N-(3-(4,4-difluorocyclohexyl)-1-(methylamino)propan-2-yl)-3-(1-(2,3,5-trifluorophenyl)-1-hydroxy-5-methoxypentyl)piperidine-1-carboxamide I-324 3-((3-ethoxypropoxy)(2,3,5-trifluorophenyl)methyl)-N-(3-(4,4-difluorocyclohexyl)-1-(methylamino)propan-2-yl)piperidine-1-carboxamide I-325 N-(3-(3,3-difluorocyclobutyl)-1-(methylamino)propan-2-yl)-3-(1-hydroxy-5-methoxy-1-(3-(trifluoromethoxy)phenyl)pentyl)piperidine-1-carboxamide I-326 3-(1-(3-hydroxypropoxy)-1-(3-chlorophenyl)-5-methoxypentyl)-N-(3-cyclohexyl-1-(methylamino)propan-2-yl)piperidine-1-carboxamide I-327 N-(1-(2-ethoxyethylamino)-3-cyclohexylpropan-2-yl)-3-(1-(3-chlorophenyl)-1-hydroxy-5-methoxypentyl)piperidine-1-carboxamide I-328 N-(3-cyclohexyl-1-(methylamino)propan-2-yl)-3-(1-hydroxy-5-methoxy-1-(2-(pyridin-3-yloxy)phenyl)pentyl)piperidine-1-carboxamide I-329 3-(1-acetamido-1-(3-chloro-2-fluorophenyl)-5-methoxypentyl)-N-(3-cyclohexyl-1-(methylamino)propan-2-yl)piperidine-1-carboxamide I-330 3-(1-(2-(allyloxy)-3-bromophenyl)-1-hydroxy-5-methoxypentyl)-N-(4-methyl-1-(methylamino)pentan-2-yl)piperidine-1-carboxamide I-331 N-(1-(2,2,2-trifluoroethylamino)-3-cyclohexylpropan-2-yl)-3-(1-(3-chlorophenyl)-1-hydroxy-5-methoxypentyl)piperidine-1-carboxamide I-332 3-(1-(3-chlorophenyl)-1-(isobutyramido)-5-methoxypentyl)-N-(3-cyclohexyl-1-(methylamino)propan-2-yl)piperidine-1-carboxamide I-333 3-(5-ethoxy-1-(2,3,5-trifluorophenyl)-1-hydroxypentyl)-N-(3-(4,4-difluorocyclohexyl)-1-(methylamino)propan-2-yl)piperidine-1-carboxamide I-334 N-(5,5,5-trifluoro-4-methyl-1-(methylamino)pentan-2-yl)-3-(1-hydroxy-5-methoxy-1-(2-phenoxyphenyl)pentyl)piperidine-1-carboxamide I-335 3-(1-(2-(benzyloxy)phenyl)-1-hydroxy-5-methoxypentyl)-N-(3-cyclohexyl-1-(methylamino)propan-2-yl)piperidine-1-carboxamide I-336 3-(1-(3-chloro-2-fluorophenyl)-5-methoxy-1-(propionamido)pentyl)-N-(3-cyclohexyl-1-(methylamino)propan-2-yl)piperidine-1-carboxamide I-337 3-(1-(2-(4-fluorophenoxy)phenyl)-1-hydroxy-5-methoxypentyl)-N-(3-cyclohexyl-1-(methylamino)propan-2-yl)piperidine-1-carboxamide I-338 N-(3-cyclohexyl-1-(methylamino)propan-2-yl)-3-(1-(5-fluoro-2-phenoxyphenyl)-1-hydroxy-5-methoxypentyl)piperidine-1-carboxamide I-339 3-(1-(2-(2-(trifluoromethyl)phenoxy)phenyl)-1-hydroxy-5-methoxypentyl)-N-(4-methyl-1-(methylamino)pentan-2-yl)piperidine-1-carboxamide I-340 3-(1-(3-chloro-2-fluorophenyl)-1-(isobutyramido)-5-methoxypentyl)-N-(3-cyclohexyl-1-(methylamino)propan-2-yl)piperidine-1-carboxamide I-341 3-(1-(3-chlorophenyl)-1-hydroxypropyl)-N-(1-cyclohexyl-3-(methylamino)propan-2-yl)piperidine-1-carboxamide I-342 N-(1-cyclohexyl-3-(methylamino)propan-2-yl)-2-(5-methoxy-1-phenylpentyl)morpholine-4-carboxamide I-343 3-(1-(3-chlorophenyl)-1-hydroxybutyl)-N-(1-cyclohexyl-3-(methylamino)propan-2-yl)piperidine-1-carboxamide I-345 3-(1-cyclohexyl-1-hydroxy-5-methoxypentyl)-N-(1-cyclohexyl-3-(methylamino)propan-2-yl)benzamide I-346 3-(1-(3-chlorophenyl)-1-hydroxypentyl)-N-(1-cyclohexyl-3-(methylamino)propan-2-yl)piperidine-1-carboxamide I-347 3-(1-cyclohexyl-1-hydroxy-5-methoxypentyl)-N-(1-cyclohexyl-3-(methylamino)propan-2-yl)piperidine-1-carboxamide I-348 3-(1-(3-chlorophenyl)-1,4-dihydroxybutyl)-N-(1-cyclohexyl-3-(methylamino)propan-2-yl)piperidine-1-carboxamide I-349 3-(1-(3-chlorophenyl)-1-hydroxy-5-methoxypentyl)-N-(3-hydroxy-4-methyl-1-(methylamino)pentan-2-yl)piperidine-1-carboxamide I-350 3-(1-(benzofuran-7-yl)-1-hydroxy-5-methoxypentyl)-N-(4,4-dimethyl-1-(methylamino)pentan-2-yl)piperidine-1-carboxamide I-351 3-(1-(2-tert-butylbenzofuran-7-yl)-1-hydroxy-5-methoxypentyl)-N-(1-(methylamino)propan-2-yl)piperidine-1-carboxamide I-352 N-(3-amino-1-cyclohexylbutan-2-yl)-3-(1-(2-fluorophenyl)-1-hydroxy-5-methoxypentyl)piperidine-1-carboxamide I-353 N-(1-cyclopentyl-1-hydroxy-3-(methylamino)propan-2-yl)-3-(1-(3-fluorophenyl)-1-hydroxy-5-methoxypentyl)piperidine-1-carboxamide I-354 N-(2-amino-3-cyclohexylpropyl)-3-(1-(3-chlorophenyl)-1-hydroxy-5-methoxypentyl)piperidine-1-carboxamide I-356 3-(1-(3-chlorophenyl)-1-hydroxy-5-methoxypentyl)-N-(4-methoxy-4-methyl-1-(methylamino)pentan-2-yl)piperidine-1-carboxamide I-357 3-(1-(3-cyanophenyl)-1-hydroxy-5-methoxypentyl)-N-(1-cyclohexyl-3-(methylamino)propan-2-yl)piperidine-1-carboxamide I-358 3-(1-(3-chloro-2-fluorophenyl)-1-hydroxy-5-methoxypentyl)-N-(4,4-dimethyl-1-(methylamino)pentan-2-yl)piperidine-1-carboxamide I-359 3-(1-(2-chloro-3-fluorophenyl)-1-hydroxy-5-methoxypentyl)-N-(4,4-dimethyl-1-(methylamino)pentan-2-yl)piperidine-1-carboxamide I-360 3-(1-(3-chloro-2-fluorophenyl)-1-hydroxy-5-methoxypentyl)-N-(3-hydroxy-4-methyl-1-(methylamino)pentan-2-yl)piperidine-1-carboxamide I-361 3-(1-(benzo[b]thiophen-4-yl)-1-hydroxy-5-methoxypentyl)-N-(4,4-dimethyl-1-(methylamino)pentan-2-yl)piperidine-1-carboxamide I-362 3-(4-acetamido-1-(2-fluorophenyl)-1-hydroxybutyl)-N-(1-cyclohexyl-3-(methylamino)propan-2-yl)piperidine-1-carboxamide I-363 N-(1-cyclohexyl-3-(methylamino)propan-2-yl)-3-(1-(3-fluoro-2-methylphenyl)-1-hydroxy-5-methoxypentyl)piperidine-1-carboxamide I-364 N-(1-cyclohexyl-3-(methylamino)propan-2-yl)-3-(1-(3-fluoro-4-methylphenyl)-1-hydroxy-5-methoxypentyl)piperidine-1-carboxamide I-365 N-(1-cyclohexyl-3-(methylamino)propan-2-yl)-3-(1-(3-fluoro-2-hydroxyphenyl)-1-hydroxy-5-methoxypentyl)piperidine-1-carboxamide I-366 N-(1-cyclohexyl-1-hydroxy-3-(methylamino)propan-2-yl)-3-(1-(2-fluorophenyl)-1-hydroxy-5-methoxypentyl)piperidine-1-carboxamide I-367 N-(3-amino-1-cyclohexylbutan-2-yl)-3-(1-(3-chlorophenyl)-1-hydroxy-5-methoxypentyl)piperidine-1-carboxamide I-368 3-(1-(3-chlorophenyl)-1-hydroxy-5-methoxypentyl)-N-(3-cyclohexyl-2-(methylamino)propyl)piperidine-1-carboxamide I-369 N-(1-(4-fluorocyclohexyl)-3-(methylamino)propan-2-yl)-3-(1-(2-fluorophenyl)-1-hydroxy-5-methoxypentyl)piperidine-1-carboxamide I-370 N-(1-(4-fluorocyclohexyl)-3-(methylamino)propan-2-yl)-3-(1-(2-fluorophenyl)-1-hydroxy-5-methoxypentyl)piperidine-1-carboxamide I-371 N-(1-cyclopentyl-1-hydroxy-3-(methylamino)propan-2-yl)-3-(1-(2,3-difluorophenyl)-1-hydroxy-5-methoxypentyl)piperidine-1-carboxamide I-372 3-(1-(2-chloro-3-fluorophenyl)-1-hydroxy-5-methoxypentyl)-N-(1-cyclopentyl-3-(methylamino)propan-2-yl)piperidine-1-carboxamide I-373 N-(2-amino-3-cyclohexylpropyl)-3-(1-(3-chloro-2-fluorophenyl)-1-hydroxy-5-methoxypentyl)piperidine-1-carboxamide I-374 3-(1-(benzofuran-4-yl)-1-hydroxy-5-methoxypentyl)-N-(1-cyclohexyl-3-(methylamino)propan-2-yl)piperidine-1-carboxamide I-375 3-(4-acetamido-1-(3,5-dimethylphenyl)-1-hydroxybutyl)-N-(1-cyclohexyl-3-(methylamino)propan-2-yl)piperidine-1-carboxamide I-376 3-(1-cyclohexyl-1-hydroxy-5-methoxypentyl)-N-(1-(4,4-difluorocyclohexyl)-3-(methylamino)propan-2-yl)piperidine-1-carboxamide I-377 N-(2-amino-3-cyclohexylpropyl)-3-(1-(benzo[b]thiophen-4-yl)-1-hydroxy-5-methoxypentyl)piperidine-1-carboxamide I-378 3-(1-(3-chloro-2-fluorophenyl)-1-hydroxy-5-methoxypentyl)-N-(4-methoxy-4-methyl-1-(methylamino)pentan-2-yl)piperidine-1-carboxamide I-379 3-(1-(2-cyano-5-fluorophenyl)-1-hydroxy-5-methoxypentyl)-N-(1-cyclohexyl-3-(methylamino)propan-2-yl)piperidine-1-carboxamide I-380 3-(1-(3-carbamoylphenyl)-1-hydroxy-5-methoxypentyl)-N-(1-cyclohexyl-3-(methylamino)propan-2-yl)piperidine-1-carboxamide I-381 N-(2-amino-3-cyclohexylpropyl)-2-(1-(benzo[b]thiophen-7-yl)-1-hydroxy-5-methoxypentyl)morpholine-4-carboxamide I-382 3-(4-acetamido-1-(3-fluoro-5-methylphenyl)-1-hydroxybutyl)-N-(1-cyclohexyl-3-(methylamino)propan-2-yl)piperidine-1-carboxamide I-383 3-(4-acetamido-1-(2-fluoro-5-methylphenyl)-1-hydroxybutyl)-N-(1-cyclohexyl-3-(methylamino)propan-2-yl)piperidine-1-carboxamide I-385 3-(1-(2-(cyclopropylmethoxy)-3-fluorophenyl)-1-hydroxy-5-methoxypentyl)-N-(4-methyl-1-(methylamino)pentan-2-yl)piperidine-1-carboxamide I-386 3-(1-(3-chloro-2-methylphenyl)-1-hydroxy-5-methoxypentyl)-N-(1-cyclohexyl-3-(methylamino)propan-2-yl)piperidine-1-carboxamide I-387 3-(1-(3-chlorophenyl)-1,5-dimethoxypentyl)-N-(1-cyclohexyl-3-(methylamino)propan-2-yl)piperidine-1-carboxamide I-388 3-(4-acetamido-1-(2,3-difluorophenyl)-1-hydroxybutyl)-N-(1-cyclohexyl-3-(methylamino)propan-2-yl)piperidine-1-carboxamide I-389 3-(4-acetamido-1-(3,5-difluorophenyl)-1-hydroxybutyl)-N-(1-cyclohexyl-3-(methylamino)propan-2-yl)piperidine-1-carboxamide I-390 3-(1-(2,3-difluorophenyl)-1-hydroxy-5-methoxypentyl)-N-(1-(methylamino)-3-(4-methylcyclohexyl)propan-2-yl)piperidine-1-carboxamide I-391 3-(1-(3-chlorophenyl)-1-hydroxy-5-methoxypentyl)-N-(1-(4-hydroxycyclohexyl)-3-(methylamino)propan-2-yl)piperidine-1-carboxamide I-392 3-(4-acetamido-1-(2,3-difluorophenyl)-1-hydroxybutyl)-N-(1-cyclopentyl-1-hydroxy-3-(methylamino)propan-2-yl)piperidine-1-carboxamide I-393 3-((2-acetamidoethoxy)(3-chloro-2-fluorophenyl)methyl)-N-(1-cyclohexyl-3-(methylamino)propan-2-yl)piperidine-1-carboxamide I-395 N-(2-amino-3-tert-butoxypropyl)-3-(1-(3-chloro-2-fluorophenyl)-1-hydroxy-5-methoxypentyl)piperidine-1-carboxamide I-395 N-(1-cyclohexyl-1-hydroxy-3-(methylamino)propan-2-yl)-3-(1-(2,3-difluorophenyl)-1-hydroxy-5-methoxypentyl)piperidine-1-carboxamide I-396 3-(1-(2,3-difluorophenyl)-1-hydroxy-5-methoxypentyl)-N-(1-(4-hydroxycyclohexyl)-3-(methylamino)propan-2-yl)piperidine-1-carboxamide I-397 N-(1-cyclohexyl-1-hydroxy-3-(methylamino)propan-2-yl)-3-(1-(2,5-difluorophenyl)-1-hydroxy-5-methoxypentyl)piperidine-1-carboxamide I-398 3-(1-(2-chloro-3-fluorophenyl)-1-hydroxy-5-methoxypentyl)-N-(1-cyclohexyl-3-(methylamino)propan-2-yl)piperidine-1-carboxamide I-399 N-(3-amino-1-cyclohexylbutan-2-yl)-3-(1-(3-chloro-2-fluorophenyl)-1-hydroxy-5-methoxypentyl)piperidine-1-carboxamide I-400 N-(1-cyclohexyl-3-(methylamino)propan-2-yl)-3-(1-hydroxy-5-methoxy-1-(2,3,4-trifluorophenyl)pentyl)piperidine-1-carboxamide I-401 N-(1-(4,4-difluorocyclohexyl)-3-(methylamino)propan-2-yl)-3-(1-(2-fluorophenyl)-1-hydroxy-5-methoxypentyl)piperidine-1-carboxamide I-402 3-(1-(2,5-difluorophenyl)-1-hydroxy-5-methoxypentyl)-N-(1-(4-fluorocyclohexyl)-3-(methylamino)propan-2-yl)piperidine-1-carboxamide I-402 3-(1-(2,5-difluorophenyl)-1-hydroxy-5-methoxypentyl)-N-(1-(4-fluorocyclohexyl)-3-(methylamino)propan-2-yl)piperidine-1-carboxamide I-403 3-(1-(2,3-difluorophenyl)-1-hydroxy-5-methoxypentyl)-N-(1-(4-fluorocyclohexyl)-3-(methylamino)propan-2-yl)piperidine-1-carboxamide I-404 2-(1-(3-chloro-2-fluorophenyl)-1-hydroxy-5-methoxypentyl)-N-(1-cyclohexyl-3-(methylamino)propan-2-yl)morpholine-4-carboxamide I-405 3-(1-(3-chloro-2-fluorophenyl)-1-hydroxy-5-methoxypentyl)-N-(1-cyclopentyl-1-hydroxy-3-(methylamino)propan-2-yl)piperidine-1-carboxamide I-406 3-(1-(3-chloro-2-fluorophenyl)-1-hydroxy-5-methoxypentyl)-N-(1-(methylamino)-3-(tetrahydro-2H-pyran-4-yl)propan-2-yl)piperidine-1-carboxamide I-408 3-(1-(benzo[b]thiophen-4-yl)-1-hydroxy-5-methoxypentyl)-N-(1-cyclohexyl-3-(methylamino)propan-2-yl)piperidine-1-carboxamide I-410 3-(1-(benzofuran-7-yl)-1-hydroxy-5-methoxypentyl)-N-(1-(4-fluorocyclohexyl)-3-(methylamino)propan-2-yl)piperidine-1-carboxamide I-411 N-(1-cyclohexyl-3-(methylamino)propan-2-yl)-3-(1-(2-fluorobenzofuran-7-yl)-1-hydroxy-5-methoxypentyl)piperidine-1-carboxamide I-412 methyl 3-(1-(1-(1-cyclohexyl-3-(methylamino)propan-2-ylcarbamoyl)piperidin-3-yl)-1-hydroxy-5-methoxypentyl)benzoate I-413 2-(1-(benzo[b]thiophen-7-yl)-1-hydroxy-5-methoxypentyl)-N-(1-cyclohexyl-3-(methylamino)propan-2-yl)morpholine-4-carboxamide I-416 3-(1-(3-chlorophenyl)-1-hydroxy-4-propionamidobutyl)-N-(1-cyclohexyl-3-(methylamino)propan-2-yl)piperidine-1-carboxamide I-417 3-(1-(2-(cyclopropylmethoxy)-3-fluorophenyl)-1-hydroxy-5-methoxypentyl)-N-(4,4-dimethyl-1-(methylamino)pentan-2-yl)piperidine-1-carboxamide I-418 3-(1-(3-chlorophenyl)-1-hydroxy-4-(3-methylureido)butyl)-N-(1-cyclohexyl-3-(methylamino)propan-2-yl)piperidine-1-carboxamide I-421 N-(3-amino-1-cyclohexylbutan-2-yl)-3-(1-(3-chlorophenyl)-1-hydroxy-5-methoxypentyl)piperidine-1-carboxamide I-423 3-(4-acetamido-1-(3-chloro-2-fluorophenyl)-1-hydroxybutyl)-N-(1-cyclohexyl-3-(methylamino)propan-2-yl)piperidine-1-carboxamide I-424 3-(4-acetamido-1-(3-chloro-5-fluorophenyl)-1-hydroxybutyl)-N-(1-cyclohexyl-3-(methylamino)propan-2-yl)piperidine-1-carboxamide I-425 3-(4-acetamido-1-(2-chloro-3-fluorophenyl)-1-hydroxybutyl)-N-(1-cyclohexyl-3-(methylamino)propan-2-yl)piperidine-1-carboxamide I-426 3-(1-(3-chloro-2-fluorophenyl)-1,5-dimethoxypentyl)-N-(1-cyclohexyl-3-(methylamino)propan-2-yl)piperidine-1-carboxamide I-427 N-(3-hydroxy-4-methyl-1-(methylamino)pentan-2-yl)-3-(1-hydroxy-5-methoxy-1-(2-phenoxyphenyl)pentyl)piperidine-1-carboxamide I-428 3-(1-(3-chloro-2-fluorophenyl)-1-hydroxy-5-methoxypentyl)-N-(1-cyclohexyl-1-hydroxy-3-(methylamino)propan-2-yl)piperidine-1-carboxamide I-429 3-(1-(3-chloro-2-fluorophenyl)-1-hydroxy-5-methoxypentyl)-N-(1-(4-hydroxycyclohexyl)-3-(methylamino)propan-2-yl)piperidine-1-carboxamide I-430 3-(1-(2-chloro-3-fluorophenyl)-1-hydroxy-5-methoxypentyl)-N-(1-cyclohexyl-1-hydroxy-3-(methylamino)propan-2-yl)piperidine-1-carboxamide I-431 3-(1-acetamido-1-(3-chlorophenyl)-5-methoxypentyl)-N-(1-cyclohexyl-3-(methylamino)propan-2-yl)benzamide I-432 3-(1-(3-chloro-2-fluorophenyl)-1-hydroxy-5-methoxypentyl)-N-(1-(4-fluorocyclohexyl)-3-(methylamino)propan-2-yl)piperidine-1-carboxamide I-432 3-(1-(3-chloro-2-fluorophenyl)-1-hydroxy-5-methoxypentyl)-N-(1-(4-fluorocyclohexyl)-3-(methylamino)propan-2-yl)piperidine-1-carboxamide I-433 3-(1-(3-chloro-2,4-difluorophenyl)-1-hydroxy-5-methoxypentyl)-N-(1-cyclohexyl-3-(methylamino)propan-2-yl)piperidine-1-carboxamide I-434 3-(1-(3-chloro-2-fluorophenyl)-1-hydroxy-5-methoxypentyl)-N-(1-(1-fluorocyclohexyl)-3-(methylamino)propan-2-yl)piperidine-1-carboxamide I-435 3-(1-(2-chloro-3-fluorophenyl)-1-hydroxy-5-methoxypentyl)-N-(1-(4-fluorocyclohexyl)-3-(methylamino)propan-2-yl)piperidine-1-carboxamide I-436 N-(1-(4-fluorocyclohexyl)-3-(methylamino)propan-2-yl)-3-(1-hydroxy-5-methoxy-1-(2,3,5-trifluorophenyl)pentyl)piperidine-1-carboxamide I-437 2-(1-(3-chloro-2-fluorophenyl)-1-hydroxy-5-methoxypentyl)-N-(1-(4-fluorocyclohexyl)-3-(methylamino)propan-2-yl)morpholine-4-carboxamide I-438 3-(1-(3-chlorophenyl)-4-(cyclopropanecarboxamido)-1-hydroxybutyl)-N-(1-cyclohexyl-3-(methylamino)propan-2-yl)piperidine-1-carboxamide I-439 3-(4-butyramido-1-(3-chlorophenyl)-1-hydroxybutyl)-N-(1-cyclohexyl-3-(methylamino)propan-2-yl)piperidine-1-carboxamide I-440 3-(1-(3-chlorophenyl)-4-(3,3-dimethylureido)-1-hydroxybutyl)-N-(1-cyclohexyl-3-(methylamino)propan-2-yl)piperidine-1-carboxamide I-442 3-(1-(3-bromophenyl)-1-hydroxy-5-methoxypentyl)-N-(1-cyclohexyl-3-(methylamino)propan-2-yl)piperidine-1-carboxamide I-447 3-(1-(3-chloro-2-fluorophenyl)-1-hydroxy-5-methoxypentyl)-N-(1-cycloheptyl-1-hydroxy-3-(methylamino)propan-2-yl)piperidine-1-carboxamide I-449 3-(1-(3-chlorophenyl)-1-hydroxy-4-(methylsulfonamido)butyl)-N-(1-cyclohexyl-3-(methylamino)propan-2-yl)piperidine-1-carboxamide I-450 3-(1-(3-chlorophenyl)-1-hydroxy-4-(sulfamoylamino)butyl)-N-(1-cyclohexyl-3-(methylamino)propan-2-yl)piperidine-1-carboxamide I-451 3-(4-acetamido-1-(2,3-difluorophenyl)-1-hydroxybutyl)-N-(1-(4,4-difluorocyclohexyl)-3-(methylamino)propan-2-yl)piperidine-1-carboxamide I-452 3-(1-(3-fluoro-2-phenoxyphenyl)-1-hydroxy-5-methoxypentyl)-N-(3-hydroxy-4-methyl-1-(methylamino)pentan-2-yl)piperidine-1-carboxamide I-454 N-(1-cyclohexyl-3-(methylamino)propan-2-yl)-3-(1-(2,3-difluorophenyl)-5-methoxy-1-propionamidopentyl)piperidine-1-carboxamide I-455 3-(1-(3-chlorophenyl)-1-hydroxy-4-(2-methoxypropanamido)butyl)-N-(1-cyclohexyl-3-(methylamino)propan-2-yl)piperidine-1-carboxamide I-456 3-(1-(3-chlorophenyl)-1-hydroxy-2-(2-methoxyethoxy)ethyl)-N-(1-cyclohexyl-3-(methylamino)propan-2-yl)piperidine-1-carboxamide I-457 N-(1-cyclopentyl-1-hydroxy-3-(methylamino)propan-2-yl)-3-(1-hydroxy-5-methoxy-1-(2-phenoxyphenyl)pentyl)piperidine-1-carboxamide I-458 2-(1-acetamido-1-(3-chloro-2-fluorophenyl)-5-methoxypentyl)-N-(1-cyclohexyl-3-(methylamino)propan-2-yl)morpholine-4-carboxamide I-459 3-(1-(2-bromo-5-fluorophenyl)-1-hydroxy-5-methoxypentyl)-N-(1-cyclohexyl-3-(methylamino)propan-2-yl)piperidine-1-carboxamide I-463 3-(1-(3-fluoro-2-(o-tolyloxy)phenyl)-1-hydroxy-5-methoxypentyl)-N-(3-hydroxy-4-methyl-1-(methylamino)pentan-2-yl)piperidine-1-carboxamide I-464 3-(1-(3-chlorophenyl)-1-hydroxy-4-(2,2,2-trifluoroacetamido)butyl)-N-(1-cyclohexyl-3-(methylamino)propan-2-yl)piperidine-1-carboxamide I-466 N-(1-cyclopentyl-1-hydroxy-3-(methylamino)propan-2-yl)-3-(1-(3-fluoro-2-phenoxyphenyl)-1-hydroxy-5-methoxypentyl)piperidine-1-carboxamide I-467 3-(1-(3'-chloro-6-fluorobiphenyl-2-yl)-1-hydroxy-5-methoxypentyl)-N-(1-cyclopentyl-3-(methylamino)propan-2-yl)piperidine-1-carboxamide I-468 N-(1-(3,3-difluorocyclobutyl)-3-(methylamino)propan-2-yl)-3-(1-(3-fluoro-2-phenoxyphenyl)-1-hydroxy-5-methoxypentyl)piperidine-1-carboxamide I-469 3-(1-butyramido-1-(3-chloro-2-fluorophenyl)-5-methoxypentyl)-N-(1-cyclohexyl-3-(methylamino)propan-2-yl)piperidine-1-carboxamide I-470 3-(1-(3-chloro-2-fluorophenyl)-5-methoxypentyl)-N-(1-cyclohexyl-3-(methylamino)propan-2-yl)piperidine-1-carboxamide I-471 2-((3-chloro-2-fluorophenyl)(3-methoxypropoxy)methyl)-N-(1-cyclohexyl-3-(methylamino)propan-2-yl)morpholine-4-carboxamide I-472  N-(2-amino-5-methoxy-4,4-dimethylpentyl)-3-(1-(3-chloro-2-fluorophenyl)-1-hydroxy-5-methoxypentyl)piperidine-1-carboxamide I-473  N-(1-amino-5-methoxy-4,4-dimethylpentan-2-yl)-3-(1-(3-chloro-2-fluorophenyl)-1-hydroxy-5-methoxypentyl)piperidine-1-carboxamide I-474  3-(1-(3-chlorophenyl)-1-hydroxy-5-methoxypentyl)-N-(1-cyclohexyl-3-(methylamino)butan-2-yl)piperidine-1-carboxamide I-475  3-(1-(3-chloro-2-fluorophenyl)-1-hydroxy-5-methoxypentyl)-N-(3-cyclohexyl-2-(methylamino)propyl)piperidine-1-carboxamide I-476  3-(1-(3-chlorophenyl)-1-hydroxy-5-methoxypentyl)-N-(1-(1-fluorocyclohexyl)-3-(methylamino)propan-2-yl)piperidine-1-carboxamide I-477  N-(3-amino-4-cyclohexylbutan-2-yl)-3-(1-(3-chloro-2-fluorophenyl)-1-hydroxy-5-methoxypentyl)piperidine-1-carboxamide I-478  3-(1-(3-chloro-2-fluorophenyl)-1-fluoro-5-methoxypentyl)-N-(1-cyclohexyl-3-(methylamino)propan-2-yl)piperidine-1-carboxamide I-479  3-(1-(benzo[b]thiophen-7-yl)-1-hydroxy-5-methoxypentyl)-N-(1-(methylamino)-3-(tetrahydro-2H-pyran-4-yl)propan-2-yl)piperidine-1-carboxamide I-480  3-(1-(2,3-dihydrobenzofuran-7-yl)-1-hydroxy-5-methoxypentyl)-N-(1-(4-fluorocyclohexyl)-3-(methylamino)propan-2-yl)piperidine-1-carboxamide I-481  3-(1-(3-chlorophenyl)-1-ethoxy-5-methoxypentyl)-N-(1-cyclohexyl-3-(methylamino)propan-2-yl)piperidine-1-carboxamide I-482  3-(1-(3-chlorophenyl)-1-hydroxy-5-methoxypentyl)-N-(1-(4-hydroxy-4-methylcyclohexyl)-3-(methylamino)propan-2-yl)piperidine-1-carboxamide I-483  3-(1-(2,3-difluorophenyl)-1-hydroxy-5-methoxypentyl)-N-(1-(4-hydroxy-4-methylcyclohexyl)-3-(methylamino)propan-2-yl)piperidine-1-carboxamide I-484  3-(1-(2,3-difluorophenyl)-1-hydroxy-5-methoxypentyl)-N-(1-(4-methoxycyclohexyl)-3-(methylamino)propan-2-yl)piperidine-1-carboxamide I-485  3-(1-(3-chloro-2-fluorophenyl)-1-hydroxy-5-methoxypentyl)-N-(1-cyclohexyl-3-(methylamino)butan-2-yl)piperidine-1-carboxamide I-488  N-(3-amino-4-cyclohexyl-1-hydroxybutan-2-yl)-3-(1-(3-chloro-2-fluorophenyl)-1-hydroxy-5-methoxypentyl)piperidine-1-carboxamide I-489  N-(1-cyclohexyl-1-hydroxy-3-(methylamino)propan-2-yl)-3-(1-hydroxy-5-methoxy-1-(2,3,5-trifluorophenyl)pentyl)piperidine-1-carboxamide I-490  3-(1-(2-chloro-3-fluorophenyl)-1-hydroxy-5-methoxypentyl)-N-(1-(1-fluorocyclohexyl)-3-(methylamino)propan-2-yl)piperidine-1-carboxamide I-491  N-(1-(4-fluorocyclohexyl)-3-(methylamino)propan-2-yl)-3-(1-hydroxy-5-methoxy-1-(2,3,5-trifluorophenyl)pentyl)piperidine-1-carboxamide I-492  N-(2-amino-3-(4,4-difluorocyclohexyl)propyl)-3-(1-(3-chloro-2-fluorophenyl)-1-hydroxy-5-methoxypentyl)piperidine-1-carboxamide I-493  N-(3-amino-1-(3-noradamantyl)-1-hydroxypropan-2-yl)-3-(1-(3-chlorophenyl)-1-hydroxy-5-methoxypentyl)piperidine-1-carboxamide I-495  3-(1-(3-chloro-2-fluorophenyl)-1-hydroxy-5-methoxypentyl)-N-(1-(4-hydroxy-4-methylcyclohexyl)-3-(methylamino)propan-2-yl)piperidine-1-carboxamide I-497  3-(1-(3-chloro-2,4-difluorophenyl)-1-hydroxy-5-methoxypentyl)-N-(1-cyclohexyl-1-hydroxy-3-(methylamino)propan-2-yl)piperidine-1-carboxamide I-498  3-(1-(3-chloro-2,4-difluorophenyl)-1-hydroxy-5-methoxypentyl)-N-(1-(4-fluorocyclohexyl)-3-(methylamino)propan-2-yl)piperidine-1-carboxamide I-499  N-(3-amino-1-(3-noradamantyl)-1-hydroxypropan-2-yl)-3-(1-(3-chloro-2-fluorophenyl)-1-hydroxy-5-methoxypentyl)piperidine-1-carboxamide I-502  3-((3-chlorophenyl)(2-hydroxyethoxy)methyl)-N-(1-cyclohexyl-3-(methylamino)propan-2-yl)piperidine-1-carboxamide I-503  N-(2-amino-3-cyclopentylpropyl)-3-(1-(3-chlorophenyl)-1-hydroxy-5-methoxypentyl)piperidine-1-carboxamide I-504  N-(2-amino-3-(tetrahydrofuran-2-yl)propyl)-3-(1-(3-chlorophenyl)-1-hydroxy-5-methoxypentyl)piperidine-1-carboxamide I-505  N-(1-amino-3-(tetrahydrofuran-2-yl)propan-2-yl)-3-(1-(3-chlorophenyl)-1-hydroxy-5-methoxypentyl)piperidine-1-carboxamide I-507  3-(1-(3-chlorophenyl)-2-(2-methoxyethoxy)ethyl)-N-(1-cyclohexyl-3-(methylamino)propan-2-yl)piperidine-1-carboxamide I-508  N-(2-amino-3-(tetrahydro-2H-pyran-4-yl)propyl)-3-(1-(3-chlorophenyl)-1-hydroxy-5-methoxypentyl)piperidine-1-carboxamide I-509  N-(1-amino-3-(tetrahydro-2H-pyran-2-yl)propan-2-yl)-3-(1-(3-chlorophenyl)-1-hydroxy-5-methoxypentyl)piperidine-1-carboxamide I-510  N-(1-amino-3-(3-methoxycyclobutyl)propan-2-yl)-3-(1-(3-chlorophenyl)-1-hydroxy-5-methoxypentyl)piperidine-1-carboxamide I-511  N-(2-amino-3-(3-methoxycyclobutyl)propyl)-3-(1-(3-chlorophenyl)-1-hydroxy-5-methoxypentyl)piperidine-1-carboxamide I-512  N-(2-amino-3-cyclohexylpropyl)-3-(1-(3-chloro-2-fluorophenyl)-5-methoxypentyl)piperidine-1-carboxamide I-513  N-(2-amino-3-(tetrahydrofuran-2-yl)propyl)-3-(1-(3-chloro-2-fluorophenyl)-1-hydroxy-5-methoxypentyl)piperidine-1-carboxamide I-514  N-(1-amino-3-(tetrahydrofuran-2-yl)propan-2-yl)-3-(1-(3-chloro-2-fluorophenyl)-1-hydroxy-5-methoxypentyl)piperidine-1-carboxamide I-515  N-(2-amino-4-phenylbutyl)-3-(1-(3-chlorophenyl)-1-hydroxy-5-methoxypentyl)piperidine-1-carboxamide I-520  N-(2-amino-4-cyclohexylbutyl)-3-(1-(3-chlorophenyl)-1-hydroxy-5-methoxypentyl)piperidine-1-carboxamide I-522  3-(1-(3-chloro-2-fluorophenyl)-5-methoxypentyl)-N-(1-cyclohexyl-3-(methylamino)propan-2-yl)piperidine-1-carboxamide I-523  3-(1-(6-fluoro-3'-methylbiphenyl-2-yl)-1-hydroxy-5-methoxypentyl)-N-(piperidin-3-yl)piperidine-1-carboxamide I-524  3-((3-chloro-2-fluorophenyl)(3-methoxypropoxy)methyl)-N-(1-cyclohexyl-3-(methylamino)propan-2-yl)piperidine-1-carboxamide I-525  N-(azetidin-3-ylmethyl)-3-(1-(3-fluoro-2-(o-tolyloxy)phenyl)-1-hydroxy-5-methoxypentyl)piperidine-1-carboxamide I-526  N-(1-amino-3-(tetrahydro-2H-pyran-2-yl)propan-2-yl)-3-(1-(3-chloro-2-fluorophenyl)-1-hydroxy-5-methoxypentyl)piperidine-1-carboxamide I-527  N-(2-amino-3-(3-methoxycyclobutyl)propyl)-3-(1-(3-chloro-2-fluorophenyl)-1-hydroxy-5-methoxypentyl)piperidine-1-carboxamide I-528 N-(1-amino-3-(3-methoxycyclobutyl)propan-2-yl)-3-(1-(3-chloro-2-fluorophenyl)-1-hydroxy-5-methoxypentyl)piperidine-1-carboxamide I-531 3-((3-chlorophenyl)(2-propionamidoethoxy)methyl)-N-(1-cyclohexyl-3-(methylamino)propan-2-yl)piperidine-1-carboxamide I-533 N-(4-cyclohexylpiperidin-3-yl)-3-(1-(2,3-difluorophenyl)-1-hydroxy-5-methoxypentyl)piperidine-1-carboxamide I-534 3-(1-(3-chlorophenyl)-1,6-dihydroxyheptyl)-N-(1-cyclohexyl-3-(methylamino)propan-2-yl)piperidine-1-carboxamide I-536 N-(1-cyclohexyl-3-(methylamino)propan-2-yl)-3-((2,3-difluorophenyl)(2-propionamidoethoxy)methyl)piperidine-1-carboxamide I-537 3-(1-(3-chlorophenyl)-1-hydroxy-2-(2-methoxyacetamido)ethyl)-N-(1-cyclohexyl-3-(methylamino)propan-2-yl)piperidine-1-carboxamide I-541 N-(3-amino-1-cyclohexylbutan-2-yl)-3-(1-(3-chloro-2-fluorophenyl)-1-hydroxy-5-methoxypentyl)piperidine-1-carboxamide I-544 3-(1-(3-chloro-2-fluorophenyl)-1-hydroxy-5-methoxypentyl)-N-(4-cyclohexylpiperidin-3-yl)piperidine-1-carboxamide I-545 3-(1-(3-chlorophenyl)-1-hydroxy-5-methoxypentyl)-N-(1-(4-methoxycyclohexyl)-3-(methylamino)propan-2-yl)piperidine-1-carboxamide I-546 3-(4-acetamido-1-(3-chloro-2-fluorophenyl)-1-hydroxybutyl)-N-(3-amino-1-cyclohexylbutan-2-yl)piperidine-1-carboxamide I-547 3-((3-chloro-2-fluorophenyl)(2-propionamidoethoxy)methyl)-N-(1-cyclohexyl-3-(methylamino)propan-2-yl)piperidine-1-carboxamide I-548 3-(1-(2,3-difluorophenyl)-1-hydroxy-5-methoxypentyl)-N-(1-(4-methoxycyclohexyl)-3-(methylamino)propan-2-yl)piperidine-1-carboxamide I-549 3-(1-(3-chloro-2-fluorophenyl)-1-hydroxy-5-methoxypentyl)-N-(4-(pentan-3-yloxy)piperidin-3-yl)piperidine-1-carboxamide I-551 N-(3-amino-1-(4-fluorocyclohexyl)-1-hydroxypropan-2-yl)-3-(1-(3-chloro-2-fluorophenyl)-1-hydroxy-5-methoxypentyl)piperidine-1-carboxamide I-552 3-(1-(3-chlorophenyl)-1-hydroxy-5-methoxypentyl)-N-(1-(3-noradamantyl)-3-(methylamino)propan-2-yl)piperidine-1-carboxamide I-553 3-(1-acetamido-5-ethoxy-1-(3-fluorophenyl)pentyl)-N-(1-cyclohexyl-3-(methylamino)propan-2-yl)piperidine-1-carboxamide I-554 3-(1-(3-chloro-2-fluorophenyl)-1-hydroxy-5-methoxypentyl)-N-(1-(3,4-difluorocyclopentyl)-3-(methylamino)propan-2-yl)piperidine-1-carboxamide I-556 3-(1-(3-chloro-2-fluorophenyl)-1-hydroxy-5-methoxypentyl)-N-(1-(4-methoxycyclohexyl)-3-(methylamino)propan-2-yl)piperidine-1-carboxamide I-558 3-(1-acetamido-1-(3-chlorophenyl)-5-ethoxypentyl)-N-(1-cyclohexyl-3-(methylamino)propan-2-yl)piperidine-1-carboxamide I-559 N-(2-amino-3-(3-noradamantyl)I-3-hydroxypropyl)-3-(1-(3-chloro-2-fluorophenyl)-1-hydroxy-5-methoxypentyl)piperidine-1-carboxamide Another embodiment of the invention is each of the compounds listed below and their salts, especially their pharmaceutically acceptable salts:

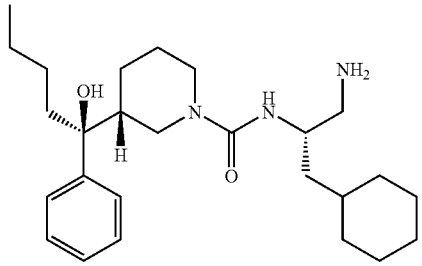

I-1a (3R)-N-((S)-1-amino-3-cyclohexylpropan-2-yl)-3-((S)-1-hydroxy-1-phenylpentyl)piperidine-1-carboxamide

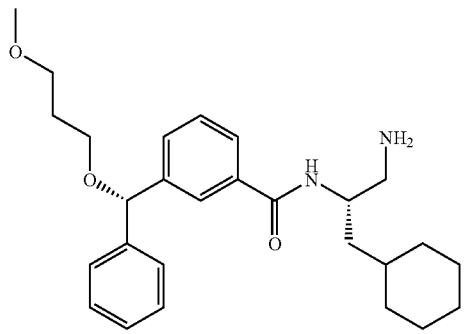

I-2a 3-((S)-(3-methoxypropoxy)(phenyl)methyl)-N-((S)-1-amino-3-cyclohexylpropan-2-yl)benzamide

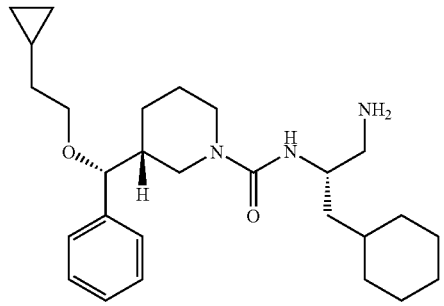

I-3a (3R)-3-((R)-(2-cyclopropylethoxy)(phenyl)methyl)-N-((S)-1-amino-3-cyclohexylpropan-2-yl)piperidine-1-carboxamide -continued

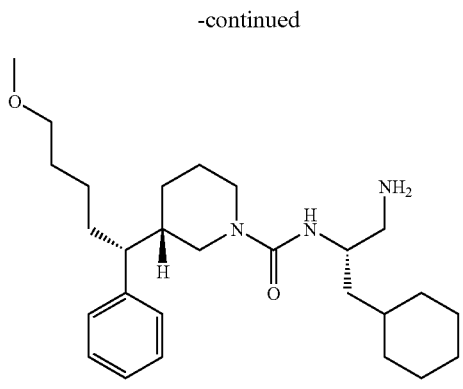

I-4a (3S)-N-((S)-1-amino-3-
cyclohexylpropan-2-yl)-3-((R)-5-
methoxy-1-
phenylpentyl)piperidine-1-
carboxamide

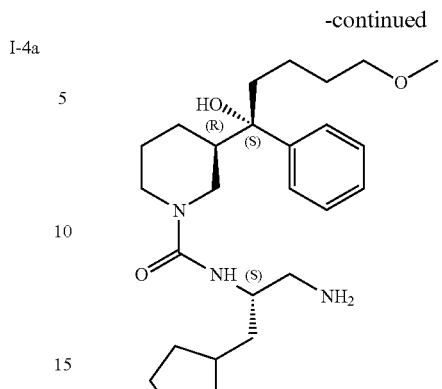

I-7a (3R)-N-((S)-1-amino-3-
cyclopentylpropan-2-yl)-3-((S)-
1-hydroxy-5-methoxy-1-
phenylpentyl)piperidine-1-
carboxamide

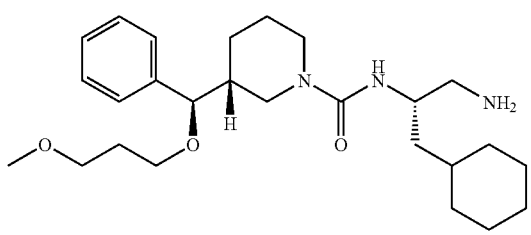

I-5a (3R)-3-((R)-(3-
methoxypropoxy)(phenyl)methyl
)-N-((S)-1-amino-3-
cyclohexylpropan-2-
yl)piperidine-1-carboxamide

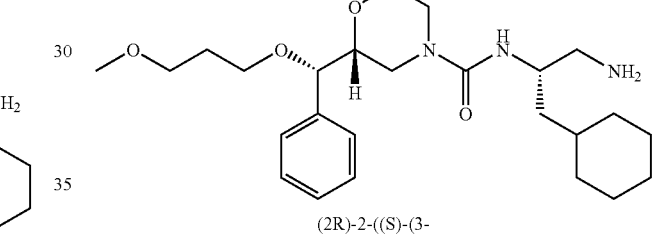

I-8a (2R)-2-((S)-(3-
methoxypropoxy)(phenyl)methyl
)-N-((S)-1-amino-3-
cyclohexylpropan-2-
yl)morpholine-4-carboxamide

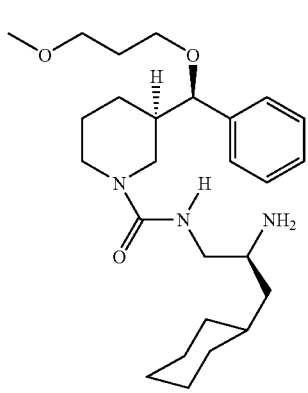

I-6a (3R)-3-((R)-(3-
methoxypropoxy)(phenyl)methyl
)-N-((S)-2-amino-3-
cyclohexylpropyl)piperidine-1-
carboxamide

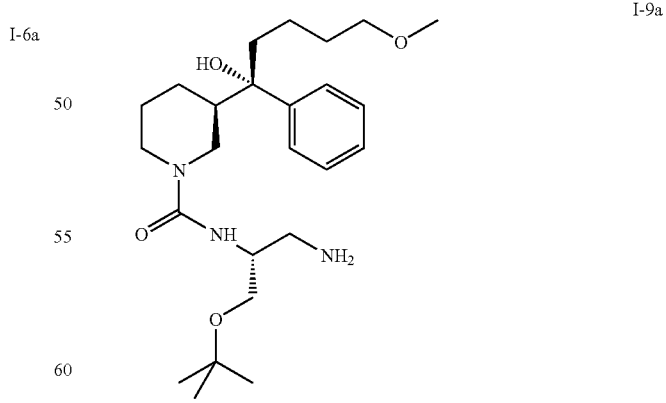

I-9a (3R)-N-((R)-3-tert-butoxy-1-
aminopropan-2-yl)-3-((S)-1-
hydroxy-5-methoxy-1-
phenylpentyl)piperidine-1-
carboxamide -continued

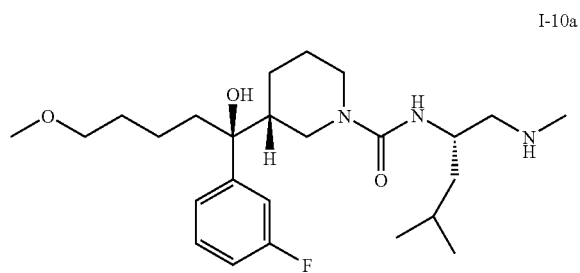

I-10a (3R)-3-((S)-(3-fluorophenyl)-
1-hydroxy-5-methoxypentyl)-N-
((S)-4-methyl-1-
(methylamino)pentan-2-
yl)piperdine-1-carboxamide

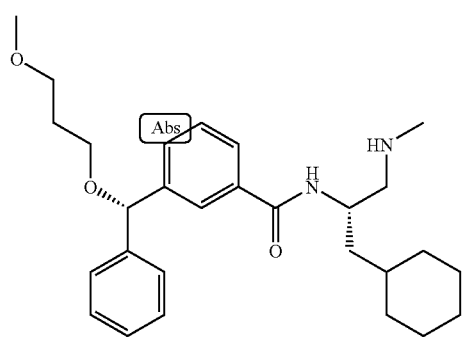

I-11a

N-((S)-1-cyclohexyl-3-
(methylamino)propan-2-yl)-3-
((S)-(3-
methoxypropoxy)(phenyl)methyl
)benzamide

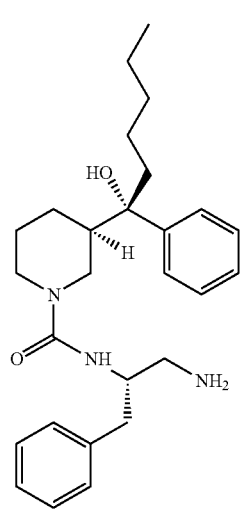

I-12a (3R)-N-((S)-1-amino-3-
phenylpropan-2-yl)-3-((S)-1-
hydroxy-5-methoxy-1-
phenylpentyl)piperidine-1-
carboxamide -continued

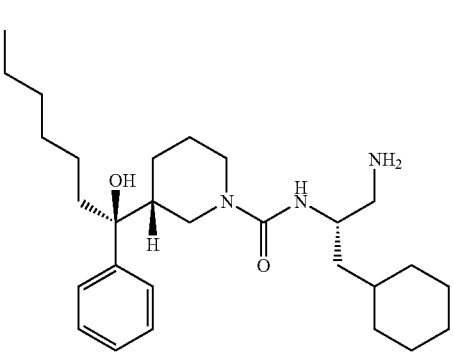

I-13a (3R)-N-((S)-1-amino-3-
cyclohexylpropan-2-yl)-3-((S)-1-
hydroxy-1-
phenylheptyl)piperidine-1-
carboxamide

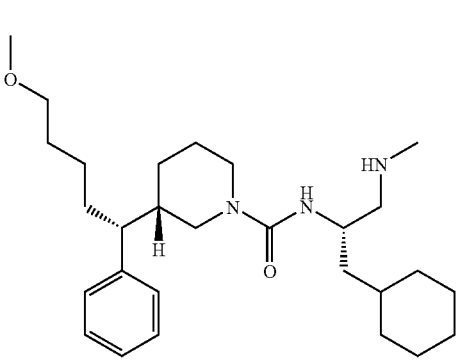

I-14a (3S)-N-((S)-3-cyclohexyl-1-
(methylamino)propan-2-yl)-3-
((R)-5-methoxy-1-
phenylpentyl)piperidine-1-
carboxamide

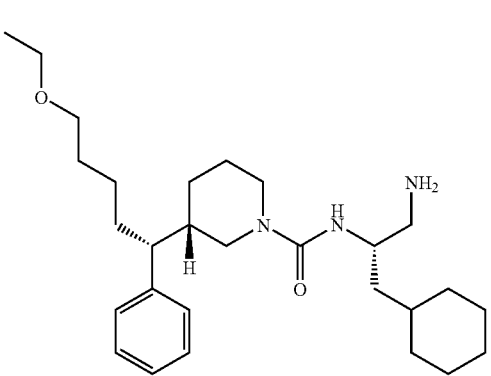

I-15a (3S)-N-((S)-1-amino-3-
cyclohexylpropan-2-yl)-3-((R)-5-
ethoxy-1-
phenylpentyl)piperidine-1-
carboxamide I-16a

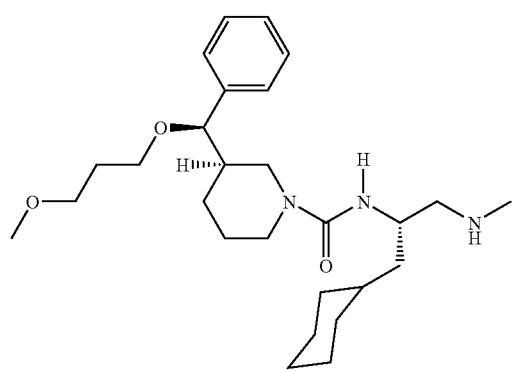

(3R)-3-((R)-(3-methoxypropoxy)(phenyl)methyl)-N-((S)-3-cyclohexyl-1-(methylamino)propan-2-yl)piperidine-1-carboxamide I-17a

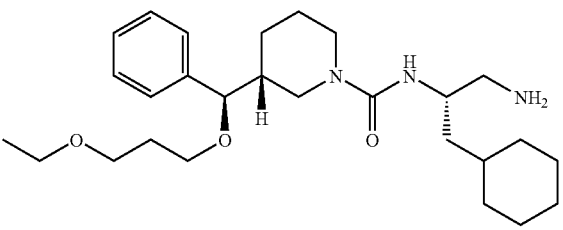

(3R)-3-((R)-(3-ethoxypropoxy)(phenyl)methyl)-N-((S)-1-amino-3-cyclohexylpropan-2-yl)piperidine-1-carboxamide I-18a

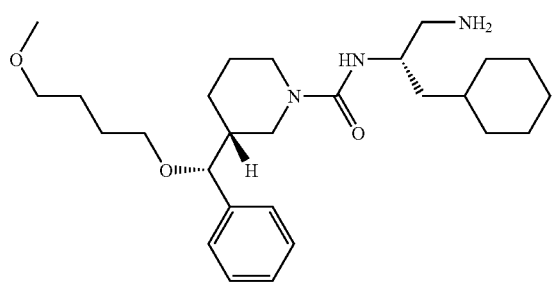

(3R)-3-((R)-(4-methoxybutoxy)(phenyl)methyl)-N-((S)-1-amino-3-cyclohexylpropan-2-yl)piperidine-1-carboxamide I-19a

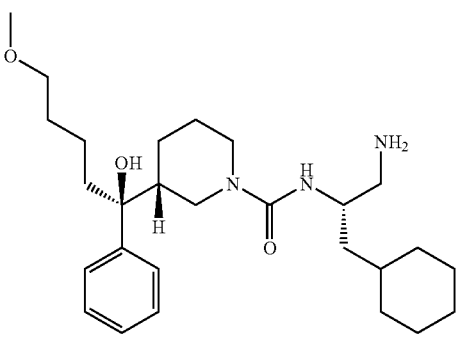

(3R)-N-((S)-1-amino-3-cyclohexylpropan-2-yl)-3-((S)-1-hydroxy-5-methoxy-1-phenylpentyl)piperidine-1-carboxamide I-20a

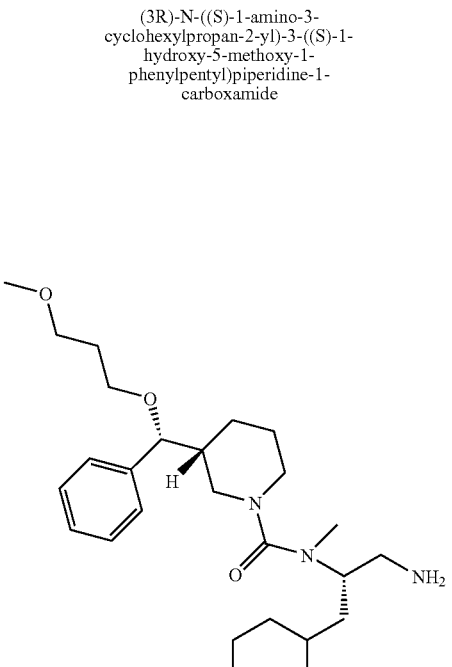

(3R)-3-((R)-(3-methoxypropoxy)(phenyl)methyl)-N-((S)-1-amino-3-cyclohexylpropan-2-yl)-N-methylpiperidine-1-carboxamide I-21a

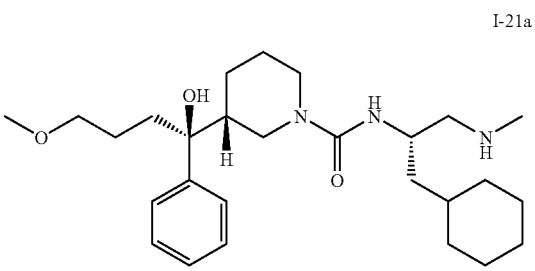

(3R)-N-((S)-3-cyclohexyl-1-(methylamino)propan-2-yl)-3-((S)-1-hydroxy-4-methoxy-1-phenylbutyl)piperidine-1-carboxamide

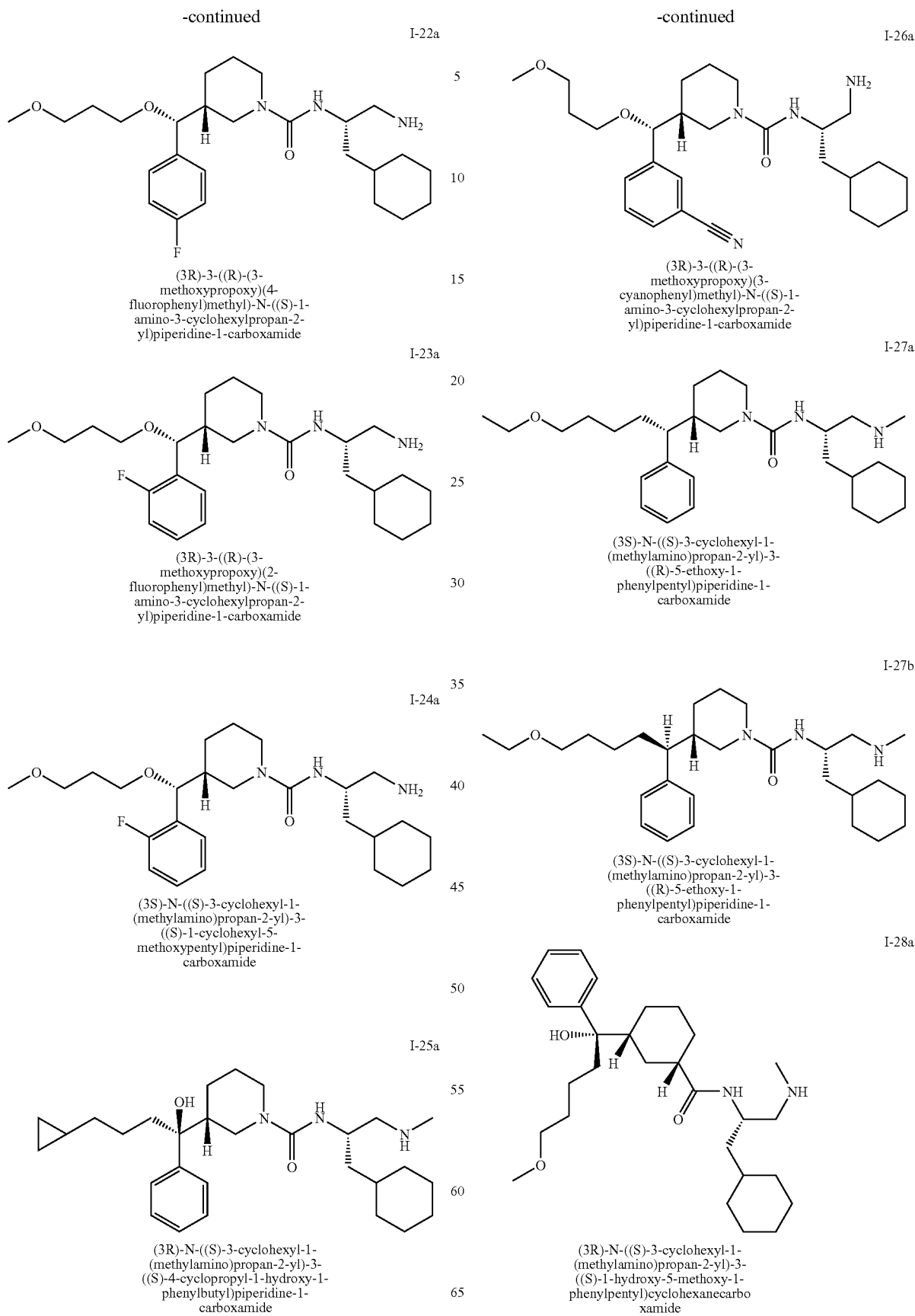

I-29a

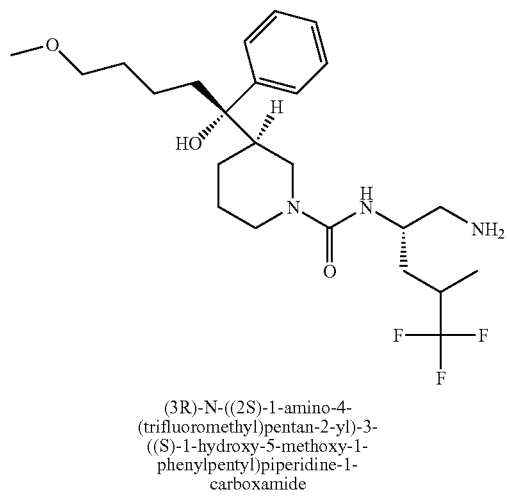

(3R)-N-((2S)-1-amino-4-
(trifluoromethyl)pentan-2-yl)-3-
((S)-1-hydroxy-5-methoxy-1-
phenylpentyl)piperidine-1-
carboxamide I-30a

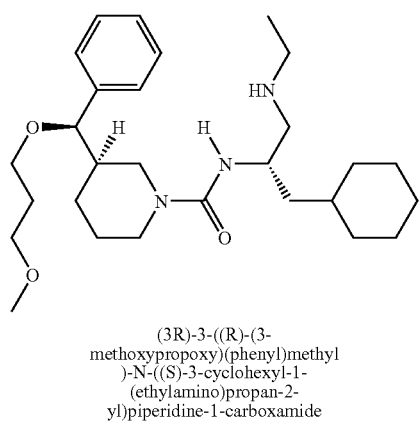

(3R)-3-((R)-(3-
methoxypropoxy)(phenyl)methyl
)-N-((S)-3-cyclohexyl-1-
(ethylamino)propan-2-
yl)piperidine-1-carboxamide I-31a

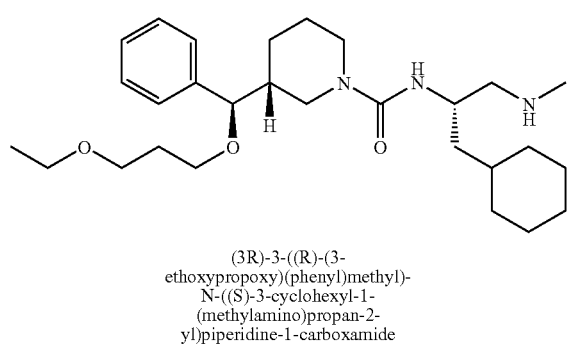

(3R)-3-((R)-(3-
ethoxypropoxy)(phenyl)methyl)-
N-((S)-3-cyclohexyl-1-
(methylamino)propan-2-
yl)piperidine-1-carboxamide I-32a

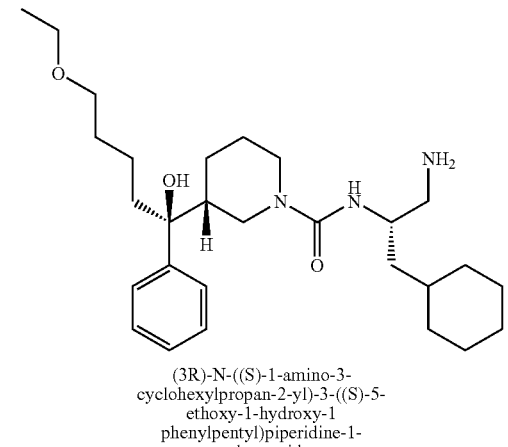

(3R)-N-((S)-1-amino-3-
cyclohexylpropan-2-yl)-3-((S)-5-
ethoxy-1-hydroxy-1
phenylpentyl)piperidine-1-
carboxamide I-33a

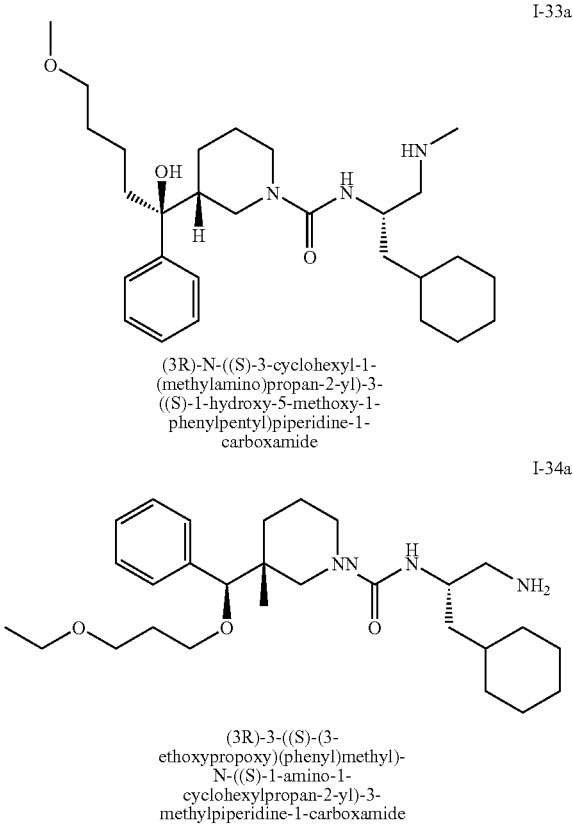

(3R)-N-((S)-3-cyclohexyl-1-
(methylamino)propan-2-yl)-3-
((S)-1-hydroxy-5-methoxy-1-
phenylpentyl)piperidine-1-
carboxamide I-34a (3R)-3-((S)-(3-
ethoxypropoxy)(phenyl)methyl)-
N-((S)-1-amino-1-
cyclohexylpropan-2-yl)-3-
methylpiperidine-1-carboxamide I-35a

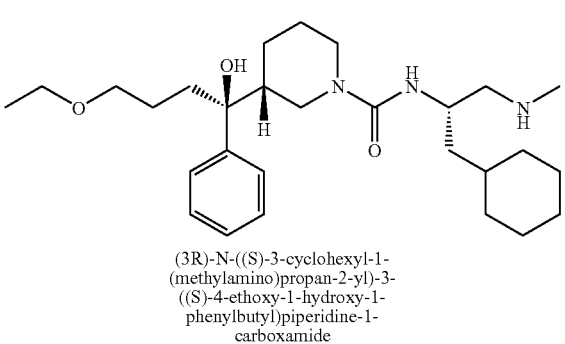

(3R)-N-((S)-3-cyclohexyl-1-
(methylamino)propan-2-yl)-3-
((S)-4-ethoxy-1-hydroxy-1-
phenylbutyl)piperidine-1-
carboxamide -continued I-36a

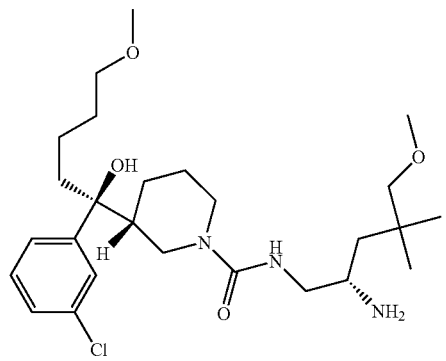

(3R)-N-((S)-2-amino-5-
methoxy-4,4-dimethylpentyl)-3-
((S)-1-(3-chlorophenyl)-1-
hydroxy-5-
methoxypentyl)piperdine-1-
carboxamide I-37a

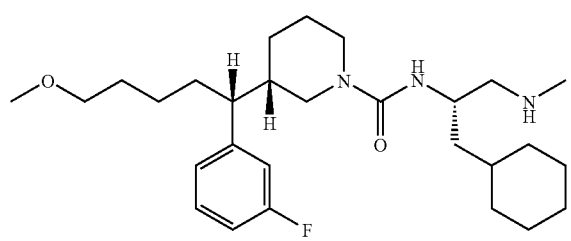

(3S)-N-((S)-3-cyclohexyl-1-
(methylamino)propan-2-yl)-3-
((R)-1-(3-fluorophenyl)-5-
methoxypentyl)piperidine-1-
carboxamide I-38a

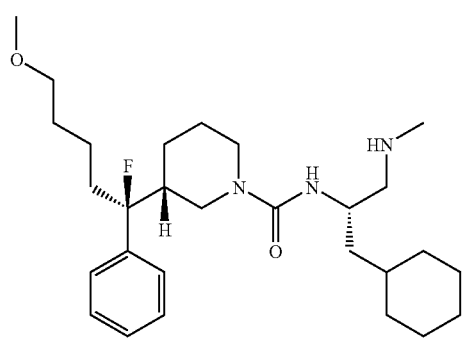

(R)-N-((S)-1-cyclohexyl-3-
(methylamino)propan-2-yl)-3-
((S)-1-fluoro-5-methoxy-1-
phenylpentyl)piperidine-1-
carboxamide -continued I-39a

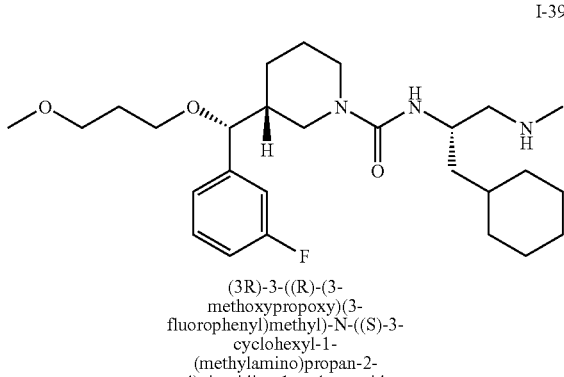

(3R)-3-((R)-(3-
methoxypropoxy)(3-
fluorophenyl)methyl)-N-((S)-3-
cyclohexyl-1-
(methylamino)propan-2-
yl)piperidine-1-carboxamide I-40a

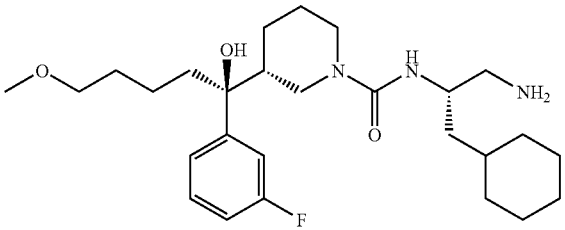

(3R)-N-((S)-1-amino-3-
cyclohexylpropan-2-yl)-3-((S)-1-
(3-fluorophenyl)-1-hydroxy-5-
methoxypentyl)piperidine-1-
carboxamide I-41a

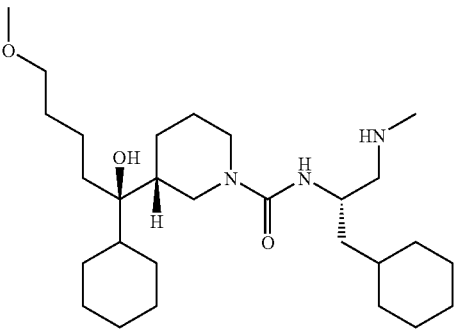

(3R)-N-((S)-3-cyclohexyl-1-
(methylamino)propan-2-yl)-3-
((R)-1-cyclohexyl-1-hydroxy-5-
methoxypentyl)piperidine-1-
carboxamide -continued I-42a

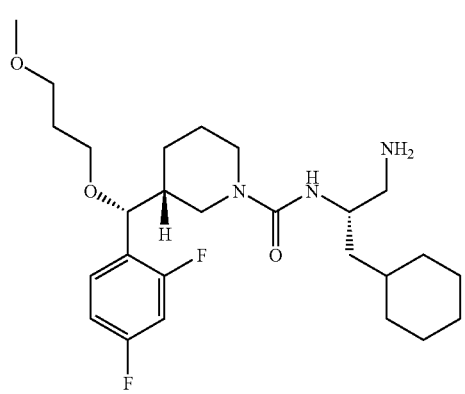

(3R)-3-((R)-(3-methoxypropoxy)(2,4-difluorophenyl)methyl)-N-((S)-1-amino-3-cyclohexylpropan-2-yl)piperidine-1-carboxamide I-43a

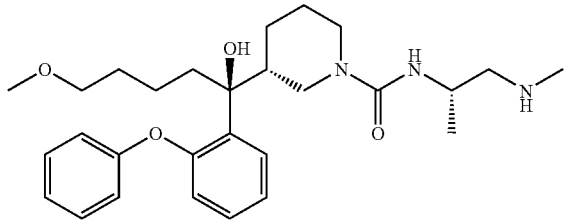

(3R)-3-((R)-(3-methoxypropoxy)(3,4-difluorophenyl)methyl)-N-((S)-1-amino-3-cyclohexylpropan-2-yl)piperidine-1-carboxamide I-44a (3R)-3-((S)-1-hydroxy-5-methoxy-1-(2-phenoxyphenyl)pentyl)-N-((S)-1-(methylamino)propan-2-yl)piperidine-1-carboxamide -continued I-45a

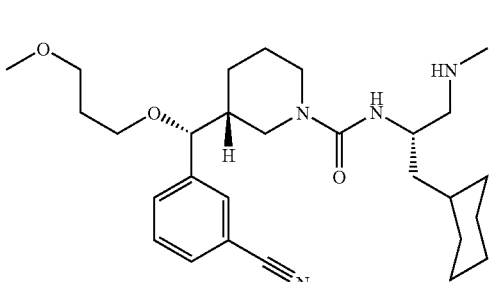

(3R)-3-((R)-(3-methoxypropoxy)(3-cyanophenyl)methyl)-N-((S)-3-cyclohexyl-1-(methylamino)propan-2-yl)piperidine-1-carboxamide I-46a

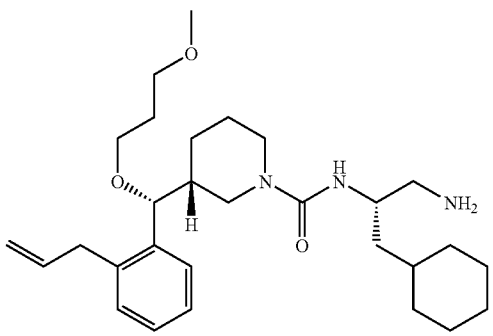

(3R)-3-((R)-(3-methoxypropoxy)(2-allylphenyl)methyl)-N-((S)-1-amino-3-cyclohexylpropan-2-yl)piperidine-1-carboxamide I-47a

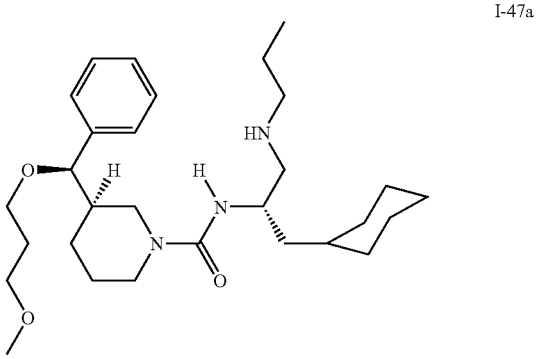

(3R)-3-((R)-(3-methoxypropoxy)(phenyl)methyl)-N-((S)-3-cyclohexyl-1-(propylamino)propan-2-yl)piperidine-1-carboxamide -continued

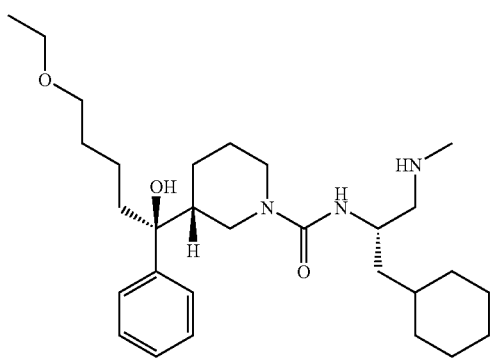

I-48a (3R)-N-((S)-3-cyclohexyl-1-
(methylamino)propan-2-yl)-3-
((S)-5-ethoxy-1-hydroxy-1-
phenylpentyl)piperidine-1-
carboxamide

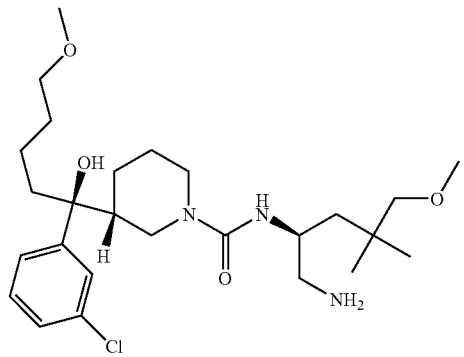

I-51a (3R)-N-((S)-1-amino-5-
methoxy-4,4-dimethylpentan-2-
yl)-3-((S)-1-(3-chlorophenyl)-1-
hydroxy-5-
methoxypentyl)piperidine-1-
carboxamide

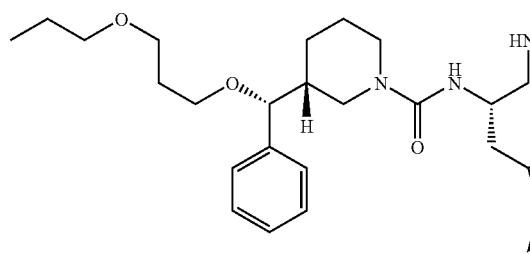

I-49a (3R)-3-((R)-(3-
propoxypropoxy)(phenyl)methyl
)-N-((S)-3-cyclohexyl-1-
(methylamino)propan-2-
yl)piperidine-1-carboxamide

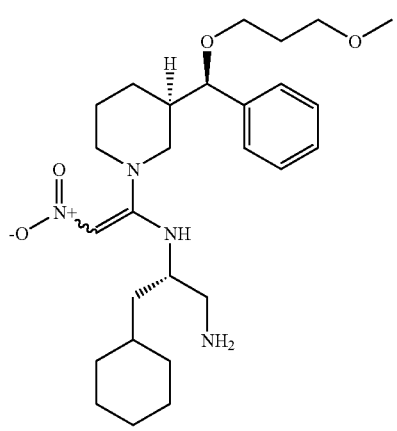

I-52a (2S)-N2-(1-((R)-3-((R)-(3-
methoxypropoxy)(phenyl)methyl
)piperidin-1-yl)-2-nitrovinyl)-3-
cyclohexylpropane-1,2-diamine

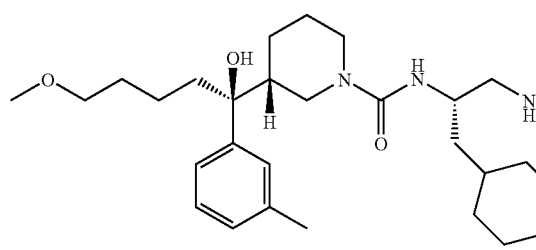

I-50a (3R)-N-((S)-3-cyclohexyl-1-
(methylamino)propan-2-yl)-3-
((S)-1-hydroxy-5-methoxy-1-m-
tolypentyl)piperidine-1-
carboxamide

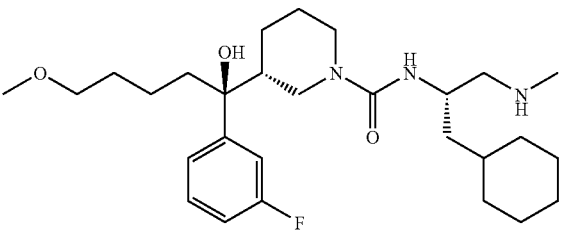

I-53a (3R)-N-((S)-3-cyclohexyl-1-
(methylamino)propan-2-yl)-3-
((S)-1-(3-fluorophenyl)-1-
hydroxy-5-
methoxypentyl)piperidine-1-
carboxamide -continued I-54a

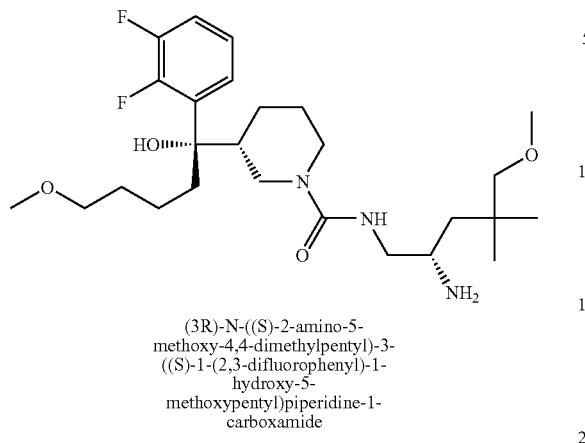

(3R)-N-((S)-2-amino-5-methoxy-4,4-dimethylpentyl)-3-((S)-1-(2,3-difluorophenyl)-1-hydroxy-5-methoxypentyl)piperidine-1-carboxamide I-55a

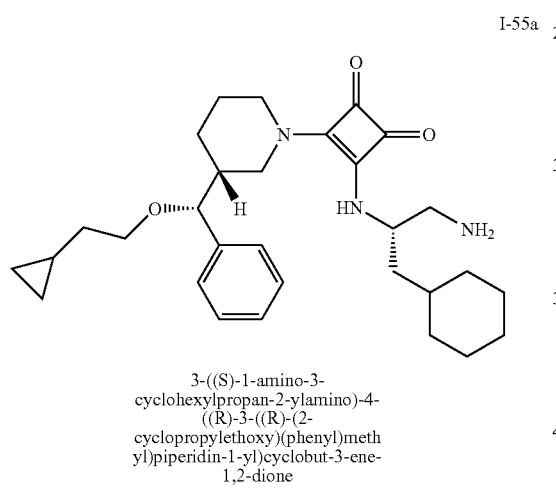

3-((S)-1-amino-3-cyclohexylpropan-2-ylamino)-4-((R)-3-((R)-(2-cyclopropylethoxy)(phenyl)methyl)piperidin-1-yl)cyclobut-3-ene-1,2-dione I-56a

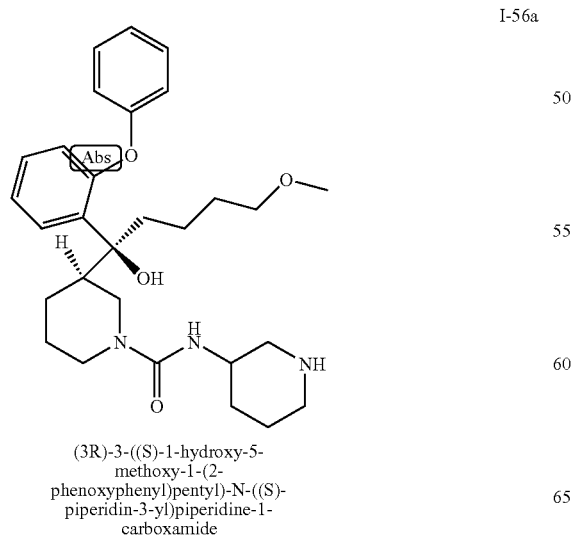

(3R)-3-((S)-1-hydroxy-5-methoxy-1-(2-phenoxyphenyl)pentyl)-N-((S)-piperidin-3-yl)piperidine-1-carboxamide -continued I-57a

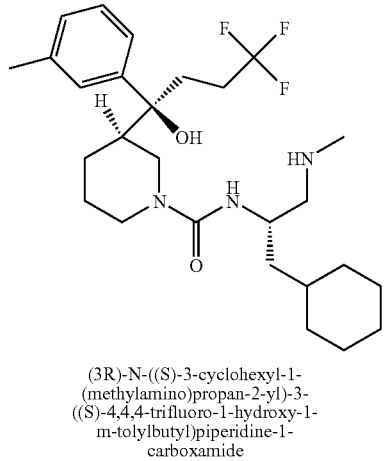

(3R)-N-((S)-3-cyclohexyl-1-(methylamino)propan-2-yl)-3-((S)-4,4,4-trifluoro-1-hydroxy-1-m-tolylbutyl)piperidine-1-carboxamide I-58a

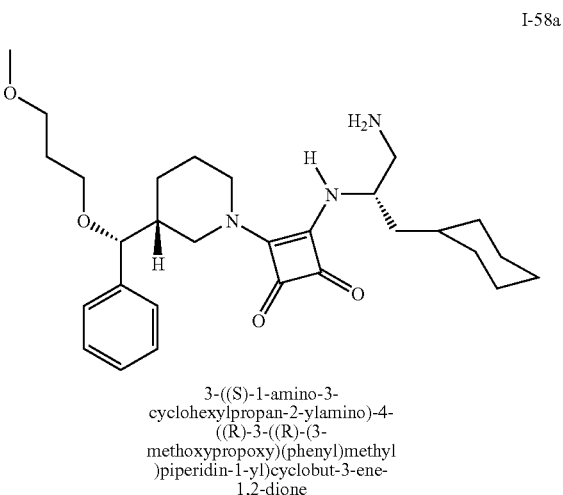

3-((S)-1-amino-3-cyclohexylpropan-2-ylamino)-4-((R)-3-((R)-(3-methoxypropoxy)(phenyl)methyl)piperidin-1-yl)cyclobut-3-ene-1,2-dione I-59a

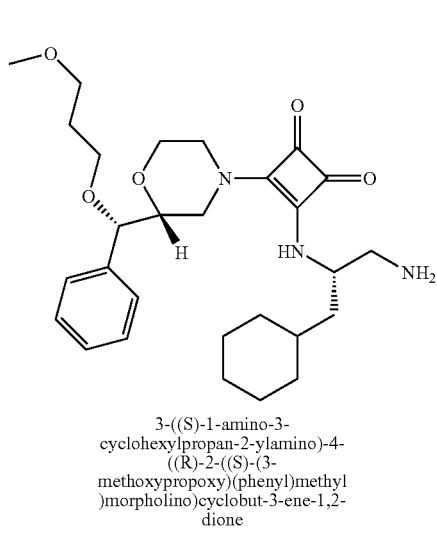

3-((S)-1-amino-3-cyclohexylpropan-2-ylamino)-4-((R)-2-((S)-(3-methoxypropoxy)(phenyl)methyl)morpholino)cyclobut-3-ene-1,2-dione -continued

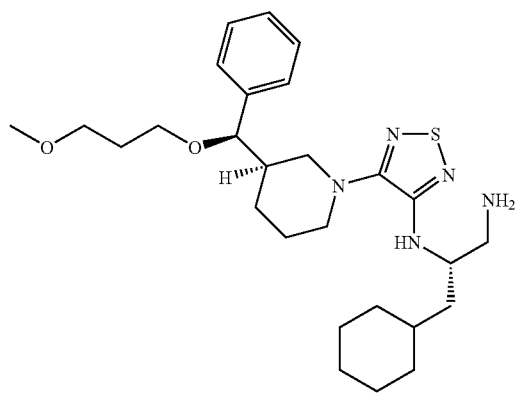

I-60a 4-((R)-3-((R)-(3-methoxypropoxy)(phenyl)methyl)piperidin-1-yl)-N-((S)-1-amino-3-cyclohexylpropan-2-yl)-1,2,5-thiadiazol-3-amine

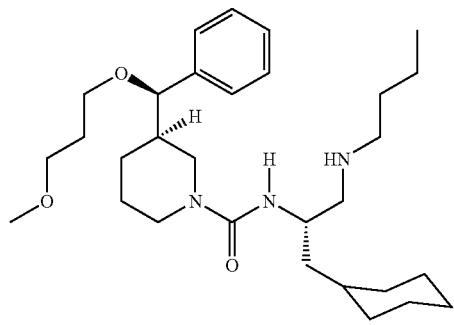

I-61a (3R)-3-((R)-(3-methoxypropoxy)(phenyl)methyl)-N-((S)-1-(butylamino)-3-cyclohexylpropan-2-yl)piperidine-1-carboxamide

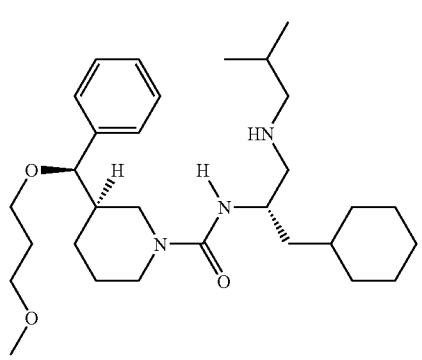

I-62a (3R)-3-((R)-(3-methoxypropoxy)(phenyl)methyl)-N-((S)-3-cyclohexyl-1-(isobutylamino)propan-2-yl)piperidine-1-carboxamide -continued

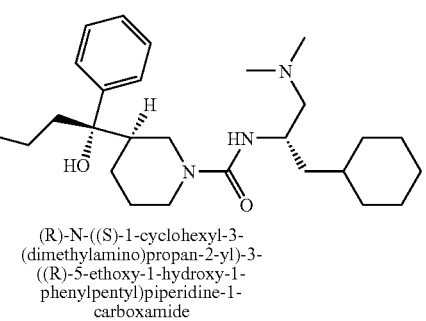

I-63a (R)-N-((S)-1-cyclohexyl-3-(dimethylamino)propan-2-yl)-3-((R)-5-ethoxy-1-hydroxy-1-phenylpentyl)piperidine-1-carboxamide

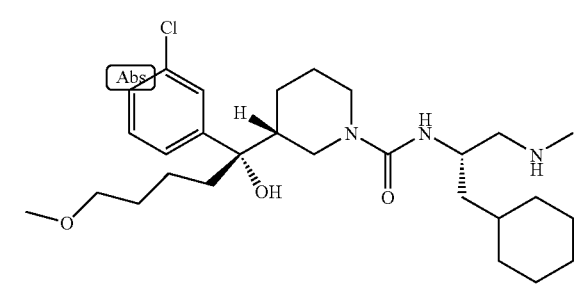

I-64a (3R)-3-((S)-1-(3-chlorophenyl)-1-hydroxy-5-methoxypentyl)-N-((S)-3-cyclohexyl-1-(methylamino)propan-2-yl)piperidine-1-carboxamide

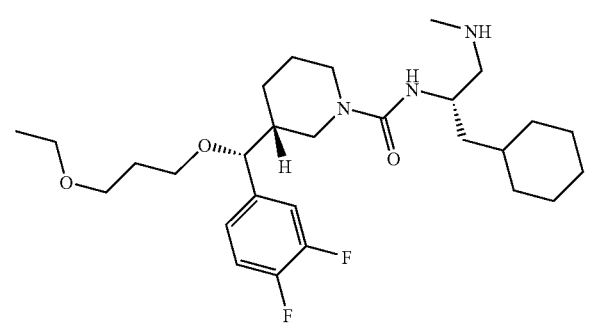

I-65a (3R)-3-((R)-(3-ethoxypropoxy)(3,4-difluorophenyl)methyl)-N-((S)-3-cyclohexyl-1-(methylamino)propan-2-yl)piperidine-1-carboxamide

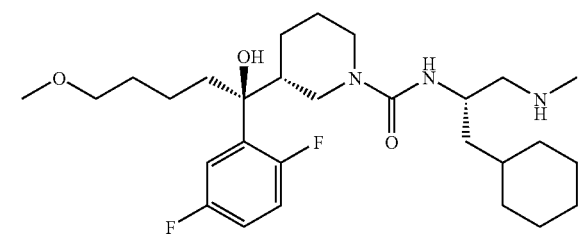

I-66a (3R)-N-((S)-3-cyclohexyl-1-(methylamino)propan-2-yl)-3-((S)-1-(2,5-difluorophenyl)-1-hydroxy-5-methoxypentyl)piperidine-1-carboxamide -continued

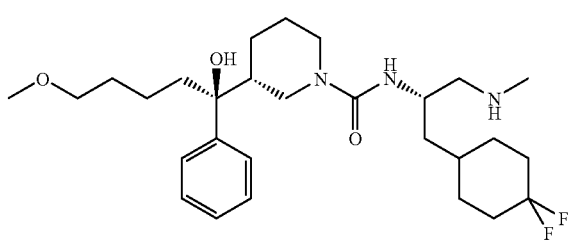

I-67a (3R)-N-((S)-3-(4,4-difluorocyclohexyl)-1-(methylamino)propan-2-yl)-3-((S)-1-hydroxy-5-methoxy-1-phenylpentyl)piperidine-1-carboxamide

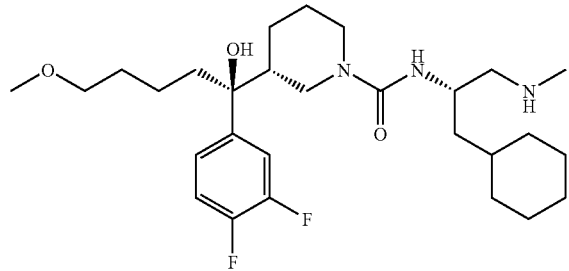

I-68a (3R)-N-((S)-3-cyclohexyl-1-(methylamino)propan-2-yl)-3-((S)-1-(3,4-difluorophenyl)-1-hydroxy-5-methoxypentyl)piperidine-1-carboxamide

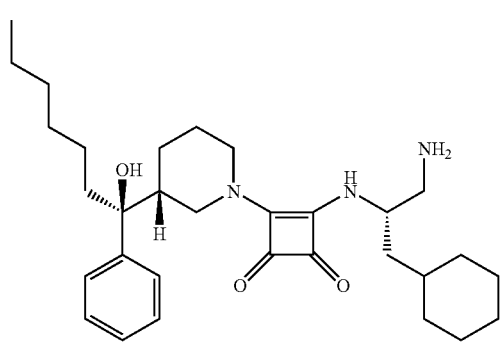

I-69a 3-((S)-1-amino-3-cyclohexylpropan-2-ylamino)-4-((R)-3-((S)-1-hydroxy-1-phenylheptyl)piperidin-1-yl)cyclobut-3-ene-1,2-dione -continued

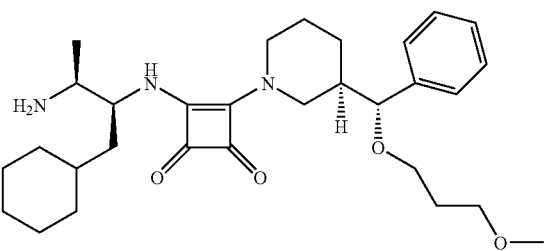

I-70a 3-((2S,3S)-3-amino-1-cyclohexylbutan-2-ylamino)-4-((R)-3-((R)-(3-methoxypropoxy)(phenyl)methyl)piperidin-1-yl)cyclobut-3-ene-1,2-dione

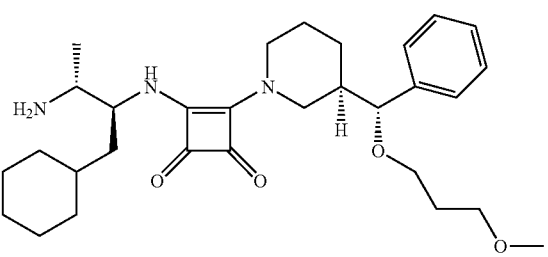

I-70b 3-((2S,3R)-3-amino-1-cyclohexylbutan-2-ylamino)-4-((R)-3-((R)-(3-methoxypropoxy)(phenyl)methyl)piperidin-1-yl)cyclobut-3-ene-1,2-dione

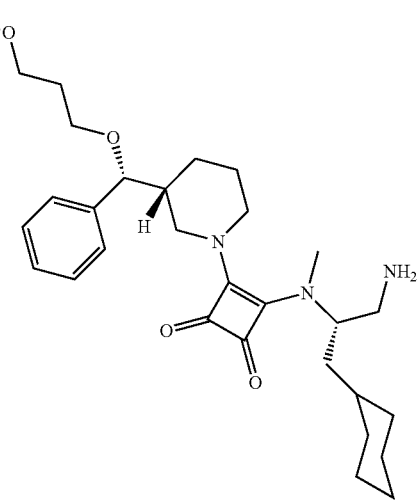

I-71a 3-((R)-3-((R)-(3-methoxypropoxy)(phenyl)methyl)piperidin-1-yl)-4-(N-((S)-1-amino-3-cyclohexylpropan-2-yl)-N-methylamino)cyclobut-3-ene-1,2-dione -continued I-72a

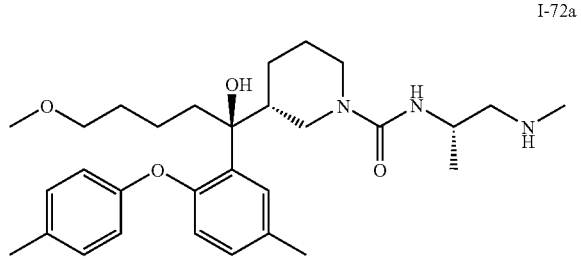

(3R)-3-((S)-1-(2-(p-tolyloxy)-5-
methylphenyl)-1-hydroxy-5-
methoxypentyl)-N-((S)-1-
(methylamino)propan-2-
yl)piperidine-1-carboxamide I-73a

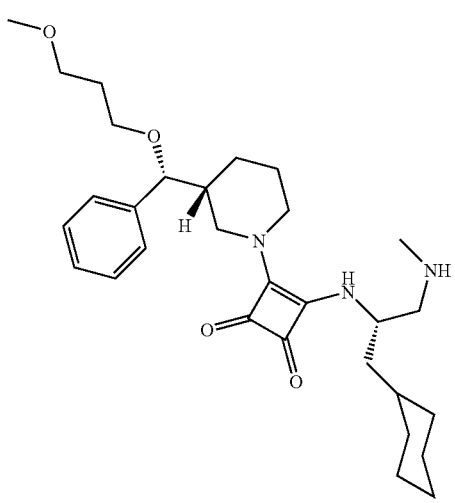

3-((S)-3-cyclohexyl-1-
(methylamino)propan-2-
ylamino)-4-((R)-3-((R)-(3-
methoxypropoxy)(phenyl)methyl
)piperidin-1-yl)cyclobut-3-ene-
1,2-dione I-74a

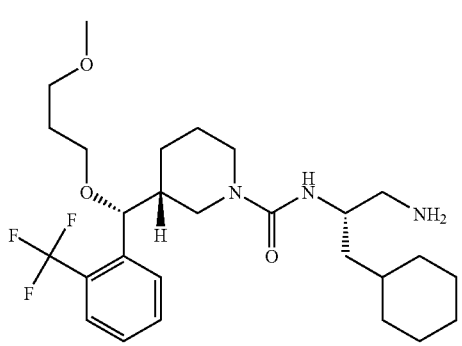

(3R)-3-((R)-(3-
methoxypropoxy)(2-
(trifluoromethyl)phenyl)methyl)-
N-((S)-1-amino-3-
cyclohexylpropan-2-
yl)piperidine-1-carboxamide -continued I-75a

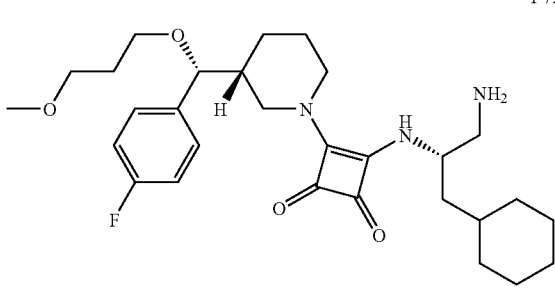

3-((S)-1-amino-3-
cyclohexylpropan-2-ylamino)-4-
((R)-3-((R)-(3-
methoxypropoxy)(4-
fluorophenyl)methyl)piperidin-1-
yl)cyclobut-3-ene-1,2-dione I-76a

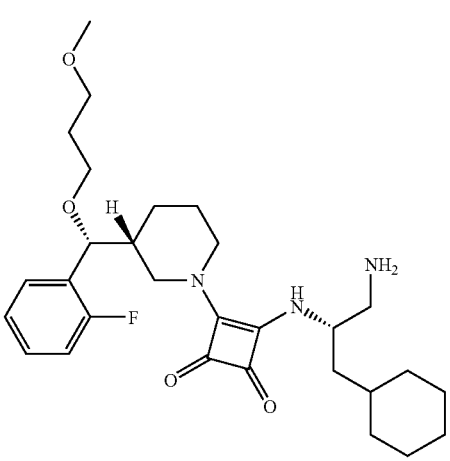

3-((S)-1-amino-3-
cyclohexylpropan-2-ylamino)-4-
((R)-3-((R)-(3-
methoxypropoxy)(2-
fluorophenyl)methyl)piperidin-1-
yl)cyclobut-3-ene-1,2-dione I-77a

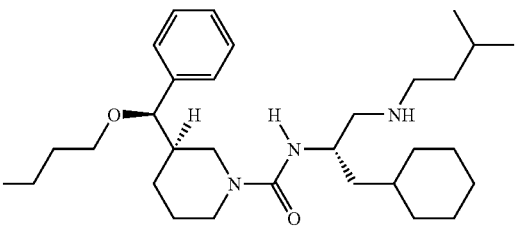

(3R)-3-((R)-(3-
methoxypropoxy)(phenyl)methyl
)-N-((S)-3-cyclohexyl-1-
(isopentylamino)propan-2-
yl)piperidine-1-carboxamide

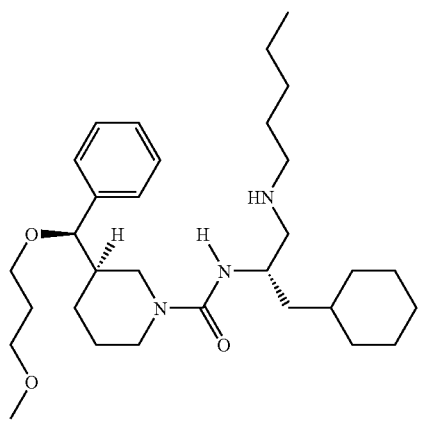

(3R)-3-((R)-(3-methoxypropoxy)(phenyl)methyl)-N-((S)-3-cyclohexyl-1-(pentylamino)propan-2-yl)piperidine-1-carboxamide I-79a

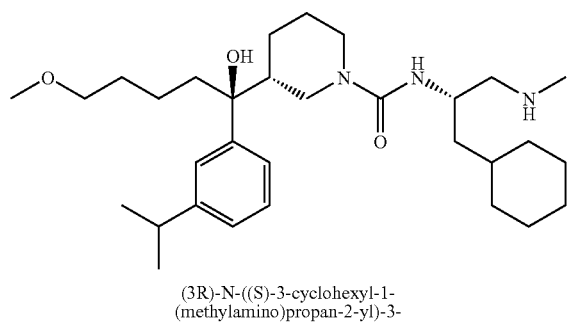

(3R)-N-((S)-3-cyclohexyl-1-(methylamino)propan-2-yl)-3-((S)-1-hydroxy-1-(3-isopropylphenyl)-5-methoxypentyl)piperidine-1-carboxamide I-80a

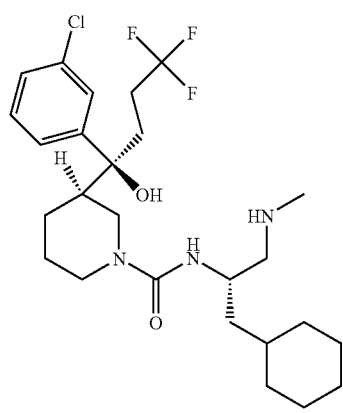

(3R)-3-((S)-1-(3-chlorophenyl)-4,4,4-trifluoro-1-hydroxybutyl)-N-((S)-3-cyclohexyl-1-(methylamino)propan-2-yl)piperidine-1-carboxamide I-81a

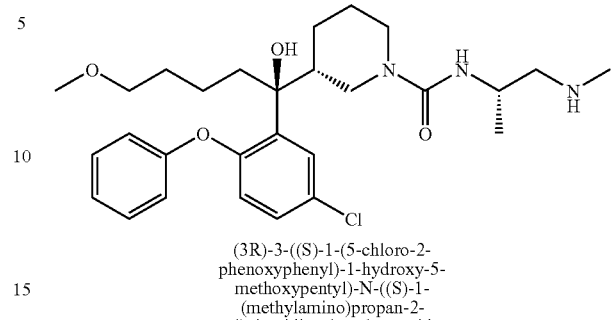

(3R)-3-((S)-1-(5-chloro-2-phenoxyphenyl)-1-hydroxy-5-methoxypentyl)-N-((S)-1-(methylamino)propan-2-yl)piperidine-1-carboxamide I-82a

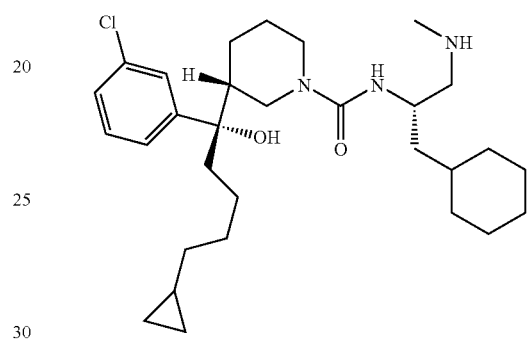

(R)-N-((S)-1-cyclohexyl-3-(methylamino)propan-2-yl)-3-((S)-5-cyclopropyl-1-hydroxy-1-phenylpentyl)piperidine-1-carboxamide I-83a

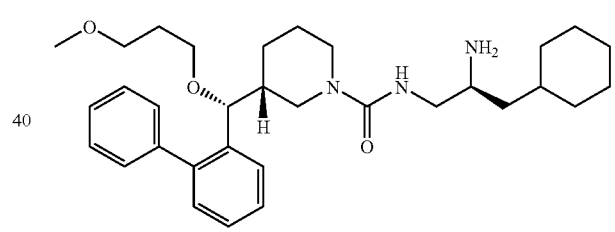

(3R)-3-((R)-(3-methoxypropoxy)(2-phenylphenyl)methyl)-N-((S)-2-amino-3-cyclohexylpropyl)piperidine-1-carboxamide I-84a

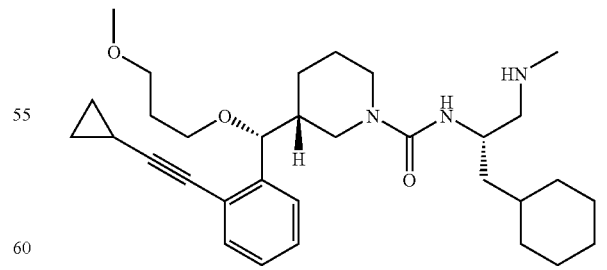

(3R)-3-((R)-(3-methoxypropoxy)(2-(2-cyclopropylethynyl)phenyl)methyl)-N-((S)-3-cyclohexyl-1-(methylamino)propan-2-yl)piperidine-1-carboxamide I-85a

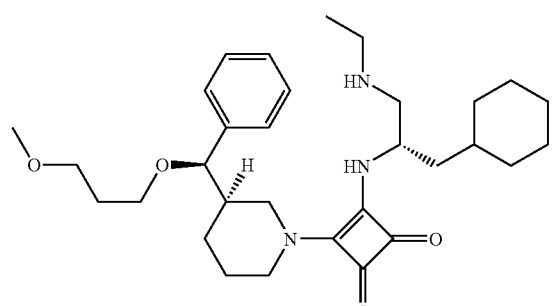

3-((S)-3-cyclohexyl-1-
(ethylamino)propan-2-ylamino)-
4-((R)-3-((R)-(3-
methoxypropoxy)(phenyl)methyl
)piperidin-1-yl)cyclobut-3-ene-
1,2-dione I-86a

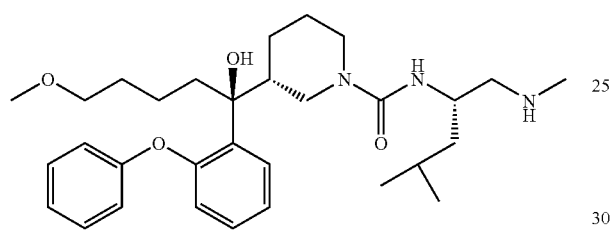

(3R)-3-((S)-1-hydroxy-5-
methoxy-1-(2-
phenoxyphenyl)pentyl)-N-((S)-
4-methyl-1-
(methylamino)pentan-2-
yl)piperidine-1-carboxamide I-87a

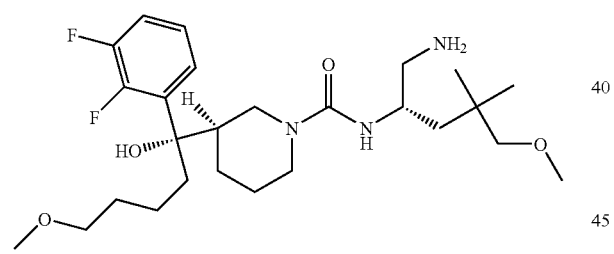

(3R)-N-((S)-1-amino-5-
methoxy-4,4-dimethylpentan-2-
yl)-3-((S)-1-(2,3-difluorophenyl)-
1-hydroxy-5-
methoxypentyl)piperidine-1-
carboxamide I-88a

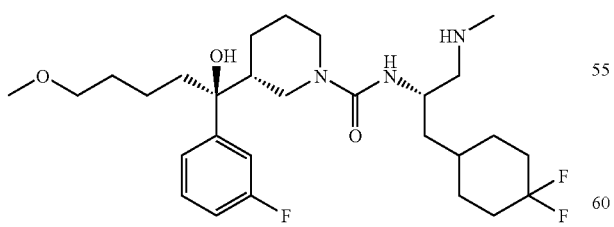

(3R)-N-((S)-3-(4,4-
difluorocyclohexyl)-1-
(methylamino)propan-2-yl)-3-
((S)-1-(3-fluorophenyl)-1-
hydroxy-5-
methoxypentyl)piperidine-1-
carboxamide I-89a

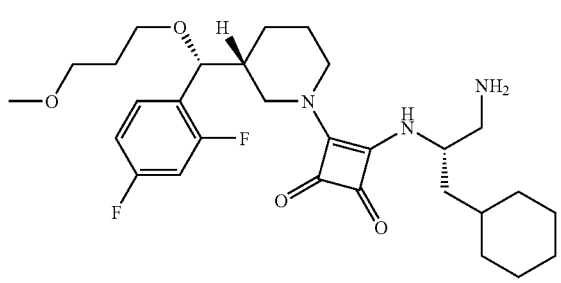

3-((S)-1-amino-3-
cyclohexylpropan-2-ylamino)-4-
((R)-3-((R)-(3-
methoxypropoxy)(2,4-
difluorophenyl)methyl)piperidin-
1-yl)cyclobut-3-ene-1,2-dione I-90a

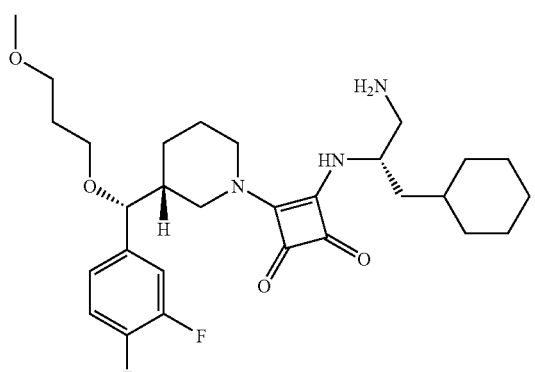

3-((S)-1-amino-3-
cyclohexylpropan-2-ylamino)-4-
((R)-3-((R)-(3-
methoxypropoxy)(3,4-
difluorophenyl)methyl)piperidin-
1-yl)cyclobut-3-ene-1,2-dione I-91a

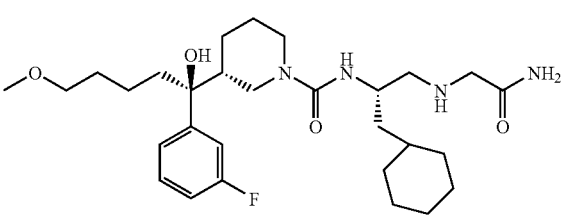

(3R)-N-((S)-1-
(carbamoylmethylamino)-3-
cyclohexylpropan-2-yl)-3-((S)-1-
(3-fluorophenyl)-1-hydroxy-5-
methoxypentyl)piperidine-1-
carboxamide -continued I-92a

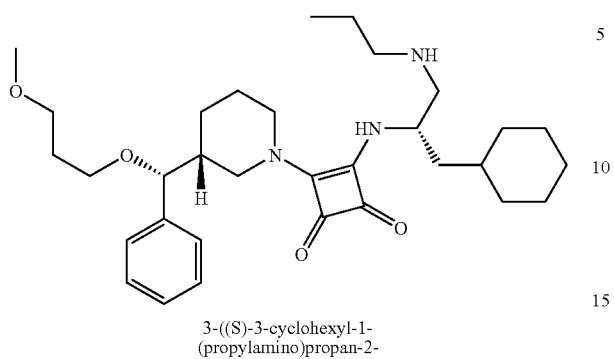

3-((S)-3-cyclohexyl-1-
(propylamino)propan-2-
ylamino)-4-((R)-3-((R)-(3-
methoxypropoxy)(phenyl)methyl
)piperidin-1-yl)cyclobut-3-ene-
1,2-dione I-93a

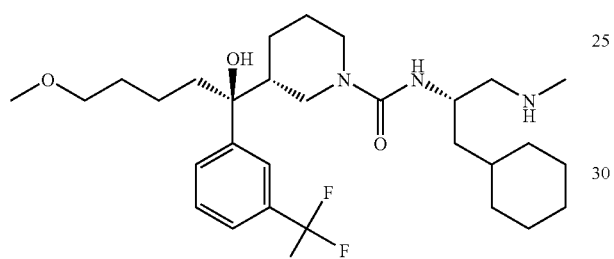

(3R)-N-((S)-3-cyclohexyl-1-
(methylamino)propan-2-yl)-3-
((S)-1-(3-
(trifluoromethyl)phenyl)-1-
hydroxy-5-
methoxypentyl)piperidine-1-
carboxamide I-94a

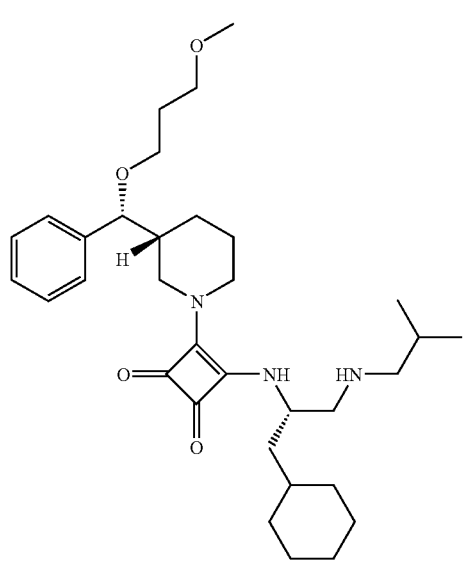

3-((S)-3-cyclohexyl-1-
(isobutylamino)propan-2-
ylamino)-4-((R)-3-((R)-(3-
methoxypropoxy)(phenyl)methyl
)piperidin-1-yl)cyclobut-3-ene-
1,2-dione -continued I-95a

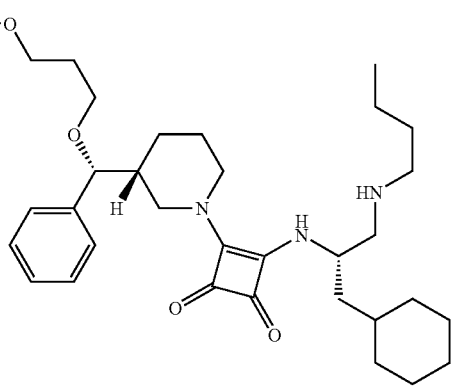

3-((S)-3-(butylamino)-1-
cyclohexylpropan-2-ylamino)-4-
((R)-3-((R)-(3-
methoxypropoxy)(phenyl)methyl
)piperidin-1-yl)cyclobut-3-ene-
1,2-dione I-96a

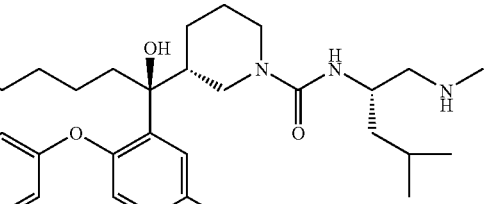

(3R)-3-((S)-1-(2-(p-tolyloxy)-5-
methylphenyl)-1-hydroxy-5-
methoxypentyl)-N-((S)-4-
methyl-1-(methylamino)pentan-
2-yl)piperidine-1-carboxamide I-97a

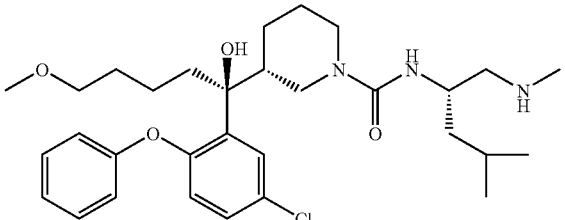

(3R)-3-((S)-1-(5-chloro-2-
phenoxyphenyl)-1-hydroxy-5-
methoxypentyl)-N-((S)-4-
methyl-1-(methylamino)pentan-
2-yl)piperidine-1-carboxamide

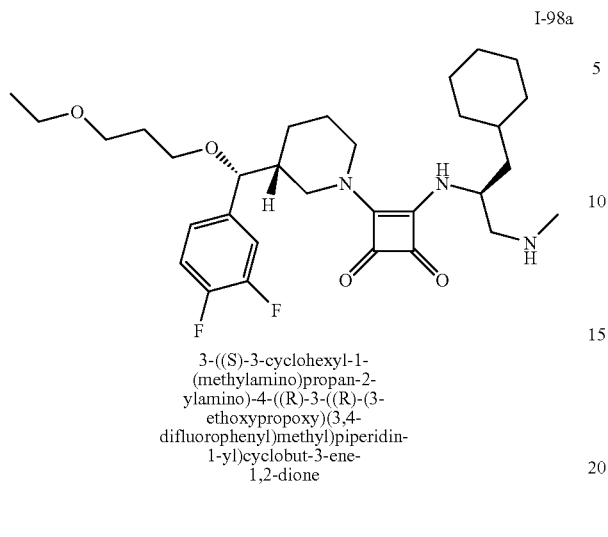

I-98a 3-((S)-3-cyclohexyl-1-
(methylamino)propan-2-
ylamino)-4-((R)-3-((R)-(3-
ethoxypropoxy)(3,4-
difluorophenyl)methyl)piperidin-
1-yl)cyclobut-3-ene-
1,2-dione

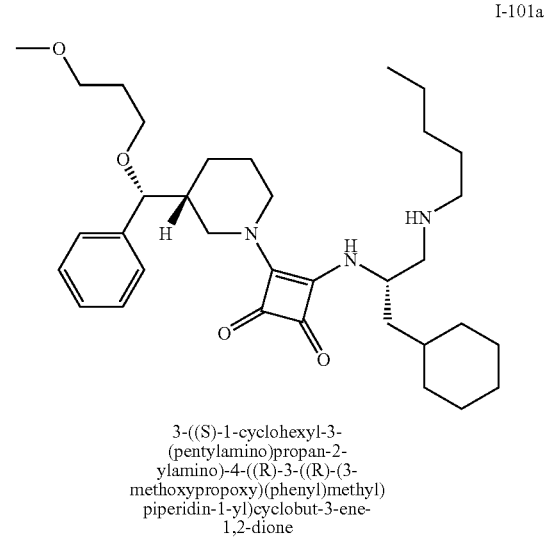

I-101a 3-((S)-1-cyclohexyl-3-
(pentylamino)propan-2-
ylamino)-4-((R)-3-((R)-(3-
methoxypropoxy)(phenyl)methyl)
piperidin-1-yl)cyclobut-3-ene-
1,2-dione

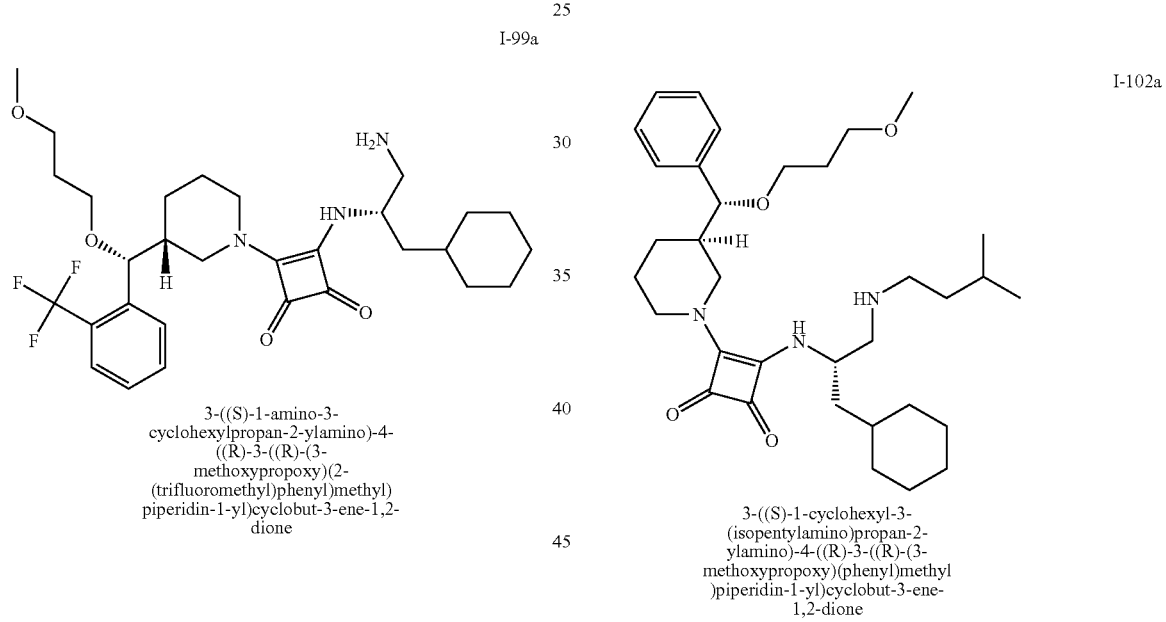

I-99a 3-((S)-1-amino-3-
cyclohexylpropan-2-ylamino)-4-
((R)-3-((R)-(3-
methoxypropoxy)(2-
(trifluoromethyl)phenyl)methyl)
piperidin-1-yl)cyclobut-3-ene-1,2-
dione I-102a 3-((S)-1-cyclohexyl-3-
(isopentylamino)propan-2-
ylamino)-4-((R)-3-((R)-(3-
methoxypropoxy)(phenyl)methyl
)piperidin-1-yl)cyclobut-3-ene-
1,2-dione

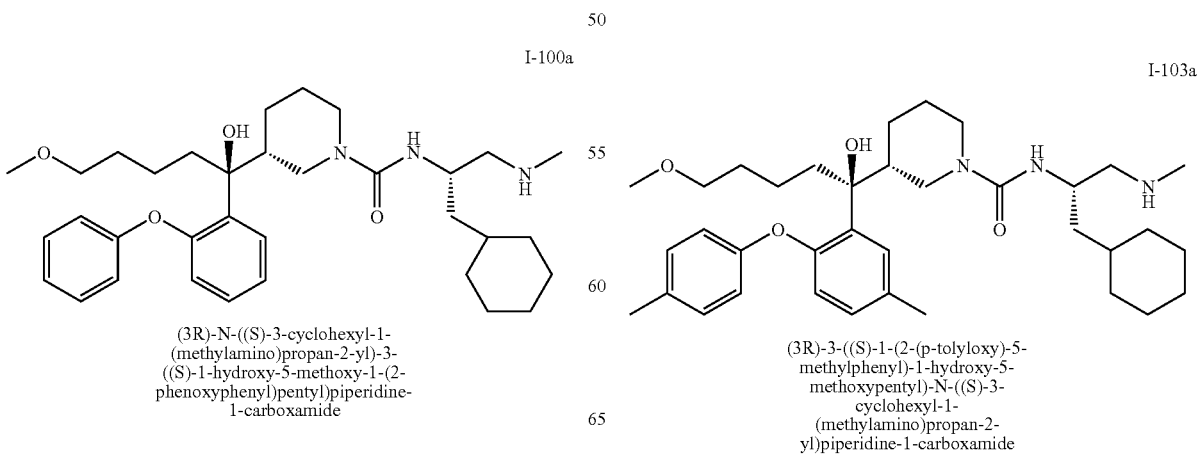

I-100a (3R)-N-((S)-3-cyclohexyl-1-
(methylamino)propan-2-yl)-3-
((S)-1-hydroxy-5-methoxy-1-(2-
phenoxyphenyl)pentyl)piperidine-
1-carboxamide I-103a (3R)-3-((S)-1-(2-(p-tolyloxy)-5-
methylphenyl)-1-hydroxy-5-
methoxypentyl)-N-((S)-3-
cyclohexyl-1-
(methylamino)propan-2-
yl)piperidine-1-carboxamide -continued

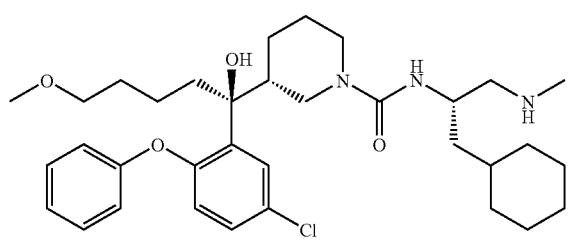

I-104a (3R)-3-((S)-1-(5-chloro-2-phenoxyphenyl)-1-hydroxy-5-methoxypentyl)-N-((S)-3-cyclohexyl-1-(methylamino)propan-2-yl)piperidine-1-carboxamide

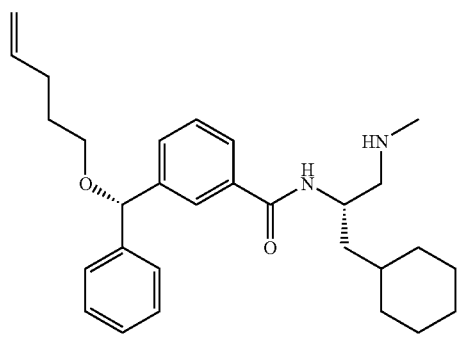

I-105a

N-((S)-3-cyclohexyl-1-(methylamino)propan-2-yl)-3-((S)-(pent-4-enyloxy)(phenyl)methyl)benzamide

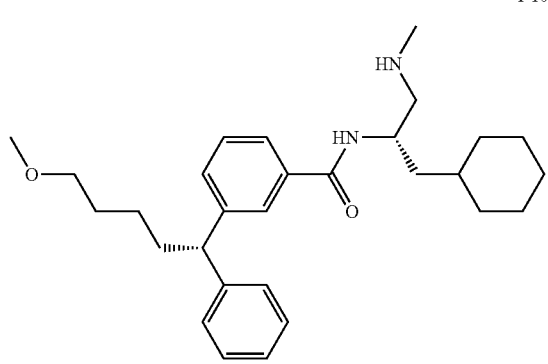

I-106a

N-((S)-3-cyclohexyl-1-(methylamino)propan-2-yl)-3-((S)-5-methoxy-1-phenylpentyl)benzamide -continued

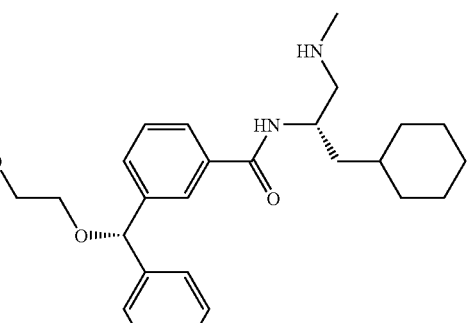

I-107a 3-((S)-(2-ethoxyethoxy)(phenyl)methyl)-N-((S)-3-cyclohexyl-1-(methylamino)propan-2-yl)benzamide

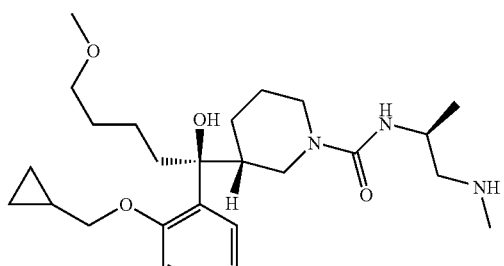

I-108a (3R)-3-((S)-1-(2-(cyclopropylmethoxy)phenyl)-1-hydroxy-5-methoxypentyl)-N-((S)-1-(methylamino)propan-2-yl)piperidine-1-carboxamide

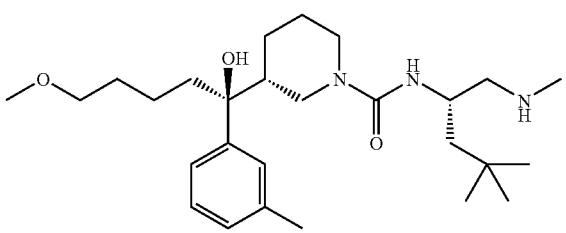

I-109a (3R)-3-((S)-1-hydroxy-5-methoxy-1-m-tolylpentyl)-N-((S)-4,4-dimethyl-1-(methylamino)pentan-2-yl)piperidine-1-carboxamide

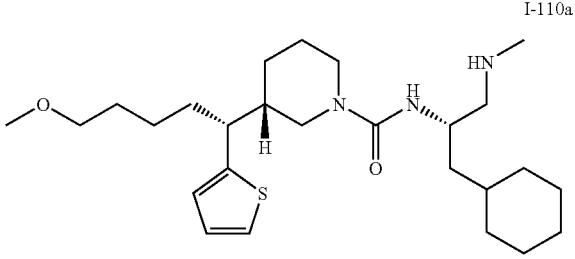

I-110a (3S)-N-((S)-3-cyclohexyl-1-(methylamino)propan-2-yl)-3-((R)-5-methoxy-1-(thiophen-2-yl)pentyl)piperidine-1-carboxamide -continued

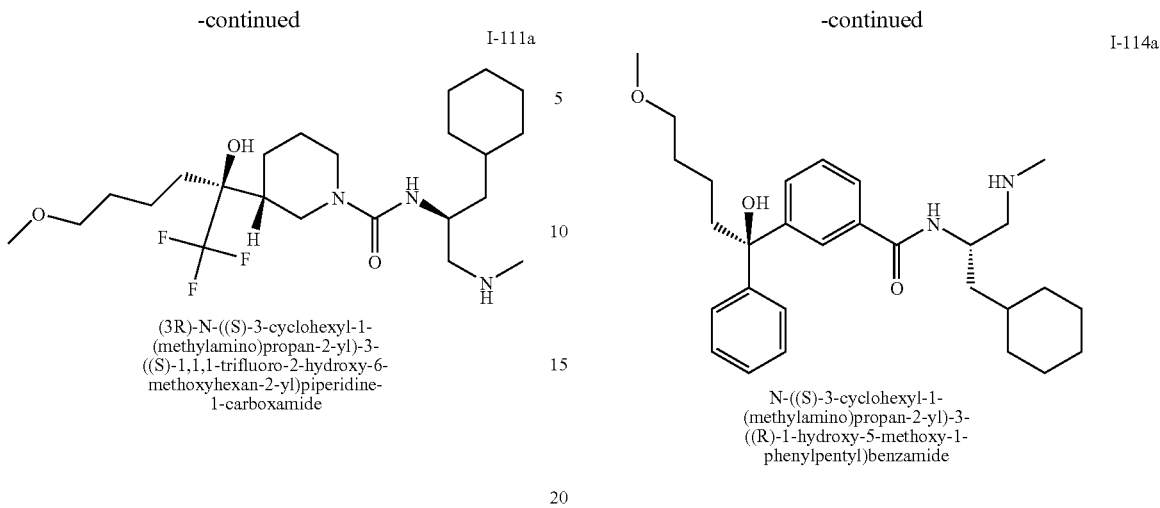

I-111a (3R)-N-((S)-3-cyclohexyl-1-
(methylamino)propan-2-yl)-3-
((S)-1,1,1-trifluoro-2-hydroxy-6-
methoxyhexan-2-yl)piperidine-
1-carboxamide I-114a N-((S)-3-cyclohexyl-1-
(methylamino)propan-2-yl)-3-
((R)-1-hydroxy-5-methoxy-1-
phenylpentyl)benzamide

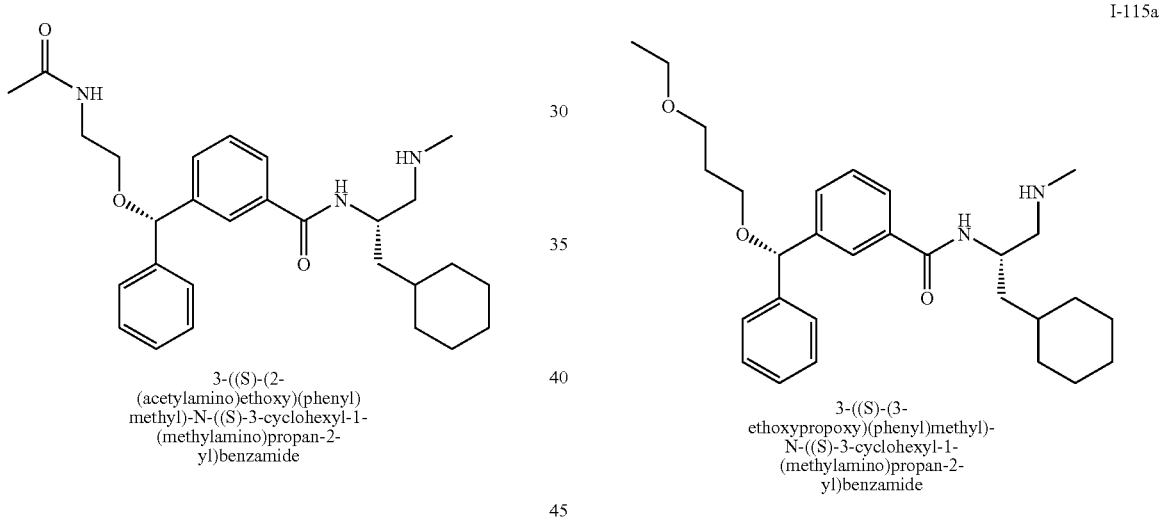

I-112a 3-((S)-(2-
(acetylamino)ethoxy)(phenyl)
methyl)-N-((S)-3-cyclohexyl-1-
(methylamino)propan-2-
yl)benzamide I-115a 3-((S)-(3-
ethoxypropoxy)(phenyl)methyl)-
N-((S)-3-cyclohexyl-1-
(methylamino)propan-2-
yl)benzamide

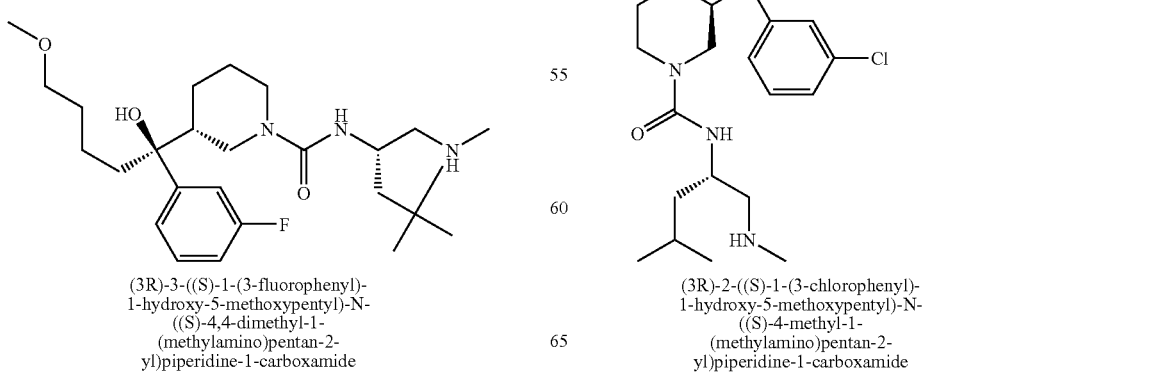

I-113a (3R)-3-((S)-1-(3-fluorophenyl)-
1-hydroxy-5-methoxypentyl)-N-
((S)-4,4-dimethyl-1-
(methylamino)pentan-2-
yl)piperidine-1-carboxamide I-116a (3R)-2-((S)-1-(3-chlorophenyl)-
1-hydroxy-5-methoxypentyl)-N-
((S)-4-methyl-1-
(methylamino)pentan-2-
yl)piperidine-1-carboxamide -continued

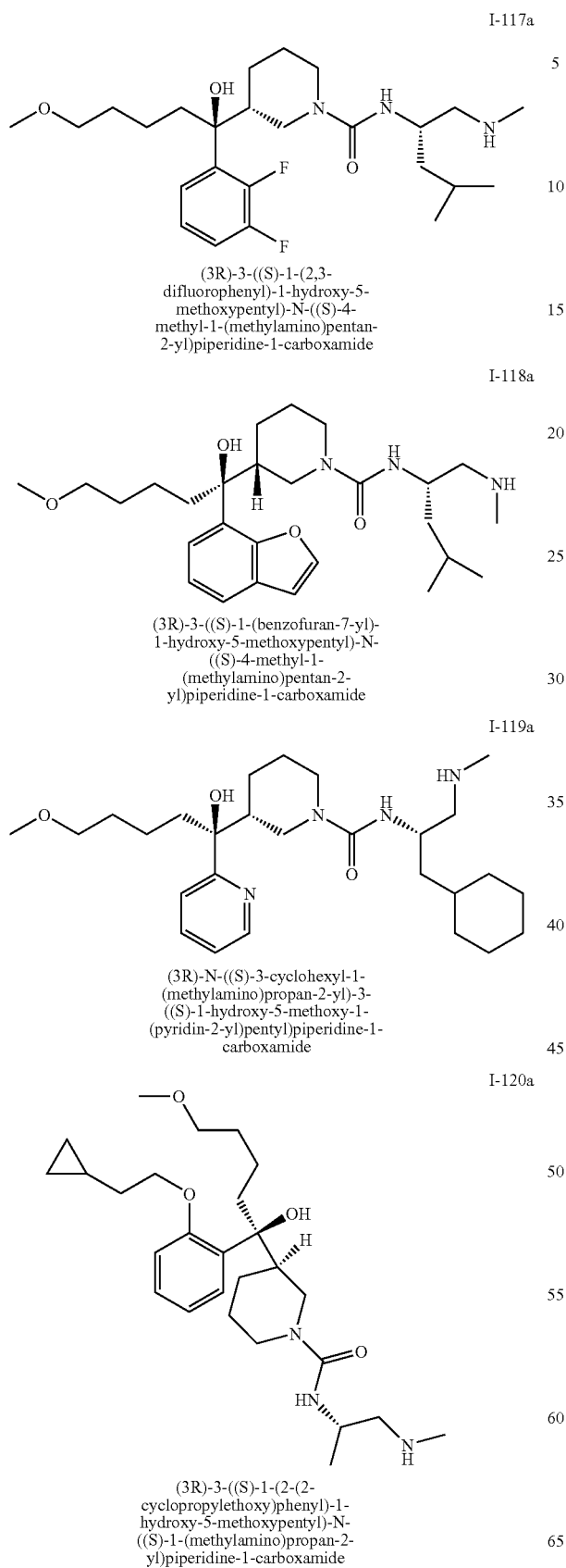

I-117a (3R)-3-((S)-1-(2,3-difluorophenyl)-1-hydroxy-5-methoxypentyl)-N-((S)-4-methyl-1-(methylamino)pentan-2-yl)piperidine-1-carboxamide I-118a (3R)-3-((S)-1-(benzofuran-7-yl)-1-hydroxy-5-methoxypentyl)-N-((S)-4-methyl-1-(methylamino)pentan-2-yl)piperidine-1-carboxamide I-119a (3R)-N-((S)-3-cyclohexyl-1-(methylamino)propan-2-yl)-3-((S)-1-hydroxy-5-methoxy-1-(pyridin-2-yl)pentyl)piperidine-1-carboxamide I-120a (3R)-3-((S)-1-(2-(2-cyclopropylethoxy)phenyl)-1-hydroxy-5-methoxypentyl)-N-((S)-1-(methylamino)propan-2-yl)piperidine-1-carboxamide

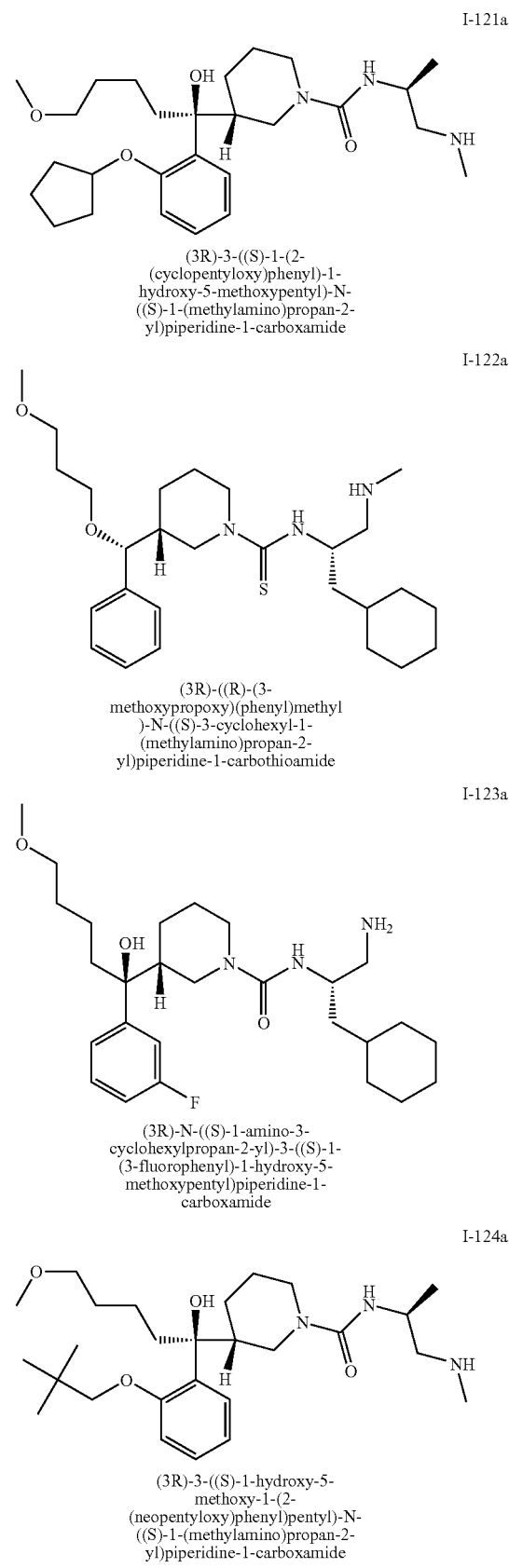

I-121a (3R)-3-((S)-1-(2-(cyclopentyloxy)phenyl)-1-hydroxy-5-methoxypentyl)-N-((S)-1-(methylamino)propan-2-yl)piperidine-1-carboxamide I-122a (3R)-((R)-(3-methoxypropoxy)(phenyl)methyl)-N-((S)-3-cyclohexyl-1-(methylamino)propan-2-yl)piperidine-1-carbothioamide I-123a (3R)-N-((S)-1-amino-3-cyclohexylpropan-2-yl)-3-((S)-1-(3-fluorophenyl)-1-hydroxy-5-methoxypentyl)piperidine-1-carboxamide I-124a (3R)-3-((S)-1-hydroxy-5-methoxy-1-(2-(neopentyloxy)phenyl)pentyl)-N-((S)-1-(methylamino)propan-2-yl)piperidine-1-carboxamide

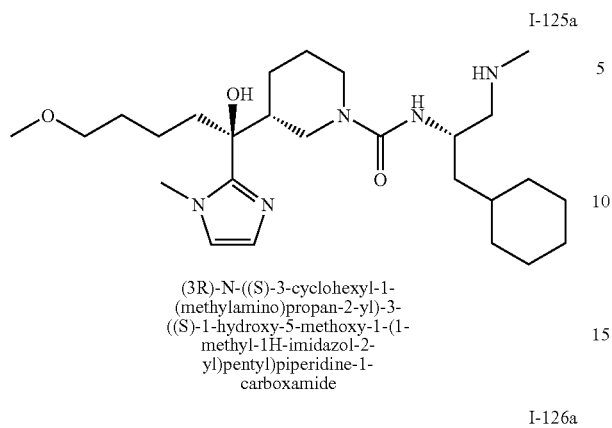

I-125a (3R)-N-((S)-3-cyclohexyl-1-
(methylamino)propan-2-yl)-3-
((S)-1-hydroxy-5-methoxy-1-(1-
methyl-1H-imidazol-2-
yl)pentyl)piperidine-1-
carboxamide

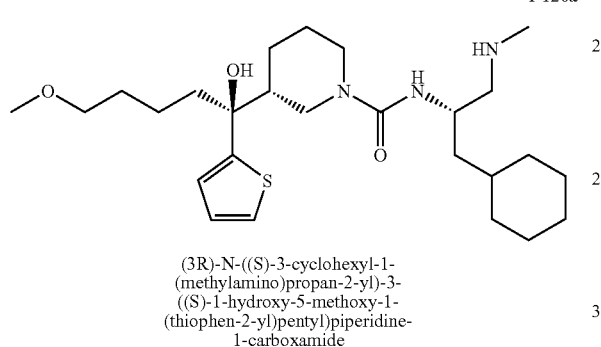

I-126a (3R)-N-((S)-3-cyclohexyl-1-
(methylamino)propan-2-yl)-3-
((S)-1-hydroxy-5-methoxy-1-
(thiophen-2-yl)pentyl)piperidine-
1-carboxamide

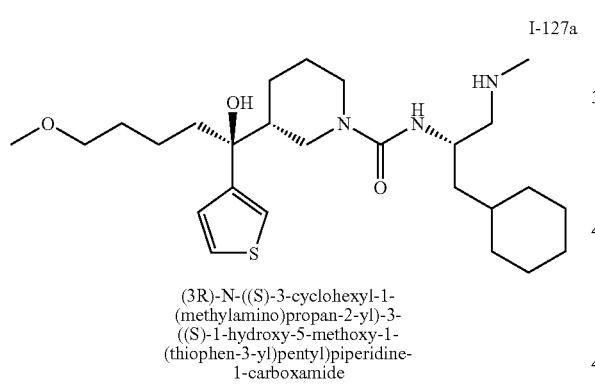

I-127a (3R)-N-((S)-3-cyclohexyl-1-
(methylamino)propan-2-yl)-3-
((S)-1-hydroxy-5-methoxy-1-
(thiophen-3-yl)pentyl)piperidine-
1-carboxamide

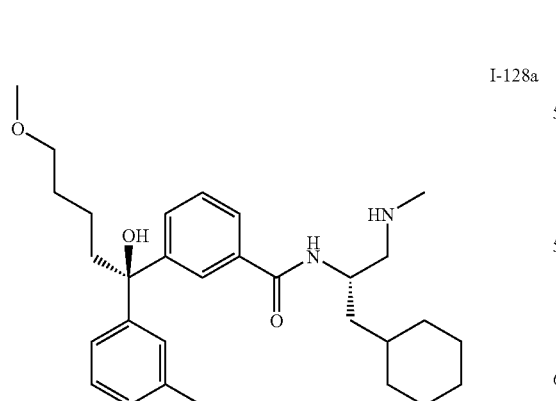

I-128a

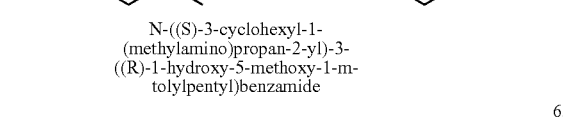

N-((S)-3-cyclohexyl-1-
(methylamino)propan-2-yl)-3-
((R)-1-hydroxy-5-methoxy-1-m-
tolylpentyl)benzamide

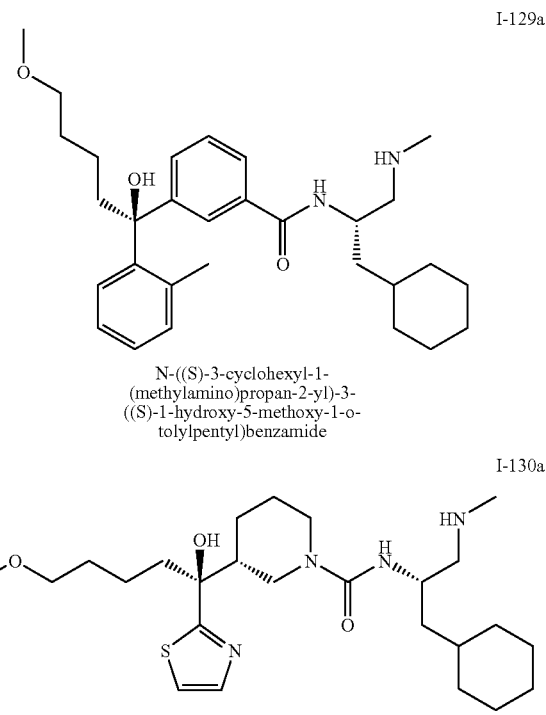

I-129a

N-((S)-3-cyclohexyl-1-
(methylamino)propan-2-yl)-3-
((S)-1-hydroxy-5-methoxy-1-o-
tolylpentyl)benzamide I-130a (3R)-N-((S)-3-cyclohexyl-1-
(methylamino)propan-2-yl)-3-
((S)-1-hydroxy-5-methoxy-1-
(thiazol-2-yl)pentyl)piperidine-1-
carboxamide

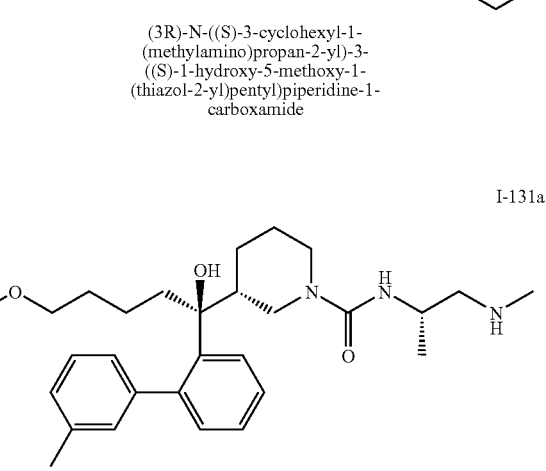

I-131a (3R)-3-((S)-1-(2-(3-
methylphenyl)phenyl)-1-
hydroxy-5-methoxypentyl)-N-
((S)-1-(methylamino)propan-2-
yl)piperidine-1-carboxamide

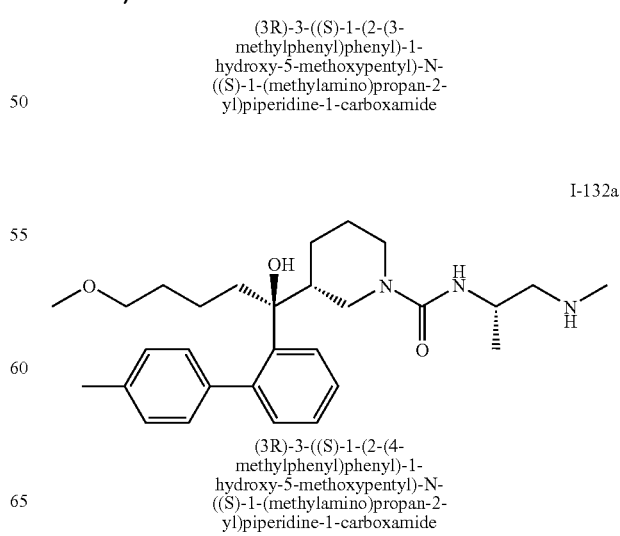

I-132a (3R)-3-((S)-1-(2-(4-
methylphenyl)phenyl)-1-
hydroxy-5-methoxypentyl)-N-
((S)-1-(methylamino)propan-2-
yl)piperidine-1-carboxamide -continued

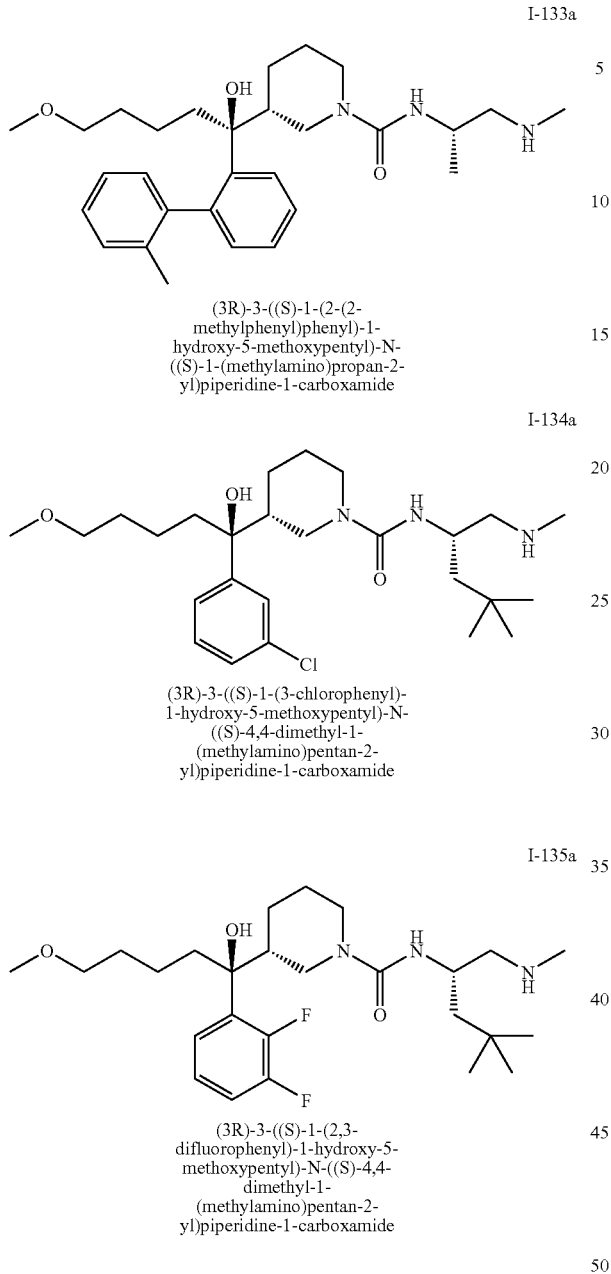

I-133a (3R)-3-((S)-1-(2-(2-methylphenyl)phenyl)-1-hydroxy-5-methoxypentyl)-N-((S)-1-(methylamino)propan-2-yl)piperidine-1-carboxamide I-134a (3R)-3-((S)-1-(3-chlorophenyl)-1-hydroxy-5-methoxypentyl)-N-((S)-4,4-dimethyl-1-(methylamino)pentan-2-yl)piperidine-1-carboxamide I-135a (3R)-3-((S)-1-(2,3-difluorophenyl)-1-hydroxy-5-methoxypentyl)-N-((S)-4,4-dimethyl-1-(methylamino)pentan-2-yl)piperidine-1-carboxamide

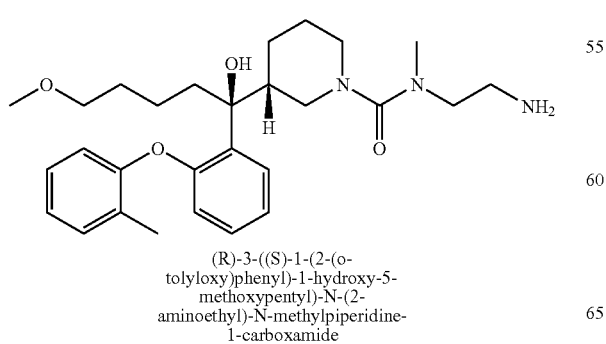

I-136a (R)-3-((S)-1-(2-(o-tolyloxy)phenyl)-1-hydroxy-5-methoxypentyl)-N-(2-aminoethyl)-N-methylpiperidine-1-carboxamide -continued

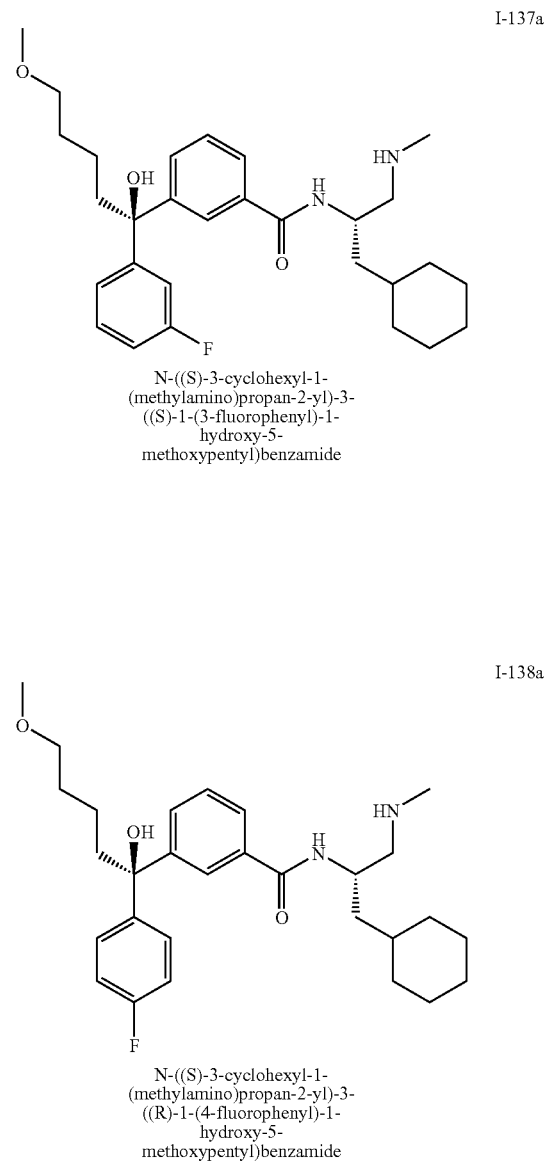

I-137a

N-((S)-3-cyclohexyl-1-(methylamino)propan-2-yl)-3-((S)-1-(3-fluorophenyl)-1-hydroxy-5-methoxypentyl)benzamide I-138a N-((S)-3-cyclohexyl-1-(methylamino)propan-2-yl)-3-((R)-1-(4-fluorophenyl)-1-hydroxy-5-methoxypentyl)benzamide

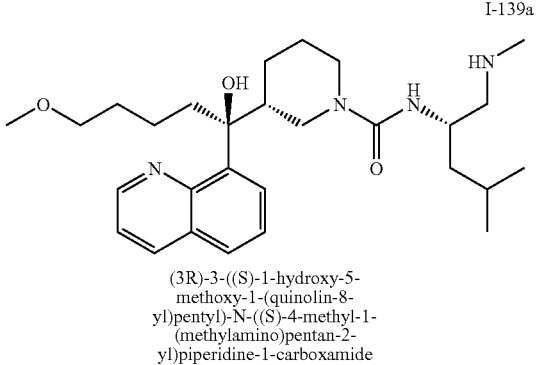

I-139a (3R)-3-((S)-1-hydroxy-5-methoxy-1-(quinolin-8-yl)pentyl)-N-((S)-4-methyl-1-(methylamino)pentan-2-yl)piperidine-1-carboxamide -continued I-140a

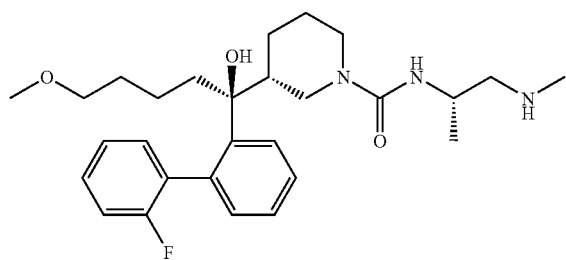

(3R)-3-((S)-1-(2-(2-fluorophenyl)phenyl)-1-hydroxy-5-methoxypentyl)-N-((S)-1-(methylamino)propan-2-yl)piperidine-1-carboxamide I-141a

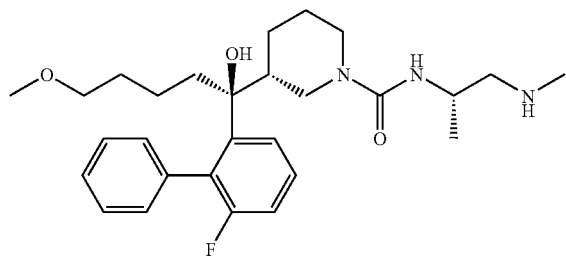

(3R)-3-((S)-1-(3-fluoro-2-phenylphenyl)-1-hydroxy-5-methoxypentyl)-N-((S)-1-(methylamino)propan-2-yl)piperidine-1-carboxamide I-142a

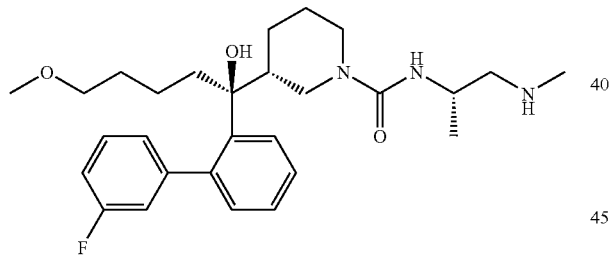

(3R)-3-((S)-1-(2-(3-fluorophenyl)phenyl)-1-hydroxy-5-methoxypentyl)-N-((S)-1-(methylamino)propan-2-yl)piperidine-1-carboxamide I-143a

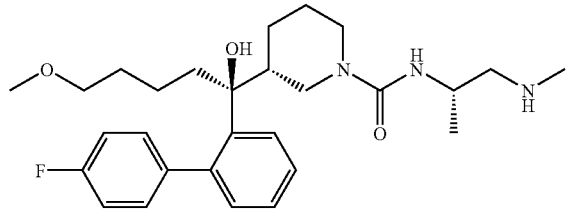

(3R)-3-((S)-1-(2-(4-fluorophenyl)phenyl)-1-hydroxy-5-methoxypentyl)-N-((S)-1-(methylamino)propan-2-yl)piperidine-1-carboxamide -continued I-144a

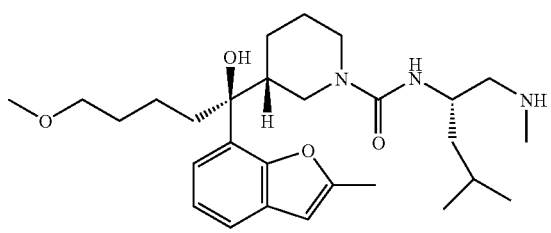

(3R)-3-((S)-1-hydroxy-5-methoxy-1-(2-methylbenzofuran-7-yl)pentyl)-N-((S)-4-methyl-1-(methylamino)pentan-2-yl)piperidine-1-carboxamide I-145a

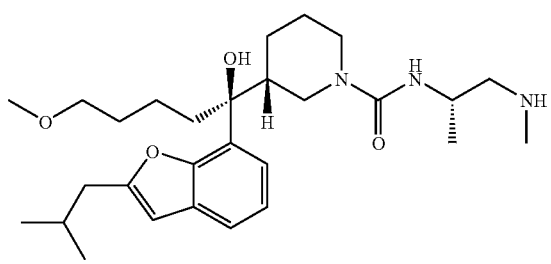

(3R)-3-((S)-1-hydroxy-1-(2-isobutylbenzofuran-7-yl)-5-methoxypentyl)-N-((S)-1-(methylamino)propan-2-yl)piperidine-1-carboxamide I-146a

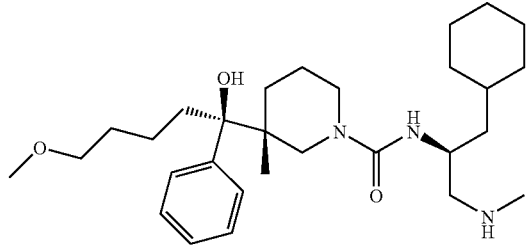

(3R)-N-((S)-3-cyclohexyl-1-(methylamino)propan-2-yl)-3-((R)-1-hydroxy-5-methoxy-1-phenylpentyl)-3-methylpiperidine-1-carboxamide I-147a

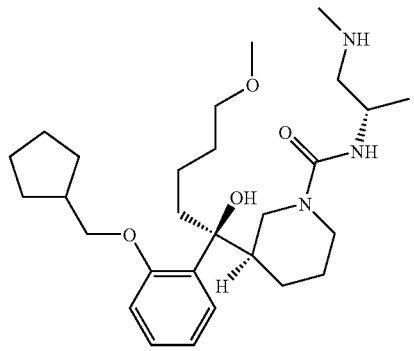

(3R)-3-((S)-1-(2-(cyclopentylmethoxy)phenyl)-1-hydroxy-5-methoxypentyl)-N-((S)-1-(methylamino)propan-2-yl)piperidine-1-carboxamide -continued I-148a

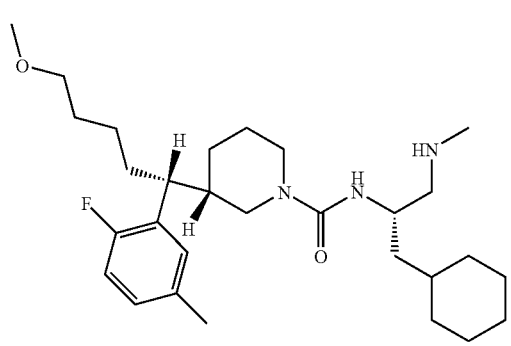

(3S)-N-((S)-3-cyclohexyl-1-(methylamino)propan-2-yl)-3-((R)-1-(2-fluoro-5-methylphenyl)-5-methoxypentyl)piperidine-1-carboxamide I-149a

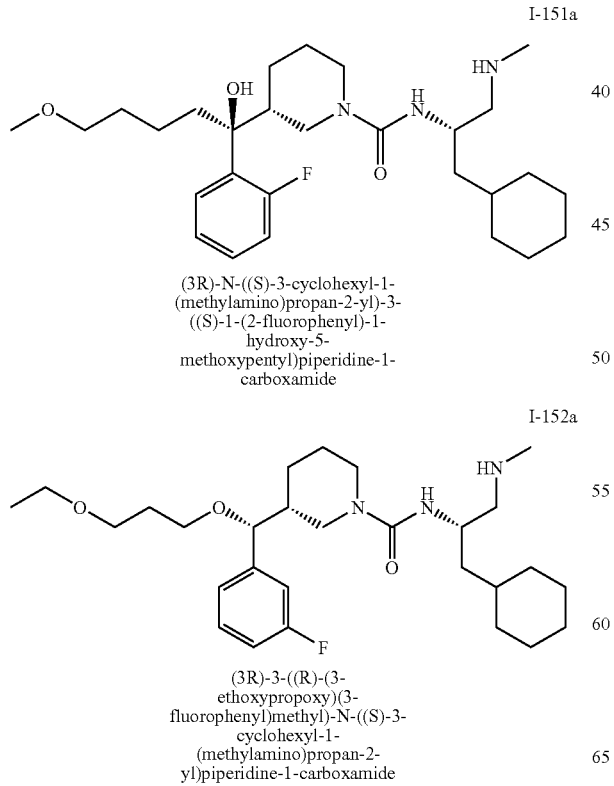

(3R)-3-((S)-1-(benzo[b]thiophen-7-yl)-1-hydroxy-5-methoxypentyl)-N-((S)-4-methyl-1-(methylamino)pentan-2-yl)piperidine-1-carboxamide I-151a (3R)-N-((S)-3-cyclohexyl-1-(methylamino)propan-2-yl)-3-((S)-1-(2-fluorophenyl)-1-hydroxy-5-methoxypentyl)piperidine-1-carboxamide I-152a (3R)-3-((R)-(3-ethoxypropoxy)(3-fluorophenyl)methyl)-N-((S)-3-cyclohexyl-1-(methylamino)propan-2-yl)piperidine-1-carboxamide -continued I-153a

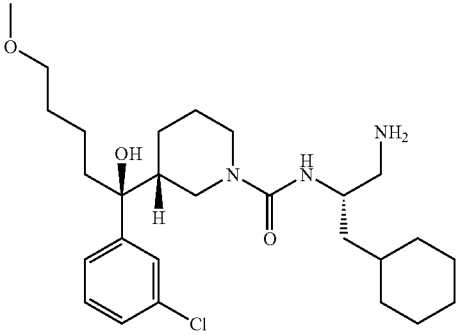

(3R)-N-((S)-1-amino-3-cyclohexylpropan-2-yl)-3-((S)-1-(3-chlorophenyl)-1-hydroxy-5-methoxypentyl)piperidine-1-carboxamide I-154a

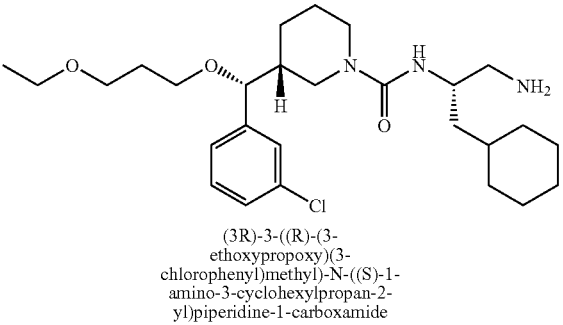

(3R)-3-((R)-(3-ethoxypropoxy)(3-chlorophenyl)methyl)-N-((S)-1-amino-3-cyclohexylpropan-2-yl)piperidine-1-carboxamide I-155a

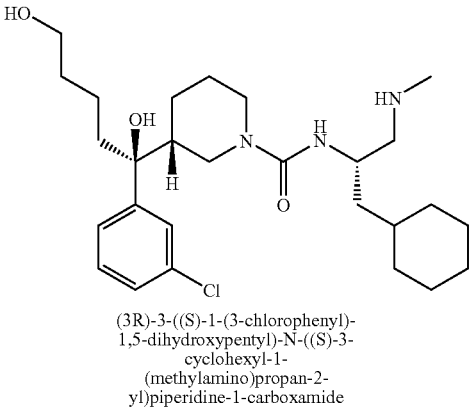

(3R)-3-((S)-1-(3-chlorophenyl)-1,5-dihydroxypentyl)-N-((S)-3-cyclohexyl-1-(methylamino)propan-2-yl)piperidine-1-carboxamide I-156a

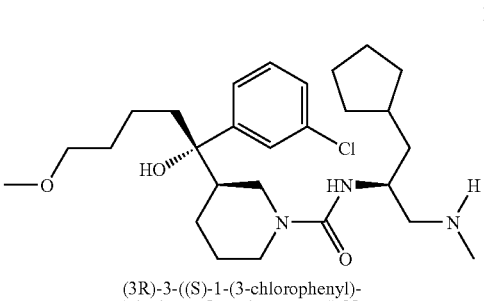

(3R)-3-((S)-1-(3-chlorophenyl)-1-hydroxy-5-methoxypentyl)-N-((S)-3-cyclopentyl-1-(methylamino)propan-2-yl)piperidine-1-carboxamide I-157a

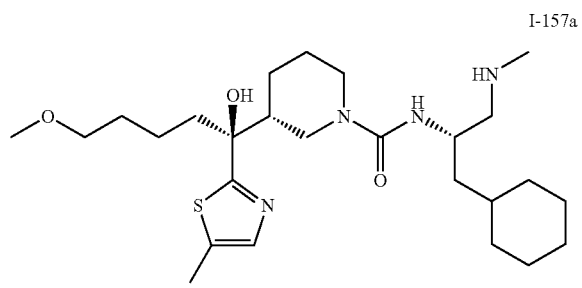

(3R)-N-((S)-3-cyclohexyl-1-
(methylamino)propan-2-yl)-3-
((S)-1-hydroxy-5-methoxy-1-(5-
methylthiazol-2-
yl)pentyl)piperidine-1-
carboxamide I-158a

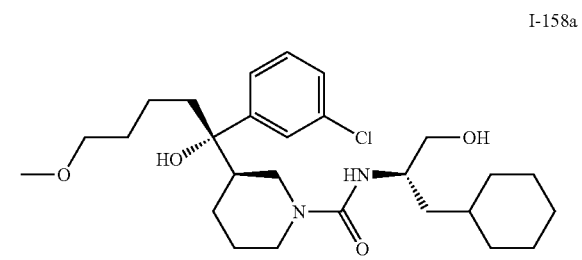

(3R)-3-((S)-1-(3-chlorophenyl)-
1-hydroxy-5-methoxypentyl)-N-
((S)-3-cyclohexyl-1-
hydroxypropan-2-yl)piperidine-
1-carboxamide I-159a

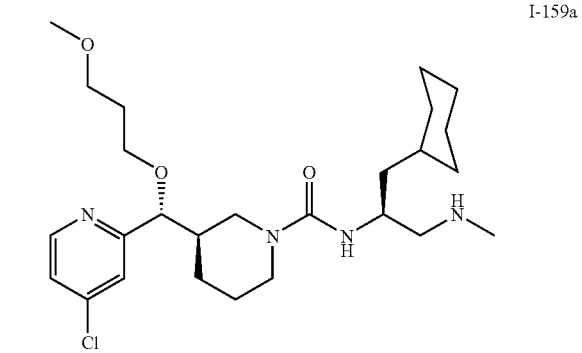

(3R)-3-((R)-(3-
methoxypropoxy)(4-
chloropyridin-2-yl)methyl)-N-
((S)-3-cyclohexyl-1-
(methylamino)propan-2-
yl)piperidine-1-carboxamide I-160a

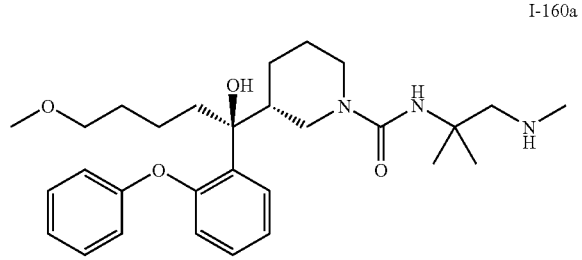

(R)-3-((S)-1-hydroxy-5-
methoxy-1-(2-
phenoxyohenyl)pentyl)-N-(2-
methyl-1-(methylamino)propan-
2-yl)piperidine-1-carboxamide I-161a

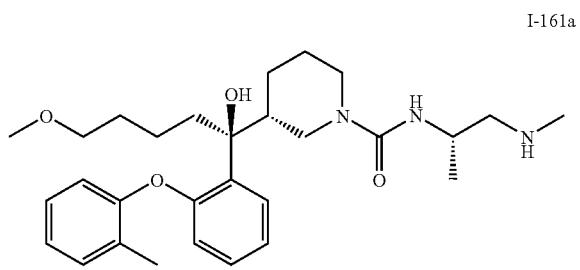

(3R)-3-((S)-1-(2-(o-
tolyloxy)phenyl)-1-hydroxy-5-
methoxypentyl)-N-((S)-1-
(methylamino)propan-2-
yl)piperidine-1-carboxamide I-162a

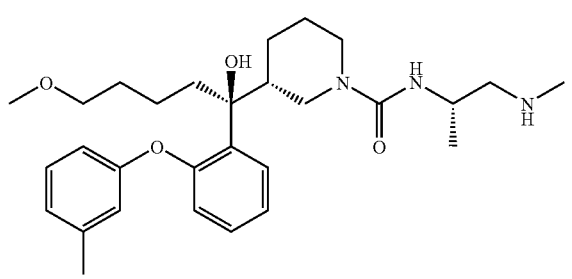

(3R)-3-((S)-1-(2-(m-
tolyloxy)phenyl)-1-hydroxy-5-
methoxypentyl)-N-((S)-1-
(methylamino)propan-2-
yl)piperidine-1-carboxamide I-163a

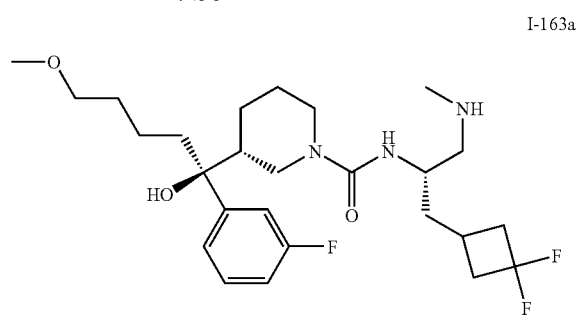

(3R)-N-((S)-3-(3,3-
difluorocyclobutyl)-1-
(methylamino)propan-2-yl)-3-
((S)-1-(3-fluorophenyl)-1-
hydroxy-5-
methoxypentyl)piperidine-1-
carboxamide I-165a

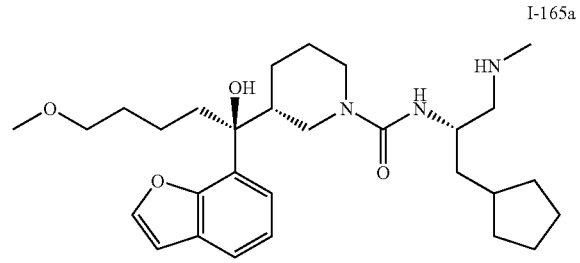

(3R)-3-((S)-1-(benzofuran-7-yl)-
1-hydroxy-5-methoxypentyl)-N-
((S)-3-cyclopentyl-1-
(methylamino)propan-2-
yl)piperidine-1-carboxamide

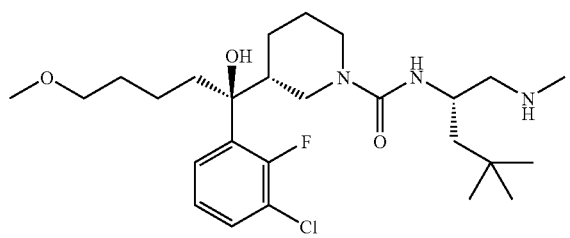

I-166a (3R)-3-((S)-1-(3-chloro-2-fluorophenyl)-1-hydroxy-5-methoxypentyl)-N-((S)-4,4-dimethyl-1-(methylamino)pentan-2-yl)piperidine-1-carboxamide

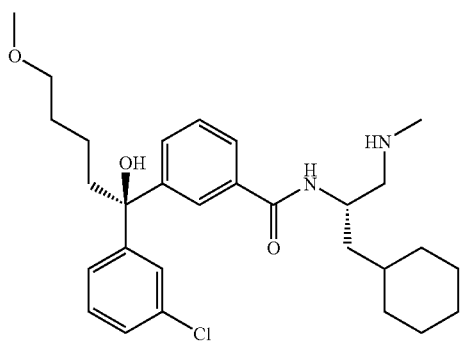

I-167a 3-((S)-1-(3-chlorophenyl)-1-hydroxy-5-methoxypentyl)-N-((S)-3-cyclohexyl-1-(methylamino)propan-2-yl)benzamide

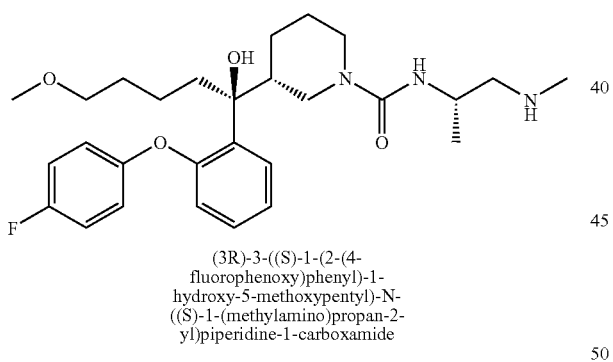

I-168a (3R)-3-((S)-1-(2-(4-fluorophenoxy)phenyl)-1-hydroxy-5-methoxypentyl)-N-((S)-1-(methylamino)propan-2-yl)piperidine-1-carboxamide

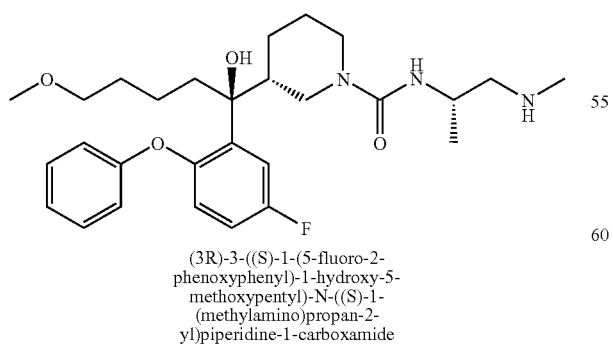

I-169a (3R)-3-((S)-1-(5-fluoro-2-phenoxyphenyl)-1-hydroxy-5-methoxypentyl)-N-((S)-1-(methylamino)propan-2-yl)piperidine-1-carboxamide

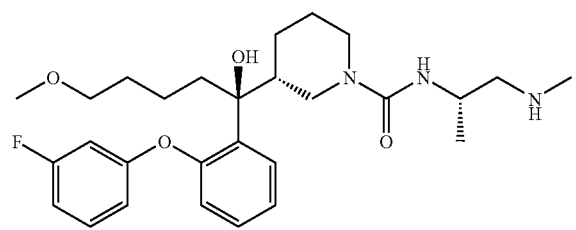

I-170a (3R)-3-((S)-1-(2-(3-fluorophenoxy)phenyl)-1-hydroxy-5-methoxypentyl)-N-((S)-1-(methylamino)propan-2-yl)piperidine-1-carboxamide

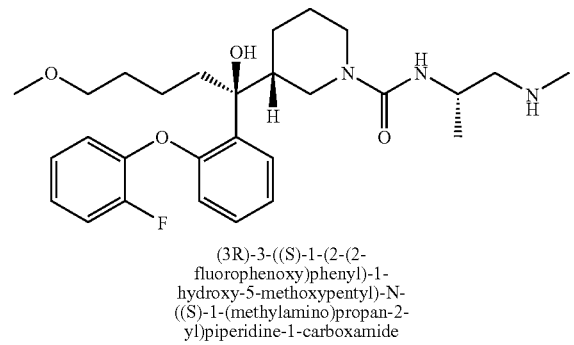

I-171a (3R)-3-((S)-1-(2-(2-fluorophenoxy)phenyl)-1-hydroxy-5-methoxypentyl)-N-((S)-1-(methylamino)propan-2-yl)piperidine-1-carboxamide

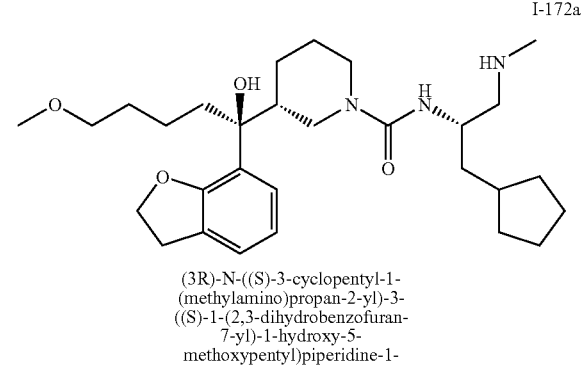

I-172a (3R)-N-((S)-3-cyclopentyl-1-(methylamino)propan-2-yl)-3-((S)-1-(2,3-dihydrobenzofuran-7-yl)-1-hydroxy-5-methoxypentyl)piperidine-1-carboxamide

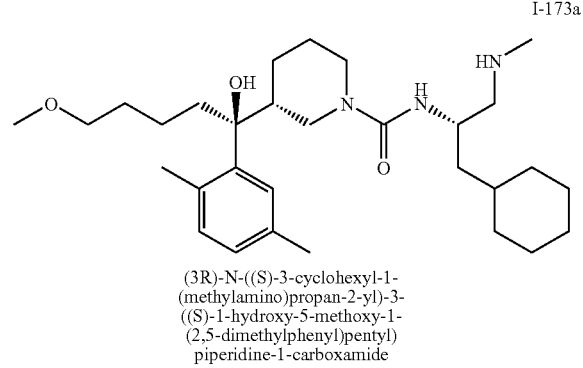

I-173a (3R)-N-((S)-3-cyclohexyl-1-(methylamino)propan-2-yl)-3-((S)-1-hydroxy-5-methoxy-1-(2,5-dimethylphenyl)pentyl)piperidine-1-carboxamide

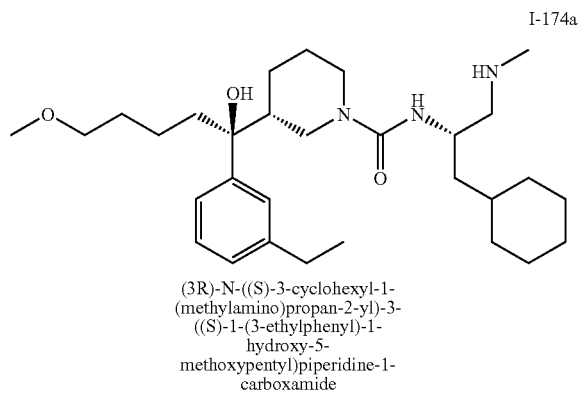

(3R)-N-((S)-3-cyclohexyl-1-
(methylamino)propan-2-yl)-3-
((S)-1-(3-ethylphenyl)-1-
hydroxy-5-
methoxypentyl)piperidine-1-
carboxamide I-174a

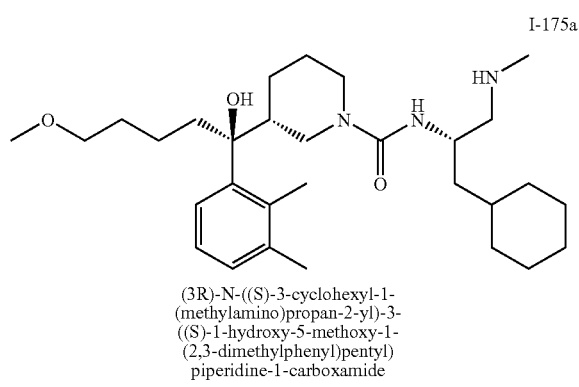

(3R)-N-((S)-3-cyclohexyl-1-
(methylamino)propan-2-yl)-3-
((S)-1-hydroxy-5-methoxy-1-
(2,3-dimethylphenyl)pentyl)
piperidine-1-carboxamide I-175a

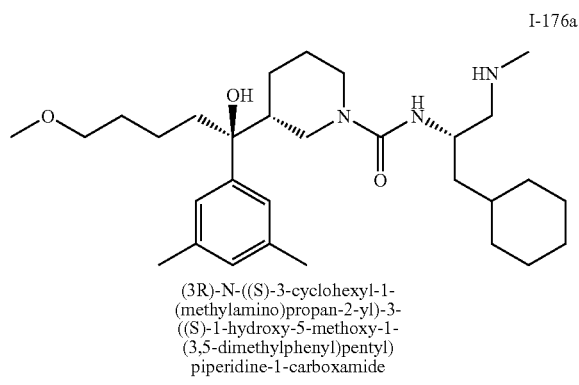

(3R)-N-((S)-3-cyclohexyl-1-
(methylamino)propan-2-yl)-3-
((S)-1-hydroxy-5-methoxy-1-
(3,5-dimethylphenyl)pentyl)
piperidine-1-carboxamide I-176a

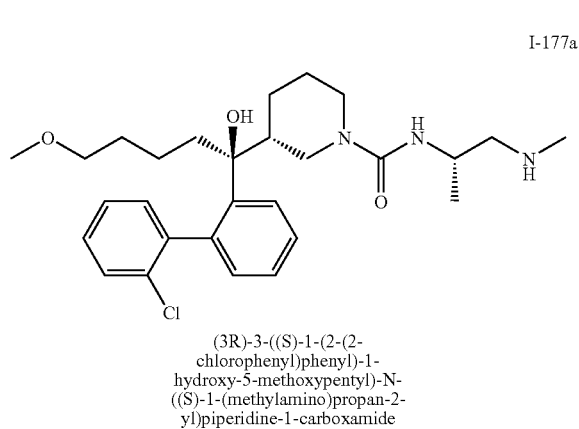

(3R)-3-((S)-1-(2-(2-
chlorophenyl)phenyl)-1-
hydroxy-5-methoxypentyl)-N-
((S)-1-(methylamino)propan-2-
yl)piperidine-1-carboxamide I-177a

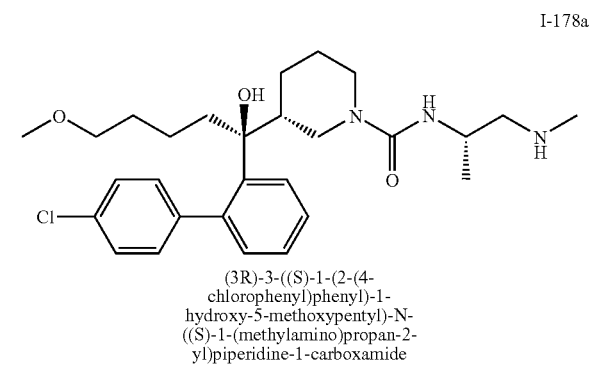

(3R)-3-((S)-1-(2-(4-
chlorophenyl)phenyl)-1-
hydroxy-5-methoxypentyl)-N-
((S)-1-(methylamino)propan-2-
yl)piperidine-1-carboxamide I-178a

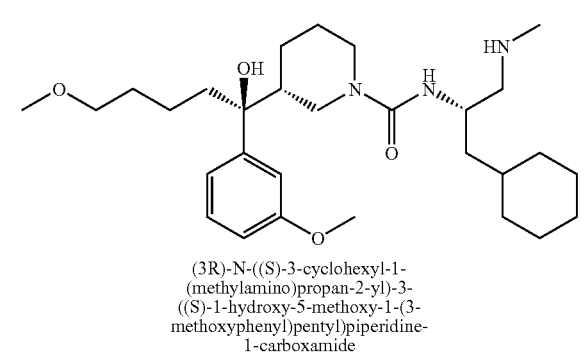

(3R)-N-((S)-3-cyclohexyl-1-
(methylamino)propan-2-yl)-3-
((S)-1-hydroxy-5-methoxy-1-(3-
methoxyphenyl)pentyl)piperidine-
1-carboxamide I-179a

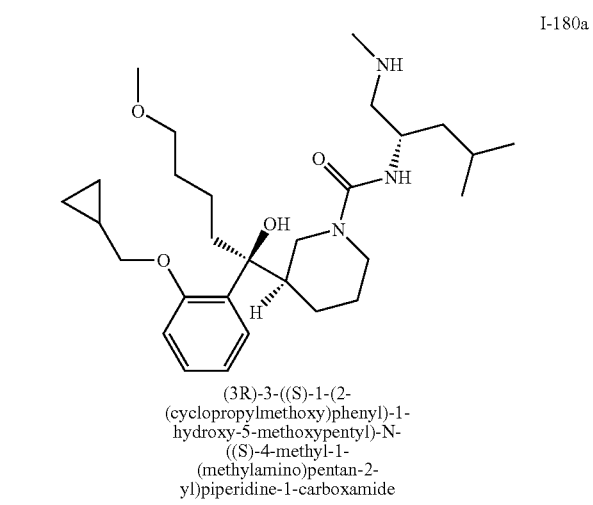

(3R)-3-((S)-1-(2-
(cyclopropylmethoxy)phenyl)-1-
hydroxy-5-methoxypentyl)-N-
((S)-4-methyl-1-
(methylamino)pentan-2-
yl)piperidine-1-carboxamide I-180a

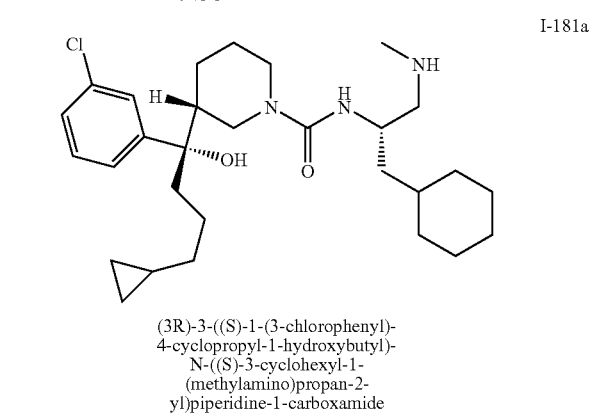

(3R)-3-((S)-1-(3-chlorophenyl)-
4-cyclopropyl-1-hydroxybutyl)-
N-((S)-3-cyclohexyl-1-
(methylamino)propan-2-
yl)piperidine-1-carboxamide I-181a

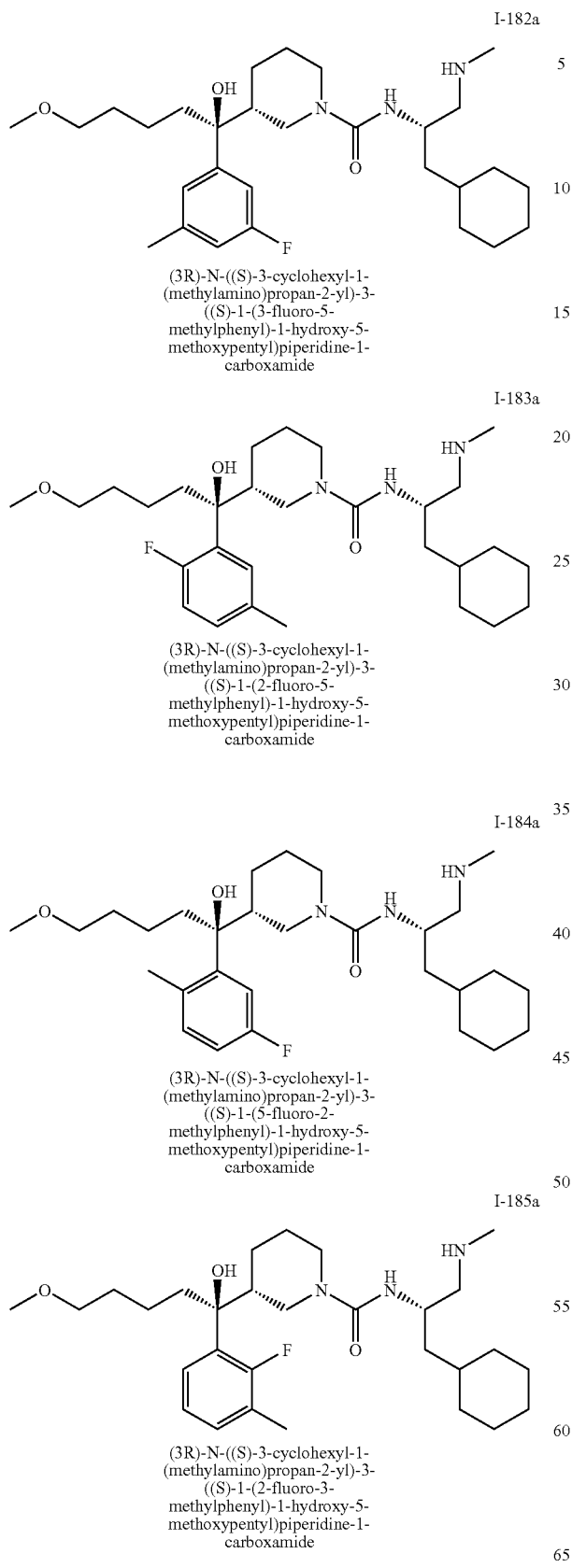
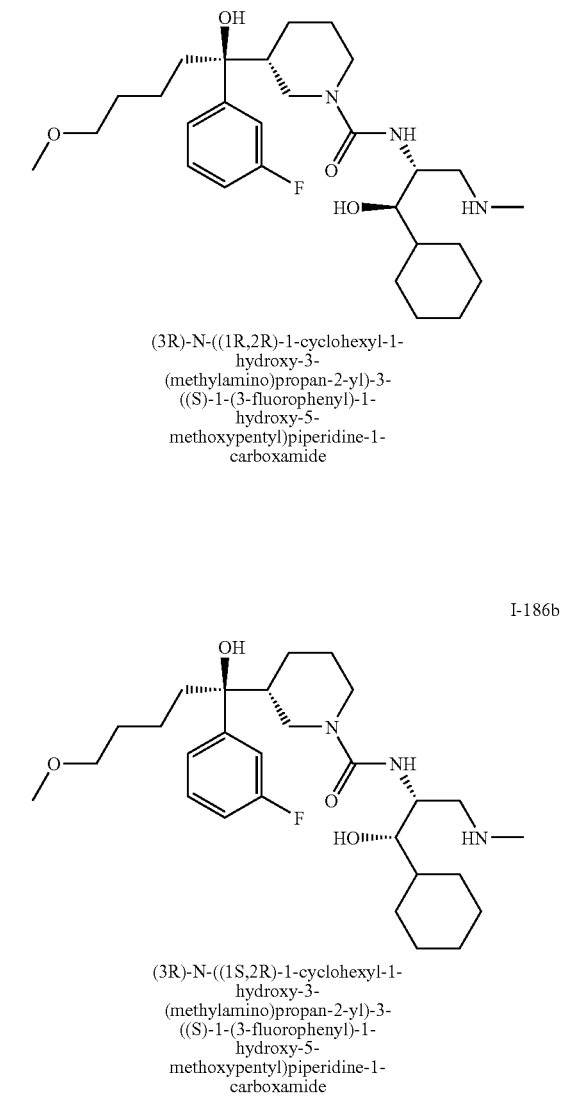

-continued

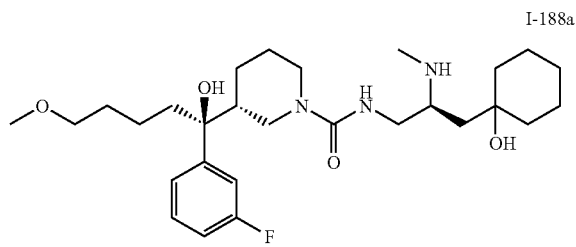

I-188a (3R)-3-((S)-1-(3-fluorophenyl)-
1-hydroxy-5-methoxypentyl)-N-
((S)-3-(1-hydroxycyclohexyl)-2-
(methylamino)propyl)piperidine-
1-carboxamide

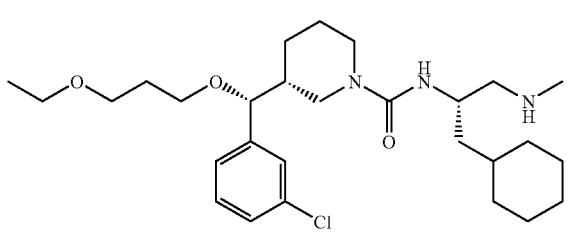

I-190a (3R)-3-((R)-(3-
ethoxypropoxy)(3-
chlorophenyl)methyl)-N-((S)-3-
cyclohexyl-1-
(methylamino)propan-2-
yl)piperidine-1-carboxamide

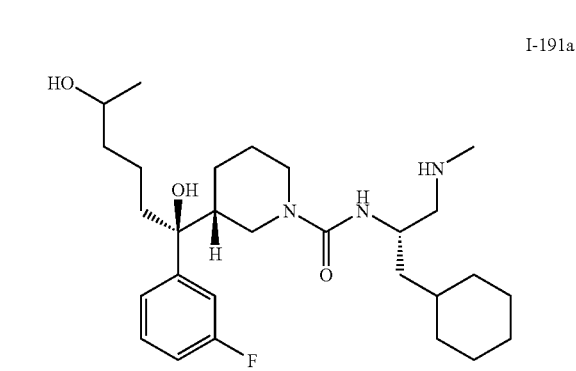

I-191a (3R)-3-((1S)-1-(3-chlorophenyl)-
1-,5-dihydroxyhexyl)-N-((S)-3-
cyclohexyl-1-
(methylamino)propan-2-
yl)piperidine-1-carboxamide

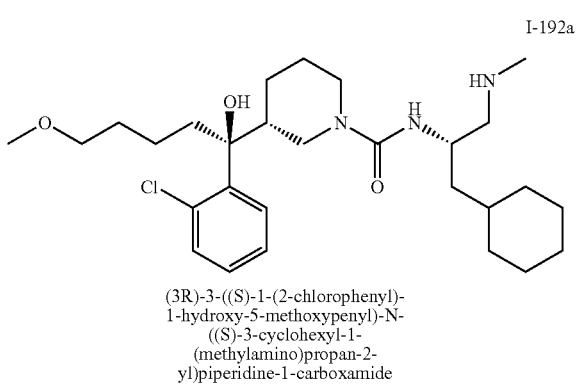

I-192a (3R)-3-((S)-1-(2-chlorophenyl)-
1-hydroxy-5-methoxypentyl)-N-
((S)-3-cyclohexyl-1-
(methylamino)propan-2-
yl)piperidine-1-carboxamide -continued

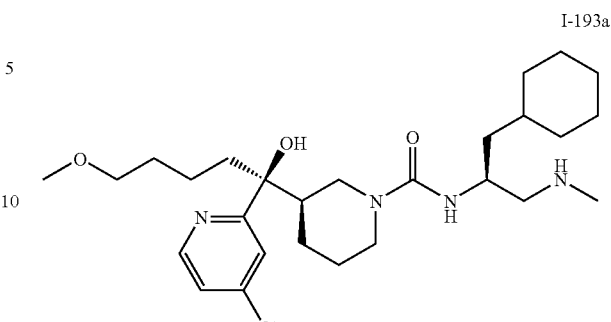

I-193a (3R)-3-((S)-1-(4-chloropyridin-2-
yl)-1-hydroxy-5-methoxypentyl)-
N-((S)-3-cyclohexyl-1-
(methylamino)propan-2-
yl)piperidine-1-carboxamide I-194a (3R)-3-((R)-(3-
ethoxypropoxy)(phenyl)methyl)-
N-((S)-3-(4,4-
difluorocyclohexyl)-1-
(methylamino)propan-2-
yl)piperidine-1-carboxamide

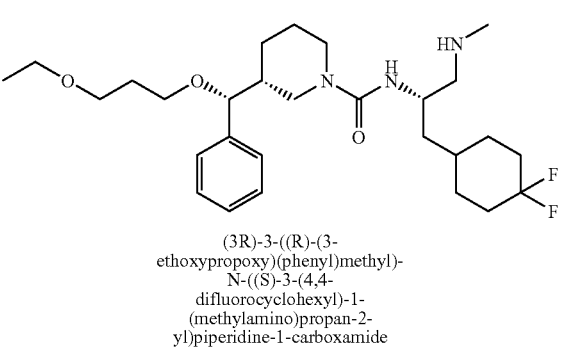

I-195a (3R)-N-((S)-3-cyclohexyl-1-
(methylamino)propan-2-yl)-3-
((S)-1-(3,5-difluorophenyl)-1-
hydroxy-5-
methoxypentyl)piperidine-1-
carboxamide

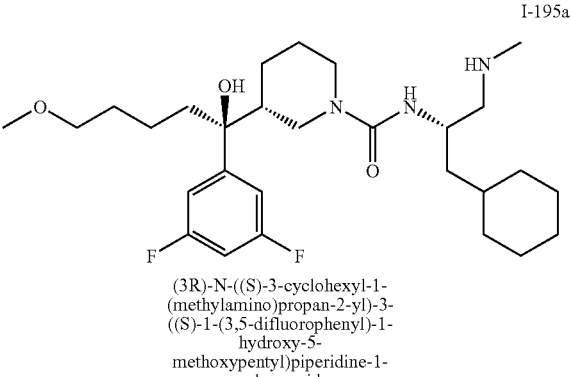

I-196a (3R)-N-((S)-3-cyclohexyl-1-
(methylamino)propan-2-yl)-3-
((S)-1-(2,3-difluorophenyl)-1-
hydroxy-5-
methoxypentyl)piperidine-1-
carboxamide -continued

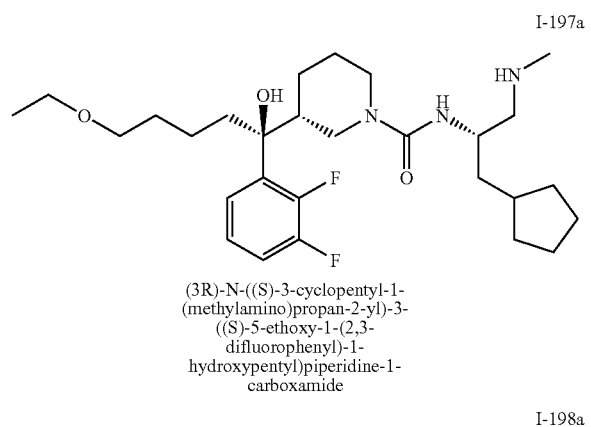

I-197a (3R)-N-((S)-3-cyclopentyl-1-
(methylamino)propan-2-yl)-3-
((S)-5-ethoxy-1-(2,3-
difluorophenyl)-1-
hydroxypentyl)piperidine-1-
carboxamide

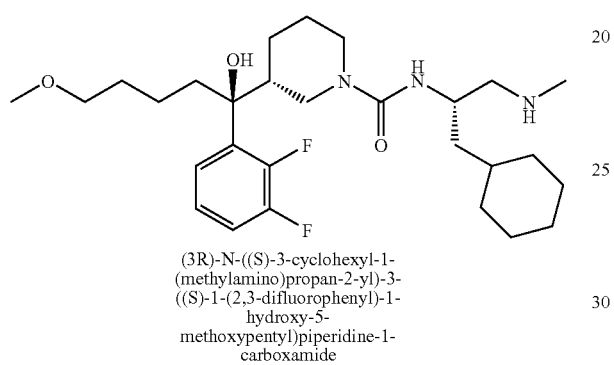

I-198a (3R)-N-((S)-3-cyclohexyl-1-
(methylamino)propan-2-yl)-3-
((S)-1-(2,3-difluorophenyl)-1-
hydroxy-5-
methoxypentyl)piperidine-1-
carboxamide

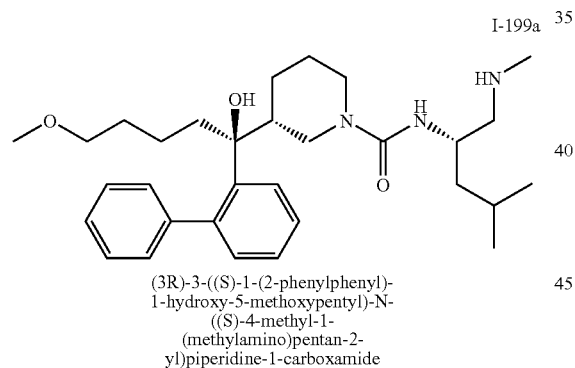

I-199a (3R)-3-((S)-1-(2-phenylphenyl)-
1-hydroxy-5-methoxypentyl)-N-
((S)-4-methyl-1-
(methylamino)pentan-2-
yl)piperidine-1-carboxamide

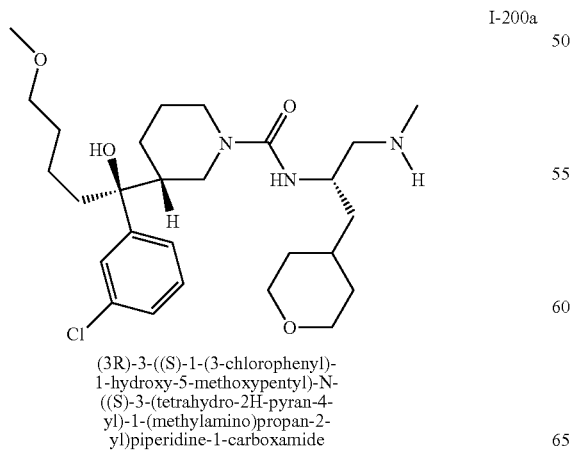

I-200a (3R)-3-((S)-1-(3-chlorophenyl)-
1-hydroxy-5-methoxypentyl)-N-
((S)-3-(tetrahydro-2H-pyran-4-
yl)-1-(methylamino)propan-2-
yl)piperidine-1-carboxamide -continued

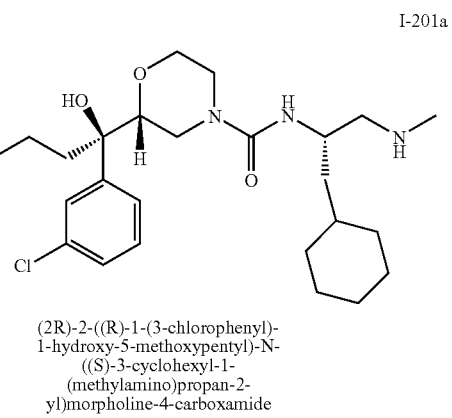

I-201a (2R)-2-((R)-1-(3-chlorophenyl)-
1-hydroxy-5-methoxypentyl)-N-
((S)-3-cyclohexyl-1-
(methylamino)propan-2-
yl)morpholine-4-carboxamide

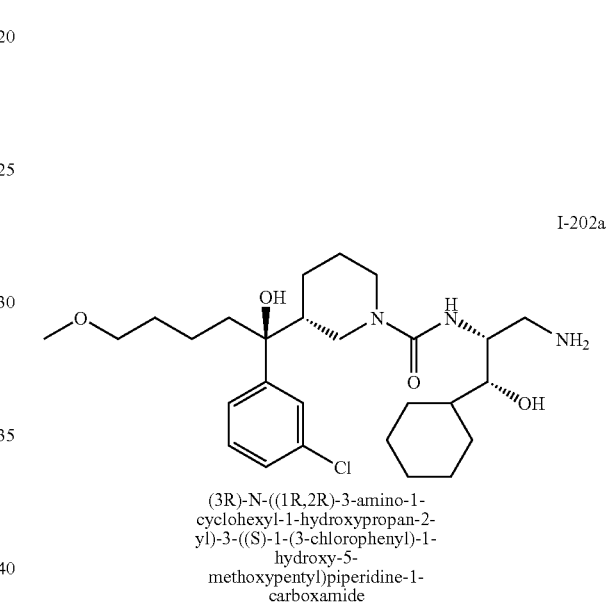

I-202a (3R)-N-((1R,2R)-3-amino-1-
cyclohexyl-1-hydroxypropan-2-
yl)-3-((S)-1-(3-chlorophenyl)-1-
hydroxy-5-
methoxypentyl)piperidine-1-
carboxamide

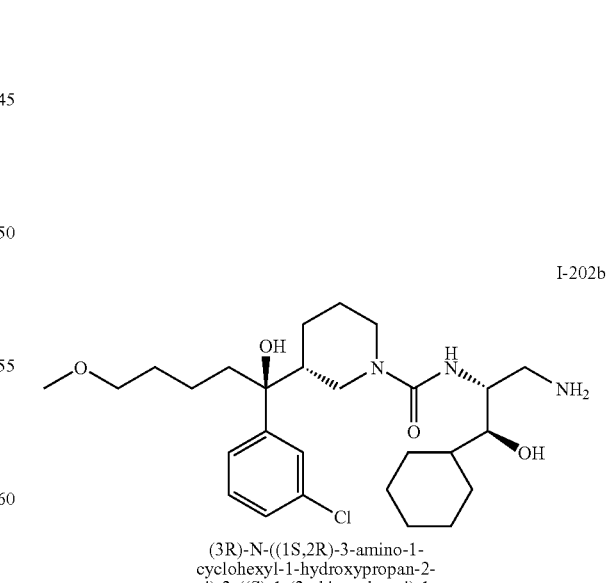

I-202b (3R)-N-((1S,2R)-3-amino-1-
cyclohexyl-1-hydroxypropan-2-
yl)-3-((S)-1-(3-chlorophenyl)-1-
hydroxy-5-
methoxypentyl)piperidine-1-
carboxamide

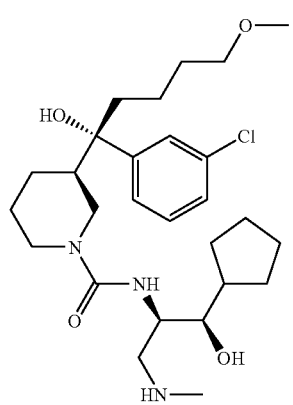

I-203a (3R)-3-((S)-1-(3-chlorophenyl)-
1-hydroxy-5-methoxypentyl)-N-
((1R,2R)-1-cyclopentyl-1-
hydroxy-3-
(methylamino)propan-2-
yl)piperidine-1-carboxamide

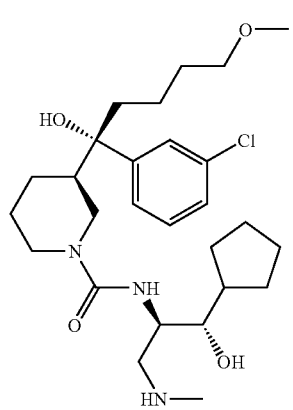

I-203b (3R)-3-((S)-1-(3-chlorophenyl)-
1-hydroxy-5-methoxypentyl)-N-
((1S,2R)-1-cyclopentyl-1-
hydroxy-3-
(methylamino)propan-2-
yl)piperidine-1-carboxamide I-204a

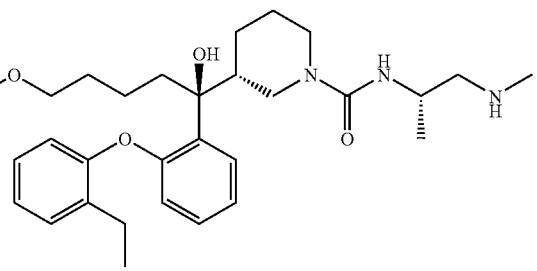

(3R)-3-((S)-1-(2-(o-
tolyloxy)phenyl)-1-hydroxy-5-
methoxypentyl)-N-(2-methyl-1-
(methylamino)propan-2-
yl)piperidine-1-carboxamide I-205a

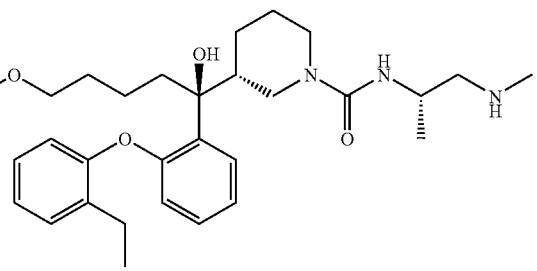

(3R)-3-((S)-1-(2-(2-
ethylphenoxy)phenyl)-1-
hydroxy-5-methoxypentyl)-N-
((S)-1-(methylamino)propan-2-
yl)piperidine-1-carboxamide I-206a

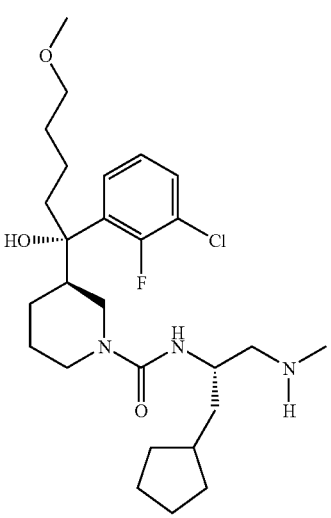

(3R)-3-((S)-1-(3-chloro-2-
fluorophenyl)-1-hydroxy-5-
methoxypentyl)-N-((S)-3-
cyclopentyl-1-
(methylamino)propan-2-
yl)piperidine-1-carboxamide -continued I-206b

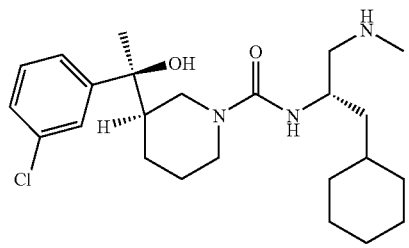

(3R)-3-((S)-1-(3-chlorophenyl)-
1-hydroxyethyl)-N-((S)-1-
cyclohexyl-3-
(methylamino)propan-2-
yl)piperidine-1-carboxamide

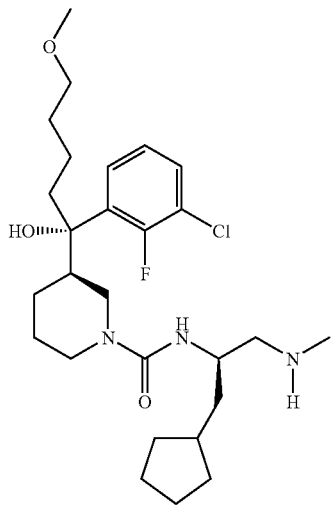

(3R)-3-((S)-1-(3-chloro-2-
fluorophenyl)-1-hydroxy-5-
methoxypentyl)-N-((R)-3-
cyclopentyl-1-
(methylamino)propan-2-
yl)piperidine-1-carboxamide I-210a

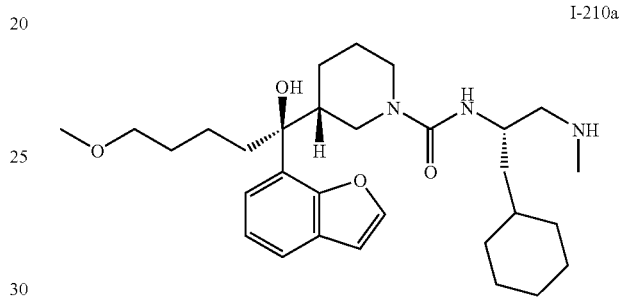

(3R)-3-((S)-1-(benzofuran-7-yl)-
1-hydroxy-5-methoxypentyl)-N-
((S)-3-cyclohexyl-1-
(methylamino)propan-2-
yl)piperidine-1-carboxamide I-207a

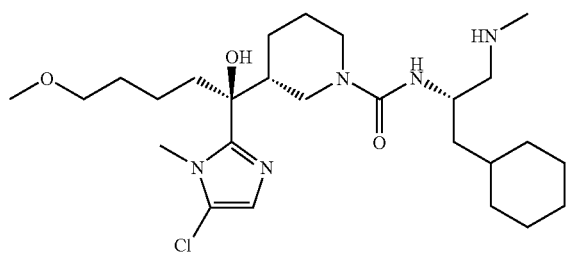

(3R)-3-((S)-1-(5-chloro-1-
methyl-1H-imidazol-2-yl)-1-
hydroxy-5-methoxypentyl)-N-
((S)-3-cyclohexyl-1-
(methylamino)propan-2-
yl)piperidine-1-carboxamide I-211a

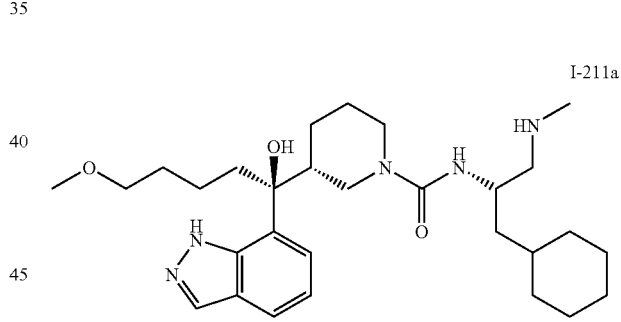

(3R)-N-((S)-3-cyclohexyl-1-
(methylamino)propan-2-yl)-3-
((S)-1-hydroxy-1-(1H-indazol-7-
yl)-5-methoxypentyl)piperidine-
1-carboxamide I-208a

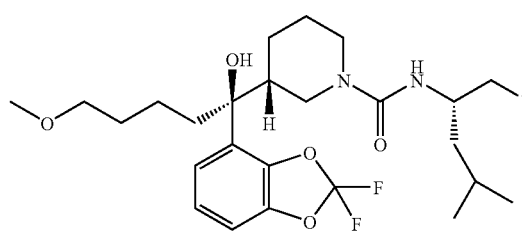

(3R)-3-((S)-1-(2,2-
difluorobenzo[d][1,3]dioxol-4-
yl)-1-hydroxy-5-methoxypentyl)-
N-((S)-4-methyl-1-
(methylamino)pentan-2-
yl)piperidine-1-carboxamide I-212a

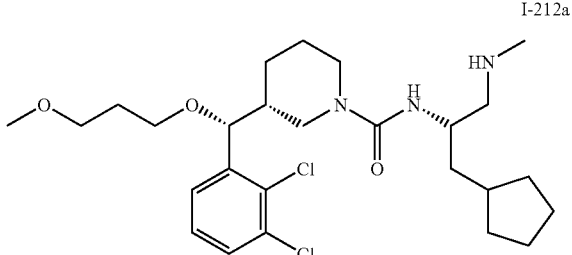

(3R)-3-((R)-(3-
methoxypropoxy)(2,3-
dichlorophenyl)methyl)-N-((S)-
3-cyclopentyl-1-
(methylamino)propan-2-
yl)piperidine-1-carboxamide -continued I-213a

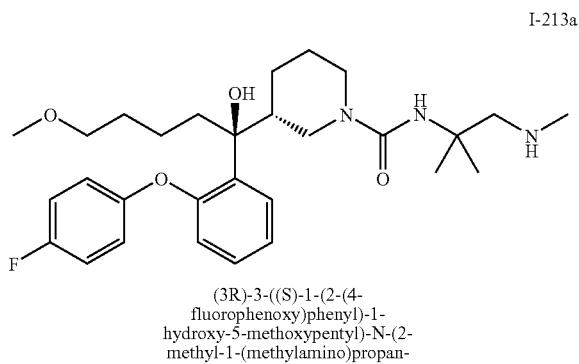

(3R)-3-((S)-1-(2-(4-fluorophenoxy)phenyl)-1-hydroxy-5-methoxypentyl)-N-(2-methyl-1-(methylamino)propan-2-yl)piperidine-1-carboxamide I-214a

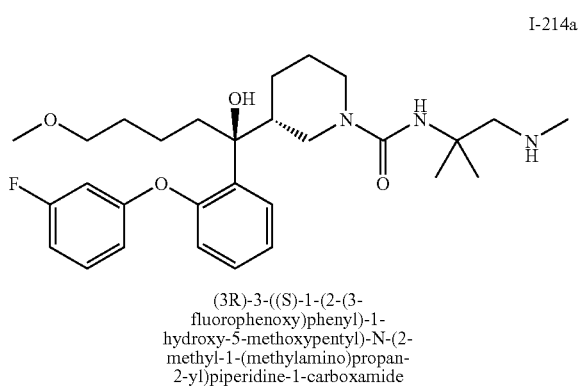

(3R)-3-((S)-1-(2-(3-fluorophenoxy)phenyl)-1-hydroxy-5-methoxypentyl)-N-(2-methyl-1-(methylamino)propan-2-yl)piperidine-1-carboxamide I-215a

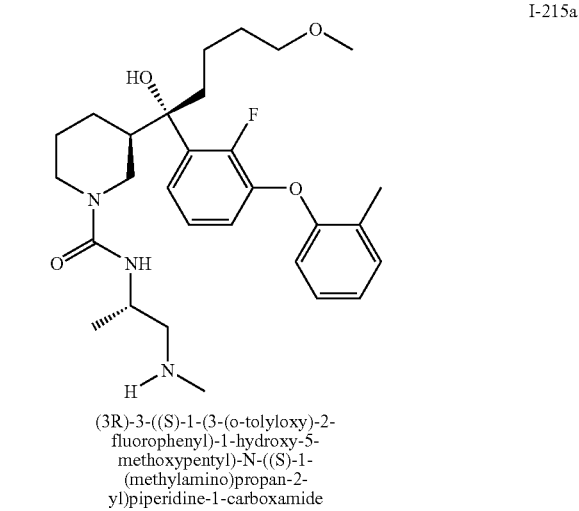

(3R)-3-((S)-1-(3-(o-tolyloxy)-2-fluorophenyl)-1-hydroxy-5-methoxypentyl)-N-((S)-1-(methylamino)propan-2-yl)piperidine-1-carboxamide I-216a

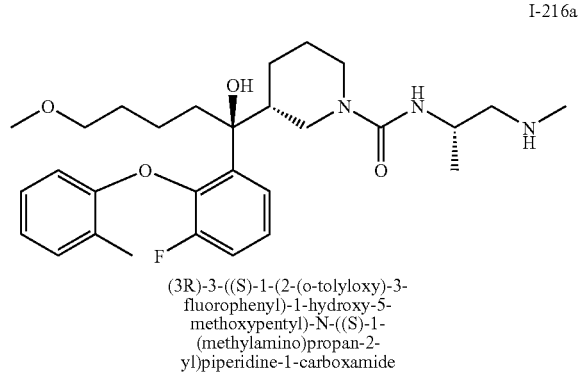

(3R)-3-((S)-1-(2-(o-tolyloxy)-3-fluorophenyl)-1-hydroxy-5-methoxypentyl)-N-((S)-1-(methylamino)propan-2-yl)piperidine-1-carboxamide -continued I-217a

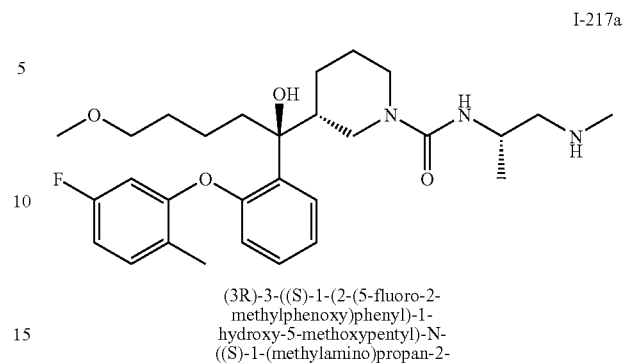

(3R)-3-((S)-1-(2-(5-fluoro-2-methylphenoxy)phenyl)-1-hydroxy-5-methoxypentyl)-N-((S)-1-(methylamino)propan-2-yl)piperidine-1-carboxamide I-218a (3R)-3-((S)-1-(2-(4-fluoro-2-methylphenoxy)phenyl)-1-hydroxy-5-methoxypentyl)-N-((S)-1-(methylamino)propan-2-yl)piperidine-1-carboxamide I-219a

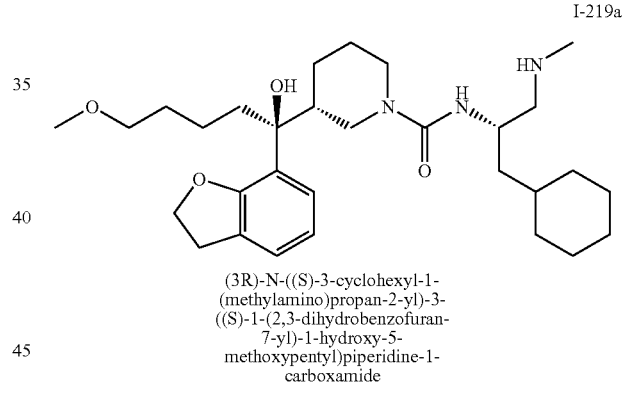

(3R)-N-((S)-3-cyclohexyl-1-(methylamino)propan-2-yl)-3-((S)-1-(2,3-dihydrobenzofuran-7-yl)-1-hydroxy-5-methoxypentyl)piperidine-1-carboxamide I-220a

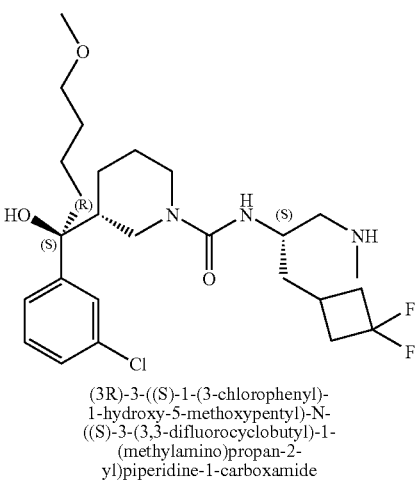

(3R)-3-((S)-1-(3-chlorophenyl)-1-hydroxy-5-methoxypentyl)-N-((S)-3-(3,3-difluorocyclobutyl)-1-(methylamino)propan-2-yl)piperidine-1-carboxamide -continued

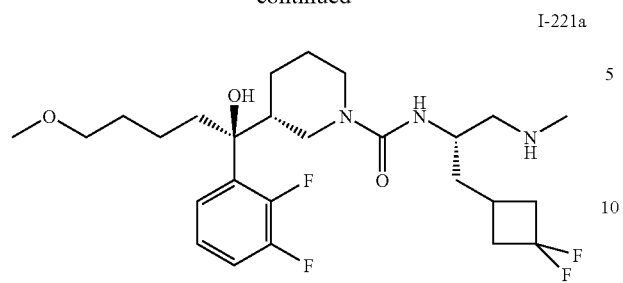

I-221a (3R)-N-((S)-3-(3,3-difluorocyclobutyl)-1-(methylamino)propan-2-yl)-3-((S)-1-(2,3-difluorophenyl)-1-hydroxy-5-methoxypentyl)piperidine-1-carboxamide

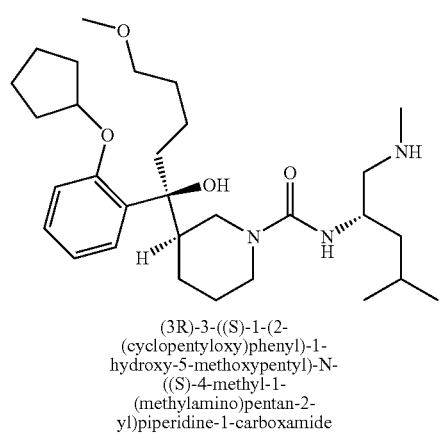

I-222a (3R)-3-((S)-1-(2-(cyclopentyloxy)phenyl)-1-hydroxy-5-methoxypentyl)-N-((S)-4-methyl-1-(methylamino)pentan-2-yl)piperidine-1-carboxamide

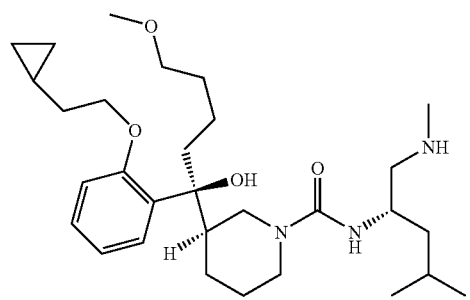

I-223a (3R)-3-((S)-1-(2-(2-cyclopropylethoxy)phenyl)-1-hydroxy-5-methoxypentyl)-N-((S)-4-methyl-1-(methylamino)pentan-2-yl)piperidine-1-carboxamide

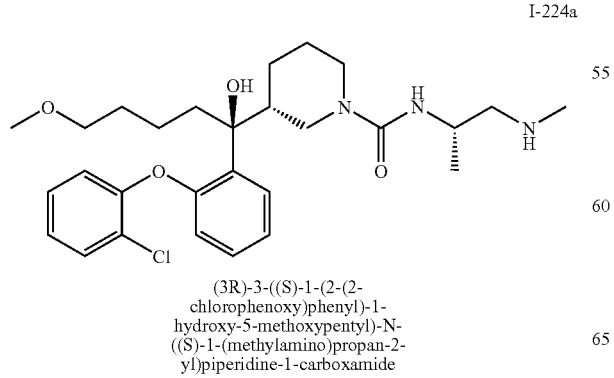

I-224a (3R)-3-((S)-1-(2-(2-chlorophenoxy)phenyl)-1-hydroxy-5-methoxypentyl)-N-((S)-1-(methylamino)propan-2-yl)piperidine-1-carboxamide

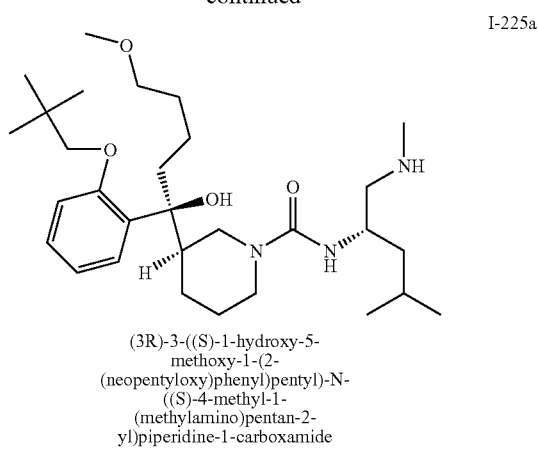

I-225a (3R)-3-((S)-1-hydroxy-5-methoxy-1-(2-(neopentyloxy)phenyl)pentyl)-N-((S)-4-methyl-1-(methylamino)pentan-2-yl)piperidine-1-carboxamide

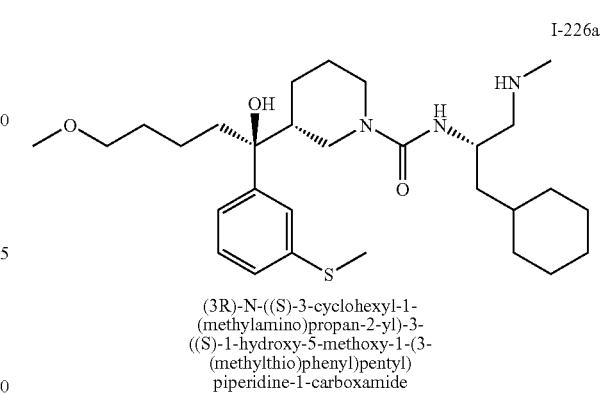

I-226a (3R)-N-((S)-3-cyclohexyl-1-(methylamino)propan-2-yl)-3-((S)-1-hydroxy-5-methoxy-1-(3-(methylthio)phenyl)pentyl)piperidine-1-carboxamide

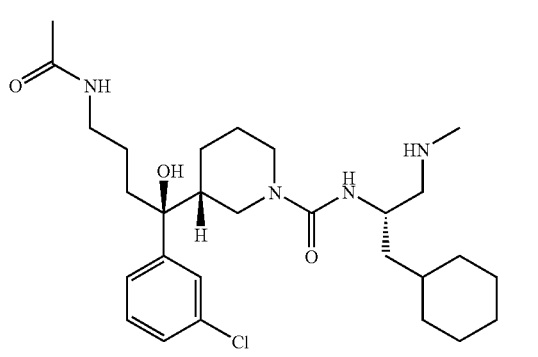

I-227a (3R)-3-((S)-4-(acetylamino)-1-(3-chlorophenyl)-1-hydroxybutyl)-N-((S)-3-cyclohexyl-1-(methylamino)propan-2-yl)piperidine-1-carboxamide -continued

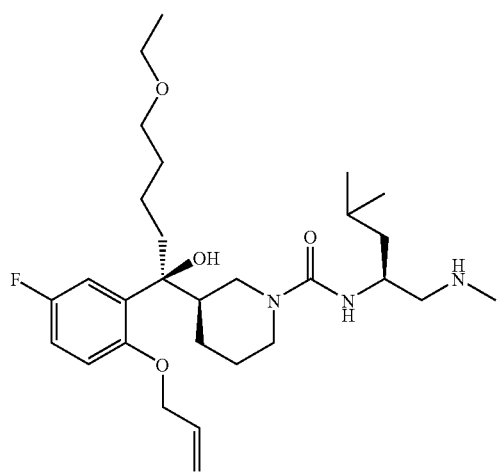

I-228a (3R)-3-((S)-1-(2-(allyloxy)-5-fluorophenyl)-1-hydroxy-5-methoxypentyl)-N-((S)-4-methyl-1-(methylamino)pentan-2-yl)piperidine-1-carboxamide

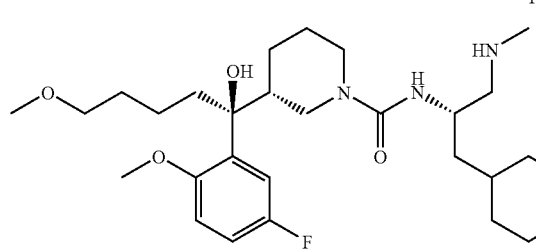

I-229a (3R)-N-((S)-3-cyclohexyl-1-(methylamino)propan-2-yl)-3-((S)-1-(5-fluoro-2-methoxyphenyl)-1-hydroxy-5-methoxypentyl)piperidine-1-carboxamide

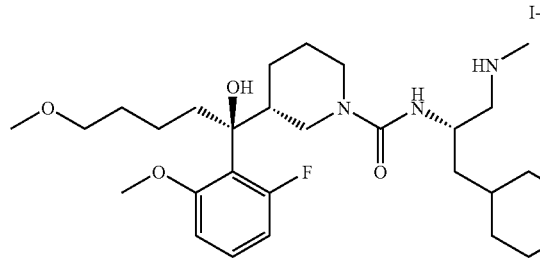

I-230a (3R)-N-((S)-3-cyclohexyl-1-(methylamino)propan-2-yl)-3-((S)-1-(2-fluoro-6-methoxyphenyl)-1-hydroxy-5-methoxypentyl)piperidine-1-carboxamide -continued

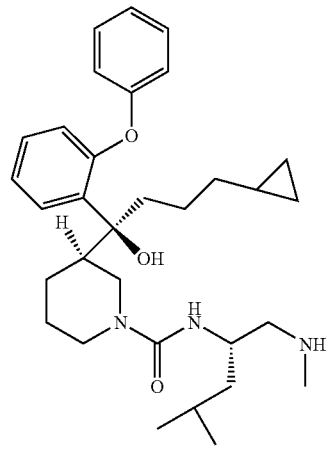

I-231a (3R)-3-((S)-4-cyclopropyl-1-hydroxy-1-(2-phenoxyphenyl)butyl)-N-((S)-4-methyl-1-(methylamino)pentan-2-yl)piperidine-1-carboxamide

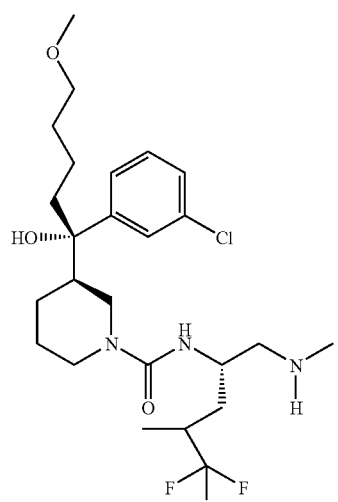

I-232a (3R)-3-((S)-1-(3-chlorophenyl)-1-hydroxy-5-methoxypentyl)-N-((2S)-5,5,5-trifluoro-4-methyl-1-(methylamino)pentan-2-yl)piperidine-1-carboxamide

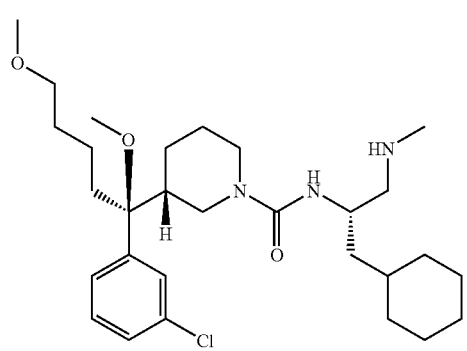

I-233a (3R)-3-((S)-1-(3-chlorophenyl)-1,5-dimethoxypentyl)-N-((S)-3-cyclohexyl-1-(methylamino)propan-2-yl)piperidine-1-carboxamide

153

-continued

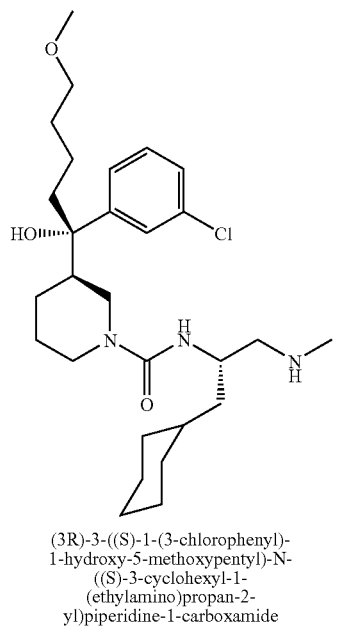

(3R)-3-((S)-1-(3-chlorophenyl)-
1-hydroxy-5-methoxypentyl)-N-
((S)-3-cyclohexyl-1-
(ethylamino)propan-2-
yl)piperidine-1-carboxamide

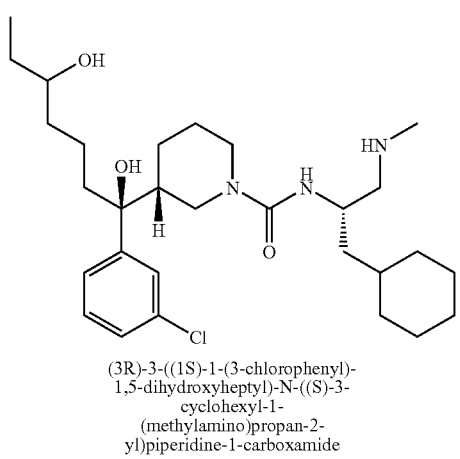

(3R)-3-((1S)-1-(3-chlorophenyl)-
1,5-dihydroxyheptyl)-N-((S)-3-
cyclohexyl-1-
(methylamino)propan-2-
yl)piperidine-1-carboxamide

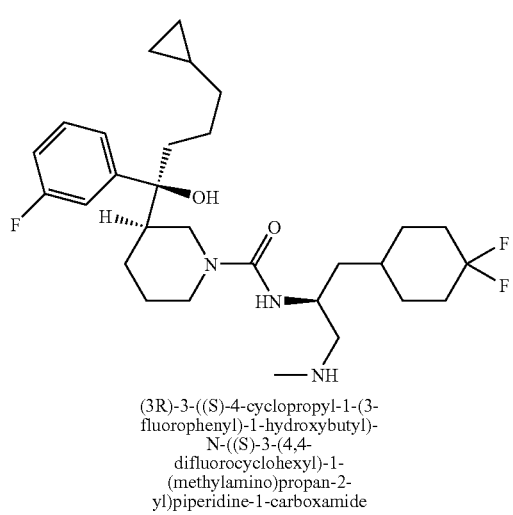

(3R)-3-((S)-4-cyclopropyl-1-(3-
fluorophenyl)-1-hydroxybutyl)-
N-((S)-3-(4,4-
difluorocyclohexyl)-1-
(methylamino)propan-2-
yl)piperidine-1-carboxamide

154

-continued

I-234a

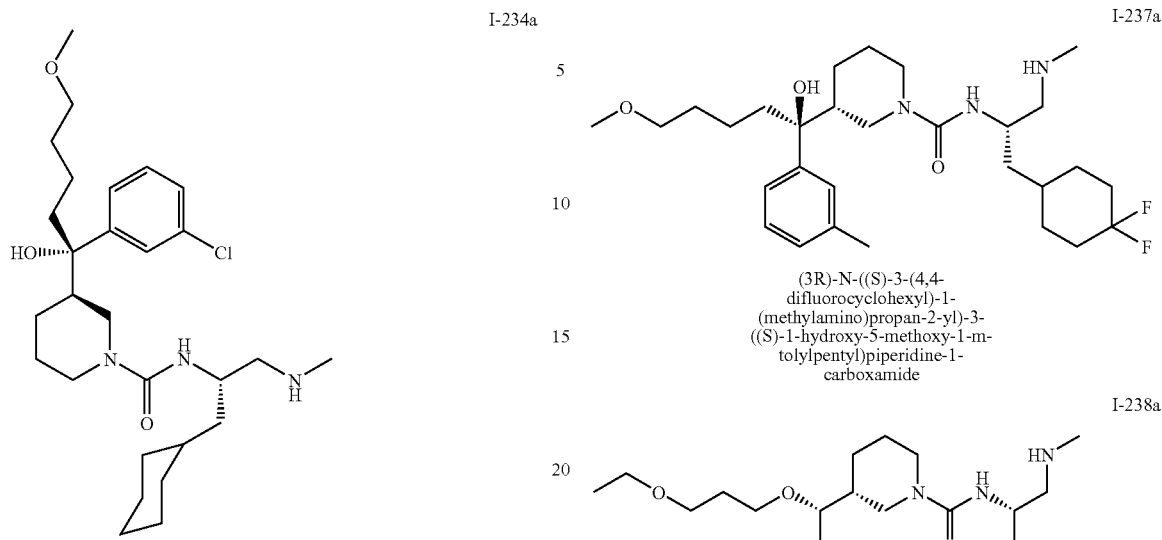

(3R)-N-((S)-3-(4,4-
difluorocyclohexyl)-1-
(methylamino)propan-2-yl)-3-
((S)-1-hydroxy-5-methoxy-1-m-
tolylpentyl)piperidine-1-
carboxamide I-237a I-238a

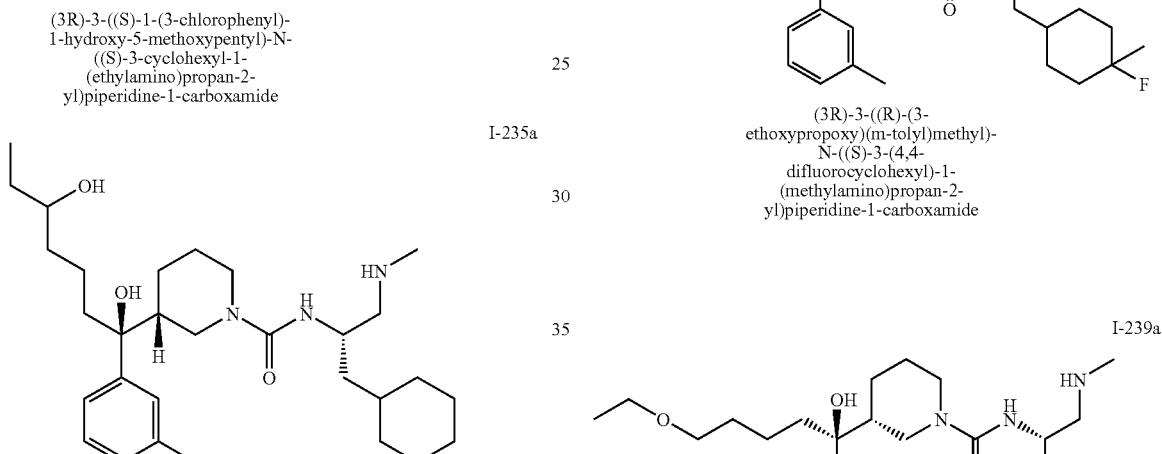

(3R)-3-((R)-(3-
ethoxypropoxy)(m-tolyl)methyl)-
N-((S)-3-(4,4-
difluorocyclohexyl)-1-
(methylamino)propan-2-
yl)piperidine-1-carboxamide I-235a I-239a

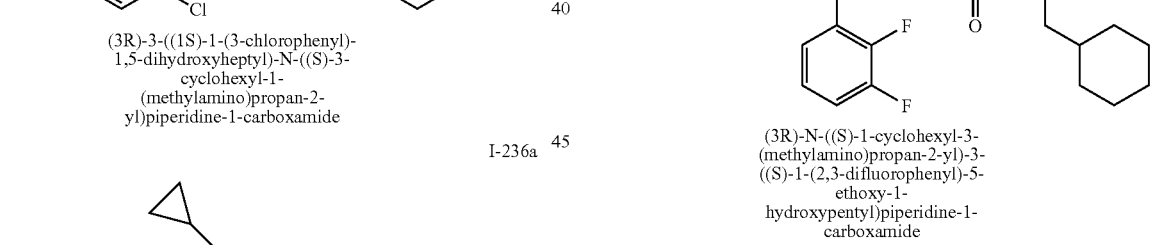

(3R)-N-((S)-1-cyclohexyl-3-
(methylamino)propan-2-yl)-3-
((S)-1-(2,3-difluorophenyl)-5-
ethoxy-1-
hydroxypentyl)piperidine-1-
carboxamide I-236a I-240a

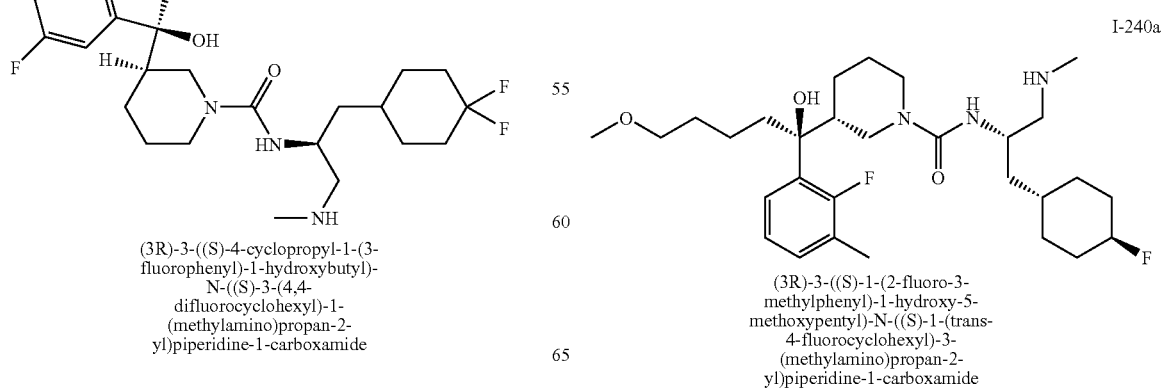

(3R)-3-((S)-1-(2-fluoro-3-
methylphenyl)-1-hydroxy-5-
methoxypentyl)-N-((S)-1-(trans-
4-fluorocyclohexyl)-3-
(methylamino)propan-2-
yl)piperidine-1-carboxamide

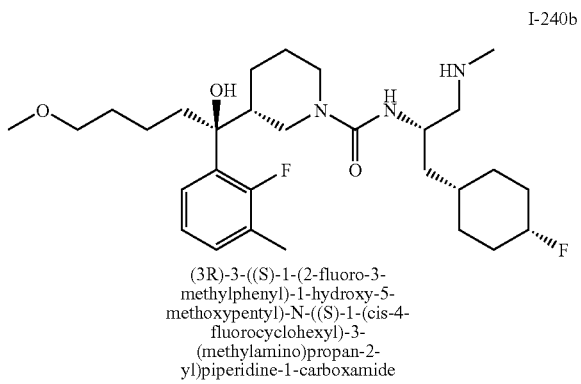

(3R)-3-((S)-1-(2-fluoro-3-methylphenyl)-1-hydroxy-5-methoxypentyl)-N-((S)-1-(cis-4-fluorocyclohexyl)-3-(methylamino)propan-2-yl)piperidine-1-carboxamide I-240b

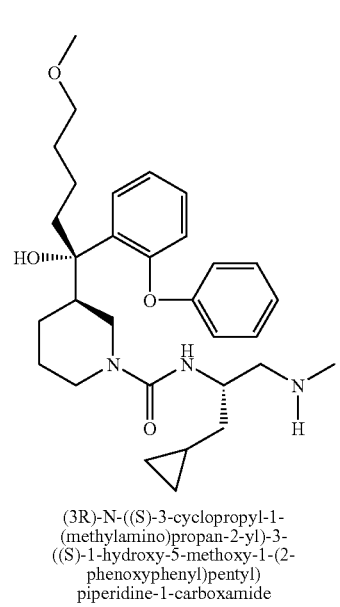

(3R)-N-((S)-3-cyclopropyl-1-(methylamino)propan-2-yl)-3-((S)-1-hydroxy-5-methoxy-1-(2-phenoxyphenyl)pentyl)piperidine-1-carboxamide I-241a

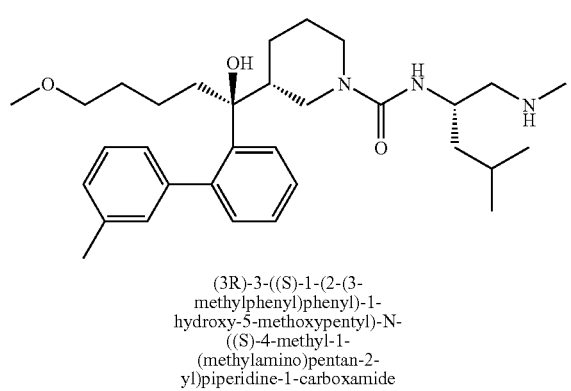

(3R)-3-((S)-1-(2-(3-methylphenyl)phenyl)-1-hydroxy-5-methoxypentyl)-N-((S)-4-methyl-1-(methylamino)pentan-2-yl)piperidine-1-carboxamide I-242a

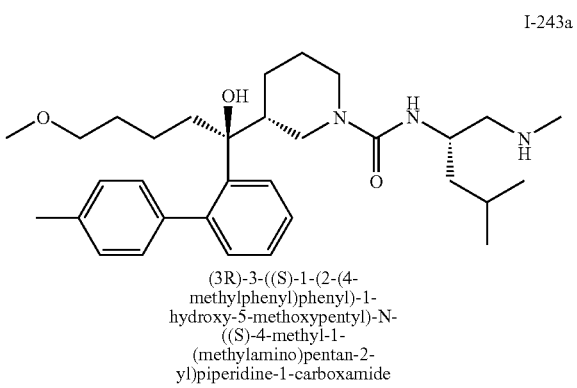

(3R)-3-((S)-1-(2-(4-methylphenyl)phenyl)-1-hydroxy-5-methoxypentyl)-N-((S)-4-methyl-1-(methylamino)pentan-2-yl)piperidine-1-carboxamide I-243a

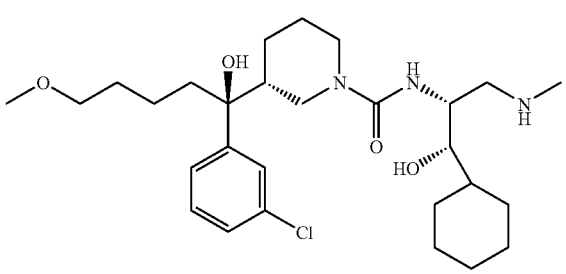

(3R)-3-((S)-1-(3-chlorophenyl)-1-hydroxy-5-methoxypentyl)-N-((1S,2R)-1-cyclohexyl-1-hydroxy-3-(methylamino)propan-2-yl)piperidine-1-carboxamide I-244a

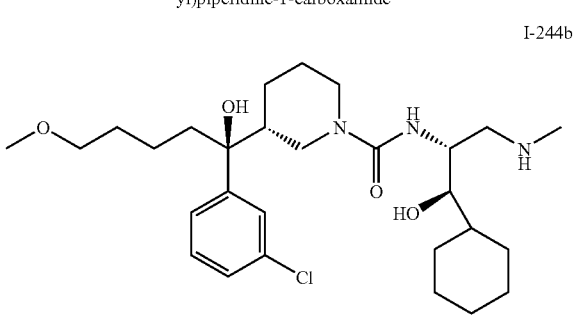

(3R)-3-((S)-1-(3-chlorophenyl)-1-hydroxy-5-methoxypentyl)-N-((1S,2R)-1-cyclohexyl-1-hydroxy-3-(methylamino)propan-2-yl)piperidine-1-carboxamide I-244b

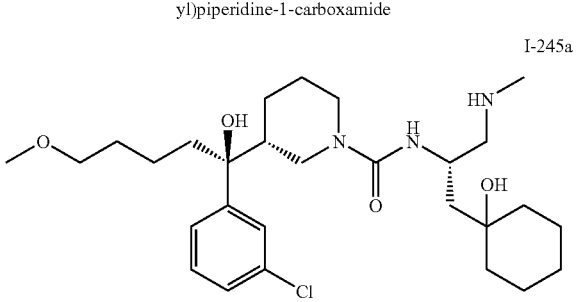

(3R)-3-((S)-1-(3-chlorophenyl)-1-hydroxy-5-methoxypentyl)-N-((S)-3-(1-hydroxycyclohexyl)-1-(methylamino)propan-2-yl)piperidine-1-carboxamide I-245a -continued

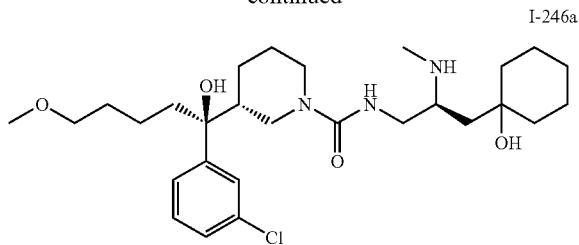

I-246a (3R)-3-((S)-1-(3-chlorophenyl)-
1-hydroxy-5-methoxypentyl)-N-
((S)-3-(1-hydroxycyclohexyl)-2-
(methylamino)propyl)piperidine-
1-carboxamide

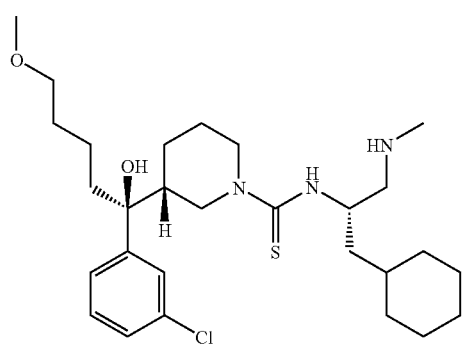

I-247a (3R)-3-((S)-1-(3-chlorophenyl)-
1-hydroxy-5-methoxypentyl)-N-
((S)-3-cyclohexyl-1-
(methylamino)propan-2-
yl)piperidine-1-carbothioamide

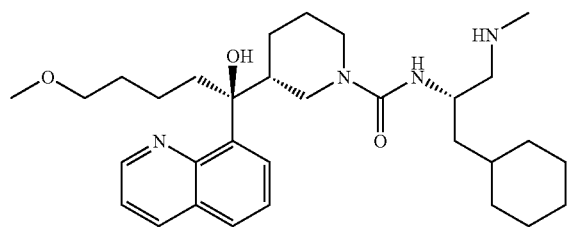

I-248a (3R)-N-((S)-3-cyclohexyl-1-
(methylamino)propan-2-yl)-3-
((S)-1-hydroxy-5-methoxy-1-
(quinolin-8-yl)pentyl)piperidine-
1-carboxamide

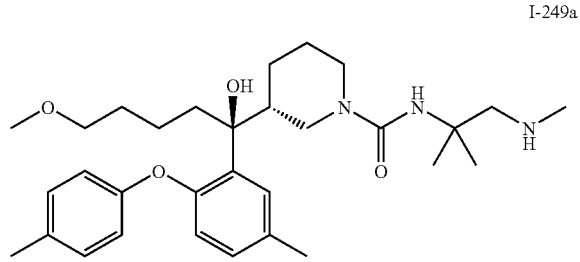

I-249a (3R)-3-((S)-1-(2-(p-tolyloxy)-5-
methylphenyl)-1-hydroxy-5-
methoxypentyl)-N-(2-methyl-1-
(methylamino)propan-2-
yl)piperidine-1-carboxamide -continued

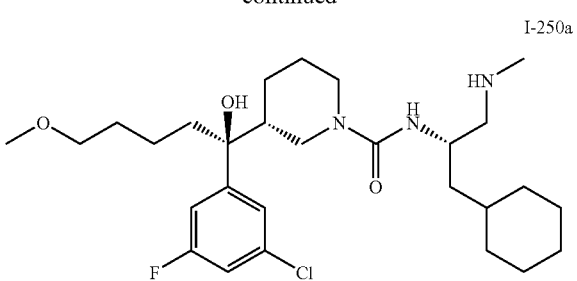

I-250a (3R)-3-((S)-1-(3-chloro-5-
fluorophenyl)-1-hydroxy-5-
methoxypentyl)-N-((S)-3-
cyclohexyl-1-
(methylamino)propan-2-
yl)piperidine-1-carboxamide

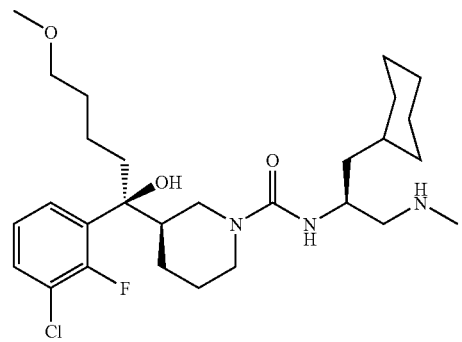

I-251a (3R)-3-((S)-1-(3-chloro-2-
fluorophenyl)-1-hydroxy-5-
methoxypentyl)-N-((S)-1-
cyclohexyl-3-
(methylamino)propan-2-
yl)piperidine-1-carboxamide

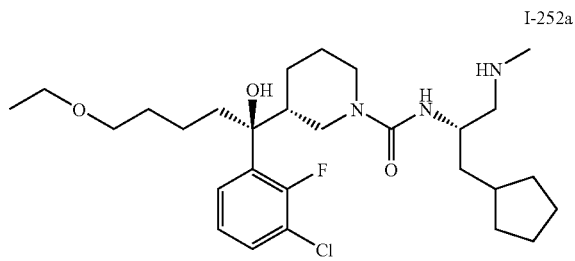

I-252a (3R)-3-((S)-1-(3-chloro-2-
fluorophenyl)-5-ethoxy-1-
hydroxypentyl)-N-((S)-3-
cyclopentyl-1-
(methylamino)propan-2-
yl)piperidine-1-carboxamide

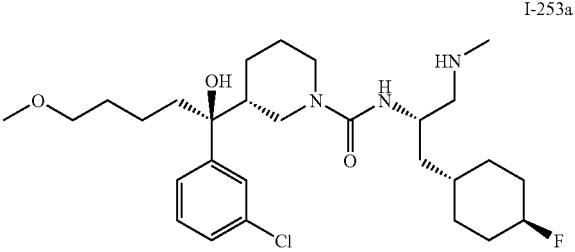

I-253a (3R)-3-((S)-1-(3-chlorophenyl)-
1-hydroxy-5-methoxypentyl)-N-
((S)-3-(trans-4-
fluorocyclohexyl)-1-
(methylamino)propan-2-
yl)piperidine-1-carboxamide -continued I-254a

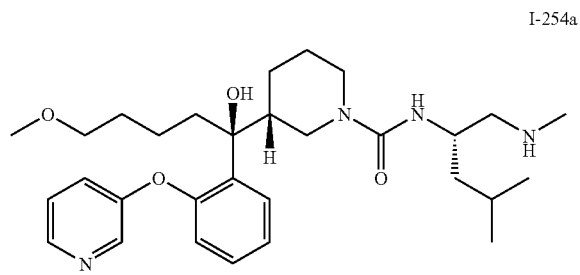

(3R)-3-((S)-1-hydroxy-5-methoxy-1-(2-(pyridin-3-yloxy)phenyl)pentyl)-N-((S)-4-methyl-1-(methylamino)pentan-2-yl)piperidine-1-carboxamide I-255a

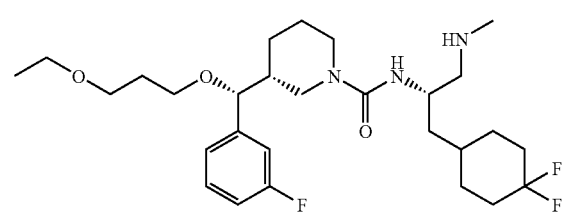

(3R)-3-((R)-(3-ethoxypropoxy)(3-fluorophenyl)methyl)-N-((S)-3-(4,4-difluorocyclohexyl)-1-(methylamino)propan-2-yl)piperidine-1-carboxamide I-256a

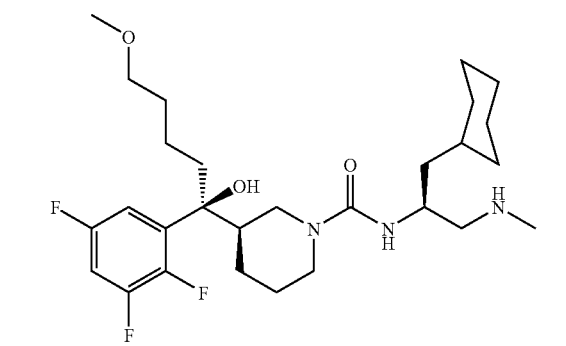

(3R)-N-((S)-3-cyclohexyl-1-(methylamino)propan-2-yl)-3-((S)-1-(2,3,5-trifluorophenyl)-1-hydroxy-5-methoxypentyl)piperidine-1-carboxamide I-257a

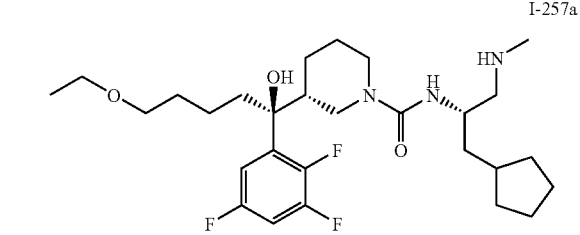

(3R)-N-((S)-3-cyclopentyl-1-(methylamino)propan-2-yl)-3-((S)-5-ethoxy-1-(2,3,5-trifluorophenyl)-1-hydroxypentyl)piperidine-1-carboxamide -continued I-258a

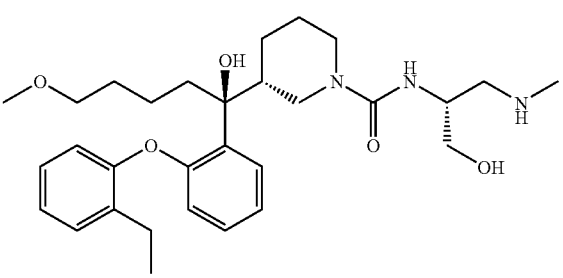

(3R)-3-((S)-1-(2-(2-ethylphenoxy)phenyl)-1-hydroxy-5-methoxypentyl)-N-((R)-3-hydroxy-1-(methylamino)propan-2-yl)piperidine-1-carboxamide I-259a

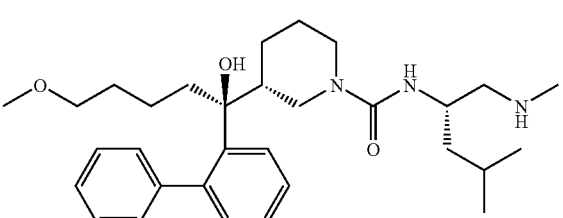

(3R)-3-((S)-1-(3-fluoro-2-phenylphenyl)-1-hydroxy-5-methoxypentyl)-N-((S)-4-methyl-1-(methylamino)pentan-2-yl)piperidine-1-carboxamide I-260a

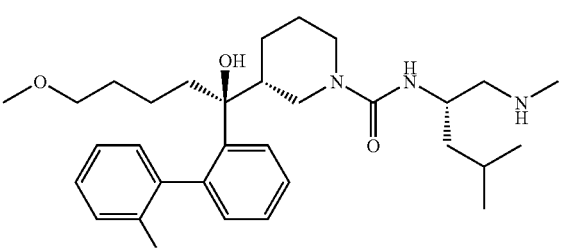

(3R)-3-((S)-1-(2-(2-fluorophenyl)phenyl)-1-hydroxy-5-methoxypentyl)-N-((S)-4-methyl-1-(methylamino)pentan-2-yl)piperidine-1-carboxamide I-261a

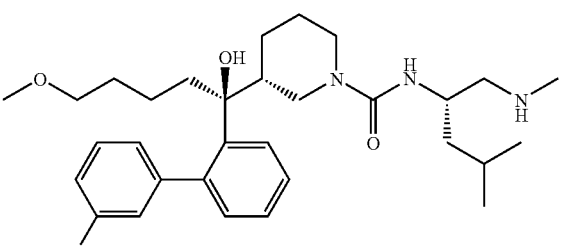

(3R)-3-((S)-1-(2-(3-fluorophenyl)phenyl)-1-hydroxy-5-methoxypentyl)-N-((S)-4-methyl-1-(methylamino)pentan-2-yl)piperidine-1-carboxamide -continued I-262a (3R)-3-((S)-1-(2-(4-fluorophenyl)phenyl)-1-hydroxy-5-methoxypentyl)-N-((S)-4-methyl-1-(methylamino)pentan-2-yl)piperidine-1-carboxamide I-263a (3R)-3-((S)-1-(3-chlorophenyl)-5,5-difluoro-1-hydroxyhexyl)-N-((S)-3-cyclohexyl-1-(methylamino)propan-2-yl)piperidine-1-carboxamide I-264a (3R)-3-((R)-(3-methoxypropoxy)(2,3-dichlorophenyl)methyl)-N-((S)-3-cyclohexyl-1-(methylamino)propan-2-yl)piperidine-1-carboxamide I-265a (3R)-3-((S)-1-(2,3-dichlorophenyl)-1-hydroxy-5-methoxypentyl)-N-((S)-3-cyclopentyl-1-(methylamino)propan-2-yl)piperidine-1-carboxamide -continued I-266a (3R)-3-((R)-(3-ethoxypropoxy)(2,3-dichlorophenyl)methyl)-N-((S)-3-cyclopentyl-1-(methylamino)propan-2-yl)piperidine-1-carboxamide I-267a (3R)-3-((S)-1-(benxo[b]thiophen-7-yl)-1-hydroxy-5-methoxypentyl)-N-((S)-3-cyclohexyl-1-(methylamino)propan-2-yl)piperidine-1-carboxamide I-268a (3R)-3-((S)-1-(benxo[b]thiophen-2-yl)-1-hydroxy-5-methoxypentyl)-N-((S)-3-cyclohexyl-1-(methylamino)propan-2-yl)piperidine-1-carboxamide I-269a (3R)-3-((S)-1-hydroxy-5-methoxy-1-(3-(trifluoromethoxy)phenyl)pentyl)-N-((S)-4,4-dimethyl-1-(methylamino)pentan-2-yl)piperidine-1-carboxamide

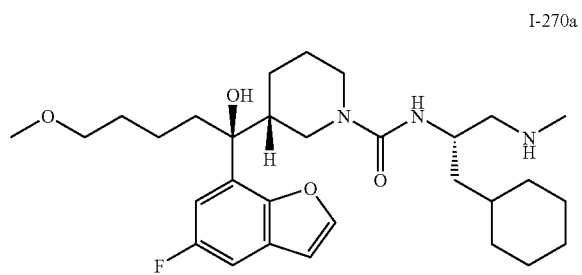

I-270a (3R)-N-((S)-3-cyclohexyl-1-
(methylamino)propan-2-yl)-3-
((S)-1-(5-fluorobenzofuran-7-yl)-
1-hydroxy-5-
methoxypentyl)piperidine-1-
carboxamide

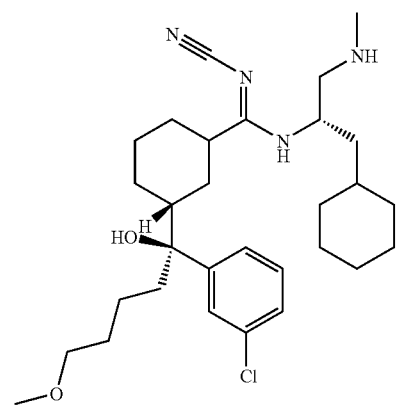

I-271a (3R)-3-((S)-1-(3-chlorophenyl)-
1-hydroxy-5-methoxypentyl)-N'-
cyano-N-((S)-3-cyclohexyl-1-
(methylamino)propan-2-
yl)piperidine-1-carboxamide

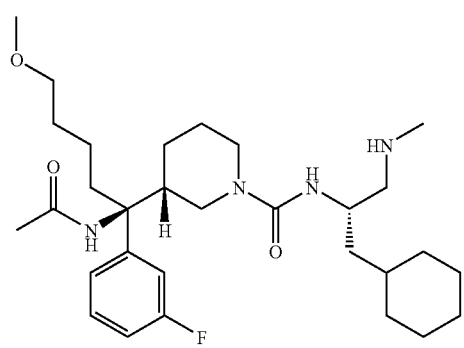

I-272a (3R)-3-((S)-1-acetamido-1-(3-
fluorophenyl)-5-methoxypentyl)-
N-((S)-3-cyclohexyl-1-
(methylamino)propan-2-
yl)piperidine-1-carboxamide

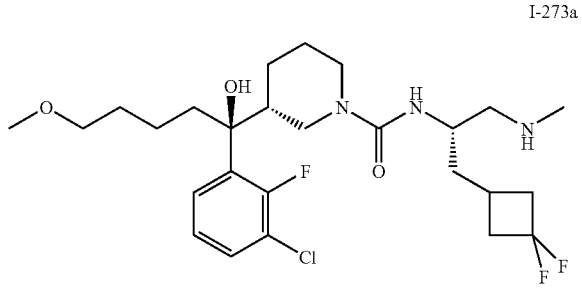

I-273a (3R)-3-((S)-1-(3-chloro-2-
fluorophenyl)-1-hydroxy-5-
methoxypentyl)-N-((S)-3-(3,3-
difluorocyclobutyl)-1-
(methylamino)propan-2-
yl)piperidine-1-carboxamide

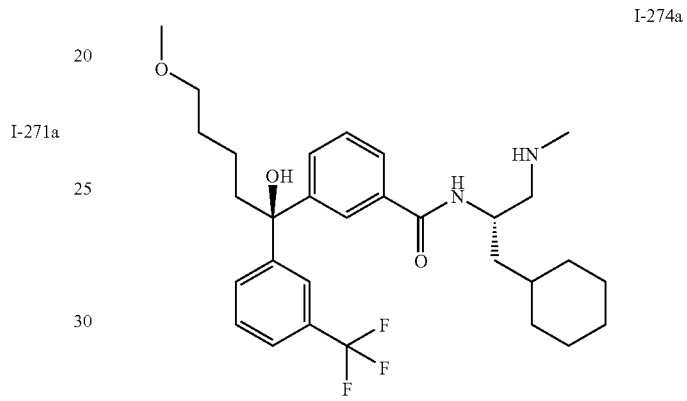

I-274a

N-((S)-3-cyclohexyl-1-
(methylamino)propan-2-yl)-3-
((S)-1-(3-
(trifluoromethyl)phenyl)-1-
hydroxy-5-
methoxypentyl)benzamide

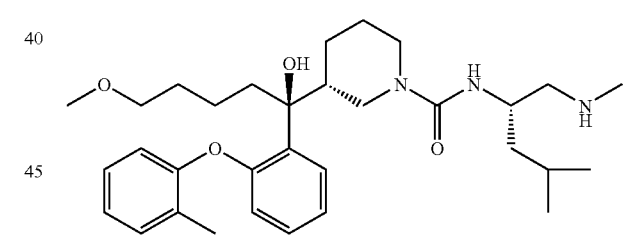

I-275a (3R)-3-((S)-1-(2-(o-
tolyloxy)phenyl)-1-hydroxy-5-
methoxypentyl)-N-((S)-4-
methyl-1-(methylamino)pentan-
2-yl)piperidine-1-carboxamide

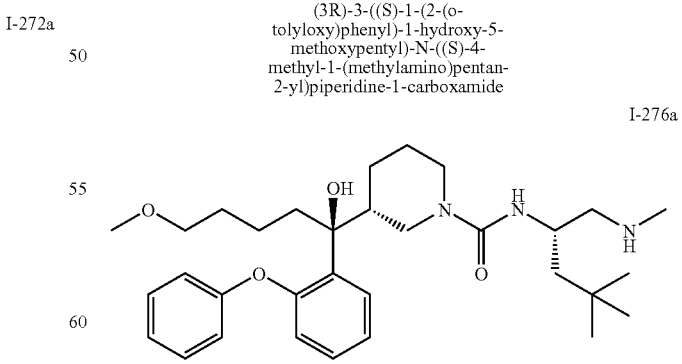

I-276a (3R)-3-((S)-1-hydroxy-5-
methoxy-1-(2-
phenoxyphenyl)pentyl)-N-((S)-
4,4-dimethyl-1-
(methylamino)pentan-2-
yl)piperidine-1-carboxamide -continued I-277a

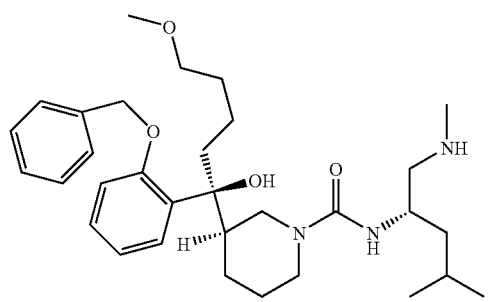

(3R)-3-((S)-1-(2-(benzyloxy)phenyl)-1-hydroxy-5-methoxypentyl)-N-((S)-4-methyl-1-(methylamino)pentan-2-yl)piperidine-1-carboxamide I-278a

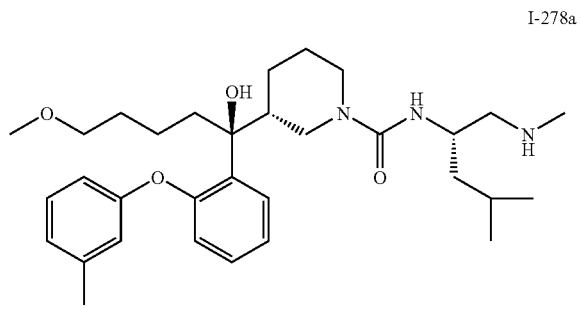

(3R)-3-((S)-1-(2-(m-tolyloxy)phenyl)-1-hydroxy-5-methoxypentyl)-N-((S)-4-methyl-1-(methylamino)pentan-2-yl)piperidine-1-carboxamide I-279a

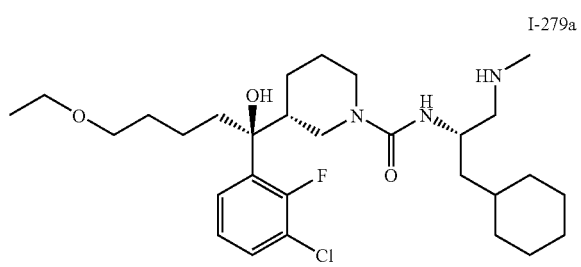

(3R)-3-((S)-1-(3-chloro-2-fluorophenyl)-5-ethoxy-1-hydroxypentyl)-N-((S)-3-cyclohexyl-1-(methylamino)propan-2-yl)piperidine-1-carboxamide I-280a

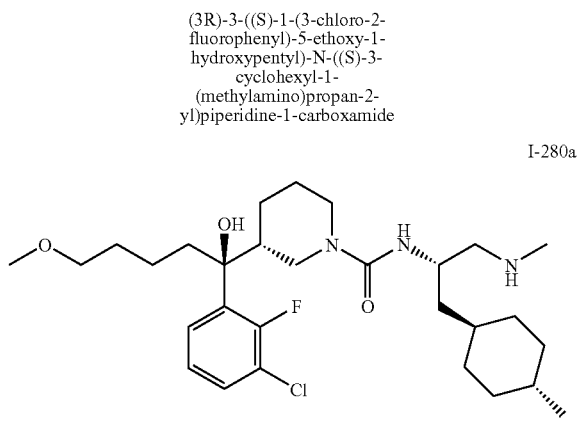

(3R)-3-((S)-1-(3-chloro-2-fluorophenyl)-1-hydroxy-5-methoxypentyl)-N-((S)-1-(methylamino)-3-(trans-4-methylcyclohexyl)propan-2-yl)piperidine-1-carboxamide -continued I-281a

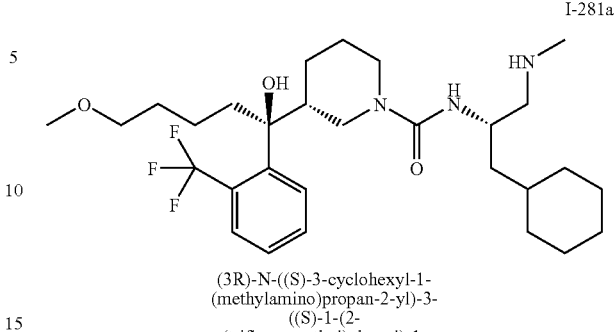

(3R)-N-((S)-3-cyclohexyl-1-(methylamino)propan-2-yl)-3-((S)-1-(2-(trifluoromethyl)phenyl)-1-hydroxy-5-methoxypentyl)piperidine-1-carboxamide I-282a

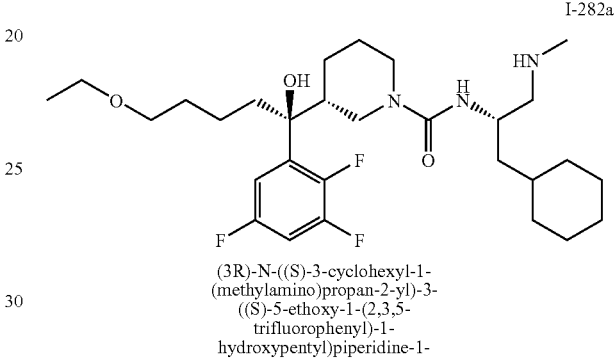

(3R)-N-((S)-3-cyclohexyl-1-(methylamino)propan-2-yl)-3-((S)-5-ethoxy-1-(2,3,5-trifluorophenyl)-1-hydroxypentyl)piperidine-1-carboxamide I-283a

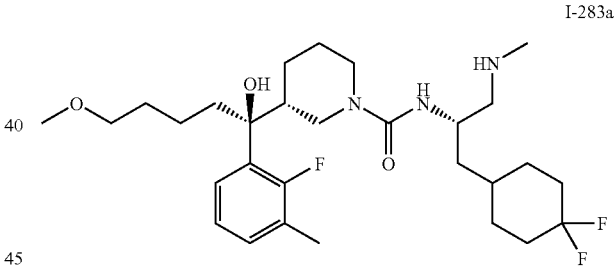

(3R)-3-((S)-1-(2-fluoro-3-methylphenyl)-1-hydroxy-5-methoxypentyl)-N-((S)-3-(4,4-difluorocyclohexyl)-1-(methylamino)propan-2-yl)piperidine-1-carboxamide I-284a

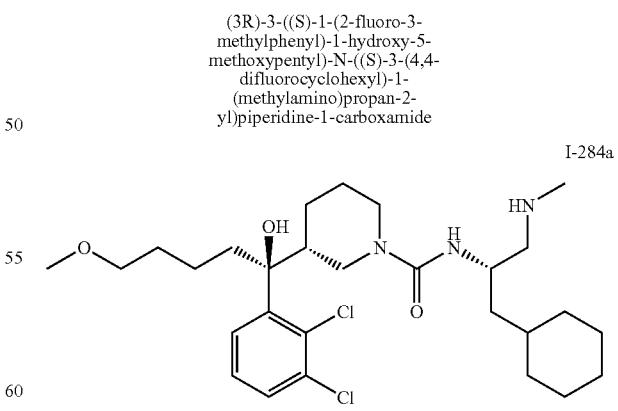

(3R)-3-((S)-1-(2,3-dichlorophenyl)-1-hydroxy-5-methoxypentyl)-N-((S)-3-cyclohexyl-1-(methylamino)propan-2-yl)piperidine-1-carboxamide -continued I-285a

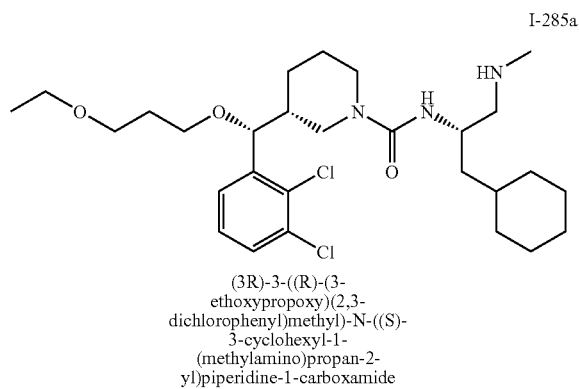

(3R)-3-((R)-(3-ethoxypropoxy)(2,3-dichlorophenyl)methyl)-N-((S)-3-cyclohexyl-1-(methylamino)propan-2-yl)piperidine-1-carboxamide I-286a

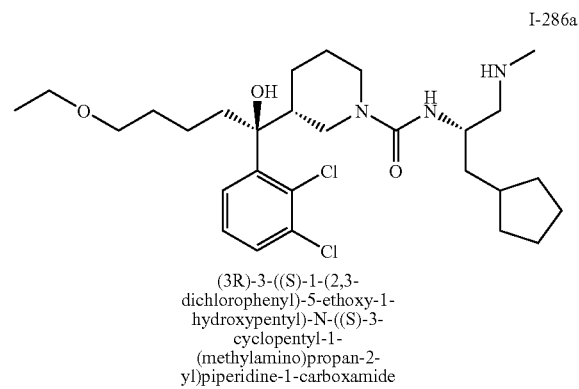

(3R)-3-((S)-1-(2,3-dichlorophenyl)-5-ethoxy-1-hydroxypentyl)-N-((S)-3-cyclopentyl-1-(methylamino)propan-2-yl)piperidine-1-carboxamide I-287a

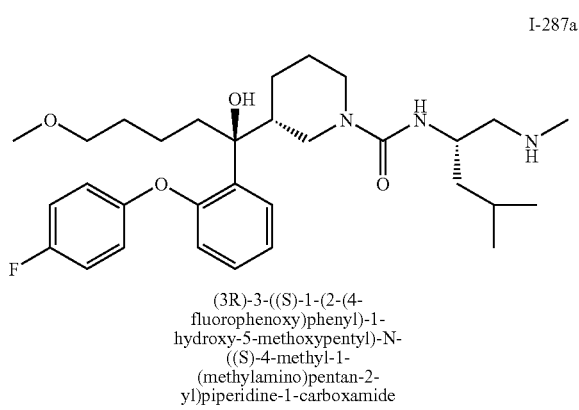

(3R)-3-((S)-1-(2-(4-fluorophenoxy)phenyl)-1-hydroxy-5-methoxypentyl)-N-((S)-4-methyl-1-(methylamino)pentan-2-yl)piperidine-1-carboxamide I-288a

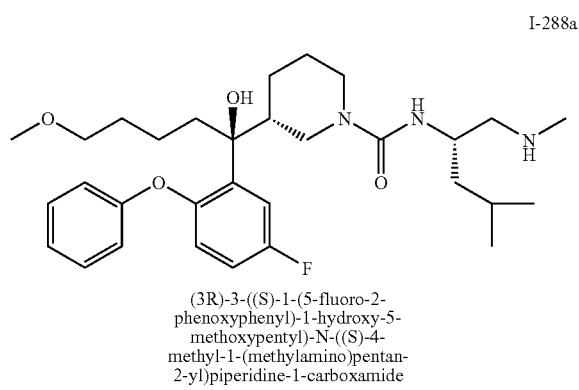

(3R)-3-((S)-1-(5-fluoro-2-phenoxyphenyl)-1-hydroxy-5-methoxypentyl)-N-((S)-4-methyl-1-(methylamino)pentan-2-yl)piperidine-1-carboxamide -continued I-289a

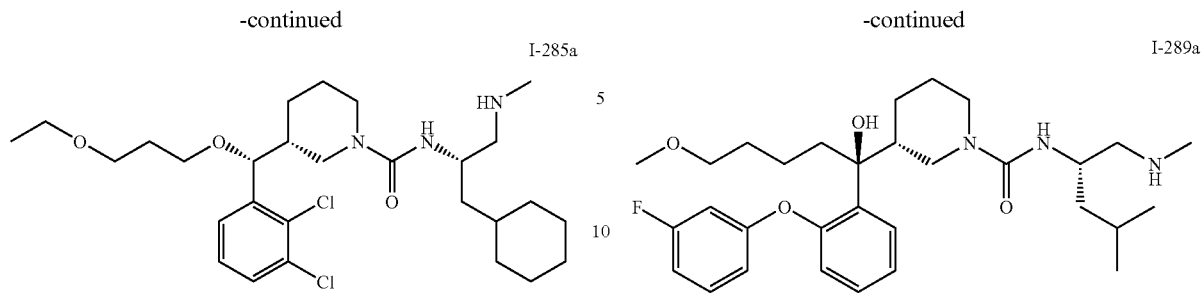

(3R)-3-((S)-1-(2-(3-fluorophenoxy)phenyl)-1-hydroxy-5-methoxypentyl)-N-((S)-4-methyl-1-(methylamino)pentan-2-yl)piperidine-1-carboxamide I-290a

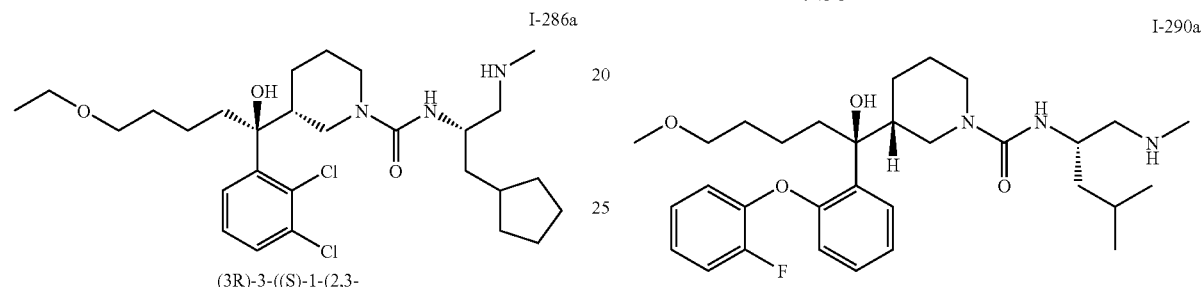

(3R)-3-((S)-1-(2-(2-fluorophenoxy)phenyl)-1-hydroxy-5-methoxypentyl)-N-((S)-4-methyl-1-(methylamino)pentan-2-yl)piperidine-1-carboxamide I-291a

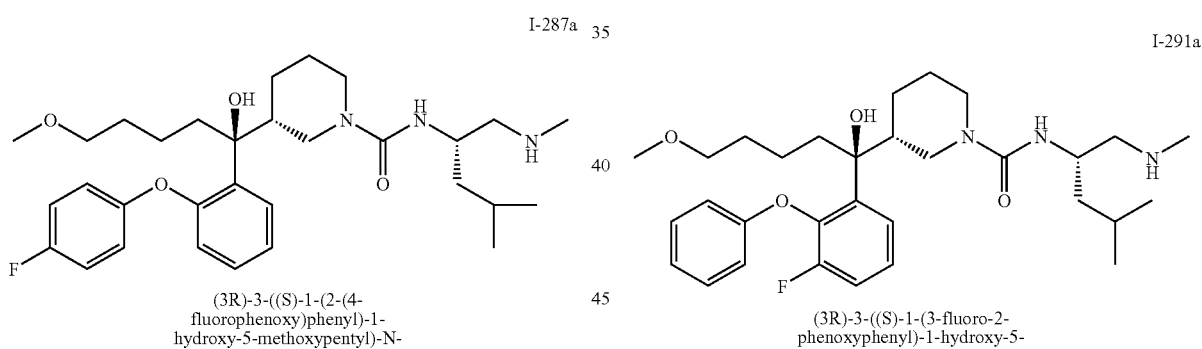

(3R)-3-((S)-1-(3-fluoro-2-phenoxyphenyl)-1-hydroxy-5-methoxypentyl)-N-((S)-4-methyl-1-(methylamino)pentan-2-yl)piperidine-1-carboxamide I-292a

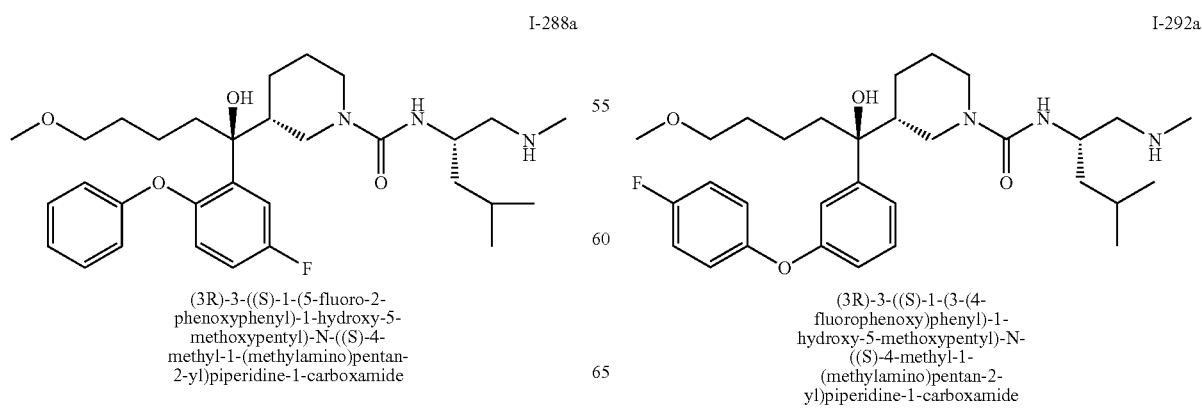

(3R)-3-((S)-1-(3-(4-fluorophenoxy)phenyl)-1-hydroxy-5-methoxypentyl)-N-((S)-4-methyl-1-(methylamino)pentan-2-yl)piperidine-1-carboxamide -continued

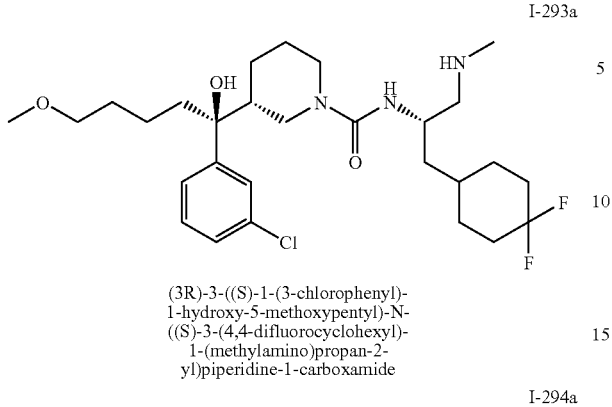

I-293a (3R)-3-((S)-1-(3-chlorophenyl)-1-hydroxy-5-methoxypentyl)-N-((S)-3-(4,4-difluorocyclohexyl)-1-(methylamino)propan-2-yl)piperidine-1-carboxamide

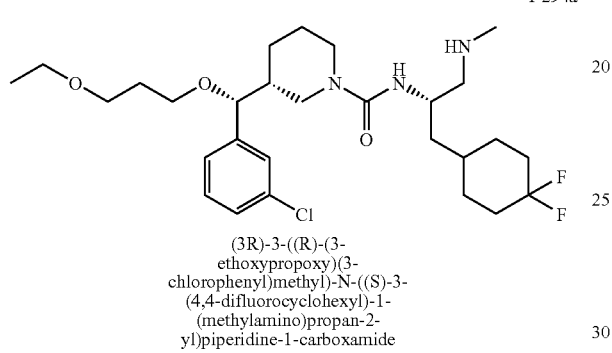

I-294a (3R)-3-((R)-(3-ethoxypropoxy)(3-chlorophenyl)methyl)-N-((S)-3-(4,4-difluorocyclohexyl)-1-(methylamino)propan-2-yl)piperidine-1-carboxamide

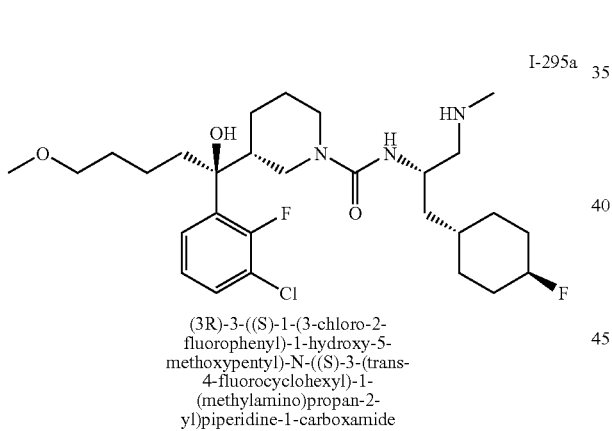

I-295a (3R)-3-((S)-1-(3-chloro-2-fluorophenyl)-1-hydroxy-5-methoxypentyl)-N-((S)-3-(trans-4-fluorocyclohexyl)-1-(methylamino)propan-2-yl)piperidine-1-carboxamide

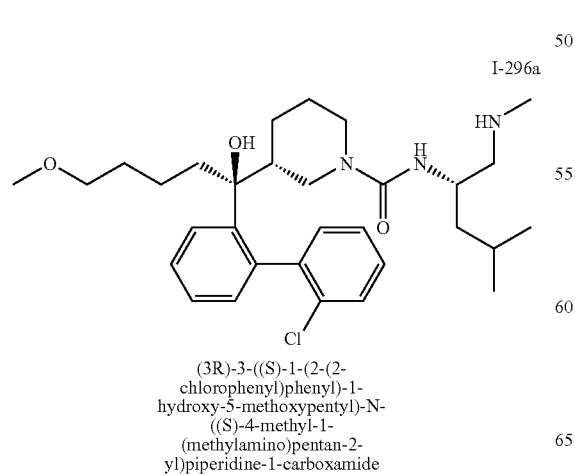

I-296a (3R)-3-((S)-1-(2-(2-chlorophenyl)phenyl)-1-hydroxy-5-methoxypentyl)-N-((S)-4-methyl-1-(methylamino)pentan-2-yl)piperidine-1-carboxamide -continued

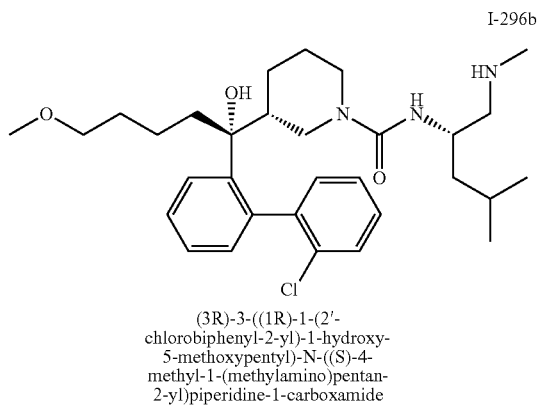

I-296b (3R)-3-((1R)-1-(2'-chlorobiphenyl-2-yl)-1-hydroxy-5-methoxypentyl)-N-((S)-4-methyl-1-(methylamino)pentan-2-yl)piperidine-1-carboxamide

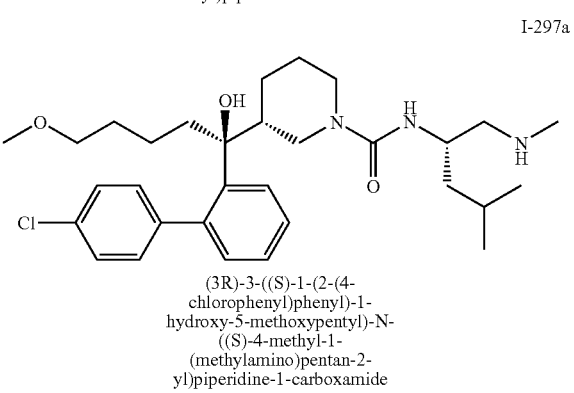

I-297a (3R)-3-((S)-1-(2-(4-chlorophenyl)phenyl)-1-hydroxy-5-methoxypentyl)-N-((S)-4-methyl-1-(methylamino)pentan-2-yl)piperidine-1-carboxamide

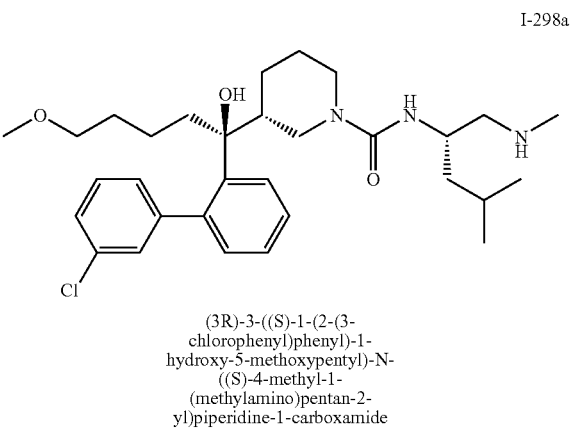

I-298a (3R)-3-((S)-1-(2-(3-chlorophenyl)phenyl)-1-hydroxy-5-methoxypentyl)-N-((S)-4-methyl-1-(methylamino)pentan-2-yl)piperidine-1-carboxamide

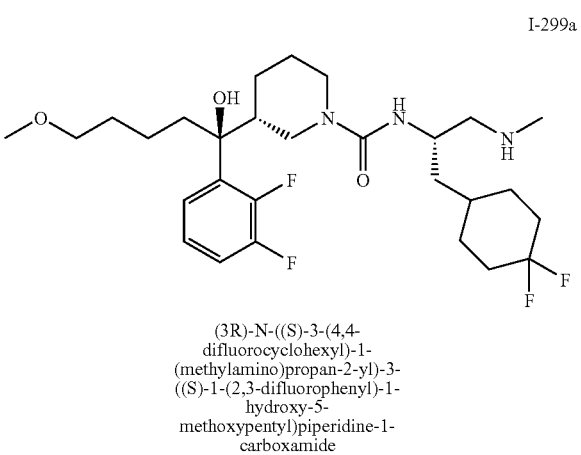

I-299a (3R)-N-((S)-3-(4,4-difluorocyclohexyl)-1-(methylamino)propan-2-yl)-3-((S)-1-(2,3-difluorophenyl)-1-hydroxy-5-methoxypentyl)piperidine-1-carboxamide -continued

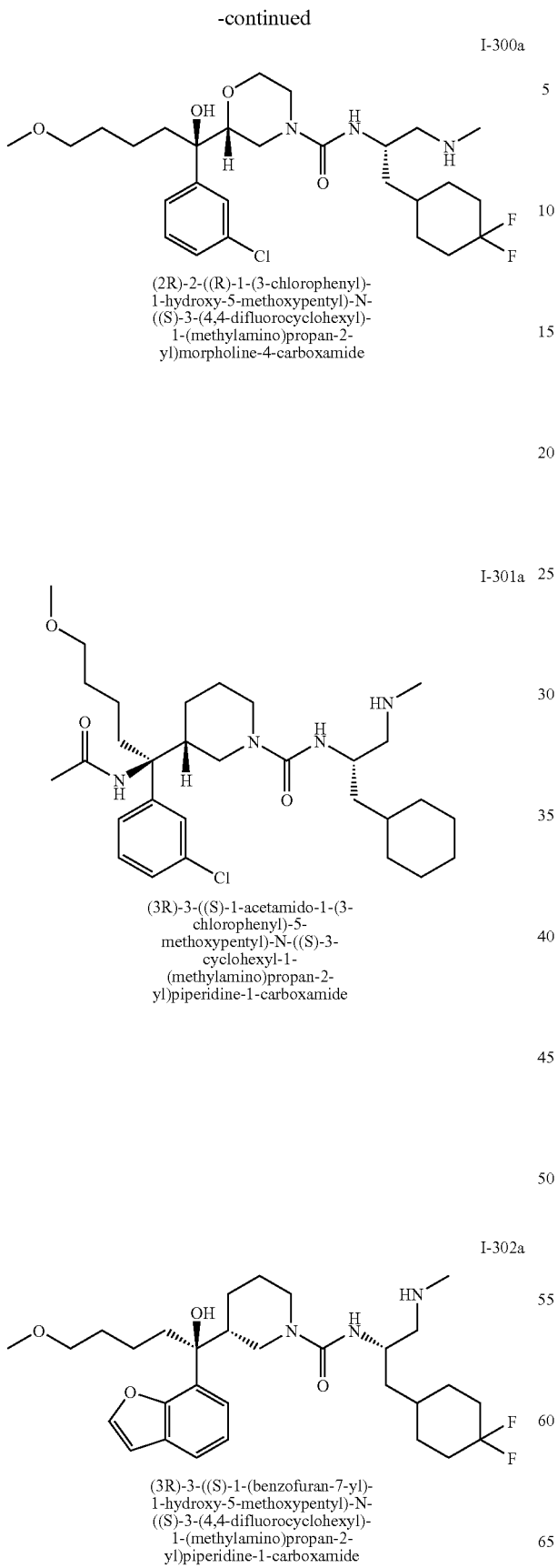

I-300a (2R)-2-((R)-1-(3-chlorophenyl)-1-hydroxy-5-methoxypentyl)-N-((S)-3-(4,4-difluorocyclohexyl)-1-(methylamino)propan-2-yl)morpholine-4-carboxamide I-301a (3R)-3-((S)-1-acetamido-1-(3-chlorophenyl)-5-methoxypentyl)-N-((S)-3-cyclohexyl-1-(methylamino)propan-2-yl)piperidine-1-carboxamide I-302a (3R)-3-((S)-1-(benzofuran-7-yl)-1-hydroxy-5-methoxypentyl)-N-((S)-3-(4,4-difluorocyclohexyl)-1-(methylamino)propan-2-yl)piperidine-1-carboxamide -continued

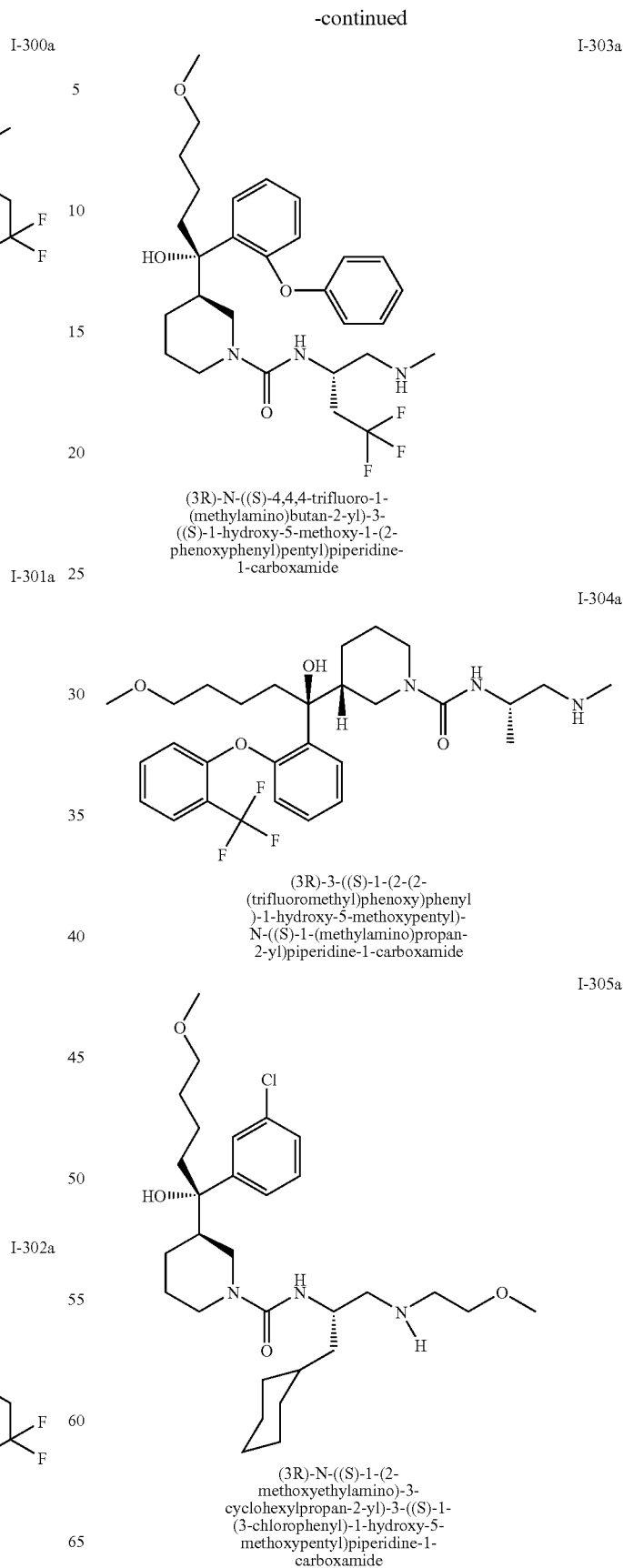

I-303a (3R)-N-((S)-4,4,4-trifluoro-1-(methylamino)butan-2-yl)-3-((S)-1-hydroxy-5-methoxy-1-(2-phenoxyphenyl)pentyl)piperidine-1-carboxamide I-304a (3R)-3-((S)-1-(2-(2-(trifluoromethyl)phenoxy)phenyl)-1-hydroxy-5-methoxypentyl)-N-((S)-1-(methylamino)propan-2-yl)piperidine-1-carboxamide I-305a (3R)-N-((S)-1-(2-methoxyethylamino)-3-cyclohexylpropan-2-yl)-3-((S)-1-(3-chlorophenyl)-1-hydroxy-5-methoxypentyl)piperidine-1-carboxamide

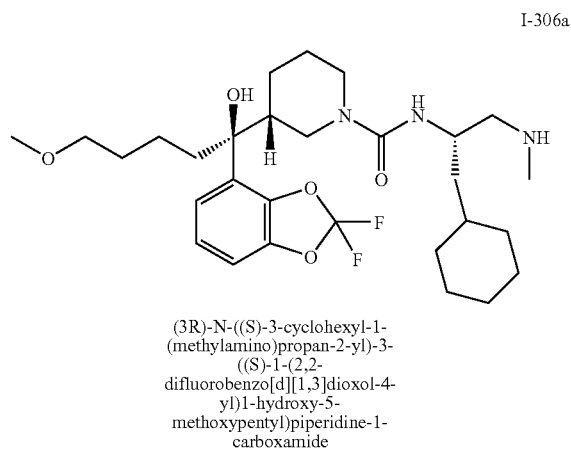

I-306a (3R)-N-((S)-3-cyclohexyl-1-
(methylamino)propan-2-yl)-3-
((S)-1-(2,2-
difluorobenzo[d][1,3]dioxol-4-
yl)1-hydroxy-5-
methoxypentyl)piperidine-1-
carboxamide

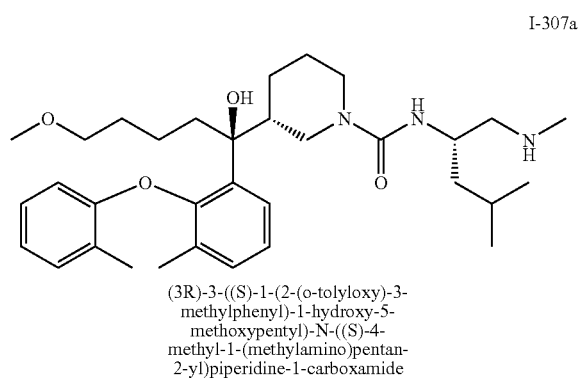

I-307a (3R)-3-((S)-1-(2-(o-tolyloxy)-3-
methylphenyl)-1-hydroxy-5-
methoxypentyl)-N-((S)-4-
methyl-1-(methylamino)pentan-
2-yl)piperidine-1-carboxamide

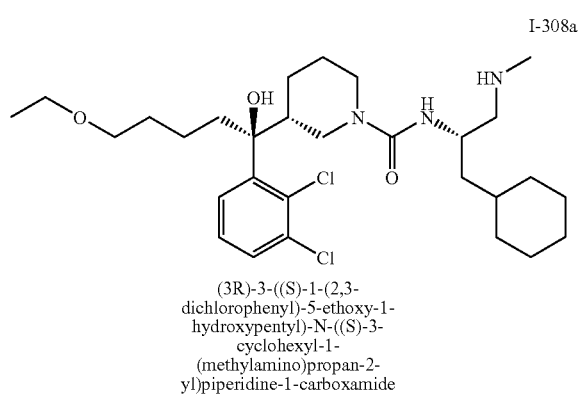

I-308a (3R)-3-((S)-1-(2,3-
dichlorophenyl)-5-ethoxy-1-
hydroxypentyl)-N-((S)-3-
cyclohexyl-1-
(methylamino)propan-2-
yl)piperidine-1-carboxamide

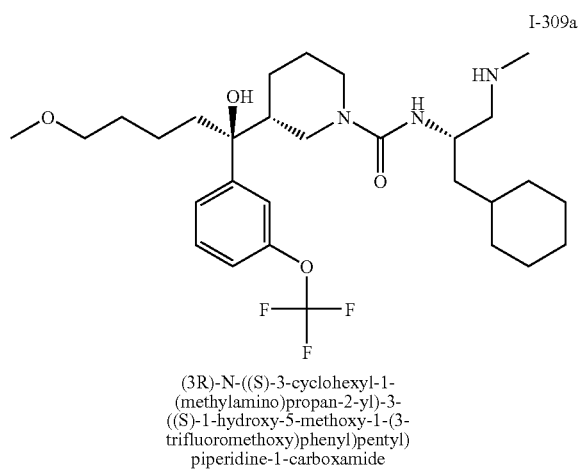

I-309a (3R)-N-((S)-3-cyclohexyl-1-
(methylamino)propan-2-yl)-3-
((S)-1-hydroxy-5-methoxy-1-(3-
trifluoromethoxy)phenyl)pentyl)
piperidine-1-carboxamide

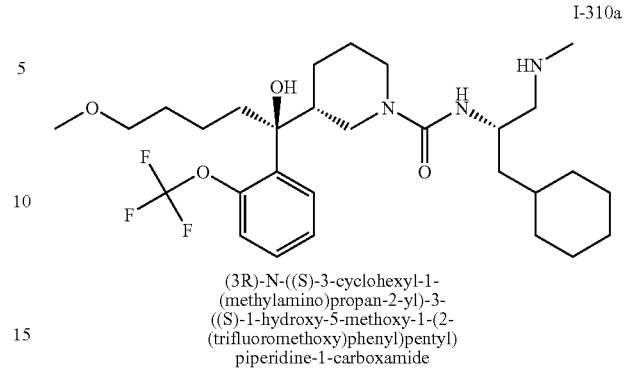

I-310a (3R)-N-((S)-3-cyclohexyl-1-
(methylamino)propan-2-yl)-3-
((S)-1-hydroxy-5-methoxy-1-(2-
(trifluoromethoxy)phenyl)pentyl)
piperidine-1-carboxamide

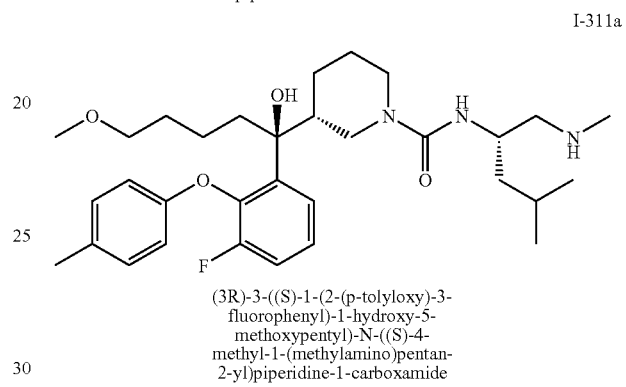

I-311a (3R)-3-((S)-1-(2-(p-tolyloxy)-3-
fluorophenyl)-1-hydroxy-5-
methoxypentyl)-N-((S)-4-
methyl-1-(methylamino)pentan-
2-yl)piperidine-1-carboxamide

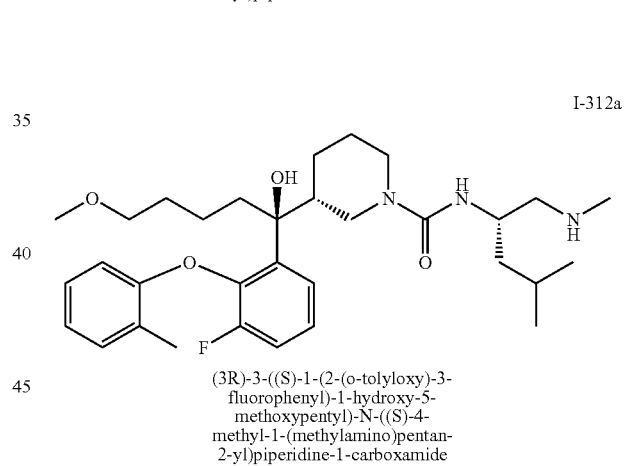

I-312a (3R)-3-((S)-1-(2-(o-tolyloxy)-3-
fluorophenyl)-1-hydroxy-5-
methoxypentyl)-N-((S)-4-
methyl-1-(methylamino)pentan-
2-yl)piperidine-1-carboxamide

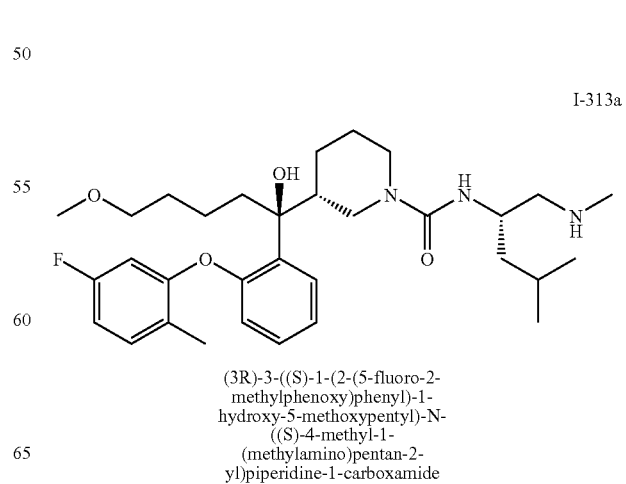

I-313a (3R)-3-((S)-1-(2-(5-fluoro-2-
methylphenoxy)phenyl)-1-
hydroxy-5-methoxypentyl)-N-
((S)-4-methyl-1-
(methylamino)pentan-2-
yl)piperidine-1-carboxamide -continued I-314a

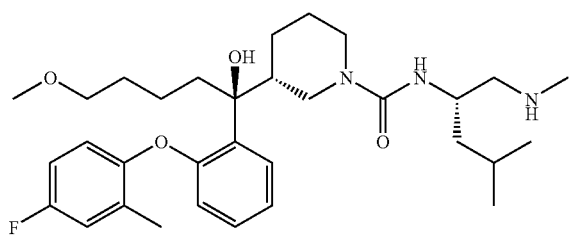

(3R)-3-((S)-1-(2-(4-fluoro-2-
methylphenoxy)phenyl)-1-
hydroxy-5-methoxypentyl)-N-
((S)-4-methyl-1-
(methylamino)pentan-2-
yl)piperidine-1-carboxamide I-315a

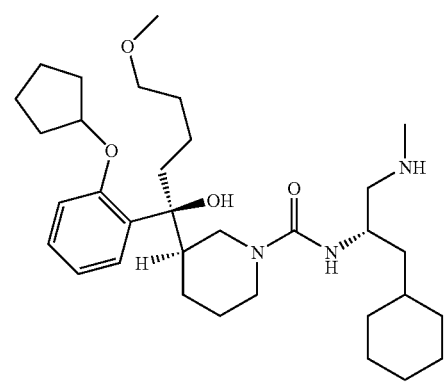

(3R)-N-((S)-3-cyclohexyl-1-
(methylamino)propan-2-yl)-3-
((S)-1-(2-
(cyclopentyloxy)phenyl)-1-
hydroxy-5-
methoxypentyl)piperidine-1-
carboxamide I-316a

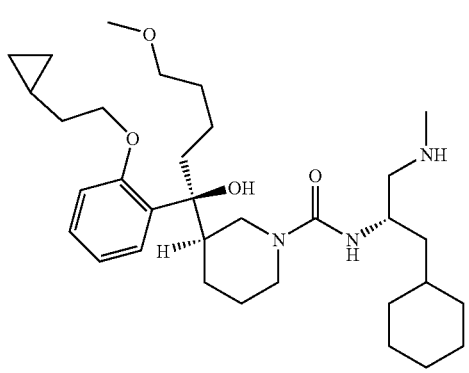

(3R)-3-((S)-1-(2-(2-
cyclopropylethoxy)phenyl)-1-
hydroxy-5-methoxypentyl)-N-
((S)-3-cyclohexyl-1-
(methylamino)propan-2-
yl)piperidine-1-carboxamide -continued I-317a

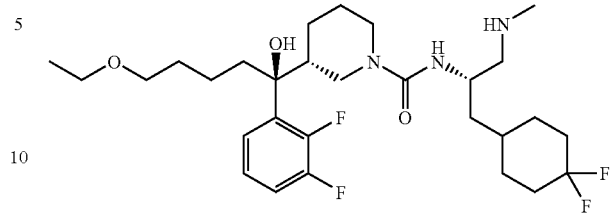

(3R)-3-((S)-5-ethoxy-1-(2,3-
difluorophenyl)-1-
hydroxypentyl)-N-((S)-3-(4,4-
difluorocyclohexyl)-1-
(methylamino)propan-2-
yl)piperidine-1-carboxamide I-318a

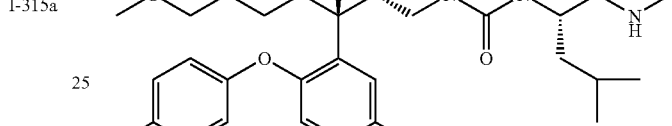

(3R)-3-((S)-1-(2-(4-
fluorophenoxy)-5-fluorophenyl)-
1-hydroxy-5-methoxypentyl)-N-
((S)-4-methyl-1-
(methylamino)pentan-2-
yl)piperidine-1-carboxamide I-319a

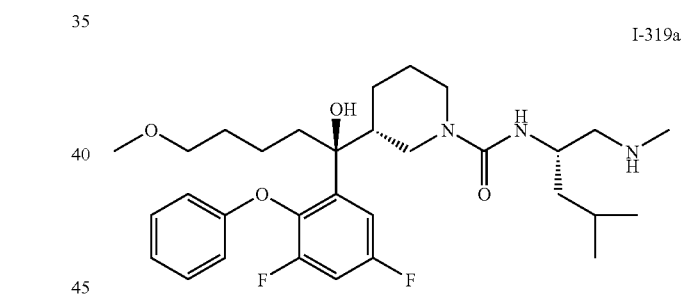

(3R)-3-((S)-1-(3,5-difluoro-2-
phenoxyphenyl)-1-hydroxy-5-
methoxypentyl)-N-((S)-4-
methyl-1-(methylamino)pentan-
2-yl)piperidine-1-carboxamide I-320a

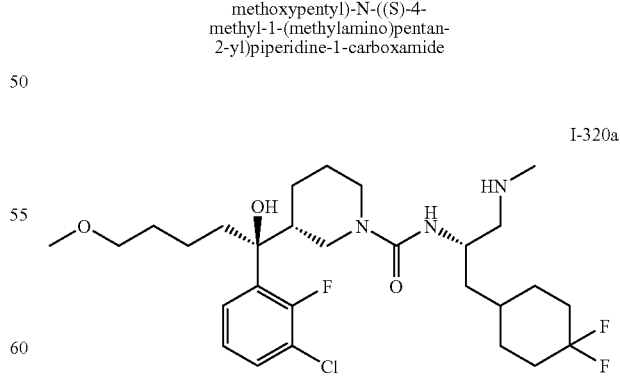

(3R)-3-((S)-1-(3-chloro-2-
fluorophenyl)-1-hydroxy-5-
methoxypentyl)-N-((S)-3-(4,4-
difluorocyclohexyl)-1-
(methylamino)propan-2-
yl)piperidine-1-carboxamide -continued

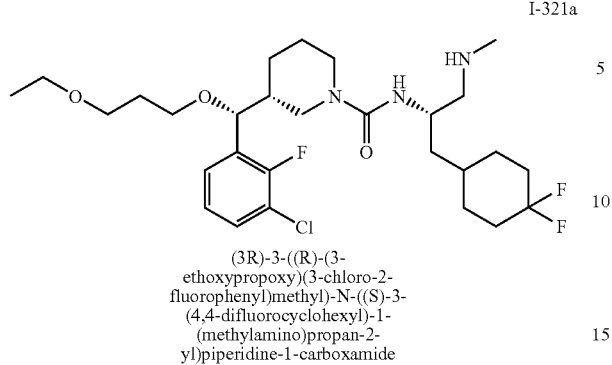

I-321a (3R)-3-((R)-(3-ethoxypropoxy)(3-chloro-2-fluorophenyl)methyl)-N-((S)-3-(4,4-difluorocyclohexyl)-1-(methylamino)propan-2-yl)piperidine-1-carboxamide

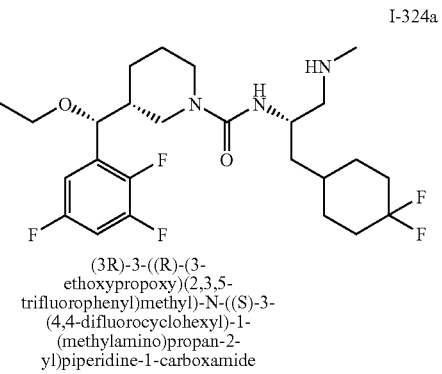

I-324a (3R)-3-((R)-(3-ethoxypropoxy)(2,3,5-trifluorophenyl)methyl)-N-((S)-3-(4,4-difluorocyclohexyl)-1-(methylamino)propan-2-yl)piperidine-1-carboxamide

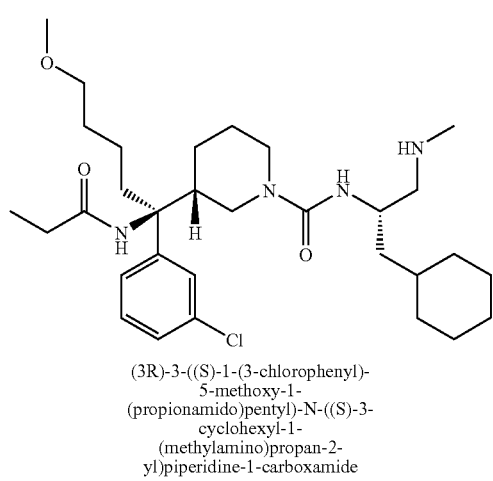

I-322a (3R)-3-((S)-1-(3-chlorophenyl)-5-methoxy-1-(propionamido)pentyl)-N-((S)-3-cyclohexyl-1-(methylamino)propan-2-yl)piperidine-1-carboxamide

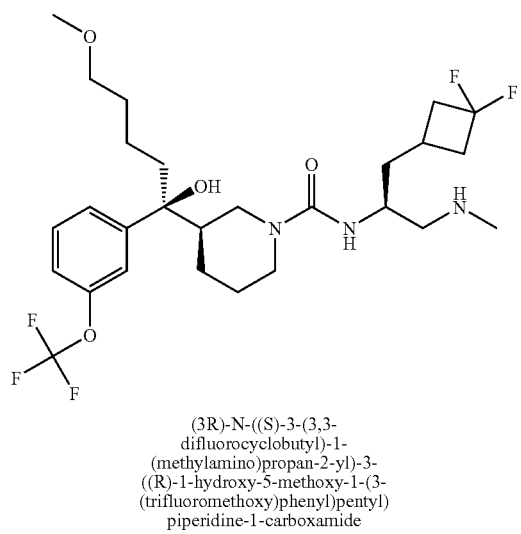

I-325a (3R)-N-((S)-3-(3,3-difluorocyclobutyl)-1-(methylamino)propan-2-yl)-3-((R)-1-hydroxy-5-methoxy-1-(3-(trifluoromethoxy)phenyl)pentyl)piperidine-1-carboxamide

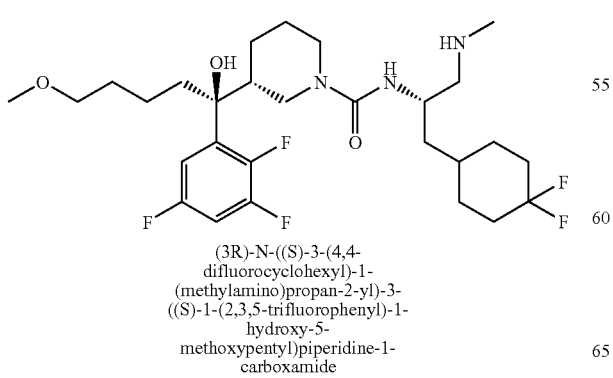

I-323a (3R)-N-((S)-3-(4,4-difluorocyclohexyl)-1-(methylamino)propan-2-yl)-3-((S)-1-(2,3,5-trifluorophenyl)-1-hydroxy-5-methoxypentyl)piperidine-1-carboxamide

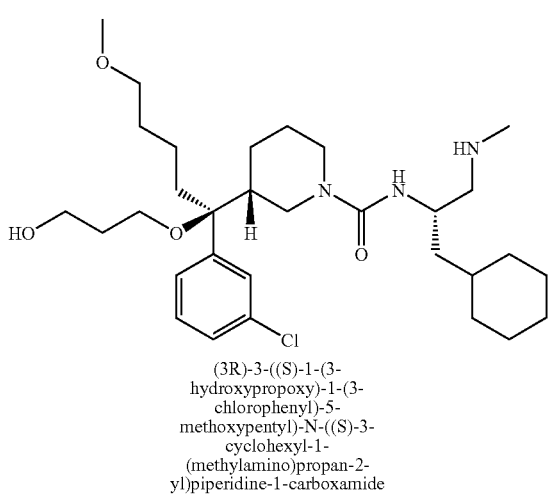

I-326a (3R)-3-((S)-1-(3-hydroxypropoxy)-1-(3-chlorophenyl)-5-methoxypentyl)-N-((S)-3-cyclohexyl-1-(methylamino)propan-2-yl)piperidine-1-carboxamide I-327a

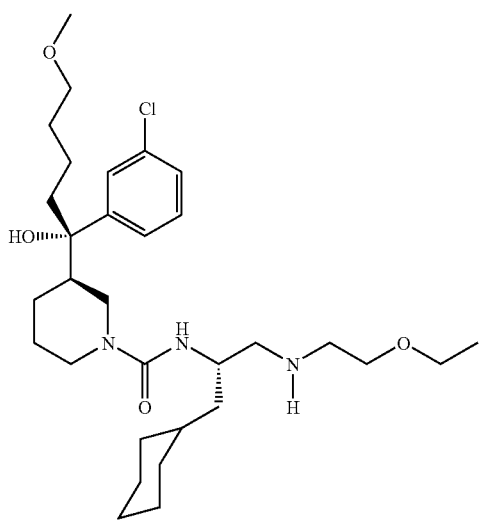

(3R)-N-((S)-1-(2-ethoxyethylamino)-3-cyclohexylpropan-2-yl)-3-((S)-1-(3-chlorophenyl)-1-hydroxy-5-methoxypentyl)piperidine-1-carboxamide I-328a

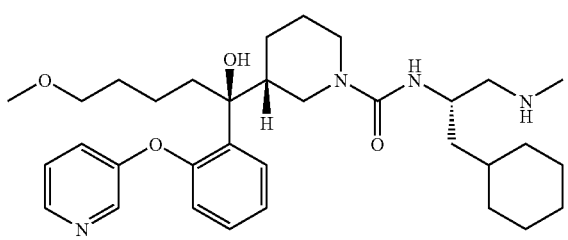

(3R)-N-((S)-3-cyclohexyl-1-(methylamino)propan-2-yl)-3-((S)-1-hydroxy-5-methoxy-1-(2-(pyridin-3-yloxy)phenyl)pentyl)piperidine-1-carboxamide I-329a

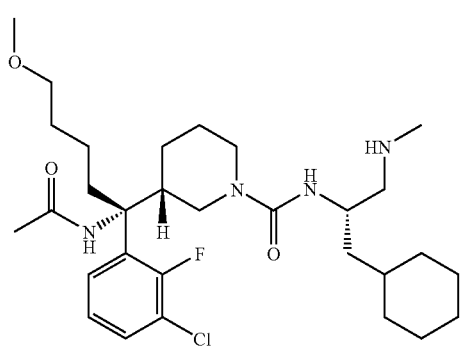

(3R)-3-((R)-1-acetamido-1-(3-chloro-2-fluorophenyl)-5-methoxypentyl)-N-((S)-3-cyclohexyl-1-(methylamino)propan-2-yl)piperidine-1-carboxamide I-329b

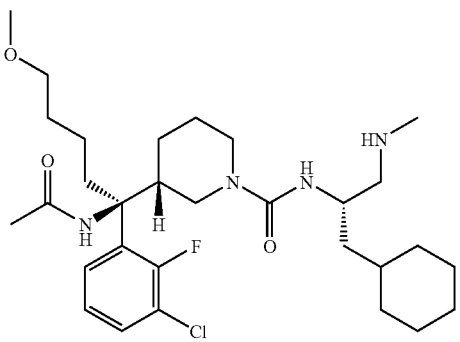

(3R)-3-((S)-1-acetamido-1-(3-chloro-2-fluorophenyl)-5-methoxypentyl)-N-((S)-3-cyclohexyl-1-(methylamino)propan-2-yl)piperidine-1-carboxamide I-330a

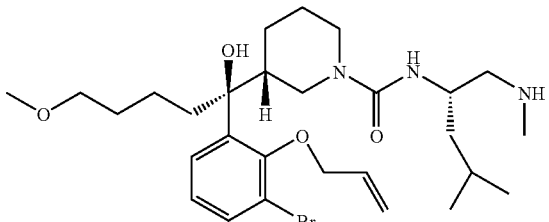

(3R)-3-((S)-1-(2-allyloxy)-3-bromophenyl)-1-hydroxy-5-methoxypentyl)-N-((S)-4-methyl-1-(methylamino)pentan-2-yl)piperidine-1-carboxamide I-331a

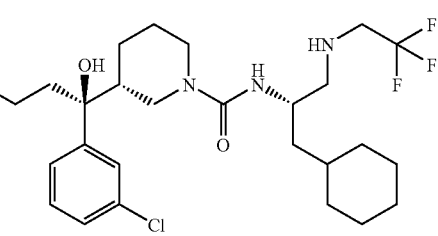

(3R)-N-((S)-1-(2,2,2-trifluoroethylamino)-3-cyclohexylpropan-2-yl)-3-((S)-1-(3-chlorophenyl)-1-hydroxy-5-methoxypentyl)piperidine-1-carboxamide -continued I-332a

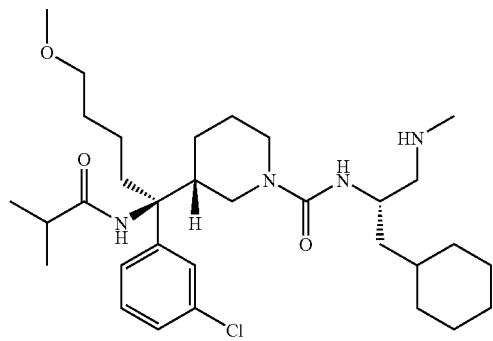

(3R)-3-((S)-1-(3-chlorophenyl)-
1-(isobutyramido)-5-
methoxypentyl)-N-((S)-3-
cyclohexyl-1-
(methylamino)propan-2-
yl)piperidine-1-carboxamide I-333a

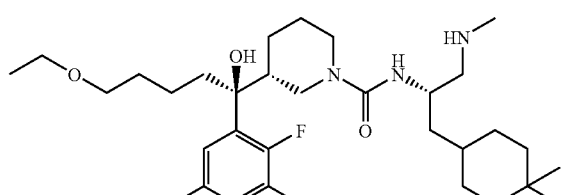

(3R)-3-((S)-5-ethoxy-1-(2,3,5-
trifluorophenyl)-1-
hydroxypentyl)-N-((S)-3-(4,4-
difluorocyclohexyl)-1-
(methylamino)propan-2-
yl)piperidine-1-carboxamide I-334a

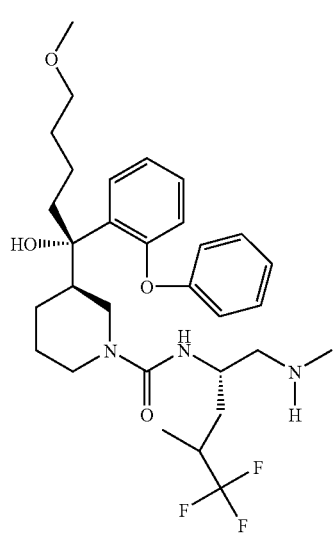

(3R)-N-((2S)-5,5,5-trifluoro-4-
methyl-1-(methylamino)pentan-
2-yl)-3-((S)-1-hydroxy-5-
methoxy-1-(2-
phenoxyphenyl)pentyl)piperidine-
1-carboxamide -continued I-335a

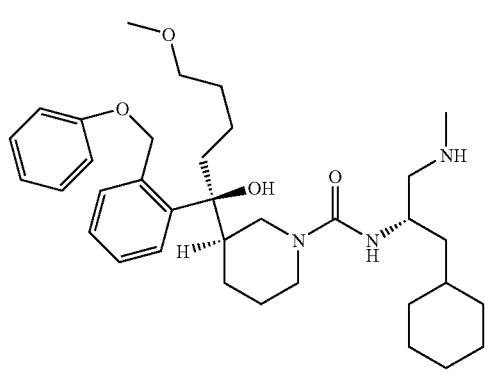

(3R)-3-((S)-1-(2-
(benzyloxy)phenyl)-1-hydroxy-
5-methoxypentyl)-N-((S)-1-
cyclohexyl-3-
(methylamino)propan-2-
yl)piperidine-1-carboxamide I-336a

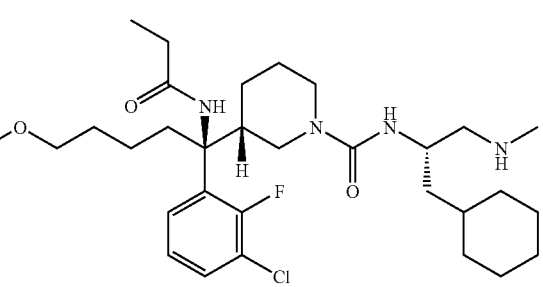

(3R)-3-((S)-1-(3-chloro-2-
fluorophenyl)-5-methoxy-1-
(propionamido)pentyl)-N-((S)-3-
cyclohexyl-1-
(methylamino)propan-2-
yl)piperidine-1-carboxamide I-337a

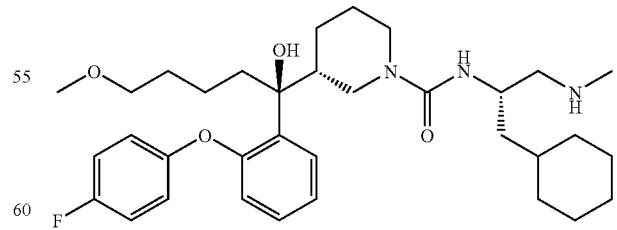

(3R)-3-((S)-1-(2-(4-
fluorophenoxy)phenyl)-1-
hydroxy-5-methoxypentyl-N-
((S)-3-cyclohexyl-1-
(methylamino)propan-2-
yl)piperidine-1-carboxamide -continued

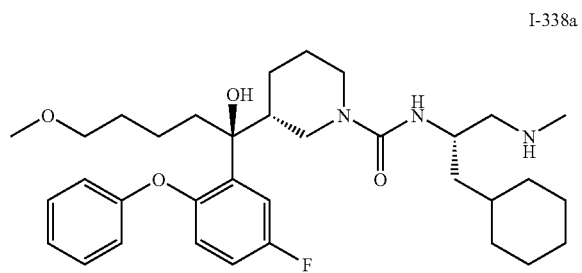

I-338a (3R)-N-((S)-3-cyclohexyl-1-
(methylamino)propan-2-yl)-3-
((S)-1-(5-fluoro-2-
phenoxyphenyl)-1-hydroxy-5-
methoxypentyl)piperidine-1-
carboxamide

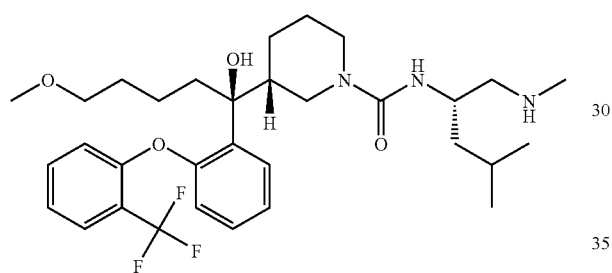

I-339a (3R)-3-((S)-1-(2-(2-
(trifluoromethyl)phenoxy)phenyl
)-1-hydroxy-5-methoxypentyl)-
N-((S)-4-methyl-1-
(methylamino)pentan-2-
yl)piperidine-1-carboxamide

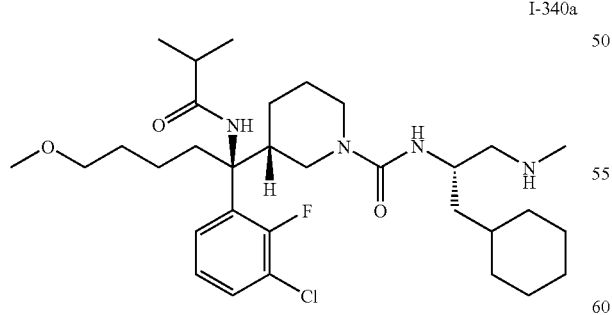

I-340a (3R)-3-((S)-1-(3-chloro-2-
fluorophenyl)-1-(isobutyramido)-
5-methoxypentyl)-N-((S)-3-
cyclohexyl-1-
(methylamino)propan-2-
yl)piperidine-1-carboxamide -continued

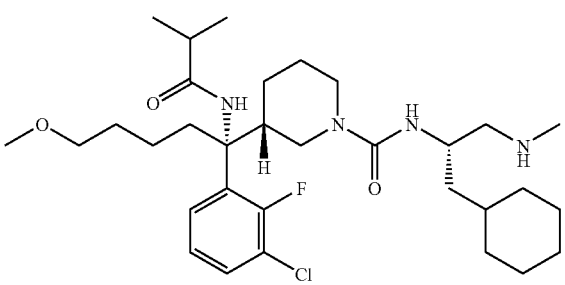

I-340b (3R)-3-((R)-1-(3-chloro-2-
fluorophenyl)-1-(isobutyramido)-
5-methoxypentyl)-N-((S)-3-
cyclohexyl-1-
(methylamino)propan-2-
yl)piperidine-1-carboxamide

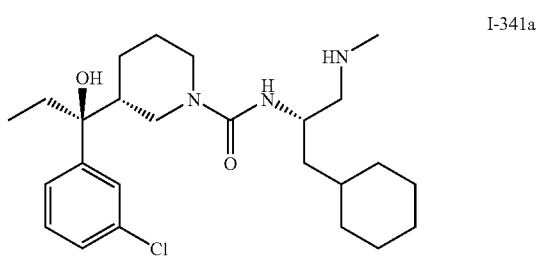

I-341a (3R)-3-((S)-1-(3-chlorophenyl)-
1-hydroxypropyl)-N-((S)-1-
cyclohexyl-3-
(methylamino)propan-2-
yl)piperidine-1-carboxamide

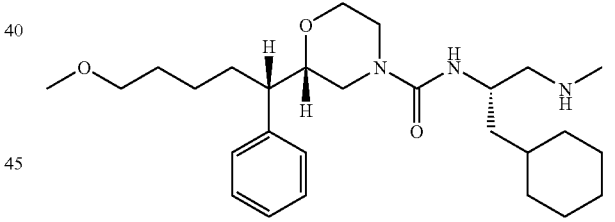

I-342a (S)-N-((S)-1-cyclohexyl-3-
(methylamino)propan-2-yl)-2-
((R)-5-methoxy-1-
phenylpentyl)morpholine-4-
carboxamide

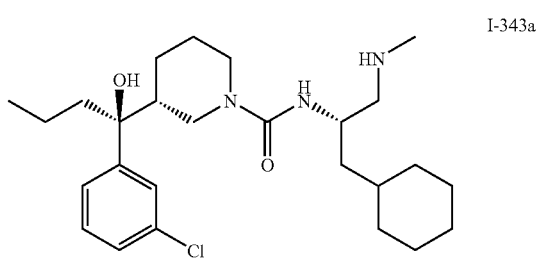

I-343a (3R)-3-((S)-1-(3-chlorophenyl)-
1-hydroxybutyl)-N-((S)-1-
cyclohexyl-3-
(methylamino)propan-2-
yl)piperidine-1-carboxamide I-345a

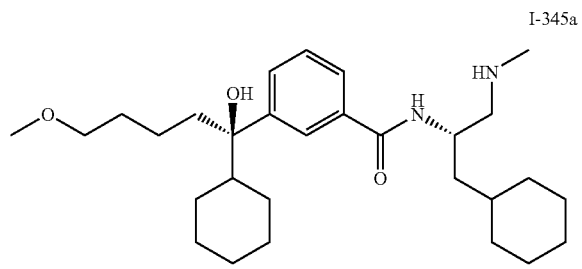

3-((R)-1-cyclohexyl-1-hydroxy-
5-methoxypentyl)-N-((S)-1-
cyclohexyl-3-
(methylamino)propan-2-
yl)benzamide I-346a

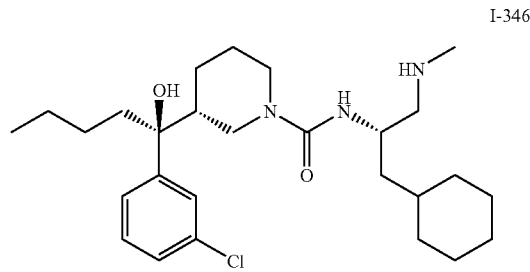

(3R)-3-((S)-1-(3-chlorophenyl)-
1-hydroxypentyl)-N-((S)-1-
cyclohexyl-3-
(methylamino)propan-2-
yl)piperidine-1-carboxamide I-349a

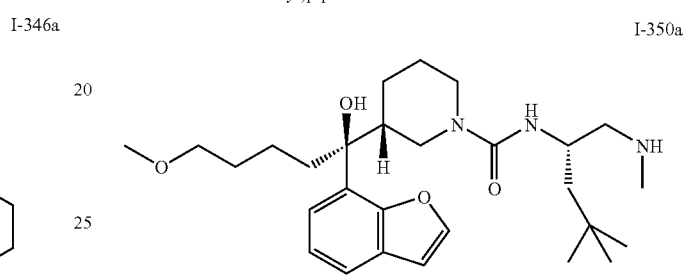

(3R)-3-((S)-1-(3-chlorophenyl)-
1-hydroxy-5-methoxypentyl)-N-
((2R,3S)-3-hydroxy-4-methyl-1-
(methylamino)pentan-2-
yl)piperidine-1-carboxamide I-350a (3R)-3-((S)-1-(benzofuran-7-yl)-
1-hydroxy-5-methoxypentyl)-N-
((S)-4,4-dimethyl-1-
(methylamino)pentan-2-
yl)piperidine-1-carboxamide I-347a

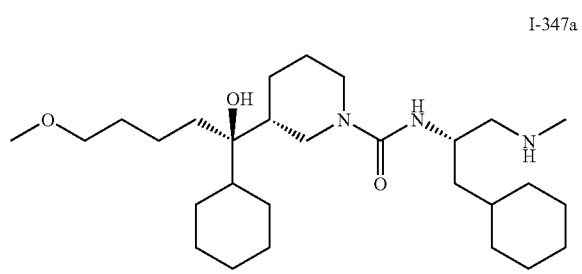

(3R)-3-((R)-1-cyclohexyl-1-
hydroxy-5-methoxypentyl)-N-
((S)-1-cyclohexyl-3-
(methylamino)propan-2-
yl)piperidine-1-carboxamide I-351a

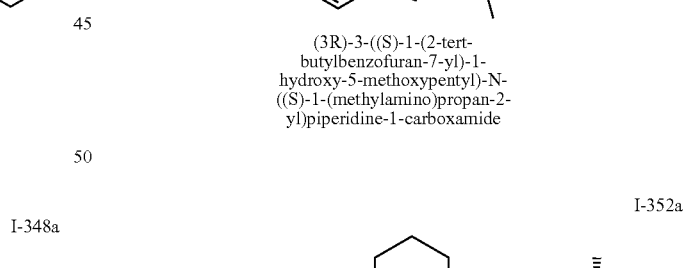

(3R)-3-((S)-1-(2-tert-
butylbenzofuran-7-yl)-1-
hydroxy-5-methoxypentyl)-N-
((S)-1-(methylamino)propan-2-
yl)piperidine-1-carboxamide I-348a

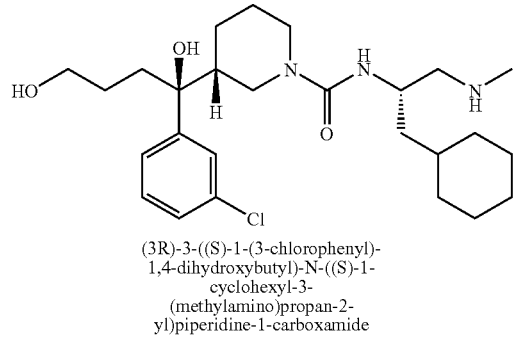

(3R)-3-((S)-1-(3-chlorophenyl)-
1,4-dihydroxybutyl)-N-((S)-1-
cyclohexyl-3-
(methylamino)propan-2-
yl)piperidine-1-carboxamide I-352a

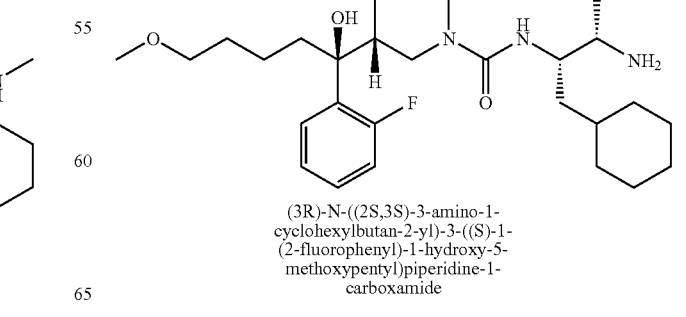

(3R)-N-((2S,3S)-3-amino-1-
cyclohexylbutan-2-yl)-3-((S)-1-
(2-fluorophenyl)-1-hydroxy-5-
methoxypentyl)piperidine-1-
carboxamide -continued

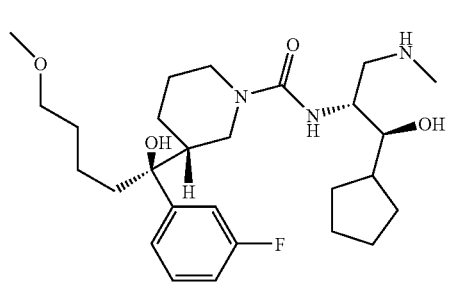

I-353a (3R)-N-((1S,2R)-1-cyclopentyl-
1-hydroxy-3-
(methylamino)propan-2-yl)-3-
((S)-1-(3-fluorophenyl)-1-
hydroxy-5-
methoxypentyl)piperidine-1-
carboxamide

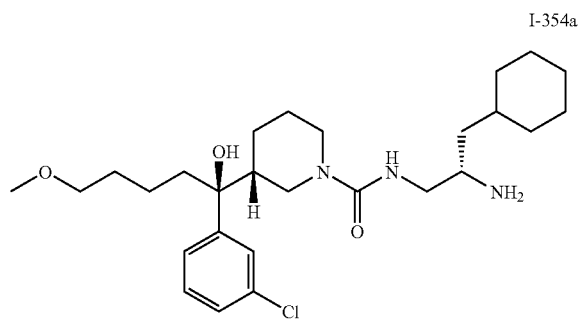

I-354a (3R)-N-((S)-2-amino-3-
cyclohexylpropyl)-3-((S)-1-(3-
chlorophenyl)-1-hydroxy-5-
methoxypentyl)piperidine-1-
carboxamide

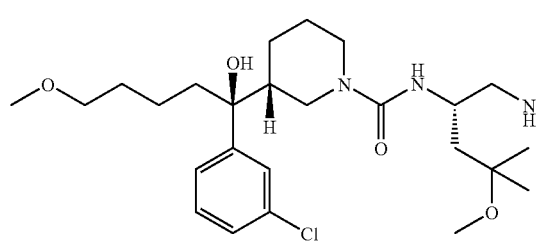

I-356a (3R)-3-((S)-1-(3-chlorophenyl)-
1-hydroxy-5-methoxypentyl)-N-
((S)-4-methoxy-4-methyl-1-
(methylamino)pentan-2-
yl)piperidine-1-carboxamide

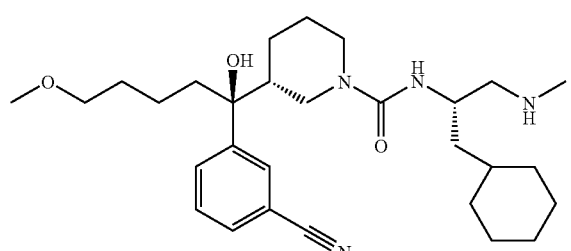

I-357a (3R)-3-((S)-1-(3-cyanophenyl)-
1-hydroxy-5-methoxypentyl)-N-
((S)-1-cyclohexyl-3-
(methylamino)propan-2-
yl)piperidine-1-carboxamide -continued I-358a (3R)-3-((R)-1-(3-chloro-2-
fluorophenyl)-1-hydroxy-5-
methoxypentyl)-N-((S)-4,4-
dimethyl-1-
(methylamino)pentan-2-
yl)piperidine-1-carboxamide

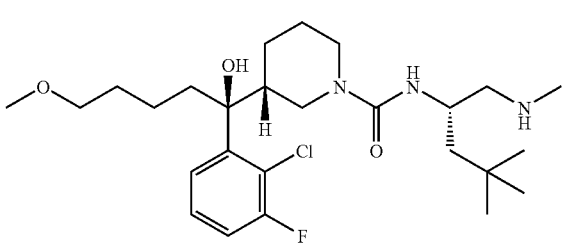

I-359a (3R)-3-((S)-1-(2-chloro-3-
fluorophenyl)-1-hydroxy-5-
methoxypentyl)-N-((S)-4,4-
dimethyl-1-
(methylamino)pentan-2-
yl)piperidine-1-carboxamide

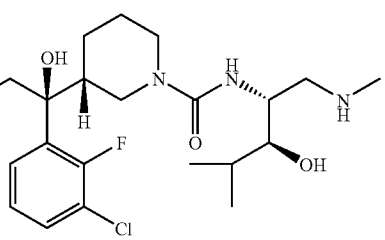

I-360a (3R)-3-((S)-1-(3-chloro-2-
fluorophenyl)-1-hydroxy-5-
methoxypentyl)-N-((2R,3S)-3-
hydroxy-4-methyl-1-
(methylamino)pentan-2-
yl)piperidine-1-carboxamide

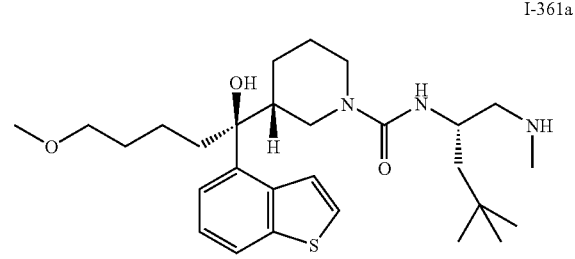

I-361a (3R)-3-((S)-1-
(benzo[b]thiophen-4-yl)-1-
hydroxy-5-methoxypentyl)-N-
((S)-4,4-dimethyl-1-
(methylamino)pentan-2-
yl)piperidine-1-carboxamide I-362a

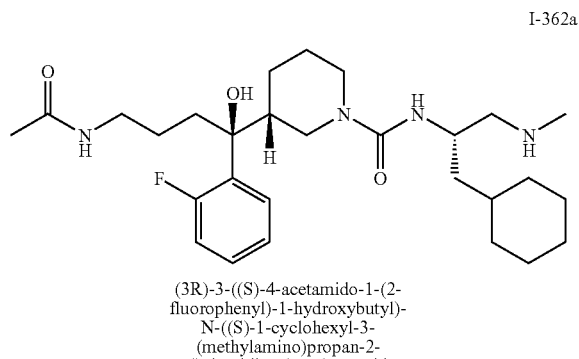

(3R)-3-((S)-4-acetamido-1-(2-fluorophenyl)-1-hydroxybutyl)-N-((S)-1-cyclohexyl-3-(methylamino)propan-2-yl)piperidine-1-carboxamide I-363a

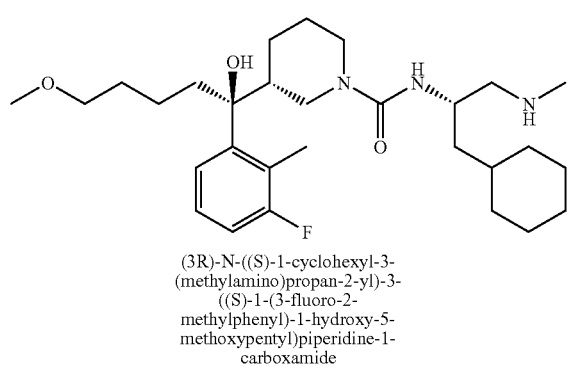

(3R)-N-((S)-1-cyclohexyl-3-(methylamino)propan-2-yl)-3-((S)-1-(3-fluoro-2-methylphenyl)-1-hydroxy-5-methoxypentyl)piperidine-1-carboxamide I-363b

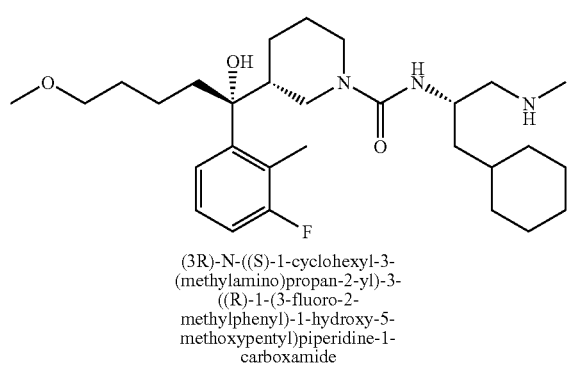

(3R)-N-((S)-1-cyclohexyl-3-(methylamino)propan-2-yl)-3-((R)-1-(3-fluoro-2-methylphenyl)-1-hydroxy-5-methoxypentyl)piperidine-1-carboxamide I-364a

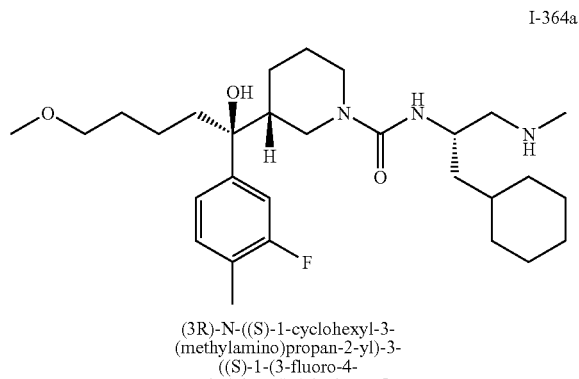

(3R)-N-((S)-1-cyclohexyl-3-(methylamino)propan-2-yl)-3-((S)-1-(3-fluoro-4-methylphenyl)-1-hydroxy-5-methoxypentyl)piperidine-1-carboxamide I-364b

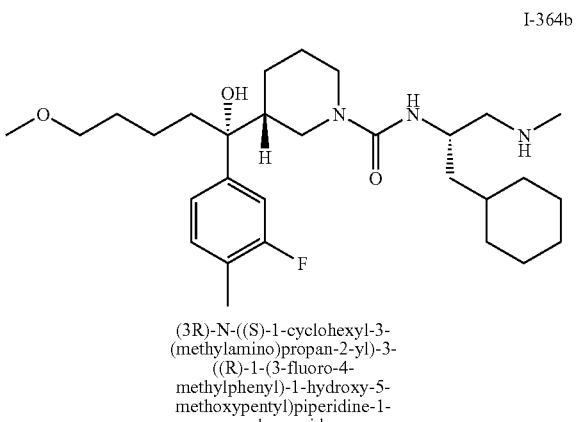

(3R)-N-((S)-1-cyclohexyl-3-(methylamino)propan-2-yl)-3-((R)-1-(3-fluoro-4-methylphenyl)-1-hydroxy-5-methoxypentyl)piperidine-1-carboxamide I-366a

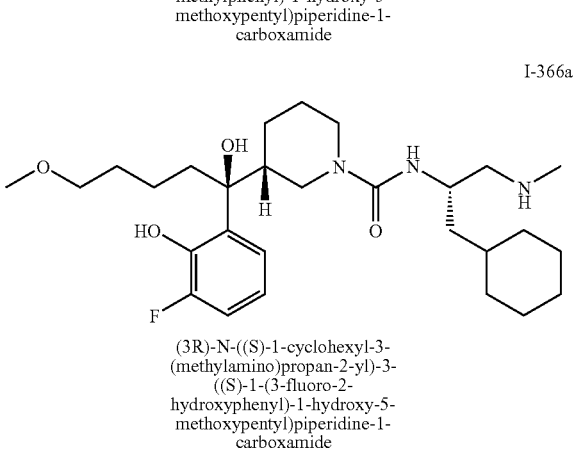

(3R)-N-((S)-1-cyclohexyl-3-(methylamino)propan-2-yl)-3-((S)-1-(3-fluoro-2-hydroxyphenyl)-1-hydroxy-5-methoxypentyl)piperidine-1-carboxamide I-367a

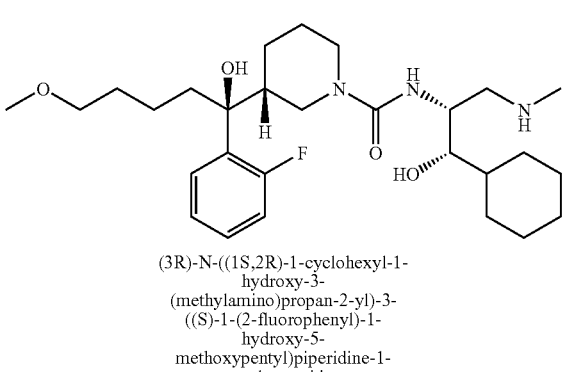

(3R)-N-((1S,2R)-1-cyclohexyl-1-hydroxy-3-(methylamino)propan-2-yl)-3-((S)-1-(2-fluorophenyl)-1-hydroxy-5-methoxypentyl)piperidine-1-carboxamide I-368a

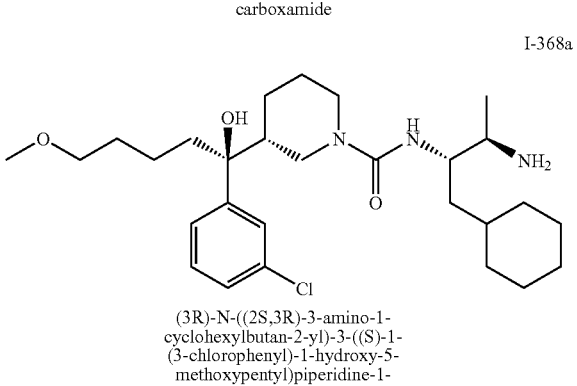

(3R)-N-((2S,3R)-3-amino-1-cyclohexylbutan-2-yl)-3-((S)-1-(3-chlorophenyl)-1-hydroxy-5-methoxypentyl)piperidine-1-carboxamide

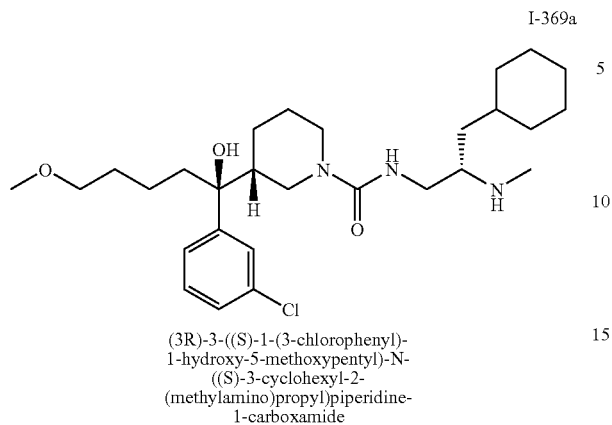

I-369a (3R)-3-((S)-1-(3-chlorophenyl)-
1-hydroxy-5-methoxypentyl)-N-
((S)-3-cyclohexyl-2-
(methylamino)propyl)piperidine-
1-carboxamide

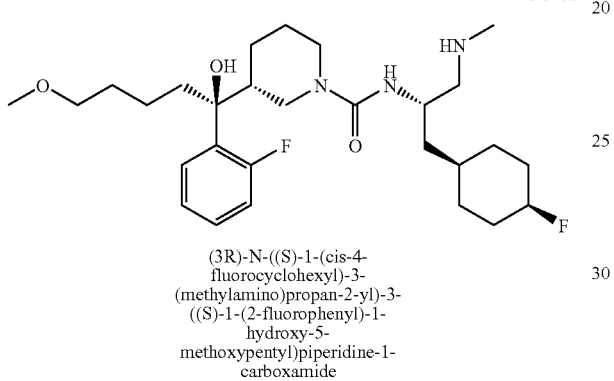

I-370a (3R)-N-((S)-1-(cis-4-
fluorocyclohexyl)-3-
(methylamino)propan-2-yl)-3-
((S)-1-(2-fluorophenyl)-1-
hydroxy-5-
methoxypentyl)piperidine-1-
carboxamide

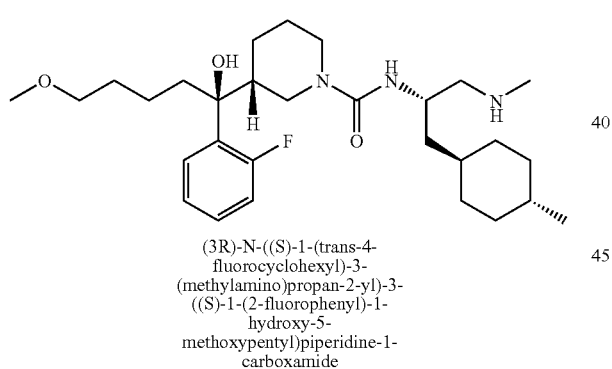

I-370b (3R)-N-((S)-1-(trans-4-
fluorocyclohexyl)-3-
(methylamino)propan-2-yl)-3-
((S)-1-(2-fluorophenyl)-1-
hydroxy-5-
methoxypentyl)piperidine-1-
carboxamide

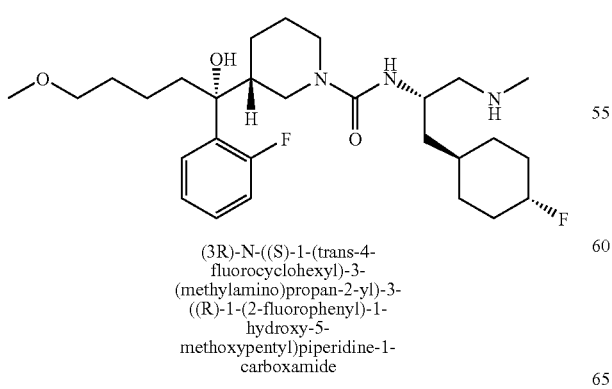

I-370c (3R)-N-((S)-1-(trans-4-
fluorocyclohexyl)-3-
(methylamino)propan-2-yl)-3-
((R)-1-(2-fluorophenyl)-1-
hydroxy-5-
methoxypentyl)piperidine-1-
carboxamide

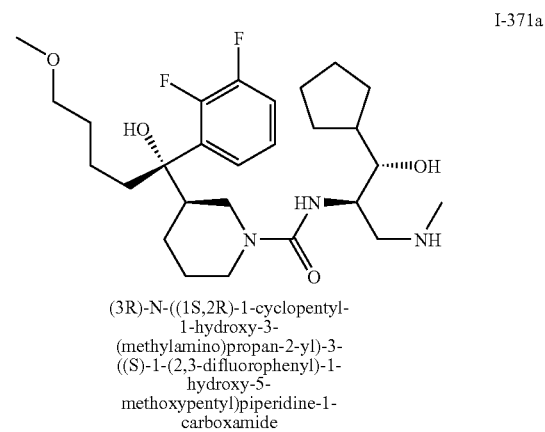

I-371a (3R)-N-((1S,2R)-1-cyclopentyl-
1-hydroxy-3-
(methylamino)propan-2-yl)-3-
((S)-1-(2,3-difluorophenyl)-1-
hydroxy-5-
methoxypentyl)piperidine-1-
carboxamide

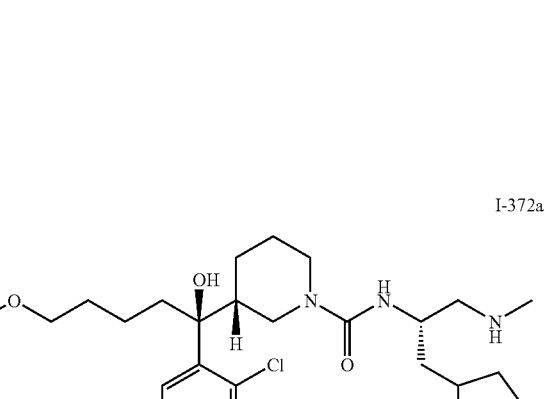

I-372a (3R)-3-((S)-1-(2-chloro-3-
fluorophenyl)-1-hydroxy-5-
methoxypentyl)-N-((S)-1-
cyclopentyl-3-
(methylamino)propan-2-
yl)piperidine-1-carboxamide

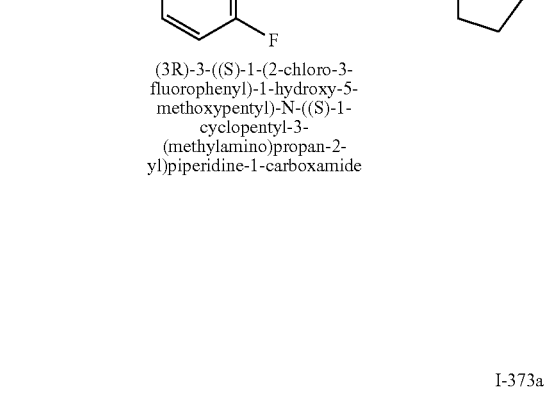

I-373a (3R)-N-((S)-2-amino-3-
cyclohexylpropyl)-3-((S)-1-(3-
chloro-2-fluorophenyl)-1-
hydroxy-5-
methoxypentyl)piperidine-1-
carboxamide I-374a

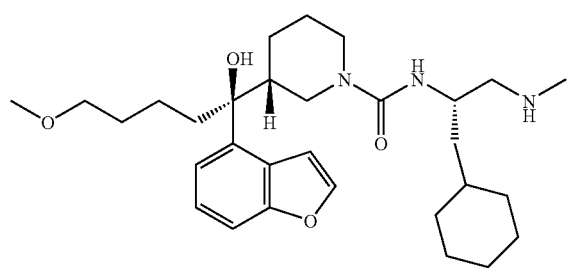

(3R)-3-((S)-1-(benzofuran-4-yl)-
1-hydroxy-5-methoxypentyl)-N-
((S)-1-cyclohexyl-3-
(methylamino)propan-2-
yl)piperidine-1-carboxamide I-375a

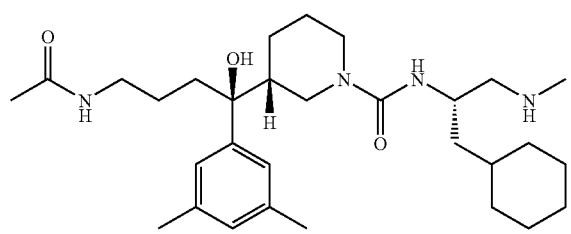

(3R)-3-((S)-4-acetamido-1-(3,5-
dimethylphenyl)-1-
hydroxybutyl)-N-((S)-1-
cyclohexyl-3-
(methylamino)propan-2-
yl)piperidine-1-carboxamide I-376a

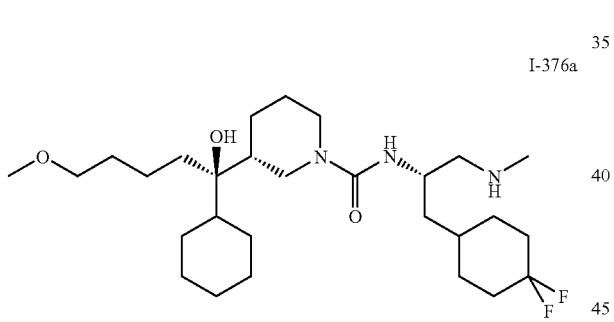

(3R)-3-((R)-1-cyclohexyl-1-
hydroxy-5-methoxypentyl)-N-
((S)-1-(4,4-difluorocyclohexyl)-
3-(methylamino)propan-2-
yl)piperidine-1-carboxamide I-377a

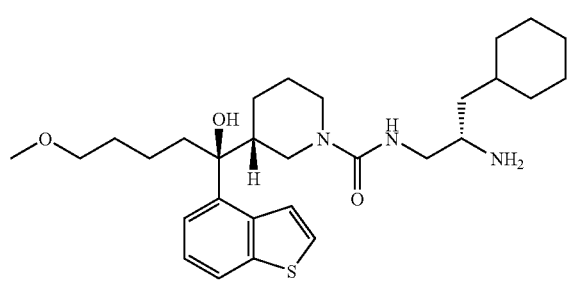

(3R)-N-((S)-2-amino-3-
cyclohexylpropyl)-3-((S)-1-
(benzo[b]thiophen-4-yl)-1-
hydroxy-5-
methoxypentyl)piperidine-1-
carboxamide I-378a

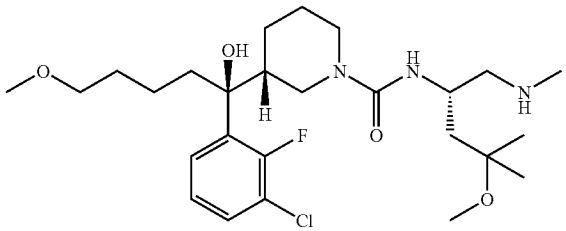

(3R)-3-((S)-1-(3-chloro-2-
fluorophenyl)-1-hydroxy-5-
methoxypentyl)-N-((S)-4-
methoxy-4-methyl-1-
(methylamino)pentan-2-
yl)piperidine-1-carboxamide I-379a

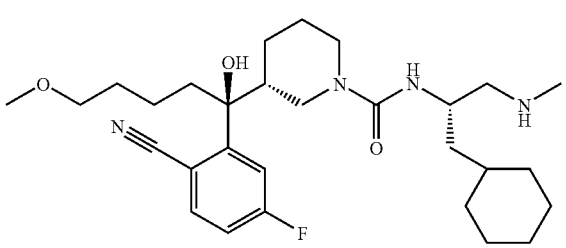

(3R)-3-((S)-1-(2-cyano-5-
fluorophenyl)-1-hydroxy-5-
methoxypentyl)-N-((S)-1-
cyclohexyl-3-
(methylamino)propan-2-
yl)piperidine-1-carboxamide I-380a

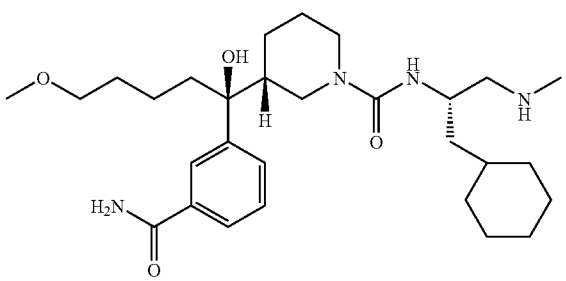

(3R)-3-((S)-1-(3-
carbamoylphenyl)-1-hydroxy-5-
methoxypentyl)-N-((S)-1-
cyclohexyl-3-
(methylamino)propan-2-
yl)piperidine-1-carboxamide I-381a

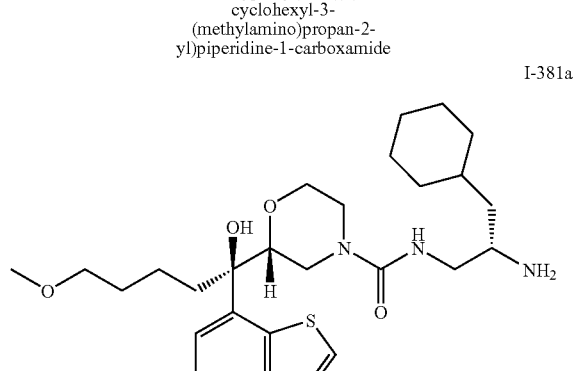

(3R)-N-((S)-2-amino-3-
cyclohexylpropyl)-2-((R)-1-
(benzo[b]thiophen-7-yl)-1-
hydroxy-5-
methoxypentyl)morpholine-4-
carboxamide

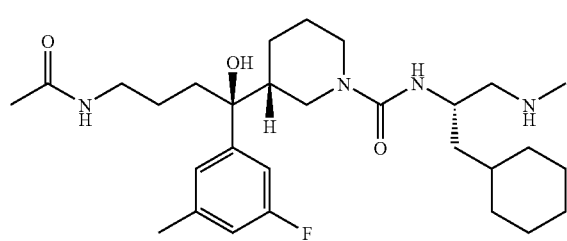

I-382a (3R)-3-((S)-4-acetamido-1-(3-fluoro-5-methylphenyl)-1-hydroxybutyl)-N-((S)-1-cyclohexyl-3-(methylamino)propan-2-yl)piperidine-1-carboxamide

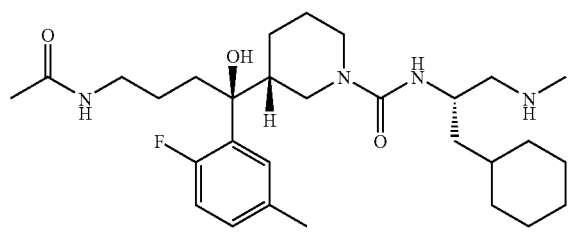

I-383a (3R)-3-((S)-4-acetamido-1-(2-fluoro-5-methylphenyl)-1-hydroxybutyl)-N-((S)-1-cyclohexyl-3-(methylamino)propan-2-yl)piperidine-1-carboxamide

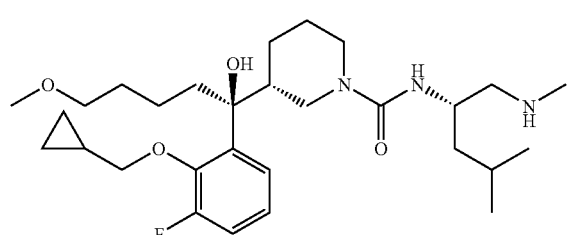

I-385a (3R)-3-((S)-1-(2-(cyclopropylmethoxy)-3-fluorophenyl)-1-hydroxy-5-methoxypentyl)-N-((S)-4-methyl-1-(methylamino)pentan-2-yl)piperidine-1-carboxamide I-386a

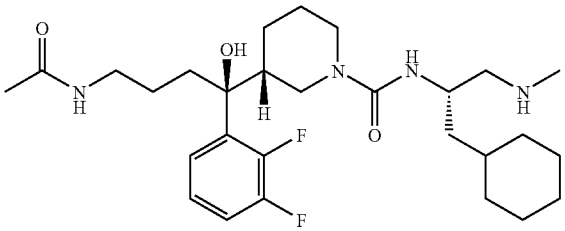

(3R)-3-((S)-1-(3-chloro-2-methylphenyl)-1-hydroxy-5-methoxypentyl)-N-((S)-1-cyclohexyl-3-(methylamino)propan-2-yl)piperidine-1-carboxamide

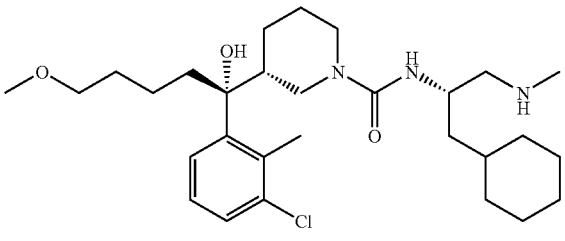

I-386b (3R)-3-((R)-1-(3-chloro-2-methylphenyl)-1-hydroxy-5-methoxypentyl)-N-((S)-1-cyclohexyl-3-(methylamino)propan-2-yl)piperidine-1-carboxamide

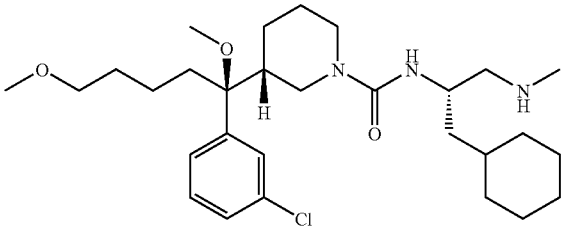

I-387a (3R)-3-((S)-1-(3-chlorophenyl)-1,5-dimethoxypentyl)-N-((S)-1-cyclohexyl-3-(methylamino)propan-2-yl)piperidine-1-carboxamide I-388a

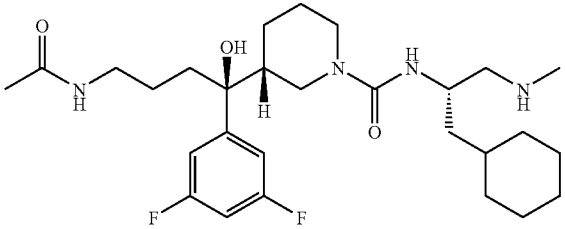

(3R)-3-((S)-4-acetamido-1-(2,3-difluorophenyl)-1-hydroxybutyl)-N-((S)-1-cyclohexyl-3-(methylamino)propan-2-yl)piperidine-1-carboxamide I-389a (3R)-3-((S)-4-acetamido-1-(3,5-difluorophenyl)-1-hydroxybutyl)-N-((S)-1-cyclohexyl-3-(methylamino)propan-2-yl)piperidine-1-carboxamide -continued I-390a

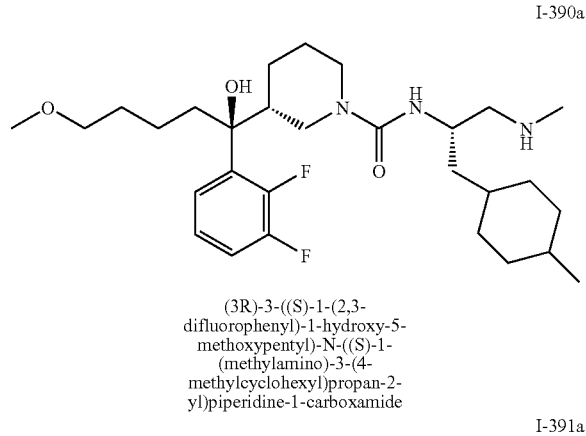

(3R)-3-((S)-1-(2,3-difluorophenyl)-1-hydroxy-5-methoxypentyl)-N-((S)-1-(methylamino)-3-(4-methylcyclohexyl)propan-2-yl)piperidine-1-carboxamide I-391a

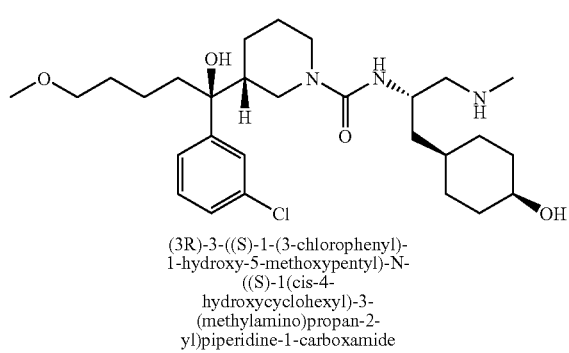

(3R)-3-((S)-1-(3-chlorophenyl)-1-hydroxy-5-methoxypentyl)-N-((S)-1(cis-4-hydroxycyclohexyl)-3-(methylamino)propan-2-yl)piperidine-1-carboxamide I-391b

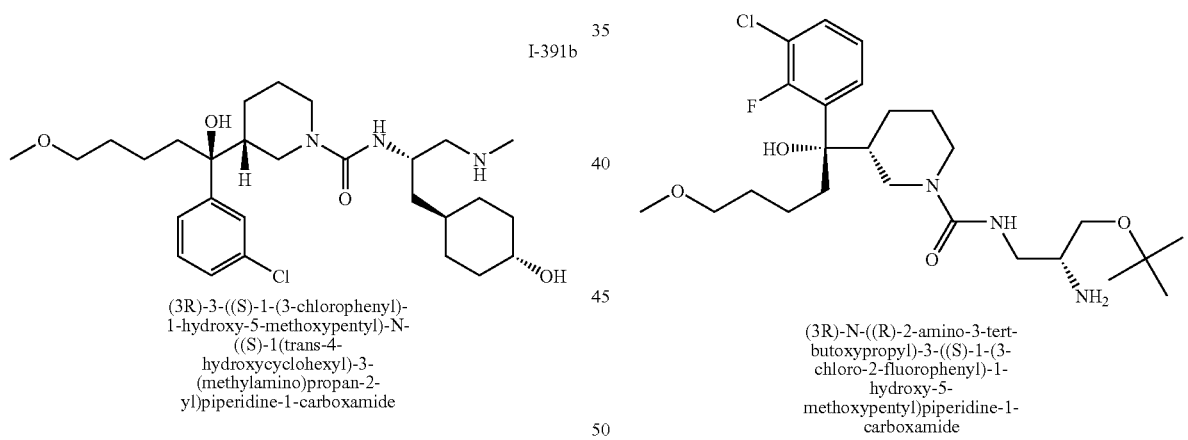

(3R)-3-((S)-1-(3-chlorophenyl)-1-hydroxy-5-methoxypentyl)-N-((S)-1(trans-4-hydroxycyclohexyl)-3-(methylamino)propan-2-yl)piperidine-1-carboxamide I-392a

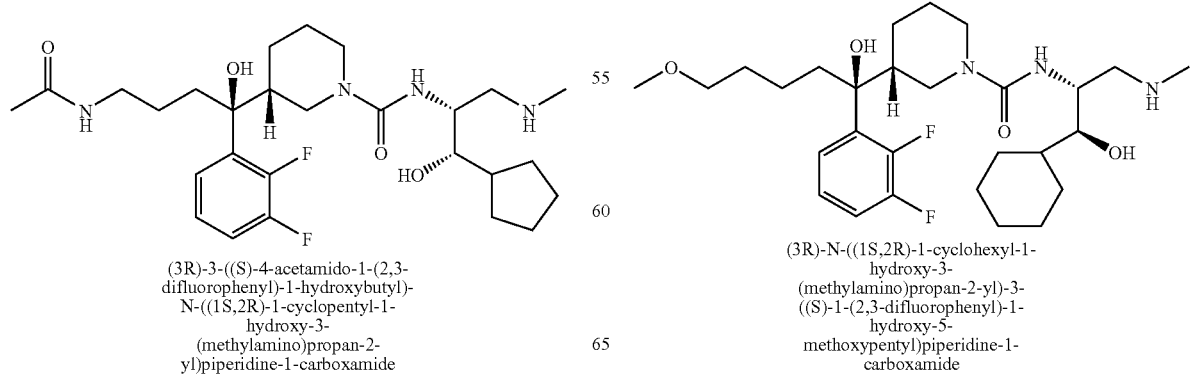

(3R)-3-((S)-4-acetamido-1-(2,3-difluorophenyl)-1-hydroxybutyl)-N-((1S,2R)-1-cyclopentyl-1-hydroxy-3-(methylamino)propan-2-yl)piperidine-1-carboxamide -continued I-393a

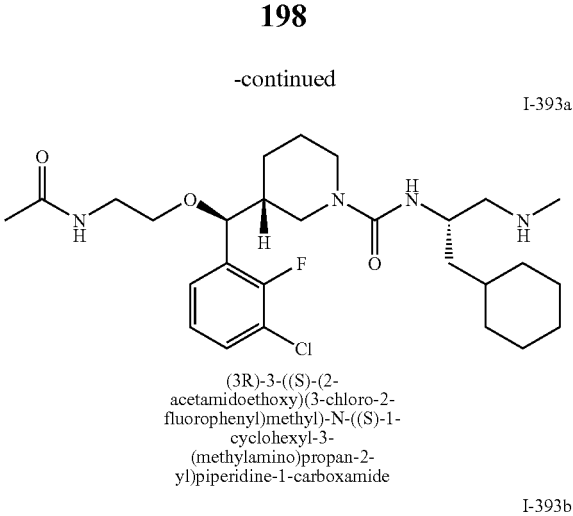

(3R)-3-((S)-(2-acetamidoethoxy)(3-chloro-2-fluorophenyl)methyl)-N-((S)-1-cyclohexyl-3-(methylamino)propan-2-yl)piperidine-1-carboxamide I-393b

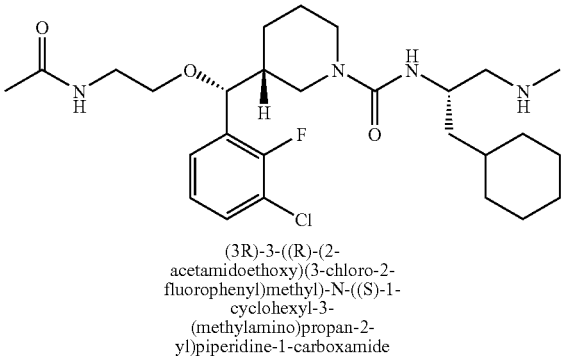

(3R)-3-((R)-(2-acetamidoethoxy)(3-chloro-2-fluorophenyl)methyl)-N-((S)-1-cyclohexyl-3-(methylamino)propan-2-yl)piperidine-1-carboxamide I-394a

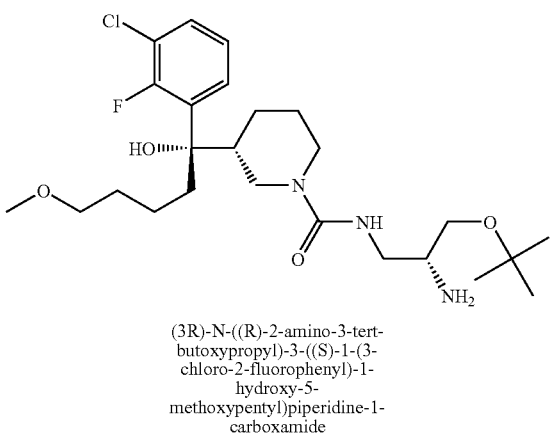

(3R)-N-((R)-2-amino-3-tert-butoxypropyl)-3-((S)-1-(3-chloro-2-fluorophenyl)-1-hydroxy-5-methoxypentyl)piperidine-1-carboxamide I-395a

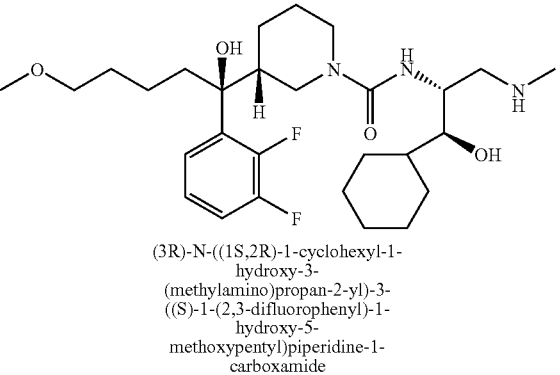

(3R)-N-((1S,2R)-1-cyclohexyl-1-hydroxy-3-(methylamino)propan-2-yl)-3-((S)-1-(2,3-difluorophenyl)-1-hydroxy-5-methoxypentyl)piperidine-1-carboxamide -continued

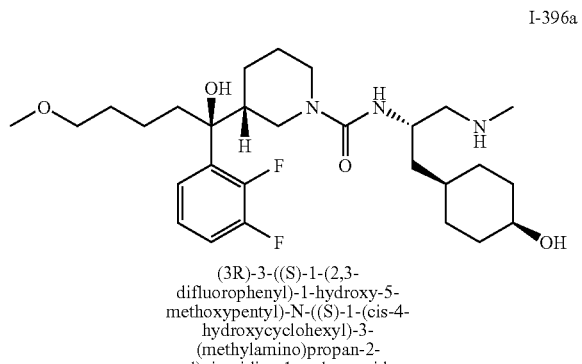

I-396a (3R)-3-((S)-1-(2,3-difluorophenyl)-1-hydroxy-5-methoxypentyl)-N-((S)-1-(cis-4-hydroxycyclohexyl)-3-(methylamino)propan-2-yl)piperidine-1-carboxamide

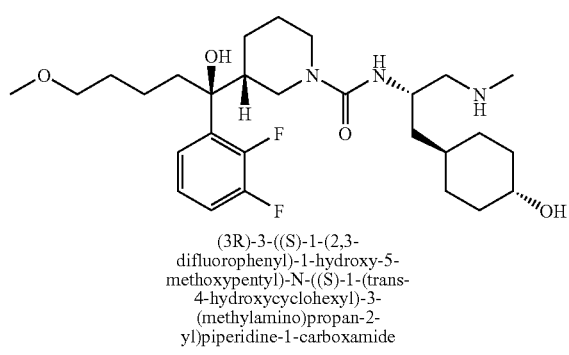

I-396b (3R)-3-((S)-1-(2,3-difluorophenyl)-1-hydroxy-5-methoxypentyl)-N-((S)-1-(trans-4-hydroxycyclohexyl)-3-(methylamino)propan-2-yl)piperidine-1-carboxamide

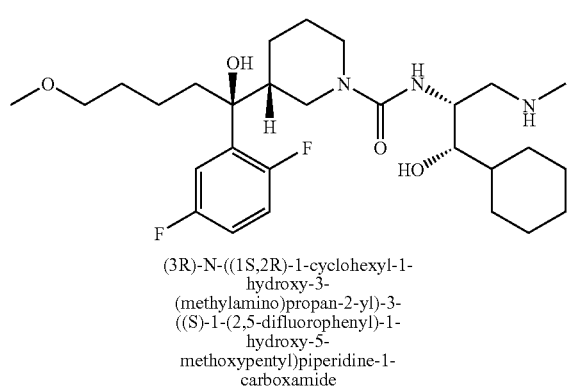

I-397a (3R)-N-((1S,2R)-1-cyclohexyl-1-hydroxy-3-(methylamino)propan-2-yl)-3-((S)-1-(2,5-difluorophenyl)-1-hydroxy-5-methoxypentyl)piperidine-1-carboxamide

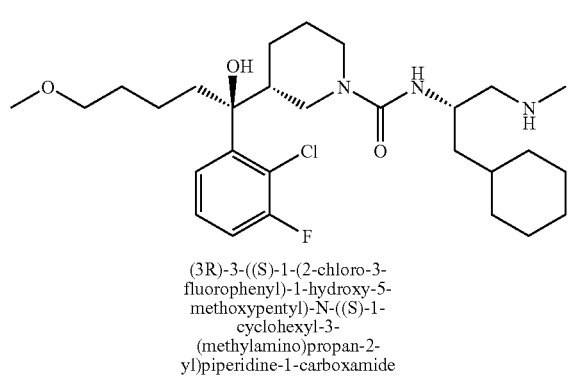

I-398a (3R)-3-((S)-1-(2-chloro-3-fluorophenyl)-1-hydroxy-5-methoxypentyl)-N-((S)-1-cyclohexyl-3-(methylamino)propan-2-yl)piperidine-1-carboxamide -continued

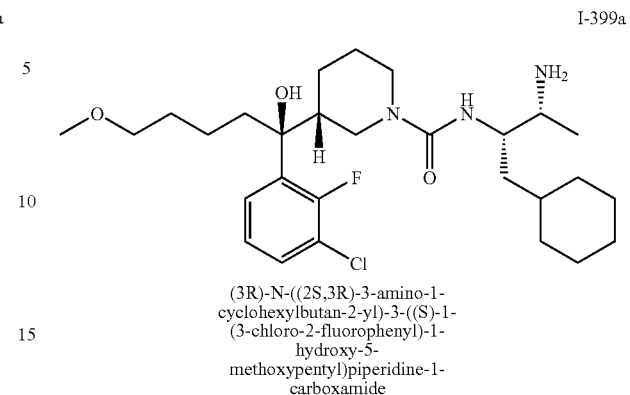

I-399a (3R)-N-((2S,3R)-3-amino-1-cyclohexylbutan-2-yl)-3-((S)-1-(3-chloro-2-fluorophenyl)-1-hydroxy-5-methoxypentyl)piperidine-1-carboxamide

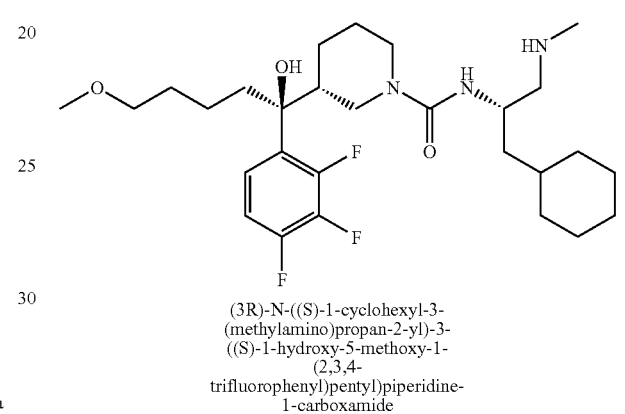

I-400a (3R)-N-((S)-1-cyclohexyl-3-(methylamino)propan-2-yl)-3-((S)-1-hydroxy-5-methoxy-1-(2,3,4-trifluorophenyl)pentyl)piperidine-1-carboxamide

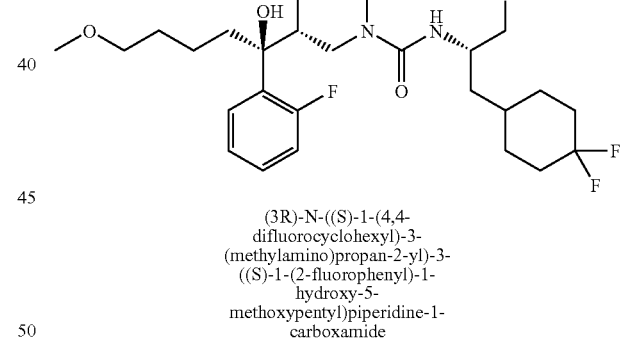

I-401a (3R)-N-((S)-1-(4,4-difluorocyclohexyl)-3-(methylamino)propan-2-yl)-3-((S)-1-(2-fluorophenyl)-1-hydroxy-5-methoxypentyl)piperidine-1-carboxamide

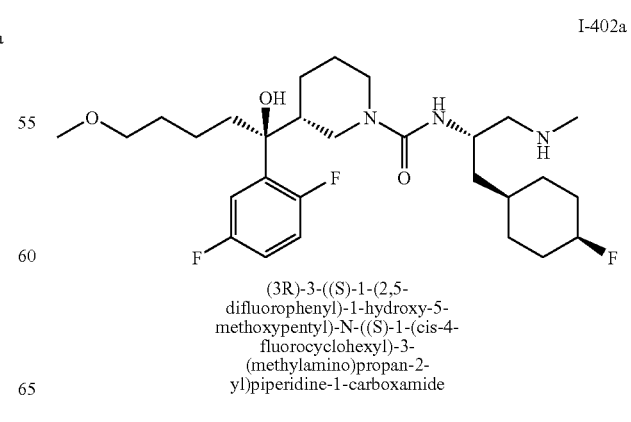

I-402a (3R)-3-((S)-1-(2,5-difluorophenyl)-1-hydroxy-5-methoxypentyl)-N-((S)-1-(cis-4-fluorocyclohexyl)-3-(methylamino)propan-2-yl)piperidine-1-carboxamide -continued

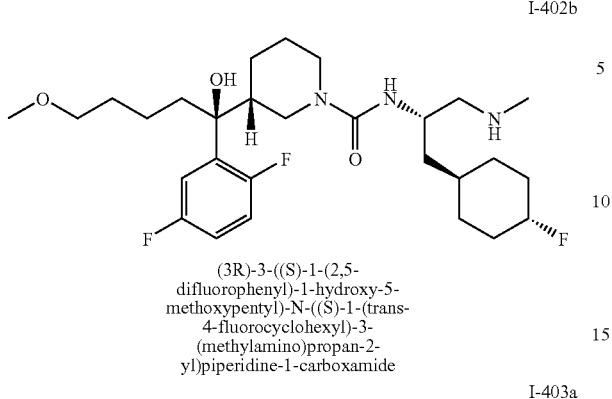

I-402b (3R)-3-((S)-1-(2,5-difluorophenyl)-1-hydroxy-5-methoxypentyl)-N-((S)-1-(trans-4-fluorocyclohexyl)-3-(methylamino)propan-2-yl)piperidine-1-carboxamide

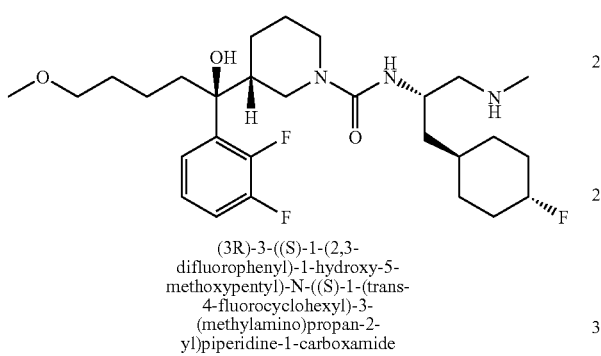

I-403a (3R)-3-((S)-1-(2,3-difluorophenyl)-1-hydroxy-5-methoxypentyl)-N-((S)-1-(trans-4-fluorocyclohexyl)-3-(methylamino)propan-2-yl)piperidine-1-carboxamide I-403b (3R)-3-((R)-1-(2,3-difluorophenyl)-1-hydroxy-5-methoxypentyl)-N-((S)-1-(trans-4-fluorocyclohexyl)-3-(methylamino)propan-2-yl)piperidine-1-carboxamide I-404a (R)-2-((R)-1-(3-chloro-2-fluorophenyl)-1-hydroxy-5-methoxypentyl)-N-((S)-1-cyclohexyl-3-(methylamino)propan-2-yl)morpholine-1-carboxamide -continued

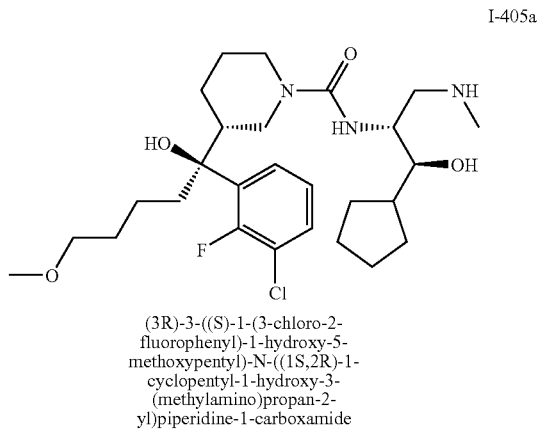

I-405a (3R)-3-((S)-1-(3-chloro-2-fluorophenyl)-1-hydroxy-5-methoxypentyl)-N-((1S,2R)-1-cyclopentyl-1-hydroxy-3-(methylamino)propan-2-yl)piperidine-1-carboxamide

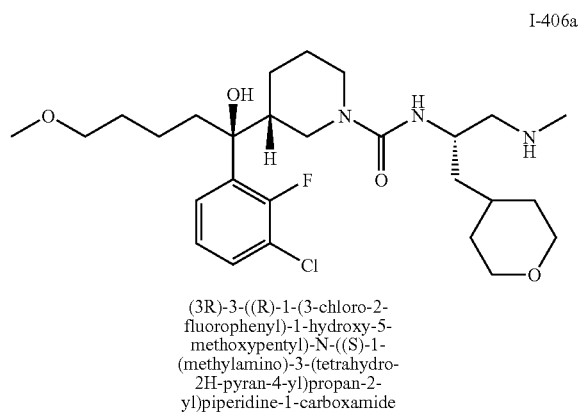

I-406a (3R)-3-((R)-1-(3-chloro-2-fluorophenyl)-1-hydroxy-5-methoxypentyl)-N-((S)-1-(methylamino)-3-(tetrahydro-2H-pyran-4-yl)propan-2-yl)piperidine-1-carboxamide I-406b

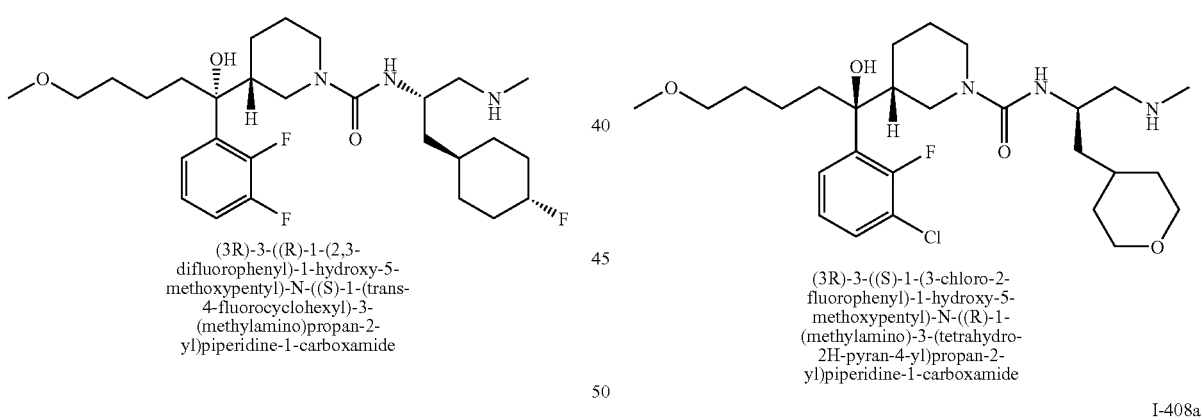

(3R)-3-((S)-1-(3-chloro-2-fluorophenyl)-1-hydroxy-5-methoxypentyl)-N-((R)-1-(methylamino)-3-(tetrahydro-2H-pyran-4-yl)propan-2-yl)piperidine-1-carboxamide I-408a

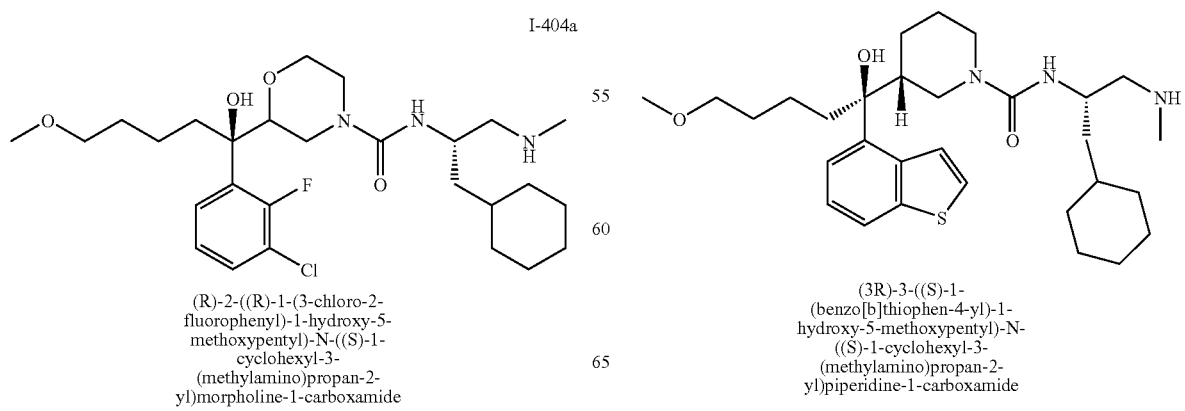

(3R)-3-((S)-1-(benzo[b]thiophen-4-yl)-1-hydroxy-5-methoxypentyl)-N-((S)-1-cyclohexyl-3-(methylamino)propan-2-yl)piperidine-1-carboxamide

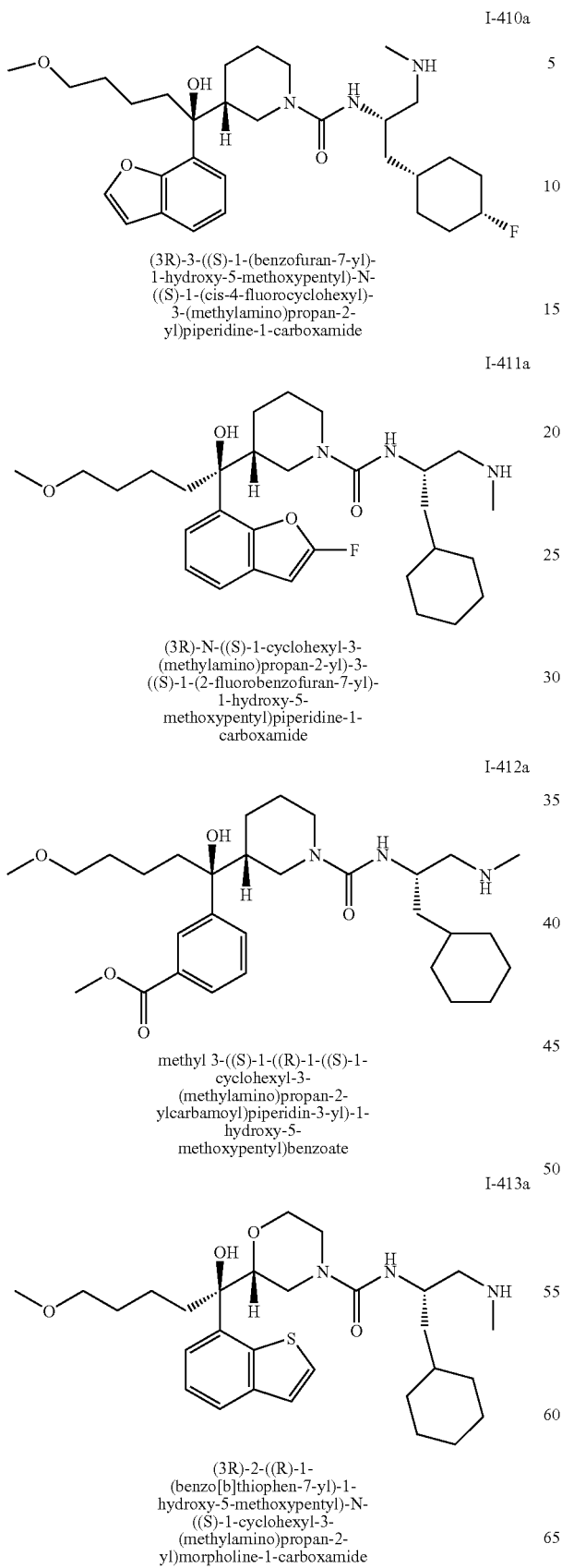

I-410a (3R)-3-((S)-1-(benzofuran-7-yl)-1-hydroxy-5-methoxypentyl)-N-((S)-1-(cis-4-fluorocyclohexyl)-3-(methylamino)propan-2-yl)piperidine-1-carboxamide I-411a (3R)-N-((S)-1-cyclohexyl-3-(methylamino)propan-2-yl)-3-((S)-1-(2-fluorobenzofuran-7-yl)-1-hydroxy-5-methoxypentyl)piperidine-1-carboxamide I-412a methyl 3-((S)-1-((R)-1-((S)-1-cyclohexyl-3-(methylamino)propan-2-ylcarbamoyl)piperidin-3-yl)-1-hydroxy-5-methoxypentyl)benzoate I-413a (3R)-2-((R)-1-(benzo[b]thiophen-7-yl)-1-hydroxy-5-methoxypentyl)-N-((S)-1-cyclohexyl-3-(methylamino)propan-2-yl)morpholine-1-carboxamide

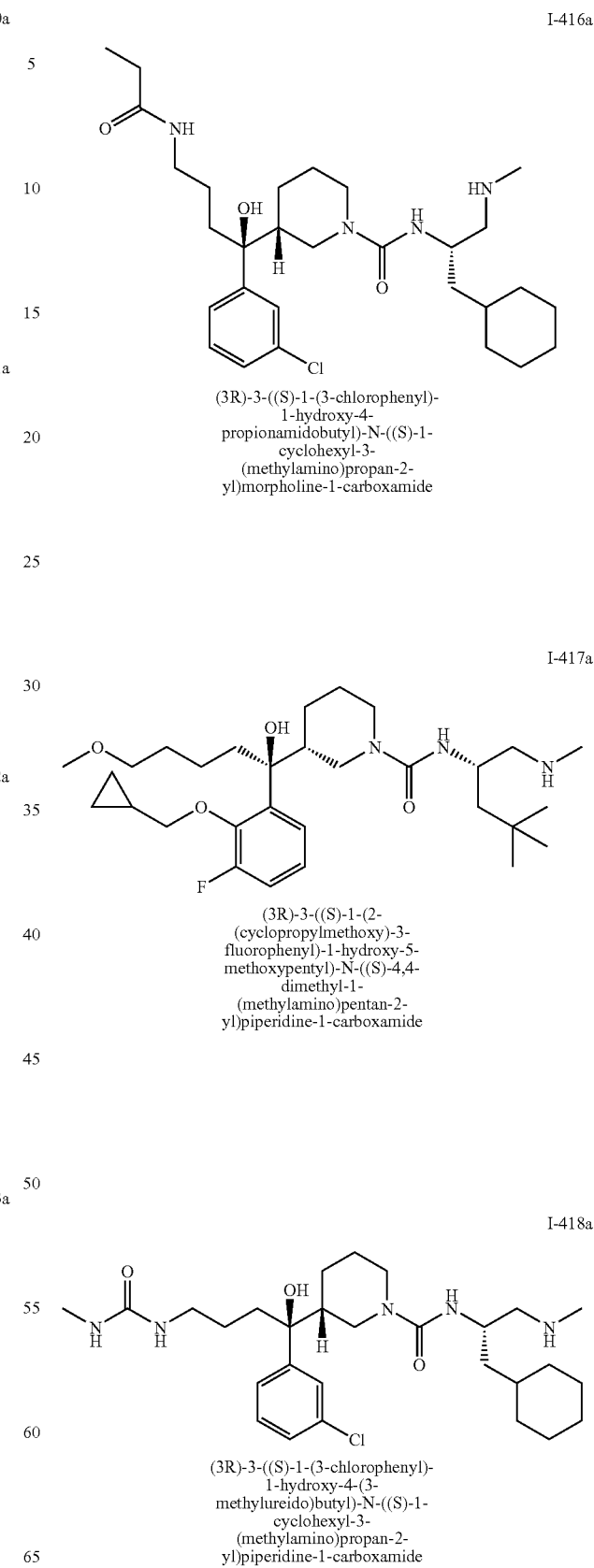

I-416a (3R)-3-((S)-1-(3-chlorophenyl)-1-hydroxy-4-propionamidobutyl)-N-((S)-1-cyclohexyl-3-(methylamino)propan-2-yl)morpholine-1-carboxamide I-417a (3R)-3-((S)-1-(2-(cyclopropylmethoxy)-3-fluorophenyl)-1-hydroxy-5-methoxypentyl)-N-((S)-4,4-dimethyl-1-(methylamino)pentan-2-yl)piperidine-1-carboxamide I-418a (3R)-3-((S)-1-(3-chlorophenyl)-1-hydroxy-4-(3-methylureido)butyl)-N-((S)-1-cyclohexyl-3-(methylamino)propan-2-yl)piperidine-1-carboxamide -continued I-421a

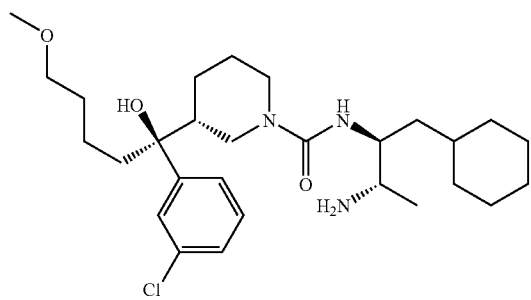

(3R)-N-((2S,3S)-3-amino-1-
cyclohexylbutan-2-yl)-3-((S)-1-
(3-chlorophenyl)-1-hydroxy-5-
methoxypentyl)piperidine-1-
carboxamide I-423a

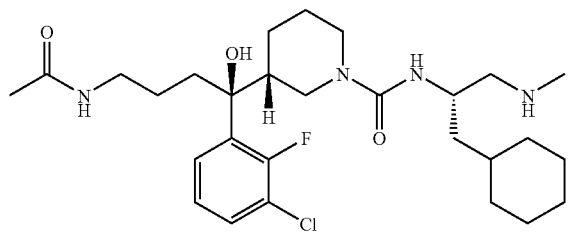

(3R)-3-((S)-4-acetamido-1-(3-
chloro-2-fluorophenyl)-1-
hydroxybutyl)-N-((S)-1-
cyclohexyl-3-
(methylamino)propan-2-
yl)piperidine-1-carboxamide I-424a

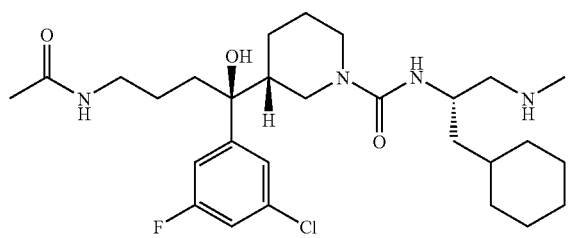

(3R)-3-((S)-4-acetamido-1-(3-
chloro-5-fluorophenyl)-1-
hydroxybutyl)-N-((S)-1-
cyclohexyl-3-
(methylamino)propan-2-
yl)piperidine-1-carboxamide I-425a

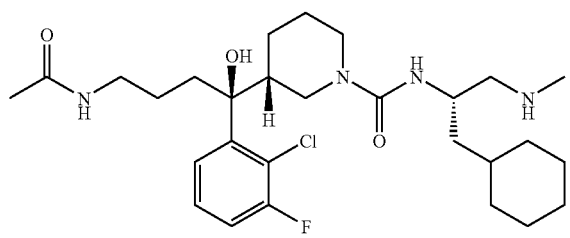

(3R)-3-((S)-4-acetamido-1-(2-
chloro-3-fluorophenyl)-1-
hydroxybutyl)-N-((S)-1-
cyclohexyl-3-
(methylamino)propan-2-
yl)piperidine-1-carboxamide -continued I-426a

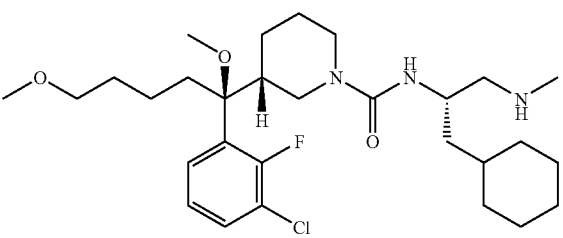

(3R)-3-((S)-1-(3-chloro-2-
fluorophenyl)-1,5-
dimethoxypentyl)-N-((S)-1-
cyclohexyl-3-
(methylamino)propan-2-
yl)piperidine-1-carboxamide I-427a

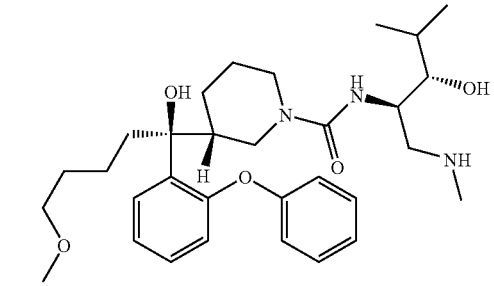

(3R)-N-((2R,3S)-3-hydroxy-4-
methyl-1-(methylamino)pentan-
2-yl)-3-((S)-1-hydroxy-5-
methoxy-1-(2-
phenoxyphenyl)pentyl)piperidin
e-1-carboxamide I-428a

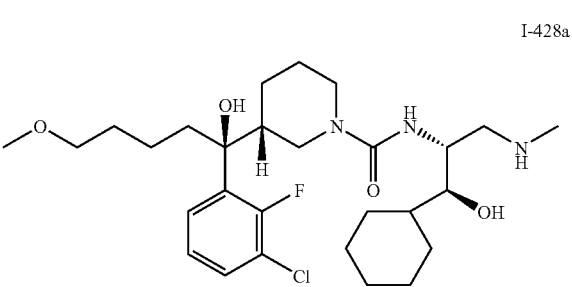

(3R)-3-((S)-1-(3-chloro-2-
fluorophenyl)-1-hydroxy-5-
methoxypentyl)-N-((1S,2R)-1-
cyclohexyl-1-hydroxy-3-
(methylamino)propan-2-
yl)piperidine-1-carboxamide I-429a

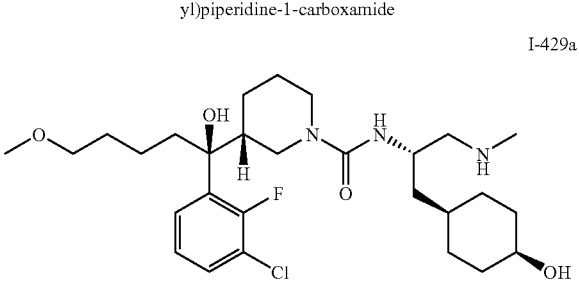

(3R)-3-((S)-1-(3-chloro-2-
fluorophenyl)-1-hydroxy-5-
methoxypentyl)-N-((S)-1-(cis-4-
hydroxycyclohexyl)-3-
(methylamino)propan-2-
yl)piperidine-1-carboxamide -continued I-429b

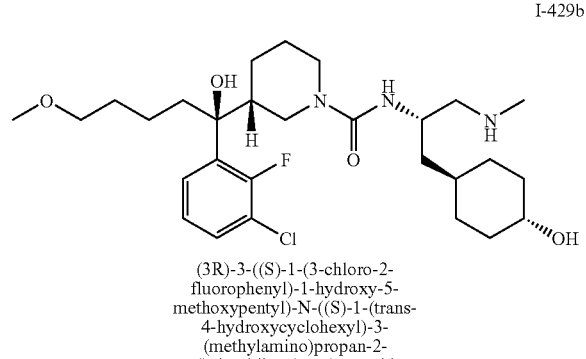

(3R)-3-((S)-1-(3-chloro-2-
fluorophenyl)-1-hydroxy-5-
methoxypentyl)-N-((S)-1-(trans-
4-hydroxycyclohexyl)-3-
(methylamino)propan-2-
yl)piperidine-1-carboxamide I-430a

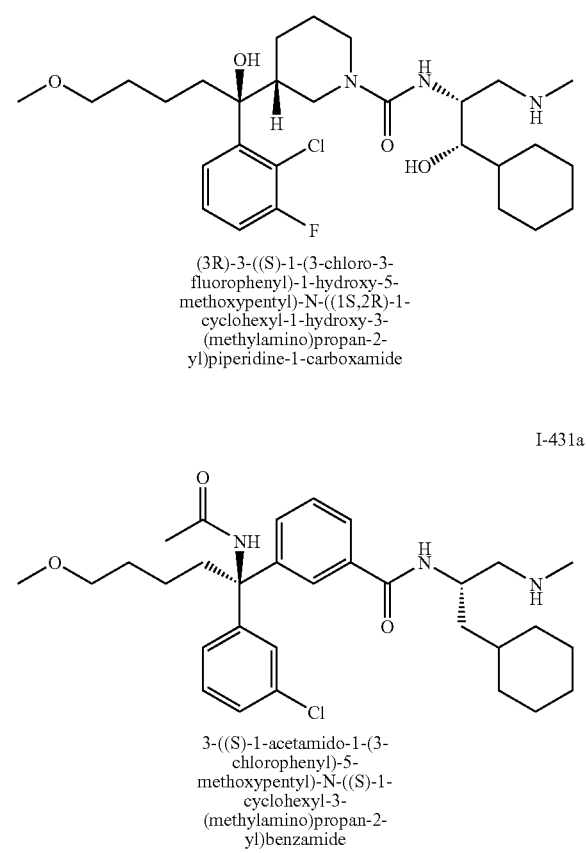

(3R)-3-((S)-1-(3-chloro-3-
fluorophenyl)-1-hydroxy-5-
methoxypentyl)-N-((1S,2R)-1-
cyclohexyl-1-hydroxy-3-
(methylamino)propan-2-
yl)piperidine-1-carboxamide I-431a 3-((S)-1-acetamido-1-(3-
chlorophenyl)-5-
methoxypentyl)-N-((S)-1-
cyclohexyl-3-
(methylamino)propan-2-
yl)benzamide I-432a

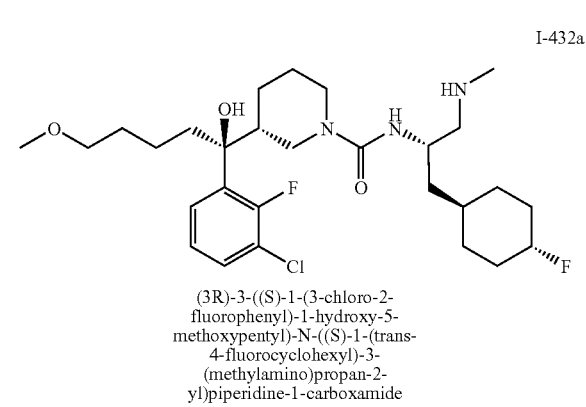

(3R)-3-((S)-1-(3-chloro-2-
fluorophenyl)-1-hydroxy-5-
methoxypentyl)-N-((S)-1-(trans-
4-fluorocyclohexyl)-3-
(methylamino)propan-2-
yl)piperidine-1-carboxamide -continued I-432b (3R)-3-((S)-1-(3-chloro-2-
fluorophenyl)-1-hydroxy-5-
methoxypentyl)-N-((S)-1-(cis-4-
fluorocyclohexyl)-3-
(methylamino)propan-2-
yl)piperidine-1-carboxamide I-433a (3R)-3-((S)-1-(3-chloro-2,4-
difluorophenyl)-1-hydroxy-5-
methoxypentyl)-N-((S)-1-
cyclohexyl-3-
(methylamino)propan-2-
yl)piperidine-1-carboxamide I-433b (3R)-3-((R)-1-(3-chloro-2,4-
difluorophenyl)-1-hydroxy-5-
methoxypentyl)-N-((S)-1-
cyclohexyl-3-
(methylamino)propan-2-
yl)piperidine-1-carboxamide I-434a (3R)-3-((S)-1-(3-chloro-2-
fluorophenyl)-1-hydroxy-5-
methoxypentyl)-N-((S)-1-(1-
fluorocyclohexyl)-3-
(methylamino)propan-2-
yl)piperidine-1-carboxamide I-435a

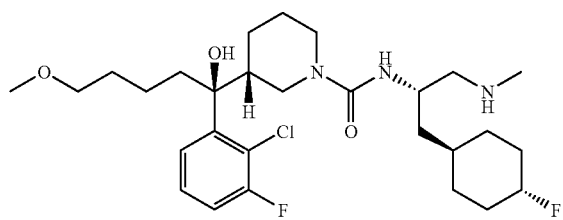

(3R)-3-((S)-1-(2-chloro-3-fluorophenyl)-1-hydroxy-5-methoxypentyl)-N-((S)-1-(trans-4-fluorocyclohexyl)-3-(methylamino)propan-2-yl)piperidine-1-carboxamide I-435b

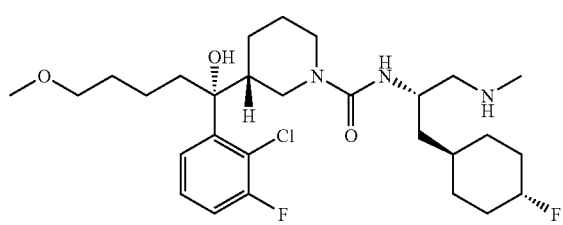

(3R)-3-((R)-1-(2-chloro-3-fluorophenyl)-1-hydroxy-5-methoxypentyl)-N-((S)-1-(trans-4-fluorocyclohexyl)-3-(methylamino)propan-2-yl)piperidine-1-carboxamide I-436a

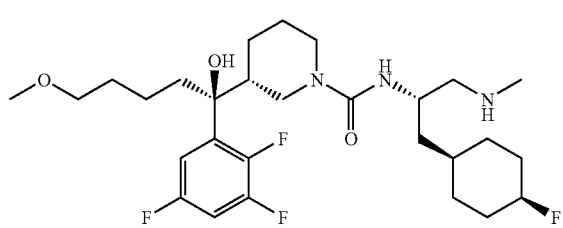

(3R)-N-((S)-1-(cis-4-fluorocyclohexyl)-3-(methylamino)propan-2-yl)-3-((S)-1-hydroxy-5-methoxy-1-(2,3,5-trifluorophenyl)pentyl)piperidine-1-carboxamide I-437a

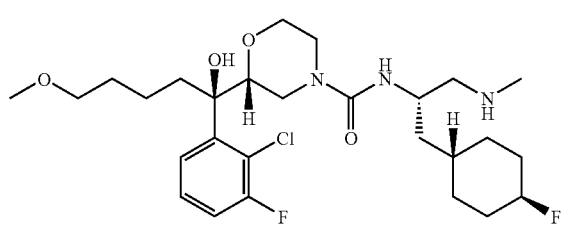

(3R)-2-((R)-1-(3-chloro-2-fluorophenyl)-1-hydroxy-5-methoxypentyl)-N-((S)-1-(trans-4-fluorocyclohexyl)-3-(methylamino)propan-2-yl)morpholine-1-carboxamide I-438a

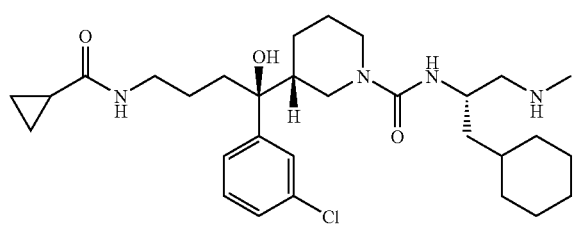

(3R)-3-((S)-1-(3-chlorophenyl)-4-(cyclopropanecarboxamido)-1-hydroxybutyl)-N-((S)-1-cyclohexyl-3-(methylamino)propan-2-yl)piperidine-1-carboxamide I-439a

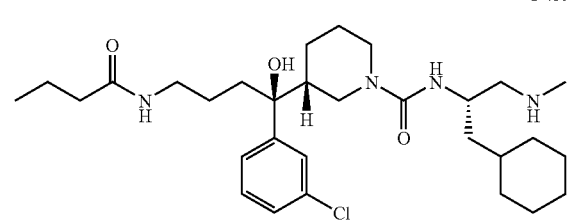

(3R)-3-((S)-4-butyramido-1-(3-chlorophenyl)-1-hydroxybutyl)-N-((S)-1-cyclohexyl-3-(methylamino)propan-2-yl)piperidine-1-carboxamide I-440a

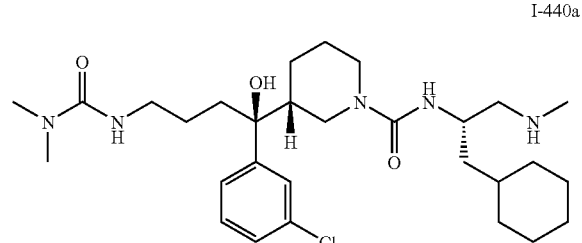

(3R)-3-((S)-1-(3-chlorophenyl)-4-(3,3-dimethylureido)-1-hydroxybutyl)-N-((S)-1-cyclohexyl-3-(methylamino)propan-2-yl)piperidine-1-carboxamide I-442a

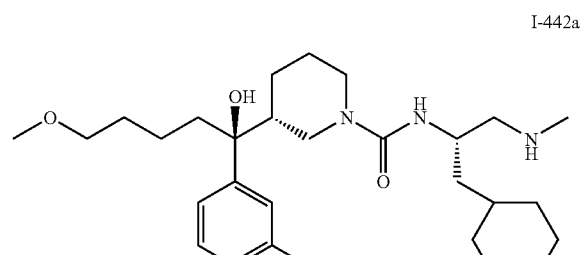

(3R)-3-((S)-1-(3-bromophenyl)-1-hydroxy-5-methoxypentyl)-N-((S)-1-cyclohexyl-3-(methylamino)propan-2-yl)piperidine-1-carboxamide -continued I-447a

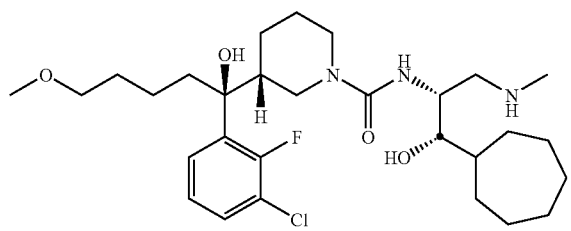

(3R)-3-((S)-1-(3-chloro-2-fluorophenyl)-1-hydroxy-5-methoxypentyl)-N-((1S,2R)-1-cycloheptyl-1-hydroxy-3-(methylamino)propan-2-yl)piperidine-1-carboxamide I-449a

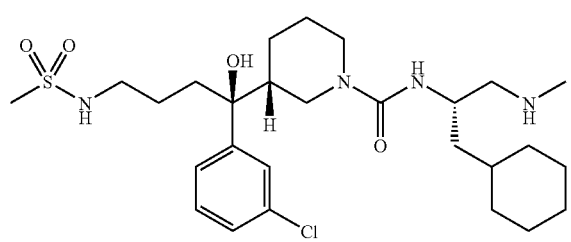

(3R)-3-((S)-1-(3-chlorophenyl)-1-hydroxy-4-(methylsulfonamido)butyl)-N-((S)-1-cyclohexyl-3-(methylamino)propan-2-yl)piperidine-1-carboxamide I-450a

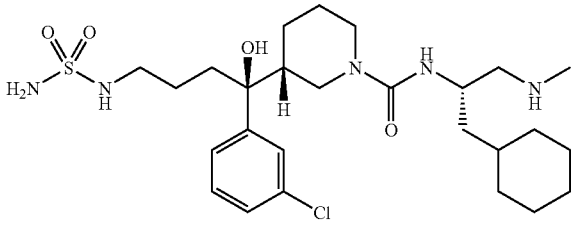

(3R)-3-((S)-1-(3-chlorophenyl)-1-hydroxy-4-(sulfamoylamino)butyl)-N-((S)-1-cyclohexyl-3-(methylamino)propan-2-yl)piperidine-1-carboxamide I-451a

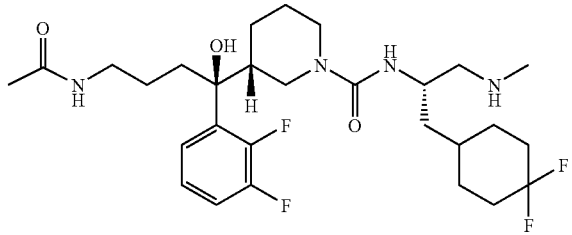

(3R)-3-((S)-4-acetamido-1-(2,3-difluorophenyl)-1-hydroxybutyl)-N-((S)-1-(4,4-difluorocyclohexyl)-3-(methylamino)propan-2-yl)piperidine-1-carboxamide -continued I-452a

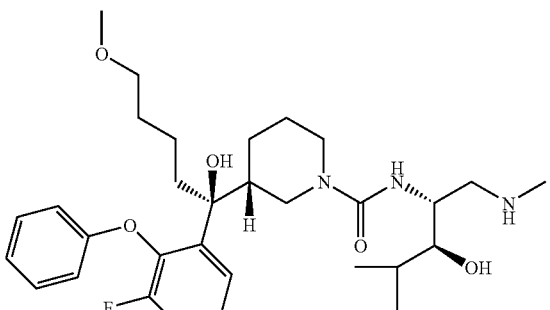

(3R)-3-((S)-1-(3-fluoro-2-phenoxyphenyl)-1-hydroxy-5-methoxypentyl)-N-((2R,3S)-3-hydroxy-4-methyl-1-(methylamino)pentan-2-yl)piperidine-1-carboxamide I-454a

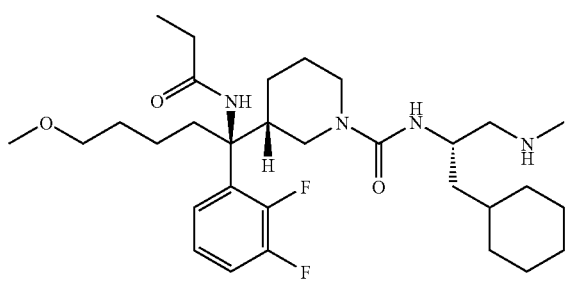

(3R)-N-((S)-1-cyclohexyl-3-(methylamino)propan-2-yl)-3-((S)-1-(2,3-difluorophenyl)-5-methoxy-1-propionamidopentyl)piperidine-1-carboxamide I-455a

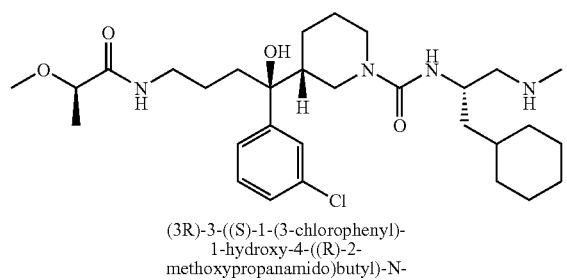

(3R)-3-((S)-1-(3-chlorophenyl)-1-hydroxy-4-((R)-2-methoxypropanamido)butyl)-N-((S)-1-cyclohexyl-3-(methylamino)propan-2-yl)piperidine-1-carboxamide I-455b

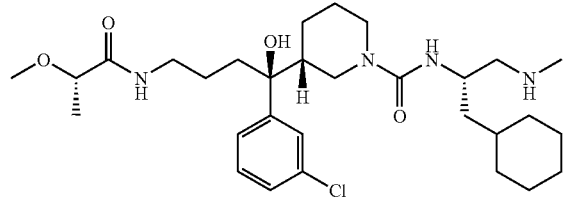

(3R)-3-((S)-1-(3-chlorophenyl)-1-hydroxy-4-((S)-2-methoxypropanamido)butyl)-N-((S)-1-cyclohexyl-3-(methylamino)propan-2-yl)piperidine-1-carboxamide -continued

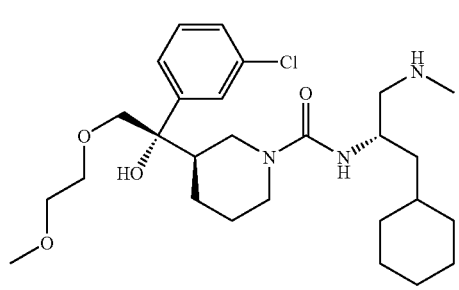

I-456a (3R)-3-((S)-1-(3-chlorophenyl)-
1-hydroxy-2-(2-
methoxyethoxy)ethyl)-N-((S)-1-
cyclohexyl-3-
(methylamino)propan-2-
yl)piperidine-1-carboxamide

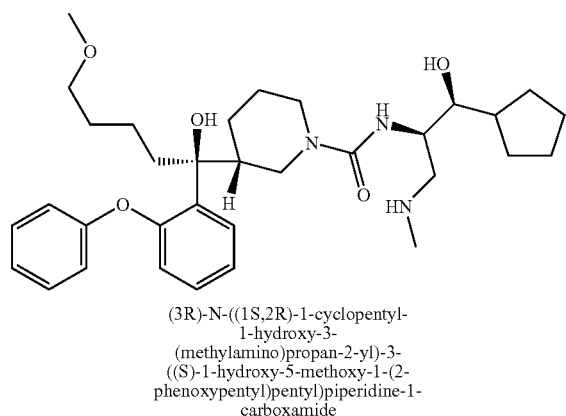

I-457a (3R)-N-((1S,2R)-1-cyclopentyl-
1-hydroxy-3-
(methylamino)propan-2-yl)-3-
((S)-1-hydroxy-5-methoxy-1-(2-
phenoxypentyl)pentyl)piperidine-1-
carboxamide I-458a 2-((R)-1-acetamido-1-(3-chloro-
2-fluorophenyl)-5-
methoxypentyl)-N-((S)-1-
cyclohexyl-3-
(methylamino)propan-2-
yl)morpholine-1-carboxamide I-459a (3R)-3-((S)-1-(2-bromo-5-
fluorophenyl)-1-hydroxy-5-
methoxypentyl)-N-((S)-1-
cyclohexyl-3-
(methylamino)propan-2-
yl)piperidine-1-carboxamide -continued

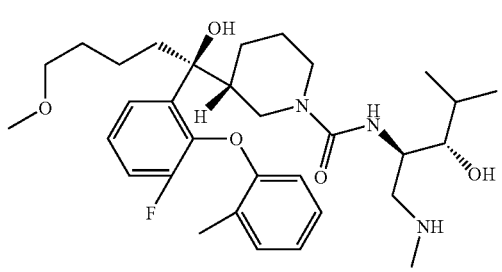

I-463a (3R)-3-((S)-1-(3-fluoro-2-(o-
tolyloxy)phenyl)-1-hydroxy-5-
methoxypentyl)-N-((2R,3S)-3-
hydroxy-4-methyl-1-
(methylamino)pentan-2-
yl)piperidine-1-carboxamide

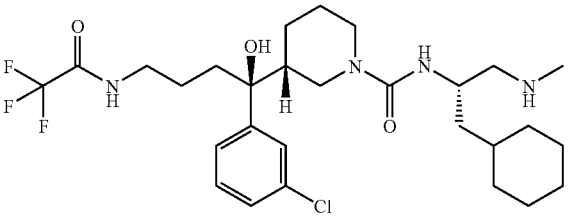

I-464a (3R)-3-((S)-1-(3-chlorophenyl)-
1-hydroxy-4-(2,2,2-
trifluoroacetamido)butyl)-N-((S)-
1-cyclohexyl-3-
(methylamino)propan-2-
yl)piperidine-1-carboxamide

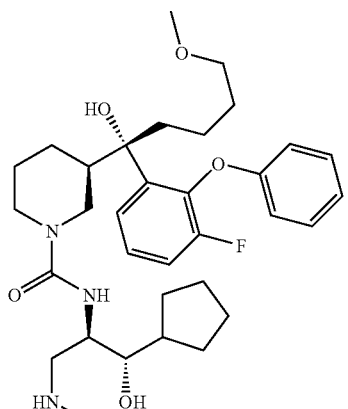

I-466a (3R)-N-((1S,2R)-1-cyclopentyl-
1-hydroxy-3-
(methylamino)propan-2-yl)-3-
((S)-1-(3-fluoro-2-
phenoxyphenyl)-1-hydroxy-5-
methoxypentyl)piperidine-1-
carboxamide -continued I-467a

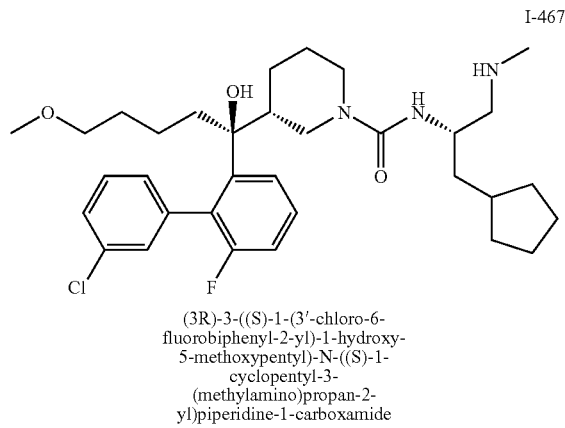

(3R)-3-((S)-1-(3'-chloro-6-fluorobiphenyl-2-yl)-1-hydroxy-5-methoxypentyl)-N-((S)-1-cyclopentyl-3-(methylamino)propan-2-yl)piperidine-1-carboxamide I-468a

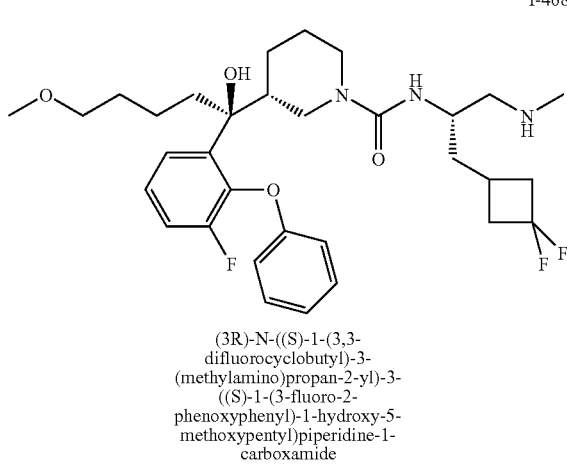

(3R)-N-((S)-1-(3,3-difluorocyclobutyl)-3-(methylamino)propan-2-yl)-3-((S)-1-(3-fluoro-2-phenoxyphenyl)-1-hydroxy-5-methoxypentyl)piperidine-1-carboxamide I-469a

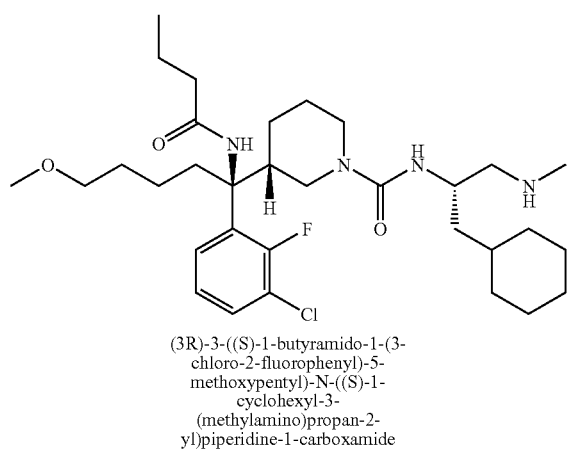

(3R)-3-((S)-1-butyramido-1-(3-chloro-2-fluorophenyl)-5-methoxypentyl)-N-((S)-1-cyclohexyl-3-(methylamino)propan-2-yl)piperidine-1-carboxamide -continued I-470a

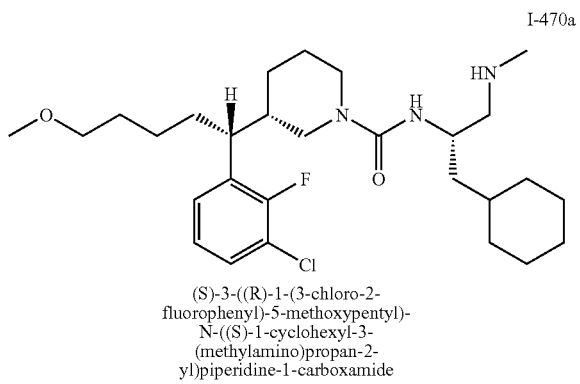

(S)-3-((R)-1-(3-chloro-2-fluorophenyl)-5-methoxypentyl)-N-((S)-1-cyclohexyl-3-(methylamino)propan-2-yl)piperidine-1-carboxamide I-471a

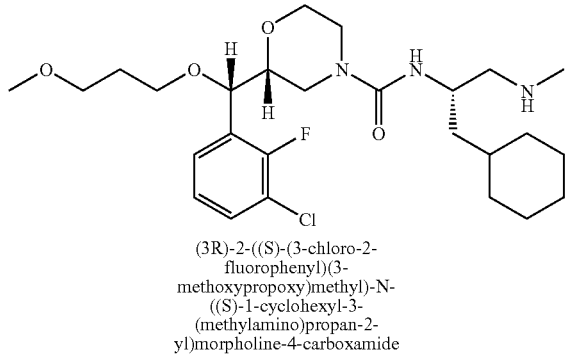

(3R)-2-((S)-(3-chloro-2-fluorophenyl)(3-methoxypropoxy)methyl)-N-((S)-1-cyclohexyl-3-(methylamino)propan-2-yl)morpholine-4-carboxamide I-472a

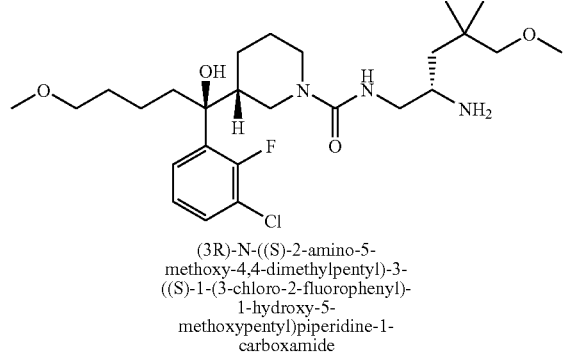

(3R)-N-((S)-2-amino-5-methoxy-4,4-dimethylpentyl)-3-((S)-1-(3-chloro-2-fluorophenyl)-1-hydroxy-5-methoxypentyl)piperidine-1-carboxamide I-473a

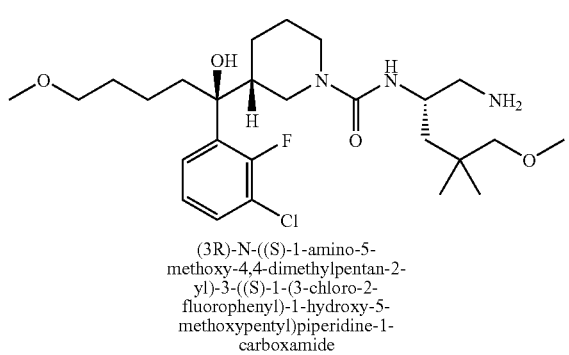

(3R)-N-((S)-1-amino-5-methoxy-4,4-dimethylpentan-2-yl)-3-((S)-1-(3-chloro-2-fluorophenyl)-1-hydroxy-5-methoxypentyl)piperidine-1-carboxamide -continued I-474a

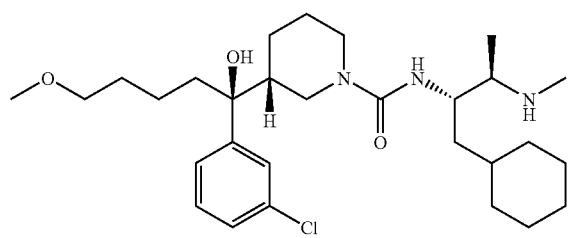

(3R)-3-((S)-1-(3-chlorophenyl)-
1-hydroxy-5-methoxypentyl)-N-
((2S,3R)-1-cyclohexyl-3-
(methylamino)butan-2-
yl)piperidine-1-carboxamide I-475a

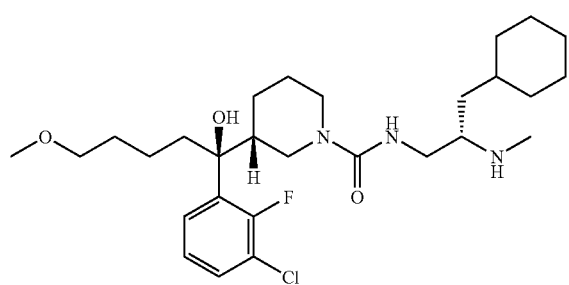

(3R)-3-((S)-1-(3-chloro-2-
fluorophenyl)-1-hydroxy-5-
methoxypentyl)-N-((S)-3-
cyclohexyl-2-
(methylamino)propyl)piperidine-
1-carboxamide I-476a

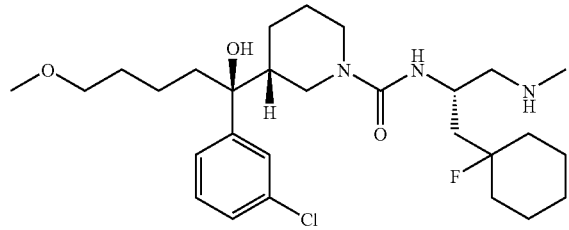

(3R)-3-((S)-1-(3-chlorophenyl)-
1-hydroxy-5-methoxypentyl)-N-
((S)-1-(1-fluorocyclohexyl)-3-
(methylamino)propan-2-
yl)piperidine-1-carboxamide I-476b

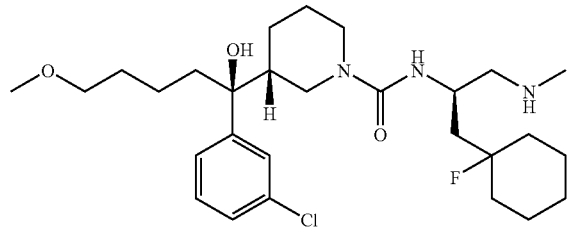

(3R)-3-((S)-1-(3-chlorophenyl)-
1-hydroxy-5-methoxypentyl)-N-
((R)-1-(1-fluorocyclohexyl)-3-
(methylamino)propan-2-
yl)piperidine-1-carboxamide -continued I-477a

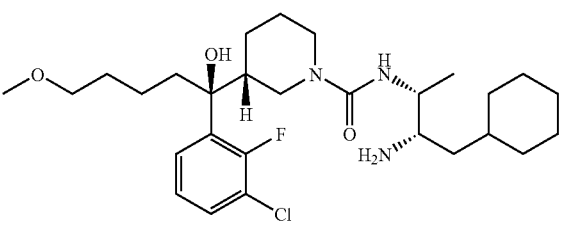

(3R)-N-((2R,3S)-3-amino-4-
cyclohexylbutan-2-yl)-3-((S)-1-
(3-chloro-2-fluorophenyl)-1-
hydroxy-5-
methoxypentyl)piperidine-1-
carboxamide I-477b

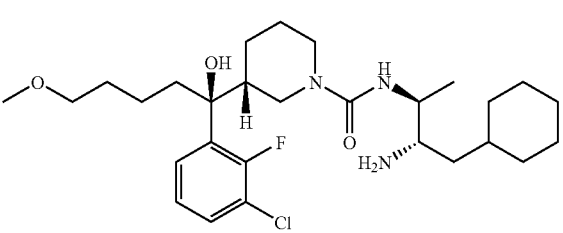

(3R)-N-((2S,3S)-3-amino-4-
cyclohexylbutan-2-yl)-3-((S)-1-
(3-chloro-2-fluorophenyl)-1-
hydroxy-5-
methoxypentyl)piperidine-1-
carboxamide I-478a

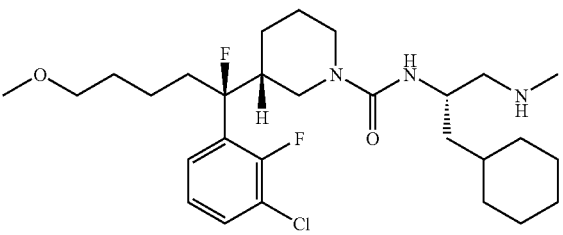

(3R)-3-((S)-1-(3-chloro-2-
fluorophenyl)-1-fluoro-5-
methoxypentyl)-N-((S)-1-
cyclohexyl-3-
(methylamino)propan-2-
yl)piperidine-1-carboxamide I-479a

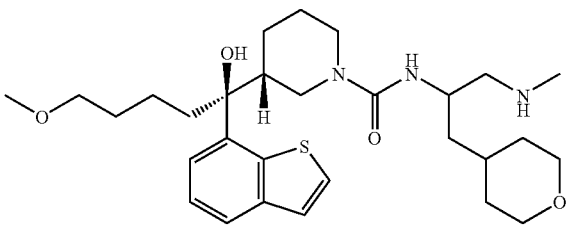

(3R)-3-((S)-1-
(benzo[b]thiopen-7-yl)-1-
hydroxy-5-methoxypentyl)-N-
((S)-1-(methylamino)-3-
(tetrahydro-2H-pyran-4-
yl)propan-2-yl)piperidine-1-
carboxamide I-480a

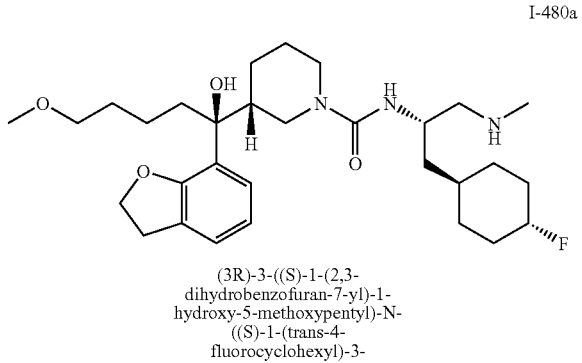

(3R)-3-((S)-1-(2,3-dihydrobenzofuran-7-yl)-1-hydroxy-5-methoxypentyl)-N-((S)-1-(trans-4-fluorocyclohexyl)-3-(methylamino)propan-2-yl)piperidine-1-carboxamide I-481a

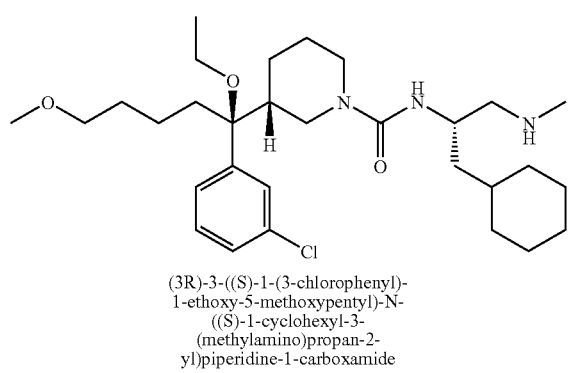

(3R)-3-((S)-1-(3-chlorophenyl)-1-ethoxy-5-methoxypentyl)-N-((S)-1-cyclohexyl-3-(methylamino)propan-2-yl)piperidine-1-carboxamide I-482a

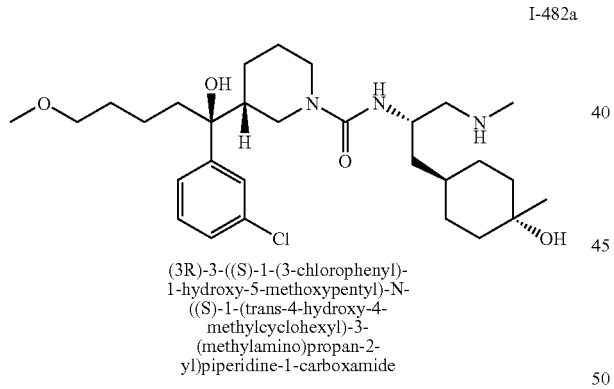

(3R)-3-((S)-1-(3-chlorophenyl)-1-hydroxy-5-methoxypentyl)-N-((S)-1-(trans-4-hydroxy-4-methylcyclohexyl)-3-(methylamino)propan-2-yl)piperidine-1-carboxamide I-483a

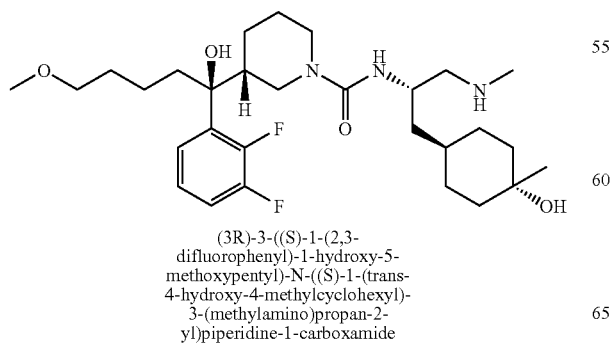

(3R)-3-((S)-1-(2,3-difluorophenyl)-1-hydroxy-5-methoxypentyl)-N-((S)-1-(trans-4-hydroxy-4-methylcyclohexyl)-3-(methylamino)propan-2-yl)piperidine-1-carboxamide I-484a

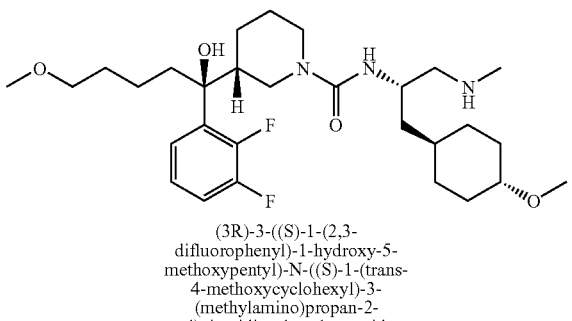

(3R)-3-((S)-1-(2,3-difluorophenyl)-1-hydroxy-5-methoxypentyl)-N-((S)-1-(trans-4-methoxycyclohexyl)-3-(methylamino)propan-2-yl)piperidine-1-carboxamide I-484b

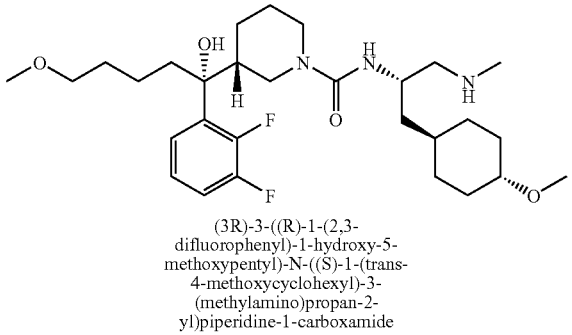

(3R)-3-((R)-1-(2,3-difluorophenyl)-1-hydroxy-5-methoxypentyl)-N-((S)-1-(trans-4-methoxycyclohexyl)-3-(methylamino)propan-2-yl)piperidine-1-carboxamide I-485a

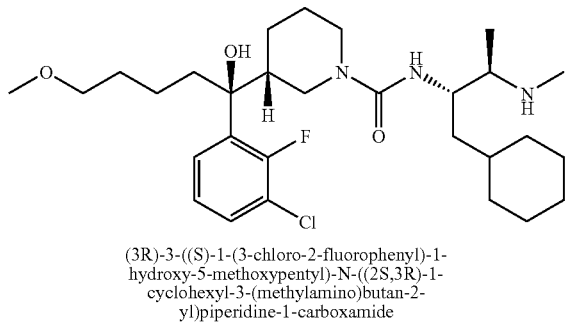

(3R)-3-((S)-1-(3-chloro-2-fluorophenyl)-1-hydroxy-5-methoxypentyl)-N-((2S,3R)-1-cyclohexyl-3-(methylamino)butan-2-yl)piperidine-1-carboxamide I-485b

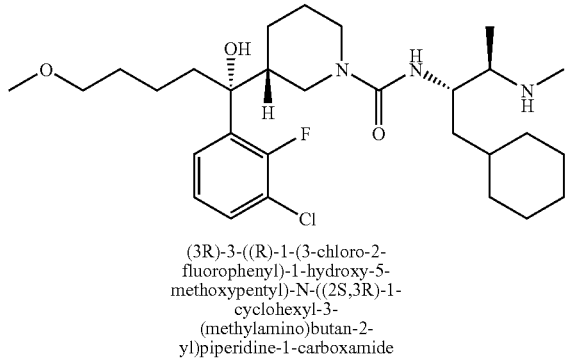

(3R)-3-((R)-1-(3-chloro-2-fluorophenyl)-1-hydroxy-5-methoxypentyl)-N-((2S,3R)-1-cyclohexyl-3-(methylamino)butan-2-yl)piperidine-1-carboxamide -continued

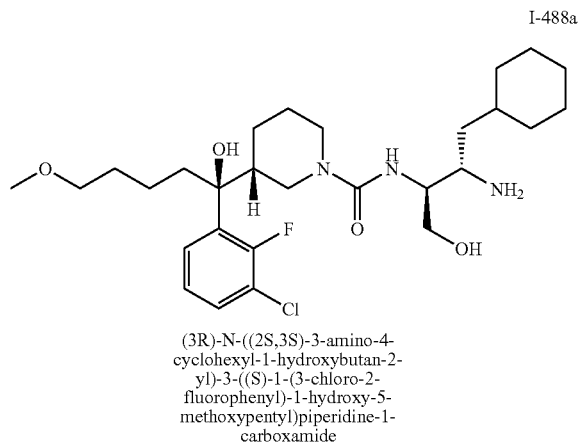

I-488a (3R)-N-((2S,3S)-3-amino-4-
cyclohexyl-1-hydroxybutan-2-
yl)-3-((S)-1-(3-chloro-2-
fluorophenyl)-1-hydroxy-5-
methoxypentyl)piperidine-1-
carboxamide

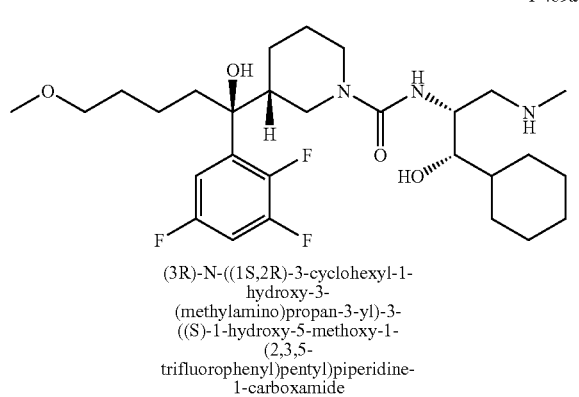

I-489a (3R)-N-((1S,2R)-3-cyclohexyl-1-
hydroxy-3-
(methylamino)propan-3-yl)-3-
((S)-1-hydroxy-5-methoxy-1-
(2,3,5-
trifluorophenyl)pentyl)piperidine-
1-carboxamide

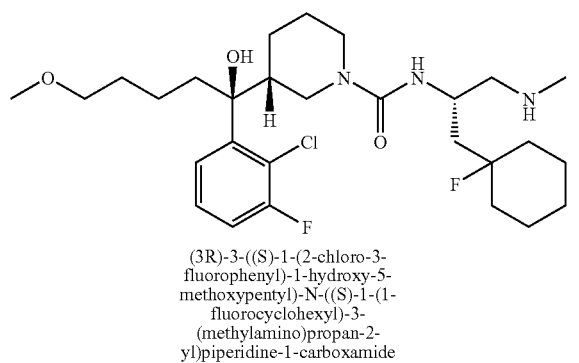

I-490a (3R)-3-((S)-1-(2-chloro-3-
fluorophenyl)-1-hydroxy-5-
methoxypentyl)-N-((S)-1-(1-
fluorocyclohexyl)-3-
(methylamino)propan-2-
yl)piperidine-1-carboxamide

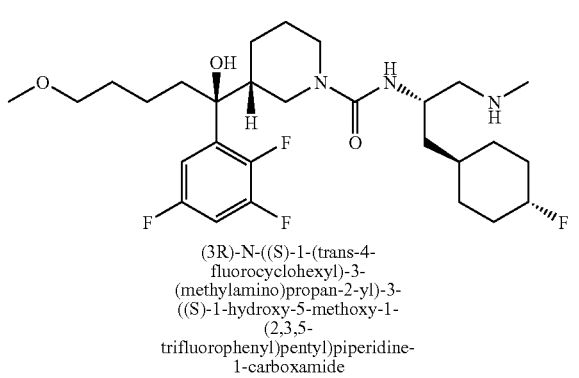

I-491a (3R)-N-((S)-1-(trans-4-
fluorocyclohexyl)-3-
(methylamino)propan-2-yl)-3-
((S)-1-hydroxy-5-methoxy-1-
(2,3,5-
trifluorophenyl)pentyl)piperidine-
1-carboxamide -continued

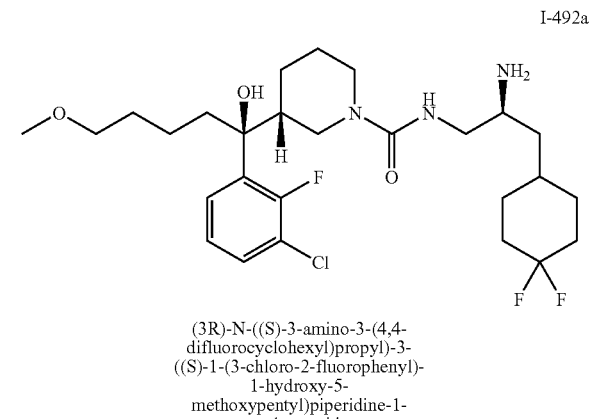

I-492a (3R)-N-((S)-3-amino-3-(4,4-
difluorocyclohexyl)propyl)-3-
((S)-1-(3-chloro-2-fluorophenyl)-
1-hydroxy-5-
methoxypentyl)piperidine-1-
carboxamide

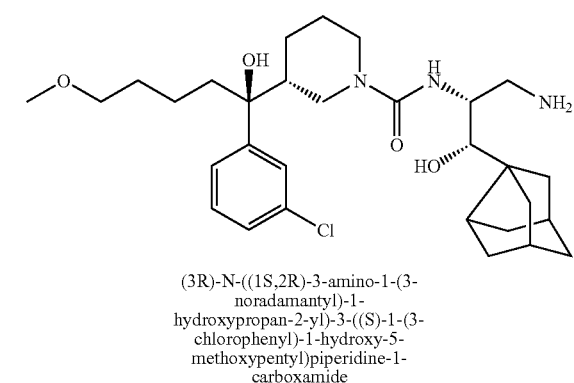

I-493a (3R)-N-((1S,2R)-3-amino-1-(3-
noradamantyl)-1-
hydroxypropan-2-yl)-3-((S)-1-(3-
chlorophenyl)-1-hydroxy-5-
methoxypentyl)piperidine-1-
carboxamide

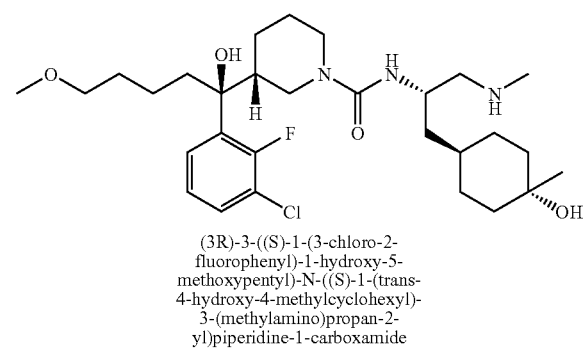

I-495a (3R)-3-((S)-1-(3-chloro-2-
fluorophenyl)-1-hydroxy-5-
methoxypentyl)-N-((S)-1-(trans-
4-hydroxy-4-methylcyclohexyl)-
3-(methylamino)propan-2-
yl)piperidine-1-carboxamide

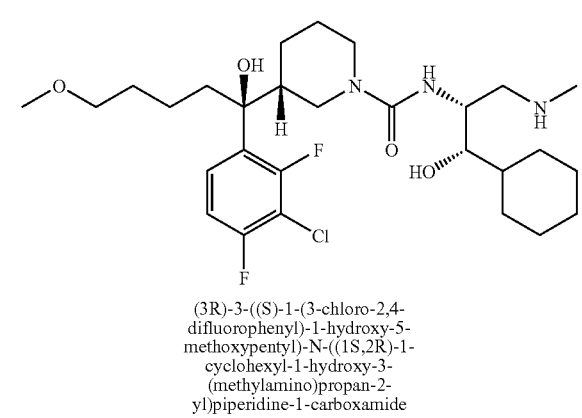

I-497a (3R)-3-((S)-1-(3-chloro-2,4-
difluorophenyl)-1-hydroxy-5-
methoxypentyl)-N-((1S,2R)-1-
cyclohexyl-1-hydroxy-3-
(methylamino)propan-2-
yl)piperidine-1-carboxamide

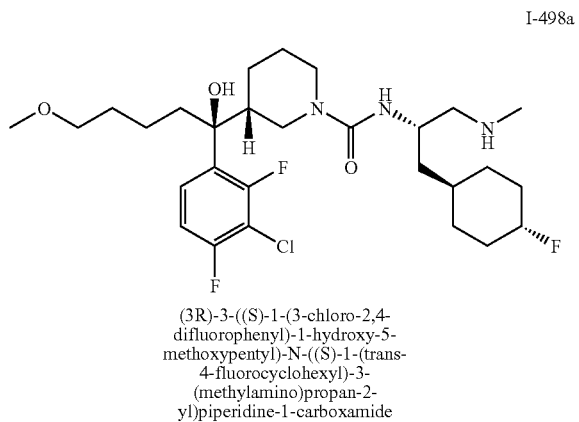

I-498a (3R)-3-((S)-1-(3-chloro-2,4-
difluorophenyl)-1-hydroxy-5-
methoxypentyl)-N-((S)-1-(trans-
4-fluorocyclohexyl)-3-
(methylamino)propan-2-
yl)piperidine-1-carboxamide

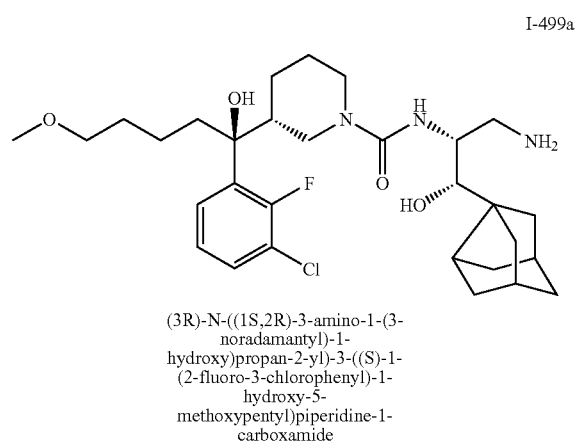

I-499a (3R)-N-((1S,2R)-3-amino-1-(3-
noradamantyl)-1-
hydroxy)propan-2-yl)-3-((S)-1-
(2-fluoro-3-chlorophenyl)-1-
hydroxy-5-
methoxypentyl)piperidine-1-
carboxamide

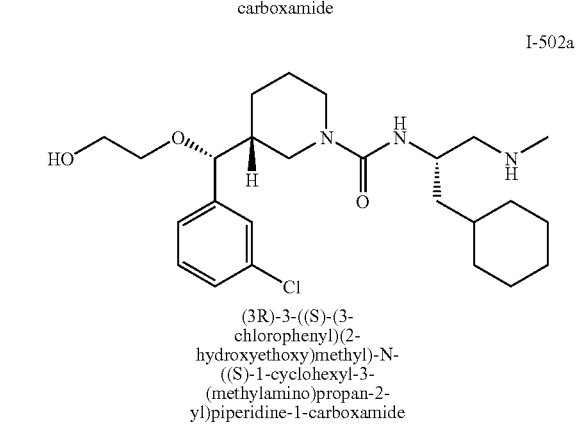

I-502a (3R)-3-((S)-(3-
chlorophenyl)(2-
hydroxyethoxy)methyl)-N-
((S)-1-cyclohexyl-3-
(methylamino)propan-2-
yl)piperidine-1-carboxamide

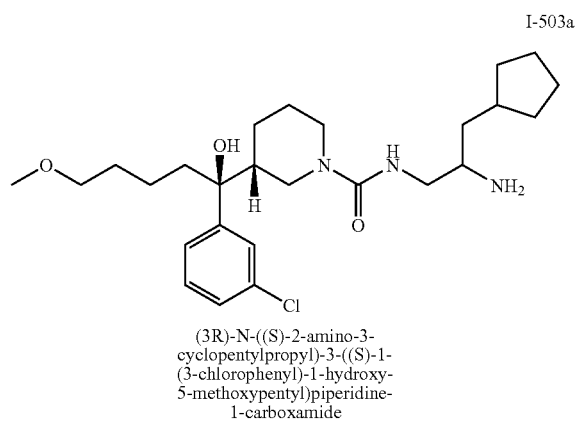

I-503a (3R)-N-((S)-2-amino-3-
cyclopentylpropyl)-3-((S)-1-
(3-chlorophenyl)-1-hydroxy-
5-methoxypentyl)piperidine-
1-carboxamide

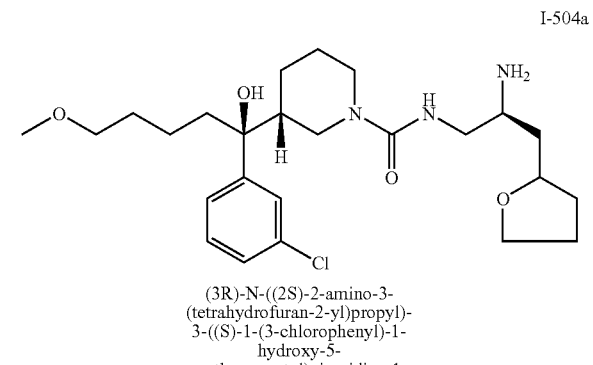

I-504a (3R)-N-((2S)-2-amino-3-
(tetrahydrofuran-2-yl)propyl)-
3-((S)-1-(3-chlorophenyl)-1-
hydroxy-5-
methoxypentyl)piperidine-1-
carboxamide

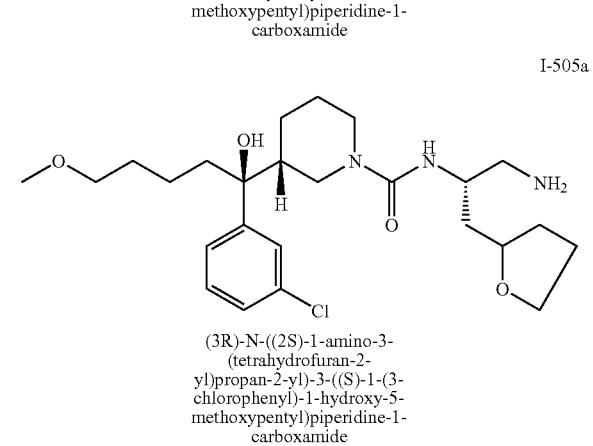

I-505a (3R)-N-((2S)-1-amino-3-
(tetrahydrofuran-2-
yl)propan-2-yl)-3-((S)-1-(3-
chlorophenyl)-1-hydroxy-5-
methoxypentyl)piperidine-1-
carboxamide

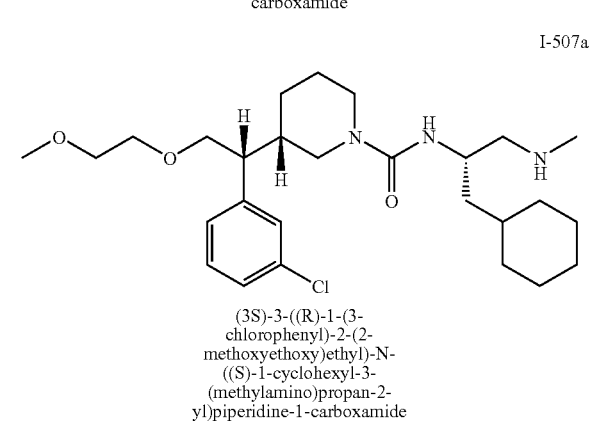

I-507a (3S)-3-((R)-1-(3-
chlorophenyl)-2-(2-
methoxyethoxy)ethyl)-N-
((S)-1-cyclohexyl-3-
(methylamino)propan-2-
yl)piperidine-1-carboxamide

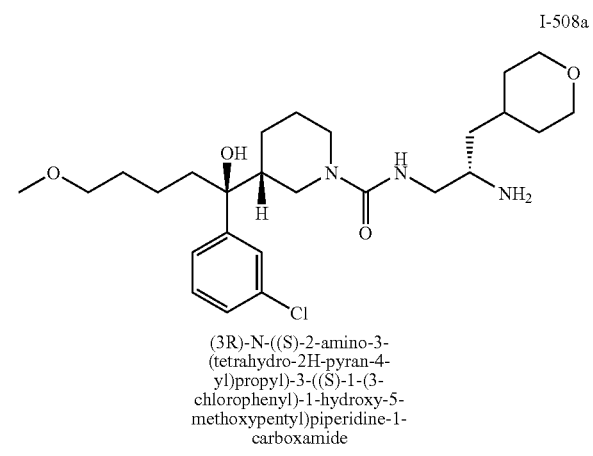

I-508a (3R)-N-((S)-2-amino-3-
(tetrahydro-2H-pyran-4-
yl)propyl)-3-((S)-1-(3-
chlorophenyl)-1-hydroxy-5-
methoxypentyl)piperidine-1-
carboxamide I-509a

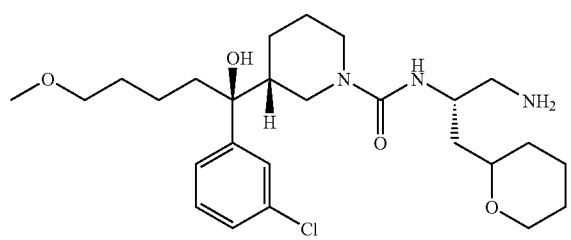

(3R)-N-((2S)-1-amino-3-
(tetrahydro-2H-pyran-2-
yl)propan-2-yl)-3-((S)-1-(3-
chlorophenyl)-1-hydroxy-5-
methoxypentyl)piperidine-1-
carboxamide I-510a

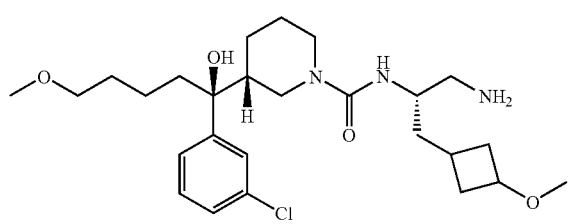

(3R)-N-((S)-1-amino-3-(3-
methoxycyclobutyl)propan-
2-yl)-3-((S)-1-(3-
chlorophenyl)-1-hydroxy-5-
methoxypentyl)piperidine-1-
carboxamide I-511a

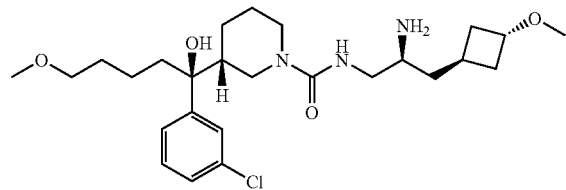

(3R)-N-((S)-2-amino-3-
(trans-3-
methoxycyclobutyl)propyl)-3-
((S)-1-(3-chlorophenyl)-1-
hydroxy-5-
methoxypentyl)piperidine-1-
carboxamide I-511b

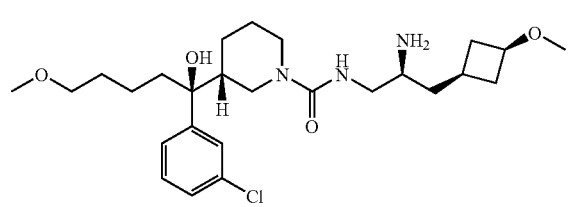

(3R)-N-((S)-2-amino-3-(cis-
3-methoxycyclobutyl)propyl)-
3-((S)-1-(3-chlorophenyl)-1-
hydroxy-5-
methoxypentyl)piperidine-1-
carboxamide I-512a

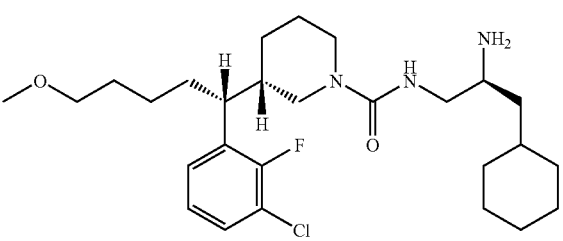

(S)-N-((S)-2-amino-3-
cyclohexylpropyl)-3-((R)-1-
(3-chloro-2-fluorophenyl)-5-
methoxypentyl)piperidine-1-
carboxamide I-512b

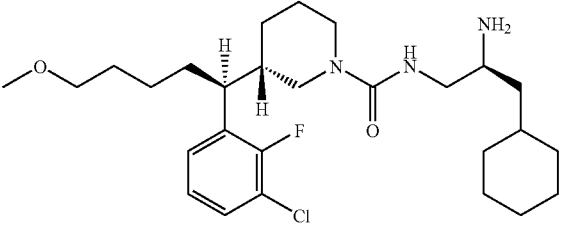

(S)-N-((S)-2-amino-3-
cyclohexylpropyl)-3-((S)-1-
(3-chloro-2-fluorophenyl)-5-
methoxypentyl)piperidine-1-
carboxamide I-513a

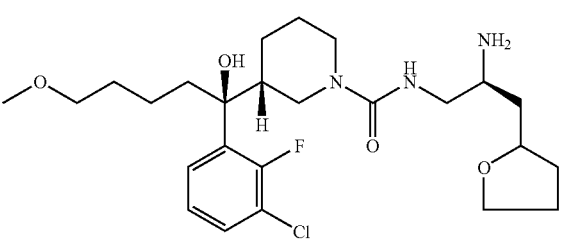

(3R)-N-((2S)-2-amino-3-
tetrahydrofuran-2-yl)propyl)-
3-((S)-1-(3-chloro-2-
fluorophenyl)-1-hydroxy-5-
methoxypentyl)piperidine-1-
carboxamide I-514a

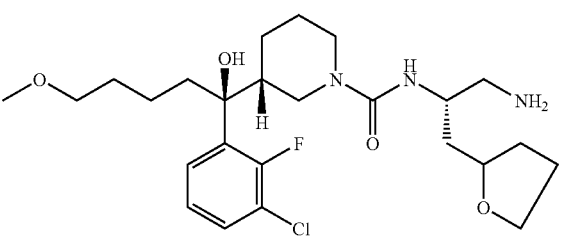

(3R)-N-((2S)-1-amino-3-
(tetrahydrofuran-2-
yl)propan-2-yl)-3-((S)-1-(3-
chloro-2-fluorophenyl)-1-
hydroxy-5-
methoxypentyl)piperidine-1-
carboxamide I-515a

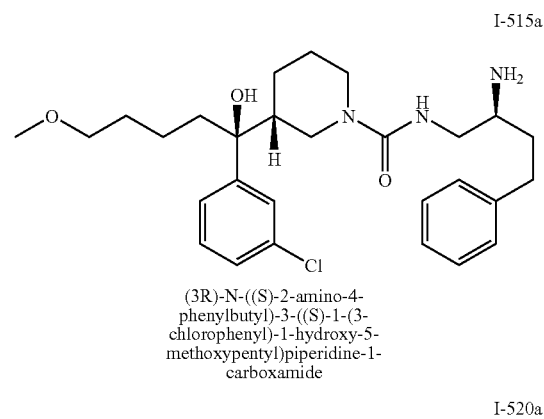

(3R)-N-((S)-2-amino-4-
phenylbutyl)-3-((S)-1-(3-
chlorophenyl)-1-hydroxy-5-
methoxypentyl)piperidine-1-
carboxamide I-520a

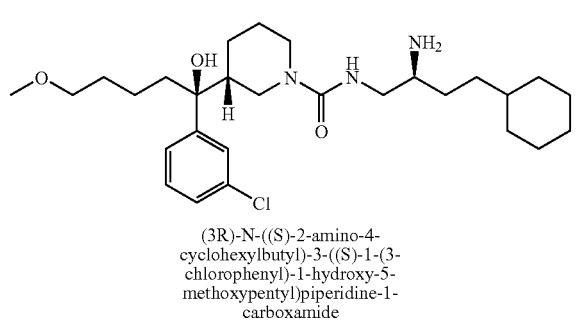

(3R)-N-((S)-2-amino-4-
cyclohexylbutyl)-3-((S)-1-(3-
chlorophenyl)-1-hydroxy-5-
methoxypentyl)piperidine-1-
carboxamide I-522a

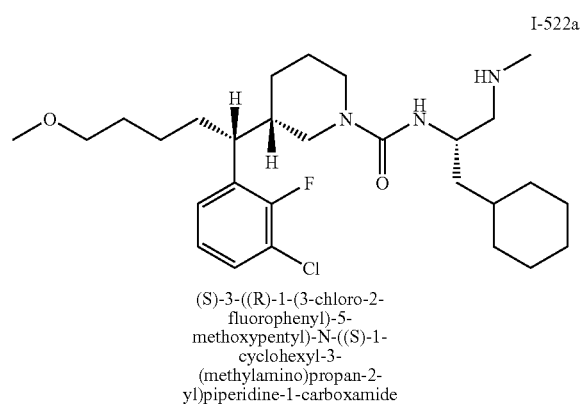

(S)-3-((R)-1-(3-chloro-2-
fluorophenyl)-5-
methoxypentyl)-N-((S)-1-
cyclohexyl-3-
(methylamino)propan-2-
yl)piperidine-1-carboxamide I-522b

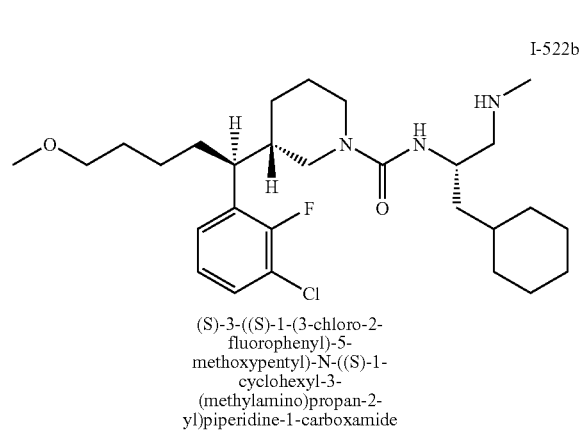

(S)-3-((S)-1-(3-chloro-2-
fluorophenyl)-5-
methoxypentyl)-N-((S)-1-
cyclohexyl-3-
(methylamino)propan-2-
yl)piperidine-1-carboxamide I-523a

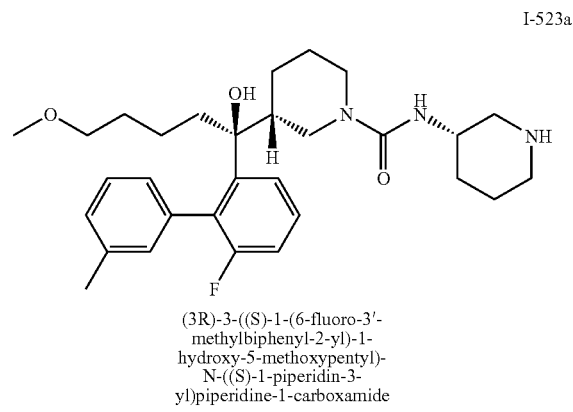

(3R)-3-((S)-1-(6-fluoro-3'-
methylbiphenyl-2-yl)-1-
hydroxy-5-methoxypentyl)-
N-((S)-1-piperidin-3-
yl)piperidine-1-carboxamide I-524a

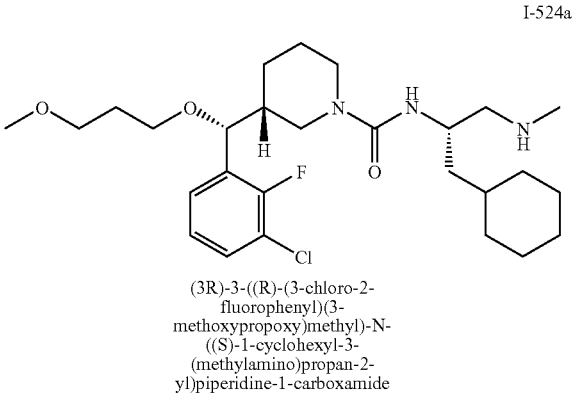

(3R)-3-((R)-(3-chloro-2-
fluorophenyl)(3-
methoxypropoxy)methyl)-N-
((S)-1-cyclohexyl-3-
(methylamino)propan-2-
yl)piperidine-1-carboxamide I-525a

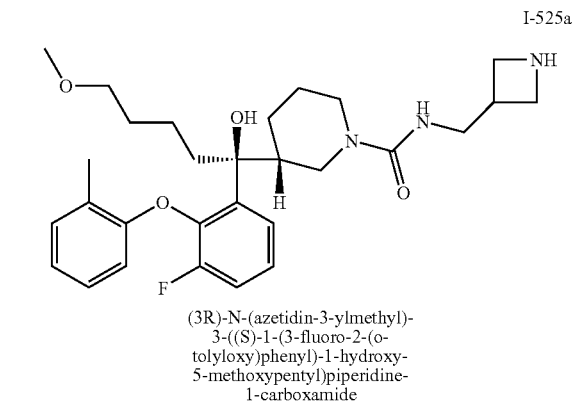

(3R)-N-(azetidin-3-ylmethyl)-
3-((S)-1-(3-fluoro-2-(o-
tolyloxy)phenyl)-1-hydroxy-
5-methoxypentyl)piperidine-
1-carboxamide I-526a

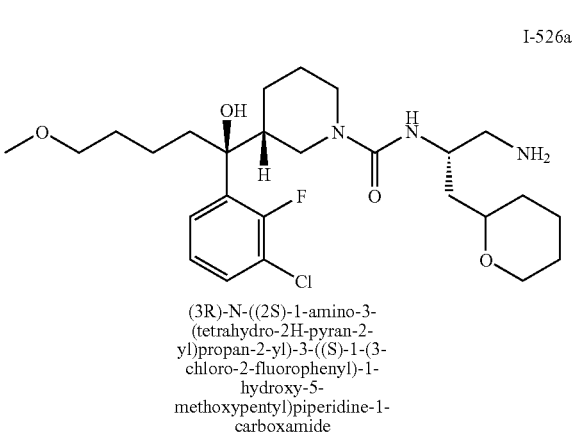

(3R)-N-((2S)-1-amino-3-
(tetrahydro-2H-pyran-2-
yl)propan-2-yl)-3-((S)-1-(3-
chloro-2-fluorophenyl)-1-
hydroxy-5-
methoxypentyl)piperidine-1-
carboxamide -continued I-527a

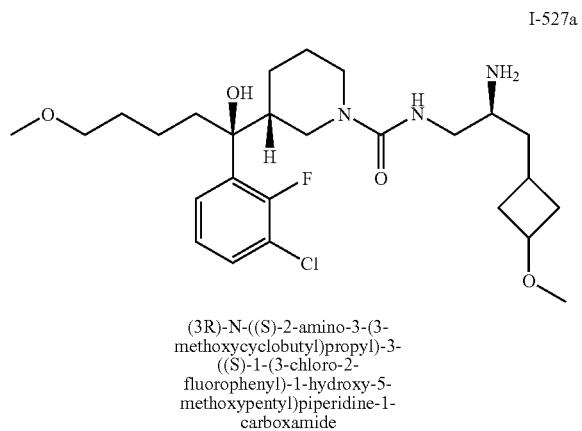

(3R)-N-((S)-2-amino-3-(3-methoxycyclobutyl)propyl)-3-((S)-1-(3-chloro-2-fluorophenyl)-1-hydroxy-5-methoxypentyl)piperidine-1-carboxamide I-528a

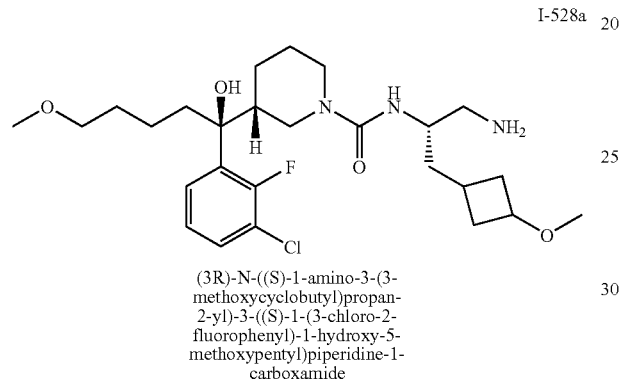

(3R)-N-((S)-1-amino-3-(3-methoxycyclobutyl)propan-2-yl)-3-((S)-1-(3-chloro-2-fluorophenyl)-1-hydroxy-5-methoxypentyl)piperidine-1-carboxamide I-531a

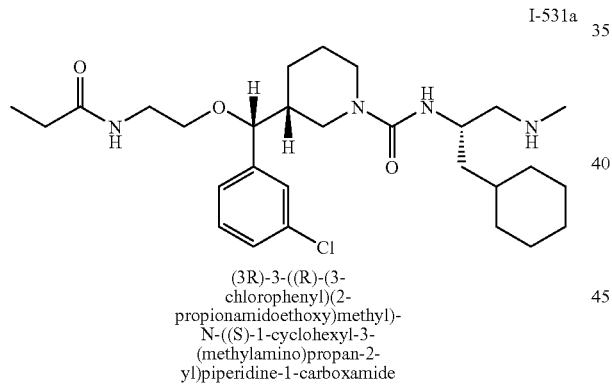

(3R)-3-((R)-(3-chlorophenyl)(2-propionamidoethoxy)methyl)-N-((S)-1-cyclohexyl-3-(methylamino)propan-2-yl)piperidine-1-carboxamide I-533a

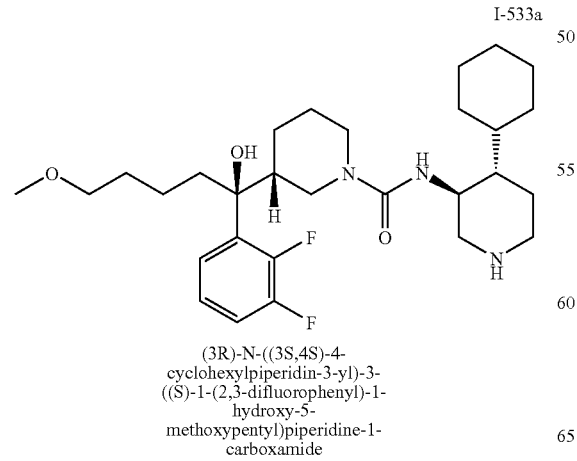

(3R)-N-((3S,4S)-4-cyclohexylpiperidin-3-yl)-3-((S)-1-(2,3-difluorophenyl)-1-hydroxy-5-methoxypentyl)piperidine-1-carboxamide -continued I-534a

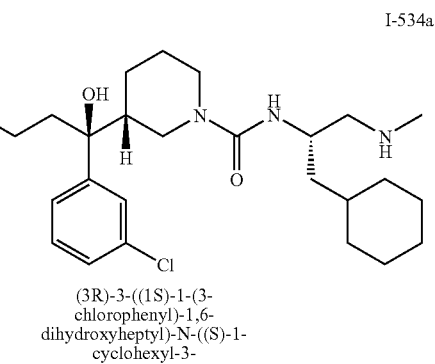

(3R)-3-((1S)-1-(3-chlorophenyl)-1,6-dihydroxyheptyl)-N-((S)-1-cyclohexyl-3-(methylamino)propan-2-yl)piperidine-1-carboxamide I-536a

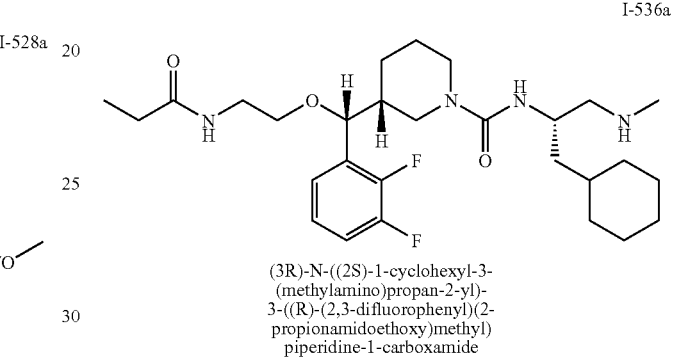

(3R)-N-((2S)-1-cyclohexyl-3-(methylamino)propan-2-yl)-3-((R)-(2,3-difluorophenyl)(2-propionamidoethoxy)methyl)piperidine-1-carboxamide I-537a

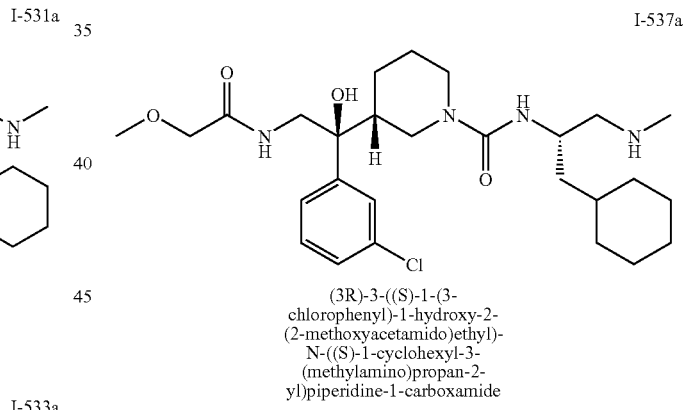

(3R)-3-((S)-1-(3-chlorophenyl)-1-hydroxy-2-(2-methoxyacetamido)ethyl)-N-((S)-1-cyclohexyl-3-(methylamino)propan-2-yl)piperidine-1-carboxamide I-541a

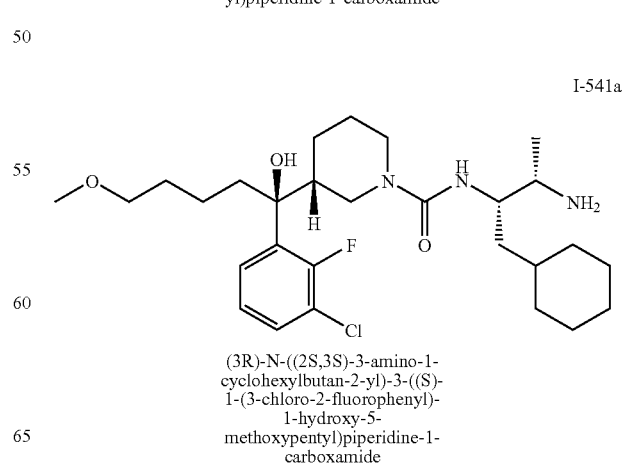

(3R)-N-((2S,3S)-3-amino-1-cyclohexylbutan-2-yl)-3-((S)-1-(3-chloro-2-fluorophenyl)-1-hydroxy-5-methoxypentyl)piperidine-1-carboxamide I-544a

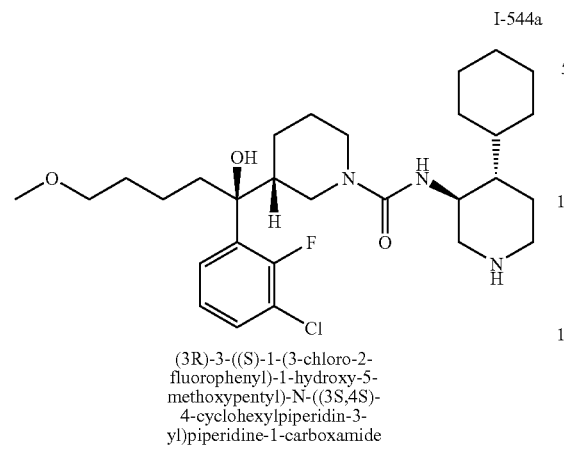

(3R)-3-((S)-1-(3-chloro-2-
fluorophenyl)-1-hydroxy-5-
methoxypentyl)-N-((3S,4S)-
4-cyclohexylpiperidin-3-
yl)piperidine-1-carboxamide I-545a

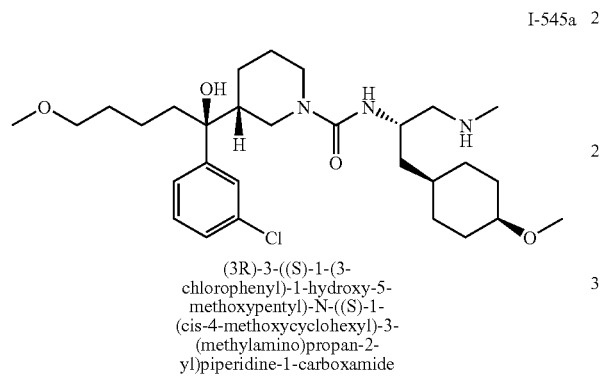

(3R)-3-((S)-1-(3-
chlorophenyl)-1-hydroxy-5-
methoxypentyl)-N-((S)-1-
(cis-4-methoxycyclohexyl)-3-
(methylamino)propan-2-
yl)piperidine-1-carboxamide I-545b

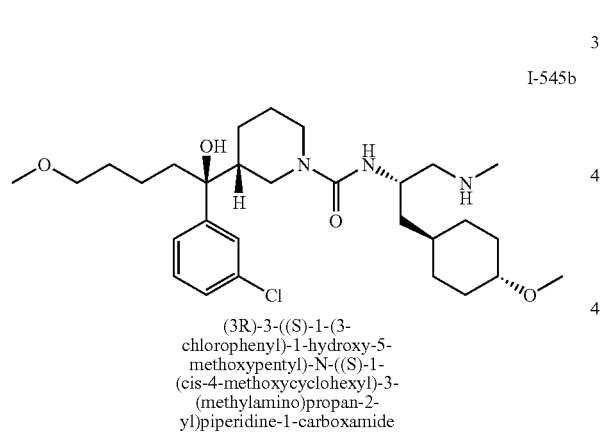

(3R)-3-((S)-1-(3-
chlorophenyl)-1-hydroxy-5-
methoxypentyl)-N-((S)-1-
(cis-4-methoxycyclohexyl)-3-
(methylamino)propan-2-
yl)piperidine-1-carboxamide I-546a

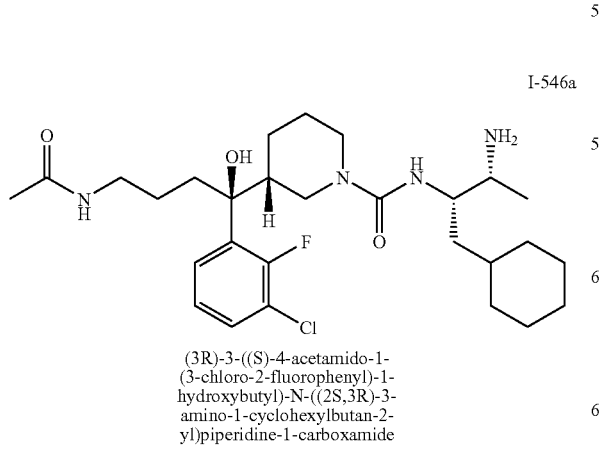

(3R)-3-((S)-4-acetamido-1-
(3-chloro-2-fluorophenyl)-1-
hydroxybutyl)-N-((2S,3R)-3-
amino-1-cyclohexylbutan-2-
yl)piperidine-1-carboxamide I-546b

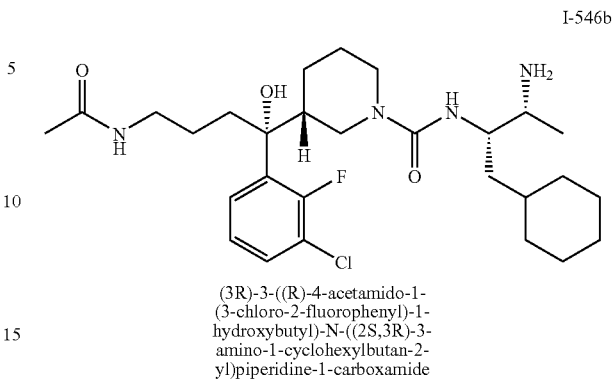

(3R)-3-((R)-4-acetamido-1-
(3-chloro-2-fluorophenyl)-1-
hydroxybutyl)-N-((2S,3R)-3-
amino-1-cyclohexylbutan-2-
yl)piperidine-1-carboxamide I-547a

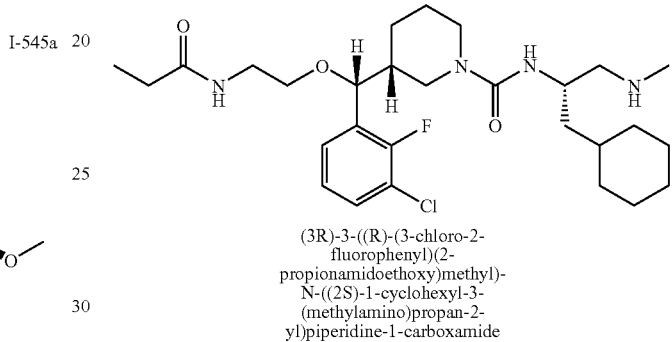

(3R)-3-((R)-(3-chloro-2-
fluorophenyl)(2-
propionamidoethoxy)methyl)-
N-((2S)-1-cyclohexyl-3-
(methylamino)propan-2-
yl)piperidine-1-carboxamide I-548a

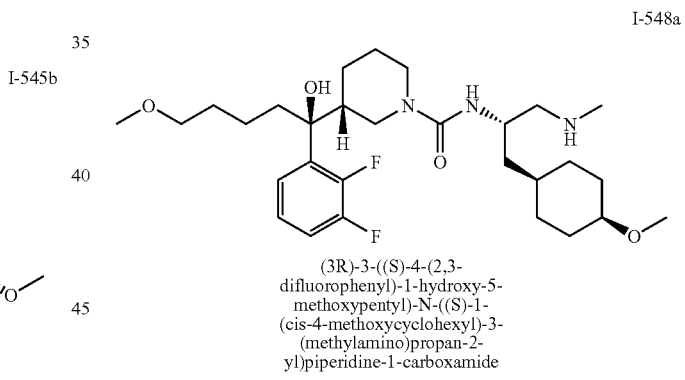

(3R)-3-((S)-4-(2,3-
difluorophenyl)-1-hydroxy-5-
methoxypentyl)-N-((S)-1-
(cis-4-methoxycyclohexyl)-3-
(methylamino)propan-2-
yl)piperidine-1-carboxamide I-549a

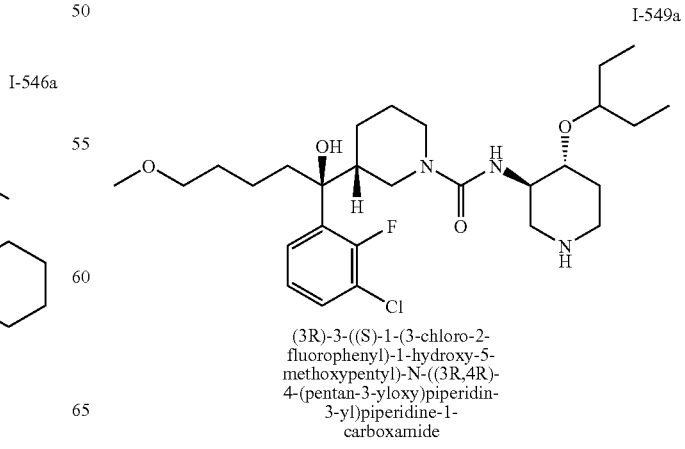

(3R)-3-((S)-1-(3-chloro-2-
fluorophenyl)-1-hydroxy-5-
methoxypentyl)-N-((3R,4R)-
4-(pentan-3-yloxy)piperidin-
3-yl)piperidine-1-
carboxamide -continued I-551a

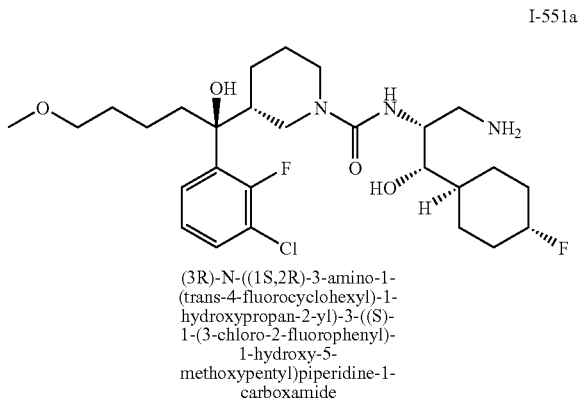

(3R)-N-((1S,2R)-3-amino-1-
(trans-4-fluorocyclohexyl)-1-
hydroxypropan-2-yl)-3-((S)-
1-(3-chloro-2-fluorophenyl)-
1-hydroxy-5-
methoxypentyl)piperidine-1-
carboxamide I-552a

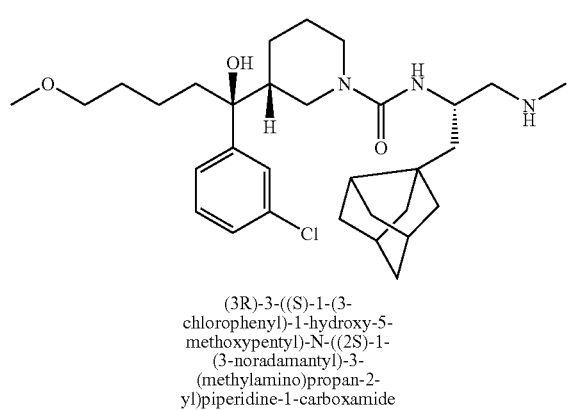

(3R)-3-((S)-1-(3-
chlorophenyl)-1-hydroxy-5-
methoxypentyl)-N-((2S)-1-
(3-noradamantyl)-3-
(methylamino)propan-2-
yl)piperidine-1-carboxamide I-553a

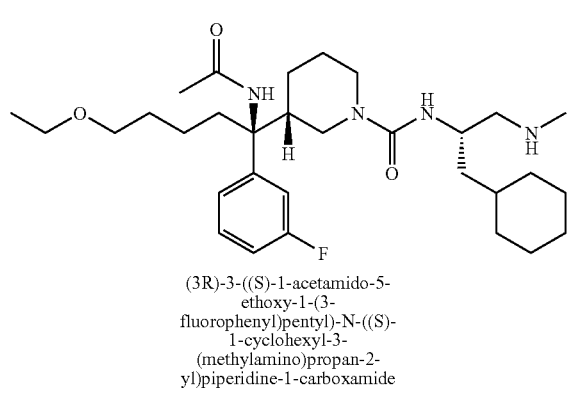

(3R)-3-((S)-1-acetamido-5-
ethoxy-1-(3-
fluorophenyl)pentyl)-N-((S)-
1-cyclohexyl-3-
(methylamino)propan-2-
yl)piperidine-1-carboxamide I-554a

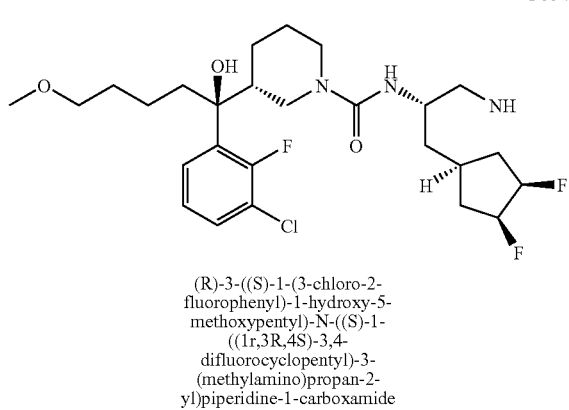

(R)-3-((S)-1-(3-chloro-2-
fluorophenyl)-1-hydroxy-5-
methoxypentyl)-N-((S)-1-
((1r,3R,4S)-3,4-
difluorocyclopentyl)-3-
(methylamino)propan-2-
yl)piperidine-1-carboxamide -continued I-556a

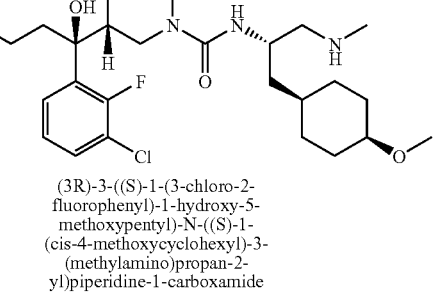

(3R)-3-((S)-1-(3-chloro-2-
fluorophenyl)-1-hydroxy-5-
methoxypentyl)-N-((S)-1-
(cis-4-methoxycyclohexyl)-3-
(methylamino)propan-2-
yl)piperidine-1-carboxamide I-556b

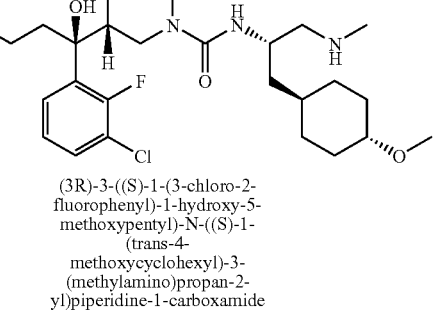

(3R)-3-((S)-1-(3-chloro-2-
fluorophenyl)-1-hydroxy-5-
methoxypentyl)-N-((S)-1-
(trans-4-
methoxycyclohexyl)-3-
(methylamino)propan-2-
yl)piperidine-1-carboxamide I-558a

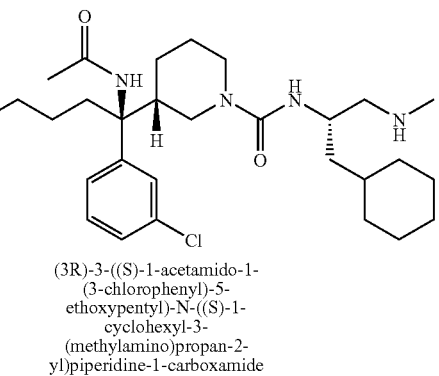

(3R)-3-((S)-1-acetamido-1-
(3-chlorophenyl)-5-
ethoxypentyl)-N-((S)-1-
cyclohexyl-3-
(methylamino)propan-2-
yl)piperidine-1-carboxamide I-559a

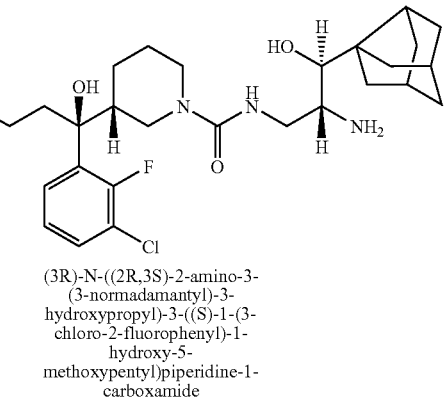

(3R)-N-((2R,3S)-2-amino-3-
(3-noradamantyl)-3-
hydroxypropyl)-3-((S)-1-(3-
chloro-2-fluorophenyl)-1-
hydroxy-5-
methoxypentyl)piperidine-1-
carboxamide The following are preferred compounds of Formula I:

I-14a (3S)—N—((S)-3-cyclohexyl-1-(methylamino)propan-2-yl)-3-((R)-5-methoxy-1-phenylpentyl)piperidine-1-carboxamide I-15a (3S)—N—((S)-1-amino-3-cyclohexylpropan-2-yl)-3-((R)-5-ethoxy-1-phenylpentyl)piperidine-1-carboxamide I-19a N—((S)-1-amino-3-cyclohexylpropan-2-yl)-3-((S)-1-hydroxy-5-methoxy-1-phenylpentyl)piperidine-1-carboxamide I-27a (3S)—N—((S)-3-cyclohexyl-1-(methylamino)propan-2-yl)-3-((R)-5-ethoxy-1-phenylpentyl)piperidine-1-carboxamide I-31a (3R)-3-((R)-(3-ethoxypropoxy)(phenyl)methyl)-N—((S)-3-cyclohexyl-1-(methylamino)propan-2-yl)piperidine-1-carboxamide I-32a (3R)—N—((S)-1-amino-3-cyclohexylpropan-2-yl)-3-((S)-5-ethoxy-1-hydroxy-1-phenylpentyl)piperidine-1-carboxamide I-33a (3R)—N—((S)-3-cyclohexyl-1-(methylamino)propan-2-yl)-3-((S)-1-hydroxy-5-methoxy-1-phenylpentyl)piperidine-1-carboxamide I-37a (3S)—N—((S)-3-cyclohexyl-1-(methylamino)propan-2-yl)-3-((R)-1-(3-fluorophenyl)-5-methoxypentyl)piperidine-1-carboxamide I-40a (3R)—N—((S)-1-amino-3-cyclohexylpropan-2-yl)-3-((S)-1-(3-fluorophenyl)-1-hydroxy-5-methoxypentyl)piperidine-1-carboxamide I-41a (3R)—N—((S)-3-cyclohexyl-1-(methylamino)propan-2-yl)-3-((R)-1-cyclohexyl-1-hydroxy-5-methoxypentyl)piperidine-1-carboxamide I-41b (3R)—N—((S)-3-cyclohexyl-1-(methylamino)propan-2-yl)-3-((S)-1-cyclohexyl-1-hydroxy-5-methoxypentyl)piperidine-1-carboxamide I-48a (3R)—N—((S)-3-cyclohexyl-1-(methylamino)propan-2-yl)-3-((S)-5-ethoxy-1-hydroxy-1-phenylpentyl)piperidine-1-carboxamide I-50a (3R)—N—((S)-3-cyclohexyl-1-(methylamino)propan-2-yl)-3-((S)-1-hydroxy-5-methoxy-1-m-tolylpentyl)piperidine-1-carboxamide I-50a (3R)—N—((S)-3-cyclohexyl-1-(methylamino)propan-2-yl)-3-((S)-1-hydroxy-5-methoxy-1-m-tolylpentyl)piperidine-1-carboxamide I-53a (3R)—N—((S)-3-cyclohexyl-1-(methylamino)propan-2-yl)-3-((S)-1-(3-fluorophenyl)-1-hydroxy-5-methoxypentyl)piperidine-1-carboxamide I-53a (3R)—N—((S)-3-cyclohexyl-1-(methylamino)propan-2-yl)-3-((S)-1-(3-fluorophenyl)-1-hydroxy-5-methoxypentyl)piperidine-1-carboxamide I-64a (3R)-3-((S)-1-(3-chlorophenyl)-1-hydroxy-5-methoxypentyl)-N—((S)-3-cyclohexyl-1-(methylamino)propan-2-yl)piperidine-1-carboxamide I-66a (3R)—N—((S)-3-cyclohexyl-1-(methylamino)propan-2-yl)-3-((S)-1-(2,5-difluorophenyl)-1-hydroxy-5-methoxypentyl)piperidine-1-carboxamide I-67a (3R)—N—((S)-3-(4,4-difluorocyclohexyl)-1-(methylamino)propan-2-yl)-3-((S)-1-hydroxy-5-methoxy-1-phenylpentyl)piperidine-1-carboxamide I-68a (3R)—N—((S)-3-cyclohexyl-1-(methylamino)propan-2-yl)-3-((S)-1-(3,4-difluorophenyl)-1-hydroxy-5-methoxypentyl)piperidine-1-carboxamide I-86a (3R)-3-((S)-1-hydroxy-5-methoxy-1-(2-phenoxyphenyl)pentyl)-N—((S)-4-methyl-1-(methylamino)pentan-2-yl)piperidine-1-carboxamide I-86a (3R)-3-((S)-1-hydroxy-5-methoxy-1-(2-phenoxyphenyl)pentyl)-N—((S)-4-methyl-1-(methylamino)pentan-2-yl)piperidine-1-carboxamide I-88a (3R)—N—((S)-3-(4,4-difluorocyclohexyl)-1-(methylamino)propan-2-yl)-3-((S)-1-(3-fluorophenyl)-1-hydroxy-5-methoxypentyl)piperidine-1-carboxamide I-93a (3R)—N—((S)-3-cyclohexyl-1-(methylamino)propan-2-yl)-3-((S)-1-(3-(trifluoromethyl)phenyl)-1-hydroxy-5-methoxypentyl)piperidine-1-carboxamide I-93a (3R)—N—((S)-3-cyclohexyl-1-(methylamino)propan-2-yl)-3-(1-(3-(trifluoromethyl)phenyl)-1-hydroxy-5-methoxypentyl)piperidine-1-carboxamide I-96a (3R)-3-((S)-1-(2-(p-tolyloxy)-5-methylphenyl)-1-hydroxy-5-methoxypentyl)-N—((S)-4-methyl-1-(methylamino)pentan-2-yl)piperidine-1-carboxamide I-97a (3R)-3-((S)-1-(5-chloro-2-phenoxyphenyl)-1-hydroxy-5-methoxypentyl)-N—((S)-4-methyl-1-(methylamino)pentan-2-yl)piperidine-1-carboxamide I-110a (3S)—N—((S)-3-cyclohexyl-1-(methylamino)propan-2-yl)-3-((R)-5-methoxy-1-(thiophen-2-yl)pentyl)piperidine-1-carboxamide I-117a (3R)-3-((S)-1-(2,3-difluorophenyl)-1-hydroxy-5-methoxypentyl)-N—((S)-4-methyl-1-(methylamino)pentan-2-yl)piperidine-1-carboxamide I-118a (3R)-3-((S)-1-(benzofuran-7-yl)-1-hydroxy-5-methoxypentyl)-N—((S)-4-methyl-1-(methylamino)pentan-2-yl)piperidine-1-carboxamide I-123a (3R)—N—((S)-1-amino-3-cyclohexylpropan-2-yl)-3-((S)-1-(3-fluorophenyl)-1-hydroxy-5-methoxypentyl)piperidine-1-carboxamide I-134a (3R)-3-((S)-1-(3-chlorophenyl)-1-hydroxy-5-methoxypentyl)-N—((S)-4,4-dimethyl-1-(methylamino)pentan-2-yl)piperidine-1-carboxamide I-135a (3R)-3-((S)-1-(2,3-difluorophenyl)-1-hydroxy-5-methoxypentyl)-N—((S)-4,4-dimethyl-1-(methylamino)pentan-2-yl)piperidine-1-carboxamide I-144a (3R)-3-((S)-1-hydroxy-5-methoxy-1-(2-methylbenzofuran-7-yl)pentyl)-N—((S)-4-methyl-1-(methylamino)pentan-2-yl)piperidine-1-carboxamide I-148a (3S)—N—((S)-3-cyclohexyl-1-(methylamino)propan-2-yl)-3-((R)-1-(2-fluoro-5-methylphenyl)-5-methoxypentyl)piperidine-1-carboxamide I-149a (3R)-3-((S)-1-(benzo[b]thiophen-7-yl)-1-hydroxy-5-methoxypentyl)-N—((S)-4-methyl-1-(methylamino)pentan-2-yl)piperidine-1-carboxamide I-151a (3R)—N—((S)-3-cyclohexyl-1-(methylamino)propan-2-yl)-3-((S)-1-(2-fluorophenyl)-1-hydroxy-5-methoxypentyl)piperidine-1-carboxamide I-152a (3R)-3-((R)-(3-ethoxypropoxy)(3-fluorophenyl)methyl)-N—((S)-3-cyclohexyl-1-(methylamino)propan-2-yl)piperidine-1-carboxamide I-153a (3R)—N—((S)-1-amino-3-cyclohexylpropan-2-yl)-3-((S)-1-(3-chlorophenyl)-1-hydroxy-5-methoxypentyl)piperidine-1-carboxamide I-154a (3R)-3-((R)-(3-ethoxypropoxy)(3-chlorophenyl)methyl)-N—((S)-1-amino-3-cyclohexylpropan-2-yl)piperidine-1-carboxamide I-155a (3R)-3-((S)-1-(3-chlorophenyl)-1,5-dihydroxypentyl)-N—((S)-3-cyclohexyl-1-(methylamino)propan-2-yl)piperidine-1-carboxamide I-161a (3R)-3-((S)-1-(2-(o-tolyloxy)phenyl)-1-hydroxy-5-methoxypentyl)-N—((S)-1-(methylamino)propan-2-yl)piperidine-1-carboxamide I-162a (3R)-3-((S)-1-(2-(m-tolyloxy)phenyl)-1-hydroxy-5-methoxypentyl)-N—((S)-1-(methylamino)propan-2-yl)piperidine-1-carboxamide I-165a (3R)-3-((S)-1-(benzofuran-7-yl)-1-hydroxy-5-methoxypentyl)-N—((S)-3-cyclopentyl-1-(methylamino)propan-2-yl)piperidine-1-carboxamide I-166a (3R)-3-((S)-1-(3-chloro-2-fluorophenyl)-1-hydroxy-5-methoxypentyl)-N—((S)-4,4-dimethyl-1-(methylamino)pentan-2-yl)piperidine-1-carboxamide I-172a (3R)—N—((S)-3-cyclopentyl-1-(methylamino)propan-2-yl)-3-((S)-1-(2,3-dihydrobenzofuran-7-yl)-1-hydroxy-5-methoxypentyl)piperidine-1-carboxamide I-173a (3R)—N—((S)-3-cyclohexyl-1-(methylamino)propan-2-yl)-3-((S)-1-hydroxy-5-methoxy-1-(2,5-dimethylphenyl)pentyl)piperidine-1-carboxamide I-174a (3R)—N—((S)-3-cyclohexyl-1-(methylamino)propan-2-yl)-3-((S)-1-(3-ethylphenyl)-1-hydroxy-5-methoxypentyl)piperidine-1-carboxamide I-175a (3R)—N—((S)-3-cyclohexyl-1-(methylamino)propan-2-yl)-3-((S)-1-hydroxy-5-methoxy-1-(2,3-dimethylphenyl)pentyl)piperidine-1-carboxamide I-176a (3R)—N—((S)-3-cyclohexyl-1-(methylamino)propan-2-yl)-3-((S)-1-hydroxy-5-methoxy-1-(3,5-dimethylphenyl)pentyl)piperidine-1-carboxamide I-179a (3R)—N—((S)-3-cyclohexyl-1-(methylamino)propan-2-yl)-3-((S)-1-hydroxy-5-methoxy-1-(3-methoxyphenyl)pentyl)piperidine-1-carboxamide I-180a (3R)-3-((S)-1-(2-(cyclopropylmethoxy)phenyl)-1-hydroxy-5-methoxypentyl)-N—((S)-4-methyl-1-(methylamino)pentan-2-yl)piperidine-1-carboxamide I-181a (3R)-3-((S)-1-(3-chlorophenyl)-4-cyclopropyl-1-hydroxybutyl)-N—((S)-3-cyclohexyl-1-(methylamino)propan-2-yl)piperidine-1-carboxamide I-182a (3R)—N—((S)-3-cyclohexyl-1-(methylamino)propan-2-yl)-3-((S)-1-(3-fluoro-5-methylphenyl)-1-hydroxy-5-methoxypentyl)piperidine-1-carboxamide I-183a (3R)—N—((S)-3-cyclohexyl-1-(methylamino)propan-2-yl)-3-((S)-1-(2-fluoro-5-methylphenyl)-1-hydroxy-5-methoxypentyl)piperidine-1-carboxamide I-184a (3R)—N—((S)-3-cyclohexyl-1-(methylamino)propan-2-yl)-3-((S)-1-(5-fluoro-2-methylphenyl)-1-hydroxy-5-methoxypentyl)piperidine-1-carboxamide I-185a (3R)—N—((S)-3-cyclohexyl-1-(methylamino)propan-2-yl)-3-((S)-1-(2-fluoro-3-methylphenyl)-1-hydroxy-5-methoxypentyl)piperidine-1-carboxamide I-186b (3R)—N-((1S,2R)-1-cyclohexyl-1-hydroxy-3-(methylamino)propan-2-yl)-3-((S)-1-(3-fluorophenyl)-1-hydroxy-5-methoxypentyl)piperidine-1-carboxamide I-190a (3R)-3-((R)-(3-ethoxypropoxy)(3-chlorophenyl)methyl)-N—((S)-3-cyclohexyl-1-(methylamino)propan-2-yl)piperidine-1-carboxamide I-192a (3R)-3-((S)-1-(2-chlorophenyl)-1-hydroxy-5-methoxypentyl)-N—((S)-3-cyclohexyl-1-(methylamino)propan-2-yl)piperidine-1-carboxamide I-193a (3R)-3-((S)-1-(4-chloropyridin-2-yl)-1-hydroxy-5-methoxypentyl)-N—((S)-3-cyclohexyl-1-(methylamino)propan-2-yl)piperidine-1-carboxamide I-194a (3R)-3-((R)-(3-ethoxypropoxy)(phenyl)methyl)-N—((S)-3-(4,4-difluorocyclohexyl)-1-(methylamino)propan-2-yl)piperidine-1-carboxamide I-195a (3R)—N—((S)-3-cyclohexyl-1-(methylamino)propan-2-yl)-3-((S)-1-(3,5-difluorophenyl)-1-hydroxy-5-methoxypentyl)piperidine-1-carboxamide I-196a (3R)—N—((S)-3-cyclohexyl-1-(methylamino)propan-2-yl)-3-((S)-1-(2,3-difluorophenyl)-1-hydroxy-5-methoxypentyl)piperidine-1-carboxamide I-197a (3R)—N—((S)-3-cyclopentyl-1-(methylamino)propan-2-yl)-3-((S)-5-ethoxy-1-(2,3-difluorophenyl)-1-hydroxypentyl)piperidine-1-carboxamide I-198a (3R)—N—((S)-3-cyclohexyl-1-(methylamino)propan-2-yl)-3-((S)-1-(2,3-difluorophenyl)-1-hydroxy-5-methoxypentyl)piperidine-1-carboxamide I-201a (2R)-2-((R)-1-(3-chlorophenyl)-1-hydroxy-5-methoxypentyl)-N—((S)-3-cyclohexyl-1-(methylamino)propan-2-yl)morpholine-4-carboxamide I-202a (3R)—N-((1R,2R)-3-amino-1-cyclohexyl-1-hydroxypropan-2-yl)-3-((S)-1-(3-chlorophenyl)-1-hydroxy-5-methoxypentyl)piperidine-1-carboxamide I-202b (3R)—N-((1S,2R)-3-amino-1-cyclohexyl-1-hydroxypropan-2-yl)-3-((S)-1-(3-chlorophenyl)-1-hydroxy-5-methoxypentyl)piperidine-1-carboxamide I-203b (3R)-3-((S)-1-(3-chlorophenyl)-1-hydroxy-5-methoxypentyl)-N-((1S,2R)-1-cyclopentyl-1-hydroxy-3-(methylamino)propan-2-yl)piperidine-1-carboxamide I-206a (3R)-3-((S)-1-(3-chloro-2-fluorophenyl)-1-hydroxy-5-methoxypentyl)-N—((S)-3-cyclopentyl-1-(methylamino)propan-2-yl)piperidine-1-carboxamide I-208a (3R)-3-((S)-1-(2,2-difluorobenzo[d][1,3]dioxol-4-yl)-1-hydroxy-5-methoxypentyl)-N—((S)-4-methyl-1-(methylamino)pentan-2-yl)piperidine-1-carboxamide I-210a (3R)-3-((S)-1-(benzofuran-7-yl)-1-hydroxy-5-methoxypentyl)-N—((S)-3-cyclohexyl-1-(methylamino)propan-2-yl)piperidine-1-carboxamide I-211a (3R)—N—((S)-3-cyclohexyl-1-(methylamino)propan-2-yl)-3-((S)-1-hydroxy-1-(1H-indazol-7-yl)-5-methoxypentyl)piperidine-1-carboxamide I-216a (3R)-3-((S)-1-(2-(o-tolyloxy)-3-fluorophenyl)-1-hydroxy-5-methoxypentyl)-N—((S)-1-(methylamino)propan-2-yl)piperidine-1-carboxamide I-217a (3R)-3-((S)-1-(2-(5-fluoro-2-methylphenoxy)phenyl)-1-hydroxy-5-methoxypentyl)-N—((S)-1-(methylamino)propan-2-yl)piperidine-1-carboxamide I-219a (3R)—N—((S)-3-cyclohexyl-1-(methylamino)propan-2-yl)-3-((S)-1-(2,3-dihydrobenzofuran-7-yl)-1-hydroxy-5-methoxypentyl)piperidine-1-carboxamide I-221a (3R)—N—((S)-3-(3,3-difluorocyclobutyl)-1-(methylamino)propan-2-yl)-3-((S)-1-(2,3-difluorophenyl)-1-hydroxy-5-methoxypentyl)piperidine-1-carboxamide I-223a (3R)-3-((S)-1-(2-(2-cyclopropylethoxy)phenyl)-1-hydroxy-5-methoxypentyl)-N—((S)-4-methyl-1-(methylamino)pentan-2-yl)piperidine-1-carboxamide I-224a (3R)-3-((S)-1-(2-(2-chlorophenoxy)phenyl)-1-hydroxy-5-methoxypentyl)-N—((S)-1-(methylamino)propan-2-yl)piperidine-1-carboxamide I-226a (3R)—N—((S)-3-cyclohexyl-1-(methylamino)propan-2-yl)-3-((S)-1-hydroxy-5-methoxy-1-(3-(methylthio)phenyl)pentyl)piperidine-1-carboxamide I-227a (3R)-3-((S)-4-(acetylamino)-1-(3-chlorophenyl)-1-hydroxybutyl)-N—((S)-3-cyclohexyl-1-(methylamino)propan-2-yl)piperidine-1-carboxamide I-229a (3R)—N—((S)-3-cyclohexyl-1-(methylamino)propan-2-yl)-3-((S)-1-(5-fluoro-2-methoxyphenyl)-1-hydroxy-5-methoxypentyl)piperidine-1-carboxamide I-230a (3R)—N—((S)-3-cyclohexyl-1-(methylamino)propan-2-yl)-3-((S)-1-(2-fluoro-6-methoxyphenyl)-1-hydroxy-5-methoxypentyl)piperidine-1-carboxamide I-234a (3R)-3-((S)-1-(3-chlorophenyl)-1-hydroxy-5-methoxypentyl)-N—((S)-3-cyclohexyl-1-(ethylamino)propan-2-yl)piperidine-1-carboxamide I-237a (3R)—N—((S)-3-(4,4-difluorocyclohexyl)-1-(methylamino)propan-2-yl)-3-((S)-1-hydroxy-5-methoxy-1-m-tolylpentyl)piperidine-1-carboxamide I-239a (3R)—N—((S)-1-cyclohexyl-3-(methylamino)propan-2-yl)-3-((S)-1-(2,3-difluorophenyl)-5-ethoxy-1-hydroxypentyl)piperidine-1-carboxamide I-240a (3R)-3-((S)-1-(2-fluoro-3-methylphenyl)-1-hydroxy-5-methoxypentyl)-N—((S)-3-(trans-4-fluorocyclohexyl)-1-(methylamino)propan-2-yl)piperidine-1-carboxamide I-241a (3R)—N—((S)-3-cyclopropyl-1-(methylamino)propan-2-yl)-3-((S)-1-hydroxy-5-methoxy-1-(2-phenoxyphenyl)pentyl)piperidine-1-carboxamide I-244a (3R)-3-((S)-1-(3-chlorophenyl)-1-hydroxy-5-methoxypentyl)-N-((1S,2R)-1-cyclohexyl-1-hydroxy-3-(methylamino)propan-2-yl)piperidine-1-carboxamide I-244b (3R)-3-((S)-1-(3-chlorophenyl)-1-hydroxy-5-methoxypentyl)-N-((1S,2R)-1-cyclohexyl-1-hydroxy-3-(methylamino)propan-2-yl)piperidine-1-carboxamide I-247a (3R)-3-((S)-1-(3-chlorophenyl)-1-hydroxy-5-methoxypentyl)-N—((S)-3-cyclohexyl-1-(methylamino)propan-2-yl)piperidine-1-carbothioamide I-250a (3R)-3-((S)-1-(3-chloro-5-fluorophenyl)-1-hydroxy-5-methoxypentyl)-N—((S)-3-cyclohexyl-1-(methylamino)propan-2-yl)piperidine-1-carboxamide I-251a (3R)-3-((S)-1-(3-chloro-2-fluorophenyl)-1-hydroxy-5-methoxypentyl)-N—((S)-1-cyclohexyl-3-(methylamino)propan-2-yl)piperidine-1-carboxamide I-251a (3R)-3-((S)-1-(3-chloro-2-fluorophenyl)-1-hydroxy-5-methoxypentyl)-N—((S)-1-cyclohexyl-3-(methylamino)propan-2-yl)piperidine-1-carboxamide I-252a (3R)-3-((S)-1-(3-chloro-2-fluorophenyl)-5-ethoxy-1-hydroxypentyl)-N—((S)-3-cyclopentyl-1-(methylamino)propan-2-yl)piperidine-1-carboxamide I-253a (3R)-3-((S)-1-(3-chlorophenyl)-1-hydroxy-5-methoxypentyl)-N—((S)-3-(trans-4-fluorocyclohexyl)-1-(methylamino)propan-2-yl)piperidine-1-carboxamide I-255a (3R)-3-((R)-(3-ethoxypropoxy)(3-fluorophenyl)methyl)-N—((S)-3-(4,4-difluorocyclohexyl)-1-(methylamino)propan-2-yl)piperidine-1-carboxamide I-256a (3R)—N—((S)-3-cyclohexyl-1-(methylamino)propan-2-yl)-3-((S)-1-(2,3,5-trifluorophenyl)-1-hydroxy-5-methoxypentyl)piperidine-1-carboxamide I-256b (3R)—N—((S)-3-cyclohexyl-1-(methylamino)propan-2-yl)-3-((S)-1-(2,3,5-trifluorophenyl)-1-hydroxy-5-methoxypentyl)piperidine-1-carboxamide I-257a (3R)—N—((S)-3-cyclopentyl-1-(methylamino)propan-2-yl)-3-((S)-5-ethoxy-1-(2,3,5-trifluorophenyl)-1-hydroxypentyl)piperidine-1-carboxamide I-265a (3R)-3-((S)-1-(2,3-dichlorophenyl)-1-hydroxy-5-methoxypentyl)-N—((S)-3-cyclopentyl-1-(methylamino)propan-2-yl)piperidine-1-carboxamide I-267a (3R)-3-((S)-1-(benzo[b]thiophen-7-yl)-1-hydroxy-5-methoxypentyl)-N—((S)-3-cyclohexyl-1-(methylamino)propan-2-yl)piperidine-1-carboxamide I-270a (3R)—N—((S)-3-cyclohexyl-1-(methylamino)propan-2-yl)-3-((S)-1-(5-fluorobenzofuran-7-yl)-1-hydroxy-5-methoxypentyl)piperidine-1-carboxamide I-271a (3R)-3-((S)-1-(3-chlorophenyl)-1-hydroxy-5-methoxypentyl)-N'-cyano-N—((S)-3-cyclohexyl-1-(methylamino)propan-2-yl)piperidine-1-carboxamidine I-273a (3R)-3-((S)-1-(3-chloro-2-fluorophenyl)-1-hydroxy-5-methoxypentyl)-N—((S)-3-(3,3-difluorocyclobutyl)-1-(methylamino)propan-2-yl)piperidine-1-carboxamide I-279a (3R)-3-((S)-1-(3-chloro-2-fluorophenyl)-5-ethoxy-1-hydroxypentyl)-N—((S)-3-cyclohexyl-1-(methylamino)propan-2-yl)piperidine-1-carboxamide I-280a (3R)-3-((S)-1-(3-chloro-2-fluorophenyl)-1-hydroxy-5-methoxypentyl)-N—((S)-1-(methylamino)-3-(trans-4-methylcyclohexyl)propan-2-yl)piperidine-1-carboxamide I-281a (3R)—N—((S)-3-cyclohexyl-1-(methylamino)propan-2-yl)-3-((S)-1-(2-(trifluoromethyl)phenyl)-1-hydroxy-5-methoxypentyl)piperidine-1-carboxamide I-282a (3R)—N—((S)-3-cyclohexyl-1-(methylamino)propan-2-yl)-3-((S)-5-ethoxy-1-(2,3,5-trifluorophenyl)-1-hydroxypentyl)piperidine-1-carboxamide I-283a (3R)-3-((S)-1-(2-fluoro-3-methylphenyl)-1-hydroxy-5-methoxypentyl)-N—((S)-3-(4,4-difluorocyclohexyl)-1-(methylamino)propan-2-yl)piperidine-1-carboxamide I-284a (3R)-3-((S)-1-(2,3-dichlorophenyl)-1-hydroxy-5-methoxypentyl)-N—((S)-3-cyclohexyl-1-(methylamino)propan-2-yl)piperidine-1-carboxamide I-286a (3R)-3-((S)-1-(2,3-dichlorophenyl)-5-ethoxy-1-hydroxypentyl)-N—((S)-3-cyclopentyl-1-(methylamino)propan-2-yl)piperidine-1-carboxamide I-287a (3R)-3-((S)-1-(2-(4-fluorophenoxy)phenyl)-1-hydroxy-5-methoxypentyl)-N—((S)-4-methyl-1-(methylamino)pentan-2-yl)piperidine-1-carboxamide I-288a (3R)-3-((S)-1-(5-fluoro-2-phenoxyphenyl)-1-hydroxy-5-methoxypentyl)-N—((S)-4-methyl-1-(methylamino)pentan-2-yl)piperidine-1-carboxamide I-289a (3R)-3-((S)-1-(2-(3-fluorophenoxy)phenyl)-1-hydroxy-5-methoxypentyl)-N—((S)-4-methyl-1-(methylamino)pentan-2-yl)piperidine-1-carboxamide I-290a (3R)-3-((S)-1-(2-(2-fluorophenoxy)phenyl)-1-hydroxy-5-methoxypentyl)-N—((S)-4-methyl-1-(methylamino)pentan-2-yl)piperidine-1-carboxamide I-291a (3R)-3-((S)-1-(3-fluoro-2-phenoxyphenyl)-1-hydroxy-5-methoxypentyl)-N—((S)-4-methyl-1-(methylamino)pentan-2-yl)piperidine-1-carboxamide I-293a (3R)-3-((S)-1-(3-chlorophenyl)-1-hydroxy-5-methoxypentyl)-N—((S)-3-(4,4-difluorocyclohexyl)-1-(methylamino)propan-2-yl)piperidine-1-carboxamide I-294a (3R)-3-((R)-(3-ethoxypropoxy)(3-chlorophenyl)methyl)-N—((S)-3-(4,4-difluorocyclohexyl)-1-(methylamino)propan-2-yl)piperidine-1-carboxamide I-295a (3R)-3-((S)-1-(3-chloro-2-fluorophenyl)-1-hydroxy-5-methoxypentyl)-N—((S)-3-(trans-4-fluorocyclohexyl)-1-(methylamino)propan-2-yl)piperidine-1-carboxamide I-295a (3R)-3-((S)-1-(3-chloro-2-fluorophenyl)-1-hydroxy-5-methoxypentyl)-N—((S)-3-(trans-4-fluorocyclohexyl)-1-(methylamino)propan-2-yl)piperidine-1-carboxamide I-296a (3R)-3-((R)-1-(2-(2-chlorophenyl)phenyl)-1-hydroxy-5-methoxypentyl)-N—((S)-4-methyl-1-(methylamino)pentan-2-yl)piperidine-1-carboxamide I-296b (3R)-3-((1R)-1-(2'-chlorobiphenyl-2-yl)-1-hydroxy-5-methoxypentyl)-N—((S)-4-methyl-1-(methylamino)pentan-2-yl)piperidine-1-carboxamide I-299a (3R)—N—((S)-3-(4,4-difluorocyclohexyl)-1-(methylamino)propan-2-yl)-3-((S)-1-(2,3-difluorophenyl)-1-hydroxy-5-methoxypentyl)piperidine-1-carboxamide I-301a (3R)-3-((S)-1-acetamido-1-(3-chlorophenyl)-5-methoxypentyl)-N—((S)-3-cyclohexyl-1-(methylamino)propan-2-yl)piperidine-1-carboxamide I-302a (3R)-3-((S)-1-(benzofuran-7-yl)-1-hydroxy-5-methoxypentyl)-N—((S)-3-(4,4-difluorocyclohexyl)-1-(methylamino)propan-2-yl)piperidine-1-carboxamide I-305a (3R)—N—((S)-1-(2-methoxyethylamino)-3-cyclohexylpropan-2-yl)-3-((S)-1-(3-chlorophenyl)-1-hydroxy-5-methoxypentyl)piperidine-1-carboxamide I-306a (3R)—N—((S)-3-cyclohexyl-1-(methylamino)propan-2-yl)-3-((S)-1-(2,2-difluorobenzo[d][1,3]dioxol-4-yl)-1-hydroxy-5-methoxypentyl)piperidine-1-carboxamide I-308a (3R)-3-((S)-1-(2,3-dichlorophenyl)-5-ethoxy-1-hydroxypentyl)-N—((S)-3-cyclohexyl-1-(methylamino)propan-2-yl)piperidine-1-carboxamide I-310a (3R)—N—((S)-3-cyclohexyl-1-(methylamino)propan-2-yl)-3-((S)-1-hydroxy-5-methoxy-1-(2-(trifluoromethoxy)phenyl)pentyl)piperidine-1-carboxamide I-311a (3R)-3-((S)-1-(2-(p-tolyloxy)-3-fluorophenyl)-1-hydroxy-5-methoxypentyl)-N—((S)-4-methyl-1-(methylamino)pentan-2-yl)piperidine-1-carboxamide I-317a (3R)-3-((S)-5-ethoxy-1-(2,3-difluorophenyl)-1-hydroxypentyl)-N—((S)-3-(4,4-difluorocyclohexyl)-1-(methylamino)propan-2-yl)piperidine-1-carboxamide
I-318a (3R)-3-((S)-1-(2-(4-fluorophenoxy)-5-fluorophenyl)-1-hydroxy-5-methoxypentyl)-N—((S)-4-methyl-1-(methylamino)pentan-2-yl)piperidine-1-carboxamide
I-319a (3R)-3-((S)-1-(3,5-difluoro-2-phenoxyphenyl)-1-hydroxy-5-methoxypentyl)-N—((S)-4-methyl-1-(methylamino)pentan-2-yl)piperidine-1-carboxamide
I-320a (3R)-3-((S)-1-(3-chloro-2-fluorophenyl)-1-hydroxy-5-methoxypentyl)-N—((S)-3-(4,4-difluorocyclohexyl)-1-(methylamino)propan-2-yl)piperidine-1-carboxamide
I-321a (3R)-3-((R)-(3-ethoxypropoxy)(3-chloro-2-fluorophenyl)methyl)-N—((S)-3-(4,4-difluorocyclohexyl)-1-(methylamino)propan-2-yl)piperidine-1-carboxamide
I-322a (3R)-3-((S)-1-(3-chlorophenyl)-5-methoxy-1-(propionamido)pentyl)-N—((S)-3-cyclohexyl-1-(methylamino)propan-2-yl)piperidine-1-carboxamide
I-323a (3R)—N—((S)-3-(4,4-difluorocyclohexyl)-1-(methylamino)propan-2-yl)-3-((S)-1-(2,3,5-trifluorophenyl)-1-hydroxy-5-methoxypentyl)piperidine-1-carboxamide
I-324a (3R)-3-((R)-(3-ethoxypropoxy)(2,3,5-trifluorophenyl)methyl)-N—((S)-3-(4,4-difluorocyclohexyl)-1-(methylamino)propan-2-yl)piperidine-1-carboxamide
I-327a (3R)—N—((S)-1-(2-ethoxyethylamino)-3-cyclohexylpropan-2-yl)-3-((S)-1-(3-chlorophenyl)-1-hydroxy-5-methoxypentyl)piperidine-1-carboxamide
I-330a (3R)-3-((S)-1-(2-(allyloxy)-3-bromophenyl)-1-hydroxy-5-methoxypentyl)-N—((S)-4-methyl-1-(methylamino)pentan-2-yl)piperidine-1-carboxamide
I-331a (3R)—N—((S)-1-(2,2,2-trifluoroethylamino)-3-cyclohexylpropan-2-yl)-3-((S)-1-(3-chlorophenyl)-1-hydroxy-5-methoxypentyl)piperidine-1-carboxamide
I-336a (3R)-3-((S)-1-(3-chloro-2-fluorophenyl)-5-methoxy-1-(propionamido)pentyl)-N—((S)-3-cyclohexyl-1-(methylamino)propan-2-yl)piperidine-1-carboxamide
I-340a (3R)-3-((S)-1-(3-chloro-2-fluorophenyl)-1-(isobutyramido)-5-methoxypentyl)-N—((S)-3-cyclohexyl-1-(methylamino)propan-2-yl)piperidine-1-carboxamide
I-343a (3R)-3-((S)-1-(3-chlorophenyl)-1-hydroxybutyl)-N—((S)-1-cyclohexyl-3-(methylamino)propan-2-yl)piperidine-1-carboxamide
I-345a 3-((R)-1-cyclohexyl-1-hydroxy-5-methoxypentyl)-N—((S)-1-cyclohexyl-3-(methylamino)propan-2-yl)benzamide
I-346a (3R)-3-((S)-1-(3-chlorophenyl)-1-hydroxypentyl)-N—((S)-1-cyclohexyl-3-(methylamino)propan-2-yl)piperidine-1-carboxamide
I-347a (3R)-3-((R)-1-cyclohexyl-1-hydroxy-5-methoxypentyl)-N—((S)-1-cyclohexyl-3-(methylamino)propan-2-yl)piperidine-1-carboxamide
I-350a (3R)-3-((S)-1-(benzofuran-7-yl)-1-hydroxy-5-methoxypentyl)-N—((S)-4,4-dimethyl-1-(methylamino)pentan-2-yl)piperidine-1-carboxamide
I-354a (3R)—N—((S)-2-amino-3-cyclohexylpropyl)-3-((S)-1-(3-chlorophenyl)-1-hydroxy-5-methoxypentyl)piperidine-1-carboxamide
I-357a (3R)-3-((S)-1-(3-cyanophenyl)-1-hydroxy-5-methoxypentyl)-N—((S)-1-cyclohexyl-3-(methylamino)propan-2-yl)piperidine-1-carboxamide
I-359a (3R)-3-((S)-1-(2-chloro-3-fluorophenyl)-1-hydroxy-5-methoxypentyl)-N—((S)-4,4-dimethyl-1-(methylamino)pentan-2-yl)piperidine-1-carboxamide
I-362a (3R)-3-((S)-4-acetamido-1-(2-fluorophenyl)-1-hydroxybutyl)-N—((S)-1-cyclohexyl-3-(methylamino)propan-2-yl)piperidine-1-carboxamide
I-363a (3R)—N—((S)-1-cyclohexyl-3-(methylamino)propan-2-yl)-3-((S)-1-(3-fluoro-2-methylphenyl)-1-hydroxy-5-methoxypentyl)piperidine-1-carboxamide
I-363b (3R)—N—((S)-1-cyclohexyl-3-(methylamino)propan-2-yl)-3-((R)-1-(3-fluoro-2-methylphenyl)-1-hydroxy-5-methoxypentyl)piperidine-1-carboxamide
I-366a (3R)—N—((S)-1-cyclohexyl-3-(methylamino)propan-2-yl)-3-((S)-1-(3-fluoro-2-hydroxyphenyl)-1-hydroxy-5-methoxypentyl)piperidine-1-carboxamide
I-367a (3R)—N-((1S,2R)-1-cyclohexyl-1-hydroxy-3-(methylamino)propan-2-yl)-3-((S)-1-(2-fluorophenyl)-1-hydroxy-5-methoxypentyl)piperidine-1-carboxamide
I-368a (3R)—N-((2S,3R)-3-amino-1-cyclohexylbutan-2-yl)-3-((S)-1-(3-chlorophenyl)-1-hydroxy-5-methoxypentyl)piperidine-1-carboxamide
I-369a (3R)-3-((S)-1-(3-chlorophenyl)-1-hydroxy-5-methoxypentyl)-N—((S)-3-cyclohexyl-2-(methylamino)propyl)piperidine-1-carboxamide
I-370a (3R)—N—((S)-1-(cis-4-fluorocyclohexyl)-3-(methylamino)propan-2-yl)-3-((S)-1-(2-fluorophenyl)-1-hydroxy-5-methoxypentyl)piperidine-1-carboxamide
I-370b (3R)—N—((S)-1-(trans-4-fluorocyclohexyl)-3-(methylamino)propan-2-yl)-3-((S)-1-(2-fluorophenyl)-1-hydroxy-5-methoxypentyl)piperidine-1-carboxamide
I-370c (3R)—N—((S)-1-(trans-4-fluorocyclohexyl)-3-(methylamino)propan-2-yl)-3-((R)-1-(2-fluorophenyl)-1-hydroxy-5-methoxypentyl)piperidine-1-carboxamide
I-371a (3R)—N-((1S,2R)-1-cyclopentyl-1-hydroxy-3-(methylamino)propan-2-yl)-3-((S)-1-(2,3-difluorophenyl)-1-hydroxy-5-methoxypentyl)piperidine-1-carboxamide
I-372a (3R)-3-((S)-1-(2-chloro-3-fluorophenyl)-1-hydroxy-5-methoxypentyl)-N—((S)-1-cyclopentyl-3-(methylamino)propan-2-yl)piperidine-1-carboxamide
I-373a (3R)—N—((S)-2-amino-3-cyclohexylpropyl)-3-((S)-1-(3-chloro-2-fluorophenyl)-1-hydroxy-5-methoxypentyl)piperidine-1-carboxamide
I-374a (3R)-3-((S)-1-(benzofuran-4-yl)-1-hydroxy-5-methoxypentyl)-N—((S)-1-cyclohexyl-3-(methylamino)propan-2-yl)piperidine-1-carboxamide
I-375a (3R)-3-((S)-4-acetamido-1-(3,5-dimethylphenyl)-1-hydroxybutyl)-N—((S)-1-cyclohexyl-3-(methylamino)propan-2-yl)piperidine-1-carboxamide
I-377a (3R)—N—((S)-2-amino-3-cyclohexylpropyl)-3-((S)-1-(benzo[b]thiophen-4-yl)-1-hydroxy-5-methoxypentyl)piperidine-1-carboxamide
I-379a (3R)-3-((S)-1-(2-cyano-5-fluorophenyl)-1-hydroxy-5-methoxypentyl)-N—((S)-1-cyclohexyl-3-(methylamino)propan-2-yl)piperidine-1-carboxamide
I-381a (3R)—N—((S)-2-amino-3-cyclohexylpropyl)-2-((R)-1-(benzo[b]thiophen-7-yl)-1-hydroxy-5-methoxypentyl)morpholine-4-carboxamide
I-382a (3R)-3-((S)-4-acetamido-1-(3-fluoro-5-methylphenyl)-1-hydroxybutyl)-N—((S)-1-cyclohexyl-3-(methylamino)propan-2-yl)piperidine-1-carboxamide
I-383a (3R)-3-((S)-4-acetamido-1-(2-fluoro-5-methylphenyl)-1-hydroxybutyl)-N—((S)-1-cyclohexyl-3-(methylamino)propan-2-yl)piperidine-1-carboxamide
I-385a (3R)-3-((S)-1-(2-(cyclopropylmethoxy)-3-fluorophenyl)-1-hydroxy-5-methoxypentyl)-N—((S)-4-methyl-1-(methylamino)pentan-2-yl)piperidine-1-carboxamide
I-386a (3R)-3-((S)-1-(3-chloro-2-methylphenyl)-1-hydroxy-5-methoxypentyl)-N—((S)-1-cyclohexyl-3-(methylamino)propan-2-yl)piperidine-1-carboxamide
I-388a (3R)-3-((S)-4-acetamido-1-(2,3-difluorophenyl)-1-hydroxybutyl)-N—((S)-1-cyclohexyl-3-(methylamino)propan-2-yl)piperidine-1-carboxamide I-389a (3R)-3-((S)-4-acetamido-1-(3,5-difluorophenyl)-1-hydroxybutyl)-N—((S)-1-cyclohexyl-3-(methylamino)propan-2-yl)piperidine-1-carboxamide I-390a (3R)-3-((S)-1-(2,3-difluorophenyl)-1-hydroxy-5-methoxypentyl)-N—((S)-1-(methylamino)-3-(4-methylcyclohexyl)propan-2-yl)piperidine-1-carboxamide I-393b (3R)-3-((R)-(2-acetamidoethoxy)(3-chloro-2-fluorophenyl)methyl)-N—((S)-1-cyclohexyl-3-(methylamino)propan-2-yl)piperidine-1-carboxamide I-395a (3R)—N-((1S,2R)-1-cyclohexyl-1-hydroxy-3-(methylamino)propan-2-yl)-3-((S)-1-(2,3-difluorophenyl)-1-hydroxy-5-methoxypentyl)piperidine-1-carboxamide I-398a (3R)-3-((S)-1-(2-chloro-3-fluorophenyl)-1-hydroxy-5-methoxypentyl)-N—((S)-1-cyclohexyl-3-(methylamino)propan-2-yl)piperidine-1-carboxamide I-399a (3R)—N-((2S,3R)-3-amino-1-cyclohexylbutan-2-yl)-3-((S)-1-(3-chloro-2-fluorophenyl)-1-hydroxy-5-methoxypentyl)piperidine-1-carboxamide I-400a (3R)—N—((S)-1-cyclohexyl-3-(methylamino)propan-2-yl)-3-((S)-1-hydroxy-5-methoxy-1-(2,3,4-trifluorophenyl)pentyl)piperidine-1-carboxamide I-401a (3R)—N—((S)-1-(4,4-difluorocyclohexyl)-3-(methylamino)propan-2-yl)-3-((S)-1-(2-fluorophenyl)-1-hydroxy-5-methoxypentyl)piperidine-1-carboxamide I-402b (3R)-3-((S)-1-(2,5-difluorophenyl)-1-hydroxy-5-methoxypentyl)-N—((S)-1-(trans-4-fluorocyclohexyl)-3-(methylamino)propan-2-yl)piperidine-1-carboxamide I-403a (3R)-3-((S)-1-(2,3-difluorophenyl)-1-hydroxy-5-methoxypentyl)-N—((S)-1-(trans-4-fluorocyclohexyl)-3-(methylamino)propan-2-yl)piperidine-1-carboxamide I-403b (3R)-3-((R)-1-(2,3-difluorophenyl)-1-hydroxy-5-methoxypentyl)-N—((S)-1-(trans-4-fluorocyclohexyl)-3-(methylamino)propan-2-yl)piperidine-1-carboxamide I-404a (R)-2-((R)-1-(3-chloro-2-fluorophenyl)-1-hydroxy-5-methoxypentyl)-N—((S)-1-cyclohexyl-3-(methylamino)propan-2-yl)morpholine-4-carboxamide I-405a (3R)-3-((S)-1-(3-chloro-2-fluorophenyl)-1-hydroxy-5-methoxypentyl)-N-((1S,2R)-1-cyclopentyl-1-hydroxy-3-(methylamino)propan-2-yl)piperidine-1-carboxamide I-406a (3R)-3-((S)-1-(3-chloro-2-fluorophenyl)-1-hydroxy-5-methoxypentyl)-N—((S)-1-(methylamino)-3-(tetrahydro-2H-pyran-4-yl)propan-2-yl)piperidine-1-carboxamide I-408a (3R)-3-((S)-1-(benzo[b]thiophen-4-yl)-1-hydroxy-5-methoxypentyl)-N—((S)-1-cyclohexyl-3-(methylamino)propan-2-yl)piperidine-1-carboxamide I-410a (3R)-3-((S)-1-(benzofuran-7-yl)-1-hydroxy-5-methoxypentyl)-N—((S)-1-(cis-4-fluorocyclohexyl)-3-(methylamino)propan-2-yl)piperidine-1-carboxamide I-411a (3R)—N—((S)-1-cyclohexyl-3-(methylamino)propan-2-yl)-3-((S)-1-(2-fluorobenzofuran-7-yl)-1-hydroxy-5-methoxypentyl)piperidine-1-carboxamide I-413a (3R)-2-((R)-1-(benzo[b]thiophen-7-yl)-1-hydroxy-5-methoxypentyl)-N—((S)-1-cyclohexyl-3-(methylamino)propan-2-yl)morpholine-4-carboxamide I-416a (3R)-3-((S)-1-(3-chlorophenyl)-1-hydroxy-4-propionamidobutyl)-N—((S)-1-cyclohexyl-3-(methylamino)propan-2-yl)piperidine-1-carboxamide I-418a (3R)-3-((S)-1-(3-chlorophenyl)-1-hydroxy-4-(3-methylureido)butyl)-N—((S)-1-cyclohexyl-3-(methylamino)propan-2-yl)piperidine-1-carboxamide I-423a (3R)-3-((S)-4-acetamido-1-(3-chloro-2-fluorophenyl)-1-hydroxybutyl)-N—((S)-1-cyclohexyl-3-(methylamino)propan-2-yl)piperidine-1-carboxamide I-424a (3R)-3-((S)-4-acetamido-1-(3-chloro-5-fluorophenyl)-1-hydroxybutyl)-N—((S)-1-cyclohexyl-3-(methylamino)propan-2-yl)piperidine-1-carboxamide I-425a (3R)-3-((S)-4-acetamido-1-(2-chloro-3-fluorophenyl)-1-hydroxybutyl)-N—((S)-1-cyclohexyl-3-(methylamino)propan-2-yl)piperidine-1-carboxamide I-428a (3R)-3-((S)-1-(3-chloro-2-fluorophenyl)-1-hydroxy-5-methoxypentyl)-N-((1S,2R)-1-cyclohexyl-1-hydroxy-3-(methylamino)propan-2-yl)piperidine-1-carboxamide I-428a (3R)-3-((S)-1-(3-chloro-2-fluorophenyl)-1-hydroxy-5-methoxypentyl)-N-((1S,2R)-1-cyclohexyl-1-hydroxy-3-(methylamino)propan-2-yl)piperidine-1-carboxamide I-432a (3R)-3-((S)-1-(3-chloro-2-fluorophenyl)-1-hydroxy-5-methoxypentyl)-N—((S)-1-(trans-4-fluorocyclohexyl)-3-(methylamino)propan-2-yl)piperidine-1-carboxamide I-432b (3R)-3-((S)-1-(3-chloro-2-fluorophenyl)-1-hydroxy-5-methoxypentyl)-N—((S)-1-(cis-4-fluorocyclohexyl)-3-(methylamino)propan-2-yl)piperidine-1-carboxamide I-433a (3R)-3-((S)-1-(3-chloro-2,4-difluorophenyl)-1-hydroxy-5-methoxypentyl)-N—((S)-1-cyclohexyl-3-(methylamino)propan-2-yl)piperidine-1-carboxamide I-433b (3R)-3-((R)-1-(3-chloro-2,4-difluorophenyl)-1-hydroxy-5-methoxypentyl)-N—((S)-1-cyclohexyl-3-(methylamino)propan-2-yl)piperidine-1-carboxamide I-434a (3R)-3-((S)-1-(3-chloro-2-fluorophenyl)-1-hydroxy-5-methoxypentyl)-N—((S)-1-(1-fluorocyclohexyl)-3-(methylamino)propan-2-yl)piperidine-1-carboxamide I-435a (3R)-3-((S)-1-(2-chloro-3-fluorophenyl)-1-hydroxy-5-methoxypentyl)-N—((S)-1-(trans-4-fluorocyclohexyl)-3-(methylamino)propan-2-yl)piperidine-1-carboxamide I-435b (3R)-3-((R)-1-(2-chloro-3-fluorophenyl)-1-hydroxy-5-methoxypentyl)-N—((S)-1-(trans-4-fluorocyclohexyl)-3-(methylamino)propan-2-yl)piperidine-1-carboxamide I-436a (3R)—N—((S)-1-(cis-4-fluorocyclohexyl)-3-(methylamino)propan-2-yl)-3-((S)-1-hydroxy-5-methoxy-1-(2,3,5-trifluorophenyl)pentyl)piperidine-1-carboxamide I-437a (3R)-2-((R)-1-(3-chloro-2-fluorophenyl)-1-hydroxy-5-methoxypentyl)-N—((S)-1-(trans-4-fluorocyclohexyl)-3-(methylamino)propan-2-yl)morpholine-4-carboxamide I-438a (3R)-3-((S)-1-(3-chlorophenyl)-4-(cyclopropanecarboxamido)-1-hydroxybutyl)-N—((S)-1-cyclohexyl-3-(methylamino)propan-2-yl)piperidine-1-carboxamide I-442a (3R)-3-((S)-1-(3-bromophenyl)-1-hydroxy-5-methoxypentyl)-N—((S)-1-cyclohexyl-3-(methylamino)propan-2-yl)piperidine-1-carboxamide I-447a (3R)-3-((S)-1-(3-chloro-2-fluorophenyl)-1-hydroxy-5-methoxypentyl)-N-((1S,2R)-1-cycloheptyl-1-hydroxy-3-(methylamino)propan-2-yl)piperidine-1-carboxamide I-450a (3R)-3-((S)-1-(3-chlorophenyl)-1-hydroxy-4-(sulfamoylamino)butyl)-N—((S)-1-cyclohexyl-3-(methylamino)propan-2-yl)piperidine-1-carboxamide I-451a (3R)-3-((S)-4-acetamido-1-(2,3-difluorophenyl)-1-hydroxybutyl)-N—((S)-1-(4,4-difluorocyclohexyl)-3-(methylamino)propan-2-yl)piperidine-1-carboxamide I-459a (3R)-3-((S)-1-(2-bromo-5-fluorophenyl)-1-hydroxy-5-methoxypentyl)-N—((S)-1-cyclohexyl-3-(methylamino)propan-2-yl)piperidine-1-carboxamide I-464a (3R)-3-((S)-1-(3-chlorophenyl)-1-hydroxy-4-(2,2,2-trifluoroacetamido)butyl)-N—((S)-1-cyclohexyl-3-(methylamino)propan-2-yl)piperidine-1-carboxamide I-469a (3R)-3-((S)-1-butyramido-1-(3-chloro-2-fluorophenyl)-5-methoxypentyl)-N—((S)-1-cyclohexyl-3-(methylamino)propan-2-yl)piperidine-1-carboxamide I-470a (S)-3-((R)-1-(3-chloro-2-fluorophenyl)-5-methoxypentyl)-N—((S)-1-cyclohexyl-3-(methylamino)propan-2-yl)piperidine-1-carboxamide I-472a (3R)—N—((S)-2-amino-5-methoxy-4,4-dimethylpentyl)-3-((S)-1-(3-chloro-2-fluorophenyl)-1-hydroxy-5-methoxypentyl)piperidine-1-carboxamide I-474a  (3R)-3-((S)-1-(3-chlorophenyl)-1-hydroxy-5-methoxypentyl)-N-((2S,3R)-1-cyclohexyl-3-(methylamino)butan-2-yl)piperidine-1-carboxamide I-475a  (3R)-3-((S)-1-(3-chloro-2-fluorophenyl)-1-hydroxy-5-methoxypentyl)-N—((S)-3-cyclohexyl-2-(methylamino)propyl)piperidine-1-carboxamide I-476a  (3R)-3-((S)-1-(3-chlorophenyl)-1-hydroxy-5-methoxypentyl)-N—((S)-1-(1-fluorocyclohexyl)-3-(methylamino)propan-2-yl)piperidine-1-carboxamide I-476b  (3R)-3-((S)-1-(3-chlorophenyl)-1-hydroxy-5-methoxypentyl)-N-((R)-1-(1-fluorocyclohexyl)-3-(methylamino)propan-2-yl)piperidine-1-carboxamide I-478a  (3R)-3-((S)-1-(3-chloro-2-fluorophenyl)-1-fluoro-5-methoxypentyl)-N—((S)-1-cyclohexyl-3-(methylamino)propan-2-yl)piperidine-1-carboxamide I-480a  (3R)-3-((S)-1-(2,3-dihydrobenzofuran-7-yl)-1-hydroxy-5-methoxypentyl)-N—((S)-1-(trans-4-fluorocyclohexyl)-3-(methylamino)propan-2-yl)piperidine-1-carboxamide I-485a  (3R)-3-((S)-1-(3-chloro-2-fluorophenyl)-1-hydroxy-5-methoxypentyl)-N-((2S,3R)-1-cyclohexyl-3-(methylamino)butan-2-yl)piperidine-1-carboxamide I-488a  (3R)—N-((2S,3S)-3-amino-4-cyclohexyl-1-hydroxybutan-2-yl)-3-((S)-1-(3-chloro-2-fluorophenyl)-1-hydroxy-5-methoxypentyl)piperidine-1-carboxamide I-490a  (3R)-3-((S)-1-(2-chloro-3-fluorophenyl)-1-hydroxy-5-methoxypentyl)-N—((S)-1-(1-fluorocyclohexyl)-3-(methylamino)propan-2-yl)piperidine-1-carboxamide I-491a  (3R)—N—((S)-1-(trans-4-fluorocyclohexyl)-3-(methylamino)propan-2-yl)-3-((S)-1-hydroxy-5-methoxy-1-(2,3,5-trifluorophenyl)pentyl)piperidine-1-carboxamide I-492a  (3R)—N—((S)-2-amino-3-(4,4-difluorocyclohexyl)propyl)-3-((S)-1-(3-chloro-2-fluorophenyl)-1-hydroxy-5-methoxypentyl)piperidine-1-carboxamide I-493a  (3R)—N-((1S,2R)-3-amino-1-(noradamant-3-yl)-1-hydroxypropan-2-yl)-3-((S)-1-(3-chlorophenyl)-1-hydroxy-5-methoxypentyl)piperidine-1-carboxamide I-497a  (3R)-3-((S)-1-(3-chloro-2,4-difluorophenyl)-1-hydroxy-5-methoxypentyl)-N-((1S,2R)-1-cyclohexyl-1-hydroxy-3-(methylamino)propan-2-yl)piperidine-1-carboxamide I-498a  (3R)-3-((S)-1-(3-chloro-2,4-difluorophenyl)-1-hydroxy-5-methoxypentyl)-N—((S)-1-(trans-4-fluorocyclohexyl)-3-(methylamino)propan-2-yl)piperidine-1-carboxamide I-499a  (3R)—N-((1S,2R)-(3-amino-1-(noradamant-3-yl)-1-hydroxy)propan-2-yl)-3-((S)-1-(2-fluoro-3-chlorophenyl)-1-hydroxy-5-methoxypentyl)piperidine-1-carboxamide I-503a  (3R)—N—((S)-2-amino-3-cyclopentylpropyl)-3-((S)-1-(3-chlorophenyl)-1-hydroxy-5-methoxypentyl)piperidine-1-carboxamide I-514a  (3R)—N-((2S)-1-amino-3-(tetrahydrofuran-2-yl)propan-2-yl)-3-((S)-1-(3-chloro-2-fluorophenyl)-1-hydroxy-5-methoxypentyl)piperidine-1-carboxamide I-520a  (3R)—N—((S)-2-amino-4-cyclohexylbutyl)-3-((S)-1-(3-chlorophenyl)-1-hydroxy-5-methoxypentyl)piperidine-1-carboxamide I-522a  (S)-3-((R)-1-(3-chloro-2-fluorophenyl)-5-methoxypentyl)-N—((S)-1-cyclohexyl-3-(methylamino)propan-2-yl)piperidine-1-carboxamide I-524a  (3R)-3-((R)-(3-chloro-2-fluorophenyl)(3-methoxypropoxy)methyl)-N—((S)-1-cyclohexyl-3-(methylamino)propan-2-yl)piperidine-1-carboxamide I-526a  (3R)—N-((2S)-1-amino-3-(tetrahydro-2H-pyran-2-yl)propan-2-yl)-3-((S)-1-(3-chloro-2-fluorophenyl)-1-hydroxy-5-methoxypentyl)piperidine-1-carboxamide I-531a  (3R)-3-((R)-(3-chlorophenyl)(2-propionamidoethoxy)methyl)-N—((S)-1-cyclohexyl-3-(methylamino)propan-2-yl)piperidine-1-carboxamide I-533a  (3R)—N-((3S,4S)-4-cyclohexylpiperidin-3-yl)-3-((S)-1-(2,3-difluorophenyl)-1-hydroxy-5-methoxypentyl)piperidine-1-carboxamide I-534a  (3R)-3-((1S)-1-(3-chlorophenyl)-1,6-dihydroxyheptyl)-N—((S)-1-cyclohexyl-3-(methylamino)propan-2-yl)piperidine-1-carboxamide I-536a  (3R)—N-((2S)-1-cyclohexyl-3-(methylamino)propan-2-yl)-3-((R)-(2,3-difluorophenyl)(2-propionamidoethoxy)methyl)piperidine-1-carboxamide I-544a  (3R)-3-((S)-1-(3-chloro-2-fluorophenyl)-1-hydroxy-5-methoxypentyl)-N-((3S,4S)-4-cyclohexylpiperidin-3-yl)piperidine-1-carboxamide I-545a  (3R)-3-((S)-1-(3-chlorophenyl)-1-hydroxy-5-methoxypentyl)-N—((S)-1-(cis-4-methoxycyclohexyl)-3-(methylamino)propan-2-yl)piperidine-1-carboxamide I-546a  (3R)-3-((S)-4-acetamido-1-(3-chloro-2-fluorophenyl)-1-hydroxybutyl)-N-((2S,3R)-3-amino-1-cyclohexylbutan-2-yl)piperidine-1-carboxamide I-546b  (3R)-3-((R)-4-acetamido-1-(3-chloro-2-fluorophenyl)-1-hydroxybutyl)-N-((2S,3R)-3-amino-1-cyclohexylbutan-2-yl)piperidine-1-carboxamide I-547a  (3R)-3-((R)-(3-chloro-2-fluorophenyl)(2-propionamidoethoxy)methyl)-N-((2S)-1-cyclohexyl-3-(methylamino)propan-2-yl)piperidine-1-carboxamide I-549a  (3R)-3-((S)-1-(3-chloro-2-fluorophenyl)-1-hydroxy-5-methoxypentyl)-N-((3R,4R)-4-(pentan-3-yloxy)piperidin-3-yl)piperidine-1-carboxamide I-551a  (3R)—N-((1S,2R)-3-amino-1-(trans-4-fluorocyclohexyl)-1-hydroxypropan-2-yl)-3-((S)-1-(3-chloro-2-fluorophenyl)-1-hydroxy-5-methoxypentyl)piperidine-1-carboxamide I-552a  (3R)-3-((S)-1-(3-chlorophenyl)-1-hydroxy-5-methoxypentyl)-N-((2S)-1-(3-noradamantyl)-3-(methylamino)propan-2-yl)piperidine-1-carboxamide I-554a  (R)-3-((S)-1-(3-chloro-2-fluorophenyl)-1-hydroxy-5-methoxypentyl)-N—((S)-1-((1R,3R,4S)-3,4-difluorocyclopentyl)-3-(methylamino)propan-2-yl)piperidine-1-carboxamide I-556a  (3R)-3-((S)-1-(3-chloro-2-fluorophenyl)-1-hydroxy-5-methoxypentyl)-N—((S)-1-(cis-4-methoxycyclohexyl)-3-(methylamino)propan-2-yl)piperidine-1-carboxamide I-558a  (3R)-3-((S)-1-acetamido-1-(3-chlorophenyl)-5-ethoxypentyl)-N—((S)-1-cyclohexyl-3-(methylamino)propan-2-yl)piperidine-1-carboxamide I-559a  (3R)—N-((2R,3S)-2-amino-3-(3-noradamantyl)-3-hydroxypropyl)-3-((S)-1-(3-chloro-2-fluorophenyl)-1-hydroxy-5-methoxypentyl)piperidine-1-carboxamide The following are more preferred compounds of Formula I:

I-50a  (3R)—N—((S)-3-cyclohexyl-1-(methylamino)propan-2-yl)-3-((S)-1-hydroxy-5-methoxy-1-m-tolylpentyl)piperidine-1-carboxamide I-53a  (3R)—N—((S)-3-cyclohexyl-1-(methylamino)propan-2-yl)-3-((S)-1-(3-fluorophenyl)-1-hydroxy-5-methoxypentyl)piperidine-1-carboxamide I-64a  (3R)-3-((S)-1-(3-chlorophenyl)-1-hydroxy-5-methoxypentyl)-N—((S)-3-cyclohexyl-1-(methylamino)propan-2-yl)piperidine-1-carboxamide I-151a  (3R)—N—((S)-3-cyclohexyl-1-(methylamino)propan-2-yl)-3-((S)-1-(2-fluorophenyl)-1-hydroxy-5-methoxypentyl)piperidine-1-carboxamide I-153a  (3R)—N—((S)-1-amino-3-cyclohexylpropan-2-yl)-3-((S)-1-(3-chlorophenyl)-1-hydroxy-5-methoxypentyl)piperidine-1-carboxamide I-176a (3R)—N—((S)-3-cyclohexyl-1-(methylamino)propan-2-yl)-3-((S)-1-hydroxy-5-methoxy-1-(3,5-dimethylphenyl)pentyl)piperidine-1-carboxamide I-180a (3R)-3-((S)-1-(2-(cyclopropylmethoxy)phenyl)-1-hydroxy-5-methoxypentyl)-N—((S)-4-methyl-1-(methylamino)pentan-2-yl)piperidine-1-carboxamide I-182a (3R)—N—((S)-3-cyclohexyl-1-(methylamino)propan-2-yl)-3-((S)-1-(3-fluoro-5-methylphenyl)-1-hydroxy-5-methoxypentyl)piperidine-1-carboxamide I-183a (3R)—N—((S)-3-cyclohexyl-1-(methylamino)propan-2-yl)-3-((S)-1-(2-fluoro-5-methylphenyl)-1-hydroxy-5-methoxypentyl)piperidine-1-carboxamide I-184a (3R)—N—((S)-3-cyclohexyl-1-(methylamino)propan-2-yl)-3-((S)-1-(5-fluoro-2-methylphenyl)-1-hydroxy-5-methoxypentyl)piperidine-1-carboxamide I-185a (3R)—N—((S)-3-cyclohexyl-1-(methylamino)propan-2-yl)-3-((S)-1-(2-fluoro-3-methylphenyl)-1-hydroxy-5-methoxypentyl)piperidine-1-carboxamide I-190a (3R)-3-((R)-(3-ethoxypropoxy)(3-chlorophenyl)methyl)-N—((S)-3-cyclohexyl-1-(methylamino)propan-2-yl)piperidine-1-carboxamide I-195a (3R)—N—((S)-3-cyclohexyl-1-(methylamino)propan-2-yl)-3-((S)-1-(3,5-difluorophenyl)-1-hydroxy-5-methoxypentyl)piperidine-1-carboxamide I-196a (3R)—N—((S)-3-cyclohexyl-1-(methylamino)propan-2-yl)-3-((S)-1-(2,3-difluorophenyl)-1-hydroxy-5-methoxypentyl)piperidine-1-carboxamide I-197a (3R)—N—((S)-3-cyclopentyl-1-(methylamino)propan-2-yl)-3-((S)-5-ethoxy-1-(2,3-difluorophenyl)-1-hydroxypentyl)piperidine-1-carboxamide I-198a (3R)—N—((S)-3-cyclohexyl-1-(methylamino)propan-2-yl)-3-((S)-1-(2,3-difluorophenyl)-1-hydroxy-5-methoxypentyl)piperidine-1-carboxamide I-202b (3R)—N—((1S,2R)-3-amino-1-cyclohexyl-1-hydroxypropan-2-yl)-3-((S)-1-(3-chlorophenyl)-1-hydroxy-5-methoxypentyl)piperidine-1-carboxamide I-206a (3R)-3-((S)-1-(3-chloro-2-fluorophenyl)-1-hydroxy-5-methoxypentyl)-N—((S)-3-cyclopentyl-1-(methylamino)propan-2-yl)piperidine-1-carboxamide I-210a (3R)-3-((S)-1-(benzofuran-7-yl)-1-hydroxy-5-methoxypentyl)-N—((S)-3-cyclohexyl-1-(methylamino)propan-2-yl)piperidine-1-carboxamide I-227a (3R)-3-((S)-4-(acetylamino)-1-(3-chlorophenyl)-1-hydroxybutyl)-N—((S)-3-cyclohexyl-1-(methylamino)propan-2-yl)piperidine-1-carboxamide I-239a (R)—N—((S)-1-cyclohexyl-3-(methylamino)propan-2-yl)-3-((S)-1-(2,3-difluorophenyl)-5-ethoxy-1-hydroxypentyl)piperidine-1-carboxamide I-240a (3R)-3-((S)-1-(2-fluoro-3-methylphenyl)-1-hydroxy-5-methoxypentyl)-N—((S)-3-(trans-4-fluorocyclohexyl)-1-(methylamino)propan-2-yl)piperidine-1-carboxamide I-247a (3R)-3-((S)-1-(3-chlorophenyl)-1-hydroxy-5-methoxypentyl)-N—((S)-3-cyclohexyl-1-(methylamino)propan-2-yl)piperidine-1-carbothioamide I-250a (3R)-3-((S)-1-(3-chloro-5-fluorophenyl)-1-hydroxy-5-methoxypentyl)-N—((S)-3-cyclohexyl-1-(methylamino)propan-2-yl)piperidine-1-carboxamide I-251a (R)-3-((S)-1-(3-chloro-2-fluorophenyl)-1-hydroxy-5-methoxypentyl)-N—((S)-1-cyclohexyl-3-(methylamino)propan-2-yl)piperidine-1-carboxamide I-251a (R)-3-((S)-1-(3-chloro-2-fluorophenyl)-1-hydroxy-5-methoxypentyl)-N—((S)-1-cyclohexyl-3-(methylamino)propan-2-yl)piperidine-1-carboxamide I-252a (3R)-3-((S)-1-(3-chloro-2-fluorophenyl)-5-ethoxy-1-hydroxypentyl)-N—((S)-3-cyclopentyl-1-(methylamino)propan-2-yl)piperidine-1-carboxamide I-253a (3R)-3-((S)-1-(3-chlorophenyl)-1-hydroxy-5-methoxypentyl)-N—((S)-3-(trans-4-fluorocyclohexyl)-1-(methylamino)propan-2-yl)piperidine-1-carboxamide I-256a (3R)—N—((S)-3-cyclohexyl-1-(methylamino)propan-2-yl)-3-((S)-1-(2,3,5-trifluorophenyl)-1-hydroxy-5-methoxypentyl)piperidine-1-carboxamide I-256b (3R)—N—((S)-3-cyclohexyl-1-(methylamino)propan-2-yl)-3-((S)-1-(2,3,5-trifluorophenyl)-1-hydroxy-5-methoxypentyl)piperidine-1-carboxamide I-265a (3R)-3-((S)-1-(2,3-dichlorophenyl)-1-hydroxy-5-methoxypentyl)-N—((S)-3-cyclopentyl-1-(methylamino)propan-2-yl)piperidine-1-carboxamide I-267a (3R)-3-((S)-1-(benzo[b]thiophen-7-yl)-1-hydroxy-5-methoxypentyl)-N—((S)-3-cyclohexyl-1-(methylamino)propan-2-yl)piperidine-1-carboxamide I-279a (3R)-3-((S)-1-(3-chloro-2-fluorophenyl)-5-ethoxy-1-hydroxypentyl)-N—((S)-3-cyclohexyl-1-(methylamino)propan-2-yl)piperidine-1-carboxamide I-280a (3R)-3-((S)-1-(3-chloro-2-fluorophenyl)-1-hydroxy-5-methoxypentyl)-N—((S)-1-(methylamino)-3-(trans-4-methylcyclohexyl)propan-2-yl)piperidine-1-carboxamide I-283a (3R)-3-((S)-1-(2-fluoro-3-methylphenyl)-1-hydroxy-5-methoxypentyl)-N—((S)-3-(4,4-difluorocyclohexyl)-1-(methylamino)propan-2-yl)piperidine-1-carboxamide I-284a (3R)-3-((S)-1-(2,3-dichlorophenyl)-1-hydroxy-5-methoxypentyl)-N—((S)-3-cyclohexyl-1-(methylamino)propan-2-yl)piperidine-1-carboxamide I-291a (3R)-3-((S)-1-(3-fluoro-2-phenoxyphenyl)-1-hydroxy-5-methoxypentyl)-N—((S)-4-methyl-1-(methylamino)pentan-2-yl)piperidine-1-carboxamide I-295a (3R)-3-((S)-1-(3-chloro-2-fluorophenyl)-1-hydroxy-5-methoxypentyl)-N—((S)-3-(trans-4-fluorocyclohexyl)-1-(methylamino)propan-2-yl)piperidine-1-carboxamide I-295a (3R)-3-((S)-1-(3-chloro-2-fluorophenyl)-1-hydroxy-5-methoxypentyl)-N—((S)-3-(trans-4-fluorocyclohexyl)-1-(methylamino)propan-2-yl)piperidine-1-carboxamide I-299a (3R)—N—((S)-3-(4,4-difluorocyclohexyl)-1-(methylamino)propan-2-yl)-3-((S)-1-(2,3-difluorophenyl)-1-hydroxy-5-methoxypentyl)piperidine-1-carboxamide I-302a (3R)-3-((S)-1-(benzofuran-7-yl)-1-hydroxy-5-methoxypentyl)-N—((S)-3-(4,4-difluorocyclohexyl)-1-(methylamino)propan-2-yl)piperidine-1-carboxamide I-306a (3R)—N—((S)-3-cyclohexyl-1-(methylamino)propan-2-yl)-3-((S)-1-(2,2-difluorobenzo[d][1,3]dioxol-4-yl)-1-hydroxy-5-methoxypentyl)piperidine-1-carboxamide I-320a (3R)-3-((S)-1-(3-chloro-2-fluorophenyl)-1-hydroxy-5-methoxypentyl)-N—((S)-3-(4,4-difluorocyclohexyl)-1-(methylamino)propan-2-yl)piperidine-1-carboxamide I-354a (3R)—N—((S)-2-amino-3-cyclohexylpropyl)-3-((S)-1-(3-chlorophenyl)-1-hydroxy-5-methoxypentyl)piperidine-1-carboxamide I-369a (3R)-3-((S)-1-(3-chlorophenyl)-1-hydroxy-5-methoxypentyl)-N—((S)-3-cyclohexyl-2-(methylamino)propyl)piperidine-1-carboxamide I-372a (3R)-3-((S)-1-(2-chloro-3-fluorophenyl)-1-hydroxy-5-methoxypentyl)-N—((S)-1-cyclopentyl-3-(methylamino)propan-2-yl)piperidine-1-carboxamide I-373a (3R)—N—((S)-2-amino-3-cyclohexylpropyl)-3-((S)-1-(3-chloro-2-fluorophenyl)-1-hydroxy-5-methoxypentyl)piperidine-1-carboxamide I-374a (3R)-3-((S)-1-(benzofuran-4-yl)-1-hydroxy-5-methoxypentyl)-N—((S)-1-cyclohexyl-3-(methylamino)propan-2-yl)piperidine-1-carboxamide I-388a (3R)-3-((S)-4-acetamido-1-(2,3-difluorophenyl)-1-hydroxybutyl)-N—((S)-1-cyclohexyl-3-(methylamino)propan-2-yl)piperidine-1-carboxamide I-390a (3R)-3-((S)-1-(2,3-difluorophenyl)-1-hydroxy-5-methoxypentyl)-N—((S)-1-(methylamino)-3-(4-methylcyclohexyl)propan-2-yl)piperidine-1-carboxamide I-393b (3R)-3-((R)-3-(2-acetamidoethoxy)(3-chloro-2-fluorophenyl)methyl)-N—((S)-1-cyclohexyl-3-(methylamino)propan-2-yl)piperidine-1-carboxamide I-398a (3R)-3-((S)-1-(2-chloro-3-fluorophenyl)-1-hydroxy-5-methoxypentyl)-N—((S)-1-cyclohexyl-3-(methylamino)propan-2-yl)piperidine-1-carboxamide I-399a (3R)—N-((2S,3R)-3-amino-1-cyclohexylbutan-2-yl)-3-((S)-1-(3-chloro-2-fluorophenyl)-1-hydroxy-5-methoxypentyl)piperidine-1-carboxamide I-403a (3R)-3-((S)-1-(2,3-difluorophenyl)-1-hydroxy-5-methoxypentyl)-N—((S)-1-(trans-4-fluorocyclohexyl)-3-(methylamino)propan-2-yl)piperidine-1-carboxamide I-403b (3R)-3-((R)-1-(2,3-difluorophenyl)-1-hydroxy-5-methoxypentyl)-N—((S)-1-(trans-4-fluorocyclohexyl)-3-(methylamino)propan-2-yl)piperidine-1-carboxamide I-404a (R)-2-((R)-1-(3-chloro-2-fluorophenyl)-1-hydroxy-5-methoxypentyl)-N—((S)-1-cyclohexyl-3-(methylamino)propan-2-yl)morpholine-4-carboxamide I-405a (3R)-3-((S)-1-(3-chloro-2-fluorophenyl)-1-hydroxy-5-methoxypentyl)-N-((1S,2R)-1-cyclopentyl-1-hydroxy-3-(methylamino)propan-2-yl)piperidine-1-carboxamide I-408a (3R)-3-((S)-1-(benzo[b]thiophen-4-yl)-1-hydroxy-5-methoxypentyl)-N—((S)-1-cyclohexyl-3-(methylamino)propan-2-yl)piperidine-1-carboxamide I-416a (3R)-3-((S)-1-(3-chlorophenyl)-1-hydroxy-4-propionamidobutyl)-N—((S)-1-cyclohexyl-3-(methylamino)propan-2-yl)piperidine-1-carboxamide I-423a (3R)-3-((S)-4-acetamido-1-(3-chloro-2-fluorophenyl)-1-hydroxybutyl)-N—((S)-1-cyclohexyl-3-(methylamino)propan-2-yl)piperidine-1-carboxamide I-424a (3R)-3-((S)-4-acetamido-1-(3-chloro-5-fluorophenyl)-1-hydroxybutyl)-N—((S)-1-cyclohexyl-3-(methylamino)propan-2-yl)piperidine-1-carboxamide I-428a (3R)-3-((S)-1-(3-chloro-2-fluorophenyl)-1-hydroxy-5-methoxypentyl)-N-((1S,2R)-1-cyclohexyl-1-hydroxy-3-(methylamino)propan-2-yl)piperidine-1-carboxamide I-432a (3R)-3-((S)-1-(3-chloro-2-fluorophenyl)-1-hydroxy-5-methoxypentyl)-N—((S)-1-(trans-4-fluorocyclohexyl)-3-(methylamino)propan-2-yl)piperidine-1-carboxamide I-432b (3R)-3-((S)-1-(3-chloro-2-fluorophenyl)-1-hydroxy-5-methoxypentyl)-N—((S)-1-(cis-4-fluorocyclohexyl)-3-(methylamino)propan-2-yl)piperidine-1-carboxamide I-433a (3R)-3-((S)-1-(3-chloro-2,4-difluorophenyl)-1-hydroxy-5-methoxypentyl)-N—((S)-1-cyclohexyl-3-(methylamino)propan-2-yl)piperidine-1-carboxamide I-434a (3R)-3-((S)-1-(3-chloro-2-fluorophenyl)-1-hydroxy-5-methoxypentyl)-N—((S)-1-(1-fluorocyclohexyl)-3-(methylamino)propan-2-yl)piperidine-1-carboxamide I-435a (3R)-3-((S)-1-(2-chloro-3-fluorophenyl)-1-hydroxy-5-methoxypentyl)-N—((S)-1-(trans-4-fluorocyclohexyl)-3-(methylamino)propan-2-yl)piperidine-1-carboxamide I-437a (3R)-2-((R)-1-(3-chloro-2-fluorophenyl)-1-hydroxy-5-methoxypentyl)-N—((S)-1-(trans-4-fluorocyclohexyl)-3-(methylamino)propan-2-yl)morpholine-4-carboxamide I-442a (3R)-3-((S)-1-(3-bromophenyl)-1-hydroxy-5-methoxypentyl)-N—((S)-1-cyclohexyl-3-(methylamino)propan-2-yl)piperidine-1-carboxamide I-447a (R)-3-((S)-1-(3-chloro-2-fluorophenyl)-1-hydroxy-5-methoxypentyl)-N-((1S,2R)-1-cycloheptyl-1-hydroxy-3-(methylamino)propan-2-yl)piperidine-1-carboxamide I-464a (3R)-3-((S)-1-(3-chlorophenyl)-1-hydroxy-4-(2,2,2-trifluoroacetamido)butyl)-N—((S)-1-cyclohexyl-3-(methylamino)propan-2-yl)piperidine-1-carboxamide I-474a (3R)-3-((S)-1-(3-chlorophenyl)-1-hydroxy-5-methoxypentyl)-N-((2S,3R)-1-cyclohexyl-3-(methylamino)butan-2-yl)piperidine-1-carboxamide I-475a (3R)-3-((S)-1-(3-chloro-2-fluorophenyl)-1-hydroxy-5-methoxypentyl)-N—((S)-3-cyclohexyl-2-(methylamino)propyl)piperidine-1-carboxamide I-476a (3R)-3-((S)-1-(3-chlorophenyl)-1-hydroxy-5-methoxypentyl)-N—((S)-1-(1-fluorocyclohexyl)-3-(methylamino)propan-2-yl)piperidine-1-carboxamide I-485a (3R)-3-((S)-1-(3-chloro-2-fluorophenyl)-1-hydroxy-5-methoxypentyl)-N-((2S,3R)-1-cyclohexyl-3-(methylamino)butan-2-yl)piperidine-1-carboxamide I-492a (3R)—N—((S)-2-amino-3-(4,4-difluorocyclohexyl)propyl)-3-((S)-1-(3-chloro-2-fluorophenyl)-1-hydroxy-5-methoxypentyl)piperidine-1-carboxamide I-498a (3R)-3-((S)-1-(3-chloro-2,4-difluorophenyl)-1-hydroxy-5-methoxypentyl)-N—((S)-1-(trans-4-fluorocyclohexyl)-3-(methylamino)propan-2-yl)piperidine-1-carboxamide I-531a (3R)-3-((R)-(3-chlorophenyl)(2-propionamidoethoxy)methyl)-N—((S)-1-cyclohexyl-3-(methylamino)propan-2-yl)piperidine-1-carboxamide I-547a (3R)-3-((R)-(3-chloro-2-fluorophenyl)(2-propionamidoethoxy)methyl)-N-((2S)-1-cyclohexyl-3-(methylamino)propan-2-yl)piperidine-1-carboxamide The following are highly preferred compounds:

I-295a (3R)-3-((S)-1-(3-chloro-2-fluorophenyl)-1-hydroxy-5-methoxypentyl)-N—((S)-3-(trans-4-fluorocyclohexyl)-1-(methylamino)propan-2-yl)piperidine-1-carboxamide I-423a (3R)-3-((S)-4-acetamido-1-(3-chloro-2-fluorophenyl)-1-hydroxybutyl)-N—((S)-1-cyclohexyl-3-(methylamino)propan-2-yl)piperidine-1-carboxamide I-432a (3R)-3-((S)-1-(3-chloro-2-fluorophenyl)-1-hydroxy-5-methoxypentyl)-N—((S)-1-(trans-4-fluorocyclohexyl)-3-(methylamino)propan-2-yl)piperidine-1-carboxamide I-531a (3R)-3-((R)-(3-chlorophenyl)(2-propionamidoethoxy)methyl)-N—((S)-1-cyclohexyl-3-(methylamino)propan-2-yl)piperidine-1-carboxamide Another embodiment of the invention is an intermediate compound of Formula III $$R^1\diagdown_X\diagdown_{\underset{R^2}{C}\underset{R^3}{C}}\diagdown_Y\diagdown_A\diagdown_E$$ III wherein $R^1$ is a) $(C_3-C_7)$cycloalkyl; or b) phenyl, heteroaryl, or bicyclic heteroaryl, optionally substituted with 1 or 2 substituents independently selected from:

1) fluorine, chlorine, bromine, iodine, trifluoromethanesulfonyloxy, cyano, nitro, $(C_1-C_6)$alkyl, $(C_3-C_6)$cycloalkyl, $(C_4-C_7)$cycloalkylalkyl, $(C_2-C_6)$alkenyl, $(C_5-C_7)$cycloalkylalkenyl, $(C_2-C_6)$alkynyl, $(C_3-C_6)$cycloalkyl$(C_2-C_4)$alkynyl, halo$(C_1-C_6)$-alkyl, halo$(C_3-C_6)$cycloalkyl, halo$(C_4-C_7)$cycloalkylalkyl, halo$(C_2-C_6)$alkenyl, halo$(C_3-C_6)$alkynyl, halo$(C_5-C_7)$cycloalkylalkynyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, and $(C_1-C_6)$alkanesulfonyl; or 2) phenyl, heteroaryl, phenoxy, heteroaryloxy, phenylthio, naphthylthio, heteroarylthio, benzyl, heteroarylmethyl, benzyloxy, or heteroaryloxy, each optionally substituted with 1 to 3 groups independently selected from:

fluorine, chlorine, cyano, $(C_1-C_3)$alkyl, halo$(C_1-C_3)$alkyl, $(C_1-C_3)$alkoxy, and halo$(C_1-C_3)$alkoxy, and aminocarbonyl;

X and Y is each a single bond;

$R^2$ is $(C_5-C_8)$cycloalkylalkyl, halo$(C_5-C_8)$alkyl, halo$(C_5-C_8)$cycloalkylalkyl, $(C_5-C_8)$alkoxy, $(C_5-C_8)$cycloalkoxy, halo$(C_5-C_8)$alkoxy, $(C_5-C_8)$alkylthio, halo$(C_5-C_8)$alkylthio, hydroxy$(C_5-C_8)$-alkyl, $(C_1-C_3)$alkoxy$(C_3-C_5)$alkyl, $(C_1-C_3)$alkoxy$(C_3-C_5)$hydroxyalkyl, $(C_3-C_6)$cycloalkoxy$(C_3-C_5)$alkyl, halo$(C_1-C_3)$alkoxy$(C_3-C_5)$alkyl, halo$(C_3-C_6)$cycloalkoxy$(C_3-C_5)$alkyl, $(C_1-C_3)$alkylthio$(C_3-C_5)$alkyl, halo$(C_1-C_3)$alkylthio$(C_3-C_5)$-alkyl, $(C_1-C_3)$alkoxy$(C_3-C_5)$alkoxy, $(C_1-C_2)$alkoxy$(C_2-C_4)$alkoxy$(C_1-C_2)$alkyl, hydroxy$(C_5-C_8)$alkoxy, $(C_3-C_6)$cycloalkoxy$(C_3-C_5)$alkoxy, halo$(C_1-C_3)$alkoxy-$(C_3-C_5)$alkoxy, halo$(C_3-C_6)$cycloalkoxy$(C_3-C_5)$alkoxy, hydroxy$(C_5-C_8)$alkylthio, $(C_1-C_3)$alkoxy$(C_3-C_5)$alkylthio, $(C_1-C_3)$alkylthio$(C_3-C_5)$alkoxy, $(C_1-C_3)$alkylthio$(C_3-C_5)$alkylthio, $(C_3-C_4)$cycloalkanecarbonylamino$(C_2-C_4)$alkyl, $(C_3-C_4)$cycloalkanecarbonylamino$(C_2-C_4)$alkoxy, $(C_3-C_4)$cycloalkanecarbonylamino$(C_2-C_4)$alkylthio, $(C_1-C_3)$alkylaminocarbonylamino$(C_2-C_4)$alkyl, $(C_1-C_3)$alkylaminocarbonylamino$(C_2-C_4)$alkoxy, $(C_1-C_3)$alkylaminocarbonylamino$(C_2-C_4)$alkylthio, di$(C_1-C_3)$alkylaminocarbonylamino$(C_2-C_4)$alkyl, di$(C_1-C_3)$alkylaminocarbonylamino$(C_2-C_4)$alkoxy, di$(C_1-C_3)$alkylaminocarbonylamino$(C_2-C_4)$alkylthio or aminocarbonyl$(C_2-C_4)$alkyl;

$R^3$ is H or OH;

provided that when $R^3$ is OH, $R^2$ is not $(C_5-C_8)$alkoxy, $(C_5-C_8)$cycloalkylalkoxy, halo$(C_5-C_8)$-alkoxy, $(C_5-C_8)$alkylthio, halo$(C_5-C_8)$alkylthio, $(C_1-C_3)$alkoxy$(C_3-C_5)$alkoxy, hydroxy$(C_5-C_8)$alkoxy, $(C_3-C_6)$cycloalkoxy$(C_3-C_5)$alkoxy, halo$(C_1-C_3)$alkoxy$(C_3-C_5)$alkoxy, halo$(C_3-C_6)$-cycloalkoxy$(C_3-C_5)$alkoxy, hydroxy$(C_5-C_8)$alkylthio, $(C_1-C_3)$alkoxy$(C_3-C_5)$alkylthio, $(C_1-C_3)$-alkylthio$(C_3-C_5)$-alkoxy, $(C_1-C_3)$alkylthio$(C_3-C_5)$alkylthio, $(C_3-C_4)$cycloalkanecarbonylamino$(C_2-C_4)$alkoxy, $(C_3-C_4)$cycloalkanecarbonylamino$(C_2-C_4)$alkylthio, $(C_1-C_3)$alkylaminocarbonylamino$(C_2-C_4)$alkoxy, $(C_1-C_3)$alkylaminocarbonylamino$(C_2-C_4)$alkylthio, di$(C_1-C_3)$alkylaminocarbonylamino$(C_2-C_4)$alkoxy, di$(C_1-C_3)$alkylaminocarbonylamino$(C_2-C_4)$alkylthio, A is 2,4-disubstituted morpholine with $R^1XCR^2R^3Y$ attached at the 2-position and E attached at the 4-position, 1,3-disubstituted piperidine with $R^1XCR^2R^3Y$ attached at the 3-position and E attached at the 1-position, or 1,3-disubstituted-3-methylpiperidine with $R^1XCR^2R^3Y$ attached at the 3-position and E attached at the 1-position; and E is hydrogen or an amine protecting group.

and the enantiomers, diastereomers and salts thereof.

Amine protecting groups include carbamate, amide, and sulfonamide protecting groups known in the art (T. W. Greene and P. G. M. Wuts "Protective Groups in Organic Synthesis" John Wiley & Sons, Inc., New York 1999).

Another embodiment of the invention is an intermediate compound of Formula IIIa

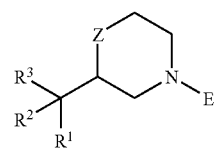

IIIa wherein:

Z is $CH_2$ or O $R^1$ is a) cyclohexyl; or b) phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl, optionally substituted with 1 to 3 substituents independently selected from:

fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl;

$R^2$ is 4,4-difluoropentyl, 3-(cyclopropyl)propyl, 4-(cyclopropyl)butyl, 4-hydroxypentyl, 4-hydroxyhexyl, 3-ethoxypropyl, 4-methoxybutyl, 4-ethoxybutyl, 2-(ethoxy)ethoxy, 3-methoxypropoxy, 3-ethoxypropoxy, 3-propoxypropoxy, or 2-cyclopropylethoxy, 2-(methoxy)ethoxymethyl, 3-(acetylamino)propyl, 3-(propionylamino)propyl, 3-(butanoylamino)propyl, 3-((2-methoxypropionyl)amino)propyl, 3-(cyclopropanecarbonylamino)propyl, 3-(trifluoroacetylamino)propyl, 3-(methylaminocarbonylamino)propyl, 3-(dimethylaminocarbonylamino)propyl, 2-(acetylamino)ethoxy, or 3-(aminosulfonylamino)propyl;

$R^3$ is H or OH;

provided that when $R^3$ is OH, $R^2$ is not 2-(ethoxy)ethoxy, 3-methoxypropoxy, 3-ethoxypropoxy, 3-propoxypropoxy, 2-cyclopropylethoxy or 2-(acetylamino)ethoxy; and E is hydrogen, tert-butoxycarbonyl, benzyloxycarbonyl, 2-(trimethylsilyl)ethoxycarbonyl, methanesulfonyl, or 2-(trimethylsilyl)ethoxysulfonyl.

and the enantiomers, diastereomers and salts thereof.

Another embodiment of the invention is an intermediate compound of Formula IIIb

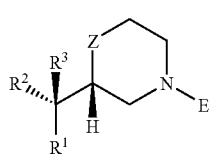

IIIb wherein:

Z is CH₂ or O

R¹ is a) cyclohexyl; or b) phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl, optionally substituted with 1 to 3 substituents independently selected from:

fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, trifluoromethyl, and aminocarbonyl;

R² is 4,4-difluoropentyl, 3-(cyclopropyl)propyl, 4-(cyclopropyl)butyl, 4-hydroxypentyl, 4-hydroxyhexyl, 3-ethoxypropyl, 4-methoxybutyl, 4-ethoxybutyl, 2-(ethoxy)ethoxy, 3-methoxypropoxy, 3-ethoxypropoxy, 3-propoxypropoxy, or 2-cyclopropylethoxy, 3-(acetylamino)propyl, 3-(propionylamino)-propyl, 3-(butanoylamino)propyl, 3-((2-methoxypropionyl)amino)propyl, 3-(cyclopropane-carbonylamino) propyl, 3-(trifluoroacetylamino)propyl, 3-(methylaminocarbonylamino)propyl, 3-(dimethylaminocarbonyl-amino)propyl, 2-(acetylamino)ethoxy, or 3-(aminosulfonylamino)propyl;

R³ is H or OH;

provided that when R³ is OH, R² is not 2-(ethoxy)ethoxy, 3-methoxypropoxy, 3-ethoxypropoxy, 3-propoxypropoxy, 2-cyclopropylethoxy or 2-(acetylamino)ethoxy and E is hydrogen, tert-butoxycarbonyl, benzyloxycarbonyl, 2-(trimethylsilyl)ethoxycarbonyl, methanesulfonyl, or 2-(trimethylsilyl)ethoxysulfonyl.

Intermediates are useful in the preparation of compounds of Formula I. An embodiment of the invention is each of the following intermediates and their enantiomers, diastereomers, and salts:

(R)-3-((R)-(2-cyclopropylethoxy)(phenyl)methyl)piperidine
(S)-2-((S)-5-methoxy-1-phenylpentyl)morpholine
(S)-4-methoxy-1-phenyl-1-((R)-piperidin-3-yl)butan-1-ol
(R)-2-((S)-(3-methoxypropoxy)(phenyl)methyl)morpholine
(S)-4-cyclopropyl-1-phenyl-1-((R)-piperidin-3-yl)butan-1-ol
(R)-3-((R)-(3-ethoxypropoxy)(phenyl)methyl)piperidine
(R)-3-((R)-(3-ethoxypropoxy)(phenyl)methyl)piperidine
(R)-3-((R)-(4-methoxybutoxy)(phenyl)methyl)piperidine
(S)-4-ethoxy-1-phenyl-1-((R)-piperidin-3-yl)butan-1-ol
(S)-5-methoxy-1-((R)-piperidin-3-yl)-1-(pyridin-2-yl)pentan-1-ol
(R)-3-((R)-(3-methoxypropoxy)(2-fluorophenyl)methyl)piperidine
(R)-3-((R)-(3-methoxypropoxy)(3-fluorophenyl)methyl)piperidine
(R)-3-((R)-(3-methoxypropoxy)(4-fluorophenyl)methyl)piperidine
(S)-1-(1H-imidazol-2-yl)-5-methoxy-1-((R)-piperidin-3-yl)pentan-1-ol
(S)-1-(3-chlorophenyl)-1-((R)-piperidin-3-yl)pentan-1-ol
(S)-5-methoxy-1-((R)-piperidin-3-yl)-1-(thiophen-3-yl)pentan-1-ol
(R)-1-cyclohexyl-5-methoxy-1-((R)-piperidin-3-yl)pentan-1-ol
(S)-1-(3-chlorophenyl)-1-((R)-piperidin-3-yl)butane-1,4-diol
(S)-5-methoxy-1-((R)-piperidin-3-yl)-1-(thiazol-2-yl)pentan-1-ol
3-((R)-(3-methoxypropoxy)((R)-piperidin-3-yl)methyl)benzonitrile
4-cyclopropyl-1-(3-fluorophenyl)-1-((R)-piperidin-3-yl)butan-1-ol
(R)-3-((R)-(3-ethoxypropoxy)(m-tolyl)methyl)piperidine
(R)-3-((R)-(3-propoxypropoxy)(phenyl)methyl)piperidine
(R)-5-methoxy-1-((R)-3-methylpiperidin-3-yl)-1-phenylpentan-1-ol
(S)-5-ethoxy-1-phenyl-1-((R)-piperidin-3-yl)pentan-1-ol
(S)-5-methoxy-1-((R)-piperidin-3-yl)-1-m-tolylpentan-1-ol
(R)-3-((R)-(3-ethoxypropoxy)(3-fluorophenyl)methyl)piperidine
(R)-3-((R)-(3-ethoxypropoxy)(3-fluorophenyl)methyl)piperidine
(S)-1-(2-fluorophenyl)-5-methoxy-1-((R)-piperidin-3-yl)pentan-1-ol
(S)-1-(3-fluorophenyl)-5-methoxy-1-((R)-piperidin-3-yl)pentan-1-ol
(S)-5-methoxy-1-(5-methylthiazol-2-yl)-1-((R)-piperidin-3-yl)pentan-1-ol
4-chloro-2-((R)-(3-methoxypropoxy)((R)-piperidin-3-yl)methyl)pyridine
(R)-3-((R)-(3-methoxypropoxy)(2,4-difluorophenyl)methyl)piperidine
(R)-3-((R)-(3-methoxypropoxy)(3,4-difluorophenyl)methyl)piperidine
2-((S)-(3-chloro-2-fluorophenyl)((R)-piperidin-3-yl)methoxy)acetamide
(S)-4,4,4-trifluoro-1-((R)-piperidin-3-yl)-1-m-tolylbutan-1-ol
3-((S)-1-hydroxy-5-methoxy-1-((R)-piperidin-3-yl)pentyl)benzonitrile
(R)-3-((R)-(3-methoxypropoxy)(2-allylphenyl)methyl)piperidine
(S)-1-(2,3-dimethylphenyl)-5-methoxy-1-((R)-piperidin-3-yl)pentan-1-ol
(S)-1-(2,5-dimethylphenyl)-5-methoxy-1-((R)-piperidin-3-yl)pentan-1-ol
(S)-1-(3,5-dimethylphenyl)-5-methoxy-1-((R)-piperidin-3-yl)pentan-1-ol
(S)-1-(3-ethylphenyl)-5-methoxy-1-((R)-piperidin-3-yl)pentan-1-ol
(S)-5-methoxy-1-(3-methoxyphenyl)-1-((R)-piperidin-3-yl)pentan-1-ol
1-(3-chlorophenyl)-4-cyclopropyl-1-((S)-piperidin-3-yl)butan-1-ol
N—((S)-4-(2-fluorophenyl)-4-hydroxy-4-((R)-piperidin-3-yl)butyl)acetamide
(S)-1-(2-fluoro-3-methylphenyl)-5-methoxy-1-((R)-piperidin-3-yl)pentan-1-ol
(S)-1-(2-fluoro-5-methylphenyl)-5-methoxy-1-((R)-piperidin-3-yl)pentan-1-ol
(S)-1-(3-fluoro-2-methylphenyl)-5-methoxy-1-((R)-piperidin-3-yl)pentan-1-ol
(S)-1-(3-fluoro-4-methylphenyl)-5-methoxy-1-((R)-piperidin-3-yl)pentan-1-ol
(S)-1-(3-fluoro-5-methylphenyl)-5-methoxy-1-((R)-piperidin-3-yl)pentan-1-ol 2-fluoro-6-((S)-1-hydroxy-5-methoxy-1-((R)-piperidin-3-yl)pentyl)phenol
(R)-3-((R)-(3-chlorophenyl)(3-ethoxypropoxy)methyl)piperidine
(S)-1-(2-chlorophenyl)-5-methoxy-1-((R)-piperidin-3-yl)pentan-1-ol
(S)-1-(3-chlorophenyl)-5-methoxy-1-((R)-piperidin-3-yl)pentan-1-ol
(S)-1-(4-chloropyridin-2-yl)-5-methoxy-1-((R)-piperidin-3-yl)pentan-1-ol
(R)-3-((R)-(3-ethoxypropoxy)(3,4-difluorophenyl)methyl)piperidine
(S)-1-(2,3-difluorophenyl)-5-methoxy-1-((R)-piperidin-3-yl)pentan-1-ol
(S)-1-(2,5-difluorophenyl)-5-methoxy-1-((R)-piperidin-3-yl)pentan-1-ol
(S)-1-(3,4-difluorophenyl)-5-methoxy-1-((R)-piperidin-3-yl)pentan-1-ol
(S)-1-(3,5-difluorophenyl)-5-methoxy-1-((R)-piperidin-3-yl)pentan-1-ol
(R)-1-(3-chlorophenyl)-5-methoxy-1-((R)-morpholin-2-yl)pentan-1-ol
(S)-1-(5-chloro-1-methyl-1H-imidazol-2-yl)-5-methoxy-1-((R)-piperidin-3-yl)pentan-1-ol
(S)-1-(benzofuran-7-yl)-5-methoxy-1-((R)-piperidin-3-yl)pentan-1-ol
(S)-1-(1H-indazol-7-yl)-5-methoxy-1-((R)-piperidin-3-yl)pentan-1-ol
(S)-1-(3-isopropylphenyl)-5-methoxy-1-((R)-piperidin-3-yl)pentan-1-ol
4-fluoro-2-((S)-1-hydroxy-5-methoxy-1-((R)-piperidin-3-yl)pentyl)benzonitrile
3-((S)-1-hydroxy-5-methoxy-1-((R)-piperidin-3-yl)pentyl)benzamide
(S)-1-(3-chlorophenyl)-5-cyclopropyl-1-((R)-piperidin-3-yl)pentan-1-ol
N—((S)-4-(2-fluoro-5-methylphenyl)-4-hydroxy-4-((R)-piperidin-3-yl)butyl)acetamide
N—((S)-4-(3-fluoro-5-methylphenyl)-4-hydroxy-4-((R)-piperidin-3-yl)butyl)acetamide
(S)-5-methoxy-1-(3-(methylthio)phenyl)-1-((R)-piperidin-3-yl)pentan-1-ol
N—((S)-4-(3-chlorophenyl)-4-hydroxy-4-((R)-piperidin-3-yl)butyl)acetamide
(S)-1-(2-fluoro-6-methoxyphenyl)-5-methoxy-1-((R)-piperidin-3-yl)pentan-1-ol
(S)-1-(5-fluoro-2-methoxyphenyl)-5-methoxy-1-((R)-piperidin-3-yl)pentan-1-ol
(R)-3-((S)-1-(3-chlorophenyl)-1,5-dimethoxypentyl)piperidine
(S)-1-(3-chloro-2-methylphenyl)-5-methoxy-1-((R)-piperidin-3-yl)pentan-1-ol
N—((S)-4-(2,3-difluorophenyl)-4-hydroxy-4-((R)-piperidin-3-yl)butyl)acetamide
N—((S)-4-(3,5-difluorophenyl)-4-hydroxy-4-((R)-piperidin-3-yl)butyl)acetamide
(R)-3-((R)-(2-(cyclopropylethynyl)phenyl)(3-methoxypropoxy)methyl)piperidine
(S)-5-methoxy-1-((R)-piperidin-3-yl)-1-(quinolin-8-yl)pentan-1-ol
N-(2-((R)-(3-chloro-2-fluorophenyl)((R)-piperidin-3-yl)methoxy)ethyl)acetamide
N-(2-((S)-(3-chloro-2-fluorophenyl)((R)-piperidin-3-yl)methoxy)ethyl)acetamide
(R)-3-((R)-(3-chloro-2-fluorophenyl)(3-ethoxypropoxy)methyl)piperidine
(S)-1-(2-chloro-3-fluorophenyl)-5-methoxy-1-((R)-piperidin-3-yl)pentan-1-ol
(S)-1-(3-chloro-2-fluorophenyl)-5-methoxy-1-((R)-piperidin-3-yl)pentan-1-ol
(S)-1-(3-chloro-5-fluorophenyl)-5-methoxy-1-((R)-piperidin-3-yl)pentan-1-ol
(R)-3-((R)-(3-ethoxypropoxy)(2,3,5-trifluorophenyl)methyl)piperidine
(R)-3-((R)-(3-methoxypropoxy)(2-(trifluoromethyl)phenyl)methyl)piperidine
(R)-3-((R)-(3-methoxypropoxy) (2-(trifluoromethyl)phenyl)methyl)piperidine
(S)-5-methoxy-1-((R)-piperidin-3-yl)-1-(2,3,4-trifluorophenyl)pentan-1-ol
(S)-5-methoxy-1-((R)-piperidin-3-yl)-1-(2,3,5-trifluorophenyl)pentan-1-ol
(S)-5-methoxy-1-(2-methylbenzofuran-7-yl)-1-((R)-piperidin-3-yl)pentan-1-ol
(1R)-1-(3-chloro-2-fluorophenyl)-5-methoxy-1-(morpholin-2-yl)pentan-1-ol
(S)-1-(3-chlorophenyl)-5,5-difluoro-1-((R)-piperidin-3-yl)hexan-1-ol
(S)-1-(benzo[b]thiophen-2-yl)-5-methoxy-1-((R)-piperidin-3-yl)pentan-1-ol
(S)-1-(benzo[b]thiophen-4-yl)-5-methoxy-1-((R)-piperidin-3-yl)pentan-1-ol
(S)-1-(benzo[b]thiophen-7-yl)-5-methoxy-1-((R)-piperidin-3-yl)pentan-1-ol
(S)-1-(2-fluorobenzofuran-7-yl)-5-methoxy-1-((R)-piperidin-3-yl)pentan-1-ol
(S)-1-(5-fluorobenzofuran-7-yl)-5-methoxy-1-((R)-piperidin-3-yl)pentan-1-ol methyl 3-((S)-1-hydroxy-5-methoxy-1-((R)-piperidin-3-yl)pentyl)benzoate
(R)-1-(benzo[b]thiophen-7-yl)-5-methoxy-1-((R)-morpholin-2-yl)pentan-1-ol
N—((S)-4-(3-chlorophenyl)-4-hydroxy-4-((R)-piperidin-3-yl)butyl)propionamide
(R)-3-((R)-biphenyl-2-yl(3-methoxypropoxy)methyl)piperidine
1-((S)-4-(3-chlorophenyl)-4-hydroxy-4-((R)-piperidin-3-yl)butyl)-3-methylurea
(R)-3-((R)-(3-methoxypropoxy)(2-bromophenyl)methyl)piperidine
(R)-3-((R)-(3-methoxypropoxy) (2-bromophenyl)methyl)piperidine
N—((S)-4-(2-chloro-3-fluorophenyl)-4-hydroxy-4-((R)-piperidin-3-yl)butyl)acetamide
N—((S)-4-(3-chloro-2-fluorophenyl)-4-hydroxy-4-((R)-piperidin-3-yl)butyl)acetamide
N—((S)-4-(3-chloro-5-fluorophenyl)-4-hydroxy-4-((R)-piperidin-3-yl)butyl)acetamide
(R)-3-((S)-1-(3-chloro-2-fluorophenyl)-1,5-dimethoxypentyl)piperidine
1-(3-chloro-2-fluorophenyl)-5-ethoxy-1-((R)-piperidin-3-yl)pentan-1-ol
(S)-1-(3-(trifluoromethyl)phenyl)-5-methoxy-1-((R)-piperidin-3-yl)pentan-1-ol
(S)-5-ethoxy-1-((R)-piperidin-3-yl)-1-(2,3,5-trifluorophenyl)pentan-1-ol
(S)-5-methoxy-1-((R)-piperidin-3-yl)-1-(2-(trifluoromethyl)phenyl)pentan-1-ol
(R)-3-((R)-(2,3-dichlorophenyl)(3-ethoxypropoxy)methyl)piperidine
(S)-1-(2,3-dichlorophenyl)-5-methoxy-1-((R)-piperidin-3-yl)pentan-1-ol
1-(2-(cyclopropylmethoxy)phenyl)-5-methoxy-1-((R)-piperidin-3-yl)pentan-1-ol (S)-1-(3-chloro-2,4-difluorophenyl)-5-methoxy-1-((R)-piperidin-3-yl)pentan-1-ol
N—((S)-4-(3-chlorophenyl)-4-hydroxy-4-((R)-piperidin-3-yl)butyl)cyclopropanecarboxamide
N—((S)-4-(3-chlorophenyl)-4-hydroxy-4-((R)-piperidin-3-yl)butyl)butyramide
(S)-1-(2-phenylphenyl)-5-methoxy-1-((R)-piperidin-3-yl)pentan-1-ol
3-((S)-4-(3-chlorophenyl)-4-hydroxy-4-((R)-piperidin-3-yl)butyl)-1,1-dimethylurea
(S)-1-(3-bromophenyl)-5-methoxy-1-((R)-piperidin-3-yl)pentan-1-ol
(S)-1-(2,2-difluorobenzo[d][1,3]dioxol-4-yl)-5-methoxy-1-((R)-piperidin-3-yl)pentan-1-ol
(S)-1-(2,3-dichlorophenyl)-5-ethoxy-1-((R)-piperidin-3-yl)pentan-1-ol
N—((S)-4-(3-chlorophenyl)-4-hydroxy-4-((R)-piperidin-3-yl)butyl)methanesulfonamide
(S)-5-methoxy-1-((R)-piperidin-3-yl)-1-(2-(trifluoromethoxy)phenyl)pentan-1-ol
(S)-5-methoxy-1-((R)-piperidin-3-yl)-1-(3-(trifluoromethoxy)phenyl)pentan-1-ol
1-(2-(2-cyclopropylethoxy)phenyl)-5-methoxy-1-((R)-piperidin-3-yl)pentan-1-ol
1-(2-(cyclobutylmethoxy)phenyl)-5-methoxy-1-((R)-piperidin-3-yl)pentan-1-ol
1-(2-(cyclopentyloxy)phenyl)-5-methoxy-1-((R)-piperidin-3-yl)pentan-1-ol
(S)-4-(aminosulfonylamino)-1-(3-chlorophenyl)-1-((R)-piperidin-3-yl)butan-1-ol
(S)-5-methoxy-1-(2-(2,2-(dimethyl)propoxy)phenyl)-1-((R)-piperidin-3-yl)pentan-1-ol
(S)-1-(2-(cyclopropylmethoxy)-3-fluorophenyl)-5-methoxy-1-((R)-piperidin-3-yl)pentan-1-ol
1-(2-(allyloxy)-5-fluorophenyl)-5-ethoxy-1-((R)-piperidin-3-yl)pentan-1-ol
(S)-4-cyclopropyl-1-(2-phenoxyphenyl)-1-((R)-piperidin-3-yl)butan-1-ol
(R)-3-((R)-(3-methoxypropoxy)(2-phenethylphenyl)methyl)piperidine
(S)-1-(2-(2-methylphenyl)phenyl)-5-methoxy-1-((R)-piperidin-3-yl)pentan-1-ol
(S)-1-(2-(3-methylphenyl)phenyl)-5-methoxy-1-((R)-piperidin-3-yl)pentan-1-ol
(S)-1-(2-(4-methylphenyl)phenyl)-5-methoxy-1-((R)-piperidin-3-yl)pentan-1-ol
(R)—N—((S)-4-(3-chlorophenyl)-4-hydroxy-4-((R)-piperidin-3-yl)butyl)-2-methoxypropanamide
N—((S)-1-(2,3-difluorophenyl)-5-methoxy-1-((R)-piperidin-3-yl)pentyl)propionamide
(S)—N—((S)-4-(3-chlorophenyl)-4-hydroxy-4-((R)-piperidin-3-yl)butyl)-2-methoxypropanamide
(S)-5-methoxy-1-(2-phenoxyphenyl)-1-((R)-piperidin-3-yl)pentan-1-ol
(S)-5-methoxy-1-(2-phenoxyphenyl)-1-((R)-piperidin-3-yl)pentan-1-ol
3-(1-(3-chlorophenyl)-5-methoxy-1-((R)-piperidin-3-yl)pentyloxy)propan-1-ol
(S)-5-methoxy-1-((R)-piperidin-3-yl)-1-(2-(pyridin-4-yloxy)phenyl)pentan-1-ol
(S)-1-(2-(2-fluorophenyl)phenyl)-5-methoxy-1-((R)-piperidin-3-yl)pentan-1-ol
(S)-1-(2-(3-fluorophenyl)phenyl)-5-methoxy-1-((R)-piperidin-3-yl)pentan-1-ol
(S)-1-(2-(4-fluorophenyl)phenyl)-5-methoxy-1-((R)-piperidin-3-yl)pentan-1-ol
(S)-1-(2-phenyl-3-fluorophenyl)-5-methoxy-1-((R)-piperidin-3-yl)pentan-1-ol
(S)-1-(2-isobutylbenzofuran-7-yl)-5-methoxy-1-((R)-piperidin-3-yl)pentan-1-ol
(S)-1-(2-tert-butylbenzofuran-7-yl)-5-methoxy-1-((R)-piperidin-3-yl)pentan-1-ol
(S)-1-(2-bromo-5-fluorophenyl)-5-methoxy-1-((R)-piperidin-3-yl)pentan-1-ol
1-(2-(cyclopentylmethoxy)phenyl)-5-methoxy-1-((R)-piperidin-3-yl)pentan-1-ol
N—((S)-4-(3-chlorophenyl)-4-hydroxy-4-((R)-piperidin-3-yl)butyl)-2,2,2-trifluoroacetamide
(S)-1-(2-(m-tolyloxy)phenyl)-5-methoxy-1-((R)-piperidin-3-yl)pentan-1-ol
(S)-1-(2-(o-tolyloxy)phenyl)-5-methoxy-1-((R)-piperidin-3-yl)pentan-1-ol
1-(2-(benzyloxy)phenyl)-5-methoxy-1-((R)-piperidin-3-yl)pentan-1-ol
(S)-1-(2-(2-fluorophenoxy)phenyl)-5-methoxy-1-((R)-piperidin-3-yl)pentan-1-ol
(S)-1-(2-(3-fluorophenoxy)phenyl)-5-methoxy-1-((R)-piperidin-3-yl)pentan-1-ol
(S)-1-(2-(4-fluorophenoxy)phenyl)-5-methoxy-1-((R)-piperidin-3-yl)pentan-1-ol
(S)-1-(3-fluoro-2-phenoxyphenyl)-5-methoxy-1-((R)-piperidin-3-yl)pentan-1-ol
(S)-1-(5-fluoro-2-phenoxyphenyl)-5-methoxy-1-((R)-piperidin-3-yl)pentan-1-ol
(3R)-tert-butyl 3-((S)-1-(2-(2-chlorophenyl)phenyl)-1-hydroxy-5-methoxypentyl)piperidine-1-carboxylate
(3R)-tert-butyl 3-((S)-1-(2-(4-chlorophenyl)phenyl)-1-hydroxy-5-methoxypentyl)piperidine-1-carboxylate
(S)-1-(2-phenyl-3-chlorophenyl)-5-methoxy-1-((R)-piperidin-3-yl)pentan-1-ol
(S)-1-(2-(3,4-difluorophenyl)phenyl)-5-methoxy-1-((R)-piperidin-3-yl)pentan-1-ol
1-(2-(cyclohexylmethoxy)phenyl)-5-methoxy-1-((R)-piperidin-3-yl)pentan-1-ol
(S)-1-(2-(2-ethylphenoxy)phenyl)-5-methoxy-1-((R)-piperidin-3-yl)pentan-1-ol
(S)-1-(2-(o-tolyloxy)-3-methylphenyl)-5-methoxy-1-((R)-piperidin-3-yl)pentan-1-ol
(S)-1-(2-(p-tolyloxy)-5-methylphenyl)-5-methoxy-1-((R)-piperidin-3-yl)pentan-1-ol
(S)-5-methoxy-1-(3-methyl-2-(o-tolyloxy)phenyl)-1-((R)-piperidin-3-yl)pentan-1-ol
N—((S)-1-(3-chloro-2-fluorophenyl)-5-methoxy-1-((R)-piperidin-3-yl)pentyl)butyramide
(S)-1-(2-(4-fluoro-2-methylphenoxy)phenyl)-5-methoxy-1-((R)-piperidin-3-yl)pentan-1-ol
(S)-1-(2-(5-fluoro-2-methylphenoxy)phenyl)-5-methoxy-1-((R)-piperidin-3-yl)pentan-1-ol
(S)-1-(2-(p-tolyloxy)-3-fluorophenyl)-5-methoxy-1-((R)-piperidin-3-yl)pentan-1-ol
(S)-1-(2-fluoro-3-(o-tolyloxy)phenyl)-5-methoxy-1-((R)-piperidin-3-yl)pentan-1-ol
(S)-1-(3-fluoro-2-(o-tolyloxy)phenyl)-5-methoxy-1-((R)-piperidin-3-yl)pentan-1-ol
1-(2-(4-fluorobenzyloxy)phenyl)-5-methoxy-1-((R)-piperidin-3-yl)pentan-1-ol
(S)-1-(2-(2-chlorophenoxy)phenyl)-5-methoxy-1-((R)-piperidin-3-yl)pentan-1-ol
(S)-1-(5-chloro-2-phenoxyphenyl)-5-methoxy-1-((R)-piperidin-3-yl)pentan-1-ol.
(S)-1-(3,5-difluoro-2-phenoxyphenyl)-5-methoxy-1-((R)-piperidin-3-yl)pentan-1-ol (S)-1-(5-fluoro-2-(4-fluorophenoxy)phenyl)-5-methoxy-1-((R)-piperidin-3-yl)pentan-1-ol (S)-5-methoxy-1-((R)-piperidin-3-yl)-1-(2-(trimethylsilyl)benzo[b]thiophen-7-yl)pentan-1-ol (S)-1-(3'-chloro-6-fluorobiphenyl-2-yl)-5-methoxy-1-((R)-piperidin-3-yl)pentan-1-ol (S)-1-(2-(allyloxy)-3-bromophenyl)-5-methoxy-1-((R)-piperidin-3-yl)pentan-1-ol (S)-1-(2-(o-tolyloxy)-3,5-difluorophenyl)-5-methoxy-1-((R)-piperidin-3-yl)pentan-1-ol (S)-1-(2-(2-(trifluoromethyl)phenoxy)phenyl)-5-methoxy-1-((R)-piperidin-3-yl)pentan-1-ol and (S)-1-(3-chlorophenyl)-2-(2-methoxyethoxy)-1-((R)-piperidin-3-yl)ethanol When any variable (e.g., aryl, heterocyclyl, $R_1$, $R_2$, etc.) occurs more than once in a compound, its definition on each occurrence is independent of any other occurrence.

"Alkyl" means a saturated aliphatic branched or straight-chain mono- or di-valent hydrocarbon radical having the specified number of carbon atoms. Thus, "$(C_1-C_8)$alkyl" means a radical having from 1-8 carbon atoms in a linear or branched arrangement. "$(C_1-C_6)$alkyl" includes methyl, ethyl, propyl, butyl, pentyl, and hexyl.

"Cycloalkyl" means a saturated aliphatic cyclic hydrocarbon radical having the specified number of carbon atoms. Thus, $(C_3-C_7)$cycloalkyl means a radical having from 3-8 carbon atoms arranged in a ring. $(C_3-C_7)$cycloalkyl includes cyclopropyl, cyclobutyl, cyclopentyl, cyclohexyl, and cycloheptyl.

Haloalkyl and halocycloalkyl include mono, poly, and perhaloalkyl groups where the halogens are independently selected from fluorine, chlorine, and bromine Saturated heterocyclic rings are 4-, 5-, 6-, and 7-membered heterocyclic rings containing 1 to 4 heteroatoms independently selected from N, O, and S, and include pyrrolidine, piperidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, morpholine, thiomorpholine, thiomorpholine 1,1-dioxide, tetrahydro-2H-1,2-thiazine 1,1-dioxide, and isothiazolidine 1,1-dioxide. Oxo substituted saturated heterocyclic rings include tetrahydrothiophene 1-oxide, tetrahydrothiophene 1,1-dioxide, thiomorpholine 1-oxide, thiomorpholine 1,1-dioxide, tetrahydro-2H-1,2-thiazine 1,1-dioxide, and isothiazolidine 1,1-dioxide, pyrrolidin-2-one, piperidin-2-one, piperazin-2-one, and morpholin-2-one.

"Heteroaryl" means a monovalent heteroaromatic monocyclic and polycylic ring radical containing 1 to 4 heteroatoms independently selected from N, O, and S. Heteroaryl rings include furyl, thienyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridinyl-N-oxide, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, cinnolinyl, phthalzinyl, quinazolinyl, quinoxalinyl, 1,8-naphthyridinyl, 1,2,3-triazolyl, 1,2,4-triazolyl, 1,3,4-oxadiazolyl, 1,2,5-thiadiazolyl, 1,2,5-thiadiazolyl-1-oxide, 1,2,5-thiadiazolyl-1,1-dioxide, 1,3,4-thiadiazolyl, 1,2,4-triazinyl, 1,3,5-triazinyl, tetrazolyl, and pteridinyl.

Bicyclic heteroaryl rings are bicyclo[4.4.0] and bicyclo[4.3.0] fused ring systems of which at least one ring is aromatic containing 1 to 4 heteroatoms independently selected from N, O, and S, and include indole, quinoline, isoquinoline, quinazoline, benzothiophene, benzofuran, 2,3-dihydrobenzofuran, benzodioxole, benzimidazole, indazole, benzisoxazole, benzoxazole, and benzothiazole.

Bicycloalkyl rings are fused, bridged and spiro ring systems and include bicyclo[1.1.0]butane, bicyclo[1.2.0]pentane, bicyclo[2.2.0]hexane, bicyclo[3.2.0]heptane, bicyclo[3.3.0]octane, bicyclo[4.2.0]octane, bicyclo[2.2.1]heptane, bicyclo[2.2.2]octane, bicyclo[3.2.1]octane, bicyclo[3.2.2]nonane, bicyclo[3.3.1]nonane, bicyclo[3.3.2]decane and bicyclo[3.3.3]undecane, spiro[2.2]pentane, spiro[2.3]hexane, spiro[3.3]heptane, spiro[2.4]heptane, spiro[3.4]octane and spiro[2.5]octane.

Tricycloalkyl rings are fused, bridged and spiro ring systems and include tricyclo[3.3.1.0$^{3,7}$]nonane (noradamantane) and tricyclo[3.3.1.1$^{3,7}$]decane (adamantane).

"Alkoxy" means an alkyl radical attached through an oxygen linking atom. "$(C_1-C_4)$-alkoxy" includes the methoxy, ethoxy, propoxy, and butoxy.

"Aromatic" means an unsaturated cycloalkyl ring system.

"Aryl" means an aromatic monocyclic or polycyclic ring system. Aryl systems include phenyl, naphthalenyl, fluorenyl, indenyl, azulenyl, and anthracenyl.

"Hetero" refers to the replacement of at least one carbon atom member in a ring system with at least one heteroatom selected from N, S, and O. A hetero ring may have 1, 2, 3, or 4 carbon atom members replaced by a heteroatom.

"Oxo" refers to =O. When an oxo group is a substituent on a carbon atom, they form a carbonyl group (—C(O)—). When one oxo group is a substituent on a sulfur atom, they form a sulfinyl (sulfoxide —S(O)—) group. When two oxo groups are a substituent on a sulfur atom, they form a sulfonyl (sulfone —S(O)$_2$—) group.

In certain instances herein when describing functional groups, "alkane", "cycloalkane" and the like are used interchangeably with "alkyl" and "cycloalkyl", respectively. Thus, by way of example, "alkanesulfonyl" means an alkyl group attached to a sulfonyl moiety, and "cycloalkanesulfonyl" refers to a cycloalkyl group attached to a sulfonyl moiety.

Enantiomers, Diastereomers, and Salts

Certain compounds of Formula I may exist in various stereoisomeric or tautomeric forms. The invention encompasses all such forms, including active compounds in the form of essentially pure enantiomers, racemic mixtures, and tautomers.

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

The compounds of the invention include pharmaceutically acceptable anionic salt forms, wherein the anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

The anionic salt form of a compound of the invention includes the acetate, bromide, camsylate, chloride, edisylate, fumarate, hydrobromide, hydrochloride, iodide, isethionate, lactate, mesylate, maleate, napsylate, salicylate, sulfate, and tosylate salts.

It may be necessary and/or desirable during synthesis to protect sensitive or reactive groups on any of the molecules concerned. Representative conventional protecting groups are described in T. W. Greene and P. G. M. Wuts "Protective Groups in Organic Synthesis" John Wiley & Sons, Inc., New York 1999. Protecting groups may be added and removed using methods well known in the art.

The invention also includes various isomers and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers).

Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms. When a chiral center is not defined as R or S, a mixture of both configurations is present.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

Atoms (other than H) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. A mixture of "cis" and "trans" species is designated "cis/trans".

"R," "S," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

Biological Assay Procedures

The compounds of the invention have enzyme-inhibiting properties. In particular, they inhibit the action of the natural enzyme renin. The latter passes from the kidneys into the blood where it effects the cleavage of angiotensinogen, releasing the decapeptide angiotensin I which is then cleaved in the blood, lungs, the kidneys and other organs by angiotensin converting enzyme to form the octapeptide angiotensin II. The octapeptide increases blood pressure both directly by binding to its receptor, causing arterial vasoconstriction, and indirectly by liberating from the adrenal glands the sodium-ion-retaining hormone aldosterone, accompanied by an increase in extracellular fluid volume. That increase can be attributed to the action of angiotensin II. Inhibitors of the enzymatic activity of renin bring about a reduction in the formation of angiotensin I. As a result a smaller amount of angiotensin II is produced. The reduced concentration of that active peptide hormone is the direct cause of the hypotensive effect of renin inhibitors.

The action of renin inhibitors in vitro is demonstrated experimentally by means of a test which measures the increase in fluorescence of an internally quenched peptide substrate. The sequence of this peptide corresponds to the sequence of human angiotensinogen. The following test protocol is used. All reactions are carried out in a flat bottom white opaque microtiter plate. A 4 µL aliquot of 400 µM renin substrate (DABCYL-γ-Abu-Ile-His-Pro-Phe-His-Leu-Val-Ile-His-Thr-EDANS) in 192 µL assay buffer (50 mM BES, 150 mM NaCl, 0.25 mg/mL bovine serum albumin, pH7.0) is added to 4 µL of test compound in DMSO at various concentrations ranging from 10 µM to 1 nM final concentrations. Next, 100 µL of trypsin-activated recombinant human renin (final enzyme concentration of 0.2-2 nM) in assay buffer is added, and the solution is mixed by pipetting. The increase in fluorescence at 495 nm (excitation at 340 nm) is measured for 60-360 minutes at rt using a Perkin-Elmer Fusion microplate reader. The slope of a linear portion of the plot of fluorescence increase as a function of time is then determined, and the rate is used for calculating percent inhibition in relation to uninhibited control. The percent inhibition values are plotted as a function of inhibitor concentration, and the $IC_{50}$ is determined from a fit of this data to a four parameter equation. The $IC_{50}$ is defined as the concentration of a particular inhibitor that reduces the formation of product by 50% relative to a control sample containing no inhibitor. In the in vitro systems the compounds of the invention exhibit inhibiting activities at minimum concentrations of from approximately $5 \times 10^{-5}$ M to approximately $10^{-12}$ M. Preferred compounds of the invention exhibit inhibiting activities at minimum concentrations of from approximately $10^{-7}$ M to approximately $10^{-12}$ M. (Wang G. T. et al. *Anal. Biochem.* 1993, 210, 351; Nakamura, N. et al. *J. Biochem.* (*Tokyo*) 1991, 109, 741; Murakami, K. et al. *Anal Biochem.* 1981, 110, 232).

The action of renin inhibitors in vitro in human plasma is demonstrated experimentally by the decrease in plasma renin activity (PRA) levels observed in the presence of the compounds. Incubations mixtures contained in the final volume of 250 μL 95.5 mM N,N-bis(2-hydroxyethyl)-2-aminoethanesulfonic acid, pH 7.0, 8 mM EDTA, 0.1 mM neomycin sulfate, 1 mg/mL sodium azide, 1 mM phenylmethanesulfonyl fluoride, 2% DMSO and 87.3% of pooled mixed-gender human plasma stabilized with EDTA. For plasma batches with low PRA (less than 1 ng/ml/hr) ~2 pM of recombinant human renin was added to achieve PRA of 3-4 ng/ml/hr. The cleavage of endogenous angiotensinogen in plasma was carried out at 37° C. for 90 min and the product angiotensin I was measured by competitive radioimmunoassay using DiaSorin PRA kit. Uninhibited incubations containing 2% DMSO and fully inhibited controls with 2 μM of isovaleryl-Phe-Nle-Sta-Ala-Sta-OH were used for deriving percent of inhibition for each concentration of inhibitors and fitting dose-response data into a four parametric model from which $IC_{50}$ values, defined as concentrations of inhibitors at which 50% inhibition occurs, were determined.

The cardiac and systemic hemodynamic efficacy of selective renin inhibitors were evaluated in vivo in sodium-depleted, normotensive cynomolgus monkeys and in sodium-depleted, normotensive beagle dogs following a single oral and intravenous administration of the test compound. Arterial blood pressure was monitored by telemetry in freely moving, conscious animals.

Cynomolgus Monkey: Six male naïve cynomolgus monkeys weighing between 2.5 and 3.5 kg were used in the studies. At least 4 weeks before the experiment, the monkeys were anesthetized with ketamine hydrochloride (15 mg/kg, i.m.) and xylazine hydrochloride (0.7 mg/kg, i.m.), and were implanted into the abdominal cavity with a transmitter (Model #TL11M2-D70-PCT, Data Sciences, St. Paul, Minn.). The pressure catheter was inserted into the lower abdominal aorta via the femoral artery. The bipotential leads were placed in Lead II configuration. The animals were housed under constant temperature (19-25° C.), humidity (>40%) and lighting conditions (12 h light and dark cycle), were fed once daily, and were allowed free access to water. The animals were sodium depleted by placing them on a low sodium diet (0.026%, Expanded Primate Diet 829552 MP-VENaCl (P), Special Diet Services, Ltd., UK) 7 days before the experiment and furosemide (3 mg/kg, intramuscularly i.m., Aventis Pharmaceuticals) was administered at −40 h and −16 h prior to administration of test compound.

For oral dosing, the renin inhibitors were formulated in 0.5% methylcellulose at dose levels of 10 and 30 mg/kg (5 mL/kg) by infant feeding tubes. For intravenous delivery, a silastic catheter was implanted into posterior vena cava via a femoral vein. The catheter was attached to the delivery pump via a tether system and a swivel joint. Test compound (dose levels of 0.1 to 10 mg/kg, formulated at 5% dextrose) was administered by continuous infusion (1.67 mL:/kg/h) or by bolus injection (3.33 mL/kg in 2 min).

Arterial blood pressures (systolic, diastolic and mean) and body temperature were recorded continuously at 500 Hz and 50 Hz, respectively, using the Dataquest™ A.R.T. (Advanced Research Technology) software. Heart rate was derived from the phasic blood pressure tracing. During the recording period, the monkeys were kept in a separate room without human presence to avoid pressure changes secondary to stress. All data were expressed as mean±SEM. Effects of the renin inhibitors on blood pressure were assessed by ANOVA, taking into account the factors dose and time compared with the vehicle group.

Beagle Dogs: Non-naive Beagle dogs (2 per sex) weighing between 9 and 11 kg were used in the studies. Each animal was implanted subcutaneously with a telemetry transmitter (Data Sciences) and the blood pressure catheter was inserted into the left femoral artery. The electrocardiogram leads were also tunneled subcutaneously to the appropriate anatomical regions. The animals were housed under constant temperature and lighting conditions, were fed once daily, and were allowed free access to water. A sodium depleted state was produced by placing them on a low-sodium diet (<4 meq/day, a combination of canned Prescription Diet canine h/d, from Hill's Pet Products and dry pellets from Bio-Serv Inc., Frenchtown, N.J.) beginning 10 days before the experiment, and furosemide (3 mg/kg i.m.; Aventis Pharmaceuticals) was administered at −40 and −16 h prior to administration of test compound.

A renin inhibitor was orally administered by orogastric gavage to all overnight fasted animals at a dose level of 30 mg/kg (4 mL/kg formulated in 0.5% methylcellulose). Food was given 4 h postdose. In some experiments, the renin inhibitor was administered by bolus i.v. at increasing dose levels of 1, 3 and 6 mg/kg (2, 6 and 20 mg/mL formulated in sterile saline). Cardiovascular parameters were collected continuously at least 80 min predose and 3 h postdose, followed by every 10 min for 5 h and every 30 min for 16 h postdose. The Dataquest™ ART (version 2.2) software package from DSI (Data Sciences International) was used to collect telemetered cardiovascular data.

The efficacy of the renin inhibitors was also evaluated in vivo in double transgenic rats engineered to express human renin and human angiotensinogen (Bohlender J, Fukamizu A, Lippoldt A, Nomura T, Dietz R, Menard J, Murakami K, Luft F C, Ganten D. High human renin hypertension in transgenic rats. *Hypertension* 1997, 29, 428-434).

Experiments were conducted in 6-week-old double transgenic rats (dTGRs). The model has been described in detail earlier. Briefly, the human renin construct used to generate transgenic animals made up the entire genomic human renin gene (10 exons and 9 introns), with 3.0 kB of the 5'-promoter region and 1.2 kB of 3' additional sequences. The human angiotensinogen construct made up the entire human angiotensinogen gene (5 exons and 4 introns), with 1.3 kB of 5'-flanking and 2.4 kB of 3'-flanking sequences. The rats were purchased from RCC Ltd (Füllinsdorf, Switzerland). Radio telemetry transmitters were surgically implanted at 4 weeks of age. The telemetry system provided 24-h recordings of systolic, mean, diastolic arterial pressure (SAP, MAP, DAP, respectively) and heart rate (HR). Beginning on day 42, animals were transferred to telemetry cages. A 24 h telemetry reading was obtained. Rats were then dosed orally on the following 4 consecutive days (days 43-46). The rats were monitored continuously and allowed free access to standard 0.3%-sodium rat chow and drinking water.

The compounds of the invention are useful for ameliorating or treating disorders or diseases in which decreasing the levels of aspartic protease products is effective in treating the disease state or in treating infections in which the infectious agent depends upon the activity of an aspartic protease. In hypertension elevated levels of angiotensin I, the product of renin catalyzed cleavage of angioteninogen are present. Elevated levels of β amyloid, the product of BACE activity on amyloid precursor protein, are believed to be responsible for the amyloid plaques present in the brains of Alzheimer's disease patients. The viruses HIV and HTLV depend on their respective aspartic proteases for viral maturation. *Plasmodium falciparum* uses plasmepsins I and II to degrade hemoglobin.

The compounds of the invention are useful for ameliorating or treating disorders or diseases in which decreasing the levels of renin products is effective in treating a disease state. In hypertension elevated levels of angiotensin I, the product of renin catalyzed cleavage of angioteninogen are present. Thus, the compounds of the invention can be used in the treatment of hypertension, congestive heart failure, cardiac hypertrophy, cardiac fibrosis, cardiomyopathy post-infarction, complications resulting from diabetes, such as nephropathy, vasculopathy and neuropathy, diseases of the coronary vessels, proteinuria, albumenuria, post-surgical hypertension, metabolic syndrome, obesity, restenosis following angioplasty, raised intra-ocular pressure, glaucoma, abnormal vascular growth, hyperaldosteronism, anxiety states, and cognitive disorders (Fisher N. D.; Hollenberg N. K. *Expert Opin. Investig. Drugs.* 2001, 10, 417-26).

A pharmaceutical composition of the invention may, alternatively or in addition to a compound of Formula I, comprise a pharmaceutically acceptable salt of a compound of Formula I or a prodrug or pharmaceutically active metabolite of such a compound or salt and one or more pharmaceutically acceptable carriers therefor.

The compositions of the invention are aspartic protease inhibitors. Said compositions contain compounds having a mean inhibition constant ($IC_{50}$) against aspartic proteases of between about 5,000 nM to about 0.001 nM; preferably between about 50 nM to about 0.001 nM; and more preferably between about 5 nM to about 0.01 nM.

The compositions of the invention reduce blood pressure. Compounds I-1 through I-559 have an $IC_{50}$ for renin of between about 5,000 nM to about 0.001 nM. Many of these compounds have an $IC_{50}$ between about 50 nM to about 0.001 nM; and others between about 5 nM to about 0.001 nM.

The invention includes a therapeutic method for treating or ameliorating an aspartic protease mediated disorder in a subject in need thereof comprising administering to a subject in need thereof an effective amount of a compound of Formula I, or the enantiomers, diastereomers, or salts thereof or composition thereof.

Administration methods include administering an effective amount (i.e., a therapeutically effective amount) of a compound or composition of the invention at different times during the course of therapy or concurrently in a combination form. The methods of the invention include all known therapeutic treatment regimens.

"Prodrug" means a pharmaceutically acceptable form of an effective derivative of a compound (or a salt thereof) of the invention, wherein the prodrug may be: 1) a relatively active precursor which converts in vivo to a compound of the invention; 2) a relatively inactive precursor which converts in vivo to a compound of the invention; or 3) a relatively less active component of the compound that contributes to therapeutic activity after becoming available in vivo (i.e., as a metabolite). See "Design of Prodrugs", ed. H. Bundgaard, Elsevier, 1985.

"Metabolite" means a pharmaceutically acceptable form of a metabolic derivative of a compound (or a salt thereof of the invention, wherein the derivative is an active compound that contributes to therapeutic activity after becoming available in vivo.

"Effective amount" means that amount of active compound agent that elicits the desired biological response in a subject. Such response includes alleviation of the symptoms of the disease or disorder being treated. The effective amount of a compound of the invention in such a therapeutic method is from about 10 mg/kg/day to about 0.01 mg/kg/day.

The invention includes the use of a compound of the invention for the preparation of a composition for treating or ameliorating an aspartic protease mediated chronic disorder or disease or infection in a subject in need thereof, wherein the composition comprises a mixture one or more compounds of the invention and an optional pharmaceutically acceptable carrier.

"Pharmaceutically acceptable carrier" means compounds and compositions that are of sufficient purity and quality for use in the formulation of a composition of the invention and that, when appropriately administered to an animal or human, do not produce an adverse reaction.

"Aspartic protease mediated disorder or disease" includes disorders or diseases associated with the elevated expression or overexpression of aspartic proteases and conditions that accompany such diseases.

An embodiment of the invention includes administering a renin inhibiting compound of Formula I or composition thereof in a combination therapy (see U.S. Pat. No. 5,821,232, U.S. Pat. No. 6,716,875, U.S. Pat. No. 5,663,188, or Fossa, A. A.; DePasquale, M. J.; Ringer, L. J.; Winslow, R. L. "Synergistic effect on reduction in blood pressure with coadministration of a renin inhibitor or an angiotensin-converting enzyme inhibitor with an angiotensin II receptor antagonist" *Drug Development Research* 1994, 33(4), 422-8) with one or more additional agents for the treatment of hypertension including α-blockers, β-blockers, calcium channel blockers, diuretics, natriuretics, saluretics, centrally acting antihypertensives, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonists.

α-Blockers include doxazosin, prazosin, tamsulosin, and terazosin.

β-Blockers for combination therapy are selected from atenolol, bisoprol, metoprolol, acetutolol, esmolol, celiprolol, taliprolol, acebutolol, oxprenolol, pindolol, propanolol, bupranolol, penbutolol, mepindolol, carteolol, nadolol, carvedilol, and their pharmaceutically acceptable salts.

Calcium channel blockers include dihydropyridines (DHPs) and non-DHPs. The preferred DHPs are amlodipine, felodipine, ryosidine, isradipine, lacidipine, nicardipine, nifedipine, nigulpidine, niludipine, nimodiphine, nisoldipine, nitrendipine, and nivaldipine, and their pharmaceutically acceptable salts. Non-DHPs are flunarizine, prenylamine, diltiazem, fendiline, gallopamil, mibefradil, anipamil, tiapamil, and verampimil, and their pharmaceutically acceptable salts.

A diuretic is, for example, a thiazide derivative selected from amiloride, chlorothiazide, hydrochlorothiazide, methylchlorothiazide, and chlorothalidon.

Centrally acting antihypertensives include clonidine, guanabenz, guanfacine and methyldopa.

ACE inhibitors include alacepril, benazepril, benazaprilat, captopril, ceronapril, cilazapril, delapril, enalapril, enalaprilat, fosinopril, lisinopril, moexipiril, moveltopril, perindopril, quinapril, quinaprilat, ramipril, ramiprilat, spirapril, temocapril, trandolapril, and zofenopril. Preferred ACE inhibitors are benazepril, enalpril, lisinopril, and ramipril.

Dual ACE/NEP inhibitors are, for example, omapatrilat, fasidotril, and fasidotrilat.

Preferred ARBs include candesartan, eprosartan, irbesartan, losartan, olmesartan, tasosartan, telmisartan, and valsartan.

Preferred aldosterone synthase inhibitors are anastrozole, fadrozole, and exemestane.

Preferred aldosterone-receptor antagonists are spironolactone and eplerenone.

A preferred endothelin antagonist is, for example, bosentan, enrasentan, atrasentan, darusentan, sitaxsentan, and tezosentan, and their pharmaceutically acceptable salts.

An embodiment of the invention includes administering an HIV protease inhibiting compound of Formula I or composition thereof in a combination therapy with one or more additional agents for the treatment of AIDS including reverse transcriptase inhibitors, non-nucleoside reverse transcriptase inhibitors, other HIV protease inhibitors, HIV integrase inhibitors, attachment and fusion inhibitors, antisense drugs, and immune stimulators.

Preferred reverse transcriptase inhibitors are zidovudine, didanosine, zalcitabine, stavudine, lamivudine, abacavir, tenofovir, and emtricitabine.

Preferred non-nucleoside reverse transcriptase inhibitors are nevirapine, delaviridine, and efavirenz.

Preferred HIV protease inhibitors are saquinavir, ritonavir, indinavir, nelfinavir, amprenavir, lopinavir, atazanavir, and fosamprenavir.

Preferred HIV integrase inhibitors are L-870,810 and S-1360.

A preferred attachment and fusion inhibitor is enfuvirtide.

An embodiment of the invention includes administering β-secretase inhibiting compound of Formula I or composition thereof in a combination therapy with one or more additional agents for the treatment of Alzheimer's disease including tacrine, donepezil, rivastigmine, galantamine, and memantine.

An embodiment of the invention includes administering a plasmepsin inhibiting compound of Formula I or composition thereof in a combination therapy with one or more additional agents for the treatment of malaria including artemisinin, chloroquine, halofantrine, hydroxychloroquine, mefloquine, primaquine, pyrimethamine, quinine, and sulfadoxine Combination therapy includes co-administration of the compound of the invention and said other agent, sequential administration of the compound and the other agent, administration of a composition containing the compound and the other agent, or simultaneous administration of separate compositions containing the compound and the other agent.

The invention further includes the process for making the composition comprising mixing one or more of the present compounds and an optional pharmaceutically acceptable carrier; and includes those compositions resulting from such a process, which process includes conventional pharmaceutical techniques.

The compositions of the invention include ocular, oral, nasal, transdermal, topical with or without occlusion, intravenous (both bolus and infusion), and injection (intraperitoneally, subcutaneously, intramuscularly, intratumorally, or parenterally). The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions of the invention may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition of the invention contains a therapeutically effective amount of the active ingredient necessary to provide a therapeutic effect. The composition may contain from about 5,000 mg to about 0.5 mg (preferably, from about 1,000 mg to about 0.5 mg) of a compound of the invention or salt form thereof and may be constituted into any form suitable for the selected mode of administration. The composition may be administered about 1 to about 5 times per day. Daily administration or post-periodic dosing may be employed.

For oral administration, the composition is preferably in the form of a tablet or capsule containing, e.g., 500 to 0.5 milligrams of the active compound. Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Compounds of the invention may also be administered via a slow release composition; wherein the composition includes a compound of the invention and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles (e.g., in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

The compound of Formula I may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The compounds may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the active ingredient in the liquid carrier whereby the final dosage unit contains from 0.005 to 10% by weight of the active ingredient. Other additives include preservatives, isotonizers, solubilizers, stabilizers, and pain-soothing agents. Injectable suspensions may also be prepared, in which case appropriate liquid carriers, suspending agents and the like may be employed.

Compounds of the invention may be administered intranasally using a suitable intranasal vehicle.

Compounds of the invention may also be administered topically using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration n the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

Methods of Preparation

In the discussion below $R^1$, $R^2$, $R^3$, X, Y, A, Q, $R^4$, L, $R^5$, $R^6$, $R^7$, $R^8$, L, G, $R^9$, and $R^{10}$ are defined as described above for compounds of Formula I and E is defined as describe above for compounds of Formula III. In cases where the synthetic intermediates and final products of Formula I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999).

A compound of Formula I is prepared by reaction of an intermediate of Formula IV with an amine intermediate of formula V:

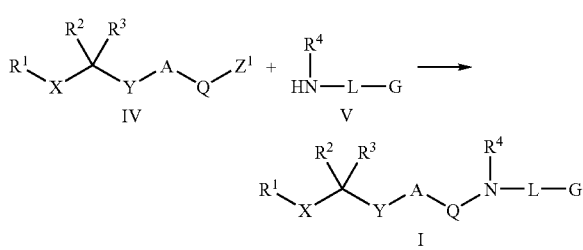

wherein $Z^1$ in IV is a leaving group such as halide, alkanesulfonate, haloalkanesulfonate, arylsulfonate, aryloxide, heteroaryloxide, azole, azolium salt, or alkoxide.

Alternatively, a compound of Formula I is prepared by reaction of a compound of formula VI with a compound of formula VII wherein $Z^1$ is a leaving group such as halide, alkanesulfonate, arylsulfonate, aryloxide, azole, azolium salt, or alkoxide:

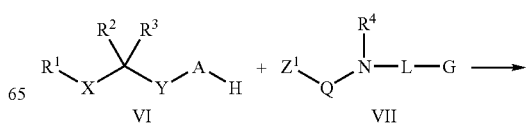

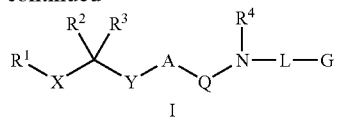

I wherein the H atom in VI is attached to a nitrogen atom that is part of A.

Furthermore, compounds of Formula I can also be prepared from other compounds of Formula I and protected compounds of Formula I:

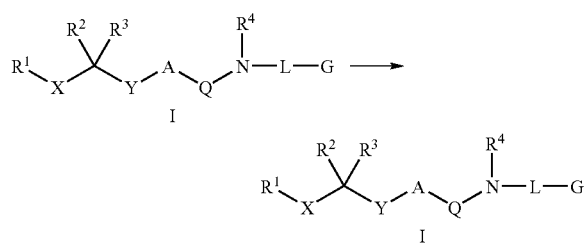

For example, when a bromophenyl, iodophenyl or trifluoromethanesulfonyloxyphenyl group is present in a compound of Formula I, it may be transformed into a biphenyl using a Suzuki coupling, to an alkynylbenzene using a Sonogashira coupling, to an allylbenzene using a Stille coupling, to a cyanobenzene using CuCN or to a methoxycarbonylbenzene using a palladium catalyzed carbonylation in the presence of methanol. Another example is the transformation of a compound of Formula I wherein $R^3$=OH to the analogous compound wherein $R^3$=H by dehydration followed by hydrogenation or in a single step by deoxygenation using Raney nickel. Another example is the deoxygenation of a compound of Formula I wherein Q=Q11 to a compound of Formula I where Q=Q10. Another example is the reaction of a compound of Formula I wherein $R^2$=OH and $R^3$=H with an alcohol in the presence of acid to afford a compound of Formula I wherein $R^2$ is a group attached through an ether linkage.

Intermediates of Formula IV wherein $Z^1$=chlorine and Q is Q1, Q6 or Q8 that is attached to a carbon atom that is part of A are prepared from intermediates VIII:

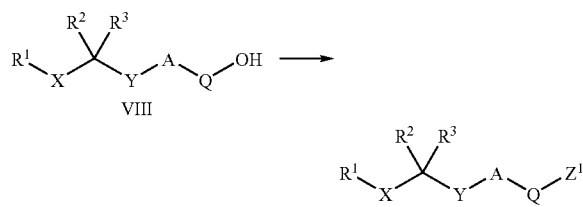

by reaction with, for example, thionyl chloride or oxalyl chloride.

Intermediates of Formula IV wherein Q is Q9 or Q11 or Q12, Q is attached to a nitrogen atom that is part of A and $Z^1$ is methoxy are prepared from intermediates VI by reaction with 3,4-dimethoxy-3-cyclobutene-1,2-dione, 3,4-dimethoxy-1,2,5-thiadiazole-1-oxide and 3,4-dimethoxy-1,2,5-thiadiazole-1,1-dioxide respectively:

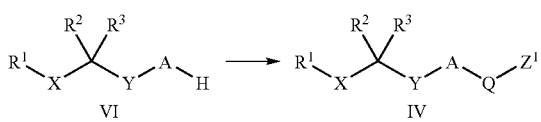

Intermediates of Formula IV wherein Q is Q1, Q1 is attached to a nitrogen atom that is part of A and Z1 is chlorine, 1-imidazolyl, or p-nitrophenoxy are prepared from intermediates of formula VI wherein H is attached to a nitrogen atom that is part of A by reaction with phosgene, 1,1'-carbonyldiimidazole, or p-nitrophenyl chloroformate respectively.

Intermediates of formula VI wherein H is attached to a nitrogen atom that is part of A are prepared from intermediates of Formula IX:

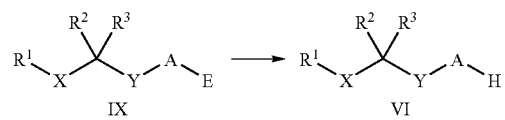

wherein E is an amine protecting group, including carbamate, amide, and sulfonamide protecting groups known in the art (T. W. Greene and P. G. M. Wuts "Protective Groups in Organic Synthesis" John Wiley & Sons, Inc., New York 1999).

Intermediates of Formula IX wherein $R^3$=OH are prepared from intermediates of formula X by addition of an organometallic reagent of formula $R^2M$ where M is for example Li, MgCl, MgBr, or MgI to the carbonyl group of X:

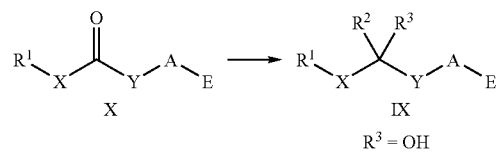

Intermediates of Formula IX wherein $R^3$=H and $R^2$ is a group attached by an ether linkage are prepared from intermediates of formula XI by reaction with an alkylating agent under basic conditions or by reaction with an alcohol of formula $R^2OH$ under acidic conditions.

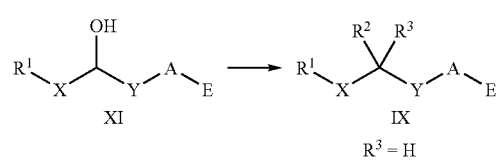

Intermediates of formula XI are prepared by reduction of intermediates of formula X:

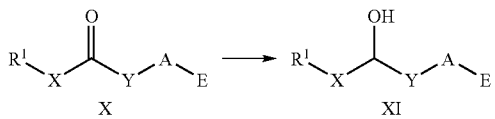

or by addition of an organometallic reagent of formula XII wherein M is, for example Li, MgCl, MgBr, or MgI to an aldehyde of Formula XIII:

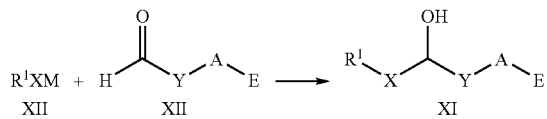

Intermediates of formula X are prepared by the addition of an organometallic reagent of formula XII to a carboxylic acid derivative of formula XIV wherein $Z^2$ is an alkoxide, dialkylamino group, or an alkoxyalkylamino group:

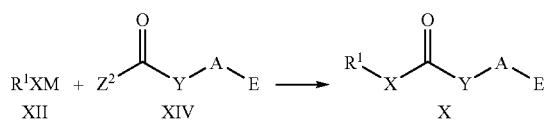

Organometallic reagents of formula XII are prepared by known process including halogen-lithium exchange, ortholithiation and treatment of halides $R^1X$-Hal with magnesium or lithium metal.

Intermediates of formula X are also prepared by oxidation of an intermediate of formula XI:

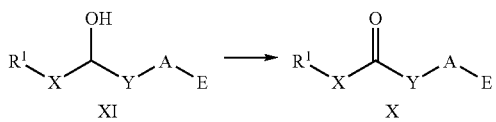

Optionally protected compounds of Formula I are prepared from compounds of formula XV by addition of an organometallic $R^2M$:

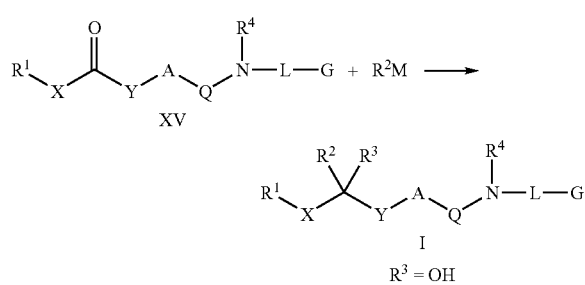

Intermediates of formula XV wherein Q is Q1 and Q1 is attached to a carbon atom that is part of A are prepared by coupling of intermediates of formula XVI and amine intermediates of formula V using peptide forming reagents or by activating XVI as an acid chloride.

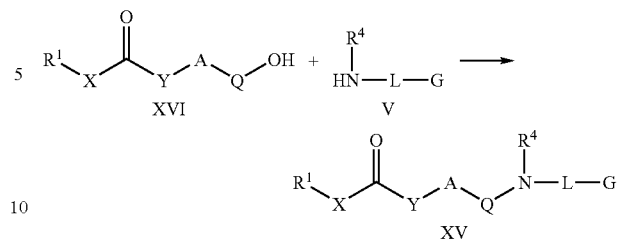

Intermediates of formula XVI in which Q=Q1, Q3, Q6, Q7 and Q8 are prepared from cyclic anhydrides of formula XVII by reaction with organometallic reagents of formula $R^1XM$:

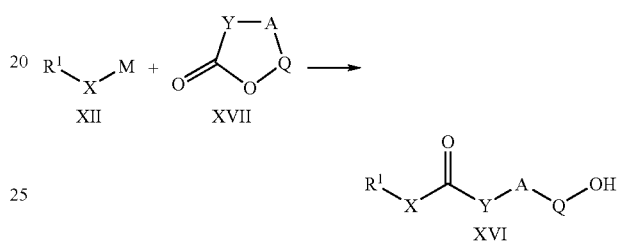

Optionally protected compounds of Formula I wherein $R^2$ is a group attached through an ether linkage are prepared from compounds of formula XVIII by reaction with an alcohol $R^2H$ of formula XIX, wherein $R^2$ is selected from the subset of $R^2$ that terminates in an oxygen atom, under acidic conditions.

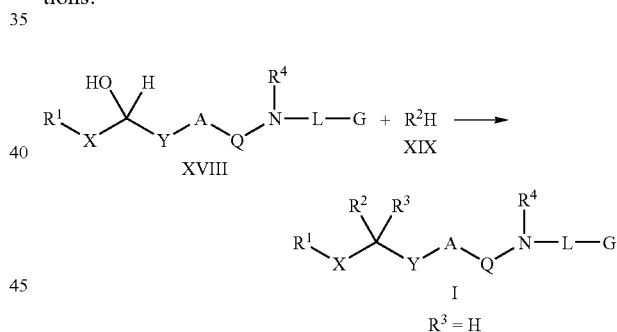

Alcohol intermediates XVIII are prepared by reduction of ketone intermediates XV.

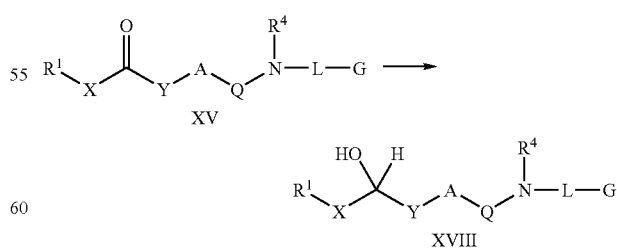

Intermediates of formula V and VII wherein L is a $C_2$ alkyl chain are prepared from natural and unnatural α-amino acids and by other methods (Lucet, D.; Le Gall, T.; Mioskowski, C. *Angew. Chem. Int. Ed.* 1998, 37, 2580-2617). Likewise, intermediates of formula V and VII wherein L is a $C_3$ or $C_4$ alkyl chain are prepared from β- and γ-amino acids, respectively.

Intermediates of Formula IX wherein $R^3$ is H and $R^2$ is a group attached through a carbon atom are prepared from intermediates of Formula IX wherein $R^3$ is OH and $R^2$ is a group attached through a carbon atom either by elimination of water and hydrogenation or by direct dehydroxylation for example using Raney nickel:

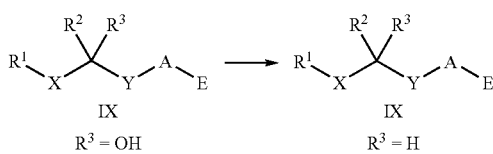

Compounds of Formula I wherein $R^1$ is a alkoxyoxyphenyl, cycloalkoxyphenyl, cycloalkylalkoxyphenyl, or arylalkoxy group can also be prepared from other compounds of Formula I in which $R^1$ is a hydroxyphenyl group:

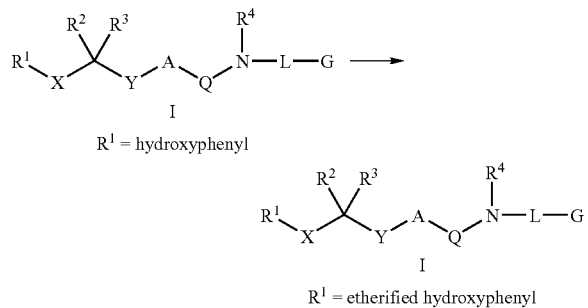

The invention is further defined by reference to the examples, which are intended to be illustrative and not limiting.

Representative compounds of the invention can be synthesized in accordance with the general synthetic schemes described above and are illustrated in the examples that follow. The methods for preparing the various starting materials used in the schemes and examples are well within the knowledge of persons skilled in the art.

The following abbreviations have the indicated meanings:

| Abbreviation | Meaning |
|---|---|
| Aq | aqueous |
| Boc | tert-butoxy carbonyl or t-butoxy carbonyl |
| (Boc)$_2$O | di-tert-butyl dicarbonate |
| Brine | saturated aqueous NaCl |
| Cbz | Benzyloxycarbonyl |
| CbzCl | Benzyl chloroformate |
| CDI | carbonyl diimidazole |
| CH$_2$Cl$_2$ | methylene chloride |
| CH$_3$CN or MeCN | acetonitrile |
| Cpd | compound |
| D | day |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIEA | N,N-diisopropylethylamine |
| DMAP | 4-(dimethylamino)pyridine |

-continued

| Abbreviation | Meaning |
|---|---|
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| EDC•HCl | 1-[3-(dimethylamino)propyl]-3-ethylcarbodiimide hydrochloride |
| Equiv | equivalents |
| Et | ethyl |
| Et$_2$O | ethyl ether |
| EtOAc | EtOAc |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazole-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| Me | methyl |
| MeCN | acetonitrile |
| MeOH | methanol |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Ph | phenyl |
| Quant | quantitative yield |
| Rt | room temperature |
| Satd | saturated |
| SOCl$_2$ | thionyl chloride |
| SPE | solid phase extraction |
| TBS | t-butyldimethylsilyl |
| TBSCl | t-butyldimethylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| TFA | trifluoroacetic acid |
| THF | tetrahydrofuran |
| Tlc | thin layer chromatography |
| TMS | trimethylsilyl |
| TMSCl | chlorotrimethylsilane or trimethylsilyl chloride |
| $t_R$ | retention time |
| TsOH | p-toluenesulfonic acid |

Purification Methods

Prep HPLC refers to preparative reverse phase HPLC on a C-18 column eluted with a water/acetonitrile gradient containing 0.01% TFA run on a Gilson 215 system.

Analytical Methods

LC-MS (3 min)

Column: Chromolith SpeedRod, RP-18e, 50×4.6 mm; Mobil phase: A: 0.01% TFA/water, B: 0.01% TFA/CH$_3$CN; Flow rate: 1 mL/min; Gradient:

LC-MS (16 min)

Column: Chromolith SpeedRod, RP-18e, 50×4.6 mm; Mobil phase: A: 0.01% TFA/water, B: 0.01% TFA/CH₃CN; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

LC-MS (16 min)

Column: Chromolith SpeedRod, RP-18e, 50×4.6 mm; Mobil phase: A: 0.01% TFA/water, B: 0.01% TFA/CH₃CN; Flow rate: 1 mL/min; Gradient:

| Time (min) | A % | B % |
|---|---|---|
| 0.0 | 90 | 10 |
| 14.0 | 10 | 90 |
| 15.0 | 10 | 90 |
| 15.1 | 90 | 10 |
| 16.0 | 90 | 10 |

Chiral HPLC

Column: Chiralpak AD-H, 0.46 cm×25 cm

Solvent A: 0.025% Diethylamine in Hexane

Solvent B: Isopropanol

Flow rate: 1 mL/min.

40 min. run

Gradient:

| Time (min) | A(%) | B(%) |
|---|---|---|
| 0 | 95 | 5 |
| 40 | 90 | 10 |

Example 1

(R)-tert-Butyl 3-((R)-(3-ethoxypropoxy)(phenyl)methyl)piperidine-1-carboxylate

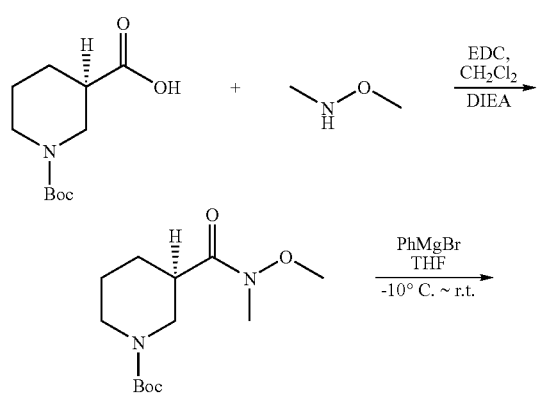

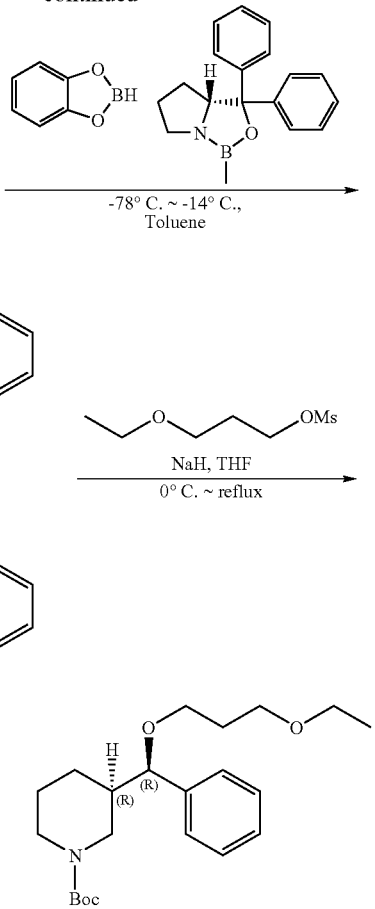

Step 1. (R)-tert-butyl 3-(N-methoxy-N-methylcarbamoyl)piperidine-1-carboxylate (R)-1-(tert-butoxycarbonyl)piperidine-3-carboxylic acid (25 g, 0.11 mol, 1.0 equiv), N,O-dimethylhydroxylamine hydrochloride, (10.5 g, 0.14 mol, 1.25 equiv) and EDC.HCl (26.3 g, 0.14 mol, 1.25 equiv) and diisopropylethylamine (48 mL, 0.28 mol, 2.5 equiv) were dissolved in 400 ml (400 mL) and stirred overnight at rt. The reaction mixture was diluted with EtOAc, washed with 5% aq HCl (2×150 mL), satd aq NaHCO₃ (150 mL), brine (100 mL), and dried over Na₂SO₄. Concentration afforded (R)-tert-butyl 3-(N-methoxy-N-methylcarbamoyl)-piperidine-1-carboxylate (24.42 g, 82%) as a clear oil. LC-MS (3 min) $t_R$=1.41 min, m/z 295 (M+Na). $^1$H NMR (CDCl₃) δ 4.19-4.00 (m, 2H), 3.77 (m, 3H), 3.12 (s, 3H), 2.79 (m, 2H), 2.64 (m, 1H), 1.89 (m, 1H), 1.71-1.52 (m, 2H), 1.51-1.33 (m, 10H). Chiral HPLC indicated 100% purity. The crude product was used for next step without further purification.

Step 2. (R)-tert-butyl 3-benzoylpiperidine-1-carboxylate (R)-tert-butyl 3-(N-methoxy-N-methylcarbamoyl)piperidine-1-carboxylate (13.6 g, 50 mmol) was dissolved in anhydrous THF (200 mL) and cooled to −10° C. (ice/MeOH bath). Phenylmagnesium bromide solution in THF (100 mL of 1.0 M, 100 mmol, 2 equiv) was added slowly. After 15 min, the reaction mixture was warmed up to rt slowly and stirred for 1 hour. LC-MS showed the reaction was complete. 5% Aq HCl (100 mL) was added slowly to quench the reaction and the mixture was stirred for 20 min. After separation, the aqueous layer was extracted with ether (2×200 mL). The combined organic layers were washed with satd aq NaHCO$_3$ (150 mL), brine (100 mL), and dried over Na$_2$SO$_4$. Concentration afforded crude (R)-tert-butyl 3-benzoylpiperidine-1-carboxylate (16.45 g, 110%) as a clear oil which was used for the next step without further purification. LC-MS (3 min) t$_R$=1.91 min, m/z 302 (M+Na). $^1$H NMR (CDCl$_3$) δ 7.94 (d, 2H), 7.54 (t, 1H), 7.47 (t, 2H), 4.28 (br d, 1H), 4.09 (d, 1H), 3.38 (t, 1H), 2.92 (br t, 1H), 2.72 (t, 1H), 2.01 (d, 1H), 1.79-1.45 (m, 3H) 1.42 (s, 9H). Chiral HPLC indicated 100% purity.

Step 3. (R)-tert-butyl 3-((R)-hydroxy(phenyl)methyl)piperidine-1-carboxylate A solution of (R)-tert-butyl 3-benzoylpiperidine-1-carboxylate (10.3 g, 35.64 mmol) anhydrous toluene (120 mL) was cooled to −78° C. and (R)-2-methyl-CBS-oxazaborolidine (1.0M in toluene, 17.8 mL, 17.8 mmol, 0.5 equiv) was added slowly. After 5 min, catecholborane (11.4 mL, 107 mmol, 3 equiv) was added slowly. The reaction mixture was then transferred into the freezer (~14.2° C.) and left overnight. LC-MS (16 min) showed 9:1 ratio of the R to S isomer. The mixture was cooled to 0° C. and water was added dropwise to quench the reaction. The reaction mixture was diluted with ether, washed with 5% aq NaOH (2×150 mL), water (150 mL), 5% aq HCl (100 mL), brine (100 mL), and dried over Na$_2$SO$_4$. After concentration, the crude product was purified by flash chromatography on a 120 g silica gel column eluted with a 4-35% EtOAc in hexanes gradient. The purified product was recrystallized from an ether hexanes mixture to afford (R)-tert-butyl 3-((R)-hydroxy(phenyl)methyl)piperidine-1-carboxylate (4.45 g, 43%) as white solid with the ratio of R/S isomers 23.5:1. LC-MS (3 min) t$_R$=1.70 min; LC-MS (3 min) t$_R$=10.62 min, m/z 314 (M+Na). $^1$H NMR (CDCl$_3$) δ 7.28 (m, 5H), 4.46 (d, 1H), 3.87 (d, 1H), 3.89-3.51 (br s, free exchange 1H), 3.00 (m, 2H), 2.68 (t, 1H), 2.52 (t, 1H), 1.94 (m, 1H), 1.76 (m, 1H), 1.65 (m, 1H), 1.42-1.20 (m, 10H).

Step 4. (R)-tert-Butyl 3-((R)-(3-ethoxypropoxy)(phenyl)methyl)piperidine-1-carboxylate An oven dried flask was charged with (R)-tert-butyl 3-((R)-hydroxy(phenyl)methyl)-piperidine-1-carboxylate (3.18 g, 10.9 mmol) and 60% NaH in mineral oil (2.19 g, 54.8, 5 equiv). The flask was purged with N$_2$ gas, cooled to 0° C. and anhydrous THF (100 mL) was added slowly. The mixture was allowed to warm to rt slowly. A solution of 3-ethoxypropyl methanesulfonate (6.0 g, 32.9 mmol, 3 equiv) in anhydrous THF (50 mL) was added. The mixture was heated at reflux for 4 h. LC-MS indicated the reaction completed. The reaction mixture was cooled to 0° C. slowly and water was added dropwise to quench the reaction. After separation, the aqueous layer was extracted with ether three times. The combined organic layers were washed with 5% aq HCl, satd aq NaHCO$_3$, brine, and dried over Na$_2$SO$_4$. After concentration, the crude product was purified by flash chromatography on a 120-g silica gel cartridge eluted with a 0-30% EtOAc in hexanes gradient) to afford (R)-tert-butyl 3-((R)-(3-ethoxypropoxy)(phenyl)methyl)piperidine-1-carboxylate (3.70 g, 90%) as a clear oil. Chiral HPLC indicated 95.5% purity. LC-MS (3 min) t$_R$=2.38 min, m/z 400 (M+Na). $^1$H NMR (CDCl$_3$) δ 7.26 (m, 5H), 4.39 (d, 1H), 3.89 (t, 2H), 3.53-3.40 (m, 4H), 3.38-3.23 (m, 2H), 2.75-2.60 (m, 2H), 1.85-1.47 (m, 4H), 1.45 (s, 9H), 1.40-1.22 (m, 2H), 1.15 (t, 3H), 1.10-0.96 (m, 1H).

Example 2

1-Phenyl-1-(piperidin-3-yl)heptan-1-ol

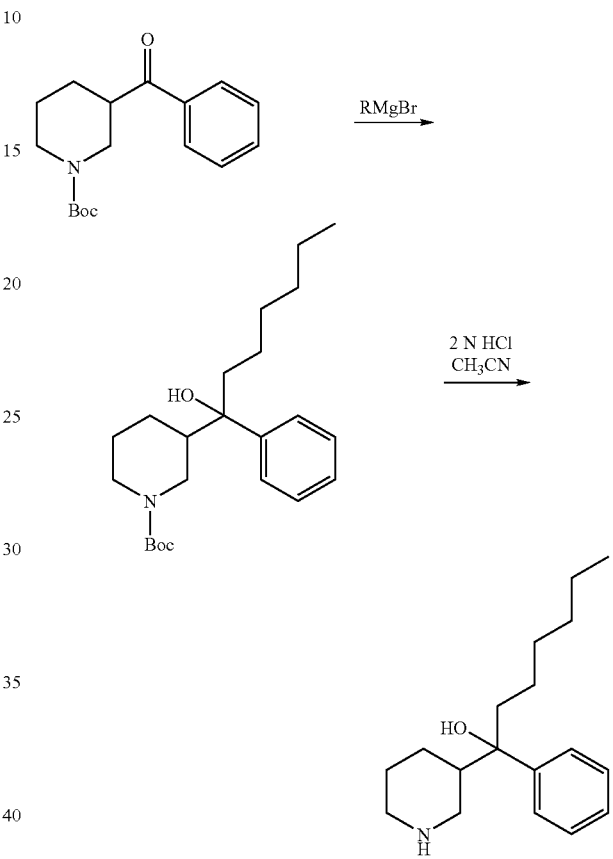

Step 1. tert-Butyl 3-(1-hydroxy-1-phenylheptyl)piperidine-1-carboxylate

To a 100-mL round bottom flask were added tert-butyl 3-(benzoyl)piperidine-1-carboxylate (0.4733 g, 1.63 mmol, 1.0 equiv) and THF (5 mL). The flask was evacuated and refilled with N$_2$. The mixture was cooled with a dry ice-acetone bath and hexylmagnesium bromide (2.0M solution in Et$_2$O, 2.5 mL, 5.0 mmol, 3.0 equiv) was added. The reaction mixture was allowed to slowly warm to −10° C. while stirring overnight (17 h). The mixture was quenched with saturated NH$_4$Cl (10 mL), extracted three times with EtOAc, and dried over Na$_2$SO$_4$. The crude product was purified by reversed-phase HPLC (XTerra® Prep MS C$_{18}$ OBD™ Column, 5 μm, 19×50 mm, 10%→90% CH$_3$CN/H$_2$O, 0.1% CF$_3$COOH over 8 min, flow rate 20 mL/min) to give tert-butyl 3-(1-hydroxy-1-phenylheptyl)piperidine-1-carboxylate. LC-MS (3 min) t$_R$=2.41 min, m/z 398 (M+Na$^+$), 376 (MH$^+$), 302, 276, 258.

Step 2. 1-Phenyl-1-(piperidin-3-yl)heptan-1-ol

A mixture of tert-Butyl 3-(1-hydroxy-1-phenylheptyl)piperidine-1-carboxylate, obtained as described above, in CH₃CN (40 mL) and 2 N HCl (40 mL) was vigorously stirred at rt for 20 h. 60 mL of the reaction mixture was quenched with saturated NaHCO₃, extracted three times with EtOAc, and dried over Na₂SO₄. The crude product (0.2709 g, 80% in two steps) was used without further purification. LC-MS (3 min) $t_R$=1.29 min in 3 min chromatography, m/z 276 (MH⁺).

Example 3

4-Cyclopropyl-1-phenyl-1-(piperidin-3-yl)butan-1-ols

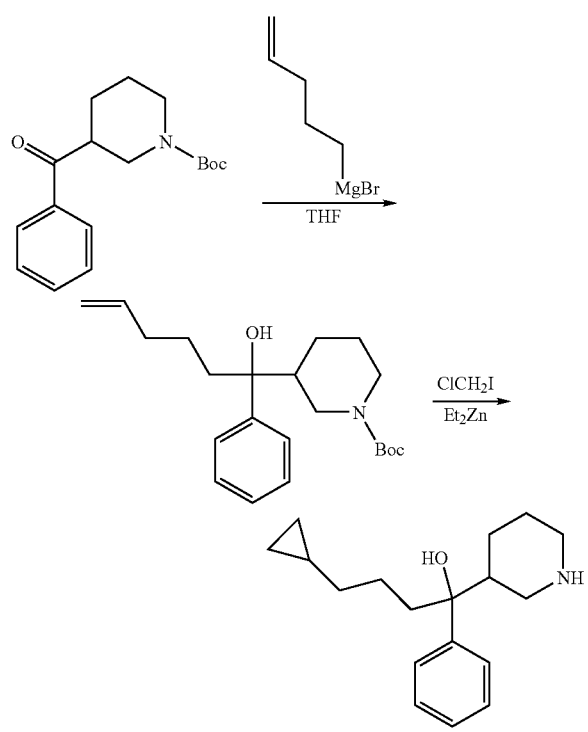

Step 1. tert-Butyl 3-((R)-1-hydroxy-1-phenylhex-5-enyl)piperidine-1-carboxylate A stirred solution of tert-butyl 3-benzoylpiperidine-1-carboxylate (160 mg, 0.55 mmol) in dry THF (2 mL) was cooled to −70° C. and 4-pentenylmagnesium bromide in THF (1.8 mL of ~2.5 M, 2.8 mmol) was added dropwise. The mixture was stirred at −78° C. and allowed to warm to rt overnight. The reaction was quenched with satd aq ammonium chloride. The aqueous layer was extracted with Et₂O (3×). The combined organic layers were washed with brine, dried over Na₂SO₄, filtered and evaporated to dryness. The crude material was purified by flash chromatography on a prepacked silica cartridge eluted with an EtOAc/hexanes gradient. tert-Butyl 3-((R)-1-hydroxy-1-phenylhex-5-enyl)piperidine-1-carboxylate (174 mg, 88%) was isolated as an oil. MS ESI+ve m/z 382 (M+Na)⁺.

Step 2. 4-Cyclopropyl-1-phenyl-1-(piperidin-3-yl)butan-1-ol

To a 0° C. solution of diethyl zinc (1.0 mL of 1M in hexane, 1 mmol) in dry dichloroethane (2 mL), chloroiodomethane (0.14 ml, 2.0 mmol) was added dropwise over five minutes. The reaction was removed from the ice bath and allowed to stir at rt for 40 min A dichloroethane solution (1 mL) of tert-butyl 3-((R)-1-hydroxy-1-phenylhex-5-enyl)piperidine-1-carboxylate (174 mg, 0.480 mmol) was added dropwise. The reaction was allowed to stir overnight. The reaction was quenched with satd ammonium chloride. The aqueous layer was extracted 3× with CH₂Cl₂. The combined organic layers were washed with brine, dried over Na₂SO₄, filtered, and evaporated to dryness. The crude material was purified via preparative HPLC (C-18 column, 10 to 90% CH₃CN in H₂O containing 0.01% CF₃CO₂H over 10 min, 20 mL/min) to afford the trifluoroacetic acid salt of 4-cyclopropyl-1-phenyl-1-(piperidin-3-yl)butan-1-ol (32 mg, 24%). MS ESI+ve m/z 274 (M+1).

Example 4 tert-Butyl 3-(hydroxy(phenyl)methyl)-3-methylpiperidine-1-carboxylate

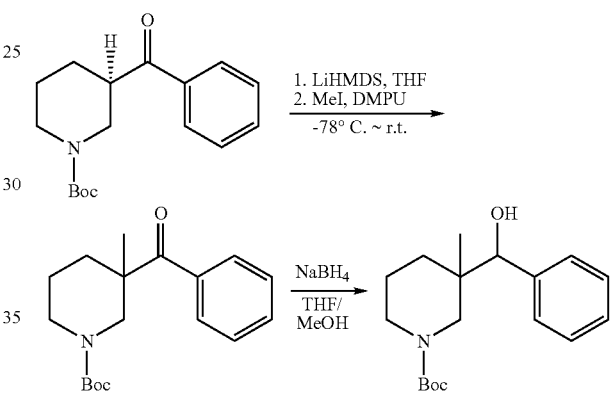

Step 1. Tert-butyl 3-benzoyl-3-methylpiperidine-1-carboxylate

A stirred solution of (R)-tert-butyl 3-benzoylpiperidine-1-carboxylate (409 mg, 1.42 mmol) in dry THF (15 mL) under N₂ was cooled to −78° C. A solution of lithium bis(trimethylsilylamide) in THF (2.84 mL of 1.0M, 2.84 mmol, 2 equiv) was added dropwise. After 30 min, a solution of iodomethane (220 μL, 3.5 mmol, 2.5 equiv) in DMPU (512 μL, 4.24 mmol, 3.0 equiv) was added slowly. After 15 min, the reaction mixture was allowed to warm to rt and stirred overnight. LC-MS showed the reaction was complete. Brine (50 mL) was added to quench the reaction. The organic layer was separated and the aqueous layer was extracted with EtOAc (2×75 mL). The combined organic layers were dried over Na₂SO₄. After concentration, the crude product was purified by chromatography on a prepacked 12-g silica gel cartridge eluted with a 0-35% EtOAc in hexanes gradient to afford tert-butyl 3-benzoyl-3-methylpiperidine-1-carboxylate (278 mg, 65%). LC-MS (3 min) $t_R$=1.92 min, m/z 326 (M+Na).

Step 2. tert-Butyl 3-(hydroxy(phenyl)methyl)-3-methylpiperidine-1-carboxylate tert-Butyl 3-benzoyl-3-methylpiperidine-1-carboxylate (278 mg, 0.92 mmol) was dissolved in 1:1 THF/MeOH (8 mL) and NaBH₄ (70 mg, 1.84 mmol, 2 equiv) was added.

After stirring 30 min at rt, LC-MS showed the reaction was complete. After concentration, the residue was partitioned between ether and diluted (~1%) aq HCl. The aqueous layer was separated and extracted twice with ether. The combined organic layers were washed with satd aq NaHCO$_3$, brine, dried over Na$_2$SO$_4$ and evaporated to afford crude product which was purified by chromatography on a 12-g prepacked silica gel cartridge eluted with a 0-35% EtOAc in hexanes gradient to afford tert-butyl 3-(hydroxy(phenyl)methyl)-3-methylpiperidine-1-carboxylate (198 mg, 71%). LC-MS (3 min) $t_R$=1.83 min, m/z 328 (M+Na).

Example 5

Using procedures analogous to those described in Examples 1-4, the following intermediates were prepared:
1-phenyl-1-(piperidin-3-yl)pentan-1-ol
2-((3-methoxypropoxy)(phenyl)methyl)morpholine
1-(3-fluorophenyl)-5-methoxy-1-(piperidin-3-yl)pentan-1-ol
3-((3-methoxypropoxy)(2-fluorophenyl)methyl)piperidine
3-((3-methoxypropoxy)(3-fluorophenyl)methyl)piperidine
5-methoxy-1-(2-phenoxyphenyl)-1-(piperidin-3-yl)pentan-1-ol
5-methoxy-1-(piperidin-3-yl)-1-m-tolylpentan-1-ol
1-(2,5-difluorophenyl)-5-methoxy-1-(piperidin-3-yl)pentan-1-ol
3-((3-methoxypropoxy)(2-(trifluoromethyl)phenyl)methyl)piperidine
3-((3-methoxypropoxy)(4-fluorophenyl)methyl)piperidine
1-(3-(trifluoromethyl)phenyl)-5-methoxy-1-(piperidin-3-yl)pentan-1-ol
3-((3-methoxypropoxy)(2-(trifluoromethyl)phenyl)methyl)piperidine
5-ethoxy-1-phenyl-1-(piperidin-3-yl)pentan-1-ol
3-((3-ethoxypropoxy)(3,4-difluorophenyl)methyl)piperidine
3-((3-methoxypropoxy)(3,4-difluorophenyl)methyl)piperidine
4-methoxy-1-phenyl-1-(piperidin-3-yl)butan-1-ol
3-((4-methoxybutoxy)(phenyl)methyl)piperidine
3-((3-methoxypropoxy)(piperidin-3-yl)methyl)benzonitrile
4-ethoxy-1-phenyl-1-(piperidin-3-yl)butan-1-ol
3-((3-propoxypropoxy)(phenyl)methyl)piperidine
3-((2-cyclopropylethoxy)(phenyl)methyl)piperidine
4,4,4-trifluoro-1-(piperidin-3-yl)-1-m-tolylbutan-1-ol
3-((3-ethoxypropoxy)(phenyl)methyl)piperidine
3-((3-methoxypropoxy)(2,4-difluorophenyl)methyl)piperidine
1-(3,4-difluorophenyl)-5-methoxy-1-(piperidin-3-yl)pentan-1-ol
1-(3-isopropylphenyl)-5-methoxy-1-(piperidin-3-yl)pentan-1-ol
1-(3-chlorophenyl)-5-cyclopropyl-1-(piperidin-3-yl)pentan-1-ol
1-(2-(p-tolyloxy)-5-methylphenyl)-5-methoxy-1-(piperidin-3-yl)pentan-1-ol
1-(5-chloro-2-phenoxyphenyl)-5-methoxy-1-(piperidin-3-yl)pentan-1-ol
(3-chlorophenyl)(piperidin-3-yl)methanol
1-(3-chlorophenyl)-1-(piperidin-3-yl)ethanol
1-(3-chlorophenyl)-1-(piperidin-3-yl)propan-1-ol
1-(3-chlorophenyl)-1-(piperidin-3-yl)butan-1-ol
1-(3-chlorophenyl)-1-(piperidin-3-yl)pentan-1-ol
5-methoxy-1-(3-methylpiperidin-3-yl)-1-phenylpentan-1-ol
(S)-1-phenyl-1-((R)-piperidin-3-yl)pentan-1-ol
(S)-1-(3-fluorophenyl)-5-methoxy-1-((R)-piperidin-3-yl)pentan-1-ol
(R)-3-((R)-(3-methoxypropoxy)(2-fluorophenyl)methyl)piperidine
(R)-3-((R)-(3-methoxypropoxy)(3-fluorophenyl)methyl)piperidine
(S)-5-methoxy-1-(2-phenoxyphenyl)-1-((R)-piperidin-3-yl)pentan-1-ol
(S)-5-methoxy-1-((R)-piperidin-3-yl)-1-m-tolylpentan-1-ol
(S)-1-(2,5-difluorophenyl)-5-methoxy-1-((R)-piperidin-3-yl)pentan-1-ol
(R)-3-((R)-(3-methoxypropoxy)(2-(trifluoromethyl)phenyl)methyl)piperidine
(R)-3-((R)-(3-methoxypropoxy)(4-fluorophenyl)methyl)piperidine
(S)-1-(3-(trifluoromethyl)phenyl)-5-methoxy-1-((R)-piperidin-3-yl)pentan-1-ol
(R)-3-((R)-(3-methoxypropoxy)(2-(trifluoromethyl)phenyl)methyl)piperidine
(S)-5-ethoxy-1-phenyl-1-((R)-piperidin-3-yl)pentan-1-ol
(R)-3-((R)-(3-ethoxypropoxy)(3,4-difluorophenyl)methyl)piperidine
(R)-3-((R)-(3-methoxypropoxy)(3,4-difluorophenyl)methyl)piperidine
(S)-4-methoxy-1-phenyl-1-((R)-piperidin-3-yl)butan-1-ol
(R)-3-((R)-(4-methoxybutoxy)(phenyl)methyl)piperidine
3-((R)-(3-methoxypropoxy)((R)-piperidin-3-yl)methyl)benzonitrile
(S)-4-ethoxy-1-phenyl-1-((R)-piperidin-3-yl)butan-1-ol
(R)-3-((R)-(3-propoxypropoxy)(phenyl)methyl)piperidine
(R)-3-((R)-(2-cyclopropylethoxy)(phenyl)methyl)piperidine
(S)-4,4,4-trifluoro-1-((R)-piperidin-3-yl)-1-m-tolylbutan-1-ol
(R)-3-((R)-(3-ethoxypropoxy)(phenyl)methyl)piperidine
(R)-3-((R)-(3-methoxypropoxy)(2,4-difluorophenyl)methyl)piperidine
(S)-1-(3,4-difluorophenyl)-5-methoxy-1-((R)-piperidin-3-yl)pentan-1-ol
(S)-1-(3-isopropylphenyl)-5-methoxy-1-((R)-piperidin-3-yl)pentan-1-ol
(S)-1-(3-chlorophenyl)-5-cyclopropyl-1-((R)-piperidin-3-yl)pentan-1-ol
(S)-1-(2-(p-tolyloxy)-5-methylphenyl)-5-methoxy-1-((R)-piperidin-3-yl)pentan-1-ol
(S)-1-(5-chloro-2-phenoxyphenyl)-5-methoxy-1-((R)-piperidin-3-yl)pentan-1-ol
(S)-(3-chlorophenyl)((R)-piperidin-3-yl)methanol
(S)-1-(3-chlorophenyl)-1-((R)-piperidin-3-yl)ethanol
(S)-1-(3-chlorophenyl)-1-((R)-piperidin-3-yl)propan-1-ol
(S)-1-(3-chlorophenyl)-1-((R)-piperidin-3-yl)butan-1-ol
(S)-1-(3-chlorophenyl)-1-((R)-piperidin-3-yl)pentan-1-ol
(R)-3-((R)-(2,3-dichlorophenyl)(3-ethoxypropoxy)methyl)piperidine
(R)-3-((R)-(3-ethoxypropoxy)(2,3,5-trifluorophenyl)methyl)piperidine
(R)-3-((R)-(3-chloro-2-fluorophenyl)(3-ethoxypropoxy)methyl)piperidine
(R)-3-((R)-(3-chlorophenyl)(3-ethoxypropoxy)methyl)piperidine
(R)-3-((R)-(3-ethoxypropoxy)(3-fluorophenyl)methyl)piperidine
(R)-3-((R)-(3-ethoxypropoxy)(m-tolyl)methyl)piperidine
(S)-4-cyclopropyl-1-(2-phenoxyphenyl)-1-((R)-piperidin-3-yl)butan-1-ol
(S)-1-(3-chlorophenyl)-4-cyclopropyl-1-((R)-piperidin-3-yl)butan-1-ol and (S)-4-cyclopropyl-1-(3-fluorophenyl)-1-((R)-piperidin-3-yl)butan-1-ol.

Example 6

3-((2-Bromophenyl)(3-methoxypropoxy)methyl)-1-(2-(trimethylsilyl)ethylsulfonyl)piperidine

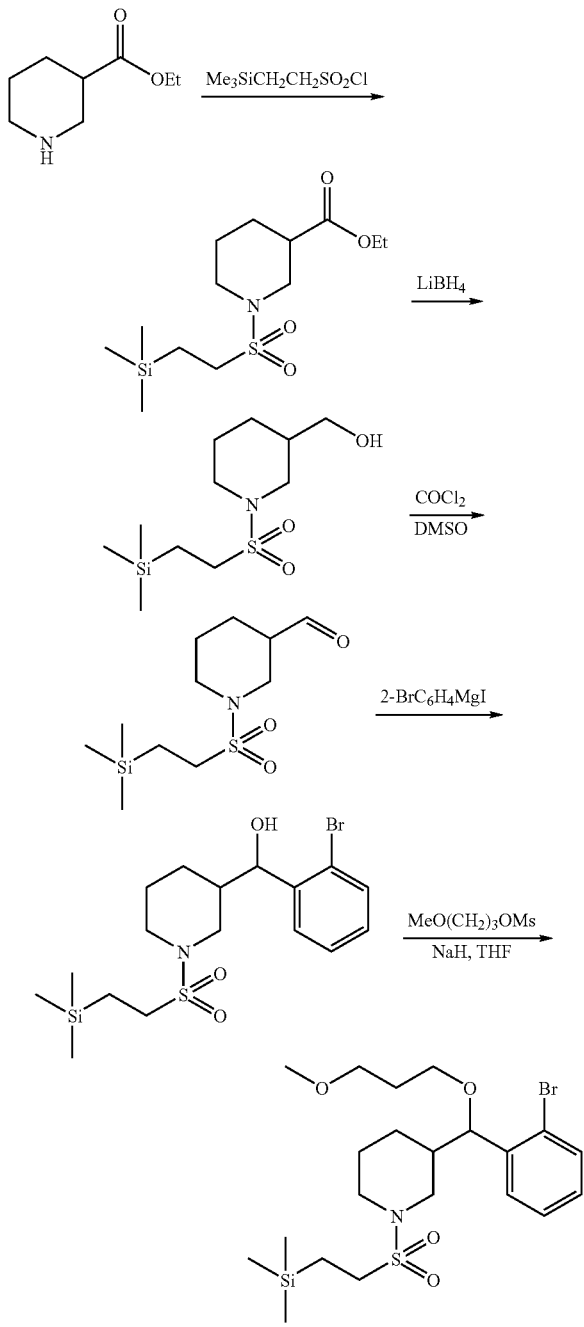

Step 1. Ethyl 1-(2-(trimethylsilyl)ethylsulfonyl)piperidine-3-carboxylate

A 1 L flask equipped with a dropping funnel was charged with 2-(trimethylsilylethane)-sulfonyl chloride (7.5 g, 0.0374 mol, 1.0 equiv) and CH$_2$Cl$_2$ (150 mL). The flask was cooled to 0° C. and the dropping funnel was charged with a solution of racemic ethyl piperidine-3-carboxylate (7.34 g, 0.0467 mol, 1.25 equiv) and diisopropylethyl amine (12.1 g, 0.0935 mol, 2.5 equiv) in CH$_2$Cl$_2$ (50 mL). The solution of the amines was added and the resulting mixture was stirred for 3 h with concomitant warming to rt temperature. Analysis of the mixture by LC-MS showed a signal for the desired product. The reaction mixture was quenched by addition of 1.0 M HCl (100 mL). The layers were separated and the organic layer washed with additional aqueous HCl, then brine. It was dried over Na$_2$SO$_4$, filtered and evaporated to yield ethyl 1-(2-(trimethylsilyl)ethanesulfonyl)piperidine-3-carboxylate (10.63 g, 88%) as an amber syrup which was of sufficient purity to use in the next step. $^1$H NMR (CDCl$_3$) δ–0.01 (s, 9H), 0.96 (m, 2H), 1.23 (t, 3H), 1.4-1.6 (m, 4H), 1.78 (M, 1H), 2.03 (m, 1H), 2.53 (m, 1H), 2.79 (m, 2H), 2.95 (d of d, 1H), 3.61 (m, 1H), 3.82 (m, 1H), 4.08, (q, 2H).

Step 2. (1-(2-(Trimethylsilyl)ethylsulfonyl)piperidin-3-yl)methanol

Ethyl 1-(2-(trimethylsilyl)ethanesulfonyl)piperidine-3-carboxylate (9.00 g, 28 mol) was dissolved in THF (200 mL) in a three-neck 500 mL flask and cooled to 0° C. A solution of LiBH$_4$ (2.0 M in THF, 28 mL, 0.056 mol, 2.0 equiv) was added via addition funnel. The mixture was allowed to warm to rt and stir for 15 h. Significant amounts of the starting ester remained; an additional charge of the LiBH$_4$ solution (28 mL, 0.056 mol) was added and the mixture stirred for an additional 17 h. After this period analysis by LC-MS showed consumption of the starting ester. The mixture was cooled to 0° C. and the excess LiBH$_4$ was quenched by dropwise addition of MeOH (100 mL). The volatile materials were removed and the residue partitioned between ether (100 mL) and 1.0 M aq HCl (100 mL). The layers were separated and the aqueous layer extracted with additional ether (3×50 mL). The combined organic extracts were washed with brine and dried over Na$_2$SO$_4$. The clear solution was evaporated to yield (1-(2-(trimethylsilyl)ethylsulfonyl)piperidin-3-yl)methanol (5.25 g, 67%) as a white solid which was of sufficient purity to use in the next step. $^1$H NMR (CDCl$_3$) δ 0.00 (s, 9H), 0.95 (m, 2H), 1.21 (m, 1H), 1.5-8 (m, 5H), 2.75-2.82 (m, 3H), 2.91 (t of d, 1H), 3.53 (m, 2H), 3.62 (d of d, 1H).

Step 3. 1-(2-(Trimethylsilyl)ethylsulfonyl)piperidine-3-carbaldehyde

A three neck 500-mL flask equipped with a dropping funnel was charged with of anhydrous CH$_2$Cl$_2$ (100 mL) and oxalyl chloride (2.64 g, 20.7 mmol, 1.1 equiv). The solution was cooled to –78° C. under nitrogen. A solution of DMSO (2.93 g, 37.6 mmol, 2.0 equiv) in CH$_2$Cl$_2$ (10 mL) was added dropwise to the oxalyl chloride over a 15 minute period, and the resulting solution stirred for 30 min at –78° C. A solution of 1-(2-(trimethylsilyl)ethanesulfonyl)-3-hydroxymethylpiperidine (5.25 g, 18.8 mmol, 1.0 equiv) in CH$_2$Cl$_2$ (30 mL) was added dropwise over a 30 min period, and the resulting mixture stirred for 30 min at –78° C. Triethylamine (9.51 g, 94.4 mmol, 5.0 equiv) was added dropwise to the mixture over a 30 min period. The resulting white slurry was allowed to warm to 0° C. and stir for 30 min. Analysis of the mixture by LC-MS showed consumption of the alcohol. Water (200 mL) was added and the layers were separated. The organic layer was washed with brine and dried over Na$_2$SO$_4$. The aldehyde was purified by flash chromatography on 120 g of silica, eluting with 0 to 50% EtOAc in hexanes. Fractions containing the desired aldehyde were visualized by staining with 2,4-dinitrophenylhydrazine on silica gel. Removal of the solvent afforded 1-(2-trimethylsilyl(ethanesulfonyl))piperidine-3-carbaldehyde (3.81 g, 73%) as a white solid. $^1$H NMR (CDCl$_3$) δ−0.15 (s, 9H), 0.96 (m, 2H), 1.5-1.77 (m, 4H), 1.95 (M, 1H), 2.54 (m, 1H), 2.82 (m, 2H), 2.95 (m, 1H), 3.17 (d of d, 1H), 3.44 (m, 1H), 3.72 (m, 1H), 9.64 (s, 1H).

Step 4. (2-Bromophenyl)(1-(2-(trimethylsilyl)ethylsulfonyl)piperidin-3-yl)methanol A three neck 200-mL flask was charged with anhydrous THF (150 mL) and 1-bromo-2-iodobenzene (5.81 g, 20.5 mmol, 1.5 equiv), and cooled to −40° C. Isopropyl magnesium bromide (1.0 M in THF, 19.9 mL, 19.9 mmol, 1.45 equiv) was added to the solution via syringe at a rate such that the internal temperature did not rise above −35° C. An aliquot was removed, quenched with water and analyzed by LC-MS. The observed amount of bromobenzene showed >90% conversion to the desired Grignard reagent. A solution of 1-(2-trimethylsilyl-(ethanesulfonyl))piperidine-3-carbaldehyde (3.8 g, 13.7 mmol) in 20 mL of THF was added to solution containing the Grignard reagent at such a rate that the internal temperature did not rise above −35° C. The mixture was stirred for 1 h at −40° C.; after this period LC-MS analysis of an aliquot showed consumption of the aldehyde and formation of two peaks with the desired mass, consistent with formation of two diastereomers. The mixture was quenched with methanol and the THF removed in vacuo. The resulting solid was partitioned between EtOAc and water, and filtered through a pad of Celite to remove a sticky white solid. The layers were separated and the aqueous layer was extracted with additional EtOAc. The combined organic extracts were washed with brine, dried over Na$_2$SO$_4$, filtered, and evaporated. The mixture of alcohols was purified by flash chromatography on 120 g silica, eluting with 0 to 50% EtOAc in hexanes. No attempt was made to separate the two diastereomers. This afforded (2-bromophenyl)(1-(2-(trimethylsilyl)ethanesulfonyl)piperidin-3-yl)methanol (3.64 g, 61%) as a white foam. $^1$H NMR (CDCl$_3$) δ 0.01 (s, 9H), 0.95-2.06 (m, 8H), 2.6-3.0 (m, 6H), 3.6-3.9 (m, 3H), 4.96 (bs, 1H), 7.13 (m, 1H), 7.29 (m, 1H), 7.44 (m, 2H).

Step 5. 3-((2-Bromophenyl)(3-methoxypropoxy)methyl)-1-(2-(trimethylsilyl)ethylsulfonyl)piperidine A 250-mL three neck flask fitted with a reflux condenser was charged with NaH (60% in mineral oil, 644 mg of material, 16.1 mmol, 5.0 equiv). Anhydrous THF (80 mL) was added. A solution of (2-bromophenyl)(1-(2-(trimethylsilyl)ethanesulfonyl)piperidin-3-yl)methanol (1.4 g, 3.22 mmol, 1.0 equiv) in 10 mL of THF was slowly added via syringe. After cessation of hydrogen evolution, a solution of 3-methoxypropyl methanesulfonate (2.2 g, 12.8 mmol, 4.0 equiv) in 10 mL of THF was added and the resulting mixture was heated to reflux. After 1.0 h the signals for the starting material in the LC-MS were consumed and a new peak with M+Na for the desired product was observed. The mixture was allowed to cool to rt and excess NaH was quenched with water. The layers were separated and the aqueous layer was extracted with EtOAc. The combined organic fractions were washed with brine and purified by flash chromatography on silica gel (40 g) eluting with 0-25% EtOAc in hexanes. This afforded 3-((2-bromophenyl)(3-methoxypropoxy)methyl)-1-(2-(trimethylsilyl)ethylsulfonyl)piperidine (1.2 g, 73%) as a clear syrup containing a mixture of two diastereomers. No attempt was made to separate the diastereomers. MS ESI+ve m/z 506 (M+1).

Example 7

1-Methanesulfonyl-3-((3-methoxypropoxy)(2-bromophenyl)methyl)piperidine 1-methanesulfonyl-3-((3-methoxypropoxy)(2-bromophenyl)methyl)piperidine was prepared following procedures analogous to those used in Example 6 using methanesulfonyl chloride in Step 1.

Example 8

N-(2-Trimethylsilyl)ethanesulfonyl)-3-((methoxypropoxy)(2-allylphenyl)methyl)piperidine

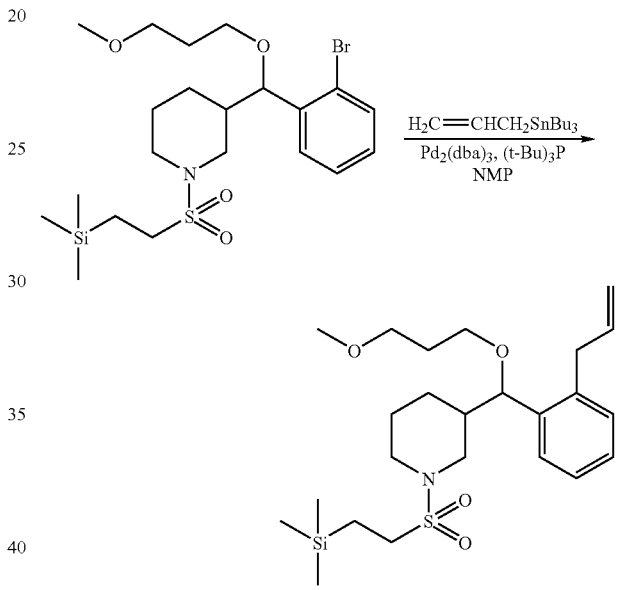

A tube designed for a microwave reactor was charged with 1-(2-(trimethylsilyl)-ethanesulfonyl)-3-((3-methoxypropoxy)(2-bromophenyl)methyl)piperidine (100 mg, 0.197 mmol, 1.0 equiv), Pd$_2$(dba)$_3$ (10 mg, 0.0099 mmol, 0.05 equiv), P($^t$Bu$_3$) (10% in hexanes, 100 μL, 0.02 mmol, 0.10 equiv), allyltributyltin (68 mg, 0.206 mmol, 1.05 equiv), and N-methylpyrrolidinone (1.0 mL). The tube was sealed and the resulting purple solution was degassed by three evacuate/N$_2$ backfill cycles, then placed in a microwave reactor and heated to 120° C. for 20 min. The resulting brown solution was analyzed by LC-MS, which showed consumption of the starting bromide and formation of a new peak with desired mass. Solid KF.H$_2$O (500 mg) was added, and the mixture stirred for 30 min in the air. The residue was partitioned between EtOAc and water. The layers were separated and the aqueous layer extracted with additional EtOAc. The combined organic extracts were washed with brine, dried over Na$_2$SO$_4$ and evaporated. The product was isolated by flash chromatography on 4 g silica, eluting with 0 to 20% EtOAc in hexanes. N-(2-Trimethylsilyl)ethane-sulfonyl)-3-((methoxypropoxy)(2-allyl)phenyl)methyl)-piperidine was isolated as a pale yellow oil (42 mg, 43%). MS ESI+ve m/z 491 (M+Na$^+$).

Example 9

3-((2-(Cyclopropylethynyl)phenyl)(3-methoxypropoxy)methyl)piperidine

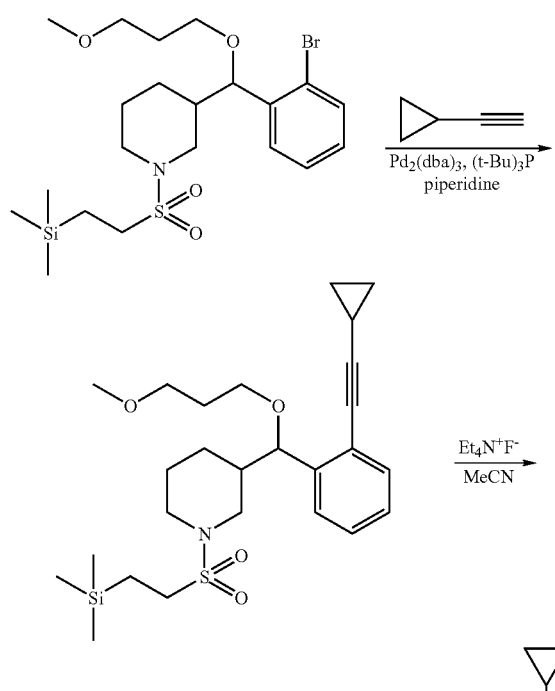

Step 1. 3-((2-(Cyclopropylethynyl)phenyl)(3-methoxypropoxy)methyl)-1-(2-(trimethylsilyl)ethylsulfonyl)piperidine A tube designed for a microwave reactor was charged with the 1-methanesulfonyl-3-((3-methoxypropoxy)(2-bromophenyl)methyl)piperidine (100 mg, 0.197 mmol, 1.0 equiv), Pd$_2$(dba)$_3$ (10 mg, 0.0099 mmol, 0.05 equiv), P($^t$Bu$_3$) (10% in hexanes, 100 μL, 0.02 mmol, 0.10 equiv), cyclopropylacetylene (70% solution in toluene, 70 μL, 0.60 mmol, 3.0 equiv), and piperidine (2.0 mL). The tube was sealed and the resulting purple solution degassed by three evacuate/N$_2$ backfill cycles, then placed in a microwave reactor and heated to 130° C. for 10 min. The resulting yellow solution containing dark solids was analyzed by LC-MS (3 min), which showed consumption of the starting bromide and formation of a new peak at t$_R$=2.43 min with m/z=M+Na for the desired product. The contents were transferred to a flask and excess piperidine was removed in vacuo. The residue was partitioned between EtOAc and 1.0 M HCl. The yellow organic layer was washed with brine, dried over Na$_2$SO$_4$ and evaporated. The product was isolated by flash chromatography on 12 g silica, eluting with 0 to 20% EtOAc in hexanes. 3-((2-(cyclopropylethynyl) phenyl)(3-methoxypropoxy)methyl)-1-(2-(trimethylsilyl) ethylsulfonyl)piperidine (68 mg, 70%) was isolated as a pale brown oil. MS ESI+ve m/z 515 (M+Na$^+$).

Step 2. 3-((2-(Cyclopropylethynyl)phenyl)(3-methoxypropoxy)methyl)piperidine A 50-mL round bottom flask was charged with 3-((2-(cyclopropylethynyl)phenyl)(3-methoxypropoxy)methyl)-1-(2-(trimethylsilyl)ethylsulfonyl)piperidine (63 mg, 0.128 mmol, 1.0 equiv), tetraethylammonium fluoride (63 mg, 0.422 mmol, 3.4 equiv) and acetonitrile (5 mL). The mixture was heated to 65° C. for 17 h. Analysis of the yellow reaction mixture by LC-MS showed consumption of the protected piperidine and formation of a new signal containing the mass of the desired product. The acetonitrile was removed under reduced pressure and the residue was partitioned between CH$_2$Cl$_2$ and water. The layers were separated and the aqueous layer was extracted twice with additional CH$_2$Cl$_2$. The combined organic layers were washed with brine, dried over Na$_2$SO$_4$ and evaporated, yielding 3-((3-methoxypropoxy)(2-(2-cyclopropylethynyl)phenyl)methyl)piperidine (40 mg, 95%). No additional purification was attempted. MS ESI+ve m/z 328 (M+H$^+$).

Example 10

3-((Methoxypropoxy)(2-phenyl)phenyl)methyl)piperidine

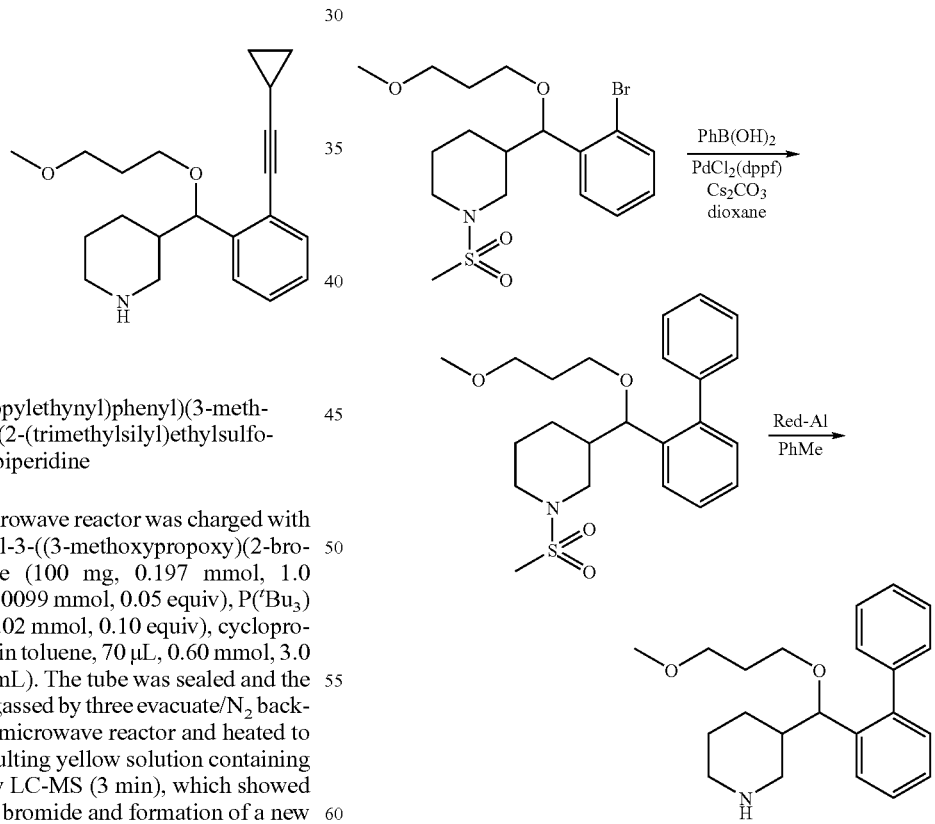

Step 1. 3-(Biphenyl-2-yl(3-methoxypropoxy)methyl)-1-(methylsulfonyl)piperidine A tube designed for a microwave reactor was charged with 1-methanesulfonyl-3-((3-methoxypropoxy)(2-bromophenyl)methyl)piperidine (200 mg, 0.0.476 mmol, 1.0 equiv), PdCl₂(dppf) (21 mg, 0.0.238 mmol, 0.05 equiv), Cs₂CO₃ (511 mg, 1.57 mmol, 3.3 equiv), phenylboronic acid (87 mg, 0.714 mmol, 1.5 equiv) and 4 mL of 1,4-dioxane. The tube was sealed and the resulting yellow solution degassed by three evacuates/N₂ backfill cycles, then placed in a microwave reactor and heated to 120° C. for 15 min. The contents were transferred to a flask and volatile materials removed in vacuo. The residue was partitioned between CH₂Cl₂ and water. The yellow organic layer was washed with brine, dried over Na₂SO₄ and evaporated. The product was purified by flash chromatography on 4 g silica, eluting with 0 to 50% EtOAc in hexanes. 3-(Biphenyl-2-yl(3-methoxypropoxy) methyl)-1-(methylsulfonyl)piperidine was isolated as an off white solid (82 mg, 91%). ¹H NMR (CDCl₃) δ 0.8-1.8 (m, 8H), 2.25-2.5 (m, 4H), 2.85 (s, 3H), 3.25-3.55 (m, 4H), 3.25 (s, 3H), 3.55 and 3.62 (bd, 1H), 4.08 and 4.13 (d, 1H), 7.07-7.56 (m, 9H).

Step 2. 3-(Biphenyl-2-yl(3-methoxypropoxy)methyl) piperidine

N-(methane-sulfonyl)-3-((methoxypropoxy)(2-phenyl) phenyl)methyl)piperidine (182 mg, 0.436 mmol) was dissolved in dry toluene (7 mL) in a 50 mL flask and stirred under a nitrogen atmosphere. Red-Al (65% in toluene, 0.30 mL, 1.3 mmol, 3.0 equiv) was added via syringe and the mixture was heated to 78° C. for 15 h. After this period LC-MS showed consumption of the starting material and formation of a new signal with m/z 340 (M+H⁺). The mixture was allowed to cool to rt and excess Red-Al was quenched by dropwise addition of 3 mL of satd NaCl solution. The mixture was stirred for 20 min, then filtered through a pad of Celite. The pad was washed with additional toluene and the filtrate was washed with brine, dried over Na₂SO₄, filtered and evaporated to yield 3-(biphenyl-2-yl(3-methoxypropoxy)methyl)piperidine (146 mg, ~99%) as a pale yellow oil. This material was used directly in the subsequent steps. ¹H NMR (CDCl₃) δ 0.65-1.8 (m, 6H), 1.8-2.5 (m, 3H), 2.83 (bd, 1H), 3.05-3.2 (m, 1H), 3.18 (2, 3H), 3.38-3.44 (m, 4H) 4.06-4.12 (m, 1H), 7.15 (m, 2H), 7.3-7.55 (m, 7H).

Example 11

1-(2-(Trimethylsilyl)ethanesulfonyl)-3-((3-methoxypropoxy)(2-(2-cyclohexylethyl)phenyl)methyl)piperidine

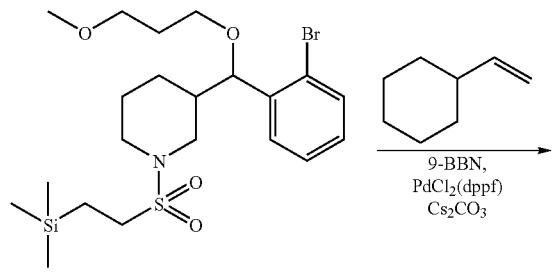

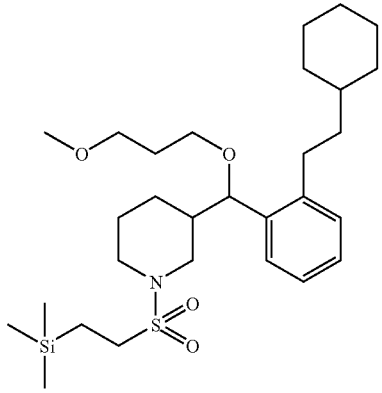

A sealed tube designed for a microwave reactor was filled with nitrogen and charged with vinylcyclohexane (66 mg, 0.595 mmol, 5.0 equiv) 9-BBN (0.5 M solution in THF, 1.07 mL, 4.5 equiv) and the clear solution was stirred overnight at rt. The flask was briefly opened and Cs₂CO₃ (213 mg, 0.119 mmol, 3.3 equiv), PdCl₂(dppf) (11 mg, 0.119 mmol, 0.05 equiv), 1-(2-(trimethylsilyl)ethanesulfonyl)-3-((3-methoxypropoxy)(2-bromophenyl)methyl)-piperidine (100 mg, 0.197 mmol, 1.0 equiv), and dioxane (4 mL) added. The tube was degassed by three evacuate/N₂ backfill cycles, then placed in a CEM microwave reactor and heated to 120° C. for 10 min. The solvent was removed and the product was extracted with EtOAc and filtered through a pad of Celite. The product was purified by flash chromatography on 12 g of silica, eluting with 0 to 27% EtOAc in hexanes, to afford 1-(2-(trimethylsilyl)ethanesulfonyl)-3-((3-methoxypropoxy)(2-(2-cyclohexylethyl)phenyl)methyl)piperidine (82%) as a mixture of diastereomers. ¹H NMR (CDCl₃) δ 0.02 (s, 9H), 0.8-1.9 (m, 24H), 2.5-2.8 (m, 4H), 3.3-4.4 (m, 11H), 7.1-7.3 (m, 4H). MS ESI+ve m/z 561 (M+Na⁺).

Example 12

(S)-2-(Trimethylsilyl)ethyl 2-amino-3-cyclohexylpropylcarbamate

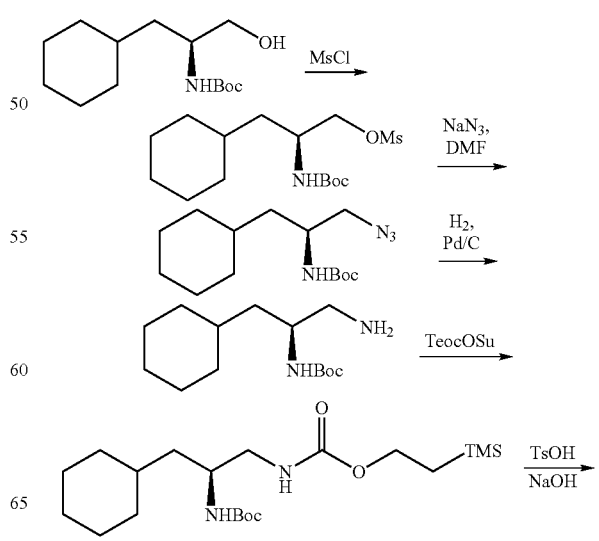

-continued

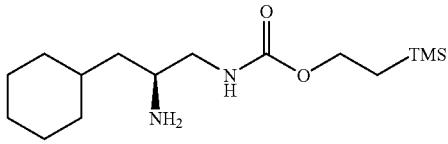

Step 1. (S)-2-(tert-Butoxycarbonylamino)-3-cyclohexylpropyl methanesulfonate A solution of (S)—N-Boc-2-amino-3-cyclohexylpropanol (20 g, 0.078 mol) in CH$_2$Cl$_2$ (400 mL) and triethylamine (19.6 g, 0.195 mol) was cooled to −20° C. Methanesulfonyl chloride (19.5 g, 0.171 mol) was added with fast dropwise addition maintaining the internal temperature at −20° C. The reaction mixture was stirred at −20° C. for an additional 30 min then for 1 h at 0° C. and then quenched with ice-cold water (200 mL). The mixture was extracted with CH$_2$Cl$_2$ (3×100 mL), washed with water (3×50 mL), dried over Na$_2$SO$_4$, concentrated to give the crude (S)-2-(tert-butoxycarbonylamino)-3-cyclohexylpropyl methanesulfonate (23.3 g, 90%), which was used for the next reaction without further purification. $^1$H NMR (400 MHz, CDCl$_3$): 4.93 (m, 1H), 4.60 (d, J=7.6 Hz, 1H), 3.67 (m, 2H), 3.12 (s, 3H), 1.87-1.50 (m, 5H), 1.45 (s, 9H), 1.40-0.72 (m, 8H), MS (E/Z): 336 (M+H$^+$).

Step 2. (S)-tert-butyl 1-azido-3-cyclohexylpropan-2-ylcarbamate

To a solution of (S)-2-(tert-butoxycarbonylamino)-3-cyclohexylpropyl methanesulfonate (23.3 g, 0.070 mol) in anhydrous DMF (300 mL) was added solid NaN$_3$ (13.5 g, 0.21 mol). The reaction mixture was heated at 80° C. overnight. After cooling to rt, the reaction solution was diluted with EtOAc (1200 mL) and water (400 mL). The organic phase was separated and washed with brine (3×300 mL), dried over Na$_2$SO$_4$ and evaporated. The residue was purified by column chromatography on silica gel to give (S)-tert-butyl 1-azido-3-cyclohexylpropan-2-ylcarbamate as a clear oil (13.6 g, 69%). $^1$H NMR (400 MHz, CDCl$_3$): 4.45 (d, J=8.0 Hz, 1H), 3.84 (m, 1H), 3.45 (m, 1H), 3.31 (m, 1H), 1.81-1.60 (m, 5H), 1.45 (s, 9H), 1.40-0.78 (m, 8H). MS (E/Z): 383 (M+H$^+$).

Step 3. (S)-tert-butyl 1-amino-3-cyclohexylpropan-2-ylcarbamate

A mixture of (S)-tert-butyl 1-azido-3-cyclohexylpropan-2-ylcarbamate (13.6 g, 0.048 mol) and Pd/C (1.4 g) in methanol (200 mL) was hydrogenated with a balloon overnight. The mixture was filtered through a pad of Celite and the solvent was removed to give (S)-tert-butyl 1-amino-3-cyclohexylpropan-2-ylcarbamate (10.5 g, 86%), which was used in the next step without purification. $^1$H NMR (400 MHz, CDCl$_3$): 4.52 (d, J=8.4 Hz, 1H), 3.68 (m, 2H), 2.73 (dd, J=13.6&4.4 Hz, 1H), 2.58 (dd, J=13.6&6.0 Hz, 1H), 1.81 (m, 1H), 1.65 (m, 4H), 1.42 (s, 9H), 1.40-1.00 (m, 6H), 1.00-0.70 (m, 2H). MS (E/Z): 257 (M+H$^+$).

Step 4. (S)-tert-Butyl 1-(2-(trimethylsilyl)ethoxycarbonylamino)-3-cyclohexylpropan-2-ylcarbamate To a vigorously stirred biphasic solution of (S)-tert-butyl 1-amino-3-cyclohexylpropan-2-ylcarbamate (10.5 g, 0.041 mol), K$_2$CO$_3$ (10.2 g, 73.8 mol), H$_2$O (60 mL), and CH$_2$Cl$_2$ (120 mL) was added 1-[2-trimethylsilyl)ethoxycarbonyloxy] pyrrolidin-2,5-dione (TeocOSu) (11.14 g, 0.043 mol). The mixture was stirred for 2 h at rt, and then the reaction was washed with brine (3×20 mL), dried over Na$_2$SO$_4$, decanted, stripped, and separated on 50 g of SiO$_2$ to give (S)-tert-butyl 1-(2-(trimethylsilyl)ethoxycarbonylamino)-3-cyclohexyl-propan-2-ylcarbamate (8.5 g, 52%) as a clear oil. $^1$H NMR (400 MHz, CDCl$_3$): 5.52 (brs, 1H), 4.42 (brs, 1H), 4.11 (m, 2H), 3.73 (brs, 1H), 3.30-3.03 (m, 2H), 1.81-1.50 (m, 5H), 1.43 (s, 9H), 1.42-1.02 (m, 6H), 1.02-0.76 (m, 4H), 0.03 (s, 9H); MS (E/Z): 401 (M+H$^+$).

Step 5. (S)-2-(Trimethylsilyl)ethyl 2-amino-3-cyclohexylpropylcarbamate (S)-tert-butyl 1-(2-(trimethylsilyl)ethoxycarbonylamino)-3-cyclohexylpropan-2-ylcarbamate (8.5 g, 0.0213 mol) was dissolved into a minimal volume of ethyl ether (120 mL) and added to a solution of tosic acid (4.46 g, 0.023 mol) in 25 mL of absolute EtOH. This solution was placed on a rotary evaporator and ethyl ether was removed at ambient temp. The flask was then lowered into the water bath (temperature: 60° C.) and the selective de-protection of the Boc group proceeded concurrently with removal of the remainder of solvent. The reaction was completed by 2 h and gave an off-white solid. This material was cooled to rt and dissolved in 100 mL of a mixture EtOH:H$_2$O (1:1, v/v). This was washed with hexanes:EtOAc (5:1, v/v, 3×12 mL), basified with 1N NaOH (pH>10), and extracted with EtOAc (3×50 mL). The combined organic extracts were washed (3×5 mL 1N NaOH, 3×5 mL brine), dried, decanted and stripped to give the free base of (S)-2-(trimethylsilyl)ethyl 2-amino-3-cyclohexylpronyl-carbamate (5.24 g, 82%). $^1$H NMR (400 MHz, CDCl$_3$): 5.09 (brs, 1H), 4.14 (t, J=8.4 Hz, 2H), 3.23 (m, 1H) 2.88 (m, 2H), 1.75-1.48 (m, 5H), 1.5-0.75 (m, 10H), 0.05 (s, 9H). MS (E/Z): 301 (M+H$^+$).

Example 13

(S)-2-(trimethylsilyl)ethyl 2-amino-3-cyclohexylpropyl(methyl)carbamate

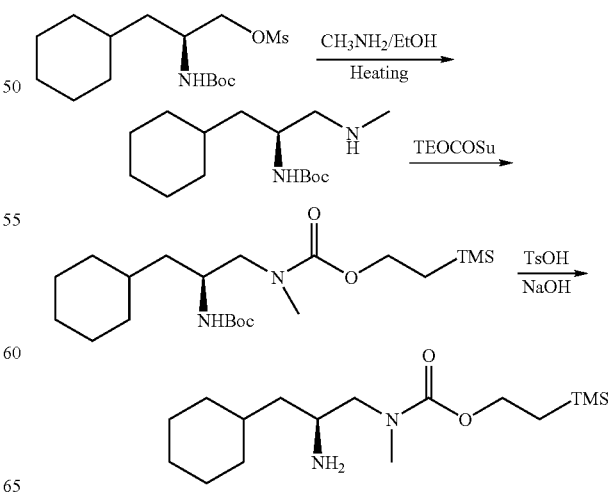

Step 1. (S)-tert-Butyl 1-cyclohexyl-3-(methylamino) propan-2-ylcarbamate (S)-2-(tert-butoxycarbonylamino)-3-cyclohexylpropyl methanesulfonate (28 g, 83.6 mmol) was dissolved into a solution of methylamine in ethanol (about 30% by weight, 300 mL). The reaction was heated at 50-60° C. overnight and concentrated in vacuo. The residue was dissolved in EtOAc, washed with brine (2×100 mL), dried over $MgSO_4$, and concentrated to give the crude product. This crude product was purified by flash chromatography (AcOEt:Hex.=2:1 first, then EtOAc:MeOH=1:1) to afford pure (S)-tert-butyl 1-cyclohexyl-3-(methylamino)propan-2-ylcarbamate (10.6 g, 47%). $^1$H NMR (400 MHz, $CDCl_3$): 4.81 (brs, 1H), 3.89 (m, 1H), 2.77 (m, 2H), 2.54 (s, 3H), 2.44 (m, 2H), 1.78 (m, 1H), 1.67 (m, 4H), 1.44 (s, 9H), 1.50-1.10 (m, 6H), 1.00-0.77 (m, 2H), 0.05 (s, 9H). MS (E/Z): 271 (M+H$^+$).

Step 2. (S)-tert-butyl 1-cyclohexyl-3-(N-methyl-N-(2-(trimethylsilyl)ethoxycarbonyl)amino)propan-2-ylcarbamate To a vigorously stirred 2-phase solution of (S)-tert-butyl 1-cyclohexyl-3-(methylamino)propan-2-ylcarbamate (7.25 g, 0.027 mol), $K_2CO_3$ (6.66 g, 0.048 mol), $H_2O$ (40 mL) and $CH_2Cl_2$ (80 mL) was added 1-[2-trimethylsilyl)ethoxycarbonyloxy]pyrrolidin-2,5-dione (TeocOSu) solid (7.3 g, 0.028 mol). After stirring for 2 h at rt, the reaction was added to $CH_2Cl_2$ (200 mL), washed with satd aq $NaHCO_3$ (3×15 mL) then brine (3×15 mL), dried over $Na_2SO_4$ and concentrated. The residue was purified by column chromatography on 40 g of silica gel to give (S)-tert-butyl 1-cyclohexyl-3-(N-methyl-N-(2-(trimethylsilyl)ethoxycarbonyl)amino)propan-2-ylcarbamate as a clear oil (5.78 g, 50%). $^1$H NMR (400 MHz, $CDCl_3$) δ 4.50 (d, J=7.6 Hz, 1H), 4.15 (t, J=7.6 Hz, 2H), 3.89 (m, 1H), 3.56-2.95 (m, 2H), 2.92&2.90 (s, 3H), 1.82 (m, 1H), 1.66 (m, 4H), 1.41 (s, 9H), 1.50-1.10 (m, 6H), 1.00-0.70 (m, 4H), 0.01 (s, 9H). MS (E/Z): 415 (M+H$^+$).

Step 3. (S)-2-(Trimethylsilyl)ethyl 2-amino-3-cyclohexylpropyl(methyl)carbamate (S)-tert-butyl 1-cyclohexyl-3-(N-methyl-N-(2-(trimethylsilyl)ethoxycarbonyl)amino)propan-2-ylcarbamate (5.78 g, 0.014 mol) was dissolved into a minimal volume of ethyl ether (100 mL) and added to a solution of TsOH (2.92 g, 0.0154 mol) in 20.0 mL of absolute EtOH. This solution was placed on a rotary evaporator and the $Et_2O$ was removed at ambient temp. The flask was then lowered into the water bath (temperature: 60° C.) and the selective de-protection of the BOC group proceeded concurrently with removal of the remainder of the solvent. The reaction was completed by 2 h and gave an off-white solid, which was washed with hexanes:EtOAc (5:1, v/v, 3×10 mL), basified with 1N NaOH (pH>10), and extracted with ethyl ether (3×50 mL). The combined organic extracts were washed with 1N NaOH (3×5 mL) and brine (3×5 mL), dried, decanted and stripped to give the free base of (S)-2-(trimethylsilyl)ethyl 2-amino-3-cyclohexylpropyl(methyl)carbamate (3.5 g, 80%). $^1$H NMR (400 MHz, $CDCl_3$): 4.15 (t, J=8.4 Hz, 2H), 3.10 (m, 3H), 2.91 (s, 3H), 1.78-1.56 (m, 5H), 1.50-1.00 (M, 6H), 1.00-0.70 (m, 4H), 0.01 (s, 9H). MS (E/Z): 315 (M+H$^+$).

Example 14

(S)-[2-Amino-3-(4,4-difluoro-cyclohexyl)-propyl]-methyl-carbamic acid 2-trimethylsilanyl-ethyl ester

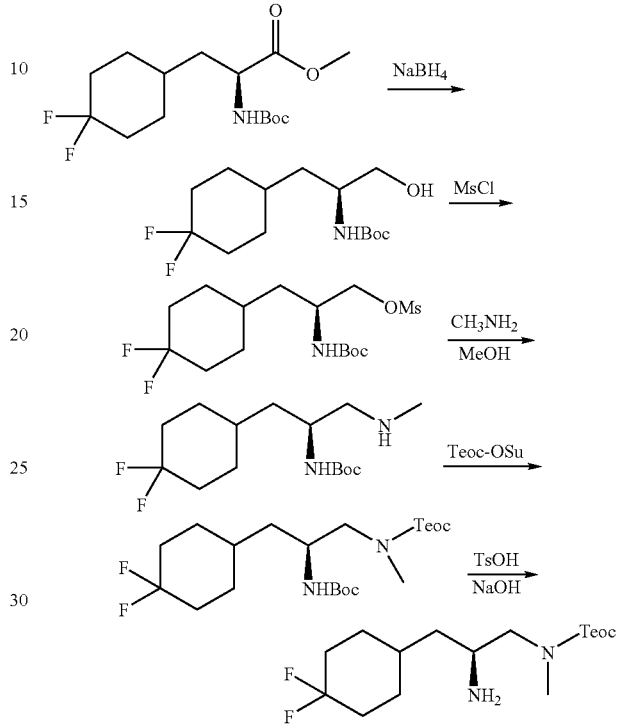

Step 1. (S)-tert-Butyl 1-(4,4-difluorocyclohexyl)-3-hydroxypropan-2-ylcarbamate To a solution of (S)-methyl 2-(tert-butoxycarbonylamino)-3-(4,4-difluorocyclohexyl)propanoate (28.6 g, 0.089 mol), prepared as described in U.S. Pat. No. 5,688,946, in ethanol (600 mL) at 0° C. was added $NaBH_4$ (27.1 g, 0.713 mol) in portions while the temp. was maintained at 0-5° C. The mixture was stirred for 2-3 h at rt and then evaporated. The residue was partitioned between water and EtOAc. The organic layer was washed with $H_2O$ and brine, dried over $Na_2SO_4$ and evaporated to give (S)-tert-butyl 1-(4,4-difluorocyclohexyl)-3-hydroxypropan-2-ylcarbamate (25.7 g, 99%), which was used in the next step without purification. $^1$H NMR (400 MHz, $CDCl_3$): 4.61 (d, J=7.6 Hz, 1H), 3.70 (m, 1H), 3.50 (m, 1H), 2.45-1.10 (m, 11H), 1.44 (s, 9H); MS (E/Z): 295 (M+H$^+$).

Step 2. (S)-2-(tert-butoxycarbonylamino)-3-(4,4-difluorocyclohexyl)propyl methanesulfonate To a solution of (S)-tert-butyl 1-(4,4-difluorocyclohexyl)-3-hydroxypropan-2-ylcarbamate (25.7 g, 0.088 mol) in dry $CH_2Cl_2$ (300 mL) was added $Et_3N$ (35.4 g, 46.2 mL) at 0 to −5° C. A solution of methanesulfonyl chloride (20.1 g, 0.1754 mol) in dry $CH_2Cl_2$ (150 mL) was added dropwise at the same temperature. After addition, the mixture was allowed to warm to rt gradually. 300 mL of water was added and the aqueous layer was extracted with $CH_2Cl_2$ (3×100 mL). The combined organic layers were washed with 10% aq citric acid, satd aq NaHCO₃ and brine, dried over Na₂SO₄, filtered and concentrated to give methanesulfonic acid (S)-2-(tert-butoxycarbonylamino)-3-(4,4-difluorocyclohexyl)propyl methanesulfonate (28.8 g, 89%), which was used in the next step without purification. ¹H NMR (400 MHz, CDCl₃): 4.57 (d, J=6.8 Hz, 1H), 4.27 (m, 1H), 4.16 (m, 1H), 3.97 (m, 1H), 3.03 (s, 3H), 2.40-1.20 (m, 11H), 1.44 (s, 9H); MS (E/Z): 372 (M+H⁺).

Step 3. (S)-tert-Butyl 1-(4,4-difluorocyclohexyl)-3-(methylamino)propan-2-ylcarbamate (S)-2-(tert-butoxycarbonylamino)-3-(4,4-difluorocyclohexyl)propyl methanesulfonate (28.8 g, 0.077 mol) was dissolved in alcoholic of methylamine solution (350 mL) and the reaction was warmed at 50-60° C. overnight. The reaction mixture was cooled to rt and the solvent was removed under reduced pressure to give an oil, which was dissolved into EtOAc, washed with water twice and brine, dried over Na₂SO₄ and concentrated. The residue was purified by flash chromatography to afford (S)-tert-butyl 1-(4,4-difluorocyclohexyl)-3-(methylamino)propan-2-ylcarbamate (8.1 g, 34.4%). ¹H NMR (400 MHz, CDCl₃): 5.12 (m, 1H), 4.97 (m, 1H), 3.82 (m, 1H), 3.63 (dd, J=14.4&4.4 Hz, 1H), 3.45 (dd, J=14.4&9.2 Hz, 1H), 2.76&2.74 (s, 1H), 2.20-1.20 (m, 11H), 1.44 (s, 9H); MS (E/Z): 307 (M+H⁺).

Step 4. (S)-tert-butyl 1-(4,4-difluorocyclohexyl)-3-(N-methyl-N-(2-(trimethylsilyl)ethoxycarbonyl)amino)propan-2-ylcarbamate Solid 1-[2-trimethylsilyl)ethoxycarbonyloxy]pyrrolidin-2,5-dione (TeocOSu, 7.2 g, 0.0278 mol) was added to a vigorously stirred 2-phase solution of (S)-tert-butyl 1-(4,4-difluorocyclohexyl)-3-(methylamino)propan-2-ylcarbamate (8.1 g, 0.0265 mol), K₂CO₃ (11.85 g, 0.0477 mol), H₂O (32 mL) and CH₂Cl₂ (64 mL). After stirring for 2 h at rt, the reaction was taken up in CH₂Cl₂ (200 mL) washed with satd aq NaHCO₃ (3×15 mL), then brine (3×15 mL), dried over Na₂SO₄ and evaporated to give an oil. Chromatography on silica gel gave (S)-tert-butyl 1-(4,4-difluorocyclohexyl)-3-(N-methyl-N-(2-(trimethylsilyl)ethoxycarbonyl)amino)propan-2-ylcarbamate (6.25 g, 52.4%). ¹H NMR (400 MHz, CDCl₃): 4.58 & 4.32 (m, 1H), 4.12 (t, J=9.6 Hz, 2H) 3.89 (m, 1H), 3.40 (m, 1H), 3.05 (m, 1H), 2.89 (s, 3H), 2.10-1.00 (m, 11H), 0.97 (t, J=9.6 Hz, 2H), 1.44 (s, 9H), 0.03 (s, 9H); MS (E/Z): 451 (M+H⁺).

Step 5. (S)-2-(trimethylsilyl)ethyl 2-amino-3-(4,4-difluorocyclohexyl)propyl(methyl)carbamate (S)-tert-Butyl 1-(4,4-difluorocyclohexyl)-3-(N-methyl-N-(2-(trimethylsilyl)ethoxycarbonyl)amino)propan-2-ylcarbamate (6.25 g, 0.0139 mol) was dissolved in a minimal volume of ether (100 mL) and added to a solution of toluenesulfonic acid (2.71 g, 0.0142 mol) in absolute EtOH (20 mL). This solution was placed on a rotary evaporator and the Et₂O was removed at ambient temp. The flask was then lowered into the water bath (temperature: 60° C.) and the selective removal of the Boc group proceeded concurrently with removal of the remainder of solvent. The reaction was completed by 2 h and gave a white solid, which was washed with hexanes:EtOAc (5:1, v/v, 3×10 mL), basified with 1N NaOH (pH>10), and extracted with Et₂O (3×50 mL) The combined Et₂O extracts were washed with 1N aq NaOH (3×5 mL), brine (3×5 mL), dried, decanted and stripped to give the free base (S)-2-(trimethylsilyl)ethyl 2-amino-3-(4,4-difluorocyclohexyl)propyl(methyl)carbamate (3.68 g, 76%). ¹H NMR (400 MHz, CD₃OD): 4.17 (t, J=8.4 Hz, 2H), 3.15 (m, 1H), 2.93 (s, 3H), 2.61 (dd, J=12.0 & 4.0 Hz, 1H), 2.36 (dd, J=12.0 & 8.4 Hz, 1H), 2.12-1.16 (m, 11H), 1.00 (t, J=8.4 Hz, 2H), 0.04 (s, 9H); MS (E/Z): 351 (M+H⁺).

Example 15

Benzyl (2S,3S)-3-amino-4-cyclohexylbutan-2-ylcarbamate

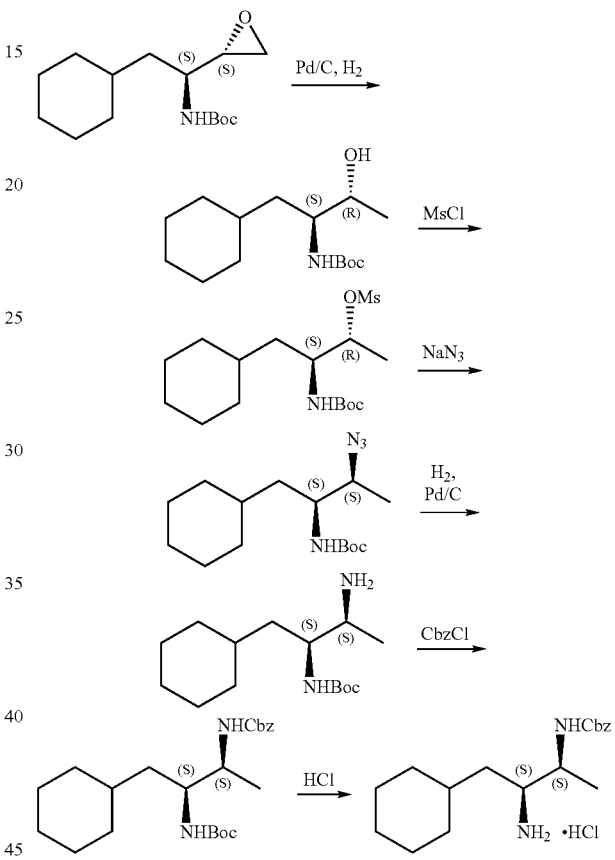

Step 1. tert-Butyl (2S,3R)-1-cyclohexyl-3-hydroxybutan-2-ylcarbamate

To a solution of tert-butyl (S)-2-cyclohexyl-1-((S)-oxiran-2-yl)ethylcarbamate (0.63 g, 2.5 mmol) and triethylamine (0.65 mL, 5 mmol) in methanol (15 mL) was added Pd/C (0.1 g), and the mixture was hydrogenated under 30 psi pressure at rt overnight. The mixture was filtered and the filtrate was concentrated to give tert-butyl (2S,3R)-1-cyclohexyl-3-hydroxybutan-2-ylcarbamate (0.44 g, 70%). ¹H NMR (400 MHz, CDCl₃): 4.48 (brs, 1H), 3.78 (m, 2H), 2.30 (brs, 1H), 1.82 (m, 1H), 1.66 (m, 4H), 1.45 (s, 9H), 1.40-1.00 (m, 6H), 1.10 (d, J=6.4 Hz, 3H), 1.00-0.70 (m, 2H); MS (E/Z): 272 (M+H⁺).

Step 2. Tert-butyl (2S,3R)-1-cyclohexyl-3-(methanesulfonyloxy)butan-2-ylcarbamate To a solution of tert-butyl (2S,3R)-1-cyclohexyl-3-hydroxybutan-2-ylcarbamate (0.44 g, 1.62 mmol) in dry CH₂Cl₂ (10 mL) was added Et₃N (0.71 g, 7 mmol, 4 eq) at 0 to −5° C. A solution of methanesulfonyl chloride (0.8 g, 7 mmol, 2 eq) in dry CH₂Cl₂ (5 mL) was added dropwise at the same temperature. The mixture was allowed to warm to rt gradually. TLC showed that the starting material had disappeared. Water (30 mL) was added. The aqueous layer was extracted with CH₂Cl₂ (3×20 mL). The combined organic layers was washed with 10% aq citric acid, satd aq NaHCO₃ and brine, then dried over Na₂SO₄, filtered and concentrated to give tert-butyl (2S,3R)-1-cyclohexyl-3-(methanesulfonyloxy)butan-2-yl-carbamate (0.46 g, 81%), which was used in the next step without purification.

Step 3. Tert-butyl (2S,3S)-3-azido-1-cyclohexylbutan-2-ylcarbamate tert-Butyl (2S,3R)-1-cyclohexyl-3-(methanesulfonyloxy)butan-2-ylcarbamate (0.46 g, 1.32 mmol) was dissolved into anhydrous DMF (10 mL), solid NaN₃ (0.26 g, 4 mmol) was added and the reaction mixture was heated to 80° C. overnight. The reaction mixture was cooled to rt and diluted with EtOAc (100 mL) and water (30 mL). The organic phase was washed with water (3×30 mL), dried over Na₂SO₄ and evaporated. The residue was separated by chromatography on a silica gel column to give tert-butyl (2S,3S)-3-azido-1-cyclohexylbutan-2-ylcarbamate (0.215 g, 55%). ¹H NMR (400 MHz, CDCl₃): 4.38 (d, J=9.2 Hz, 1H), 3.72 (m, 1H), 3.60 (m, 1H), 1.82 (m, 1H), 1.67 (m, 4 h), 1.44 (s, 9H), 1.40-1.00 (m, 6H), 1.28 (d, J=6.4 Hz, 3H), 1.00-0.75 (m, 2H); MS (E/Z): 297 (M+H⁺).

Step 4. Tert-butyl (2S,3S)-3-amino-1-cyclohexylbutan-2-ylcarbamate

A solution of tert-butyl (2S,3S)-3-azido-1-cyclohexylbutan-2-ylcarbamate (0.215 g, 0.73 mmol) in methanol (10 mL) was added to wetted Pd/C (0.1 g) and was hydrogenated with a balloon overnight. The reaction mixture was filtered through a pad of Celite and the solvent was removed to give tert-butyl (2S,3S)-3-amino-1-cyclohexylbutan-2-ylcarbamate (0.153 g, 78%), which was used in the next step without purification.

Step 5. Benzyl (2S,3S)-3-(tert-butoxycarbonyl)amino-4-cyclohexylbutan-2-ylcarbamate To a mixture of tert-butyl (2S,3S)-3-amino-1-cyclohexylbutan-2-ylcarbamate (0.153 g, 0.57 mmol) and Et₃N (0.19 mL, 1.42 mmol) in methanol (5 mL) at 0° C. was added dropwise a solution of CBZCl (0.116 g, 0.68 mmol) in methanol (3 mL). The mixture was warmed to rt, stirred 2 h, evaporated to remove methanol, diluted with water (15 mL) and extracted with EtOAc (3×10 mL). The combined organic layers were washed with brine (15 mL), dried and evaporated to give benzyl (2S,3S)-3-(tert-butoxycarbonyl)amino-4-cyclohexylbutan-2-ylcarbamate (0.117 g, 51%) that was used in the next step without further purification. ¹H NMR (400 MHz, CDCl₃): 7.32 (m, 5H), 5.37 (brs, 1H), 5.09 (s, 2H), 4.36 (brs 1H), 3.76 (m, 2H), 1.82 (m, 1H), 1.66 (m, 4H), 1.44 (s, 9H), 1.35-1.10 (m, 6H), 1.07 (d, J=6.4 Hz, 3H), 1.00-0.78 (m, 2H); MS (E/Z): 405 (M+H⁺).

Step 6. Benzyl (2S,3S)-3-amino-4-cyclohexylbutan-2-ylcarbamate

Benzyl (2S,3S)-3-(tert-butoxycarbonyl)amino-4-cyclohexylbutan-2-ylcarbamate (0.117 g, 0.29 mmol) was dissolved in 2 N HCl in methanol (10 mL, 20 mmol). The mixture was allowed to stir at 40-50° C. for 2 h. The mixture was concentrated in vacuo to give the HCl salt of benzyl (2S,3S)-3-amino-4-cyclohexylbutan-2-ylcarbamate (0.077 g, 78%).

Example 16

Benzyl (2R,3S)-3-amino-4-cyclohexylbutan-2-ylcarbamate

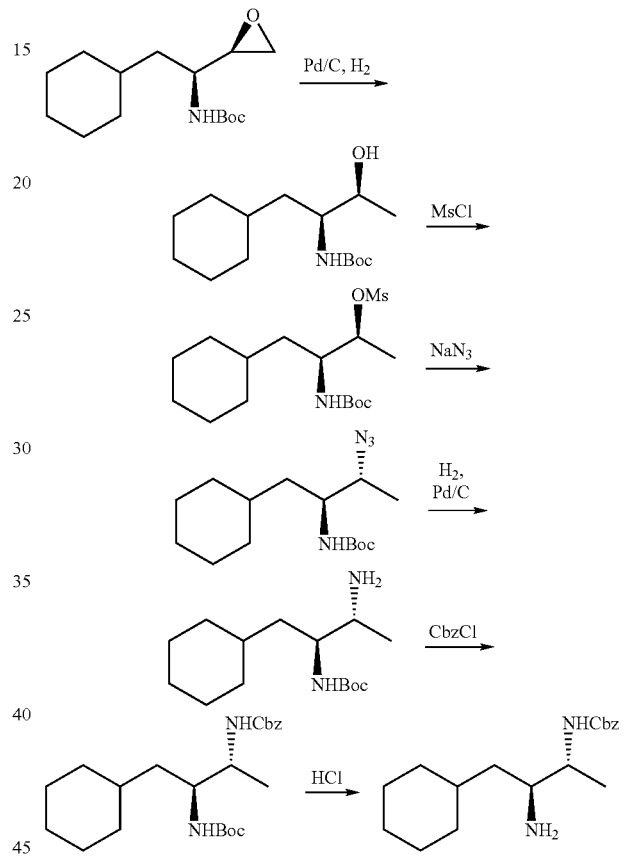

The procedure in Example 15 was followed starting with (1S,R)-(2-cyclohexyl-1-oxiranyl-ethyl)-carbamic acid tert-butyl ester.

Example 17 tert-Butyl (S)-1-amino-3-cyclohexylpropan-2-ylcarbamate

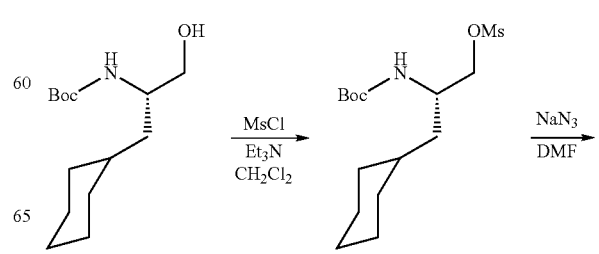

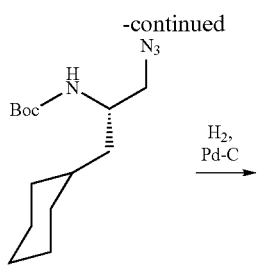 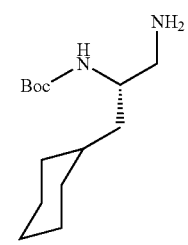

Step 1. (S)-2-(tert-Butoxycarbonylamino)-3-cyclohexylpropyl methanesulfonate A solution of tert-butyl (S)-3-cyclohexyl-1-hydroxypropan-2-ylcarbamate (3.02 g, 11.7 mmole) in $CH_2Cl_2$ (50 mL) and triethylamine (4.0 mL, 28.6 mmol) was cooled to –20° C. (internal temperature). Neat methanesulfonyl chloride (2.0 mL, 25.7 mmol) was added dropwise, maintaining the internal temperature at –20° C. (+/–5° C.). The reaction mixture was stirred at –20° C. for an additional 30 min and at 0° C. for 1 h. Reaction progress was followed by TLC and LC-MS. The reaction was quenched with ice-cold water, extracted with $CH_2Cl_2$ (3×20 mL), washed with water (3×10 mL), dried ($Na_2SO_4$), decanted, and stripped to give 4.13 g (quant) of product. $^1H$ NMR ($CDCl_3$) δ 0.80-1.40 (10H), 1.40 (s, 9H), 1.65 (t, 2H), 1.75 (d, 1H), 2.95 (s, 3H), 3.94 (m, 1H), 4.10 (m, 1H), 4.24 (m, 1H), 4.60 (m, 1H). MS ESI+ve m/z 236 (M(–BOC)+1).

Step 2. (S)-tert-Butyl 1-azido-3-cyclohexylpropan-2-ylcarbamate (S)-2-(tert-Butoxycarbonylamino)-3-cyclohexylpropyl methanesulfonate (13.3 g, 39.3 mmol) from Step 1 was dissolved in anhydrous DMF (140 mL). Solid $NaN_3$ (5.18 g, 79.7 mmol) was added and the reaction was warmed to 50° C. for 5 h. The reaction mixture was permitted to cool to rt and the solvent was removed under reduced pressure (150 Torr, 55° C.). This material was taken up into $Et_2O$ (150 mL), washed with water (3×10 mL) and brine (3×10 mL), dried ($Na_2SO_4$), decanted, and stripped to give 13.9 g crude product. This was separated on a silica column using a gradient from 0-100% EtOAc in hexanes. Solvent was stripped from appropriate fractions to give (S)-tert-butyl 1-azido-3-cyclohexylpropan-2-ylcarbamate (7.21 g, 65%) as a clear oil. $^1H$ NMR ($CDCl_3$) δ 0.60-1.80 (m 12H), 1.40 (s, 9H), 2.86 (d, 1H), 3.29 (d, 1H), 4.85 (d, 1H), 4.51 (m, 1H), 8.00 (s, 1H). MS ESI+ve m/z 183 (M(–BOC)+1).

Step 3. (S)-tert-Butyl 1-amino-3-cyclohexylpropan-2-ylcarbamate

A solution of (S)-tert-butyl 1-azido-3-cyclohexylpropan-2-ylcarbamate (7.2 g, 25.5 mmol) in methanol (250 mL) was added to wetted Pd/C (1.0 g) in a $N_2$-filled Parr bottle. After 3 vac/purge cycles with $H_2$, the vessel was charged to 50 psi and shaken on a Parr apparatus overnight. Theoretical equivalents (36 psi) of $H_2$ were consumed. The reaction mixture was filtered through a pad of Celite and the solvent was removed to give (S)-tert-butyl 1-amino-3-cyclohexylpropan-2-ylcarbamate (5.9 g, 90%) as a white solid. $^1H$ NMR (D6-DMSO) δ 0.70-1.30 (m 10H), 1.38 (s, 9H), 1.58 (d, 2H), 1.80 (d, 1H), 2.66 (m, 1H), 2.78 (d, 1H), 3.74 (m, 1H), 6.77 (d, 1H), 8.0 (bs, 2H). MS ESI+ve m/z 157 (M(–BOC)+1).

Example 18

(S)-3-Cyclohexyl-$N^1,N^1$-dimethylpropane-1,2-diamine

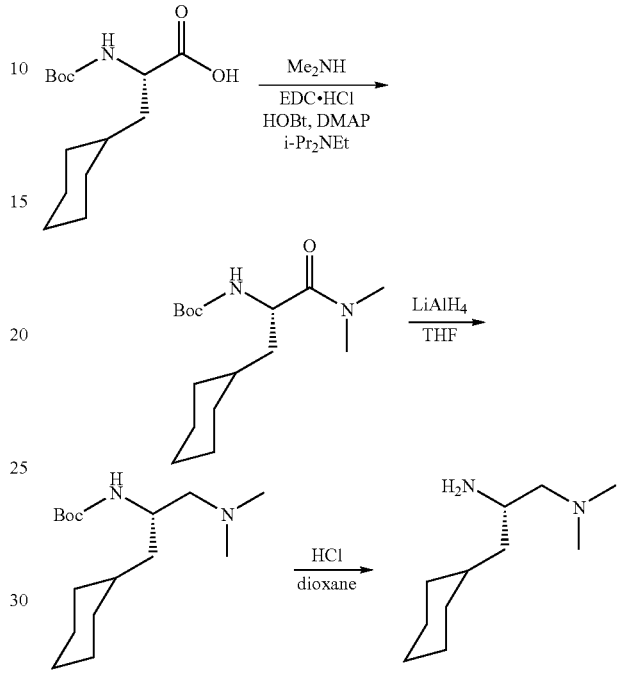

Step 1. (S)-tert-Butyl 3-cyclohexyl-1-(dimethylamino)-1-oxopropan-2-ylcarbamate Solid EDC.HCl (4.62 g, 24.1 mmol) was added to a solution of (S)-2-(tert-butoxycarbonylamino)-3-cyclohexylpropanoic acid (5.08 g, 19.0 mmol), diisopropylethylamine (10.0 mL, 57 mmol), HOBt (0.38 g, 2.8 mmol), DMAP (0.16 g, 1.3 mmol), dimethylamine (15 mL of a 2 M THF solution, 30 mmol), and anhydrous DMF (50 mL). The resultant clear light yellow solution was stirred at rt and the reaction progress was followed by LC-MS. After 5 h, the solvent was removed (50° C., 150 Torr). The residue was taken up in ether (200 mL) and washed with satd aq $NaHCO_3$ (3×25 mL). Hexanes (100 mL) was added to the $Et_2O$ extract and this was washed with water (5×10 mL) and brine (3×10 mL), dried ($Na_2SO_4$), decanted and stripped. The crude material was purified using 40 g $SiO_2$ with an eluent of hexanes to EtOAc. Combining appropriate fractions and removal of solvent gave (S)-tert-butyl 3-cyclohexyl-1-(dimethylamino)-1-oxopropan-2-ylcarbamate (3.85 g, 69%) as a white solid. MS ESI+ve m/z 321 $(M+Na)^+$.

Step 2. (S)-tert-Butyl 1-cyclohexyl-3-(dimethylamino)propan-2-ylcarbamate

A 1 M solution of $LiAlH_4$ in THF (35 mL, 35.0 mmol) was added to a solution of (S)-tert-butyl 3-cyclohexyl-1-(dimethylamino)-1-oxopropan-2-ylcarbamate (3.85 g, 12.9 mmol) in THF at –78° C. at a rate to maintain the temperature below –60° C. The reaction was permitted to warm to 25° C. and conversion to product was monitored by LC-MS. After 6 h, the reaction was cooled to 0° C., and $H_2O$ (3.0 mL) was added dropwise, followed by 1 N aq NaOH (3.0 mL), maintaining the temperature below 10° C. Ether (100 mL) and Celite (10 g) were added to the heterogenous mixture, stirred for 30 minutes and filtered through a pad of Celite. The solvent was removed and the residue was separated on 12 g of SiO$_2$ with an eluent gradient from hexanes to 30% MeOH in EA. Appropriate fractions were combined and the solvent was removed to afford (S)-tert-butyl 1-cyclohexyl-3-(dimethylamino)propan-2-ylcarbamate (0.26 g, 7%) as a white solid. MS ESI+ve m/z 285 (M+Na)$^+$.

Step 3. (S)-3-Cyclohexyl-N$^1$,N$^1$-dimethylpropane-1,2-diamine

Solid (S)-tert-butyl 1-cyclohexyl-3-(dimethylamino)propan-2-ylcarbamate (263 mg, 0.97 mmol) was dissolved in 4 M HCl in dioxane (10 mL, 40 mmol) and H$_2$O (1 mL). After 2 h, the solvent was removed (50° C., 150 mm) and the residual solvent was azeotroped with toluene (2×10 mL) to afford (S)-3-Cyclohexyl-N$^1$,N$^1$-dimethylpropane-1,2-diamine dihydrochloride (245.3 mg, 100%) as a white solid. MS ESI+ve m/z 185 (M(−BOC)+1)$^+$.

Example 19

The following intermediates were prepared according to procedures analogous to those used in Example 18:
2-(trimethylsilyl)ethyl (S)-2-amino-4-methylpentylmethylcarbamate
2-(trimethylsilyl)ethyl (S)-2-aminopropylmethylcarbamate.

Example 20

(2S)-2-amino-1-(N-butyl-N-(2-(trimethylsilyl)ethoxycarbonyl)amino)-3-cyclohexylpropane

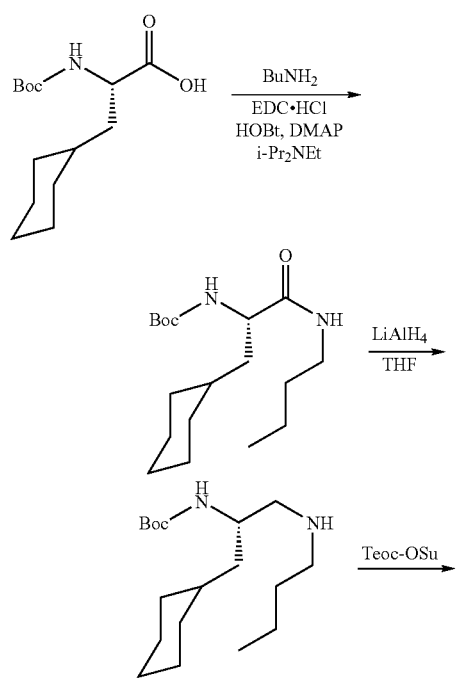

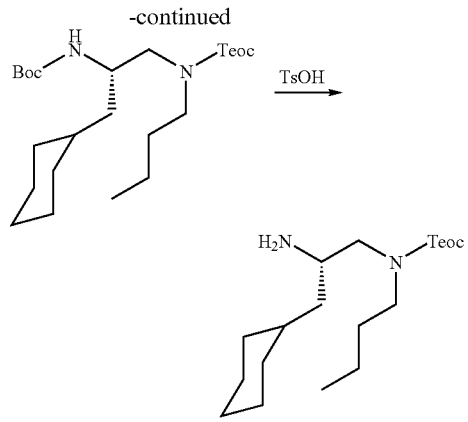

Step 1. (S)-tert-Butyl 1-(butylamino)-3-cyclohexyl-1-oxopropan-2-ylcarbamate

Solid EDC.HCl (518 mg, 3.3 mmol) was added to a solution of (S)-2-(tert-butoxycarbonylamino)-3-cyclohexylpropanoic acid (405 mg, 1.5 mmol), diisopropylethylamine (2.5 mL, 14 mmol), HOBt (130 mg, 1.0 mmol), DMAP (18 mg, 0.15 mmol), butylamine (0.30 mL, 3 mmol), and anhydrous DMF (25 mL). The resulting clear light yellow solution was stirred at rt for 12 h. The solvent was removed (50° C., 150 Torr) and the residue was taken up in ether (100 mL) and washed with satd aq NaHCO$_3$ (3×10 mL). Hexanes (30 mL) was added to the ether extract and this was washed with water (5×5 mL) and brine (3×5 mL), dried (Na$_2$SO$_4$), decanted, stripped and the crude material was purified using 40 g SiO$_2$ with an eluent of hexanes to 30% MeOH in EA. Combining appropriate fractions and removal of solvent gave (S)-tert-butyl 1-(butylamino)-3-cyclohexyl-1-oxopropan-2-ylcarbamate (417 mg, 85%) as a white solid. $^1$H NMR (CDCl$_3$) δ 0.80-1.80 (m 20H), 1.50 (s, 9H), 3.20 (m, 2H), 4.01 (d, 1H), 5.01 (d, 1H), 6.50 (bs, 1H). MS ESI+ve m/z 321 (M+Na).

Step 2. (2S)-2-(tert-Butoxycarbonylamino)-1-butylamino-3-cyclohexylpropane

A 1 M solution of LiAlH$_4$ in THF (2.5 mL, 2.5 mmol) was added to a solution of (S)-tert-butyl 1-(butylamino)-3-cyclohexyl-1-oxopropan-2-ylcarbamate (384.7 mg, 1.18 mmol) in THF (10 mL) at 0° C. The reaction was permitted to warm to 25° C. and stirred for 12 h. The reaction was cooled to 0° C., and H$_2$O (0.2 mL) and then 1 N NaOH (0.2 mL) were introduced with cautious dropwise addition maintaining the temperature below 10° C. The resulting gel was filtered through a pad of Celite and the solids were washed with Et$_2$O (50 mL). The solvent was removed to yield crude (2S)-2-(tert-butoxycarbonylamino)-1-butylamino-3-cyclohexylpropane (312.8 mg, 85%) as a white solid. MS ESI+ve m/z 313 (M+1). The crude amine was used without further purification.

Step 3. (2S)-2-(tert-Butoxycarbonylamino)-1-(N-butyl-N-(2-(trimethylsilyl)ethoxycarbonyl)amino)-3-cyclohexylpropane Solid Teoc-OSu (390 mg, 1.5 mmol) was added to a vigorously stirred 2-phase mixture of (2S)-2-(tert-butoxycarbonylamino)-1-butylamino-3-cyclohexylpropane (312.8 mg, 1.0 mmol), Na$_2$CO$_3$ (525 mg, 5.0 mmol), H$_2$O (5.0 mL), and CH$_2$Cl$_2$ (25.0 mL). The mixture was stirred for 90 min at rt and the reaction was taken up in CH$_2$Cl$_2$ (50 mL), washed with brine (3×10 mL), dried over Na$_2$SO$_4$, decanted, and stripped to give a clear oil. This oil was separated on a 4 g SiO$_2$ column to give crude (2S)-2-(tert-butoxycarbonylamino)-1-(N-butyl-N-(2-(trimethylsilyl)ethoxycarbonyl)amino)-3-cyclohexylpropane (486.5 mg, 106%) as a clear oil (quant). MS ESI+ve m/z 479 (M+Na). The crude product was used without further purification.

Step 4. (2S)-2-amino-1-(N-butyl-N-(2-(trimethylsilyl)ethoxycarbonyl)amino)-3-cyclohexylpropane A solution of toluenesulfonic acid monohydrate (199.4 mg, 1.0 mmol) in absolute EtOH (1.0 mL) was added to a solution of (2S)-2-(tert-butoxycarbonylamino)-1-(N-butyl-N-(2-(trimethylsilyl)ethoxycarbonyl)amino)-3-cyclohexylpropane (468.5 mg, 1.03 mmol) in Et$_2$O (10 mL). This solution was placed in a flask on a rotary evaporator and the Et$_2$O was removed at rt. The flask was then lowered into the water bath (temperature: 60° C.) and the selective removal of the Boc group proceeded concurrently with removal of the remainder of solvent to afford (2S)-2-amino-1-(N-butyl-N-(2-(trimethylsilyl)ethoxycarbonyl)amino)-3-cyclohexylpropane (556.7 mg, 98%) as a white solid.

Example 21

The following intermediates were prepared using procedures analogous to those used in Example 20:

(2S)-1-(N-ethyl-N-(2-(trimethylsilyl)ethoxycarbonyl)amino)-3-cyclohexylpropyl-2-amine (2S)-1-(N-propyl-N-(2-(trimethylsilyl)ethoxycarbonyl)amino)-3-cyclohexylpropyl-2-amine (2S)-1-(N-isobutyl-N-(2-(trimethylsilyl)ethoxycarbonyl)amino)-3-cyclohexylpropyl-2-amine (2S)-1-(N-isopentyl-N-(2-(trimethylsilyl)ethoxycarbonyl)amino)-3-cyclohexylpropyl-2-amine (2S)-1-(N-pentyl-N-(2-(trimethylsilyl)ethoxycarbonyl)amino)-3-cyclohexylpropyl-2-amine and (S)-2-(trimethylsilyl)ethyl 2-amino-3-cyclohexylpropyl(2-methoxyethyl)carbamate.

Example 22

2-(Trimethylsilyl)ethyl (S)-3-cyclohexyl-2-(methylamino)propylcarbamate

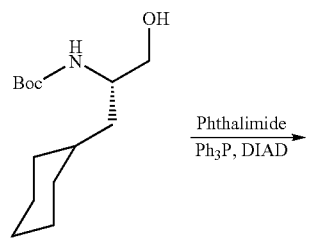

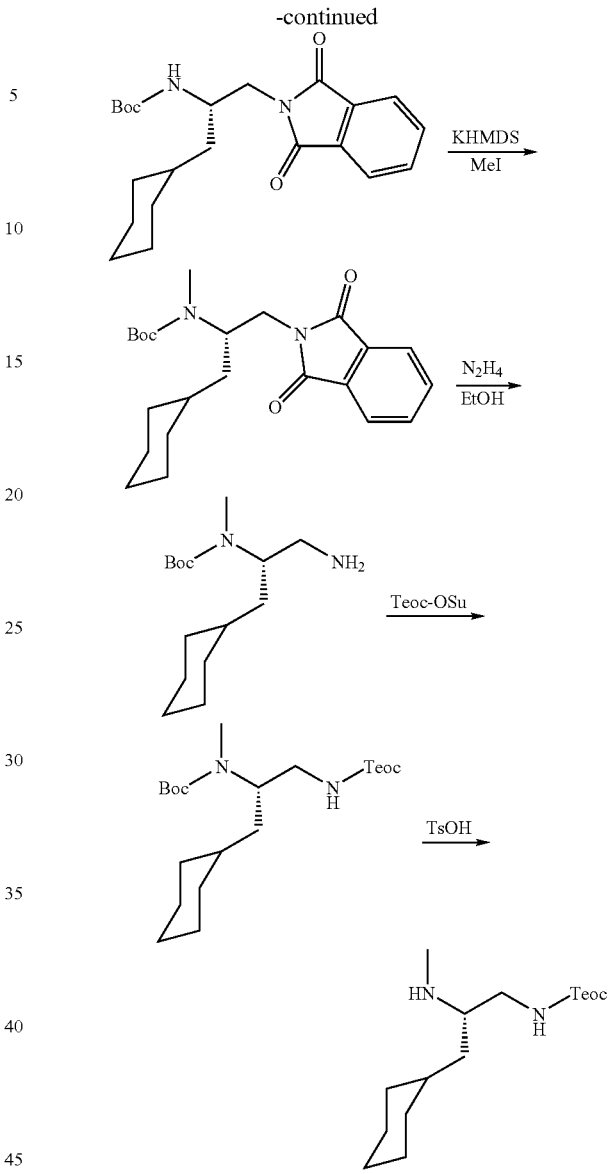

Step 1. (2S)-tert-Butyl 1-cyclohexyl-3-(N-phthalimido)propan-2-ylcarbamate

A solution of (S)-tert-butyl 1-cyclohexyl-3-hydroxypropan-2-ylcarbamate (0.992 g, 3.86 mmol), triphenylphosphine (1.502 g, 5.8 mmol), and phthalimide (0.8505 g, 5.8 mmol) in THF (40 mL) was cooled to 0° C. Neat diisopropyl azodicarboxylate (1.15 mL, 5.94 mmol) was introduced with fast dropwise addition resulting in a persistent yellow color. The reaction mixture was stirred 12 h at rt. Reaction progress was followed by LC-MS. The reaction solvent was removed under reduced pressure and the crude residue was taken up in CH$_2$Cl$_2$ (50 mL) and filtered through a pad of Celite. The solvent was removed and this material was separated on 40 g SiO$_2$ using an eluent gradient from hexanes to EtOAc. Appropriate fractions were combined and stripped to afford (2S)-tert-butyl 1-cyclohexyl-3-(N-phthalimido)propan-2-ylcarbamate (1.36 g, 92%) as a white solid. MS ESI+ve m/z 409 (M+Na).

Step 2. (2S)-tert-Butyl 1-cyclohexyl-3-(N-phthalimido)propan-2-yl(methyl)carbamate A solution of (2S)-tert-butyl 1-cyclohexyl-3-(N-phthalimido)propan-2-ylcarbamate (523.6 mg, 1.38 mmol) in anhydrous THF (10 mL) was cooled to 0° C. A 0.5 M solution of potassium hexamethyldisilazide in toluene (6.0 mL, 3.0 mmol) was added over 15 minutes. The resulting deep yellow solution was stirred for an additional 15 minutes at 0° C. and neat methyl iodide (0.5 mL, 8.0 mmol) was added. The resulting mixture was permitted to warm to rt and stirred for an additional 4 h. The solvent was removed under reduced pressure, dissolved in a minimal amount of CH$_2$Cl$_2$ and separated on 4 g of silica using a gradient from hexanes to EtOAc. Solvent was stripped from appropriate fractions to give (2S)-tert-butyl 1-cyclohexyl-3-(N-phthalimido)propan-2-yl(methyl)carbamate (284 mg, 52%) as a white solid. $^1$H NMR (CDCl$_3$) δ 0.80-1.80 (m 13H), 1.14 (s, 9H), 3.54 (m, 1H), 3.68 (m, 1H), 4.63 (m, 1H), 7.67 (m, 2H), 7.79 (m, 2H). MS ESI+ve m/z 423 (M+Na).

Step 3

A solution of tert-butyl (S)-3-cyclohexyl-1-(1,3-dioxoisoindolin-2-yl)propan-2-ylmethyl-carbamate (244 mg, 0.61 mmol), hydrazine monohydrate (0.15 mL, 3.0 mmol), and absolute ethanol (100 mL) was warmed to 50° C. for 4 h. The reaction was then warmed to reflux for an additional 6 h. LC-MS indicated full conversion to the deprotected amine. The reaction mixture was cooled to 25° C., suspended in Et$_2$O (25 mL) and filtered through a pad of Celite. Solvent was removed and the crude material (189.1 mg, theoretical: 164.7 mg) was carried on to the next step directly. MS ESI+ve m/z 271 (M+1).

Step 4

Solid Teoc-OSu (23.7 mg, 1.3 mmol) was added to a vigorously stirred 2-phase mixture of tert-butyl (S)-1-amino-3-cyclohexylpropan-2-ylmethylcarbamate (19.2 mg, 0.07 mmol), K$_2$CO$_3$ (500 mg, 3.6 mmol), H$_2$O (5.0 mL), and CH$_2$Cl$_2$ (10.0 mL). This mixture was stirred for 90 minutes at rt and then the reaction was taken up in CH$_2$Cl$_2$ (50 mL) washed with brine (3×10 mL), dried over Na$_2$SO$_4$, decanted, and stripped to give a clear oil. This oil was separated on a 4 g SiO$_2$ column to give 2-(trimethylsilyl)ethyl (S)-3-cyclohexyl-2-((tert-butylcarbamoyl)methylamino)propylcarbamate (21.3 mg, 72%) as a clear oil. $^1$H NMR (CDCl$_3$) δ 0.00 (s, 9H), 0.80-1.80 (m 13H), 1.37 (s, 9H), 2.63 (s, 3H), 3.03 (m, 1H), 3.17 (m, 1H), 4.10 (m, 2H), 4.2 (m, 1H). MS ESI+ve m/z 438 (M+Na).

Step 5

A solution of toluenesulfonic acid monohydrate (10 mg, 0.053 mmol) in absolute ethanol (1 mL) was added to a solution of 2-(trimethylsilyl)ethyl (S)-3-cyclohexyl-2-((tert-butyl-carbamoyl)methylamino)propylcarbamate (21.3 mg, 0.51 mmol) in Et$_2$O (10 mL). This solution was placed in a flask on a rotary evaporator and the Et$_2$O was removed at ambient temp. The flask was then lowered into a water bath (60° C.) and selective removal of the Boc group proceeded concurrently with removal of the solvent. The reaction was complete within 2 h. This material was taken up in CH$_2$Cl$_2$ (20 mL) and 1N aq NaOH (10 mL) and extracted with CH$_2$Cl$_2$ (2×10 mL). The combined organic layers were washed with brine (2×5 mL), dried over Na$_2$SO$_4$, decanted, and stripped to afford 2-(trimethylsilyl)ethyl (S)-3-cyclohexyl-2-(methylamino)propylcarbamate (15.0 mg, 94%) as a clear film. MS ESI+ve m/z 315 (M+1).

Example 23

3-((S)-1-Amino-3-cyclohexylpropan-2-ylamino)-4-(3-((2-fluorophenyl)(3-methoxypropoxy)methyl)piperidin-1-yl)cyclobut-3-ene-1,2-dione (I-76A)

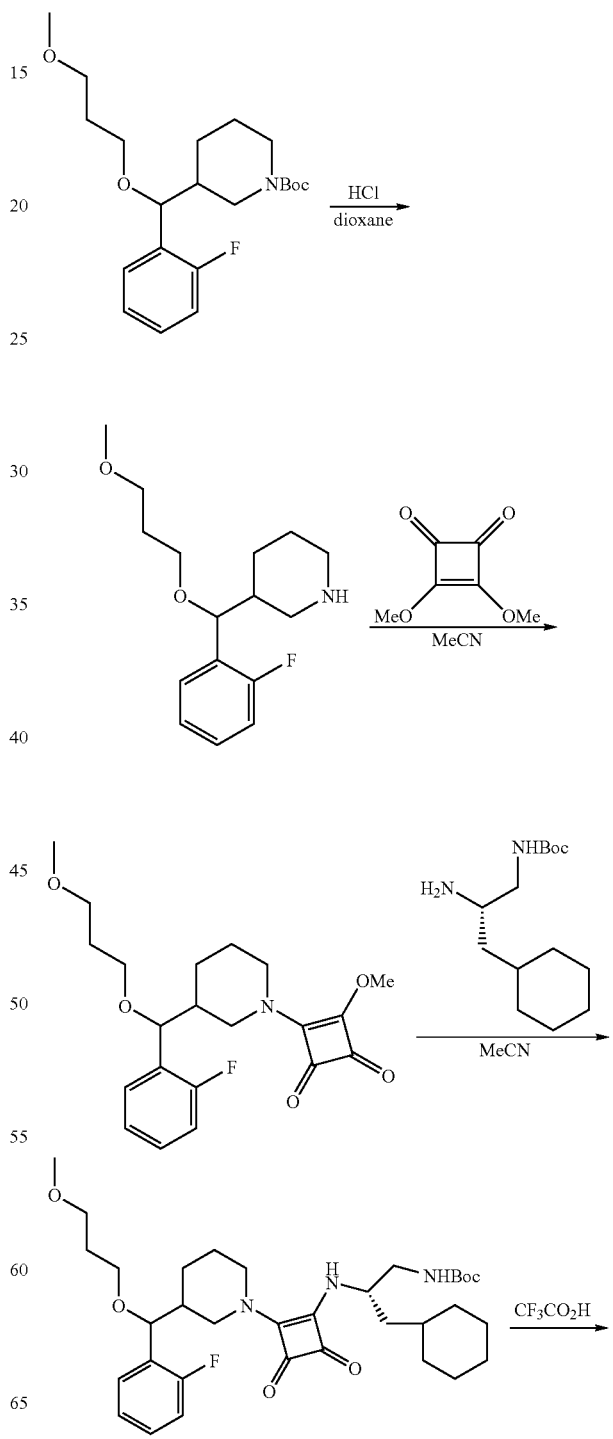

-continued

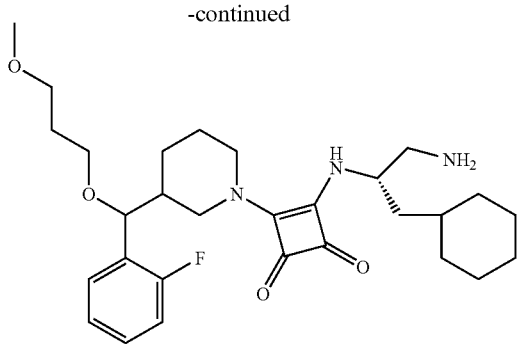

Step 1. 3-((3-methoxypropoxy)(2-fluorophenyl)methyl)piperidine tert-Butyl 3-((3-methoxypropoxy)(2-fluorophenyl)methyl)piperidine-1-carboxylate (28.0 mg, 0.07 mmol) was dissolved in 4 N HCl in dioxane. The resulting solution was stirred at rt until no starting material was left (~30 min). The solvent was removed in vacuo to give 3-((3-methoxypropoxy)(2-fluorophenyl)methyl)piperidine hydrochloride as an oil. MS ESI+ve m/z 282 (M+1).

Step 2. 3-(3-((2-fluorophenyl)(3-methoxypropoxy)methyl)piperidin-1-yl)-4-methoxycyclobut-3-ene-1,2-dione To a solution of 3-((3-methoxypropoxy)(2-fluorophenyl)methyl)piperidine hydrochloride (0.07 mmol), and triethylamine (0.2 mL) in MeCN (0.8 mL) was added 3,4-dimethoxycyclobut-3-ene-1,2-dione (8.5 mg, 0.08 mmol). The mixture was stirred at rt until no starting material remained (~10 min) and the crude 3-(3-((2-fluorophenyl)(3-methoxypropoxy)methyl)piperidin-1-yl)-4-methoxycyclobut-3-ene-1,2-dione was used for next steps without isolation. MS ESI+ve m/z 414 (M+Na).

Step 3. tert-Butyl (2S)-3-cyclohexyl-2-(2-(3-((2-fluorophenyl)(3-methoxypropoxy)methyl)piperidin-1-yl)-3,4-dioxocyclobut-1-enylamino)propylcarbamate To the crude 3-(3-((2-fluorophenyl)(3-methoxypropoxy)methyl)piperidin-1-yl)-4-methoxycyclobut-3-ene-1,2-dione in MeCN there was added tert-butyl (S)-2-amino-3-cyclohexylpropylcarbamate (27.0 mg, 0.11 mmol), the resulting solution was stirred at rt for 10 min, filtered through HPLC filter, purified by HPLC to give tert-butyl (2S)-3-cyclohexyl-2-(2-(3-((2-fluorophenyl)(3-methoxypropoxy)methyl)piperidin-1-yl)-3,4-dioxocyclobut-1-enylamino)propylcarbamate (17.4 mg, 40%) as on oil. MS ESI+ve m/z 616 (M+1).

Step 4. 3-((S)-1-amino-3-cyclohexylpropan-2-ylamino)-4-(3-((2-fluorophenyl)(3-methoxypropoxy)methyl)piperidin-1-yl)cyclobut-3-ene-1,2-dione tert-butyl (2S)-3-cyclohexyl-2-(2-(3-((2-fluorophenyl)(3-methoxypropoxy)methyl)piperidin-1-yl)-3,4-dioxocyclobut-1-enylamino)propylcarbamate (17.4 mg, 0.03 mmol) was treated with neat TFA for 30 min. TFA was removed in vacuo, and the residue was purified by HPLC to give 3-((S)-1-amino-3-cyclohexylpropan-2-ylamino)-4-(3-((2-fluorophenyl)(3-methoxypropoxy)methyl)piperidin-1-yl)cyclobut-3-ene-1,2-dione (8.7 mg, 60%) as a TFA salt. $^1$H NMR (CD$_3$OD) δ 0.8-2.1 (20H), 3.0 (1H), 3.1 (1H), 3.25 (s, 3H), 3.3 (m, 6H), 3.5 (2H), 4.45 (d, 1H), 4.63 (m, 1H), 7.15 (1H), 7.21 (1H), 7.35 (1H), 7.40 (1H). MS ESI+ve m/z 516 (M+1).

Example 24

3-(1S,2S-2-Amino-1-cyclohexylmethyl-propylamino)-4-{3-[(3-methoxy-propoxy)phenyl-methyl]-piperidin-1-yl}-cyclobut-3-ene-1,2-dione (I-70A)

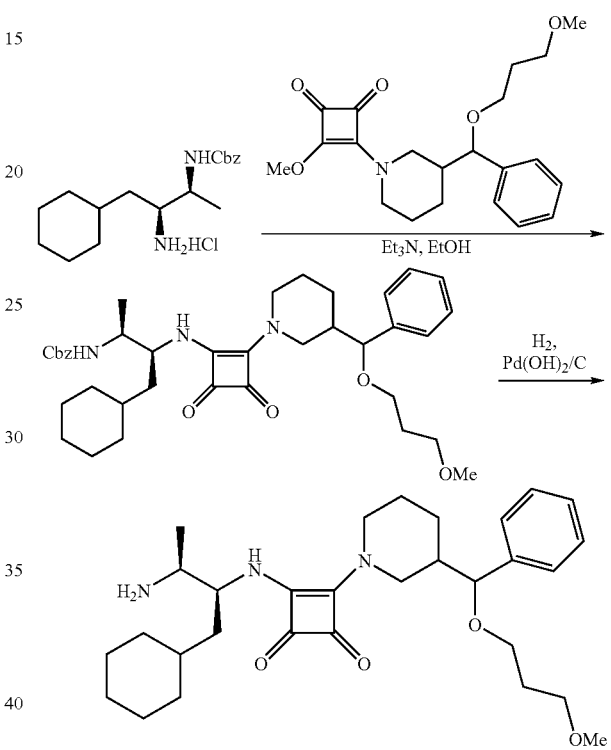

Step 1. [(2S,3S)-cyclohexyl-2-(2-{3-[(3-methoxy-propoxy)-phenyl-methyl]-piperidin-1-yl}-3,4-dioxo-cyclobut-1-enylamino)-1-methyl-propyl]-carbamic acid benzyl ester A solution of the HCl salt of (2S,3S)-(2-amino-3-cyclohexyl-1-methyl-propyl)carbamic acid benzyl ester (77 mg, 0.226 mmol), 3-methoxy-4-{3-[(3-methoxy-propoxy)-phenyl-methyl]-piperidin-1-yl}-cyclobut-3-ene-1,2-dione (67.4 mg, 0.181 mmol) and triethylamine (59.5 mg, 0.452 mmol) in ethanol (10 mL) was stirred at rt until the reaction was completed (about 8-10 h). The solvent was removed by evaporation and the crude product purified by preparative HPLC to give (2S,3S)-cyclohexyl-2-(2-{3-[(3-methoxy-propoxy)-phenyl-methyl]-piperidin-yl}-3,4-dioxo-cyclobut-1-enylamino)-1-methyl-propyl]-carbamic acid benzyl ester (5 mg, 3.5%). MS m/z 405 (M+H$^+$).

Step 2. 3-(1S,2S-2-amino-1-cyclohexylmethyl-propylamino)-4-{3-[(3-methoxy-propoxy)-phenyl-methyl]-piperidin-1-yl}-cyclobut-3-ene-1,2-dione To a solution of [(2S,3S)-cyclohexyl-2-(2-{3-[(3-methoxy-propoxy)-phenyl-methyl]-piperidin-1-yl}-3,4-dioxocyclobut-1-enylamino)-1-methyl-propyl]-carbamic acid benzyl ester (5 mg, 0.00775 mmol) in EtOAc (5 mL) was added palladium hydroxide 20 wt. % on carbon (2 mg). The mixture was stirred under a hydrogen balloon at rt overnight. The mixture was filtered and the filtrate was evaporated to give a residue, which was purified by preparative HPLC to give 3-(1S,2S-2-amino-1-cyclohexylmethyl-propylamino)-4-{3-[(3-methoxy-propoxy)-phenyl-methyl]-piperidin-1-yl}-cyclobut-3-ene-1,2-dione (0.6 mg, 15.1%) as a TFA salt $^1$H NMR (400 MHz, CDCl$_3$): 7.32 (m, 5H), 4.68 (m, 2H), 4.21 (m, 1H), 3.55-3.05 (m, 8H) (1H), 3.32 (s, 3H), 2.05-0.75 (m, 21H), MS m/z 512 (M+H$^+$).

Example 25

3-(1S,2R-2-Amino-1-cyclohexylmethyl-propylamino)-4-{3-[(3-methoxy-propoxy)-phenyl-methyl]-piperidin-1-yl}-cyclobut-3-ene-1,2-dione (I-70B)

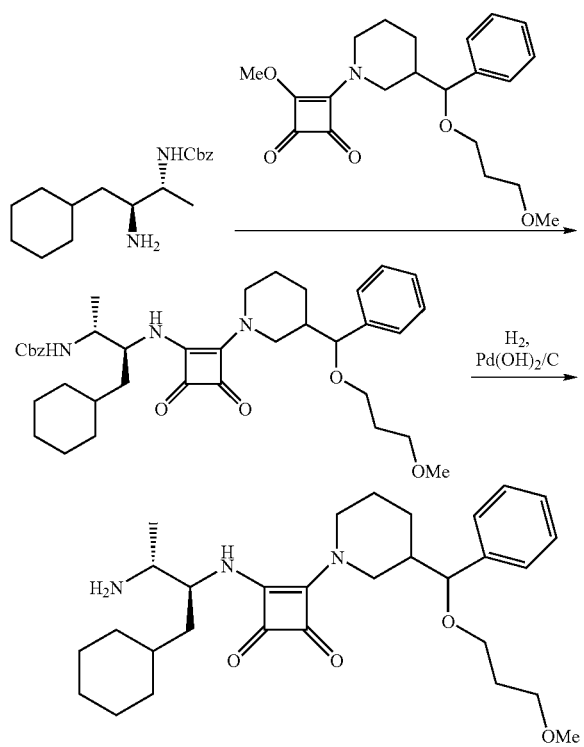

Procedures analogous to those used in Example 24 were followed to afford 3-(1S,2R-2-amino-1-cyclohexylmethyl-propylamino)-4-{3-[(3-methoxy-propoxy)-phenyl-methyl]-piperidin-1-yl}-cyclobut-3-ene-1,2-dione TFA salt. $^1$H NMR (400 MHz, CDCl$_3$): 7.32 (m, 5H), 4.68 (m, 3H), 4.21 (m, 1H), 3.55-3.10 (m, 8H), 3.32 (s, 3H), 1.95-0.80 (m, 21H). MS (E/Z): 512 (M+H$^+$).

Example 26

The following compounds of Formula I were prepared following procedures analogous to those used in Example 23, 24, and 25:

| Cpd. No. | Name |
|---|---|
| I-58A | 3-((S)-1-amino-3-cyclohexylpropan-2-ylamino)-4-((R)-3-((R)-(3-methoxypropoxy)(phenyl)methyl)piperidin-1-yl)cyclobut-3-ene-1,2-dione |
| I-58A | 3-((S)-1-amino-3-cyclohexylpropan-2-ylamino)-4-((R)-3-((R)-(3-methoxypropoxy)(phenyl)methyl)piperidin-1-yl)cyclobut-3-ene-1,2-dione |
| I-58A | 3-((S)-1-amino-3-cyclohexylpropan-2-ylamino)-4-(3-((3-methoxypropoxy)(phenyl)methyl)piperidin-1-yl)cyclobut-3-ene-1,2-dione |
| I-75A | 3-((S)-1-amino-3-cyclohexylpropan-2-ylamino)-4-(3-((3-methoxypropoxy)(4-fluorophenyl)methyl)piperidin-1-yl)cyclobut-3-ene-1,2-dione |
| I-99A | 3-((S)-1-amino-3-cyclohexylpropan-2-ylamino)-4-(3-((3-methoxypropoxy)(2-(trifluoromethyl)phenyl)methyl)-piperidin-1-yl)cyclobut-3-ene-1,2-dione |

Example 27

3-((S)-1-amino-3-cyclohexyl-propan-2-ylamino)-4-(3-((2-cyclopropylethoxy)(phenyl)methyl)piperidin-1-yl)cyclobut-3-ene-1,2-dione (I-55A)

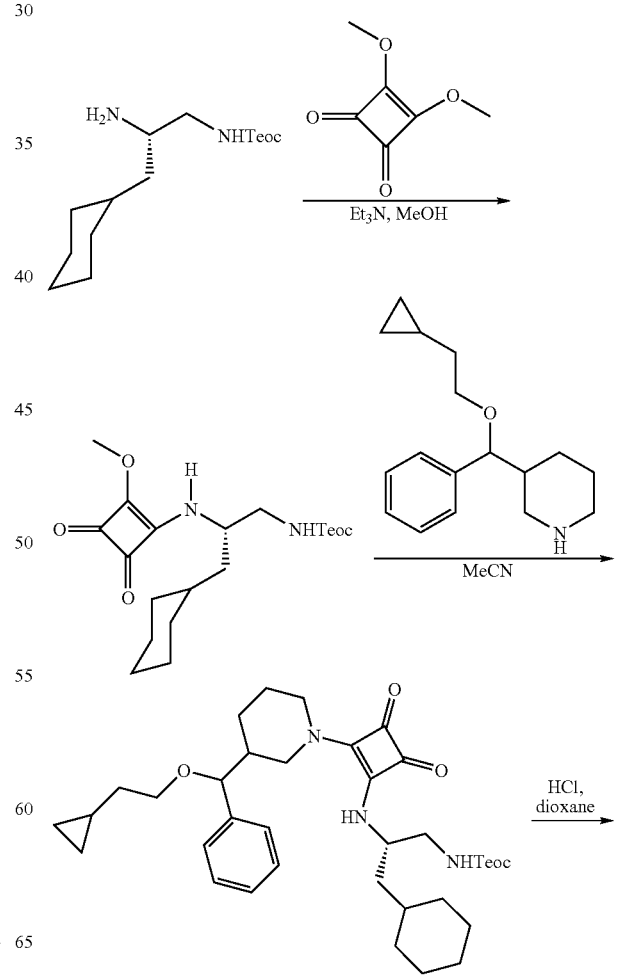

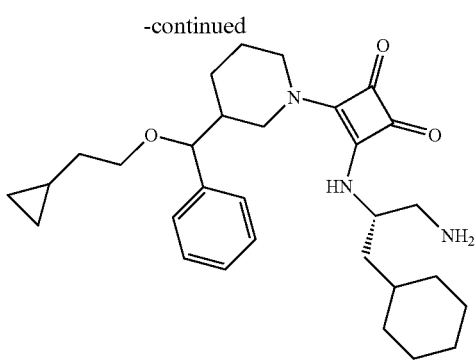

Step 1. (S)-2-(trimethylsilyl)ethyl 3-cyclohexyl-2-(2-methoxy-3,4-dioxocyclobut-1-enylamino)propylcarbamate Solid 3,4-dimethoxycyclobut-3-ene-1,2-dione (87.5 mg, 0.61 mmol) was added to a solution of (S)—N$^1$-((2-(trimethylsilyl)ethoxy)methyl)-3-cyclohexylpropane-1,2-diamine (173.1 mg, 0.57) and triethylamine (0.2 mL, 1.4 mmol) in MeOH (10 mL). After stirring at rt for 2 h, the solvent was removed and the residue was purified using 4 g SiO$_2$ with an eluent of hexanes to EtOAc. Removal of solvent from appropriate fractions yielded (S)-2-(trimethylsilyl)ethyl 3-cyclohexyl-2-(2-methoxy-3,4-dioxocyclobut-1-enylamino)propylcarbamate (186.2 mg, 80%) as a clear film. MS ESI+ve m/z 433 (M+Na).

Steps 2 and 3. 3-((S)-1-amino-3-cyclohexylpropan-2-ylamino)-4-(3-((2-cyclopropylethoxy)(phenyl)methyl)piperidin-1-yl)cyclobut-3-ene-1,2-dione A solution of 3-((S)-1-((2-(trimethylsilyl)ethoxy)methylamino)-3-cyclohexylpropan-2-ylamino)-4-methoxycyclobut-3-ene-1,2-dione (13.4 mg, 0.034 mmol) in dry CH$_3$CN (0.2 mL) was added to neat 3-((2-cyclopropylethoxy)(phenyl)methyl)piperidine (24.4 mg, 0.094 mmol). The mixture was stirred at rt overnight and heated to reflux for several h until no further reaction was evident as monitored by LC-MS. The solvent was evaporated and purified via preparative HPLC (C-18 column, 10 to 90% CH$_3$CN in H$_2$O containing 0.01% CF$_3$CO$_2$H over 10 min, 20 mL/min) to afford 2-(trimethylsilyl)ethyl (S)-2-(2-(3-((2-cyclopropylethoxy)-(phenyl)-methyl)piperidin-1-yl)-3,4-dioxocyclobut-1-enylamino)-3-cyclohexylpropylcarbamate (12.3 mg, 55%) as an oil. MS ESI+ve m/z 638 (M+1).

The N—((S)-2-(2-(3-((2-cyclopropylethoxy)(phenyl)methyl)piperidin-1-yl)-3,4-dioxocyclobut-1-enylamino)-3-cyclohexylpropyl)-4-(trimethylsilyl)butanamide (12.3 mg, 0.02 mmol) was dissolved in dioxane (1 mL) and treated with 4M HCl in dioxane (0.5 mL, 2.0 mmol). The solution was allowed to stir for 1.5 h before evaporation of solvent. The residual oil was redissolved in methanol and evaporated under reduced pressure to afford 3-((S)-1-amino-3-cyclohexylpropan-2-ylamino)-4-(3-((2-cyclopropylethoxy)(phenyl)methyl)piperidin-1-yl)cyclobut-3-ene-1,2-dione hydrochloride as an oil (10 mg, >99%). MS ESI+ve m/z 494 (M+1).

Example 28

The following compounds of Formula I were prepared following procedures analogous to those used in Example 27:

| Cpd. No. | Name |
|---|---|
| I-58A | 3-((S)-1-amino-3-cyclohexylpropan-2-ylamino)-4-(3-((3-methoxypropoxy)(phenyl)methyl)piperidin-1-yl)cyclobut-3-ene-1,2-dione |
| I-58A | 3-((S)-1-amino-3-cyclohexylpropan-2-ylamino)-4-(3-((3-methoxypropoxy)(phenyl)methyl)piperidin-1-yl)cyclobut-3-ene-1,2-dione |
| I-59A | 3-((S)-1-amino-3-cyclohexylpropan-2-ylamino)-4-(2-((3-methoxypropoxy)(phenyl)methyl)morpholino)cyclobut-3-ene-1,2-dione |
| I-69A | 3-((S)-1-amino-3-cyclohexylpropan-2-ylamino)-4-(3-(1-hydroxy-1-phenylheptyl)piperidin-1-yl)cyclobut-3-ene-1,2-dione |
| I-71A | 3-(3-((3-methoxypropoxy)(phenyl)methyl)piperidin-1-yl)-4-(N-((S)-1-amino-3-cyclohexylpropan-2-yl)-N-methylamino)cyclobut-ene-1,2-dione |
| I-73A | 3-((S)-3-cyclohexyl-1-(methylamino)propan-2-ylamino)-4-(3-((3-methoxypropoxy)(phenyl)methyl)piperidin-1-yl)cyclobut-3-ene-1,2-dione |
| I-85A | 3-(3-cyclohexyl-1-(ethylamino)propan-2-ylamino)-4-(3-((3-methoxypropoxy)(phenyl)methyl)piperidin-1-yl)cyclobut-3-ene-1,2-dione |
| I-89A | 3-((S)-1-amino-3-cyclohexylpropan-2-ylamino)-4-(3-((3-methoxypropoxy)(2,4-difluorophenyl)methyl)piperidin-1-yl)cyclobut-3-ene-1,2-dione |
| I-90A | 3-((S)-1-amino-3-cyclohexylpropan-2-ylamino)-4-(3-((3-methoxypropoxy)(3,4-difluorophenyl)methyl)piperidin-1-yl)cyclobut-3-ene-1,2-dione |
| I-92A | 3-(3-cyclohexyl-1-(propylamino)propan-2-ylamino)-4-(3-((3-methoxypropoxy)(phenyl)methyl)piperidin-1-yl)cyclobut-3-ene-1,2-dione |
| I-94A | 3-(3-cyclohexyl-1-(isobutylamino)propan-2-ylamino)-4-(3-((3-methoxypropoxy)(phenyl)methyl)piperidin-1-yl)cyclobut-3-ene-1,2-dione |
| I-95A | 3-(3-(butylamino)-1-cyclohexylpropan-2-ylamino)-4-(3-((3-methoxypropoxy)(phenyl)methyl)piperidin-1-yl)cyclobut-3-ene-1,2-dione |
| I-98A | 3-(3-cyclohexyl-1-(methylamino)propan-2-ylamino)-4-(3-((3-ethoxypropoxy)(3,4-difluorophenyl)methyl)piperidin-1-yl)cyclobut-3-ene-1,2-dione |
| I-101A | 3-(1-cyclohexyl-3-(pentylamino)propan-2-ylamino)-4-(3-((3-methoxypropoxy)(phenyl)methyl)piperidin-1-yl)cyclobut-3-ene-1,2-dione |
| I-102A | 3-(1-cyclohexyl-3-(isopentylamino)propan-2-ylamino)-4-(3-((3-methoxypropoxy)(phenyl)methyl)piperidin-1-yl)cyclobut-3-ene-1,2-dione |

Example 29

(3R)-3-((R)-(3-methoxypropoxy)(phenyl)methyl)-
N—((S)-1-amino-3-cyclohexylpropan-2-yl)piperi-
dine-1-carboxamide (I-5A)

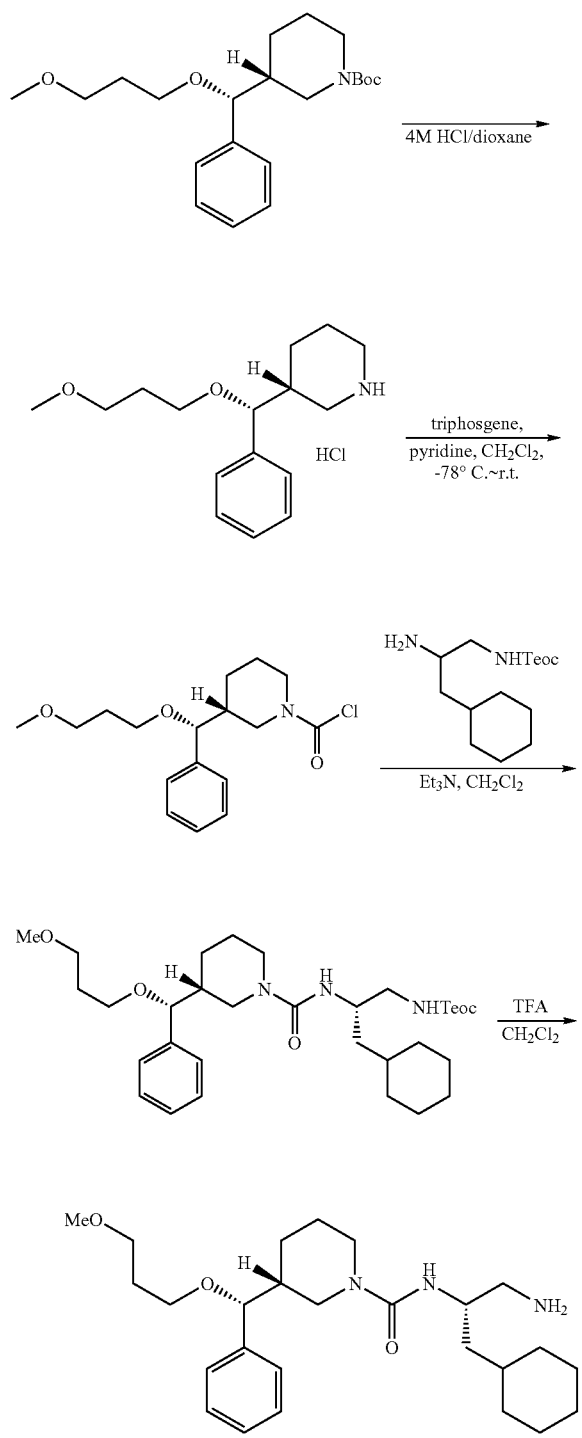

Step 1. (R)-3-((R)-(3-methoxypropoxy)(phenyl)-methyl)piperidine-1-carbonyl chloride (R)-tert-butyl 3-((R)-(3-methoxypropoxy)(phenyl)methyl)piperidine-1-carboxylate (219 mg, 0.603 mmol) was dissolved in 4M HCl in 1,4-dioxane (20 mL, 80 mmol) and stirred for 30 min. LC-MS showed removal of the Boc protecting group. The reaction mixture was concentrated and redissolved dry $CH_2Cl_2$ (5 mL). Pyridine (122 μL, 1.51 mmol, 2.5 equiv) was added. This solution was added dropwise under $N_2$ to a solution of triphosgene (188 mg, 0.63 mmol, 1.05 equiv) in dry $CH_2Cl_2$ (5 mL) at −78° C. After 10 min, the reaction mixture was warmed to rt and stirred for 2 h. LC-MS showed the reaction was complete. 5% aq HCl (15 mL) was added and the layers were separated. The aqueous layer was extracted with $CH_2Cl_2$ (2×30 ml). The combined organic layers were washed with satd aq $NaHCO_3$ and brine, and dried over $Na_2SO_4$. Concentration afforded (R)-3-((R)-(3-methoxypropoxy)(phenyl)-methyl)piperidine-1-carbonyl chloride (188 mg, 96%) as a yellow oil. LC-MS (3 min) $t_R$=1.83 min, m/z 344 (M+$H_2O$). The crude product was used for the next step without further purification.

Step 2. 2-(trimethylsilyl)ethyl (S)-2-((R)-3-((R)-(3-methoxypropoxy)-(phenyl)methyl)piperidine-1-carboxamido)-3-cyclohexyl-propylcarbamate Crude (R)-3-((R)-(3-methoxypropoxy)(phenyl)methyl)piperidine-1-carbonyl chloride (60 mg, 0.184 mmol), 2-(trimethylsilyl)ethyl (S)-2-amino-3-cyclohexylpropylcarbamate (69 mg, 0.23 mmol, 1.25 equiv) and triethylamine (64 μL, 0.46 mmol, 2.5 equiv) were combined in $CH_2Cl_2$ (1 mL) at rt and left on the shaker overnight. After concentration, the product was isolated by prep HPLC to afford 2-(trimethylsilyl)ethyl (S)-2-((R)-3-((R)-(3-methoxypropoxy)-(phenyl)methyl)piperidine-1-carboxamido)-3-cyclohexyl-propylcarbamate (85.3 mg, 79%). LC-MS (3 min) $t_R$=2.44 min, m/z 590 (M+1).

Step 3. (3R)-3-((R)-(3-methoxypropoxy)(phenyl)methyl)-N—((S)-1-amino-3-cyclohexylpropan-2-yl)piperidine-1-carboxamide 2-(Trimethylsilyl)ethyl (S)-2-((R)-3-((R)-(3-methoxypropoxy)(phenyl)methyl)piperidine-1-carboxamido)-3-cyclohexylpropylcarbamate (85.3 mg, 0.14 mmol) was dissolved in 6 mL 1:1 TFA/$CH_2Cl_2$ (6 mL) and stirred for 30 min. LC-MS showed the reaction was complete. After concentration, (3R)-3-((R)-(3-methoxypropoxy)(phenyl)methyl)-N—((S)-1-amino-3-cyclohexylpropan-2-yl)piperidine-1-carboxamide trifluoroacetic acid salt was isolated by prep HPLC. LC-MS (3 min) $t_R$=1.56 min, m/z 446 (M+1). $^1$H NMR ($CD_3OD$) δ 7.37-7.25 (m, 5H), 4.30 (d, 1H), 4.03 (m, 1H), 4.97-4.90 (m, 2H), 3.50-3.39 (m, 2H), 3.27 (s, 3H), 3.00 (dd, 1H), 2.85-2.75 (m, 3H), 1.81-0.82 (m, 22H).

Example 30

The following compounds of Formula I were prepared using procedures analogous to those used in Example 29:

| Cpd. No. | Name |
|---|---|
| I-10A | (3R)-3-((S)-1-(3-fluorophenyl)-1-hydroxy-5-methoxypentyl)-N-((S)-4-methyl-1-(methylamino)pentan-2-yl)piperidine-1-carboxamide |
| I-16A | 3-((3-methoxypropoxy)(phenyl)methyl)-N-(3-cyclohexyl-1-(methylamino)propan-2-yl)piperidine-1-carboxamide |
| I-20A | (3R)—N-((S)-3-cyclohexyl-1-(methylamino)propan-2-yl)-3-((R)-1-hydroxy-4-methoxy-1-phenylbutyl)piperidine-1-carboxamide |
| I-26A | 3-((3-methoxypropoxy)(3-cyanophenyl)methyl)-N-((S)-1-amino-3-cyclohexylpropan-2-yl)piperidine-1-carboxamide |
| I-30A | 3-((3-methoxypropoxy)(phenyl)methyl)-N-(3-cyclohexyl-1-(ethylamino)propan-2-yl)piperidine-1-carboxamide |
| I-45A | 3-((3-methoxypropoxy)(3-cyanophenyl)methyl)-N-((S)-3-cyclohexyl-1-(methylamino)propan-2-yl)piperidine-1-carboxamide |
| I-47A | 3-((3-methoxypropoxy)(phenyl)methyl)-N-(3-cyclohexyl-1-(propylamino)propan-2-yl)piperidine-1-carboxamide |
| I-49A | 3-((3-propoxypropoxy)(phenyl)methyl)-N-((S)-3-cyclohexyl-1-(methylamino)propan-2-yl)piperidine-1-carboxamide |
| I-61A | 3-((3-methoxypropoxy)(phenyl)methyl)-N-(1-(butylamino)-3-cyclohexylpropan-2-yl)piperidine-1-carboxamide |
| I-62A | 3-((3-methoxypropoxy)(phenyl)methyl)-N-(3-cyclohexyl-1-(isobutylamino)propan-2-yl)piperidine-1-carboxamide |
| I-63A | (3R)—N-((S)-3-cyclohexyl-1-(dimethylamino)propan-2-yl)-3-((R)-5-ethoxy-1-hydroxy-1-phenylpentyl)piperidine-1-carboxamide |
| I-77A | 3-((3-methoxypropoxy)(phenyl)methyl)-N-(3-cyclohexyl-1-(isopentylamino)propan-2-yl)piperidine-1-carboxamide |
| I-78A | 3-((3-methoxypropoxy)(phenyl)methyl)-N-(3-cyclohexyl-1-(pentylamino)propan-2-yl)piperidine-1-carboxamide |

Example 31

4-Nitrophenyl (S)-3-cyclohexyl-1-((2-(trimethylsilyl)ethylcarbamate)methylamino)propan-2-yl)carbamate

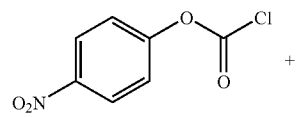

+

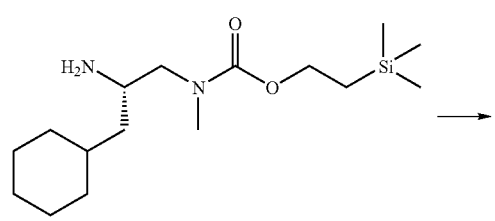

⟶

-continued

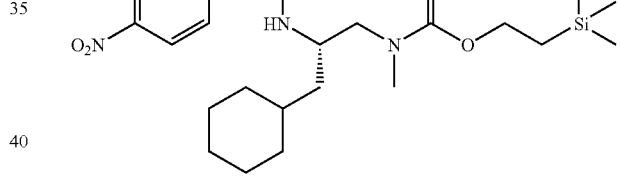

A 100-mL round bottom-flask was charged with diisopropylethylamine (820 mg, 6.34 mmol, 2.0 equiv), 2-(trimethylsilyl)ethyl (S)-2-amino-3-cyclohexylpropylmethylcarbamate (996 mg, 3.17 mmol, 1.0 equiv) and 30 mL of $CH_2Cl_2$, and the resulting solution cooled to 0° C. A solution of 4-nitrophenylchloroformate (733 mg, 3.64 mmol, 1.15 equiv) in 20 mL of $CH_2Cl_2$ was added at a rate such that the internal temperature did not rise above 5° C. After 1 h an aliquot was examined by LC-MS which showed no remaining starting material. The reaction was quenched with water and separated. The organic layer was washed with of 5% aq $K_2CO_3$ (2×40 mL), 0.25 M aq HCl, and brine, dried over $Na_2SO_4$ and evaporated. Excess 4-nitrophenyl-chloroformate was removed by flash chromatography on silica, eluting with 0 to 10% methanol in $CH_2Cl_2$. This afforded 4-nitrophenyl (S)-3-cyclohexyl-1-((2-(trimethylsilyl)ethylcarbamate)-methylamino)propan-2-yl)carbamate (990 mg, 65%). MS ESI+ve m/z 503 (M+Na⁺).

Example 32

(3R)-3-((R)-(3-ethoxypropoxy)(phenyl)methyl)-N—((S)-3-cyclohexyl-1-(methylamino)propan-2-yl)piperidine-1-carboxamide (I-31B)

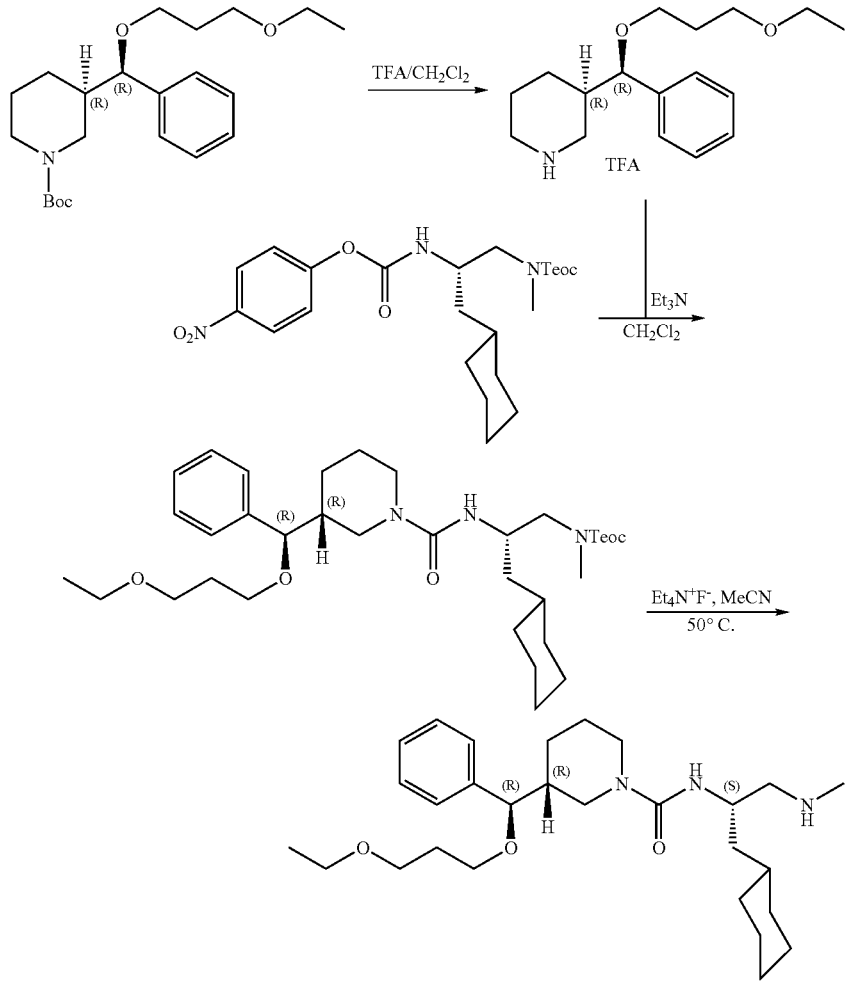

(172.5 mg, 72%). LC-MS (3 min) $t_R$=2.64 min, m/z 618 (M+1), 640 (M+Na). $^1$H NMR (CDCl$_3$) δ 7.24 (m, 5H), 5.16 (d, 1H), 4.11-4.00 (m, 4H), 3.92 (m, 1H), 3.71 (d, 1H), 3.56-3.21 (m, 7H), 3.00-2.90 (m, 1H), 2.90 (s, 3H), 2.73 (t, 1H), 2.61 (m, 1H), 1.81-1.51 (m, 9H), 1.20-0.75 (m, 16H), 0.01 (s, 9H). Chiral HPLC indicated 94.5% purity.

Step 1. 2-(trimethylsilyl)ethyl (S)-2-((R)-3-((R)-(3-ethoxypropoxy)(phenyl)methyl)piperidine-1-carboxamido)-3-cyclohexylpropylmethylcarbamate (R)-tert-butyl 3-((R)-(3-ethoxypropoxy)(phenyl)methyl)piperidine-1-carboxylate (150 mg, 0.39 mmol) was dissolved in 1:1 TFA/CH$_2$Cl$_2$ (8 mL) and stirred for 30 min at rt. LC-MS showed the Boc protecting group had been removed. The reaction mixture was concentrated, redissolved in CH$_2$Cl$_2$ (5 mL) and Et$_3$N (2 mL). A solution of 4-nitrophenyl (S)-3-cyclohexyl-1-((2-(trimethylsilyl)ethylcarbamate)methylamino)propan-2-yl)carbamate (185 mg, 0.39 mmol, 1 equiv) in CH$_2$Cl$_2$ (4 mL) was added. After stirring overnight at rt, the reaction mixture was concentrated and purified by reverse phase preparative HPLC to afford 2-(trimethylsilyl)ethyl (S)-2-((R)-3-((R)-(3-ethoxypropoxy)(phenyl)methyl)piperidine-1-carboxamido)-3-cyclohexylpropylmethylcarbamate (172.5 mg, 72%).

Step 2. (3R)-3-((R)-(3-ethoxypropoxy)(phenyl)methyl)-N—((S)-3-cyclohexyl-1-(methylamino)propan-2-yl)piperidine-1-carboxamide 2-(trimethylsilyl)ethyl (S)-2-((R)-3-((R)-(3-ethoxypropoxy)(phenyl)methyl)piperidine-1-carboxamido)-3-cyclohexylpropylmethylcarbamate (172 mg, 0.28 mmol) was dissolved in acetonitrile (8 mL) and tetraethylammonium fluoride (123 mg, 0.84 mmol, 3 equiv) was added. The mixture was heated at 50° C. overnight. LC-MS showed the reaction was complete. The crude product was purified by reverse phase preparative HPLC to afford (3R)-3-((R)-(3-ethoxypropoxy)(phenyl)methyl)-N—((S)-3-cyclohexyl-1-(methylamino)propan-2-yl)piperidine-1-carboxamide as its trifluoroacetic acid salt (90 mg, 68%). LC-MS (3 min) $t_R$=1.58 min, m/z 474 (M+1). $^1$H NMR (CD$_3$OD) δ 7.38-7.23 (m, 5H), 4.29 (d, 1H), 4.09 (m, 1H), 3.94 (m, 2H), 3.55-3.38 (m, 4H), 3.30 (s, 3H), 3.05 (d, 1H), 2.89 (t, 1H), 2.81-2.70 (m, 2H), 2.69 (s, 3H), 1.93-0.92 (m, 24H). Chiral HPLC indicated 94.6% purity.

Example 33

The following compounds of Formula I were prepared by procedures analogous to those used in Example 32:

| Cpd. No. | Name |
|---|---|
| I-3A | 3-((2-cyclopropylethoxy)(phenyl)methyl)-N-((S)-1-amino-3-cyclohexylpropan-2-yl)piperidine-1-carboxamide |
| I-4A | N-((S)-1-amino-3-cyclohexylpropan-2-yl)-3-(5-methoxy-1-phenylpentyl)piperidine-1-carboxamide |
| I-5C | (3R)-3-((R)-(3-methoxypropoxy)(phenyl)methyl)-N-((S)-1-amino-3-cyclohexylpropan-2-yl)piperidine-1-carboxamide |
| I-5A | 3-((3-methoxypropoxy)(phenyl)methyl)-N-((S)-1-amino-3-cyclohexylpropan-2-yl)piperidine-1-carboxamide |
| I-5B | (3S)-3-((3-methoxypropoxy)(phenyl)methyl)-N-((S)-1-amino-3-cyclohexylpropan-2-yl)piperidine-1-carboxamide |
| I-8A | 2-((3-methoxypropoxy)(phenyl)methyl)-N-((S)-1-amino-3-cyclohexylpropan-2-yl)morpholine-4-carboxamide |
| I-13A | N-((S)-1-amino-3-cyclohexylpropan-2-yl)-3-(1-hydroxy-1-phenylheptyl)piperidine-1-carboxamide |
| I-17A | 3-((4-methoxybutoxy)(phenyl)methyl)-N-((S)-1-amino-3-cyclohexylpropan-2-yl)piperidine-1-carboxamide |
| I-17A | 3-((3-ethoxypropoxy)(phenyl)methyl)-N-((S)-1-amino-3-cyclohexylpropan-2-yl)piperidine-1-carboxamide |
| I-18A | N-((S)-1-amino-3-cyclohexylpropan-2-yl)-3-(1-hydroxy-5-methoxy-1-phenylpentyl)piperidine-1-carboxamide |
| I-19A | (3R)—N-((S)-1-amino-3-cyclohexylpropan-2-yl)-3-((S)-1-hydroxy-5-methoxy-1-phenylpentyl)piperidine-1-carboxamide |
| I-19A | 3-((3-methoxypropoxy)(phenyl)methyl)-N-(1-amino-3-cyclohexylpropan-2-yl)-N-methylpiperidine-1-carboxamide |
| I-21A | (3R)-3-((R)-(3-ethoxypropoxy)(phenyl)methyl)-N-((S)-1-amino-3-cyclohexylpropan-2-yl)piperidine-1-carboxamide |
| I-22A | 3-((3-methoxypropoxy)(4-fluorophenyl)methyl)-N-((S)-1-amino-3-cyclohexylpropan-2-yl)piperidine-1-carboxamide |
| I-23A | 3-((3-methoxypropoxy)(2-fluorophenyl)methyl)-N-((S)-1-amino-3-cyclohexylpropan-2-yl)piperidine-1-carboxamide |
| I-25A | (3R)—N-((S)-3-cyclohexyl-1-(methylamino)propan-2-yl)-3-(4-cyclopropyl-1-hydroxy-1-phenylbutyl)piperidine-1-carboxamide |
| I-31A | 3-((3-ethoxypropoxy)(phenyl)methyl)-N-((S)-3-cyclohexyl-1-(methylamino)propan-2-yl)piperidine-1-carboxamide |
| I-32A | (3R)—N-((S)-1-amino-3-cyclohexylpropan-2-yl)-3-((S)-5-ethoxy-1-hydroxy-1-phenylpentyl)piperidine-1-carboxamide |
| I-33A | (3R)—N-((S)-3-cyclohexyl-1-(methylamino)propan-2-yl)-3-((S)-1-hydroxy-5-methoxy-1-phenylpentyl)piperidine-1-carboxamide |
| I-34A | 3-((3-ethoxypropoxy)(phenyl)methyl)-N-((S)-1-amino-3-cyclohexylpropan-2-yl)-3-methylpiperidine-1-carboxamide |
| I-35A | (3R)—N-((S)-3-cyclohexyl-1-(methylamino)propan-2-yl)-3-((R)-4-ethoxy-1-hydroxy-1-phenylbutyl)piperidine-1-carboxamide |
| I-39A | (3R)-3-((R)-(3-methoxypropoxy)(3-fluorophenyl)methyl)-N-((S)-3-cyclohexyl-1-(methylamino)propan-2-yl)piperidine-1-carboxamide |
| I-40A | (3R)—N-((S)-1-amino-3-cyclohexylpropan-2-yl)-3-((S)-1-(3-fluorophenyl)-1-hydroxy-5-methoxypentyl)piperidine-1-carboxamide |
| I-41A | (3R)—N-((S)-3-cyclohexyl-1-(methylamino)propan-2-yl)-3-((R)-1-cyclohexyl-1-hydroxy-5-methoxypentyl)piperidine-1-carboxamide |
| I-41A | (3R)—N-((S)-3-cyclohexyl-1-(methylamino)propan-2-yl)-3-((S)-1-cyclohexyl-1-hydroxy-5-methoxypentyl)piperidine-1-carboxamide |
| I-42A | 3-((3-methoxypropoxy)(2,4-difluorophenyl)methyl)-N-((S)-1-amino-3-cyclohexylpropan-2-yl)piperidine-1-carboxamide |
| I-43A | 3-((3-methoxypropoxy)(3,4-difluorophenyl)methyl)-N-((S)-1-amino-3-cyclohexylpropan-2-yl)piperidine-1-carboxamide |
| I-44A | (3R)-3-((S)-1-hydroxy-5-methoxy-1-(2-phenoxyphenyl)pentyl)-N-((S)-1-(methylamino)propan-2-yl)piperidine-1-carboxamide |
| I-46A | 3-((3-methoxypropoxy)(2-allylphenyl)methyl)-N-((S)-1-amino-3-cyclohexylpropan-2-yl)piperidine-1-carboxamide |
| I-48A | (3R)—N-((S)-3-cyclohexyl-1-(methylamino)propan-2-yl)-3-((S)-5-ethoxy-1-hydroxy-1-phenylpentyl)piperidine-1-carboxamide |
| I-50A | (3R)—N-((S)-3-cyclohexyl-1-(methylamino)propan-2-yl)-3-((R)-1-hydroxy-5-methoxy-1-m-tolylpentyl)piperidine-1-carboxamide |
| I-50B | (3R)—N-((S)-3-cyclohexyl-1-(methylamino)propan-2-yl)-3-((S)-1-hydroxy-5-methoxy-1-m-tolylpentyl)piperidine-1-carboxamide |
| I-53B | (3R)—N-((S)-3-cyclohexyl-1-(methylamino)propan-2-yl)-3-((S)-1-(3-fluorophenyl)-1-hydroxy-5-methoxypentyl)piperidine-1-carboxamide |
| I-53A | (3R)—N-((S)-3-cyclohexyl-1-(methylamino)propan-2-yl)-3-((R)-1-(3-fluorophenyl)-1-hydroxy-5-methoxypentyl)piperidine-1-carboxamide |
| I-56A | (3R)-3-(1-hydroxy-5-methoxy-1-(2-phenoxyphenyl)pentyl)-N-(piperidin-3-yl)piperidine-1-carboxamide |

-continued

| Cpd. No. | Name |
|---|---|
| I-57A | (3R)—N-((S)-3-cyclohexyl-1-(methylamino)propan-2-yl)-3-(4,4,4-trifluoro-1-hydroxy-1-m-tolylbutyl)piperidine-1-carboxamide |
| I-64A | (3R)-3-((S)-1-(3-chlorophenyl)-1-hydroxy-5-methoxypentyl)-N-((S)-3-cyclohexyl-1-(methylamino)propan-2-yl)piperidine-1-carboxamide |
| I-65A | 3-((3-ethoxypropoxy)(3,4-difluorophenyl)methyl)-N-((S)-3-cyclohexyl-1-(methylamino)propan-2-yl)piperidine-1-carboxamide |
| I-66A | (3R)—N-((S)-3-cyclohexyl-1-(methylamino)propan-2-yl)-3-((S)-1-(2,5-difluorophenyl)-1-hydroxy-5-methoxypentyl)piperidine-1-carboxamide |
| I-67A | (3R)—N-((S)-3-(4,4-difluorocyclohexyl)-1-(methylamino)propan-2-yl)-3-((S)-1-hydroxy-5-methoxy-1-phenylpentyl)piperidine-1-carboxamide |
| I-68A | (3R)—N-((S)-3-cyclohexyl-1-(methylamino)propan-2-yl)-3-((S)-1-(3,4-difluorophenyl)-1-hydroxy-5-methoxypentyl)piperidine-1-carboxamide |
| I-72A | (3R)-3-((S)-1-(2-(p-tolyloxy)-5-methylphenyl)-1-hydroxy-5-methoxypentyl)-N-((S)-1-(methylamino)propan-2-yl)piperidine-1-carboxamide + ~10% of alcohol epimer |
| I-74A | 3-((3-methoxypropoxy)(2-(trifluoromethyl)phenyl)methyl)-N-((S)-1-amino-3-cyclohexylpropan-2-yl)piperidine-1-carboxamide |
| I-79A | (3R)—N-((S)-3-cyclohexyl-1-(methylamino)propan-2-yl)-3-((S)-1-hydroxy-1-(3-isopropylphenyl)-5-methoxypentyl)piperidine-1-carboxamide |
| I-80A | (3R)-3-((R)-1-(3-chlorophenyl)-4,4,4-trifluoro-1-hydroxybutyl)-N-((S)-3-cyclohexyl-1-(methylamino)propan-2-yl)piperidine-1-carboxamide |
| I-81A | (3R)-3-((S)-1-(5-chloro-2-phenoxyphenyl)-1-hydroxy-5-methoxypentyl)-N-((S)-1-(methylamino)propan-2-yl)piperidine-1-carboxamide + ~10% of alcohol epimer |
| I-82A | (3R)-3-(1-(3-chlorophenyl)-5-cyclopropyl-1-hydroxypentyl)-N-((S)-3-cyclohexyl-1-(methylamino)propan-2-yl)piperidine-1-carboxamide |
| I-83A | 3-((3-methoxypropoxy)(3-phenylphenyl)methyl)-N-((S)-2-amino-3-cyclohexylpropyl)piperidine-1-carboxamide |
| I-84A | 3-((3-methoxypropoxy)(2-(2-cyclopropylethynyl)phenyl)methyl)-N-((S)-3-cyclohexyl-1-(methylamino)propan-2-yl)piperidine-1-carboxamide |
| I-86B | (3R)-3-((S)-1-hydroxy-5-methoxy-1-(2-phenoxyphenyl)pentyl)-N-((S)-4-methyl-1-(methylamino)pentan-2-yl)piperidine-1-carboxamide |
| I-86A | (3R)-3-((S)-1-hydroxy-5-methoxy-1-(2-phenoxyphenyl)pentyl)-N-((S)-4-methyl-1-(methylamino)pentan-2-yl)piperidine-1-carboxamide + ~10% of alcohol epimer |
| I-88A | (3R)—N-((S)-3-(4,4-difluorocyclohexyl)-1-(methylamino)propan-2-yl)-3-((S)-1-(3-fluorophenyl)-1-hydroxy-5-methoxypentyl)piperidine-1-carboxamide |
| I-91A | (3R)—N-((S)-1-(carbamoylmethylamino)-3-cyclohexylpropan-2-yl)-3-((S)-1-(3-fluorophenyl)-1-hydroxy-5-methoxypentyl)piperidine-1-carboxamide |
| I-93A | (3R)—N-((S)-3-cyclohexyl-1-(methylamino)propan-2-yl)-3-((S)-1-(3-(trifluoromethyl)phenyl)-1-hydroxy-5-methoxypentyl)piperidine-1-carboxamide |
| I-93A | (3R)—N-((S)-3-cyclohexyl-1-(methylamino)propan-2-yl)-3-(1-(3-(trifluoromethyl)phenyl)-1-hydroxy-5-methoxypentyl)piperidine-1-carboxamide |
| I-96A | (3R)-3-((S)-1-(2-(p-tolyloxy)-5-methylphenyl)-1-hydroxy-5-methoxypentyl)-N-((S)-4-methyl-1-(methylamino)pentan-2-yl)piperidine-1-carboxamide + ~10% of alcohol epimer |
| I-97A | (3R)-3-((S)-1-(5-chloro-2-phenoxyphenyl)-1-hydroxy-5-methoxypentyl)-N-((S)-4-methyl-1-(methylamino)pentan-2-yl)piperidine-1-carboxamide + ~10% of alcohol epimer |
| I-100A | (3R)—N-((S)-3-cyclohexyl-1-(methylamino)propan-2-yl)-3-((S)-1-hydroxy-5-methoxy-1-(2-phenoxyphenyl)pentyl)piperidine-1-carboxamide + ~10% of alcohol epimer |
| I-103A | (3R)-3-((S)-1-(2-(p-tolyloxy)-5-methylphenyl)-1-hydroxy-5-methoxypentyl)-N-((S)-3-cyclohexyl-1-(methylamino)propan-2-yl)piperidine-1-carboxamide + ~10% of alcohol epimer |
| I-104A | (3R)-3-((S)-1-(5-chloro-2-phenoxyphenyl)-1-hydroxy-5-methoxypentyl)-N-((S)-3-cyclohexyl-1-(methylamino)propan-2-yl)piperidine-1-carboxamide + ~10% of alcohol epimer |
| I-108A | 3-(1-(2-(cyclopropylmethoxy)phenyl)-1-hydroxy-5-methoxypentyl)-N-((S)-1-(methylamino)propan-2-yl)piperidine-1-carboxamide |
| I-109A | (3R)-3-((S)-1-hydroxy-5-methoxy-1-m-tolylpentyl)-N-((S)-4,4-dimethyl-1-(methylamino)pentan-2-yl)piperidine-1-carboxamide |
| I-111A | N-((S)-3-cyclohexyl-1-(methylamino)propan-2-yl)-3-(1,1,1-trifluoro-2-hydroxy-6-methoxyhexan-2-yl)piperidine-1-carboxamide |
| I-113A | (3R)-3-((S)-1-(3-fluorophenyl)-1-hydroxy-5-methoxypentyl)-N-((S)-4,4-dimethyl-1-(methylamino)pentan-2-yl)piperidine-1-carboxamide |
| I-116A | (3R)-3-((S)-1-(3-chlorophenyl)-1-hydroxy-5-methoxypentyl)-N-((S)-4-methyl-1-(methylamino)pentan-2-yl)piperidine-1-carboxamide |
| I-117A | (3R)-3-((S)-1-(2,3-difluorophenyl)-1-hydroxy-5-methoxypentyl)-N-((S)-4-methyl-1-(methylamino)pentan-2-yl)piperidine-1-carboxamide |
| I-118A | (3R)-3-((S)-1-(benzofuran-7-yl)-1-hydroxy-5-methoxypentyl)-N-((S)-4-methyl-1-(methylamino)pentan-2-yl)piperidine-1-carboxamide |
| I-120A | (3R)-3-(1-(2-(2-cyclopropylethoxy)phenyl)-1-hydroxy-5-methoxypentyl)-N-((S)-1-(methylamino)propan-2-yl)piperidine-1-carboxamide |

-continued

| Cpd. No. | Name |
| --- | --- |
| I-121A | (3R)-3-(1-(2-(cyclopentyloxy)phenyl)-1-hydroxy-5-methoxypentyl)-N-((S)-1-(methylamino)propan-2-yl)piperidine-1-carboxamide |
| I-123A | (3R)—N-((S)-1-amino-3-cyclohexylpropan-2-yl)-3-((S)-1-(3-fluorophenyl)-1-hydroxy-5-methoxypentyl)piperidine-1-carboxamide |
| I-124A | (3R)-3-(1-hydroxy-5-methoxy-1-(2-(neopentyloxy)phenyl)pentyl)-N-((S)-1-(methylamino)propan-2-yl)piperidine-1-carboxamide |
| I-130A | (3R)—N-((S)-3-cyclohexyl-1-(methylamino)propan-2-yl)-3-((S)-1-hydroxy-5-methoxy-1-(thiazol-2-yl)pentyl)piperidine-1-carboxamide |
| I-134A | (3R)-3-((S)-1-(3-chlorophenyl)-1-hydroxy-5-methoxypentyl)-N-((S)-4,4-dimethyl-1-(methylamino)pentan-2-yl)piperidine-1-carboxamide |
| I-135A | (3R)-3-((S)-1-(2,3-difluorophenyl)-1-hydroxy-5-methoxypentyl)-N-((S)-4,4-dimethyl-1-(methylamino)pentan-2-yl)piperidine-1-carboxamide |
| I-144A | (3R)-3-((S)-1-hydroxy-5-methoxy-1-(2-methylbenzofuran-7-yl)pentyl)-N-((S)-4-methyl-1-(methylamino)pentan-2-yl)piperidine-1-carboxamide |
| I-145A | (3R)-3-((S)-1-hydroxy-1-(2-isobutylbenzofuran-7-yl)-5-methoxypentyl)-N-((S)-1-(methylamino)propan-2-yl)piperidine-1-carboxamide |
| I-146A | N-((S)-3-cyclohexyl-1-(methylamino)propan-2-yl)-3-(1-hydroxy-5-methoxy-1-phenylpentyl)-3-methylpiperidine-1-carboxamide |
| I-147A | (3R)-3-(1-(2-(cyclopentylmethoxy)phenyl)-1-hydroxy-5-methoxypentyl)-N-((S)-1-(methylamino)propan-2-yl)piperidine-1-carboxamide |
| I-149A | (3R)-3-((S)-1-(benzo[b]thiophen-7-yl)-1-hydroxy-5-methoxypentyl)-N-((S)-4-methyl-1-(methylamino)pentan-2-yl)piperidine-1-carboxamide |
| I-151A | (3R)—N-((S)-3-cyclohexyl-1-(methylamino)propan-2-yl)-3-((S)-1-(2-fluorophenyl)-1-hydroxy-5-methoxypentyl)piperidine-1-carboxamide |
| I-152A | (3R)-3-((R)-(3-ethoxypropoxy)(3-fluorophenyl)methyl)-N-((S)-3-cyclohexyl-1-(methylamino)propan-2-yl)piperidine-1-carboxamide |
| I-153A | (3R)—N-((S)-1-amino-3-cyclohexylpropan-2-yl)-3-((S)-1-(3-chlorophenyl)-1-hydroxy-5-methoxypentyl)piperidine-1-carboxamide |
| I-154A | (3R)-3-((R)-(3-ethoxypropoxy)(3-chlorophenyl)methyl)-N-((S)-1-amino-3-cyclohexylpropan-2-yl)piperidine-1-carboxamide |
| I-159A | (3R)-3-((3-methoxypropoxy)(4-chloropyridin-2-yl)methyl)-N-((S)-3-cyclohexyl-1-(methylamino)propan-2-yl)piperidine-1-carboxamide |
| I-160A | (R)-3-((S)-1-hydroxy-5-methoxy-1-(2-phenoxyphenyl)pentyl)-N-(2-methyl-1-(methylamino)propan-2-yl)piperidine-1-carboxamide |
| I-161A | (3R)-3-((S)-1-(2-(o-tolyloxy)phenyl)-1-hydroxy-5-methoxypentyl)-N-((S)-1-(methylamino)propan-2-yl)piperidine-1-carboxamide |
| I-162A | (3R)-3-((S)-1-(2-(m-tolyloxy)phenyl)-1-hydroxy-5-methoxypentyl)-N-((S)-1-(methylamino)propan-2-yl)piperidine-1-carboxamide |
| I-166A | (3R)-3-((S)-1-(3-chloro-2-fluorophenyl)-1-hydroxy-5-methoxypentyl)-N-((S)-4,4-dimethyl-1-(methylamino)pentan-2-yl)piperidine-1-carboxamide |
| I-168A | (3R)-3-((S)-1-(2-(4-fluorophenoxy)phenyl)-1-hydroxy-5-methoxypentyl)-N-((S)-1-(methylamino)propan-2-yl)piperidine-1-carboxamide |
| I-169A | (3R)-3-((S)-1-(5-fluoro-2-phenxoyphenyl)-1-hydroxy-5-methoxypentyl)-N-((S)-1-(methylamino)propan-2-yl)piperidine-1-carboxamide |
| I-170A | (3R)-3-((S)-1-(2-(3-fluorophenoxy)phenyl)-1-hydroxy-5-methoxypentyl)-N-((S)-1-(methylamino)propan-2-yl)piperidine-1-carboxamide |
| I-171A | (3R)-3-((S)-1-(2-(2-fluorophenoxy)phenyl)-1-hydroxy-5-methoxypentyl)-N-((S)-1-(methylamino)propan-2-yl)piperidine-1-carboxamide |
| I-173A | (3R)—N-((S)-3-cyclohexyl-1-(methylamino)propan-2-yl)-3-((S)-1-hydroxy-5-methoxy-1-(2,5-dimethylphenyl)pentyl)piperidine-1-carboxamide |
| I-174A | (3R)—N-((S)-3-cyclohexyl-1-(methylamino)propan-2-yl)-3-((S)-1-(3-ethylphenyl)-1-hydroxy-5-methoxypentyl)piperidine-1-carboxamide |
| I-175A | (3R)—N-((S)-3-cyclohexyl-1-(methylamino)propan-2-yl)-3-((S)-1-hydroxy-5-methoxy-1-(2,3-dimethylphenyl)pentyl)piperidine-1-carboxamide |
| I-179A | (3R)—N-((S)-3-cyclohexyl-1-(methylamino)propan-2-yl)-3-((S)-1-hydroxy-5-methoxy-1-(3-methoxyphenyl)pentyl)piperidine-1-carboxamide |
| I-180A | (3R)-3-(1-(2-(cyclopropylmethoxy)phenyl)-1-hydroxy-5-methoxypentyl)-N-((S)-4-methyl-1-(methylamino)pentan-2-yl)piperidine-1-carboxamide |
| I-181A | (3R)-3-(1-(3-chlorophenyl)-4-cyclopropyl-1-hydroxybutyl)-N-((S)-3-cyclohexyl-1-(methylamino)propan-2-yl)piperidine-1-carboxamide |
| I-190A | (3R)-3-((R)-(3-ethoxypropoxy)(3-chlorophenyl)methyl)-N-((S)-3-cyclohexyl-1-(methylamino)propan-2-yl)piperidine-1-carboxamide |
| I-193A | (3R)-3-((S)-1-(4-chloropyridin-2-yl)-1-hydroxy-5-methoxypentyl)-N-((S)-3-cyclohexyl-1-(methylamino)propan-2-yl)piperidine-1-carboxamide |
| I-194A | (3R)-3-((R)-(3-ethoxypropoxy)(phenyl)methyl)-N-((S)-3-(4,4-difluorocyclohexyl)-1-(methylamino)propan-2-yl)piperidine-1-carboxamide |
| I-195A | (3R)—N-((S)-3-cyclohexyl-1-(methylamino)propan-2-yl)-3-((S)-1-(3,5-difluorophenyl)-1-hydroxy-5-methoxypentyl)piperidine-1-carboxamide |
| I-198A | (3R)—N-((S)-3-cyclohexyl-1-(methylamino)propan-2-yl)-3-((S)-1-(2,3-difluorophenyl)-1-hydroxy-5-methoxypentyl)piperidine-1-carboxamide |
| I-200A | (3R)-3-((S)-1-(3-chlorophenyl)-1-hydroxy-5-methoxypentyl)-N-((S)-3-(tetrahydro-2H-pyran-4-yl)-1-(methylamino)propan-2-yl)piperidine-1-carboxamide |
| I-201A | (2RS)-2-((RS)-1-(3-chlorophenyl)-hydroxy-5-methoxypentyl)-N-((S)-3-cyclohexyl-1-(methylamino)propan-2-yl)morpholine-4-carboxamide |

| Cpd. No. | Name |
|---|---|
| I-204A | (R)-3-((S)-1-(2-(o-tolyloxy)phenyl)-1-hydroxy-5-methoxypentyl)-N-(2-methyl-1-(methylamino)propan-2-yl)piperidine-1-carboxamide |
| I-205A | (3R)-3-((S)-1-(2-(2-ethylphenoxy)phenyl)-1-hydroxy-5-methoxypentyl)-N-((S)-1-(methylamino)propan-2-yl)piperidine-1-carboxamide |
| I-208A | (3R)-3-((S)-1-(2,2-difluorobenzo[d][1,3]dioxol-4-yl)-1-hydroxy-5-methoxypentyl)-N-((S)-4-methyl-1-(methylamino)pentan-2-yl)piperidine-1-carboxamide |
| I-210A | (3R)-3-((S)-1-(benzofuran-7-yl)-1-hydroxy-5-methoxypentyl)-N-((S)-3-cyclohexyl-1-(methylamino)propan-2-yl)piperidine-1-carboxamide |
| I-213A | (R)-3-((S)-1-(2-(4-fluorophenoxy)phenyl)-1-hydroxy-5-methoxypentyl)-N-(2-methyl-1-(methylamino)propan-2-yl)piperidine-1-carboxamide |
| I-214A | (R)-3-((S)-1-(2-(3-fluorophenoxy)phenyl)-1-hydroxy-5-methoxypentyl)-N-(2-methyl-1-(methylamino)propan-2-yl)piperidine-1-carboxamide |
| I-215A | (3R)-3-((S)-1-(3-(o-tolyloxy)-2-fluorophenyl)-1-hydroxy-5-methoxypentyl)-N-((S)-1-(methylamino)propan-2-yl)piperidine-1-carboxamide |
| I-216A | (3R)-3-((S)-1-(2-(o-tolyloxy)-3-fluorophenyl)-1-hydroxy-5-methoxypentyl)-N-((S)-1-(methylamino)propan-2-yl)piperidine-1-carboxamide |
| I-217A | (3R)-3-((S)-1-(2-(5-fluoro-2-methylphenoxy)phenyl)-1-hydroxy-5-methoxypentyl)-N-((S)-1-(methylamino)propan-2-yl)piperidine-1-carboxamide |
| I-218A | (3R)-3-((S)-1-(2-(4-fluoro-2-methylphenoxy)phenyl)-1-hydroxy-5-methoxypentyl)-N-((S)-1-(methylamino)propan-2-yl)piperidine-1-carboxamide |
| I-222A | (3R)-3-(1-(2-(cyclopentyloxy)phenyl)-1-hydroxy-5-methoxypentyl)-N-((S)-4-methyl-1-(methylamino)pentan-2-yl)piperidine-1-carboxamide |
| I-223A | (3R)-3-(1-(2-(2-cyclopropylethoxy)phenyl)-1-hydroxy-5-methoxypentyl)-N-((S)-4-methyl-1-(methylamino)pentan-2-yl)piperidine-1-carboxamide |
| I-224A | (3R)-3-((S)-1-(2-(2-chlorophenoxy)phenyl)-1-hydroxy-5-methoxypentyl)-N-((S)-1-(methylamino)propan-2-yl)piperidine-1-carboxamide |
| I-225A | (3R)-3-(1-hydroxy-5-methoxy-1-(2-(neopentyloxy)phenyl)pentyl)-N-((S)-4-methyl-1-(methylamino)pentan-2-yl)piperidine-1-carboxamide |
| I-227A | (3R)-3-((S)-4-(acetylamino)-1-(3-chlorophenyl)-1-hydroxybutyl)-N-((S)-3-cyclohexyl-1-(methylamino)propan-2-yl)piperidine-1-carboxamide |
| I-228A | (3R)-3-(1-(2-(allyloxy)-5-fluorophenyl)-5-ethoxyl-hydroxypentyl)-N-((S)-4-methyl-1-(methylamino)pentan-2-yl)piperidine-1-carboxamide |
| I-229A | (3R)—N-((S)-3-cyclohexyl-1-(methylamino)propan-2-yl)-3-((S)-1-(5-fluoro-2-methoxyphenyl)-1-hydroxy-5-methoxypentyl)piperidine-1-carboxamide |
| I-231A | (3R)-3-(4-cyclopropyl-1-hydroxy-1-(2-phenoxyphenyl)butyl)-N-((S)-4 methyl-1-(methylamino)pentan-2-yl)piperidine-1-carboxamide |
| I-232A | (3R)-3-((S)-1-(3-chlorophenyl)-1-hydroxy-5-methoxypentyl)-N-(5,5,5-trifluoro-4-methyl-1-(methylamino)pentan-2-yl)piperidine-1-carboxamide |
| I-233A | (3R)-3-(1-(3-chlorophenyl)-1,5-dimethoxypentyl)-N-((S)-3-cyclohexyl-1-(methylamino)propan-2-yl)piperidine-1-carboxamide |
| I-234A | (3R)-3-((S)-1-(3-chlorophenyl)-1-hydroxy-5-methoxypentyl)-N-((S)-3-cyclohexyl-1-(ethylamino)propan-2-yl)piperidine-1-carboxamide |
| I-236A | (3R)-3-(4-cyclopropyl-1-(3-fluorophenyl)-1-hydroxybutyl)-N-((S)-3-(4,4-difluorocyclohexyl)-1-(methylamino)propan-2-yl)piperidine-1-carboxamide |
| I-240A | (3R)-3-((S)-1-(2-fluoro-3-methylphenyl)-1-hydroxy-5-methoxypentyl)-N-((S)-3-(cis-4-fluorocyclohexyl)-1-(methylamino)propan-2-yl)piperidine-1-carboxamide |
| I-249A | (R)-3-((S)-1-(2-(p-tolyloxy)-5-methylphenyl)-1-hydroxy-5-methoxypentyl)-N-(2-methyl-1-(methylamino)propan-2-yl)piperidine-1-carboxamide |
| 1-251B | (3R)-3-((S)-1-(3-chloro-2-fluorophenyl)-1-hydroxy-5-methoxypentyl)-N-((S)-3-cyclohexyl-1-(methylamino)propan-2-yl)piperidine-1-carboxamide |
| I-251A | (3R)-3-(1-(3-chloro-2-fluorophenyl)-1-hydroxy-5-methoxypentyl)-N-((S)-3-cyclohexyl-1-(methylamino)propan-2-yl)piperidine-1-carboxamide |
| I-254A | (3R)-3-((S)-1-hydroxy-5-methoxy-1-(2-(pyridin-3-yloxy)phenyl)pentyl)-N-((S)-4-methyl-1-(methylamino)pentan-2-yl)piperidine-1-carboxamide |
| I-256A | (3R)—N-((S)-3-cyclohexyl-1-(methylamino)propan-2-yl)-3-(1-(2,3,5-trifluorophenyl)-1-hydroxy-5-methoxypentyl)piperidine-1-carboxamide |
| I-256B | (3R)—N-((S)-3-cyclohexyl-1-(methylamino)propan-2-yl)-3-((S)-1-(2,3,5-trifluorophenyl)-1-hydroxy-5-methoxypentyl)piperidine-1-carboxamide |
| I-263A | (3R)-3-(1-(3-chlorophenyl)-5,5-difluoro-1-hydroxyhexyl)-N-((S)-3-cyclohexyl-1-(methylamino)propan-2-yl)piperidine-1-carboxamide |
| I-267A | (3R)-3-((S)-1-(benzo[b]thiophen-7-yl)-1-hydroxy-5-methoxypentyl)-N-((S)-3-cyclohexyl-1-(methylamino)propan-2-yl)piperidine-1-carboxamide |
| I-268A | (3R)-3-((S)-1-(benzo[b]thiophen-2-yl)-1-hydroxy-5-methoxypentyl)-N-((S)-3-cyclohexyl-1-(methylamino)propan-2-yl)piperidine-1-carboxamide |
| I-269A | (3R)-3-((S)-1-hydroxy-5-methoxy-1-(3-(trifluoromethoxy)pheny)pentyl)-N-((S)-4,4-dimethyl-1-(methylamino)pentan-2-yl)piperidine-1-carboxamide |
| I-270A | (3R)—N-((S)-3-cyclohexyl-1-(methylamino)propan-2-yl)-3-((S)-1-(5-fluorobenzofuran-7-yl)-1-hydroxy-5-methoxypentyl)piperidine-1-carboxamide |
| I-275A | (3R)-3-((S)-1-(2-(o-tolyloxy)phenyl)-1-hydroxy-5-methoxypentyl)-N-((S)-4-methyl-1-(methylamino)pentan-2-yl)piperidine-1-carboxamide |

-continued

| Cpd. No. | Name |
|---|---|
| I-276A | (3R)-3-((S)-1-hydroxy-5-methoxy-1-(2-phenoxyphenyl)pentyl)-N-((S)-4,4-dimethyl-1-(methylamino)pentan-2-yl)piperidine-1-carboxamide |
| I-277A | (3R)-3-(1-(2-(benzyloxy)phenyl)-1-hydroxy-5-methoxypentyl)-N-((S)-4-methyl-1-(methylamino)pentan-2-yl)piperidine-1-carboxamide |
| I-278A | (3R)-3-((S)-1-(2-(m-tolyloxy)phenyl)-1-hydroxy-5-methoxypentyl)-N-((S)-4-methyl-1-(methylamino)pentan-2-yl)piperidine-1-carboxamide |
| I-279A | (3R)-3-(1-(3-chloro-2-fluorophenyl)-5-ethoxy-1-hydroxypentyl)-N-((S)-3-cyclohexyl-1-(methylamino)propan-2-yl)piperidine-1-carboxamide |
| I-287A | (3R)-3-((S)-1-(2-(4-fluorophenoxy)phenyl)-1-hydroxy-5-methoxypentyl)-N-((S)-4-methyl-1-(methylamino)pentan-2-yl)piperidine-1-carboxamide |
| I-288A | (3R)-3-((S)-1-(5-fluoro-2-phenoxyphenyl)-1-hydroxy-5-methoxypentyl)-N-((S)-4-methyl-1-(methylamino)pentan-2-yl)piperidine-1-carboxamide |
| I-289A | (3R)-3-((S)-1-(2-(3-fluorophenoxy)phenyl)-1-hydroxy-5-methoxypentyl)-N-((S)-4-methyl-1-(methylamino)pentan-2-yl)piperidine-1-carboxamide |
| I-290A | (3R)-3-((S)-1-(2-(2-fluorophenoxy)phenyl)-1-hydroxy-5-methoxypentyl)-N-((S)-4-methyl-1-(methylamino)pentan-2-yl)piperidine-1-carboxamide |
| I-290B | (3R)-3-((R)-1-(2-(2-fluorophenoxy)phenyl)-1-hydroxy-5-methoxypentyl)-N-((S)-4-methyl-1-(methylamino)pentan-2-yl)piperidine-1-carboxamide |
| I-291A | (3R)-3-((S)-1-(3-fluoro-2-phenoxyphenyl)-1-hydroxy-5-methoxypentyl)-N-((S)-4-methyl-1-(methylamino)pentan-2-yl)piperidine-1-carboxamide |
| I-292A | (3R)-3-((S)-1-(3-(4-fluorophenoxy)phenyl)-1-hydroxy-5-methoxypentyl)-N-((S)-4-methyl-1-(methylamino)pentan-2-yl)piperidine-1-carboxamide |
| I-293A | (3R)-3-((S)-1-(3-chlorophenyl)-1-hydroxy-5-methoxypentyl)-N-((S)-3-(4,4-difluorocyclohexyl)-1-(methylamino)propan-2-yl)piperidine-1-carboxamide |
| I-294A | (3R)-3-((R)-(3-ethoxypropoxy)(3-chlorophenyl)methyl)-N-((S)-3-(4,4-difluorocyclohexyl)-1-(methylamino)propan-2-yl)piperidine-1-carboxamide |
| I-299A | (3R)—N-((S)-3-(4,4-difluorocyclohexyl)-1-(methylamino)propan-2-yl)-3-((S)-1-(2,3-difluorophenyl)-1-hydroxy-5-methoxypentyl)piperidine-1-carboxamide |
| I-300A | (2RS)-2-((RS)-1-(3-chlorophenyl)-1-hydroxy-5-methoxypentyl)-N-((S)-3-(4,4-difluorocyclohexyl)-1-(methylamino)propan-2-yl)morpholine-4-carboxamide |
| I-303A | (3R)—N-((S)-4,4,4-trifluoro-1-(methylamino)butan-2-yl)-3-((S)-1-hydroxy-5-methoxy-1-(2-phenoxyphenyl)pentyl)piperidine-1-carboxamide |
| I-304A | (3R)-3-((S)-1-(2-(2-(trifluoromethyl)phenoxy)phenyl)-1-hydroxy-5-methoxypentyl)-N-((S)-1-(methylamino)propan-2-yl)piperidine-1-carboxamide |
| I-305A | (3R)—N-((S)-1-(2-methoxyethylamino)-3-cyclohexylpropan-2-yl)-3-((S)-1-(3-chlorophenyl)-1-hydroxy-5-methoxypentyl)piperidine-1-carboxamide |
| I-306A | (3R)—N-((S)-3-cyclohexyl-1-(methylamino)propan-2-yl)-3-((S)-1-(2,2-difluorobenzo[d][1,3]dioxol-4-yl)-1-hydroxy-5-methoxypentyl)piperidine-1-carboxamide |
| I-307A | (3R)-3-((S)-1-(2-(o-tolyloxy)-3-methylphenyl)-1-hydroxy-5-methoxypentyl)-N-((S)-4-methyl-1-(methylamino)pentan-2-yl)piperidine-1-carboxamide |
| I-311A | (3R)-3-((S)-1-(2-(p-tolyloxy)-3-fluorophenyl)-1-hydroxy-5-methoxypentyl)-N-((S)-4-methyl-1-(methylamino)pentan-2-yl)piperidine-1-carboxamide |
| I-312A | (3R)-3-((S)-1-(2-(o-tolyloxy)-3-fluorophenyl)-1-hydroxy-5-methoxypentyl)-N-((S)-4-methyl-1-(methylamino)pentan-2-yl)piperidine-1-carboxamide |
| I-313A | (3R)-3-((S)-1-(2-(5-fluoro-2-methylphenoxy)phenyl)-1-hydroxy-5-methoxypentyl)-N-((S)-4-methyl-1-(methylamino)pentan-2-yl)piperidine-1-carboxamide |
| I-314A | (3R)-3-((S)-1-(2-(4-fluoro-2-methylphenoxy)phenyl)-1-hydroxy-5-methoxypentyl)-N-((S)-4-methyl-1-(methylamino)pentan-2-yl)piperidine-1-carboxamide |
| I-315A | (3R)—N-((S)-3-cyclohexyl-1-(methylamino)propan-2-yl)-3-(1-(2-(cyclopentyloxy)phenyl)-1-hydroxy-5-methoxypentyl)piperidine-1-carboxamide |
| I-316A | (3R)-3-(1-(2-(2-cyclopropylethoxy)phenyl)-1-hydroxy-5-methoxypentyl)-N-((S)-3-cyclohexyl-1-(methylamino)propan-2-yl)piperidine-1-carboxamide |
| I-318A | (3R)-3-((S)-1-(2-(4-fluorophenoxy)-5-fluorophenyl)-1-hydroxy-5-methoxypentyl)-N-((S)-4-methyl-1-(methylamino)pentan-2-yl)piperidine-1-carboxamide |
| I-318A | (3R)-3-((R)-1-(2-(4-fluorophenoxy)-5-fluorophenyl)-1-hydroxy-5-methoxypentyl)-N-((S)-4-methyl-1-(methylamino)pentan-2-yl)piperidine-1-carboxamide |
| I-319A | (3R)-3-((S)-1-(3,5-difluoro-2-phenoxyphenyl)-1-hydroxy-5-methoxypentyl)-N-((S)-4-methyl-1-(methylamino)pentan-2-yl)piperidine-1-carboxamide |
| I-327A | (3R)—N-((S)-1-(2-ethoxyethylamino)-3-cyclohexylpropan-2-yl)-3-((S)-1-(3-chlorophenyl)-1-hydroxy-5-methoxypentyl)piperidine-1-carboxamide |
| I-328A | (3R)—N-((S)-3-cyclohexyl-1-(methylamino)propan-2-yl)-3-((S)-1-hydroxy-5-methoxy-1-(2-(pyridin-3-yloxy)phenyl)pentyl)piperidine-1-carboxamide |

| Cpd. No. | Name |
|---|---|
| I-330A | (3R)-3-((S)-1-(2-(allyloxy)-3-bromophenyl)-1-hydroxy-5-methoxypentyl)-N-((S)-4-methyl-1-(methylamino)pentan-2-yl)piperidine-1-carboxamide |
| I-334A | (3R)—N-(5,5,5-trifluoro-4-methyl-1-(methylamino)pentan-2-yl)-3-((S)-1-hydroxy-5-methoxy-1-(2-phenoxyphenyl)pentyl)piperidine-1-carboxamide |
| I-335A | (3R)-3-(1-(2-(benzyloxy)phenyl)-1-hydroxy-5-methoxypentyl)-N-((S)-1-cyclohexyl-3-(methylamino)propan-2-yl)piperidine-1-carboxamide |
| I-337A | (3R)-3-((S)-1-(2-(4-fluorophenoxy)phenyl)-1-hydroxy-5-methoxypentyl)-N-((S)-3-cyclohexyl-1-(methylamino)propan-2-yl)piperidine-1-carboxamide |
| I-338A | (3R)—N-((S)-3-cyclohexyl-1-(methylamino)propan-2-yl)-3-((S)-1-(5-fluoro-2-phenoxyphenyl)-1-hydroxy-5-methoxypentyl)piperidine-1-carboxamide |
| I-339A | (3R)-3-((S)-1-(2-(2-(trifluoromethyl)phenoxy)phenyl)-1-hydroxy-5-methoxypentyl)-N-((S)-4-methyl-1-(methylamino)pentan-2-yl)piperidine-1-carboxamide |
| I-350A | (R)-3-((S)-1-(benzofuran-7-yl)-1-hydroxy-5-methoxypentyl)-N-((S)-4,4-dimethyl-1-(methylamino)pentan-2-yl)piperidine-1-carboxamide |
| I-356A | (R)-3-((S)-1-(3-chlorophenyl)-1-hydroxy-5-methoxypentyl)-N-((S)-4-methoxy-4-methyl-1-(methylamino)pentan-2-yl)piperidine-1-carboxamide |
| I-361A | (R)-3-((S)-1-(benzo[b]thiophen-4-yl)-1-hydroxy-5-methoxypentyl)-N-((S)-4,4-dimethyl-1-(methylamino)pentan-2-yl)piperidine-1-carboxamide |
| I-374A | (R)-3-((S)-1-(benzofuran-4-yl)-1-hydroxy-5-methoxypentyl)-N-((S)-1-cyclohexyl-3-(methylamino)propan-2-yl)piperidine-1-carboxamide |
| I-378A | (R)-3-((S)-1-(3-chloro-2-fluorophenyl)-1-hydroxy-5-methoxypentyl)-N-((S)-4-methoxy-4-methyl-1-(methylamino)pentan-2-yl)piperidine-1-carboxamide |
| I-380A | (R)-3-((S)-1-(3-carbamoylphenyl)-1-hydroxy-5-methoxypentyl)-N-((S)-1-cyclohexyl-3-(methylamino)propan-2-yl)piperidine-1-carboxamide |
| I-387A | (R)-3-((S)-1-(3-chlorophenyl)-1,5-dimethoxypentyl)-N-((S)-1-cyclohexyl-3-(methylamino)propan-2-yl)piperidine-1-carboxamide |
| I-388A | (R)-3-((S)-4-acetamido-1-(2,3-difluorophenyl)-1-hydroxybutyl)-N-((S)-1-cyclohexyl-3-(methylamino)propan-2-yl)piperidine-1-carboxamide |
| I-390A | (R)-3-((S)-1-(2,3-difluorophenyl)-1-hydroxy-5-methoxypentyl)-N-((S)-1-(methylamino)-3-(4-methylcyclohexyl)propan-2-yl)piperidine-1-carboxamide |
| I-404A | 2-((R)-1-(3-chloro-2-fluorophenyl)-1-hydroxy-5-methoxypentyl)-N-((S)-1-cyclohexyl-3-(methylamino)propan-2-yl)morpholine-4-carboxamide |
| I-406A | (R)-3-((S)-1-(3-chloro-2-fluorophenyl)-1-hydroxy-5-methoxypentyl)-N-((S)-1-(methylamino)-3-(tetrahydro-2H-pyran-4-yl)propan-2-yl)piperidine-1-carboxamide |
| I-406B | (R)-3-((S)-1-(3-chloro-2-fluorophenyl)-1-hydroxy-5-methoxypentyl)-N-((R)-1-(methylamino)-3-(tetrahydro-2H-pyran-4-yl)propan-2-yl)piperidine-1-carboxamide |
| I-408A | (R)-3-((S)-1-(benzo[b]thiophen-4-yl)-1-hydroxy-5-methoxypentyl)-N-((S)-1-cyclohexyl-3-(methylamino)propan-2-yl)piperidine-1-carboxamide |
| I-411A | (R)—N-((S)-1-cyclohexyl-3-(methylamino)propan-2-yl)-3-((S)-1-(2-fluorobenzofuran-7-yl)-1-hydroxy-5-methoxypentyl)piperidine-1-carboxamide |
| I-413A | (RS)-2-((RS)-1-(benzo[b]thiophen-7-yl)-1-hydroxy-5-methoxypentyl)-N-((S)-1-cyclohexyl-3-(methylamino)propan-2-yl)morpholine-4-carboxamide |
| I-416A | (R)-3-((S)-1-(3-chlorophenyl)-1-hydroxy-4-propionamidobutyl)-N-((S)-1-cyclohexyl-3-(methylamino)propan-2-yl)piperidine-1-carboxamide |
| I-418A | (R)-3-((S)-1-(3-chlorophenyl)-1-hydroxy-4-(3-methylureido)butyl)-N-((S)-1-cyclohexyl-3-(methylamino)propan-2-yl)piperidine-1-carboxamide |
| I-426A | (R)-3-((S)-1-(3-chloro-2-fluorophenyl)-1,5-dimethoxypentyl)-N-((S)-1-cyclohexyl-3-(methylamino)propan-2-yl)piperidine-1-carboxamide |
| I-437A | (R)-2-((R)-1-(3-chloro-2-fluorophenyl)-1-hydroxy-5-methoxypentyl)-N-((S)-1-(trans-4-fluorocyclohexyl)-3-(methylamino)propan-2-yl)morpholine-4-carboxamide |
| I-438A | (R)-3-((S)-1-(3-chlorophenyl)-4-(cyclopropanecarboxamido)-1-hydroxybutyl)-N-((S)-1-cyclohexyl-3-(methylamino)propan-2-yl)piperidine-1-carboxamide |
| I-439A | (R)-3-((S)-4-butyramido-1-(3-chlorophenyl)-1-hydroxybutyl)-N-((S)-1-cyclohexyl-3-(methylamino)propan-2-yl)piperidine-1-carboxamide |
| I-440A | (R)-3-((S)-1-(3-chlorophenyl)-4-(3,3-dimethylureido)-1-hydroxybutyl)-N-((S)-1-cyclohexyl-3-(methylamino)propan-2-yl)piperidine-1-carboxamide |
| I-442A | (R)-3-((S)-1-(3-bromophenyl)-1-hydroxy-5-methoxypentyl)-N-((S)-1-cyclohexyl-3-(methylamino)propan-2-yl)piperidine-1-carboxamide |
| I-449A | (R)-3-((S)-1-(3-chlorophenyl)-1-hydroxy-4-(methylsulfonamido)butyl)-N-((S)-1-cyclohexyl-3-(methylamino)propan-2-yl)piperidine-1-carboxamide |
| I-450A | (R)-3-((S)-1-(3-chlorophenyl)-1-hydroxy-4-(sulfamoylamino)butyl)-N-((S)-1-cyclohexyl-3-(methylamino)propan-2-yl)piperidine-1-carboxamide |
| I-451A | (R)-3-((S)-4-acetamido-1-(2,3-difluorophenyl)-1-hydroxybutyl)-N-((S)-1-(4,4-difluorocyclohexyl)-3-(methylamino)propan-2-yl)piperidine-1-carboxamide |
| I-455A | (R)-3-((S)-1-(3-chlorophenyl)-1-hydroxy-4-((R)-2-methoxypropanamido)butyl)-N-((S)-1-cyclohexyl-3-(methylamino)propan-2-yl)piperidine-1-carboxamide |

-continued

| Cpd. No. | Name |
| --- | --- |
| I-455B | (R)-3-((S)-1-(3-chlorophenyl)-1-hydroxy-4-((S)-2-methoxypropanamido)butyl)-N-((S)-1-cyclohexyl-3-(methylamino)propan-2-yl)piperidine-1-carboxamide |
| I-459A | (R)-3-((S)-1-(2-bromo-5-fluorophenyl)-1-hydroxy-5-methoxypentyl)-N-((S)-1-cyclohexyl-3-(methylamino)propan-2-yl)piperidine-1-carboxamide |
| I-464A | (R)-3-((S)-1-(3-chlorophenyl)-1-hydroxy-4-(2,2,2-trifluoroacetamido)butyl)-N-((S)-1-cyclohexyl-3-(methylamino)propan-2-yl)piperidine-1-carboxamide |
| I-470A | (3S)-3-(1-(3-chloro-2-fluorophenyl)-5-methoxypentyl)-N-((S)-1-cyclohexyl-3-(methylamino)propan-2-yl)piperidine-1-carboxamide |
| I-471A | (R)-2-((S)-(3-chloro-2-fluorophenyl)(3-methoxypropoxy)methyl)-N-((S)-1-cyclohexyl-3-(methylamino)propan-2-yl)morpholine-4-carboxamide |
| I-479A | (3R)-3-((S)-1-(benzo[b]thiophen-7-yl)-1-hydroxy-5-methoxypentyl)-N-(1-(methylamino)-3-(tetrahydro-2H-pyran-4-yl)propan-2-yl)piperidine-1-carboxamide |
| I-478A | (3R)-3-(1-(3-chloro-2-fluorophenyl)-1-fluoro-5-methoxypentyl)-N-((S)-1-cyclohexyl-3-(methylamino)propan-2-yl)piperidine-1-carboxamide |
| I-502A | (3R)-3-((R)-(3-chlorophenyl)(2-hydroxyethoxy)methyl)-N-((S)-1-cyclohexyl-3-(methylamino)propan-2-yl)piperidine-1-carboxamide |
| I-505A | (3R)—N-((2S)-1-amino-3-(tetrahydrofuran-2-yl)propan-2-yl)-3-((S)-1-(3-chlorophenyl)-1-hydroxy-5-methoxypentyl)piperidine-1-carboxamide |
| I-509A | (3R)—N-((2S)-1-amino-3-(tetrahydro-2H-pyran-2-yl)propan-2-yl)-3-((S)-1-(3-chlorophenyl)-1-hydroxy-5-methoxypentyl)piperidine-1-carboxamide |
| I-510A | (3R)—N-((S)-1-amino-3-(3-methoxycyclobutyl)propan-2-yl)-3-((S)-1-(3-chlorophenyl)-1-hydroxy-5-methoxypentyl)piperidine-1-carboxamide |
| I-514A | (3R)—N-((2S)-1-amino-3-(tetrahydrofuran-2-yl)propan-2-yl)-3-((S)-1-(3-chloro-2-fluorophenyl)-1-hydroxy-5-methoxypentyl)piperidine-1-carboxamide |
| I-522A | (S)-3-((R)-1-(3-chloro-2-fluorophenyl)-5-methoxypentyl)-N-((S)-1-cyclohexyl-3-(methylamino)propan-2-yl)piperidine-1-carboxamide |
| I-522B | (S)-3-((S)-1-(3-chloro-2-fluorophenyl)-5-methoxypentyl)-N-((S)-1-cyclohexyl-3-(methylamino)propan-2-yl)piperidine-1-carboxamide |
| I-524A | (3R)-3-((R)-(3-chloro-2-fluorophenyl)(3-methoxypropoxy)methyl)-N-((S)-1-cyclohexyl-3-(methylamino)propan-2-yl)piperidine-1-carboxamide |
| I-526A | (3R)—N-((2S)-1-amino-3-(tetrahydro-2H-pyran-2-yl)propan-2-yl)-3-((S)-1-(3-chloro-2-fluorophenyl)-1-hydroxy-5-methoxypentyl)piperidine-1-carboxamide |
| I-528A | (3R)—N-((S)-1-amino-3-(3-methoxycyclobutyl)propan-2-yl)-3-((S)-1-(3-chloro-2-fluorophenyl)-1-hydroxy-5-methoxypentyl)piperidine-1-carboxamide |

The following compounds were prepared using procedures analogous to those described in Example 32 Step 1 followed by acid catalyzed removal of a Boc protecting group following the conditions described in Example 126, Step 2:

(3R)-3-((S)-1-(3-chlorophenyl)-1-hydroxy-5-methoxypentyl)-N—((S)-3-cyclohexyl-1-hydroxypropan-2-yl)piperidine-1-carboxamide (I-158A) was prepared by applying analogous procedures to those described in Example 32 Step

| Cpd. No. | Name |
| --- | --- |
| I-163A | (3R)—N-(3-(3,3-difluorocyclobutyl)-1-(methylamino)propan-2-yl)-3-((S)-1-(3-fluorophenyl)-1-hydroxy-5-methoxypentyl)piperidine-1-carboxamide |
| I-220A | (3R)-3-((S)-1-(3-chlorophenyl)-1-hydroxy-5-methoxypentyl)-N-(3-(3,3-difluorocyclobutyl)-1-(methylamino)propan-2-yl)piperidine-1-carboxamide |
| I-221A | (3R)—N-(3-(3,3-difluorocyclobutyl)-1-(methylamino)propan-2-yl)-3-((S)-1-(2,3-difluorophenyl)-1-hydroxy-5-methoxypentyl)piperidine-1-carboxamide |
| I-273A | (3R)-3-((S)-1-(3-chloro-2-fluorophenyl)-1-hydroxy-5-methoxypentyl)-N-(3-(3,3-difluorocyclobutyl)-1-(methylamino)propan-2-yl)piperidine-1-carboxamide |
| I-325A | (3R)—N-(3-(3,3-difluorocyclobutyl)-1-(methylamino)propan-2-yl)-3-((R)-1-hydroxy-5-methoxy-1-(3-(trifluoromethoxy)phenyl)pentyl)piperidine-1-carboxamide |
| I-369A | (R)-3-((S)-1-(3-chlorophenyl)-1-hydroxy-5-methoxypentyl)-N-((S)-3-cyclohexyl-2-(methylamino)propyl)piperidine-1-carboxamide |
| I-468A | (3R)—N-(1-(3,3-difluorocyclobutyl)-3-(methylamino)propan-2-yl)-3-((S)-1-(3-fluoro-2-phenoxyphenyl)-1-hydroxy-5-methoxypentyl)piperidine-1-carboxamide |

1 to (S)-4-nitrophenyl 1-(tert-butyldimethylsilyloxy)-3-cyclohexylpropan-2-ylcarbamate and (S)-1-(3-chlorophenyl)-5-methoxy-1-((R)-piperidin-3-yl)pentan-1-ol to afford (R)—N—((S)-1-(tert-butyldimethylsilyloxy)-3-cyclohexylpropan-2-yl)-3-((S)-1-(3-chlorophenyl)-1-hydroxy-5-methoxypentyl)piperidine-1-carboxamide followed by removal of the t-butyldimethylsilyl group with aqueous acid.

Example 34

N2-((Z)-1-(3-((3-methoxypropoxy)(phenyl)methyl)piperidin-1-yl)-2-nitrovinyl)-3-cyclohexylpropane-1,2-diamine (I-52A)

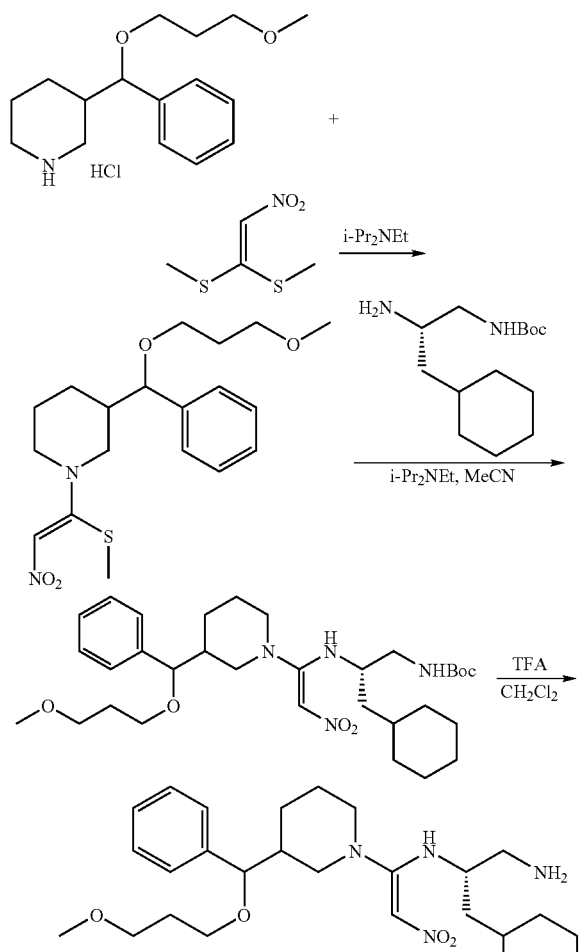

Step 1. tert-butyl (S)-2-(1-(3-((3-methoxypropoxy)(phenyl)methyl)piperidin-1-yl)-2-nitrovinylamino)-3-cyclohexylpropylcarbamate 3-((3-Methoxypropoxy)(phenyl)methyl)piperidine hydrochloride (177 mg, 0.59 mmol), 1,1-bis(methylthio)-2-nitroethene (117 mg, 0.71 mmol, 1.2 equiv), and diisopropylethylamine (500 µL, 2.8 mmol, 5 equiv) were dissolved in acetonitrile (5 mL) and put on a shaker for 2 h. LC-MS indicated the presence of 3-((3-methoxypropoxy)(phenyl) methyl)-1-((Z)-1-(methylthio)-2-nitrovinyl)piperidine. Tert-butyl (S)-2-amino-3-cyclohexylpropylcarbamate (~300 mg, 1.17 mmol, 2 equiv) was added to the mixture and shaking was continued overnight. The mixture was concentrated and purified by prep HPLC to afford tert-butyl (S)-2-(1-(3-((3-methoxypropoxy)(phenyl)methyl)piperidin-1-yl)-2-nitrovinylamino)-3-cyclohexylpropylcarbamate (22 mg, 6.6%). LC-MS (3 min) $t_R$=1.92 min. m/z 589 (M+1).

Step 2. (2S)—N$^2$-(1-(3-((3-methoxypropoxy)(phenyl)methyl)piperidin-1-yl)-2-nitrovinyl)-3-cyclohexylpropane-1,2-diamine Tert-butyl (S)-2-(1-(3-((3-methoxypropoxy)(phenyl)methyl)piperidin-1-yl)-2-nitrovinylamino)-3-cyclohexylpropylcarbamate (12 mg, 0.02 mmol) was dissolved in 1:1 TFA/CH$_2$Cl$_2$ (3 mL) and stirred for 30 min at rt. LC-MS showed the reaction was complete. After concentration, the mixture was purified by prep HPLC to afford (2S)—N$^2$-(1-(3-((3-methoxypropoxy)(phenyl)methyl)piperidin-1-yl)-2-nitrovinyl)-3-cyclohexylpropane-1,2-diamine (12.4 mg, 68%). LC-MS (3 min) $t_R$=1.38 min. m/z 489 (M+1).

Example 35

(3S)—N—((S)-3-cyclohexyl-1-(methylamino)propan-2-yl)-3-((R)-5-ethoxy-1-phenylpentyl)piperidine-1-carboxamide (I-27A)

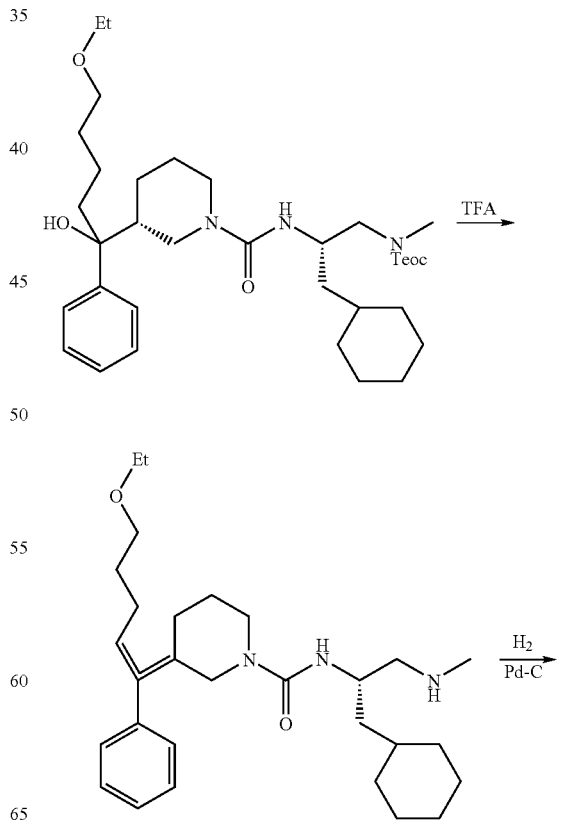

-continued

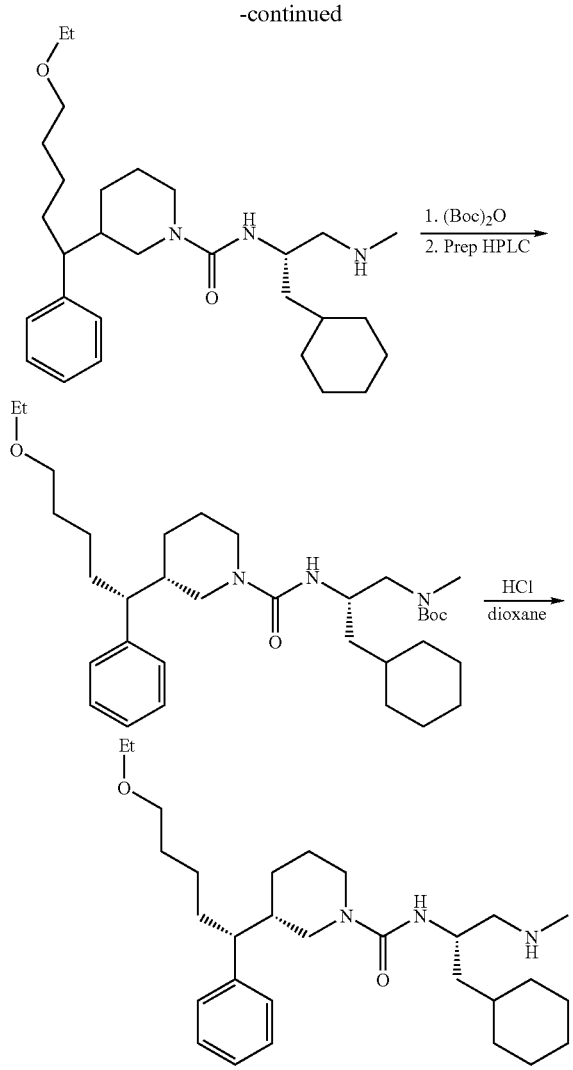

Step 1

2-(Trimethylsilyl)ethyl (S)-2-((R)-3-(5-ethoxy-1-hydroxy-1-phenylpentyl)piperidine-1-carboxamido)-3-cyclohexylpropylmethylcarbamate (310 mg, 0.49 mmol) was dissolved in neat TFA (2 mL). The resulting solution was stirred at rt until no starting material remained (~1 h). TFA was removed in vacuo to give a mixture of N—((S)-3-cyclohexyl-1-(methylamino)propan-2-yl)-3-((E)-5-ethoxy-1-phenylpent-1-enyl)piperidine-1-carboxamide and (Z)-N—((S)-3-cyclohexyl-1-(methylamino)propan-2-yl)-3-(5-ethoxy-1-phenylpentylidene)-piperidine-1-carboxamide as an oil, which was used in the next step without purification. MS ESI+ve m/z 470 (M+1).

Step 2. N—((S)-3-cyclohexyl-1-(methylamino)propan-2-yl)-3-(5-ethoxy-1-phenylpentyl)piperidine-1-carboxamide To a solution of above mixture in methanol (5 mL), there was added 10% Pd—C (wet, excess). The resulting suspension was stirred under a H₂-balloon at rt overnight. The mixture was filtered through Celite and the solvent was removed under reduced pressure to give N—((S)-3-cyclohexyl-1-(methylamino)propan-2-yl)-3-(5-ethoxy-1-phenylpentyl)piperidine-1-carboxamide (194.4 mg, 84%) as an oil. MS ESI+ve m/z 472 (M+1).

Step 3. tert-butyl (S)-2-((S)-3-((R)-5-ethoxy-1-phenylpentyl)piperidine-1-carboxamido)-3-cyclohexylpropyl-methylcarbamate To the solution of N—((S)-3-cyclohexyl-1-(methylamino)propan-2-yl)-3-(5-ethoxy-1-phenylpentyl)piperidine-1-carboxamide in acetone (3 mL) was added 5% aqueous K₂CO₃ (2 mL), followed by excess (Boc)₂O. The resulting solution was stirred at rt for 10 min, acetone was removed, and the aqueous layer was extracted with ether (4×5 mL). The combined organic layers was washed with water (5 mL), brine (2 mL), dried over Na₂SO₄, and upon removal of solvent, the residue was purified by chiral HPLC to give tert-butyl (S)-2-((S)-3-((R)-5-ethoxy-1-phenylpentyl)piperidine-1-carboxamido)-3-cyclohexylpropyl-methylcarbamate (40.7 mg, 17%) as an oil. MS ESI+ve m/z 572 (M+1).

Step 4. (3S)—N—((S)-3-cyclohexyl-1-(methylamino)propan-2-yl)-3-((R)-5-ethoxy-1-phenylpentyl)-piperidine-1-carboxamide tert-butyl (S)-2-((S)-3-((R)-5-ethoxy-1-phenylpentyl)piperidine-1-carboxamido)-3-cyclohexylpropylmethylcarbamate (40.7 mg, 0.071 mmol) was stirred in HCl/dioxane (4 N, 4 mL) at rt until no starting material remained. The solvent was removed to give (3S)—N—((S)-3-cyclohexyl-1-(methylamino)propan-2-yl)-3-((R)-5-ethoxy-1-phenylpentyl)-piperidine-1-carboxamide (32.9 mg, 91%) as its HCl salt. ¹H NMR (CD₃OD) δ 0.9 (m, 3H), 1.0 (m, 2H), 1.11 (t, 3H), 1.2-2.0 (20H), 2.40 (m, 1H), 2.65 (m, 1H), 2.70 (s, 3H), 3.93 (m, 1H), 3.05 (m, 2H), 3.31 (m, 1H), 3.40 (q, 2H), 3.91 (d, 1H), 4.13 (m, 2H), 7.13 (2H), 7.19 (1H), 7.28 (2H). MS ESI+ve m/z 472 (M+1).

Example 36

(3S)—N—((S)-3-cyclohexyl-1-(methylamino)propan-2-yl)-3-((R)-5-methoxy-1-phenylpentyl)piperidine-1-carboxamide (I-14A)

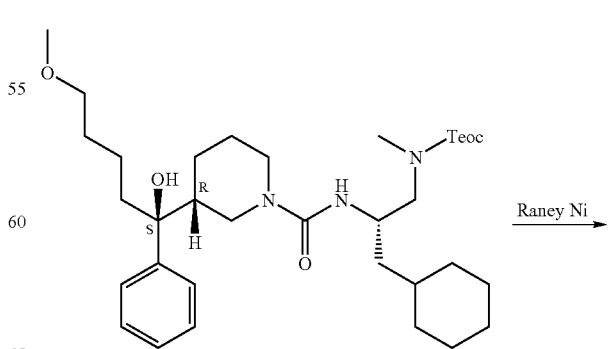

-continued

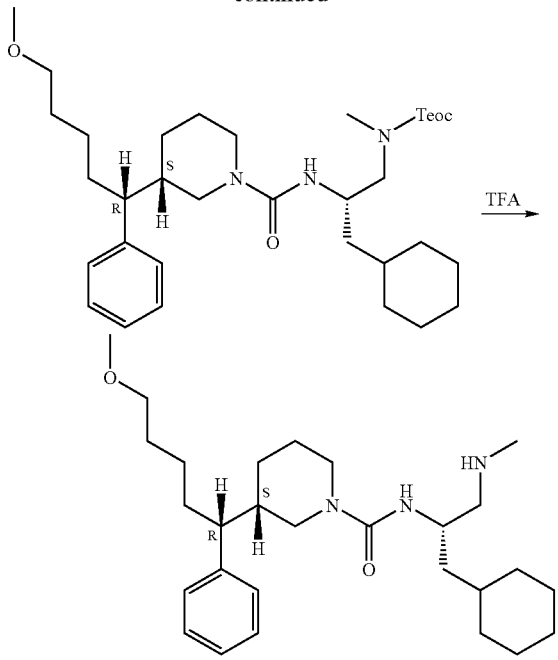

Step 1. 2-(trimethylsilyl)ethyl (S)-2-((S)-3-((R)-5-methoxy-1-phenylpentyl)piperidine-1-carboxamido)-3-cyclohexylpropylmethylcarbamate A 100-mL round bottom flask was charged with of 2-(trimethylsilyl)ethyl (S)-2-((R)-3-((S)-1-hydroxy-5-methoxy-1-phenylpentyl)piperidine-1-carboxamido)-3-cyclohexylpropyl-methylcarbamate (0.9806 g, 1.59 mol, 1.0 equiv), absolute ethanol (6 mL), and Raney nickel (2.15 g, ca. 20 equiv) (Aldrich Raney® 2800 nickel, slurry in water, washed with distilled water prior to use until the washings were neutral, then washed three times with absolute ethanol and stored under ethanol until needed.) The reaction mixture was heated to 100° C. for 3 h and then stirred at rt overnight. LC-MS showed about 60% conversion. The ethanolic solution was decanted from the catalyst. The catalyst was washed with absolute ethanol three times, the solvent being removed by decanting in each case. The organic solutions were combined and concentrated in vacuo. The residue was purified by reversed-phase HPLC (Phenomenex® Luna 5μ C18(2) 100 A, 250×21.20 mm, 5 micron, 70%→90% CH$_3$CN/H$_2$O, 0.1% CF$_3$COOH over 8 min and then 90% CH$_3$CN/H$_2$O, 0.1% CF$_3$COOH over 16 min, flow rate 25 mL/min) to give of 2-(trimethylsilyl)ethyl (S)-2-((S)-3-((R)-5-methoxy-1-phenylpentyl)-piperidine-1-carboxamido)-3-cyclohexylpropyl-methylcarbamate (0.5422 g, 57%). LC-MS (3 min) $t_R$=2.61 min, m/z 624 (M+Na$^+$), 602 (M+H$^+$). $^1$H NMR (400 MHz, CDCl$_3$) δ 8.28 (br s, 2H), 7.29-7.25 (m, 2H), 7.21-7.17 (m, 1H), 7.09-7.06 (m, 2H), 5.46 (m, 1H), 4.21-4.06 (m, 4H), 3.68-3.59 (m, 2H), 3.33-3.27 (m, 2H), 3.28 (s, 3H), 2.92 (s, 3H), 2.68-2.63 (m, 1H), 2.43-2.29 (m, 2H), 1.80-0.83 (m, 25H), 0.02 (s, 9H); $^{13}$C NMR (100 MHz, CDCl$_3$) δ 158.5, 158.0, 142.8, 128.4, 128.2, 126.2, 72.7, 64.3, 58.3, 52.8, 49.4, 49.1, 47.9, 45.1, 41.2, 41.1, 34.7, 34.3, 33.4, 33.3, 32.4, 29.2, 28.7, 26.4, 26.2, 26.1, 25.1, 24.1, 17.7, −1.5.

Unconsumed starting material (0.3570 g, 36%) was recovered as well. LC-MS (3 min) $t_R$=2.40 min, m/z 640 (M+Na$^+$), 618 (M+H$^+$). $^1$H NMR (400 MHz, CDCl$_3$) δ 7.35-7.20 (m, 5H), 5.31 (m, 1H), 5.11 (br s, 1H), 4.30 (dm, J=13.2 Hz, 1H), 4.18-4.04 (m, 3H), 3.69-3.58 (m, 2H), 3.31-3.25 (m, 2H), 3.26 (s, 3H), 2.97-2.91 (m, 1H), 2.90 (s, 3H), 2.63-2.49 (m, 2H), 2.03-0.84 (m, 26H), −0.01 (s, 9H); $^{13}$C NMR (100 MHz, CDCl$_3$) δ 158.3, 157.7, 144.2, 127.9, 126.3, 125.6, 77.8, 72.5, 63.8, 58.4, 52.6, 47.7, 46.1, 45.1, 44.9, 41.3, 39.0, 34.6, 34.4, 33.4, 33.3, 29.5, 26.4, 26.2, 26.1, 25.4, 25.2, 20.1, 17.6, −1.5.

Step 2. (3S)—N—((S)-3-cyclohexyl-1-(methylamino)-propan-2-yl)-3-((R)-5-methoxy-1-phenylpentyl)piperidine-1-carboxamide A 100 mL round bottom flask was charged with 2-(trimethylsilyl)ethyl (S)-2-((S)-3-((R)-5-methoxy-1-phenylpentyl)piperidine-1-carboxamido)-3-cyclohexylpropylmethylcarbamate (0.5420 g, 0.90 mmol) and trifluoroacetic acid (8 mL). The reaction mixture was stirred at rt for 2 h. The solvent was removed in vacuo and the residue was purified by reversed-phase HPLC (Phenomenex® Luna 5μ C18(2) 100 A, 250×21.20 mm, 5 micron, 10%→90% CH$_3$CN/H$_2$O, 0.1% CF$_3$COOH over 13 min, flow rate 25 mL/min) to give the trifluoroacetate salt of (3S)—N—((S)-3-cyclohexyl-1-(methylamino)propan-2-yl)-3-((R)-5-methoxy-1-phenylpentyl)piperidine-1-carboxamide, which was treated with 1 N NaOH (1.5 mL), extracted with CH$_2$Cl$_2$, dried over K$_2$CO$_3$, filtered and then concentrated in vacuo. The residue was dissolved into Et$_2$O and the solution was filtered through HPLC filter. The filtrate was concentrated in vacuo to give (3S)—N—((S)-3-cyclohexyl-1-(methylamino)propan-2-yl)-3-((R)-5-methoxy-1-phenylpentyl)piperidine-1-carboxamide (0.3342 g, 81%) as an oil. LC-MS (3 min) $t_R$=1.63 min, m/z 458 (M+H$^+$), 262. $^1$H NMR (400 MHz, CDCl$_3$) δ 7.29-7.25 (m, 2H), 7.21-7.16 (m, 1H), 7.09-7.07 (m, 2H), 4.60 (d, J=7.9 Hz, 1H), 4.18 (dm, J=12.9 Hz, 1H), 4.03-3.98 (m, 1H), 3.71 (dm, J=12.3 Hz, 1H), 3.26 (s, 3H), 3.28-3.22 (m, 2H), 2.70-2.61 (m, 3H), 2.44 (t, J=12.0 Hz, 1H), 2.43 (s, 3H), 2.36-2.30 (m, 1H), 1.86-0.86 (m, 25H); $^{13}$C NMR (100 MHz, CDCl$_3$) δ 157.6, 143.2, 128.4, 128.2, 126.1, 72.6, 58.4, 56.4, 49.5, 48.9, 47.5, 45.0, 41.3, 41.2, 36.6, 34.6, 33.7, 33.1, 32.6, 29.6, 29.1, 26.5, 26.32, 26.25, 25.2, 24.2.

A solution of (3S)—N—((S)-3-cyclohexyl-1-(methylamino)propan-2-yl)-3-((R)-5-methoxy-1-phenylpentyl)piperidine-1-carboxamide (0.3342 g, 0.73 mmol, 1.0 equiv), obtained as described above, in methanol was added to a solution of fumaric acid (0.0398 g, 0.34 mmol, 0.47 equiv) in methanol. The methanol solvent was then removed in vacuo. The residue was dried under high vacuum. The resulting white solid was washed twice with Et$_2$O to remove excess free base to afford 0.3194 g (90%) fumarate salt of (3S)—N—((S)-3-cyclohexyl-1-(methylamino)-propan-2-yl)-3-((R)-5-methoxy-1-phenylpentyl)piperidine-1-carboxamide. $^1$H NMR (400 MHz, CD$_3$OD) δ 7.18-7.14 (m, 2H), 7.08-7.04 (m, 1H), 7.02-6.99 (m, 2H), 6.53 (s, 1H), 4.07-4.01 (m, 2H), 3.78 (br d, J=12.9 Hz, 1H), 3.15 (t, J=6.6 Hz, 1H), 3.12 (s, 3H), 2.94-2.82 (m, 2H), 2.57 (s, 3H), 2.61-2.49 (m, 2H), 2.29-2.23 (m, 1H), 1.82-0.74 (m, 25H); $^{13}$C NMR (100 MHz, CD$_3$OD) δ 174.2, 159.5, 144.3, 137.1, 129.4, 129.3, 127.2, 73.6, 58.6, 55.1, 50.3, 50.1, 46.7, 45.8, 42.7, 41.0, 35.4, 34.8, 33.8, 33.4, 30.5, 30.0, 27.52, 27.47, 27.3, 26.1, 25.3.

Example 37

The following compounds of Formula I were prepared using procedures analogous to those described in Examples 35:

| Cpd. No. | Name |
|---|---|
| I-14A | N-((S)-3-cyclohexyl-1-(methylamino)propan-2-yl)-3-(5-methoxy-1-phenylpentyl)piperidine-1-carboxamide |
| I-15A | (3S)—N-((S)-3-cyclohexyl-1-(methylamino)propan-2-yl)-3-((R)-5-methoxy-1-phenylpentyl)piperidine-1-carboxamide |
| I-27A | N-((S)-3-cyclohexyl-1-(methylamino)propan-2-yl)-3-(5-ethoxy-1-phenylpentyl)piperidine-1-carboxamide |
| I-27A | (3S)—N-((S)-3-cyclohexyl-1-(methylamino)propan-2-yl)-3-((S)-5-ethoxy-1-phenylpentyl)piperidine-1-carboxamide |
| I-37A | (3S)—N-((S)-3-cyclohexyl-1-(methylamino)propan-2-yl)-3-((R)-1-(3-fluorophenyl)-5-methoxypentyl)piperidine-1-carboxamide |
| I-110A | N-((S)-3-cyclohexyl-1-(methylamino)propan-2-yl)-3-(5-methoxy-1-(thiophen-2-yl)pentyl)piperidine-1-carboxamide |
| I-148A | (3S)—N-((S)-3-cyclohexyl-1-(methylamino)propan-2-yl)-3-((R)-1-(2-fluoro-5-methylphenyl)-5-methoxypentyl)piperidine-1-carboxamide |
| I-342A | (SR)—N-((S)-1-cyclohexyl-3-(methylamino)propan-2-yl)-2-((RS)-5-methoxy-1-phenylpentyl)morpholine-4-carboxamide |

Example 38

The following compounds of Formula I were prepared using procedures analogous to those described in Examples 36:

| Cpd. No. | Name |
|---|---|
| I-24A | (3S)—N-((S)-3-cyclohexyl-1-(methylamino)propan-2-yl)-3-((S)-1-cyclohexyl-5-methoxypentyl)piperidine-1-carboxamide |

-continued

| Cpd. No. | Name |
|---|---|
| I-24B | (3S)—N-((S)-3-cyclohexyl-1-(methylamino)propan-2-yl)-3-((R)-1-cyclohexyl-5-methoxypentyl)piperidine-1-carboxamide |

Example 39

4-(3-((2-methoxyethoxy)(phenyl)methyl)piperidin-1-yl)-N—((S)-1-amino-3-cyclohexylpropan-2-yl)-1,2,5-thiadiazol-3-amine (I-60A)

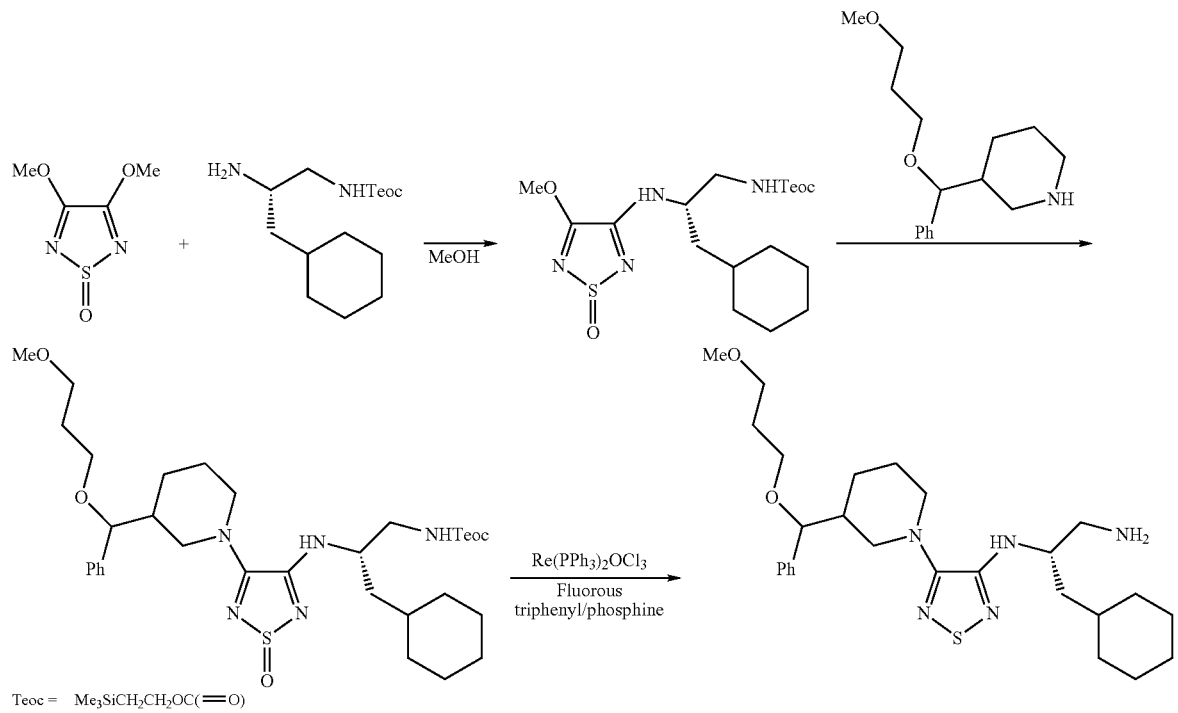

Step 1. 2-(trimethylsilyl)-ethyl (S)-2-(4-methoxy-1-oxo-1,2,5-thiadiazol-3-ylamino)-3-cyclohexylpropylcarbamate To a stirred, ice-cold solution of 3,4-dimethoxy-1,2,5-thiadiazole 1-oxide (219 mg, 1.35 mmol) (prepared as described in U.S. Pat. No. 4,374,248) in methanol (40 mL) was added a solution of 2-(trimethylsilyl)ethyl (S)-2-amino-3-cyclohexylpropylcarbamate (406 mg, 1.35 mmol) in methanol (5 mL). The ice bath was allowed to melt and the mixture was stirred at rt for 2 days. The mixture was evaporated to dryness under reduced pressure to afford a syrup (577 mg). The crude product was triturated with methanol (5 mL) to afford 2-(trimethylsilyl)-ethyl (S)-2-(4-methoxy-1-oxo-1,2,5-thiadiazol-3-ylamino)-3-cyclohexylpropylcarbamate as a sticky solid (547 mg, 94%) which was used without further purification. $^1$H NMR (CD$_3$OD) δ 0.03 (s, 9H), 0.8-1.9 (15H), 3.0-3.4 (3H), 4.08 (m, 2H), 4.15 (s, 3H).

Step 2. 2-(trimethylsilyl)ethyl (S)-2-(4-(3-((3-methoxypropoxy)(phenyl)methyl)piperidin-1-yl)-1-oxo-1,2,5-thiadiazol-3-ylamino)-3-cyclohexylpropylcarbamate To a solution of 2-(trimethylsilyl)ethyl (S)-2-(4-methoxy-1-oxo-1,2,5-thiadiazol-3-ylamino)-3-cyclohexylpropylcarbamate (547 mg, 1.27 mmol) in methanol (5 mL) was added a solution of 3-((2-methoxypropoxy)(phenyl)methyl)piperidine (360 mg, 1.39 mmol) in methanol (5 mL). The mixture was stirred at rt for 3 days and the solvent was removed under reduced pressure. The residue was taken up in EtOAc (100 mL), washed with 5% aq HCl (2×50 mL) and satd aq NaHCO$_3$ (50 mL), and dried over MgSO$_4$. Removal of the solvent afforded crude product as a yellow solid (465 mg, 51%).

A 100 mg portion of crude product was applied to a 2-g silica cartridge and eluted sequentially with 0, 10, 25, 50, 75, and 100% EtOAc in hexanes (15 mL of each) to afford six fractions. Fractions 3 and 4 were combined and evaporated to give 2-(trimethylsilyl)ethyl (S)-2-(4-(3-((3-methoxypropoxy)(phenyl)methyl)piperidin-1-yl)-1-oxo-1,2,5-thiadiazol-3-ylamino)-3-cyclohexylpropylcarbamate as an oil. $^1$H NMR (CDCl$_3$) δ 0.03 (s, 9H), 0.8-1.9 (22H), 2.8-3.5 (11H), 3.30 (s, 3H), 4.0-4.2 (5H), 7.2-7.4 (5H). MS ESI+ve m/z 662 (M+1).

Step 3. 4-(3-((2-methoxypropoxy)(phenyl)methyl)piperidin-1-yl)-N—((S)-1-amino-3-cyclohexylpropan-2-yl)-1,2,5-thiadiazol-3-amine A stirred solution of 2-(trimethylsilyl)ethyl (S)-2-(4-(3-((2-methoxypropoxy)(phenyl)-methyl)piperidin-1-yl)-1-oxo-1,2,5-thiadiazol-3-ylamino)-3-cyclohexylpropylcarbamate (51 mg, 0.077 mmol), bis[4-(1H,1H,2H,2H-perfluorooctyl)phenyl]phenylphosphine (101 mg, 0.078 mmol), Re(PPh$_3$)$_2$OCl$_3$ (7 mg, 0.008 mmol), and 1,2-dichloroethane (2 mL) was heated at 100° C. for 10 min in a microwave. The mixture was evaporated to dryness, taken up in methanol (1 mL) and applied to a 2-g fluorous SPE cartridge that had been prewetted with 20% water in methanol. The cartridge was eluted with 20% water in methanol (15 mL) and the eluate was evaporated to afford an oil (41 mg) which was applied to a 2 g silica SPE cartridge and eluted sequentially with 0, 10, 25, 50, 75, and 100% EtOAc in hexanes (15 mL of each) to afford six fractions. Fractions 3 and 4 were combined and evaporated to give 2-(trimethylsilyl)ethyl (S)-2-(4-(3-((2-methoxypropoxy)(phenyl)methyl)piperidin-1-yl)-1,2,5-thiadiazol-3-ylamino)-3-cyclohexylpropylcarbamate as an oil (18 mg). This material was dissolved in CH$_2$Cl$_2$ (0.5 mL) and CF$_3$CO$_2$H (0.5 mL) was added. The mixture was stirred at rt for 1.5 h and evaporated under reduced pressure to leave an oil (24 mg) which was submitted to preparative HPLC (C-18 column, 10 to 90% CH$_3$CN in H$_2$O containing 0.01% CF$_3$CO$_2$H over 10 min, 20 mL/min) to afford 4-(3-((2-methoxypropoxy)(phenyl)methyl)piperidin-1-yl)-N—((S)-1-amino-3-cyclohexylpropan-2-yl)-1,2,5-thiadiazol-3-amine as its trifluoroacetic acid salt (6.8 mg, 14%) as an oil. $^1$H NMR (CD$_3$OD) δ 0.8-1.9 (18H), 2.1 (2H), 2.5-3.5 (10H), 3.3 (s, 3H), 3.8-4.3 (3H), 7.2-7.4 (5H). MS ESI+ve m/z 502 (M+1).

Example 40

N—((S)-3-cyclohexyl-1-(methylamino)propan-2-yl)-3-(1-hydroxy-5-methoxy-1-phenylpentyl)cyclohexanecarboxamide (I-28A)

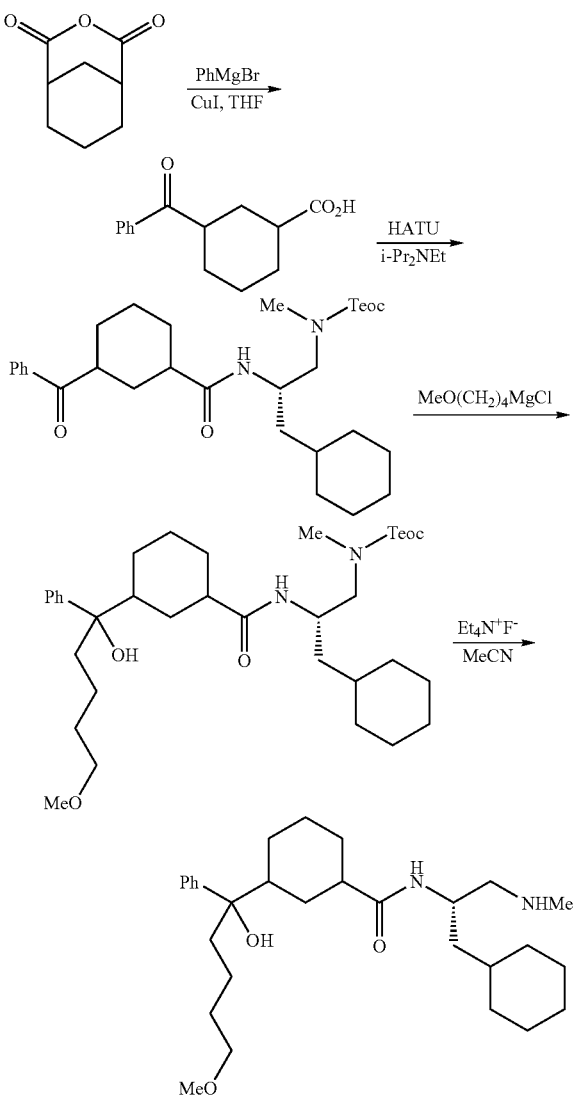

Step 1. cis-3-benzoylcyclohexane-1-carboxylic acid

A stirred solution of 1,3-cyclohexanedicarboxylic anhydride (67 mg, 0.43 mmol) (prepared from 1,3-cyclohexanedicarboxylic acid as described in patent application US 2004010005) and copper(I) iodide (8 mg, 0.04 mmol) in dry THF (3 mL) was cooled to −70° C. and phenmagnesium bromide in THF (0.4 mL of 1 M, 0.40 mmol) was added dropwise over 2 min. The mixture was stirred at −70° C. for 1 h and allowed to warm slowly to rt. After 2 h the mixture was poured into ether (75 mL) and extracted with satd aqueous NaHCO$_3$ (2×30 mL). The combined aqueous extracts were acidified to pH 1 by cautious addition of concentrated HCl and back extracted with ether (2×50 mL). These ether extracts were combined, dried over Na$_2$SO$_4$ and evaporated under reduced pressure to afford cis-3-benzoylcyclohexane-1-carboxylic acid (78 mg, 77%) as an oil which solidified on standing. $^1$H NMR (CDCl$_3$) δ 1.3-2.8 (9H), 3.32 (m, 1H), 7.45 (m, 2H), 7.55 (1=m, 1H), 7.92 (m, 2H). MS ESI+ve m/z 233 (M+1).

Step 2. 2-(Trimethylsilyl)ethyl (S)-2-(3-benzoylcyclohexane-carboxamido)-3-cyclohexylpropylmethylcarbamate To a stirred solution of cis-3-benzoylcyclohexane-1-carboxylic acid (78 mg, 0.34 mmol), 2-(trimethylsilyl)ethyl (S)-2-amino-3-cyclohexylpropylcarbamate (116 mg, 0.37 mmol) and diisopropylethylamine (0.13 mL, 0.70 mmol) in CH$_2$Cl$_2$ (2 mL) were added solid 2-(7-aza-1H-benzotriazole-1-yl)-1,1,3,3-tetramethyluronium hexafluorophosphate (HATU, 200 mg, 0.53 mmol) and DMF (0.5 mL). The mixture was stirred at rt for 3 h, diluted with ether (90 mL), washed with 5% aqueous HCl (25 mL), sat'd aqueous NaHCO$_3$ (25 mL), and brine (25 mL) and dried over Na$_2$SO$_4$. Removal of the solvent under reduced pressure left an oil (260 mg) which was applied to a 2-g silica SPE cartridge and eluted sequentially with 0, 10, 25, 50, 75, and 100% EtOAc in hexanes (15 mL of each) to give six fractions. Fractions 2-4 were pooled and evaporated to afford 2-(trimethylsilyl)ethyl (S)-2-(3-benzoylcyclohexane-carboxamido)-3-cyclohexylpropylmethylcarbamate (170 mg, 91%) as an oil. MS ESI+ve m/z 528 (M+1).

Step 3 2-(trimethylsilyl)ethyl (S)-2-(3-(1-hydroxy-5-methoxy-1-phenylpentyl)cyclohexanecarboxamido)-3-cyclohexylpropyl-methylcarbamate A stirred solution of 2-(trimethylsilyl)ethyl (S)-2-(3-benzoylcyclohexanecarboxamido)-3-cyclohexylpropylmethylcarbamate (111 mg, 0.21 mmol) in dry THF (2 mL) was cooled to −70° C. and methoxybutylmagnesium chloride in THF (0.5 mL of 2 M, 1.0 mmol) was added dropwise over 2 min. The cooling bath was allowed to expire and the mixture was stirred as it warmed to rt. After 2 h, the mixture was poured into sat'd aqueous NaHCO$_3$ (20 mL) and sat'd aqueous NH$_4$Cl (20 mL) was added. The mixture was extracted with EtOAc (2×50 mL). The combined organic extracts were washed with brine (15 mL), dried over Na$_2$SO$_4$ and evaporated under reduced pressure to leave crude 2-(trimethylsilyl)ethyl (S)-2-(3-(1-hydroxy-5-methoxy-1-phenylpentyl)cyclohexanecarboxamido)-3-cyclohexylpropyl-methylcarbamate as an oil (124 mg, 95%). MS ESI+ve m/z 617 (M+1).

Step 4. N—((S)-3-cyclohexyl-1-(methylamino)propan-2-yl)-3-(1-hydroxy-5-methoxy-1-phenylpentyl)-cyclohexane-carboxamide A solution of 2-(trimethylsilyl)ethyl (S)-2-(3-(1-hydroxy-5-methoxy-1-phenylpentyl)-cyclohexanecarboxamido)-3-cyclohexylpropylmethylcarbamate (62 mg, 0.10 mmol) and tetraethylammonium fluoride (80 mg, 0.50 mmol) in acetonitrile (2 mL) was heated at 100° C. for 10 min in a microwave. The mixture was directly submitted to preparative HPLC (C-18 column, 10 to 90% CH$_3$CN in H$_2$O containing 0.01% CF$_3$CO$_2$H over 10 min, 20 mL/min) to afford N—((S)-3-cyclohexyl-1-(methylamino)propan-2-yl)-3-(1-hydroxy-5-methoxy-1-phenylpentyl)-cyclohexane-carboxamide as its trifluoroacetic acid salt (28 mg, 48%) as an oil. $^1$H NMR (CD$_3$OD) δ 0.8-2.3 (29H), 2.62 (s, 3H), 2.8-3.1 (2H), 3.25 (s, 3H), 3.30 (m, 2H), 4.1-4.3 (1H), 7.15 (1H), 7.25 (2H), 7.35 (2H), 8.8 (1H). MS ESI+ve m/z 473 (M+1).

Example 41

3-((3-Methoxypropoxy)(phenyl)methyl)benzoic acid

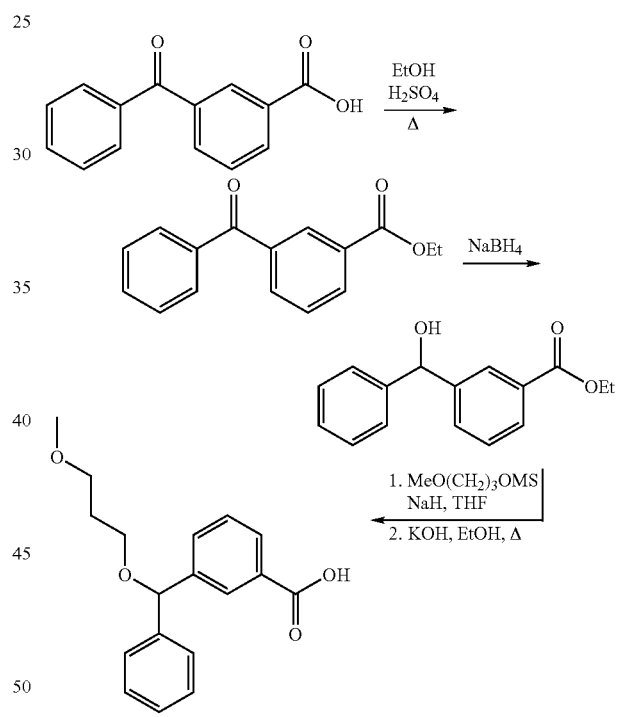

Step 1. Ethyl 3-benzoylbenzoate

A 100-mL round bottom flask was charged with of 3-benzoylbenzoic acid (2.20 g, 9.7 mmol), ethanol (40 mL), and sulfuric acid (3 mL). The reaction mixture was heated at 100° C. for 15 h, poured into ice water and extracted twice with Et$_2$O. The combined organic phase was washed with satd aq NaHCO$_3$ and dried over K$_2$CO$_3$. The crude ethyl 3-benzoylbenzoate was used in the next step without further purification. LC-MS (3 min) t$_R$=1.87 min in 3 min chromatography, m/z 255 (MH$^+$). $^1$H NMR (400 MHz, CDCl$_3$) δ 8.45-8.44 (m, 1H), 8.28-8.25 (m, 1H), 8.00-7.97 (m, 1H), 7.82-7.79 (m, 2H), 7.64-7.48 (m, 4H), 4.40 (q, J=7.1 Hz, 2H), 1.40 (t, J=7.2 Hz, 3H).

347

Step 2. Ethyl 3-(hydroxy(phenyl)methyl)benzoate

To a solution of ethyl 3-benzoylbenzoate (1.0197 g, 4.0 mmol, 1.0 equiv) in ethanol (10 mL) was added of $NaBH_4$ (0.32 g, 2.1 equiv). The reaction mixture was stirred at rt for 1.5 h, quenched with 10% aq $Na_2CO_3$, extracted three times with $CH_2Cl_2$, and dried over $Na_2SO_4$. The crude product was used in the next step without further purification. LC-MS (3 min) $t_R$=1.64 min, m/z 239 ($M^+$—OH). $^1H$ NMR (400 MHz, $CDCl_3$) δ 8.09 (m, 1H), 7.93-7.96 (m, 1H), 7.56-7.59 (m, 1H), 7.26-7.43 (m, 6H), 5.89 (s, 1H), 4.36 (q, J=7.2 Hz, 2H), 2.38 (br s, 1H), 1.40 (t, J=7.2 Hz, 3H).

Step 3. 3-((3-Methoxypropoxy)-(phenyl)methyl)benzoic acid

To a mixture of ethyl 3-(hydroxy)(phenyl)methyl)benzoate (1.0202 g, 3.98 mmol), 60% NaH in mineral oil (1.50 g, 37.5 mmol) and THF (20 mL) was added of 3-methoxypropyl methanesulfonate (3.00 g, 17.8 mmol). The reaction mixture was heated at 70° C. for 16 h, quenched with water, extracted twice with EtOAc, and dried over $Na_2SO_4$. After solvents were removed in vacuo, 4.20 g of KOH (4.20 g) and ethanol (25 mL) were added to 1.050 g of the residue. The reaction mixture was heated at 100° C. for 15 h and then the solvent ethanol was removed in vacuo. The residue was treated with water and extracted twice with $Et_2O$. The aqueous phase was treated with 2N aq HCl (60 mL), extracted twice with $CH_2Cl_2$ and dried over $Na_2SO_4$. Removal of the solvent afforded crude 3-((3-methoxypropoxy)(phenyl)methyl)benzoic acid (0.255 g), which was used in the next step without further purification. LC-MS $t_R$=1.63 min in 3 min chromatography, m/z 421, 211 ($M^+$—$OCH_2CH_2CH_2OCH_3$). $^1H$ NMR (400 MHz, $CDCl_3$) δ 8.10 (m, 1H), 7.99 (dm, J=7.6 Hz, 1H), 7.59 (dm, J=7.6 Hz, 1H), 7.42 (t, J=7.7 Hz, 1H), 7.36-7.23 (m, 5H), 5.40 (s, 1H), 3.57-3.50 (m, 4H), 3.33 (s, 3H), 1.93 (p, J=6.3 Hz, 2H); $^{13}C$ NMR (100 MHz, $CDCl_3$) δ 171.9, 143.2, 141.8, 132.2, 129.4, 129.2, 128.63, 128.60, 128.5, 127.7, 126.9, 83.2, 69.7, 66.1, 58.6, 30.0.

Example 42

The compounds listed below were prepared following procedures analogous to those described in Example 40 Step 2 followed by Step 4:

| Cpd. No. | Name |
|---|---|
| I-2A | 3-((3-methoxypropoxy)(phenyl)methyl)-N-((S)-1-amino-3-cyclohexylpropan-2-yl)benzamide |
| I-11A | 3-((3-methoxypropoxy)(phenyl)methyl)-N-((S)-3-cyclohexyl-1-(methylamino)propan-2-yl)benzamide |
| I-105A | N-((S)-3-cyclohexyl-1-(methylamino)propan-2-yl)-3-((pent-4-enyloxy)(phenyl)methyl)benzamide |
| I-107A | 3-((2-ethoxyethoxy)(phenyl)methyl)-N-((S)-3-cyclohexyl-1-(methylamino)propan-2-yl)benzamide |
| I-115A | 3-((3-ethoxypropoxy)(phenyl)methyl)-N-((S)-3-cyclohexyl-1-(methylamino)propan-2-yl)benzamide |

Example 43

(3R)—N—((S)-3-cyclohexyl-1-(methylamino)propan-2-yl)-3-(1-fluoro-5-methoxy-1-phenylpentyl)piperidine-1-carboxamide (I-38A)

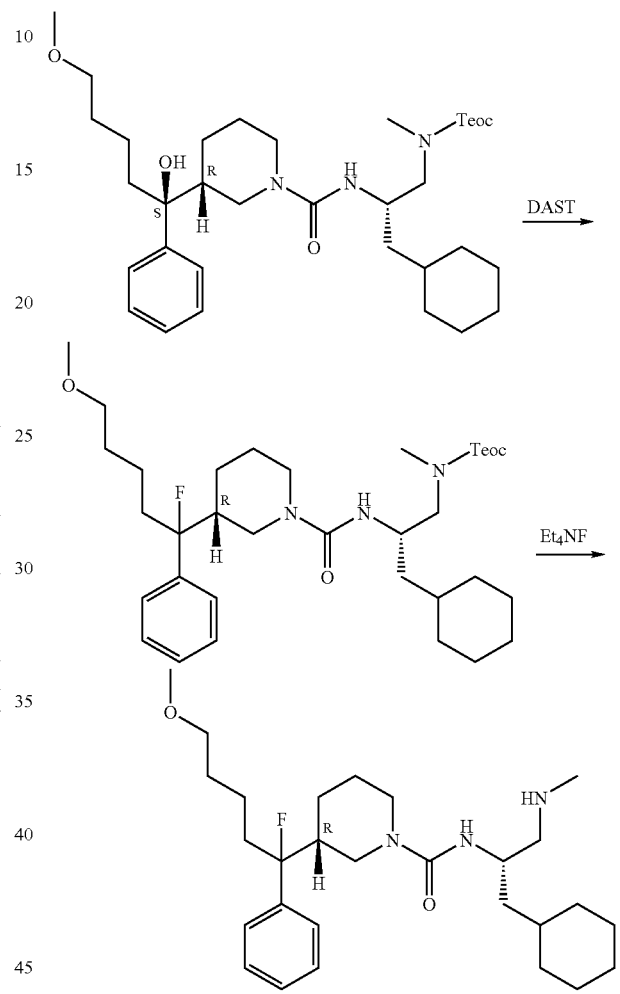

Step 1. 2-(trimethylsilyl)ethyl (S)-2-((R)-3-(1-fluoro-5-methoxy-1-phenylpentyl)piperidine-1-carboxamido)-3-cyclohexylpropylmethylcarbamate To a 50 mL round bottom flask were added 0.0597 g (0.097 mmol, 1.0 equiv) of 2-(trimethylsilyl)ethyl (S)-2-((R)-3-((S)-1-hydroxy-5-methoxy-1-phenylpentyl)piperidine-1-carboxamido)-3-cyclohexylpropylmethylcarbamate and 5 mL of $CH_2Cl_2$. The flask was evacuated and refilled with $N_2$. The mixture was cooled with a dry ice-acetone bath and 0.1860 g (ca. 10 equiv) of (diethylamino)sulfur trifluoride (DAST) was added. After 5 min, the dry ice-acetone bath was replaced by an ice-MeOH bath (−10° C.). After an additional hour, the reaction mixture was quenched with 10% $Na_2CO_3$ (10 mL), extracted three times with $Et_2O$, and dried over $Na_2SO_4$. The crude product was purified by reversed-phase HPLC (Phenomenex® Luna 5μ C18(2) 100 A, 250×21.20 mm, 5 micron, 70%→90% CH$_3$CN/H$_2$O, 0.1% CF$_3$COOH over 8 min and then 90% CH$_3$CN/H$_2$O, 0.1% CF$_3$COOH over 15 min, flow rate 25 mL/min) to give 0.0478 g (80%) of 2-(trimethylsilyl) ethyl (S)-2-((R)-3-(1-fluoro-5-methoxy-1-phenylpentyl)-piperidine-1-carboxamido)-3-cyclohexylpropylmethylcarbamate. LC-MS t$_R$=2.59 min in 3 min chromatography, m/z 642 (M+Na$^+$), 620 (M+H$^+$). $^1$H NMR (400 MHz, CDCl$_3$) δ 8.83 (br s, 1H), 7.36-7.19 (m, 5H), 5.42 (br s, 0.69H), 5.00 (br s, 0.31H), 4.39-4.36 (m, 1H), 4.14-4.03 (m, 3H), 3.72-3.46 (m, 2H), 3.28-3.24 (m, 5H), 2.94-2.86 (m, 4H), 2.62-2.40 (m, 2H), 2.11-0.81 (m, 25H), 0.03 and −0.01 (s, 9H); $^{13}$C NMR (100 MHz, CDCl$_3$) δ 158.4, 157.8, 141.3, 141.0, 128.2, 128.1, 127.3, 126.9, 124.7, 124.6, 101.3, 99.5, 72.52, 72.46, 63.9, 63.8, 58.4, 58.3, 52.7, 52.6, 47.9, 47.6, 45.0, 44.82, 44.77, 44.6, 41.3, 41.1, 37.1, 36.9, 34.7, 34.6, 34.4, 34.3, 33.5, 33.4, 33.2, 29.6, 29.5, 26.4, 26.2, 26.13, 26.09, 25.1, 25.0, 24.6, 19.8, 17.7, −1.6.

Step 2. (3R)—N—((S)-3-cyclohexyl-1-(methylamino)propan-2-yl)-3-(1-fluoro-5-methoxy-1-phenylpentyl)piperidine-1-carboxamide A 50 mL round bottom flask was charged with 2-(trimethylsilyl)ethyl (S)-2-((R)-3-(1-fluoro-5-methoxy-1-phenylpentyl)piperidine-1-carboxamido)-3-cyclohexylpropylmethyl-carbamate (0.0453 g, 0.073 mmol), 0.3786 g of tetraethylammonium fluoride, and 5 mL of acetonitrile. The reaction mixture was stirred at 80° C. for 16 h. The solvent was removed in vacuo and then purified by reversed-phase HPLC (Phenomenex® Luna 5μ C18(2) 100 A, 250×21.20 mm, 5 micron, 10%→90% CH$_3$CN/H$_2$O, 0.1% CF$_3$COOH over 13 min, flow rate 25 mL/min) to give 0.0325 g (75%) of trifluoroacetate salt of (3R)—N—((S)-3-cyclohexyl-1-(methylamino)propan-2-yl)-3-(1-fluoro-5-methoxy-1-phenylpentyl)piperidine-1-carboxamide. LC-MS t$_R$=1.64 min in 3 min chromatography, m/z 476 (MH$^+$), 280, 260. $^1$H NMR (400 MHz, CDCl$_3$) δ 7.29-7.15 (m, 5H), 4.23 (dm, J=13.2 Hz, 1H), 4.05-3.92 (m, 1H), 3.86 and 3.71 (dm, J=13.2 Hz, 1H), 3.20-3.15 (m, 1H), 3.13 (s, 3H), 3.00-2.73 (m, 2H), 2.59 and 2.55 (s, 3H), 2.51-2.39 (m, 2H), 2.08-0.74 (m, 25H). Chiral HPLC indicated a mixture of two isomers (72:28).

Example 44 tert (3R)—N—((S)-1-Amino-3-phenylpropan-2-yl)-3-((S)-1-hydroxy-5-methoxy-1-phenylpentyl)piperidine-1-carboxamide (I-12A)

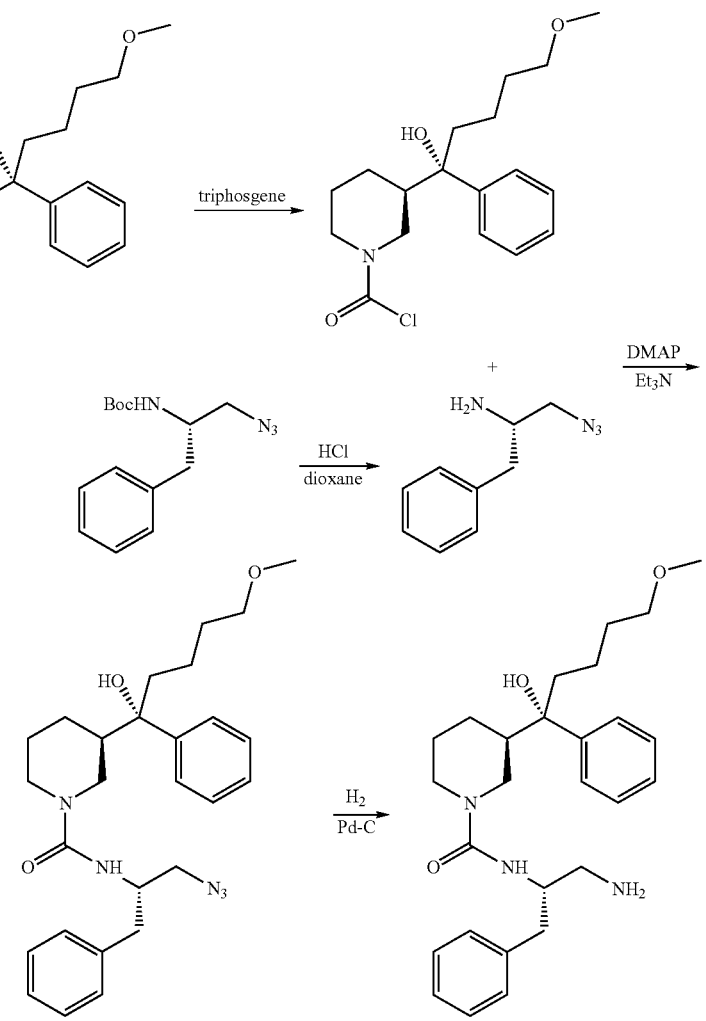

Step 1. (S)-1-azido-3-phenylpropan-2-amine

A solution of tert-butyl (S)-3-azido-1-phenylpropan-2-yl-carbamate (1.0045 g, 3.6 mmol) was dissolved in 4 M HCl in dioxane (20 mL, 80 mmol) and stirred at rt for 2 h. The solvent was stripped. The residue was taken up in $CH_2Cl_2$ (50 mL) and 1 N aq NaOH (10 mL), extracted with $CH_2Cl_2$ (3×10 mL), washed with brine (3×5 mL), dried ($Na_2SO_4$), decanted, and stripped to afford (S)-1-azido-3-phenylpropan-2-amine (812.9 mg, quant, 80% purity) as a clear oil. MS ESI+ve m/z 177 (M+1).

Step 2. (R)-3-((S)-1-hydroxy-5-methoxy-1-phenylpentyl)piperidine-1-carbonyl chloride A solution of (S)-5-methoxy-1-phenyl-1-((R)-piperidin-3-yl)pentan-1-ol (455.6 mg, 1.8 mmol) and triethylamine (1.50 mL, 10.7 mmol) in $CH_2Cl_2$ (100 mL) was cooled to 0° C. A solution of triphosgene (278.6 mg, 1.0 mmol) in $CH_2Cl_2$ (10 mL) was added with fast dropwise addition. The solution was stirred for 30 min at 0° C. and then for 2 h at rt. The reaction mixture was cooled to 0° C., washed with ice-cold satd aq $NaHCO_3$ (3×10 mL) and ice-cold brine (3×10 mL), dried ($Na_2SO_4$), decanted, and stripped to afford (R)-3-((S)-1-hydroxy-5-methoxy-1-phenylpentyl)piperidine-1-carbonyl chloride (540.8 mg, 99%) as a yellow oil. This material was carried on directly to the next step.

Step 3. (3R)—N—((S)-3-azido-1-phenylpropan-2-yl)-3-((S)-1-hydroxy-5-methoxy-1-phenylpentyl)piperidine-1-carboxamide A solution of (R)-3-((S)-1-hydroxy-5-methoxy-1-phenylpentyl)piperidine-1-carbonyl chloride (135 mg, 0.4 mmol) in $CH_2Cl_2$ (10 mL) was added to a solution of (S)-1-azido-3-phenylpropan-2-amine (156.3 mg, 0.73 mmol), triethylamine (0.6 mL, 4.3 mmol), and DMAP (16.6 mg, 0.13 mmol) in $CH_2Cl_2$. After stirring for 12 h, the reaction was taken up in $CH_2Cl_2$ (50 mL), washed with satd aq NaHCO3 (3×10 mL), and brine (3×10 mL), dried ($Na_2SO_4$), decanted, and stripped to afford (3R)—N—((S)-3-azido-1-phenylpropan-2-yl)-3-((S)-1-hydroxy-5-methoxy-1-phenylpentyl)piperidine-1-carboxamide (210.7 mg) as a brown residue (theoretical yield: 192.0 mg). MS ESI+ve m/z 502 (M+Na).

Step 4. (3R)—N—((S)-1-amino-3-phenylpropan-2-yl)-3-((S)-1-hydroxy-5-methoxy-1-phenylpentyl)piperidine-1-carboxamide Crude (3R)—N—((S)-3-azido-1-phenylpropan-2-yl)-3-((S)-1-hydroxy-5-methoxy-1-phenylpentyl)piperidine-1-carboxamide (210.7 mg, 91% purity, 0.4 mmol) from the previous step was dissolved in MeOH (10 mL) and was added to 0.2 g of Pd/C previously wetted with a drop of $H_2O$. After 3 vacuum/purge cycles using 12 torr vacuum and 14 psi $H_2$, the reaction was stirred under an atmosphere of $H_2$ at 14 psi for 30 minutes. The crude mixture was filtered through a plug of Celite and the solvent was removed. The resulting oil was dissolved in a minimal volume of 1:1 acetonitrile:$H_2O$ then separated by prep HPLC on a C-18 column using a gradient of 0.05% TFA in $H_2O$ and acetonitrile. Appropriate fractions were combined, made slightly basic with 1 N NaOH, and the solvent was removed at 50° C. and 150 torr. The residue was taken up in $CH_2Cl_2$ (50 mL) and 1 N NaOH (10 mL). The organic layer was dried ($Na_2SO_4$), decanted and stripped to afford (3R)—N—((S)-1-amino-3-phenylpropan-2-yl)-3-((S)-1-hydroxy-5-methoxy-1-phenylpentyl)piperidine-1-carboxamide (61.5 mg, 34% overall yield from (R)-3-((S)-1-hydroxy-5-methoxy-1-phenylpentyl)piperidine-1-carbonyl chloride) as a clear colorless film. MS ESI+ve m/z 454 (M+1).

Example 45

The following compounds of Formula I were prepared following procedures analogous to those described in Example 44:

| Cpd. No. | Name |
|---|---|
| I-7A | (3R)—N-(1-amino-3-cyclopentylpropan-2-yl)-3-((S)-1-hydroxy-5-methoxy-1-phenylpentyl)piperidine-1-carboxamide |
| I-9A | (3R)—N-((R)-3-tert-butoxy-1-aminopropan-2-yl)-3-((S)-1-hydroxy-5-methoxy-1-phenylpentyl)piperidine-1-carboxamide |
| I-29A | N-(1-amino-4-(trifluoromethyl)pentan-2-yl)-3-(1-hydroxy-5-methoxy-1-phenylpentyl)piperidine-1-carboxamide |

Example 46

(2S)-1-(N-(aminocarbonylmethyl)-N-(2-(trimethylsilyl)ethoxycarbonyl)amino)-3-cyclohexylpropyl-2-amine

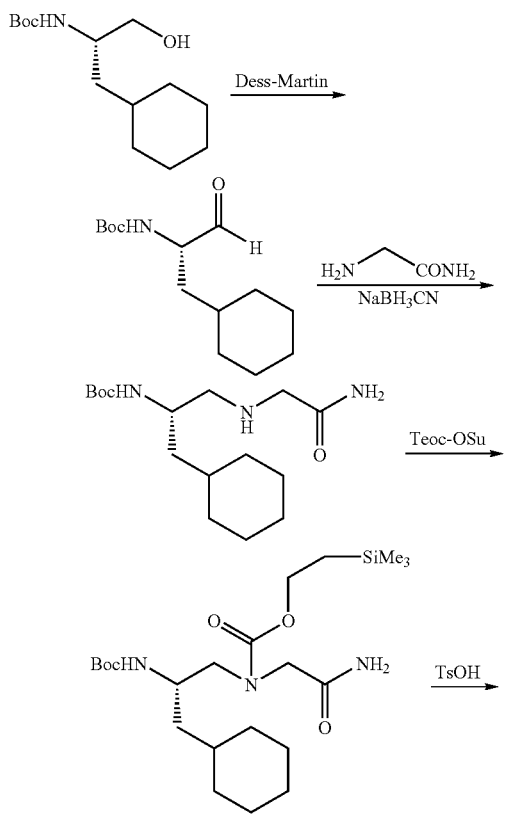

-continued

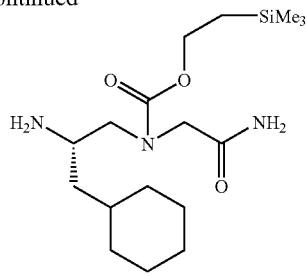

Step 1. (S)-tert-Butyl 1-cyclohexyl-3-oxopropan-2-ylcarbamate

To a stirred solution of tert-butyl (S)-3-cyclohexyl-1-hydroxypropan-2-ylcarbamate (0.23 g, 0.9 mmol) in 1,2-dichloroethane (5 mL), was added Dess-Martin periodinane (0.49 g, 1.34 mmol). The resulting mixture was heated in a CEM microwave synthesizer at 70° C. for 3 min, diluted with ether (100 mL), and washed with 1 N NaOH (2×10 mL). The ether layer was dried over $Na_2SO_4$, and the solvent was removed in vacuo to give (S)-tert-butyl 1-cyclohexyl-3-oxopropan-2-ylcarbamate as an oil. MS ESI+ve m/z 256 (M+1).

Step 2. tert-butyl (S)-1-(carbamoylmethylamino)-3-cyclohexyl-propan-2-ylcarbamate To a solution of 2-aminoacetamide hydrochloride (0.13 g, 1.13 mmol) in MeOH (1 mL) was added KOH (18 mg). When the solid had completely dissolved, the tert-butyl (S)-2-cyclohexyl-1-formylethylcarbamate from Step 1 was added in one portion, and the resulting suspension was stirred for 15 minutes. A solution of sodium cyanoborohydride (0.18 g, 2.7 mmol) in MeOH (1 mL) was added dropwise. The resulting solution was stirred at rt until no aldehyde remained (~40 min). The solvent was removed under vacuum and the residue was distributed between ether and water (10 mL/10 mL). The water layer was extracted with ether (2×5 mL). The combined ether layers were dried, and solvent was removed under vacuum to give tert-butyl (S)-1-(carbamoylmethylamino)-3-cyclohexyl-propan-2-ylcarbamate as an oil, which was used for the next step without purification. MS ESI+ve m/z 314 (M+1).

Step 3. $N^1$-(tert-butoxycarbonyl)-$N^2$-(2-(trimethylsilyl)ethoxycarbonyl)-$N^2$-(aminocarbonylmethyl)-(S)-3-cyclohexylpropane-1,2-diamine To a solution of tert-butyl (S)-1-(carbamoylmethylamino)-3-cyclohexylpropan-2-ylcarbamate from Step 2 in acetone (4 mL) and water (2 mL), was added $NaHCO_3$ (0.23 g, 2.7 mmol) followed by 1-[2-trimethylsilyl)ethoxycarbonyloxy]pyrrolidin-2,5-dione (excess). The mixture was stirred at rt for 2 h, acetone was removed in vacuo, and the aqueous layer was extracted with $CH_2Cl_2$. After removing solvent under vacuum, the residue was purified by flash chromatography on a silica gel column to give $N^1$-(tert-butoxycarbonyl)-$N^2$-(2-(trimethylsilyl)ethoxycarbonyl)-$N^2$-(aminocarbonylmethyl)-(S)-3-cyclohexylpropane-1,2-diamine (183.2 mg, 44% in three steps). MS ESI+ve m/z 480 (M+Na).

Step 4. (2S)-1-(N-(aminocarbonylmethyl)-N-(2-(trimethylsilyl)ethoxycarbonyl)amino)-3-cyclohexylpropyl-2-amine To a solution of above $N^1$-(tert-butoxycarbonyl)-$N^2$-(2-(trimethylsilyl)ethoxycarbonyl)-$N^2$-(aminocarbonylmethyl)-(S)-3-cyclohexylpropane-1,2-diamine in ether (2 mL) was added $TsOH.H_2O$ (36.9 mg, 0.22 mmol) in ethanol (1 mL). The resulting solution was put on a rotatory vaporator, ether was removed in vacuum at rt, the bath temperature was raised to 60-65° C., and the mixture was heated in vacuo for 30 min to give (2S)-1-(N-(aminocarbonylmethyl)-N-(2-(trimethylsilyl)ethoxycarbonyl)amino)-3-cyclohexylpropyl-2-amine as a p-toluenesulfonic acid salt. MS ESI+ve m/z 358 (M+1).

Example 47

(S)-1-(3-chlorophenyl)-5,5-difluoro-1-((R)-piperidin-3-yl)hexan-1-ol

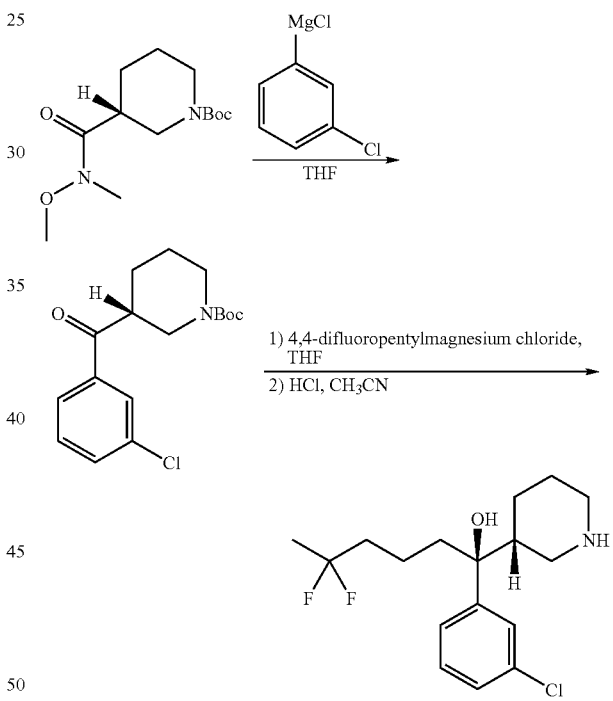

Step 1. (3R)-1-(tert-butoxycarbonyl)-3-(3-chlorobenzoyl)piperidine

At −20° C., 3-chlorophenyl magnesium chloride (11 mL, 5.5 mmol, 0.5M THF solution) was added dropwise to a solution of (R)-tert-butyl 3-(N-methoxy-N-methylcarbamoyl)piperidine-1-carboxylate (500 mg, 1.84 mmol) in THF (5 mL). The solution was stirred for 2 h and allowed to warm to rt. The reaction was quenched with satd ammonium chloride solution. The aqueous layer was extracted with ether (3×). The combined organic layers were washed with brine, dried over $MgSO_4$ and filtered. Evaporation of solvent provided (3R)-1-(tert-butoxycarbonyl)-3-(3-chlorobenzoyl)piperidine (0.79 g) as an oil that was used without purification.

Step 2. 4,4-difluoropentylmagnesium chloride

To a solution of 5-chloropentan-2-one (19.0 mL, 166 mmol) in CH$_2$Cl$_2$ (50 mL) was added Deoxo-Fluor™ (bis-(2-methoxyethyl)aminosulfur trifluoride, 41.6 mL, 226 mmol) in CH$_2$Cl$_2$ (30 mL) followed by ethanol (1.9 mL, 33 mmol). The mixture was stirred at rt overnight. Reaction was poured slowly into satd NaHCO3 solution. The aqueous layer was extracted with CH$_2$Cl$_2$ (3×). The combined organic layers were washed with brine, dried over Na$_2$SO$_4$, and filtered. After evaporation of solvent, the crude product was distilled under reduced pressure to afford 1-chloro-4,4-difluoropentane as a clear liquid (7 g). $^1$H NMR (400 MHz, CDCl$_3$) δ 3.59 (t, 2H, J=5 Hz), 2.02-1.97 (m, 4H), 1.62 (t, 3H, J=18 Hz).

To Rieke Mg® (1 M suspension of finely divided Mg in THF, 7 mL, 7 mmol) at reflux, 1-chloro-4,4-difluoropentane (1.7 mL, 6.9 mmol) was added dropwise. The mixture was maintained at reflux for 2 h and used in Step 3.

Step 3. (S)-1-(3-chlorophenyl)-5,5-difluoro-1-((R)-piperidin-3-yl)hexan-1-ol

A solution of (3R)-1-(tert-butoxycarbonyl)-3-(3-chlorobenzoyl)piperidine (100 mg, 0.33 mmol) in THF (2 mL) was cooled to −20° C. and 4,4-difluoropentylmagnesium chloride (~0.79M in THF, 5.0 mL, 4.0 mmol) was added. The mixture was stirred for 2 h and quenched with sat'd NH$_4$Cl. The aqueous layer was extracted with ether. The combined organic layers were washed with brine, dried over sodium sulfate and filtered. The solvent was removed on a rotoevaporator. The crude product was purified using flash chromatography (hexanes/EtOAc). N-Boc-(S)-1-(3-chlorophenyl)-5,5-difluoro-1-((R)-piperidin-3-yl)hexan-1-ol was isolated as an oil (70 mg) MS m/z 454 (M+Na).

N-Boc-(S)-1-(3-chlorophenyl)-5,5-difluoro-1-((R)-piperidin-3-yl)hexan-1-ol (70 mg, 0.16 mmol) was dissolved in acetonitrile (16 mL) and 2M aq HCl (16 mL) and allowed to stir at rt overnight. The solvent was removed under high vacuum. The crude material was redissolved in CH$_2$Cl$_2$ and washed with satd NaHCO$_3$ 2×. The aqueous layer was extracted with CH$_2$Cl$_2$ 3×. The combined organic layers were washed with brine and dried over sodium sulfate. After removing solvent under vacuum (S)-1-(3-chlorophenyl)-5,5-difluoro-1-((R)-piperidin-3-yl)hexan-1-ol was isolated as an oil (28 mg) MS m/z 332 (M+H$^+$).

Example 48

(S)-1-(benzo[b]thiophen-2-yl)-5-methoxy-1-((R)-piperidin-3-yl)pentan-1-ol

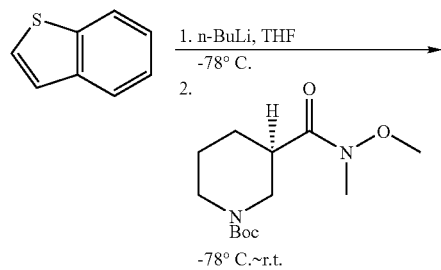

Step 1. (R)-tert-butyl 3-(benzo[b]thiophene-2-carbonyl)piperidine-1-carboxylate

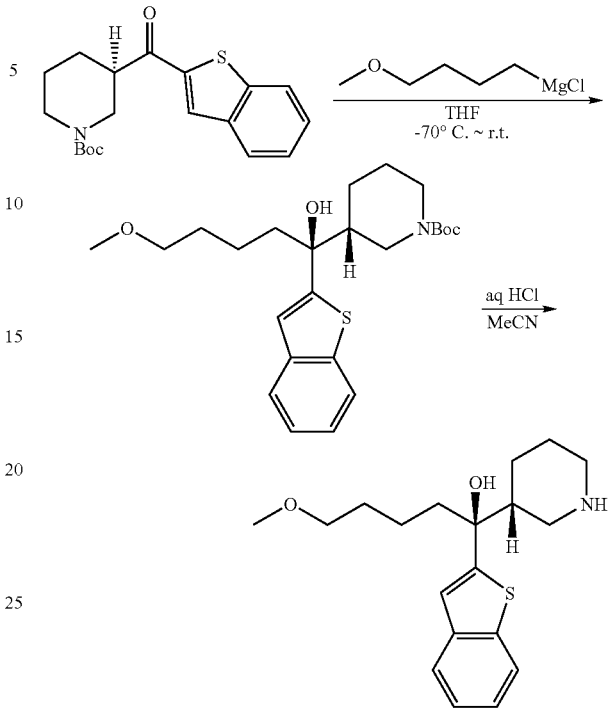

A solution of benzothiophene (117 µL, 1 mmol) in dry THF (4 mL) was cooled to −70° C. A solution of 1.6M n-BuLi in hexanes (950 µL, 1.5 equiv) was added dropwise. After 10 min, a solution of Weinreb amide (282 mg, 1 equiv) in dry THF (2.5 mL) was added dropwise. The mixture was allowed to warm to rt and stirred overnight. Sat'd aq NH$_4$Cl (30 mL) was added and the mixture was extracted with ether (2×50 mL). The combined ether layers were washed with brine (20 mL) and dried over Na$_2$SO$_4$. After concentration, the crude product was purified by chromatography on a 12-g silica cartridge eluted with a gradient from 0 to 15% EtOAc in hexanes to afford (R)-tert-butyl 3-(benzo[b]thiophene-2-carbonyl)piperidine-1-carboxylate (292 mg, 85%).

Step 2. (R)-tert-butyl 3-((S)-1-(benzo[b]thiophen-2-yl)-1-hydroxy-5-methoxypentyl)piperidine-1-carboxylate A solution of (R)-tert-butyl 3-(benzo[b]thiophene-2-carbonyl)piperidine-1-carboxylate (146 mg, 0.423 mmol) in dry THF (5 mL) was cooled to −70° C. A solution of 1.34 M 4-methoxybutylmagnesium chloride in THF (630 µL, 2 equiv) was added slowly. After 10 min, the reaction mixture was allowed to warm up to rt slowly and stirred for another 2 h. Sat'd aq NH$_4$Cl (20 mL) was added and the mixture was extracted with ether (2×40 mL). The combined ether layers were washed with brine (20 mL) and dried over Na$_2$SO$_4$. After concentration, the crude product was purified by chromatography on a 12-g silica cartridge eluted with a gradient from 0 to 35% EtOAc in hexanes to afford (R)-tert-butyl 3-((S)-1-(benzo[b]thiophen-2-yl)-1-hydroxy-5-methoxypentyl)piperidine-1-carboxylate (160.7 mg, 88%).

Step 3. (S)-1-(benzo[b]thiophen-2-yl)-5-methoxy-1-((R)-piperidin-3-yl)pentan-1-ol hydrochloride (R)-tert-butyl 3-((S)-1-(benzo[b]thiophen-2-yl)-1-hydroxy-5-methoxypentyl)piperidine-1-carboxylate (160 mg, 0.37 mmol) was dissolved in 1:1 2 N aq HCl solution/acetonitrile (50 mL). The mixture was stirred overnight at rt and neutralized with 5% aq NaOH. The acetonitrile was removed by evaporation. The aqueous residue was extracted by CH₂Cl₂ (2×40 mL). The combined organic layers were concentrated to afford (S)-1-(benzo[b]thiophen-2-yl)-5-methoxy-1-((R)-piperidin-3-yl)pentan-1-ol (102 mg, 83%) which was used without purification.

Example 49

The following piperidines were prepared using procedures analogous to those described in Example 48 using the heterocycle and base indicated below in Step 1.
(S)-1-(2,2-difluorobenzo[d][1,3]dioxol-4-yl)-5-methoxy-1-((R)-piperidin-3-yl)pentan-1-ol using 2,2-difluorobenzo[d][1,3]dioxole and s-BuLi in Step 1.
(S)-5-methoxy-1-(1-methyl-1H-imidazol-2-yl)-1-((R)-piperidin-3-yl)pentan-1-ol using 1-methylimidazole and n-BuLi in Step 1.
1-(5-chloro-1-methyl-1H-imidazol-2-yl)-5-methoxy-1-(piperidin-3-yl)pentan-1-ol using 5-chloro-1-methyl-1H-imidazole and n-BuLi in Step 1.
(S)-5-methoxy-1-((R)-piperidin-3-yl)-1-(thiazol-2-yl)pentan-1-ol using thiazole and n-BuLi in Step 1.
(S)-5-methoxy-1-(5-methylthiazol-2-yl)-1-((R)-piperidin-3-yl)pentan-1-ol using 5-methylthiazole and n-BuLi in Step 1.
4-chloro-2-((R)-(3-methoxypropoxy)((R)-piperidin-3-yl)methyl)pyridine using 4-chloropyridine and n-BuLi/Me₂N(CH₂)₂OLi in Step 1.

Example 50

Halodiphenyl Ethers from Halophenols and Benzeneboronic Acids 1-(3-Fluorophenoxy)-2-bromobenzene

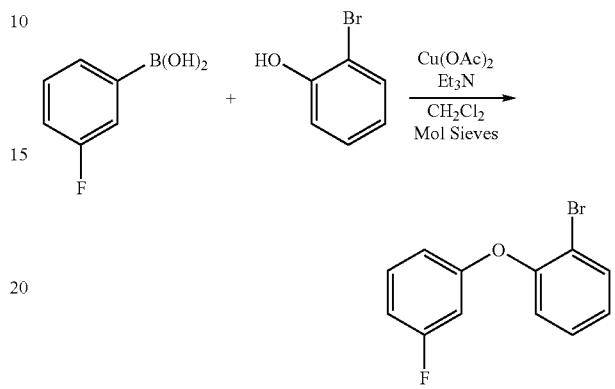

To a stirred solution of 3-fluorophenylboronic acid (2.10 g, 15 mmol), 2-bromophenol (1.77 g, 10 mmol) and Cu(OAc)₂ (0.93 g, 5 mmol) in anhydrous CH₂Cl₂ (25 mL) was added activated 4 Å molecular sieves (~0.1 g), followed by anhydrous Et₃N (3.5 mL, 25 mmol). The resulting dark green solution was stirred at rt for 48 h. The mixture was evaporated under reduced pressure and the residue was washed several times with Et₂O (~150 mL). The Et₂O solution was washed with sat'd aq NH₄Cl, and 1 N aq HCl. The organic layer was evaporated and the crude product was purified by flash column chromatography to give 1-(3-fluorophenoxy)-2-bromobenzene (1.28 g, 48%) as clear oil.

Example 51

The following halodiphenyl ethers were prepared following procedures analogous to those described in Example 50.

| Halodiphenyl ether | Phenol | Boronic Acid |
| --- | --- | --- |
| 1-(2-ethylphenoxy)-2-bromobenzene | 2-bromophenol | 2-ethylphenylboronic acid |
| 1-(4-fluorophenoxy)-2-bromobenzene | 2-bromophenol | 4-fluorophenylboronic acid |
| 1-(2-bromophenoxy)-3-methylbenzene | 2-bromophenol | 3-methylphenylboronic acid |
| 2-(o-tolyloxy)-1-bromo-3-methylbenzene | 2-bromo-6-methylphenol | 2-methylphenylboronic acid |
| 2-(o-tolyloxy)-1-bromo-3,5-difluorobenzene | 2-bromo-4,6-difluorophenol | 2-methylphenylboronic acid |
| 1-(4-fluoro-2-methylphenoxy)-2-bromobenzene | 2-bromophenol | 4-fluoro-2-methylphenylboronic acid |
| 1-(5-fluoro-2-methylphenoxy)-2-bromobenzene | 2-bromophenol | 5-fluoro-2-methylphenylboronic acid |
| 1-chloro-3-fluoro-2-phenoxybenzene | 2-chloro-6-fluorophenol | phenylboronic acid |
| 2-(p-tolyloxy)-1-chloro-3-fluorobenzene | 2-chloro-6-fluorophenol | 4-methylphenylboronic acid |
| 2-bromo-4-fluoro-1-(4-fluorophenoxy)benzene | 2-bromo-6-fluorophenol | 2-methylphenylboronic acid |
| 2-bromo-4-fluoro-1-phenoxybenzene | 2-bromo-4-fluorophenol | phenylboronic acid |

-continued

| Halodiphenyl ether | Phenol | Boronic Acid |
|---|---|---|
| 2-bromo-4-fluoro-1-(4-fluorophenoxy)benzene | 2-bromo-4-fluorophenol | 4-fluorophenylboronic acid |

Example 52

1-(o-tolyloxy)-2-iodobenzene

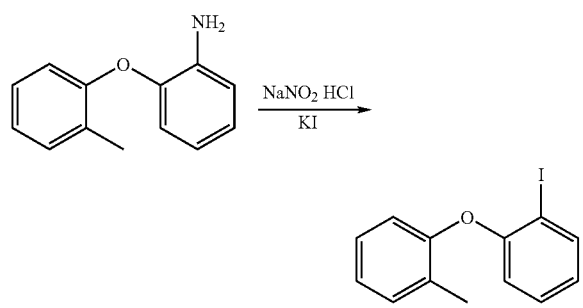

To a solution of 2-(o-tolyloxy)aniline (40 g, 0.2 mol) in 1N aq HCl (400 mL, 0.4 mol, 2 equiv) cooled to 0° C. was added dropwise a solution of NaNO$_2$ (18 g, 0.26 mol, 1.3 equiv) in water (520 mL). The mixture was stirred for 1 h at 0° C. and a solution of Ki (83 g, 0.5 mol, 2.5 equiv) in water (500 mL) was added dropwise with vigorous stirring. After 0.5 h the mixture was warmed to 90-100° C. for 1 h, cooled to rt and washed with sat'd NaHSO$_3$ until the aqueous layer become clear. The mixture was extracted with EtOAc (3×200 mL) and the combined organic layers were washed with aq Na$_2$S$_2$O$_4$ and dried over Na$_2$SO$_4$. After evaporation of the solvent, the solution was passed through a short silica gel column to afford 1-(o-tolyloxy)-2-iodobenzene (40.0 g, 65%).

Example 53

1-(2-Iodophenoxy)-2-chlorobenzene

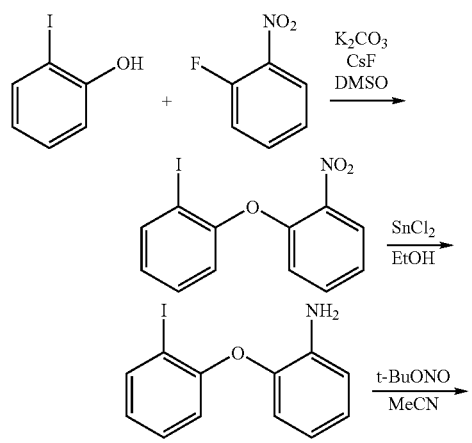

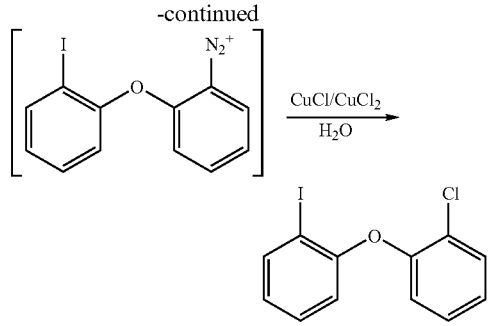

Step 1. 1-(2-Iodophenoxy)-2-nitrobenzene

To a solution of 2-iodophenol (11.82 g, 52.7 mmol) and 1-fluoro-2-nitrobenzene (5.0 g, 35.1 mmol) in DMSO (50 mL was added K$_2$CO$_3$ (14.5 g, 105.3 mmol), followed by CsF (8.0 g, 52.7 mmol). The resulting suspension was stirred at 50° C. until no starting material remained (~5 h), cooled to rt and partitioned between water (50 mL) and CH$_2$Cl$_2$ (50 mL). The water layer was separated and extracted with CH$_2$Cl$_2$ (2×10 mL). The combined organic layers were washed with 1 aq N NaOH (10 mL) and brine, and dried over Na$_2$SO$_4$. Solvent was removed under vacuum to give 1-(2-iodophenoxy)-2-nitrobenzene (11.2 g, 93%) as an oil, which was used for next step without purification.

Step 2. 2-(2-Iodophenoxy)benzenamine

A solution of 1-(2-iodophenoxy)-2-nitrobenzene (9.60 g, 28.1 mmol) and SnCl$_2$.2H$_2$O (13.0 g, 56.0 mmol) in ethanol (25 mL) and water (5 mL) was refluxed until no starting material remained (~1 h). The ethanol was removed in vacuo and the aq layer was basified to pH>10 and extracted with CH$_2$Cl$_2$ (4×10 mL). The combined organic layers were dried over Na$_2$SO$_4$, and the solvent was removed to give a crude 2-(2-Iodophenoxy)benzenamine (8.57 g, 98%), which was used for the next step without purification.

Step 3. 1-(2-Iodophenoxy)-2-chlorobenzene

A solution of crude 2-(2-iodophenoxy)benzenamine (8.57 g, 27.6 mmol) in MeCN (60 mL) was cooled to 0° C. and treated with HBF$_4$ (54 wt % in Et$_2$O, 4.93 mL, 35.9 mmol). The reaction mixture was stirred at 0° C. for 5 min and of t-BuONO (4.10 g, 35.9 mmol) was added dropwise. The resulting mixture was stirred at 0° C. for 10 min, cooled to −20° C., and added to a solution of CuCl (41 g, 414.1 mmol) and CuCl$_2$ (70 g, 414.1 mmol) in water (500 mL) at 0° C. The mixture was stirred vigorously at 25° C. for 2 h, and partitioned between EtOAc and water. The water layer was extracted with EtOAc (3×10 mL) and the combined organic layers were washed with brine, dried over Na$_2$SO$_4$ and concentrated under vacuum. Flash column chromatography gave 1-(2-iodophenoxy)-2-chlorobenzene (5.35 g, 58%).

Example 54

The following halodiphenyl ethers were prepared following procedures analogous to those described in Example 52 using the starting materials and reagents indicated:

| Halopdiphenyl ether | Phenol in Step 1 | Halide in Step 3 |
| --- | --- | --- |
| 1-(2-iodophenoxy)-2-(trifluoromethyl)benzene | 2-(trifluoromethyl)phenol | KI |
| 1-(2-iodophenoxy)-2-fluorobenzene | 2-fluorophenol | KI |

Example 55

(S)-5-methoxy-1-(2-phenoxyphenyl)-1-((R)-piperidin-3-yl)pentan-1-ol

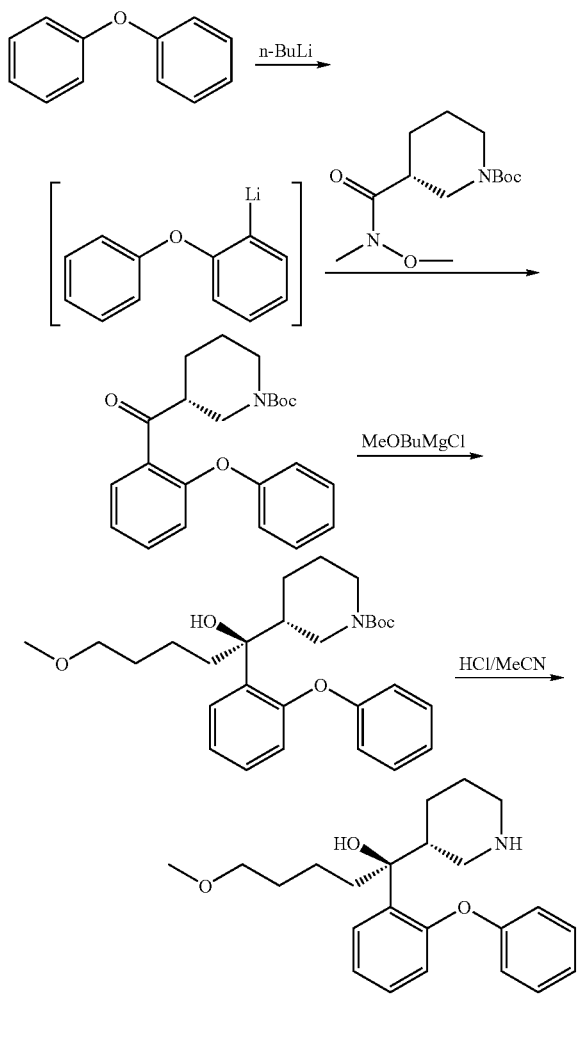

Step 1. 2-(phenoxy)phenyllithium

To a solution of diphenyl ether (8.60 g, 50.0 mmol) in Et$_2$O (75 mL) was added n-BuLi (1.6 M in hexane, 32.8 mL, 52.5 mmol). The mixture was refluxed for 48 h, and the resulting solution of 2-(phenoxy)phenyllithium was used in the next step without any further analysis.

Step 2. (3R)-1-(tert-butoxycarbonyl)-3-(2-phenoxybenzoyl)piperidine

To a solution of (R)-tert-butyl 3-(N-methoxy-N-methylcarbamoyl)piperidine-1-carboxylate (4.40 g, 16.2 mmol) in anhydrous THF (18 mL) at −10° C., was added dropwise the solution of 2-phenoxyphenyllithium prepared in Step 1 (80 mL, 32 mmol). The mixture was then warmed to rt, and stirred until no starting material remained (~30 min). The reaction was quenched with 1 N HCl (~30 mL) and extracted with Et$_2$O (4×10 mL). The combined organic layers were washed with sat'd aq NaHCO$_3$ and brine, and dried over Na$_2$SO$_4$. The solvent was removed to give (3R)-1-(tert-butoxycarbonyl)-3-(2-phenoxybenzoyl)piperidine (7.44 g, quantitative).

Step 3. (R)-tert-Butyl 3-((S)-1-hydroxy-5-methoxy-1-(2-phenoxyphenyl)pentyl)piperidine-1-carboxylate To a solution of (3R)-1-(tert-butoxycarbonyl)-3-(2-phenoxybenzoyl)piperidine (6.17 g, 16.2 mmol) in THF (30 mL) at −10° C. was added dropwise 2.54 M 4-methoxybutylmagnesium chloride in THF (15 mL, 38 mmol). The resulting solution was warmed to rt slowly, and stirred over night. The reaction was quenched with sat'd NH$_4$Cl (10 mL) and extracted with Et$_2$O (4×10 mL). The combined organic layers were washed with water and brine. The solvent was removed and the residue was purified by flash chromatography to give (R)-tert-butyl 3-((S)-1-hydroxy-5-methoxy-1-(2-phenoxyphenyl)pentyl)piperidine-1-carboxylate (1.97 g, 26% from (R)-tert-butyl 3-(N-methoxy-N-methylcarbamoyl)piperidine-1-carboxylate).

Step 4. (S)-5-Methoxy-1-(2-phenoxyphenyl)-1-((R)-piperidin-3-yl)pentan-1-ol

To a solution of (R)-tert-butyl 3-((S)-1-hydroxy-5-methoxy-1-(2-phenoxyphenyl)pentyl)piperidine-1-carboxylate (1.97 g, 4.19 mmol) in MeCN (100 mL) was added 2 N aq HCl (100 mL) slowly at rt. The resulting solution was stirred at rt until no starting material remained (~16 h), basified to pH=10 with 10 N aq NaOH, and evaporated under reduced pressure to remove MeCN. The aq layer was extracted with CH$_2$Cl$_2$ (4×10 mL). The combined organic layers were washed with brine and dried over Na$_2$SO$_4$. The solvent was removed in vacuo to afford (S)-5-methoxy-1-(2-phenoxyphenyl)-1-((R)-piperidin-3-yl)pentan-1-ol (1.56 g, quantitative) as a free amine.

Example 56

(S)-1-(2-(3-Fluorophenoxy)phenyl)-5-methoxy-1-((R)-piperidin-3-yl)pentan-1-ol

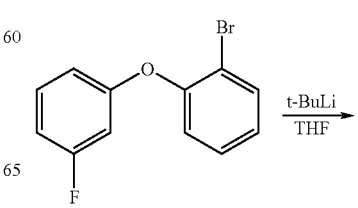

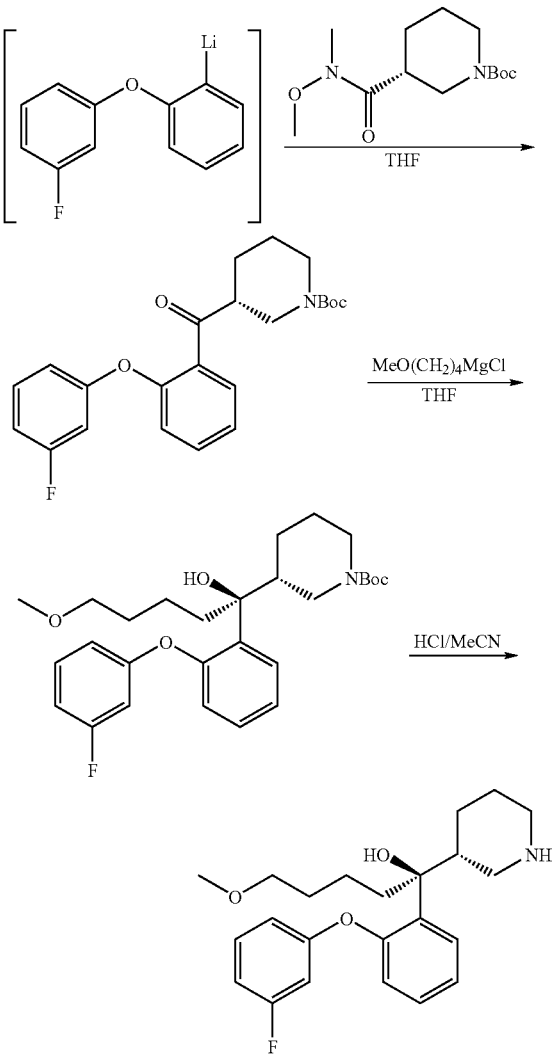

Step 1. 2-(3-fluorophenoxy)phenyllithium

To a stirred solution of 1-(3-fluorophenoxy)-2-bromobenzene (1.27 g, 4.75 mmol) in THF (10 mL) at −70° C. was added 1.7 M t-BuLi in pentane (5.6 mL, 9.50 mmol) dropwise to keep the temperature below −70° C. The resulting solution was stirred at −70° C. for 30 min, and used for the next step directly.

Step 2. (3R)-1-(tert-butoxycarbonyl)-3-((3-fluorophenoxy)benzoyl)piperidine

To a solution of (R)-tert-butyl 3-(N-methoxy-N-methylcarbamoyl)piperidine-1-carboxylate (0.65 g, 2.37 mmol) in THF (4 mL) at −20° C. was added dropwise the solution of 2-(3-fluorophenoxy)phenyllithium prepared in Step 2 above. After the addition was complete, the resulting solution was allowed to warm to rt slowly, and left at rt for 1 h. The reaction was quenched with 1N HCl (~6 mL), and extracted with Et$_2$O (4×10 mL). The combined organic layers were washed with sat'd aq NaHCO$_3$ and brine, and dried over Na$_2$SO$_4$. Removal of the solvent left the crude ketone (1.49 g, quantitative), which was used for next step without further purification.

Step 3. (R)-tert-Butyl 3-((S)-1-(2-(3-fluorophenoxy)phenyl)-1-hydroxy-5-methoxy pentyl)piperidine-1-carboxylate To a solution of (3R)-1-(tert-butoxycarbonyl)-3-((3-fluorophenoxy)benzoyl)piperidine (0.95 g, 2.37 mmol) in THF (3 mL) at −20° C. was added 1.45 M 4-methoxybutyl magnesium chloride in THF (3.3 mL, 4.76 mmol) dropwise. The resulting solution was warmed to rt slowly, and the completion of reaction was confirmed by LC-MS (~20 min). The reaction was quenched with sat'd aq NH$_4$Cl (4 mL) and extracted with Et$_2$O (4×5 mL). The combined organic layers were washed with water and brine, and the solvent was removed in vacuo to give a crude product which was purified by flash column chromatography to afford (R)-tert-butyl 3-((S)-1-(2-(3-fluorophenoxy)phenyl)-1-hydroxy-5-methoxypentyl)piperidine-1-carboxylate (0.50 g, 43%).

Step 4. (S)-1-(2-(3-Fluorophenoxy)phenyl)-5-methoxy-1-((R)-piperidin-3-yl)pentan-1-ol To a solution of (R)-tert-butyl 3-((S)-1-(2-(3-fluorophenoxy)phenyl)-1-hydroxy-5-methoxy pentyl)piperidine-1-carboxylate (0.50 g, 1.03 mmol) in MeCN (60 mL) was added 2 N aq HCl (60 mL) slowly at rt. The resulting solution was stirred at rt overnight, then basified to pH=10 with 10 N aq NaOH. The mixture was evaporated under reduced pressure to remove MeCN. The aq layer was extracted with CH$_2$Cl$_2$ (4×10 mL), and the combined organic layers were washed with brine and dried over Na$_2$SO$_4$. The solvent was removed under vacuum to give (S)-1-(2-(3-fluorophenoxy)phenyl)-5-methoxy-1-((R)-piperidin-3-yl)pentan-1-ol (0.40 g, quantitative) as a free amine.

Example 57

The following piperidines were prepared following procedures analogous to those described in Example 56 using the halodiphenyl ethers listed below in Step 1.

| Piperidine | Halodiphenyl ether |
| --- | --- |
| (S)-1-(2-(2-ethylphenoxy)phenyl)-5-methoxy-1-((R)-piperidin-3-yl)pentan-1-ol | 1-(2-ethylphenoxy)-2-bromobenzene |
| (S)-1-(2-(4-fluorophenoxy)phenyl)-5-methoxy-1-((R)-piperidin-3-yl)pentan-1-ol | 1-(4-fluorophenoxy)-2-bromobenzene |
| (S)-1-(2-(m-tolyloxy)phenyl)-5-methoxy-1-((R)-piperidin-3-yl)pentan-1-ol | 1-(2-bromophenoxy)-3-methylbenzene |
| (S)-1-(2-(o-tolyloxy)-3-methylphenyl)-5-methoxy-1-((R)-piperidin-3-yl)pentan-1-ol | 2-(o-tolyloxy)-1-bromo-3-methylbenzene |
| (S)-1-(2-(o-tolyloxy)-3,5-difluorophenyl)-5- | 2-(o-tolyloxy)-1-bromo-3,5- |

-continued

| Piperidine | Halodiphenyl ether |
|---|---|
| methoxy-1-((R)-piperidin-3-yl)pentan-1-ol | difluorobenzene |
| (S)-1-(2-(4-fluoro-2-methylphenoxy)phenyl)-5-methoxy-1-((R)-piperidin-3-yl)pentan-1-ol | 1-(4-fluoro-2-methylphenoxy)-2-bromobenzene |
| (S)-1-(2-(5-fluoro-2-methylphenoxy)phenyl)-5-methoxy-1-((R)-piperidin-3-yl)pentan-1-ol | 1-(5-fluoro-2-methylphenoxy)-2-bromobenzene |
| (S)-1-(3,5-difluoro-2-phenoxyphenyl)-5-methoxy-1-((R)-piperidin-3-yl)pentan-1-ol | 2-(o-tolyloxy)-1-bromo-3,5-difluorobenzene |
| (S)-1-(5-fluoro-2-phenoxyphenyl)-5-methoxy-1-((R)-piperidin-3-yl)pentan-1-ol | 2-bromo-4-fluoro-1-phenoxybenzene |
| (S)-1-(3-fluoro-2-(o-tolyloxy)phenyl)-5-methoxy-1-((R)-piperidin-3-yl)pentan-1-ol | 1-bromo-3-fluoro-2-(o-tolyloxy)benzene |
| (S)-5-methoxy-1-(3-methyl-2-(o-tolyloxy)phenyl)-1-((R)-piperidin-3-yl)pentan-1-ol | 1-bromo-3-methyl-2-(o-tolyloxy)benzene |
| (S)-1-(5-fluoro-2-(4-fluorophenoxy)phenyl)-5-methoxy-1-((R)-piperidin-3-yl)pentan-1-ol | 2-bromo-4-fluoro-1-(4-fluorophenoxy)benzene |

Example 58

The following piperidines were prepared following procedures analogous to those described in Example 56 except that in Step 1 Grignard reagents were prepared from the halodiphenyl ethers listed below instead of organolithiums.

| Piperidine | Halodiphenyl ether |
|---|---|
| (S)-1-(3-fluoro-2-phenoxyphenyl)-5-methoxy-1-((R)-piperidin-3-yl)pentan-1-ol | 1-chloro-3-fluoro-2-phenoxybenzene |
| (S)-1-(2-(p-tolyloxy)-3-fluorophenyl)-5-methoxy-1-((R)-piperidin-3-yl)pentan-1-ol | 2-(p-tolyloxy)-1-chloro-3-fluorobenzene |

Example 59

(S)-1-(2-(o-tolyloxy)phenyl)-5-methoxy-1-((R)-piperidin-3-yl)pentan-1-ol

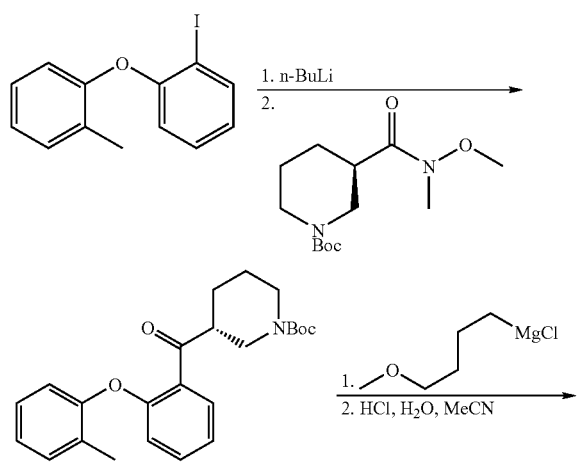

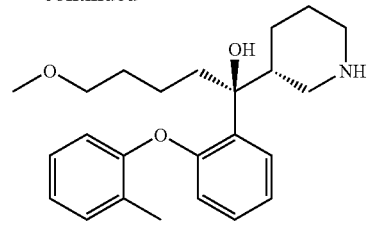

Step 1. (2-(o-tolyloxy)phenyl)((R)-1-(tert-butoxycarbonyl)piperidin-3-yl)methanone To a solution of 1-(o-tolyloxy)-2-iodobenzene (40 g, 0.13 mol) in anhydrous THF (500 mL) cooled to −78° C. was added dropwise 1.6 M n-BuLi in hexanes (52 mL, 0.13 mol). After stirring for 1 h at −78° C., a solution of (R)-tert-butyl 3-(N-methoxy-N-methylcarbamoyl)-piperidine-1-carboxylate (35 g, 0.13 mol) in anhydrous THF (500 mL) was added dropwise. The mixture was allowed to warm to rt and stirred overnight. Sat'd aq NH₄Cl (500 mL) was added and the mixture was extracted with EtOAc (3×150 mL). The combined organic layers were dried over Na₂SO₄. Solvent removal and flash column chromatography afforded (2-(o-tolyloxy)phenyl)((R)-1-(tert-butoxycarbonyl)piperidin-3-yl)methanone (23 g, 45%).

Step 2. (R)-tert-butyl 3-((S)-1-(2-(o-tolyloxy)phenyl)-1-hydroxy-5-methoxypentyl)piperidine-1-carboxylate A 500-mL, three-necked flask was charged with magnesium turnings (12 g, 0.5 mol) and a small crystal of iodine. The flask was evacuated and refilled with N₂. A solution of 1-chloro-4-methoxybutane (50 g, 0.4 mol) in THF (200 mL) was added dropwise to the mixture. The reaction mixture was stirred at reflux for 2 h and most of magnesium was consumed. The solution of Grignard reagent was cooled to rt.

A 1000-mL, three-necked flask was charged with the (2-(o-tolyloxy)phenyl)((R)-1-(tert-butoxycarbonyl)piperidin-3-yl)methanone (20 g, 0.05 mol) and THF (250 mL). The flask was evacuated and refilled with N₂, the mixture was cooled with a dry ice-acetone bath and the Grignard reagent was added dropwise. The mixture was allowed to warm slowly to rt and stirred overnight. After quenching with sat'd aq NH₄Cl (500 mL), the mixture was extracted with EtOAc (3×150 mL) and the combined organic layers were dried over Na₂SO₄. The solvent was removed and the crude product was purified by flash column chromatography to afford the (R)-tert-butyl 3-((S)-1-(2-(o-tolyloxy)phenyl)-1-hydroxy-5-methoxypentyl)piperidine-1-carboxylate (20 g, 83%).

Step 3. (S)-1-(2-(o-tolyloxy)phenyl)-5-methoxy-1-((R)-piperidin-3-yl)pentan-1-ol The Boc protecting group was removed using the protocol described in Example 56 Step 4.

Example 60

The following piperidines were prepared using the procedures analogous to those described above from the halodiphenyl ether indicated.

| Piperidine | Iododiphenyl ether |
|---|---|
| (S)-1-(2-(2-chlorophenoxy)phenyl)-5-methoxy-1-((R)-piperidin-3-yl)pentan-1-ol | 1-(2-iodophenoxy)-2-chlorobenzene |
| (S)-1-(2-(2-(trifluoromethyl)phenoxy)phenyl)-5-methoxy-1-((R)-piperidin-3-yl)pentan-1-ol | 1-(2-iodophenoxy)-2-(trifluoromethyl)benzene |
| (S)-1-(2-(2-fluorophenoxy)phenyl)-5-methoxy-1-((R)-piperidin-3-yl)pentan-1-ol | 1-(2-iodophenoxy)-2-fluorobenzene |
| (S)-5-methoxy-1-((R)-piperidin-3-yl)-1-(2-(pyridin-4-yloxy)phenyl)pentan-1-ol | 1-(3-pyridyloxy)-2-bromobenzene |

Example 61

(S)-5-methoxy-1-(2-(2,2-(dimethyl)propoxy)phenyl)-1-((R)-piperidin-3-yl)pentan-1-ol hydrochloride

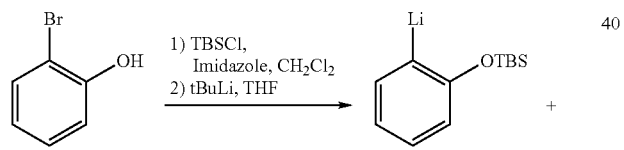

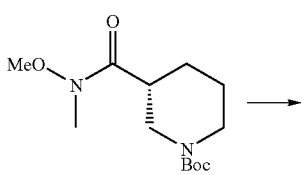

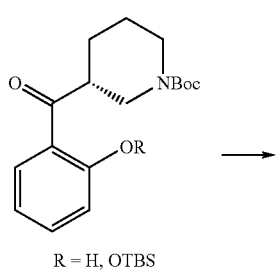

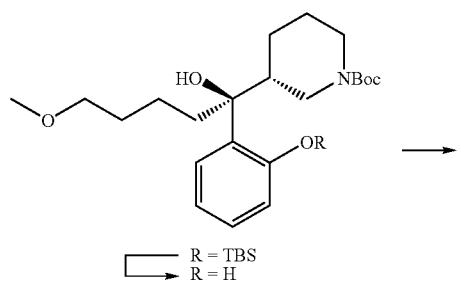

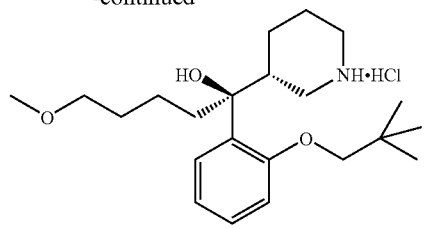

Step 1. Bromo-2-[(tert-butyl)dimethylsiloxy]benzene

A solution of 2-bromophenol (5 mL, 47 mmol), imidazole (8 g, 118 mmol) and tert-butyldimethylsilyl chloride (8.6 g, 57 mmol) in DMF (50 mL) was stirred at rt overnight. The reaction was treated with water (150 mL) and extracted with Et₂O (4×25 mL). The organic phase was washed with 50% aq lithium chloride solution twice, dried over MgSO₄ and filtered. The solvent was evaporated and the crude product was purified by filtration through silica gel, washing with 1:1 EtOAc/hexanes to afford bromo-2-[(tert-butyl)dimethylsiloxy]benzene (13.4 g, 99%).

Step 2. 2-((S)-1-hydroxy-5-methoxy-1-((R)—N-Boc-piperidin-3-yl)pentyl)[tert-butyldimethylsiloxy]benzene A solution of bromo-2-[(tert-butyl)dimethylsiloxy]benzene (2.1 g, 7.4 mmol) in Et₂O (35 mL) was cooled to −78° C. and treated with 1.7 M tert-butyllithium in hexanes (8.6 mL, 15 mmol). The reaction was stirred for 30 min and a solution of (R)-tert-butyl 3-(N-methoxy-N-methylcarbamoyl)piperidine-1-carboxylate (1.0 g, 3.7 mmol) in Et₂O was added slowly. The reaction was allowed to stir and warm to rt over a two hour period. Sat'd aq ammonium chloride was added to quench the reaction. The aq phase was extracted with Et$_2$O three times. The combined organic layers were washed with brine and dried over MgSO$_4$. The solvent was removed by evaporation and the crude product was purified by flash chromatography on silica gel eluting with EtOAc/hexanes to give a mixture of (2-tert-butyldimethylsiloxyphenyl)((R)—N-Boc-piperidin-3-yl)methanone and (2-hydroxyphenyl)((R)—N-Boc-piperidin-3-yl)methanone. A −20° C. solution of the crude mixture in tetrahydrofuran was treated with 1.3 M 4-methoxybutylmagensium chloride in THF (14.9 mL, 19.4 mmol). The reaction was stirred and allowed to warm to rt over a two hour period. The reaction was quenched with ammonium chloride. The aq layer was extracted with Et$_2$O. The combined organic layers were dried over MgSO$_4$ and filtered. The solvent was evaporated and the crude product was purified by flash chromatography on silica gel eluting with EtOAc/hexanes to afford 2-((S)-1-hydroxy-5-methoxy-1-((R)—N-Boc-piperidin-3-yl)pentyl)[tert-butyldimethylsiloxy]benzene (874 mg, 47%) and 2-((S)-1-hydroxy-5-methoxy-1-((R)—N-Boc-piperidin-3-yl)pentyl)phenol (650 mg, 45%).

To a solution of 2-((S)-1-hydroxy-5-methoxy-1-((R)—N-Boc-piperidin-3-yl)pentyl)[tert-butyldimethylsiloxy]benzene (710 mg, 1.40 mmol) in tetrahydrofuran (7 mL) was added 1M tetrabutylammonium fluoride in THF (2.1 mL, 2.1 mmol). The mixture was stirred at rt for one hour. The mixture was diluted with EtOAc (20 mL) and washed with brine twice. The organic layer was dried over sodium sulfate and filtered. The filtrate was evaporated to give a residue, which was purified by flash chromatography on silica gel eluting with EtOAc/hexanes to give 2-((S)-1-hydroxy-5-methoxy-1-((R)—N-Boc-piperidin-3-yl)pentyl)[tert-butyldimethylsiloxy]benzene (450 mg, 81%).

Step 3. ((S)-5-methoxy-1-(2-(2,2-(dimethyl)propoxy)phenyl)-1-((R)-piperidin-3-yl)pentan-1-ol hydrochloride A solution of 2-((S)-1-hydroxy-5-methoxy-1-((R)—N-Boc-piperidin-3-yl)pentyl)phenol (195 mg, 0.500 mmol), 1-bromo-2,2-dimethylpropane (1.0 ml, 7.5 mmol), and cesium carbonate (230 mg, 0.71) in NMP (2 mL) was heated and stirred in a microwave reactor for 20 min at 130° C. After removal of solvent, the mixture was redissolved in CH$_2$Cl$_2$ and filtered. The filtrate was evaporated to give a residue which was used without any further purification.

A solution of crude (R)-tert-butyl-3-((S)-1-hydroxy-5-methoxy-1-(2-(2,2-(dimethyl)propoxy)phenyl)pentyl)piperidine-1-carboxylate in MeCN (50 mL) was treated with 2M aq hydrochloric acid (50 mL) and stirred at rt overnight. The solvent was evaporated to afford ((S)-5-methoxy-1-(2-(2,2-(dimethyl)propoxy)phenyl)-1-((R)-piperidin-3-yl)pentan-1-ol hydrochloride (122 mg, 67%) as an oil.

Example 62

The following piperidines were prepared following procedures analogous to those described in Example 61, replacing 1-bromo-2,2-dimethylpropane in Step 3 with the alkylating agent indicated and using DMF as solvent at rt in place of NMP at elevated temperature:

| Piperidine | Alkyl halide |
|---|---|
| 1-(2-(cyclopentylmethoxy)phenyl)-5-methoxy-1-((R)-piperidin-3-yl)pentan-1-ol | bromomethylcyclopentane |
| 1-(2-(cyclopentyloxy)phenyl)-5-methoxy-1-((R)-piperidin-3-yl)pentan-1-ol | bromocyclopentane |
| 1-(2-(cyclobutylmethoxy)phenyl)-5-methoxy-1-((R)-piperidin-3-yl)pentan-1-ol | bromomethylcyclobutane |
| 1-(2-(cyclopropylmethoxy)phenyl)-5-methoxy-1-((R)-piperidin-3-yl)pentan-1-ol | bromomethylcyclopropane |
| 1-(2-(2-cyclopropylethoxy)phenyl)-5-methoxy-1-((R)-piperidin-3-yl)pentan-1-ol | (2-bromoethyl)cyclopropane |
| 1-(2-(benzyloxy)phenyl)-5-methoxy-1-((R)-piperidin-3-yl)pentan-1-ol | benzyl bromide |
| 1-(2-(4-fluorobenzyloxy)phenyl)-5-methoxy-1-((R)-piperidin-3-yl)pentan-1-ol | 4-fluorobenzyl bromide |
| 1-(2-(cyclohexylmethoxy)phenyl)-5-methoxy-1-((R)-piperidin-3-yl)pentan-1-ol | bromomethylcyclohexane |

Example 63

(3R)-tert-butyl 3-((S)-1-(2-(2-chlorophenyl)phenyl)-1-hydroxy-5-methoxypentyl)piperidine-1-carboxylate

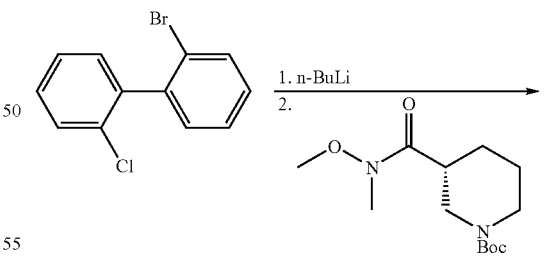

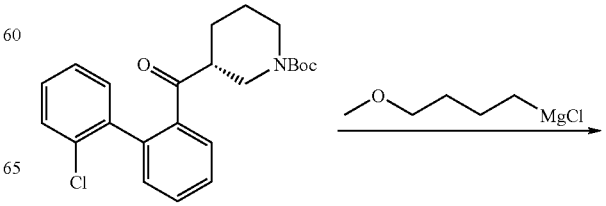

-continued

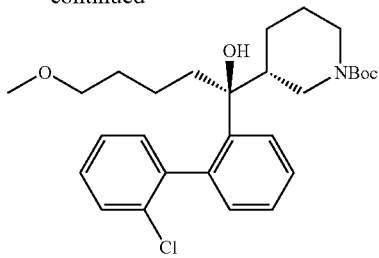

Step 1. (3R)-1-(tert-butoxycarbonyl)-3-((2-(2-chlorophenyl))benzoyl)piperidine

To a solution of 2-bromo-2-chloro-biphenyl (5.34 g, 20 mmol) in anhydrous THF (50 mL) cooled to −78° C. was added dropwise a solution of 1.6 M n-BuLi in hexane (12.5 mL, 20 mmol). The reaction mixture was stirred at −78° C. for 1 h and a solution of (R)-tert-butyl 3-(N-methoxy-N-methylcarbamoyl)-piperidine-1-carboxylate (5.44 g, 20 mmol) in anhydrous THF (50 mL) was added. The mixture was allowed to warm to rt and stirred overnight. The mixture was quenched with sat'd aq $NH_4Cl$ (100 mL) and extracted with EtOAc (3×75 mL). The combined organic layers were dried over $Na_2SO_4$ and concentrated to give the crude product, which was purified by flash column chromatography to afford (3R)-1-(tert-butoxycarbonyl)-3-((2-(2-chlorophenyl))benzoyl)piperidine (4.43 g, 55%).

Step 2. (3R)-tert-butyl 3-((S)-1-(2-(2-chlorophenyl)phenyl)-1-hydroxy-5-methoxypentyl)-piperidine-1-carboxylate A 250-mL three-necked flask was charged with magnesium turning (2.88 g, 0.12 mol) and a small crystal of iodine. The flask was evacuated and refilled with $N_2$. A solution of 1-chloro-4-methoxybutane (15 g, 0.12 mol) in THF (60 mL) was added dropwise to the above mixture. After heating under reflux for 2 h most of magnesium had been consumed and the Grignard solution was cooled to rt. A 250-mL three-necked flask was charged with (3R)-1-(tert-butoxycarbonyl)-3-((2-(2-chlorophenyl))benzoyl)piperidine (4.43 g, 11 mmol) and THF (50 ml), evacuated and refilled with $N_2$. The mixture was cooled in a dry ice-acetone bath and the Grignard reagent was added dropwise. The mixture was allowed to warm slowly to rt and stirred overnight. The mixture was quenched with sat'd aq $NH_4Cl$ (100 mL) and extracted with EtOAc. The combined organic layers were dried over $Na_2SO_4$ and concentrated to give the crude product which was purified by flash column chromatography to afford pure (3R)-tert-butyl 3-((S)-1-(2-(2-chlorophenyl)phenyl)-1-hydroxy-5-methoxypentyl)piperidine-1-carboxylate (2.5 g, 47%).

Example 64

The following piperidines were prepared following procedures analogous to those described in Example 63 employing the bromobiphenyls indicated in Step 1:

| Piperidine | Bromobiphenyl |
|---|---|
| (S)-1-(2-phenylphenyl)-5-methoxy-1-((R)-piperidin-3-yl)pentan-1-ol | 2-bromo-1,1'-biphenyl |
| (S)-1-(2-phenyl-3-fluorophenyl)-5-methoxy-1-((R)-piperidin-3-yl)pentan-1-ol | 2-bromo-6-fluoro-1,1'-biphenyl |
| (S)-1-(2-phenyl-3-chlorophenyl)-5-methoxy-1-((R)-piperidin-3-yl)pentan-1-ol | 2-bromo-6-chloro-1,1'-biphenyl |
| (S)-1-(2-(2-methylphenyl)phenyl)-5-methoxy-1-((R)-piperidin-3-yl)pentan-1-ol | 2-bromo-2'-methylbiphenyl |
| (S)-1-(2-(3-methylphenyl)phenyl)-5-methoxy-1-((R)-piperidin-3-yl)pentan-1-ol | 2-bromo-3'-methyl-1,1'-biphenyl |
| (S)-1-(2-(4-methylphenyl)phenyl)-5-methoxy-1-((R)-piperidin-3-yl)pentan-1-ol | 2-bromo-4'-methylbiphenyl |
| (S)-1-(2-(2-fluorophenyl)phenyl)-5-methoxy-1-((R)-piperidin-3-yl)pentan-1-ol | 2-bromo-2'-fluorobiphenyl |
| (S)-1-(2-(3-fluorophenyl)phenyl)-5-methoxy-1-((R)-piperidin-3-yl)pentan-1-ol | 2-bromo-3'-fluorobiphenyl |
| (S)-1-(2-(4-fluorophenyl)phenyl)-5-methoxy-1-((R)-piperidin-3-yl)pentan-1-ol | 2-bromo-4'-fluorobiphenyl |
| (3R)-tert-butyl 3-((S)-1-(2-(4-chlorophenyl)phenyl)-1-hydroxy-5-methoxypentyl)piperidine-1-carboxylate | 2-bromo-4'-chlorobiphenyl |
| (S)-1-(6-fluoro-3'-methylbiphenyl-2-yl)-5-methoxy-1-((R)-piperidin-3-yl)pentan-1-ol | 2-bromo-6-fluoro-3'-methylbiphenyl |
| (S)-1-(3'-chloro-6-fluorobiphenyl-2-yl)-5-methoxy-1-((R)-piperidin-3-yl)pentan-1-ol | 2-bromo-3'-chloro-6-fluorobiphenyl |

Example 65

(S)-1-(3-(o-tolyloxy)-2-fluorophenyl)-5-methoxy-1-((R)-piperidin-3-yl)pentan-1-ol

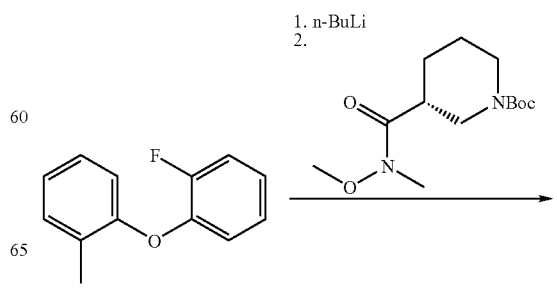

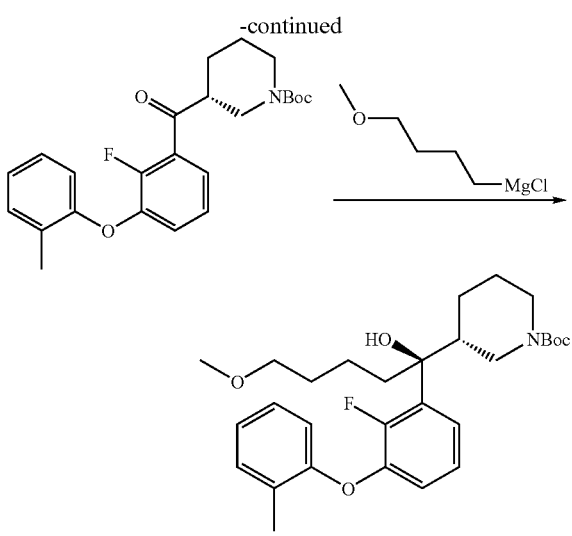

Step 1. (3R)-1-tert-butoxycarbonyl-3-(2-fluoro-3-(o-tolyloxy)benzoyl)piperidine

A solution of 2.0 mL of 2.0 M n-BuLi (2.0 mL, 4.0 mmol) was added dropwise to a solution of 1-(o-tolyloxy)-2-fluorobenzene (0.7009 g, 3.5 mmol) in THF (15 mL); the internal temperature was maintained below −70° C. during the addition. A pale, yellow slurry resulted. Confirmation of proton abstraction was confirmed by quenching an aliquot on solid 12. A solution of (R)-tert-butyl 3-(N-methoxy-N-methylcarbamoyl)piperidine-1-carboxylate (1.1159 g, 4.1 mmol) in THF (15 mL) was added dropwise. The reaction was permitted to warm to rt and stirred at for 12 h. The reaction was quenched at 0° C. with satd aq NH₄Cl and extracted with Et₂O. The Et₂O extracts were washed with aq NH₄Cl and brine and dried over Na₂SO₄. Removal of the solvent left crude (3R)-1-tert-butoxycarbonyl-3-(2-fluoro-3-(o-tolyloxy)benzoyl)piperidine (1.79 g, ~80% pure, quantitative) which was used directly without further purification.

Step 2. (R)-tert-butyl 3-((S)-1-(3-(o-tolyloxy)-2-fluorophenyl)-1-hydroxy-5-methoxypentyl)-piperidine-1-carboxylate A solution of crude (3R)-1-tert-butoxycarbonyl-3-(2-fluoro-3-(o-tolyloxy)benzoyl)-piperidine (1.79 g, ~80% pure, 3.5 mmol) in THF (15 mL) was cooled to 0° C. A 1.63 M solution of 4-methoxybutylmagnesium chloride in THF was added with fast dropwise addition. The reaction was stirred for 1 h at rt, cooled to 0° C. and then quenched with sat'd aq NH₄Cl. The crude mixture was taken up into Et₂O, washed with sat'd aq NH₄Cl and brine, and dried over Na₂SO₄. Removal of the solvent gave an oil (1.82 g). Flash chromatography on a 40-g silica cartridge eluting with a gradient from 0 to 100% EtOAc in hexanes. Appropriate fractions were combined and stripped to give (R)-tert-butyl 3-((S)-1-(3-(o-tolyloxy)-2-fluorophenyl)-1-hydroxy-5-methoxypentyl)piperidine-1-carboxylate (0.66 g, 30%).

Example 66

N—((S)-4-(3-chlorophenyl)-4-hydroxy-4-((R)-piperidin-3-yl)butyl)acetamide

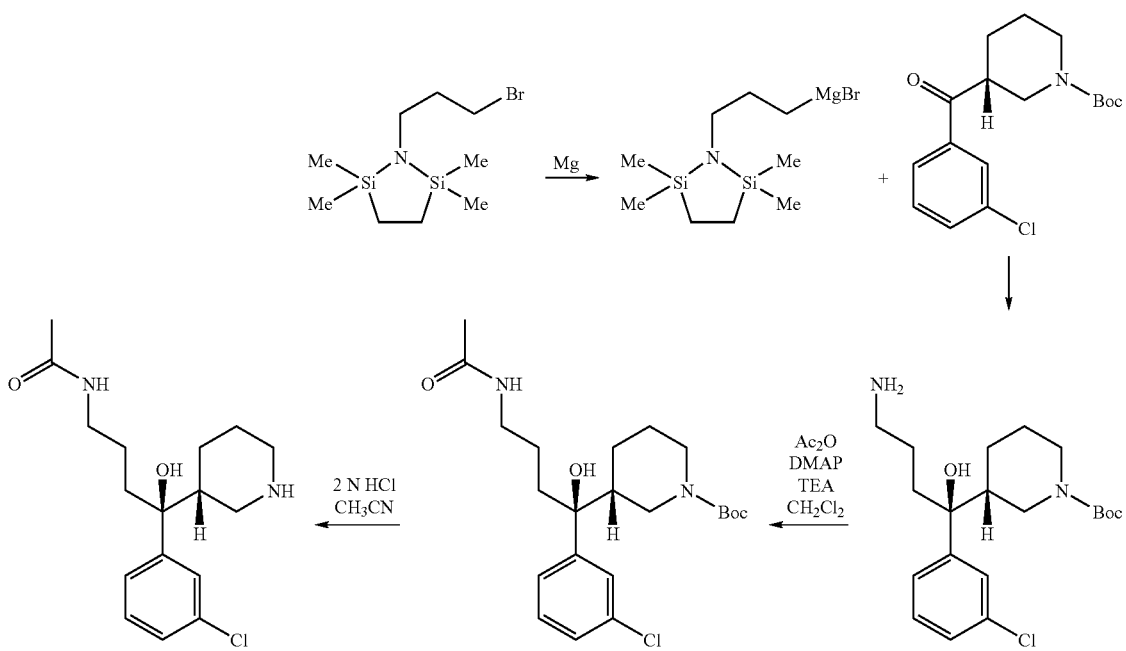

Step 1. [3-(2,2,5,5-tetramethyl-1-aza-2,5-disilacyclopent-1-yl)propyl]magnesium bromide A 250 mL, round bottom flask was charged with magnesium turnings (0.528 g, 21.7 mmol, 1.16 equiv) and THF (10 mL). The flask was degassed and heated to 100° C. A small crystal of iodine was then added. A solution of 1-(3-bromopropyl)-2,2,5,5-tetramethyl-1-aza-2,5-disilacyclopentane (5.239 g, 18.7 mmol, 1.0 equiv) in THF (15 mL) was added dropwise to the boiling THF mixture over 10 min. The reaction mixture was stirred and heated under reflux for 2.5 h and most of magnesium was consumed. The resulting Grignard reagent was used in the next step.

Step 2. (R)-tert-butyl 3-((S)-4-amino-1-(3-chlorophenyl)-1-hydroxybutyl)piperidine-1-carboxylate To a 250 mL, round bottom flask were added (3-chlorophenyl)((R)—N-Boc-piperidin-3-yl)methanone (0.800 g, 2.47 mmol) and THF (10 mL). The flask was evacuated and refilled with $N_2$. The mixture was cooled with a dry ice-acetone bath and the [3-(2,2,5,5-tetramethyl-1-aza-2,5-disilacyclopent-1-yl)propyl]magnesium bromide solution, obtained in Step 1, was added via a cannula. The reaction mixture was allowed to slowly warm to −8° C. while stirring overnight. The mixture was quenched with 10% aq $Na_2CO_3$ (10 mL), stirred at rt for 3 h, extracted with $CH_2Cl_2$ (3×) and dried over $Na_2SO_4$. The crude product was purified by reversed-phase HPLC (Phenomenex® Luna 5μ C18(2) 100 A, 250×21.20 mm, 5 micron, 10%→90% $CH_3CN/H_2O$, 0.1% $CF_3COOH$ over 13 min and then 90% $CH_3CN/H_2O$, 0.1% $CF_3COOH$ over 3.5 min, flow rate 25 mL/min) to give 0.883 g (72%) of TFA salt of (R)-tert-butyl 3-((S)-4-amino-1-(3-chlorophenyl)-1-hydroxybutyl)piperidine-1-carboxylate. LC-MS (3 min) $t_R$=1.30 min, m/z 383, 385 ($MH^+$), 327, 329; $^1H$ NMR (400 MHz, $CD_3OD$) δ 7.36 (m, 1H), 7.27-7.13 (m, 3H), 4.26 (br s, 1H), 3.89 (d, J=12.9 Hz, 1H), 2.82-2.68 (m, 2H), 2.44 (br s, 1H), 2.36 (t, J=12.2 Hz, 1H), 1.97-1.79 (m, 2H), 1.64-1.08 (m, 16H), 1.34 (s); $^{13}C$ NMR (100 MHz, $CD_3OD$) δ 156.69, 148.15, 135.39, 130.69, 127.74, 127.36, 125.41, 81.04, 78.10, 40.95, 28.69, 26.64, 26.51, 23.30.

Step 3. (R)-tert-butyl 3-((S)-4-acetamido-1-(3-chlorophenyl)-1-hydroxybutyl)piperidine-1-carboxylate To a 100 mL, round bottom flask were added TFA salt of (R)-tert-butyl 3-((S)-4-amino-1-(3-chlorophenyl)-1-hydroxybutyl)piperidine-1-carboxylate (0.374 g, 0.75 mmol, 1.0 equiv), DMAP (0.1615 g), $CH_2Cl_2$ (10 mL), and triethylamine (3 mL). The mixture was cooled in an ice bath and a solution of acetic anhydride (0.280 g, 2.74 mmol, 3.6 equiv) in $CH_2Cl_2$ (10 mL) was added. The reaction mixture was allowed to slowly warm to rt while stirring overnight (16 h). After the solvents were removed in vacuo, the residue was purified by reversed-phase HPLC (Phenomenex® Luna 5μ C18(2) 100 A, 250×21.20 mm, 5 micron, 70%→90% $CH_3CN/H_2O$, 0.1% $CF_3COOH$ over 8 min and then 90% $CH_3CN/H_2O$, 0.1% $CF_3COOH$ over 1.5 min, flow rate 25 mL/min) to give 0.2589 g (81%) of (R)-tert-butyl 3-((S)-4-acetamido-1-(3-chlorophenyl)-1-hydroxybutyl)-piperidine-1-carboxylate. LC-MS (3 min) $t_R$=1.72 min, m/z 447, 449 ($MNa^+$), 425 ($MH^+$), 325, 327; $^1H$ NMR (400 MHz, $CDCl_3$) δ 7.38-7.37 (m, 1H), 7.28-7.18 (m, 3H), 6.06 (br s, 1H), 4.36-4.34 (m, 1H), 3.97-3.95 (m, 1H), 3.35-3.26 (m, 1H), 3.13-3.05 (m, 1H), 2.99 (br s, 2H), 2.55-2.49 (m, 2H), 1.97 (s, 3H), 1.44 (s, 9H), 1.95-1.15 (m, 6H); $^{13}C$ NMR (100 MHz, $CDCl_3$) δ 171.41, 155.17, 146.75, 134.24, 129.33, 126.63, 126.01, 123.83, 79.68, 77.60, 46.34, 44.69, 39.71, 35.91, 28.43, 25.40, 25.23, 24.15, 22.99.

Step 4. N—((S)-4-(3-chlorophenyl)-4-hydroxy-4-((R)-piperidin-3-yl)butyl)acetamide A mixture of (R)-tert-butyl 3-((S)-4-acetamido-1-(3-chlorophenyl)-1-hydroxybutyl)-piperidine-1-carboxylate (0.1773 g, 0.4172 mmol) in $CH_3CN$ (50 mL) and 2 N aq HCl (45 mL) was vigorously stirred at rt for 24 h. The solvents were removed in vacuo to give the HCl salt of N—((S)-4-(3-chlorophenyl)-4-hydroxy-4-((R)-piperidin-3-yl)butyl)acetamide, which was used in the next step without further purification. LC-MS (3 min) $t_R$=0.91 min, m/z 325, 327 ($MH^+$).

Example 67

The following piperidines were prepared following procedures analogous to those described in Example 66:

N—((S)-4-(2-fluorophenyl)-4-hydroxy-4-((R)-piperidin-3-yl)butyl)acetamide using (2-fluorophenyl)((R)—N-Boc-piperidin-3-yl)methanone in Step 2.

N—((S)-4-(2-fluoro-5-methylphenyl)-4-hydroxy-4-((R)-piperidin-3-yl)butyl)acetamide using (2-fluoro-5-methylphenyl)((R)—N-Boc-piperidin-3-yl)methanone in Step 2.

N—((S)-4-(3-fluoro-5-methylphenyl)-4-hydroxy-4-((R)-piperidin-3-yl)butyl)acetamide using (3-fluoro-5-methylphenyl)((R)—N-Boc-piperidin-3-yl)methanone in Step 2.

N—((S)-4-(2,3-difluorophenyl)-4-hydroxy-4-((R)-piperidin-3-yl)butyl)acetamide using (2,3-difluorophenyl)((R)—N-Boc-piperidin-3-yl)methanone in Step 2.

N—((S)-4-(3,5-difluorophenyl)-4-hydroxy-4-((R)-piperidin-3-yl)butyl)acetamide using (3,5-difluorophenyl)((R)—N-Boc-piperidin-3-yl)methanone in Step 2.

N—((S)-4-(2-chloro-3-fluorophenyl)-4-hydroxy-4-((R)-piperidin-3-yl)butyl)acetamide using (2-chloro-3-fluorophenyl)((R)—N-Boc-piperidin-3-yl)methanone in Step 2.

N—((S)-4-(3-chloro-2-fluorophenyl)-4-hydroxy-4-((R)-piperidin-3-yl)butyl)acetamide using (3-chloro-2-fluorophenyl)((R)—N-Boc-piperidin-3-yl)methanone in Step 2.

N—((S)-4-(3-chloro-5-fluorophenyl)-4-hydroxy-4-((R)-piperidin-3-yl)butyl)acetamide using (3-chloro-5-fluorophenyl)((R)—N-Boc-piperidin-3-yl)methanone in Step 2.

N—((S)-4-(3-chlorophenyl)-4-hydroxy-4-((R)-piperidin-3-yl)butyl)-2,2,2-trifluoroacetamide using trifluoroacetic anhydride in Step 3.

N—((S)-4-(3-chlorophenyl)-4-hydroxy-4-((R)-piperidin-3-yl)butyl)butyramide using butyric anhydride in Step 3.

(R) —N—((S)-4-(3-chlorophenyl)-4-hydroxy-4-((R)-piperidin-3-yl)butyl)-2-methoxypropanamide using (R)-2-methoxypropanoic acid and EDC in place of acetic anhydride in Step 3.

(S)—N—((S)-4-(3-chlorophenyl)-4-hydroxy-4-((R)-piperidin-3-yl)butyl)-2-methoxypropanamide using (S)-2-methoxypropanoic acid and EDC in place of acetic anhydride in Step 3.

N—((S)-4-(3-chlorophenyl)-4-hydroxy-4-((R)-piperidin-3-yl)butyl)propionamide using propionic anhydride in Step 3.

N—((S)-4-(3-chlorophenyl)-4-hydroxy-4-((R)-piperidin-3-yl)butyl)cyclopropanecarboxamide using cyclopropanecarboxylic acid and EDC in place of the anhydride in Step 3.

Example 68

(S)-1-(benzofuran-7-yl)-5-methoxy-1-((R)-piperidin-3-yl)pentan-1-ol

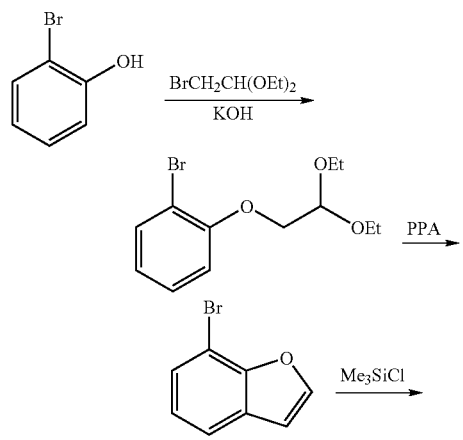

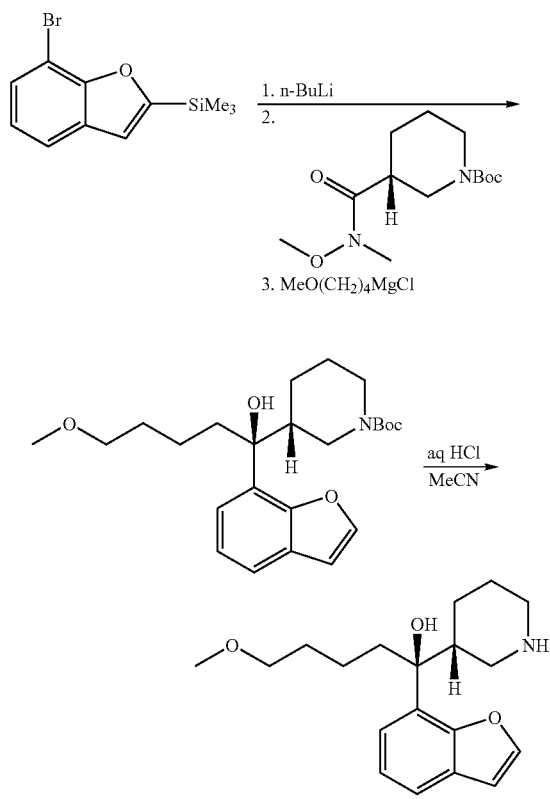

Step 1. 1-(2,2-diethoxyethoxy)-2-bromobenzene

A solution of KOH pellets (85%, 0.68 g, 10.3 mmol) in water (1.5 mL) was added to 2-bromophenol (1 mL, 8.6 mmol). The mixture was diluted with DMSO (20 mL) and bromoacetaldehyde diethyl acetal (1.43 mL, 9.5 mmol) was added. The mixture was heated at 100° C. for 6 h, cooled to rt, diluted with ether (175 mL), washed with water (3×40 mL) and 5% aq NaOH (40 mL), and dried over MgSO$_4$. Removal of the solvent left 1-(2,2-diethoxyethoxy)-2-bromobenzene (2.62 g, quant) as an oil.

Step 2. 7-bromobenzofuran

A stirred mixture of polyphosphoric acid (~5 g) and chlorobenzene (8 mL) was heated at reflux and a solution of 1-(2,2-diethoxyethoxy)-2-bromobenzene (2.62 g, 9.0 mmol) in chlorobenzene (3 mL) was added dropwise over 10 min. The mixture was heated at reflux for 1.5 h. The mixture was allowed to cool to rt and 1 M aq NaOH (20 mL) was added, followed by ether (175 mL). The mixture was washed with water (2×20 mL) and brine (20 mL), and dried over MgSO$_4$. Evaporation of the solvent left a residue which was purified by a chromatography on a 140-g silica cartridge eluted with hexanes and a 0-10% EtOAc in hexanes gradient. Appropriate fractions were pooled and concentrated to afford 7-bromobenzofuran (0.65 g, 38% from 2-bromophenol) as a clear colorless oil.

Step 3. 7-Bromo-2-(trimethylsilyl)benzofuran

A stirred solution of diisopropylamine (0.65 mL, 4.7 mmol) in THF (15 L) was cooled to 5° C. and n-BuLi (2.5 M in hexanes, 1.9 mL, 4.7 mmol) was added dropwise over 5 min. The mixture was stirred at 5° C. for 15 min and cooled to −70° C. Chlorotrimethylsilane (0.59 mL, 4.7 mmol) was added followed by a solution of 7-bromobenzofuran (0.46 g, 2.35 mmol) in THF (5 mL). The mixture was stirred at −70° C. for 1.5 h and poured into sat'd aq NH$_4$Cl (80 mL). The mixture was diluted with 5% aq HCl (20 mL) and extracted with ether (2×80 mL). The combined ether extracts were washed with sat'd aq NaHCO$_3$ (50 mL), dried over MgSO$_4$ and concentrated to leave crude 7-bromo-2-(trimethylsilyl)benzofuran (0.62 g, 98%) as a yellow oil.

Step 4. (R)-tert-butyl 3-((S)-1-(benzofuran-7-yl)-1-hydroxy-5-methoxypentyl)piperidine-1-carboxylate A stirred solution of 7-bromo-2-(trimethylsilyl)benzofuran (620 mg, 2.3 mmol) in THF (15 mL) was cooled to −70° C. and n-BuLi (2.5 M in hexanes, 0.85 mL, 2.1 mmol) was added dropwise over 2 min. The mixture was stirred at −70° C. for 15 min and a solution of (R)-tert-butyl 3-(N-methoxy-N-methylcarbamoyl)piperidine-1-carboxylate (341 mg, 1.30 mmol) in THF (5 mL) was added dropwise over 2 min. The mixture was stirred at −70° C. for 1 h, poured into satd aq NaHCO$_3$ (100 mL) and extracted with ether (2×100 mL). The combined ether extracts were washed with brine (40 mL) and dried over MgSO$_4$. Removal of the solvent afforded crude (R)-tert-butyl 3-((benzofuran-7-yl)carbonyl)piperidine-1-carboxylate (727 mg) as an oil. This material was dissolved in THF (15 mL) and cooled to −70° C. 4-Methoxybutylmagnesium chloride (1.52 M in THF, 2.0 mL, 3.04 mmol) was added dropwise over 2 min. The mixture was stirred at −70° C. for 2 h and poured into sat'd aq NaHCO$_3$ (100 mL). The mixture was extracted with ether (2×100 mL) and the combined ether extracts were washed with brine (35 mL) and dried over MgSO$_4$. Removal of the solvent left an oil which was purified by chromatography on a 40-g silica cartridge eluted with a gradient from 0 to 100% EtOAc in hexanes to afford (R)-tert-butyl 3-((S)-1-(benzofuran-7-yl)-1-hydroxy-5-methoxypentyl)piperidine-1-carboxylate (240 mg, 44%) as an oil.

Step 4. (S)-1-(benzofuran-7-yl)-5-methoxy-1-((R)-piperidin-3-yl)pentan-1-ol (R)-tert-butyl 3-((S)-1-(benzofuran-7-yl)-1-hydroxy-5-methoxypentyl)piperidine-1-carboxylate (240 mg, 0.58 mmol) was dissolved in MeCN (20 mL) and 5% aq HCl (10 mL) was added. The mixture was stirred at rt for 1 d and solid K$_2$CO$_3$ was added. The mixture was diluted with water (40 mL) and extracted with EtOAc (2×100 mL). The combined organic extracts were washed with brine (25 mL), dried over MgSO$_4$ and concentrated to leave an oil (150 mg) which was purified by reverse phase preparative HPLC to afford (S)-1-(benzofuran-7-yl)-5-methoxy-1-((R)-piperidin-3-yl)pentan-1-ol (120 mg, 81%) as an oil.

Example 69

The following piperidines were prepared following procedures analogous to those described in Example 68:
- (S)-5-methoxy-1-(2-methylbenzofuran-7-yl)-1-((R)-piperidin-3-yl)pentan-1-ol using 7-bromo-2-methylbenzofuran and n-BuLi in Step 4.
- (S)-1-(2-isobutylbenzofuran-7-yl)-5-methoxy-1-((R)-piperidin-3-yl)pentan-1-ol using 7-bromo-2-isobutylbenzofuran and n-BuLi in Step 4.
- (S)-5-methoxy-1-((R)-piperidin-3-yl)-1-(thiophen-3-yl)pentan-1-ol using 3-bromothiophene and n-BuLi in Step 4.
- (S)-5-methoxy-1-((R)-piperidin-3-yl)-1-(pyridin-2-yl)pentan-1-ol from 2-bromopyridine and n-BuLi in Step 4.
- (S)-5-methoxy-1-((R)-piperidin-3-yl)-1-(quinolin-8-yl)pentan-1-ol from 8-bromoquinoline and n-BuLi in Step 4.
- (S)-1-(1H-indazol-7-yl)-5-methoxy-1-((R)-piperidin-3-yl)pentan-1-ol from 7-bromoindazole and n-BuLi
- (S)-5-methoxy-1-((R)-piperidin-3-yl)-1-(2-(trimethylsilyl)benzo[b]thiophen-7-yl)pentan-1-ol from 7-bromo-2-(trimethylsilyl)benzothiophene and n-BuLi in Step 4.
- (S)-5-methoxy-1-(2-methylbenzofuran-7-yl)-1-((R)-piperidin-3-yl)pentan-1-ol from 7-bromo-2-methylbenzofuran and n-BuLi in Step 4.
- (S)-1-(2-fluorobenzofuran-7-yl)-5-methoxy-1-((R)-piperidin-3-yl)pentan-1-ol from 7-bromo-2-fluorobenzofuran and n-BuLi in Step 4.
- (S)-1-(5-fluorobenzofuran-7-yl)-5-methoxy-1-((R)-piperidin-3-yl)pentan-1-ol from 7-bromo-5-fluoro-2-(trimethylsilyl)benzofuran and n-BuLi in Step 4.
- (S)-1-(2-tert-butylbenzofuran-7-yl)-5-methoxy-1-((R)-piperidin-3-yl)pentan-1-ol from 7-bromo-2-(t-butyl)benzofuran and n-BuLi in Step 4.
- (S)-5-methoxy-1-((R)-piperidin-3-yl)-1-(2-(trimethylsilyl)benzo[b]thiophen-4-yl)pentan-1-ol from 4-bromo-2-(trimethylsilyl)benzothiophene and n-BuLi in Step 4.

Example 70

(±)-(RS)-1-(3-chlorophenyl)-5-methoxy-1-((RS)-morpholin-2-yl)pentan-1-ol

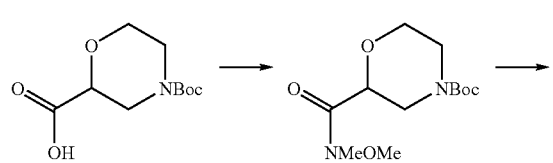

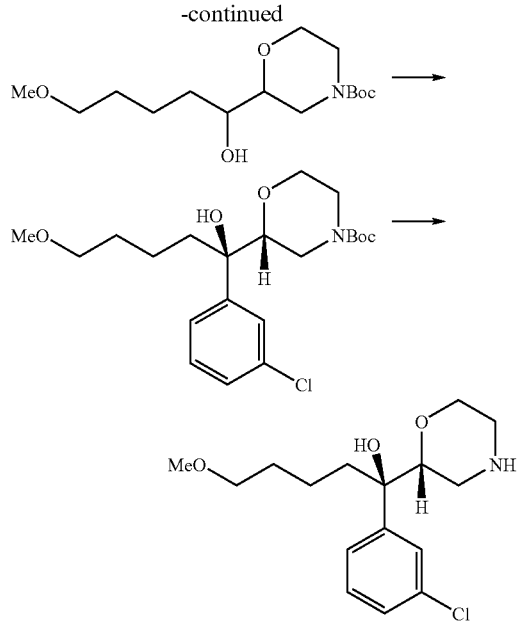

Step 1. (±)-tert-butyl 2-(methoxy(methyl)carbamoyl)morpholine-4-carboxylate

To a stirred solution of (±)-4-(tert-butoxycarbonyl)morpholine-2-carboxylic acid (1.51 g, 6.53 mmol), N,O-dimethylhydroxylamine hydrochloride (0.83 g, 8.49 mmol) and i-Pr$_2$NEt (3.1 mL, 17.6 mmol) in CH$_2$Cl$_2$ (30 mL) was added solid HATU (3.01 g, 7.85 mmol). The mixture was stirred at rt for 3 d, diluted with ether (175 mL), washed with 5% aq HCl (2×50 mL) and satd aq NaHCO3 (50 mL) and dried over MgSO$_4$. Removal of the solvent left (±)-tert-butyl 2-(methoxy(methyl)carbamoyl)morpholine-4-carboxylate (1.73 g, 96%) as an oil.

Step 2. (±)-tert-butyl 2-(5-methoxypentanoyl)morpholine-4-carboxylate

A stirred solution of (±)-tert-butyl 2-(methoxy(methyl)carbamoyl)morpholine-4-carboxylate (1.73 g, 6.4 mmol) in dry THF (40 mL) was cooled in an ice-salt bath and 1.34 M 4-methoxybutylmagnesium chloride in THF (10 mL, 1.34 mmol) was added dropwise over 3 min. The cooling bath was allowed to expire and the mixture was stirred at rt for 6 h, poured into ice cold 3% aq HCl (100 mL) and extracted with ether (2×100 mL). The combined ether extracts were washed with satd aq NaHCO$_3$ (35 mL), dried over MgSO$_4$ and concentrated to afford (±)-tert-butyl 2-(5-methoxypentanoyl)morpholine-4-carboxylate (1.78 g, 93%) as an oil.

Step 3. (±)-(R)-tert-butyl 2-((R)-1-(3-chlorophenyl)-1-hydroxy-5-methoxypentyl)morpholine-4-carboxylate A stirred solution of (±)-tert-butyl 2-(5-methoxypentanoyl)morpholine-4-carboxylate (258 mg, 0.86 mmol) in CH$_2$Cl$_2$ (5 mL) was cooled to −70 C and 0.5 M 3-chlorophenylmagnesium bromide in THF (4 mL, 2.0 mmol) was added dropwise over 5 min. The cooling bath was allowed to expire. After 1.5 h the mixture had reached rt and was poured into satd aq NaHCO$_3$ (50 mL). The mixture was extracted with ether (2×50 mL). The combined ether extracts were washed with brine (10 mL), dried over MgSO₄ and concentrated to afford an oil (398 mg). This material was chromatographed on a 12-g silica cartridge eluted with a gradient of 0-100% EtOAc in hexanes to afford (±)-(R)-tert-butyl 2-((R)-1-(3-chlorophenyl)-1-hydroxy-5-methoxypentyl)morpholine-4-carboxylate (274 mg, 76%).

Step 4. (±)-(R)-1-(3-chlorophenyl)-5-methoxy-1-((R)-morpholin-2-yl)pentan-1-ol (±)-(R)-tert-butyl 2-((R)-1-(3-chlorophenyl)-1-hydroxy-5-methoxypentyl)morpholine-4-carboxylate (274 mg, 0.66 mmol) was dissolved in MeCN (10 mL) and 5% aq HCl (5 mL) was added. The mixture was stirred at rt for 2 d. Solid K₂CO₃ (~1 g) was added to the mixture, followed by water (25 mL). The mixture was extracted with ether (2×50 mL). The combined ether extracts were washed with brine (10 mL), dried over MgSO₄ and concentrated to afford a white solid (0.15 g). This material was purified by prep HPLC to afford the TFA salt of (±)-(R)-1-(3-chlorophenyl)-5-methoxy-1-((R)-morpholin-2-yl)pentan-1-ol (163 mg, 55%) as a syrup.

Example 71

The following morpholines were prepared following procedures analogous to those described in Example 70:

(RS)-1-(3-chloro-2-fluorophenyl)-5-methoxy-1-((RS)-morpholin-2-yl)pentan-1-ol using 2-fluoro-3-chlorophenyllithium and THF as solvent in Step 3.

(RS)-1-(benzo[b]thiophen-7-yl)-5-methoxy-1-((RS)-morpholin-2-yl)pentan-1-ol using 7-lithiobenzothiophene, generated from 7-bromobenzothiophene and n-BuLi, and ether as solvent in Step 3.

(R)-1-(3-chloro-2-fluorophenyl)-5-methoxy-1-((R)-morpholin-2-yl)pentan-1-ol using (R)-4-(tert-butoxycarbonyl)morpholine-2-carboxylic acid in Step 1 and 2-fluoro-3-chlorophenyllithium and THF as solvent in Step 3.

Example 72

1,1,1-trifluoro-6-methoxy-2-(piperidin-3-yl)hexan-2-ol

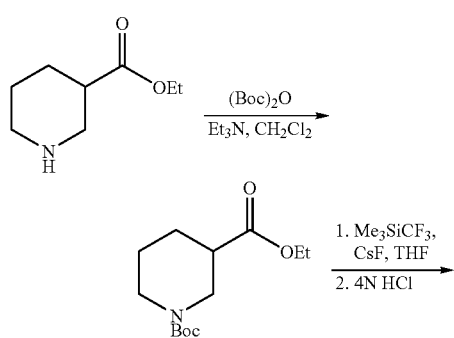

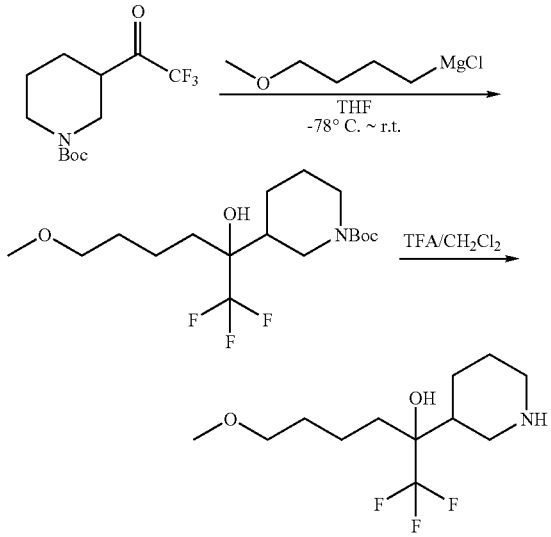

Step 1. 1-tert-butyl 3-ethyl piperidine-1,3-dicarboxylate

Ethyl nipecotate (1.55 mL, 10 mmol), (Boc)₂O (2.4 g, 1.1 equiv), triethylamine (2.8 mL, 2.1 equiv) and dichloromethane (70 mL) were mixed and stirred overnight at rt. The reaction mixture was diluted with EtOAc (200 mL), washed with 5% aq HCl (2×25 mL), sat'd aq NaHCO₃ (30 mL) and brine (20 mL), and dried over Na₂SO₄. After concentration, the crude product was purified by chromatography on a 40-g silica cartridge eluted with a 0-30% EtOAc in hexanes gradient to afford 1-tert-butyl 3-ethyl piperidine-1,3-dicarboxylate (2.61 g, 100%) as a clear oil.

Step 2. tert-butyl 3-(2,2,2-trifluoroacetyl)piperidine-1-carboxylate 1-tert-butyl 3-ethyl piperidine-1,3-dicarboxylate (424 mg, 1.65 mmol) and CsF (ca 10 mg) were combined in a vial under N₂. Dry THF (3 mL) was added, followed by Me₃SiCF₃ (256 μL, 1.05 equiv). After stirring for 3 h, 4N aq HCl (4 mL) was added to the vial and the mixture was stirred for 1 h. The mixture was extracted with diethyl ether (2×15 mL). The combined organic layers were washed with brine (8 mL), dried over Na₂SO₄, and concentrated to afford tert-butyl 3-(2,2,2-trifluoroacetyl)piperidine-1-carboxylate (173 mg. 37%)

Step 3. tert-butyl 3-(1,1,1-trifluoro-2-hydroxy-6-methoxyhexan-2-yl)piperidine-1-carboxylate Under protection of N₂ gas, tert-butyl 3-(2,2,2-trifluoroacetyl)piperidine-1-carboxylate (102 mg, 0.363 mmol) was dissolved dry THF (8 mL) and cooled to −78° C. (dry ice/acetone bath). 1.22 M methoxybutylmagnesium chloride in THF (600 μL, 2 equiv) solution was added slowly. After 10 min, the reaction was allowed to warm up to rt slowly. After 2 h, satd aq NH₄Cl (15 mL) solution was added to the reaction mixture. The mixture was diluted with diethyl ether and the layers were separated. The aqueous layer was extracted with diethyl ether (3×10 mL). The combined organic layers were washed with brine (10 mL) and dried over Na₂SO₄. After concentration, the crude product was purified by prep HPLC to afford tert-butyl 3-(1,1,1-trifluoro-2-hydroxy-6-methoxy-hexan-2-yl)piperidine-1-carboxylate (20 mg, 15%).

Step 4. 1,1,1-trifluoro-6-methoxy-2-(piperidin-3-yl)hexan-2-ol

Tert-butyl 3-(1,1,1-trifluoro-2-hydroxy-6-methoxyhexan-2-yl)piperidine-1-carboxylate (20 mg) was dissolved in 1:1 TFA/dichloromethane (4 mL). The mixture was stirred for 30 min. The mixture was concentrated to afford 1,1,1-trifluoro-6-methoxy-2-(piperidin-3-yl)hexan-2-ol which was used without purification.

Example 73

(S)-1-(3-chlorophenyl)-5-methoxy-1-((R)-piperidin-3-yl)pentan-1-ol

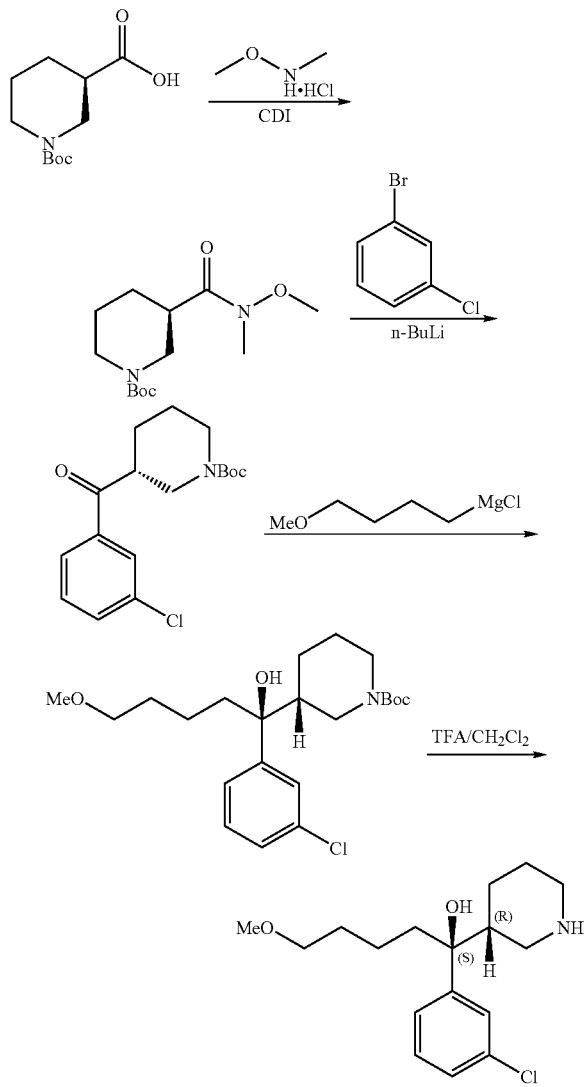

Step 1. (R)-tert-butyl 3-(methoxy(methyl)carbamoyl)piperidine-1-carboxylate

To a stirred solution of R-piperidine-1,3-dicarboxylic acid 1-tert-butyl ester (233 g, 1.2 mol) in THF (1.2 L) was added carbonyldiimidazole (230 g, 1.42 mol). The mixture was stirred for 1 h in an ice-water bath. A suspension of triethylamine (207 mL, 1.41 mol) and N,O-dimethylhydroxylamine hydrochloride (138 g, 1.42 mol) in THF (900 mL) was added. The reaction mixture was allowed to warm to rt and stirred overnight. After TLC showed the reaction was complete, solvent was evaporated to give a residue, which was dissolved in $CH_2Cl_2$ (1.2 L) and washed successively with 0.5 N aq HCl, sat'd aq $Na_2CO_3$ and brine, dried over anhydrous sodium sulfate and evaporated to give the crude compound (R)-tert-butyl 3-(methoxy(methyl)-carbamoyl)piperidine-1-carboxylate (250 g, 91%), which was used in the next step directly without purification. $^1$H NMR (400 MHz, $CDCl_3$): 1.44 (s, 9H), 1.60-1.78 (m, 2H), 1.90 (m, 1H), 2.65 (m, 1H), 2.75-2.85 (m, 2H), 3.16 (s, 3H), 3.71 (s, 3H), 4.05-4.19 (m, 2H). MS (E/Z): 273 (M+H$^+$).

Step 2. (R)-tert-butyl 3-(3-chlorobenzoyl)piperidine-1-carboxylate

To a solution of 1-bromo-3-chlorobenzene (15 g, 78.3 mmol) in anhydrous THF (150 mL) cooled to −78° C. was added dropwise a solution of 2.5 M n-BuLi in hexane (31.3 mL, 78.34 mmol). The reaction mixture was stirred at −78° C. for 1 h and a solution of (R)-tert-butyl 3-(methoxy(methyl)carbamoyl)piperidine-1-carboxylate (17.8 g, 65.3 mmol) in anhydrous THF (50 mL) was added dropwise. After addition, the mixture was allowed to warm to rt and stirred for 2 h. The mixture was quenched with saturated $NH_4Cl$ (250 mL) and extracted with EtOAc (3×150 mL). The combined organic layers were washed with brine, dried over $Na_2SO_4$ and concentrated in vacuo. The residue was purified by flash column chromatography (PE/EtOAc 5:95) to give (R)-tert-butyl 3-(3-chlorobenzoyl)piperidine-1-carboxylate (12.9 g, 51%). $^1$H NMR (400 MHz, $CDCl_3$): 1.45 (s, 9H), 1.54-1.73 (m, 2H), 1.75 (m, 1H), 2.00 (m, 1H), 2.71-2.78 (m, 1H), 2.93 (m, 2H), 3.30-3.35 (m, 1H), 4.22 (m, 1H), 7.39-7.42 (t, 1H), 7.52 (d, 1H), 7.89 (d, 1H), 7.90 (m, 1H). MS (E/Z): 324 (M+H$^+$).

Step 3. (R)-tert-butyl 3-((S)-1-(3-chlorophenyl)-1-hydroxy-5-methoxypentyl)piperidine-1-carboxylate A 250 mL three-necked flask was charged with magnesium turnings (2.88 g, 0.12 mol) and a small crystal of iodine in THF (20 mL). The flask was evacuated and refilled with $N_2$. A solution of 1-chloro-4-methoxybutane (15 g, 0.12 mol) in THF (40 mL) was added dropwise to the above mixture. After heating under reflux for 1 h, most of magnesium was consumed, the reaction mixture cooled to rt. Another 250 mL three-necked flask was charged with (R)-3-(3-chloro-benzoyl)-piperidine-1-carboxylic acid tert-butyl ester (3.24 g, 10 mmol) and THF (50 mL), which was evacuated and refilled with $N_2$. The mixture was cooled with dry ice-acetone bath and the Grignard reagent derived from 1-chloro-4-methoxybutane (20 mL) was added dropwise. After addition, the mixture was allowed to warm slowly to rt and stirred for 2 h. The mixture was quenched with sat'd aq $NH_4Cl$ (100 mL), extracted with EtOAc (3×80 mL). The combined organic layers were washed with brine, dried over $Na_2SO_4$ and concentrated in vacuo. The residue was purified by flash column chromatography (EA/PE 10:90) to give (R)-tert-butyl 3-((S)-1-(3-chlorophenyl)-1-hydroxy-5-methoxypentyl)piperidine-1-carboxylate (3.0 g, 73%). $^1$H NMR (400 MHz, $CDCl_3$): 1.45 (s, 9H), 1.52-1.58 (m, 3H), 1.75 (m, 1H), 1.92 (m, 2H), 2.52 (m, 2H), 3.25 (s, 3H), 3.27 (m, 2H), 3.95 (m, 1H), 4.35 (m, 1H), 7.20-7.26 (m, 3H), 7.36 (m, 1H). MS (E/Z): 412 (M+H$^+$).

Step 4. (S)-1-(3-chlorophenyl)-5-methoxy-1-((R)-piperidin-3-yl)pentan-1-ol (R)-tert-butyl 3-((S)-1-(3-chlorophenyl)-1-hydroxy-5-methoxypentyl)piperidine-1-carboxylate (4.1 g, 0.01 mol) was dissolved in 20% TFA/CH$_2$Cl$_2$ (40 mL). The reaction mixture was stirred at rt for 2 h, TLC showed the reaction was completed. A solution of sat'd aq Na$_2$CO$_3$ was added dropwise to adjust the pH to 8~9 and the mixture was extracted with EtOAc (3×50 mL). The combined organic layers were washed with brine, dried over Na$_2$SO$_4$ and concentrated in vacuo to give crude (S)-1-(3-chlorophenyl)-5-methoxy-1-((R)-piperidin-3-yl)pentan-1-ol (3.0 g, 97%), which was used without purification.

Example 74

The compounds listed below were prepared following procedures analogous to those described in Example 73:

(S)-1-(3-fluoro-4-methylphenyl)-5-methoxy-1-((R)-piperidin-3-yl)pentan-1-ol using 3-fluoro-4-methylbromobenzene in Step 2

(S)-5-methoxy-1-((R)-piperidin-3-yl)-1-(2,3,5-trifluorophenyl)pentan-1-ol using 2,3,5-trifluorobromobenzene in Step 2.

(S)-5-ethoxy-1-((R)-piperidin-3-yl)-1-(2,3,5-trifluorophenyl)pentan-1-ol using 2,3,5-trifluorobromobenzene in Step 2 and 4-ethoxybutylmagnesium chloride in Step 3.

(S)-1-(3-fluoro-5-methylphenyl)-5-methoxy-1-((R)-piperidin-3-yl)pentan-1-ol using 3-fluoro-5-methylbromobenzene in Step 2

(S)-1-(2-fluorophenyl)-5-methoxy-1-((R)-piperidin-3-yl)pentan-1-ol using 2-fluorobromobenzene in Step 2.

(S)-1-(3,5-difluorophenyl)-5-methoxy-1-((R)-piperidin-3-yl)pentan-1-ol using 3,5-difluorobromobenzene in Step 2.

(S)-1-(2,3-difluorophenyl)-5-methoxy-1-((R)-piperidin-3-yl)pentan-1-ol using 2,3-difluorobromobenzene in Step 2.

(S)-1-(2-fluoro-3-methylphenyl)-5-methoxy-1-((R)-piperidin-3-yl)pentan-1-ol using 2-fluoro-3-methyliododbenzene in Step 2.

(S)-1-(3-fluoro-2-methylphenyl)-5-methoxy-1-((R)-piperidin-3-yl)pentan-1-ol using 2-methyl-3-fluorobromobenzene in Step 2.

(S)-1-(2-fluoro-5-methylphenyl)-5-methoxy-1-((R)-piperidin-3-yl)pentan-1-ol using 2-fluoro-5-methylbromobenzene and n-BuLi in Step 2.

(S)-1-(5-fluoro-2-methylphenyl)-5-methoxy-1-((R)-piperidin-3-yl)pentan-1-ol using 2-methyl-5-fluorobromobenzene in Step 2.

(S)-1-(2-chlorophenyl)-5-methoxy-1-((R)-piperidin-3-yl)pentan-1-ol using 2-chlorobromobenzene in Step 2.

(S)-5-methoxy-1-((R)-piperidin-3-yl)pentan-1-ol-1-(2-(trifluoromethoxy)phenyl)pentan-1-ol using 2-(trifluoromethoxy)bromobenzene and n-BuLi in Step 2.

(S)-1-(3,5-dimethylphenyl)-5-methoxy-1-((R)-piperidin-3-yl)pentan-1-ol using 3,5-dimethylbromobenzene in Step 2.

(S)-5-methoxy-1-(3-(methylthio)phenyl)-1-((R)-piperidin-3-yl)pentan-1-ol using 3-(methylthio)bromobenzene and n-BuLi in Step 2.

(S)-1-(2-fluoro-6-methoxyphenyl)-5-methoxy-1-((R)-piperidin-3-yl)pentan-1-ol using 2-fluoro-6-methoxybromobenzene and n-BuLi in Step 2.

(S)-5-methoxy-1-((R)-piperidin-3-yl)-1-(2-(trifluoromethyl)phenyl)pentan-1-ol using 2-(trifluoromethyl)bromobenzene and n-BuLi in Step 2.

(S)-1-(5-fluoro-2-methoxyphenyl)-5-methoxy-1-((R)-piperidin-3-yl)pentan-1-ol using 2-methoxy-5-fluorobromobenzene and n-BuLi in Step 2.

(S)-5-methoxy-1-((R)-piperidin-3-yl)-1-(3-(trifluoromethoxy)phenyl)pentan-1-ol using 3-(trifluoromethoxy)bromobenzene and n-BuLi in Step 2.

(S)-1-(3-fluoro-5-methylphenyl)-5-methoxy-1-((R)-piperidin-3-yl)pentan-1-ol using 3-fluoro-5-methylbromobenzene and n-BuLi in Step 2.

(S)-1-(2,3-dimethylphenyl)-5-methoxy-1-((R)-piperidin-3-yl)pentan-1-ol using 2,3-dimethylbromobenzene and n-BuLi in Step 2.

(S)-1-(2,5-dimethylphenyl)-5-methoxy-1-((R)-piperidin-3-yl)pentan-1-ol using 2,5-dimethylbromobenzene and n-BuLi in Step 2.

(S)-5-methoxy-1-(3-methoxyphenyl)-1-((R)-piperidin-3-yl)pentan-1-ol using 3-methoxybromobenzene and n-BuLi in Step 2.

(S)-1-(2,3-difluorophenyl)-5-methoxy-1-((R)-piperidin-3-yl)pentan-1-ol using 2,3-difluorobromobenzene and n-BuLi in Step 2.

(S)-1-(3-chloro-2-methylphenyl)-5-methoxy-1-((R)-piperidin-3-yl)pentan-1-ol using 3-chloro-2-methylbromobenzene and n-BuLi in Step 2.

(S)-1-(3-chloro-5-fluorophenyl)-5-methoxy-1-((R)-piperidin-3-yl)pentan-1-ol using 3-bromo-5-chloroiodobenzene and n-BuLi in Step 2.

(S)-1-(3-chloro-2,4-difluorophenyl)-5-methoxy-1-((R)-piperidin-3-yl)pentan-1-ol using 3-chloro-2,4-difluorobromobenzene in Step 2.

(S)-1-(2-(allyloxy)-3-bromophenyl)-5-methoxy-1-((R)-piperidin-3-yl)pentan-1-ol using 2-allyloxy-1,3-dibromobenzene and n-BuLi in Step 2.

1-(2-(allyloxy)-5-fluorophenyl)-5-ethoxy-1-((R)-piperidin-3-yl)pentan-1-ol using 2-allyloxy-5-fluorobromobenzene and n-BuLi in Step 2.

(S)-5-methoxy-1-((R)-piperidin-3-yl)-1-(2,3,5-trifluorophenyl)pentan-1-ol using 2,3,5-trifluorobromobenzene and n-BuLi in Step 2.

Example 75

(S)-1-(3-chloro-2-fluorophenyl)-5-methoxy-1-((R)-piperidin-3-yl)pentan-1-ol

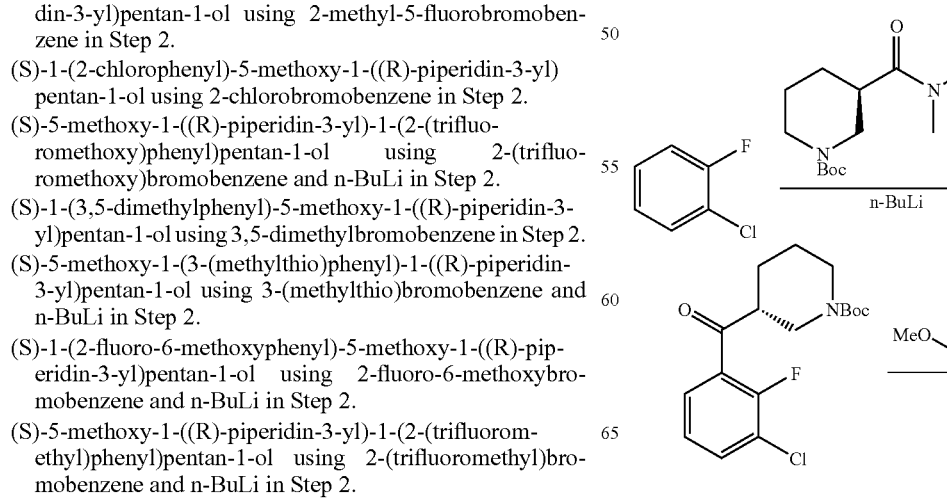

-continued

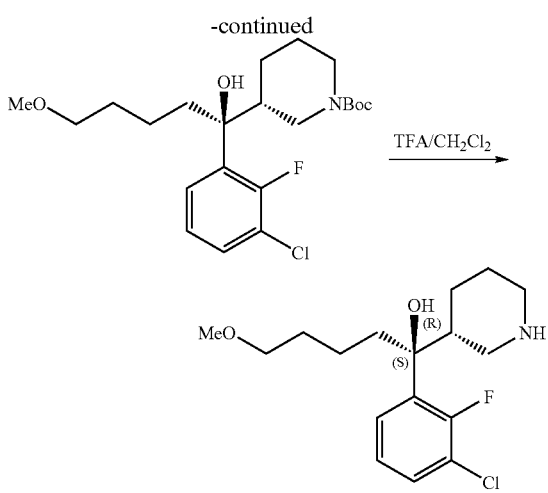

Step 1. (R)-tert-butyl 3-(3-chloro-2-fluorobenzoyl)piperidine-1-carboxylate

To a stirred solution of 1-chloro-2-fluoro-benzene (13.0 g, 0.1 mol) in THF (250 mL) at −75° C. was added dropwise 2.5 M BuLi in hexane (40 mL, 0.1 mol) during 45 min. After additional stirring for 30 min at −75° C., a solution of (R)-tert-butyl 3-(methoxy(methyl)-carbamoyl)piperidine-1-carboxylate (21.76 g, 0.08 mol) in THF (100 mL) was added dropwise over 30 min. The mixture was allowed to warm from −70° C. to 0° C. The mixture was quenched with sat'd aq $NH_4Cl$, extracted with EtOAc (3×) and the combined organic layers were dried over $Na_2SO_4$. Solvent removal and flash column chromatography, eluting with 5% EtOAc/PE afforded (R)-tert-butyl 3-(3-chloro-2-fluorobenzoyl)piperidine-1-carboxylate (19.2 g, 70%). $^1$H NMR (400 MHz, $CDCl_3$): 1.45 (s, 9H), 1.63 (m, 2H), 1.76 (m, 1H), 2.06 (m, 1H), 2.87 (m, 1H), 3.15 (m, 1H), 3.25 (m, 1H), 3.9 (m, 1H), 4.2 (m, 1H), 7.18 (m, 1H), 7.60 (m, 2H). MS (E/Z): 342 (M+H$^+$).

Step 2. (R)-tert-butyl 3-((S)-1-(3-chloro-2-fluorophenyl)-1-hydroxy-5-methoxypentyl)piperidine-1-carboxylate A flame dried 250 mL three-necked flask was charged with magnesium turnings (7.02 g, 0.293 mol), a small crystal of iodine and THF (30 mL). The flask was evacuated and refilled with $N_2$. A solution of 1-chloro-4-methoxybutane (28.69 g, 0.234 mol) in THF (120 mL) was added dropwise slowly to the mixture. The reaction mixture was stirred under reflux for 2.5 h and most of magnesium was consumed. The resulting Grignard reagent was used as follows To another 100 mL three-necked flask was added (R)-tert-butyl 3-(3-chloro-2-fluorobenzoyl)piperidine-1-carboxylate (10 g, 0.0293 mol) and THF (100 mL). The flask was evacuated and refilled with $N_2$. The mixture was cooled with dry ice-acetone bath and the Grignard reagent (250 mL) was added. The reaction mixture was allowed to warm slowly to rt while stirring overnight. The mixture was quenched with satd aq $NH_4Cl$ (50 mL), extracted with EtOAc (3×), and the combined organic layers were dried over $Na_2SO_4$. Evaporation of the solvent gave the crude product. The LC-MS analysis of the crude product indicated the presence of two isomers (95:5). Flash column chromatography, eluting with 10% EtOAc/PE afforded (R)-tert-butyl 3-((S)-1-(3-chloro-2-fluorophenyl)-1-hydroxy-5-methoxypentyl)piperidine-1-carboxylate (9.4 g, 75% yield). $^1$H NMR (400 MHz, DMSO): 0.68 (m, 1H), 1.50-1.01 (m, 7H), 1.37 (s, 9H), 1.75 (m, 2H), 2.01 (m, 1H), 3.11 (s, 3H), 3.17 (m, 2H), 3.85 (m, 1H), 7.2 (t, 1H), 7.45 (m, 2H). MS (E/Z): 430 (M+H$^+$).

Step 3. (S)-1-(3-chloro-2-fluorophenyl)-5-methoxy-1-((R)-piperidin-3-yl)pentan-1-ol A solution of (R)-tert-butyl 3-((S)-1-(3-chloro-2-fluorophenyl)-1-hydroxy-5-methoxypentyl)piperidine-1-carboxylate (100 mg) in 20% TFA/$CH_2Cl_2$ was stirred at 0° C. for 30 min. The mixture was neutralized by addition of sat'd aq $NaHCO_3$, extracted with $CH_2Cl_2$ (3×) and dried over $Na_2SO_4$. Evaporation of the solvent gave (S)-1-(3-chloro-2-fluorophenyl)-5-methoxy-1-((R)-piperidin-3-yl)pentan-1-ol (70 mg, 91%), which was used without further purification. $^1$H NMR (400 MHz, $CDCl_3$): 0.90 (m, 1H), 1.52-1.24 (m, 6H), 1.78 (m, 1H), 1.83 (m, 1H), 1.93 (m, 1H), 2.21 (m, 1H), 2.40 (m, 1H), 2.83 (m, 1H), 3.00 (m, 1H), 3.12 (s, 3H), 3.31 (m, 2H), 3.63 (m, 1H), 7.06 (m, 1H), 7.30 (m, 1H), 7.55 (t, 1H). MS (E/Z): 330 (M+H$^+$).

Example 76

The compounds listed below were prepared following procedures analogous to those described in Example 75:

(S)-1-(2,3-dichlorophenyl)-5-methoxy-1-((R)-piperidin-3-yl)pentan-1-ol using 1,2-dichlorobenzene in Step 1.

(S)-5-methoxy-1-((R)-piperidin-3-yl)-1-(2,3,4-trifluorophenyl)pentan-1-ol using 1,2,3-trifluorobenzene in Step 1.

1-(3-chloro-2-fluorophenyl)-5-ethoxy-1-((R)-piperidin-3-yl)pentan-1-ol using 4-(ethoxy)butylmagnesium chloride in Step 2.

(S)-1-(2,3-dichlorophenyl)-5-ethoxy-1-((R)-piperidin-3-yl)pentan-1-ol using 1,2-dichlorobenzene in Step 1 and 4-(ethoxy)butylmagnesium chloride in Step 2.

Example 77

(S)-1-(2-(cyclopropylmethoxy)-3-fluorophenyl)-5-methoxy-1-((R)-piperidin-3-yl)pentan-1-ol

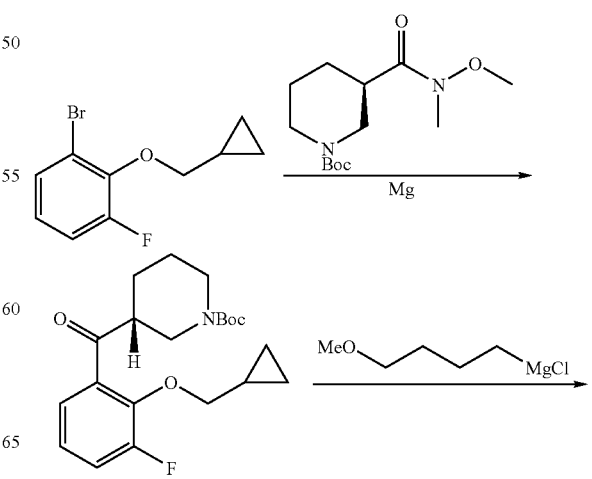

-continued

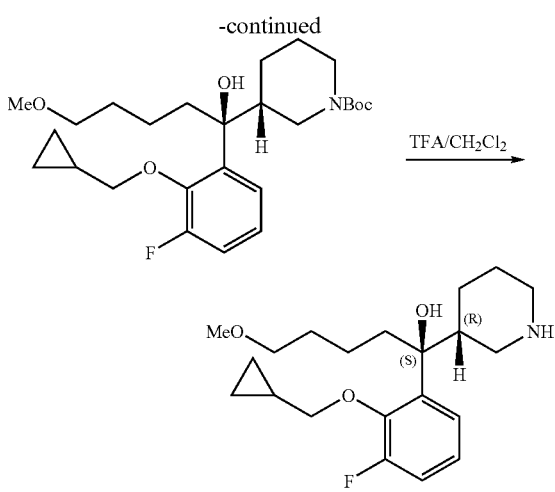

Step 1. (R)-tert-butyl 3-(2-(cyclopropylmethoxy)-3-fluorobenzoyl)piperidine-1-carboxylate A 50 mL three-necked flask was charged with magnesium turning (240 mg, 10 mmol) and a small crystal of iodine. The flash was evacuated and refilled with $N_2$. A portion of a solution of 1-bromo-2-cyclopropylmethyl-3-fluoro-benzene (2.1 g, 8.57 mmol) in dry THF (10 mL) was added dropwise to trigger the reaction. When the color of iodine had disappeared, the residual solution was added dropwise slowly. The mixture was stirred under reflux for 2.5 h and most of magnesium was consumed. The resulting Grignard reagent was used for the next step. To another 100-mL three-necked flask was added (R)-tert-butyl 3-(methoxy(methyl)carbamoyl)piperidine-1-carboxylate (1.55 g, 5.7 mmol) and THF (15 mL). The flask was evacuated and refilled with $N_2$. The mixture was cooled in a dry ice-acetone bath and the Grignard reagent prepared above (10 mL) was added slowly. The reaction mixture was stirred at −20 to −10° C. for 2.5 h. The mixture was quenched with sat'd aq $NH_4Cl$ (20 mL), extracted with EtOAc (3×), and the combined organic layers were dried over $Na_2SO_4$. Solvent removal and flash column chromatography, eluting with 5% EtOAc/PE afforded (R)-tert-butyl 3-(2-(cyclopropylmethoxy)-3-fluorobenzoyl)piperidine-1-carboxylate (1.5 g, 70%). $^1$H NMR (400 MHz, $CDCl_3$): 0.27 (m, 2H), 0.57 (m, 2H) 1.20 (m, 1H), 1.43 (s, 9H), 1.60-1.51 (m, 4H), 1.73 (m, 1H), 2.02 (m, 1H), 2.79 (m, 1H), 3.47 (m, 1H), 3.98 (m, 3H), 4.20 (m, 1H), 7.04 (m, 1H), 7.20 (m, 2H). MS (E/Z): 378 (M+H$^+$).

Step 2. (R)-tert-butyl 3-((S)-1-(2-(cyclopropylmethoxy)-3-fluorophenyl)-1-hydroxy-5-methoxypentyl)piperidine-1-carboxylate A flame dried 50 mL three-necked flask was charged with magnesium turnings (380 mg, 15.8 mmol) and a small crystal of iodine in THF (5 mL). The flask was evacuated and refilled with $N_2$. Then a solution of 1-chloro-4-methoxybutane (1.6 g, 13.2 mmol) in THF (10 mL) was added dropwise slowly to the mixture. The reaction mixture was stirred under reflux for 2.5 h and most of the magnesium was consumed. The resulting Grignard reagent was used as follows. To another 100 mL three-necked flask was added (R)-tert-butyl 3-(2-(cyclopropylmethoxy)-3-fluorobenzoyl)piperidine-1-carboxylate (0.5 g, 1.32 mmol) and THF (10 mL). The flask was evacuated and refilled with $N_2$. The mixture was cooled with a dry ice-acetone bath and the Grignard reagent (250 mL) was added. The reaction mixture was allowed to warm slowly to rt while stirring overnight. The mixture was quenched with sat'd aq $NH_4Cl$ (10 mL), extracted with EtOAc (3×), and the combined organic layers were dried over $Na_2SO_4$. Evaporation of the solvent and purification by flash column chromatography, eluting with 10% EtOAc/PE afforded (R)-tert-butyl 3-((S)-1-(2-(cyclopropylmethoxy)-3-fluorophenyl)-1-hydroxy-5-methoxypentyl)piperidine-1-carboxylate (560 mg, 91%). $^1$H NMR (400 MHz, $CDCl_3$): 0.35 (m, 2H), 0.63 (m, 2H), 1.05 (m, 1H), 1.43 (s, 9H), 1.55-1.20 (m, 9H), 1.85 (m, 1H), 2.55 (m, 1H), 2.67 (m, 1H), 3.27 (s, 3H), 3.33 (m, 2H), 3.85 (m, 1H), 4.05 (m, 2H), 4.25 (m, 1H), 6.97 (m, 3H). MS (E/Z): 466 (M+H$^+$).

Step 3. (S)-1-(2-(cyclopropylmethoxy)-3-fluorophenyl)-5-methoxy-1-((R)-piperidin-3-yl)pentan-1-ol A solution of (R)-tert-butyl 3-((S)-1-(2-(cyclopropylmethoxy)-3-fluorophenyl)-1-hydroxy-5-methoxypentyl)piperidine-1-carboxylate (120 mg) in 20% $TFA/CH_2Cl_2$ (20 mL) was stirred at 0° C. for 5 min. The solvent was neutralized by addition of sat'd aq $NaHCO_3$, and the mixture was extracted with $CH_2Cl_2$ (3×). The combined organic layers were dried over $Na_2SO_4$ and evaporated to give the crude product. LC-MS analysis of the crude product indicated the presence of two isomers (10:1). The crude product was purified by reverse phase prep HPLC to afford the major isomer, (S)-1-(2-(cyclopropylmethoxy)-3-fluorophenyl)-5-methoxy-1-((R)-piperidin-3-yl)pentan-1-ol (40 mg, 42%). $^1$H NMR (400 MHz, $CD_4O$): 0.36 (m, 2H), 0.63 (m, 2H), 0.86 (m, 1H), 1.55-1.11 (m, 1H), 1.82 (m, 1H), 2.29 (m, 2H), 2.45 (m, 1H), 2.66 (t, 1H), 2.94 (d, 1H), 3.24 (s, 3H), 3.31 (m, 2H), 3.91 (m, 2H), 6.98 (m, 2H), 726 (m, 1H). MS (E/Z): 366 (M+1). In addition, 2-fluoro-6-((S)-1-hydroxy-5-methoxy-1-((R)-piperidin-3-yl)pentyl)phenol was isolated as a byproduct.

Example 78

The following compounds were prepared using procedures analogous to those described in Example 77:

(S)-1-(2-chloro-3-fluorophenyl)-5-methoxy-1-((R)-piperidin-3-yl)pentan-1-ol using 2-chloro-3-fluorophenylmagnesium bromide prepared from 2-chloro-3-fluorobromobenzene and Mg turnings in Step 1.

(R)-1-cyclohexyl-5-methoxy-1-((R)-piperidin-3-yl)pentan-1-ol using cyclohexylmagnesium bromide prepared from bromocyclohexane and Mg turnings in Step 1.

(S)-1-(3-ethylphenyl)-5-methoxy-1-((R)-piperidin-3-yl)pentan-1-ol using 3-ethylphenyl-magnesium bromide prepared from 3-ethylbromobenzene and Mg turnings in Step 1.

(S)-1-(3-bromophenyl)-5-methoxy-1-((R)-piperidin-3-yl)pentan-1-ol using 3-bromphenyl-magnesium iodide prepared from 3-bromo-1-iodobenzene and i-PrMgBr in Step 1.

(S)-1-(2-bromo-5-fluorophenyl)-5-methoxy-1-((R)-piperidin-3-yl)pentan-1-ol using 2-bromo-5-fluorophenylmagnesium iodide prepared from 2-bromo-5-fluoro-1-iodobenzene and i-PrMgBr in Step 1.

Example 79
N-(2-((R)-(3-chloro-2-fluorophenyl)((R)-piperidin-3-yl)methoxy)ethyl)acetamide
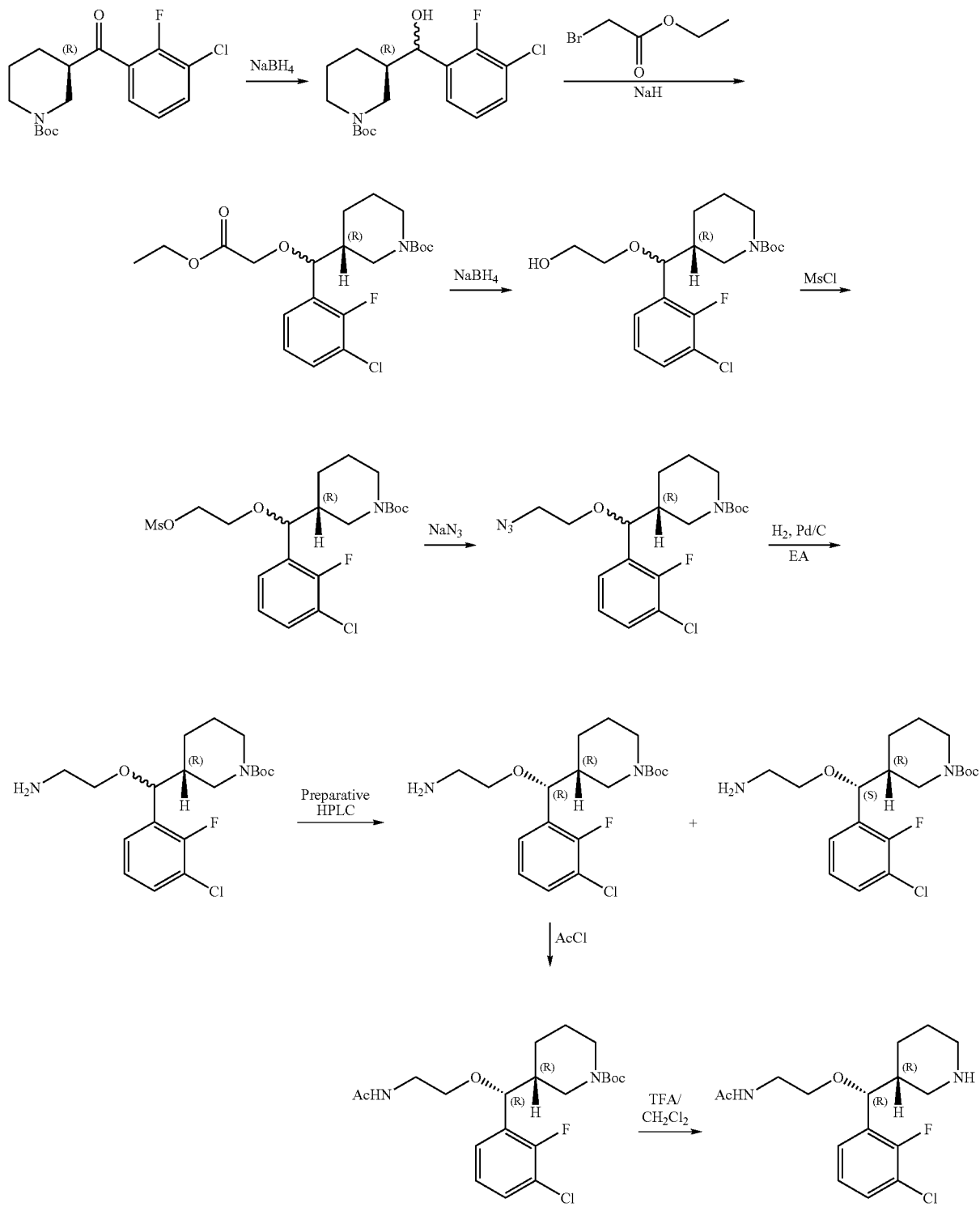

Step 1. (R)-tert-butyl 3-((3-chloro-2-fluorophenyl)(hydroxy)methyl)piperidine-1-carboxylate To a solution of (R)-tert-butyl 3-(3-chloro-2-fluorobenzoyl)piperidine-1-carboxylate (7.75 g, 22.7 mmol) in MeOH (160 mL) was added NaBH₄ (6.9 g, 182 mmol) in portions such that the temperature remained below 40° C. After addition, the mixture was stirred at rt for 3 h. TLC showed the start material had disappeared. The solvent was removed in vacuo and the residue was partitioned between water and EtOAc. The organic layer was washed with H₂O and brine, dried over Na₂SO₄ and evaporated to give (R)-tert-butyl 3-((3-chloro-2-fluorophenyl)(hydroxy)methyl)piperidine-1-carboxylate (4.35 g, 56%) which was used in the next step without purification. MS (E/Z): 344 (M+H⁺).

Step 2. (R)-tert-butyl 3-((3-chloro-2-fluorophenyl)(2-ethoxy-2-oxoethoxy)methyl)piperidine-1-carboxylate To a stirred suspension of NaH (0.608 g, 15.2 mmol) in THF (100 mL) at 0-5° C. was added dropwise a solution of (R)-tert-butyl 3-((3-chloro-2-fluorophenyl)(hydroxy)methyl)-piperidine-1-carboxylate (4.35 g, 12.68 mmol) in THF (30 mL). The reaction mixture was stirred for an additional 1 h at rt. A solution of ethyl bromoacetate (2.52 g, 15.2 mmol) in THF (30 mL) was added dropwise and the mixture was refluxed for 5 h. TLC showed the starting material had disappeared. The reaction mixture was poured into sat'd aq NH₄Cl, extracted with EtOAc (3×100 mL), dried over Na₂SO₄, filtered and concentrated in vacuo. The residue was purified by chromatography on silica gel to afford (R)-tert-butyl 3-((3-chloro-2-fluorophenyl)(2-ethoxy-2-oxoethoxy)methyl)piperidine-1-carboxylate (4.368 g, 80%). ¹H NMR (400 MHz, CDCl₃): 0.861 (m, 2H), 1.25 (m, 6H), 1.38&1.43 (s, 9H), 1.59-2.10 (m, 3H), 2.75 (m, 1H), 3.80 (s, 1H), 3.96 (m, 2H), 4.18 (m, 2H), 4.62 (m, 1H), 7.12 (m, 1H), 7.33 (m, 2H); MS (E/Z): 430 (M+1)

Step 3. (R)-tert-butyl 3-((3-chloro-2-fluorophenyl)(2-hydroxyethoxy)methyl)piperidine-1-carboxylate To a solution of (R)-tert-butyl 3-((3-chloro-2-fluorophenyl)(2-ethoxy-2-oxoethoxy)-methyl)piperidine-1-carboxylate (4.368 g, 10.2 mmol) in MeOH (85 mL) was added NaBH₄ (3.18 g, 81.5 mmol) in portions such that the temperature remained below 40° C. After addition, the mixture was stirred at rt for 2~3 h. TLC showed the starting material had disappeared. The solvent was removed in vacuo and the residue was partitioned between water and EtOAc. The organic layer was washed with H₂O and brine, dried over Na₂SO₄ and evaporated to give (R)-tert-butyl 3-((3-chloro-2-fluorophenyl)(2-hydroxyethoxy)methyl)piperidine-1-carboxylate (3.5 g, 89%). ¹H NMR (400 MHz, CDCl₃): 1.18 (m, 1H), 1.38-1.46 (s, 9H), 1.65 (m, 1H), 1.85 (m, 2H), 2.66 (m, 1H), 3.25 (m, 1H), 3.38 (m, 2H), 3.69 (m, 3H), 3.93 (m, 1H), 4.52 (m, 6H); MS (E/Z): 388 (M+1)

Step 4. (R)-tert-butyl 3-((3-chloro-2-fluorophenyl)(2-(methylsulfonyloxy)ethoxy)methyl)-piperidine-1-carboxylate To a solution of (R)-tert-butyl 3-((3-chloro-2-fluorophenyl)(2-hydroxyethoxy)methyl)-piperidine-1-carboxylate (3.5 g, 9 mmol) in dry CH₂Cl₂ (50 mL) was added Et₃N (3.2 g, 4.2 mL, 27 mmol, 4 eq) at 0~−5° C. Then a solution of MsCl (1.23 g, 10.8 mmol, 1.2 eq) in dry CH₂Cl₂ (20 mL) was added dropwise at the same temperature. After addition, the mixture was allowed to warm to rt gradually. TLC showed the starting material had disappeared. Water (30 mL) was added and the mixture was extracted with CH₂Cl₂ (3×20 mL). The combined organic layers were washed with 10% aq citric acid, sat'd aq NaHCO₃ and brine, then dried over Na₂SO₄, filtered and concentrated to give 3R-3-[(3-chloro-2-fluoro-phenyl)-(2-methanesulfonyloxy-ethoxy)-methyl]-piperidine-1-carboxylic acid tert-butyl ester (4.13 g, 99%), which was used in the next step without purification. ¹H NMR (400 MHz, CDCl₃): 1.35 (m, 4H), 1.46 (s, 9H), 1.62 (m, 3H), 1.83 (m, 1H), 2.52-2.81 (m, 2H), 3.05 (m, 3H), 3.56 (m, 2H), 3.92 (m, 1H), 4.30 (m, 2H), 4.48 (m, 1H), 7.13 (m, 1H), 7.28 (m, 1H), 7.35 (m, 1H); MS (E/Z): 466 (M+)

Step 5. (R)-tert-butyl 3-((2-azidoethoxy)(3-chloro-2-fluorophenyl)methyl)piperidine-1-carboxylate 3R-3-[(3-chloro-2-fluoro-phenyl)-(2-methanesulfonyloxy-ethoxy)-methyl]-piperidine-1-carboxylic acid tert-butyl ester (4 g, 8.6 mmol) was dissolved in anhydrous DMF (30 mL), solid NaN₃ (0.84 g, 12.9 mmol) was added and the reaction mixture was heated at 80° C. overnight. The reaction mixture was cooled to rt and EtOAc (100 mL) was added. The mixture was washed with water (3×30 mL), dried over Na₂SO₄ and evaporated. The residue was separated on a silica column to give (R)-tert-butyl 3-((2-azidoethoxy)(3-chloro-2-fluorophenyl)methyl)piperidine-1-carboxylate (2.6 g, 73%). ¹H NMR: (400 MHz, CDCl₃): 1.24 (m, 1H), 1.38&1.46 (s, 9H), 1.67 (m, 3H), 1.83 (m, 1H), 2.58-2.81 (m, 2H), 3.32 (m, 2H), 3.45 (m, 2H), 3.92 (m, 1H), 4.20 (m, 1H), 4.50 (m, 1H), 7.13 (t, 1H), 7.34 (m, 2H), 8.02 (s, 1H);

Step 6. (R)-tert-butyl 3-((R)-(2-aminoethoxy)(3-chloro-2-fluorophenyl)methyl)piperidine-1-carboxylate To a solution of (R)-tert-butyl 3-((2-azidoethoxy)(3-chloro-2-fluorophenyl)methyl)-piperidine-1-carboxylate (2.6 g, 6.31 mmol) in EtOAc (50 mL) was added wetted Pd/C (0.1 g) and the mixture was stirred overnight under a hydrogen atmosphere maintained by a balloon. The reaction mixture was filtered through a pad of Celite and the solvent was removed to give (R)-tert-butyl 3-((2-aminoethoxy)(3-chloro-2-fluorophenyl)methyl)piperidine-1-carboxylate which was submitted to reverse phase the preparative HPLC to give (R)-tert-butyl 3-((S)-(2-aminoethoxy)(3-chloro-2-fluorophenyl)methyl)piperidine-1-carboxylate (990 mg, 81%) and (R)-tert-butyl 3-((R)-(2-aminoethoxy)(3-chloro-2-fluorophenyl)methyl)piperidine-1-carboxylate (792 mg, 65%). MS (E/Z): 387 (M+H⁺).

Step 7. (R)-tert-butyl 3-((R)-(2-acetamidoethoxy)(3-chloro-2-fluorophenyl)methyl)piperidine-1-carboxylate To a solution of (R)-tert-butyl 3-((R)-(2-aminoethoxy)(3-chloro-2-fluorophenyl)methyl)-piperidine-1-carboxylate (160 mg, 0.41 mmol) and Et₃N (1 mL) at 0° C. was added acetyl chloride (32.3 mg, 0.41 mmol). The mixture was allowed to warm to rt and stirred overnight. The mixture was concentrated in vacuo to give crude (R)-tert-butyl 3-((R)-(2-acetamidoethoxy)-(3-chloro-2-fluorophenyl)methyl)piperidine-1-carboxylate (95 mg, 54%), which was used in the next step without further purification. ¹H NMR: (400 MHz, CDCl$_3$): 1.20 (m, 1H), 1.40 (s, 9H), 1.70 (m, 2H), 1.98 (s, 3H), 2.60 (m, 2H), 3.48 (m, 4H), 3.90 (m, 1H), 4.42 (m, 1H), 5.82 (m, 1H), 7.10 (m, 1H), 7.20 (m, 1H), 7.34 (m, 1H); MS (E/Z): 429 (M+1). MS (E/Z): 429 (M+)

Step 8. N-(2-((R)-(3-chloro-2-fluorophenyl)((R)-piperidin-3-yl)methoxy)ethyl)acetamide (R)-tert-butyl 3-((R)-(2-acetamidoethoxy)(3-chloro-2-fluorophenyl)methyl)piperidine-1-carboxylate (95 mg, 1.88 mmol) was dissolved in 20% v/v TFA/CH$_2$Cl$_2$ (8 mL) at 0° C., the mixture was allowed to warm to rt for 1 h and then concentrated in vacuo to give N-(2-((R)-(3-chloro-2-fluorophenyl)((R)-piperidin-3-yl)methoxy)ethyl)acetamide (63 mg, 87%), which was used without further purification. MS (E/Z): 329 (M+)

tertterttert

Example 81

(R)-3-((S)-1-(3-Chlorophenyl)-1,5-dimethoxypentyl)piperidine

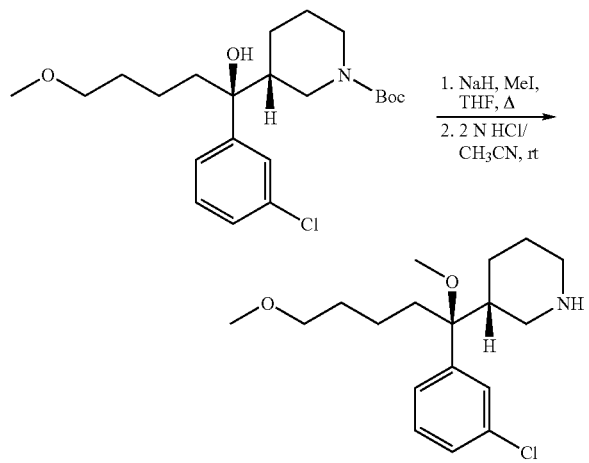

Step 1. (R)-tert-butyl 3-((S)-1-(3-chlorophenyl)-1,5-dimethoxypentyl)piperidine-1-carboxylate To a mixture of (R)-tert-butyl 3-((S)-1-(3-chlorophenyl)-1-hydroxy-5-methoxypentyl)-piperidine-1-carboxylate (0.1874 g, 0.45 mmol, 1.0 equiv) and 60% NaH in oil (0.345 g, 8.6 mmol, 19 equiv) in THF (15 mL) was added iodomethane (1.195 g, 8.4 mmol, 18.5 equiv). The resulting mixture was heated at 70° C. for 16 h and then quenched with water, extracted with EtOAc and dried over Na$_2$SO$_4$. After the solvent was removed, the crude (R)-tert-butyl 3-((S)-1-(3-chlorophenyl)-1,5-dimethoxypentyl)piperidine-1-carboxylate (0.3175 g) was used in the next step without further purification. LC-MS (3 min) t$_R$=2.44 min m/z 450, 448 (M+Na$^+$), 426 (M+H$^+$), 340, 338, 294.

Step 2. (R)-3-((S)-1-(3-chlorophenyl)-1,5-dimethoxypentyl)piperidine

A quarter of the (R)-tert-butyl 3-((S)-1-(3-chlorophenyl)-1,5-dimethoxypentyl)piperidine-1-carboxylate obtained in Step 1 (ca. 75 mg, ca. 0.1 mmol) was dissolved in CH$_3$CN (30 mL) and 2 N HCl (25 mL). The mixture was vigorously stirred at rt for 2 d. The solvents were removed in vacuo to give the HCl salt of (R)-3-((S)-1-(3-chlorophenyl)-1,5-dimethoxypentyl)-piperidine, which was used without further purification. LC-MS (3 min) t$_R$=1.22 min, m/z 328, 326 (M+H$^+$).

Example 82

(R)-3-((S)-1-(3-chloro-2-fluorophenyl)-1,5-dimethoxypentyl)piperidine (R)-3-((S)-1-(3-chloro-2-fluorophenyl)-1,5-dimethoxypentyl)piperidine was prepared using procedures analogous to those described in Example 81, using (R)-tert-butyl 3-((S)-1-(3-chloro-2-fluorophenyl)-1-hydroxy-5-methoxypentyl)piperidine-1-carboxylate in Step 1.

Example 83

1-((S)-4-(3-Chlorophenyl)-4-hydroxy-4-((R)-piperidin-3-yl)butyl)-3-methylurea

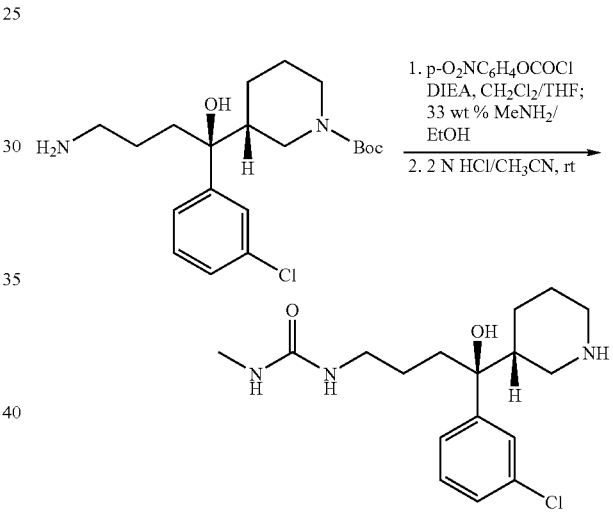

Step 1. (R)-tert-butyl 3-((S)-4-(methylaminocarbonylamino)-1-(3-chlorophenyl)-1-hydroxybutyl)-piperidine-1-carboxylate To a stirred mixture of the TFA salt of (R)-tert-butyl 3-((S)-4-amino-1-(3-chlorophenyl)-1-hydroxybutyl)piperidine-1-carboxylate (0.0388 g, 0.078 mmol, 1.0 equiv) in THF (5 mL) and CH$_2$Cl$_2$ (5 mL) at rt were added of DIEA (0.7 mL) and p-nitrophenyl chloroformate (0.0350 g, 0.17 mmol, 2.2 equiv). The mixture was stirred at rt for 3 h. One half of the resulting solution was withdrawn and 33 wt % MeNH$_2$ in EtOH (1.5 mL) was added. The resulting mixture was stirred at rt for 1 h. The solvents were removed in vacuo and the residue was purified by reversed-phase preparative HPLC (Phenomenex® Luna 5µ C18(2) 100 A, 250×21.20 mm, 5 micron, 70%→90% CH$_3$CN/H$_2$O, 0.1% CF$_3$COOH over 8 min and then 90% CH$_3$CN/H$_2$O, 0.1% CF$_3$COOH over 7 min, flow rate 25 mL/min) to give (R)-tert-butyl 3-((S)-4-(methylamino-carbonylamino)-1-(3-chlorophenyl)-1-hydroxybutyl)piperidine-1-carboxylate (0.0043 g). LC-MS (3 min) t$_R$=1.71 min, m/z 442, 440 (M+H$^+$), 340.

Step 2. 1-((S)-4-(3-chlorophenyl)-4-hydroxy-4-((R)-piperidin-3-yl)butyl)-3-methylurea A mixture of (R)-tert-butyl 3-((S)-4-(methylaminocarbonylamino)-1-(3-chlorophenyl)-1-hydroxybutyl)piperidine-1-carboxylate, CH$_3$CN (20 mL) and 2 N aq HCl (15 mL) was vigorously stirred at rt for 2 d. The solvents were removed in vacuo to give the HCl salt of 1-((S)-4-(3-chlorophenyl)-4-hydroxy-4-((R)-piperidin-3-yl)butyl)-3-methylurea, which was used without further purification. LC-MS (3 min) $t_R$=0.93 min, m/z 342, 340 (M+H$^+$).

Example 84

3-((S)-4-(3-chlorophenyl)-4-hydroxy-4-((R)-piperidin-3-yl)butyl)-1,1-dimethylurea 3-((S)-4-(3-chlorophenyl)-4-hydroxy-4-((R)-piperidin-3-yl)butyl)-1,1-dimethylurea was prepared using procedures analogous to those described in Example 83, using dimethylamine in Step 1.

Example 85

Example 86

N—((S)-4-(3-chlorophenyl)-4-hydroxy-4-((R)-piperidin-3-yl)butyl)methanesulfonamide was prepared by reaction of (R)-tert-butyl 3-((S)-4-amino-1-(3-chlorophenyl)-1-hydroxybutyl)piperidine-1-carboxylate with methanesulfonyl chloride followed by Boc removal using the conditions described in Example 83 Step 2.

Example 87

(S)-4-(Aminosulfonylamino)-1-(3-chlorophenyl)-1-((R)-piperidin-3-yl)butan-1-ol

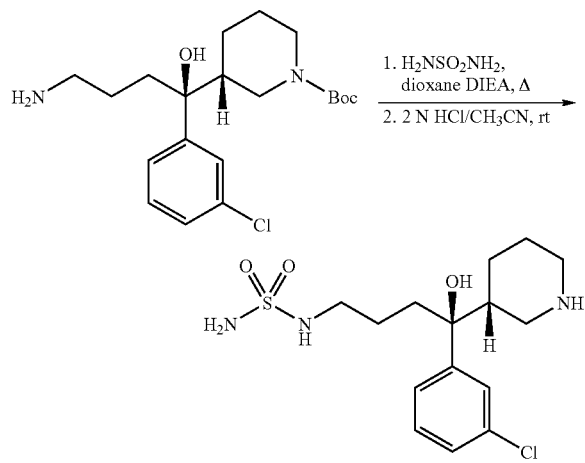

Step 1. (R)-tert-butyl 3-((S)-4-(aminosulfonylamino)-1-(3-chlorophenyl)-1-hydroxybutyl)-piperidine-1-carboxylate To a 50 mL round bottom flask were added the TFA salt of (R)-tert-butyl 3-((S)-4-amino-1-(3-chlorophenyl)-1-hydroxybutyl)piperidine-1-carboxylate (0.0803 g, 0.16 mmol, 1.0 equiv), sulfamide (0.2368 g, 2.46 mmol, 15 equiv), 1,4-dioxane (5 mL) and DIEA (1 mL). The resulting mixture was heated at 110° C. for 2 h. After the solvents were removed in vacuo, the residue was purified by reversed-phase HPLC (Phenomenex® Luna 5µ C18(2) 100 A, 250×21.20 mm, 5 micron, 70%→90% CH$_3$CN/H$_2$O, 0.1% CF$_3$COOH over 8 min and then 90% CH$_3$CN/H$_2$O, 0.1% CF$_3$COOH over 1.5 min, flow rate 25 mL/min) to give 0.0438 g (59%) of (R)-tert-butyl 3-((S)-4-(aminosulfonylamino)-1-(3-chlorophenyl)-1-hydroxybutyl)piperidine-1-carboxylate. LC-MS (3 min) $t_R$=1.74 min, m/z 486, 484 (MNa$^+$), 362.

Step 2. (S)-4-(aminosulfonylamino)-1-(3-chlorophenyl)-1-((R)-piperidin-3-yl)butan-1-ol A mixture of (R)-tert-butyl 3-((S)-4-(aminosulfonylamino)-1-(3-chlorophenyl)-1-hydroxybutyl)piperidine-1-carboxylate (0.0438 g, 0.095 mmol), CH$_3$CN (35 mL) and 2 N aq HCl (30 mL) was vigorously stirred at rt for 24 h. The solvents were removed in vacuo to give the HCl salt of (S)-4-(aminosulfonylamino)-1-(3-chlorophenyl)-1-((R)-piperidin-3-yl)butan-1-ol, which was used without further purification. LC-MS (3 min) $t_R$=0.93 min, m/z 364, 362 (MH$^+$), 285, 283.

Example 88

(R)-4-(tert-Butoxycarbonyl)morpholine-2-carboxylic acid

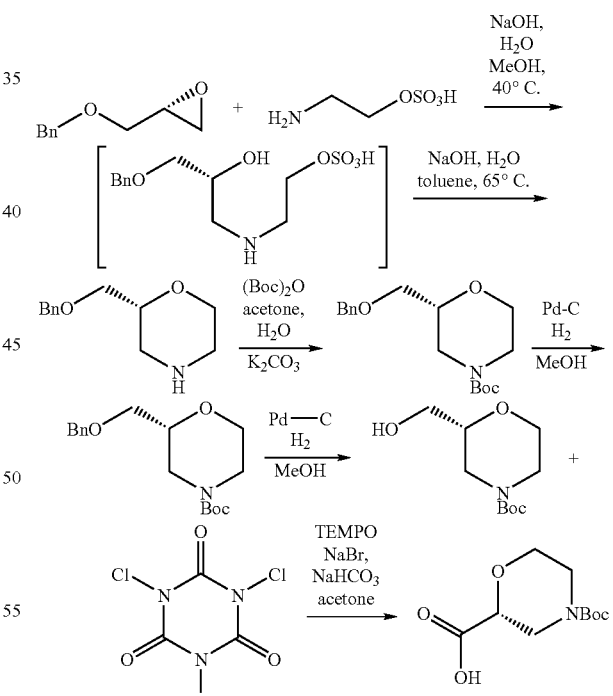

Step 1. (R)-2-(Benzyloxymethyl)morpholine

To a stirred mixture of (R)-2-(benzyloxymethyl)oxirane (10.0 g, 60.9 mmol) and NaOH (19.49 g, 487.2 mmol) in H$_2$O (46 mL) and MeOH (18 mL), there was added 2-aminoethyl hydrogen sulfate (36.8 g, 255.8 mmol) in portions. After addition the reaction mixture was stirred at 40° C. for 2 h. After cooling, the mixture was treated with NaOH (15.0 g, 375.0 mmol) then toluene (70 mL) and stirred at 65° C. overnight. The mixture was cooled, diluted with toluene (27 mL) and H$_2$O (92 mL). The toluene layer was separated and the aqueous layer was extracted with CH$_2$Cl$_2$ (2×50 mL). The combined organic layers were concentrated to give crude (R)-2-(benzyloxymethyl)morpholine (~14 g), which was used without purification. MS m/z 208 (M+H$^+$).

Step 2. (R)-tert-Butyl 2-(benzyloxymethyl)morpholine-4-carboxylate

To a solution of crude (R)-2-(benzyloxymethyl)morpholine (~14 g) in acetone (100 mL) and H$_2$O (30 mL) at 0° C., there was added K$_2$CO$_3$ (25.2 g, 182.7 mmol), followed by (Boc)$_2$O (14.6 g, 67.0 mmol). The resulting solution was warmed to rt, and stirred until no starting material remained (~30 min), acetone was removed under vacuum, and the aqueous solution was extracted with CH$_2$Cl$_2$ (4×10 mL). The combined organic layers were washed with H$_2$O (10 mL) and the solvent was removed. The residue was purified by flash column chromatography to give (R)-tert-butyl 2-(benzyloxymethyl)morpholine-4-carboxylate (8.33 g, 44% over 2 steps). $^1$H NMR (400 MHz, CDCl$_3$): 7.34 (m, 5H), 4.56 (s, 2H), 3.88 (d, 2H), 3.82 (br, 1H), 3.40 (m, 1H), 3.48 (m, 3H), 2.94 (m, 1H), 2.76 (m, 1H), 1.44 (s, 9H); MS m/z 330 (M+Na$^+$).

Step 3. (R)-tert-Butyl 2-(hydroxymethyl)morpholine-4-carboxylate

To a solution of (R)-tert-butyl 2-(benzyloxymethyl)morpholine-4-carboxylate (8.33 g, 27.1 mmol) in EtOH was added Pd—C (wet, 3.6 g), and the resulting mixture was stirred at rt under a H$_2$ balloon overnight. After filtration, the solvent was removed under vacuum, and the residue was purified by flash column chromatography to give (R)-tert-butyl 2-(hydroxymethyl)morpholine-4-carboxylate (5.84 g, 99%) as a clear oil. $^1$H NMR (400 MHz, CDCl$_3$): 3.88 (d, 2H), 3.82 (br, 1H), 3.64 (d, 1H), 3.56 (m, 3H), 2.94 (m, 1H), 2.76 (m, 1H), 1.90 (br, 1H), 1.44 (s, 9H); MS m/z 218 (M+H$^+$).

Step 4. (R)-4-(tert-Butoxycarbonyl)morpholine-2-carboxylic acid

Sat'd aq NaHCO$_3$ (15 mL) was added to a solution of (R)-tert-butyl 2-(hydroxymethyl)-morpholine-4-carboxylate (1.09 g, 5.0 mmol) in acetone (50 mL), stirred and maintained at 0° C. Solid NaBr (0.1 g, 1 mmol) and TEMPO (0.015 g, 0.1 mmol) were added. Trichloroisocyanuric acid (2.32 g, 10.0 mmol) was then added slowly within 20 min at 0° C. After addition the mixture was warmed to rt and stirred overnight. 2-Propanol (3 mL) was added, and the resulting solution was stirred at rt for 30 min, filtered through a pad of Celite, concentrated under vacuum, and treated with sat'd aq Na$_2$CO$_3$ (15 mL). The aqueous solution was washed with EtOAc (5 mL), acidified with 6 N HCl, and extracted with EtOAc (5×10 mL). The combined organic layers were dried over Na$_2$SO$_4$ and the solvent was removed to give (R)-4-(tert-butoxycarbonyl)morpholine-2-carboxylic acid (1.07 g, 92%) as a white solid. $^1$H NMR (400 MHz, CDCl$_3$): 4.20 (br, 1H), 4.12 (d, 1H), 4.02 (d, 1H), 3.84 (m, 1H), 3.62 (m, 1H), 3.04 (m, 2H), 1.44 (s, 9H); MS m/z 232 (M+H$^+$).

Example 89

6-Bromo-2-fluoro-3'-methyl-biphenyl

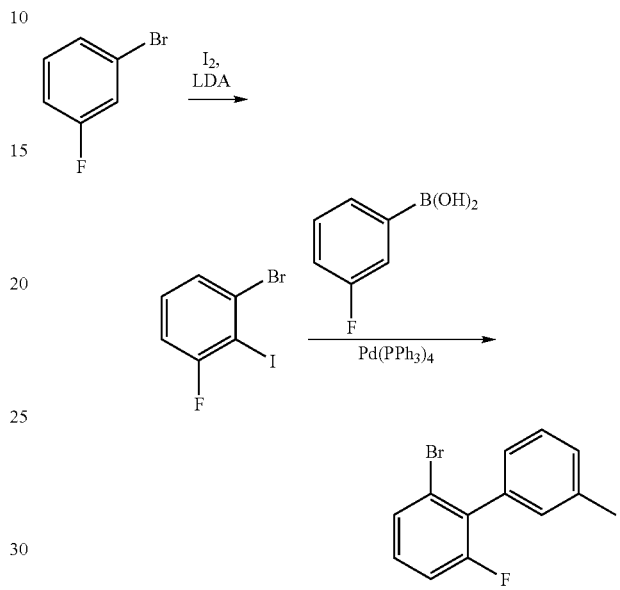

Step 1. Preparation of 1-Bromo-3-fluoro-2-iodo-benzene

To a solution of diisopropylamine (76 mL, 0.4 mol) in dry THF (664 mL) and n-hexane (220 mL) was added 2.5 M/L n-BuLi (160 mL. 0.4 mol) dropwise at −78° C. during a period of 1 h. The mixture was stirred for 1 h at −78° C. Then a solution of 1-bromo-3-fluoro-benzene (69 g, 0.4 mol) in dry THF (300 mL) at −78° C. was added to the above mixture dropwise. After stirring for an additional 1 h at −78° C., the mixture was added a solution of iodine (101 g, 0.4 mol) in dry THF (400 mL) dropwise at −78° C. The temperature was raised from −78° C. to rt during 2 h. After stirring for 18 h at rt, the mixture was concentrated in vacuo to give crude product (120 g) which was distilled under reduced pressure to afford 1-bromo-3-fluoro-2-iodo-benzene (110 g). $^1$H NMR (400 MHz, DMSO): 7.24-7.19 (t, 1H), 7.38-7.32 (m, 1H), 7.55-7.53 (d, 1H).

Step 2. 6-Bromo-2-fluoro-3'-methyl-biphenyl

Pd(Ph$_3$P)$_4$ in a 500-mL round-bottom flask under N$_2$ atmosphere was treated sequentially with a solution of 1-bromo-3-fluoro-2-iodo-benzene (30 g, 0.1 mol) in toluene (250 mL), a solution of 2N aq Na$_2$CO$_3$ (200 mL) and 3-methyl phenylboronic acid in ethanol (62 mL). This mixture was heated at reflux under N$_2$ for 12 h, then cooled to rt. The mixture was partitioned between water and EtOAc, the combined organic layers were washed with brine, dried over MgSO$_4$, evaporated and purified by column chromatography to give 6-bromo-2-fluoro-3'-methyl-biphenyl (12 g). ¹H NMR (400 MHz, CD₃OD): 7.03 (m, 2H), 7.48-7.04 (m, 4H), 7.50 (d, 1H).

Example 90

4-bromo-2-(trimethylsilyl)benzothiophene

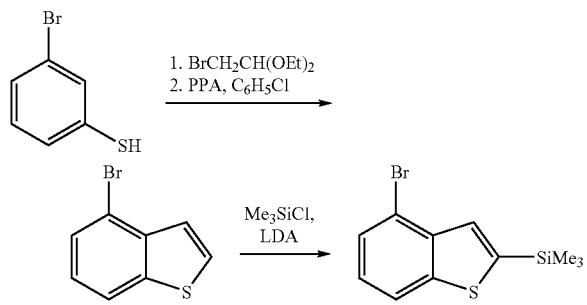

Step 1. (3-bromophenyl)(2,2-diethoxyethyl)sulfane

To a stirred solution of 3-bromothiophenol (5.0 g, 26 mmol) in DMSO (40 mL) was added a solution of KOH pellets (85% by wt, 2.15 g, 32 mmol) in water (4 mL) followed by bromoacetaldehyde diethyl acetal (4.5 mL, 29 mmol). The mixture was stirred at rt for 5 d, diluted with ether (300 mL) and washed with water (3×100 mL). The combined water washes were extracted with ether (100 mL). The combined ether extracts were washed with brine (100 mL), dried over MgSO₄ and concentrated to afford (3-bromophenyl)(2, 2-diethoxyethyl)sulfane (8.23 g, 100%) as a colorless oil.

Step 2. 4-bromobenzothiophene

A stirred mixture of (3-bromophenyl)(2,2-diethoxyethyl) sulfane (8.23 g, 26 mmol), polyphosphoric acid (20 mL) and chlorobenzene (30 mL) was heated at 130° C. for 1 h. The mixture was allowed to cool to rt and 1 M aq NaOH (100 mL) was added. The mixture was extracted with ether (2×100 mL). The combined ether extracts were washed with water (25 m) and brine (25 mL) and dried over MgSO₄. Removal of the solvent left an oil (29.55 g) which was chromatographed on a 120-g silica cartridge eluted with hexanes. Fractions containing the desired product were concentrated to afford an oil (3.33 g) which resubmitted to chromatography under the same conditions to afford ~80% pure 4-bromobenzothiophene (1.16 g, 20%).

Step 3. 4-bromo-2-(trimethylsilyl)benzothiophene

A stirred solution of ~80% pure 4-bromobenzothiophene (580 mg, 2.7 mmol) and chlorotrimethylsilane (0.70 mL, 5.4 mmol) in dry THF (10 mL) was cooled to −70° C. and 2 M LDA in 1:1 THF/heptane (1.35 mL, 5.4 mmol) was added dropwise over 2 min. The mixture was stirred at −70° C. for 1.5 h and diluted with ether (80 mL) and 5% aq HCl (20 mL). The organic layer was separated, washed with sat'd aq NaHCO₃ (20 mL) and dried over MgSO₄. Removal of the solvent left 4-bromo-2-(trimethylsilyl)benzothiophene (740 mg, 95%) as an amber oil.

Example 91

4-bromo-2-(trimethylsilyl)-benzofuran

4-Bromo-2-(trimethylsilyl)-benzofuran was made following procedures analogous to those described in Example 90, using 3-bromophenol in Step 1.

Example 92

(S)-2-(trimethylsilyl)ethyl 3-amino-5,5-dimethyl-hexyl(methyl)carbamate

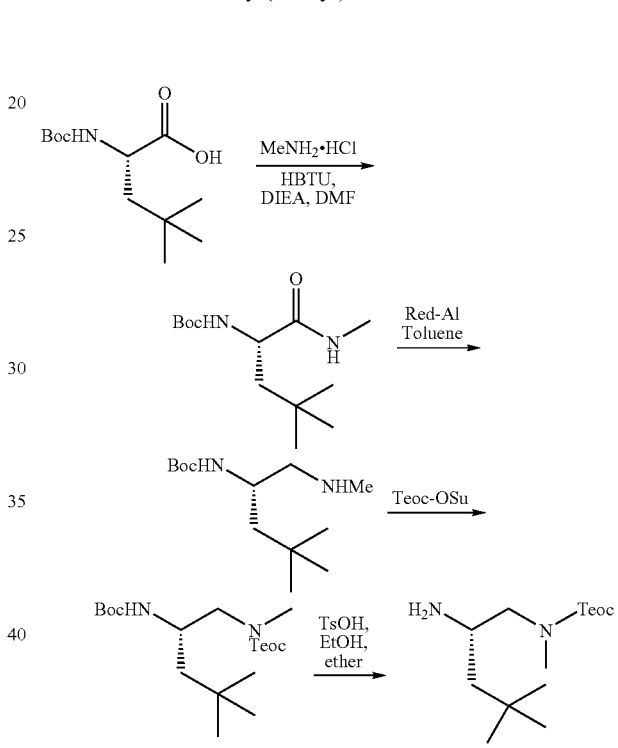

Step 1. tert-Butyl (S)-1-(methylcarbamoyl)-3,3-dimethylbutylcarbamate

To a solution of (S)-2-(t-butoxyaminocarbonylamino)-4,4-dimethylpentanoic acid (1.0 g, 4.08 mmol) and methylamine hydrochloride in DMF (10 mL) was added DIEA (2.1 mL, 12.2 mmol), followed by HBTU (1.55 g, 4.08 mmol). The resulting solution was stirred at rt until no starting material remained (~2 h). The solution was diluted with EtOAc (10 mL), washed with 1 N aq HCl (2×5 mL), sat'd aq NaHCO₃ (10 mL) and brine, and dried over Na₂SO₄. After removal of the solvent, the crude product was purified by flash column chromatography to give tert-butyl (S)-1-(methylcarbamoyl)-3,3-dimethylbutyl carbamate (1.05 g, quant.) as a clear oil. MS m/z 281 (M+Na⁺).

Step 2. tert-Butyl (S)-4,4-dimethyl-1-(methylamino) pentan-2-ylcarbamate

To a solution of tert-butyl (S)-1-(methylcarbamoyl)-3,3-dimethylbutyl carbamate (1.05 g, 4.08 mmol) in toluene (10 mL) at 0° C., there was added Red-Al (65 wt % in toluene, 3.73 mL, 12.2 mmol) dropwise. The solution was warmed to rt slowly and stirred overnight. The reaction was quenched with ice water, filtered through Celite, and solvent was removed to give tert-butyl (S)-4,4-dimethyl-1-(methylamino)pentan-2-ylcarbamate (0.79 g, 79%) as a clear oil. MS m/z 245 (M+H$^+$).

Step 3. 2-(Trimethylsilyl)ethyl (S)-2-tert-butylcarboxylamino-4,4-dimethylpentylmethyl carbamate To a solution of tert-butyl (S)-4,4-dimethyl-1-(methylamino)pentan-2-ylcarbamate (0.79 g, 3.24 mmol) in acetone (10 mL) and water (3 mL) was added K$_2$CO$_3$ (1.34 g, 9.72 mmol), followed by Teoc-OSu (0.84 g, 3.24 mmol). The resulting mixture was stirred at rt until no starting material remained (~1 h). Acetone was removed in vacuo, and the aqueous residue was extracted with CH$_2$Cl$_2$ (4×5 mL), the combined organic layers were concentrated, and the crude residue was purified by flash column chromatography to give 2-(trimethylsilyl)ethyl (S)-2-tert-butylcarboxylamino-4,4-dimethylpentylmethyl carbamate (0.74 g, 59%) as a clear oil. MS m/z 389 (M+H$^+$).

Step 4. (S)-2-(trimethylsilyl)ethyl 3-amino-5,5-dimethylhexyl(methyl)carbamate

To a solution of 2-(trimethylsilyl)ethyl (S)-2-tert-butylcarboxylamino-4,4-dimethylpentylmethyl carbamate (0.74 g, 1.90 mmol) in ether (7 mL) was added a solution of p-toluenesulfonic acid (0.37 g, 1.92 mmol) in 1.5 mL of ethanol (1.5 mL). Transfer of the p-toluenesulfonic acid was completed with the aid of ether (1 mL). The solution was placed on a rotary evaporator and the ether removed under reduced pressure at rt. Then, with continuing evacuation, the bath temperature was raised to 60-65° C. for 20 min, during which gas evolution was evident. The solid residue of the toluensulfonate salt of (S)-2-(trimethylsilyl)ethyl 3-amino-5,5-dimethylhexyl(methyl)carbamate was used without purification in the next step. MS m/z 289 (M+H$^+$).

Example 93

The following compounds were prepared using procedures analogous to those described in Example 92:
2-(trimethylsilyl)ethyl (S)-2-amino-4-methylpentylmethylcarbamate
2-(trimethylsilyl)ethyl (S)-2-aminopropylmethylcarbamate
2-(trimethylsilyl)ethyl 2-amino-3-(tetrahydro-2H-pyran-4-yl)propyl(methyl)carbamate
2-(trimethylsilyl)ethyl 2-amino-5,5,5-trifluoro-4-methylpentyl(methyl)carbamate
2-(trimethylsilyl)ethyl 2-amino-4,4,4-trifluorobutyl(methyl)carbamate
(S)-2-(trimethylsilyl)ethyl 2-amino-3-cyclopropylpropyl(methyl)carbamate
2-(trimethylsilyl)ethyl 2-amino-2-methylpropyl(methyl)carbamate.
(R)-2-(trimethylsilyl)ethyl 1-amino-3-tert-butoxypropan-2-ylcarbamate Example 94

2-(Trimethylsilyl)ethyl (2R,3R)-2-amino-3-cyclohexyl-3-hydroxypropylmethylcarbamate

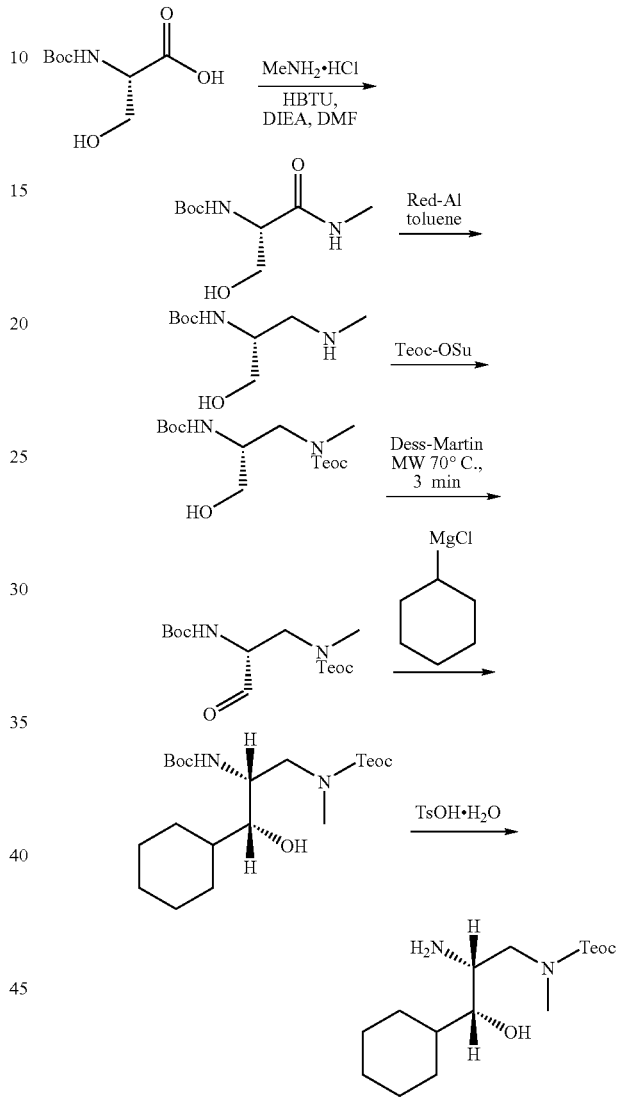

Step 1. tert-Butyl (S)-1-(methylcarbamoyl)-2-hydroxyethylcarbamate

To a solution of L-N-Boc-serine (6.33 g, 30.8 mmol) and methylamine hydrochloride (3.12 g, 46.2 mmol) in DMF (30 mL) was added DIEA (16.0 mL, 92.4 mmol), followed by HBTU (11.90 g, 31.0 mmol). The resulting solution was stirred at rt until no starting material remained (~2 h). The solution was diluted with EtOAc (30 mL), washed with 1 N aq HCl (2×10 mL), sat'd aq NaHCO$_3$ (15 mL) and brine, and dried over Na$_2$SO$_4$. After removal of the solvent, the crude product was purified by flash column chromatography to give tert-butyl (S)-1-(methylcarbamoyl)-2-hydroxyethyl carbamate (6.93 g, quant.) as a clear oil. MS m/z 219 (M+H$^+$).

Step 2. tert-Butyl (R)-3-hydroxy-1-(methylamino) propan-2-ylcarbamate

To a solution of tert-butyl (S)-1-(methylcarbamoyl)-2-hydroxyethyl carbamate (6.93 g, 30.8 mmol) in toluene (50 mL) at 0° C. was added dropwise Red-Al (65 wt % in toluene, 28.3 mL, 92.4 mmol) dropwise. The solution was warmed to rt slowly and stirred overnight. The reaction was quenched with ice water, filtered through Celite, and solvent was removed to give crude tert-butyl (R)-3-hydroxy-1-(methylamino)propan-2-ylcarbamate (~13 g) which used for next step without purification. MS m/z 205 (M+H$^+$).

Step 3. (2R)-2-(t-butoxycarbonylamino)-3-(N-methyl-N-(2-(trimethylsilyl)ethoxycarbonyl)-amino) propan-1-ol To a solution of crude tert-butyl (R)-3-hydroxy-1-(methylamino)propan-2-ylcarbamate in acetone (30 mL) and water (10 mL), there was added K$_2$CO$_3$ (12.8 g, 92.4 mmol), followed by Teoc-OSu (8.0 g, 30.8 mmol). The resulting mixture was stirred at rt until no starting material remained (~1 h). Acetone was removed under vacuum and the aqueous residue was extracted with CH$_2$Cl$_2$ (4×15 mL). The combined organic layers were concentrated and the crude residue was purified by flash column chromatography to give (2R)-2-(t-butoxycarbonylamino)-3-(N-methyl-N-(2-(trimethylsilyl)ethoxycarbonyl)amino)propan-1-ol (2.12 g, 20% steps). $^1$H NMR (400 MHz, CDCl$_3$): 5.08 (br, 1H), 4.14 (m, 2H), 3.66-3.42 (m, 4H), 3.02 (m, 1H), 2.90 (s, 3H), 1.40 (S, 9H), 0.98 (m, 2H), 0.02 (s, 9H); MS m/z 349 (M+H$^+$).

Step 4. (2-(trimethylsilyl)ethyl)(R)-2-(t-butoxycarbonylamino)-2-formylethylmethylcarbamate To a solution of tert-butyl (R)-3-hydroxy-1-(methyl-N-Teoc-amino)propan-2-ylcarbamate (0.97 g, 2.79 mmol) in 1,2-dichloroethane (10 mL) was added Dess-Martin periodinane (1.76 g, 3.63 mmol), and the resulting mixture was heated in a CEM microwave reactor at 70° C. for 3 min. The completion of the reaction was confirmed by TLC. The mixture was diluted with ether (20 mL), washed with 1 N aq NaOH (2×10 mL) and brine, and dried over Na$_2$SO$_4$. The solvent was removed to give a crude (2-(trimethylsilyl)ethyl) (R)-2-(t-butoxycarbonylamino)-2-formylethylmethylcarbamate (0.71 g, 73%), which was used without purification.

Step 5. 2-(Trimethylsilyl)ethyl (2R,3R)-2-N-tert-butylcarboxyamino-3-cyclohexyl-3-hydroxypropyl-methylcarbamate To a solution of above crude (2-(trimethylsilyl)ethyl)(R)-2-(t-butoxycarbonylamino)-2-formylethylmethylcarbamate (0.71 g, 2.05 mmol) in toluene (6 mL) at −78° C. was added cyclohexylmagnesium chloride (2 M in ether, 5.13 mL) dropwise. The resulting solution was stirred at −78° C. for 1 h, allowed to warm slowly to rt, and quenched with sat'd aq NH$_4$Cl (5 mL). The organic layer was separated, and aqueous layer was extracted with ether (2×5 mL). The combined organic layers were concentrated in vacuo, and the residue was purified by flash column chromatography to give (1R,2R)-2-(t-butoxycarbonylamino)-1-cyclohexyl-3-(N-methyl-N-(2-(trimethylsilyl)ethoxycarbonyl)amino)propan-1-ol (209.7 mg, 24%). $^1$H NMR (400 MHz, CDCl$_3$): 4.94 (d, 1H), 4.16 (m, 2H), 3.80 (m, 1H), 3.78 (m, 1H), 3.04 (m, 1H), 2.88 (m, 1H), 2.86 (s, 3H), 2.10 (m, 1H), 1.64 (m, 4H), 1.42 (m, 1H), 1.40 (s, 9H), 1.28-1.02 (m, 4H), 0.98 (m, 2H), 0.82 (m, 4H), 0.02 (s, 9H); MS m/z 431 (M+H$^+$).

Step 6. 2-(Trimethylsilyl)ethyl (2R,3R)-2-amino-3-cyclohexyl-3-hydroxypropyl methyl carbamate To a solution of 2-(trimethylsilyl)ethyl (2R,3R)-2-N-tert-butylcarboxyamino-3-cyclohexyl-3-hydroxypropylmethyl-carbamate (220 mg, 0.51 mmol) in ether (2 mL) was added a solution of p-toluenesulfonic acid (99 mg, 0.52 mmol) in 1.0 mL of ethanol. Transfer of the p-toluene-sulfonic acid was completed with the aid of ether (0.5 mL). The solution was placed on a rotary evaporator and the ether removed under reduced pressure at rt. Then, with continuing evacuation, the bath temperature was raised to 60-65° C. for 20 min, during which gas evolution was evident. The crude p-toluene-sulfonic acid salt of 2-(trimethylsilyl)ethyl (2R,3R)-2-amino-3-cyclohexyl-3-hydroxypropyl methyl carbamate obtained was used without purification. MS m/z 331 (M+H$^+$).

Example 95

2-(Trimethylsilyl)ethyl (2R,3S)-2-amino-3-cyclohexyl-3-hydroxypropylmethylcarbamate

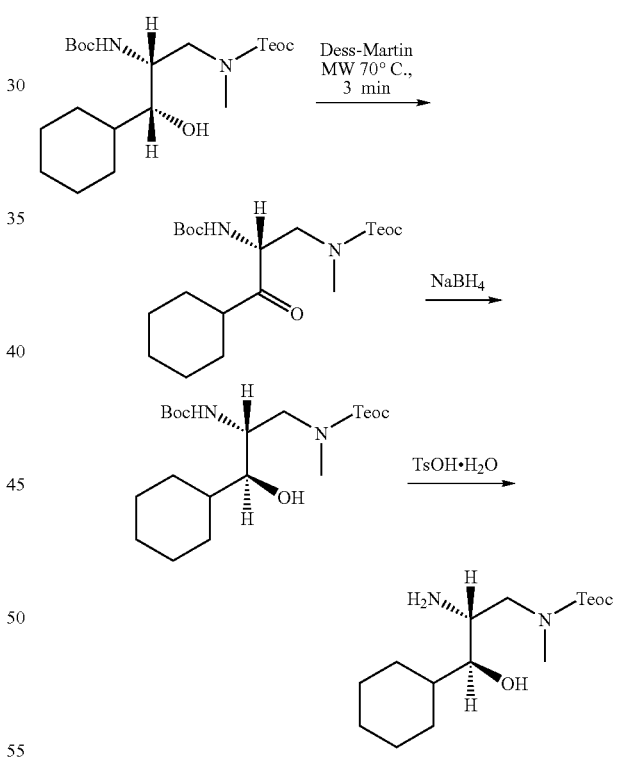

Step 1. (R)-2-(t-butoxycarbonylamino)-1-cyclohexyl-3-(N-methyl-N-(2-(trimethylsilyl)-ethoxycarbonyl)amino)propan-1-one To a solution of (1R,2R)-2-(t-butoxycarbonylamino)-1-cyclohexyl-3-(N-methyl-N-(2-(trimethylsilyl)ethoxycarbonyl)amino)propan-1-ol (0.76 g, 1.76 mmol) in 1,2-dichloroethane (4 mL) was added Dess-Martin periodinane (1.05 g, 2.29 mmol), and the resulting mixture was heated in a CEM microwave reactor at 70° C. for 3 min. Completion of reaction was confirmed by TLC. The mixture was diluted with ether (20 mL), washed with 1 N aq NaOH (2×10 mL) and brine, dried over $Na_2SO_4$, and concentrated to give crude (R)-2-(t-butoxycarbonylamino)-1-cyclohexyl-3-(N-methyl-N-(2-(trimethylsilyl)ethoxycarbonyl)amino)propan-1-one (0.74 g), which was used without purification.

Step 2. 2-(Trimethylsilyl)ethyl (2R,3S)-2-N-tert-butylcarboxyamino-3-cyclohexyl-3-hydroxypropyl methylcarbamate To a solution of (R)-2-(t-butoxycarbonylamino)-1-cyclohexyl-3-(N-methyl-N-(2-(trimethylsilyl)ethoxycarbonyl) amino)propan-1-one (0.74 g) in methanol (4 mL) at 0° C., was added $NaBH_4$ (0.11 g) in one portion. The resulting solution was stirred at 0° C. until no starting material remained (~20 min) and the reaction was quenched with ice water. Methanol was removed in vacuo and the residue was distributed between ether (10 mL) and water (10 mL). The aqueous layer was extracted with ether (2×5 mL) and the combined organic layers were concentrated. The residue was purified by flash column chromatography to give 2-(trimethylsilyl)ethyl (2R,3S)-2-N-tert-butylcarboxy amino-3-cyclohexyl-3-hydroxypropylmethyl carbamate (0.21 g, 22% two steps). $^1$H NMR (400 MHz, $CDCl_3$): 4.96 (d, 1H), 4.12 (m, 2H), 3.88 (m, 1H), 3.64 (m, 1H), 3.40-3.14 (m, 2H), 2.86 (s, 3H), 1.94 (m, 1H), 1.80-1.50 (m, 4H), 1.40 (sm, 10H), 1.18 (m, 5H), 0.98 (m, 2H), 0.02 (s, 9H); MS m/z 431 (M+H$^+$).

Step 3. 2-(Trimethylsilyl)ethyl (2R,3S)-2-amino-3-cyclohexyl-3-hydroxypropyl methylcarbamate To a solution of 2-(trimethylsilyl)ethyl (2R,3S)-2-N-tert-butylcarboxyamino-3-cyclohexyl-3-hydroxypropylmethyl-carbamate (210 mg, 0.49 mmol) in ether (2 mL) was added a solution of p-toluenesulfonic acid (95.0 mg, 0.50 mmol) in 1.0 mL of ethanol. Transfer of the p-toluenesulfonic acid was completed with the aid of ether (0.5 mL). The solution was placed on a rotary evaporator and the ether removed under reduced pressure at rt. Then, with continuing evacuation, the bath temperature was raised to 60-65° C. for 20 min, during which gas evolution was evident. The crude p-toluenesulfonate salt of 2-(trimethylsilyl)ethyl (2R,3S)-2-amino-3-cyclohexyl-3-hydroxypropyl methylcarbamate was used without further purification. MS m/z 331 (M+H$^+$).

Example 96

(2R)-2-amino-3-(N-methyl-N-(2-(trimethylsilyl)ethoxycarbonyl)amino)-1-(trimethylsilyloxy)propane

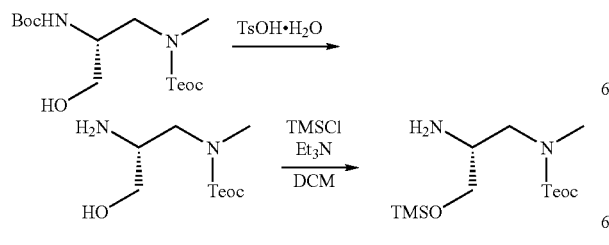

Step 1. (2-(Trimethylsilyl)ethyl)(R)-2-amino-3-hydroxypropylmethylcarbamate

To a solution of (2R)-2-(t-butoxycarbonylamino)-3-(N-methyl-N-(2-(trimethylsilyl)-ethoxycarbonyl)amino)pro-pan-1-ol (0.55 g, 1.58 mmol) in ether (5 mL) was added a solution of p-toluenesulfonic acid (0.31 g, 1.60 mmol) in ethanol (2 mL). Transfer of the p-toluenesulfonic acid was completed with the aid of ether (1 mL). The solution was placed on a rotary evaporator and the ether removed under vacuum at rt. Then, with continuing evacuation, the bath temperature was raised to 60-65° C. for 30 min, during which gas evolution was evident. The solid residue was dissolved in 1 N aq NaOH solution (5 mL) and extracted with $CH_2Cl_2$ (4×5 mL). The combined organic layers were washed with brine and dried over $Na_2SO_4$. Solvent was removed in vacuo to give (2-(trimethylsilyl)ethyl)(R)-2-amino-3-hydroxypropyl-methylcarbamate (0.35 g, 90%) as a free amine, which was without purification. MS m/z 249 (M+H$^+$).

Step 2. (2R)-2-amino-3-(N-methyl-N-(2-(trimethylsilyl)ethoxycarbonyl)amino)-1-(trimethylsilyloxy) propane To a solution of above (2-(trimethylsilyl)ethyl)(R)-2-amino-3-hydroxypropylmethyl carbamate (0.35 g, 1.41 mmol) in anhydrous $CH_2Cl_2$ (4 mL) at 0° C. was added triethylamine (1.0 mL), followed by trimethylsilyl chloride (0.54 mL, 4.23 mmol). The resulting solution was warmed to rt slowly and stirred at rt until no starting material remained (~1 h). Solvent was removed in vacuo. The residue was redissolved in $CH_2Cl_2$ (2 mL) and the solvent was again removed in vacuo to give (2R)-2-amino-3-(N-methyl-N-(2-(trimethylsilyl)ethoxycarbonyl)amino)-1-(trimethylsilyloxy)propane as a clear oil which was used for the next reaction without purification. MS m/z 321 (M+H$^+$).

Example 97

2-(Trimethylsilyl)ethyl 3-(1-hydroxycyclohexyl)-2-amino-propylmethylcarbamate

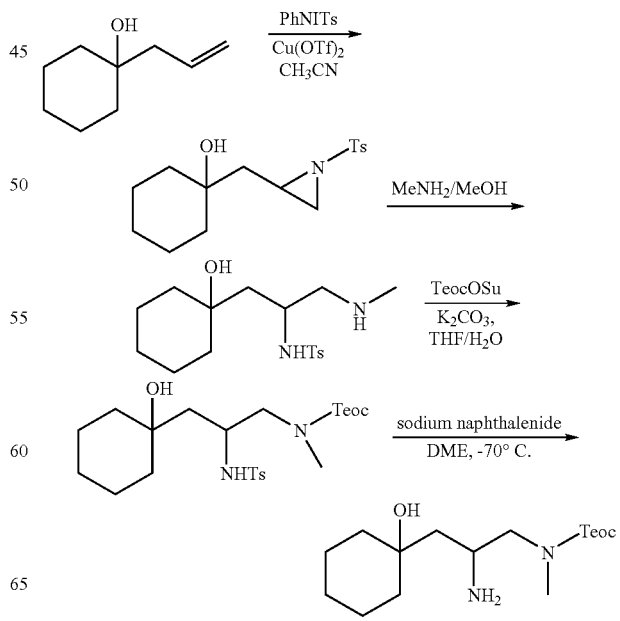

Step 1. 1-((1-Tosylaziridin-2-yl)methyl)cyclohexanol

A flame-dried 100 mL three-necked flask was purged with N₂, and charged with Cu(OTf)₂ (95 mg, 0.26 mmol), 1-allyl-cyclohexanol (960 mg, 9.86 mmol) and acetonitrile (HPLC grade). Solid [N-(p-Toluenesulfonyl)imino]phenyliodinane (PhINTs, prepared as described in *Inorgania Chimica Acta* 2003, 342, 301-304, 1.97 g, 5.28 mmol) was added in a single portion and the mixture was stirred at rt until all PhINTs had dissolved (within 5 to 30 min). The solvent was removed and the residue was chromatographied on silica gel eluted with hexane/EtOAc to give 1-((1-tosylaziridin-2-yl)methyl)cyclohexanol (217 mg, 13%). MS m/z 310 (M+H⁺).

Step 2. 1-(3-(Methylamino)-2-(tosylamino)propyl)cyclohexanol

A solution of 1-((1-tosylaziridin-2-yl)methyl)cyclohexanol (270 mg, 0.87 mmol) and methylamine in MeOH was stirred at rt for 4 h and concentrated to give 1-(3-(methylamino)-2-(tosylamino)propyl)cyclohexanol. The crude product was used in the next step without purification. MS m/z 341 (M+H⁺).

Step 3. 2-(Trimethylsilyl)ethyl 3-(1-hydroxycyclohexyl)-2-(tosylamino)propylmethylcarbamate To a solution of 1-(3-(methylamino)-2-(tosylamino)propyl)cyclohexanol in 3:1 THF/H₂O v/v (4 mL) was added K₂CO₃ (240 mg, 1.74 mmol), followed by Teoc-OSu (248 mg, 0.96 mmol). The resulting solution was stirred at rt for 30 min and the organic solvent was removed under reduced pressure. The residue was extracted with EtOAc (2×). The combined organic phases were washed with brine, dried, filtered and concentrated under vacuum. The residue was chromatographied on silica gel to give 2-(trimethylsilyl)ethyl 3-(1-hydroxycyclohexyl)-2-(tosylamino)propylmethylcarbamate (300 mg, 74% for two steps). MS m/z 469 (M+H⁺).

Step 4. 2-(Trimethylsilyl)ethyl 3-(1-hydroxycyclohexyl)-2-amino-propylmethylcarbamate Sodium naphthalenide solution was prepared as described in *J. Org. Chem.* 1989, 54, 1548-1562. To a well stirred, cooled (−70° C.) solution of 2-(trimethylsilyl)ethyl 3-(1-hydroxycyclohexyl)-2-(tosylamino)propylmethyl carbamate (113 mg, 0.233 mmol) in anhydrous DME (20 mL) under a N₂ atmosphere was added dropwise freshly prepared sodium naphthalenide solution until a light green color persisted. The reaction was quenched with water, diluted with EtOAc and washed with 1 N aq HCl. The acidic aqueous phase was basified with K₂CO₃, and extracted with EtOAc (2×). The combined organic phases were dried over anhydrous Na₂SO₄, filtered and evaporated under reduced pressure to give pure 2-(trimethylsilyl)ethyl 3-(1-hydroxycyclohexyl)-2-amino-propylmethylcarbamate (36.6 mg, 43.6%). MS m/z 331 (M+H⁺).

Example 98

1-(2-(N-methyl-N-(2-(trimethylsilyl)ethoxycarbonyl)amino)-3-(p-nitrophenoxycarbonylamino)propyl)-1-(trimethylsilyloxy)cyclohexane

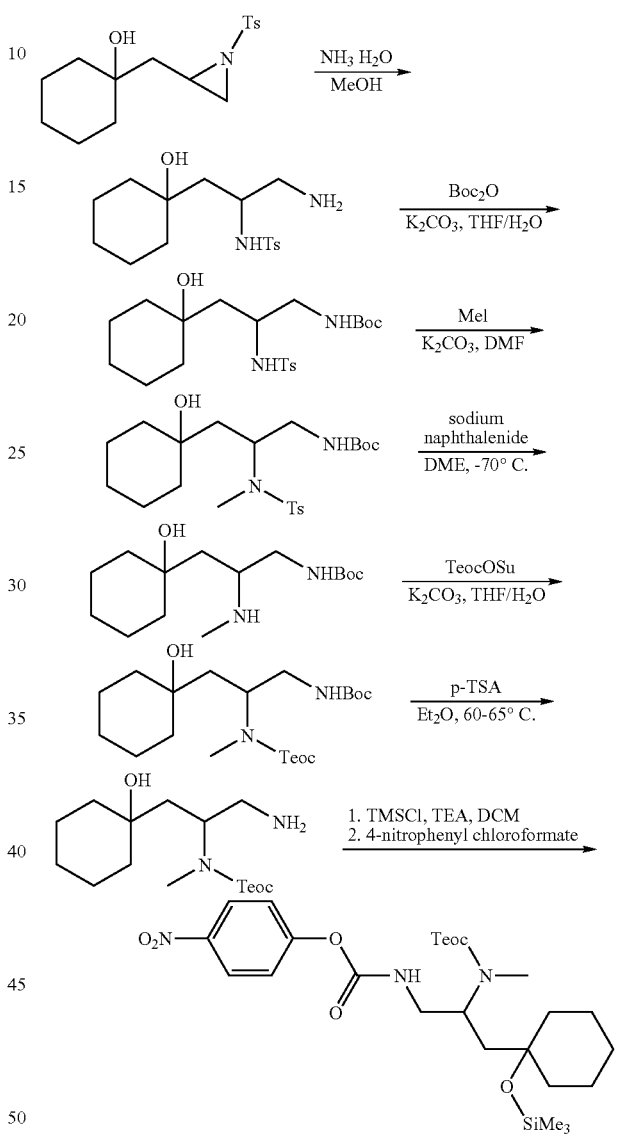

Step 1. 1-(3-Amino-2-(tosylamino)propyl)cyclohexanol

To a solution of 1-((1-tosylaziridin-2-yl)methyl)cyclohexanol (107 mg, 0.346 mmol) in MeOH (2 mL) was added satd aq ammonia (2 mL). The resulting solution was stirred at rt for 4 h and concentrated to give 1-(3-amino-2-(tosylamino)propyl)cyclohexanol which was used for the next step without purification. MS m/z 327 (M+H⁺).

Step 2. tert-Butyl 3-(1-hydroxycyclohexyl)-2-(tosylamino)propylcarbamate

To a solution of above 1-(3-amino-2-(tosylamino)propyl)cyclohexanol in 3:1 THF/H₂O v/v (4 mL) was added K₂CO₃

(143 mg, 1.038 mmol), followed by Boc$_2$O (80 mg, 0.367 mmol). The resulting solution was stirred at rt for 30 min and the organic solvent was removed under reduced pressure. The aqueous residue was extracted with EtOAc (2×). The combined organic layers were washed with brine, dried, filtered and concentrated in vacuo. The residue was chromatographed on silica gel to give tert-butyl 3-(1-hydroxycyclohexyl)-2-(tosylamino)-propylcarbamate (138 mg, 91% for two steps). MS m/z 449 (M+Na$^+$).

Step 3. tert-Butyl 3-(1-hydroxycyclohexyl)-2-(N-methyl-N-tosylamino)propyl carbamate To a solution of tert-butyl 3-(1-hydroxycyclohexyl)-2-(tosylamino)propylcarbamate (115 mg, 0.27 mmol) in dry DMF (2 mL) was added K$_2$CO$_3$ (110 mg, 0.80 mmol). The mixture was stirred at rt for 30 min before MeI (57.5 mg, 25 µL, 0.41 mmol) was added. The mixture was stirred for 1 h and the organic solvent was removed under vacuum. The residue was partitioned between EtOAc and H$_2$O. The separated aqueous phase was extracted with EtOAc (2×) and the combined organic phases were washed with brine and dried over Na$_2$SO$_4$. Removal of the solvent under reduced pressure gave crude tert-butyl 3-(1-hydroxycyclohexyl)-2-(N-methyl-N-tosylamino)propyl carbamate (117 mg), which was used without further purification. MS m/z 463 (M+Na$^+$).

Step 4. tert-Butyl 3-(1-hydroxycyclohexyl)-2-(methylamino)propylcarbamate

To a well-stirred, cooled (−70° C.) solution of crude tert-butyl 3-(1-hydroxycyclohexyl)-2-(N-methyl-N-tosylamino) propyl carbamate (117 mg, ca. 0.27 mmol) in anhydrous DME (20 mL) under N$_2$ atmosphere was added freshly prepared sodium naphthalenide solution dropwise until a light green color persisted. The reaction was quenched with water, diluted with EtOAc, washed with H$_2$O and brine successively, and dried over Na$_2$SO$_4$. Removal of the solvent afforded a mixture of tert-butyl 3-(1-hydroxycyclohexyl)-2-(methylamino)propylcarbamate and naphthalene which was used for next step without further purification. MS m/z 287 (M+H$^+$).

Step 5. 1-(3-(t-butoxycarbonylamino)-2-(N-methyl-N-(2-(trimethylsilyl)ethoxycarbonyl)-amino)propyl)cyclohexanol To a solution of above mixture of tert-butyl 3-(1-hydroxycyclohexyl)-2-(methylamino)-propylcarbamate and naphthalene in 3:1 THF/H$_2$O V/V (4 mL) was added K$_2$CO$_3$ (100 mg, 0.72 mmol), followed by Teoc-OSu (70 mg, 0.27 mmol). The resulting solution was stirred at rt for 30 min and the organic solvent was removed under reduced pressure. The residue was extracted with EtOAc (2×). The combined organic phases were washed with brine, dried, filtered, and concentrated under vacuum. The residue was chromatographed on silica gel to give 1-(3-(t-butoxycarbonylamino)-2-(N-methyl-N-(2-(trimethylsilyl)ethoxycarbonyl)amino) propyl)cyclohexanol (100 mg, 86% for three steps). MS m/z 453 (M+Na$^+$).

Step 6. 1-(3-Amino-2-(N-methyl-N-(2-(trimethylsilyl)ethoxycarbonyl)amino)propyl)cyclohexanol A solution of p-TsOH.H$_2$O (25 mg) in ethanol (0.5 mL) was added to 1-(3-(t-butoxy-carbonylamino)-2-(N-methyl-N-(2-(trimethylsilyl)ethoxycarbonyl)amino)propyl)cyclohexanol (50 mg, 0.12 mmol) dissolved in ether (12 mL). The transfer was completed with additional ether (2 mL). The resulting solution was evaporated under reduced pressure at rt to remove Et$_2$O and heated at 60-65° C. for 20 min under reduced pressure to remove ethanol. The residue was dissolved in MeOH and aqueous K$_2$CO$_3$ was added. The mixture was evaporated and extracted with EtOAc (3×). The combined organic phases were dried over Na$_2$SO$_4$, filtered and evaporated to give 1-(3-amino-2-(N-methyl-N-(2-(trimethylsilyl)ethoxycarbonyl)-amino)propyl)cyclohexanol (43 mg, 89%). MS m/z 453 (M+Na$^+$).

Step 7. 1-(2-(N-methyl-N-(2-(trimethylsilyl)ethoxycarbonyl)amino)-3-(p-nitrophenoxycarbonyl-amino) propyl)-1-(trimethylsilyloxy)cyclohexane To a solution of 1-(3-amino-2-(N-methyl-N-(2-(trimethylsilyl)ethoxycarbonyl)amino)-propyl)cyclohexanol (21 mg, 0.064 mmol) in CH$_2$Cl$_2$ (2 mL) were added Et$_3$N (0.2 mL) and Me$_3$SiCl (13.9 mg, 16 µL, 0.13 mmol). The resulting solution was stirred for 1 h and evaporated under vacuum. The residue was dissolved in CH$_2$Cl$_2$ (2 mL) and pyridine (0.05 mL) was added, followed by 4-nitrophenyl chloroformate (15 mg, 0.077 mmol). The mixture was stirred for 30 min to afford a solution of 1-(2-(N-methyl-N-(2-(trimethylsilyl) ethoxycarbonyl)amino)-3-(p-nitrophenoxycarbonylamino) propyl)-1-(trimethylsilyloxy)cyclohexane which was used directly without isolation.

Example 99

(2-(Trimethylsilyl)ethyl)(S)-2-amino-3-(4-methylcyclohexyl)propylmethylcarbamate

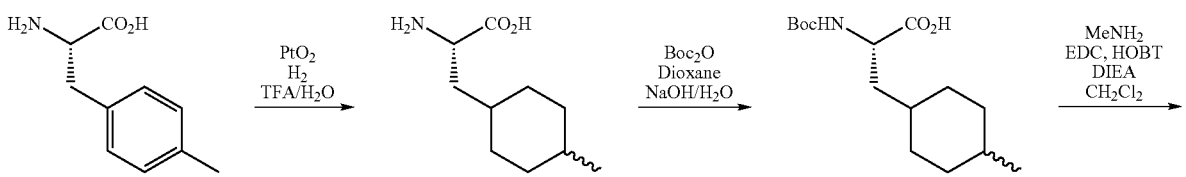

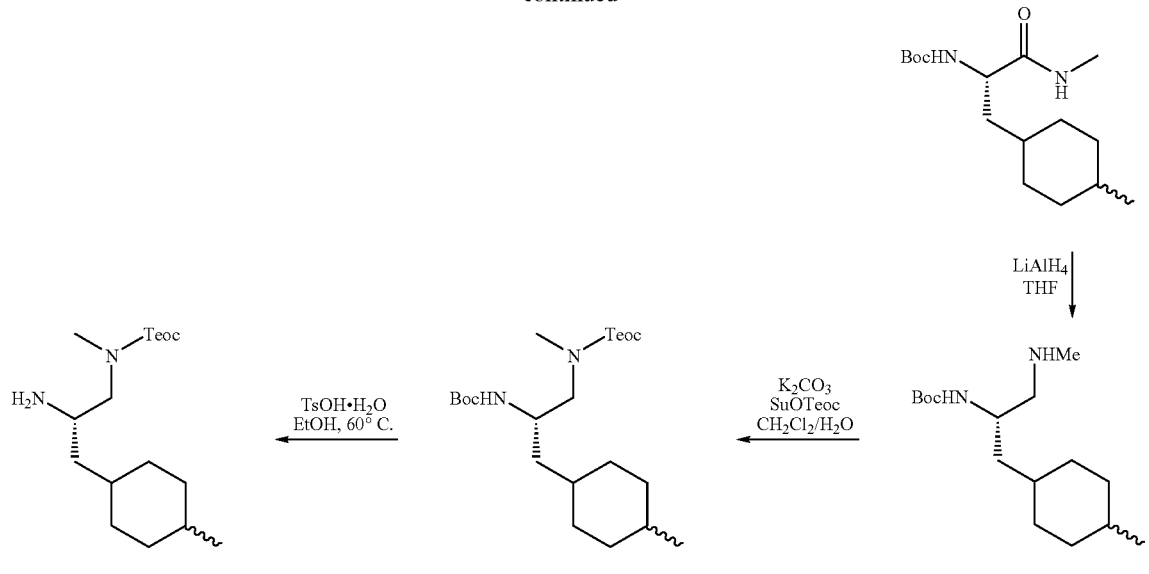

Step 1.
(S)-2-amino-3-(4-methylcyclohexyl)propanoic acid

A 250 mL Parr shaker vessel was charged with of 4-methylphenylalanine (1.0 g, 5.6 mmol), PtO$_2$ (63 mg, 0.28 mmol, 5 mol %) and 1:1 TFA/water (10 mL). The vessel was placed in a Parr hydrogenation shaker and pressurized/evacuated with hydrogen gas (3×), then pressurized to 50 psi. The reaction vessel was shaken for 2 d, then carefully vented. Analysis of the mixture by LC-MS showed no remaining starting material and two peaks with the desired mass, consistent with a ca 1:1 mixture of cis:trans isomers. The contents were filtered through a pad of Celite and the spent catalyst washed with additional water. The clear filtrate was evaporated to afford the TFA salt of (S)-2-amino-3-(4-methylcyclohexyl)propanoic acid, which used directly in the next step.

Step 2. (S)-2-(tert-butoxycarbonylamino)-3-(4-methylcyclohexyl)propanoic acid The crude TFA salt of (S)-2-amino-3-(4-methylcyclohexyl)propanoic acid from Step 1 was dissolved in dioxane (20 mL) and 0.67 M aq NaOH (30 mL). The pH of the solution was raised to >14 by addition of solid KOH, then di-tert-butyl dicarbonate (3.03 g, 13.9 mmol, 1.05 equiv) was added. After stirring for 1 h, LC-MS analysis showed ca. 80% conversion to the desired carbamate. Addition di-tert-butyl dicarbonate (600 mg) was added and the mixture stirred overnight. After this time all the free amine had been consumed. The mixture was cooled to 0° C. and solution pH lowered to <4 by addition of sat'd aq citric acid. Most of the dioxane was removed using a rotary evaporator and the aqueous residue was extracted with EtOAc (5×25 mL). The combined organic extracts were dried over Na$_2$SO$_4$, filtered and evaporated to yield (S)-2-(tert-butoxycarbonylamino)-3-(4-methylcyclohexyl)propanoic acid as a tacky solid.

Step 3. tert-Butyl (S)-1-(methylcarbamoyl)-2-(4-methylcyclohexyl)ethylcarbamate A mixture of (S)-2-(tert-butoxycarbonylamino)-3-(4-methylcyclohexyl)propanoic acid (2.080 g, 7.29 mmol, 1.0 equiv), EDC.HCl (3.308 g, 2.37 equiv), HOBt (1.752 g, 1.78 equiv), DIEA (7.6 mL, 6 equiv) and 33% wt. methylamine in EtOH (2.771 g, 4 equiv) in CH$_2$Cl$_2$ (80 mL) was stirred at rt for 21 h. The solvents were removed in vacuo and 1 N aq HCl (200 mL) was added. The mixture was extracted with EtOAc (3×). The combined organic extracts were washed with brine and dried over Na$_2$SO$_4$. After the solvents were removed in vacuo, the residue was purified by reversed-phase HPLC (Phenomenex® Luna 5μ C18(2) 100 A, 250×21.20 mm, 5 micron, 10%→90% CH$_3$CN/H$_2$O, 0.1% CF$_3$COOH over 13 min and then 90% CH$_3$CN/H$_2$O, 0.1% CF$_3$COOH over 3.5 min, flow rate 25 mL/min) to give tert-butyl (S)-1-(methylcarbamoyl)-2-(4-methylcyclohexyl)ethylcarbamate (1.0167 g, 47%). LC-MS (3 min) t$_R$=1.72 min, m/z 321 (M+Na$^+$), 243, 199; $^1$H NMR (400 MHz, CDCl$_3$) δ 6.27 (br s, 1H), 4.91 (br s, 1H), 4.11-4.07 (m, 1H), 2.802, 2.798 (d, J=4.8 Hz, 3H), 1.85-1.20 (m, 21H), 0.886, 0.851 (d, J=6.4 Hz, 3H).

Step 4. tert-Butyl (S)-1-(methylamino)-3-(4-methylcyclohexyl)propan-2-ylcarbamate To a solution of tert-butyl (S)-1-(methylcarbamoyl)-2-(4-methylcyclohexyl)ethylcarbamate (1.0075 g, 3.38 mmol, 1.0 equiv) in THF (40 mL) at 0° C. under N$_2$ was added 1.0 M LiAlH$_4$ in THF (7 mL, 7 mmol, 2.1 equiv). The mixture was stirred at rt for 19 h and sodium sulfate decahydrate (6.45 g, 20 mmol) was added carefully to quench excess LiAlH$_4$. The mixture was filtered and the solid was washed with ether. After the solvents were removed in vacuo, the crude product (1.04 g) was used in the next step without further purification. LC-MS (3 min) t$_R$=1.37 min, m/z 285 (MH$^+$), 229.

Step 5. 2-(Trimethylsilyl)ethyl (S)-2-amino-3-(4-methylcyclohexyl)propylmethylcarbamate A mixture of tert-butyl (S)-1-(methylamino)-3-(4-methylcyclohexyl)propan-2-ylcarbamate (1.04 g), obtained as described above, K$_2$CO$_3$ (2.17 g, 15.7 mmol, 4.65 equiv), Teoc-OSu (1.53 g, 5.90 mmol, 1.75 equiv), H$_2$O (20 mL) and CH$_2$Cl$_2$ (100 mL) was stirred vigorously at rt for 4 h. The mixture was diluted brine and extracted with CH$_2$Cl$_2$ (3×). The combined organic extracts were dried over Na$_2$SO$_4$ and concentrated in vacuo. The residue was purified by column chromatography (40 g silica gel cartridge, 0%→30% EtOAc/hexanes over 30 min, flow rate 40 mL/min) to give (0.534 g, 37% in two steps) of N-Boc-N'-Teoc protected diamine which was used in the next step. LC-MS $t_R$=2.60 min in 3 min chromatography, m/z 451 (MNa$^+$), 301.

A mixture of N-Boc-N'-Teoc protected diamine (0.534 g, 1.25 mmol, 1.0 equiv) and TsOH.H$_2$O (0.234 g, 1.23 mmol, 0.99 equiv) in ethanol was heated with a 60° C. water bath and the solvent was removed under reduced pressure. 1 N aq NaOH (3 mL) was added to the residue. After water was removed in vacuo, the residue was extracted with CH$_2$Cl$_2$. The organic extract was dried over Na$_2$SO$_4$, filtered through an HPLC filter and dried in vacuo to give of 2-(trimethylsilyl)ethyl (S)-2-amino-3-(4-methylcyclohexyl)-propylmethyl-carbamate (0.3492 g, 85%). LC-MS $t_R$=1.59 min in 3 min chromatography, m/z 329 (MH$^+$), 301.

Example 100

2-(2-(trimethylsilyl)ethoxycarbonylamino)-1-(3,3-difluorocyclobutyl)-3-(N-(t-butoxycarbonyl)-N-methylamino)-propane

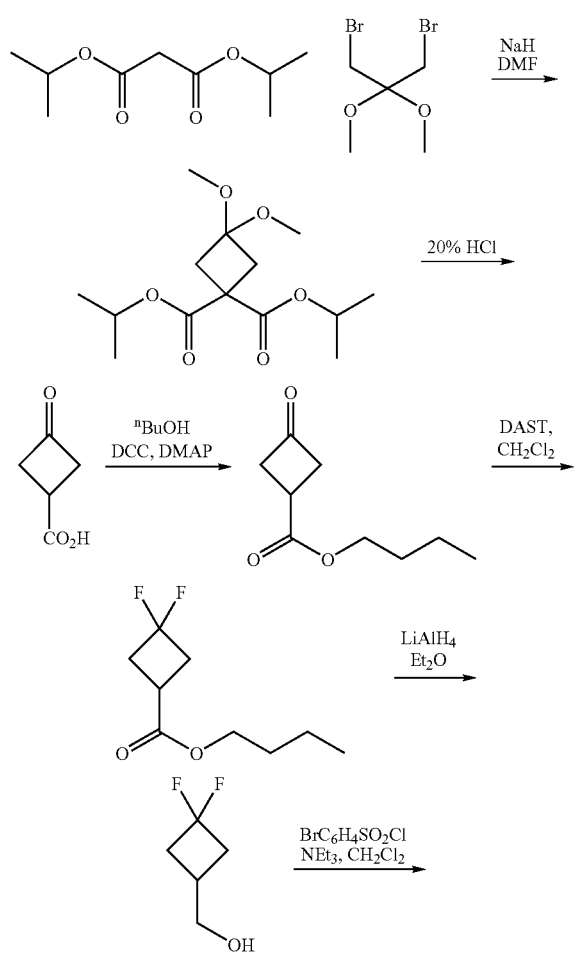

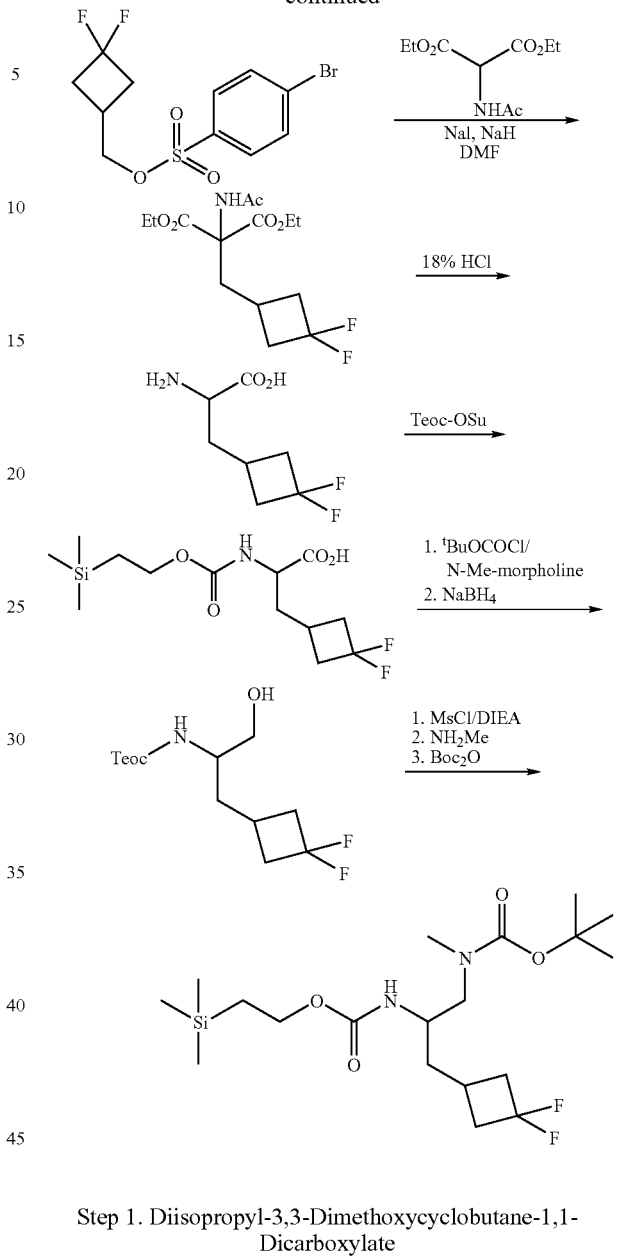

Step 1. Diisopropyl-3,3-Dimethoxycyclobutane-1,1-Dicarboxylate

Following the procedure of Pigou and Scheisser (*J. Org. Chem.* 1988, 53, 3841), a 500 mL, 3-neck flask, fitted with a reflux condenser and thermocouple, was charged with NaH (60% in mineral oil, 4 g, 0.210 mol). DMF (100 mL) was added via syringe and the slurry was stirred under N$_2$. Diisopropyl malonate was added at a rate so that the internal temperature did not rise above 70° C. After the H$_2$ evolution had ceased, the flask was briefly opened and 1,3-dibromo-2,2-dimethoxypropane was added. The bath temperature was raised to 145° C. The reaction mixture was maintained at this temperature for 48 h. After this time the dark brown mixture was allowed to cool to rt. Water (50 mL) was added and the solvents were removed in vacuo. The residue was partitioned between ether (200 mL) and sat'd aq NH$_4$Cl (200 mL) and the mixture filtered through a pad of Celite to remove solid impurities. The aqueous layer was extracted with ether (2×100 mL). The combined ether extracts were washed with brine, dried over Na$_2$SO$_4$, filtered and evaporated. Flash chromatography (SiO$_2$, O-25% EtOAc in hexanes) gave semi-pure diisopropyl-3,3-dimethoxycyclobutane-1,1-dicarboxylate (28.5 g), which was used in the next step.

Step 2. 3-Oxocylobutanecarboxylic Acid

Diisopropyl-3,3-dimethoxycyclobutane-1,1-dicarboxylate (28.5 g) was added to 75 mL of 20% aq HCl. The mixture was heated to reflux for 60 h. The brown solution was cooled to rt and satd with NaCl. The aqueous layer was extracted with ether (7×75 mL) and stripped to yield 3-oxocylobutanecarboxylic acid (12.2 g) as a brown oil.

Step 3. Butyl 3-oxocylobutanecarboxylate

3-Oxocylobutanecarboxylic acid (12.2 g, <0.107 mol, 1.0 equiv) and DMAP (10.5 g, 0.856 mol) were dissolved in butanol (100 mL) and the mixture cooled to 0° C. DCC (24.2 g, 0.118 mol, 1.2 equiv) was added as a solid. The mixture was allowed to stir for 15 h with concomitant warming to rt. The mixture was filtered through a pad of Celite. The filter cake was washed with hexanes. The filtrate was washed with 1.0 M aq HCl, sat'd aq NaHCO$_3$ and brine. Evaporation of the solvent afforded a brown oil. This was purified by flash chromatography (SiO$_2$, O-20% EtOAc). The fractions which stained with 2,4-dinitrophenylhydrazine on tlc were pooled and evaporated to yield a pale yellow oil which was dissolved in hexane and filtered through Celite. The filtrate was evaporated to yield butyl 3-oxocylobutanecarboxylate (4.97 g) as a clear oil.

Step 4. Butyl 3,3-difluorocylobutanecarboxylate

The ester (4.97 g, 0.0292 mol, 1.0 equiv) was dissolved in CH$_2$Cl$_2$ and cooled to 0° C. DAST (11.5 mL, 0.0876 mol, 3.0 equiv) was added via syringe and the mixture was stirred overnight with warming to rt. TLC analysis showed no spots which stain with 2,4-dinitrophenylhydrazine. The mixture was cooled to 0° C. and sat'd NaHCO$_3$ was added, followed by 1.0 M aq NaOH till the pH>14. The layers were separated and the aqueous layer was extracted with CH$_2$Cl$_2$. The combined organic layers were dried over Na$_2$SO$_4$ and evaporated to leave butyl 3,3-difluorocylobutanecarboxylate (5.5 g) as a brown oil, which was used in the next step.

Step 5. (3,3-Difluorocylobutyl)methanol

A three-neck, 500 mL flask was charged with LiAlH$_4$ (2.4 g, 63 mmol, 2.2 equiv) and ether (140 mL) and cooled to −40° C. A solution of butyl 3,3-difluorocylobutanecarboxylate (5.5 g, 28.6 mmol, 1.0 equiv) in ether (20 mL) was added dropwise over a 20 min. The excess LiAlH$_4$ was quenched by sequential addition of water (2.5 mL), 10% aq NaOH (2.5 mL) and celite (10 g). The mixture was stirred for 30 min and diluted with EtOAc (100 mL). The mixture was filtered through a pad of celite. The filtrate was washed with brine, dried over Na$_2$SO$_4$, filtered and evaporated. This afforded (3,3-difluorocylobutyl)methanol (2.4 g) contaminated with ca 10% butanol. This crude material was used in the subsequent step.

Step 6. (3,3-difluorocyclobutyl)methyl 4-bromobenzenesulfonate

A round bottom flask was charged with (3,3-difluorocylobutyl)methanol (1.0 g, 8.2 mmol, 1.0 equiv), 4-bromobenzenesulphonyl chloride (2.2 g, 8.6 mmol, 1.05 equiv) and CH$_2$Cl$_2$ (50 mL). The mixture was cooled to 0° C. and triethylamine (2.07 g, 2.89 mL, 20.5 mmol, 2.5 equiv) was added via syringe. The mixture stirred for 12 h with warming to rt. After this time 1.0 M aq HCl (50 mL) was added. The layers were separated, the organic layer was extracted with CH$_2$Cl$_2$ (50 mL) and the combined organic layers were washed with brine, dried over Na$_2$SO$_4$, filtered and evaporated. The compound was purified by flash chromatography on silica, eluting with 0-30% EtOAc in hexanes. This afforded (3,3-difluorocyclobutyl)methyl 4-bromobenzenesulfonate (2.7 g, 95%) as an off white solid.

Step 7. Diethyl 2-acetamido-2-((3,3-difluorocyclobutyl)methyl)malonate (3,3-Difluorocyclobutyl)methyl 4-bromobenzenesulfonate (500 mg, 1.47 mmol) and NaI (220 mg, 1.47 mmol, 1.0 equiv) were stirred in dry DMF (4 mL). In a separate 3-neck, 100 mL flask NaH (60 wt % in oil, 352 mg, 8.82 mmol, 6 equiv) was slurried in dry DMF (20 mL). The flask was cooled to 0° C. and diethyl-2-acetamidomalonate was added via syringe. After gas evolution ceased, the solution of the (3,3-difluorocyclobutyl)methyl 4-bromobenzenesulfonate and NaI In DMF was added. The resulting solution was heated to 45° C. for 17 h. After this time no remaining brosylate or iodide was observed by TLC and LC-MS. The mixture was quenched by dropwise addition of water (10 mL) and the DMF was removed in vacuo. The residue was partitioned between ether and water and the layers separated. The aqueous layer was extracted with additional ether and the combined organic layers were washed with brine. The residue was evaporated and the desired product was purified by flash chromatography on silica, eluting with 0 to 50% EtOAc in hexanes. The fractions were stained with ceric ammonium molybdate; the desired product is contained in the second spot. This afforded diethyl 2-acetamido-2-((3,3-difluorocyclobutyl)methyl)malonate (474 mg, 99%).

Step 8.
2-Amino-3-(3,3-difluorocyclobutyl)propanoic acid, HCl salt

Diethyl 2-acetamido-2-((3,3-difluorocyclobutyl)methyl)malonate (474 mg, 1.47 mmol) was slurried in 18% HCl (30 mL) and the mixture was heated to reflux for 8 h. After this time LC-MS showed complete conversion to the desired product. The solvent was removed to leave the hydrochloride of 2-amino-3-(3,3-difluorocyclobutyl)propanoic acid as an off-white solid which was used directly in the next step. A quantitative yield was assumed.

Step 9. 2-(2-(Trimethylsilyl)ethoxycarbonyl)amino-3-(3,3-difluorocyclobutyl)propanoic acid The crude HCl salt 2-amino-3-(3,3-difluorocyclobutyl) propanoic acid (0.74 mmol) was dissolved in dioxane (5 mL) and 1.0 M aq NaOH 2.5 mL). Teoc-OSu (213 mg, 0.820 mmol, 1.1 equiv) was added and the mixture was stirred overnight at rt. The solvent was removed and the residue was taken up in water (~5 mL). Citric acid (10% weight solution) was added till pH<4 and the mixture was extracted with EtOAc. The organic extract was dried over Na$_2$SO$_4$, filtered and solvent was removed to yield 2-(2-(trimethylsilyl) ethoxycarbonyl)amino-3-(3,3-difluorocyclobutyl)propanoic acid (273 mg) as a white foam. $^1$H and $^{19}$F NMR were consistent with the desired product contaminated with Teoc-OSu.

Step 10. 2-(Trimethylsilyl)ethyl 3-(3,3-difluorocyclobutyl)-1-hydroxypropan-2-ylcarbamate Crude 2-(2-(trimethylsilyl)ethoxycarbonyl)amino-3-(3,3-difluorocyclobutyl)propanoic acid (273 mg, 0.844 mmol) was dissolved in THF (5 mL) and the solution was cooled to −10° C. N-methylmorpholine (95 mg, 0.929 mmol, 1.1 equiv) was added and the mixture stirred for 15 min. After this time isobutyl chloroformate (127 mg, 0.929 mmol, 1.1 equiv) was added. After stirring for 30 min LC-MS showed remaining starting material. The procedure was repeated with an additional 0.55 equiv of the amine and chloroformate. This consumed all of the starting material. The reaction mixture was quickly filtered through a pad of celite into a solution of NaBH$_4$ (128 mmol, 3.4 mmol, 4.0 equiv) in water (4 mL). The filter cake was washed with an additional dry THF (5 mL). LC-MS analysis showed formation of the desired alcohol. The solvent was removed and the residue partitioned between EtOAc and brine. The layers were separated and the aqueous layer extracted with additional EtOAc. The combined organic layers were dried over Na$_2$SO$_4$. The solvent was removed to yield 2-(trimethylsilyl)ethyl 3-(3,3-difluorocyclobutyl)-1-hydroxypropan-2-ylcarbamate (240 mg, 90%) as an orange oil. $^1$H and $^{19}$F NMR were consistent with the desired product.

Step 11. 2-(2-(Trimethylsilyl)ethoxycarbonylamino)-1-(3,3-difluorocyclobutyl)-3-(N-(t-butoxycarbonyl)-N-methylamino)-propane 2-(Trimethylsilyl)ethyl 3-(3,3-difluorocyclobutyl)-1-hydroxypropan-2-ylcarbamate (240 mg, 0.776 mmol) was dissolved in CH$_2$Cl$_2$ (4 mL) and the solution was cooled to 0° C. DIEA (301 mg, 2.32 mmol, 3.0 equiv) was added followed by MsCl (133 mg, 1.16 mmol, 1.5 equiv) and the mixture was stirred for 30 min at 0° C. LC-MS analysis showed consumption of the alcohol and formation of the desired mesylate. The reaction was quenched by addition of aq citric acid (10% by weight). The layers were separated and the aqueous phase was extracted with additional CH$_2$Cl$_2$. The combined organic layers were dried over Na$_2$SO$_4$, filtered and solvent was removed. The residue was taken up in methylamine solution (30 wt % in ethanol, 10 mL). Methanol was added dropwise to aid dissolution. The mixture was divided into three 4 mL portions. Each portion was separately heated to 150° C. for 7 min in a CEM microwave reactor. The four reaction mixtures were combined and volatile materials were removed. The residue was dissolved in acetonitrile (7 mL) and 1.0 M aq NaOH (2.0 mL) was added, followed by Boc$_2$O (186 mg, 0.854 mmol, 1.1 equiv). After 1 h starting amine was still observed by LC-MS and additional Boc$_2$O (1.1 equiv) was added. After 1 h all the amine was converted into the Boc derivative. The solvent was removed in vacuo and the residue was taken up in EtOAc and water. The layers were separated and the organic layer was washed with sat'd aq NaHCO$_3$, brine and evaporated. The diamine was purified by flash chromatography on 12 g of silica, eluting with a 0 to 50% EtOAc in hexanes gradient. The fractions which stained with ninhydrin were combined and evaporated to yield 2-(2-(trimethylsilyl)ethoxycarbonylamino)-1-(3,3-difluorocyclobutyl)-3-(N-(t-butoxycarbonyl)-N-methylamino)-propane (56 mg, 15%) of the deprotected amine. $^1$H and $^{19}$F NMR were consistent with the desired product.

Example 101

(1R,2R)-2-amino-1-cyclopentyl-3-(N-methyl-N-(2-(trimethylsilyl)ethoxycarbonyl)amino)-propan-1-ol

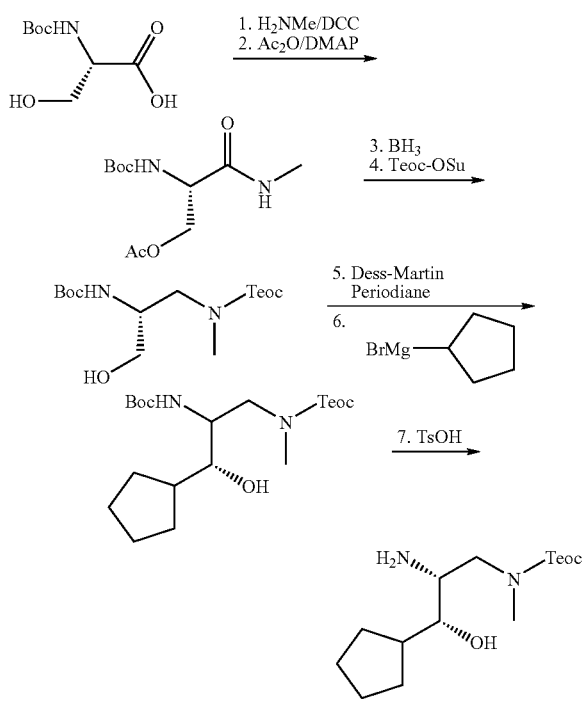

Step 1. (2S)-3-acetoxy-2-(t-butoxycarbonylamino)-N-methylpropanamide

A three-neck, 3 L flask was dried under N$_2$, cooled, equipped with an overhead stirrer and charged with a solution of DCC (20.6 g, 0.1 mol) in CH$_2$Cl$_2$ (0.65 L). This was cooled to 0° C. and solid Boc-Ser-OH (20.06 g, 0.1 mole) was added in one portion. This mixture was stirred for 5 min. Methylamine (33% w/w solution in EtOH, 12.5 mL, 0.1 mol) was added dropwise over 10 min maintaining the internal temperature below 8° C. The reaction was stirred for an additional 10 min, the cooling bath was emptied, and the reaction was stirred for 12 h; LC-MS (3 min) t$_R$=0.75 min, m/z 241 (M+Na) indicated full conversion. DMAP (1.0 g, 0.008 mol) then acetic anhydride (105.0 mL, 1.1 mol) were added using an external water bath to moderate the exotherm (internal temp<30° C.). The reaction was stirred for 60 min. Celite (25 g) and Et$_2$O (1 L) were added, the mixture was cooled to 0° C. and filtered through a pad of Celite and then a pad of SiO$_2$. The filtrate was evaporated under reduced pressure. The resulting oil was chased with toluene (3×100 mL) and separated by chromatography on a SiO$_2$ column to yield (2S)-3-acetoxy-2-(t-butoxycarbonylamino)-N-methylpropanamide (20.4 g, 78%). LC-MS (3 min) t$_R$=0.75 min, m/z, 283 (M+Na).

Step 2. (2R)-2-(t-butoxycarbonylamino)-3-(N-methyl-N-((2-trimethylsilyl)ethoxycarbonyl)-amino)propan-1-ol A solution of BH₃ in THF (1.0 M, 0.25 L, 250 mmol) was added dropwise over 15 min to a solution of (2S)-3-acetoxy-2-(t-butoxycarbonylamino)-N-methylpropanamide (20.4 g, 78.5 mmol) in THF (0.5 L) at 0° C. The cooling bath was removed and the reaction was permitted to come to rt overnight. The reaction mixture was cooled to 0° C. (internal temp) and H₂O (20 mL, 1.11 mol) was added dropwise over 30 min (internal temp maintained below 5° C.). The pH was adjusted (pH<1) with a slight excess of 5 N aq HCl and the mixture was stirred for 30 min at 0° C. A solution of K₂CO₃ (57.96 g, 420 mmol) in H₂O (210 mL) and Teoc-OSu (21 g, 81 mmol) were added. The reaction mixture was permitted to warm to rt and stirred for 2 h. The solvent was stripped and the residue was taken up in EtOAc (0.5 L), washed with 1N aq HCl and brine, dried over Na₂SO₄, decanted, stripped and purified on a SiO₂ column to give (2R)-2-(t-butoxycarbonylamino)-3-(N-methyl-N-((2-trimethylsilyl)ethoxycarbonyl)amino)propan-1-ol (11.54 g) as a white solid. LC-MS (3 min) $t_R$=1.78 min, m/z=371 (M+Na).

Step 3. (1R,2R)-2-(t-butoxycarbonylamino)-1-cyclopentyl-3-(N-methyl-N-(2-(trimethylsilyl)-ethoxycarbonyl)amino)propan-1-ol A suspension of (2R)-2-(t-butoxycarbonylamino)-3-(N-methyl-N-((2-trimethylsilyl)-ethoxycarbonyl)amino)propan-1-ol (627.6 mg, 1.8 mmol) and Dess-Martin periodinane (941.4 mg, 2.2 mmol) in 1,2-dichloroethane (5 mL) was heated in a CEM microwave reactor at 70° C. for 3 min. Loss of starting material was confirmed by LC-MS and generation of aldehyde was confirmed by TLC ($R_f$=0.4, 5:1 hexanes/EtOAc, 2,4-DNP: yellow). The mixture was taken up in 100 mL CH₂Cl₂ (100 mL), washed with 1 N aq NaOH, water and brine, dried over Na₂SO₄, decanted, stripped. The residue (772.3 mg) was carried on directly without further purification. The crude aldehyde was taken up in THF (5.0 mL), cooled to –20° C., and cyclopentyl magnesium bromide (0.81 M in THF, 5.0 mL) was added with fast dropwise addition. The reaction was permitted to warm to rt, stirred for 12 h and quenched with sat'd aq NH₄Cl. The mixture was extracted with ether. The ether extracts were washed with sat'd aq NH₄Cl and brine, and dried over Na₂SO₄, decanted, and stripped. Chromatography on a 12-g SiO₂ cartridge afforded (1R,2R)-2-(t-butoxycarbonylamino)-1-cyclopentyl-3-(N-methyl-N-(2-(trimethylsilyl)ethoxycarbonyl)amino)propan-1-ol (225.9 mg, 30% overall) as a white solid ( ). LC-MS (3 min) $t_R$=2.19, m/z 439 (M+Na).

Step 4. (1R,2R)-2-amino-1-cyclopentyl-3-(N-methyl-N-(2-(trimethylsilyl)ethoxycarbonyl)-amino)propan-1-ol A solution of TsOH (36.8 mg, 0.194 mg) in 1.0 mL EtOH (1 mL) was added to (1R,2R)-2-(t-butoxycarbonylamino)-1-cyclopentyl-3-(N-methyl-N-(2-(trimethylsilyl)ethoxycarbonyl)-amino)propan-1-ol (68.2 mg, 0.164 mmol) in 3.0 mL Et₂O (3 mL). The solvent was removed under reduced pressure at 60° C. and the residue maintained at this temperature for 1 h. The residue was taken up into CH₂Cl₂ (50 mL), washed with 1 N aq NaOH and brine, and dried over Na₂SO₄. Removal of the solvent left (1R,2R)-2-amino-1-cyclopentyl-3-(N-methyl-N-(2-(trimethylsilyl)ethoxycarbonyl)amino)propan-1-ol which was used without purification.

Example 102 tert-Butyl (2R,3S)-2-amino-3-cyclopentyl-3-hydroxypropylmethylcarbamate

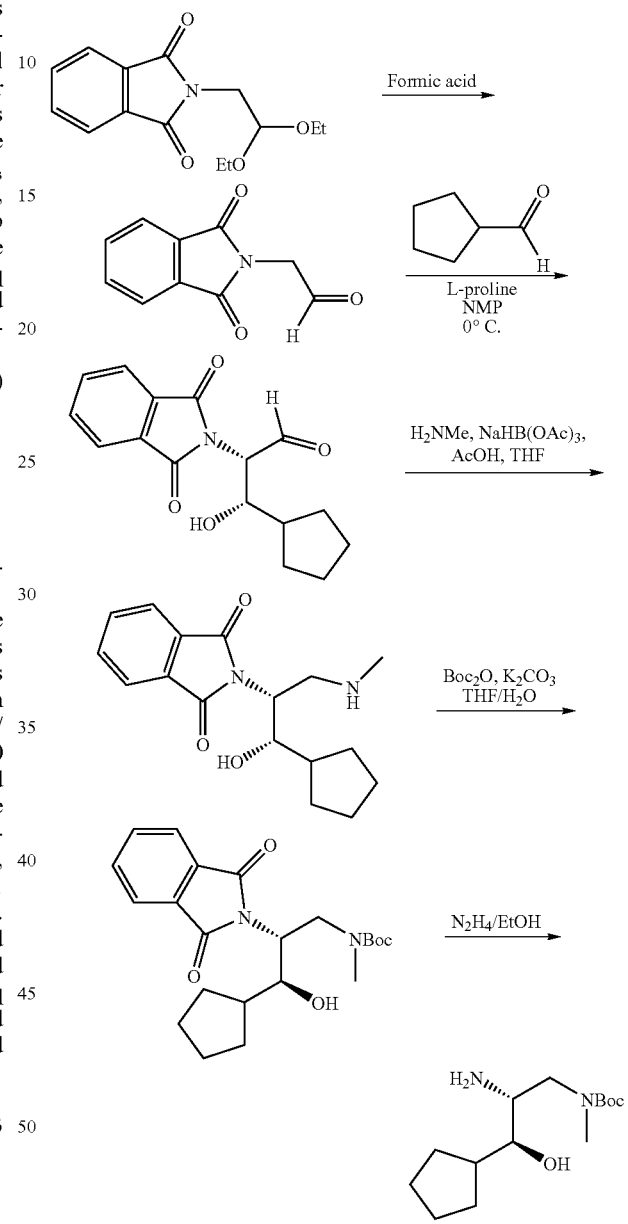

Step 1. 2-(1,3-dioxoisoindolin-2-yl)acetaldehyde

Phthalimidoacetaldehyde diethyl acetal (76.40 g, 0.32 mol, Aldrich) was dissolved in 85% formic acid (300 mL) and stirred for 2 h at rt. After TLC analysis indicated full conversion to the aldehyde (Rf=0.34 1:1 hexanes/EtOAc, 2,4-DNP: yellow), the solvent was removed and the residue was dried under vacuum (150 mm Hg) to afford 2-(1,3-dioxoisoindolin-2-yl)acetaldehyde (56.34 g, 93%) as a white solid. ¹H NMR: 4.57 (s, 2H), 7.76 (m, 2H), 7.77 (m, 2H), 9.66 (s, 1H).

Step 2. (2S,3S)-3-cyclopentyl-3-hydroxy-2-(1,3-dioxoisoindolin-2-yl)propanal 2-(1,3-Dioxoisoindolin-2-yl)acetaldehyde (2.017 g, 10.7 mmol) was dissolved in a minimal amount of anhydrous NMP (5.0 mL). Heating was required for full dissolution. The solution was cooled to rt and cyclopentanecarboxaldehyde (4.91 g, 50 mmol) was added. The solution was cooled to 0° C. and solid L-proline (0.4025 g, 3.4 mmol) was added in one portion. The reaction was stirred for 1 h at 0° C. and then the orange mixture was stored in the refrigerator at 6° C. for 36 h. The mixture was taken up in EtOAc (100 mL), washed with sat'd aq NH$_4$Cl (3×10 mL) and brine (3×10 mL), dried over Na$_2$SO$_4$, decanted and stripped to give an orange oil (5.4 g). Chromatography isolation of the UV active aldehyde (R$_f$=0.53 1:1 hexanes/EtOAc) gave (2S,3S)-3-cyclopentyl-3-hydroxy-2-(1,3-dioxoisoindolin-2-yl)propanal (1.33 g, 44%) as a yellow solid. LC-MS (3 min) t$_R$=1.65 min, m/z 287 (M+1).

Step 3. 2-((1S,2R)-1-cyclopentyl-1-hydroxy-3-(methylamino)propan-2-yl)isoindoline-1,3-dione A solution of (2S,3S)-3-cyclopentyl-3-hydroxy-2-(1,3-dioxoisoindolin-2-yl)propanal (1.339 g, 4.7 mmol) in dry THF (20 mL) was cooled to 0° C. Acetic acid (2.5 mL, 44 mmol), methylamine (33% in EtOH, 2.5 mL, 20 mmol), and NaHB(OAc)3 (4.4937 g, 21.3 mmol) were added sequentially in single portions. The ice bath was removed and the mixture was stirred for 2 h at rt. The solvent was stripped and the crude 2-((1S,2R)-1-cyclopentyl-1-hydroxy-3-(methylamino)propan-2-yl)isoindoline-1,3-dione was used directly in the next step. LC-MS (3 min) t$_R$=1.07, m/z=303 (M+1).

Step 4. 2-((1S,2R)-1-cyclopentyl-1-hydroxy-3-(N-methyl-N-(t-butoxycarbonyl)amino)propan-2-yl)isoindoline-1,3-dione Crude 2-((1S,2R)-1-cyclopentyl-1-hydroxy-3-(methylamino)propan-2-yl)isoindoline-1,3-dione (<4.7 mmol) was dissolved in THF (20 mL). A solution of K$_2$CO$_3$ (8.3 g, 60 mmol) in water (20 mL) was added followed by Boc$_2$O (6.1 g, 27 mmol). The two-phase system was stirred for 1 h at rt. The mixture was extracted with ether, washed with sat'd aq NaHCO$_3$ and brine, dried, decanted, and stripped. Chromatography on silica gel gave 2-((11S,2R)-1-cyclopentyl-1-hydroxy-3-(N-methyl-N-(t-butoxycarbonyl)amino)propan-2-yl)isoindoline-1,3-dione (1.25 g, 65%) of a highly crystalline solid. LC-MS (3 min) t$_R$=1.8 min, m/z=403 (M+1).

Step 5. tert-Butyl (2R,3S)-2-amino-3-cyclopentyl-3-hydroxypropylmethylcarbamate 2-((1S,2R)-1-cyclopentyl-1-hydroxy-3-(N-methyl-N-(t-butoxycarbonyl)amino)propan-2-yl)isoindoline-1,3-dione (0.7961 mg, 2.0 mmol) was dissolved in a minimal volume of EtOH (20 mL) and hydrazine monohydrate (0.5 mL, 10.3 mmol) was added. The solution was heated at 55° C. for 45 min and at reflux for 2 h. A white solid (precipitation of the hydrazone) resulted and the reaction was cooled to rt. Ether (50 mL) was added and the reaction was filtered through #1 Whatman filter paper. The filtrate was stripped and the residue was stirred in ether (15 mL) for 1 h, filtered, and stripped to give tert-butyl (2R,3S)-2-amino-3-cyclopentyl-3-hydroxypropyl-methylcarbamate (199.7 mg, 36%). LC-MS (3 min) t$_R$=1.10 min, m/z=272 (M+).

Example 103

The following compounds were prepared using procedures analogous to those described in Example 102:

(2R,3R)-1-(N-(t-butoxycarbonyl)-N-methylamino)-3-cycloheptyl-3-hydroxypropyl-2-amine using cycloheptanecarboxaldehyde in Step 2.

tert-butyl (2R,3S)-2-amino-3-hydroxy-4-methylpentyl(methyl)carbamate using isobutyraldehyde in Step 2.

Example 104 tert-Butyl 2-(methylamino)ethylcarbamate

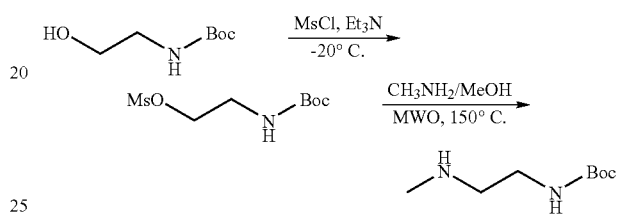

Step 1. tert-butyl 2-(methanesulfonatyl)ethylcarbamate

A solution of N-Boc-2-aminoethanol (5.0 g, 27.6 mmol) in CH$_2$Cl$_2$ (100 mL) was cooled to −20° C. (ice/MeOH bath). Triethylamine (4.8 mL, 1.25 equiv) was added, followed by MsCl (2.25 mL, 1.05 equiv) dropwise. Some white precipitate formed after the addition of MsCl. After 10 min, the reaction mixture was warmed to rt slowly. After stirring 2 h, the reaction mixture was diluted with ether (400 mL), washed with 5% HCl solution (2×50 mL), water (50 mL) and brine (40 mL), and dried over Na$_2$SO$_4$. Evaporation afforded crude tert-butyl 2-(methanesulfonatyl)ethylcarbamate (7.82 g, quant) which was used without purification.

Step 2. tert-Butyl 2-(methylamino)ethylcarbamate tert-Butyl 2-(methanesulfonatyl)ethylcarbamate (417 mg, 1.61 mmol) and methylamine in methanol solution (33%, 3.81 g, 25 equiv) were mixed and heated in a CEM microwave oven for 5 min at 150° C. The reaction mixture was concentrated to afford crude tert-butyl 2-(methylamino)ethylcarbamate (305 mg, quant). LC-MS showed the reaction was complete and the crude product was used without purification.

Example 105

Benzyl (S)-2-amino-3-cyclohexylpropyl-2,2,2-trifluoroethylcarbamate

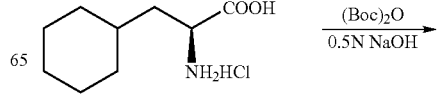

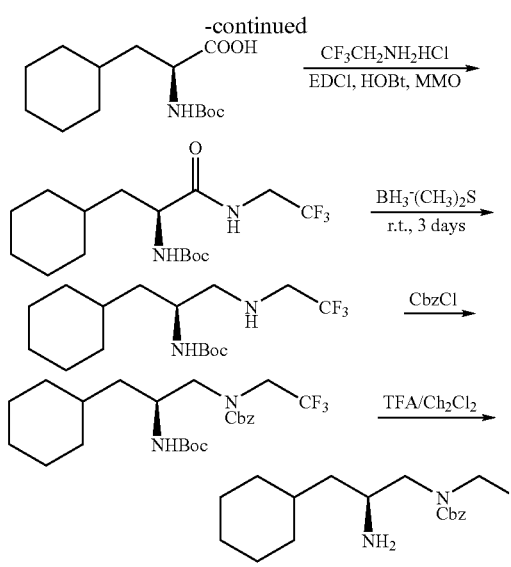

Step 1. (2S)-2-tert-Butoxycarbonylamino-3-cyclohexyl-propionic acid

To a solution of (S)-2-amino-3-cyclohexylpropanoic acid hydrochloride salt (41.5 g, 0.2 mol) in 0.5 N aqueous NaOH (840 mL) was added a solution of Boc$_2$O (48 g, 0.22 mol) in THF (420 mL) and the mixture was stirred for about 2 h. After removing the organic solvent, the aqueous layer was extracted with ether (2×200 mL) and the organic layer was discarded. The aqueous layer was treated with 2N aq HCl until pH 5 and extracted with EtOAc (3×200 mL). The combined organic layers were washed with brine, and dried over Na$_2$SO$_4$, then evaporated to give (2S)-2-tert-butoxycarbonylamino-3-cyclohexyl-propionic acid as an oil that was used in the next step without further purification. $^1$H NMR (CDCl$_3$, 400 MHz) δ 0.90 (m, 2H), 1.18 (m, 2H), 1.44 (s, 9H), 1.50 (m, 2H), 1.68 (m, 6H), 1.82 (m, 1H), 4.30 (brs, 1H), 5.00 (brs, 1H).

Step 2. tert-Butyl (S)-1-(2,2,2-trifluoroethylcarbamoyl)-2-cyclohexylethylcarbamate A mixture of (2S)-2-tert-butoxycarbonylamino-3-cyclohexyl-propionic acid (2.98 g, 11 mmol), 2,2,2-trifluoroethylamine (1.35 g, 10 mmol), EDC (2.87 g, 15 mmol), HOBt (2.03 g, 15 mmol) and NMM (5.05 g, 50 mmol) in 100 mL of CH$_2$Cl$_2$ was stirred overnight. The mixture was poured into water (50 mL) and extracted with CH$_2$Cl$_2$ (3×50 mL). The combined organic extracts were washed with brine (50 mL), dried over Na$_2$SO$_4$, and evaporated to give the residue. The residue was purified by silica chromatography to give tert-butyl (S)-1-(2,2,2-trifluoroethylcarbamoyl)-2-cyclohexylethylcarbamate (2.8 g, 80%). $^1$H NMR (CDCl$_3$, 400 MHz) δ 0.90 (m, 2H), 1.25 (m, 4H), 1.44 (s, 9H), 1.68 (m, 7H), 3.89 (m, 1H), 4.16 (brs, 1H), 4.82 (brs, 1H), 6.78 (brs, 1H).

Step 3. tert-Butyl (S)-1-(2,2,2-trifluoroethylamino)-3-cyclohexylpropan-2-ylcarbamate To a solution of tert-butyl (S)-1-(2,2,2-trifluoroethylcarbamoyl)-2-cyclohexylethyl-carbamate (1.8 g, 5.1 mmol) in anhydrous THF (30 mL) was added 2 M BH$_3$·Me$_2$S in THF (25 mL, 50 mmol) and the mixture was stirred at rt for 3 d. The reaction was quenched with MeOH (20 mL), the solvent was removed in vacuo and the residue was purified by silica chromatography to give crude tert-butyl (S)-1-(2,2,2-trifluoroethylamino)-3-cyclohexylpropan-2-ylcarbamate (1.7 g).

Step 3. Benzyl (S)-2-(t-butoxycarbonylamino)-3-cyclohexylpropyl-2,2,2-trifluoroethylcarbamate To a solution of tert-butyl (S)-1-(2,2,2-trifluoroethylamino)-3-cyclohexylpropan-2-ylcarbamate (1.7 g, 5 mmol) and Et$_3$N (2 mL, 15 mmol) in CH$_2$Cl$_2$ (20 mL) was added dropwise a solution of CbzCl (1.02 g, 6 mmol) in CH$_2$Cl$_2$ (10 mL) at 0° C. After stirring for an additional 2 h, water (30 mL) was added. The mixture was extracted with CH$_2$Cl$_2$ (2×20 mL), the organic layers were washed with brine, dried over MgSO$_4$, and evaporated. The residue was purified by silica chromatography to obtain benzyl (S)-2-(t-butoxycarbonylamino)-3-cyclohexylpropyl-2,2,2-trifluoroethylcarbamate (250 mg, yield 10% for 2 steps) as an oil. $^1$H NMR (CDCl$_3$, 400 MHz) δ 0.90 (m, 2H), 1.25 (m, 4H), 1.44 (s, 9H), 1.70 (m, 7H), 3.33 (m, 2H), 3.85 (m, 3H), 4.45 (brs, 1H), 5.20 (s, 2H), 7.36 (m, 5H).

Step 4. Benzyl (S)-2-amino-3-cyclohexylpropyl-2,2,2-trifluoroethylcarbamate

A solution of benzyl (S)-2-(t-butoxycarbonylamino)-3-cyclohexyl-propyl-2,2,2-trifluoroethylcarbamate (250 mg) in TFA/CH$_2$Cl$_2$ (8 mL, 20% v/v) was stirred for 2 h at 0° C. The reaction was neutralized with satd aq NaHCO$_3$ and extracted with CH$_2$Cl$_2$ (3×30 mL). The combined extracts were washed with brine (30 mL), dried over Na$_2$SO$_4$ and evaporated to give benzyl (S)-2-amino-3-cyclohexylpropyl-2,2,2-trifluoroethylcarbamate (205 mg) that was used without further purification.

Example 106

Benzyl (S)-2-amino-3-cyclopentylpropylmethylcarbamate

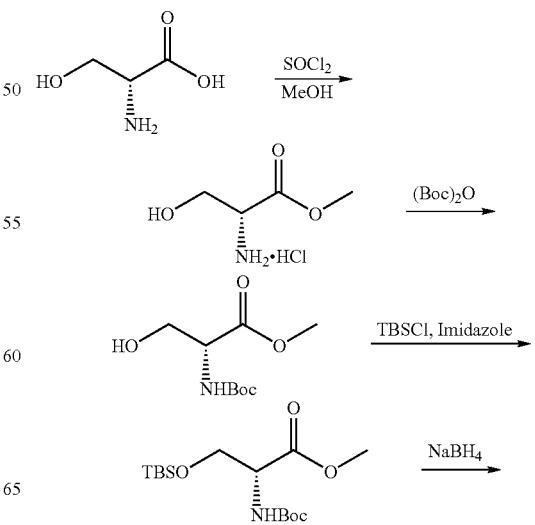

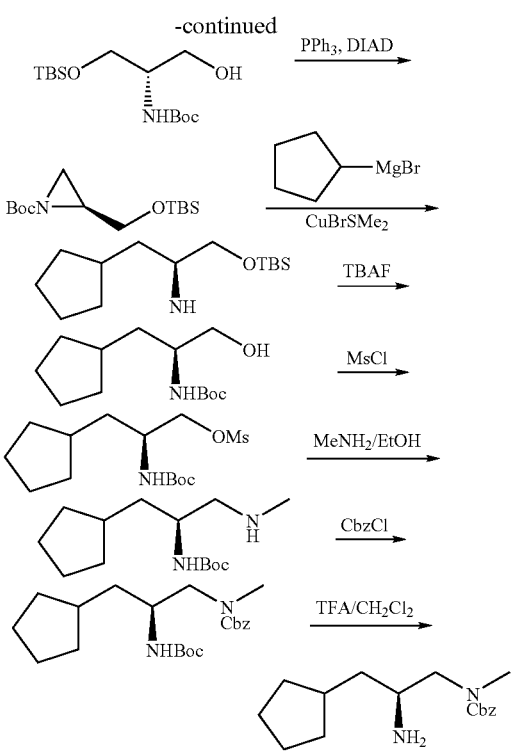

Step 1. (R)-2-Amino-3-hydroxy-propionic acid methyl ester hydrochloride

To a solution of serine (105 g, 1 mol) in methanol (1200 mL) was added thionyl chloride (87.6 mL, 142.8 g, 1.2 mol) dropwise at 0° C. After addition, the reaction mixture was heated under reflux for 12 h. Volatiles were evaporated to give (R)-2-amino-3-hydroxy-propionic acid methyl ester hydrochloride (155 g, 100%) as a solid that was used without further purification. $^1$H NMR (CDCl$_3$, 400 MH$_z$) δ 3.71 (s, 3H), 3.79 (m, 2H), 4.08 (s, 1H), 8.51 (br s, 2H).

Step 2. tert-Butyl (R)-1-(methoxycarbonyl)-2-hydroxyethylcarbamate

DIEA (194 g, 1.5 mol) was added to a stirred suspension of (R)-2-amino-3-hydroxy-propionic acid methyl ester hydrochloride (155 g, 1 mol) in CH$_2$Cl$_2$ (1200 mL). A solution of Boc$_2$O (218 g, 1 mol) in CH$_2$Cl$_2$ (800 mL) was added dropwise to the above mixture and the reaction mixture was allowed to stir overnight. The solution was washed with 1 N aqueous HCl (600 mL), then with sat'd NaHCO$_3$ (500 mL) and brine (500 mL), dried, filtered, evaporated to give tert-butyl (R)-1-(methoxycarbonyl)-2-hydroxyethylcarbamate (245 g, 96%) as an oil that was used without further purification. $^1$H NMR (CDCl$_3$, 400 MHz) δ 1.44 (s, 9H), 2.37 (br s, 1H), 3.77 (s, 3H), 3.91 (dd, J=18, 3.2 Hz, 2H), 4.35 (s, 1H), 5.29 (br s, 1H).

Step 3. tert-Butyl (R)-1-(methoxycarbonyl)-2-(t-butyldimethylsilyloxy)ethylcarbamate To a solution of tert-butyl (R)-1-(methoxycarbonyl)-2-hydroxyethylcarbamate (27.5 g, 0.126 mol) in DMF (250 mL) was added imidazole (25.7 g, 0.378 mol), followed by TBSCl (20.9 g, 0.139 mol) and the reaction mixture was stirred for 4 h. The solvents were removed in vacuo. EtOAc (300 mL) was added and the solution was washed with sat'd aq NH$_4$Cl (2×100 mL), sat'd aq NaHCO$_3$ (100 mL) and brine (100 mL), dried, filtered and evaporated to give tert-butyl (R)-1-(methoxycarbonyl)-2-(t-butyldimethylsilyloxy)ethylcarbamate (40 g, yield 95%) as an oil that was used without further purification. $^1$H NMR (CDCl3, 400 MHz): δ=0.02 (s, 6H), 0.86 (s, 9H), 1.45 (s, 9H), 3.73 (s, 3H), 3.82 (dd, J=14, 4.4 Hz, 1H), 4.05 (dd, J=13.2, 3.6 Hz, 1H), 4.35 (m, 1H), 5.34 (brs, 1H).

Step 4. (S)-2-(t-butoxycarbonylamino)-3-(t-butyldimethylsilyloxy)propan-1-ol To a solution of tert-butyl (R)-1-(methoxycarbonyl)-2-(t-butyldimethylsilyloxy)ethylcarbamate (40 g, 0.12 mol) in MeOH (500 mL) at 0° C. was added NaBH$_4$ (38 g, 1 mol) in portions. The mixture was stirred for 2 h at rt and then evaporated. The residue was partitioned between water (200 mL) and EtOAc (2×200 mL). The organic layers were washed with sat'd aq NaHCO$_3$ and brine, dried over MgSO$_4$ and evaporated to obtain the alcohol (S)-2-(t-butoxycarbonylamino)-3-(t-butyldimethylsilyloxy)propan-1-ol (36 g, 98%). $^1$H NMR (CDCl$_3$, 400 MHz): δ 0.07 (s, 6H), 0.89 (s, 9H), 1.45 (s, 9H), 2.25 (brs, 1H), 3.68 (m, 2H), 3.78 (m, 2H), 5.15 (brs, 1H).

Step 5. (S)-tert-butyl 2-(t-butyldimethylsilyloxymethyl)aziridine-1-carboxylate Ph$_3$P (19.65 g, 75 mmol) was dissolved in 9:1 THF/CH$_3$CN (600 mL) and cooled to 0° C., DIAD (14.7 mL, 75 mmol) was added dropwise over 15 min. After stirring for 30 min, a solution of (S)-2-(t-butoxycarbonylamino)-3-(t-butyldimethylsilyloxy)propan-1-ol (15.25 g, 50 mmol) in THF (100 mL) was added dropwise over 15 min, the reaction mixture was allowed to rt and stirred for 24 h. Water (100 mL) was added and volatiles were evaporated. The residue was partitioned between water (100 mL) and EtOAc (2×100 mL). The organic layers were washed with brine, dried over MgSO$_4$ and evaporated. The residue was purified by silica chromatography to provide (S)-tert-butyl 2-(t-butyldimethylsilyloxymethyl)aziridine-1-carboxylate (7.8 g, 54%) as an oil. $^1$H NMR (CDCl$_3$, 400 MHz): δ 0.07 (s, 6H), 0.89 (s, 9H), 1.45 (s, 9H), 2.06 (d, J=3.6 Hz 1H), 2.26 (d, J=6 Hz 1H), 2.55 (m, 1H), 3.64 (dd, J=16.4, 4.8 Hz, 1H), 3.82 (dd, J=16.4, 4.4 Hz, 1H).

Step 6. tert-Butyl (S)-3-cyclopentyl-1-(t-butyldimethylsilyloxy)propan-2-ylcarbamate A 100 mL, three-neck flask was charged with Mg powder (720 mg, 30 mmol), and a solution of cyclopentylbromide (3.73 g, 25 mmol) in THF (25 mL) was added dropwise while the flask was heated with a heat gun. After stirring for about 2 h, most of the Mg had been consumed. The Grignard reagent was added to a suspension of CuBr.SMe$_2$ (307.5 mg, 1.5 mmol) in THF (80 mL) at −78° C., the cuprate was stirred for 30 min and a solution of (S)-tert-butyl 2-(t-butyldimethylsilyloxymethyl)aziridine-1-carboxylate (2.87 g, 10 mmol) in ether (30 mL) was added. The mixture was stirred for 2 h, washed with sat'd aq NaHCO$_3$ (2×20 mL) and brine (30 mL), dried over MgSO$_4$, and evaporated. The residue was purified by silica chromatography to obtain tert-butyl (S)-3-cyclopentyl-1-(t-butyldimethylsilyloxy)propan-2-ylcarbamate (2.9 g, 81%) as an oil. $^1$H NMR (CDCl$_3$, 400 MHz) δ 0.04 (s, 6H), 0.89 (s, 9H), 1.10 (m, 2H), 1.44 (s, 9H), 1.50 (m, 3H), 1.60 (m, 3H), 1.81 (m, 3H), 3.58 (m, 3H), 4.60 (brs, 1H).

Step 7. tert-Butyl (S)-3-cyclopentyl-1-hydroxypropan-2-ylcarbamate tert-Butyl (S)-3-cyclopentyl-1-(t-butyldimethylsilyloxy) propan-2-ylcarbamate (2.9 g, 8.1 mmol) was stirred with 1 M Bu$_4$NF in THF (24.3 mL) at 0° C. for 1 h. Water (30 mL) was added and the mixture was extracted with EtOAc (3×40 mL). The combined organic layers were washed with brine, dried over MgSO$_4$ and evaporated to give crude tert-butyl (S)-3-cyclopentyl-1-hydroxypropan-2-ylcarbamate that was used in the next step without further purification. $^1$H NMR (CDCl$_3$, 400 MHz) δ 1.09 (m, 2H), 1.44 (s, 9H), 1.50 (m, 3H), 1.60 (m, 3H), 1.81 (m, 3H), 3.52 (m, 1H), 3.68 (m, 2H), 4.60 (brs, 1H).

Step 8. tert-Butyl (S)-3-cyclopentyl-1-(methanesulfonyloxy)propan-2-ylcarbamate Crude tert-butyl (S)-3-cyclopentyl-1-hydroxypropan-2-ylcarbamate from the previous step was dissolved in CH$_2$Cl$_2$ (30 mL). Et$_3$N (3.2 mL, 24.3 mmol) was added and the mixture was cooled to 0° C. A solution of MsCl (1.1 g, 9.7 mmol) in CH$_2$Cl$_2$ (10 mL) added dropwise. After stirring for an additional 2 h, water (30 mL) was added and the mixture was extracted with CH$_2$Cl$_2$ (2×30 mL). The combined organic layers were washed with brine, dried over MgSO$_4$, and evaporated to give crude tert-butyl (S)-3-cyclopentyl-1-(methanesulfonyloxy)propan-2-ylcarbamate that was used in the next step without further purification. $^1$H NMR (CDCl$_3$, 400 MHz) δ 1.09 (m, 2H), 1.46 (s, 9H), 1.50 (m, 3H), 1.60 (m, 3H), 1.81 (m, 3H), 3.02 (s, 3H), 3.86 (m, 1H), 4.17 (dd, J=10, 4 Hz, 1H), 4.27 (dd, J=10, 3.2 Hz, 1H), 4.59 (brs, 1H).

Step 9. tert-Butyl (S)-3-cyclopentyl-1-(methylamino) propan-2-ylcarbamate

A mixture of crude tert-butyl (S)-3-cyclopentyl-1-(methanesulfonyloxy)propan-2-ylcarbamate in ethanolic methylamine (30 mL) was heated under reflux overnight. The solvent was removed in vacuo and the residue was purified by silica chromatography to obtain tert-butyl (S)-3-cyclopentyl-1-(methylamino)propan-2-ylcarbamate (900 mg, 43% for 3 steps from) as a solid (900 mg, yield 43% for 3 steps from tert-butyl (S)-3-cyclopentyl-1-(t-butyldimethylsilyloxy)propan-2-ylcarbamate). $^1$H NMR (CDCl$_3$, 400 MHz) δ 1.10 (m, 2H), 1.44 (s, 9H), 1.49 (m, 3H), 1.60 (m, 3H), 1.81 (m, 3H), 2.69 (s, 3H), 2.90 (m, 1H), 3.17 (m, 1H), 3.92 (brs, 1H), 5.66 (brs, 1H).

Step 10. Benzyl (S)-2-(t-butoxycarbonylamino)-3-cyclopentylpropylmethylcarbamate To a mixture of tert-butyl (S)-3-cyclopentyl-1-(methylamino)propan-2-ylcarbamate (900 mg, 3.52 mmol) and Et$_3$N (1.5 mL, 10.6 mmol) in CH$_2$Cl$_2$ (10 mL) was added dropwise a solution of CbzCl (720 mg, 4.22 mmol) in CH$_2$Cl$_2$ (5 mL) at 0° C. After stirring for an additional 2 h, water (30 mL) was added and the mixture was extracted with CH$_2$Cl$_2$ (2×10 mL). The combined organic layers were washed with brine, dried over MgSO$_4$ and concentrated. The residue was purified by silica chromatography to obtain benzyl (S)-2-(t-butoxycarbonylamino)-3-cyclopentylpropylmethylcarbamate (550 mg, 40%) as an oil. $^1$H NMR (CDCl$_3$, 400 MHz) δ 1.10 (m, 2H), 1.43 (s, 9H), 1.49 (m, 3H), 1.60 (m, 3H), 1.81 (m, 3H), 2.96 (s, 3H), 3.15 (m, 1H), 3.40 (m, 1H), 3.83 (brs, 1H), 4.57 (brs, 1H), 5.16 (s, 2H), 7.33 (m, 5H).

Step 11. Benzyl (S)-2-amino-3-cyclopentylpropylmethylcarbamate

A solution of benzyl (S)-2-(t-butoxycarbonylamino)-3-cyclopentylpropylmethylcarbamate (550 mg) in TFA/CH$_2$Cl$_2$ (10 mL, 20% v/v) was stirred for 2 h at 5° C. The mixture was neutralized with sat'd aq NaHCO$_3$ and extracted with CH$_2$Cl$_2$ (3×30 mL). The combined organic extracts were washed with brine (30 mL), dried over Na$_2$SO$_4$ and evaporated to give benzyl (S)-2-amino-3-cyclopentylpropylmethylcarbamate (420 mg) that was used in the next step without further purification.

Example 107

Benzyl (S)-2-amino-3-(cis-4-fluorocyclohexyl)propylmethylcarbamate

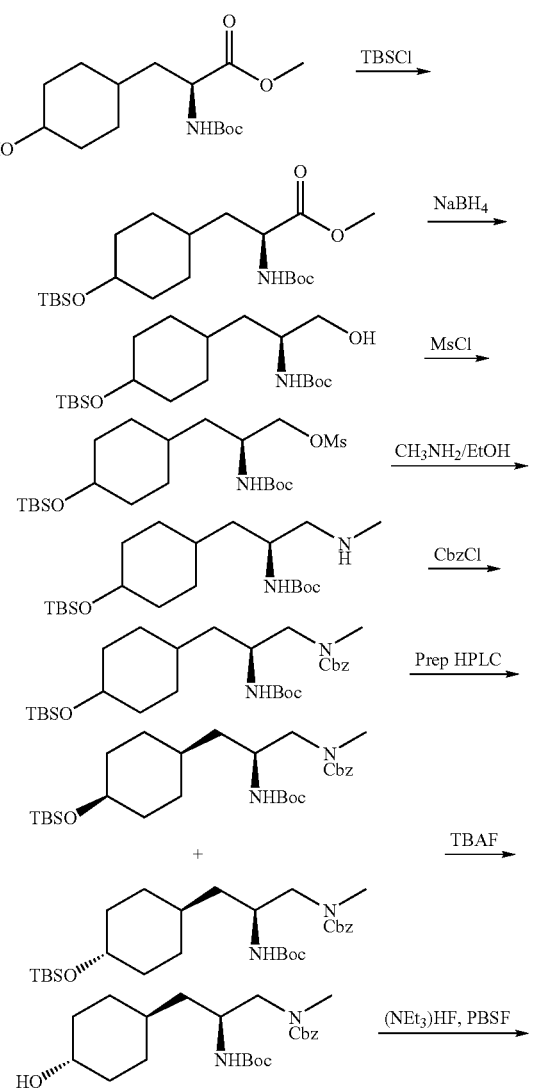

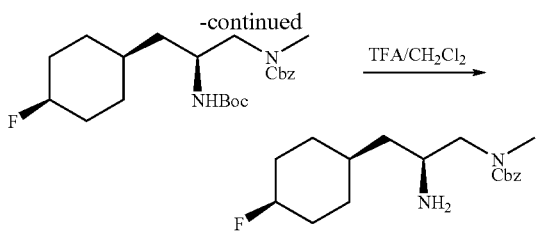

Step 1. tert-butyl (S)-1-(methoxycarbonyl)-2-(4-(t-butyldimethylsilyloxy)cyclohexyl)ethylcarbamate To a solution of TBSCl (12.7 g, 85 mmol) in dichloromethane (20 mL) was added dropwise a mixture of 2-tert-butoxycarbonylamino-3-(4-hydroxy-cyclohexyl)propionic acid methyl ester (17 g, 56 mmol) and imidazole (7.68 g, 113 mmol) in dichloromethane (200 mL) at 0° C. After stirring at rt for 5 h, the reaction mixture was washed with water and brine. The organic layer was dried over $Na_2SO_4$ and concentrated to give tert-butyl (S)-1-(methoxycarbonyl)-2-(4-(t-butyldimethylsilyloxy)cyclohexyl)ethylcarbamate (21 g, 91%) that was used in the next step without further purification. $^1$H NMR ($CDCl_3$, 400 MHz) δ 0.08 (d, 6H), 0.89 (d, 9H), 1.45 (s, 9H), 1.51 (m, 4H), 1.58 (m, 1H), 1.68 (t, 4H), 1.85 (d, 1H) 3.71 (d, 3H), 3.91 (m, 1H), 4.34 (m, 1H), 4.86 (m, 1H).

Step 2. (2S)-2-(t-butoxycarbonylamino)-3-(4-(t-butyldimethylsilyloxy)cyclohexyl)propan-1-ol To a solution of tert-butyl (S)-1-(methoxycarbonyl)-2-(4-(t-butyldimethylsilyloxy)-cyclohexyl)ethylcarbamate (25 g, 60 mmol) in EtOH (500 mL) at 0° C. was added $NaBH_4$ (18 g, 480 mmol) in portions. The mixture was stirred for 6 h at rt and then evaporated. The residue was partitioned between water (200 mL) and EtOAc (2×200 mL). The combined organic layers were washed with brine, dried over $MgSO_4$, and evaporated to give (2S)-2-(t-butoxycarbonylamino)-3-(4-(t-butyldimethylsilyloxy)cyclohexyl)propan-1-ol (23 g, yield 98%). $^1$H NMR ($CDCl_3$, 400 MHz) δ 0.08 (d, 6H), 0.89 (d, 9H), 1.30 (m, 4H), 1.40 (t, 2H), 1.45 (s, 9H), 1.61 (m, 1H), 1.58 (m, 1H), 1.68 (t, 4H), 1.85 (d, 1H) 3.50 (m, 1H), 3.65 (m, 1H), 3.73 (m, 1H), 3.91 (s, 1H), 4.53 (s, 1H).

Step 3. (2S)-2-(t-butoxycarbonylamino)-3-(4-(t-butyldimethylsilyloxy)cyclohexyl)-1-methanesulfonyloxypropane To a solution of (2S)-2-(t-butoxycarbonylamino)-3-(4-(t-butyldimethylsilyloxy)-cyclohexyl)propan-1-ol (23 g, 59 mmol) in $CH_2Cl_2$ (250 mL) was added $Et_3N$ (15 g, 148 mmol). The reaction mixture was cooled to −20° C. and a solution of MsCl (14.9 g, 131 mmol) in $CH_2Cl_2$ (40 mL) added dropwise. After returning to rt then stirring for an additional 1 h, at which point TLC showed no starting material, water (100 mL) was added and the mixture was extracted with $CH_2Cl_2$ (2×150 mL). The combined organic layers were washed with brine, dried over $MgSO_4$ and evaporated to give crude (2S)-2-(t-butoxycarbonylamino)-3-(4-(t-butyldimethyl-silyloxy)cyclohexyl)-1-methanesulfonyloxypropane (30 g) that was used in the next step without further purification.

Step 4. tert-Butyl (S)-1-(4-(t-butyldimethylsilyloxy)cyclohexyl)-3-(methylamino)propan-2-ylcarbamate A solution of crude (2S)-2-(t-butoxycarbonylamino)-3-(4-(t-butyldimethylsilyloxy)cyclohexyl)-1-methanesulfonyloxypropane (30 g) in methylamine alcohol solution (300 mL) was heated under reflux overnight. The solvent was removed in vacuo and the residue was purified by silica chromatography to obtain tert-butyl (S)-1-(4-(t-butyldimethylsilyloxy)cyclohexyl)-3-(methylamino)propan-2-ylcarbamate as a solid (15 g, 63% for 2 steps). $^1$H NMR ($CDCl_3$, 400 MHz) δ 0.08 (d, 6H), 0.89 (d, 9H), 1.25 (t, 3H), 1.45 (s, 9H), 1.61 (m, 2H), 1.82 (t, 2H), 2.01 (d, 1H), 2.56 (d, 2H), 2.80 (d, 2H), 2.95 (t, 2H), 3.49 (m, 1H), 3.61 (m, 1H), 3.90 (s, 1H), 5.35 (d, 1H), 7.15 (m, 1H).

Step 5. tert-Butyl (S)-1-(4-(t-butyldimethylsilyloxy)cyclohexyl)-3-(N-(benzyloxycarbonyl)-N-methylamino)propan-2-ylcarbamate To a mixture solution of tert-butyl (S)-1-(4-(t-butyldimethylsilyloxy)cyclohexyl)-3-(methylamino)propan-2-ylcarbamate (112 g, 209 mmol) and $Et_3N$ (52.8 g, 522 mmol) in $CH_2Cl_2$ (1200 mL) was added dropwise a solution of benzyl chloroformate (39 g, 230 mmol) in $CH_2Cl_2$ (40 mL) at −20° C. After stirring for an additional 2 h, water (400 mL) was added and the mixture was extracted with $CH_2Cl_2$ (2×200 mL). The organic layers were washed with brine, dried over $MgSO_4$, and evaporated. The residue was purified by silica chromatography to afford crude tert-butyl (S)-1-(4-(t-butyldimethylsilyloxy)cyclohexyl)-3-(N-(benzyloxycarbonyl)-N-methylamino)propan-2-ylcarbamate (90 g) as an oil which was a mixture of two isomers. The isomers were separated by preparative HPLC. $^1$H NMR (CDCl3, 400 MHz): δ=0.08 (s, 6H), 0.89 (s, 9H), 1.28 (m, 4H), 1.40 (d, 9H), 1.59 (m, 4H), 2.96 (d, 3H), 3.05 (d, 1H), 3.15 (d, 1H), 3.45 (t, 3H), 3.90 (s, 1H), 5.12 (d, 2H), 7.33 (m, 5H).

Step 6. tert-Butyl (S)-1-(trans-4-hydroxycyclohexyl)-3-(N-(benzyloxycarbonyl)-N-methylamino)propan-2-ylcarbamate tert-Butyl (S)-1-(trans-4-(t-butyldimethylsilyloxy)cyclohexyl)-3-(N-(benzyloxycarbonyl)-N-methylamino)propan-2-ylcarbamate (18 g, 34 mmol) was treated with 4 M $nBu_4NF$/THF (50 mL) at 50° C. for 6 h. Water (30 mL) was added and the mixture was extracted with EtOAc (3×100 mL). The combined organic layers were washed with brine, dried over $MgSO_4$ and evaporated to give crude tert-butyl (S)-1-(trans-4-hydroxycyclohexyl)-3-(N-(benzyloxycarbonyl)-N-methylamino)propan-2-ylcarbamate (9 g, 64%) that was purified by silica chromatography. $^1$H NMR ($CDCl_3$, 400 MHz) δ 1.41 (d, 9H), 1.65 (m, 6H), 1.95 (m, 3H), 2.98 (d, 3H), 3.10 (m, 1H), 3.52 (m, 1H), 3.90 (m, 1H), 5.13 (d, 2H), 7.33 (m, 5H).

Step 7. tert-Butyl (S)-1-(cis-4-fluorocyclohexyl)-3-(N-(benzyloxycarbonyl)-N-methylamino)propan-2-ylcarbamate A mixture of tert-butyl (S)-1-(trans-4-hydroxycyclohexyl)-3-(N-(benzyloxycarbonyl)-N-methylamino)propan-2-ylcarbamate (3 g, 7 mmol), $Et_3N$ (12 mL, 88 mmol), $NEt_3$ $(HF)_3$ (4.71 mL, 29 mmol) and perfluorobutanesulfonyl fluoride (5.21 mL, 29 mmol) was stirred in THF (70 mL, 1 mmol/10 mL) at 50° C. until HPLC revealed complete conversion. The reaction mixture was quenched with water and extracted with EtOAc (2×100 mL), dried over MgSO₄ and evaporated. The residue was then purified by prep HPLC to give tert-butyl (S)-1-(trans-4-fluorocyclohexyl)-3-(N-(benzyloxycarbonyl)-N-methylamino)propan-2-ylcarbamate (1.16 g, 40%) as a white solid. ¹H NMR (CDCl₃, 400 MHz) δ 1.41 (d, 9H), 1.68 (m, 6H), 1.96 (m, 3H), 2.98 (d, 3H), 3.20 (m, 1H), 3.52 (m, 1H), 3.90 (m, 1H), 5.13 (d, 2H), 7.33 (m, 5H).

Step 8. Benzyl (S)-2-amino-3-(cis-4-fluorocyclohexyl)propylmethylcarbamate

A solution of tert-butyl (S)-1-(trans-4-fluorocyclohexyl)-3-(N-(benzyloxycarbonyl)-N-methylamino)propan-2-ylcarbamate (550 mg, 1.3 mmol) in TFA/CH₂Cl₂ (20 mL, v/v 20%) was stirred for 1 h at rt, quenched with satd aq NaHCO₃ until no further gas evolution was visible and extracted with CH₂Cl₂ (2×50 mL). The combined organic layers were washed with brine, dried over MgSO₄, filtered and condensed under reduced pressure to obtain benzyl (S)-2-amino-3-(cis-4-fluorocyclohexyl)propylmethylcarbamate (400 mg, yield 95%). ¹H NMR (CDCl₃, 400 MHz) δ 1.42 (m, 4H), 1.64 (m, 4H), 2.98 (d, 3H), 3.21 (m, 1H), 3.50 (m, 1H), 3.90 (m, 1H), 5.13 (d, 2H), 7.33 (m, 5H).

Example 108

Benzyl (S)-2-amino-3-(trans-4-fluorocyclohexyl)propylmethylcarbamate

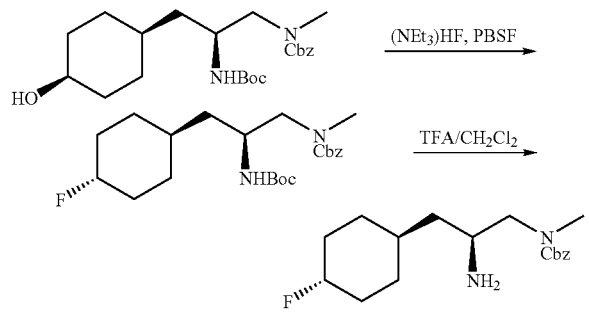

Step 1. Benzyl (S)-2-(t-butoxycarbonylamino)-3-(trans-4-fluorocyclohexyl)propyl(methyl)carbamate A mixture of benzyl (S)-2-(t-butoxycarbonylamino)-3-(cis-4-hydroxycyclohexyl)-propyl(methyl)carbamate (1 g, 2.38 mmol), base Et₃N (5 mL, 28 mmol), a fluoride source NEt₃(HF)₃ (1.9 mL, 9.52 mmol) and perfluorobutanesulfonyl fluoride (2.1 mL, 9.52 mmol) were stirred in THF (24 mL, 1 mmol/10 mL) in a capped vial or flask at 50° C. until LC revealed complete conversion. The reaction mixture was quenched with water and extracted with EtOAc (2×100 mL), dried over MgSO₄, and evaporated. The residue was then purified by preparative HPLC to give benzyl (S)-2-(t-butoxycarbonylamino)-3-(trans-4-fluorocyclohexyl)propyl(methyl)carbamate (200 mg, 20%) as a white solid.

Step 2. (2-Amino-3-(4-fluoro-cyclohexyl)-propyl)-methyl-carbamic acid benzyl ester A solution of benzyl (S)-2-(t-butoxycarbonylamino)-3-(trans-4-fluorocyclohexyl)-propyl(methyl)carbamate (200 mg, 0.47 mmol) in TFA/CH₂Cl₂ (15 mL, v/v 20%) was stirred for 1 h at rt, then quenched by addition of sat'd aq NaHCO₃ solution until gas evolution ceased. The mixture was extracted with CH₂Cl₂ (2×50 mL). The combined organic layers were washed with brine, dried over MgSO₄, filtered and concentrated under reduced pressure to obtain benzyl (S)-2-amino-3-(trans-4-fluorocyclohexyl)propyl(methyl)carbamate (140 mg, yield 93%). ¹H NMR (CDCl₃, 400 MHz): δ 1.42 (m, 4H), 1.64 (m, 4H), 2.98 (d, 3H), 3.21 (m, 1H), 3.50 (m, 1H), 3.90 (m, 1H), 5.13 (d, 2H), 7.33 (m, 5H).

Example 109

(S)-2-(trimethylsilyl)ethyl 2-amino-3-(4-(tert-butyldimethylsilyloxy)cyclohexyl)propyl(methyl)carbamate

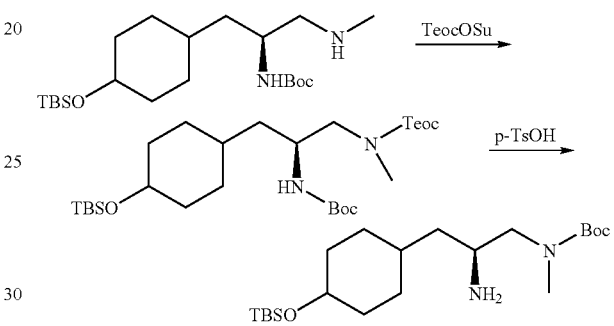

Step 1. (S)-tert-butyl 1-(4-(tert-butyldimethylsilyloxy)cyclohexyl)-3-(N-methyl-N-(2-(trimethylsilyl)ethoxycarbonyl)amino)propan-2-ylcarbamate Solid Teoc-OSu (1.35 g, 5.25 mmol) was added to a two-phase solution of (S)-tert-butyl 1-(4-(tert-butyldimethylsilyloxy)cyclohexyl)-3-(methylamino)propan-2-ylcarbamate (2.0 g, 5.0 mmol), K₂CO₃ (0.75 g, 9.0 mmol) in H₂O (6 ml) and CH₂Cl₂ (12 mL). The mixture was vigorously stirred for 2 h at rt. The product was extracted with CH₂Cl₂. The combined organic layers were washed with sat'd aq NaHCO₃ and brine, dried over Na₂SO₄ and evaporated. The residue was purified by column chromatography to provide (S)-tert-butyl 1-(4-(tert-butyldimethylsilyloxy)cyclohexyl)-3-(N-methyl-N-(2-(trimethylsilyl)ethoxycarbonyl)amino)propan-2-ylcarbamate (1.9 g, 3.49 mmol, 70% yield). ¹H NMR (400 MHz, CD₃OD): 0.05 (s, 15H), 0.87 (s, 9H), 1.40 (s, 9H), 1.69 (s, 3H), 2.96 (m, 3H), 3.40-3.52 (m, 1H), 3.81-3.92 (m, 1H), 4.12-4.29 (m, 2H). MS (E/Z): 545 (M+H⁺)

Step 2. (S)-2-(trimethylsilyl)ethyl 2-amino-3-(4-(tert-butyldimethylsilyloxy)cyclohexyl)-propyl(methyl)carbamate (S)-tert-butyl 1-(4-(tert-butyldimethylsilyloxy)cyclohexyl)-3-(N-methyl-N-(2-(trimethylsilyl)ethoxycarbonyl)amino)propan-2-ylcarbamate (1.9 g, 3.49 mmol) was dissolved into a minimal volume of Et₂O (23.4 mL) and added to a solution of TsOH (0.66 g, 3.49 mmol) in absolute EtOH (5 mL). This solution was placed on a rotary evaporator and the Et₂O was removed at ambient temperature. The flask was then lowed into the water bath (temperature: 60° C.) and the selective deprotection of the Boc group proceeded concurrent with removal of the remainder of solvent. The reaction was complete after 2 h and gave a pale yellow oil. The residue was dissolved into EtOAc (30 mL) and washed with 1 M aq NaOH (3×5 mL), brine (4×5 mL). The combined organic layers were dried and concentrated to provide (S)-2-(trimethylsilyl)ethyl 2-amino-3-(4-(tert-butyldimethylsilyloxy)cyclohexyl)propyl(methyl)carbamate (1.15 g, 74%). MS (E/Z): 445 (M+H⁺).

Example 110 tert-Butyl 2-amino-3-(1-fluorocyclohexyl)propyl (methyl)carbamate

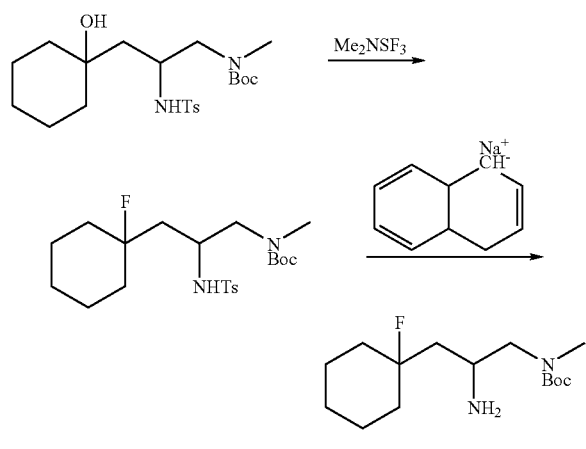

Step 1. tert-Butyl 3-(1-fluorocyclohexyl)-2-(4-methylphenylsulfonamido)propyl(methyl)carbamate To a solution of tert-butyl 3-(1-hydroxycyclohexyl)-2-(4-methylphenylsulfonamido)-propyl(methyl)carbamate (9.23 g, 21 mmol) in dry CH₂Cl₂ (100 mL) at −78° C. was added (dimethylamino)sulfur trifluoride (4.2 g, 32 mmol). The reaction mixture was poured into water (80 mL) and extracted with CH₂Cl₂ (3×50 mL). The combined organic layers were washed with brine, dried over Na₂SO₄ and concentrated in vacuo. The residue was purified by column chromatography on silica eluted with 10:90 hexanes/EtOAc to afford a light yellow solid. The crude product was purified further by preparative HPLC to give tert-butyl 3-(1-fluorocyclohexyl)-2-(4-methylphenylsulfonamido)propyl(methyl)carbamate (1.85 g). ¹H NMR (400 MHz, CDCl₃): 1.24-1.52 (m, 19H), 1.74-1.79 (m, 3H), 2.42 (s, 3H), 2.50 (s, 3H), 3.15 (m, 1H), 3.40 (m, 2H), 7.30 (d, 2H), 7.72 (d, J=8.4, 2H). MS (E/Z): 443 (M+H⁺).

Step 2. tert-Butyl 2-amino-3-(1-fluorocyclohexyl) propyl(methyl)carbamate

A solution of sodium naphalenide in anhydrous DME was prepared by adding anhydrous DME (20 mL) to a mixture of sodium (0.3 g, 13 mmol) and naphthalene (2.1 g, 16 mmol) and stirring the resulting mixture at rt for 2 h. A solution of tert-butyl 3-(1-fluorocyclohexyl)-2-(4-methylphenylsulfonamido)propyl(methyl)carbamate (200 mg, 0.43 mmol) in anhydrous DME (15 mL) was cooled in dry ice-isopropyl alcohol bath. The sodium naphthalenide solution was added dropwise to the well-stirred tosylamide solution until a light green color persisted. The reaction was quenched with water, diluted with EtOAc and washed with 1 N aq HCl. The aqueous phase was basified with K₂CO₃, and extracted with EtOAc (3×20 mL). The combined organic layers were washed with brine, dried over Na₂SO₄ and concentrated in vacuo to give (S)-[2-amino-3-(1-fluoro-cyclohexyl)-propyl]-methyl-carbamic acid tert-butyl ester (50 mg, 45%).

Example 111

(S)-2-(Trimethylsilyl)ethyl 2-amino-4-methoxy-4-methylpentyl(methyl)carbamate

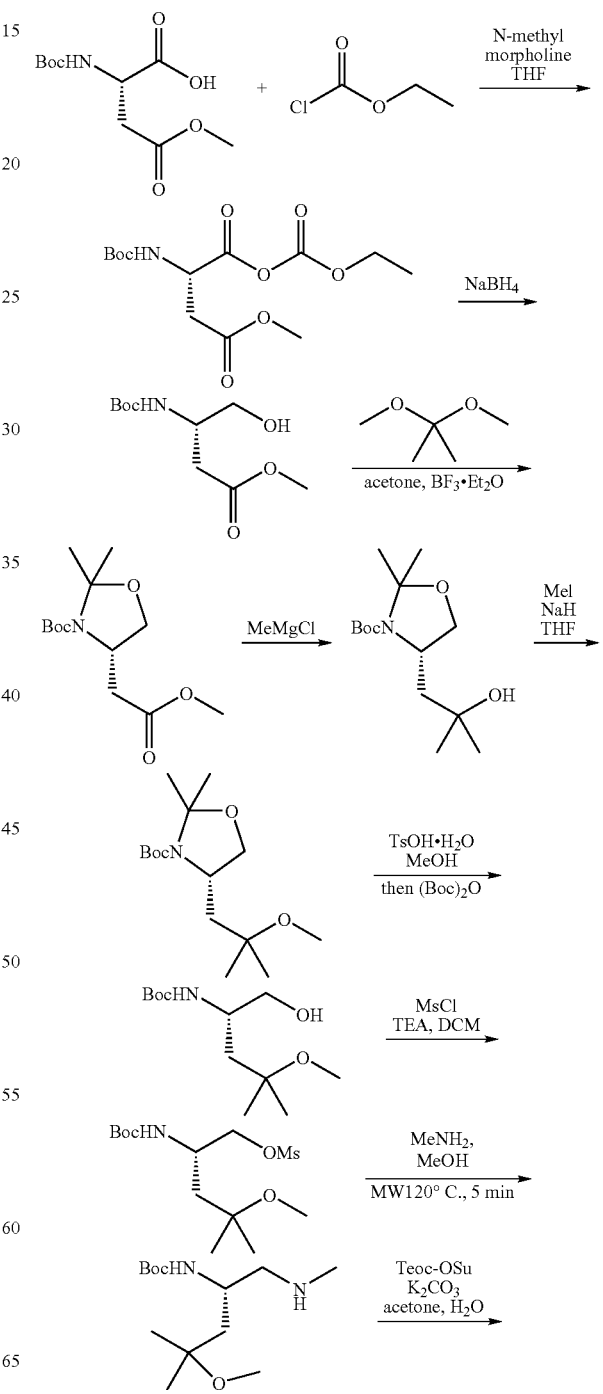

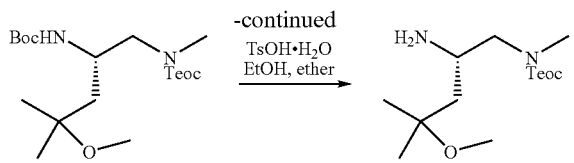

Step 1. (S)-Methyl 3-(tert-butoxycarbonylamino)-4-hydroxybutanoate

To a stirred solution of (S)-2-(tert-butoxycarbonylamino)-4-methoxy-4-oxobutanoic acid (9.0 g, 35.7 mmol) in THF (180 mL) at −10° C. was added N-methylmorpholine (3.9 mL, 35.7 mmol) followed by ethyl chloroformate (3.91 g, 35.7 mmol). After 10 min, the mixture was transferred slowly to a mixture of NaBH$_4$ (2.7 g, 71.4 mmol) and ice water (900 mL). The resulting solution was stirred for 1 h, NaHCO$_3$ (~20 g) was added, and the organic layer was separated. The aqueous layer was extracted with EtOAc (4×200 mL). The combined organic layers were washed with 1 N aq HCl (20 mL) and brine (15 mL), dried over Na$_2$SO$_4$, and concentrated to give (S)-methyl 3-(tert-butoxycarbonylamino)-4-hydroxybutanoate (7.06 g, 85%) as an oil. MS m/z 234 (M+H$^+$).

Step 2. (S)-tert-Butyl 4-(2-methoxy-2-oxoethyl)-2,2-dimethyloxazolidine-3-carboxylate To a solution of (S)-methyl 3-(tert-butoxycarbonylamino)-4-hydroxybutanoate (7.0 g, 30.0 mmol) in acetone (90 mL), there was added 2,2-dimethoxypropane (37 mL, 300 mmol) followed by BF$_3$·Et$_2$O (0.11 mL, 0.9 mmol). The resulting solution was stirred at rt overnight. Solvents were removed under vacuum, and the residue was redissolved in ether (100 mL), washed with sat'd NaHCO$_3$ (20 mL). Upon concentrating under vacuum, the residue was purified by flash column chromatography to give (S)-tert-butyl 4-(2-methoxy-2-oxoethyl)-2,2-dimethyloxazolidine-3-carboxylate (7.51 g, 92%). MS m/z 296 (M+Na$^+$).

Step 3. (S)-tert-Butyl 4-(2-hydroxy-2-methylpropyl)-2,2-dimethyloxazolidine-3-carboxylate To a stirred solution of (S)-tert-butyl 4-(2-methoxy-2-oxoethyl)-2,2-dimethyloxazolidine-3-carboxylate (1.56 g, 5.71 mmol) in toluene (10 mL) at −20° C., was added methylmagnesium chloride in THF (3 M, 7.61 mL) dropwise to keep the solution temperature below −20° C. After addition, the solution was allowed to warm to rt slowly, and stirred for another 1 h. Sat'd aq NH$_4$Cl (5 mL) was added, and the organic layer was washed with water (10 mL), and concentrated under vacuum. The residue was purified by flash column chromatography to give (S)-tert-butyl 4-(2-hydroxy-2-methylpropyl)-2,2-dimethyloxazolidine-3-carboxylate (0.93 g, 60%) as an oil. $^1$H NMR (400 MHz, CDCl$_3$): 4.18 (m, 1H), 4.00 (m, 2H), 3.80 (m, 1H), 1.92 (m, 1H), 1.74 (m, 1H), 1.44 (ss, 15H), 1.24 (s, 6H); MS m/z 296 (M+Na$^+$).

Step 4. (S)-tert-Butyl 4-(2-methoxy-2-methylpropyl)-2,2-dimethyloxazolidine-3-carboxylate To a stirred solution of (S)-tert-butyl 4-(2-hydroxy-2-methylpropyl)-2,2-dimethyl-oxazolidine-3-carboxylate (0.93 g, 3.4 mmol) in anhydrous THF (8 mL), there was added NaH (60 wt % in mineral oil, 0.41 g, 10.2 mmol) followed by iodomethane (1.46 g, 10.2 mmol). The resulting mixture was stirred at rt until no starting material remained (~5 h). The reaction was quenched by slow addition of water, the organic layer was separated, and aqueous layer was extracted with ether (2×5 mL). The combined organic layers were washed with 1 N aq HCl (5 mL), sat'd aq NaHCO$_3$ (5 mL) and brine (5 mL), dried over Na$_2$SO$_4$ and concentrated to give crude (S)-tert-butyl 4-(2-methoxy-2-methylpropyl)-2,2-dimethyloxazolidine-3-carboxylate (1.2 g, quant.) which was used without purification. MS m/z 310 (M+Na$^+$).

Step 5. (S)-tert-Butyl 1-hydroxy-4-methoxy-4-methylpentan-2-ylcarbamate

To a solution of (S)-tert-butyl 4-(2-methoxy-2-methylpropyl)-2,2-dimethyloxazolidine-3-carboxylate (1.2 g, 3.40 mmol) in MeOH (5 mL) at rt, there was added 4-methylbenzenesulfonic acid (0.65 g, 3.40 mmol). The resulting solution was stirred until no starting material remained (~1 h). Solvent was removed under vacuum, and the residue was redissolved in acetone (3 mL) and H$_2$O (1 mL). Excess K$_2$CO$_3$ was added to keep the solution basic, followed by (Boc)$_2$O. The mixture was stirred for 20 min, acetone was removed under vacuum, and the aqueous solution was extracted with CH$_2$Cl$_2$ (4×5 mL). After concentration, the residue was purified by flash column chromatography to give (S)-tert-butyl 1-hydroxy-4-methoxy-4-methylpentan-2-ylcarbamate (0.76 g, 78%, 2 steps). $^1$H NMR (400 MHz, CDCl$_3$): 5.38 (br, 1H), 3.78 (m, 1H), 3.66 (m, 1H), 3.56 (m, 1H), 3.20 (s, 3H), 1.66 (m, 2H), 1.62 (br, 1H), 1.44 (s, 9H), 1.20 (s, 6H); MS m/z 248 (M+H$^+$).

Step 6. (S)-2-(tert-Butoxycarbonylamino)-4-methoxy-4-methylpentyl methanesulfonate To a solution of (S)-tert-butyl 1-hydroxy-4-methoxy-4-methylpentan-2-yl carbamate (0.74 g, 2.99 mmol) in anhydrous CH$_2$Cl$_2$ (15 mL) and triethylamine (1.67 mL, 12.0 mmol) at −20° C., there was added methanesulfonyl chloride (0.69 g, 6.0 mmol) dropwise to keep the solution temperature below −20° C. After addition, the solution was warmed to rt slowly, and stirred for another 2 h. Water (5 mL) was added, and the organic layer was separated. The aqueous layer was extracted with CH$_2$Cl$_2$ (2×5 mL), and the combined organic layers were washed with 1 N aq HCl (5 mL), water (5 mL) and brine (5 mL), and dried over Na$_2$SO$_4$. Solvent was removed under vacuum to give (S)-2-(tert-butoxycarbonylamino)-4-methoxy-4-methylpentyl methane-sulfonate (1.08 g, quant.), which was used for the next step without purification. MS m/z 348 (M+Na$^+$).

Step 7. (S)-tert-Butyl 4-methoxy-4-methyl-1-(methylamino)pentan-2-ylcarbamate To a solution of (S)-2-(tert-butoxycarbonylamino)-4-methoxy-4-methylpentyl methane-sulfonate (1.08 g, 2.99 mmol) in MeOH was added methylamine in methanol (33 wt %, 4.0 mL). The resulting solution was heated in CEM microwave reactor at 120° C. for 5 min. Reaction completion was confirmed by LC-MS. Solvent was removed under vacuum to give a crude (S)-tert-butyl 4-methoxy-4-methyl-1-(methylamino)pentan-2-ylcarbamate, which was used for the next step without purification. MS m/z 261 (M+H$^+$).

Step 8. (S)-tert-butyl 4-methoxy-4-methyl-1-(N-methyl-N-(2-(trimethylsilyl)ethoxycarbonyl)-amino)pentan-2-ylcarbamate To a solution of the above (S)-tert-butyl 4-methoxy-4-methyl-1-(methylamino)pentan-2-ylcarbamate (~2.99 mmol) in acetone (9 mL) and water (3 mL), there was added K₂CO₃ (1.24 g, 9.0 mmol), followed by Teoc-OSu (0.85 g, 3.29 mmol). The resulting mixture was stirred at rt until no starting material remained (~1 h). Acetone was removed under vacuum, and the aqueous residue was extracted with CH₂Cl₂ (4×5 mL). The combined organic layers were concentrated, and crude residue was purified with flash column chromatography to give (S)-tert-butyl 4-methoxy-4-methyl-1-(N-methyl-N-(2-(trimethylsilyl)ethoxycarbonyl)amino)pentan-2-ylcarbamate (0.18 g, 15%, 3 steps) as a clear oil. ¹H NMR (400 MHz, CDCl₃): 4.82, 4.92 (br, 1H), 4.16 (m, 2H), 3.88 (m, 1H), 3.44 (m, 1H), 3.24 (m, 1H), 3.16 (s, 3H), 2.88, 2.90 (s, 3H), 1.44 (s, 9H), 1.18, 1.20 (s, 6H), 0.98 (m, 2H), 0.02 (s, 9H); MS m/z 405 (M+H⁺).

Step 9. (S)-2-(Trimethylsilyl)ethyl 2-amino-4-methoxy-4-methylpentyl(methyl)carbamate To a solution of (S)-tert-butyl 4-methoxy-4-methyl-1-(N-methyl-N-(2-(trimethylsilyl)-ethoxycarbonyl)amino)pentan-2-ylcarbamate (0.17 g, 0.42 mmol) in ether (2.0 mL) was added a solution of p-toluenesulfonic acid (80.7 mg, 0.43 mmol) in ethanol (1.0 mL). Transfer of the p-toluenesulfonic acid was completed with the aid of additional ether (1.0 mL). The solution was placed on a rotary evaporator and the ether was removed at rt. Then, with continuing evacuation, the bath temperature was raised to 60-65° C. for 20 min, during which gas evolution was evident. After cooling down to rt, the solid residue (S)-2-(trimethylsilyl)ethyl 2-amino-4-methoxy-4-methylpentyl(methyl)-carbamate was used without further purification as a p-toluenesulfonic acid salt. MS m/z 291 (M+H⁺).

Example 112

(3R)-3-((S)-1-(2-(2-Ethylphenoxy)phenyl)-1-hydroxy-5-methoxypentyl)-N—((R)-1-hydroxy-3-(methylamino)propan-2-yl)piperidine-1-carboxamide

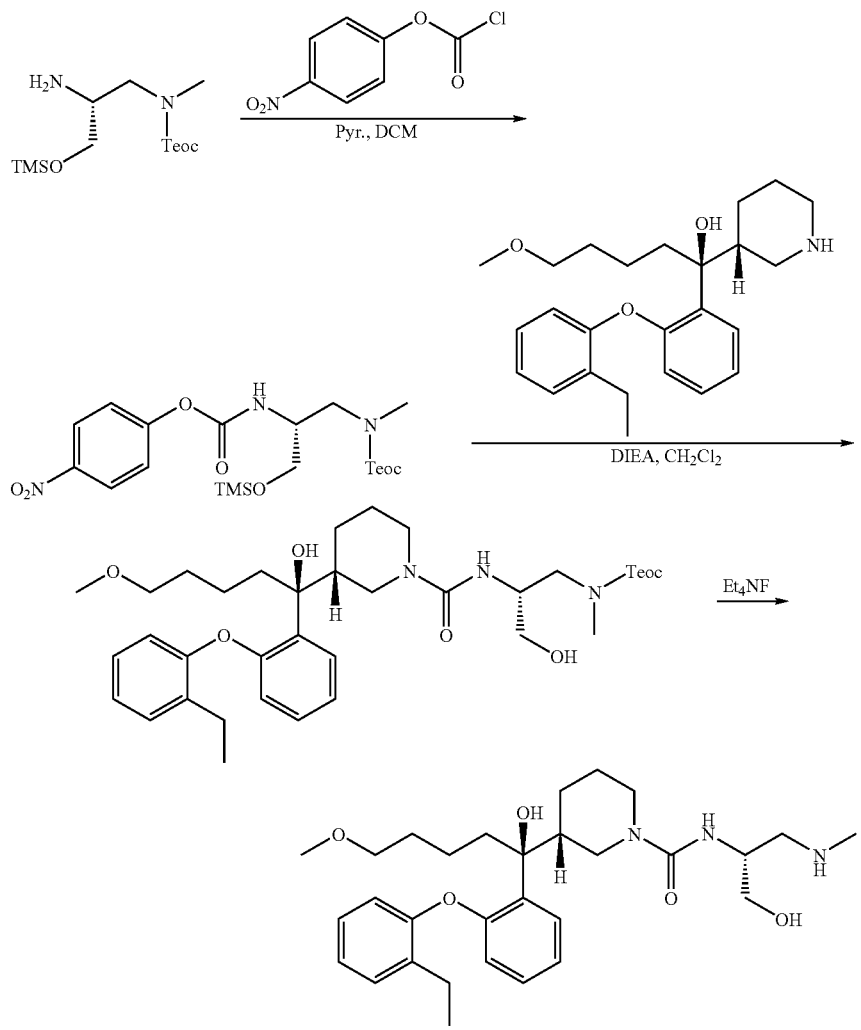

Step 1. (2R)-2-(p-nitrophenoxycarbonylamino)-3-(N-methyl-N-(2-(trimethylsilyl)ethoxy-carbonyl)amino)-1-(trimethylsilyloxy)propane (2-(Trimethylsilyl)ethyl)(R)-2-amino-3-trimethylsilyhydroxypropylmethyl carbamate was dissolved in dry $CH_2Cl_2$ (4 mL) and pyridine (0.35 mL) was added, followed by 4-nitrophenyl chloroformate (0.35 g, 2.11 mmol) at rt. The resulting solution was stirred until no starting material remained (~1 h), and the solution of (2R)-2-(p-nitrophenoxycarbonylamino)-3-(N-methyl-N-(2-(trimethylsilyl)ethoxycarbonyl)amino)-1-(trimethylsilyloxy)propane was used directly without isolation. MS m/z 486 (M+H$^+$).

Step 2. (3R)-3-((S)-1-(2-(2-Ethylphenoxy)phenyl)-1-hydroxy-5-methoxypentyl)-N-((R)-1-hydroxy-3-(N-methyl-N-(2-(trimethylsilyl)ethoxycarbonyl)amino)propan-2-yl)piperidine-1-carboxamide To a solution of (S)-1-(2-(2-ethylphenoxy)phenyl)-5-methoxy-1-((R)-piperidin-3-yl)pentan-1-ol (19.9 mg, 0.05 mmol) in $CH_2Cl_2$ (0.5 mL) was added the solution of (2R)-2-(p-nitrophenoxycarbonylamino)-3-(N-methyl-N-(2-(trimethylsilyl)ethoxycarbonyl)amino)-1-(trimethylsilyloxy)propane (0.05 mmol), followed by DIEA (26 µL, 0.15 mmol). The resulting yellow solution was stirred at rt for 30 min. $CH_2Cl_2$ was removed in vacuo and the residue was redissolved in acetonitrile, and purified by prep HPLC to give (3R)-3-((S)-1-(2-(2-ethylphenoxy)phenyl)-1-hydroxy-5-methoxypentyl)-N—((R)-1-hydroxy-3-(N-methyl-N-(2-(trimethylsilyl)ethoxycarbonyl)amino)propan-2-yl)piperidine-1-carboxamide (10.0 mg, 30%). MS m/z 672 (M+H$^+$).

Step 3. (3R)-3-((S)-1-(2-(2-Ethylphenoxy)phenyl)-1-hydroxy-5-methoxypentyl)-N-((R)-1-hydroxy-3-(methylamino)propan-2-yl)piperidine-1-carboxamide To a solution of (3R)-3-((S)-1-(2-(2-ethylphenoxy)phenyl)-1-hydroxy-5-methoxypentyl)-N—((R)-1-hydroxy-3-(N-methyl-N-(2-(trimethylsilyl)ethoxycarbonyl)amino)propan-2-yl)piperidine-1-carboxamide (10.0 mg, 0.01 mmol) in acetonitrile (1.0 mL) was added excess tetraethylammonium fluoride. The resulting solution was heated at 50° C. for 2 h, and concentrated under vacuum. The residue was purified by prep HPLC to give (3R)-3-((S)-1-(2-(2-ethylphenoxy)phenyl)-1-hydroxy-5-methoxypentyl)-N—((R)-1-hydroxy-3-(methylamino)propan-2-yl)piperidine-1-carboxamide (2 mg) as its TFA salt. $^1$H NMR (400 MHz, $CD_3OD$) 7.62 (d, 1H), 7.32 (d, 1H), 7.04-7.20 (m, 4H), 6.74 (d, 1H), 6.56 (d, 1H), 4.40 (d, 1H), 4.00 (m, 1H), 3.92 (d, 1H), 3.60 (m, 1H), 3.54 (m, 1H), 3.26 (t, 2H), 3.24 (s, 3H), 3.22 (m, 1H), 3.04 (m, 1H), 2.82 (m, 1H), 2.64 (s, 3H), 2.62 (q, 2H), 2.42 (m, 2H), 1.94 (m, 1H), 1.24-1.64 (m, 7H), 1.08 (t, 3H), 0.98 (m, 1H); MS m/z 528 (M+H$^+$).

Example 113

(3R)-3-((S)-1-(3-chlorophenyl)-1-hydroxy-5-methoxypentyl)-N-(3-(1-hydroxycyclohexyl)-1-(methylamino)propan-2-yl)piperidine-1-carboxamide (I-245A)

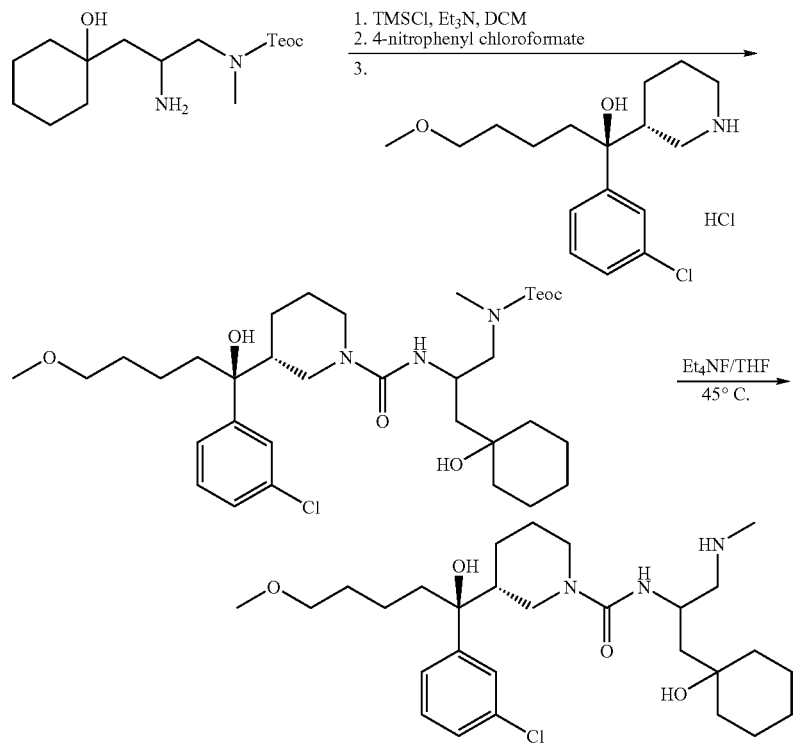

Step 1. (3R)-3-((S)-1-(3-chlorophenyl)-1-hydroxy-5-methoxypentyl)-N-(3-(1-hydroxycyclo-hexyl)-1-(N-methyl-N-(2-(trimethylsilyl)ethoxycarbonyl)amino)propan-2-yl)piperidine-1-carboxamide To a solution of (2-(trimethylsilyl)ethyl 3-(1-hydroxycyclohexyl)-2-aminopropylmethylcarbamate (18.3 mg, 0.055 mmol) in CH$_2$Cl$_2$ (2 mL) were added Et$_3$N (0.2 mL) and Me$_3$SiCl (12 mg, 14 µL, 0.11 mmol). The resulting solution was stirred for 1 h and evaporated under vacuum. The residue was dissolved in CH$_2$Cl$_2$ (2 mL), then pyridine (0.05 mL) was added, followed by 4-nitrophenyl chloroformate (13.5 mg, 0.66 mmol). The mixture was stirred for 30 min and (S)-1-(3-chlorophenyl)-5-methoxy-1-((R)-piperidin-3-yl)pentan-1-ol hydrochloride (19 mg, 0.055 mmol) was added. The mixture was stirred for 10 min and evaporated. The residue was purified by prep HPLC to give (3R)-3-((S)-1-(3-chlorophenyl)-1-hydroxy-5-methoxypentyl)-N-(3-(1-hydroxycyclohexyl)-1-(N-methyl-N-(2-(trimethylsilyl)ethoxycarbonyl)amino)propan-2-yl)piperidine-1-carboxamide (20 mg, 54%). MS m/z 668 (M+H$^+$).

Step 2. (3R)-3-((S)-1-(3-Chlorophenyl)-1-hydroxy-5-methoxypentyl)-N-(3-(1-hydroxycyclohexyl)-1-(methylamino)propan-2-yl)piperidine-1-carboxamide To a solution of (3R)-3-((S)-1-(3-chlorophenyl)-1-hydroxy-5-methoxypentyl)-N-(3-(1-hydroxycyclohexyl)-1-(N-methyl-N-(2-(trimethylsilyl)ethoxycarbonyl)amino)propan-2-yl)piperidine-1-carboxamide (20 mg, 0.03 mmol) in anhydrous THF (1 mL) was added Et$_4$NF (3 mg). The solution was stirred at 45° C. for 2 h and evaporated under reduced pressure. The residue was purified by prep HPLC to give (3R)-3-((S)-1-(3-chlorophenyl)-1-hydroxy-5-methoxypentyl)-N-(3-(1-hydroxycyclohexyl)-1-(methylamino)propan-2-yl)piperidine-1-carboxamide (13.2 mg, 71%) as its TFA salt. $^1$H NMR (400 MHz, CD$_3$OD): 7.43 (t, 1H), 7.32-7.21 (m, 3H), 4.42 and 4.29 (two isomers on 1 to 1 ratio, d, 1H), 4.15 (m, 1H), 3.95 and 3.83 (two isomers on 1 to 1 ratio, d, 1H), 3.34 (m, 1H), 3.27 (s, 3H), 3.14 (m, 1H), 2.99 (m, 1H), 2.80 (s, 3H), 2.64-2.38 (m, 3H), 1.94 (t, 2H), 1.76 (m, 2H), 1.68-1.18 (m, 20H), 0.98 (m, 1H); MS m/z 524 (M+H$^+$).

Example 114

(3R)-3-((S)-1-(3-fluorophenyl)-1-hydroxy-5-methoxypentyl)-N-(3-(1-hydroxycyclohexyl)-1-(methylamino)propan-2-yl)piperidine-1-carboxamide (I-187A)

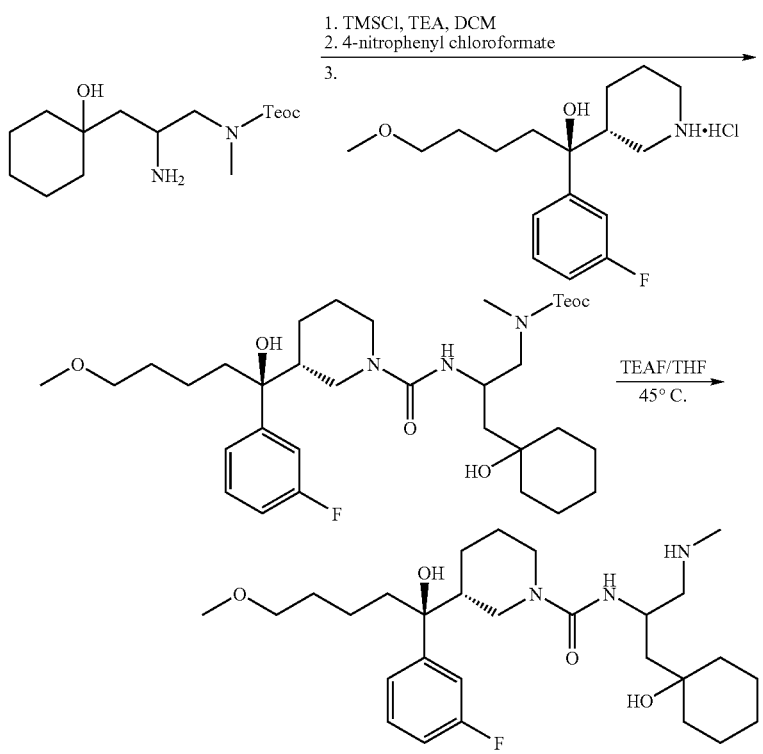

Step 1. (3R)-3-((S)-1-(3-fluorophenyl)-1-hydroxy-5-methoxypentyl)-N-(3-(1-hydroxycyclohexyl)-1-(N-methyl-N-(2-(trimethylsilyl)ethoxycarbonyl)amino)propan-2-yl)piperidine-1-carboxamide To a solution of 2-(trimethylsilyl)ethyl 3-(1-hydroxycyclohexyl)-2-aminopropylmethylcarbamate (18.3 mg, 0.055 mmol) in CH$_2$Cl$_2$ (2 mL) was added Et$_3$N (0.2 mL) and TMSCl (12 mg, 14 µL, 0.11 mmol). The resulting solution was stirred for 1 h and evaporated under vacuum. The residue was dissolved in CH$_2$Cl$_2$ (2 mL) and pyridine (0.05 mL) was added, followed by 4-nitrophenyl chloroformate (13.5 mg, 0.66 mmol). The solution was stirred for 30 min and (S)-1-(3-fluorophenyl)-5-methoxy-1-((R)-piperidin-3-yl)pentan-1-ol hydrochloride (18 mg, 0.055 mmol). The resulting mixture was stirred for 10 min and evaporated. The residue was purified by prep HPLC to give (3R)-3-((S)-1-(3-fluorophenyl)-1-hydroxy-5-methoxypentyl)-N-(3-(1-hydroxycyclohexyl)-1-(N-methyl-N-(2-(trimethylsilyl)ethoxycarbonyl)amino)propan-2-yl)piperidine-1-carboxamide (17.8 mg, 50%). MS m/z 652 (M+H$^+$).

Step 2. (3R)-3-((S)-1-(3-Fluorophenyl)-1-hydroxy-5-methoxypentyl)-N-(3-(1-hydroxycyclohexyl)-1-(methylamino)propan-2-yl)piperidine-1-carboxamide To a solution of (3R)-3-((S)-1-(3-fluorophenyl)-1-hydroxy-5-methoxypentyl)-N-(3-(1-hydroxycyclohexyl)-1-(N-methyl-N-(2-(trimethylsilyl)ethoxycarbonyl)amino)propan-2-yl)-piperidine-1-carboxamide (17.8 mg, mmol) in anhydrous THF (1 mL) was added Et$_4$NF (3 mg). The solution was stirred at 45° C. for 2 h and evaporated under reduced pressure. The residue was purified by prep HPLC to give (3R)-3-((S)-1-(3-fluorophenyl)-1-hydroxy-5-methoxypentyl)-N-(3-(1-hydroxycyclohexyl)-1-(methylamino)propan-2-yl)piperidine-1-carboxamide (9.5 mg, 58%) as a TFA salt. $^1$H NMR (400 MHz, CD$_3$OD) δ 7.32 (q, 1H), 7.16 (m, 1H), 7.14 (m. 1H), 6.94 (m, 1H), 4.42 and 4.28 (two isomers in a 3:2 ratio, d, 1H), 4.15 (m, 1H), 3.95 and 3.84 (two isomers on 3 to 2 ratio, d, 1H), 3.32 (m, 1H), 3.26 (s, 3H), 3.14 (dd, 1H), 2.95 (m, 1H), 2.70 (s, 3H), 2.60-2.39 (m 3H), 1.94 (t, 2H), 1.79-1.22 (m, 20H), 1.00 (m, 1H); MS m/z 508 (M+H$^+$).

Example 115

(3R)-3-((S)-1-(3-Fluorophenyl)-1-hydroxy-5-methoxypentyl)-N-(3-(1-hydroxycyclohexyl)-2-(methylamino)propyl)piperidine-1-carboxamide (I-188A)

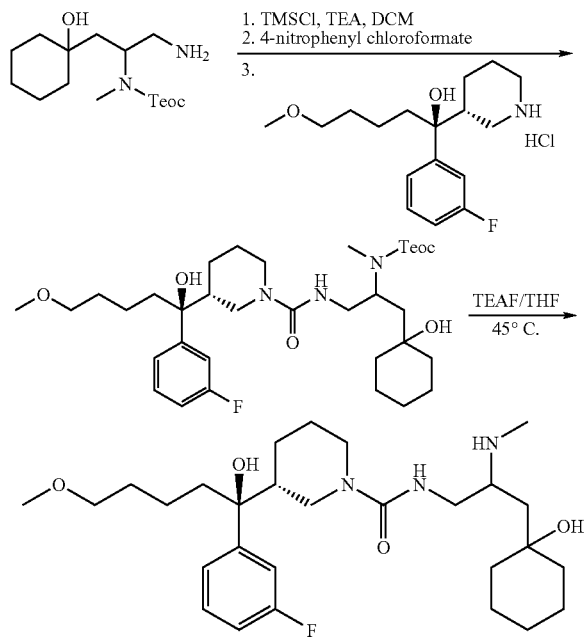

Step 1. (3R)-3-((S)-1-(3-fluorophenyl)-1-hydroxy-5-methoxypentyl)-N-(3-(1-hydroxycyclohexyl)-2-(N-methyl-N-(2-(trimethylsilyl)ethoxycarbonyl)amino)propyl)piperidine-1-carboxamide To a solution of 1-(3-amino-2-(N-methyl-N-(2-(trimethylsilyl)ethoxycarbonyl)amino)propyl)cyclohexanol (12 mg, 0.036 mmol) in CH$_2$Cl$_2$ (1.5 mL) was added Et$_3$N (0.1 mL) and TMSCl (7.8 mg, 9 μL, 0.073 mmol). The resulting solution was stirred for 1 h and evaporated under vacuum. The residue was dissolved in CH$_2$Cl$_2$ (1.5 mL) and pyridine (0.03 mL) was added, followed by 4-nitrophenyl chloroformate (9 mg, 0.043 mmol). The solution was stirred for 30 min and (S)-1-(3-chlorophenyl)-5-methoxy-1-((R)-piperidin-3-yl)pentan-1-ol hydrochloride (14 mg, 0.043 mmol) was added. The resulting mixture was stirred for 10 min and evaporated. The residue was purified by prep HPLC to give (3R)-3-((S)-1-(3-fluorophenyl)-1-hydroxy-5-methoxypentyl)-N-(3-(1-hydroxycyclohexyl)-2-(N-methyl-N-(2-(trimethylsilyl)ethoxycarbonyl)amino)propyl)piperidine-1-carboxamide (12.5 mg, 53%). MS m/z 652 (M+H$^+$).

Step 2. (3R)-3-((S)-1-(3-Fluorophenyl)-1-hydroxy-5-methoxypentyl)-N-(3-(1-hydroxycyclohexyl)-2-(methylamino)propyl)piperidine-1-carboxamide To a solution of (3R)-3-((S)-1-(3-fluorophenyl)-1-hydroxy-5-methoxypentyl)-N-(3-(1-hydroxycyclohexyl)-2-(N-methyl-N-(2-(trimethylsilyl)ethoxycarbonyl)amino)propyl)piperidine-1-carboxamide (9.7 mg, 0.015 mmol) in anhydrous THF (1 mL) was added Et$_4$NF (3 mg). The solution was stirred at 45° C. for 2 h and evaporated under reduced pressure. The residue was purified by prep HPLC to give (3R)-3-((S)-1-(3-fluorophenyl)-1-hydroxy-5-methoxypentyl)-N-(3-(1-hydroxycyclohexyl)-2-(methylamino)propyl)piperidine-1-carboxamide (4.5 mg, 50%) as its TFA salt. $^1$H NMR (400 MHz, CD$_3$OD): 7.32 (t, 1H), 7.16 (d, 1H), 7.14 (d, 1H), 6.94 (td, 1H), 4.36 (t, 1H), 3.88 (t, 1H), 3.53 (m, 1H), 3.40 (m, 1H), 3.26 (s, 3H), 2.61 (s, 3H), 2.48 (m, 1H), 2.47 (m, 1H), 1.94 (t, 2H), 1.90 (td, 1H), 1.76 (tt, 1H), 1.69-1.22 (m, 18H), 0.99 (m, 1H); MS m/z 524 (M+H$^+$).

Example 116

(3R)-3-((S)-1-(3-chlorophenyl)-1-hydroxy-5-methoxypentyl)-N-(3-(1-hydroxycyclohexyl)-2-(methylamino)propyl)piperidine-1-carboxamide (I-246A)

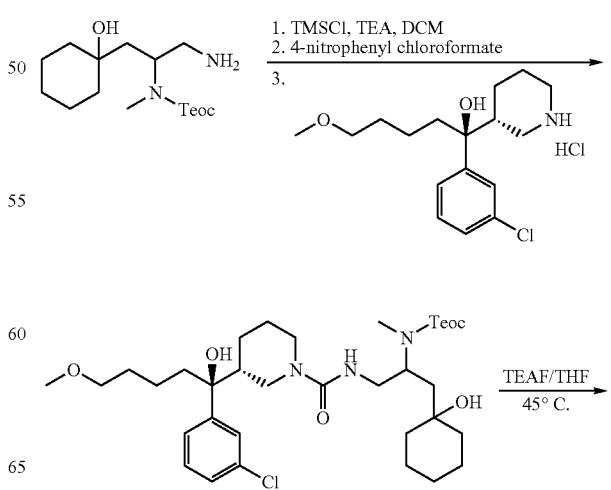

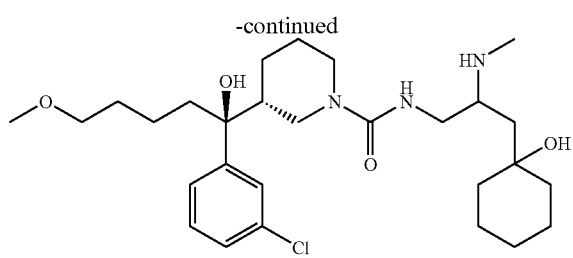

Step 1. (3R)-3-((S)-1-(3-chlorophenyl)-1-hydroxy-5-methoxypentyl)-N-(3-(1-hydroxy-cyclohexyl)-2-(N-methyl-N-(2-(trimethylsilyl)ethoxycarbonyl)amino) propyl)piperidine-1-carboxamide To a solution of 1-(3-amino-2-(N-methyl-N-(2-(trimethylsilyl)ethoxycarbonyl)amino)propyl)cyclohexanol (21 mg, 0.064 mmol) in $CH_2Cl_2$ (2 mL) was added $Et_3N$ (0.2 mL) and TMSCl (13.9 mg, 16 µL, 0.13 mmol). The resulting solution was stirred for 1 h and evaporated under vacuum The residue was dissolved in $CH_2Cl_2$ (2 mL) and pyridine (0.05 mL) was added, followed by 4-nitrophenyl chloroformate (15 mg, 0.077 mmol). The solution was stirred for 30 min and (S)-1-(3-chlorophenyl)-5-methoxy-1-((R)-piperidin-3-yl)pentan-1-ol hydrochloride (27 mg, 0.077 mmol) was added. The resulting mixture was stirred for 10 min and evaporated. The residue was purified by preparative HPLC to give (3R)-3-((S)-1-(3-chlorophenyl)-1-hydroxy-5-methoxypentyl)-N-(3-(1-hydroxycyclohexyl)-2-(N-methyl-N-(2-(trimethylsilyl)ethoxycarbonyl)amino)propyl)piperidine-1-carboxamide (22 mg, 51%). MS m/z 668 (M+H$^+$).

Step 2. (3R)-3-((S)-1-(3-chlorophenyl)-1-hydroxy-5-methoxypentyl)-N-(3-(1-hydroxycyclohexyl)-2-(methylamino)propyl)piperidine-1-carboxamide To a solution of (3R)-3-((S)-1-(3-chlorophenyl)-1-hydroxy-5-methoxypentyl)-N-(3-(1-hydroxycyclohexyl)-2-(N-methyl-N-(2-(trimethylsilyl)ethoxycarbonyl)amino)propyl)piperidine-1-carboxamide (10.7 mg, 0.016 mmol) in anhydrous THF (1 mL) was added Et4NF (3 mg). The solution was stirred at 45° C. for 2 h and evaporated under reduced pressure. The residue was purified by preparative HPLC to give (3R)-3-((S)-1-(3-chlorophenyl)-1-hydroxy-5-methoxypentyl)-N-(3-(1-hydroxycyclohexyl)-1-(methylamino)propan-2-yl)piperidine-1-carboxamide (6.3 mg, 64%) as its TFA salt. $^1$H NMR (400 MHz, CD$_3$OD): 7.43 (d, 1H), 7.33-7.21 (m, 3), 4.37 (t, 1H), 3.88 (t, 1H), 3.54 (m, 1H), 3.40 (m, 1H), 3.33 (m, 1H), 3.27 (s, 3H), 2.60 (q, 1H), 2.46 (m, 1H), 1.94 (t, 2H), 1.86 (dt, 1H), 1.76 (tt, 1H), 1.68-1.21 (m 18H), 0.99 (m, 1H); MS m/z 524 (M+H$^+$).

Example 117

The following compounds were prepared using procedures analogous to those described in Examples 113-116:

| Cpd. No. | Name |
| --- | --- |
| I-186A | (3R)—N-((2R)-1-cyclohexyl-1-hydroxy-3-(methylamino)propan-2-yl)-3-((S)-1-(3-fluorophenyl)-1-hydroxy-5-methoxypentyl)piperidine-1-carboxamide |
| I-186B | (3R)—N-((1S,2R)-1-cyclohexyl-1-hydroxy-3-(methylamino)propan-2-yl)-3-((S)-1-(3-fluorophenyl)-1-hydroxy-5-methoxypentyl)piperidine-1-carboxamide |
| I-202A | (3R)—N-((1R,2R)-3-amino-1-cyclohexyl-1-hydroxypropan-2-yl)-3-((S)-1-(3-chlorophenyl)-1-hydroxy-5-methoxypentyl)piperidine-1-carboxamide |
| I-202B | (3R)—N-((1S,2R)-3-amino-1-cyclohexyl-1-hydroxypropan-2-yl)-3-((S)-1-(3-chlorophenyl)-1-hydroxy-5-methoxypentyl)piperidine-1-carboxamide |
| I-203A | (3R)-3-((S)-1-(3-chlorophenyl)-1-hydroxy-5-methoxypentyl)-N-((1R,2R)-1-cyclopentyl-1-hydroxy-3-(methylamino)propan-2-yl)piperidine-1-carboxamide |
| I-203B | (3R)-3-((S)-1-(3-chlorophenyl)-1-hydroxy-5-methoxypentyl)-N-((1S,2R)-1-cyclopentyl-1-hydroxy-3-(methylamino)propan-2-yl)piperidine-1-carboxamide |
| I-244A | (3R)-3-((S)-1-(3-chlorophenyl)-1-hydroxy-5-methoxypentyl)-N-((1R,2R)-1-cyclohexyl-1-hydroxy-3-(methylamino)propan-2-yl)piperidine-1-carboxamide |
| I-244B | (3R)-3-((S)-1-(3-chlorophenyl)-1-hydroxy-5-methoxypentyl)-N-((1S,2R)-1-cyclohexyl-1-hydroxy-3-(methylamino)propan-2-yl)piperidine-1-carboxamide |
| I-353A | (R)—N-((1S,2R)-1-cyclopentyl-1-hydroxy-3-(methylamino)propan-2-yl)-3-((S)-1-(3-fluorophenyl)-1-hydroxy-5-methoxypentyl)piperidine-1-carboxamide |
| I-360A | (R)-3-((S)-1-(3-chloro-2-fluorophenyl)-1-hydroxy-5-methoxypentyl)-N-((2R,3S)-3-hydroxy-4-methyl-1-(methylamino)pentan-2-yl)piperidine-1-carboxamide |
| I-371A | (R)—N-((1S,2R)-1-cyclopentyl-1-hydroxy-3-(methylamino)propan-2-yl)-3-((S)-1-(2,3-difluorophenyl)-1-hydroxy-5-methoxypentyl)piperidine-1-carboxamide |
| I-392A | (3R)-3-((S)-4-acetamido-1-(2,3-difluorophenyl)-1-hydroxybutyl)-N-((2R)-1-cyclopentyl-1-hydroxy-3-(methylamino)propan-2-yl)piperidine-1-carboxamide |
| I-395A | (R)—N-((1S,2R)-1-cyclohexyl-1-hydroxy-3-(methylamino)propan-2-yl)-3-((S)-1-(2,3-difluorophenyl)-1-hydroxy-5-methoxypentyl)piperidine-1-carboxamide |

-continued

| Cpd. No. | Name |
|---|---|
| I-405A | (R)-3-((S)-1-(3-chloro-2-fluorophenyl)-1-hydroxy-5-methoxypentyl)-N-((1S,2R)-1-cyclopentyl-1-hydroxy-3-(methylamino)propan-2-yl)piperidine-1-carboxamide |
| I-427A | (R)—N-((2R,3S)-3-hydroxy-4-methyl-1-(methylamino)pentan-2-yl)-3-((S)-1-hydroxy-5-methoxy-1-(2-phenoxyphenyl)pentyl)piperidine-1-carboxamide |
| I-428A | (R)-3-((S)-1-(3-chloro-2-fluorophenyl)-1-hydroxy-5-methoxypentyl)-N-((1S,2R)-1-cyclohexyl-1-hydroxy-3-(methylamino)propan-2-yl)piperidine-1-carboxamide |
| I-447A | (R)-3-((S)-1-(3-chloro-2-fluorophenyl)-1-hydroxy-5-methoxypentyl)-N-((1R,2R)-1-cycloheptyl-1-hydroxy-3-(methylamino)propan-2-yl)piperidine-1-carboxamide |
| I-452A | (R)-3-((S)-1-(3-fluoro-2-phenoxyphenyl)-1-hydroxy-5-methoxypentyl)-N-((2R,3S)-3-hydroxy-4-methyl-1-(methylamino)pentan-2-yl)piperidine-1-carboxamide |
| I-457A | (R)—N-((1S,2R)-1-cyclopentyl-1-hydroxy-3-(methylamino)propan-2-yl)-3-((S)-1-hydroxy-5-methoxy-1-(2-phenoxyphenyl)pentyl)piperidine-1-carboxamide |
| I-463A | (R)-3-((S)-1-(3-fluoro-2-(o-tolyloxy)phenyl)-1-hydroxy-5-methoxypentyl)-N-((2R,3S)-3-hydroxy-4-methyl-1-(methylamino)pentan-2-yl)piperidine-1-carboxamide |
| I-466A | (R)—N-((1S,2R)-1-cyclopentyl-1-hydroxy-3-(methylamino)propan-2-yl)-3-((S)-1-(3-fluoro-2-phenoxyphenyl)-1-hydroxy-5-methoxypentyl)piperidine-1-carboxamide |
| I-489A | (3R)—N-((1S,2R)-1-cyclohexyl-1-hydroxy-3-(methylamino)propan-2-yl)-3-((S)-1-hydroxy-5-methoxy-1-(2,3,5-trifluorophenyl)pentyl)piperidine-1-carboxamide |
| I-497A | (3R)-3-((S)-1-(3-chloro-2,4-difluorophenyl)-1-hydroxy-5-methoxypentyl)-N-((1S,2R)-1-cyclohexyl-1-hydroxy-3-(methylamino)propan-2-yl)piperidine-1-carboxamide |

Example 118

(3R)—N—((S)-1-(2,2,2-trifluoroethylamino)-3-cyclohexylpropan-2-yl)-3-((S)-1-(3-chlorophenyl)-1-hydroxy-5-methoxypentyl)piperidine-1-carboxamide (I-331A)

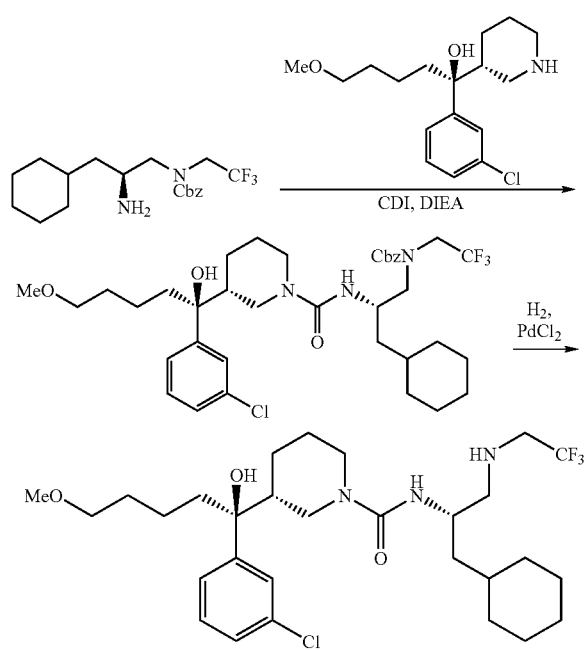

Step 1. Benzyl (S)-2-((R)-3-((S)-1-(3-chlorophenyl)-1-hydroxy-5-methoxypentyl)piperidine-1-carboxamido)-3-cyclohexylpropyl-2,2,2-trifluoroethylcarbamate A solution of benzyl (S)-2-amino-3-cyclohexylpropyl-2,2,2-trifluoroethylcarbamate (74.4 mg, 0.2 mmol) and CDI (32.4 mg, 0.2 mmol) in CH$_2$Cl$_2$ (5 mL) cooled to 0~5° C. and DIEA (0.5 mL) was added. After stirring for 30 min, a solution of 1-(3-chloro-phenyl)-5-methoxy-1-piperidin-3-yl-pentan-1-ol (62.2 mg, 0.2 mmol) in CH$_2$Cl$_2$ (3 mL) was added dropwise. The mixture was allowed to warm to rt and stirred overnight. The mixture was washed with water (10 mL). The aqueous layer was extracted with CH$_2$Cl$_2$ (2×15 mL) and the combined organic layers were washed with brine, dried over Na$_2$SO$_4$, filtered and evaporated. The residue was purified by prep HPLC to give benzyl (S)-2-((R)-3-((S)-1-(3-chlorophenyl)-1-hydroxy-5-methoxypentyl)piperidine-1-carboxamido)-3-cyclohexylpropyl-2,2,2-trifluoroethylcarbamate (85.2 mg, 60%).

Step 2. (3R)—N—((S)-1-(2,2,2-trifluoroethylamino)-3-cyclohexylpropan-2-yl)-3-((S)-1-(3-chlorophenyl)-1-hydroxy-5-methoxypentyl)piperidine-1-carboxamide To a solution of benzyl (S)-2-((R)-3-((S)-1-(3-chlorophenyl)-1-hydroxy-5-methoxypentyl)piperidine-1-carboxamido)-3-cyclohexylpropyl-2,2,2-trifluoroethylcarbamate (85.2 mg, 0.12 mmol) in EtOAc (10 mL) was added PdCl$_2$ (25 mg) and the mixture was stirred under a hydrogen balloon at rt for 3~5 hrs. After filtration, the filtrate was evaporated to give a residue, which was purified by prep HPLC to give (3R)—N—((S)-1-(2,2,2-trifluoroethylamino)-3-cyclohexylpropan-2-yl)-3-((S)-1-(3-chlorophenyl)-1-hydroxy-5-methoxypentyl)piperidine-1-carboxamide (25.2 mg, yield 36.5%). ¹H NMR (CDCl₃, 400 MHz) δ 0.90-1.5 (m, 10H), 1.54 (m, 2H), 1.69 (m, 8H), 1.82 (m, 1H), 2.96 (m, 1H), 2.33 (m, 1H), 2.61 (t, 1H), 3.25 (m, 2H), 3.28 (s, 3H), 3.33 (m, 2H), 3.68 (m, 2H), 3.94 (m, 1H), 4.18 (m, 2H), 5.56 (brs, 1H), 7.16 (m, 1H), 7.25 (m, 2H), 7.33 (s, 1H).

Example 119

The following compounds were prepared using procedures analogous to those described in Example 118:

| Cpd. No. | Name |
| --- | --- |
| I-156A | (3R)-3-((S)-1-(3-chlorophenyl)-1-hydroxy-5-methoxypentyl)-N-((S)-3-cyclopentyl-1-(methylamino)propan-2-yl)piperidine-1-carboxamide |
| I-165A | (3R)-3-((S)-1-(benzofuran-7-yl)-1-hydroxy-5-methoxypentyl)-N-((S)-3-cyclopentyl-1-(methylamino)propan-2-yl)piperidine-1-carboxamide |
| I-197A | (3R)—N-((S)-3-cyclopentyl-1-(methylamino)propan-2-yl)-3-((S)-5-ethoxy-1-(2,3-difluorophenyl)-1-hydroxypentyl)piperidine-1-carboxamide |
| I-206A | (3R)-3-((S)-1-(3-chloro-2-fluorophenyl)-1-hydroxy-5-methoxypentyl)-N-((S)-3-cyclopentyl-1-(methylamino)propan-2-yl)piperidine-1-carboxamide |
| I-206B | (3R)-3-((S)-1-(3-chloro-2-fluorophenyl)-1-hydroxy-5-methoxypentyl)-N-((R)-3-cyclopentyl-1-(methylamino)propan-2-yl)piperidine-1-carboxamide |
| I-212A | (3R)-3-((R)-(3-methoxypropoxy)(2,3-dichlorophenyl)methyl)-N-((S)-3-cyclopentyl-1-(methylamino)propan-2-yl)piperidine-1-carboxamide |
| I-239A | (R)—N-((S)-1-cyclohexyl-3-(methylamino)propan-2-yl)-3-((S)-1-(2,3-difluorophenyl)-5-ethoxy-1-hydroxypentyl)piperidine-1-carboxamide |
| I-240B | (3R)—N-((S)-3-cyclopropyl-1-(methylamino)propan-2-yl)-3-((S)-1-hydroxy-5-methoxy-1-(2-phenoxyphenyl)pentyl)piperidine-1-carboxamide |
| I-252A | (3R)-3-((S)-1-(3-chloro-2-fluorophenyl)-5-ethoxy-1-hydroxypentyl)-N-((S)-3-cyclopentyl-1-(methylamino)propan-2-yl)piperidine-1-carboxamide |
| I-253A | (3R)-3-((S)-1-(3-chlorophenyl)-1-hydroxy-5-methoxypentyl)-N-((S)-3-(4-fluorocyclohexyl)-1-(methylamino)propan-2-yl)piperidine-1-carboxamide |
| I-257A | (3R)—N-((S)-3-cyclopentyl-1-(methylamino)propan-2-yl)-3-((S)-5-ethoxy-1-(2,3,5-trifluorophenyl)-1-hydroxypentyl)piperidine-1-carboxamide |
| I-265A | (3R)-3-((S)-1-(2,3-dichlorophenyl)-1-hydroxy-5-methoxypentyl)-N-((S)-3-cyclopentyl-1-(methylamino)propan-2-yl)piperidine-1-carboxamide |
| I-266A | (3R)-3-((R)-(3-ethoxypropoxy)(2,3-dichlorophenyl)methyl)-N-((S)-3-cyclopentyl-1-(methylamino)propan-2-yl)piperidine-1-carboxamide |
| I-286A | (3R)-3-((S)-1-(2,3-dichlorophenyl)-5-ethoxy-1-hydroxypentyl)-N-((S)-3-cyclopentyl-1-(methylamino)propan-2-yl)piperidine-1-carboxamide |
| I-295A | (3R)-3-((S)-1-(3-chloro-2-fluorophenyl)-1-hydroxy-5-methoxypentyl)-N-((S)-3-(trans-4-fluorocyclohexyl)-1-(methylamino)propan-2-yl)piperidine-1-carboxamide |
| I-295B | (3R)-3-((S)-1-(3-chloro-2-fluorophenyl)-1-hydroxy-5-methoxypentyl)-N-((S)-3-(4-fluorocyclohexyl)-1-(methylamino)propan-2-yl)piperidine-1-carboxamide |
| I-139A | (3R)-3-((S)-1-hydroxy-5-methoxy-1-(quinolin-8-yl)pentyl)-N-((S)-4-methyl-1-(methylamino)pentan-2-yl)piperidine-1-carboxamide |
| I-199A | (3R)-3-((S)-1-(2-phenylphenyl)-1-hydroxy-5-methoxypentyl)-N-((S)-4-methyl-1-(methylamino)pentan-2-yl)piperidine-1-carboxamide |
| I-242A | (3R)-3-((S)-1-(2-(3-methylphenyl)phenyl)-1-hydroxy-5-methoxypentyl)-N-((S)-4-methyl-1-(methylamino)pentan-2-yl)piperidine-1-carboxamide |
| I-243A | (3R)-3-((S)-1-(2-(4-methylphenyl)phenyl)-1-hydroxy-5-methoxypentyl)-N-((S)-4-methyl-1-(methylamino)pentan-2-yl)piperidine-1-carboxamide |
| I-259A | (3R)-3-((S)-1-(3-fluoro-2-phenylphenyl)-1-hydroxy-5-methoxypentyl)-N-((S)-4-methyl-1-(methylamino)pentan-2-yl)piperidine-1-carboxamide |
| I-260A | (3R)-3-((S)-1-(2-(2-fluorophenyl)phenyl)-1-hydroxy-5-methoxypentyl)-N-((S)-4-methyl-1-(methylamino)pentan-2-yl)piperidine-1-carboxamide |
| I-261A | (3R)-3-((S)-1-(2-(3-fluorophenyl)phenyl)-1-hydroxy-5-methoxypentyl)-N-((S)-4-methyl-1-(methylamino)pentan-2-yl)piperidine-1-carboxamide |
| I-262A | (3R)-3-((S)-1-(2-(4-fluorophenyl)phenyl)-1-hydroxy-5-methoxypentyl)-N-((S)-4-methyl-1-(methylamino)pentan-2-yl)piperidine-1-carboxamide |
| I-296B | (3R)-3-((R)-1-(2-(2-chlorophenyl)phenyl)-1-hydroxy-5-methoxypentyl)-N-((S)-4-methyl-1-(methylamino)pentan-2-yl)piperidine-1-carboxamide |
| I-296A | (3R)-3-((S)-1-(2-(2-chlorophenyl)phenyl)-1-hydroxy-5-methoxypentyl)-N-((S)-4-methyl-1-(methylamino)pentan-2-yl)piperidine-1-carboxamide |
| I-296A | (3R)-3-((S)-1-(2-(2-chlorophenyl)phenyl)-1-hydroxy-5-methoxypentyl)-N-((S)-4-methyl-1-(methylamino)pentan-2-yl)piperidine-1-carboxamide |
| I-297A | (3R)-3-((S)-1-(2-(4-chlorophenyl)phenyl)-1-hydroxy-5-methoxypentyl)-N-((S)-4-methyl-1-(methylamino)pentan-2-yl)piperidine-1-carboxamide |
| I-298A | (3R)-3-((S)-1-(2-(3-chlorophenyl)phenyl)-1-hydroxy-5-methoxypentyl)-N-((S)-4-methyl-1-(methylamino)pentan-2-yl)piperidine-1-carboxamide |
| I-359A | (R)-3-((S)-1-(2-chloro-3-fluorophenyl)-1-hydroxy-5-methoxypentyl)-N-((S)-4,4-dimethyl-1-(methylamino)pentan-2-yl)piperidine-1-carboxamide |

-continued

| Cpd. No. | Name |
| --- | --- |
| I-368A | (R)—N-((2S,3R)-3-amino-1-cyclohexylbutan-2-yl)-3-((S)-1-(3-chlorophenyl)-1-hydroxy-5-methoxypentyl)piperidine-1-carboxamide |
| I-370A | (R)—N-((S)-1-(cis-4-fluorocyclohexyl)-3-(methylamino)propan-2-yl)-3-((S)-1-(2-fluorophenyl)-1-hydroxy-5-methoxypentyl)piperidine-1-carboxamide |
| I-370B | (R)—N-((S)-1-(trans-4-fluorocyclohexyl)-3-(methylamino)propan-2-yl)-3-((S)-1-(2-fluorophenyl)-1-hydroxy-5-methoxypentyl)piperidine-1-carboxamide |
| I-370C | (R)—N-((S)-1-(trans-4-fluorocyclohexyl)-3-(methylamino)propan-2-yl)-3-((R)-1-(2-fluorophenyl)-1-hydroxy-5-methoxypentyl)piperidine-1-carboxamide |
| I-399A | (R)—N-((2S,3R)-3-amino-1-cyclohexylbutan-2-yl)-3-((S)-1-(3-chloro-2-fluorophenyl)-1-hydroxy-5-methoxypentyl)piperidine-1-carboxamide |
| I-402A | (R)-3-((S)-1-(2,5-difluorophenyl)-1-hydroxy-5-methoxypentyl)-N-((S)-1-(cis-4-fluorocyclohexyl)-3-(methylamino)propan-2-yl)piperidine-1-carboxamide |
| I-402B | (R)-3-((S)-1-(2,5-difluorophenyl)-1-hydroxy-5-methoxypentyl)-N-((S)-1-(trans-4-fluorocyclohexyl)-3-(methylamino)propan-2-yl)piperidine-1-carboxamide |
| I-403A | (R)-3-((S)-1-(2,3-difluorophenyl)-1-hydroxy-5-methoxypentyl)-N-((S)-1-(trans-4-fluorocyclohexyl)-3-(methylamino)propan-2-yl)piperidine-1-carboxamide |
| I-403B | (R)-3-((R)-1-(2,3-difluorophenyl)-1-hydroxy-5-methoxypentyl)-N-((S)-1-(trans-4-fluorocyclohexyl)-3-(methylamino)propan-2-yl)piperidine-1-carboxamide |
| I-410A | (R)-3-((S)-1-(benzofuran-7-yl)-1-hydroxy-5-methoxypentyl)-N-((S)-1-(cis-4-fluorocyclohexyl)-3-(methylamino)propan-2-yl)piperidine-1-carboxamide |
| I-432A | (R)-3-((S)-1-(3-chloro-2-fluorophenyl)-1-hydroxy-5-methoxypentyl)-N-((S)-1-(trans-4-fluorocyclohexyl)-3-(methylamino)propan-2-yl)piperidine-1-carboxamide |
| I-432B | (R)-3-((S)-1-(3-chloro-2-fluorophenyl)-1-hydroxy-5-methoxypentyl)-N-((S)-1-(cis-4-fluorocyclohexyl)-3-(methylamino)propan-2-yl)piperidine-1-carboxamide |
| I-435A | (R)-3-((S)-1-(2-chloro-3-fluorophenyl)-1-hydroxy-5-methoxypentyl)-N-((S)-1-(trans-4-fluorocyclohexyl)-3-(methylamino)propan-2-yl)piperidine-1-carboxamide |
| I-435B | (R)-3-((R)-1-(2-chloro-3-fluorophenyl)-1-hydroxy-5-methoxypentyl)-N-((S)-1-(trans-4-fluorocyclohexyl)-3-(methylamino)propan-2-yl)piperidine-1-carboxamide |
| I-436A | (R)—N-((S)-1-(cis-4-fluorocyclohexyl)-3-(methylamino)propan-2-yl)-3-((S)-1-hydroxy-5-methoxy-1-(2,3,5-trifluorophenyl)pentyl)piperidine-1-carboxamide |
| I-467A | (R)-3-((S)-1-(3'-chloro-6-fluorobiphenyl-2-yl)-1-hydroxy-5-methoxypentyl)-N-((S)-1-cyclopentyl-3-(methylamino)propan-2-yl)piperidine-1-carboxamide |
| I-421A | (3R)—N-((2S,3S)-3-amino-1-cyclohexylbutan-2-yl)-3-((S)-1-(3-chlorophenyl)-1-hydroxy-5-methoxypentyl)piperidine-1-carboxamide |
| I-474A | (3R)-3-((S)-1-(3-chlorophenyl)-1-hydroxy-5-methoxypentyl)-N-((2S,3R)-1-cyclohexyl-3-(methylamino)butan-2-yl)piperidine-1-carboxamide |
| I-482A | (3R)-3-((S)-1-(3-chlorophenyl)-1-hydroxy-5-methoxypentyl)-N-((S)-1-((1r,4S)-4-hydroxy-4-methylcyclohexyl)-3-(methylamino)propan-2-yl)piperidine-1-carboxamide |
| I-483A | (R)-3-((S)-1-(2,3-difluorophenyl)-1-hydroxy-5-methoxypentyl)-N-((S)-1-((1r,4S)-4-hydroxy-4-methylcyclohexyl)-3-(methylamino)propan-2-yl)piperidine-1-carboxamide |
| I-485A | (3R)-3-((S)-1-(3-chloro-2-fluorophenyl)-1-hydroxy-5-methoxypentyl)-N-((2S,3R)-1-cyclohexyl-3-(methylamino)butan-2-yl)piperidine-1-carboxamide |
| I-485B | (3R)-3-((R)-1-(3-chloro-2-fluorophenyl)-1-hydroxy-5-methoxypentyl)-N-((2S,3R)-1-cyclohexyl-3-(methylamino)butan-2-yl)piperidine-1-carboxamide |

Example 120

(3R)-3-((S)-1-(3-chloro-2-fluorophenyl)-1-hydroxy-5-methoxypentyl)-N-((2S)-1-(4-hydroxycyclohexyl)-3-(methylamino)propan-2-yl)piperidine-1-carboxamide (I-429A)

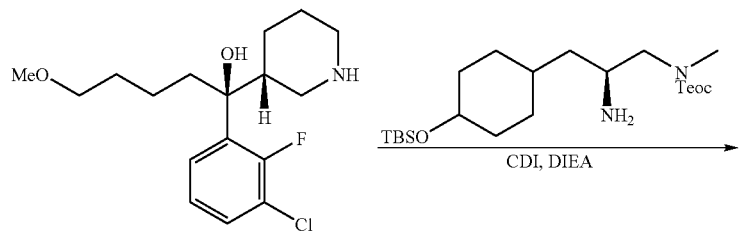

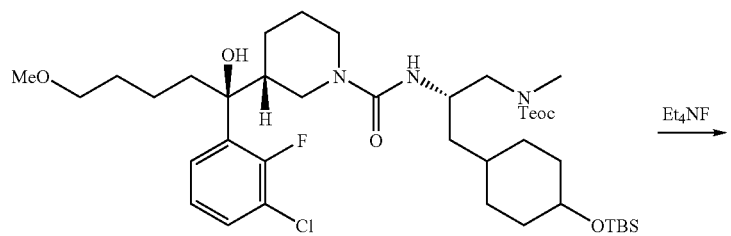

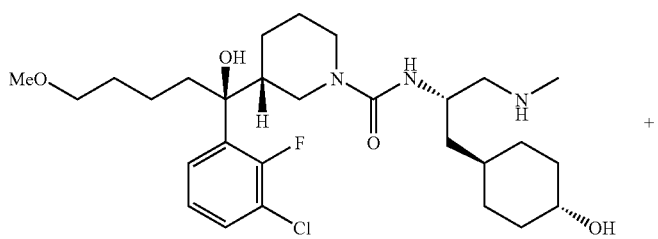

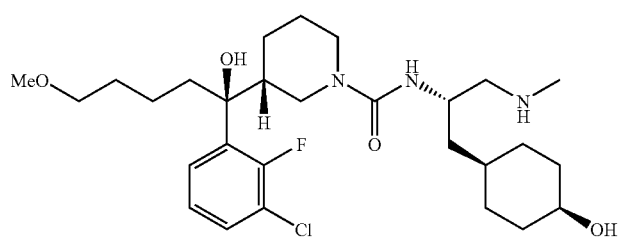

Step 1. 2-(Trimethylsilyl)ethyl (S)-3-(4-((tert-butyldimethylsilyl)methyl)cyclohexyl)-2-((R)-3-((S)-1-(3-chloro-2-fluorophenyl)-1-hydroxy-5-methoxypentyl)piperidine-1-carboxamido)-propyl(methyl)carbamate To a solution of (S)-2-(trimethylsilyl)ethyl 2-amino-3-(4-(tert-butyldimethylsilyloxy)-cyclohexyl)propyl(methyl)carbamate (249 mg, 0.561 mmol) and DIEA (241 mg, 1.87 mmol) in dry $CH_2Cl_2$ (3.5 mL) was added CDI (91 mg, 0.561 mmol) at 0° C. After addition, the reaction mixture was stirred for 1 h at 0° C. and added to a solution of (S)-1-(3-chloro-2-fluorophenyl)-5-methoxy-1-((R)-piperidin-3-yl)pentan-1-ol (123 mg, 0.374 mmol) in $CH_2Cl_2$ (3.5 mL). The reaction mixture was allowed to warm to rt and stirred overnight. After the reaction was completed by analysis of HPLC, the reaction solution was washed with water and brine, dried over $Na_2SO_4$, filtered and concentrated in vacuo. The product was purified by preparative TLC to afford 2-(trimethylsilyl)ethyl (S)-3-(4-((tert-butyldimethylsilyl)methyl)cyclohexyl)-2-((R)-3-((S)-1-(3-chloro-2-fluorophenyl)-1-hydroxy-5-methoxypentyl)piperidine-1-carboxamido)-propyl(methyl)carbamate (79 mg, 0.0991 mmol, 31%). MS (E/Z): 800 (M+H$^+$).

Step 2. (3R)-3-((S)-1-(3-chloro-2-fluorophenyl)-1-hydroxy-5-methoxypentyl)-N-((2S)-1-(4-hydroxycyclohexyl)-3-(methylamino)propan-2-yl)piperidine-1-carboxamide A solution of 2-(trimethylsilyl)ethyl (S)-3-(4-((tert-butyldimethylsilyl)methyl)cyclohexyl)-2-((R)-3-((S)-1-(3-chloro-2-fluorophenyl)-1-hydroxy-5-methoxypentyl)piperidine-1-carboxamido)propyl(methyl)carbamate (79 mg, 0.0991 mmol) and Et$_4$NF (36.9 mg, 0.248 mmol) in dry CH$_3$CN (8 mL) was heated under reflux for 2 h. After the reaction was completed by analysis of HPLC, the mixture was concentrated in vacuo. The product was purified by preparative HPLC to give two isomeric compounds: (3R)-3-((S)-1-(3-chloro-2-fluorophenyl)-1-hydroxy-5-methoxypentyl)-N-((2S)-1-(trans-4-hydroxycyclohexyl)-3-(methylamino)propan-2-yl)piperidine-1-carboxamide (16 mg, 0.0295 mmol) $^1$H NMR (400 MHz, CD$_3$OD): 2.14 (m, 1H), 2.71 (s, 3H), 3.25 (s, 3H), 3.44-3.49 (m, 1H), 3.94-3.98 (m, 1H), 4.12 (m, 1H), 4.33-4.37 (m, 1H), 7.16-7.11 (t, 1H), 7.33-7.39 (m, 1H), 7.50-7.55 (m, 1H). MS (E/Z): 542 (M+H$^+$) and (3R)-3-((S)-1-(3-chloro-2-fluorophenyl)-1-hydroxy-5-methoxypentyl)-N-((2S)-1-(cis-4-hydroxycyclohexyl)-3-(methylamino)propan-2-yl)piperidine-1-carboxamide (10 mg, 0.0185 mmol) $^1$H NMR (400 MHz, CD$_3$OD): 2.14 (m, 1H), 2.71 (s, 3H), 3.25 (s, 3H), 3.94-4.02 (m, 1H), 4.12 (m, 1H), 4.33-4.37 (m, 1H), 7.16-7.11 (t, 1H), 7.34-7.39 (m, 1H), 7.50-7.54 (m, 1H). MS (E/Z): 542 (M+H$^+$).

Example 121

The following compounds were prepared using procedures analogous to those described in Example 120:

| Cpd. No. | Name |
| --- | --- |
| I-119A | (3R)—N-((S)-3-cyclohexyl-1-(methylamino)propan-2-yl)-3-((S)-1-hydroxy-5-methoxy-1-(pyridin-2-yl)pentyl)piperidine-1-carboxamide |
| I-125A | (3R)—N-((S)-3-cyclohexyl-1-(methylamino)propan-2-yl)-3-((S)-1-hydroxy-5-methoxy-1-(1-methyl-1H-imidazol-2-yl)pentyl)piperidine-1-carboxamide |
| I-126A | (3R)—N-((S)-3-cyclohexyl-1-(methylamino)propan-2-yl)-3-((S)-1-hydroxy-5-methoxy-1-(thiophen-2-yl)pentyl)piperidine-1-carboxamide |
| I-127A | (3R)—N-((S)-3-cyclohexyl-1-(methylamino)propan-2-yl)-3-((S)-1-hydroxy-5-methoxy-1-(thiophen-3-yl)pentyl)piperidine-1-carboxamide |
| I-157A | (3R)—N-((S)-3-cyclohexyl-1-(methylamino)propan-2-yl)-3-((S)-1-hydroxy-5-methoxy-1-(5-methylthiazol-2-yl)pentyl)piperidine-1-carboxamide |
| I-176A | (3R)—N-((S)-3-cyclohexyl-1-(methylamino)propan-2-yl)-3-((S)-1-hydroxy-5-methoxy-1-(3,5-dimethylphenyl)pentyl)piperidine-1-carboxamide |
| I-182A | (3R)—N-((S)-3-cyclohexyl-1-(methylamino)propan-2-yl)-3-((S)-1-(3-fluoro-5-methylphenyl)-1-hydroxy-5-methoxypentyl)piperidine-1-carboxamide |
| I-183A | (3R)—N-((S)-3-cyclohexyl-1-(methylamino)propan-2-yl)-3-((S)-1-(2-fluoro-5-methylphenyl)-1-hydroxy-5-methoxypentyl)piperidine-1-carboxamide |
| I-184A | (3R)—N-((S)-3-cyclohexyl-1-(methylamino)propan-2-yl)-3-((S)-1-(5-fluoro-2-methylphenyl)-1-hydroxy-5-methoxypentyl)piperidine-1-carboxamide |
| I-185A | (3R)—N-((S)-3-cyclohexyl-1-(methylamino)propan-2-yl)-3-((S)-1-(2-fluoro-3-methylphenyl)-1-hydroxy-5-methoxypentyl)piperidine-1-carboxamide |
| I-192A | (3R)-3-((S)-1-(2-chlorophenyl)-1-hydroxy-5-methoxypentyl)-N-((S)-3-cyclohexyl-1-(methylamino)propan-2-yl)piperidine-1-carboxamide |
| I-196A | (3R)—N-((S)-3-cyclohexyl-1-(methylamino)propan-2-yl)-3-((S)-1-(2,3-difluorophenyl)-1-hydroxy-5-methoxypentyl)piperidine-1-carboxamide |
| I-207A | (3R)-3-((S)-1-(5-chloro-1-methyl-1H-imidazol-2-yl)-1-hydroxy-5-methoxypentyl)-N-((S)-3-cyclohexyl-1-(methylamino)propan-2-yl)piperidine-1-carboxamide |
| I-211A | (3R)—N-((S)-3-cyclohexyl-1-(methylamino)propan-2-yl)-3-((R)-1-hydroxy-1-(1H-indazol-7-yl)-5-methoxypentyl)piperidine-1-carboxamide |
| I-219A | (3R)—N-((S)-3-cyclohexyl-1-(methylamino)propan-2-yl)-3-((S)-1-(2,3-dihydrobenzofuran-7-yl)-1-hydroxy-5-methoxypentyl)piperidine-1-carboxamide |
| I-226A | (3R)—N-((S)-3-cyclohexyl-1-(methylamino)propan-2-yl)-3-((S)-1-hydroxy-5-methoxy-1-(3-(methylthio)phenyl)pentyl)piperidine-1-carboxamide |
| I-230A | (3R)—N-((S)-3-cyclohexyl-1-(methylamino)propan-2-yl)-3-((S)-1-(2-fluoro-6-methoxyphenyl)-1-hydroxy-5-methoxypentyl)piperidine-1-carboxamide |
| I-237A | (3R)—N-((S)-3-(4,4-difluorocyclohexyl)-1-(methylamino)propan-2-yl)-3-((S)-1-hydroxy-5-methoxy-1-m-tolylpentyl)piperidine-1-carboxamide |
| I-238A | (3R)-3-((R)-(3-ethoxypropoxy)(m-tolyl)methyl)-N-((S)-3-(4,4-difluorocyclohexyl)-1-(methylamino)propan-2-yl)piperidine-1-carboxamide |
| I-240A | (3R)-3-((S)-1-(2-fluoro-3-methylphenyl)-1-hydroxy-5-methoxypentyl)-N-((S)-3-(4-fluorocyclohexyl)-1-(methylamino)propan-2-yl)piperidine-1-carboxamide |
| I-248A | (3R)—N-((S)-3-cyclohexyl-1-(methylamino)propan-2-yl)-3-((S)-1-hydroxy-5-methoxy-1-(quinolin-8-yl)pentyl)piperidine-1-carboxamide |
| I-250A | (3R)-3-((S)-1-(3-chloro-5-fluorophenyl)-1-hydroxy-5-methoxypentyl)-N-((S)-3-cyclohexyl-1-(methylamino)propan-2-yl)piperidine-1-carboxamide |
| I-255A | (3R)-3-((R)-(3-ethoxypropoxy)(3-fluorophenyl)methyl)-N-((S)-3-(4,4-difluorocyclohexyl)-1-(methylamino)propan-2-yl)piperidine-1-carboxamide |
| I-264A | (3R)-3-((R)-(3-methoxypropoxy)(2,3-dichlorophenyl)methyl)-N-((S)-3-cyclohexyl-1-(methylamino)propan-2-yl)piperidine-1-carboxamide |
| I-279A | (3R)-3-((S)-1-(3-chloro-2-fluorophenyl)-5-ethoxy-1-hydroxypentyl)-N-((S)-3-cyclohexyl-1-(methylamino)propan-2-yl)piperidine-1-carboxamide |

| Cpd. No. | Name |
|---|---|
| I-280A | (3R)-3-((S)-1-(3-chloro-2-fluorophenyl)-1-hydroxy-5-methoxypentyl)-N-(1-(methylamino)-3-(4-methylcyclohexyl)propan-2-yl)piperidine-1-carboxamide |
| I-281A | (3R)—N-((S)-3-cyclohexyl-1-(methylamino)propan-2-yl)-3-((S)-1-(2-(trifluoromethyl)phenyl)-1-hydroxy-5-methoxypentyl)piperidine-1-carboxamide |
| I-282A | (3R)—N-((S)-3-cyclohexyl-1-(methylamino)propan-2-yl)-3-((S)-5-ethoxy-1-(2,3,5-trifluorophenyl)-1-hydroxypentyl)piperidine-1-carboxamide |
| I-283A | (3R)-3-((S)-1-(2-fluoro-3-methylphenyl)-1-hydroxy-5-methoxypentyl)-N-((S)-3-(4,4-difluorocyclohexyl)-1-(methylamino)propan-2-yl)piperidine-1-carboxamide |
| I-284A | (3R)-3-((S)-1-(2,3-dichlorophenyl)-1-hydroxy-5-methoxypentyl)-N-((S)-3-cyclohexyl-1-(methylamino)propan-2-yl)piperidine-1-carboxamide |
| I-285A | (3R)-3-((R)-(3-ethoxypropoxy)(2,3-dichlorophenyl)methyl)-N-((S)-3-cyclohexyl-1-(methylamino)propan-2-yl)piperidine-1-carboxamide |
| I-302A | (3R)-3-((S)-1-(benzofuran-7-yl)-1-hydroxy-5-methoxypentyl)-N-((S)-3-(4,4-difluorocyclohexyl)-1-(methylamino)propan-2-yl)piperidine-1-carboxamide |
| I-308A | (3R)-3-((S)-1-(2,3-dichlorophenyl)-5-ethoxy-1-hydroxypentyl)-N-((S)-3-cyclohexyl-1-(methylamino)propan-2-yl)piperidine-1-carboxamide |
| I-309A | (3R)—N-((S)-3-cyclohexyl-1-(methylamino)propan-2-yl)-3-((S)-1-hydroxy-5-methoxy-1-(3-(trifluoromethoxy)phenyl)pentyl)piperidine-1-carboxamide |
| I-310A | (3R)—N-((S)-3-cyclohexyl-1-(methylamino)propan-2-yl)-3-((S)-1-hydroxy-5-methoxy-1-(2-(trifluoromethoxy)phenyl)pentyl)piperidine-1-carboxamide |
| I-317A | (3R)-3-((S)-5-ethoxy-1-(2,3-difluorophenyl)-1-hydroxypentyl)-N-((S)-3-(4,4-difluorocyclohexyl)-1-(methylamino)propan-2-yl)piperidine-1-carboxamide |
| I-320A | (3R)-3-((S)-1-(3-chloro-2-fluorophenyl)-1-hydroxy-5-methoxypentyl)-N-((S)-3-(4,4-difluorocyclohexyl)-1-(methylamino)propan-2-yl)piperidine-1-carboxamide |
| I-321A | (3R)-3-((R)-(3-ethoxypropoxy)(3-chloro-2-fluorophenyl)methyl)-N-((S)-3-(4,4-difluorocyclohexyl)-1-(methylamino)propan-2-yl)piperidine-1-carboxamide |
| I-323A | (3R)—N-((S)-3-(4,4-difluorocyclohexyl)-1-(methylamino)propan-2-yl)-3-((S)-1-(2,3,5-trifluorophenyl)-1-hydroxy-5-methoxypentyl)piperidine-1-carboxamide |
| I-324A | (3R)-3-((R)-(3-ethoxypropoxy)(2,3,5-trifluorophenyl)methyl)-N-((S)-3-(4,4-difluorocyclohexyl)-1-(methylamino)propan-2-yl)piperidine-1-carboxamide |
| I-333A | (3R)-3-((S)-5-ethoxy-1-(2,3,5-trifluorophenyl)-1-hydroxypentyl)-N-((S)-3-(4,4-difluorocyclohexyl)-1-(methylamino)propan-2-yl)piperidine-1-carboxamide |
| I-209A | (R)-3-((S)-1-(3-chlorophenyl)-1-hydroxyethyl)-N-((S)-1-cyclohexyl-3-(methylamino)propan-2-yl)piperidine-1-carboxamide |
| I-341A | (R)-3-((S)-1-(3-chlorophenyl)-1-hydroxypropyl)-N-((S)-1-cyclohexyl-3-(methylamino)propan-2-yl)piperidine-1-carboxamide |
| I-343A | (R)-3-((S)-1-(3-chlorophenyl)-1-hydroxybutyl)-N-((S)-1-cyclohexyl-3-(methylamino)propan-2-yl)piperidine-1-carboxamide |
| I-345A | 3-((R)-1-cyclohexyl-1-hydroxy-5-methoxypentyl)-N-((S)-1-cyclohexyl-3-(methylamino)propan-2-yl)benzamide |
| I-346A | (R)-3-((S)-1-(3-chlorophenyl)-1-hydroxypentyl)-N-((S)-1-cyclohexyl-3-(methylamino)propan-2-yl)piperidine-1-carboxamide |
| I-347A | (R)-3-((R)-1-cyclohexyl-1-hydroxy-5-methoxypentyl)-N-((S)-1-cyclohexyl-3-(methylamino)propan-2-yl)piperidine-1-carboxamide |
| I-352A | (R)—N-((2S,3S)-3-amino-1-cyclohexylbutan-2-yl)-3-((S)-1-(2-fluorophenyl)-1-hydroxy-5-methoxypentyl)piperidine-1-carboxamide |
| I-358A | (R)-3-((R)-1-(3-chloro-2-fluorophenyl)-1-hydroxy-5-methoxypentyl)-N-((S)-4,4-dimethyl-1-(methylamino)pentan-2-yl)piperidine-1-carboxamide |
| I-362A | (R)-3-((S)-4-acetamido-1-(2-fluorophenyl)-1-hydroxybutyl)-N-((S)-1-cyclohexyl-3-(methylamino)propan-2-yl)piperidine-1-carboxamide |
| I-363A | (R)—N-((S)-1-cyclohexyl-3-(methylamino)propan-2-yl)-3-((S)-1-(3-fluoro-2-methylphenyl)-1-hydroxy-5-methoxypentyl)piperidine-1-carboxamide |
| I-363B | (R)—N-((S)-1-cyclohexyl-3-(methylamino)propan-2-yl)-3-((R)-1-(3-fluoro-2-methylphenyl)-1-hydroxy-5-methoxypentyl)piperidine-1-carboxamide |
| I-364A | (R)—N-((S)-1-cyclohexyl-3-(methylamino)propan-2-yl)-3-((S)-1-(3-fluoro-4-methylphenyl)-1-hydroxy-5-methoxypentyl)piperidine-1-carboxamide |
| I-364B | (R)—N-((S)-1-cyclohexyl-3-(methylamino)propan-2-yl)-3-((R)-1-(3-fluoro-4-methylphenyl)-1-hydroxy-5-methoxypentyl)piperidine-1-carboxamide |
| I-366A | (R)—N-((S)-1-cyclohexyl-3-(methylamino)propan-2-yl)-3-((S)-1-(3-fluoro-2-hydroxyphenyl)-1-hydroxy-5-methoxypentyl)piperidine-1-carboxamide |
| I-372A | (R)-3-((S)-1-(2-chloro-3-fluorophenyl)-1-hydroxy-5-methoxypentyl)-N-((S)-1-cyclopentyl-3-(methylamino)propan-2-yl)piperidine-1-carboxamide |
| I-375A | (R)-3-((S)-4-acetamido-1-(3,5-dimethylphenyl)-1-hydroxybutyl)-N-((S)-1-cyclohexyl-3-(methylamino)propan-2-yl)piperidine-1-carboxamide |

-continued

| Cpd. No. | Name |
|---|---|
| I-376A | (R)-3-((R)-1-cyclohexyl-1-hydroxy-5-methoxypentyl)-N-((S)-1-(4,4-difluorocyclohexyl)-3-(methylamino)propan-2-yl)piperidine-1-carboxamide |
| I-382A | (R)-3-((S)-4-acetamido-1-(3-fluoro-5-methylphenyl)-1-hydroxybutyl)-N-((S)-1-cyclohexyl-3-(methylamino)propan-2-yl)piperidine-1-carboxamide |
| I-383A | (R)-3-((S)-4-acetamido-1-(2-fluoro-5-methylphenyl)-1-hydroxybutyl)-N-((S)-1-cyclohexyl-3-(methylamino)propan-2-yl)piperidine-1-carboxamide |
| I-385A | (3R)-3-(1-(2-(cyclopropylmethoxy)-3-fluorophenyl)-1-hydroxy-5-methoxypentyl)-N-((S)-4-methyl-1-(methylamino)pentan-2-yl)piperidine-1-carboxamide |
| I-386A | (R)-3-((S)-1-(3-chloro-2-methylphenyl)-1-hydroxy-5-methoxypentyl)-N-((S)-1-cyclohexyl-3-(methylamino)propan-2-yl)piperidine-1-carboxamide |
| I-386B | (R)-3-((R)-1-(3-chloro-2-methylphenyl)-1-hydroxy-5-methoxypentyl)-N-((S)-1-cyclohexyl-3-(methylamino)propan-2-yl)piperidine-1-carboxamide |
| I-389A | (R)-3-((S)-4-acetamido-1-(3,5-difluorophenyl)-1-hydroxybutyl)-N-((S)-1-cyclohexyl-3-(methylamino)propan-2-yl)piperidine-1-carboxamide |
| I-391A | (R)-3-((S)-1-(3-chlorophenyl)-1-hydroxy-5-methoxypentyl)-N-((S)-1-(cis-4-hydroxycyclohexyl)-3-(methylamino)propan-2-yl)piperidine-1-carboxamide |
| I-391A | (R)-3-((S)-1-(3-chlorophenyl)-1-hydroxy-5-methoxypentyl)-N-((S)-1-(trans-4-hydroxycyclohexyl)-3-(methylamino)propan-2-yl)piperidine-1-carboxamide |
| I-393A | (R)-3-((S)-(2-acetamidoethoxy)(3-chloro-2-fluorophenyl)methyl)-N-((S)-1-cyclohexyl-3-(methylamino)propan-2-yl)piperidine-1-carboxamide |
| I-393B | (R)-3-((R)-(2-acetamidoethoxy)(3-chloro-2-fluorophenyl)methyl)-N-((S)-1-cyclohexyl-3-(methylamino)propan-2-yl)piperidine-1-carboxamide |
| I-396A | (R)-3-((S)-1-(2,3-difluorophenyl)-1-hydroxy-5-methoxypentyl)-N-((S)-1-(cis-4-hydroxycyclohexyl)-3-(methylamino)propan-2-yl)piperidine-1-carboxamide |
| I-396B | (R)-3-((S)-1-(2,3-difluorophenyl)-1-hydroxy-5-methoxypentyl)-N-((S)-1-(trans-4-hydroxycyclohexyl)-3-(methylamino)propan-2-yl)piperidine-1-carboxamide |
| I-398A | (R)-3-((S)-1-(2-chloro-3-fluorophenyl)-1-hydroxy-5-methoxypentyl)-N-((S)-1-cyclohexyl-3-(methylamino)propan-2-yl)piperidine-1-carboxamide |
| I-400A | (R)—N-((S)-1-cyclohexyl-3-(methylamino)propan-2-yl)-3-((S)-1-hydroxy-5-methoxy-1-(2,3,4-trifluorophenyl)pentyl)piperidine-1-carboxamide |
| I-401A | (R)—N-((S)-1-(4,4-difluorocyclohexyl)-3-(methylamino)propan-2-yl)-3-((S)-1-(2-fluorophenyl)-1-hydroxy-5-methoxypentyl)piperidine-1-carboxamide |
| I-417A | (3R)-3-(1-(2-(cyclopropylmethoxy)-3-fluorophenyl)-1-hydroxy-5-methoxypentyl)-N-((S)-4,4-dimethyl-1-(methylamino)pentan-2-yl)piperidine-1-carboxamide |
| I-423A | (R)-3-((S)-4-acetamido-1-(3-chloro-2-fluorophenyl)-1-hydroxybutyl)-N-((S)-1-cyclohexyl-3-(methylamino)propan-2-yl)piperidine-1-carboxamide |
| I-424A | (R)-3-((S)-4-acetamido-1-(3-chloro-5-fluorophenyl)-1-hydroxybutyl)-N-((S)-1-cyclohexyl-3-(methylamino)propan-2-yl)piperidine-1-carboxamide |
| I-425A | (R)-3-((S)-4-acetamido-1-(2-chloro-3-fluorophenyl)-1-hydroxybutyl)-N-((S)-1-cyclohexyl-3-(methylamino)propan-2-yl)piperidine-1-carboxamide |
| I-429B | (R)-3-((S)-1-(3-chloro-2-fluorophenyl)-1-hydroxy-5-methoxypentyl)-N-((S)-1-(trans-4-hydroxycyclohexyl)-3-(methylamino)propan-2-yl)piperidine-1-carboxamide |
| I-433A | (R)-3-((S)-1-(3-chloro-2,4-difluorophenyl)-1-hydroxy-5-methoxypentyl)-N-((S)-1-cyclohexyl-3-(methylamino)propan-2-yl)piperidine-1-carboxamide |
| I-433B | (R)-3-((R)-1-(3-chloro-2,4-difluorophenyl)-1-hydroxy-5-methoxypentyl)-N-((S)-1-cyclohexyl-3-(methylamino)propan-2-yl)piperidine-1-carboxamide |
| I-476B | (3R)-3-((S)-1-(3-chlorophenyl)-1-hydroxy-5-methoxypentyl)-N-((S)-1-(1-fluorocyclohexyl)-3-(methylamino)propan-2-yl)piperidine-1-carboxamide |
| I-476B | (3R)-3-((S)-1-(3-chlorophenyl)-1-hydroxy-5-methoxypentyl)-N-((S)-1-(1-fluorocyclohexyl)-3-(methylamino)propan-2-yl)piperidine-1-carboxamide |
| I-476C | (3R)-3-((S)-1-(3-chlorophenyl)-1-hydroxy-5-methoxypentyl)-N-((R)-1-(1-fluorocyclohexyl)-3-(methylamino)propan-2-yl)piperidine-1-carboxamide |
| I-495A | (3R)-3-((S)-1-(3-chloro-2-fluorophenyl)-1-hydroxy-5-methoxypentyl)-N-((S)-1-((1r,4S)-4-hydroxy-4-methylcyclohexyl)-3-(methylamino)propan-2-yl)piperidine-1-carboxamide |
| I-507A | (3S)-3-((R)-1-(3-chlorophenyl)-2-(2-methoxyethoxy)ethyl)-N-((S)-1-cyclohexyl-3-(methylamino)propan-2-yl)piperidine-1-carboxamide |
| I-531A | (3R)-3-((R)-(3-chlorophenyl)(2-propionamidoethoxy)methyl)-N-((S)-1-cyclohexyl-3-(methylamino)propan-2-yl)piperidine-1-carboxamide |
| I-536A | (3R)—N-((2S)-1-cyclohexyl-3-(methylamino)propan-2-yl)-3-((R)-(2,3-difluorophenyl)(2-propionamidoethoxy)methyl)piperidine-1-carboxamide |
| I-537A | (3R)-3-((S)-1-(3-chlorophenyl)-1-hydroxy-2-(2-methoxyacetamido)ethyl)-N-((S)-1-cyclohexyl-3-(methylamino)propan-2-yl)piperidine-1-carboxamide |
| I-541A | (3R)—N-((2S,3S)-3-amino-1-cyclohexylbutan-2-yl)-3-((S)-1-(3-chloro-2-fluorophenyl)-1-hydroxy-5-methoxypentyl)piperidine-1-carboxamide |
| I-545A | (3R)-3-((S)-1-(3-chlorophenyl)-1-hydroxy-5-methoxypentyl)-N-((S)-1-(cis-4-methoxycyclohexyl)-3-(methylamino)propan-2-yl)piperidine-1-carboxamide |

-continued

| Cpd. No. | Name |
| --- | --- |
| I-545B | (3R)-3-((S)-1-(3-chlorophenyl)-1-hydroxy-5-methoxypentyl)-N-((S)-1-(cis-4-methoxycyclohexyl)-3-(methylamino)propan-2-yl)piperidine-1-carboxamide |
| I-546A | (3R)-3-((S)-4-acetamido-1-(3-chloro-2-fluorophenyl)-1-hydroxybutyl)-N-((2S,3R)-3-amino-1-cyclohexylbutan-2-yl)piperidine-1-carboxamide |
| I-546B | (3R)-3-((R)-4-acetamido-1-(3-chloro-2-fluorophenyl)-1-hydroxybutyl)-N-((2S,3R)-3-amino-1-cyclohexylbutan-2-yl)piperidine-1-carboxamide |
| I-547A | (3R)-3-((R)-(3-chloro-2-fluorophenyl)(2-propionamidoethoxy)methyl)-N-((2S)-1-cyclohexyl-3-(methylamino)propan-2-yl)piperidine-1-carboxamide |
| I-548A | (3R)-3-((S)-1-(2,3-difluorophenyl)-1-hydroxy-5-methoxypentyl)-N-((S)-1-(cis-4-methoxycyclohexyl)-3-(methylamino)propan-2-yl)piperidine-1-carboxamide |
| I-556A | (3R)-3-((S)-1-(3-chloro-2-fluorophenyl)-1-hydroxy-5-methoxypentyl)-N-((S)-1-(cis-4-methoxycyclohexyl)-3-(methylamino)propan-2-yl)piperidine-1-carboxamide |
| I-556B | (3R)-3-((S)-1-(3-chloro-2-fluorophenyl)-1-hydroxy-5-methoxypentyl)-N-((S)-1-(trans-4-methoxycyclohexyl)-3-(methylamino)propan-2-yl)piperidine-1-carboxamide |

The following compounds were prepared using procedures analogous to those described in Example 120 Step 1 followed by acid catalyzed removal of a Boc protecting group following the conditions described in Example 126 Step 2:

| Cpd. No. | Name |
| --- | --- |
| I-131A | (3R)-3-((S)-1-(2-(3-methylphenyl)phenyl)-1-hydroxy-5-methoxypentyl)-N-((S)-1-(methylamino)propan-2-yl)piperidine-1-carboxamide |
| I-132A | (3R)-3-((S)-1-(2-(4-methylphenyl)phenyl)-1-hydroxy-5-methoxypentyl)-N-((S)-1-(methylamino)propan-2-yl)piperidine-1-carboxamide |
| I-133A | (3R)-3-((S)-1-(2-(2-methylphenyl)phenyl)-1-hydroxy-5-methoxypentyl)-N-((S)-1-(methylamino)propan-2-yl)piperidine-1-carboxamide |
| I-140A | (3R)-3-((S)-1-(2-(2-fluorophenyl)phenyl)-1-hydroxy-5-methoxypentyl)-N-((S)-1-(methylamino)propan-2-yl)piperidine-1-carboxamide |
| I-141A | (3R)-3-((S)-1-(3-fluoro-2-phenylphenyl)-1-hydroxy-5-methoxypentyl)-N-((S)-1-(methylamino)propan-2-yl)piperidine-1-carboxamide |
| I-142A | (3R)-3-((S)-1-(2-(3-fluorophenyl)phenyl)-1-hydroxy-5-methoxypentyl)-N-((S)-1-(methylamino)propan-2-yl)piperidine-1-carboxamide |
| I-143A | (3R)-3-((S)-1-(2-(4-fluorophenyl)phenyl)-1-hydroxy-5-methoxypentyl)-N-((S)-1-(methylamino)propan-2-yl)piperidine-1-carboxamide |
| I-177A | (3R)-3-((S)-1-(2-(2-chlorophenyl)phenyl)-1-hydroxy-5-methoxypentyl)-N-((S)-1-(methylamino)propan-2-yl)piperidine-1-carboxamide |
| I-178A | (3R)-3-((S)-1-(2-(4-chlorophenyl)phenyl)-1-hydroxy-5-methoxypentyl)-N-((S)-1-(methylamino)propan-2-yl)piperidine-1-carboxamide |
| I-351A | (R)-3-((S)-1-(2-tert-butylbenzofuran-7-yl)-1-hydroxy-5-methoxypentyl)-N-((S)-1-(methylamino)propan-2-yl)piperidine-1-carboxamide |
| I-434A | (R)-3-((S)-1-(3-chloro-2-fluorophenyl)-1-hydroxy-5-methoxypentyl)-N-((S)-1-(1-fluorocyclohexyl)-3-(methylamino)propan-2-yl)piperidine-1-carboxamide |
| I-367A | (R)—N-((1S,2R)-1-cyclohexyl-1-hydroxy-3-(methylamino)propan-2-yl)-3-((S)-1-(2-fluorophenyl)-1-hydroxy-5-methoxypentyl)piperidine-1-carboxamide |
| I-397A | (R)—N-((1S,2R)-1-cyclohexyl-1-hydroxy-3-(methylamino)propan-2-yl)-3-((S)-1-(2,5-difluorophenyl)-1-hydroxy-5-methoxypentyl)piperidine-1-carboxamide |
| I-428A | (R)-3-((S)-1-(3-chloro-2-fluorophenyl)-1-hydroxy-5-methoxypentyl)-N-((1S,2R)-1-cyclohexyl-1-hydroxy-3-(methylamino)propan-2-yl)piperidine-1-carboxamide |
| I-430A | (R)-3-((S)-1-(2-chloro-3-fluorophenyl)-1-hydroxy-5-methoxypentyl)-N-((1S,2R)-1-cyclohexyl-1-hydroxy-3-(methylamino)propan-2-yl)piperidine-1-carboxamide |
| I-456A | (3R)-3-((S)-1-(3-chlorophenyl)-1-hydroxy-2-(2-methoxyethoxy)ethyl)-N-((S)-1-cyclohexyl-3-(methylamino)propan-2-yl)piperidine-1-carboxamide |
| I-484A | (3R)-3-((S)-1-(2,3-difluorophenyl)-1-hydroxy-5-methoxypentyl)-N-((S)-1-((1r,4S)-4-methoxycyclohexyl)-3-(methylamino)propan-2-yl)piperidine-1-carboxamide |
| I-484B | (3R)-3-((R)-1-(2,3-difluorophenyl)-1-hydroxy-5-methoxypentyl)-N-((S)-1-((1r,4S)-4-methoxycyclohexyl)-3-(methylamino)propan-2-yl)piperidine-1-carboxamide |
| I-490A | (3R)-3-((S)-1-(2-chloro-3-fluorophenyl)-1-hydroxy-5-methoxypentyl)-N-((S)-1-(1-fluorocyclohexyl)-3-(methylamino)propan-2-yl)piperidine-1-carboxamide |

Example 122

(3R)—N—((S)-3-cyclopentyl-1-(methylamino)pro-pan-2-yl)-3-((S)-1-(2,3-dihydrobenzofuran-7-yl)-1-hydroxy-5-methoxypentyl)piperidine-1-carboxamide (I-172A)

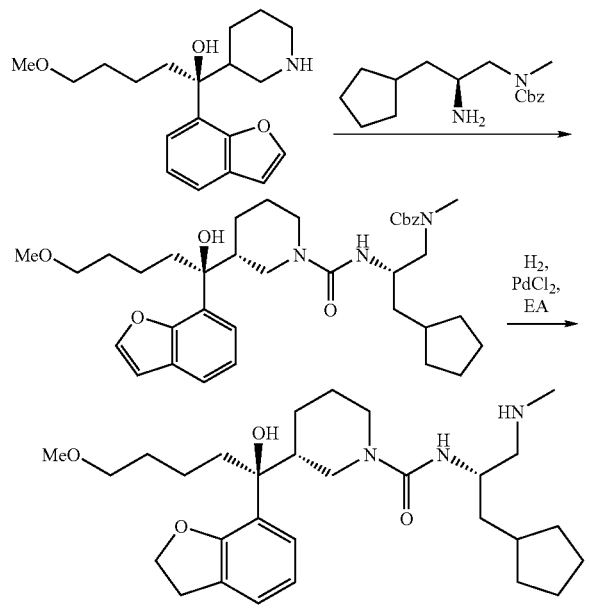

Step 1. Benzyl (S)-2-((R)-3-((S)-1-(benzofuran-7-yl)-1-hydroxy-5-methoxypentyl)piperidine-1-carboxamido)-3-cyclopentylpropylmethylcarbamate To a solution of (2-amino-3-cyclopentyl-propyl)-methylcarbamic acid benzyl ester (87 mg, 0.3 mmol) and CDI (48.6 mg, 0.3 mmol) in $CH_2Cl_2$ (5 mL) cooled to 0~5° C. was added DIEA (0.5 mL). After stirring for 30 minutes, a solution of (S)-1-(benzofuran-7-yl)-5-methoxy-1-((R)-piperidin-3-yl)pentan-1-ol (95.1 mg, 0.3 mmol) in $CH_2Cl_2$ (3 mL) was added dropwise. The reaction mixture was allowed to warm to rt and stirred overnight. The mixture was washed with water (10 mL). The aqueous layer was extracted with $CH_2Cl_2$ (2×15 mL) and the combined organic layers were washed with brine, dried over $Na_2SO_4$, filtered and evaporated. The residue was purified by prep HPLC to give benzyl (S)-2-((R)-3-((S)-1-(benzofuran-7-yl)-1-hydroxy-5-methoxypentyl)piperidine-1-carboxamido)-3-cyclopentylpropylmethylcarbamate (98.5 mg, 51.9%).

Step 2. (3R)—N—((S)-3-cyclopentyl-1-(methylamino)propan-2-yl)-3-((S)-1-(2,3-dihydrobenzofuran-7-yl)-1-hydroxy-5-methoxypentyl)piperidine-1-carboxamide To a solution of benzyl (S)-2-((R)-3-((S)-1-(benzofuran-7-yl)-1-hydroxy-5-methoxypentyl)piperidine-1-carboxamido)-3-cyclopentylpropylmethylcarbamate (98.5 mg, 0.156 mmol) in EtOAc (10 mL) was added $PdCl_2$ (30 mg) and the mixture was stirred under a hydrogen balloon at rt for 3~5 hrs. After filtration, the filtrate was evaporated and the residue, was purified by prep HPLC to afford (3R)—N—((S)-3-cyclopentyl-1-(methylamino)propan-2-yl)-3-((S)-1-(2,3-dihydrobenzofuran-7-yl)-1-hydroxy-5-methoxypentyl)piperidine-1-carboxamide (36.2 mg, 46.5%). $^1$H NMR ($CD_3OD$, 400 MHz) δ 0.89 (m, 1H), 1.12-2.15 (m, H), 2.58 (m, 2H), 2.71 (s, 3H), 2.93 (m, 1H), 3.15 (m, 3H), 3.23 (s, 3H), 3.98 (m, 2H), 4.26 (m, 1H), 4.48 (m, 2H), 6.83 (m, 1H), 7.12 (m, 1H), 7.21 (m, 1H).

Example 123

(3R)—N—((S)-3-cyclohexyl-1-(methylamino)pro-pan-2-yl)-3-((S)-1-hydroxy-5-methoxy-1-phenylpen-tyl)piperidine-1-carbothioamide (I-247A)

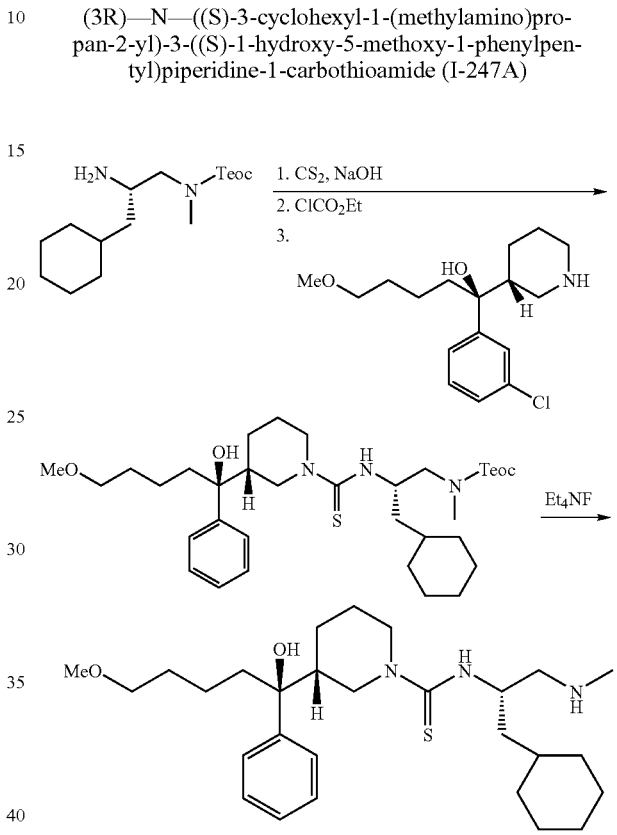

Step 1. (3R)—N—((S)-3-cyclohexyl-1-(N-methyl-N-(2-(trimethylsilyl)ethoxycarbonyl)amino)propan-2-yl)-3-((S)-1-hydroxy-5-methoxy-1-phenylpentyl)piperidine-1-carbothioamide A stirred solution of (2-(trimethylsilyl)ethyl)(S)-2-amino-3-cyclohexylpropylmethylcarbamate (484 mg, 1.54 mmol) and $CS_2$ (96 µL, 1.62 mmol) in THF (5 mL) was cooled in an ice bath and a solution of NaOH (65 mg, 1.62 mmol) in water (0.15 mL) was added. The mixture was heated at reflux for 1.5 h, cooled to 40° C. and treated with ethyl chloroformate (0.155 mL, 1.62 mmol). The mixture was heated at 40° C. for 30 min, cooled and poured into ether (90 mL). The ether layer was washed with water (25 mL), brine (25 mL) and dried over $MgSO_4$. Removal of the solvent left an oil (660 mg). An aliquot of this oil (83 mg) and (S)-1-(3-chlorophenyl)-5-methoxy-1-((R)-piperidin-3-yl)pentan-1-ol (42 mg, 0.13 mmol) were dissolved in MeCN (1 mL) and heated at 100° C. in a microwave for 10 min. The mixture was concentrated to leave an oil which was applied to a 2-g silica SPE cartridge and eluted sequentially with 0, 10, 25, 50, 75 and 100% EtOAc in hexanes (15 mL of each) to afford six fractions. The third fraction was evaporated to afford (3R)—N—((S)-3-cyclohexyl-1-(N-methyl-N-(2-(trimethylsilyl)ethoxycarbonyl)amino)propan-2-yl)-3-((S)-1-hydroxy-5-methoxy-1-phenylpentyl)piperidine-1-carbothioamide (35 mg) as an oil.

Step 2. (3R)—N—((S)-3-cyclohexyl-1-(methylamino)propan-2-yl)-3-((S)-1-hydroxy-5-methoxy-1-phenylpentyl)piperidine-1-carbothioamide A solution of (3R)—N—((S)-3-cyclohexyl-1-(N-methyl-N-(2-(trimethylsilyl)ethoxycarbonyl)-amino)propan-2-yl)-3-((S)-1-hydroxy-5-methoxy-1-phenylpentyl)piperidine-1-carbothioamide (35 mg, 52 μmol) and Et$_4$NF (40 mg, 0.26 mmol) in MeCN (1 mL) was heated at 60° C. in a microwave for 10 min. The reaction mixture was submitted directly to prep HPLC to afford (3R)—N—((S)-3-cyclohexyl-1-(methylamino)propan-2-yl)-3-((S)-1-hydroxy-5-methoxy-1-phenylpentyl)piperidine-1-carbothioamide (6.4 mg, 23%) and recovered (3R)—N—((S)-3-cyclohexyl-1-(N-methyl-N-(2-(trimethylsilyl)ethoxycarbonyl)amino)propan-2-yl)-3-((S)-1-hydroxy-5-methoxy-1-phenylpentyl)piperidine-1-carbothioamide (11.2 mg).

Example 124

The following compound was prepared using procedures analogous to those described in Example 123:

| Cpd. No. | Name |
|---|---|
| I-122A | N-((S)-1-cyclohexyl-3-(methylamino)propan-2-yl)-3-((3-methoxypropoxy)(phenyl)methyl)piperidine-1-carbothioamide using 3-((3-methoxypropoxy)(phenyl)methyl)piperidine in Step 1 |

Example 125

(3R)—N'-cyano-N—((S)-3-cyclohexyl-1-(methylamino)propan-2-yl)-3-((S)-1-hydroxy-5-methoxy-1-phenylpentyl)piperidine-1-carboxamidine (I-271A)

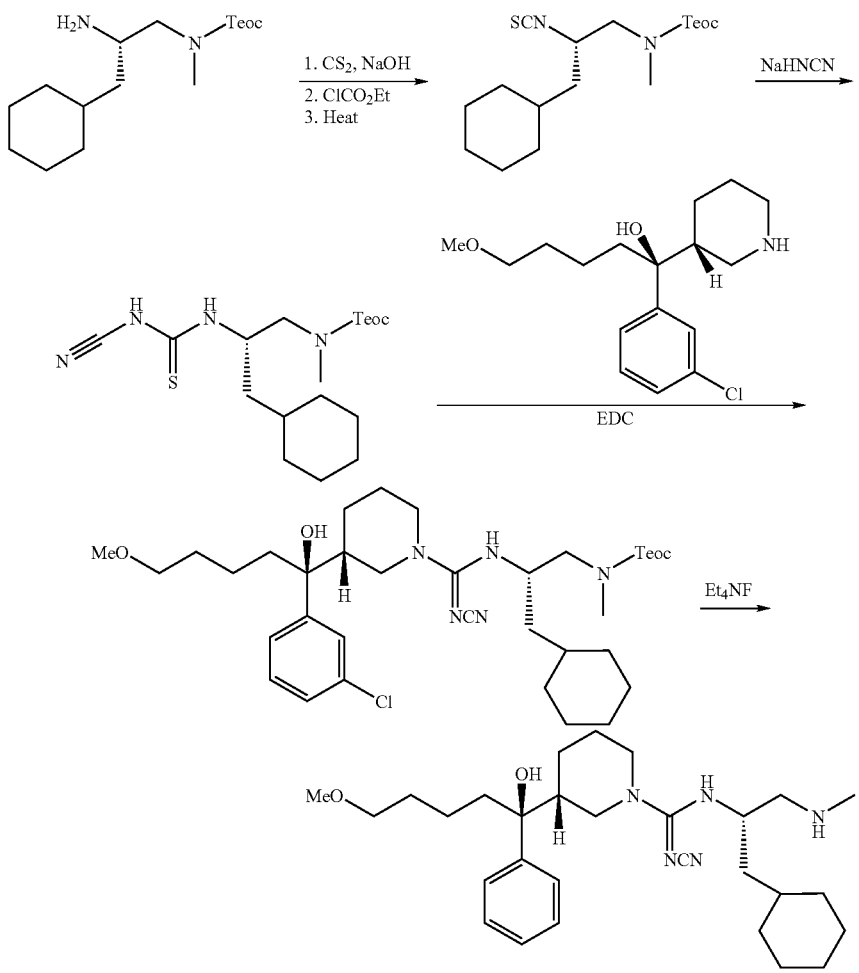

Step 1. (2-(Trimethylsilyl)ethyl)(S)-3-cyclohexyl-2-isothiocyanatopropylmethylcarbamate A stirred solution of (2-(trimethylsilyl)ethyl)(S)-2-amino-3-cyclohexylpropylmethylcarbamate (484 mg, 1.54 mmol) and CS$_2$ (96 μL, 1.62 mmol) in THF (5 mL) was cooled in an ice bath and a solution of NaOH (65 mg, 1.62 mmol) in water (0.15 mL) was added. The mixture was heated at reflux for 1.5 h, cooled to 40° C. and treated with ethyl chloroformate (0.155 mL, 1.62 mmol). The mixture was heated at 40° C. for 30 min, cooled and poured into ether (90 mL). The ether layer was washed with water (25 mL), brine (25 mL) and dried over MgSO₄. Removal of the solvent left an oil (660 mg). An aliquot of this oil (354 mg) was dissolved in MeCN (4 mL) and heated at 150° C. in a microwave for 10 min. The mixture was concentrated to afford an oil (403 mg) which was purified by chromatography on a 12-g silica cartridge eluted with hexane/EtOAc gradient to afford (2-(trimethylsilyl)ethyl)(S)-3-cyclohexyl-2-isothiocyanatopropylmethylcarbamate (278 mg) as an oil.

Step 2. 1-Cyano-3-((S)-3-cyclohexyl-1-(N-methyl-N-(2-(trimethylsilyl)ethoxycarbonyl)-amino)propan-2-yl)thiourea To a stirred solution of (2-(trimethylsilyl)ethyl)(S)-3-cyclohexyl-2-isothiocyanatopropyl-methylcarbamate (190 mg, 0.53 mmol) in ethanol (5 mL) was added solid sodium hydrogen cyanamide (38 mg, 0.59 mmol). The mixture was stirred at rt for 2 d, diluted with 1:1 sat'd aq NH₄Cl/H₂O (40 mL) and extracted with ether (2×60 mL). The combined ether extracts were dried over MgSO₄ and rotovaped to leave 1-cyano-3-((S)-3-cyclohexyl-1-(N-methyl-N-(2-(trimethylsilyl)ethoxycarbonyl)amino)propan-2-yl)thiourea (230 mg, quant) as a white solid.

Step 3. (3R)—N'-cyano-N—((S)-3-cyclohexyl-1-(N-methyl-N-(2-(trimethylsilyl)ethoxycarbonyl)-amino)propan-2-yl)-3-((S)-1-hydroxy-5-methoxy-1-phenylpentyl)piperidine-1-carboxamidine To a stirred solution of 1-cyano-3-((S)-3-cyclohexyl-1-(N-methyl-N-(2-(trimethylsilyl)ethoxycarbonyl)amino)propan-2-yl)thiourea (230 mg, 0.58 mmol) and (S)-1-(3-chlorophenyl)-5-methoxy-1-((R)-piperidin-3-yl)pentan-1-ol (180 mg, 0.58 mmol) in DMF (5 mL) was added EDC (0.17 g, 0.87 mmol). The mixture was stirred for 16 h at rt, diluted with ether (175 mL) and washed with 5% aq HCl (2×50 mL) and brine (50 mL). The combined aqueous washes were back extracted with ether. The combined ether extracts were concentrated to afford crude product (290 mg). The mixture was purified by prep HPLC to afford (3R)—N'-cyano-N—((S)-3-cyclohexyl-1-(N-methyl-N-(2-(trimethylsilyl)ethoxycarbonyl)amino)propan-2-yl)-3-((S)-1-hydroxy-5-methoxy-1-phenylpentyl)piperidine-1-carboxamidine (145 mg, 37%).

Step 4. (3R)—N'-cyano-N—((S)-3-cyclohexyl-1-(methylamino)propan-2-yl)-3-((S)-1-hydroxy-5-methoxy-1-phenylpentyl)piperidine-1-carboxamidine A solution of (3R)—N'-cyano-N—((S)-3-cyclohexyl-1-(N-methyl-N-(2-(trimethylsilyl)ethoxycarbonyl)amino)propan-2-yl)-3-((S)-1-hydroxy-5-methoxy-1-phenylpentyl)piperidine-1-carboxamidine (145 mg, 0.21 mmol) and Et₄NF (160 mg, 1.1 mmol) in MeCN (5 mL) was heated at 100° C. in the microwave for 7 min. The reaction mixture was directly submitted to prep HPLC to afford (3R)—N'-cyano-N—((S)-3-cyclohexyl-1-(methylamino)propan-2-yl)-3-((S)-1-hydroxy-5-methoxy-1-phenylpentyl)piperidine-1-carboxamidine (16 mg, 14%).

Example 126

(R)—N—((S)-2-amino-3-cyclohexylpropyl)-3-((S)-1-(3-chlorophenyl)-1-hydroxy-5-methoxypentyl)piperidine-1-carboxamide (I-354A)

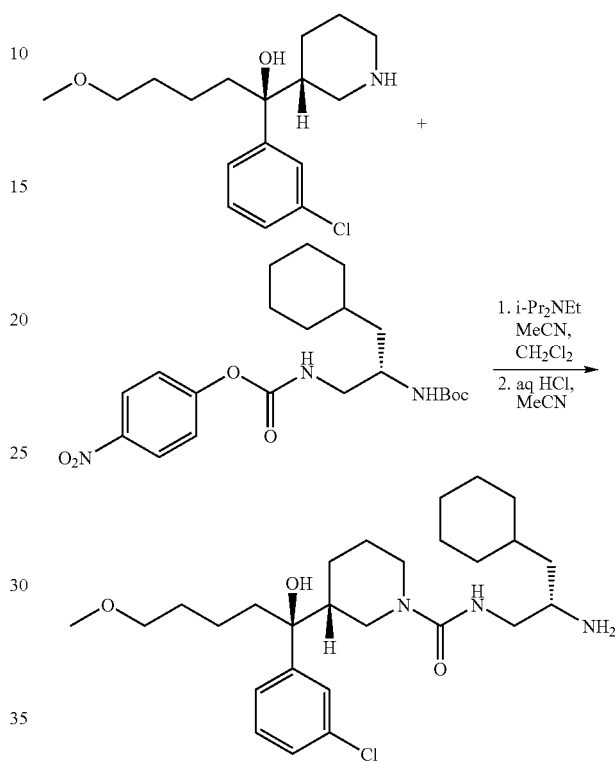

Step 1. tert-Butyl (S)-1-((R)-3-((S)-1-(3-chlorophenyl)-1-hydroxy-5-methoxypentyl)piperidine-1-carboxamido)-3-cyclohexylpropan-2-ylcarbamate To a stirred solution of (S)-1-(3-chlorophenyl)-5-methoxy-1-((R)-piperidin-3-yl)pentan-1-ol (31 mg, 0.10 mmol) and (S)-tert-butyl 1-(p-nitrophenoxycarbonylamino)-3-cyclohexylpropan-2-ylcarbamate (40 mg, 0.10 mmol) in MeCN (1 mL) and CH₂Cl₂ (1 mL) was added DIEA (50 μL, 0.28 mmol). The mixture was stirred at rt for 20 h, diluted with ether (90 mL), washed with 5% aq HCl (20 mL) and 1 M aq NaOH (20 mL) and dried over MgSO₄. Removal of the solvent left an oil (82 mg) which was applied to a 2-g silica SPE cartridge which was eluted sequentially with 10, 25, 50, 75 and 100% ethyl acetate in hexanes (15 mL of each) to afford 5 fractions. The 4th fraction was concentrated to afford tert-butyl (S)-1-((R)-3-((S)-1-(3-chlorophenyl)-1-hydroxy-5-methoxypentyl)piperidine-1-carboxamido)-3-cyclohexylpropan-2-ylcarbamate (29 mg, 49%) as an oil.

Step 2. (R)—N—((S)-2-amino-3-cyclohexylpropyl)-3-((S)-1-(3-chlorophenyl)-1-hydroxy-5-methoxypentyl)piperidine-1-carboxamide tert-Butyl (S)-1-((R)-3-((S)-1-(3-chlorophenyl)-1-hydroxy-5-methoxypentyl)piperidine-1-carboxamido)-3-cyclohexylpropan-2-ylcarbamate (29 mg, 0.05 mmol) was dissolved in MeCN (5 mL) and 5% aq HCl (5 mL) was added.

The mixture was stirred at rt overnight and solid K₂CO₃ was added. MeCN was removed on the rotary evaporator and the aqueous residue was extracted with CH₂Cl₂ (2×50 mL). The combined organic extracts were dried over Na₂SO₄ and evaporated to leave an oil (55.5 mg). Preparative HPLC afforded (R)—N—((S)-2-amino-3-cyclohexylpropyl)-3-((S)-1-(3-chlorophenyl)-1-hydroxy-5-methoxypentyl)piperidine-1-carboxamide (22.7 mg, 93%) as a solid.

Example 127

The following compounds were prepared using procedures analogous to those described in Example 126:

| Cpd. No. | Name |
|---|---|
| I-6A | 3-((3-methoxypropoxy)(phenyl)methyl)-N-(2-amino-3-cyclohexylpropyl)piperidine-1-carboxamide using 3-((3-methoxypropoxy)(phenyl)methyl)piperidine in Step 1. |
| I-83A | 3-((3-methoxypropoxy)(2-phenylphenyl)methyl)-N-((S)-2-amino-3-cyclohexylpropyl)piperidine-1-carboxamide using 3-(biphenyl-2-yl(3-methoxypropoxy)methyl)piperidine in Step 1. |
| I-373A | (R)—N-((S)-2-amino-3-cyclohexylpropyl)-3-((S)-1-(3-chloro-2-fluorophenyl)-1-hydroxy-5-methoxypentyl)piperidine-1-carboxamide using (S)-1-(3-chloro-2-fluorophenyl)-5-methoxy-1-((R)-piperidin-3-yl)pentan-1-ol in Step 1. |
| I-377A | (R)—N-((S)-2-amino-3-cyclohexylpropyl)-3-((S)-1-(benzo[b]thiophen-4-yl)-1-hydroxy-5-methoxypentyl)piperidine-1-carboxamide using (S)-1-(benzo[b]thiophen-4-yl)-5-methoxy-1-((R)-piperidin-3-yl)pentan-1-ol in Step 1. |
| I-381A | (RS)—N-((S)-2-amino-3-cyclohexylpropyl)-2-((RS)-1-(benzo[b]thiophen-7-yl)-1-hydroxy-5-methoxypentyl)morpholine-4-carboxamide using (RS)-1-(benzo[b]thiophen-7-yl)-5-methoxy-1-((RS)-morpholin-2-yl)pentan-1-ol in Step 1. |
| I-394A | (3R)—N-((R)-2-amino-3-tert-butoxypropyl)-3-((S)-1-(3-chloro-2-fluorophenyl)-1-hydroxy-5-methoxypentyl)piperidine-1-carboxamide |
| I-475A | (3R)-3-((S)-1-(3-chloro-2-fluorophenyl)-1-hydroxy-5-methoxypentyl)-N-((S)-3-cyclohexyl-2-(methylamino)propyl)piperidine-1-carboxamide |
| I-36A | (3R)—N-((S)-2-amino-5-methoxy-4,4-dimethylpentyl)-3-((S)-1-(3-chlorophenyl)-1-hydroxy-5-methoxypentyl)piperidine-1-carboxamide |
| I-54A | (3R)—N-((S)-2-amino-5-methoxy-4,4-dimethylpentyl)-3-((S)-1-(2,3-difluorophenyl)-1-hydroxy-5-methoxypentyl)piperidine-1-carboxamide |
| I-472A | (3R)—N-((S)-2-amino-5-methoxy-4,4-dimethylpentyl)-3-((S)-1-(3-chloro-2-fluorophenyl)-1-hydroxy-5-methoxypentyl)piperidine-1-carboxamide |
| I-477A | (3R)—N-((2R,3S)-3-amino-4-cyclohexylbutan-2-yl)-3-((S)-1-(3-chloro-2-fluorophenyl)-1-hydroxy-5-methoxypentyl)piperidine-1-carboxamide |
| I-477B | (3R)—N-((2S,3S)-3-amino-4-cyclohexylbutan-2-yl)-3-((S)-1-(3-chloro-2-fluorophenyl)-1-hydroxy-5-methoxypentyl)piperidine-1-carboxamide |
| I-492A | (3R)—N-((S)-2-amino-3-(4,4-difluorocyclohexyl)propyl)-3-((S)-1-(3-chloro-2-fluorophenyl)-1-hydroxy-5-methoxypentyl)piperidine-1-carboxamide |
| I-503A | (3R)—N-(2-amino-3-cyclopentylpropyl)-3-((S)-1-(3-chlorophenyl)-1-hydroxy-5-methoxypentyl)piperidine-1-carboxamide |
| I-504A | (3R)—N-((2S)-2-amino-3-(tetrahydrofuran-2-yl)propyl)-3-((S)-1-(3-chlorophenyl)-1-hydroxy-5-methoxypentyl)piperidine-1-carboxamide |
| I-508A | (3R)—N-(2-amino-3-(tetrahydro-2H-pyran-4-yl)propyl)-3-((S)-1-(3-chlorophenyl)-1-hydroxy-5-methoxypentyl)piperidine-1-carboxamide |
| I-511A | (3R)—N-((S)-2-amino-3-(trans-3-methoxycyclobutyl)propyl)-3-((S)-1-(3-chlorophenyl)-1-hydroxy-5-methoxypentyl)piperidine-1-carboxamide |
| I-511B | (3R)—N-((S)-2-amino-3-(cis-3-methoxycyclobutyl)propyl)-3-((S)-1-(3-chlorophenyl)-1-hydroxy-5-methoxypentyl)piperidine-1-carboxamide |
| I-512A | (S)—N-((S)-2-amino-3-cyclohexylpropyl)-3-((S)-1-(3-chloro-2-fluorophenyl)-5-methoxypentyl)piperidine-1-carboxamide |
| I-512B | (S)—N-((S)-2-amino-3-cyclohexylpropyl)-3-((R)-1-(3-chloro-2-fluorophenyl)-5-methoxypentyl)piperidine-1-carboxamide |
| I-513A | (3R)—N-((2S)-2-amino-3-(tetrahydrofuran-2-yl)propyl)-3-((S)-1-(3-chloro-2-fluorophenyl)-1-hydroxy-5-methoxypentyl)piperidine-1-carboxamide |
| I-515A | (3R)—N-((S)-2-amino-4-phenylbutyl)-3-((S)-1-(3-chlorophenyl)-1-hydroxy-5-methoxypentyl)piperidine-1-carboxamide |
| I-520A | (3R)—N-((S)-2-amino-4-cyclohexylbutyl)-3-((S)-1-(3-chlorophenyl)-1-hydroxy-5-methoxypentyl)piperidine-1-carboxamide |
| I-527A | (3R)—N-((S)-2-amino-3-(3-methoxycyclobutyl)propyl)-3-((S)-1-(3-chloro-2-fluorophenyl)-1-hydroxy-5-methoxypentyl)piperidine-1-carboxamide |

Example 128

N—((S)-3-Cyclohexyl-1-(methylamino)propan-2-yl)-3-(1-hydroxy-5-methoxy-1-phenylpentyl)benzamide (I-114A)

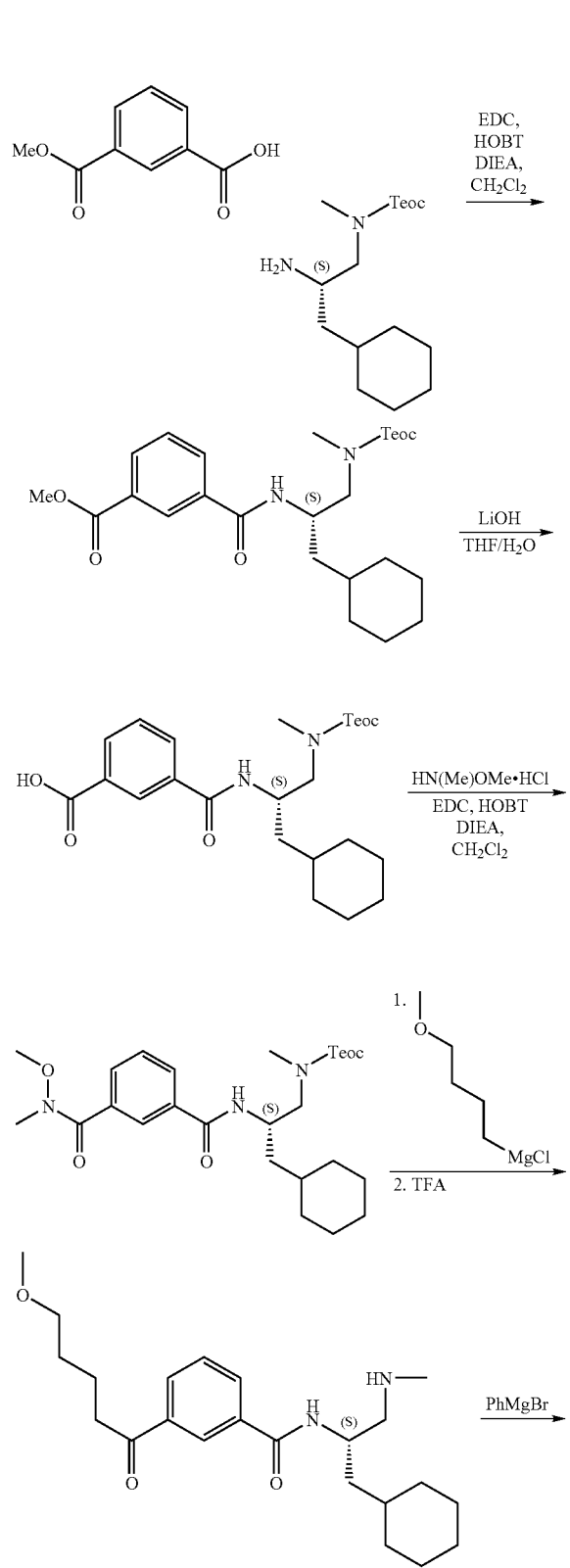

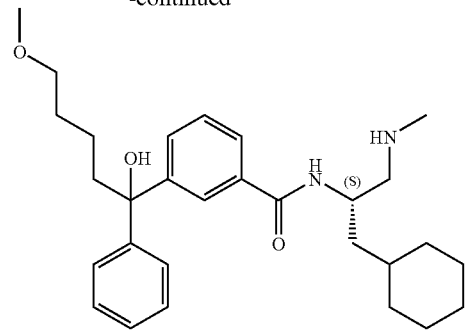

Step 1. (S)-methyl 3-(1-cyclohexyl-3-(N-methyl-N-(2-(trimethylsilyl)ethoxycarbonyl)amino)propan-2-ylcarbamoyl)benzoate A mixture of mono-methyl isophthalate (0.3230 g, 1.79 mmol, 1.0 equiv), 2-(trimethylsilyl)ethyl (S)-2-amino-3-cyclohexylpropylmethylcarbamate (0.5573 g, 1.77 mmol, 0.99 equiv), EDC (0.6200 g, 1.8 equiv), HOBT (0.4035 g, 1.66 equiv), and DIEA (3.6 mL, 11 equiv) in $CH_2Cl_2$ (20 mL) was stirred at rt for 18 h. The reaction mixture was quenched with 10% aq $Na_2CO_3$, extracted with $CH_2Cl_2$ and dried over $Na_2SO_4$. After the solvent was removed, the crude (S)-methyl 3-(1-cyclohexyl-3-(N-methyl-N-(2-(trimethylsilyl)ethoxycarbonyl)amino)propan-2-ylcarbamoyl)benzoate (1.397 g) was used in the next step without further purification. LC-MS (3 min) $t_R$=2.29 min, m/z 499 (M+Na$^+$), 449, 359.

Step 2. (S)-3-(1-cyclohexyl-3-(N-methyl-N-(2-(trimethylsilyl)ethoxycarbonyl)amino)propan-2-ylcarbamoyl)benzoic acid A mixture of (S)-methyl 3-(1-cyclohexyl-3-(N-methyl-N-(2-(trimethylsilyl)ethoxycarbonyl)-amino)propan-2-ylcarbamoyl)benzoate (1.397 g) and LiOH.$H_2O$ (0.430 g, 10 mmol, 5.7 equiv) in THF (50 mL) and $H_2O$ (10 mL) was vigorously stirred at rt for 23 h. The reaction mixture was quenched with 2 N HCl (6 mL). After the organic solvent was removed in vacuo, the aqueous phase was extracted with $CH_2Cl_2$ (3×) and the combined organic layers were dried over $Na_2SO_4$. The crude (S)-3-(1-cyclohexyl-3-(N-methyl-N-(2-(trimethylsilyl)ethoxycarbonyl)amino)propan-2-ylcarbamoyl)benzoic acid (0.923 g) was used in the next step without further purification. LC-MS (3 min) $t_R$=2.06 min, m/z 485 (M+Na$^+$), 435, 391. $^{13}$C NMR (100 MHz, CDCl$_3$) δ 168.45, 166.95, 157.89, 135.27, 132.73, 132.34, 129.95, 128.47, 128.42, 64.25, 52.86, 45.49, 40.59, 34.58, 34.26, 33.77, 33.13, 26.46, 26.23, 26.11, 17.64, −1.61.

Step 3. (S)—N$^1$-(1-cyclohexyl-3-(N-methyl-N-(2-(trimethylsilyl)ethoxycarbonyl)amino)propan-2-yl)-N$^3$-methoxy-N$^3$-methylisophthalamide A mixture of (S)-3-(1-cyclohexyl-3-(N-methyl-N-(2-(trimethylsilyl)ethoxycarbonyl)-amino)propan-2-ylcarbamoyl) benzoic acid (0.923 g, 1.77 mmol, 1.0 equiv), obtained as described above, N,O-dimethylhydroxylamine hydrochloride (0.378 g, 2.2 equiv), EDC (0.600 g, 1.8 equiv), HOBt (0.384 g, 1.6 equiv), and DIEA (3 mL, 9.7 equiv) in $CH_2Cl_2$ (20 mL) was stirred at rt for 3 d. The reaction mixture was diluted with brine and extracted with $CH_2Cl_2$ (3×). The combined organic extracts were dried over $Na_2SO_4$. After the solvent was removed, the crude product was purified by chromatography on a 40-g silica gel cartridge eluted with a gradient from 0% to 40% EtOAc in hexanes to give (S)—N'-(1-cyclohexyl-3-(N-methyl-N-(2-(trimethylsilyl)ethoxycarbonyl)amino)propan-2-yl)-N-3-methoxy-N³-methylisophthalamide (0.7388 g, 83%). TLC r$_f$=0.38 (50% EtOAc in hexanes); LC-MS (3 min) t$_R$=2.12 min, m/z 528 (MNa⁺), 506 (M+H⁺), 478; ¹H NMR (400 MHz, CDCl$_3$) δ 8.09 (s, 1H), 7.84 (dt, J=7.9, 1.5 Hz, 1H), 7.75 (d, J=7.6 Hz, 1H), 7.42 (t, J=7.8 Hz, 1H), 6.77 (d, J=8.2 Hz, 1H), 4.48-4.39 (m, 1H), 4.11-3.97 (m, 2H), 3.72 (dd, J=14.3, 10.5 Hz, 1H), 3.54 (s, 3H), 3.33 (s, 3H), 3.01 (dd, J=14.3, 4.1 Hz, 1H), 2.90 (s, 3H), 1.85-0.80 (m, 15H), −0.06 (s, 9H); ¹³C NMR (100 MHz, CDCl$_3$) δ 169.03, 166.25, 158.12, 134.41, 130.84, 128.80, 128.12, 126.89, 63.75, 61.06, 52.51, 46.78, 40.64, 34.60, 34.35, 33.53, 33.15, 26.36, 26.13, 26.06, 17.56, −1.61.

Step 4. (S)—N-(1-cyclohexyl-3-(N-methyl-N-(2-(trimethylsilyl)ethoxycarbonyl)amino)propan-2-yl)-3-(5-methoxypentanoyl)benzamide To a solution of (S)—N¹-(1-cyclohexyl-3-(N-methyl-N-(2-(trimethylsilyl)ethoxycarbonyl)-amino)propan-2-yl)-N³-methoxy-N³-methylisophthalamide (0.7361 g, 1.46 mmol, 1.0 equiv) in THF (15 mL) was added 1.45 M 4-methoxybutylmagnesium chloride in THF (4 mL, 5.8 mmol, 4.0 equiv) at 0° C. under N$_2$. After 2 h, the reaction mixture was quenched with 1 N aq HCl (15 mL) and extracted EtOAc (3×). The combined EtOAc extracts were dried over Na$_2$SO$_4$ and concentrated to afford crude (S)—N-(1-cyclohexyl-3-(N-methyl-N-(2-(trimethylsilyl)-ethoxycarbonyl)amino)propan-2-yl)-3-(5-methoxypentanoyl)benzamide (0.758 g), which was used in the next step without further purification. LC-MS (3 min) t$_R$=2.34 min, m/z 555 (M+Na⁺), 534, 505.

Step 5. (S)—N-(1-cyclohexyl-3-(methylamino)propan-2-yl)-3-(5-methoxypentanoyl)benzamide A mixture of crude (S)—N-(1-cyclohexyl-3-(N-methyl-N-(2-(trimethylsilyl)ethoxycarbonyl)-amino)propan-2-yl)-3-(5-methoxypentanoyl)benzamide (0.310 g), and TFA (4 mL) was stirred at rt for 3 h. After the solvent was removed in vacuo, the crude product was purified by preparative HPLC (Phenomenex® Luna 5μ C18(2) 100 A, 250×21.20 mm, 5 micron, 10%→90% CH$_3$CN/H$_2$O, 0.1% CF$_3$COOH over 13 min, flow rate 25 mL/min) to give 0.0382 g of TFA salt of (S)—N-(1-cyclohexyl-3-(methylamino)propan-2-yl)-3-(5-methoxypentanoyl)benzamide. LC-MS (3 min) t$_R$=1.34 min, m/z 389 (M+H⁺), 372, 358. ¹H NMR (400 MHz, CD$_3$OD) δ 8.50 (d, J=8.5 Hz, 1H), 8.35 (s, 1H), 8.03 (d, J=7.6 Hz, 1H), 7.97 (d, J=7.9 Hz, 1H), 7.48 (t, J=7.8 Hz, 1H), 4.46-4.41 (m, 1H), 3.30 (t, J=6.2 Hz, 2H), 3.18 (s, 3H), 3.09-2.95 (m, 2H), 2.97 (t, J=7.0 Hz, 2H), 2.60 (s, 3H), 1.76-0.78 (m, 17H).

Step 6. N—((S)-1-cyclohexyl-3-(methylamino)propan-2-yl)-3-(1-hydroxy-5-methoxy-1-phenylpentyl)benzamide A 50 mL round bottom flask was charged with the TFA salt of (S)—N-(1-cyclohexyl-3-(methylamino)propan-2-yl)-3-(5-methoxypentanoyl)benzamide (0.0357 g, 0.071 mmol) and THF (5 mL). The flask was evacuated and refilled with N$_2$. The mixture was cooled in a dry ice-acetone bath and 1 M phenylmagnesium bromide in THF (4 mL, 4 mmol) was added. After 1 h, the cooling bath was removed and the reaction mixture was stirred at rt for 5 h. The mixture was quenched with 10% aq Na$_2$CO$_3$ (10 mL) and extracted with CH$_2$Cl$_2$ (3×). The combined organic extracts were dried over Na$_2$SO$_4$. The crude product was purified by preparative HPLC (Phenomenex® Luna 5μ C18(2) 100 A, 250×21.20 mm, 5 micron, 10%→90% CH$_3$CN/H$_2$O, 0.1% CF$_3$COOH over 13 min, flow rate 25 mL/min) to give the TFA salt of N—((S)-1-cyclohexyl-3-(methylamino)propan-2-yl)-3-(1-hydroxy-5-methoxy-1-phenylpentyl)-benzamide (0.0342 g, 83%). LC-MS (3 min) t$_R$=1.47 min, m/z 467 (MH⁺); ¹H NMR (400 MHz, CD$_3$OD) δ 8.26 (d, J=8.2 Hz, 1H), 7.89-7.03 (m, 9H), 4.40-4.38 (m, 1H), 3.23 (t, J=6.4 Hz, 2H), 3.15 (s, 3H), 3.06-2.91 (m, 2H), 2.584, 2.579 (s, 3H), 2.23 (t, J=8.2 Hz, 2H), 1.74-0.78 (m, 17H).

Example 129

The following compounds were prepared using procedures analogous to those described in Example 128:

| Cpd. No. | Name |
| --- | --- |
| I-128A | N-((S)-3-cyclohexyl-1-(methylamino)propan-2-yl)-3-(1-hydroxy-5-methoxy-1-m-tolylpentyl)benzamide |
| I-129A | N-((S)-3-cyclohexyl-1-(methylamino)propan-2-yl)-3-(1-hydroxy-5-methoxy-1-o-tolylpentyl)benzamide |
| I-137A | N-((S)-3-cyclohexyl-1-(methylamino)propan-2-yl)-3-(1-(3-fluorophenyl)-1-hydroxy-5-methoxypentyl)benzamide |
| I-138A | N-((S)-3-cyclohexyl-1-(methylamino)propan-2-yl)-3-(1-(4-fluorophenyl)-1-hydroxy-5-methoxypentyl)benzamide |
| I-167A | 3-(1-(3-chlorophenyl)-1-hydroxy-5-methoxypentyl)-N-((S)-3-cyclohexyl-1-(methylamino)propan-2-yl)benzamide |
| I-274A | N-((S)-1-cyclohexyl-3-(methylamino)propan-2-yl)-3-((S)-1-hydroxy-5-methoxy-1-(3-(trifluoromethyl)phenyl)pentyl)benzamide |

Example 130

N—((S)-3-cyclohexyl-1-(methylamino)propan-2-yl)-3-(5-methoxy-1-phenylpentyl)benzamide (I-106A)

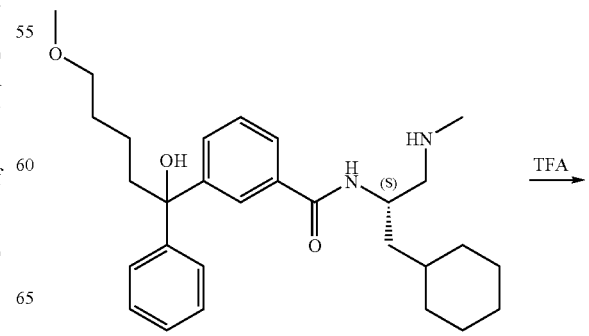

-continued

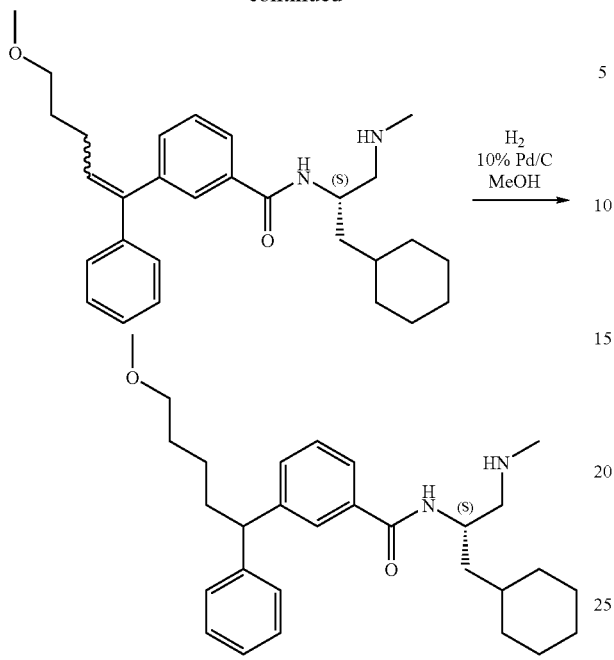

Step 1. (S)—N-(1-cyclohexyl-3-(methylamino)propan-2-yl)-3-(5-methoxy-1-phenylpent-1-enyl)benzamide A mixture of the TFA salt of N—((S)-1-cyclohexyl-3-(methylamino)propan-2-yl)-3-(1-hydroxy-5-methoxy-1-phenylpentyl)benzamide (0.0257 g, 0.0442 mmol) and TFA (2 mL) was stirred at rt for 20 h. Removal of the solvent in vacuo, afforded the crude TFA salt of (S)—N-(1-cyclohexyl-3-(methylamino)propan-2-yl)-3-(5-methoxy-1-phenylpent-1-enyl)benzamide, which was used in the next step without further purification. LC-MS (3 min) $t_R$=1.72 min, m/z 449 (M+H$^+$).

Step 2. N—((S)-1-cyclohexyl-3-(methylamino)propan-2-yl)-3-(5-methoxy-1-phenylpentyl)benzamide A 250 mL Parr shaker vessel was charged with the TFA salt of (S)—N-(1-cyclohexyl-3-(methylamino)propan-2-yl)-3-(5-methoxy-1-phenylpent-1-enyl)benzamide, obtained as described above, 10% Pd/C (0.140 g) and methanol. The vessel was placed in a Parr hydrogenation shaker and pressurized/evacuated 3 times with H$_2$ gas, then pressurized to 55 psi. The reaction vessel was shaken for 5 h, then carefully vented. The contents were filtered through an HPLC filter. After the solvent was removed in vacuo, the crude product was purified by preparative HPLC (Phenomenex® Luna 5μ C18(2) 100 A, 250×21.20 mm, 5 micron, 10%→90% CH$_3$CN/H$_2$O, 0.1% CF$_3$COOH over 13 min, flow rate 25 mL/min) to give the TFA salt of N—((S)-1-cyclohexyl-3-(methylamino)propan-2-yl)-3-(5-methoxy-1-phenylpentyl)benzamide. LC-MS (3 min) $t_R$=1.67 min, m/z 451 (M+H$^+$); $^1$H NMR (400 MHz, CD$_3$OD) δ 8.29 (d, J=8.2 Hz, 1H), 7.71-7.05 (m, 9H), 4.43-4.41 (m, 1H), 3.91 (t, J=7.9 Hz, 1H), 3.26 (t, J=6.4 Hz, 2H), 3.18 (s, 3H), 3.10-2.92 (m, 2H), 2.616, 2.613 (s, 3H), 2.06-2.00 (m, 2H), 1.77-0.81 (m, 17H).

Example 131

Example omitted.

Example 132

(3R)-3-((S)-1-(3-chloro-2-fluorophenyl)-1-(isobutyramido)-5-methoxypentyl)-N—((S)-3-cyclohexyl-1-(methylamino)propan-2-yl)piperidine-1-carboxamide (I-340A)

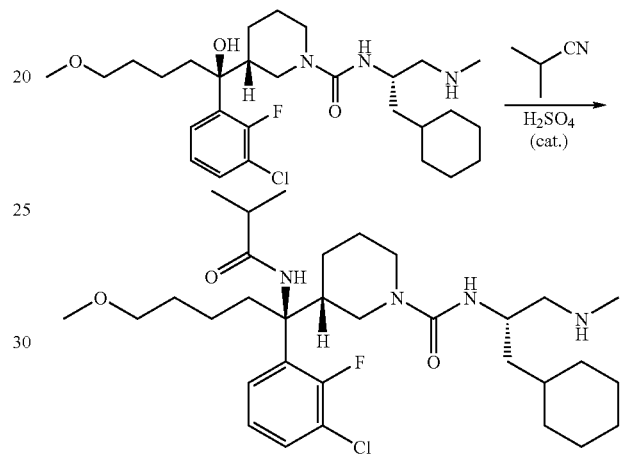

(3R)-3-((S)-1-(3-chloro-2-fluorophenyl)-1-hydroxy-5-methoxypentyl)-N—((S)-3-cyclohexyl-1-(methylamino) propan-2-yl)piperidine-1-carboxamide (70 mg, 0.133 mmol) was mixed with isobutyronitrile (8 mL) and conc H$_2$SO$_4$ (23 drops). After stirring vigorously overnight at rt, the mixture was neutralized with K$_2$CO$_3$ (ca. 100 mg). A few drops of water were added and the mixture was filtered. The filtrate was concentrated and the residue was purified by preparative HPLC to afford (3R)-3-((S)-1-(3-chloro-2-fluorophenyl)-1-(isobutyramido)-5-methoxypentyl)-N—((S)-3-cyclohexyl-1-(methylamino)propan-2-yl)piperidine-1-carboxamide (11.4 mg, 14%) as a TFA salt. $^1$H NMR (400 MHz, CDCl$_3$): 7.94 (s, 1H), 7.41 (td, 1H), 7.27 (td, 1H), 7.15 (t, 1H), 4.25 (d, 1H), 4.11 (m, 1H), 3.92 (d, 1H), 3.37 (t, 1H), 3.28 (s, 3H), 3.07 (dd, 1H), 2.96 (dd, 1H), 2.71 (s, 3H), 2.66 (m, 1H), 2.54 (td, 1H), 1.14 (dd, 6H). 3 min. LC-MS: R/T 1.59 min., m/z 596 (M+H$^+$). In addition, (3R)-3-((R)-1-(3-chloro-2-fluorophenyl)-1-(isobutyramido)-5-methoxypentyl)-N—((S)-3-cyclohexyl-1-(methylamino)propan-2-yl)piperidine-1-carboxamide and (S)-3-(1-(3-chloro-2-fluorophenyl)-1-(isobutyramido)-5-methoxypentyl)-N—((S)-3-cyclohexyl-1-(methylamino)propan-2-yl)piperidine-1-carboxamide and (S)-3-(1-(3-chloro-2-fluorophenyl)-5-methoxypent-1-enyl)-N—((S)-1-cyclohexyl-3-(methylamino)propan-2-yl)piperidine-1-carboxamide were isolated.

Example 133

The following compounds were prepared using procedures analogous to those described in Example 132:

| Cpd. No. | Name |
|---|---|
| I-272A | (3R)-3-((S)-1-acetamido-1-(3-fluorophenyl)-5-methoxypentyl)-N-((S)-3-cyclohexyl-1-(methylamino)propan-2-yl)piperidine-1-carboxamide |
| I-301A | (3R)-3-((S)-1-acetamido-1-(3-chlorophenyl)-5-methoxypentyl)-N-((S)-3-cyclohexyl-1-(methylamino)propan-2-yl)piperidine-1-carboxamide |
| I-322A | (3R)-3-((S)-1-(3-chlorophenyl)-5-methoxy-1-(propionamido)pentyl)-N-((S)-3-cyclohexyl-1-(methylamino)propan-2-yl)piperidine-1-carboxamide |
| I-329A | (3R)-3-((R)-1-acetamido-1-(3-chloro-2-fluorophenyl)-5-methoxypentyl)-N-((S)-3-cyclohexyl-1-(methylamino)propan-2-yl)piperidine-1-carboxamide |
| I-329B | (3R)-3-((S)-1-acetamido-1-(3-chloro-2-fluorophenyl)-5-methoxypentyl)-N-((S)-3-cyclohexyl-1-(methylamino)propan-2-yl)piperidine-1-carboxamide |
| I-332A | (3R)-3-(1-(3-chlorophenyl)-1-(isobutyramido)-5-methoxypentyl)-N-((S)-3-cyclohexyl-1-(methylamino)propan-2-yl)piperidine-1-carboxamide |
| I-336A | (3R)-3-((S)-1-(3-chloro-2-fluorophenyl)-5-methoxy-1-(propionamido)pentyl)-N-((S)-3-cyclohexyl-1-(methylamino)propan-2-yl)piperidine-1-carboxamide |
| I-340A | (3R)-3-((R)-1-(3-chloro-2-fluorophenyl)-1-(isobutyramido)-5-methoxypentyl)-N-((S)-3-cyclohexyl-1-(methylamino)propan-2-yl)piperidine-1-carboxamide |
| I-431A | 3-(1-acetamido-1-(3-chlorophenyl)-5-methoxypentyl)-N-((S)-1-cyclohexyl-3-(methylamino)propan-2-yl)benzamide |
| I-454A | (R)—N-((S)-1-cyclohexyl-3-(methylamino)propan-2-yl)-3-((S)-1-(2,3-difluorophenyl)-5-methoxy-1-propionamidopentyl)piperidine-1-carboxamide |
| I-458A | 2-(1-acetamido-1-(3-chloro-2-fluorophenyl)-5-methoxypentyl)-N-((S)-1-cyclohexyl-3-(methylamino)propan-2-yl)morpholine-4-carboxamide |
| I-469A | (R)-3-((S)-1-butyramido-1-(3-chloro-2-fluorophenyl)-5-methoxypentyl)-N-((S)-1-cyclohexyl-3-(methylamino)propan-2-yl)piperidine-1-carboxamide |
| I-553A | (3R)-3-((S)-1-acetamido-5-ethoxy-1-(3-fluorophenyl)pentyl)-N-((S)-1-cyclohexyl-3-(methylamino)propan-2-yl)piperidine-1-carboxamide |
| I-558A | (3R)-3-((S)-1-acetamido-1-(3-chlorophenyl)-5-ethoxypentyl)-N-((S)-1-cyclohexyl-3-(methylamino)propan-2-yl)piperidine-1-carboxamide |

Example 134

(3R)-3-((S)-1-(3-Chlorophenyl)-1,5-dihydroxypentyl)-N—((S)-3-cyclohexyl-1-(methylamino)propan-2-yl)piperidine-1-carboxamide (I-155A)

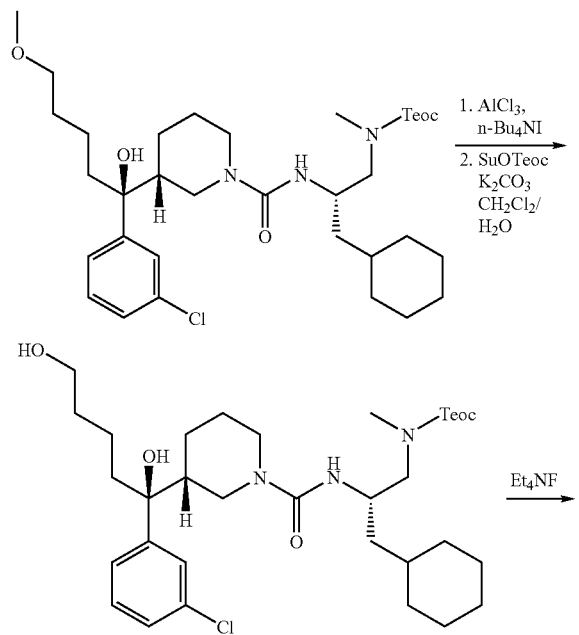

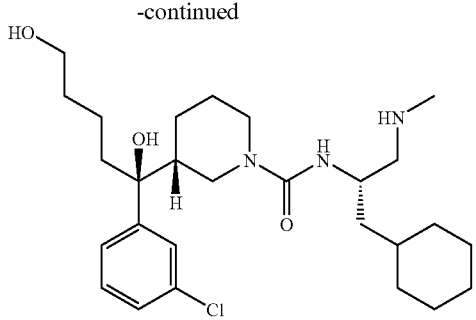

Step 1. (3R)-3-((S)-1-(3-chlorophenyl)-1,5-dihydroxypentyl)-N—((S)-3-cyclohexyl-1-(N-methyl-N-(2-(trimethylsilyl)ethoxycarbonyl)amino)propan-2-yl)piperidine-1-carboxamide A 100 mL round-bottom flask was charged with of (3R)-3-((S)-1-(3-chlorophenyl)-1-hydroxy-5-methoxypentyl)-N—((S)-3-cyclohexyl-1-(N-methyl-N-(2-(trimethylsilyl)ethoxycarbonyl)-amino)propan-2-yl)piperidine-1-carboxamide (0.6557 g, 1.0 mmol, 1.0 equiv), n-Bu$_4$NI (3.765 g, 10 mmol, 10 equiv), and CH$_3$CN (15 mL). To the flask was added AlCl$_3$ (1.345 g, 10 mmol, 10 equiv) at 0° C. After 4 h, the reaction mixture was quenched with 10% aq Na$_2$CO$_3$ (18 mL) and 1 N aq NaOH (10 mL) and extracted with CH$_2$Cl$_2$ (3×). The combine organic extracts were dried over Na$_2$SO$_4$ and the solvent was removed in vacuo. The crude product was treated with Teoc-OSu (0.534 g, 2.06 mmol), K$_2$CO$_3$ (4.080 g, 29.5 mmol), water (5 mL) and CH$_2$Cl$_2$ (50 mL) at rt for 2.5 h. The mixture was diluted with brine, extracted with CH₂Cl₂ and dried over Na₂SO₄. After the solvent was removed in vacuo, the crude product was purified by prep HPLC (Phenomenex® Luna 5μ C18(2) 100 A, 250×21.20 mm, 5 micron, 70%→90% CH₃CN/H₂O, 0.1% CF₃COOH over 8 min and then 90% CH₃CN/H₂O, 0.1% CF₃COOH over 10 min, flow rate 25 mL/min) to give (3R)-3-((S)-1-(3-chlorophenyl)-1,5-dihydroxypentyl)-N—((S)-3-cyclohexyl-1-(N-methyl-N-(2-(trimethylsilyl)ethoxycarbonyl)amino)propan-2-yl)piperidine-1-carboxamide (0.1625 g). LC-MS (3 min) $t_R$=2.29 min, m/z 660, 662 (MNa⁺), 638, 640 (MH⁺).

Step 2. (3R)-3-((S)-1-(3-chlorophenyl)-1,5-dihydroxypentyl)-N—((S)-3-cyclohexyl-1-(methylamino)propan-2-yl)piperidine-1-carboxamide A 50 mL, round-bottom flask was charged with (3R)-3-((S)-1-(3-chlorophenyl)-1,5-dihydroxypentyl)-N—((S)-3-cyclohexyl-1-(N-methyl-N-(2-(trimethylsilyl)ethoxycarbonyl)-amino)propan-2-yl)piperidine-1-carboxamide (0.1081 g, 0.1693 mmol), Et₄NF (0.6045 g), and acetonitrile (8 mL). The reaction mixture was stirred at 80° C. for 2 h and then purified by prep HPLC (Phenomenex® Luna 5μ C18(2) 100 A, 250×21.20 mm, 5 micron, 10%→90% CH₃CN/H₂O, 0.1% CF₃COOH over 13 min, flow rate 25 mL/min) to give the trifluoroacetate salt of (3R)-3-((S)-1-(3-chlorophenyl)-1,5-dihydroxypentyl)-N—((S)-3-cyclohexyl-1-(methylamino)-propan-2-yl)piperidine-1-carboxamide. LC-MS (3 min) $t_R$=1.40 min, m/z 494, 496 (MH⁺); ¹H NMR (400 MHz, CD₃OD) δ 7.33-7.32 (m, 1H), 7.21-7.09 (m, 3H), 4.19 (d, J=11.7 Hz, 1H), 4.06-3.98 (m, 1H), 3.86 (d, J=12.9 Hz, 1H), 3.37 (t, J=6.6 Hz, 2H), 2.95 (dd, J=12.6, 3.2 Hz, 1H), 2.83 (dd, J=12.6, 10.0 Hz, 1H), 2.59 (s, 3H), 2.47-2.41 (m, 2H), 1.92-0.74 (m, 24H); ¹³C NMR (100 MHz, CD₃OD) δ 159.94, 148.89, 135.14, 130.38, 127.44, 127.33, 125.43, 78.43, 62.77, 56.01, 47.58, 47.02, 46.89, 45.87, 40.89, 40.47, 35.44, 34.89, 34.03, 33.88, 33.38, 27.54, 27.31, 26.64, 26.50, 20.95.

Example 135

The following compound was prepared using procedures analogous to those described in Example 134:

| Cpd. No. | Name |
|---|---|
| I-348A | (R)-3-((S)-1-(3-chlorophenyl)-1,4-dihydroxybutyl)-N-((S)-1-cyclohexyl-3-(methylamino)propan-2-yl)piperidine-1-carboxamide |

Example 136

(3R)-3-((1S)-1-(3-chlorophenyl)-1,5-dihydroxyhexyl)-N—((S)-3-cyclohexyl-1-(methylamino)propan-2-yl)piperidine-1-carboxamide (I-191A)

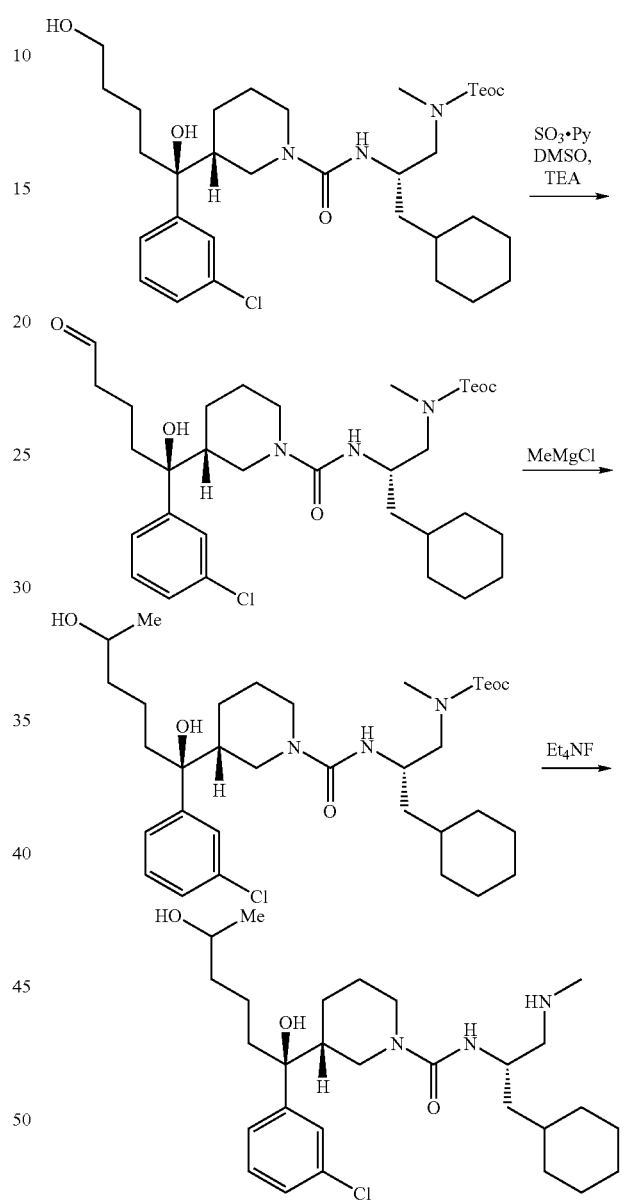

Step 1. (3R)-3-((S)-1-(3-chlorophenyl)-4-formyl-1-hydroxybutyl)-N—((S)-3-cyclohexyl-1-(N-methyl-N-(2-(trimethylsilyl)ethoxycarbonyl)amino)propan-2-yl)piperidine-1-carboxamide A 100 mL, round-bottom flask was charged with (3R)-3-((S)-1-(3-chlorophenyl)-1,5-dihydroxypentyl)-N—((S)-3-cyclohexyl-1-(N-methyl-N-(2-(trimethylsilyl)ethoxycarbonyl)-amino)propan-2-yl)piperidine-1-carboxamide (0.0544 g, 0.0852 mmol), DMSO (2.5 mL) and Et₃N (1 mL). The flask was cooled in an ice bath and a mixture of pyridine-sulphur trioxide complex (0.24 g, 1.51 mmol) and dry DMSO (2.5 mL) was added. After 10 min, the ice bath was removed. The reaction mixture was allowed to stir at rt for 3 h. The mixture was quenched with brine, extracted with EtOAc (3×) and dried over $Na_2SO_4$. Removal of the solvent left crude (3R)-3-((S)-1-(3-chlorophenyl)-4-formyl-1-hydroxybutyl)-N—((S)-3-cyclohexyl-1-(N-methyl-N-(2-(trimethylsilyl) ethoxycarbonyl)amino)propan-2-yl)piperidine-1-carboxamide (0.1036 g), which was carried on to the next step without further purification. LC-MS (3 min) $t_R$=2.43 min, m/z 658, 660 (MNa$^+$), 636 (MH$^+$), 618, 620.

Step 2. (3R)-3-((1S)-1-(3-chlorophenyl)-1,5-dihydroxyhexyl)-N—((S)-3-cyclohexyl-1-(N-methyl-N-(2-(trimethylsilyl)ethoxycarbonyl)amino)propan-2-yl)piperidine-1-carboxamide To a solution of crude (3R)-3-((S)-1-(3-chlorophenyl)-4-formyl-1-hydroxybutyl)-N—((S)-3-cyclohexyl-1-(N-methyl-N-(2-(trimethylsilyl)ethoxycarbonyl)amino)propan-2-yl)piperidine-1-carboxamide, obtained as described above, in THF (5 mL) was added methylmagnesium chloride (3 M in THF, 5 mL, 15 mmol) at −78° C. under $N_2$. After 17 h, the mixture was quenched with 10% aq $Na_2CO_3$ (3 mL), extracted (3×) with $CH_2Cl_2$ (3×) and dried over $Na_2SO_4$. The crude product was treated with Teoc-OSu (0.0785 g, 0.30 mmol) and $K_2CO_3$ (0.760 g) in $H_2O/CH_2Cl_2$. The product was purified by preparative HPLC (Phenomenex® Luna 5µ C18(2) 100 A, 250×21.20 mm, 5 micron, 70%→90% $CH_3CN/H_2O$, 0.1% $CF_3COOH$ over 8 min and then 90% $CH_3CN/H_2O$, 0.1% $CF_3COOH$ over 18.5 min, flow rate 25 mL/min) to give (3R)-3-((1S)-1-(3-chlorophenyl)-1,5-dihydroxyhexyl)-N—((S)-3-cyclohexyl-1-(N-methyl-N-(2-(trimethylsilyl)ethoxycarbonyl)amino)propan-2-yl)piperidine-1-carboxamide (0.0028 g). LC-MS (3 min) $t_R$=2.36 min, m/z 674, 676 (MNa$^+$), 652, 650 (MH$^+$).

Step 3. (3R)-3-((1S)-1-(3-chlorophenyl)-1,5-dihydroxyhexyl)-N—((S)-3-cyclohexyl-1-(methylamino) propan-2-yl)piperidine-1-carboxamide A 50 mL, round-bottom flask was charged with (3R)-3-((1S)-1-(3-chlorophenyl)-1,5-dihydroxyhexyl)-N—((S)-3-cyclohexyl-1-(N-methyl-N-(2-(trimethylsilyl)ethoxycarbonyl)-amino)propan-2-yl)piperidine-1-carboxamide, $Et_4NF$ (0.2274 g) and MeCN (4 mL). The reaction mixture was stirred at 80° C. for 2.5 h and then purified by prep HPLC (Phenomenex® Luna 5µ C18(2) 100 A, 250×21.20 mm, 5 micron, 10%→90% $CH_3CN/H_2O$, 0.1% $CF_3COOH$ over 13 min, flow rate 25 mL/min) to give the TFA salt of (3R)-3-((1S)-1-(3-chlorophenyl)-1,5-dihydroxyhexyl)-N—((S)-3-cyclohexyl-1-(methylamino)propan-2-yl)piperidine-1-carboxamide. LC-MS (3 min) $t_R$=1.53 min, m/z 508, 510 (MH$^+$); $^1$H NMR (400 MHz, $CD_3OD$) δ 7.36-7.34 (m, 1H), 7.24-7.13 (m, 3H), 4.20 (d, J=15 Hz, 1H), 4.06-3.99 (m, 1H), 3.88 (d, J=13.2 Hz, 1H), 3.58-3.53 (m, 1H), 2.97 (dd, J=12.8, 3.1 Hz, 1H), 2.82 (dd, J=12.6, 10.2 Hz, 1H), 2.61 (s, 3H), 2.49-2.41 (m, 2H), 0.987, 0.982 (d, J=6 Hz, 3H), 1.94-0.80 (m, 24H).

Example 137

The following compound was prepared using procedures analogous to those described in Example 136:

| Cpd. No. | Name |
| --- | --- |
| I-235A | (3R)-3-((1S)-1-(3-chlorophenyl)-1,5-dihydroxyheptyl)-N-((S)-3-cyclohexyl-1-(methylamino)propan-2-yl)piperidine-1-carboxamide |

Example 139

(3R)-3-((S)-1-(3-Cyanophenyl)-1-hydroxy-5-methoxypentyl)-N—((S)-1-cyclohexyl-3-(methylamino) propan-2-yl)piperidine-1-carboxamide (I-357A)

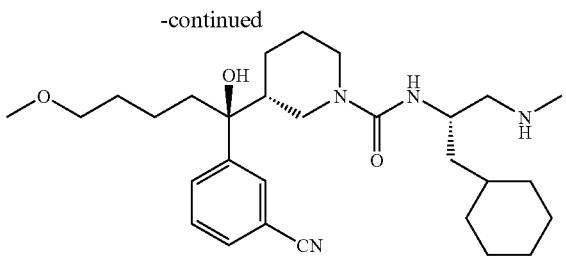

Step 1. (3R)-3-((S)-1-(3-Cyanophenyl)-1-hydroxy-5-methoxypentyl)-N—((S)-1-cyclohexyl-3-(N-methyl-N-(2-(trimethylsilyl)ethoxycarbonyl)amino)propan-2-yl)piperidine-1-carboxamide To a stirred mixture of (3R)-3-((S)-1-(3-bromophenyl)-1-hydroxy-5-methoxypentyl)-N—((S)-1-cyclohexyl-3-(N-methyl-N-(2-(trimethylsilyl)ethoxycarbonyl)amino)propan-2-yl)piperidine-1-carboxamide (40.0 mg, 0.06 mmol) in DMF (0.5 mL), was added CuCN (excess), and the resulting solution was heated in a CEM microwave reactor at 220° C. for 20 min. The mixture was cooled to rt, and purified by preparative HPLC to give (3R)-3-((S)-1-(3-Cyanophenyl)-1-hydroxy-5-methoxypentyl)-N—((S)-1-cyclohexyl-3-(N-methyl-N-(2-(trimethylsilyl)ethoxycarbonyl)-amino)propan-2-yl)piperidine-1-carboxamide (8.0 mg, 22%). MS m/z 665 (M+Na+).

Step 2. (3R)-3-((S)-1-(3-Cyanophenyl)-1-hydroxy-5-methoxypentyl)-N—((S)-1-cyclohexyl-3-(methylamino)propan-2-yl)piperidine-1-carboxamide To a solution (3R)-3-((S)-1-(3-cyanophenyl)-1-hydroxy-5-methoxypentyl)-N—((S)-1-cyclohexyl-3-(N-methyl-N-(2-(trimethylsilyl)ethoxycarbonyl)amino)propan-2-yl)piperidine-1-carboxamide (8.0 mg, 0.012 mmol) in acetonitrile (1.0 mL) was added Et4NF (excess). The resulting solution was stirred at 50° C. until no starting material remained (~1 h). Solvent was removed under vacuum and the residue was purified by preparative HPLC to give the TFA salt of (3R)-3-((S)-1-(3-Cyanophenyl)-1-hydroxy-5-methoxypentyl)-N—((S)-1-cyclohexyl-3-(methylamino)propan-2-yl)piperidine-1-carboxamide (4.0 mg, 52%). $^1$H NMR (400 MHz, CD$_3$OD): 7.78 (s, 1H), 7.68 (d, 1H), 7.62 (d, 1H), 7.56 (dd, 1H), 4.34 (d, 1H), 4.14 (m, 1H), 3.98 (d, 1H), 3.30 (t, 2H), 3.24 (s, 3H), 3.06 (dd, 1H), 2.94 (dd, 1H), 2.72 (s, 3H), 2.54 (m, 2H), 1.18-2.06 (m, 21H), 0.84-1.10 (m, 3H); MS m/z 499 (M+H+).

Example 140

The following compound was prepared using procedures analogous to those described in Example 139:

| Cpd. No. | Name |
|---|---|
| I-379A | (R)-3-((S)-1-(2-cyano-5-fluorophenyl)-1-hydroxy-5-methoxypentyl)-N-((S)-1-cyclohexyl-3-(methylamino)propan-2-yl)piperidine-1-carboxamide |

Example 141

Methyl 3-((S)-1-((R)-1-((S)-1-cyclohexyl-3-(methylamino)propan-2-ylcarbamoyl)piperidin-3-yl)-1-hydroxy-5-methoxypentyl)benzoate (I-412A)

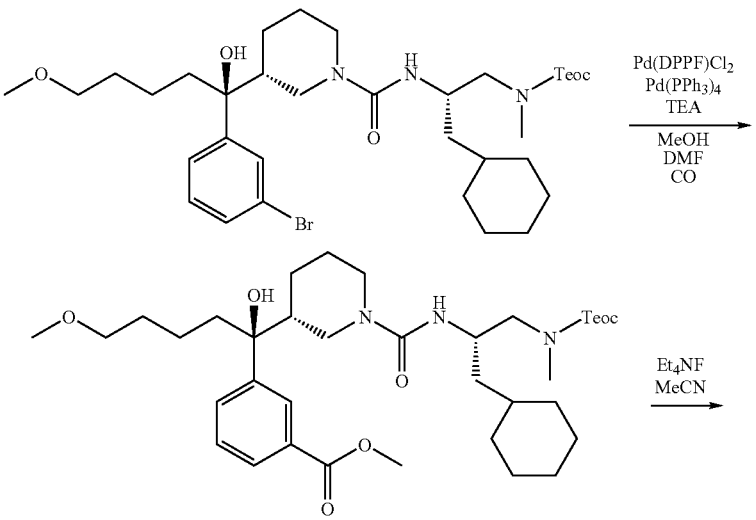

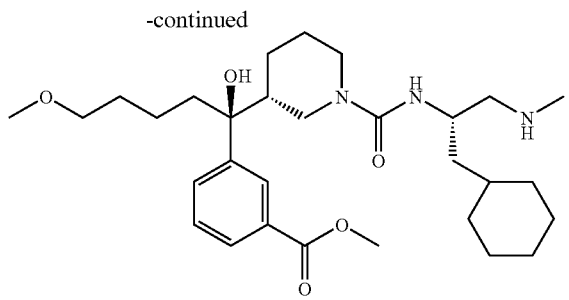

Step 1. Methyl 3-((S)-1-((R)-1-((S)-1-cyclohexyl-3-(N-methyl-N-(2-(trimethylsilyl)ethoxy-carbonyl)amino)propan-2-ylcarbamoyl)piperidin-3-yl)-1-hydroxy-5-methoxypentyl)benzoate Triethylamine (50 μL) was added to a stirred suspension of (3R)-3-((S)-1-(3-bromophenyl)-1-hydroxy-5-methoxypentyl)-N—((S)-1-cyclohexyl-3-(N-methyl-N-(2-(trimethylsilyl)ethoxycarbonyl)amino)propan-2-yl)piperidine-1-carboxamide (21.0 mg, 0.03 mmol), Pd(dppf)Cl$_2$ (5 mg) and Pd(PPh$_3$)$_4$ (5 mg) in 4:1 DMF/MeOH (2 mL). A carbon monoxide atmosphere was established in the reaction vessel and the mixture was stirred at 70° C. overnight. After cooling to ambient temperature, the mixture was extracted with EtOAc (2×5 mL) and the combined organic layers were washed with 1 N aq HCl (2×1 mL) and concentrated. The residue was purified by preparative HPLC to give methyl 3-((S)-1-((R)-1-((S)-1-cyclohexyl-3-(N-methyl-N-(2-(trimethylsilyl)ethoxycarbonyl)amino)propan-2-ylcarbamoyl)-piperidin-3-yl)-1-hydroxy-5-methoxypentyl)benzoate (5.4 mg, 27%). MS m/z 698 (M+Na$^+$).

Step 2. Methyl 3-((S)-1-((R)-1-((S)-1-cyclohexyl-3-(methylamino)propan-2-ylcarbamoyl)-piperidin-3-yl)-1-hydroxy-5-methoxypentyl)benzoate To a solution of the above methyl 3-((S)-1-((R)-1-((S)-1-cyclohexyl-3-(N-methyl-N-(2-(trimethylsilyl)ethoxycarbonyl)amino)propan-2-ylcarbamoyl)piperidin-3-yl)-1-hydroxy-5-methoxypentyl)benzoate (5.4 g, 0.008 mmol) in acetonitrile (1.0 mL) was added Et$_4$NF (excess). The resulting solution was stirred at 50° C. until no starting material remained (~1 h). Solvent was removed under vacuum, and the residue was purified by preparative HPLC to give the TFA salt of methyl 3-((S)-1-((R)-1-((S)-1-cyclohexyl-3-(methylamino)propan-2-ylcarbamoyl)piperidin-3-yl)-1-hydroxy-5-methoxypentyl)benzoate (2.2 mg, 59%). $^1$H NMR (400 MHz, CD$_3$OD): 8.06 (s, 1H), 7.90 (d, 1H), 7.62 (d, 1H), 7.44 (dd, 1H), 4.32 (d, 1H), 4.14 (m, 1H), 3.98 (d, 1H), 3.92 (s, 3H), 3.30 (t, 2H), 3.24 (s, 3H), 3.04 (dd, 1H), 2.93 (dd, 1H), 2.70 (s, 3H), 2.54 (m, 2H), 1.18-2.06 (m, 21H), 0.84-1.14 (m, 3H); MS m/z 532 (M+H$^+$).

Example 142

(1S)-1-(3-chlorophenyl)-2-(2-methoxyethoxy)-1-((3R)-piperidin-3-yl)ethanol

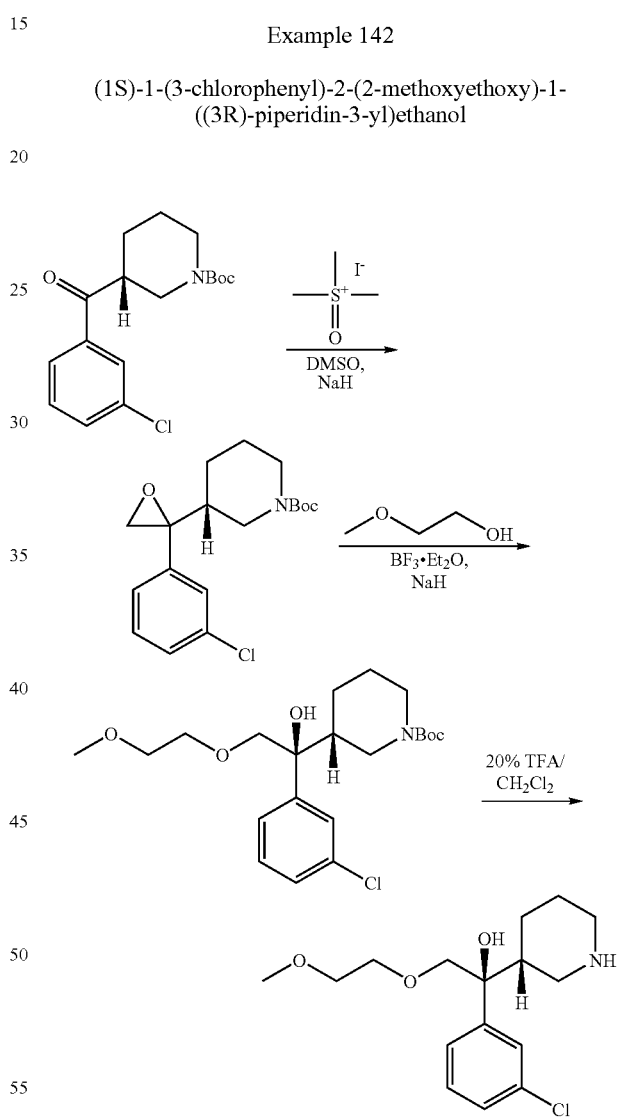

Step 1. (3R)-tert-butyl 3-(2-(3-chlorophenyl)oxiran-2-yl)piperidine-1-carboxylate A flame dried 250 mL round bottom flask was charged with sodium hydride (60% in oil, 1.45 g, 36.2 mmol) and trimethyloxosulfonium iodide (8.05 g, 36.5 mmol). The flask was evacuated and refilled with N$_2$. Dry DMSO (50 mL) was added and the mixture was stirred at rt for 1 h. A portion of this solution (14.5 mL, 10.5 mmol, 1.5 equiv) was added by syringe to a 150 mL round bottom flask which had been charged with (R)-tert-butyl 3-(3-chlorobenzoyl)-piperidine-1-carboxylate (2.27 g, 7 mmol) and THF (30 mL) and placed under N$_2$. The resulting mixture was stirred for 1 h at rt. The reaction mixture was quenched with brine and extracted with EtOAc (3×). The combined organic phase was washed with brine, dried over Na$_2$SO$_4$, filtered and concentrated in vacuo to give (3R)-tert-butyl 3-(2-(3-chlorophenyl)oxiran-2-yl)piperidine-1-carboxylate as a mixture of two isomers (2.32 g, 6.9 mmol, 99% yield), which was used in the next step without further purification. $^1$H NMR (400 MHz, CDCl$_3$): 1.40 (s, 9H), 1.55-1.72 (m, 3H), 1.85 (m, 1H), 2.01 (m, 1H), 2.35-2.60 (m, 2H), 2.65 (d, 1H), 3.063 (d, 1H), 4.05 (m, 1H), 4.15 (m, 1H), 7.26 (m, 3H), 7.34 (s, 1H); MS (E/Z): 338 (M+H$^+$)

Step 2. (R)-tert-butyl 3-((S)-1-(3-chlorophenyl)-1-hydroxy-2-(2-methoxyethoxy)ethyl)piperidine-1-carboxylate A stirred solution of BF$_3$.Et$_2$O (12.9 mg, 0.0592 mmol) and NaH (22.6 mg, 0.296 mmol) in 2-methoxyethanol (10 mL) was warmed to 55-60° C. and (3R)-tert-butyl 3-(2-(3-chlorophenyl)oxiran-2-yl)piperidine-1-carboxylate (100 mg, 0.296 mmol) was added dropwise. After addition, the reaction mixture was stirred at the same temperature overnight. The reaction mixture was concentrated and the residue was partitioned between H$_2$O and EtOAc. The organic layer washed with water and brine, dried over Na$_2$SO$_4$, filtered and concentrated in vacuo. LC-MS analysis of the crude product indicated the presence of two isomers. The crude product was purified by preparative HPLC to give the major isomer (R)-tert-butyl 3-((S)-1-(3-chlorophenyl)-1-hydroxy-2-(2-methoxyethoxy)ethyl)piperidine-1-carboxylate (30 mg, 0.073 mmol); $^1$H NMR (400 MHz, CDCl$_3$): 1.33 (s, 9H), 1.65 (m, 1H), 1.74 (m, 1H), 1.96 (m, 1H), 2.47 (m, 2H), 3.26 (m, 2H), 3.33 (s, 3H), 3.46 (m, 2H), 3.61 (m, 2H), 3.79 (m, 1H), 3.84 (m, 1H), 3.99 (m, 1H), (m, 1H), 7.22 (m, 3H), 7.42 (s, 1H); MS (E/Z): 414 (M+H$^+$)

The minor isomer (R)-tert-butyl 3-((R)-1-(3-chlorophenyl)-1-hydroxy-2-(2-methoxyethoxy)ethyl)piperidine-1-carboxylate was also isolated (25 mg, 0.061 mmol). $^1$H NMR (400 MHz, CDCl$_3$): 1.26 (m, 2H), 1.45 (s, 9H), 1.57 (m, 1H), 1.76 (m, 1H), 2.51 (m, 2H), 3.27 (m, 2H), 3.33 (s, 3H), 3.47 (m, 2H), 3.62 (m, 2H), 3.80 (m, 1H), 3.87 (m, 1H), 4.01 (m, 1H), 4.33 (m, 1H), 7.24 (m, 3H), 7.40 (s, 1H); MS (E/Z): 414 (M+H$^+$)

Step 3. (1S)-1-(3-chlorophenyl)-2-(2-methoxyethoxy)-1-((3R)-piperidin-3-yl)ethanol A solution of (R)-tert-butyl 3-((S)-1-(3-chlorophenyl)-1-hydroxy-2-(2-methoxyethoxy)-ethyl)piperidine-1-carboxylate (30 mg, 0.073 mmol) in 20% TFA/CH$_2$Cl$_2$ (5 mL) was stirred at 0° C. for 30 min. Evaporation of the solvent afforded (1S)-1-(3-chlorophenyl)-2-(2-methoxy-ethoxy)-1-((3R)-piperidin-3-yl)ethanol (30 mg, 0.073 mmol 100%). MS (E/Z): 314 (M+H$^+$).

Example 143

(R)-tert-Butyl 3-((S)-1-(3-carbamoylphenyl)-1-hydroxy-5-methoxypentyl)piperidine-1-carboxylate

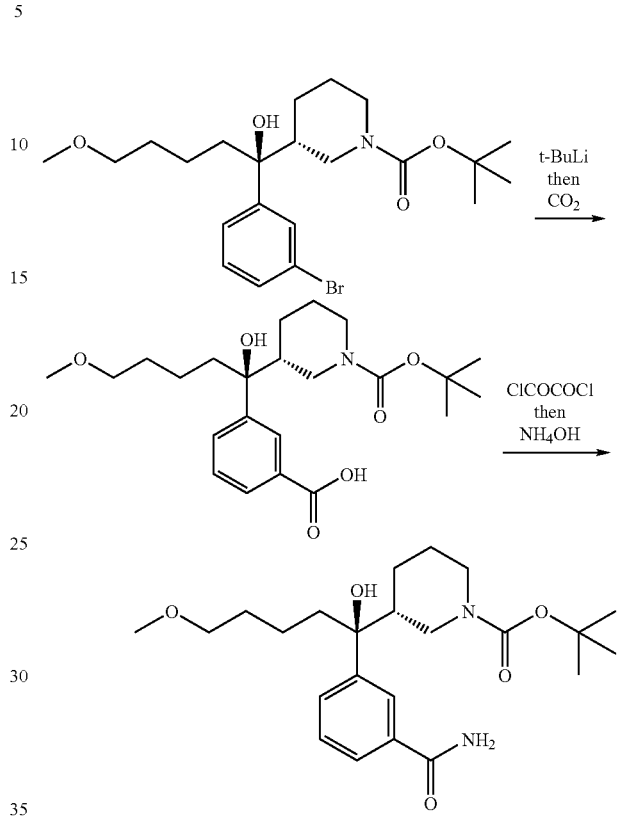

Step 1. 3-((S)-1-((R)-1-(tert-Butoxycarbonyl)piperidin-3-yl)-1-hydroxy-5-methoxypentyl)benzoic acid To a solution of (R)-tert-butyl 3-((S)-1-(3-bromophenyl)-1-hydroxy-5-methoxy-pentyl)piperidine-1-carboxylate (279.1 mg, 0.61 mmol) in THF (5 mL) at −70° C. was added t-butyllithium in pentane (1.7 M, 0.71 mL, 1.22 mmol) dropwise. When the addition was complete dried carbon dioxide was bubbled through the reaction system for 10 min, and completion of reaction was confirmed by LC-MS. The solution was warmed to rt, and sat'd aq Na$_2$CO$_3$ solution (5 mL) was added. The organic layer was separated, and washed once with 1 N NaOH (2 mL). The combined aqueous solutions were acidified with 1 N aq HCl and extracted with EtOAc (5×5 mL). The organic layer was dried over Na$_2$SO$_4$, and concentrated under vacuum to give 3-((S)-1-((R)-1-(tert-butoxycarbonyl)piperidin-3-yl)-1-hydroxy-5-methoxy-pentyl) benzoic acid (152.4 mg, 59%) as a white solid. MS m/z 422 (M+H$^+$).

Step 2. (R)-tert-Butyl 3-((S)-1-(3-carbamoylphenyl)-1-hydroxy-5-methoxypentyl)piperidine-1-carboxylate To a solution of 3-((S)-1-((R)-1-(tert-butoxycarbonyl)piperidin-3-yl)-1-hydroxy-5-methoxypentyl)benzoic acid (51.0 mg, 0.12 mmol) in CH$_2$Cl$_2$ (2 mL) was added oxalyl chloride (17.3 mg, 0.13 mmol) followed by DMF (1 drop). The resulting mixture was stirred until gas evolution ceased (~10 min), and completion of reaction was confirmed by LC-MS. To the reaction flask was added excess NH₄OH, and reaction was stirred at rt for another 10 min. Water (5 mL) was added and organic layer was separated. The aqueous layer was extracted with CH₂Cl₂ (2×5 mL) and the combined organic layers were washed with brine (5 mL), dried over Na₂SO₄, and concentrated under vacuum to give (R)-tert-butyl 3-((S)-1-(3-carbamoylphenyl)-1-hydroxy-5-methoxypentyl)piperidine-1-carboxylate (26.2 mg, 52%). MS m/z 443 (M+Na⁺).

Example 144

(S)-tert-butyl 1-(p-nitrophenoxycarbonylamino)-3-cyclohexylpropan-2-ylcarbamate

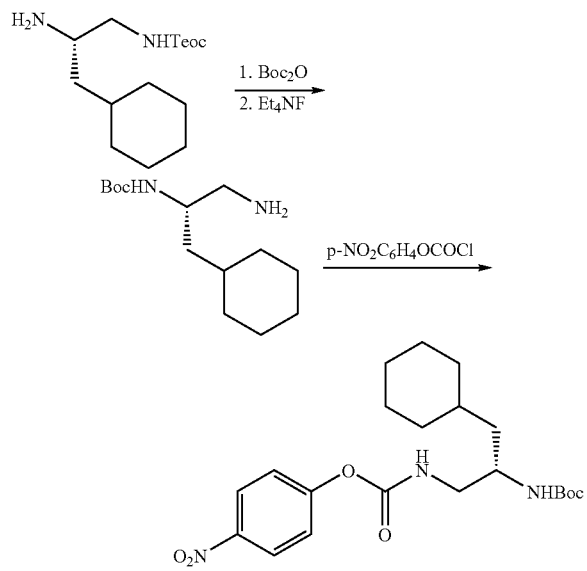

Step 1. (S)-tert-butyl 1-(2-(trimethylsilyl)ethoxycarbonylamino)-3-cyclohexylpropan-2-ylcarbamate To a stirred mixture of (S)-2-(trimethylsilyl)ethyl 2-amino-3-cyclohexylpropylcarbamate (4.61 g, 15.4 mmol), dioxane (50 mL) and 10% aq K₂CO₃ (50 mL) was added solid Boc₂O (3.50 g, 15.4 mmol). The mixture was stirred at rt for 18 h. Dioxane was removed on the rotary evaporator and the aqueous residue was extracted with ether (175 mL). The ether layer was washed with 5% aq HCl (50 mL), satd aq NaHCO₃ (50 mL) and brine (50 mL) and dried over MgSO₄. Removal of the solvent afforded (S)-tert-butyl 1-(2-(trimethylsilyl)ethoxycarbonyl-amino)-3-cyclohexylpropan-2-ylcarbamate (6.55 g, quant) as a yellow oil.

Step 2. (S)-tert-butyl 1-amino-3-cyclohexylpropan-2-ylcarbamate

To a stirred solution of (S)-tert-butyl 1-(2-(trimethylsilyl)ethoxycarbonylamino)-3-cyclohexylpropan-2-ylcarbamate (6.55 g, 15.4 mmol) in MeCN (100 mL) was added Et₄NF (7.5 g, 50 mmol). The mixture was stirred overnight at rt and at 60° C. for 7 h. The mixture was concentrated and the oily residue was taken up in EtOAc (175 mL). The mixture was washed with water (2×50 mL) and brine (50 mL) and dried over Na₂SO₄. Removal of the solvent afforded (S)-tert-butyl 1-amino-3-cyclohexylpropan-2-ylcarbamate (3.39 g, 80%) as a syrup.

Step 3. (S)-tert-butyl 1-(p-nitrophenoxycarbonylamino)-3-cyclohexylpropan-2-ylcarbamate To a stirred solution of (S)-tert-butyl 1-amino-3-cyclohexylpropan-2-ylcarbamate (0.65 g, 2.54 mmol) in MeCN (20 mL) and THF (5 mL) was added powdered NaHCO₃ (0.43 g, 5.08 mmol) followed by a solution of p-nitrophenyl chloroformate (0.51 g, 5.08 mmol) in MeCN (20 mL) dropwise over 10 min. The mixture was stirred at rt for 2 h, filtered through a pad of Celite and concentrated to leave a white solid. This material was purified by chromatography on a 40-g silica cartridge eluted with a gradient from 0-100% EtOAc in hexanes to afford (S)-tert-butyl 1-(p-nitrophenoxycarbonylamino)-3-cyclohexylpropan-2-ylcarbamate (0.67 g, 67%) as an off-white solid.

Example 145

3-((2-acetamidoethoxy)(phenyl)methyl)-N—((S)-1-cyclohexyl-3-(methylamino)propan-2-yl)benzamide
(I-112A)

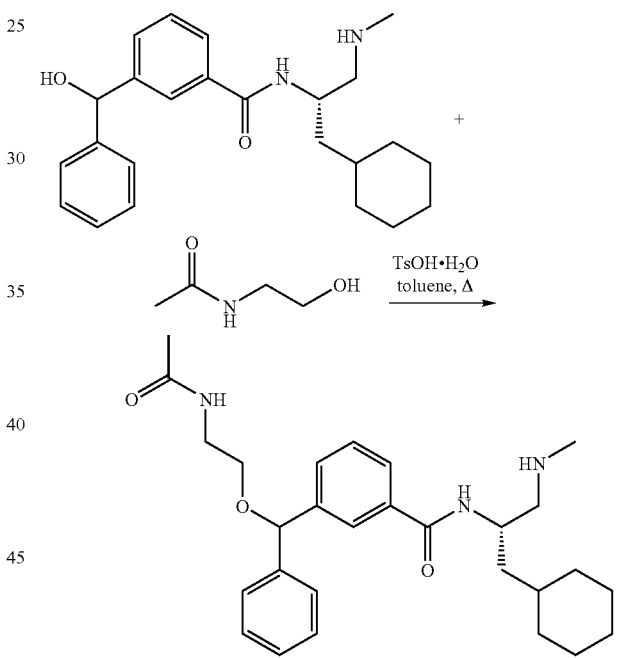

A mixture of the TFA salt of N—((S)-1-cyclohexyl-3-(methylamino)propan-2-yl)-3-(hydroxy)(phenyl)methyl)benzamide (0.0160 g, 0.0323 mmol), N-(2-hydroxyethyl)acetamide (0.1570 g, 1.52 mmol), p-toluenesulfonic acid monohydrate (0.1158 g, 0.61 mmol) and toluene (1.5 mL) was heated at 140° C. for 2 h. After the solvent was removed in vacuo, the crude product was purified by reversed-phase HPLC (Phenomenex® Luna 5µ C18(2) 100 A, 250×21.20 mm, 5 micron, 10%→90% CH₃CN/H₂O, 0.1% CF₃COOH over 13 min, flow rate 25 mL/min) to give the TFA salt of 3-((2-acetamidoethoxy)(phenyl)methyl)-N—((S)-1-cyclohexyl-3-(methylamino)propan-2-yl)benzamide (0.0061 g). LC-MS (3 min) $t_R$=1.37 min, m/z 466 (MH⁺); ¹H NMR (400 MHz, CD₃OD) δ 8.34-8.29 (m, 1H), 7.86-7.12 (m, 9H), 5.76 (s, 1H), 5.41 (d, J=2 Hz, 1H), 4.45-4.38 (m, 1H), 3.44 (t, J=5 Hz, 2H), 3.35-3.31 (m, 2H), 3.10-3.06 (m, 1H), 3.00-2.93 (m, 1H), 2.62 (s, 3H), 1.844, 1.839 (s, 3H), 1.77-0.82 (m, 13H).

Example 146

The following compound was prepared using procedures analogous to those described in Example 145:

| Cpd. No. | Name |
|---|---|
| I-326A | (3R)-3-(1-(3-hydroxypropoxy)-1-(3-chlorophenyl)-5-methoxypentyl)-N-((S)-3-cyclohexyl-1-(methylamino)propan-2-yl)piperidine-1-carboxamide |

Example 147

7-bromo-2-methylbenzofuran

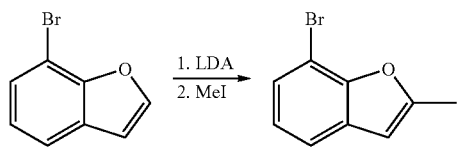

A stirred solution of 7-bromobenzofuran (493 mg, 2.5 mmol) in dry THF (5 mL) was cooled to −70° C. and 2M LDA in 1:1 THF/heptane (1.4 mL, 2.8 mmol) was added dropwise over 2 min. The mixture was stirred at −70° C. for 1 h and methyl iodide (0.19 mL, 3.0 mmol) was added. The mixture was stirred at −70° C. for 3 h and at 0° C. for 1 h. The mixture was poured into 5% aq HCl (60 mL) and extracted with ether (2×50 mL). The combined ether extracts were washed with sat'd aq NaHCO$_3$ (20 mL) and dried over MgSO$_4$. Removal of the solvent left an oil (470 mg) which was purified by chromatography on a 40-g silica cartridge eluted with hexanes to afford 7-bromo-2-methylbenzofuran (277 mg, 52%, estimated purity 80%).

Example 148

7-bromo-2-isobutylbenzofuran

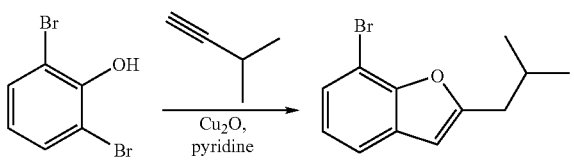

A stirred mixture of 2,6-dibromophenol (946 mg, 3.76 mmol), Cu$_2$O (322 mg, 2.25 mmol), 4-methylpentyne (0.5 mL, 3.9 mmol) and pyridine (5 mL) was heated at vigorous reflux for 0.5 h. The mixture was concentrated under reduced pressure to remove pyridine, diluted with ether (100 mL), washed with water (50 mL), 5% aq HCl (2×50 mL) and 1M aq NaOH (50 mL) and dried over MgSO$_4$. Removal of the solvent left an oil (650 mg) containing 7-bromo-2-isobutylbenzofuran (~70% pure).

Example 149

(3R)-3-(1-(3-chloro-2-fluorophenyl)-1-fluoro-5-methoxypentyl)-N—((S)-1-cyclohexyl-3-(methylamino)propan-2-yl)piperidine-1-carboxamide (I-478A) was prepared by procedures analogous to those described in Example 43.

Example 150

(3R)—N-((2S,3S)-3-amino-4-cyclohexyl-1-hydroxybutan-2-yl)-3-((S)-1-(3-chloro-2-fluorophenyl)-1-hydroxy-5-methoxypentyl)piperidine-1-carboxamide (I-488A) was prepared by procedures analogous to those described in Example 112.

Example 151

(3R)-3-((S)-1-(2,3-dihydrobenzofuran-7-yl)-1-hydroxy-5-methoxypentyl)-N—((S)-1-(((1r,4S)-4-fluorocyclohexyl)-3-(methylamino)propan-2-yl)piperidine-1-carboxamide (I-480A) was prepared by procedures analogous to those described in Example 122.

Example 152

(R)-tert-butyl 3-(methoxy(methyl)carbamoyl)piperidine-1-carboxylate

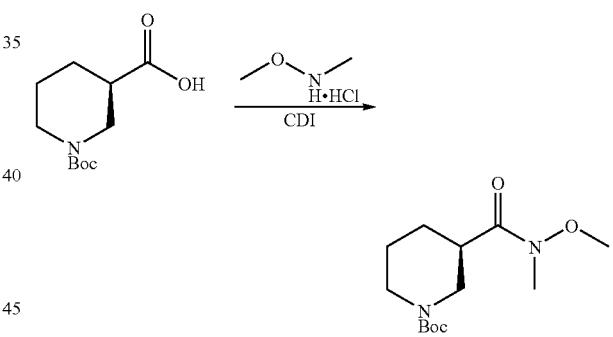

To a stirred, ice-cold solution of (R)-1-(tert-butoxycarbonyl)piperidine-3-carboxylic acid (233 g, 1.2 mol) in THF (1.2 L) was added carbonyldiimidazole (230 g, 1.42 mol) under stirring. The mixture was stirred for 1 h in the ice-water bath. A suspension of triethylamine (207 mL, 1.41 mol) and N,O-dimethylhydroxylamine hydrochloride (138 g, 1.42 mol) in THF (900 mL) was added. The reaction mixture was allowed to warm to rt and stirred overnight. Tlc showed the reaction was complete. Solvent was evaporated, and the residue was dissolved in CH$_2$Cl$_2$ (1.2 L), washed successively with 0.5 N aq HCl, satd aq Na$_2$CO$_3$ and brine, dried over Na$_2$SO$_4$ and evaporated to give (R)-tert-butyl 3-(methoxy(methyl)carbamoyl)piperidine-1-carboxylate (250 g, 90.6%), which was used in the next step directly without further purification. Chiral HPLC indicated that the product had an enantiomeric excess of 96%~98%. $^1$H NMR (400 MHz, CDCl$_3$): 4.05-4.19 (m, 2H), 3.71 (s, 3H), 3.16 (s, 3H), 2.75-2.85 (m, 2H), 2.65 (t, 1H), 1.90 (d, 1H), 1.60-1.78 (m, 2H), 1.44 (s, 9H).

Example 153

(3R)-3-(1-hydroxy-5-methoxy-1-(2-phenoxyphenyl)pentyl)-N-(piperidin-3-yl)piperidine-1-carboxamide (I-56A)

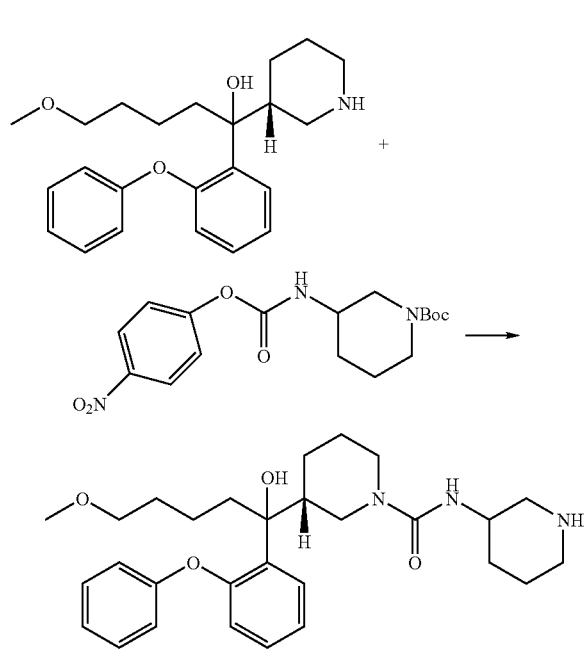

tert-butyl 3-((4-nitrophenoxy)carbonylamino)piperidine-1-carboxylate (29 mg, 0.079 mmol) was added to an acetonitrile (2 mL) solution of 5-methoxy-1-(2-phenoxyphenyl)-1-((R)-piperidin-3-yl)pentan-1-ol (28 mg, 0.076 mmol), diisopropylamine (20 μL, 0.11 mmol), and DMAP (10 mg, 0.084 mmol). The reaction was allowed to stir overnight at rt. The solvent was evaporated and the crude material was redissolved in methylene chloride. The solution was washed with 1 N aq NaOH, 1 M aq HCl and brine. The organic layer was separated and the solvent was evaporated. The crude material was dissolved in acetonitrile (9 mL) and treated with 2 M aq HCl (9 mL). The reaction was allowed to stir overnight. The solvent was evaporated and the crude mixture purified by preparative HPLC to give (3R)-3-(1-hydroxy-5-methoxy-1-(2-phenoxyphenyl)pentyl)-N-(piperidin-3-yl)piperidine-1-carboxamide as its TFA salt (38.7 mg). MS ESI+ve m/z 496 (M+1).

Example 154

(3R)-3-((S)-1-(6-fluoro-3'-methylbiphenyl-2-yl)-1-hydroxy-5-methoxypentyl)-N-(piperidin-3-yl)piperidine-1-carboxamide (I-523A)

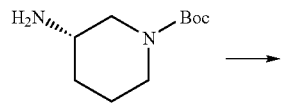

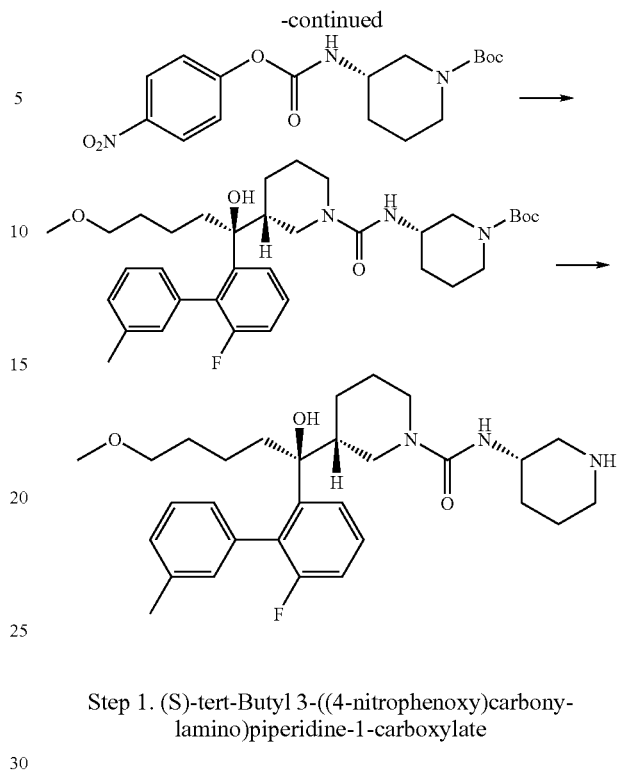

Step 1. (S)-tert-Butyl 3-((4-nitrophenoxy)carbonylamino)piperidine-1-carboxylate To a stirred solution 4-nitrophenyl chloroformate (26.0 mg, 0.13 mmol) in anhydrous CH$_2$Cl$_2$ was added a solution of (S)-tert-butyl 3-aminopiperidine-1-carboxylate (27.0 mg, 0.13 mmol) and pyridine (7 μL) in CH$_2$Cl$_2$ (0.5 mL). The mixture was stirred for 30 min. LC-MS showed complete conversion. This intermediate was used as a solution for the next step.

Step 2. (S)-tert-Butyl 3-((R)-3-((S)-1-(6-fluoro-3'-methylbiphenyl-2-yl)-1-hydroxy-5-methoxypentyl)piperidine-1-carboxamido)piperidine-1-carboxylate A solution of (S)-1-(6-fluoro-3'-methylbiphenyl-2-yl)-5-methoxy-1-((R)-piperidin-3-yl)pentan-1-ol TFA salt (62.7 mg, 0.13 mmol) in anhydrous CH$_2$Cl$_2$ (0.5 mL) containing triethyl amine (0.1 mL) was added to above solution of (S)-tert-butyl 3-((4-nitrophenoxy)carbonylamino)piperidine-1-carboxylate within 1 min. The mixture was stirred for 30 min. The reaction mixture was evaporated and the residue was purified by preparative HPLC to afford (S)-tert-Butyl 3-((R)-3-((S)-1-(6-fluoro-3'-methylbiphenyl-2-yl)-1-hydroxy-5-methoxypentyl)piperidine-1-carboxamido)piperidine-1-carboxylate (35 mg). MS m/z 612 (M+H)$^+$.

Step 3. (3R)-3-((S)-1-(6-fluoro-3'-methylbiphenyl-2-yl)-1-hydroxy-5-methoxypentyl)-N-(piperidin-3-yl)piperidine-1-carboxamide (S)-tert-Butyl 3-((R)-3-((S)-1-(6-fluoro-3'-methylbiphenyl-2-yl)-1-hydroxy-5-methoxypentyl)piperidine-1-carboxamido)piperidine-1-carboxylate (20 mg, 0.033 mmol) was dissolved in TFA/dichloromethane (1 mL, 1:3, v/v), stirred 20 min, evaporated, and purified by preparative HPLC to give the (3R)-3-((S)-1-(6-fluoro-3'-methylbiphenyl-2-yl)-1-hydroxy-5-methoxypentyl)-N-(piperidin-3-yl)piperidine-1-carboxamide (9.39 mg) as its TFA salt. $^1$H NMR (400 MHz, CD$_3$OD): δ ppm 7.57 (d, J=8.4 Hz, 1H), 7.36-7.20 (m, 3H), 7.04-7.02 (m, 2H), 6.92 (m, 1H), 4.03 (m, 1H), 3.85-3.75 (m, 2H), 3.39-3.32 (m, 3H), 3.29 (s, 3H), 2.86 (m, 1H), 2.71-2.56 (m, 3H), 2.37, 2.35 (two s, 3H, rotamer), 1.99 (m, 2H), 1.88-1.26 (m, 13H), 0.92 (m, 1H). MS m/z 512 (M+H)⁺.

Example 155

The following compounds were prepared using procedures analogous to those described in Example 154:

(3R)—N-(azetidin-3-ylmethyl)-3-((S)-1-(3-fluoro-2-(o-tolyloxy)phenyl)-1-hydroxy-5-methoxypentyl)piperidine-1-carboxamide (I-525A)

Example 156

(3S,4S)-benzyl 3-amino-4-cyclohexylpiperidine-1-carboxylate

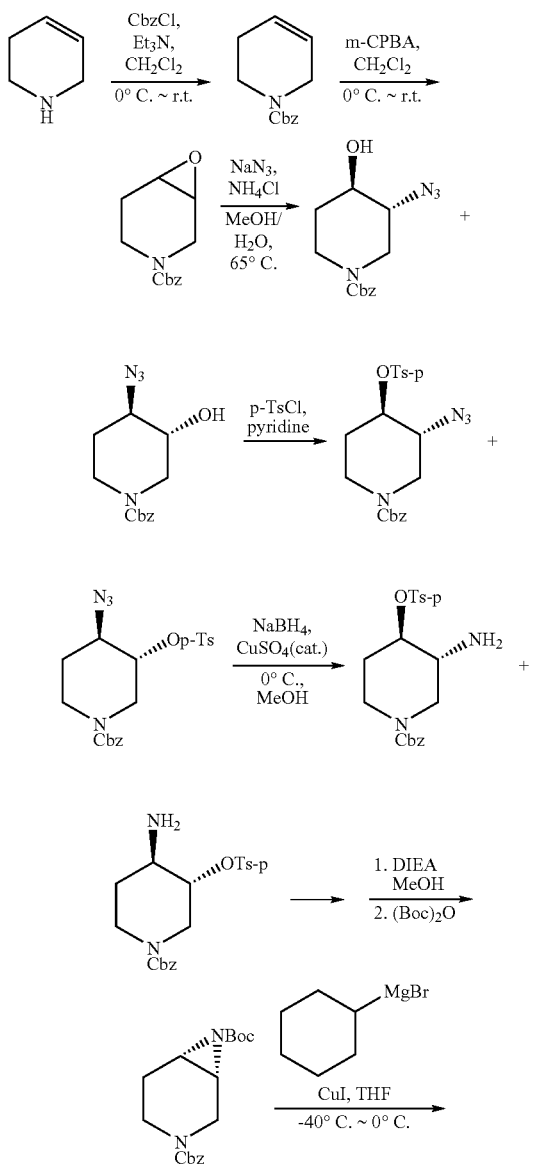

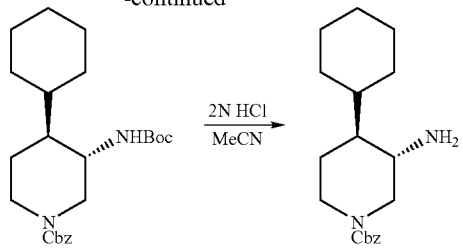

Step 1. Benzyl 5,6-dihydropyridine-1(2H)-carboxylate

A solution of 1,2,3,6-tetrahydropyridine (5.0 g, 60.15 mmol) and triethylamine (16.77 mL, 2 equiv) in CH$_2$Cl$_2$ (50 mL) was cooled to 0° C. (ice/water bath), Benzyl chloroformate (9.7 mL, 1.1 equiv) was added slowly. After 30 min, the reaction mixture was allowed to warm slowly to rt and stirred for 4 h. LC-MS showed the reaction was complete. The mixture was diluted with ether (300 mL), washed with 5% aq HCl (2×50 mL), satd aq NaHCO$_3$ (40 mL) and brine (40 mL), and dried over Na$_2$SO$_4$. After concentration, benzyl 5,6-dihydropyridine-1(2H)-carboxylate (9.93 g, 78% yield) was left. LC-MS (3 min) t$_R$=1.74 min., m/z 218 (M+1).

Step 2. Benzyl 7-oxa-3-azabicyclo[4.1.0]heptane-3-carboxylate

A solution of benzyl 5,6-dihydropyridine-1(2H)-carboxylate (9.93 g, 45.76 mmol) in CH$_2$Cl$_2$ (75 mL) was cooled to 0° C. (ice/water bath), Solid m-chloroperoxybenzoic acid (77%, 15.38 g, 1.5 equiv) was added. After 10 min, the reaction mixture was warmed slowly to rt. A white precipitate formed after 1 h. After stirring for another 1 h, LC-MS showed the reaction was complete. The mixture was diluted with ether (300 mL), washed by with 5% aq NaOH (2×40 mL), 25% aq Na$_2$S$_2$O$_3$ solution (3×20 mL) and brine (30 mL), and dried over Na$_2$SO$_4$. After concentration, the residue was purified by flash chromatography (120 g silica gel column, 12%-70% EtOAc in hexanes gradient, 2$^{nd}$ UV peak) to afford benzyl 7-oxa-3-azabicyclo[4.1.0]heptane-3-carboxylate (7.87 g, 74% yield). LC-MS (3 min) t$_R$=1.41 min., m/z 234 (M+1).

Step 3. (±)-(3R,4R)-Benzyl 3-azido-4-hydroxypiperidine-1-carboxylate

Benzyl 7-oxa-3-azabicyclo[4.1.0]heptane-3-carboxylate (6.78 g, 29.1 mmol), sodium azide (3.78 g, 2 equiv), and ammonium chloride (1.56 g, 1 equiv) were dissolved in methanol (100 mL) and water (20 mL). The mixture was heated at 65° C. for 18 h. The mixture was cooled to rt and methanol was removed under vacuum. The aqueous residue was extracted with ether (3×120 mL). The combined ether layers were washed with brine (30 mL) and dried over Na$_2$SO$_4$. Concentration afforded (3R,4R)-benzyl 3-azido-4-hydroxypiperidine-1-carboxylate (8.07 g, quant.) which was used for without further purification. LC-MS (3 min) t$_R$=1.45 min., m/z 277 (M+1).

Step 4. (±)-(3R,4R)-Benzyl 3-azido-4-(tosyloxy) piperidine-1-carboxylate (3R,4R)-benzyl 3-azido-4-hydroxypiperidine-1-carboxylate (8.07 g, 29.1 mmol) and pyridine (6 mL, 2.55 equiv) were dissolved in CH₂Cl₂ (20 mL) and cooled to 0° C. (ice/water bath). Solid p-TsCl (11.1 g, 2.1 equiv) was added. After 5 min, the reaction mixture was allowed to warm to rt slowly and stirred overnight. LC-MS showed the reaction was complete. The mixture was diluted with ether (300 mL), washed with 5% HCl (3×35 mL), satd aq NaHCO₃ (40 mL) and brine (30 mL), and dried over Na₂SO₄. After concentration, the residue was purified by flash chromatography (120 g silica gel column, 0-50% EtOAc in hexanes gradient, 2$^{nd}$ UV peak) to afford (3R,4R)-benzyl 3-azido-4-(tosyloxy)piperidine-1-carboxylate (12.18 g, 97%). LC-MS (3 min) $t_R$=1.99 min., m/z 431 (M+1).

Step 5. (±)-(3R,4R)-benzyl 3-amino-4-(tosyloxy) piperidine-1-carboxylate

To a cooled (0° C., ice/water bath) solution of CuSO₄.5H₂O (642 mg, 0.5 equiv) in methanol (30 mL) was added slowly NaBH₄ (200 mg, 1.05 equiv). To the stirred black suspension was added a solution of (3R,4R)-benzyl 3-azido-4-(tosyloxy)piperidine-1-carboxylate (2.21 g, 5.14 mmol) in methanol (20 mL). Additional NaBH₄ (578 mg, 3 equiv) was introduced into the reaction in four portions over the course of 1 h. LC-MS showed the reaction was complete. The reaction mixture was filtered through a pad of Celite, and concentrated. The residue was diluted with CH₂Cl₂ (70 mL), washed with water (15 mL), satd aq NH₄Cl solution (2×10 mL) and brine (15 mL), and dried over Na₂SO₄. Concentration afforded (3R,4R)-benzyl 3-amino-4-(tosyloxy)piperidine-1-carboxylate (1.34 g, 64%). LC-MS (3 min) $t_R$=1.26 min., m/z 405 (M+1). The product was used for the next step without further purification.

Step 6. (±)-(1R,6S)-3-benzyl 7-tert-butyl 3,7-diazabicyclo[4.1.0]heptane-3,7-dicarboxylate (3R,4R)-benzyl 3-amino-4-(tosyloxy)piperidine-1-carboxylate (274 mg, 0.678 mmol) and DIEA (177 µL, 1.5 equiv) were dissolved in methanol (8 mL) and heated to 80° C. for 20 min in a CEM Microwave reactor. LC-MS showed the reaction was complete. The reaction mixture was concentrated and redissolved in CH₂Cl₂ (10 mL). (Boc)₂O (150 mg, 1 equiv) was added and the mixture was stirred overnight at rt. LC-MS showed the reaction was complete. The reaction mixture was concentrated and purified by flash chromatography (40 g silica gel column, 0~45% EtOAc in hexanes gradient, major UV peak) to afford (1R,6S)-3-benzyl 7-tert-butyl 3,7-diazabicyclo[4.1.0]heptane-3,7-dicarboxylate (227 mg, quant). LC-MS (3 min) $t_R$=1.86 min., m/z 355 (M+Na).

Step 7. (±)-(3S,4S)-benzyl 3-(tert-butoxycarbonylamino)-4-cyclohexylpiperidine-1-carboxylate (1R,6S)-3-benzyl 7-tert-butyl 3,7-diazabicyclo[4.1.0]heptane-3,7-dicarboxylate (220 mg, 0.663 mmol), CuI (25 mg, 0.2 equiv), and a stirring bar were put in a 100-mL flask. The flask was evacuated and backfilled with N₂ gas (3×). Dry THF (5 mL) was added and the mixture was cooled to −40° C. 1 M Cyclohexylmagnesium bromide in THF (2.0 mL, 3 equiv) was added slowly. After 8 min, the reaction mixture was allowed warmed slowly to rt. After 20 min, the reaction mixture turned into black. After stirring a further 2 h, LC-MS showed the reaction was complete. Satd aq NH₄Cl solution (5 mL) was added to quench the reaction. The reaction mixture was partitioned between EtOAc (50 mL) and satd aq NH₄Cl solution (20 mL). The aqueous layer was extracted with EtOAc (20 mL). The combined EtOAc layers were washed with water (15 mL) and brine (15 mL), and dried over Na₂SO₄. After concentration, the residue was purified by preparative HPLC to afford (3S,4S)-benzyl 3-(tert-butoxycarbonylamino)-4-cyclohexylpiperidine-1-carboxylate (62.3 mg, 23% yield) and (3S,4S)-benzyl 4-(tert-butoxycarbonylamino)-3-cyclohexylpiperidine-1-carboxylate (15 mg). LC-MS (3 min) $t_R$=2.33 min., m/z 439 (M+Na).

Step 8. (±)-(3S,4S)-benzyl 3-amino-4-cyclohexylpiperidine-1-carboxylate (3S,4S)-benzyl 3-(tert-butoxycarbonylamino)-4-cyclohexylpiperidine-1-carboxylate (35 mg, 0.084 mmol) was dissolved in 1:1 2N aq HCl/acetonitrile (8 mL) and stirred overnight at rt. LC-MS showed the reaction was complete. The reaction mixture was basified with 5% aq NaOH solution to about pH=9. The acetonitrile was removed under vacuum. The aqueous residue was extracted with CH₂Cl₂ (3×20 mL). The combined organic layers were washed with brine (10 mL) and dried over Na₂SO₄. Concentration afforded (3S,4S)-benzyl 3-amino-4-cyclohexylpiperidine-1-carboxylate (23 mg, 86% yield). The crude product was used in the next step without further purification. LC-MS (3 min) $t_R$=1.31 min., m/z 317 (M+1).

Example 157

(3R)-3-((S)-1-(3-chloro-2-fluorophenyl)-1-hydroxy-5-methoxypentyl)-N-((3RS,4RS)-4-cyclohexylpiperidin-3-yl)piperidine-1-carboxamide (I-544A)

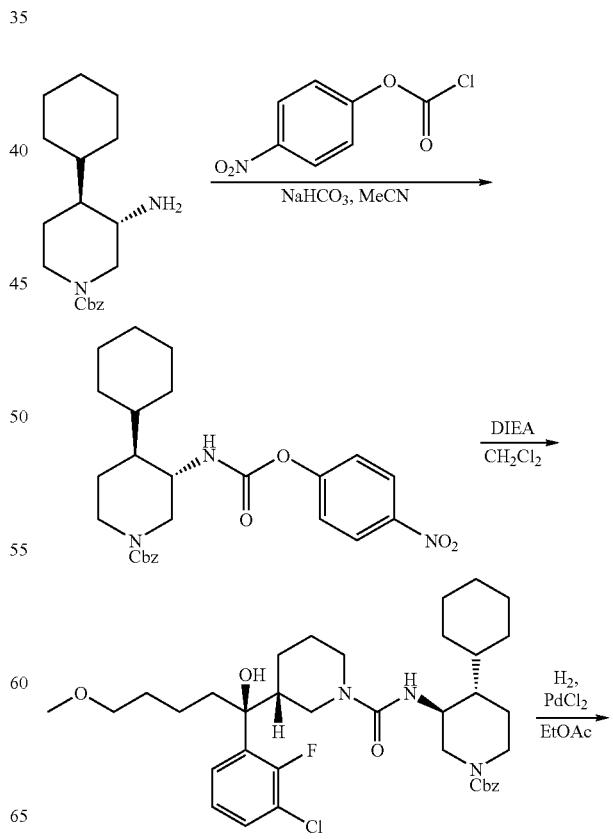

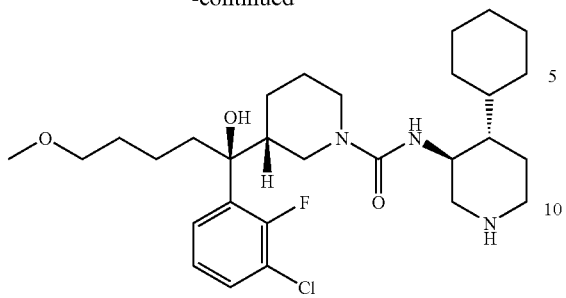

Step 1. (±)-(3S,4S)-benzyl 4-cyclohexyl-3-((4-nitrophenoxy)carbonylamino)piperidine-1-carboxylate (3S,4S)-benzyl 3-amino-4-cyclohexylpiperidine-1-carboxylate (23 mg, 0.073 mmol), 4-nitrophenyl chloroformate (16 mg, 1.1 equiv) and powdered NaHCO₃ (13 mg, 2 equiv) were mixed with acetonitrile (3 mL). The mixture was stirred 1 h at rt. LC-MS showed the reaction was complete. The reaction mixture was concentrated to afford (3S,4S)-benzyl 4-cyclohexyl-3-((4-nitrophenoxy)carbonylamino)piperidine-1-carboxylate which was used directly in the next step. LC-MS (3 min) $t_R$=2.24 min., m/z 482 (M+1).

Step 2. (3SR,4SR)-benzyl 3-((R)-3-((S)-1-(3-chloro-2-fluorophenyl)-1-hydroxy-5-methoxypentyl)piperidine-1-carboxamido)-4-cyclohexylpiperidine-1-carboxylate Half of the crude (3S,4S)-benzyl 4-cyclohexyl-3-((4-nitrophenoxy)carbonylamino)piperidine-1-carboxylate from Step 1 was added to a solution of (S)-1-(3-chloro-2-fluorophenyl)-5-methoxy-1-((R)-piperidin-3-yl)pentan-1-ol (29 mg, 2 equiv) and DIEA (15 μL, 3 equiv) in CH₂Cl₂ (2 mL). The mixture was stirred for 1 h at rt. LC-MS showed the reaction was complete. The mixture was concentrated and purified by preparative HPLC to afford (3S,4S)-benzyl 3-((R)-3-((S)-1-(3-chloro-2-fluorophenyl)-1-hydroxy-5-methoxypentyl)piperidine-1-carboxamido)-4-cyclohexylpiperidine-1-carboxylate (18.4 mg, 63%). LC-MS (3 min) $t_R$=2.40 min., m/z 672 (M+1).

Step 3. (3R)-3-((S)-1-(3-chloro-2-fluorophenyl)-1-hydroxy-5-methoxypentyl)-N-((3RS,4RS)-4-cyclohexylpiperidin-3-yl)piperidine-1-carboxamide (3S,4S)-benzyl 3-((R)-3-((S)-1-(3-chloro-2-fluorophenyl)-1-hydroxy-5-methoxypentyl)piperidine-1-carboxamido)-4-cyclohexylpiperidine-1-carboxylate (18.4 mg, 0.027 mmol) and palladium(II) chloride (catalytic amount, c.a. 4 mg) were mixed with EtOAc (3 mL). The flask was evacuated and filled by H₂ gas (3×). A balloon filled with H₂ gas was attached to the flask to maintain the H₂ gas atmosphere for 2 h. LC-MS showed most of the starting material had been converted to product. The mixture was concentrated, redissolved in acetonitrile (3 mL), filtered and purified by preparative HPLC to afford (3R)-3-((S)-1-(3-chloro-2-fluorophenyl)-1-hydroxy-5-methoxypentyl)-N-((3RS,4RS)-4-cyclohexylpiperidin-3-yl)piperidine-1-carboxamide (16.6 mg, quant). LC-MS (3 min) $t_R$=1.58 min., m/z 538 (M+1).

Example 158

The following compounds were prepared using procedures analogous to those described in Example 157:
(3R)—N-((3RS,4RS)-4-cyclohexylpiperidin-3-yl)-3-((S)-1-(2,3-difluorophenyl)-1-hydroxy-5-methoxypentyl)piperidine-1-carboxamide (I-533A) using (S)-1-(3-chloro-2-fluorophenyl)-5-methoxy-1-((R)-piperidin-3-yl)pentan-1-ol in Step 2.
(3R)-3-((S)-1-(3-chloro-2-fluorophenyl)-1-hydroxy-5-methoxypentyl)-N-((3RS,4RS)-4-(pentan-3-yloxy)piperidin-3-yl)piperidine-1-carboxamide (I-549A) using (±)-(3R,4R)-benzyl 3-amino-4-(pentan-3-yloxy)piperidine-1-carboxylate in Step 1.

Example 159

(1S,2R)-2-amino-3-azido-1-(3-noradamantyl)propan-1-ol

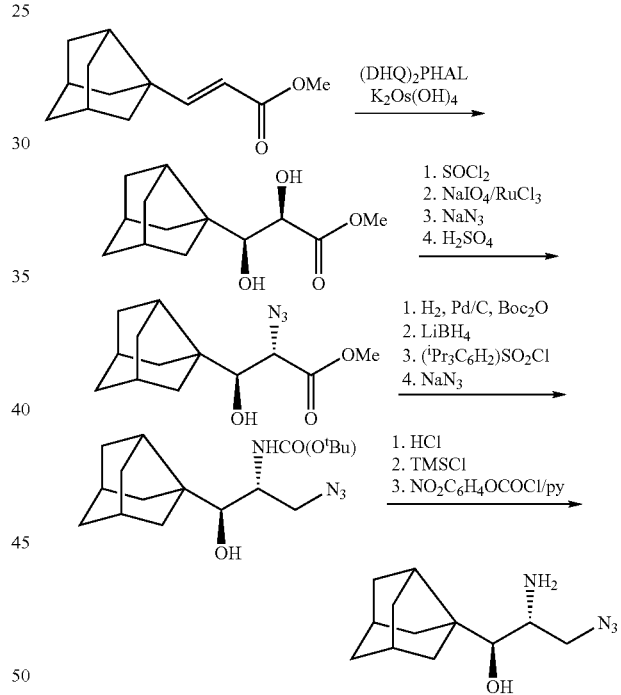

Step 1. (2R,3S)-methyl 3-(3-noradamantyl)-2,3-dihydroxypropanoate

A 250-mL flask containing 180 mL of 1:1 ᵗBuOH/H₂O (180 mL) at 0° C. was charged with the following reagents: (E)-methyl 3-(3-noradamantyl)acrylate (4.1 g, 19.87 mmol), (DHQ)₂PHAL (155 mg, 0.1987 mmol, 1 mol %), K₂Os(OH)₄ (36 mg, 0.0994 mmol, 0.5 mol %), K₃Fe(CN)₆ (19.63 g, 59.6 mmol, 3.0 equiv), MeSO₂NH₂ (1.89 g, 19.87 mmol, 1.0 equiv), K₂CO₃ (8.24 g, 59.6 mmol, 3.0 equiv) and NaHCO₃ (5.12 g, 59.6 mmol, 3.0 equiv). The mixture was placed in a refrigerator and allowed to stir for 3 d at 5° C. After this time Na₂S₂O₅ (15.8 g, 83.4 mmol, 4.0 equiv) was added to the yellow slurry and the mixture stirred for 1 h. The contents were transferred to a separatory funnel and the layers were separated. The aqueous layer was extracted with EtOAc (4×30 mL). The combined organic layers were washed with 1.0 M aq NaOH and brine, dried over $Na_2SO_4$, filtered, and evaporated to afford an off-white solid (7.15 g). Flash chromatography on silica, eluting with 0-47% EtOAc in hexanes afforded (2R,3S)-methyl 3-(3-noradamantyl)-2,3-dihydroxypropanoate (3.4 g, 71%). The ee of the product was not determined.

Step 2a-c. (2S,3S)-methyl 2-azido-3-(3-noradamantyl)-3-hydroxypropanoate

A flask was charged with (2R,3S)-methyl 3-(3-noradamantyl)-2,3-dihydroxypropanoate (3.4 g, 14.1 mmol, 1.0 equiv), pyridine (4.5 mL, 56.4 mmol, 4.0 equiv) and $CH_2Cl_2$ (30 mL) and the resulting solution was cooled to 0° C. Thionyl chloride (2.5 g, 21.2 mmol, 1.5 equiv) was added via syringe and the mixture was stirred at 0° C. The reaction was monitored by LC-MS till the starting material was consumed. The mixture was diluted with water and additional $CH_2Cl_2$ and transferred to a separatory funnel. The layers were separated and aqueous layer was extracted with additional $CH_2Cl_2$. The combined organic layers were washed with brine, dried over $Na_2SO_4$, filtered, and evaporated. The crude cyclic sulfite was used directly in the next step.

The cyclic sulfite was dissolved in 1:1 $CCl_4/CH_3CN$ (20 mL). A solution of $NaIO_4$ (4.5 g, 21.2 mmol, 1.5 equiv) of in $H_2O$ (30 mL), and $RuCl_3.xH2O$ (~50 mg) were added and the resulting biphasic mixture was stirred rapidly overnight. Monitoring by LC-MS showed formation of the desired cyclic sulfate. The mixture was diluted with EtOAc and the layers were separated. The aqueous layer was extracted with EtOAc (2×50 mL). The combined organic layers were washed with satd aq $NaHCO_3$ and brine, and evaporated. The crude cyclic sulfate was dissolved in 5:1 acetone/water (100 mL). Solid $NaN_3$ (1.84 g, 28.2.5 mmol, 3.0 equiv) was added and the mixture was stirred rapidly for 72 h. Analysis by LC-MS showed consumption of the cyclic sulfate. The mixture was concentrated to a volume of ~10 mL. To the residual solution was added 1:1 2.0N $H_2SO_4/Et_2O$ (200 mL) and the mixture was stirred at rt for 18 h. The mixture was diluted with additional $Et_2O/H_2O$ and the layers were separated. The aqueous phase was extracted with additional $Et_2O$. The combined organic extracts were washed with brine, dried over $Na_2SO_4$, filtered, and evaporated. Flash chromatography on silica gel, eluting with 0-47% EtOAc in hexanes afforded (2S,3S)-methyl 2-azido-3-(3-noradamantyl)-3-hydroxypropanoate (2.0 g, 7.7 mmol, 55%).

Steps 3a-d. tert-butyl (1S,2R)-3-azido-1-(3-noradamantyl)-1-hydroxypropan-2-ylcarbamate A 250-mL pressure bottle was charged with (2S,3S)-methyl 2-azido-3-(3-noradamantyl)-3-hydroxypropanoate (2.0 g, 7.7 mmol), $Boc_2O$ (1.7 g, 7.7 mmol), 10% Pd/C (~100 mg) and MeOH (30 mL). The bottle was fitted to a Parr hydrogenation shaker, pressurized to 45 psi with $H_2$, evacuated and backfilled with $H_2$ (3×). The reaction mixture was shaken under 45 psi of $H_2$ for 8 h. LC-MS analysis showed no remaining azide. The mixture was filtered through a pad of Celite. The spent catalyst was washed with additional methanol and the combined filtrates were evaporated to dryness. The residuelt was purified by flash chromatography on silica, eluting with 0-49% EtOAc in hexanes. This afforded (2S,3S)-methyl 2-(tert-butoxycarbonylamino)-3-(3-noradamantyl)-3-hydroxypropanoate (1.6 g, 61% yield).

(2S,3S)-methyl 2-(tert-butoxycarbonylamino)-3-(3-noradamantyl)-3-hydroxypropanoate (1.6 g, 4.7 mmol, 1.0 equiv) was dissolved in THF (40 mL) and the mixture was cooled to 0° C. $LiBH_4$ (2.0 M in THF, 4.7 mL, 9.4 mmol, 2.0 equiv) was added via syringe and the mixture was stirred overnight with concomitant warming to ambient temperature. LC-MS analysis showed consumption of the starting ester. The solution was cooled to 0° C. and excess $LiBH_4$ was quenched with satd aq $NH_4Cl$. The mixture was diluted with water and the layers were separated. The aqueous phase was extracted with EtOAc. The combined organic layers were washed with brine, dried over $Na_2SO_4$, filtered, and evaporated to afford tert-butyl (1S,2R)-1-(3-noradamantyl)-1,3-dihydroxypropan-2-ylcarbamate of sufficient purity for use in the next step.

tert-Butyl (1S,2R)-1-(3-noradamantyl)-1,3-dihydroxypropan-2-ylcarbamate (852 mg, 2.74 mmol), 2,4,6-triisopropylphenylsulfonylchloride (2.48 g, 8.21 mmol, 3.0 equiv), DABCO (922 mg, 8.21 mmol, 3.0 equiv) and DMAP (334 mg, 2.74 mmol, 1.0 equiv) were dissolved in $CH_2Cl_2$ and the mixture was heated at reflux overnight. After this time tlc analysis showed ca 50% conversion to the desired sulfonate ester. The mixture was diluted with $CH_2Cl_2$ and 0.5 M aq HCl. The layers were separated and the aqueous layer was extracted with additional $CH_2Cl_2$. The combined organic extracts were washed with brine, dried over $Na_2SO_4$, filtered, and evaporated. The residue was purified by flash chromatography on silica, eluting with 0-19% EtOAc in hexanes to afford (2R,3S)-2-(tert-butoxycarbonylamino)-3-(3-noradamantyl)-3-hydroxypropyl 2,4,5-triisopropylbenzenesulfonate (905 mg). Unreacted starting diol was recovered by eluting the column with EtOAc.

The sulfonate ester (70 mg, 0.133 mmol, 1.0 equiv) and $NaN_3$ (70 mg, 1.1 mmol, 8.0 equiv) were dissolved in 3 mL of DMF and the mixture was heated to 70° C. for 18 h. Volatile materials were removed in vacuo and the residue was dissolved in EtOAc, washed with brine, dried over $Na_2SO_4$, filtered, and evaporated. Flash chromatography on silica, eluting with 0-41% EtOAc in hexanes gave tert-butyl (1S,2R)-3-azido-1-(3-noradamantyl)-1-hydroxypropan-2-ylcarbamate.

Step 4. (1S,2R)-2-amino-3-azido-1-(3-noradamantyl) propan-1-ol tert-butyl (1S,2R)-3-azido-1-(3-noradamantyl)-1-hydroxypropan-2-ylcarbamate (134 mg, 0.399 mmol, 1.0 equiv) was dissolved in $CH_2Cl_2$. Hydrogen chloride solution (4.0 M in dioxane, 4 mL, 40 equiv) was added and the mixture was stirred at ambient temperature till the none of the starting material was detected by LC-MS. The solvents were removed to afford (1S,2R)-2-amino-3-azido-1-(3-noradamantyl)propan-1-ol as its HCl salt which was used directly in the next step.

Example 160

The following compounds were prepared using procedures analogous to those described in Example 159:
(1S,2R)-2-amino-3-azido-1-(trans-4-fluorocyclohexyl)propan-1-ol using (E)-methyl 3-(trans-4-fluorocyclohexyl) acrylate in Step 1.

Example 161

(3R)—N-((1S,2R)-3-amino-1-(3-noradamantyl)-1-hydroxypropan-2-yl)-3-((S)-1-(3-chlorophenyl)-1-hydroxy-5-methoxypentyl)piperidine-1-carboxamide (I-493A)

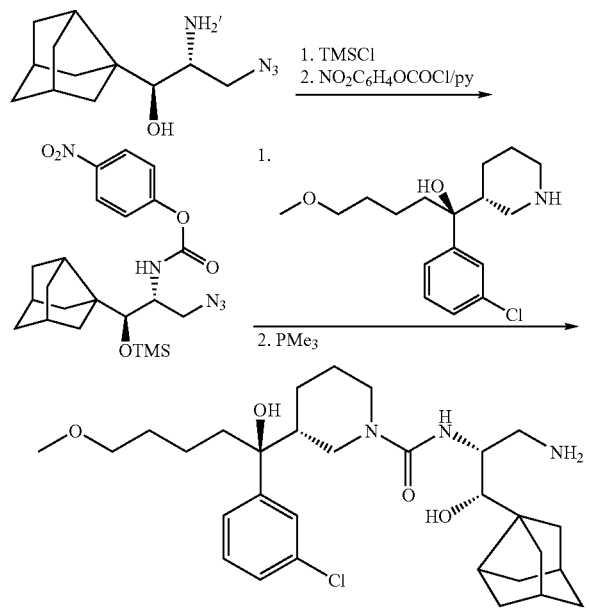

Step 1. 4-nitrophenyl (1S,2R)-3-azido-1-(3-noradamantyl)-1-(trimethylsilyloxy)propan-2-ylcarbamate (1S,2R)-2-amino-3-azido-1-(3-noradamantyl)propan-1-ol HCl salt was dissolved in CH$_2$Cl$_2$ (5 mL) and cooled to 0° C. Et$_3$N (0.5 mL) was added, followed by TMSCl (173 mg, 1.6 mmol, 4.0 equiv). After stirring for 3 h, LC-MS analysis showed complete conversion to the desired silyl ether. The volatile materials were removed in vacuo and the residue was dissolved in CH$_2$Cl$_2$ (4.0 mL). This solution was treated with pyridine (0.35 mL) and p-NO$_2$C$_6$H$_4$OCOCl (120 mg, 0.599 mmol, 1.5 equiv). The mixture was stirred for 3 h. After this time LC-MS analysis showed formation of the desired 4-nitrophenyl carbamate. This solution of 4-nitrophenyl (1S,2R)-3-azido-1-(3-noradamantyl)-1-(trimethylsilyloxy)propan-2-ylcarbamate was employed directly in the subsequent steps.

Step 2. (3R)—N-((1S,2R)-3-amino-1-(3-noradamantyl)-1-hydroxypropan-2-yl)-3-((S)-1-(3-chlorophenyl)-1-hydroxy-5-methoxypentyl)piperidine-1-carboxamide A solution of the 4-nitrophenyl (1S,2R)-3-azido-1-(3-noradamantyl)-1-(trimethylsilyloxy)propan-2-ylcarbamate (0.092 M in CH$_2$Cl$_2$, 0.5 mL, 0.46 mmol, 1.0 equiv) was treated with (S)-1-(3-chlorophenyl)-5-methoxy-1-((R)-piperidin-3-yl)pentan-1-ol (16 mg, 0.051 mmol, 1.1 equiv) and DIPEA (0.3 mL). The solution was allowed to stir for 16 h. After this time LC/MS analysis showed consumption of the starting carbamate. The solution was evaporated, dissolved in EtOAc, and washed with 1.0 M aq NaOH (3×3 mL), 1.0 M aq HCl (3 mL) and brine. The organic layer was evaporated and dissolved in 6:1 THF/H$_2$O (3.5 mL). A solution of PMe$_3$ (1.0 M in THF, 3.0 mL, 3.0 mmol, 6 equiv) was added and the mixture heated to 50° C. under nitrogen. The solvent was removed and the residue was purified by prep HPLC to afford (3R)—N-((1S,2R)-3-amino-1-(3-noradamantyl)-1-hydroxypropan-2-yl)-3-((S)-1-(3-chlorophenyl)-1-hydroxy-5-methoxypentyl)piperidine-1-carboxamide. The product was shown to have an optical purity of 50% ee.

Example 162

The following compounds were prepared using procedures analogous to those described in Example 161:

(3R)—N-((1S,2R)-(3-amino-1-(3-noradamantyl)-1-hydroxy)propan-2-yl)-3-((S)-1-(2-fluoro-3-chlorophenyl)-1-hydroxy-5-methoxypentyl)piperidine-1-carboxamide (I-499A) using (S)-1-(3-chloro-2-fluorophenyl)-5-methoxy-1-((R)-piperidin-3-yl)pentan-1-ol in Step 2.

(3R)—N-((1S,2R)-3-amino-1-(trans-4-fluorocyclohexyl)-1-hydroxypropan-2-yl)-3-((S)-1-(3-chloro-2-fluorophenyl)-1-hydroxy-5-methoxypentyl)piperidine-1-carboxamide (I-551A) using (1S,2R)-2-amino-3-azido-1-(trans-4-fluorocyclohexyl)propan-1-ol in Step 1 and (S)-1-(3-chloro-2-fluorophenyl)-5-methoxy-1-((R)-piperidin-3-yl)pentan-1-ol in Step 2.

Example 163

(S)-2-(trimethylsilyl)ethyl 2-amino-3-cyclopentylpropyl(methyl)carbamate

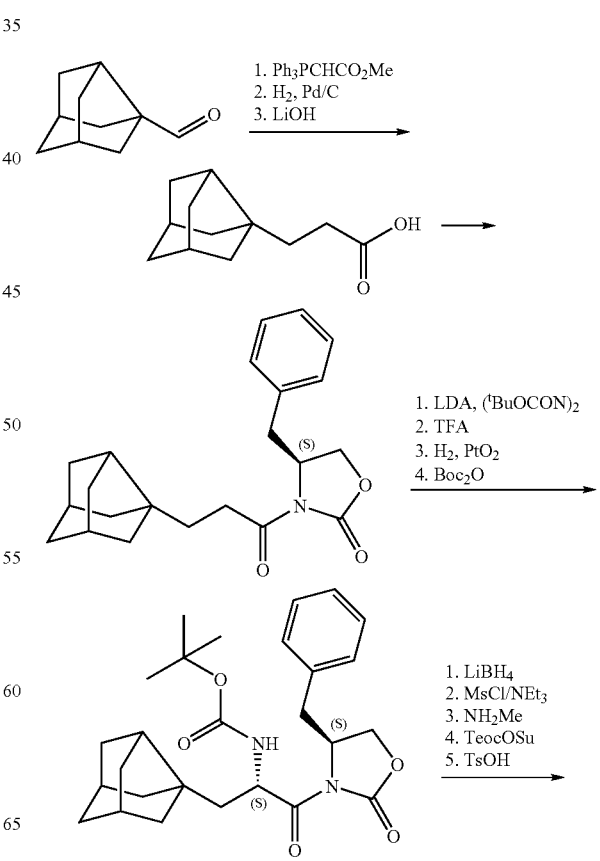

-continued

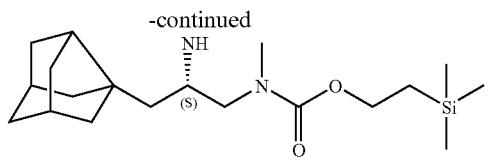

Step 1a-c. 3-(3-noradamantyl)propanoic acid

A 250-mL flask was charged with 3-noradamantylcarboxaldehyde (3.3 g, 22 mol), Ph₃PCHCO₂Me (9.2 g, 27.5 mmol, 1.25 equiv) and CHCl₃ (100 mL). The mixture was heated to reflux for 18 h. The clear solution was allowed to cool to ambient and evaporated. The sticky residue was taken up in 4:1 hexanes/EtOAc (200 mL) and filtered through a pad of silica gel. The pad was washed with additional 4:1 hexanes/EtOAc (200 mL) and the filtrate was evaporated. The product was isolated by flash chromatography on 120 g of silica, eluting with 0-17% EtOAc in hexanes. This afforded (E)-methyl 3-(3-noradamantyl)acrylate (4.13 g, 0.2 mmol, 90%).

A 500-mL pressure bottle was charged with (E)-methyl 3-(3-noradamantyl)acrylate (7.8 g, 37.8 mmol), 10% Pd/C (1.8 g), and (MeOH) 100 mL. The bottle was fitted to a Parr hydrogenation shaker, pressurized to 50 psi with H₂, and evacuated. The fill/evacuation procedure was repeated 3×, and the apparatus pressurized with 50 psi H₂ and shoken for 3 h. After this time tlc analysis showed no remaining enoate. The mixture was filtered through a pad of celite. The spent catalyst was washed with additional methanol and the combined filtrates were evaporated to yield methyl 3-(3-noradamantyl)propanoate (7.8 g, 37.8 mmol) in quantitative yield.

Methyl 3-(3-noradamantyl)propanoate (7.8 g, 37.8 mmol) was dissolved in THF (150 mL) and the solution was cooled to 0° C. To this was added 1.0 M aqueous LiOH (148 mL). The biphasic reaction mixture was vigorously stirred at 0° C. After 3 h, a homogeneous solution was produced and LC-MS analysis showed no ester remained. The pH of the solution was lowered to ~4 by the dropwise addition of concentrated HCl. The mixture was transferred to a separatory funnel and the layers were separated. The aqueous layer was extracted with EtOAc (4×30 mL). The combined organic layers were dried over Na₂SO₄, filtered, and evaporated to afford 3-(3-noradamantyl)propanoic acid (7.15 g, 36.8 mmol) as a tacky solid.

Step 2. (S)-4-benzyl-3-(3-(3-noradamantyl)propanoyl)oxazolidin-2-one 3-(3-Noradamantyl)propanoic acid (7.15 g, 36.8 mmol, 1.0 equiv) was dissolved in THF (70 mL) and the solution was cooled to 0° C. To the stirred solution were added N-methylmorpholine (4.25 mL, 38.7 mmol, 1.05 equiv) and isobutyl chloroformate (4.52 mL, 38.7 mmol, 1.05 equiv). A white precipitate rapidly formed and the mixture containing the 3-(noradamantyl)propanoic(isobutylcarbonic) anhydride was allowed to stir for 0.5 h at 0° C. A separate 500-mL 3-neck flask was charged with S-(−)-4-benzyloxazolidinone (8.5 g, 47.8 mmol, 1.35 equiv) and THF (100 mL). The mixture was cooled to −78° C. and ″BuLi (19.1 mL of a 2.5 M solution) was added over a 10 min period. This was allowed to stir for 0.5 h at −78° C. The first solution was rapidly filtered through a pad of Celite and the resulting clear filtrate transferred via cannula to the solution of the deprotonated oxazolidinone. After stirring for 0.5 h at −78° C. LC-MS analysis showed consumption of the mixed anhydride. The mixture was quenched with brine and allowed to warm to rt. The mixture was transferred to a separatory funnel. The organic layer was separated and evaporated. Flash chromatography (120 g SiO₂, O-27% EtOAc in hexanes) afforded (S)-4-benzyl-3-(3-(3-noradamantyl)propanoyl)oxazolidin-2-one.

Step 3a-d. tert-butyl (S)-1-((S)-4-benzyl-2-oxooxazolidin-3-yl)-3-(3-noradamantyl)-1-oxopropan-2-ylcarbamate A solution of LDA was generated by charging an oven-dried 50-mL flask with dry THF (10 mL) and diisopropylamine (152 mg, 1.5 mmol, 1.5 equiv). The mixture was cooled to −0° C. and ″BuLi (2.5 M, 0.6 mL, 1.5 mmol, 1.5 equiv) added dropwise over 5 min. The mixture was stirred for 0.5 h and cooled to −78° C. A solution of (S)-4-benzyl-3-(3-(3-noradamantyl)propanoyl)oxazolidin-2-one (335 mg, 1.0 mmol, 1.0 equiv) in THF (9 mL) was cooled to −78° C. and added to the solution of LDA via cannula. The mixture was allowed to stir for 0.5 h. A separate flask was charged with ′BuCO₂N═NCO₂′Bu (345 mg, 1.5 mmol, 1.5 equiv) and THF (9 mL) and cooled to −78° C. This solution was transferred to the enolate solution with the aid of a cannula. The resulting mixture was allowed to stir at −78° C. for 0.5 h. Tlc analysis showed consumption of the starting material. The mixture was quenched with HOAc (0.5 mL), and allowed to warm to rt. The solution was transferred to a separatory funnel and the organic layer was washed with water and brine, dried over Na₂SO₄ and filtered. The product was purified by flash chromatography on SiO₂, eluting with 0-37% EtOAc in hexanes. This yielded di-tert-butyl 1-((S)-1-((S)-4-benzyl-2-oxooxazolidin-3-yl)-3-(3-noradamantyl)-1 oxopropan-2-yl) hydrazine-1,2-dicarboxylate (477 mg, 0.82 mmol, 82%).

The Boc protected hydrazine was dissolved in 3:1 CH₂Cl₂/TFA (20 mL) and stirred for 4 h. LC-MS analysis showed only the presence of the desired product. The mixture was evaporated to afford (S)-4-benzyl-3-((S)-3-(3-noradamantyl)-2-hydrazinylpropanoyl)oxazolidin-2-one as its TFA salt which was used directly in the next step.

The hydrazine TFA salt was dissolved in EtOH (10 mL) of and transferred to a Parr hydrogenation shaker. PtO₂ (56 mg, 0.25 mmol, 0.3 equiv) was added and the vessel pressurized to 60 psi with H₂, and evacuated. The fill/evacuation procedure was repeated 3 times, and then the apparatus pressurized with 60 psi H₂ and shaken for 4 h. After this time the hydrazine was no longer observed in the LC/MS. The mixture was filtered and evaporated to give crude (S)-3-((S)-2-amino-3-cyclopentylpropanoyl)-4-benzyloxazolidin-2-one which was used without purification.

Crude (S)-3-((S)-2-amino-3-cyclopentylpropanoyl)-4-benzyloxazolidin-2-one from the previous step was dissolved in 1:1 acetonitrile/10% aqueous K₂CO₃ (20 mL). Boc₂O (327 mg, 1.5 mmol, 1.8 equiv) was added and mixture was stirred for 4 h. LC-MS showed consumption of the free amine. The acetonitrile was removed in vacuo and the product was extracted with EtOAc (2×20 mL). The combined organic extracts were dried over Na₂SO₄, filtered, and evaporated. Flash chromatography afforded tert-butyl (S)-1-((S)-4-benzyl-2-oxooxazolidin-3-yl)-3-(3-noradamantyl)-1-oxopropan-2-ylcarbamate (148 mg, 0.32 mmol).

Step 4a-e. (S)-2-(trimethylsilyl)ethyl 2-amino-3-(3-noradamantyl)propyl(methyl)carbamate tert-butyl (S)-1-((S)-4-benzyl-2-oxooxazolidin-3-yl)-3-(3-noradamantyl)-1-oxopropan-2-ylcarbamate (2.0 g, 4.23 mmol) was dissolved in THF and the solution was cooled to 0° C. Methanol (250 μL) was added, followed by a solution of LiBH$_4$ (2.0 M in THF, 8.6 mL, 4.0 equiv). The mixture was allowed to stir at 0° C. until LC-MS analysis indicated that the starting material had been consumed. Excess LiBH$_4$ was quenched by addition of satd aq NH$_4$Cl and the contents were transferred to a separatory funnel. The layers were separated, the aqueous layer was extracted with EtOAc, and the combined organic layers were washed with brine, dried over Na$_2$SO$_4$, filtered and evaporated. The protected residue was purified by flash chromatography on silica, eluting with 0-29% EtOAc in hexanes. This afforded (S)-tert-butyl 1-(3-noradamantyl)-3-hydroxypropan-2-ylcarbamate (1.24 g, >98%).

(S)-tert-butyl 1-(3-noradamantyl)-3-hydroxypropan-2-yl-carbamate (75 mg, 0.25 mmol, 1.0 equiv) was dissolved in CH$_2$Cl$_2$ and cooled to 0° C. Triethylamine (101 mg, 1.0 mmol, 4.0 equiv) was added, followed by methanesulfonyl chloride (58 mg, 0.50 mmol, 2.0 equiv). The mixture was allowed to stir till the starting material was consumed by LC.MS analysis. The mixture was quenched by addition of satd aq NH$_4$Cl and the contents were transferred to a separatory funnel. The layers were separated and the organic layer was washed with brine, dried over Na$_2$SO$_4$, filtered, and evaporated to afford (S)-2-(tert-butoxycarbonylamino)-3-(3-noradamantyl)methanesulfonate which was used directly in the next step.

The crude mesylate was dissolved in of 33 wt % methylamine in ethanol (20 mL). The mixture was heated to reflux overnight. The solution was evaporated and the residue was taken up in EtOAc. The solution was washed with saturated NaHCO$_3$ and brine, and evaporated to afford crude (S)-tert-butyl 1-(3-noradamantyl)-3-(methylamino)propan-2-ylcarbamate which was used directly in the next step.

The crude amine was dissolved in 1:1 acetonitrile/10% aqueous K$_2$CO$_3$ (20 mL). TeocOSu (97 mg, 0.375 mmol, 1.5 equiv) was added and mixture was stirred for 4 h. LC-MS showed consumption of the free amine. The acetonitrile was removed in vacuo and the aqueous residue was extracted with EtOAc (2×20 mL). The combined organic extracts were dried over Na$_2$SO$_4$, filtered, and evaporated. The product was isolated by flash chromatography on silica eluting with 0-27% EtOAc. (S)-2-(trimethylsilyl)ethyl 2-(t-butoxycarbonylamino)-3-(3-noradamantyl)propyl(methyl)carbamate (36 mg, 0.080 mmol, 32% yield for Steps 4b-d) was isolated.

(S)-2-(trimethylsilyl)ethyl 2-(t-butoxycarbonylamino)-3-(3-noradamantyl)propyl(methyl)carbamate (36 mg, 0.080 mmol, 1.0 equiv) was dissolved in MeOH (5 mL). Toluenesulfonic acid hydrate (16 mg, 0.088 mmol, 1.1 equiv) was added and the solvent was removed at 65° C. under vacuum to afford (S)-2-(trimethylsilyl)ethyl 2-amino-3-(3-noradamantyl)propyl(methyl)carbamate. This material was used without purification.

Example 164

(3R)-3-((S)-1-(3-chlorophenyl)-1-hydroxy-5-methoxypentyl)-N-((2S)-1-(3-noradamantyl)-3-(methylamino)propan-2-yl)piperidine-1-carboxamide
(I-552A)

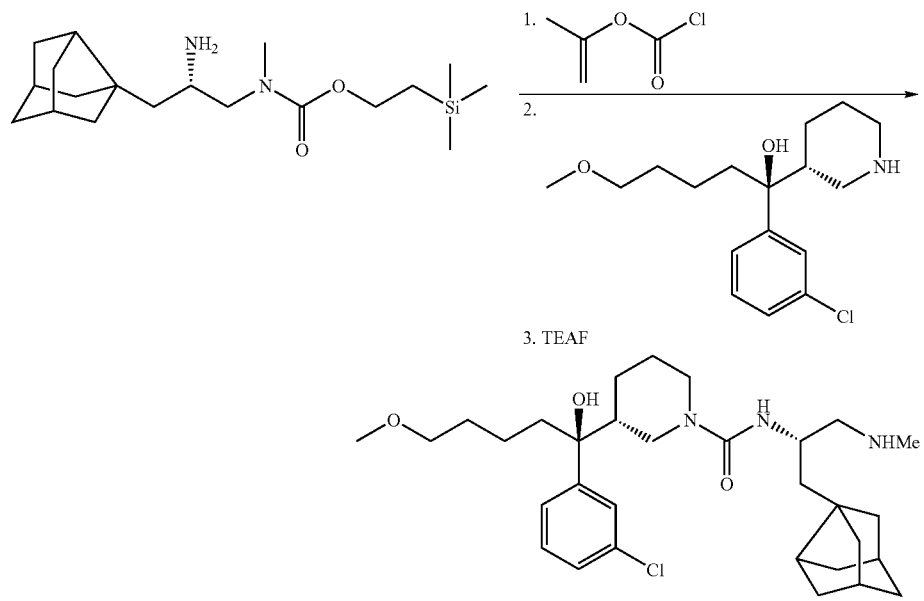

(S)-2-(trimethylsilyl)ethyl 2-amino-3-(3-noradamantyl)propyl(methyl)carbamate was dissolved in acetonitrile (5 mL) and 10% aq Na$_2$CO$_3$ (1 mL) was added. Isopropenylchloroformate (17 μL, 0.159 mmol, 2.0 equiv) was added and the solution was stirred for 1 h at rt. LC-MS analysis showed complete conversion to the desired isopropenyl carbamate. The acetonitrile was removed in vacuo and EtOAc was added. The mixture was transferred to a separatory funnel and the layers were separated. The organic layer was dried over Na$_2$SO$_4$, filtered, and evaporated. The crude (S)-2-(trimethylsilyl)ethyl 2-(isopropenyloxycarbonylamino)-3-(3-noradamantyl)propyl(methyl)carbamate was dissolved in acetonitrile and used in the subsequent step without further purification.

To the above isopropenyl carbamate solution (0.016 mmol, 1.0 equiv) was added a solution of (S)-1-(3-chlorophenyl)-5-methoxy-1-((R)-piperidin-3-yl)pentan-1-ol (20 mg, 0.064 mmol, 4.0 equiv) and DMAP (20 mg, 0.16 mmol, 10 equiv) in acetonitrile. The mixture was heated to 45° C. for 18 h. The solvent was removed and the residue was dissolved in EtOAc, washed with 0.5 M aq HCl (2×10 mL) and brine, and concentrated. The residue was dissolved in acetonitrile (2 mL) and transferred to a vial fitted for a microwave reactor. $Et_4NF$ (ca 50 mg, 0.34 mmol, ~20 equiv) was added. The vial was sealed, placed in the microwave reactor and heated to 119° C. for 7 min. LC-MS analysis showed formation of the desired amine. The solvent was removed and (3R)-3-((S)-1-(3-chlorophenyl)-1-hydroxy-5-methoxypentyl)-N-((2S)-1-(3-noradamantyl)-3-(methylamino)propan-2-yl)piperidine-1-carboxamide was isolated by prep HPLC.

Example 165

2-(trimethylsilyl)ethyl (R)-2-amino-3-((1r,3R,4S)-3,4-difluorocyclopentyl)propyl(methyl)carbamate

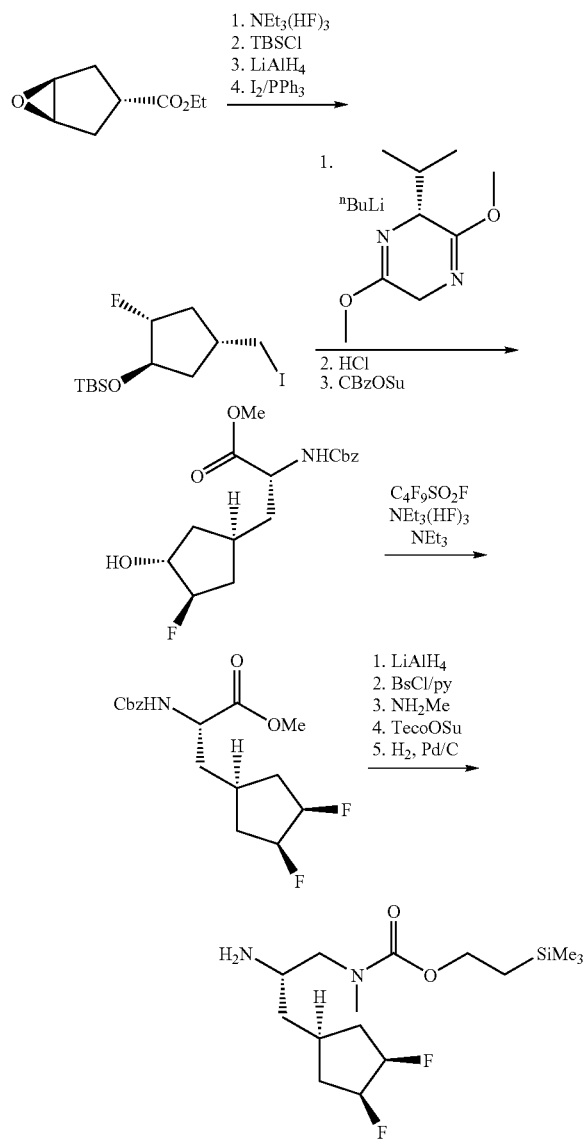

Step 1a-d tert-butyl((1R,2R,4R)-2-fluoro-4-(iodomethyl)cyclopentyloxy)dimethylsilane A 100-mL flask was charged with 7.2 g (50.7 mol) of the (1R,3s,5S)-ethyl 6-oxabicyclo[3.1.0]hexane-3-carboxylate and $NEt_3(HF)_3$ (12.3 g, 76 mmol, 1.5 equiv). The mixture was heated to 120° C. for 16 h. After this time tlc analysis showed consumption of the starting epoxide. The mixture was cooled to 0° C. and quenched by addition of satfd aq $NaHCO_3$. The mixture was allowed to stir for 1 h, and diluted with EtOAc. The layers were separated and the aqueous layer extracted with additional EtOAc. The combined organic extracts were washed with brine, dried over $Na_2SO_4$ filtered, and evaporated. The residue was purified by flash chromatography on silica, eluting with 0-47% EtOAc in hexanes. This afforded (1S,3S,4S)-ethyl 3-fluoro-4-hydroxycyclopentanecarboxylate (6.73 g, 75% yield).

A solution of the (1S,3S,4S)-ethyl 3-fluoro-4-hydroxycyclopentanecarboxylate (6.73 g, 38.2 mmol, 1.0 equiv), TBSCl (11.5 g, 76.4 mmol, 2.0 equiv) and imidazole (12 g, 0.17 mol, 4.0 equiv) in DMF (10 mL) was stirred at rt for 4 h. After this time the free alcohol was consumed by tlc analysis. The DMF was removed in vacuo and the residue was partitioned between ether and water. The layers were separated and the organic layer washed with brine, dried over $Na_2SO_4$ filtered, and evaporated. (1S,3S,4S)-ethyl 3-(tert-butyldimethylsilyloxy)-4-fluorocyclopentanecarboxylate was isolated in quantitative yield.

A slurry of $LiAlH_4$ (2.99 g, 78.5 mmol, 2.0 equiv) in THF (100 mL) was cooled to −78° C. A solution of the above (1S,3S,4S)-ethyl 3-(tert-butyldimethylsilyloxy)-4-fluorocyclopentanecarboxylate in THF (50 mL) was added over 20 min, and the mixture was stirred at −78° C. for 0.5 h. Analysis by tlc showed consumption of the ester. The mixture was allowed to warm to 0° C., then brine (10 mL) was added dropwise over a 15 min, followed by ~20 g of Celite. The thick slurry was diluted with EtOAc and allowed to stir for 0.5 h. The mixture was filtered through a pad of Celite. The filter cake was washed with additional EtOAc. The resulting clear solution was dried over $Na_2SO_4$, filtered, and evaporated. This afforded ((1S,3S,4S)-3-(tert-butyldimethylsilyloxy)-4-fluorocyclopentyl)methanol 7.24 g (76% yield).

The above alcohol (7.24 g, 29.1 mmol, 1.0 equiv), triphenylphosphine (9.2 g (35 mmol, 1.2 equiv), and imidazole (4.0 g, 58.3 mmol, 2.0 equiv) were dissolved in THF (100 mL) and cooled to 0° C. Iodine (8.15 g, 32.4 mmol, 1.1 equiv) was added in 3 equal portions over a 20 min. The mixture was stirred for 1 h at 0° C. After this time additional triphenylphosphine (0.125 equiv) was added, followed by additional iodine (0.125 equiv). After stirring for 20 min tlc analysis showed no remaining alcohol. The mixture was filtered through a pad of silica. The silica was washed with ether and the filtrate was evaporated. tert-butyl((1R,2R,4R)-2-fluoro-4-(iodomethyl)cyclopentyloxy)dimethylsilane was isolated by flash chromatography on silica, eluting with 0-9% EtOAc in hexanes.

Step 2a-b. (S)-methyl 2-(benzyloxycarbonylamino)-3-((1R,3R,4R)-3-fluoro-4-hydroxycyclopentyl)propanoate An oven-dried 250-mL flask was charged with dry THF (75 mL) and (R)-2-isopropyl-3,6-dimethoxy-2,5-dihydropyrazine (4.02 g, 21.8 mmol, 1.5 equiv). The mixture was cooled to −78° C. (dry ice/IPA) and "BuLi (2.5 M, 8.72 mL, 21.8 mmol, 1.5 equiv) was added dropwise over a 20 min. After addition was complete the flask was maintained at −78° C. for 1 h. After this time a solution of tert-butyl((1R,2R,4R)-2- fluoro-4-(iodomethyl)cyclopentyloxy)dimethylsilane (5.2 g, 14.5 mmol, 1.0 equiv) in THF (25 mL) was added over 10 min. The mixture was stirred at −78° C. for 2 h, then tightly stoppered and the dry ice/IPA bath placed in a −15 C freezer for 19 h. After this time LC-MS analysis showed consumption of the iodide and formation of the desired product (M+H⁺). The reaction was quenched by addition of satd aq NH$_4$Cl (10 mL) and the THF removed in vacuo. The residue was partitioned between EtOAc and H$_2$O. The water layer was extracted with additional EtOAc and the combined organic layers washed with brine, dried over dried over Na$_2$SO$_4$, filtered and evaporated. The desired (2S,5R)-2-(((1r,3R,4S)-3,4-difluorocyclopentyl)methyl)-5-isopropyl-3,6-dimethoxy-2,5-dihydropyrazine, contaminated with the starting and (R)-2-isopropyl-3,6-dimethoxy-2,5-dihydropyrazine, was used directly in the next step.

The pyrazine mixture was dissolved in 1:1 acetonitrile/1.0 M aqueous HCl (200 mL). The mixture was stirred for 7 h at rt. The volatile components were removed in vacuo. The residue was dissolved in 1:1 acetonitrile/water (100 mL). To this solution was added K$_2$CO$_3$ (15.2 g, 0.110 mol, 5.0 equiv) and CbzOSu (10.9 g, 43.6 mmol, 3.0 equiv) and the resulting mixture allowed to stir for 17 h. After this time the volatile materials were removed and the residue was partitioned between EtOAc and water. The layers were separated and the organic layer was washed with satd aq NaHCO$_3$ and brine, dried over Na$_2$SO$_4$ filtered, and evaporated. The crude amino acid derivative was purified by flash chromatography, on silica, eluting with 0 to 47% EtOAc in hexanes. This afforded (S)-methyl 2-(benzyloxycarbonylamino)-3-((1R,3R,4R)-3-fluoro-4-hydroxycyclopentyl)propanoate (4.4 g, 89% yield).

Step 3. (S)-methyl 2-(benzyloxycarbonylamino)-3-((1r,3R,4S)-3,4-difluorocyclopentyl)propanoate (S)-methyl 2-(benzyloxycarbonylamino)-3-((1R,3R,4R)-3-fluoro-4-hydroxycyclopentyl)propanoate (4.4 g, 12.9 mmol, 1.0 equiv) was dissolved in THF (50 mL) and cooled to 0° C. To this solution was added C$_4$F$_9$SO$_2$F (7.86 g, 25.93 mmol, 2.0 equiv), NEt$_3$(HF)$_3$ (4.18 g, 25.93 mmol, 2.0 equiv), and NEt$_3$ (7.84 g, 77.8 mmol, 6.0 equiv). The resulting mixture was allowed to stir for 72 h. After this time the solution was filtered through a pad of silica. The silica was washed with additional THF and the filtrate was transferred to a separatory funnel. The solution was washed with saturated NaHCO$_3$ and brine and evaporated. The desired vicinal difluoride was purified by flash chromatography on silica. This afforded (S)-methyl 2-(benzyloxycarbonylamino)-3-((1r,3R,4S)-3,4-difluorocyclopentyl)propanoate (3.0 g). Unreacted starting alcohol (818 mg) was also recovered.

Step 4. 2-(trimethylsilyl)ethyl (R)-2-amino-3-((1r,3R,4S)-3,4-difluorocyclopentyl)propyl(methyl)carbamate LiAlH$_4$ (1.0 g, 26.5 mmol, 3.0 equiv) was slurried in THF (100 mL) and cooled to −78° C. A solution of (S)-methyl 2-(benzyloxycarbonylamino)-3-((1r,3R,4S)-3,4-difluorocyclopentyl)propanoate (3.0 g, 8.84 mmol) in THF (20 mL) was added over 20 min. After this time LC-MS analysis showed no remaining starting material. The mixture was warmed to 0° C. and brine (7 mL) was added dropwise, followed by ca 10 g of Celite. The thick slurry was stirred for 0.5 h, and filtered through a pad of Celite. The clear solution was evaporated to yield benzyl (S)-1-((1r,3R,4S)-3,4-difluorocyclopentyl)-3-hydroxypropan-2-ylcarbamate as a thick syrup (1.8 g, 65% yield).

A 250-mL flask was charged with the above alcohol (1.8 g, 5.75 mmol), brosyl chloride (2.94 g, 11.5 mmol, 2.0 equiv), DMAP (351 mg, 2.87 mmol, 0.5 equiv) and 5:1 CH$_2$Cl$_2$: pyridine (120 mL). The mixture was allowed to stir for 17 h at rt. After this time the volatile materials were removed in vacuo and the residue was partitioned between EtOAc and 1.0 M aq HCl. The layers were separated, and the organic layer evaporated. (S)-2-(benzyloxycarbonylamino)-3-((1r,3R,4S)-3,4-difluorocyclopentyl)propyl 4-bromobenzenesulfonate was purified by flash chromatography on silica gel, eluting with 0-80% EtOAc in hexanes.

The above brosylate was dissolved in 30% NH$_2$Me in EtOH (100 mL). The mixture was heated at reflux for 15 h. After this time the solvent was removed and the residue was dissolved in fresh 30% NH$_2$Me in EtOH (100 mL), and the mixture was heated to reflux for an additional 8 h. After this time the volatile materials were removed and the residue was dissolved in 1:1 CH$_3$CN:10% aqueous K$_2$CO$_3$ (40 mL). TeocOSu (2.22 g, 8.83 mmol, 1.5 equiv) was added and mixture stirred for 4 h. LC-MS showed consumption of the free amine. The acetonitrile was removed in vacuo and the product was extracted with EtOAc (2×20 mL). The combined organic extracts were dried over Na$_2$SO$_4$, filtered, and evaporated. 2-(trimethylsilyl)ethyl (S)-2-(benzyloxycarbonylamino)-3-((1r,3R,4S)-3,4-difluorocyclopentyl)propyl(methyl)carbamate was isolated by flash chromatography on silica gel eluting with 0-7% MeOH in CH$_2$Cl$_2$.

A crude sample of the above diamine dissolved in MeOH (10 mL) was added to a 250-mL Parr pressure bottle containing 10% Pd (ca 100 mg) on carbon and MeOH (7 mL). The bottle was placed in a hydrogenation shaker and pressurized to 45 psi of H$_2$, then evaporated. This procedure was repeated twice, the mixture was placed in the shaker for 3 h. After this time the Cbz group was cleanly removed. The catalyst was removed by filtration through Celite and the volatile materials removed to afford 2-(trimethylsilyl)ethyl (R)-2-amino-3-((1r,3R,4S)-3,4-difluorocyclopentyl)propyl(methyl)carbamate (109 mg) as a clear oil. This amine was of sufficient purity to employ in subsequent steps.

Example 166

The following compounds were prepared using procedures analogous to those described in Example 165:

2-(trimethylsilyl)ethyl (2S)-2-amino-3-(tetrahydro-2H-pyran-2-yl)propylcarbamate using 2-(iodomethyl)tetrahydro-2H-pyran in step 2.

2-(trimethylsilyl)ethyl (2S)-2-amino-3-(tetrahydrofuran-2-yl)propylcarbamate using 2-(iodomethyl)tetrahydrofuran in step 2.

(S)-2-(trimethylsilyl)ethyl 2-amino-3-(3-methoxycyclobutyl)propylcarbamate using 1-(iodomethyl)-3-methoxycyclobutane in step 2.

The following are compounds of the invention. Compound names were generated with the assistance of ChemDraw® versions 8.0 and 9.0 (CambridgeSoft Corporation, 100 CambridgePark Drive, Cambridge, Mass. 02140 USA). When the stereochemistry at a chiral center is not defined in the compound name this indicates that the sample prepared contained a mixture of isomers at this center.

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-1A | N-((S)-1-amino-3-cyclohexylpropan-2-yl)-3-(1-hydroxy-1-phenylpentyl)-piperidine-1-carboxamide | 33 | 1.57 | 430 | 7.26-7.05 (m), 4.29-3.70 (m), 2.89-2.21 (m), 1.83-0.69 (m) |
| I-2A | 3-(3-methoxypropoxy)(phenyl)methyl)-N-((S)-1-amino-3-cyclohexylpropan-2-yl)benzamide | 42 | 1.55 | 439 | 8.29 (m), 7.82-7.10 (m), 5.36-5.32 (m), 4.33 (m), 3.46-2.82 (m), 1.83-0.76 (m) |
| I-3A | 3-((2-cyclopropylethoxy)(phenyl)methyl)-N-((S)-1-amino-3-cyclohexylpropan-2-yl)piperidine-1-carboxamide | 33 | 1.72 | 442 | 7.13-7.27 (m), 4.17-4.33 (m), 3.69-4.05 (m), 2.54-2.92 (m), 0.61-1.71 (m), 0.25-0.31 (m), −0.15-−0.09 (m) |
| I-4A | N-((S)-1-amino-3-cyclohexylpropan-2-yl)-3-(5-methoxy-1-phenylpentyl)piperidine-1-carboxamide | 33 | 1.68 | 444 | 7.26-6.99 (m), 3.95-3.46 (m), 3.11 (m), 2.89-1.94 (m), 1.70-0.71 (m) |
| I-5A | 3-((3-methoxypropoxy)(phenyl)methyl)-N-((S)-1-amino-3-cyclohexylpropan-2-yl)piperidine-1-carboxamide | 33 | 1.53 | 446 | 7.24-7.12 (m), 4.27-4.15 (m), 3.99-3.55 (m), 3.38-3.10 (m), 2.90-2.42 (m), 1.86-0.71 (m) |
| I-5B | (3S)-3-((3-methoxypropoxy)(phenyl)methyl)-N-((S)-1-amino-3-cyclohexylpropan-2-yl)piperidine-1-carboxamide | 33 | 1.53 | 446 | 7.38-7.33 (m, 2H), 7.32-7.26 (m, 3H), 4.09 (d, 1H), 3.98 (m, 1H), 3.70 (dd, 1H), 3.50-3.43 (m, 2H), 3.36 (m, 1H), 2.97 (dd, 1H), 2.78-2.64 (m, 3H), 2.00 (dm, 1H) |
| I-5C | (3R)-3-((R)-(3-methoxypropoxy)(phenyl)methyl)-N-((S)-1-amino-3-cyclohexylpropan-2-yl)piperidine-1-carboxamide | 33 | 1.55 | 446 | 7.37-7.32 (m, 2H), 7.32-7.25 (m, 3H), 4.32 (d, 1H), 4.04 (m, 1H), 4.00-3.88 (m, 2H), 3.51-3.39 (m, 2H), 3.02 (dd, 1H), 2.86-2.74 (m, 3H) |
| I-6A[b] | 3-((3-methoxypropoxy)(phenyl)methyl)-N-(2-amino-3-cyclohexylpropyl)piperidine-1-carboxamide | 127 | 1.44 | 446 | 0.80-1.80 (m)2.10 (m), 3.20 (s), 4.10 (m) 7.10-7.50 (m) |
| I-7A[b] | (3R)—N-(1-amino-3-cyclopentylpropan-2-yl)-3-((S)-1-hydroxy-5-methoxy-1-phenylpentyl)piperidine-1-carboxamide | 45 | 1.43 | 446 | 3.70-3.90 (m), 4.20 (m), 7.10-7.40 (m) |
| I-8A[c] | 2-((3-methoxypropoxy)(phenyl)methyl)-N-((S)-1-amino-3-cyclohexylpropan-2-yl)morpholine-4-carboxamide | 33 | 1.41 | 448 | 1.80 (m), 2.79 (m), 2.99 (m), 3.30 (s), 3.78 (br t), 4.07 (m), 4.22 (m) |
| I-9A[b] | (3R)—N-((R)-3-tert-butoxy-1-aminopropan-2-yl)-3-((S)-1-hydroxy-5-methoxy-1-phenylpentyl)piperidine-1-carboxamide | 45 | 1.32 | 450 | 1.15 (s), 3.25 (s), 3.75 (m), 4.20 (m), 7.10-7.25 (m) |
| I-10A | (3R)-3-((S)-1-(3-fluorophenyl)-1-hydroxy-5-methoxypentyl)-N-((S)-4-methyl-1-(methylamino)pentan-2-yl)piperidine-1-carboxamide | 30 | 1.37 | 452 | 0.92 (d), 0.98 (d), 1.2-2.0 (m), 2.54 (m), 2.70 (m), 2.96 (m), 3.06 (m), 3.24 (s), 3.3 (m), 3.96 (d), 4.08 (m), 4.32 (d), 6.94 (m), 7.16 (m), 7.32 (m) |
| I-11A | 3-((3-methoxypropoxy)(phenyl)methyl)-N-((S)-3-cyclohexyl-1-(methylamino)propan-2-yl)benzamide | 42 | 1.57 | 453 | 7.77-7.06 (m), 5.30 (s), 4.37 (m), 3.40-3.35 (m), 3.14 (s), 3.04-2.91 (m), 2.56 (s), 1.77-0.74 (m) |
| I-12A[b] | (3R)—N-((S)-1-amino-3-phenylpropan-2-yl)-3-((S)-1-hydroxy-5-methoxy-1-phenylpentyl)piperidine-1-carboxamide | 44 | 1.32 | 454 | 2.50-2.80 (m), 2.60-2.90 (m), 3.30 (s), 4.10 (m), 7.10-7.40 (m) |
| I-13A | N-((S)-1-amino-3-cyclohexylpropan-2-yl)-3-(1-hydroxy-1-phenylheptyl)piperidine-1-carboxamide | 33 | 1.79 | 458 | 7.28-7.08 (m), 4.32-3.72 (m), 2.91-2.24 (m), 1.90-0.73 (m) |
| I-14A | N-((S)-1-amino-3-cyclohexylpropan-2-yl)-3-(5-ethoxy-1-phenylpentyl)piperidine-1-carboxamide | 36 | 1.64 | 458 | not determined |
| I-14A | N-((S)-3-cyclohexyl-1-(methylamino)propan-2-yl)-3-(5-methoxy-1-phenylpentyl)piperidine-1-carboxamide | 37 | 1.7 | 458 | not determined |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-15A | (3S)—N-((S)-3-cyclohexyl-1-(methylamino)propan-2-yl)-3-((R)-5-methoxy-1-phenylpentyl)piperidine-1-carboxamide | 37 | 1.76 | 458 | not determined |
| I-16A[b] | 3-((3-methoxypropoxy)(phenyl)methyl)-N-(3-cyclohexyl-1-(methylamino)propan-2-yl)piperidine-1-carboxamide | 30 | 2.77 | 460 | 2.65 (s), 2.95 (m), 3.35 (s), 4.17 (m), 7.10-7.50 (m) |
| I-17A | 3-((4-methoxybutoxy)(phenyl)methyl)-N-((S)-1-amino-3-cyclohexylpropan-2-yl)piperidine-1-carboxamide | 33 | 1.61 | 460, 482 | 7.34-7.24 (m, 5H), 4.29 (d, 1H), 4.02 (m, 1H), 3.92 (m, 1H), 3.51-3.38 (m, 4H), 2.99 (dd, 1H), 2.82-2.73 (m, 2H) |
| I-17A | 3-((3-ethoxypropoxy)(phenyl)methyl)-N-((S)-1-amino-3-cyclohexylpropan-2-yl)piperidine-1-carboxamide | 33 | 1.63 | 460 | 3.28 (m), 4.28 (d), 4.38 (d), 7.24-7.38 (m) |
| I-18A | N-((S)-1-amino-3-cyclohexylpropan-2-yl)-3-(1-hydroxy-5-methoxy-1-phenylpentyl)piperidine-1-carboxamide | 33 | 1.6 | 460 | 3.27 (m), 3.70 (m), 3.81 (m), 3.95 (m), 4.02 (m), 4.10 (m), 4.29 (d), 4.39 (d), 7.25-7.36 (m) |
| I-19A | (3R)—N-((S)-1-amino-3-cyclohexylpropan-2-yl)-3-((S)-1-hydroxy-5-methoxy-1-phenylpentyl)piperidine-1-carboxamide | 33 | 1.48 | 460 | 7.24-7.00 (m, 5H), 4.12 (dm, J = 12.8 Hz, 1H), 3.93-3.86 (m, 1H), 3.79 (dm, J = 12.8 Hz, 1H), 3.14-3.11 (m, 2H), 3.07 (s, 3H), 2.84 (dd, J = 12.6, 3.4 Hz, 1H), 2.68 (dd, J = 12.6, 9.8 Hz, 1H), 2.33 (t, J = 12.2 Hz, 2H), 1.84-0.66 (m, 25H) |
| I-19A | 3-((3-methoxypropoxy)(phenyl)methyl)-N-(1-amino-3-cyclohexylpropan-2-yl)-N-methylpiperidine-1-carboxamide | 33 | 1.47 | 460 | 7.25-7.05 (m), 4.29-3.70 (m), 3.12 (m), 2.89-2.21 (m), 1.86-0.72 (m) |
| I-20A | (3R)—N-((S)-3-cyclohexyl-1-(methylamino)propan-2-yl)-3-((R)-1-hydroxy-4-methoxy-1-phenylbutyl)piperidine-1-carboxamide | 30 | 1.58 | 460 | 2.70 (s), 3.30 (s), 3.90 (br m), 7.20-7.50 (m) |
| I-21A | (3R)-3-((R)-(3-ethoxypropoxy)(phenyl)methyl)-N-((S)-1-amino-3-cyclohexylpropan-2-yl)piperidine-1-carboxamide | 33 | 1.59 | 460 | 0.85-1.08 (m), 2.00 (m), 2.65 (s), 2.69 (s), 3.04 (d), 3.07 (d), 3.25 (s), 3.26 (s), 3.29-3.34 (m), 3.98 (m), 4.13 (m), 4.28 (d), 7.19-7.42 (m) |
| I-22A | 3-((3-methoxypropoxy)(4-fluorophenyl)methyl)-N-((S)-1-amino-3-cyclohexylpropan-2-yl)piperidine-1-carboxamide | 33 | 1.59 | 464 | 0.8-2.0 (m), 3.30 (s), 7.08 (t), 7.28 (t) |
| I-23A | 3-((3-methoxypropoxy)(2-fluorophenyl)methyl)-N-((S)-1-amino-3-cyclohexylpropan-2-yl)piperidine-1-carboxamide | 33 | 1.59 | 464 | 0.8-1.9 (m), 3.28 (s), 4.0 (m), 7.04 (t), 7.20 (t), 7.35 (m), 7.41 (m) |
| I-24A | (3S)—N-((S)-3-cyclohexyl-1-(methylamino)propan-2-yl)-3-((S)-1-cyclohexyl-5-methoxypentyl)piperidine-1-carboxamide | 38 | 1.89 | 464 | 4.03-3.98 (m, 1H), 3.91 (dm, J = 12.8 Hz, 1H), 3.82 (dm, J = 12.8 Hz, 1H), 3.28 (t, J = 6.6 Hz, 2H), 3.20 (s, 3H), 2.93 (dd, J = 12.4, 3.2 Hz, 1H), 2.80 (dd, J = 12.4, 10.0 Hz, 1H), 2.58 (s, 3H), 2.61-2.48 (m, 2H), 1.70-0.72 (m, 37H) |
| I-24B | (3S)—N-((S)-3-cyclohexyl-1-(methylamino)propan-2-yl)-3-((R)-1-cyclohexyl-5-methoxypentyl)piperidine-1-carboxamide | 38 | 1.98 | 464 | 4.05-3.99 (m, 1H), 3.93 (dm, J = 12.8 Hz, 1H), 3.84 (dm, J = 13.0 Hz, 1H), 3.31 (t, J = 6.4 Hz, 2H), 3.23 (s, 3H), 2.96 (dd, J = 12.6, 3.4 Hz, 1H), 2.80 (dd, J = 12.6, 10.2 Hz, 1H), 2.60 (s, 3H), 2.64-2.51 (m, 2H), 1.71-0.74 (m, 37H) |
| I-25A | (3R)—N-((S)-3-cyclohexyl-1-(methylamino)propan-2-yl)-3-(4-cyclopropyl-1-hydroxy-1-phenylbutyl)piperidine-1-carboxamide | 33 | 1.71 | 470 | |
| I-26A | 3-((3-methoxypropoxy)(3-cyanophenyl)methyl)-N-((S)-1-amino-3-cyclohexylpropan-2-yl)piperidine-1-carboxamide | 30 | 1.84 | 514 | 3.30 (m), 4.12 (m), 7.34 (m) |
| I-27A | N-((S)-3-cyclohexyl-1-(methylamino)propan-2-yl)-3-(5-ethoxy-1-phenylpentyl)piperidine-1-carboxamide | 37 | 1.78 | 472 | 7.14-6.93 (m), 3.97-3.45 (m), 3.24-3.11 (m), 2.89-2.59 (m), 2.51 (s), 2.46 (s), 2.28-2.18 (m), 1.92-1.89 (m), 1.75-0.65 (m) |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-28A[d] | N-((S)-3-cyclohexyl-1-(methylamino)propan-2-yl)-3-(1-hydroxy-5-methoxy-1-phenylpentyl)cyclohexanecarboxamide | 40 | 1.45 | 473 | 2.62 (s), 2.74 (s), 2.76 (s) 3.90 (m), 3.26 (s), 7.18 (m), 7.27 (m), 7.38 (m) |
| I-29A[b] | N-(1-amino-4-(trifluoromethyl)pentan-2-yl)-3-(1-hydroxy-5-methoxy-1-phenylpentyl)piperidine-1-carboxamide | 45 | 1.37 | 474 | 1.15 (m), 2.60 (m), 3.80 (m), 3.25 (s), 4.10 (m), 7.10-7.25 (m) |
| I-30[b] | 3-((3-methoxypropoxy)(phenyl)methyl)-N-(3-cyclohexyl-1-(ethylamino)propan-2-yl)piperidine-1-carboxamide | 30 | 1.6 | 474 | 0.95 (m), 2.9 (m), 3.80 (m), 4.1 (m) 7.20-7.50 (m) |
| I-31A | 3-((3-ethoxypropoxy)(phenyl)methyl)-N-((S)-3-cyclohexyl-1-(methylamino)propan-2-yl)piperidine-1-carboxamide | 33 | 1.67 | 474 | |
| I-31B | (3R)-3-((R)-(3-ethoxypropoxy)(phenyl)methyl)-N-((S)-3-cyclohexyl-1-(methylamino)propan-2-yl)piperidine-1-carboxamide | 32 | 1.58 | 474 | 7.34 (m, 2H), 7.27 (m, 3H), 4.30 (d, 1H), 4.10 (m, 1H), 3.94 (m, 2H), 3.52-3.40 (m, 4H), 3.01-2.87 (m, 2H), 2.76 (td, 2H), 2.65 (s, 3H) |
| I-32A | (3R)—N-((S)-1-amino-3-cyclohexylpropan-2-yl)-3-((S)-5-ethoxy-1-hydroxy-1-phenylpentyl)piperidine-1-carboxamide | 33 | 1.56 | 474 | 7.30-7.09 (m, 5H), 4.19 (dm, J = 12.8 Hz, 1H), 3.95 (m, 1H), 3.87 (dm, J = 12.8 Hz, 1H), 3.34-3.19 (m, 4H), 2.93-2.87 (m, 1H), 2.77-2.69 (m, 1H), 2.44-2.37 (m, 2H), 1.90-0.78 (m, 28H) |
| I-33A | (3R)—N-((S)-3-cyclohexyl-1-(methylamino)propan-2-yl)-3-((S)-1-hydroxy-5-methoxy-1-phenylpentyl)piperidine-1-carboxamide | 33 | 1.49 | 474 | 7.14-6.94 (m, 5H), 4.05 (dm, J = 12.8 Hz, 1H), 3.93-3.87 (m, 1H), 3.73 (dm, J = 12.4 Hz, 1H), 3.08-3.05 (m, 2H), 3.01 (s, 3H), 2.82 (dd, J = 12.8, 3.2 Hz, 1H), 2.71 (dd, J = 12.4, 10.0 Hz, 1H), 2.46 (s, 3H), 2.28 (t, J = 12.2 Hz, 2H), 1.78-0.63 (m, 25H) |
| I-34A | 3-((3-ethoxypropoxy)(phenyl)methyl)-N-((S)-1-amino-3-cyclohexylpropan-2-yl)-3-methylpiperidine-1-carboxamide | 33 | 1.76 | 474 | 7.35-7.25 (m, 5H), 4.05 (s, 2H), 3.89 (m, 1H), 3.64 (d, 1H), 3.52 (m, 2H), 3.45 (m, 2H), 3.37-3..18 (m, 3H), 3.50-2.90 (m, 2H), 2.81 (1H) |
| I-35A | (3R)—N-((S)-3-cyclohexyl-1-(methylamino)propan-2-yl)-3-((R)-4-ethoxy-1-hydroxy-1-phenylbutyl)piperidine-1-carboxamide | 33 | 1.65 | 475 | 2.02 (m), 2.65 (s), 2.70 (s), 2.91 (m), 3.04 (d), 3.07 (d), 3.30 (m), 3.33-3.43 (m), 3.98 (d), 4.13 (m), 4.29 (d), 7.19-7.43 (m) |
| I-36A | (3R)—N-((S)-2-amino-5-methoxy-4,4-dimethylpentyl)-3-((S)-1-(3-chlorophenyl)-1-hydroxy-5-methoxypentyl)piperidine-1-carboxamide | 126.1 | 1.41 | 498 | 0.98 (s), 1.00 (s), 1.20-1.80 (m), 1.94 (m), 2.44 (dd), 2.58 (dd), 3.16 (d), 3.22 (d), 3.24 (s), 3.30 (m), 3.38 (s), 3.88 (d), 4.38 (d), 7.20-7.32 (m), 7.42 (s). |
| I-37A | (3S)—N-((S)-3-cyclohexyl-1-(methylamino)propan-2-yl)-3-((R)-1-(3-fluorophenyl)-5-methoxypentyl)piperidine-1-carboxamide | 37 | 1.68 | 476 | 0.9-1.9 (m), 2.40 (m), 2.68 (s), 2.92 (dd), 3.06 (m), 3.24 (s), 3.90 (d), 4.16 (m), 6.88 (m), 6.92 (m), 7.28 (m) |
| I-38A | (3R)—N-((S)-3-cyclohexyl-1-(methylamino)propan-2-yl)-3-(1-fluoro-5-methoxy-1-phenylpentyl)piperidine-1-carboxamide | 43 | 1.64 | 476 | 7.29-7.15 (m, 5H), 4.23 (dm, J = 13.2 Hz, 1H), 4.05-3.92 (m, 1H), 3.86 and 3.71 (dm, J = 13.2 Hz, 1H), 3.20-3.15 (m, 1H), 3.13 (s, 3H), 3.00-2.73 (m, 2H), 2.59 and 2.55 (s, 3H), 2.51-2.39 (m, 2H), 2.08-0.74 (m, 25H) |
| I-39A | (3R)-3-((R)-(3-methoxypropoxy)(3-fluorophenyl)methyl)-N-((S)-3-cyclohexyl-1-(methylamino)propan-2-yl)piperidine-1-carboxamide | 33 | | 478 | 2.73 (d, 3H), 3.31 (s, 1H), 3.48 (m, 2H), 3.56 (t, 1H), 3.77 (m, 1H), 3.92 (br d, 1H), 4.02 (brd, 1H), 4.12 (m, 1H), 4.26 (br d, 1H), 7.03 (m, 2H), 7.10 (d, 1H), 7.37 (m, 1H) |
| I-40A | (3R)—N-((S)-1-amino-3-cyclohexylpropan-2-yl)-3-((S)-1-(3-fluorophenyl)-1-hydroxy-5-methoxypentyl)piperidine-1-carboxamide | 33 | | 478 | 3.26 (s), 3.84 (br d), 3.97 (br d), 4.05 (m), 4.29 (br d), 4.42 (br d), 6.93 (m), 7.15 (m), 7.34 (m) |
| I-41A | (3R)—N-((S)-3-cyclohexyl-1-(methylamino)propan-2-yl)-3-((R)-1- | 33 | 1.59 | 480 | 4.05-4.00 (m, 1H), 3.93 (dm, J = 12.8 Hz, 2H), 3.31 (t, J = 6.4 Hz, 2H), 3.22 (s, 3H), |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | cyclohexyl-1-hydroxy-5-methoxypentyl)piperidine-1-carboxamide | | | | 2.95 (dd, J = 12.4, 3.2 Hz, 1H), 2.81 (dd, J = 12.4, 10.2 Hz, 1H), 2.59 (s, 3H), 2.67-2.54 (m, 2H), 1.78-0.72 (m, 36H) |
| I-41A | (3R)—N-((S)-3-cyclohexyl-1-(methylamino)propan-2-yl)-3-((S)-1-cyclohexyl-1-hydroxy-5-methoxypentyl)piperidine-1-carboxamide | 33 | 1.6 | 480 | 4.07-4.01 (m, 1H), 3.94 (dm, J = 12.8 Hz, 2H), 3.32 (t, J = 6.4 Hz, 2H), 3.22 (s, 3H), 2.96 (dd, J = 12.6, 3.4 Hz, 1H), 2.80 (dd, J = 12.8, 10.2 Hz, 1H), 2.59 (s, 3H), 2.67-2.54 (m, 2H), 1.79-0.73 (m, 36H) |
| I-42A | 3-((3-methoxypropoxy)(2,4-difluorophenyl)methyl)-N-((S)-1-amino-3-cyclohexylpropan-2-yl)piperidine-1-carboxamide | 33 | 1.55 | 482 | not determined |
| I-43A | 3-((3-methoxypropoxy)(3,4-difluorophenyl)methyl)-N-((S)-1-amino-3-cyclohexylpropan-2-yl)piperidine-1-carboxamide | 33 | 1.59 | 482 | 7.15-7.06 (m), 4.42-3.66 (m), 3.40-3.11 (m), 2.91-2.46 (m), 1.82-0.73 (m) |
| I-44A | (3R)-3-((S)-1-hydroxy-5-methoxy-1-(2-phenoxyphenyl)pentyl)-N-((S)-1-(methylamino)propan-2-yl)piperidine-1-carboxamide | 33 | 1.40 | 484 | 1.18 (d), 2.60 (s), 3.22 (s), 3.82 (d), 4.00 (m), 4.32 (d), 6.72 (m), 6.84 (d), 7.04 (m), 7.14 (m), 7.28 (m), 7.60 (d) |
| I-45A | 3-((3-methoxypropoxy)(3-cyanophenyl)methyl)-N-((S)-3-cyclohexyl-1-(methylamino)propan-2-yl)piperidine-1-carboxamide | 30 | 1.5 | 485 | 3.01 (m), 3.24 (m), 3.41 (m), 4.03 (m), 7.49-7.64 (m) |
| I-46A | 3-((3-methoxypropoxy)(2-allylphenyl)methyl)-N-((S)-1-amino-3-cyclohexylpropan-2-yl)piperidine-1-carboxamide | 33 | 1.75 | 486 | 0.9-1.8 (m), 2.8 (m), 3.28 (s), 5.06 (m), 5.98 (m), 7.20 (m), 7.35 (m) |
| I-47A[b] | 3-((3-methoxypropoxy)(phenyl)methyl)-N-(3-cyclohexyl-1-(propylamino)propan-2-yl)piperidine-1-carboxamide | 30 | 1.69 | 488 | 0.95 (m). 1.75 (m), 2.9 (m), 3.80 (m), 4.1 (m) 7.20-7.50 (m) |
| I-48A | (3R)—N-((S)-3-cyclohexyl-1-(methylamino)propan-2-yl)-3-((S)-5-ethoxy-1-hydroxy-1-phenylpentyl)piperidine-1-carboxamide | 33 | 1.59 | 488 | 7.22-7.02 (m, 5H), 4.13 (dm, J = 12.8 Hz, 1H), 4.01-3.94 (m, 1H), 3.80 (dm, J = 12.8 Hz, 1H), 3.24 (q, J = 6.9 Hz, 2H), 3.18 (t, J = 6.6 Hz, 2H), 2.89 (dd, J = 12.8, 3.6 Hz, 1H), 2.78 (dd, J = 12.4, 10.0 Hz, 1H), 2.53 (s, 3H), 2.35 (t, J = 12.2 Hz, 2H), 0.95 (t, J = 7.0 Hz, 3H), 1.87-0.68 (m, 25H) |
| I-49A | 3-((3-propoxypropoxy)(phenyl)methyl)-N-((S)-3-cyclohexyl-1-(methylamino)propan-2-yl)piperidine-1-carboxamide | 30 | 1.83 | 488 | 0.87 (m), 2.65 (s), 2.69 (s), 3.30 (m), 3.30 (m), 3.74 (d), 4.10 (d), 4.30 (d), 4.42 (d), 7.39-7.23 (m) |
| I-50A | (3R)—N-((S)-3-cyclohexyl-1-(methylamino)propan-2-yl)-3-((R)-1-hydroxy-5-methoxy-1-m-tolylpentyl)piperidine-1-carboxamide | 33 | | 488 | 2.34 (s), 2.71 (s), 2.72 (s), 3.07 (dd), 3.84 (br d), 3.98 (br d), 4.13 (br d), 4.26 (br d), 4.41 (br d) |
| I-50B | (3R)—N-((S)-3-cyclohexyl-1-(methylamino)propan-2-yl)-3-((S)-1-hydroxy-5-methoxy-1-m-tolylpentyl)piperidine-1-carboxamide | 33 | | 488 | |
| I-51A | (3R)—N-((S)-1-amino-5-methoxy-4,4-dimethylpentan-2-yl)-3-((S)-1-(3-chlorophenyl)-1-hydroxy-5-methoxypentyl)piperidine-1-carboxamide | 33 | 1.41 | 498 | 0.96 (s), 0.98 (m), 1.08-1.80 (m), 1.96 (m), 2.46 (m), 2.58 (m), 2.84 (m), 2.98 (m), 3.08 (s), 3.24 (s), 3.30 (m), 3.92 (d), 4.08 (d), 4.36 (d), 7.20-7.34 (m), 7.42 (m) |
| I-52A | (2S)-N2-(1-(3-((3-methoxypropoxy)(phenyl)methyl)piperidin-1-yl)-2-nitrovinyl)-3-cyclohexylpropane-1,2-diamine | 34 | 1.92 | 589 | 7.41-7.23 (m, 5H), 4.40-4.00 (m, 3H), 3.73 (m, 1H) |
| I-53A | (3R)—N-((S)-3-cyclohexyl-1-(methylamino)propan-2-yl)-3-((R)-1-(3-fluorophenyl)-1-hydroxy-5-methoxypentyl)piperidine-1-carboxamide | 33 | | 492 | 2.59 (s), 3.05 (dd), 3.29 (S), 3.84 (brd), 3.98 (br d) 4.13 (m),, 4.19 (br d), 4.28 (br d), 4.45 (br d), 6.95 (m, 1H), 7.15 (m, 2H), 7.33 (m, 1H) |
| I-53B | (3R)—N-((S)-3-cyclohexyl-1-(methylamino)propan-2-yl)-3-((S)-1-(3-fluorophenyl)-1-hydroxy-5- | 33 | 1.47 | 492 | 7.14-7.09 (m, 1H), 6.97-6.93 (m, 2H), 6.75-6.70 (m, 1H), 6.49 (s, 2H), 4.11 (dm, J = 12.8 Hz, 1H), 3.99-3.92 (m, 1H), |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | methoxypentyl)piperidine-1-carboxamide | | | | 3.76 (dm, J = 12.8 Hz, 1H), 3.11 (t, J = 6.4 Hz, 2H), 3.05 (s, 3H), 2.86 (dd, J = 12.8, 3.6 Hz, 1H), 2.79 (dd, J = 12.8, 9.6 Hz, 1H), 2.50 (s, 3H), 2.33 (t, J = 12.2 Hz, 2H), 1.82-0.64 (m, 25H) |
| I-54A | (3R)—N-((S)-2-amino-5-methoxy-4,4-dimethylpentyl)-3-((S)-1-(2,3-difluorophenyl)-1-hydroxy-5-methoxypentyl)piperidine-1-carboxamide | 127 | 1.38 | 500 | 0.84 (m), 1.00 (s), 1.22-1.68 (m), 1.96 (m), 2.18 (m), 2.66 (m), 3.18 (d), 3.24 (sd), 3.30 (m), 3.38 (s), 3.84 (d), 4.42 (d), 7.16 (m), 7.38 (m). |
| I-55A | 3-((S)-1-amino-3-cyclohexylpropan-2-ylamino)-4-(3-((2-cyclopropylethoxy)(phenyl)methyl)piperidin-1-yl)cyclobut-3-ene-1,2-dione | 27 | 1.78 | 494 | −.032 (m), 0.35 (m), 0.86 (m), 3.26 (m), 3.61 (m), 4.03 (br s), 4.62 (br s), 7.30 (m) |
| I-56A | (3R)-3-(1-hydroxy-5-methoxy-1-(2-phenoxyphenyl)pentyl)-N-(piperidin-3-yl)piperidine-1-carboxamide | 33 | 1.41 | 496 | 0.91 (m), 1.75 (m), 1.95 (m), 2.21 (m), 2.35 (m), 2.87 (m), 3.2 (s), 3.84 (m), 4.38 (br m), 6.78 (d), 6.92 (m), 7.01 (d), 7.11 (m), 7.19 (m), 7.34 (m), 7.67 (m) |
| I-57A | (3R)—N-((S)-3-cyclohexyl-1-(methylamino)propan-2-yl)-3-(4,4,4-trifluoro-1-hydroxy-1-m-tolylbutyl)piperidine-1-carboxamide | 33 | 1.72 | 498 | 0.82-0.93 (m), 1.98 (t), 2.32 (s), 2.81 (s), 3.28 (d), 3.59 (d), 4.25 (d), 6.19 (d), 7.03-7.17 (m), 9.29 (br s), 9.91 (br s) |
| I-58A[be] | 3-((S)-1-amino-3-cyclohexylpropan-2-ylamino)-4-((R)-3-((R)-(3-methoxypropoxy)(phenyl)methyl)piperidin-1-yl)cyclobut-3-ene-1,2-dione | 26 | 1.43 | 498 | 8.20 (br s, 2H), 7.37-7.19 (m, 5H), 4.58 (br s, 1H), 4.00-3.62 (m, 2H), 3.57-2.90 (m, 10H) |
| I-58B | 3-((S)-1-amino-3-cyclohexylpropan-2-ylamino)-4-((R)-3-((R)-(3-methoxypropoxy)(phenyl)methyl)piperidin-1-yl)cyclobut-3-ene-1,2-dione | 26 | 1.48 | 498 | 7.39-7.24 (m, 5H), 4.65 (m, 1H), 4.20 (brs, 1H), 3.52-3.45 (m, 2H), 3.40 (m, 1H), 3.22-3.09 (m, 3H), 3.03-2.97 (m, 1H) |
| I-58C[f] | 3-((S)-1-amino-3-cyclohexylpropan-2-ylamino)-4-(3-((3-methoxypropoxy)(phenyl)methyl)piperidin-1-yl)cyclobut-3-ene-1,2-dione | 26 | 1.48 | 498 | 7.38-7.24 (m, 5H), 4.66 (m, 1H), 4.24 (m, 1H), 3.53-3.35 (m, 3H), 3.30 (3H), 3.22-3.07 (m, 3H), 2.99 (m, 1H) |
| I.58D[g] | 3-((S)-1-amino-3-cyclohexylpropan-2-ylamino)-4-(3-((3-methoxypropoxy)(phenyl)methyl)piperidin-1-yl)cyclobut-3-ene-1,2-dione | 28 | 1.46 | 498 | 2.95 (m), 3.30 (s), 4.05 (m), 7.10-7.50 (m) |
| I-59A[c] | 3-((S)-1-amino-3-cyclohexylpropan-2-ylamino)-4-(2-((3-methoxypropoxy)(phenyl)methyl)morpholino)cyclobut-3-ene-1,2-dione | 28 | 1.37 | 500 | 1.80 (m), 3.30 (s), 3.70 (m), 3.89 (br d), 4.65 (m), |
| I-60A | 4-(3-((3-methoxypropoxy)(phenyl)methyl)piperidin-1-yl)-N-((S)-1-amino-3-cyclohexylpropan-2-yl)-1,2,5-thiadiazol-3-amine | 39 | 1.87 | 503 | 1.77 (m), 2.70 (m), 3.25 (s), 3.43 (m), 4.10 (m), 7.2-7.4 (m) |
| I-61A | 3-((3-methoxypropoxy)(phenyl)methyl)-N-(1-(butylamino)-3-cyclohexylpropan-2-yl)piperidine-1-carboxamide | 30 | 1.75 | 502 | 0.95 (m). 1.20 (m), 1.40 (m), 2.90 (m), 3.80 (m), 4.1 (m) 7.20-7.50 (m) |
| I-62A | 3-((3-methoxypropoxy)(phenyl)methyl)-N-(3-cyclohexyl-1-(isobutylamino)propan-2-yl)piperidine-1-carboxamide | 30 | 1.74 | 502 | 1.10 (m), 2.10 (m), 3.80 (m), 4.1 (m) 7.20-7.50 (m) |
| I-63A | (3R)—N-((S)-3-cyclohexyl-1-(dimethylamino)propan-2-yl)-3-((R)-5-ethoxy-1-hydroxy-1-phenylpentyl)piperidine-1-carboxamide | 30 | 1.59 | 502 | |
| I-64A | (3R)-3-((S)-1-(3-chlorophenyl)-1-hydroxy-5-methoxypentyl)-N-((S)-3-cyclohexyl-1-(methylamino)propan-2-yl)piperidine-1-carboxamide | 33 | 1.55 | 508 | 7.43 (s, 1H), 7.32-7.25 (m, 2H), 7.22 (dd, 1H), 4.31 (d, 1H), 4.15 (m, 1H), 3.97 (d, 1H), 3.25 (s, 3H), 3.08-2.95 (m, 2H), 2.67 (s, 3H), 2.52 (m, 2H). |
| I-65A | 3-((3-ethoxypropoxy)(3,4-difluorophenyl)methyl)-N-((S)-3-cyclohexyl-1-(methylamino)propan-2-yl)piperidine-1-carboxamide | 33 | 1.77 | 510 | 2.63 (m), 3.24 (m), 3.27 (m), 3.37 (m), 4.23 (m), 4.36 (m), 7.04-7.24 (m) |
| I-65A | (3R)—N-((S)-3-cyclohexyl-1-(methylamino)propan-2-yl)-3-((S)-1-(2,5-difluorophenyl)-1-hydroxy-5- | 33 | | 510 | 271 (s, 3H), 2.92 (dd, 1H), 3.06 (dd), 3.25 (s, 3H), 3.98 (br d, 1H), 4.12 9m, 1H), 4.31 (br d, 1H), 7.01 (m, 2H), 7.31 (m, |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | methoxypentyl)piperidine-1-carboxamide | | | | 1H) |
| I-67A[b] | (3R)—N-((S)-3-(4,4-difluorocyclohexyl)-1-(methylamino)propan-2-yl)-3-((S)-1-hydroxy-5-methoxy-1-phenylpentyl)piperidine-1-carboxamide | 33 | | 510 | 2.31 (t, 1H), 2.53 (t, 1H), 2.76 (s, 3H), 2.89 (m, 1H), 3.29 (s, 3H), 3.31 (t, 1H), 3.75 (br d, 1H), 4.24 (m, 2H), 6.16 (m, 1H) |
| I-68A | (3R)—N-((S)-3-cyclohexyl-1-(methylamino)propan-2-yl)-3-((S)-1-(3,4-difluorophenyl)-1-hydroxy-5-methoxypentyl)piperidine-1-carboxamide | 33 | | 510 | 2.55 (t, 3H), 2.79 (s, 3H), 2.91 (m, 1H), 3.28 (s, 3h), 3.31 (t, 1H), 3.78 (br d, 1H), 4.27 (m, 2H), 6.11 (m, 1H), 7.32 (m, 3H) |
| I-69A | 3-((S)-1-amino-3-cyclohexylpropan-2-ylamino)-4-(3-(1-hydroxy-1-phenylheptyl)piperidin-1-yl)cyclobut-3-ene-1,2-dione | 28 | 1.71 | 510 | 7.26-7.08 (m), 4.52 (m), 3.01-2.87 (m), 1.90-0.70 (m) |
| I-70A[b] | 3-((2S,3S)-3-amino-1-cyclohexylbutan-2-ylamino)-4-(3-((3-methoxypropoxy)(phenyl)methyl)piperidin-1-yl)cyclobut-3-ene-1,2-dione | 24 | | 512 | 4.68 (m), 4.21 (m), 3.55-3.05 (m, 8H), 3.32 (s, 3H), 2.05-0.75 (m, 21H) |
| I-70B[b] | 3-((2S,3R)-3-amino-1-cyclohexylbutan-2-ylamino)-4-(3-((3-methoxypropoxy)(phenyl)methyl)piperidin-1-yl)cyclobut-3-ene-1,2-dione | 25 | | 512 | 4.68 (m, 3H), 4.21 (m, 1H), 3.55-3.10 (m, 8H), 3.32 (s, 3H), 1.95-0.80 (m, 21H) |
| I-71A | 3-(3-((3-methoxypropoxy)(phenyl)methyl)piperidin-1-yl)-4-(N-((S)-1-amino-3-cyclohexylpropan-2-yl)-N-methylamino)cyclobut-3-ene-1,2-dione | 28 | 1.5 | 512 | 2.75 (m), 3.30 (s), 3.50 (s), 4.20 (m), 7.20-7.50 (m) |
| I-72A | (3R)-3-((S)-1-(2-(p-tolyloxy)-5-methylphenyl)-1-hydroxy-5-methoxypentyl)-N-((S)-1-(methylamino)propan-2-yl)piperidine-1-carboxamide + ~10% of alcohol epimer | 33 | 1.57 | 512 | 1.18 (d), 2.32 (s), 2.34 (s), 2.64 (s), 3.24 (s), 3.86 (d), 4.0 (m), 4.36 (d), 6.60 (d), 6.78 (d), 6.98 (dd), 7.14 (d), 7.42 (d) |
| I-73A | 3-((S)-3-cyclohexyl-1-(methylamino)propan-2-ylamino)4-(3-((3-methoxypropoxy)(phenyl)methyl)piperidin-1-yl)cyclobut-3-ene-1,2-dione | 28 | 1.53 | 512 | 2.80 (s), 3.38 (s), 4.05 (br m), 7.20-7.50 (m) |
| I-74A | 3-((3-methoxypropoxy)(2-(trifluoromethyl)phenyl)methyl)-N-((S)-1-amino-3-cyclohexylpropan-2-yl)piperidine-1-carboxamide | 33 | 1.71 | 514 | 0.8-1.9 (m), 2.8 (m), 3.28 (s), 4.03 (m), 4.40 (m), 4.56 (m), 7.48 (m), 7.70 (m) |
| I-75A | 3-((S)-1-amino-3-cyclohexylpropan-2-ylamino)-4-(3-((3-methoxypropoxy)(4-fluorophenyl)methyl)piperidin-1-yl)cyclobut-3-ene-1,2-dione | 26 | 1.49 | 516 | 0.9 (m), 3.34 (s), 4.02 (m), 4.67 (m), 7.12 (m), 7.30 (m) |
| I-76A | 3-((S)-1-amino-3-cyclohexylpropan-2-ylamino)-4-(3-((3-methoxypropoxy)(2-fluorophenyl)methyl)piperidin-1-yl)cyclobut-3-ene-1,2-dione | 23 | 1.48 | 516 | 0.9-2.1 (m), 3.0 (m), 3.14 (m), 3.36 (s), 3.52 (m), 4.44 (d), 4.64 (m), 7.12 (t), 7.24 (t), 7.36 (m), 7.41 (m) |
| I-77A | 3-((3-methoxypropoxy)(phenyl)methyl)-N-(3-cyclohexyl-1-(isopentylamino)propan-2-yl)piperidine-1-carboxamide | 30 | 1.83 | 516 | 0.90 (m), 1.80 (m), 3.30 (s), 4.17 (br m), 7.20-7.60 (m) |
| I-78A[b] | 3-((3-methoxypropoxy)(phenyl)methyl)-N-(3-cyclohexyl-1-(pentylamino)propan-2-yl)piperidine-1-carboxamide | 30 | 1.83 | 516 | 0.95 (m), 1.20 (m), 1.35-1.45 (m), 2.90 (m), 3.80 (m), 4.1 (m) 7.20-7.50 (m) |
| I-79A[b] | (3R)—N-((S)-3-cyclohexyl-1-(methylamino)propan-2-yl)-3-((S)-1-hydroxy-1-(3-isopropylphenyl)-5-methoxypentyl)piperidine-1-carboxamide | 33 | | 516 | 1.25 (d, 6H), 2.51 (t, 1H), 2.81 (s, 3H), 3.27 (s, 3H), 3.31 (t, 1H), 3.75 (br d, 1H), 4.23 (m, 2H), 6.06 (br s, 1H), 7.12 (m 3H), 7.23 (t, 1H) |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-80A | (3R)-3-((R)-1-(3-chlorophenyl)-4,4,4-trifluoro-1-hydroxybutyl)-N-((S)-3-cyclohexyl-1-(methylamino)propan-2-yl)piperidine-1-carboxamide | 33 | 1.72 | 518 | 0.91 (m), 1.03 (m), 2.49 (t), 2.58 (q), 2.71 (s), 2.93 (t), 3.07 (ap d), 3.30-3.33 (m), 3.84 (d), 3.96 (d) 4.13 (m), 4.33 (d), 4.48 (d), 7.29 (m), 7.34 (m), 7.46 (ap s) |
| I-81A | (3R)-3-((S)-1-(5-chloro-2-phenoxyphenyl)-1-hydroxy-5-methoxypentyl)-N-((S)-1-(methylamino)propan-2-yl)piperidine-1-carboxamide + ~10% of alcohol epimer | 33 | 1.53 | 518 | 1.18 (m), 2.64 (s), 3.24 (s), 3.85 (d), 4.06 (m), 4.38 (d), 6.66 (d), 6.94 (d), 7.14 (m), 7.38 (dd), 7.64 (d) |
| I-82A | (3R)-3-(1-(3-chlorophenyl)-5-cyclopropyl-1-hydroxypentyl)-N-((S)-3-cyclohexyl-1-(methylamino)propan-2-yl)piperidine-1-carboxamide | 33 | 1.95 | 518 | −.0.84 (m), 0.33 (,), 0.57 (m), 2.53 (t), 2.68 (s), 2.91 (m), 3.04 (s), 3.29 (m), 3.47 (m), 3.96 (d), 4.11 (m), 4.27 (d), 7.20-7.31 (m), 7.41 (ap s) |
| I-83A | 3-((3-methoxypropoxy)(2-phenylphenyl)methyl)-N-((S)-2-amino-3-cyclohexylpropyl)piperidine-1-carboxamide | 127 | 1.72 | 522 | 0.94 (m), 2.31 (m), 2.49 (m), 2.65 (m), 3.30 (m), 7.16-7.78 (m) |
| I-84A | 3-((3-methoxypropoxy)(2-(2-cyclopropylethynyl)phenyl)methyl)-N-((S)-3-cyclohexyl-1-(methylamino)propan-2-yl)piperidine-1-carboxamide | 33 | 1.87 | 524 | 2.67 (m), 3.02 (m), 3.30 (m), 3.41-3.49 (m), 3.79 (d), 3.95 (m), 4.07 (m), 4.18 (d), 4.33 (d), 4.59 (m), 7.27 (m), 7.34 (m) |
| I-85A | 3-(3-cyclohexyl-1-(ethylamino)propan-2-ylamino)-4-(3-((3-methoxypropoxy)(phenyl)methyl)piperidin-1-yl)cyclobut-3-ene-1,2-dione | 28 | 1.55 | 526 | 1.30 (m), 3.00-3.20 (m), 3.30 (s), 4.10 (m), 7.02-7.45 (m) |
| I-86A | (3R)-3-((S)-1-hydroxy-5-methoxy-1-(2-phenoxyphenyl)pentyl)-N-((S)-4-methyl-1-(methylamino)pentan-2-yl)piperidine-1-carboxamide + ~10% of alcohol epimer | 33 | 1.56 | 526 | 0.78 (d), 0.84 (d), 2.64 (s), 3.24 (s), 4.00 (m), 4.26 (d), 6.74 (d), 6.92 (d), 7.1 (m), 7.38 (dd), 7.64 (d) |
| I-86B | (3R)-3-((S)-1-hydroxy-5-methoxy-1-(2-phenoxyphenyl)pentyl)-N-((S)-4-methyl-1-(methylamino)pentan-2-yl)piperidine-1-carboxamide | 33 | 1.56 | 526 | 0.78 (d), 0.84 (d), 2.64 (s), 3.24 (s), 4.00 (m), 4.26 (d), 6.68 (s), 6.74 (d), 6.92 (d), 7.1 (m), 7.38 (dd), 7.64 (d) |
| I-87A | (3R)—N-((S)-1-amino-5-methoxy-4,4-dimethylpentan-2-yl)-3-((S)-1-(2,3-difluorophenyl)-1-hydroxy-5-methoxypentyl)piperidine-1-carboxamide | 33 | 1.38 | 500 | 0.84 (m), 0.98 (s), 1.20-1.64 (m), 1.98 (m), 2.18 (m), 2.64 (m), 2.78 (dd), 2.84 (dd), 2.98 (dd), 3.10 (s), 3.24 (s), 3.30 (m), 3.34 (m), 3.96 (d), 4.12 (m), 4.38 (d), 7.14 (m), 7.36 (m). |
| I-88A[b] | (3R)—N-((S)-3-(4,4-difluorocyclohexyl)-1-(methylamino)propan-2-yl)-3-((S)-1-(3-fluorophenyl)-1-hydroxy-5-methoxypentyl)piperidine-1-carboxamide | 33 | | 528 | 2.54 (t, 1H), 2.81 (s, 3H), 2.89 (m, 1H), 3.28 (s, 3H), 3.32 (t, 1H), 3.73 (br d, 1H), 4.22 (m, 2H), 6.22 (br s, 1H), 6.93 (t, 1H), 7.07 (m, 2H), 7.29 (m, 1H) |
| I-89A | 3-((S)-1-amino-6-cyclohexylpropan-2-ylamino)-4-(3-((3-methoxypropoxy)(2,4-difluorophenyl)methyl)piperidin-1-yl)cyclobut-3-ene-1,2-dione | 28 | 1.43 | 534 | 7.31-7.24 (m), 6.90-6.83 (m), 4.56-4.43 (m), 3.38-2.83 (m), 2.30 (m), 1.79-0.78 (m) |
| I-90A | 3-((S)-1-amino-3-cyclohexylpropan-2-ylamino)-4-(3-((3-methoxypropoxy)(3,4-difluorophenyl)methyl)piperidin-1-yl)cyclobut-3-ene-1,2-dione | 28 | 1.48 | 534 | 7.13-7.07 (m), 4.55 (m), 4.38-4.35 (m), 3.44-2.86 (m), 1.93-0.78 (m) |
| I-91A | (3R)—N-((S)-1-(carbamoylmethylamino)-3-cyclohexylpropan-2-yl)-3-((S)-1-(3-fluorophenyl)-1-hydroxy-5-methoxypentyl)piperidine-1-carboxamide | 33 | 1.51 | 535 | 0.9-2.0 (m), 2.58 (m), 2.98 (m), 3.16 (m), 3.24 (s), 3.80 (d), 3.86 (d), 3.94 (d), 4.14 (m), 4.32 (d), 6.96 (m), 7.16 (m), 7.32 (m) |
| I-92A | 3-(3-cyclohexyl-1-(propylamino)propan-2-ylamino)-4-(3-((3-methoxypropoxy)(phenyl)methyl)piperidin-1-yl)cyclobut-3-ene-1,2-dione | 28 | 1.57 | 540 | 0.90 (m), 1.45 (m), 2.95 (m), 3.30 (s), 4.10 (m), 7.20-7.40 (m) |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-93A[b] | (3R)—N-((S)-3-cyclohexyl-1-(methylamino)propan-2-yl)-3-((S)-1-(3-(trifluoromethyl)phenyl)-1-hydroxy-5-methoxypentyl)piperidine-1-carboxamide | 33 | | 542 | 2.55 (t, 1H), 2.82 (s, 3H), 3.29 (s, 3H), 3.32 (t 1H), 3.72 (br d, 1H), 4.25 (m, 2H), 6.05 (s, 1H), 7.43 (m, 1H), 7.50 (m, 2H), 7.64 (s, 1H) |
| I-93A | (3R)—N-((S)-3-cyclohexyl-1-(methylamino)propan-2-yl)-3-(1-(3-(trifluoromethyl)phenyl)-1-hydroxy-5-methoxypentyl)piperidine-1-carboxamide | 33 | | 542 | 2.71 (s), 2.72 (s), 3.26 (s), 3.84 (br d), 3.96 (br d), 4.12 (br d), 4.33 (br d), 4.48 (br d) |
| I-94A | 3-(3-cyclohexyl-1-(isobutylamino)propan-2-ylamino)-4-(3-((3-methoxypropoxy)(phenyl)methyl)piperidin-1-yl)cyclobut-3-ene-1,2-dione | 28 | 1.6 | 554 | 1.01 (m), 2.05 (m), 2.95 (m), 3.30 (s), 4.01 (m), 7.02-7.45 (m) |
| I-95A | 3-(3-(butylamino)-1-cyclohexylpropan-2-ylamino)-4-(3-((3-methoxypropoxy)(phenyl)methyl)piperidin-1-yl)cyclobut-3-ene-1,2-dione | 28 | 1.66 | 554 | 0.90 (m), 1.33 (m), 1.45 (m), 2.90 (m), 3.30 (s), 4.10 (m), 7.20-7.40 (m) |
| I-96A | (3R)-3-((S)-1-(2-(p-tolyloxy)-5-methylphenyl)-1-hydroxy-5-methoxypentyl)-N-((S)-4-methyl-1-(methylamino)pentan-2-yl)piperidine-1-carboxamide + ~10% of alcohol epimer | 33 | 1.74 | 554 | 0.78 (d), 0.84 (d), 2.32 (s), 2.34 (s), 2.64 (s), 3.24 (s), 4.0 (m), 4.24 (d), 6.58 (d), 6.78 (d), 6.96 (dd), 7.16 (d), 7.42 (d) |
| I-97A | (3R)-3-((S)-1-(5-chloro-2-phenoxyphenyl)-1-hydroxy-5-methoxypentyl)-N-((S)-4-methyl-1-(methylamino)pentan-2-yl)piperidine-1-carboxamide + ~10% of alcohol epimer | 33 | 1.67 | 560 | 0.78 (d), 0.82 (d), 1.2-1.7 (m), 2.62 (s), 3.24 (s), 4.0 (m), 4.24 (d), 6.64 (d), 6.94 (d), 7.16 (m), 7.38 (dd), 7.64 (d) |
| I-98A | 3-(3-cyclohexyl-1-(methylamino)propan-2-ylamino)-4-(3-((3-ethoxypropoxy)(3,4-difluorophenyl)methyl)piperidin-1-yl)cyclobut-3-ene-1,2-dione | 28 | 1.67 | 562 | 1.05 (t), 2.75 (m), 3.35 (m), 3.38 (s), 4.10 (d), 7.00-7.40 (m) |
| I-99A | 3-((S)-1-amino-3-cyclohexylpropan-2-ylamino)-4-(3-((3-methoxypropoxy)(2-(trifluoromethyl)phenyl)methyl)piperidin-1-yl)cyclobut-3-ene-1,2-dione | 26 | 1.61 | 566 | 0.9-2.1 (m), 3.35 (s), 4.46 (m), 4.65 (m), 7.52 (t), 7.71 (m) |
| I-100A | (3R)—N-((S)-3-cyclohexyl-1-(methylamino)propan-2-yl)-3-((S)-1-hydroxy-5-methoxy-1-(2-phenoxyphenyl)pentyl)piperidine-1-carboxamide + ~10% of alcohol epimer | 33 | 1.72 | 566 | 0.8-1.7 (m), 1.98 (m), 2.64 (s), 3.24 (s), 4.0 (m), 4.26 (d), 6.68 (d), 6.92 (d), 7.1 (m), 7.36 (dd), 7.62 (d) |
| I-101A | 3-(1-cyclohexyl-3-(pentylamino)propan-2-ylamino)-4-(3-((3-methoxypropoxy)(phenyl)methyl)piperidin-1-yl)cyclobut-3-ene-1,2-dione | 28 | 1.71 | 568 | 0.90 (m), 1.01 (m), 1.25 (m), 1.50 (m), 2.90 (m), 3.30 (s), 4.10 (m), 7.20-7.40 (m) |
| I-102A | 3-(1-cyclohexyl-3-(isopentylamino)propan-2-ylamino)-4-(3-((3-methoxypropoxy)(phenyl)methyl)piperidin-1-yl)cyclobut-3-ene-1,2-dione | 28 | 1.72 | 568 | 0.90 (m), 1.20 (m), 1.40 (m), 1.80 (m), 3.10 (m), 3.30 (s), 4.10 (m), 7.20-7.50 (m) |
| I-103A | (3R)-3-((S)-1-(2-(p-tolyloxy)-5-methylphenyl)-1-hydroxy-5-methoxypentyl)-N-((S)-cyclohexyl-1-(methylamino)propan-2-yl)piperidine-1-carboxamide + ~10% of alcohol epimer | 33 | 1.87 | 594 | 0.8-1.7 (m), 2.32 (s), 2.34 (s), 2.64 (s), 3.24 (s), 4.0 (m), 4.24 (d), 6.58 (d), 6.78 (d), 6.96 (dd), 7.16 (d), 7.42 (d) |
| I-104A | (3R)-3-((S)-1-(5-chloro-2-phenoxyphenyl)-1-hydroxy-5-methoxypentyl)-N-((S)-3-cyclohexyl-1-(methylamino)propan-2-yl)piperidine-1-carboxamide + ~10% of alcohol epimer | 33 | 1.83 | 600 | 0.8-1.7 (m), 2.64 (s), 3.24 (s), 4.0 (m), 4.24 (d), 6.64 (d), 6.96 (d), 7.16 (m), 7.38 (dd), 7.64 (d) |
| I-105A | N-((S)-3-cyclohexyl-1-(methylamino)propan-2-yl)-3-((pent- | 42 | 1.87 | 449 | 8.33 (d, J = 8.5 Hz, 1H), 7.82-7.13 (m, 9H), 5.75-5.68 (m, 1H), 5.36 (s, 1H), |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | 4-enyloxy)(phenyl)methyl)benzamide | | | | 4.92-4.84 (m, 2H), 4.43-4.40 (m, 1H), 3.39 (t, J = 6.4 Hz, 2H), 3.09-2.93 (m, 2H), 2.61 (s, 3H), 2.10-2.05 (m, 2H), 1.77-0.81 (m, 15H). |
| I-106A | N-((S)-3-cyclohexyl-1-(methylamino)propan-2-yl)-3-(5-methoxy-1-phenylpentyl)benzamide | 130 | 1.67 | 451 | 8.29 (d, J = 8.2 Hz, 1H), 7.71-7.05 (m, 9H), 4.43-4.41 (m, 1H), 3.91 (t, J = 7.9 Hz, 1H), 3.26 (t, J = 6.4 Hz, 2H), 3.18 (s, 3H), 3.10-2.92 (m, 2H), 2.616, 2.613 (s, 3H), 2.06-2.00 (m, 2H), 1.77-0.81 (m, 17H). |
| I-107A | 3-((2-ethoxyethoxy)(phenyl)methyl)-N-((S)-3-cyclohexyl-1-(methylamino)propan-2-yl)benzamide | 42 | 1.65 | 453 | 7.83-7.16 (m, 9H), 5.45, 5.43 (s, 1H), 4.41 (br s, 1H), 2.61, 2.59 (s, 3H). |
| I-108A | 3-(1-(2-(cyclopropylmethoxy)phenyl)-1-hydroxy-5-methoxypentyl)-N-((S)-1-(methylamino)propan-2-yl)piperidine-1-carboxamide | 33 | 1.36 | 462 | 7.39-7.34 (m), 7.07 (t), 6.77 (m), 3.20 (m), 3.13 (s), 2.60 (s), 0.73 (br s), 0.51 (d), 0.23 (m). |
| I-109A | (3R)-3-((S)-1-hydroxy-5-methoxy-1-m-tolylpentyl)-N-((S)-4,4-dimethyl-1-(methylamino)pentan-2-yl)piperidine-1-carboxamide | 33 | 1.49 | 462 | 0.96 (s), 1.00-1.78 (m), 1.92 (m), 2.34 (s), 2.48 (m), 2.70 (s), 2.92 (dd), 3.02 (dd), 3.24 (s), 3.26 (t), 3.98 (d), 4.18 (m), 4.26 (d), 7.02 (d), 7.14 (m), 7.20 (m) |
| I-110A[b] | N-((S)-3-cyclohexyl-1-(methylamino)propan-2-yl)-3-(5-methoxy-1-(thiophen-2-yl)pentyl)piperidine-1-carboxamide | 37 | | 464.3 | 2.03 (m, 1H), 3.28 (s, 3H), 5.14&5.73 (m, 1H), 6.76 (m, 1H), 6.92 (m, 1H), 7.14 (m, 1H), 8.21 (brs, 1H), 9.84 (brs, 1H) |
| I-111A | N-((S)-3-cyclohexyl-1-(methylamino)propan-2-yl)-3-(1,1,1-trifluoro-2-hydroxy-6-methoxyhexan-2-yl)piperidine-1-carboxamide | 33 | 1.42 | 466 | 4.11 (m, 1H), 3.72 (m, 1H), 3.41 (t, 2H), 3.05 (d, 1H), 2.69 (s, 3H), 1.92 (d, 1H), 1.02 (q, 1H), 0.89 (m, 1H) |
| I-112A | 3-((2-acetamidoethoxy)(phenyl)methyl)-N-((S)-1-cyclohexyl-3-(methylamino)propan-2-yl)benzamide | 145 | 1.37 | 466 | 8.34-8.29 (m, 1H), 7.86-7.12 (m, 9H), 5.76 (s, 1H), 5.41 (d, J = 2 Hz, 1H), 4.45-4.38 (m, 1H), 3.45-3.43 (m, 2H), 3.35-3.31 (m, 2H), 3.10-3.06 (m, 1H), 3.00-2.93 (m, 1H), 2.62 (s, 3H), 1.844, 1.839 (s, 3H), 1.77-0.82 (m, 13H). |
| I-113A | (3R)-3-((S)-1-(3-fluorophenyl)-1-hydroxy-5-methoxypentyl)-N-((S)-4,4-dimethyl-1-(methylamino)pentan-2-yl)piperidine-1-carboxamide | 33 | 1.45 | 466 | 0.96 (s), 1.08-1.98 (m), 2.44 (m), 2.64 (s), 2.86 (m), 2.98 (m), 3.24 (s), 3.26 (t), 3.94 (d), 4.14 (m), 4.24 (d), 6.86 (m), 7.08 (m), 7.26 (m) |
| I-114A | N-((S)-3-cyclohexyl-1-(methylamino)propan-2-yl)-3-(1-hydroxy-5-methoxy-1-phenylpentyl)benzamide | 128 | 1.47 | 467 | 8.26 (d, J = 8.2 Hz, 1H), 7.89-7.03 (m, 9H), 4.40-4.38 (m, 1H), 3.23 (t, J = 6.4 Hz, 2H), 3.15 (s, 3H), 3.06-2.91 (m, 2H), 2.584, 2.579 (s, 3H), 2.23 (t, J = 8.2 Hz, 2H), 1.74-0.78 (m, 17H). |
| I-115A | 3-((3-ethoxypropoxy)(phenyl)methyl)-N-((S)-3-cyclohexyl-1-(methylamino)propan-2-yl)benzamide | 42 | 1.74 | 467 | 8.32 (d, J = 7.6 Hz, 1H), 7.82-7.13 (m, 9H), 5.37 (s, 1H), 4.43-4.38 (m, 1H), 3.48-3.44 (m, 4H), 3.37 (q, J = 7.0 Hz, 2H), 3.07 (dd, J = 12.6, 3.2 Hz, 1H), 2.95 (dd, J = 12.4, 10.4 Hz, 1H), 2.61 (s, 3H), 1.05 (t, J = 7.0 Hz, 3H), 1.83-0.81 (m, 15H). |
| I-116A[b] | (3R)-3-((S)-1-(3-chlorophenyl)-1-hydroxy-5-methoxypentyl)-N-((S)-4-methyl-1-(methylamino)pentan-2-yl)piperidine-1-carboxamide | 33 | 1.48 | 469 | 0.92 (m, 6H), 1.2-2.0 (m) 2.53 (s, 3H), 3.8 (m, 1H) 7.2-7.6 (m, 4H) |
| I-117A | (3R)-3-((S)-1-(2,3-difluorophenyl)-1-hydroxy-5-methoxypentyl)-N-((S)-4-methyl-1-(methylamino)pentan-2-yl)piperidine-1-carboxamide | 33 | 1.37 | 470 | 7.23 (m), 7.06-6.96 (m), 4.22 (d), 3.97 (m), 3.83 (d), 3.17 (s), 3.12 (s), 2.94 (d), 2.80 (t), 2.65 (t), 2.60 (s), 2.50 (s), 0.83 (m). |
| I-118A | (3R)-3-((S)-1-(benzofuran-7-yl)-1-hydroxy-5-methoxypentyl)-N-((S)-4-methyl-1-(methylamino)pentan-2-yl)piperidine-1-carboxamide | 33 | 1.32 | 474 | 0.98 (d, 3H), 1.01 (d, 3H), 2.72 (s, 3H), 3.19 (s, 3H), 3.95 (br d, 1H), 4.10 (m, 1H), 4.42 (br d, 1H), 6.86 (d, 1H), 7.21 (m, 1H), 7.43 (d, 1H), 7.52 (d, 1H), 7.69 (d, 1H) |
| I-119A[b] | (3R)—N-((S)-3-cyclohexyl-1-(methylamino)propan-2-yl)-3-((S)-1-hydroxy-5-methoxy-1-(pyridin-2-yl)pentyl)piperidine-1-carboxamide | 121 | | 475.3 | 2.09 (m, 3H), 2.41 (t, 3H), 2.56 (t, 1H), 2.77 (s, 3H), 3.08 (m, 2H), 3.78 (d, 1H), 4.23 (m, 1H), 4.47 (d, 1H), 6.01 (m, 1H), 7.83 (dd, 2H), 8.36 (t, 1H), 8.42 (m, 1H), 8.84 (d, 1H), 9.05 (brs, 1H) |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-120A | (3R)-3-(1-(2-(2-cyclopropylethoxy)phenyl)-1-hydroxy-5-methoxypentyl)-N-((S)-1-(methylamino)propan-2-yl)piperidine-1-carboxamide | 33 | 1.45 | 476 | 7.44-7.36 (m), 7.10 (m), 7.10 (m), 4.40 (d), 4.19 (d), 3.94 (m), 3.84 (d), 3.68 (m), 3.48 (d), 3.21 (m), 3.16 (m), 3.13 (s), 3.00-2.87 (m), 2.61 (s), 2.53 (s), 0.76 (m), 0.41 (q), 0.05 (m). |
| I-121A | (3R)-3-(1-(2-(cyclopentyloxy)phenyl)-1-hydroxy-5-methoxypentyl)-N-((S)-1-(methylamino)propan-2-yl)piperidine-1-carboxamide | 33 | 1.42 | 476 | 7.41 (m), 7.35 (m), 7.06 (m), 6.76 (m), 4.37 (d), 4.17 (d), 4.00 (m), 3.83 (d), 3.69 (m), 3.19 (m), 3.16 (m), 3.12 (s), 2.59 (s), 2.52 (s). |
| I-122A | 3-((3-methoxypropoxy)(phenyl)methyl)-N-((S)-3-cyclohexyl-1-(methylamino)propan-2-yl)piperidine-1-carbothioamide | 124 | 1.73 | 476 | 2.60 (s), 2.63 (s), 3.4 (br m), 4.91 (m), 4.06 (m), 4.25 (br d), 4.33 (br d), 5.08 (br m), 7.18-7.26 (m) |
| I-123A | (3R)—N-((S)-1-amino-3-cyclohexylpropan-2-yl)-3-((S)-1-(3-fluorophenyl)-1-hydroxy-5-methoxypentyl)piperidine-1-carboxamide | 33 | 1.45 | 478 | 7.22-7.16 (m, 1H), 7.03-7.00 (m, 2H), 6.83-6.78 (m, 1H), 4.17 (d, J = 13.2 Hz, 1H), 3.96-3.89 (m, 1H), 3.83 (d, J = 12.9 Hz, 1H), 3.12 (s, 3H), 2.88 (dd, J = 12.7, 3.4 Hz, 1H), 2.71 (dd, J = 12.4, 9.8 Hz, 1H), 2.44-2.32 (m, 2H), 1.89-0.71 (m, 24H). |
| I-124A | (3R)-3-(1-hydroxy-5-methoxy-1-(2-(neopentyloxy)phenyl)pentyl)-N-((S)-1-(methylamino)propan-2-yl)piperidine-1-carboxamide | 33 | 1.48 | 478 | 7.43-7.36 (m), 7.09 (m), 6.80, (m), 3.19 (m), 3.10 (m), 2.59 (s), 2.51 (s), 0.96 (m). |
| I-125A[b] | (3R)—N-((S)-3-cyclohexyl-1-(methylamino)propan-2-yl)-3-((S)-1-hydroxy-5-methoxy-1-(1-methyl-1H-imidazol-2-yl)pentyl)piperidine-1-carboxamide | 121 | | 478.3 | 2.17 (s, 3H), 2.25 (m, 1H), 2.97 (m, 1H), 3.18 (m, 1H), 3.30 (s, 3H), 3.41 (m, 1H), 3.69 (m, 1H), 4.02 (m, 2H), 4.32 (m, 1H), 5.78 (m, 1H), 6.94 (m, 1H), 7.33 (m, 1H), 8.38 (brs, 1H), 9.10 (brs, 1H) |
| I-126A[b] | (3R)—N-((S)-3-cyclohexyl-1-(methylamino)propan-2-yl)-3-((S)-1-hydroxy-5-methoxy-1-(thiophen-2-yl)pentyl)piperidine-1-carboxamide | 121 | | 480.2 | 0.92 (m, 5H), 2.85 (m, 3H), 3.18 (m, 2H), 3.26 (s, 3H), 4.05 (m, 2H), 4.23 (m, 3H), 6.78 (m, 1H), 7.00 (m, 1H), 7.52 (m, 1H), 7.70 (m, 1H) |
| I-127A[b] | (3R)—N-((S)-3-cyclohexyl-1-(methylamino)propan-2-yl)-3-((S)-1-hydroxy-5-methoxy-1-(thiophen-3-yl)pentyl)piperidine-1-carboxamide | 121 | | 480.3 | 2.53 (m, 2H), 2.78 (s, 3H), 3.28 (s, 3H), 3.68 (m, 1H), 4.12 (m, 1H), 4.32 (m, 2H), 6.18 (m, 1H), 6.77 (m, 1H), 6.97 (m, 1H), 7.18 (m, 1H) |
| I-128A | N-((S)-3-cyclohexyl-1-(methylamino)propan-2-yl)-3-(1-hydroxy-5-methoxy-1-m-tolylpentyl)benzamide | 129 | 1.62 | 481 | 8.25 (d, J = 8.8 Hz, 1H), 7.92-6.92 (m, 8H), 4.44-4.41 (m, 1H), 3.28 (t, J = 6.4 Hz, 2H), 3.20 (s, 3H), 3.11-2.93 (m, 2H), 2.635 2.628 (s, 3H), 2.26 (t, J = 8.0 Hz, 2H), 2.21 (s, 3H), 1.78-0.82 (m, 17H). |
| I-129A | N-((S)-3-cyclohexyl-1-(methylamino)propan-2-yl)-3-(1-hydroxy-5-methoxy-1-o-tolylpentyl)benzamide | 129 | 1.61 | 481 | 8.24 (d, J = 8.4 Hz, 1H), 7.79-6.96 (m, 8H), 4.42-4.39 (m, 1H), 3.27 (t, J = 6.4 Hz, 2H), 3.20 (s, 3H), 3.10-2.95 (m, 2H), 2.635, 2.622 (s, 3H), 2.35-2.16 (m, 2H), 1.90 (s, 3H), 1.75-0.82 (m, 17H). |
| I-130A[b] | (3R)—N-((S)-3-cyclohexyl-1-(methylamino)propan-2-yl)-3-((S)-1-hydroxy-5-methoxy-1-(thiazol-2-yl)pentyl)piperidine-1-carboxamide | 33 | | 481.3 | 2.17 (m, 2H), 3.28 (s, 3H), 3.75 (m, 1H), 4.27 (m, 2H), 6.07 (m, 1H), 7.76 (m, 1H), 9.10 (brs, 1H), 9.73 (brs, 1H) |
| I-131A | (3R)-3-((S)-1-(2-(3-methylphenyl)phenyl)-1-hydroxy-5-methoxypentyl)-N-((S)-1-(methylamino)propan-2-yl)piperidine-1-carboxamide | 121 | | 482.3 | 0.92 (m, 1H), 1.14 (m, 3H), 1.26 (m, 4H), 1.45 (m, 2H), 1.59 (m, 3H), 1.74 (m, 1H), 2.35 (s, 3H), 2.56 (m, 1H), 2.68 (s, 3H), 2.74 (m, 1H), 2.91 (m, 1H), 3.03 (m, 1H), 3.26 (m, 3H), 3.95 (m, 3H), 6.95 (m, 3H), 7.19 (m, 3H), 7.32 (t, 1H), 7.72 (d, 1H) |
| I-132A | (3R)-3-((S)-1-(2-(4-methylphenyl)phenyl)-1-hydroxy-5-methoxypentyl)-N-((S)-1-(methylamino)propan-2-yl)piperidine-1-carboxamide | 121 | | 482.3 | 0.92 (m, 1H), 1.14 (d, 3H), 2.36 (s, 3H), 2.55 (m, 1H), 2.68 (s, 3H), 2.73 (m, 1H), 2.90 (m, 1H), 3.04 (m, 1H), 3.94 (m, 3H), 6.92 (m, 1H), 6.95-7.24 (m, 5H), 7.32 (t, 1H), 7.72 (m, 1H) |
| I-133A | (3R)-3-((S)-1-(2-(2-methylphenyl)phenyl)-1-hydroxy-5-methoxypentyl)-N-((S)-1-(methylamino)propan-2-yl)piperidine-1-carboxamide | 121 | | 482.3 | 0.94 (m, 1H), 1.15 (d, 3H), 1.30 (m, 3H), 2.58 (m, 1H), 2.68 (s, 3H), 2.75 (m, 1H), 2.94 (m, 1H), 3.01 (m, 1H), 3.26 (m, 3H), 3.87 (m, 1H), 4.02 (m, 2H), 6.96 (m, 1H), 7.10-7.28 (m, 4H), 7.35 (m, 2H), 7.74 (m, 1H) |
| I-134A | (3R)-3-((S)-1-(3-chlorophenyl)-1-hydroxy-5-methoxypentyl)-N-((S)-4,4-dimethyl-1- | 33 | 1.52 | 482 | 0.98 (s), 1.10-1.78 (m), 1.92 (m), 2.48 (m), 2.68 (s), 2.92 (dd), 3.02 (dd), 3.24 (s), 3.26 (t), 3.98 (d), 4.18 (m), 4.28 (d), |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | (methylamino)pentan-2-yl)piperidine-1-carboxamide | | | | 7.22-7.34 (m), 7.42 (s) |
| I-135A | (3R)-3-((S)-1-(2,3-difluorophenyl)-1-hydroxy-5-methoxypentyl)-N-((S)-4,4-dimethyl-1-(methylamino)pentan-2-yl)piperidine-1-carboxamide | 33 | 1.44 | 484 | 7.24 (m) 7.03 (m), 4.23 (d), 4.08 (t), 3.88 (d), 3.19 (s), 3.4 (s), 2.59 (s), 0.87 (s). |
| I-136A | (R)-3-((S)-1-(2-(o-tolyloxy)phenyl)-1-hydroxy-5-methoxypentyl)-N-(2-aminoethyl)-N-methylpiperidine-1-carboxamide | 33 | 1.5 | 484 | 7.65 (dd, 1H), 7.28 (d, 1H), 7.16 (td, 2H), 7.08-7.03 (m, 2H), 6.73 (d, 1H), 6.57 (d, 1H), 4.01 (d, 1H), 3.38 (td, 2H), 3.24 (s, 3H), 3.09 (t, 2H), 2.87 (s, 3H), 2.24 (s, 3H), 0.96 (m, 1H). |
| I-137A | N-((S)-3-cyclohexyl-1-(methylamino)propan-2-yl)-3-(1-(3-fluorophenyl)-1-hydroxy-5-methoxypentyl)benzamide | 129 | 1.54 | 485 | 829-6.80 (m, 9H), 4.40 (br s, 1H), 3.17 (s, 3H), 2.61 (s, 3H). |
| I-138A | N-((S)-3-cyclohexyl-1-(methylamino)propan-2-yl)-3-(1-(4-fluorophenyl)-1-hydroxy-5-methoxypentyl)benzamide | 129 | 1.53 | 485 | 828-6.87 (m, 9H), 4.43-4.39 (m, 1H), 3.17 (s, 3H), 2.61 (s, 3H). |
| I-139A[b] | (3R)-3-((S)-1-hydroxy-5-methoxy-1-(quinolin-8-yl)pentyl)-N-((S)-4-methyl-1-(methylamino)pentan-2-yl)piperidine-1-carboxamide | 119 | | 485.3 | 0.85 (t, 6H), 2.06 (m, 2H), 2.30 (m, 3H), 2.70 (s, 3H), 2.99 (m, 1H), 3.14 (m, 1H), 3.22 (s, 3H), 3.85 (m, 1H), 4.16 (m, 1H), 4.43 (m, 1H), 6.16 (m, 1H), 7.70 (d, 1H), 7.80 (t, 1H), 7.99 (d, 1H), 8.70 (d, 1H), 8.80 (m, 1H), 9.14 (m, 1H), 9.28 (m, 1H) |
| I-140A | (3R)-3-((S)-1-(2-(2-fluorophenyl)phenyl)-1-hydroxy-5-methoxypentyl)-N-((S)-1-(methylamino)propan-2-yl)piperidine-1-carboxamide | 121 | | 486.3 | 0.95 (m, 3H), 1.15 (d, 3H), 2.56 (m, 1H), 2.68 (s, 3H), 2.74 (m, 1H), 2.92 (m, 1H), 3.05 (m, 1H), 3.25 (m, 3H), 3.86 (m, 1H), 4.03 (m, 2H), 6.98 (m, 1H), 7.20 (m, 4H), 7.37 (m, 2H), 7.75 (m, 1H) |
| I-141A[b] | (3R)-3-((S)-1-(3-fluoro-2-phenylphenyl)-1-hydroxy-5-methoxypentyl)-N-((S)-1-(methylamino)propan-2-yl)piperidine-1-carboxamide | 121 | | 486.2 | 1.05 (m, 1H), 1.22 (d, 3H), 1.48 (m, 2H), 1.69 (m, 4H), 2.55 (m, 1H), 2.70 (s, 3H), 2.95 (m, 1H), 3.15 (m, 1H), 3.28 (s, 3H), 3.32 (m, 2H), 3.71 (m, 1H), 3.86 (m, 1H), 4.18 (m, 1H), 5.62 (m, 1H), 7.03 (t, 1H), 7.12-7.48 (m, 7H), 8.58 (brs, 1H), 9.50 (brs, 1H) |
| I-142A | (3R)-3-((S)-1-(2-(3-fluorophenyl)phenyl)-1-hydroxy-5-methoxypentyl)-N-((S)-1-(methylamino)propan-2-yl)piperidine-1-carboxamide | 121 | | 486.3 | 1.16 (d, 3H), 1.78 (m, 1H), 2.58 (m, 1H), 2.68 (s, 3H), 3.00 (m, 3H), 3.28 (s, 3H), 3.97 (m, 1H), 4.03 (m, 2H), 6.73-7.12 (m, 4H), 7.23 (m, 1H), 7.35 (m, 2H), 7.71 (m, 1H) |
| I-143A | (3R)-3-((S)-1-(2-(4-fluorophenyl)phenyl)-1-hydroxy-5-methoxypentyl)-N-((S)-1-(methylamino)propan-2-yl)piperidine-1-carboxamide | 121 | | 486.2 | 1.15 (m, 3H), 1.76 (m, 1H), 2.53 (m, 1H), 2.57 (s, 3H), 2.97 (m, 2H), 3.28 (m, 3H), 3.86 (m, 1H), 4.03 (m, 3H), 6.94 (m, 1H), 7.07-7.23 (m, 5H), 7.31 (m, 1H), 7.71 (m, 1H) |
| I-144A | (3R)-3-((S)-1-hydroxy-5-methoxy-1-(2-methylbenzofuran-7-yl)pentyl)-N-((S)-4-methyl-1-(methylamino)pentan-2-yl)piperidine-1-carboxamide | 33 | 1.36 | 488 | 0.98 (d, 3H), 1.01 (d, 3H), 2.42 (s, 3H), 3.72 (s, 3H), 3.20 (s, 3H), 3.96 (br d, 1H), 4.08 (m, 1H), 4.39 (br, d), 6.43 (s, 1H), 7.14 (m, 1H), 7.30 (d, 1H), 7.37 (d, 1H) |
| I-145A | (3R)-3-((S)-1-hydroxy-1-(2-isobutylbenzofuran-7-yl)-5-methoxypentyl)-N-((S)-1-(methylamino)propan-2-yl)piperidine-1-carboxamide | 33 | 1.47 | 488 | 0.98 (m, 6H), 1.24 (d, 3H), 2.70 (s, 3H), 3.20 (s, 3H), 0.93 (br d, 1H), 4.10 (m, 1H), 4.40 (br d, 1H), 6.43 (s, 1H), 7.14 (m, 1H), 7.32 (d, 1H), 7.38 (d, 1H) |
| I-146A | N-((S)-3-cyclohexyl-1-(methylamino)propan-2-yl)-3-(1-hydroxy-5-methoxy-1-phenylpentyl)-3-methylpiperidine-1-carboxamide | 33 | 1.59 | 488 | 7.41 (t, 2H), 7.34-7.28 (m, 2H), 7.24-7.18 (m, 1H), 4.16-3.96 (m, 2H), 3.80 (t, 1H), 3.26 (s, 3H), 2.25 (m, 1H). |
| I-147A | (3R)-3-(1-(2-(cyclopentylmethoxy)phenyl)-1-hydroxy-5-methoxypentyl)-N-((S)-1-(methylamino)propan-2-yl)piperidine-1-carboxamide | 33 | 1.49 | 490 | 7.36 (m), 7.10 (m), 6.80 (m), 3.19 (m), 3.11 (s), 2.59 (s), 2.51 (s). |
| I-148A | (3S)—N-((S)-3-cyclohexyl-1-(methylamino)propan-2-yl)-3-((R)-1-(2-fluoro-5-methylphenyl)-5-methoxypentyl)piperidine-1-carboxamide | 37 | 1.79 | 490 | 6.93-6.78 (m, 3H), 4.07-4.00 (m, 2H), 3.78 (d, J = 13.5 Hz, 1H), 3.19 (t, J = 6.4 Hz, 2H), 3.15 (s, 3H), 2.96 (dd, J = 12.4, 3.4 Hz, 1H), 2.81 (dd, J = 12.6, 10.2 Hz, 1H), 2.71-2.59 (m, 2H), 2.61 (s, 3H), 2.20 (s, 3H), 1.82-0.79 (m, 25H). |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-149A | (3R)-3-((S)-1-(benzo[b]thiophen-7-yl)-1-hydroxy-5-methoxypentyl)-N-((S)-4-methyl-1-(methylamino)pentan-2-yl)piperidine-1-carboxamide | 33 | 1.47 | 490 | 7.72 (d, 1H), 7.49 (d, 1H), 7.36-7.26 (m, 3H), 4.36 (d, 1H), 4.09 (m, 1H), 3.93 (d, 1H), 3.25 (t, 2H), 3.20 (s, 3H), 3.07 (dd, 1H), 2.93 (dd, 1H), 2.71 (s, 3H), 1.75 (m, 1H), 0.97 (dd, 6H). |
| I-151A[b] | (3R)—N-((S)-3-cyclohexyl-1-(methylamino)propan-2-yl)-3-((S)-1-(2-fluorophenyl)-1-hydroxy-5-methoxypentyl)piperidine-1-carboxamide | 33 | | 492.3 | 2.33 (m, 2H), 2.66 (m, 2H), 2.77 (s, 3H), 2.95 (m, 1H), 3.28 (s, 3H), 4.20 (m, 2H), 5.94 (m, 1H), 6.96 (m, 1H), 7.13 (t, 1H), 7.24 (m, 1H), 7.56 (dd, 1H), 8.87 (brs, 1H), 9.83 (brs, 1H) |
| I-152A[b] | (3R)-3-((R)-(3-ethoxypropoxy)(3-fluorophenyl)methyl)-N-((S)-3-cyclohexyl-1-(methylamino)propan-2-yl)piperidine-1-carboxamide | 33 | | 492 | 1.15 (m, 3H), 1.80 (t, 2H), 3.77 (d, 1H), 3.91 (d, 1H), 4.06 (d, 1H), 4.20 (s, 1H), 5.65 (s, 1H), 6.97 (m, 3H), 7.30 (m, 1H), 8.70 (brs, 1H), 9.59 (brs, 1H) |
| I-153A | (3R)—N-((S)-1-amino-3-cyclohexylpropan-2-yl)-3-((S)-1-(3-chlorophenyl)-1-hydroxy-5-methoxypentyl)piperidine-1-carboxamide | 33 | 1.53 | 494, 496 | 7.32 (m, 1H), 7.22-7.10 (m, 3H), 4.20 (d, J = 12.9 Hz, 1H), 3.99-3.92 (m, 1H), 3.86 (d, J = 13.2 Hz, 1H), 3.15 (s, 3H), 2.91 (dd, J = 12.7, 3.4 Hz, 1H), 2.74 (dd, J = 12.4, 9.8 Hz, 1H), 2.48-2.40 (m, 2H), 1.92-0.74 (m, 24H). |
| I-154A | (3R)-3-((R)-(3-ethoxypropoxy)(3-chlorophenyl)methyl)-N-((S)-1-amino-3-cyclohexylpropan-2-yl)piperidine-1-carboxamide | 33 | 1.73 | 494 | 7.36-7.29 (m, 3H), 7.20 (dd, 1H), 4.27 (d, 1H), 4.03 (m, 1H), 3.00 (dd, 1H), 2.84-2.74 (m, 2H), 1.12 (t, 3H), 1.02 (m, 1H), 0.93 (m, 1H) |
| I-155A | (3R)-3-((S)-1-(3-chlorophenyl)-1,5-dihydroxypentyl)-N-((S)-3-cyclohexyl-1-(methylamino)propan-2-yl)piperidine-1-carboxamide | 134 | 1.4 | 494, 496 | 7.33-7.32 (m, 1H), 7.21-7.09 (m, 3H), 4.19 (d, J = 11.7 Hz, 1H), 4.06-3.98 (m, 1H), 3.86 (d, J = 12.9 Hz, 1H), 3.37 (t, J = 6.6 Hz, 2H), 2.95 (dd, J = 12.6, 3.2 Hz, 1H), 2.83 (dd, J = 12.6, 10.0 Hz, 1H), 2.59 (s, 3H), 2.47-2.41 (m, 2H), 1.92-0.74 (m, 24H). |
| I-156A[b] | (3R)-3-((S)-1-(3-chlorophenyl)-1-hydroxy-5-methoxypentyl)-N-((S)-3-cyclopentyl-1-(methylamino)propan-2-yl)piperidine-1-carboxamide | 119 | 1.56 | 495 | 1.40-1.75 (m, 9H), 3.20 (s, 3H), 2.20 (s, 3H), 7.10-7.80 (m, 4H) |
| I-157A[b] | (3R)—N-((S)-3-cyclohexyl-1-(methylamino)propan-2-yl)-3-((S)-1-hydroxy-5-methoxy-1-(5-methylthiazol-2-yl)pentyl)piperidine-1-carboxamide | 121 | | 495.3 | 2.51 (s, 3H), 2.72 (s, 3H), 3.32 (s, 3H), 3.40 (m, 2H), 3.70 (m, 1H), 4.26 (m, 2H), 5.88 (m, 1H), 7.61 (m, 1H), 8.48 (brs, 1H), 9.27 (brs, 1H) |
| I-158A[b] | (3R)-3-((S)-1-(3-chlorophenyl)-1-hydroxy-5-methoxypentyl)-N-((S)-3-cyclohexyl-1-hydroxypropan-2-yl)piperidine-1-carboxamide | 33 | 1.9 | 496 | 3.25 (s, 3H), 3.80 (m, 1H), 4.18 (d, 1H), 4.50 (d, 1H), 7.00-7.40 (m, 5H) |
| I-159A | (3R)-3-((3-methoxypropoxy)(4-chloropyridin-2-yl)methyl)-N-((S)-3-cyclohexyl-1-(methylamino)propan-2-yl)piperidine-1-carboxamide | 33 | 1.52 | 486 | 8.47 (d, J = 4.7, 1H), 8.12 (d, 9.4, 0.5H), 7.52 (s, 1H), 7.44 (m, 1H), 6.89 (d, J = 9.4, 0.5H), 4.27 (d, J = 5.5, 0.5H), 4.15 (d, J = 7.4, 0.5H), 3.29 (s, 3H), 2.68 (s, 3H) |
| I-160A | (R)-3-((S)-1-hydroxy-5-methoxy-1-(2-phenoxyphenyl)pentyl)-N-(2-methyl-1-(methylamino)propan-2-yl)piperidine-1-carboxamide | 33 | 1.47 | 498 | 0.96 (m), 1.18-1.60 (m), 1.26 (s), 1.88 (m), 2.22 (m), 2.36 (m), 2.64 (s), 2.72 (m), 3.14 (m), 3.24 (s), 3.26 (t), 3.84 (d), 4.38 (d), 6.78 (d), 6.94 (d), 7.10 (m), 7.20 (m), 7.36 (m), 7.64 (d) |
| I-161A | (3R)-3-((S)-1-(2-(o-tolyloxy)phenyl)-1-hydroxy-5-methoxypentyl)-N-((S)-1-(methylamino)propan-2-yl) piperidine-1-carboxamide | 33 | 1.48 | 498 | 0.96 (m), 1.18 (d), 1.20-1.64 (m), 1.94 (m), 2.22 (s), 2.38 (m), 2.62 (s), 2.80 (m), 2.94 (dd), 3.04 (dd), 3.24 (s), 3.26 (t), 3.90 (d), 4.02 (m), 4.38 (d), 6.54 (d), 6.74 (d), 7.04 (m), 7.16 (m), 7.28 (d), 7.64 (d) |
| I-162A | (3R)-3-((S)-1-(2-(m-tolyloxy)phenyl)-1-hydroxy-5-methoxypentyl)-N-((S)-1-(methylamino)propan-2-yl)piperidine-1-carboxamide | 33 | 1.47 | 498 | 0.96 (m), 1.20 (d), 1.22-1.60 (m), 1.92 (m), 2.22 (m), 2.26 (s), 2,62 (m), 2.64 (s), 2.78 (m), 2.96 (dd), 3.04 (dd), 3.24 (s), 3.26 (t), 3.86 (d), 4.04 (m), 4.36 (d), 6.72 (m), 6.76 (d), 6.92 (d), 7.08 (m), 7.18 (m), 7.64 (d) |
| I-163A | (3R)—N-(3-(3,3-difluorocyclobutyl)-1-(methylamino)propan-2-yl)-3-((S)-1-(3-fluorophenyl)-1-hydroxy-5-methoxypentyl)piperidine-1-carboxamide | 33 | 1.37 | 500 | 7.32 (m, 1H), 7.15 (d, J = 7.0, 2H), 6.94 (m, 1H), 4.42 (d, J = 12.5, 0.5H), 4.30 (d, J = 13.6, 0.5H), 3.99 (m, 1H), 3.94 (d, J = 16, 0.5H), 3.84 (d, J = 12.9, 0.5H), 3.30 (s, 3H), 2.70 (s, 1H) |
| I-165A | (3R)-3-((S)-1-(benzofuran-7-yl)-1-hydroxy-5-methoxypentyl)-N-((S)-3-cyclopentyl-1-(methylamino)propan- | 119 | | 500.3 | 0.72 (m, 1H), 2.26 (m, 1H), 2.42 (m, 1H), 2.60 (m, 1H), 2.72 (s, 3H), 2.78 (m, 1H), 2.94 (m, 1H), 3.09 (m, 1H), 3.18 (s, 3H), |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | 2-yl)piperidine-1-carboxamide | | | | 4.01 (m, 2H), 4.42 (m, 1H), 6.84 (m, 1H), 7.22 (t, 1H), 7.41 (m, 1H), 7.51 (m, 1H), 7.67 (m, 1H) |
| I-166A | (3R)-3-((S)-1-(3-chloro-2-fluorophenyl)-1-hydroxy-5-methoxypentyl)-N-((S)-4,4-dimethyl-1-(methylamino)pentan-2-yl)piperidine-1-carboxamide | 33 | 1.51 | 500 | 7.42 (t), 7.26 (t), 7.03 (t), 4.24 (d), 4.09 (m), 3.89 (d), 3.19 (m), 3.15 (m), 2.93 (d), 2.83 (t), 2.68 (t), 2.60 (s), 2.51 (t), 2.05 (t), 1.86 (m), 0.89 (s). |
| I-167A | 3-(1-(3-chlorophenyl)-1-hydroxy-5-methoxypentyl)-N-((S)-3-cyclohexyl-1-(methylamino)propan-2-yl)benzamide | 129 | 1.55 | 501, 503 | 8.30 (d, J = 8.5 Hz, 1H), 7.91-7.07 (m, 8H), 4.43-4.40 (m, 1H), 3.26 (t, J = 6.3 Hz, 2H), 3.17 (s, 3H), 3.09-2.93 (m, 2H), 2.61 (s, 3H), 2.27-2.22 (m, 2H), 1.76-0.80 (m, 17H). |
| I-168A | (3R)-3-((S)-1-(2-(4-fluorophenoxy)phenyl)-1-hydroxy-5-methoxypentyl)-N-((S)-1-(methylamino)propan-2-yl)piperidine-1-carboxamide | 33 | 1.42 | 502 | 0.92 (m), 1.18 (d), 1.20-1.62 (m), 1.92 (m), 2.20 (m), 2.32 (m), 2.64 (s), 2.78 (m), 2.96 (dd), 3.04 (dd), 3.24 (s), 3.26 (t), 3.86 (d), 4.04 (m), 4.38 (d), 6.74 (d), 6.94 (dd), 7.08 (m), 7.38 (m), 7.44 (dd) |
| I-169A | (3R)-3-((S)-1-(5-fluoro-2-phenoxyphenyl)-1-hydroxy-5-methoxypentyl)-N-((S)-1-(methylamino)propan-2-yl)piperidine-1-carboxamide | 33 | 1.44 | 502 | 0.92 (m), 1.18 (d), 1.20-1.62 (m), 1.90 (m), 2.20 (m), 2.28 (m), 2.64 (s), 2.76 (m), 2.96 (m), 3.04 (dd), 3.24 (s), 3.26 (t), 3.86 (d), 4.04 (m), 4.36 (d), 6.80 (dd), 6.92 (m), 7.08 (m), 7.36 (m), 7.40 (dd) |
| I-170A | (3R)-3-((S)-1-(2-(3-fluorophenoxy)phenyl)-1-hydroxy-5-methoxypentyl)-N-((S)-1-(methylamino)propan-2-yl)piperidine-1-carboxamide | 33 | 1.45 | 502 | 0.84 (m), 1.18 (d), 1.24-1.60 (m), 1.92 (m), 2.16 (m), 2.24 (m), 2.62 (m), 2.64 (s), 2.78 (dd), 2.96 (dd), 3.04 (dd), 3.24 (s), 3.26 (t), 3.86 (d), 4.04 (m), 4.36 (d), 6.64 (d), 6.74 (d), 6.84 (m), 7.18 (m), 7.24 (m), 7.34 (m), 7.68 (d) |
| I-171A | (3R)-3-((S)-1-(2-(2-fluorophenoxy)phenyl)-1-hydroxy-5-methoxypentyl)-N-((S)-1-(methylamino)propan-2-yl)piperidine-1-carboxamide | 33 | 1.44 | 502 | 7.66 (d, 1H), 7.27-7.23 (m, 1H), 7.19-7.12 (m, 3H), 7.08 (t, 1H), 7.01 (m, 1H), 6.62 (d, 1H), 4.42 (dd, 1H), 4.05 (m, 1H), 3.86 (dd, 1H), 3.72 (m, 2H), 2.67 (d, 3H), 1.93 (td, 1H). |
| I-172A | (3R)—N-((S)-3-cyclopentyl-1-(methylamino)propan-2-yl)-3-((S)-1-(2,3-dihydrobenzofuran-7-yl)-1-hydroxy-5-methoxypentyl)piperidine-1-carboxamide | 122 | | 502.3 | 1.95 (m, 1H), 2.10 (m, 1H), 2.26 (m, 1H), 2.72 (s, 3H), 3.26 (s, 3H), 4.02 (m, 2H), 4.28 (m, 1H), 4.49 (m, 2H), 6.83 (m, 2H), 7.11 (m, 1H), 7.21 (m, 1H) |
| I-173A[b] | (3R)—N-((S)-3-cyclohexyl-1-(methylamino)propan-2-yl)-3-((S)-1-hydroxy-5-methoxy-1-(2,5-dimethylphenyl)pentyl)piperidine-1-carboxamide | 33 | | 502.4 | 1.05 (m, 4H), 2.30 (s, 3H), 2.37 (s, 3H), 2.93 (m, 2H), 3.78 (d, 1H), 4.10 (d, 1H), 4.20 (m, 1H), 5.79 (m, 1H), 8.72 (brs, 1H), 10.06 (brs, 1H) |
| I-174A[b] | (3R)—N-((S)-3-cyclohexyl-1-(methylamino)propan-2-yl)-3-((S)-1-(3-ethylphenyl)-1-hydroxy-5-methoxypentyl)piperidine-1-carboxamide | 33 | | 502..4 | 2.31 (dd, 1H), 2.32 (s, 3H), 3.32 (s, 3H), 4.22 (m, 2H), 5.90 (m, 1H), 8.96 (brs, 1H), 9.97 (brs, 1H) |
| I-175A[b] | (3R)—N-((S)-3-cyclohexyl-1-(methylamino)propan-2-yl)-3-((S)-1-hydroxy-5-methoxy-1-(2,3-dimethylphenyl)pentyl)piperidine-1-carboxamide | 33 | | 502.4 | 2.26 (s, 3H), 2.29 (s, 3H), 3.26 (s, 3H), 4.18 (m, 2H), 5.72 (m, 1H), 7.05 (d, 2H), 7.34 (m, 1H), 8.72 (brs, 1H), 9.99 (brs, 1H) |
| I-176A[b] | (3R)—N-((S)-3-cyclohexyl-1-(methylamino)propan-2-yl)-3-((S)-1-hydroxy-5-methoxy-1-(3,5-dimethylphenyl)pentyl)piperidine-1-carboxamide | 121 | | 502 | 1.54 (dd, 1H), 2.30 (s, 3H), 2.55 (t, 1H), 3.27 (s, 3H), 3.32 (t, 3H), 3.76 (m, 1H), 4.26 (m, 2H), 5.95 (m, 1H), 6.86 (s, 1H), 6.91 (s, 2H), 8.67 (brs, 1H), 9.54 (brs, 1H) |
| I-177A | (3R)-3-((S)-1-(2-(2-chlorophenyl)phenyl)-1-hydroxy-5-methoxypentyl)-N-((S)-1-(methylamino)propan-2-yl)piperidine-1-carboxamide | 121 | | 502.2 | 1.02 (m, 1H), 1.15 (d, 3H), 1.76 (m, 2H), 2.60 (m, 1H), 2.69 (m, 2H), 2.72 (m, 1H), 3.00 (m, 2H), 3.26 (m, 3H), 3.37 (m, 1H), 3.82-4.13 (m, 3H), 6.94 (m, 1H), 7.16-7.48 (m, 6H), 7.69 (m, 1H) |
| I-178A | (3R)-3-((S)-1-(2-(4-chlorophenyl)phenyl)-1-hydroxy-5-methoxypentyl)-N-((S)-1-(methylamino)propan-2-yl)piperidine-1-carboxamide | 121 | | 502.3 | 0.99 (m, 1H), 1.18 (d, 3H), 1.85 (m, 1H), 2.59 (m, 1H), 2.68 (s, 3H), 2.75 (m, 1H), 2.94 (m, 1H), 3.04 (m, 1H), 3.25 (m, 3H), 3.88 (m, 1H), 4.05 (m, 1H), 6.94 (m, 1H), 7.05-7.50 (m, 6H), 7.72 (m, 1H) |
| I-179A[b] | (3R)—N-((S)-3-cyclohexyl-1-(methylamino)propan-2-yl)-3-((S)-1-hydroxy-5-methoxy-1-(3- | 33 | | 504.4 | 2.15 (m, 2H), 2.54 (dd, 1H), 3.26 (s, 3H), 3.80 (s, 3H), 4.20 (m, 2H), 6.04 (m, 1H), 6.75 (d, 1H), 6.77 (t, 2H), 7.24 (d, 1H), |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | methoxyphenyl)pentyl)piperidine-1-carboxamide | | | | 9.18 (brs, 1H), 9.86 (brs, 1H) |
| I-180A | (3R)-3-(1-(2-(cyclopropylmethoxy)phenyl)-1-hydroxy-5-methoxypentyl)-N-((S)-4-methyl-1-(methylamino)pentan-2-yl)piperidine-1-carboxamide | 33 | 1.56 | 504 | 7.41 (m), 7.35 (m), 7.08 (q), 6.78 (m), 4.15 (m), 3.91 (br m), 3.71 (m), 3.19 (m), 3.12 (s), 2.59 (s), 2.51 (s), 0.50 (t), 0.22 (m). |
| I-181A | (3R)-3-(1-(3-chlorophenyl)-4-cyclopropyl-1-hydroxybutyl)-N-((S)-3-cyclohexyl-1-(methylamino)propan-2-yl)piperidine-1-carboxamide | 33 | 1.87 | 504 | 7.32 (s), 7.22-7.11 (m), 4.17 (d), 4.00 (m), 3.86 (d), 3.18 (m), 2.94 (d), 2.79 (t), 2.58 (s), 2.41 (q), 0.49 (m), 0.24 (m), −0.18 (q). |
| I-182A[b] | (3R)—N-((S)-3-cyclohexyl-1-(methylamino)propan-2-yl)-3-((S)-1-(3-fluoro-5-methylphenyl)-1-hydroxy-5-methoxypentyl)piperidine-1-carboxamide | 121 | | 506 | 1.57 (dd, 1H), 2.04 (t, 1H), 2.21 (m, 1H), 2.82 (s, 3H), 2.55 (t, 1H), 2.82 (s, 3H), 3.28 (s, 3H), 4.25 (m, 2H), 6.05 (m, 1H), 6.74 (d, 1H), 6.86 (m, 2H), 8.99 (brs, 1H), 9.74 (brs, 1H) |
| I-183A[b] | (3R)—N-((S)-3-cyclohexyl-1-(methylamino)propan-2-yl)-3-((S)-1-(2-fluoro-5-methylphenyl)-1-hydroxy-5-methoxypentyl)piperidine-1-carboxamide | 121 | | 506.4 | 2.32 (s, 3H), 2.76 (s, 3H), 3.27 (s, 3H), 3.33 (m, 2H), 4.13 (m, 1H), 4.26 (m, 1H), 5.96 (m, 1H), 6.84 (t, 1H), 6.87 (m, 1H), 7.31 (d, 1H), 8.75 (brs, 1H), 9.67 (brs, 1H) |
| I-184A[b] | (3R)—N-((S)-3-cyclohexyl-1-(methylamino)propan-2-yl)-3-((S)-1-(5-fluoro-2-methylphenyl)-1-hydroxy-5-methoxypentyl)piperidine-1-carboxamide | 121 | | 506.4 | 2.22 (m, 1H), 2.35 (s, 3H), 2.67 (m, 1H), 2.73 (s, 3H), 2.93 (m, 2H), 3.26 (s, 3H), 3.78 (m, 1H), 4.12 (m, 1H), 4.23 (m, 1H), 5.98 (m, 1H), 6.80 (m, 1H), 7.02 (m, 1H), 7.31 (m, 1H), 8.87 (brs, 1H), 9.84 (brs, 1H) |
| I-185A[b] | (3R)—N-((S)-3-cyclohexyl-1-(methylamino)propan-2-yl)-3-((S)-1-(2-fluoro-3-methylphenyl)-1-hydroxy-5-methoxypentyl)piperidine-1-carboxamide | 121 | | 506.3 | 2.24 (s, 3H), 2.45 (t, 1H), 2.63 (m, 2H), 2.79 (s, 3H), 2.92 (m, 1H), 3.28 (s, 3H), 3.76 (m, 1H), 4.14 (m, 1H), 4.26 (m, 1H), 5.99 (m, 1H), 7.00 (t, 1H), 7.09 (t, 1H), 7.43 (t, 1H), 8.88 (brs, 1H), 9.89 (brs, 1H) |
| I-186A | (3R)—N-((2R)-1-cyclohexyl-1-hydroxy-3-(methylamino)propan-2-yl)-3-((S)-1-(3-fluorophenyl)-1-hydroxy-5-methoxypentyl)piperidine-1-carboxamide | 117 | 1.44 | 508 | 0.98 (m), 1.18-2.06 (m), 2.60 (m), 2.74 (s), 3.14 (dd), 3.22 (dd), 3.24 (s), 3.28 (tm), 4.00 (d), 4.24 (m), 6.94 (m), 7.16 (m), 7.36 (m) |
| I-186B | (3R)—N-((1S,2R)-1-cyclohexyl-1-hydroxy-3-(methylamino)propan-2-yl)-3-((S)-1-(3-fluorophenyl)-1-hydroxy-5-methoxypentyl)piperidine-1-carboxamide | 117 | 1.38 | 508 | 0.98-2.02 (m), 2.54 (m), 2.72 (s), 3.04 (m), 3.24 (s), 3.26 (t), 3.42 (m), 3.84, 3.98 (d), 4.08 (m), 4.26, 4.42 (d), 6.96 (m), 7.18 (m), 7.34 (m) |
| I-187A | (3R)-3-((S)-1-(3-fluorophenyl)-1-hydroxy-5-methoxypentyl)-N-(3-(1-hydroxycyclohexyl)-1-(methylamino)propan-2-yl)piperidine-1-carboxamide | 114 | 1.37 | 508 | 7.32 (q, 1H), 7.16 (m, 1H), 7.14 (m, 1H), 6.94 (m, 1H), 4.42 and 4.28 (two isomers on 3 to 2 ratio, d, 1H), 4.15 (m, 1H), 3.95 and 3.84 (two isomers on 3 to 2 ratio, d, 1H), 3.32 (m, 1H), 3.26 (s, 3H), 3.14 (dd, 1H), 2.95 (m, 1H), 2.70 (s, 3H), 2.60-2.39 (m 3H), 1.94 (t, 2H), 1.79-1.22 (m, 20H), 1.00 (m, 1H). |
| I-188A | (3R)-3-((S)-1-(3-fluorophenyl)-1-hydroxy-5-methoxypentyl)-N-(3-(1-hydroxycyclohexyl)-2-(methylamino)propyl)piperidine-1-carboxamide | 115 | 1.34 | 508 | 7.32 (t, 1H), 7.16 (d, 1H), 7.14 (d, 1H), 6.94 (td, 1H), 4.36 (t, 1H), 3.88 (t, 1H), 3.53 (m, 1H), 3.40 (m, 1H), 3.26 (s, 3H), 2.61 (s, 3H), 2.48 (m, 1H), 2.47 (m, 1H), 1.94 (t, 2H), 1.90 (td, 1H), 1.76 (tt, 1H), 1.69-1.22 (m, 18H), 0.99 (m, 1H). |
| I-190A | (3R)-3-((R)-(3-ethoxypropoxy)(3-chlorophenyl)methyl)-N-((S)-3-cyclohexyl-1-(methylamino)propan-2-yl)piperidine-1-carboxamide | 33 | 1.75 | 508 | 7.36-7.29 (m, 3H), 7.25 (d, 1H), 4.28 (d, 1H), 4.10 (m, 1H), 3.05 (dd, 2H), 2.90 (m, 1H), 2.69 (s, 3H), 1.12 (t, 3H). |
| I-191A | (3R)-3-((1S)-1-(3-chlorophenyl)-1,5-dihydroxyhexyl)-N-((S)-3-cyclohexyl-1-(methylamino)propan-2-yl)piperidine-1-carboxamide | 136 | 1.53 | 508, 510 | 7.36-7.34 (m, 1H), 7.24-7.13 (m, 3H), 4.20 (d, J = 15 Hz, 1H), 4.06-3.99 (m, 1H), 3.88 (d, J = 13.2 Hz, 1H), 3.58-3.53 (m, 1H), 2.97 (dd, J = 12.8, 3.1 Hz, 1H), 2.82 (dd, J = 12.6, 10.2 Hz, 1H), 2.61 (s, 3H), 2.49-2.41 (m, 2H), 0.987, 0.982 (d, J = 6 Hz, 3H), 1.94-0.80 (m, 24H). |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-192A[b] | (3R)-3-((S)-1-(2-chlorophenyl)-1-hydroxy-5-methoxypentyl)-N-((S)-3-cyclohexyl-1-(methylamino)propan-2-yl)piperidine-1-carboxamide | 121 | | 508.3 | 1.54 (m, 2H), 2.97 (m, 1H), 3.26 (s, 3H), 3.82 (m, 1H), 4.06 (m, 1H), 4.28 (m, 1H), 5.91 (m, 1H), 7.18&7.30 (m, 3H), 7.75 (m, 1H), 8.28 (brs, 1H), 9.66 (brs, 1H) |
| I-193A | (3R)-3-((S)-1-(4-chloropyridin-2-yl)-1-hydroxy-5-methoxypentyl)-N-((S)-3-cyclohexyl-1-(methylamino)propan-2-yl)piperidine-1-carboxamide | 33 | 1.44 | 510 | 8.51 (d, J = 5.8, 1H), 8.12 (d, J = 9.0, 0.5H), 7.81 (bs, 1H), 7.52 (bs, 1H), 6.88 (d, J = 9.0, 0.5H), 4.35 (d, J = 12.1, 1H), 4.12 (m, 1H), 3.94 (d, J = 12.1, 1H), 3.29 (s, 3H), 2.70 (s, 3H) |
| I-194A[b] | (3R)-3-((R)-(3-ethoxypropoxy)(phenyl)methyl)-N-((S)-3-(4,4-difluorocyclohexyl)-1-(methylamino)propan-2-yl)piperidine-1-carboxamide | 33 | | 510.3 | 1.14 (t, 3H), 2.71 (m, 1H), 3.79 (m, 1H), 3.93 (dd, 1H), 5.78 (m, 1H), 7.20 (m, 2H), 7.34 (m, 3H), 8.77 (brs, 1H), 9.87 (brs, 1H) |
| I-195A[b] | (3R)—N-((S)-3-cyclohexyl-1-(methylamino)propan-2-yl)-3-((S)-1-(3,5-difluorophenyl)-1-hydroxy-5-methoxypentyl)piperidine-1-carboxamide | 33 | | 510 | 1.52 (m, 1H), 2.04 (t, 1H), 2.18 (m, 1H), 2.58 (t, 1H), 2.81 (s, 3H), 2.88 (m, 1H), 3.28 (s, 3H), 3.30 (t, 3H), 3.71 (m, 1H), 4.25 (m, 2H), 6.04 (m, 1H), 6.68 (dd, 1H), 6.87 (m, 2H), 8.96 (brs, 1H), 9.65 (brs, 1H) |
| I-196A[b] | (3R)—N-((S)-3-cyclohexyl-1-(methylamino)propan-2-yl)-3-((S)-1-(2,3-difluorophenyl)-1-hydroxy-5-methoxypentyl)piperidine-1-carboxamide | 121 | | 510 | 2.41 (m, 1H), 2.64 (s, 3H), 3.22 (s, 3H), 3.77 (m, 1H), 4.13 (m, 1H), 4.28 (m, 1H), 6.02 (m, 1H), 7.05 (m, 2H), 7.30 (m, 1H), 8.81 (brs, 1H), 9.49 (brs, 1H) |
| I-197A[b] | (3R)—N-((S)-3-cyclopentyl-1-(methylamino)propan-2-yl)-3-((S)-5-ethoxy-1-(2,3-difluorophenyl)-1-hydroxypentyl)piperidine-1-carboxamide | 119 | | 510.6 | 1.24 (t, 3H), 2.42 (m, 2H), 2.65 (t, 1H), 2.71 (s, 3H), 2.94 (m, 2H), 3.26 (m, 1H), 3.35 (t, 2H), 3.45 (m, 2H), 3.72 (m, 1H), 4.19 (m, 1H), 6.15 (m, 1H), 7.06 (m, 2H), 7.31 (t, 1H), 9.10 (brs, 1H), 10.13 (brs, 1H) |
| I-198A | (3R)—N-((S)-3-cyclohexyl-1-(methylamino)propan-2-yl)-3-((S)-1-(2,3-difluorophenyl)-1-hydroxy-5-methoxypentyl)piperidine-1-carboxamide | 33 | 1.44 | 510 | 7.24 (m), 7.01 (m), 4.21 (d), 4.01 (m), 3.87 (d), 3.18 (s), 3.13 (s), 2.95 (d) 2.80 (t), 2.69 (t), 2.58 (s), 2.51 (t). |
| I-199A[b] | (3R)-3-((S)-1-(2-phenylphenyl)-1-hydroxy-5-methoxypentyl)-N-((S)-4-methyl-1-(methylamino)pentan-2-yl)piperidine-1-carboxamide | 119 | | 510.3 | 0.89 (t, 6H), 2.71 (m, 4H), 3.15 (m, 1H), 3.28 (s, 3H), 3.30 (m, 2H), 3.75 (m, 1H), 3.93 (m, 1H), 4.12 (m, 1H), 5.58 (m, 1H), 7.00 (d, 1H), 7.21 (m, 3H), 7.34 (m, 5H), 8.62 (brs, 1H), 9.86 (brs, 1H) |
| I-200A[b] | (3R)-3-((S)-1-(3-chlorophenyl)-1-hydroxy-5-methoxypentyl)-N-((S)-3-(tetrahydro-2H-pyran-4-yl)-1-(methylamino)propan-2-yl)piperidine-1-carboxamide | 33 | 1.3 | 511 | 2.40 (s, 3H), 3.20 (s, 3H), 3.2-3.3 (m, 4H), 3.80 (m, 1H), 7.10-7.40 (m, 4H) |
| I-201A | (2RS)-2-((RS)-1-(3-chlorophenyl)-1-hydroxy-5-methoxypentyl)-N-((S)-3-cyclohexyl-1-(methylamino)propan-2-yl)morpholine-4-carboxamide | 33 | 1.5 | 510 | 2.26 (dd), 2.42 (dd), 2.67 (s), 3.52 (m), 3.66 (br d), 3.80 (br d), 3.92 (m), 4.12 (m), 7.2-7.6 |
| I-202A | (3R)—N-((1R,2R)-3-amino-1-cyclohexyl-1-hydroxypropan-2-yl)-3-((S)-1-(3-chlorophenyl)-1-hydroxy-5-methoxypentyl)piperidine-1-carboxamide | 117 | 1.50 | 510 | 1.00 (m), 1.18-2.08 (m), 2.42 (m), 2.62 (m), 3.10 (m), 3.26 (s), 3.28 (t), 3.82, 3.98 (d), 4.08 (m), 4.24, 4.42 (d), 7.20-7.34 (m), 7.42 (s) |
| I-202B | (3R)—N-((1S,2R)-3-amino-1-cyclohexyl-1-hydroxypropan-2-yl)-3-((S)-1-(3-chlorophenyl)-1-hydroxy-5-methoxypentyl)piperidine-1-carboxamide | 117 | 1.48 | 510 | 1.00-2.00 (m), 2.40-2.64 (m), 2.96 (m), 3.26 (s), 3.28 (t), 3.42 (m), 3.84, 3.98 (d), 4.04 (m), 4.28, 4.42 (d), 7.22-7.36 (m), 7.42 (s) |
| I-203A | (3R)-3-((S)-1-(3-chlorophenyl)-1-hydroxy-5-methoxypentyl)-N-((1R,2R)-1-cyclopentyl-1-hydroxy-3-(methylamino)propan-2-yl)piperidine-1-carboxamide | 117 | 1.48 | 510 | 2.72 (s, 3H), 3.30 (s, 3H), 3.95 (m, 1H), 4.19 (m, 1H), 7.20-7.50 (m, 4H) |
| I-203B | (3R)-3-((S)-1-(3-chlorophenyl)-1-hydroxy-5-methoxypentyl)-N-((1S,2R)-1-cyclopentyl-1-hydroxy-3-(methylamino)propan-2-yl)piperidine-1-carboxamide | 117 | 1.37 | 510 | 2.70 (s, 3H), 3.30 (s, 3H), 3.95 (m, 1H), 4.25 (d, 1H), 7.20-7.50 (m, 4H) |
| I-204A | (R)-3-((S)-1-(2-(o-tolyloxy)phenyl)-1-hydroxy-5-methoxypentyl)-N-(2-methyl-1-(methylamino)propan-2-yl)piperidine-1-carboxamide | 33 | 1.53 | 512 | 0.96 (m), 1.20-1.60 (m), 1.26, 1.28 (s), 1.92 (m), 2.24 (s), 2.40 (m), 2.64 (s), 2.74 (m), 3.14 (dd), 3.24 (s), 3.26 (t), 3.84 (d), 4.42 (d), 6.58 (d), 6.76 (d), 7.04 (m), 7.16 (m), 7.26 (d), 7.64 (d) |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-205A | (3R)-3-((S)-1-(2-(2-ethylphenoxy)phenyl)-1-hydroxy-5-methoxypentyl)-N-((S)-1-(methylamino)propan-2-yl)piperidine-1-carboxamide | 33 | 1.55 | 512 | 0.96 (m), 1.18 (d), 1.20 (t), 1.22-1.64 (m), 1.96 (m), 2.40 (m), 2.64 (s), 2.82 (dd), 2.94 (dd), 3.02 (dd), 3.24 (s), 3.26 (t), 3.94 (d), 4.02 (m), 4.38 (d), 6.56 (d), 6.74 (d), 7.00-7.20 (m), 7.30 (d), 7.64 (d) |
| I-206A | (3R)-3-((S)-1-(3-chloro-2-fluorophenyl)-1-hydroxy-5-methoxypentyl)-N-((S)-3-cyclopentyl-1-(methylamino)propan-2-yl)piperidine-1-carboxamide | 119 | 1.6 | 512 | 2.50 (s, 3H) 3.20 (s, 3H), 6.80-7.50 (m, 4H) |
| I-206B | (3R)-3-((S)-1-(3-chloro-2-fluorophenyl)-1-hydroxy-5-methoxypentyl)-N-((R)-3-cyclopentyl-1-(methylamino)propan-2-yl)piperidine-1-carboxamide | 119 | 1.63 | 563 | 2.60 (s, 3H), 3.25 (s, 3H), 7.0-7.5 (m, 3H) |
| I-207A[b] | (3R)-3-((S)-1-(5-chloro-1-methyl-1H-imidazol-2-yl)-1-hydroxy-5-methoxypentyl)-N-((S)-3-cyclohexyl-1-(methylamino)propan-2-yl)piperidine-1-carboxamide | 121 |  | 512.3 | 2.26 (m, 3H), 2.72 (s, 3H), 2.75 (m, 2H), 3.01 (m, 1H), 3.10 (m, 1H), 3.27 (s, 3H), 3.34 (m, 2H), 3.74 (m, 1H), 3.94 (s, 3H), 4.19 (m, 1H), 4.32 (m, 1H), 6.03 (m, 1H), 7.35 (m, 1H), 8.84 (brs, 1H), 9.24 (brs, 1H) |
| I-208A | (3R)-3-((S)-1-(2,2-difluorobenzo[d][1,3]dioxol-4-yl)-1-hydroxy-5-methoxypentyl)-N-((S)-4-methyl-1-(methylamino)pentan-2-yl)piperidine-1-carboxamide | 33 | 1.52 | 514 | 0.94 (d), 1.00 (d), 2.61 (m), 2.72 (s), 2.92 (dd), 3.06 (dd), 3.15 (s), 3.98 (br d), 4.10 (m), 4.35 (br dd), 7.13 (m), 7.30 (dd) |
| I-209A | (R)-3-((S)-1-(3-chlorophenyl)-1-hydroxyethyl)-N-((S)-1-cyclohexyl-3-(methylamino)propan-2-yl)piperidine-1-carboxamide | 121 |  | 436 | 0.90 (m, 1H), 1.58 (s, 3H), 2.57 (m, 2H), 2.66 (s, 3H), 2.89 (m, 1H), 3.04 (m, 1H), 3.97 (d, 1H), 4.12 (m, 1H), 4.24 (d, 1H), 7.24 (m, 1H), 7.32 (m, 2H), 7.46 (s, 1H) |
| I-210A | (3R)-3-((S)-1-(benzofuran-7-yl)-1-hydroxy-5-methoxypentyl)-N-((S)-3-cyclohexyl-1-(methylamino)propan-2-yl)piperidine-1-carboxamide | 33 | 1.55 | 514 | 2.10 (m), 2.26 (m), 2.44 (m), 2.60 (m), 2.70 (s), 2.82 (m), 2.93 (m), 3.19 (s), 4.00 (br d), 4.15 (m), 4.39 (br d), 6.86 (s), 7.20 (dd), 7.41 (d), 7.52 (d), 7.65 (s) |
| I-211A | (3R)—N-((S)-3-cyclohexyl-1-(methylamino)propan-2-yl)-3-((R)-1-hydroxy-1-(1H-indazol-7-yl)-5-methoxypentyl)piperidine-1-carboxamide | 121 |  | 514.3 | 2.12 (m, 2H), 2.48 (m, 2H), 2.69 (s, 3H), 2.90 (m, 1H), 3.08 (m, 1H), 2.37 (s, 3H), 2.93 (m, 2H), 3.25 (s, 3H), 3.95 (m, 1H), 4.14 (m, 1H), 4.43 (m, 1H), 7.15 (m, 2H), 7.66 (m, 1H), 8.02 (m, 1H) |
| I-212A[b] | (3R)-3-((R)-(3-methoxypropoxy)(2,3-dichlorophenyl)methyl)-N-((S)-3-cyclopentyl-1-(methylamino)propan-2-yl)piperidine-1-carboxamide | 119 |  | 516.5 | 2.69 (s, 3H), 2.75 (m, 1H), 2.96 (m, 1H), 3.10 (m, 1H), 3.28 (s, 3H), 3.42 (m, 2H), 3.81 (m, 1H), 4.08 (m, 2H), 4.46 (m, 1H), 5.65 (m, 1H), 7.29 (m, 2H), 7.40 (d, 1H), 8.62 (brs, 1H), 9.73 (brs, 1H) |
| I-213A | (R)-3-((S)-1-(2-(4-fluorophenoxy)phenyl)-1-hydroxy-5-methoxypentyl)-N-(2-methyl-1-(methylamino)propan-2-yl)piperidine-1-carboxamide | 33 | 1.49 | 516 | 0.96 (m), 1.20-1.60 (m), 1.32 (s), 1.88 (m), 2.20 (m), 2.36 (m), 2.64 (s), 2.72 (m), 3.16 (dd), 3.24 (s), 3.26 (t), 3.82 (d), 4.38 (d), 6.74 (d), 6.96 (m), 7.08 (m), 7.20 (m), 7.64 (d) |
| I-214A | (R)-3-((S)-1-(2-(3-fluorophenoxy)phenyl)-1-hydroxy-5-methoxypentyl)-N-(2-methyl-1-(methylamino)propan-2-yl)piperidine-1-carboxamide | 33 | 1.49 | 516 | 0.96 (m), 1.12-1.60 (m), 1.32 (s), 1.88 (m), 2.10 (m), 2.24 (m), 2.64 (s), 2.72 (m), 3.16 (dd), 3.24 (s), 3.26 (t), 3.82 (d), 4.38 (d), 6.64 (dd), 6.74 (dd), 6.82 (m), 6.84 (d), 7.18 (m), 7.24 (m), 7.34 (m), 7.68 (dd) |
| I-215A | (3R)-3-((S)-1-(3-(o-tolyloxy)-2-fluorophenyl)-1-hydroxy-5-methoxypentyl)-N-((S)-1-(methylamino)propan-2-yl)piperidine-1-carboxamide | 33 | 1.52 | 516 | 1.10 (2s, 3H), 2.25 (s, 3H), 3.30 (s, 3H), 4.10 (m, 1H), 6.65 (d, 1H), 6.85 (t, 1H), 7.00 (t, 1H), 7.10 (m, 2H), 7.25 (d, 1H), 7.39 (t, 1H) |
| I-216A | (3R)-3-((S)-1-(2-(o-tolyloxy)-3-fluorophenyl)-1-hydroxy-5-methoxypentyl)-N-((S)-1-(methylamino)propan-2-yl)piperidine-1-carboxamide | 33 | 1.44 | 516 | 0.70-1.00 (m), 1.18, 1.22 (two d), 1.28-1.78 (m), 1.92 (m), 2.36, 2.38 (two s), 2.52 (m), 2.62, 2.70 (two s), 2.78 (m), 2.92, 3.02 (m), 3.04, 3.36 (two t), 3.18, 3.24 (two s), 3.76, 3.98 (d), 3.96, 4.08 (m), 4.30 (d), 6.40, 6.42 (two d), 6.90 (m), 7.00 (m), 7.12 (m), 7.22 (m), 7.56 (d) |
| I-217A | (3R)-3-((S)-1-(2-(5-fluoro-2-methylphenoxy)phenyl)-1-hydroxy-5-methoxypentyl)-N-((S)-1-(methylamino)propan-2-yl)piperidine-1-carboxamide | 33 | 1.48 | 516 | 0.94 (m), 1.20 (d), 1.22-1.64 (m), 1.94 (m), 2.22 (s), 2.30 (m), 2.64 (s), 2.80 (dd), 2.99 (dd), 3.04 (dd), 3.24 (s), 3.26 (t), 3.92 (d), 4.04 (m), 4.38 (d), 6.44 (d), 6.66 (d), 6.80 (m), 7.14 (m), 7.22 (m), 7.26 (m), 7.68 (d) |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-218A | (3R)-3-((S)-1-(2-(4-fluoro-2-methylphenoxy)phenyl)-1-hydroxy-5-methoxypentyl)-N-((S)-1-(methylamino)propan-2-yl)piperidine-1-carboxamide | 33 | 1.49 | 516 | 0.94 (m), 1.18 (d), 1.22-1.64 (m), 1.94 (m), 2.22 (s), 2.38 (m), 2.64 (s), 2.80 (dd), 2.98 (m), 3.04 (m), 3.24 (s), 3.26 (t), 3.92 (d), 4.04 (m), 4.40 (m), 6.46 (d), 6.74 (m), 6.92 (m), 7.06 (m), 7.16 (m), 7.62 (d) |
| I-219A[b] | (3R)—N-((S)-3-cyclohexyl-1-(methylamino)propan-2-yl)-3-((S)-1-(2,3-dihydrobenzofuran-7-yl)-1-hydroxy-5-methoxypentyl)piperidine-1-carboxamide | 121 | | 516.3 | 2.93 (m), 315 (m, 1H), 3.28 (s, 3H), 3.34 (m, 1H), 3.88 (m, 1H), 4.25 (m, 1H), 4.54 (t, 2H), 5.85 (m, 1H), 6.84 (m, 1H), 7.11 (m, 2H), 8.51 (brs, 1H), 9.12 (brs, 1H) |
| I-220A | (3R)-3-((S)-1-(3-chlorophenyl)-1-hydroxy-5-methoxypentyl)-N-(3-(3,3-difluorocyclobutyl)-1-(methylamino)propan-2-yl)piperidine-1-carboxamide | 33 | 1.5 | 517 | 7.26 (m, 4H), 4.64 (d, J = 20.2, 0.5H), 4.31 (d, 14.8, 0.5H), 4.01 (m, 1H), 3.94 (d, J = 12.1, 0.5H), 3.30 (s, 3H), 2.70 (2, 3H) |
| I-221A | (3R)—N-(3-(3,3-difluorocyclobutyl)-1-(methylamino)propan-2-yl)-3-((S)-1-(2,3-difluorophenyl)-1-hydroxy-5-methoxypentyl)piperidine-1-carboxamide | 33 | 1.52 | 591 | 7.42 (d), 7.19-7.11 (m), 7.05 (t), 6.91 (m), 6.70 (d), 4.33 (d), 4.14 (d) 3.88 (m), 3.77 (d), 3.62 (d), 3.20 (m), 3.13 (s), 2.58 (s). |
| I-222A | (3R)-3-(1-(2-(cyclopentyloxy)phenyl)-1-hydroxy-5-methoxypentyl)-N-((S)-4-methyl-1-(methylamino)pentan-2-yl)piperidine-1-carboxamide | 33 | 1.65 | 518 | 7.41 (m), 7.34 (m), 7.06 (m), 6.75 (m), 4.09, (d), 3.92 (m), 3.75 (br s), 3.18 (br s), 3.12 (s), 2.95 (m), 2.59 (s), 2.52 (s). |
| I-223A | (3R)-3-(1-(2-(2-cyclopropylethoxy)phenyl)-1-hydroxy-5-methoxypentyl)-N-((S)-4-methyl-1-(methylamino)pentan-2-yl)piperidine-1-carboxamide | 33 | 1.65 | 518 | 7.44 (m), 7.35 (m), 7.10 (q), 6.82 (m), 4.12 (m), 3.93 (m), 3.75 (br s), 3.18 (br s), 3.12 (s), 2.60 (s), 2.50 (s), 0.40 (m), 0.04 (m). |
| I-224A | (3R)-3-((S)-1-(2-(2-chlorophenoxy)phenyl)-1-hydroxy-5-methoxypentyl)-N-((S)-1-(methylamino)propan-2-yl)piperidine-1-carboxamide | 33 | 1.44 | 518 | 0.94 (m), 1.20 (d), 1.22-1.60 (m), 1.94 (m), 2.38 (m), 2.64 (s), 2.80 (m), 2.94 (m), 3.04 (m), 3.24 (s), 3.26 (t), 3.92 (d), 4.04 (m), 4.38 (d), 6.60 (d), 6.94 (d), 7.10-7.22 (m), 7.28 (m), 7.52 (d), 7.68 (d) |
| I-225A | (3R)-3-(1-hydroxy-5-methoxy-1-(2-(neopentyloxy)phenyl)pentyl)-N-((S)-4-methyl-1-(methylamino)pentan-2-yl)piperidine-1-carboxamide | 33 | 1.71 | 520 | 7.37 (br s), 7.08 (m), 6.81 (m), 4.47 (m), 4.12 (m), 3.95 (m), 3.67 (m), 3.54 (m), 3.19 (m), 3.12 (s, 2.60 (s), 0.98 (s). |
| I-226A[b] | (3R)—N-((S)-3-cyclohexyl-1-(methylamino)propan-2-yl)-3-((S)-1-hydroxy-5-methoxy-1-(3-(methylthio)phenyl)pentyl)piperidine-1-carboxamide | 121 | | 520.4 | 2.12 (m, 2H), 2.48 (s, 3H), 3.27 (s, 3H), 3.74 (m, 1H), 4.27 (m, 2H), 6.09 (m, 1H), 7.06 (d, 1H), 7.11 (d, 1H), 7.24 (m, 1H), 7.28 (m, 1H), 9.18 (brs, 1H), 9.87 (brs, 1H) |
| I-227A | (3R)-3-((S)-4-(acetylamino)-1-(3-chlorophenyl)-1-hydroxybutyl)-N-((S)-3-cyclohexyl-1-(methylamino)propan-2-yl)piperidine-1-carboxamide | 33 | 1.32 | 521, 523 | 7.30 (t, J = 1.8 Hz, 1H), 7.20-7.08 (m, 3H), 4.16 (d, J = 12.9 Hz, 1H), 4.05-3.97 (m, 1H), 3.84 (d, J = 12.6 Hz, 1H), 2.99-2.91 (m, 3H), 2.81 (dd, J = 12.7, 10.1 Hz, 1H), 2.57 (s, 3H), 2.45-2.37 (m, 2H), 1.76 (s, 3H), 1.88-0.75 (m, 22H). |
| I-228A | (3R)-3-(1-(2-(allyloxy)-5-fluorophenyl)-5-ethoxy-1-hydroxypentyl)-N-((S)-4-methyl-1-(methylamino)pentan-2-yl)piperidine-1-carboxamide | 33 | 1.53 | 521 | 7.26 (d, J = 10.9, 1H), 6.88 (2H), 6.04 (m, 1H), 5.36 (d, J = 17.1, 1H), 5.23 (d, J = 10.5, 1H), 4.53 (bs, 1H), 4.26 (d, J = 13.3, 1H), 4.08 (m, 1H), 3.97 (d, J = 12.9, 1H), 3.40 (q, J = 5.9, 2H), 2.70 (s, 3H), |
| I-229A[b] | (3R)—N-((S)-3-cyclohexyl-1-(methylamino)propan-2-yl)-3-((S)-1-(5-fluoro-2-methoxyphenyl)-1-hydroxy-5-methoxypentyl)piperidine-1-carboxamide | 33 | | 522.3 | 2.08 (m, 1H), 2.25 (m, 1H), 2.75 (s, 3H), 3.28 (s, 3H), 3.78 (s, 3H), 4.08 (m, 1H), 4.18 (m, 1H), 5.69 (m, 1H), 6.77 (m, 1H), 6.89 (m, 1H), 7.15 (m, 1H), 8.75 (brs, 1H) 10.03 (brs, 1H) |
| I-230A[b] | (3R)—N-((S)-3-cyclohexyl-1-(methylamino)propan-2-yl)-3-((S)-1-(2-fluoro-6-methoxyphenyl)-1-hydroxy-5-methoxypentyl)piperidine-1-carboxamide | 121 | | 522 | 1.91 (m, 1H), 2.18 (m, 1H), 3.14 (m, 1H), 3.27 (s, 3H), 3.30 (t, 3H), 3.90 (s, 3H), 4.05 (m, 1H), 4.16 (m, 1H), 5.66 (m, 1H), 6.72 (m, 1H), 7.20 (m, 1H), 8.74 (brs, 1H), 9.78 (brs, 1H) |
| I-231A | (3R)-3-(4-cyclopropyl-1-hydroxy-1-(2-phenoxyphenyl)butyl)-N-((S)-4-methyl-1-(methylamino)pentan-2- | 33 | 1.79 | 522 | 7.54 (d), 7.23 (t), 7.07 (t), 6.99 (m), 6.80 (d), 6.61 (m), 4.16 (d), 3.88 (m), 3.19 (m), 2.91 (d), 2.76 (q), 2.54 (s), 2.50 (m), |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | yl)piperidine-1-carboxamide | | | | 2.18 (q), 1.82 (t), 0.72 (d), 0.66 (d), 0.45 (br m), 0.21 (d), −0.23 (br s). |
| I-232A[b] | (3R)-3-((S)-1-(3-chlorophenyl)-1-hydroxy-5-methoxypentyl)-N-(5,5,5-trifluoro-4-methyl-1-(methylamino)pentan-2-yl)piperidine-1-carboxamide | 33 | 1.5 | 522 | 1.20 (m, 3H), 2.39 (2s, 3H), 3.25 (s, 3H), 3.75 (m, 1H) 7.10-7.20 (m, 4H) |
| I-233A[b] | (3R)-3-(1-(3-chlorophenyl)-1,5-dimethoxypentyl)-N-((S)-3-cyclohexyl-1-(methylamino)propan-2-yl)piperidine-1-carboxamide | 33 | 1.78 | 522, 490, 492 | 7.28-6.93 (m), 5.48 (t, J = 7.3 Hz), 4.79 (d, J = 7.6 Hz), 4.01-3.86 (m), 3.27 (s), 2.46 (s). |
| I-234A[b] | (3R)-3-((S)-1-(3-chlorophenyl)-1-hydroxy-5-methoxypentyl)-N-((S)-3-cyclohexyl-1-(ethylamino)propan-2-yl)piperidine-1-carboxamide | 33 | 1.63 | 522 | 1.00 (t, 3H), 2.65 (m, 2H), 3.27 (s, 3H), 3.95 (m, 1H), 7.10-7.30 (m, 4H) |
| I-235A | (3R)-3-((1S)-1-(3-chlorophenyl)-1,5-dihydroxyheptyl)-N-((S)-3-cyclohexyl-1-(methylamino)propan-2-yl)piperidine-1-carboxamide | 137 | 1.59 | 522, 524 | 7.36-7.14 (m, 4H), 4.21 (d, J = 14.4 Hz, 1H), 4.07-4.01 (m, 1H), 3.89 (d, J = 11.6 Hz, 1H), 2.622, 2.607 (s, 3H). |
| I-236A[b] | (3R)-3-(4-cyclopropyl-1-(3-fluorophenyl)-1-hydroxybutyl)-N-((S)-3-(4,4-difluorocyclohexyl)-1-(methylamino)propan-2-yl)piperidine-1-carboxamide | 33 | 1.68 | 524 | 9.77 (d), 8.98 (d), 7.29 (q), 7.08 (m), 6.94 (m), 6.16 (br s), 5.12 (d), 4.23 (br s), 3.73 (d), 3.30 (br s), 2.89 (d), 2.81 (s), 2.54 (t), 0.57 (m), 0.35 (d), −0.06 (d). |
| I-237A[b] | (3R)—N-((S)-3-(4,4-difluorocyclohexyl)-1-(methylamino)propan-2-yl)-3-((S)-1-hydroxy-5-methoxy-1-m-tolylpentyl)piperidine-1-carboxamide | 121 | | 524.4 | 2.08 (m, 3H), 2.46 (s, 3H), 2.54 (t, 1H), 2.79 (s, 3H), 2.91 (m, 1H), 3.29 (s, 3H), 3.76 (m, 1H), 4.24 (m, 2H), 6.13 (m, 2H), 7.06 (m, 3H), 7.22 (m, 1H), 8.87 (brs, 1H), 9.78 (brs, 1H) |
| I-238A[b] | (3R)-3-((R)-(3-ethoxypropoxy)(m-tolyl)methyl)-N-((S)-3-(4,4-difluorocyclohexyl)-1-(methylamino)propan-2-yl)piperidine-1-carboxamide | 121 | | 524.4 | 1.15 (t, 3H), 2.08 (m, 2H), 2.37 (m, 6H), 3.49 (m, 4H), 4.06 (m, 2H), 4.51 (m, 2H), 7.10 (m, 4H) |
| I-239A[b] | (R)—N-((S)-1-cyclohexyl-3-(methylamino)propan-2-yl)-3-((S)-1-(2,3-difluorophenyl)-5-ethoxy-1-hydroxypentyl)piperidine-1-carboxamide | 119 | | 524.4 | 1.16 (t, 3H), 2.43 (m, 2H), 2.54 (t, 1H), 2.81 (s, 3H), 2.94 (m, 2H), 3.27 (m, 1H), 3.35 (t, 2H), 3.45 (m, 2H), 3.71 (m, 1H), 4.20 (m, 1H), 6.15 (m, 1H), 7.04 (m, 2H), 7.31 (t, 1H), 9.13 (brs, 1H), 10.13 (brs, 1H) |
| I-240A[b] | (3R)-3-((S)-1-(2-fluoro-3-methylphenyl)-1-hydroxy-5-methoxypentyl)-N-((S)-3-(cis-4-fluorocyclohexyl)-1-(methylamino)propan-2-yl)piperidine-1-carboxamide | 33 | 1.53 | 524 | 0.00 (m, 2H), 0.20 (m, 1H), 0.4 (m, 2H), 2.40 (s, 3H), 3.20 (s, 3H), 3.75 (m, 1H), 6.75 (m, 1H), 6.90 (m, 2H), 7.10 (m, 2H), 7.30 (m, 2H), 7.50 (m, 1H), 8.2 (d, 1H) |
| I-240B[b] | (3R)—N-((S)-3-cyclopropyl-1-(methylamino)propan-2-yl)-3-((S)-1-hydroxy-5-methoxy-1-(2-phenoxyphenyl)pentyl)piperidine-1-carboxamide | 119 | | 524.4 | 2.04 (m, 2H), 2.25 (s, 3H), 2.65 (s, 3H), 2.79 (m, 1H), 3.01 (m, 1H), 3.28 (s, 3H), 3.35 (m, 2H), 4.34 (m, 1H), 4.81 (m, 1H), 7.04 (m, 1H), 7.07 (m, 1H), 7.36 (m, 1H) |
| I-241A[b] | (3R)-3-((S)-1-(2-fluoro-3-methylphenyl)-1-hydroxy-5-methoxypentyl)-N-((S)-3-(4-fluorocyclohexyl)-1-(methylamino)propan-2-yl)piperidine-1-carboxamide | 121 | | 524.3 | 2.24 (s, 3H), 2.32 (m, 2H), 2.75 (s, 3H), 3.26 (s, 3H), 3.32 (m, 2H), 3.76 (m, 1H), 4.22 (m, 2H), 6.05 (m, 1H), 6.97 (m, 1H), 7.00 (m, 1H), 7.35 (m, 1H), 8.82 (brs, 1H), 9.91 (brs, 1H) |
| I-242A | (3R)-3-((S)-1-(2-(3-methylphenyl)phenyl)-1-hydroxy-5-methoxypentyl)-N-((S)-4-methyl-1-(methylamino)pentan-2-yl)piperidine-1-carboxamide | 119 | | 524.3 | 0.85 (m, 6H), 2.34 (m, 3H), 2.55 (m, 1H), 2.66 (s, 3H), 2.75 (m, 1H), 2.92 (m, 1H), 3.28 (s, 3H), 3.91 (m, 3H), 6.96 (m, 3H), 7.15 (m, 3H), 7.30 (m, 1H), 7.58 (m, 1H) |
| I-243A | (3R)-3-((S)-1-(2-(4-methylphenyl)phenyl)-1-hydroxy-5-methoxypentyl)-N-((S)-4-methyl-1-(methylamino)pentan-2-yl)piperidine-1-carboxamide | 119 | | 524.4 | 0.88 (m, 6H), 1.75 (m, 1H), 2.37 (s, 3H), 2.57 (m, 1H), 2.66 (s, 3H), 2.86 (m, 1H), 3.03 (m, 1H), 3.27 (m, 3H), 3.98 (m, 3H), 6.90 (d, 1H), 6.926-7.22 (m, 5H), 7.32 (t, 1H), 7.70 (d, 1H) |
| I-244A | (3R)-3-((S)-1-(3-chlorophenyl)-1-hydroxy-5-methoxypentyl)-N-((1R,2R)-1-cyclohexyl-1-hydroxy-3-(methylamino)propan-2-yl)piperidine-1-carboxamide | 117 | 1.51 | 524 | 0.98 (m), 1.20-2.04 (m), 2.60 (m), 2.74 (s), 3.14 (dd), 3.22 (dd), 3.24 (s), 3.28 (tm), 3.98 (d), 4.24 (m), 7.22-7.34 (m), 7.42 (s) |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-244B | (3R)-3-((S)-1-(3-chlorophenyl)-1-hydroxy-5-methoxypentyl)-N-((1S,2R)-1-cyclohexyl-1-hydroxy-3-(methylamino)propan-2-yl)piperidine-1-carboxamide | 117 | 1.45 | 524 | 0.98-2.02 (m), 2.54 (m), 2.74 (s), 3.04 (m), 3.26 (s), 3.28 (t), 3.42 (m), 3.84, 3.98 (d), 4.08 (m), 4.28, 4.42 (d), 7.22-7.34 (m), 7.42 (s) |
| I-245A | (3R)-3-((S)-1-(3-chlorophenyl)-1-hydroxy-5-methoxypentyl)-N-(3-(1-hydroxycyclohexyl)-1-(methylamino)propan-2-yl)piperidine-1-carboxamide | 113 | 1.47 | 524, 526 | 7.43 (t, 1H), 7.32-7.21 (m, 3H), 4.42 and 4.29 (two isomers on 1 to 1 ratio, d, 1H), 4.15 (m, 1H), 3.95 and 3.83 (two isomers on 1 to 1 ratio, d, 1H), 3.34 (m, 1H), 3.27 (s, 3H), 3.14 (m, 1H), 2.99 (m, 1H), 2.80 (s, 3H), 2.64-2.38 (m, 3H), 1.94 (t, 2H), 1.76 (m, 2H), 1.68-1.18 (m, 20H), 0.98 (m, 1H) |
| I-246A | (3R)-3-((S)-1-(3-chlorophenyl)-1-hydroxy-5-methoxypentyl)-N-(3-(1-hydroxycyclohexyl)-2-(methylamino)propyl)piperidine-1-carboxamide | 116 | 1.41 | 524, 526 | 7.43 (d, 1H), 7.33-7.21 (m, 3), 4.37 (t, 1H), 3.88 (t, 1H), 3.54 (m, 1H), 3.40 (m, 1H), 3.33 (m, 1H), 3.27 (s, 3H), 2.60 (q, 1H), 2.46 (m, 1H), 1.94 (t, 2H), 1.86 (dt, 1H), 1.76 (tt, 1H), 1.68-1.21 (m 18H), 0.99 (m, 1H). |
| I-247A | (3R)-3-((S)-1-(3-chlorophenyl)-1-hydroxy-5-methoxypentyl)-N-((S)-3-cyclohexyl-1-(methylamino)propan-2-yl)piperidine-1-carbothioamide | 123 | 1.77 | 525 | 2.67 (s), 3.20 (s), 5.12 (m), 7.39 (s) |
| I-248A[b] | (3R)—N-((S)-3-cyclohexyl-1-(methylamino)propan-2-yl)-3-((S)-1-hydroxy-5-methoxy-1-(quinolin-8-yl)pentyl)piperidine-1-carboxamide | 121 | | 525.3 | 2.18 (s, 3H), 2.40 (m, 1H), 2.73 (m, 2H), 3.03 (m, 1H), 3.26 (s, 3H), 3.90 (m, 1H), 4.26 (m, 1H), 4.62 (m, 1H), 6.34 (m, 1H), 7.80-8.11 (m, 3H), 8.35 (m, 1H), 8.90 (m, 1H), 9.18 (m, 1H), 9.39 (m, 1H) |
| I-249A | (R)-3-((S)-1-(2-(p-tolyloxy)-5-methylphenyl)-1-hydroxy-5-methoxypentyl)-N-(2-methyl-1-(methylamino)propan-2-yl)piperidine-1-carboxamide | 33 | 1.66 | 526 | 0.92 (m), 1.20-1.60 (m), 1.30 (s), 1.84 (m), 2.20 (m), 2.28 (s), 2.30 (s), 2.64 (s), 2.72 (s), 3.10 (dd), 3.24 (s), 3.26 (t), 3.82 (d), 4.38 (d), 6.62 (d), 6.78 (d), 6.98 (dd), 7.12 (d), 7.42 (d) |
| I-250A[b] | (3R)-3-((S)-1-(3-chloro-5-fluorophenyl)-1-hydroxy-5-methoxypentyl)-N-((S)-3-cyclohexyl-1-(methylamino)propan-2-yl)piperidine-1-carboxamide | 121 | | 526.3 | 2.62 (m, 1H), 2.82 (s, 3H), 3.28 (s, 3H), 3.79 (m, 1H), 4.28 (m, 2H), 5.95 (m, 1H), 6.98 (m, 2H), 7.12 (m, 1H), 8.91 (brs, 1H), 9.76 (brs, 1H) |
| I-251A | (3R)-3-(1-(3-chloro-2-fluorophenyl)-1-hydroxy-5-methoxypentyl)-N-((S)-3-cyclohexyl-1-(methylamino)propan-2-yl)piperidine-1-carboxamide | 33 | 1.63 | 526 | 7.52 (m, 1H), 7.36 (m, 1H), 7.12 (m, 1H), 4.32 (d, J = 12.9, 1H), 4.12 (m, 1H), 3.99 (d, J = 12.9, 1H), 3.30 (s, 3H), 2.70, (s, 3H) |
| I-251B | (3R)-3-((S)-1-(3-chloro-2-fluorophenyl)-1-hydroxy-5-methoxypentyl)-N-((S)-3-cyclohexyl-1-(methylamino)propan-2-yl)piperidine-1-carboxamide | 33 | 1.63 | 526 | 7.52 (m, 1H), 7.36 (m, 1H), 7.12 (m, 1H), 6.76 (s, 2H), 4.32 (d, J = 12.9, 1H), 4.12 (m, 1H), 3.99 (d, J = 12.9, 1H), 3.30 (s, 3H), 2.70, (s, 3H) |
| I-252A[b] | (3R)-3-((S)-1-(3-chloro-2-fluorophenyl)-5-ethoxy-1-hydroxypentyl)-N-((S)-3-cyclopentyl-1-(methylamino)propan-2-yl)piperidine-1-carboxamide | 119 | | 526.3 | 1.16 (t, 3H), 2.32 (m, 1H), 2.73 (s, 3H), 3.16 (m, 1H), 3.35 (s, 3H), 3.74 (m, 1H), 4.15 (m, 2H), 5.94 (m, 1H), 7.06 (dd, 1H), 7.28 (dd, 1H), 7.49 (dd, 1H), 8.99 (brs, 1H), 9.84 (brs, 1H) |
| I-253A[b] | (3R)-3-((S)-1-(3-chlorophenyl)-1-hydroxy-5-methoxypentyl)-N (S)-3-(4-fluorocyclohexyl)-1-(methylamino)propan-2-yl)piperidine-1-carboxamide | 119 | | 526.5 | 2.52 (m, 1H), 2.73 (s, 3H), 3.76 (m, 1H), 4.28 (m, 2H), 6.24 (m, 1H), 7.22 (m, 3H), 7.36 (m, 1H), 9.21 (brs, 1H), 9.78 (brs, 1H) |
| I-254A | (3R)-3-((S)-1-hydroxy-5-methoxy-1-(2-(pyridin-3-yloxy)phenyl)pentyl)-N-((S)-4-methyl-1-(methylamino)pentan-2-yl)piperidine-1-carboxamide | 33 | 1.22 | 527 | 8.47 (d, 2H), 7.85-7.72 (m, 3H), 7.33 (m, 2H), 6.93 (dd, 1H), 4.05 (m, 1H), 3.03 (d, 1H), 2.68 (s, 3H) |
| I-255A[b] | (3R)-3-((R)-(3-ethoxypropoxy)(3-fluorophenyl)methyl)-N-((S)-3-(4,4-difluorocyclohexyl)-1-(methylamino)propan-2-yl)piperidine-1-carboxamide | 121 | | 528 | 1.14 (m, 3H), 2.06 (m, 2H), 2.70 (s, 3H), 3.79 (m, 1H), 3.93 (d, 1H), 4.15 (m, 2H), 5.83 (m, 1H), 6.98 (m, 3H), 7.32 (m, 1H), 8.80 (brs, 1H), 9.82 (brs, 1H) |
| I-256A | (3R)—N-((S)-3-cyclohexyl-1-(methylamino)propan-2-yl)-3-(1-(2,3,5-trifluorophenyl)-1-hydroxy-5-methoxypentyl)piperidine-1-carboxamide | 33 | 1.56 | 528 | 7.15 (m, 1H), 7.05 (m, 1H), 6.38 (d, J = 8.6, 1H), 4.32 (d, J = 12.5, 1H), 4.12 (m, 1H), 3.99 (d, J = 13.7, 1H), 3.29 (s, 3H), 2.70, (s, 3H) |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-256B | (3R)—N-((S)-3-cyclohexyl-1-(methylamino)propan-2-yl)-3-((S)-1-(2,3,5-trifluorophenyl)-1-hydroxy-5-methoxypentyl)piperidine-1-carboxamide | 33 | 1.56 | 528 | 7.15 (m, 1H), 7.05 (m, 1H), 6.70 (s, 2H), 4.32 (d, J = 12.5, 1H), 4.12 (m, 1H), 3.99 (d, J = 13.7, 1H), 3.29 (s, 3H), 2.70, (s, 3H) |
| I-257A[b] | (3R)—N-((S)-3-cyclopentyl-1-(methylamino)propan-2-yl)-3-((S)-5-ethoxy-1-(2,3,5-trifluorophenyl)-1-hydroxypentyl)piperidine-1-carboxamide | 119 | | 530.6 | 1.15 (t, 3H), 2.42 (m, 1H), 2.55 (m, 1H), 2.64 (t, 1H), 2.73 (m, 1H), 2.80 (s, 3H), 2.96 (m, 1H), 3.28 (m, 2H), 3.36 (t, 2H), 3.44 (m, 2H), 3.75 (m, 1H), 4.23 (m, 1H), 4.36 (m, 1H), 6.18 (m, 1H), 6.80 (m, 1H), 7.06 (m, 1H), 9.01 (brs, 1H), 9.87 (brs, 1H) |
| I-258A | (3R)-3-((S)-1-(2-(2-ethylphenoxy)phenyl)-1-hydroxy-5-methoxypentyl)-N-((R)-3-hydroxyl-1-(methylamino)propan-2-yl)piperidine-1-carboxamide | 112 | 1.47 | 528 | 0.98 (m), 1.08 (t), 1.24-1.64 (m), 1.94 (m), 2.42 (m), 2.62 (q), 2.64 (s), 2.82 (m), 3.04 (m), 3.22 (m), 3.24 (s), 3.26 (t), 6.56 (d), 6.74 (d), 7.04-7.20 (m), 7.32 (d), 7.62 (d) |
| I-259A[b] | (3R)-3-((S)-1-(3-fluoro-2-phenylphenyl)-1-hydroxy-5-methoxypentyl)-N-((S)-4-methyl-1-(methylamino)pentan-2-yl)piperidine-1-carboxamide | 119 | | 528.3 | 0.86 (t, 6H), 2.69 (s, 3H), 3.14 (m, 1H), 3.28 (s, 3H), 3.80 (m, 2H), 4.13 (m, 1H), 5.70 (m, 1H), 7.00 (t, 1H), 7.28 (m, 7H), 8.46 (brs, 1H), 9.54 (brs, 1H) |
| I-260A | (3R)-3-((S)-1-(2-(2-fluorophenyl)phenyl)-1-hydroxy-5-methoxypentyl)-N-((S)-4-methyl-1-(methylamino)pentan-2-yl)piperidine-1-carboxamide | 119 | | 528.4 | 0.91 (m, 6H), 2.67 (s, 3H), 3.33 (m, 3H), 3.98 (m, 3H), 6.96 (m, 1H), 7.13-7.38 (m, 6H), 7.38 (m, 1H) |
| I-261A | (3R)-3-((S)-1-(2-(3-fluorophenyl)phenyl)-1-hydroxy-5-methoxypentyl)-N-((S)-4-methyl-1-(methylamino)pentan-2-yl)piperidine-1-carboxamide | 119 | | 528.4 | 0.90 (m, 6H), 1.78 (m, 1H), 2.56 (m, 1H), 2.67 (s, 3H), 2.83 (m, 2H), 3.04 (m, 1H), 3.30 (s, 3H), 3.98 (m, 3H), 6.83-6.95 (m, 4H), 7.32 (m, 1H), 7.37 (m, 2H), 7.71 (m, 1H) |
| I-262A | (3R)-3-((S)-1-(2-(4-fluorophenyl)phenyl)-1-hydroxy-5-methoxypentyl)-N-((S)-4-methyl-1-(methylamino)pentan-2-yl)piperidine-1-carboxamide | 119 | | 528.4 | 0.89 (m, 6H), 1.74 (m, 1H), 2.56 (m, 1H), 2.68 (s, 3H), 2.87 (m, 2H), 3.05 (m, 1H), 3.30 (s, 3H), 3.99 (m, 3H), 6.93 (m, 1H), 7.07-7.24 (m, 5H), 7.35 (t, 1H), 7.72 (m, 1H) |
| I-263A | (3R)-3-(1-(3-chlorophenyl)-5,5-difluoro-1-hydroxyhexyl)-N-((S)-3-cyclohexyl-1-(methylamino)propan-2-yl)piperidine-1-carboxamide | 33 | 1.71 | 528 | 7.33 (s), 7.22-7.11 (m), 4.18 (d), 4.00 (m), 3.84 (d), 3.18 (m), 2.94 (d), 2.80 (t), 2.58 (s), 2.46-2.34 (m), 1.35 (t). |
| I-264A[b] | (3R)-3-((R)-(3-methoxypropoxy)(2,3-dichlorophenyl)methyl)-N-((S)-3-cyclohexyl-1-(methylamino)propan-2-yl)piperidine-1-carboxamide | 121 | | 528.3 | 1.15 (t, 3H), 3.28 (s, 3H), 3.82 (m, 1H), 4.02 (m, 1H), 4.17 (m, 1H), 4.57 (m, 1H), 5.61 (m, 1H), 7.22 (m, 1H), 7.31 (m, 1H), 7.39 (m, 1H), 8.79 (brs, 1H), 9.85 (brs, 1H) |
| I-265A[b] | (3R)-3-((S)-1-(2,3-dichlorophenyl)-1-hydroxy-5-methoxypentyl)-N-((S)-3-cyclopentyl-1-(methylamino)propan-2-yl)piperidine-1-carboxamide | 119 | | 528.3 | 3.28 (s, 3H), 3.83 (m, 1H), 3.95 (m, 1H), 2.78 (s, 3H), 3.42 (t, 3H), 5.85 (m, 1H), 7.10 (m, 1H), 7.21 (s, 1H), 7.28 (m, 2H), 8.65 (brs, 1H), 9.71 (brs, 1H) |
| I-266A[b] | (3R)-3-((R)-(3-ethoxypropoxy)(2,3-dichlorophenyl)methyl)-N-((S)-3-cyclopentyl-1-(methylamino)propan-2-yl)piperidine-1-carboxamide | 119 | | 528.5 | 1.15 (t, 3H), 2.68 (s, 3H), 2.96 (m, 1H), 3.09 (m, 1H), 3.28 (t, 3H), 3.45 (m, 1H), 3.83 (m, 1H), 4.58 (d, 2H), 5.60 (m, 1H), 7.24 (m, 1H), 7.30 (m, 1H), 7.40 (d, 1H), 8.69 (brs, 1H), 9.87 (brs, 1H) |
| I-267A | (3R)-3-((S)-1-(benzo[b]thiophen-7-yl)-1-hydroxy-5-methoxypentyl)-N-((S)-3-cyclohexyl-1-(methylamino)propan-2-yl)piperidine-1-carboxamide | 33 | 1.67 | 530 | 7.72 (dd, 1H), 7.48 (d, 1H), 7.35-7.24 (m, 3H), 4.12 (m, 1H), 3.05 (dt, 1H), 2.71 (s, 3H), 1.83 (d, 1H), 1.03 (m, 1H), 0.91 (m, 1H). |
| I-268A | (3R)-3-((S)-1-(benzo[b]thiophen-2-yl)-1-hydroxy-5-methoxypentyl)-N-((S)-3-cyclohexyl-1-(methylamino)propan-2-yl)piperidine-1-carboxamide | 33 | 1.63 | 530 | 7.78 (d, 1H), 7.71 (d, 1H), 7.33-7.23 (m, 2H), 7.16 (d, 1H), 4.29 (d, 1H), 4.12 (m, 1H), 4.01 (d, 2H). |
| I-269A | (3R)-3-((S)-1-hydroxy-5-methoxy-1-(3-(trifluoromethoxy)phenyl)pentyl)-N-((S)-4,4-dimethyl-1-(methylamino)pentan-2-yl)piperidine-1-carboxamide | 33 | 1.62 | 532 | 0.98 (s), 1.08-1.78 (m), 1.94 (m), 2.46 (m), 2.68 (s), 2.94 (dd), 3.02 (dd), 3.24 (s), 3.26 (t), 3.98 (d), 4.18 (d), 4.32 (d), 7.14 (d), 7.34 (m), 7.42 (m) |
| I-270A | (3R)—N-((S)-3-cyclohexyl-1-(methylamino)propan-2-yl)-3-((S)-1-(5-fluorobenzofuran-7-yl)-1- | 33 | 1.55 | 532 | 7.73 (s, 0.5H), 7.39 (m, 0.5H), 7.32-7.19 (m, 1.5H), 6.98 (t, 0.5H), 6.85 (m, 0.5H), 6.73 (s, 0.5H), 2.43 (td, 1H), 2.26 (t, |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | hydroxy-5-methoxypentyl)piperidine-1-carboxamide | | | | 1H). |
| I-271A | (3R)-3-((S)-1-(3-chlorophenyl)-1-hydroxy-5-methoxypentyl)-N'-cyano-N-((S)-3-cyclohexyl-1-(methylamino)propan-2-yl)piperidine-1-carboxamide | 125 | 1.62 | 532 | 2.98 (m), 3.25 (s), 4.09 (m), 4.33 (m), 7.11-7.18 (m), 7.46 (s) |
| I-272A | (3R)-3-((S)-1-acetamido-1-(3-fluorophenyl)-5-methoxypentyl)-N-((S)-3-cyclohexyl-1-(methylamino)propan-2-yl)piperidine-1-carboxamide | 133 | 1.4 | 533 | 7.84 (s, 1H), 7.30-7.24 (m, 1H), 7.06-6.89 (m, 3H), 4.10 (d, J = 12.6 Hz, 1H), 4.05-3.98 (m, 1H), 3.79 (d, J = 12.9 Hz, 1H), 3.30 (t, J = 6.3 Hz, 2H), 3.00-2.86 (m, 2H), 2.63 (s, 3H), 1.99 (s, 3H). |
| I-273A | (3R)-3-((S)-1-(3-chloro-2-fluorophenyl)-1-hydroxy-5-methoxypentyl)-N-(3-(3,3-difluorocyclobutyl)-1-(methylamino)propan-2-yl)piperidine-1-carboxamide | 33 | 1.45 | 534 | 7.42 (t), 7.26 (t), 7.03 (t), 4.30 (m), 3.91 (m), 3.78 (m), 3.20 (s), 3.14 (s), 3.08 (m), 2.88 (t) 2.60 (s). |
| I-274A | N-((S)-3-cyclohexyl-1-(methylamino)propan-2-yl)-3-(1-(3-(trifluoromethyl)phenyl)-1-hydroxy-5-methoxypentyl)benzamide | 129 | 1.65 | 535 | not determined |
| I-275A | (3R)-3-((S)-1-(2-(o-tolyloxy)phenyl)-1-hydroxy-5-methoxypentyl)-N-((S)-4-methyl-1-(methylamino)pentan-2-yl)piperidine-1-carboxamide | 33 | 1.59 | 540 | 0.64, 0.78 (d), 0.96 (m), 1.14-1.66 (m), 1.98 (m), 2.20 (s), 2.42 (m), 2.62 (m), 2.64 (s), 2.86 (m), 3.00 (m), 3.24 (s), 3.26 (t), 4.04 (m), 4.26 (d), 6.42 (d), 6.78 (d), 7.02 (m), 7.08 (m), 7.18 (d), 7.28 (d), 7.62 (d) |
| I-276A | (3R)-3-((S)-1-hydroxy-5-methoxy-1-(2-phenoxyphenyl)pentyl)-N-((S)-4,4-dimethyl-1-(methylamino)pentan-2-yl)piperidine-1-carboxamide | 33 | 1.64 | 540 | 0.86 (s), 1.20-1.64 (m), 1.94 (m), 2.24 (m), 2.32 (m), 2.58 (m), 2.64 (s), 2.88 (m), 2.98 (dd), 3.24 (s), 3.26 (t), 4.02 (d), 4.12 (m), 4.24 (d), 6.76 (d), 6.92 (d), 7.12 (m), 7.18 (m), 7.36 (m), 7.64 (d) |
| I-277A | (3R)-3-(1-(2-(benzyloxy)phenyl)-1-hydroxy-5-methoxypentyl)-N-((S)-4-methyl-1-(methylamino)pentan-2-yl)piperidine-1-carboxamide | 33 | 1.61 | 540 | 7.49-6.82 (m), 5.01 (m), 4.13 (br m), 3.88 (m), 3.77 (m), 3.20 (s), 3.13 (d), 2.57 (s), 2.51 (s), 0.83-0.70 (m) |
| I-278A | (3R)-3-((S)-1-(2-(m-tolyloxy)phenyl)-1-hydroxy-5-methoxypentyl)-N-((S)-4-methyl-1-(methylamino)pentan-2-yl)piperidine-1-carboxamide | 33 | 1.63 | 540 | 0.88 (d), 0.94 (d), 0.96 (m), 1.20-1.70 (m), 1.94 (m), 2.26 (s), 2.60 (m), 2.66 (s), 2.88 (m), 3.04 (dd), 3.24 (s), 3.26 (t), 4.00 (m), 4.26 (d), 6.72 (m), 6.96 (d), 7.06 (m), 7.18 (m), 7.22 (m), 7.62 (d) |
| I-279A[b] | (3R)-3-(1-(3-chloro-2-fluorophenyl)-5-ethoxy-1-hydroxypentyl)-N-((S)-3-cyclohexyl-1-(methylamino)propan-2-yl)piperidine-1-carboxamide | 33 | 1.65 | 541 | 7.53 (t, J = 6.6, 1H), 7.37 (t, J = 7.02, 1H), 7.14 (t, J = 7.8, 1H), 4.33 (d, J = 14, 1H), 4.13 (m, 1H), 3.99 (d, J = 12.5 1H), 33.40 (q, J = 7.0, 2H), 2.70 (s, 3H) |
| I-279A | (3R)-3-((S)-1-(3-chloro-2-fluorophenyl)-5-ethoxy-1-hydroxypentyl)-N-((S)-3-cyclohexyl-1-(methylamino)propan-2-yl)piperidine-1-carboxamide | 121 | | 540.3 | 1.19 (t, 3H), 1.86 (m), 2.33 (m, 1H), 2.68 (m, 2H), 2.77 (s, 3H), 2.92 (m, 1H), 3.22 (m, 1H), 3.37 (t, 2H), 3.42 (t, 2H), 3.74 (m, 1H), 4.14 (m, 1H), 4.26 (m, 1H), 5.98 (m, 1H), 7.06 (dd, 1H), 7.30 (dd, 1H), 7.50 (dd, 1H), 8.81 (brs, 1H), 9.76 (brs, 1H) |
| I-280A | (3R)-3-((S)-1-(3-chloro-2-fluorophenyl)-1-hydroxy-5-methoxypentyl)-N-(1-(methylamino)-3-(4-methylcyclohexyl)propan-2-yl)piperidine-1-carboxamide | 121 | 1.68 | 540 | 7.43 (t), 7.28 (t), 7.04 (t), 3.21 (m), 3.16 (s), 2.62 (s), 0.84 (m). |
| I-281A[b] | (3R)—N-((S)-3-cyclohexyl-1-(methylamino)propan-2-yl)-3-((S)-1-(2-(trifluoromethyl)phenyl)-1-hydroxy-5-methoxypentyl)piperidine-1-carboxamide | 121 | | 542.3 | 0.92 (m, 3H), 2.75 (s, 3H), 3.27 (s, 3H), 3.77 (m, 1H), 4.24 (m, 2H), 5.75 (m, 1H), 7.32 (t, 1H), 7.76 (d, 1H), 8.08 (m, 1H), 8.38 (brs, 1H), 9.64 (brs, 1H) |
| I-282A[b] | (3R)—N-((S)-3-cyclohexyl-1-(methylamino)propan-2-yl)-3-((S)-5-ethoxy-1-(2,3,5-trifluorophenyl)-1-hydroxypentyl)piperidine-1-carboxamide | 121 | | 542.6 | 1.15 (t, 3H), 2.34 (t, 1H), 2.68 (m, 2H), 2.79 (s, 3H), 2.92 (m, 1H), 3.24 (m, 1H), 3.39 (t, 2H), 3.49 (m, 2H), 3.79 (m, 1H), 4.26 (m, 1H), 6.02 (m, 1H), 6.80 (m, 1H), 7.06 (m, 1H), 8.68 (brs, 1H), 9.76 (brs, 1H) |
| I-283A | (3R)-3-((S)-1-(2-fluoro-3-methylphenyl)-1-hydroxy-5-methoxypentyl)-N-((S)-3-(4,4- | 121 | | 542.4 | 0.85 (m, 1H), 2.25 (m, 3H), 2.54 (m, 1H), 2.72 (s, 3H), 2.88 (m, 2H), 3.10 (m, 1H), 3.26 (s, 3H), 3.30 (t, 2H), 4.02 (m, 1H), |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | difluorocyclohexyl)-1-(methylamino)propan-2-yl)piperidine-1-carboxamide | | | | 4.14 (m, 1H), 4.30 (m, 1H), 7.02 (m, 1H), 7.11 (t, 1H), 7.36 (t, 1H) |
| I-284A[b] | (3R)-3-((S)-1-(2,3-dichlorophenyl)-1-hydroxy-5-methoxypentyl)-N-((S)-3-cyclohexyl-1-(methylamino)propan-2-yl)piperidine-1-carboxamide | 121 | | 542.3 | 1.88 (m, 1H), 2.52 (m, 1H), 2.75 (s, 3H), 2.96 (m, 1H), 3.28 (s, 3H), 3.34 (m, 2H), 3.79 (m, 1H), 3.97 (m, 1H), 4.24 (m, 1H), 5.80 (m, 1H), 7.19 (m, 1H), 7.38 (m, 1H), 7.72 (m, 1H), 8.59 (brs, 1H), 9.70 (brs, 1H) |
| I-285A[b] | (3R)-3-((R)-(3-ethoxypropoxy)(2,3-dichlorophenyl)methyl)-N-((S)-3-cyclohexyl-1-(methylamino)propan-2-yl)piperidine-1-carboxamide | 121 | | 542.3 | 1.19 (t, 3H), 2.90 (m, 1H), 3.06 (m, 1H), 3.30 (t, 3H), 3.82 (m, 1H), 4.02 (m, 1H), 4.13 (m, 1H), 4.57 (m, 1H), 4.91 (m, 1H), 5.59 (m, 1H), 7.22 (m, 1H), 7.30 (m, 1H), 7.41 (m, 1H), 8.76 (brs, 1H), 9.81 (brs, 1H) |
| I-286A[b] | (3R)-3-((S)-1-(2,3-dichlorophenyl)-5-ethoxy-1-hydroxypentyl)-N-((S)-3-cyclopentyl-1-(methylamino)propan-2-yl)piperidine-1-carboxamide | 119 | | 542.4 | 1.15 (t, 3H), 2.52 (m, 1H), 2.73 (s, 3H), 3.05 (m, 2H), 3.24 (m, 1H), 3.35 (m, 2H), 3.45 (m, 2H), 4.06 (m, 1H), 4.18 (m, 1H), 5.87 (m, 1H), 7.19 (m, 1H), 7.38 (d, 1H), 7.75 (d, 1H), 8.68 (brs, 1H), 9.80 (brs, 1H) |
| I-287A | (3R)-3-((S)-1-(2-(4-fluorophenoxy)phenyl)-1-hydroxy-5-methoxypentyl)-N-((S)-4-methyl-1-(methylamino)pentan-2-yl)piperidine-1-carboxamide | 33 | 1.56 | 544 | 0.78, 0.84 (d), 0.94 (m), 1.20-1.68 (m), 1.96 (m), 2.24 (m), 2.62 (m), 2.64 (s), 2.88 (m), 3.04 (dd), 3.24 (s), 3.26 (t), 4.00 (m), 4.26 (d), 6.64 (d), 6.94 (m), 7.06-7.20 (m), 7.64 (dd) |
| I-288A | (3R)-3-((S)-1-(5-fluoro-2-phenoxyphenyl)-1-hydroxy-5-methoxypentyl)-N-((S)-4-methyl-1-(methylamino)pentan-2-yl)piperidine-1-carboxamide | 33 | 1.60 | 544 | 0.78, 0.84 (d), 0.94 (m), 1.20-1.68 (m), 1.96 (m), 2.24 (m), 2.62 (m), 2.64 (s), 2.84 (m), 3.04 (dd), 3.24 (s), 3.26 (t), 3.98 (d), 4.00 (m), 4.26 (d), 6.74 (dd), 6.92 (m), 7.12 (m), 7.38 (m), 7.40 (dd) |
| I-289A | (3R)-3-((S)-1-(2-(3-fluorophenoxy)phenyl)-1-hydroxy-5-methoxypentyl)-N-((S)-4-methyl-1-(methylamino)pentan-2-yl)piperidine-1-carboxamide | 33 | 1.55 | 544 | 0.82, 0.86 (d), 1.20-1.70 (m), 1.96 (m), 2.18 (m), 2.60 (m), 2.66 (s), 2.86 (m), 3.04 (m), 3.24 (s), 3.26 (t), 3.98 (d), 4.02 (m), 4.26 (d), 6.64 (dd), 6.76 (dd), 6.84 (m), 7.16 (m), 7.24 (m), 7.38 (m), 7.64 (dd) |
| I-290A | (3R)-3-((S)-1-(2-(2-fluorophenoxy)phenyl)-1-hydroxy-5-methoxypentyl)-N-((S)-4-methyl-1-(methylamino)pentan-2-yl)piperidine-1-carboxamide | 33 | 1.53 | 544 | 7.63 (dd, 1H), 7.28-7.13 (m, 4H), 7.08 (m, 2H), 6.57 (d, 1H), 4.28 (d, 1H), 4.00 (m, 2H), 3.24 (s, 3H), 3.02 (dd, 1H), 2.66 (s, 3H), 1.96 (td, 1H), 0.93 (m, 1H), 0.83-0.71 (dd, 6H). |
| I-290B | (3R)-3-((R)-1-(2-(2-fluorophenoxy)phenyl)-1-hydroxy-5-methoxypentyl)-N-((S)-4-methyl-1-(methylamino)pentan-2-yl)piperidine-1-carboxamide | 33 | 1.6 | 544 | 7.65 (dd, 1H), 7.26-7.13 (m, 4H), 7.09-6.99 (m, 2H), 6.59 (d, 1H), 4.48 (d, 1H), 4.06 (m, 1H), 3.24ls, 3H), 3.03 (dd, 1H), 2.89 (t, 1H), 2.67 (s, 3H), 1.94 (td, 1H), 0.92-0.81 (dd, 6H), |
| I-291A | (3R)-3-((S)-1-(3-fluoro-2-phenoxyphenyl)-1-hydroxy-5-methoxypentyl)-N-((S)-4-methyl-1-(methylamino)pentan-2-yl)piperidine-1-carboxamide | 33 | 1.56 | 544 | 0.82 (m), 0.88, 0.92 (d), 1.08-1.70 (m), 1.92 (m), 2.04 (m), 2.58 (m), 2.64 (s), 2.84 (m), 3.04 (m), 3.20 (t), 3.22 (s), 3.94 (d), 4.02 (m), 4.24 (d), 6.80 (d), 7.02 (m), 7.14 (m), 7.22 (m), 7.26 (m), 7.52 (d) |
| I-292A | (3R)-3-((S)-1-(3-(4-fluorophenoxy)phenyl)-1-hydroxy-5-methoxypentyl)-N-((S)-4-methyl-1-(methylamino)pentan-2-yl)piperidine-1-carboxamide | 33 | 1.57 | 544 | 0.92 (d), 0.96 (d), 1.04 (m), 1.20-1.78 (m), 1.84 (m), 1.92 (m), 2.56 (m), 2.68 (s), 2.92 (dd), 3.06 (dd), 3.24 (s), 3.26 (t), 3.96 (d), 4.06 (m), 4.28 (d), 6.82 (d), 6.96-7.14 (m), 7.32 (m) |
| I-293A[b] | (3R)-3-((S)-1-(3-chlorophenyl)-1-hydroxy-5-methoxypentyl)-N-((S)-3-(4,4-difluorocyclohexyl)-1-(methylamino)propan-2-yl)piperidine-1-carboxamide | 33 | | 544.3 | 2.25 (dd, 1H), 2.56 (dd, 1H), 2.80 (s, 3H), 3.28 (s, 3H), 3.31 (t, 3H), 3.73 (m, 1H), 3.74 (m, 1H), 6.14 (m, 1H), 7.16-7.24 (m, 2H), 7.35 (s, 1H), 8.84 (brs, 1H), 9.62 (brs, 1H) |
| I-294A[b] | (3R)-3-((R)-(3-ethoxypropoxy)(3-chlorophenyl)methyl)-N-((S)-3-(4,4-difluorocyclohexyl)-1-(methylamino)propan-2-yl)piperidine-1-carboxamide | 33 | | 544.3 | 1.13 (t, 3H), 2.78 (s, 3H), 3.42 (t, 3H), 5.85 (m, 1H), 7.10 (m, 1H), 7.21 (s, 1H), 7.28 (m, 2H), 8.65 (brs, 1H), 9.71 (brs, 1H) |
| I-295A[b] | (3R)-3-((S)-1-(3-chloro-2-fluorophenyl)-1-hydroxy-5-methoxypentyl)-N-((S)-3-(trans-4-fluorocyclohexyl)-1-(methylamino)propan-2-yl)piperidine-1-carboxamide | 119 | | 544.5 | 2.77 (s, 3H), 2.92 (m, 2H), 3.29 (s, 3H), 3.33 (m, 2H), 3.89 (m, 1H), 4.12 (m, 1H), 4.39&4.52 (m, 1H), 6.08 (m, 1H), 7.06 (t, 1H), 7.29 (t, 1H), 7.51 (t, 1H), 8.88 (brs, 1H), 9.47 (brs, 1H) |
| I-295B[b] | (3R)-3-((S)-1-(3-chloro-2-fluorophenyl)-1-hydroxy-5-methoxypentyl)-N-((S)-3-(4- | 119 | | 544.5 | 0.92 (m, 2H), 2.75 (s, 3H), 3.29 (s, 3H), 3.93 (m, 1H), 4.12 (m, 1H), 4.32 (m, 1H), 6.15 (m, 1H), 7.06 (t, 1H), 7.28 (m, 1H), |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | fluorocyclohexyl)-1-(methylamino)propan-2-yl)piperidine-1-carboxamide | | | | 7.51 (t, 1H), 8.84 (brs, 1H), 9.28 (brs, 1H) |
| I-296A | (3R)-3-((S)-1-(2-(2-chlorophenyl)phenyl)-1-hydroxy-5-methoxypentyl)-N-((S)-4-methyl-1-(methylamino)pentan-2-yl)piperidine-1-carboxamide | 119 | | 544.4 | 0.88 (m, 6H), 2.59 (m, 1H), 2.68 (m, 3H), 2.72 (m, 2H), 3.05 (m, 1H), 3.25 (m, 3H), 3.46 (m, 2H), 4.00 (m, 3H), 6.94 (m, 3H), 7.16-7.48 (m, 6H), 7.58 (m, 1H) |
| I-296A[b] | (3R)-3-((S)-1-(2-(2-chlorophenyl)phenyl)-1-hydroxy-5-methoxypentyl)-N-((S)-4-methyl-1-(methylamino)pentan-2-yl)piperidine-1-carboxamide | 119 | | 544.2 | 0.94 (m, 6H), 2.72 (m, 3H), 2.98 (m, 3H), 3.28 (s, 3H), 3.33 (m, 2H), 3.72 (m, 1H), 4.15 (m, 2H), 5.72 (m, 1H), 6.98 (m, 2H), 7.20 (m, 2H), 7.48 (m, 4H), 8.75 (brs, 1H), 10.08 (brs, 1H) |
| I-296B[b] | (3R)-3-((R)-1-(2-(2-chlorophenyl)phenyl)-1-hydroxy-5-methoxypentyl)-N-((S)-4-methyl-1-(methylamino)pentan-2-yl)piperidine-1-carboxamide | 119 | | 544.2 | 0.88 (m, 6H), 2.73 (s, 3H), 3.29 (s, 3H), 3.33 (m, 2H), 3.80 (m, 1H), 4.28 (m, 2H), 5.42 (m, 1H), 7.00 (m, 2H), 7.19 (m, 2H), 7.38 (m, 1H), 7.52 (m, 3H), 8.70 (brs, 1H), 10.02 (brs, 1H) |
| I-297A | (3R)-3-((S)-1-(2-(4-chlorophenyl)phenyl-1-hydroxy-5-methoxypentyl)-N-((S)-4-methyl-1-(methylamino)pentan-2-yl)piperidine-1-carboxamide | 119 | | 544.3 | 0.90 (m, 6H), 1.78 (m, 1H), 2.57 (m, 1H), 2.68 (s, 3H), 2.82 (m, 2H), 3.03 (m, 1H), 3.25 (m, 3H), 3.98 (m, 3H), 6.94 (m, 1H), 7.05-7.42 (m, 6H), 7.72 (m, 1H) |
| I-298A | (3R)-3-((S)-1-(2-(3-chlorophenyl)phenyl)-1-hydroxy-5-methoxypentyl)-N-((S)-4-methyl-1-(methylamino)pentan-2-yl)piperidine-1-carboxamide | 119 | | 544.3 | 0.92 (m, 6H), 1.76 (m, 1H), 2.67 (s, 3H), 2.82 (m, 1H), 3.02 (m, 1H), 3.28 (s, 3H), 3.99 (m, 1H), 6.95 (m, 1H), 7.05-7.39 (m, 6H), 7.71 (m, 1H) |
| I-299A | (3R)—N-((S)-3-(4,4-difluorocyclohexyl)-1-(methylamino)propan-2-yl)-3-((S)-1-(2,3-difluorophenyl)-1-hydroxy-5-methoxypentyl)piperidine-1-carboxamide | 33 | 1.43 | 546 | 7.25 (m), 7.02 (m), 4.24 (d), 4.02 (m), 3.86 (d), 3.19 (s), 3.14 (s), 2.99 (d), 2.83 (t), 2.67 (t), 2.60 (s), 2.54 (t). |
| I-300A | (2RS)-2-((RS)-1-(3-chlorophenyl)-1-hydroxy-5-methoxypentyl)-N-((S)-3-(4,4-difluorocyclohexyl)-1-(methylamino)propan-2-yl)morpholine-4-carboxamide | 33 | 1.43 | 546 | 7.53 (d, 1H), 7.42 (t, 1H), 7.28 (t, 1H), 7.22 (d, 1H), 4.11 (m, 2H), 3.07 (d, 1H), 2.68 (s, 3H), 1.05 (m, 1H). |
| I-301A | (3R)-3-((S)-1-acetamido-1-(3-chlorophenyl)-5-methoxypentyl)-N-((S)-3-cyclohexyl-1-(methylamino)propan-2-yl)piperidine-1-carboxamide | 133 | 1.53 | 549, 551 | 7.86 (s, 1H), 7.27-7.15 (m, 4H), 4.10 (d, J = 11.4 Hz, 1H), 4.03-3.98 (m, 1H), 3.79 (d, J = 13.5 Hz, 1H), 3.30 (t, J = 6.1 Hz, 2H), 3.00-2.85 (m, 2H), 2.62 (s, 3H), 1.98 (s, 3H). |
| I-302A | (3R)-3-((S)-1-(benzofuran-7-yl)-1-hydroxy-5-methoxypentyl)-N-((S)-3-(4,4-difluorocyclohexyl)-1-(methylamino)propan-2-yl)piperidine-1-carboxamide | 121 | | 550.3 | 0.72 (m, 1H), 2.72 (s, 3H), 2.79 (m, 1H), 2.96 (m, 1H), 3.10 (m, 1H), 3.18 (s, 3H), 3.22 (m, 2H), 3.30 (t, 2H), 3.98 (m, 1H), 4.13 (m, 1H), 4.40 (m, 1H), 6.84 (t, 1H), 7.22 (m, 1H), 7.42 (m, 1H), 7.52 (m, 1H), 7.68 (m, 1H) |
| I-303A[b] | (3R)—N-((S)-4,4,4-trifluoro-1-(methylamino)butan-2-yl)-3-((S)-1-hydroxy-5-methoxy-1-(2-phenoxyphenyl)pentyl)piperidine-1-carboxamide | 33 | 1.49 | 552 | 2.40 (d, 3H), 3.25 (s, 3H), 3.79 (m, 1H), 6.75 (d, 1H), 6.90 (d, 2H), 7.10 (m, 3H), 7.38 (m, 2H), 7.58 (d, 1H) |
| I-304A | (3R)-3-((S)-1-(2-(trifluoromethyl)phenoxy)phenyl)-1-hydroxy-5-methoxypentyl)-N-((S)-1-(methylamino)propan-2-yl)piperidine-1-carboxamide | 33 | 1.5 | 552 | 7.71 (dd, 2H), 7.56 (t, 1H), 7.28-7.21 (m, 2H), 7.16 (t, 1H), 7.00-6.83 (br d, 1H), 6.71 (d, 1H), 4.31 (d, 1H), 2.81 (t, 1H), 2.48 (br s, 1H), 0.89 (m, 2H). |
| I-305A[b] | (3R)—N-((S)-1-(2-methoxyethylamino)-3-cyclohexylpropan-2-yl)-3-((S)-1-(3-chlorophenyl)-1-hydroxy-5-methoxypentyl)piperidine-1-carboxamide | 33 | 1.72 | 552 | 3.25 (s, 3H), 3.75 (m, 1H), 7.10-7.60 (m, 4H) |
| I-306A | (3R)—N-((S)-3-cyclohexyl-1-(methylamino)propan-2-yl)-3-((S)-1-(2,2-difluorobenzo[d][1,3]dioxol-4-yl)-1-hydroxy-5-methoxypentyl)piperidine-1-carboxamide | 33 | 1.61 | 554 | 2.60 (m), 2.71 (s), 2.92 (dd), 3.06 (dd), 3.13 (s), 4.02 (br d), 4.12 (m), 4.35 (br d), 7.03-7.09 (m), 7.30 (dd) |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-307A | (3R)-3-((S)-1-(2-(o-tolyloxy)-3-methylphenyl)-1-hydroxy-5-methoxypentyl)-N-((S)-4-methyl-1-(methylamino)pentan-2-yl)piperidine-1-carboxamide | 33 | 1.64 | 554 | 0.76-1.04 (m), 1.20-1.68 (m), 1.92, 1.94 (two s), 2.38, 2.40 (two s), 2.50 (m), 2.64, 2.70 (two s), 2.80-3.16 (m), 3.20, 3.24 (two s), 3.80 (d), 3.92-4.22 (m), 6.24 (d), 6.86 (m), 6.98 (m), 7.12-7.24 (m), 7.56 (d) |
| I-308A[b] | (3R)-3-((S)-1-(2,3-dichlorophenyl)-5-ethoxy-1-hydroxypentyl)-N-((S)-3-cyclohexyl-1-(methylamino)propan-2-yl)piperidine-1-carboxamide | 121 | | 556.3 | 1.16 (t, 3H), 1.94 (m, 1H), 2.62 (m, 1H), 2.74 (s, 3H), 2.96 (m, 1H), 3.13 (m, 2H), 3.36 (t, 3H), 3.45 (m, 2H), 4.22 (m, 1H), 5.83 (m, 1H), 7.19 (dd, 1H), 7.38 (d, 1H), 7.75 (d, 1H), 8.77 (brs, 1H), 9.78 (brs, 1H) |
| I-309A[b] | (3R)—N-((S)-3-cyclohexyl-1-(methylamino)propan-2-yl)-3-((S)-1-hydroxy-5-methoxy-1-(3-(trifluoromethoxy)phenyl)pentyl)piperidine-1-carboxamide | 121 | | 558.4 | 1.54 (t, 1H), 2.08 (m, 1H), 2.20 (m, 1H), 2.55 (t, 1H), 2.82 (s, 3H), 2.88 (m, 1H), 3.27 (s, 3H), 3.75 (m, 1H), 3.24 (m, 1H), 4.24 (m, 2H), 6.03 (m, 1H), 7.10 (d,1H), 7.23 (m, 1H), 7.34 (t, 1H), 8.95 (brs, 1H), 9.73 (brs, 1H) |
| I-310A[b] | (3R)—N-((S)-3-cyclohexyl-1-(methylamino)propan-2-yl)-3-((S)-1-hydroxy-5-methoxy-1-(2-(trifluoromethoxy)phenyl)pentyl)piperidine-1-carboxamide | 121 | | 558.3 | 2.311.88 (m, 1H), 2.02 (m, 1H), 2.25 (m, 1H), 2.74 (s, 3H), 2.95 (m, 2H), 3.28 (s, 3H), 3.78 (m, 1H), 4.04 (m, 1H), 5.92 (m, 1H), 7.24 (m, 3H), 7.69 (d, 1H), 8.80 (brs, 1H), 9.62 (brs, 1H) |
| I-311A | (3R)-3-((S)-1-(2-(p-tolyloxy)-3-fluorophenyl)-1-hydroxy-5-methoxypentyl)-N-((S)-4-methyl-1-(methylamino)pentan-2-yl)piperidine-1-carboxamide | 33 | 1.63 | 558 | 0.82 (m), 0.88, 0.92 (d), 1.08-1.68 (m), 1.92 (m), 2.04 (m), 2.24 (s), 2.58 (m), 2.64 (s), 2.84 (m), 3.04 (m), 3.24 (s), 3.26 (t), 3.94 (d), 4.02 (m), 4.24 (d), 6.66 (d), 7.08 (m), 7.20 (m), 7.46 (d) |
| I-312A | (3R)-3-((S)-1-(2-(o-tolyloxy)-3-fluorophenyl)-1-hydroxy-5-methoxypentyl)-N-((S)-4-methyl-1-(methylamino)pentan-2-yl)piperidine-1-carboxamide | 33 | 1.59 | 558 | 0.70-1.10 (m), 1.20-1.78 (m), 1.92 (m), 2.36, 2.38 (two s), 2.50 (m), 2.62, 2.72 (two s), 2.80-3.08 (m), 3.10, 3.36 (two t), 3.20, 3.26 (two s), 3.82 (d), 3.96-4.08 (m), 4.22 (d), 6.42, 6.44 (two d), 6.92 (m), 7.02 (m), 7.14 (m), 7.22 (m), 7.54 (d) |
| I-313A | (3R)-3-((S)-1-(2-(5-fluoro-2-methylphenoxy)phenyl)-1-hydroxy-5-methoxypentyl)-N-((S)-4-methyl-1-(methylamino)pentan-2-yl)piperidine-1-carboxamide | 33 | 1.62 | 558 | 0.72 (d), 0.80 (d), 0.92 (m), 1.20-1.68 (m), 1.98 (m), 2.20 (s), 2.32 (m), 2.60 (m), 2.64 (s), 2.84-3.04 (m), 3.24 (s), 3.26 (t), 4.02 (m), 4.24 (d), 6.48 (d), 6.58 (d), 6.84 (m), 7.08 (m), 7.18 (m), 7.28 (m), 7.64 (d) |
| I-314A | (3R)-3-((S)-1-(2-(4-fluoro-2-methylphenoxy)phenyl)-1-hydroxy-5-methoxypentyl)-N-((S)-4-methyl-1-(methylamino)pentan-2-yl)piperidine-1-carboxamide | 33 | 1.61 | 558 | 0.70 (d), 0.80 (d), 0.92 (m), 1.18-1.68 (m), 1.98 (m), 2.20 (s), 2.40 (m), 2.62 (m), 2.64 (s), 2.84-3.04 (m), 3.24 (s), 3.26 (t), 4.02 (m), 4.26 (d), 6.40 (d), 6.78 (m), 6.94 (m), 7.00-7.14 (m), 7.62 (d) |
| I-315A | (3R)—N-((S)-3-cyclohexyl-1-(methylamino)propan-2-yl)-3-(1-(2-(cyclopentyloxy)phenyl)-1-hydroxy-5-methoxypentyl)piperidine-1-carboxamide | 33 | 1.76 | 558 | 7.40 (d), 7.34 (d), 7.06 (s), 6.76 (s), 4.10 (m), 3.96 (m), 3.89-3.80 (m), 3.18 (m), 3.14 (m), 3.12 (m), 2.95 (m), 2.84 (q), 2.72 (m), 2.58 (s), 2.51 (s). |
| I-316A | (3R)-3-(1-(2-(2-cyclopropylethoxy)phenyl)-1-hydroxy-5-methoxypentyl)-N-((S)-3-cyclohexyl-1-(methylamino)propan-2-yl)piperidine-1-carboxamide | 33 | 1.79 | 558 | 7.47 (d), 7.37 (d), 7.13 (q), 6.89-6.05 (m), 4.14 (d), 3.97 (m), 3.88 (m), 3.21 (m), 3.17 (m), 3.14 (m), 2.61 (s), 2.54 (s), 0.77 (br s), 0.42 (d), 0.06 (s). |
| I-317A | (3R)-3-((S)-5-ethoxy-1-(2,3-difluorophenyl)-1-hydroxypentyl)-N-((S)-3-(4,4-difluorocyclohexyl)-1-(methylamino)propan-2-yl)piperidine-1-carboxamide | 121 | | 560.3 | 0.89 (m, 1H), 1.12 (t, 3H), 2.72 (s, 3H), 2.95 (m, 1H), 3.09 (m, 1H), 3.32 (t, 2H), 3.38 (m, 2H), 3.96 (m, 1H), 4.15 (m, 1H), 4.36 (m, 1H), 7.13 (m, 1H), 7.36 (m, 1H) |
| I-318A | (3R)-3-((S)-1-(2-(4-fluorophenoxy)-5-fluorophenyl)-1-hydroxy-5-methoxypentyl)-N-((S)-4-methyl-1-(methylamino)pentan-2-yl)piperidine-1-carboxamide | 33 | 1.59 | 562 | 0.78, 0.86 (d), 0.94 (m), 1.20-1.68 (m), 1.96 (m), 2.24 (m), 2.62 (m), 2.64 (s), 2.86 (m), 3.04 (m), 3.24 (s), 3.26 (t), 3.98 (d), 4.02 (m), 4.28 (d), 6.84 (dd), 6.94 (m), 7.10 (m), 7.40 (dd) |
| I-318A | (3R)-3-((R)-1-(2-(4-fluorophenoxy)-5-fluorophenyl)-1-hydroxy-5-methoxypentyl)-N-((S)-4-methyl-1-(methylamino)pentan-2-yl)piperidine-1-carboxamide | 33 | 1.65 | 562 | 0.94, 0.98 (d), 1.24-1.64 (m), 1.78 (m), 1.96 (m), 2.14 (m), 2.64 (m), 2.70 (s), 2.78 (m), 2.92 (m), 3.08 (m), 3.24 (s), 3.26 (t), 3.98 (d), 4.08 (m), 4.34 (d), 6.84 (m), 6.96-7.12 (m), 7.24 (m) |
| I-319A | (3R)-3-((S)-1-(3,5-difluoro-2-phenoxyphenyl)-1-hydroxy-5-methoxypentyl)-N-((S)-4-methyl-1-(methylamino)pentan-2-yl)piperidine-1-carboxamide | 33 | 1.60 | 562 | 0.88, 0.90 (d), 1.10-1.70 (m), 1.96 (m), 2.04 (m), 2.58 (m), 2.64 (s), 2.80 (m), 3.04 (m), 3.24 (st), 3.94 (m), 4.02 (m), 4.24 (d), 6.80 (d), 7.04 (m), 7.28 (m) |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-320A[b] | (3R)-3-((S)-1-(3-chloro-2-fluorophenyl)-1-hydroxy-5-methoxypentyl)-N-((S)-3-(4,4-difluorocyclohexyl)-1-(methylamino)propan-2-yl)piperidine-1-carboxamide | 121 | | 562.1 | 1.03 (m, 1H), 2.24 (m, 1H), 2.78 (s, 3H), 2.98 (m, 1H), 3.30 (s, 3H), 3.36 (m, 2H), 4.10 (m, 1H), 4.28 (m, 1H), 6.16 (m, 1H), 7.08 (t, 3H), 7.31 (t, 1H), 7.48 (t, 1H), 8.16 (brs, 1H), 9.56 (brs, 1H) |
| I-321A[b] | (3R)-3-((R)-(3-ethoxypropoxy)(3-chloro-2-fluorophenyl)methyl)-N-((S)-3-(4,4-difluorocyclohexyl)-1-(methylamino)propan-2-yl)piperidine-1-carboxamide | 121 | | 562.2 | 1.16 (t, 3H), 2.08 (m, 2H), 2.73 (s, 3H), 2.94 (m, 1H), 3.15 (m, 1H), 3.32 (m, 2H), 3.42 (m, 2H), 3.45 (m, 3H), 3.78 (m, 2H), 4.16 (m, 2H), 4.34 (d, 1H), 5.79 (m, 1H), 7.11 (m, 1H), 7.23 (t, 1H), 7.33 (t, 1H), 8.68 (brs, 1H), 10.02 (brs, 1H) |
| I-322A | (3R)-3-((S)-1-(3-chlorophenyl)-5-methoxy-1-(propionamido)pentyl)-N-((S)-3-cyclohexyl-1-(methylamino)propan-2-yl)piperidine-1-carboxamide | 133 | 1.53 | 563, 565 | 7.76 (s, 1H), 7.27-7.15 (m, 4H), 4.09 (d, J = 12.9 Hz, 1H), 4.05-3.99 (m, 1H), 3.81 (d, J = 11.4 Hz, 1H), 3.30 (t, J = 6.3 Hz, 2H), 3.01-2.85 (m, 2H), 2.63 (s, 3H), 1.08 (t, J = 7.6 Hz, 3H). |
| I-323A[b] | (3R)—N-((S)-3-(4,4-difluorocyclohexyl)-1-(methylamino)propan-2-yl)-3-((S)-1-(2,3,5-trifluorophenyl)-1-hydroxy-5-methoxypentyl)piperidine-1-carboxamide | 121 | | 564.3 | 2.05 (m, 2H), 2.29 (m, 1H), 2.72 (s, 3H), 3.28 (s, 3H), 3.32 (m, 2H), 3.86 (m, 1H), 4.25 (m, 2H), 6.11 (m, 2H), 6.81 (m, 2H), 7.08 (m, 1H), 8.74 (brs, 1H), 9.78 (brs, 1H) |
| I-324A[b] | (3R)-3-((R)-(3-ethoxypropoxy)(2,3,5-trifluorophenyl)methyl)-N-((S)-3-(4,4-difluorocyclohexyl)-1-(methylamino)propan-2-yl)piperidine-1-carboxamide | 121 | | 564.3 | 1.08 (t, 3H), 2.73 (s, 3H), 2.99 (m, 1H), 3.13 (m, 1H), 3.36 (m, 2H), 3.45 (m, 2H), 3.82 (m, 1H), 4.23 (m, 2H), 4.38 (d, 1H), 5.39 (m, 1H), 6.83 (t, 1H), 7.10 (m, 1H), 8.70 (brs, 1H), 9.75 (brs, 1H) |
| I-325A | (3R)—N-(3-(3,3-difluorocyclobutyl)-1-(methylamino)propan-2-yl)-3-((R)-1-hydroxy-5-methoxy-1-(3-(trifluoromethoxy)phenyl)pentyl)piperidine-1-carboxamide | 33 | 1.55 | 566 | 7.40 (m, 3H), 7.10 (d, J = 8.2, 1H), 4.42 (d, J = 11.7, 0.5H), 4.31 (d, J = 13.3, 0.5H), 3.99 (m, 1H), 3.91 (d, J = 10.1, 0.5H), 3.81 (d, J = 11.3, 0.5H), 3.27 (s, 3H), 2.68 (s, 3H) |
| I-326A | (3R)-3-(1-(3-hydroxypropoxy)-1-(3-chlorophenyl)-5-methoxypentyl)-N-((S)-3-cyclohexyl-1-(methylamino)propan-2-yl)piperidine-1-carboxamide | 146 | 1.71 | 566, 568 | not determined |
| I-327A[b] | (3R)—N-((S)-1-(2-ethoxyethylamino)-3-cyclohexylpropan-2-yl)-3-((S)-1-(3-chlorophenyl)-1-hydroxy-5-methoxypentyl)piperidine-1-carboxamide | 33 | 1.71 | 566 | 1.10 (m, 3H), 2.75 (m, 2H), 3.25 (s, 3H), 3.55 (m, 2H), 3.75 (m, 1H), 7.1-7.40 (m, 4H) |
| I-328A | (3R)—N-((S)-3-cyclohexyl-1-(methylamino)propan-2-yl)-3-((S)-1-hydroxy-5-methoxy-1-(2-(pyridin-3-yloxy)phenyl)pentyl)piperidine-1-carboxamide | 33 | 1.38 | 567 | 8.45 (s, 2H), 7.80-7.70 (m, 3H), 7.34-7.22 (m, 2H), 6.96-6.88 (dd, 1H), 4.09 (m, 1H), 3.04 (dd, 1H), 2.93-2.82 (m, 1H), 2.68 (s, 3H), 2.22 (td, 1H), 2.11 (tt, 1H). |
| I-329A | (3R)-3-((R)-1-acetamido-1-(3-chloro-2-fluorophenyl)-5-methoxypentyl)-N-((S)-3-cyolohexyl-1-(methylamino)propan-2-yl)piperidine-1-carboxamide | 133 | 1.44 | 567, 569 | 7.90 (s, 1H), 7.31-7.27 (m, 1H), 7.21-7.17 (m, 1H), 7.02 (t, J = 7.9 Hz, 1H), 4.06-3.98 (m, 2H), 3.89 (d, J = 12.9 Hz, 1H), 3.24 (t, J = 6.3 Hz, 2H), 3.17 (s, 3H), 2.98-2.77 (m, 2H), 2.58 (s, 3H), 1.91 (s, 3H). |
| I-329B | (3R)-3-((S)-1-acetamido-1-(3-chloro-2-fluorophenyl)-5-methoxypentyl)-N-((S)-3-cyclohexyl-1-(methylamino)propan-2-yl)piperidine-1-carboxamide | 133 | 1.46 | 567, 569 | 7.98 (s, 1H), 7.32-7.28 (m, 1H), 7.19-7.15 (m, 1H), 7.04 (t, J = 8.1 Hz, 1H), 4.19 (d, J = 9.1 Hz, 1H), 4.03-3.98 (m, 1H), 3.80 (d, J = 13.2 Hz, 1H), 2.99-2.86 (m, 2H), 2.61 (s, 3H), 1.95 (s, 3H). |
| I-330A | (3R)-3-((S)-1-(2-(allyloxy)-3-bromophenyl)-1-hydroxy-5-methoxypentyl)-N-((S)-4-methyl-1-(methylamino)pentan-2-yl)piperidine-1-carboxamide | 33 | 1.55 | 568, 570 | 0.96 (d, 3H), 0.99 (d, 3H), 2.70 (s, 3H), 3.26 (s, 3H), 3.98 (br d, 1H), 4.08 (br d, 1H), 4.30 (br d, 1H), 4.58 (m, 1H), 5.27 (d, 1H), 5.42 (d, 1H), 6.12 (m, 1H), 7.01 (m, 1H), 7.53 (m, 2H) |
| I-331A[b] | (3R)—N-((S)-1-(2,2,2-trifluoroethylamino)-3-cyclohexylpropan-2-yl)-3-((S)-1-(3-chlorophenyl)-1-hydroxy-5-methoxypentyl)piperidine-1-carboxamide | 118 | | 576.1 | 1.52 (m, 2H), 2.03 (m, 1H), 2.33 (m, 1H), 2.57 (t, 1H), 3.28 (s, 3H), 3.31 (t, 2H), 3.71 (m, 2H), 3.94 (m, 1H), 4.15 (m, 2H), 5.53 (m, 1H), 7.16 (d, 1H), 7.23 (m, 2H), 7.34 (s, 1H) |
| I-332A | (3R)-3-(1-(3-chlorophenyl)-1-(isobutyramido)-5-methoxypentyl)- | 133 | 1.55, 1.59 | 577, 579 | 7.68, 7.55 (s, 1H), 7.18-7.06 (m, 4H), 4.03-3.91 (m, 2H), 3.78 (d, J = 12.4 Hz, |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | N-((S)-3-cyclohexyl-1-(methylamino)propan-2-yl)piperidine-1-carboxamide | | | | 1H), 3.71 (d, J = 12.8 Hz, 1H), 3.127, 3.121 (s, 3H), 2.536, 2.522 (s, 3H). |
| I-333A[b] | (3R)-3-((S)-5-ethoxy-1-(2,3,5-trifluorophenyl)-1-hydroxypentyl)-N-((S)-3-(4,4-difluorocyclohexyl)-1-(methylamino)propan-2-yl)piperidine-1-carboxamide | 121 | | 578.3 | 1.15 (t, 3H), 2.43 (m, 1H), 2.54 (m, 1H), 2.65 (t, 1H), 2.79 (s, 3H), 2.96 (m, 1H), 3.27 (m, 1H), 3.36 (t, 2H), 3.45 (t, 2H), 3.76 (m, 1H), 4.23 (m, 1H), 4.35 (m, 1H), 6.18 (m, 1H), 6.82 (m, 1H), 7.09 (m, 1H), 9.01 (brs, 1H), 9.87 (brs, 1H) |
| I-334A[b] | (3R)—N-(5,5,5-trifluoro-4-methyl-1-(methylamino)pentan-2-yl)-3-((S)-1-hydroxy-5-methoxy-1-(2-phenoxyphenyl)pentyl)piperidine-1-carboxamide | 33 | 1.61 | 580 | 1.15 (m, 3H), 2.50 (2s, 3H), 3.25 (s, 3H), 3.80 (m, 1H), 6.77 (d, 1H), 6.95 (m, 2H), 7.10-7.30 (m, 3H), 7.35 (m, 2H) 7.52 (m, 1H) |
| I-335A | (3R)-3-(1-(2-(benzyloxy)phenyl)-1-hydroxy-5-methoxypentyl)-N-((S)-1-cyclohexyl-3-(methylamino)propan-2-yl)piperidine-1-carboxamide | 33 | 1.74 | 580 | 7.50-6.89 (m), 5.02 (m), 4.15 (d), 3.96 (m), 3.85 (m), 3.21 (m), 3.12 (d), 2.58 (s), 2.51 (s). |
| I-336A | (3R)-3-((S)-1-(3-chloro-2-fluorophenyl)-5-methoxy-1-(propionamido)pentyl)-N-((S)-3-cyclohexyl-1-(methylamino)propan-2-yl)piperidine-1-carboxamide | 133 | 1.52 | 581 | 7.99 (s, 0.5H), 7.40 (t, 1H), 7.27 (t, 1H), 7.14 (t, 1H), 4.28 (d, 1H), 4.11 (m, 1H), 3.91 (d, 1H), 3.88 (t, 2H), 3.29 (s, 3H), 3.07 (dd, 1H), 2.71 (s, 3H), 2.54 (t, 1H), 1.92 (d, 1H), 1.83 (d, 1H), 1.16 (t, 3H). |
| I-337A | (3R)-3-((S)-1-(2-(4-fluorophenoxy)phenyl)-1-hydroxy-5-methoxypentyl)-N-((S)-3-cyclohexyl-1-(methylamino)propan-2-yl)piperidine-1-carboxamide | 33 | 1.71 | 584 | 0.78-1.76 (m), 1.98 (m), 2.30 (m), 2.62 (m), 2.64 (s), 2.86 (m), 3.04 (m), 3.24 (s), 3.26 (t), 4.04 (m), 4.26 (d), 6.64 (d), 6.96 (m), 7.08-7.20 (m), 7.64 (d) |
| I-338A | (3R)—N-((S)-3-cyclohexyl-1-(methylamino)propan-2-yl)-3-((S)-1-(5-fluoro-2-phenoxyphenyl)-1-hydroxy-5-methoxypentyl)piperidine-1-carboxamide | 33 | 1.74 | 584 | 0.78-1.76 (m), 1.96 (m), 2.24 (m), 2.62 (m), 2.64 (s), 2.86 (m), 3.04 (m), 3.24 (s), 3.26 (t), 3.98 (d), 4.02 (m), 4.24 (d), 6.74 (dd), 6.92 (m), 7.14 (m), 7.36 (m), 7.40 (dd) |
| I-339A | (3R)-3-((S)-1-(2-(2-(trifluoromethyl)phenoxy)phenyl)-1-hydroxy-5-methoxypentyl)-N-((S)-4-methyl-1-(methylamino)pentan-2-yl)piperidine-1-carboxamide | 33 | 1.62 | 594 | 7.75-7.67 (dd, 2H), 7.59 (br s, 1H), 7.29 (t, 1H), 7.23-7.12 (m, 2H), 6.99-6.84 (br d, 1H), 6.65 (d, 1H), 4.23 (m, 1H), 3.99 (m, 2H), 3.01 (m, 1H), 0.99-0.68 (m, 6H). |
| I-340A | (3R)-3-((S)-1-(3-chloro-2-fluorophenyl)-1-(isobutyramido)-5-methoxypentyl)-N-((S)-3-cyclohexyl-1-(methylamino)propan-2-yl)piperidine-1-carboxamide | 132 | 1.59 | 595 | 7.94 (s, 1H), 7.41 (t, 1H), 7.27 (t, 1H), 7.15 (t, 1H), 4.25 (d, 1H), 4.12 (m, 1H), 3.93 (d, 1H), 3.38 (t, 2H), 3.28 (s, 3H), 3.08 (dd, 1H), 2.71 (s, 3H), 2.54 (t, 1H), 1.13 (dd, 6H). |
| I-340A | (3R)-3-((R)-1-(3-chloro-2-fluorophenyl)-1-(isobutyramido)-5-methoxypentyl)-N-((S)-3-cyclohexyl-1-(methylamino)propan-2-yl)piperidine-1-carboxamide | 133 | 1.57 | 595 | 7.83 (s, 1H), 7.39 (t, 1H), 7.29 (t, 1H), 7.13 (t, 1H), 4.14 (m, 2H), 3.99 (d, 1H), 3.27 (s, 3H), 3.07 (dd, 1H), 2.92 (dd, 1H), 2.54 (tm, 1H), 2.03 (d, 1H), 1.11 (m, 6H), 1.02 (m, 1H), 0.91 (m, 1H). |
| I-341A | (3R)-3-((S)-1-(3-chlorophenyl)-1-hydroxypropyl)-N-((S)-1-cyclohexyl-3-(methylamino)propan-2-yl)piperidine-1-carboxamide | 121 | | 450 | 2.53 (m, 2H), 2.70 (s, 3H), 2.92 (m, 1H), 3.08 (m, 1H), 3.96 (m, 1H), 4.12 (m, 1H), 4.28 (m, 1H), 7.24-7.32 (m, 3H), 7.43 (s, 1H) |
| I-342A | (SR)—N-((S)-1-cyclohexyl-3-(methylamino)propan-2-yl)-2-((RS)-5-methoxy-1-phenylpentyl)morpholine-4-carboxamide | 37 | 1.55 | 460 | 7.31 (t, 1H), 7.25-7.18 (m, 2H), 3.23 (s, 3H), 2.62 (s, 3H), 2.10 (m, 1H), 0.97 (m, 1H), 0.84 (m, 1H). |
| I-343A | (3R)-3-((S)-1-(3-chlorophenyl)-1-hydroxybutyl)-N-((S)-1-cyclohexyl-3-(methylamino)propan-2-yl)piperidine-1-carboxamide | 121 | | 464 | 0.88 (t, 3H), 2.56 (m, 2H), 2.70 (s, 3H), 2.91 (m, 1H), 3.06 (m, 1H), 3.98 (m, 1H), 4.12 (m, 1H), 4.39 (m, 1H), 7.24-7.31 (m, 3H), 7.43 (s, 1H) |
| I-345A[b] | 3-((R)-1-cyclohexyl-1-hydroxy-5-methoxypentyl)-N-((S)-1-cyclohexyl-3-(methylamino)propan-2-yl)benzamide | 121 | | 473 | 2.74 (s, 3H), 3.28 (s, 3H), 3.09 (m, 1H), 4.64 (m, 1H), 7.40 (m, 2H), 7.71 (m, 1H), 8.03 (m, 1H), 8.51 (brs, 1H), 9.18 (brs, 1H) |
| I-346A | (3R)-3-((S)-1-(3-chlorophenyl)-1-hydroxypentyl)-N-((S)-1-cyclohexyl-3-(methylamino)propan-2-yl)piperidine-1-carboxamide | 121 | | 478 | 0.86 (t, 3H), 2.53 (m, 2H), 2.70 (s, 3H), 2.93 (m, 1H), 3.04 (m, 1H), 3.96 (d, 1H), 4.12 (m, 1H), 4.28 (d, 1H), 7.22-7.31 (m, 3H), 7.43 (s, 1H) |
| I-347A | (3R)-3-((R)-1-cyclohexyl-1-hydroxy-5-methoxypentyl)-N-((S)-1- | 121 | | 480 | 2.70 (s, 3H), 2.92 (m, 1H), 3.06 (m, 1H), 3.31 (s, 3H), 4.12 (m, 3H), |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-348A | cyclohexyl-3-(methylamino)propan-2-yl)piperidine-1-carboxamide (3R)-3-((S)-1-(3-chlorophenyl)-1,4-dihydroxybutyl)-N-((S)-1-cyclohexyl-3-(methylamino)propan-2-yl)piperidine-1-carboxamide | 135 | 1.39 | 480, 482 | 7.37-7.36 (m, 1H), 7.26-7.14 (m, 3H), 4.22 (d, J = 14.6 Hz, 1H), 4.08-4.01 (m, 1H), 3.90 (d, J = 12.3 Hz, 1H), 3.42 (t, J = 6.3 Hz, 2H), 2.98 (dd, J = 12.7, 3.4 Hz, 1H), 2.83 (dd, J = 12.4, 10.4 Hz, 1H), 2.62 (s, 3H), 2.50-2.44 (m, 2H), 1.93 (t, J = 8.0 Hz, 2H), 1.75-0.78 (m, 20H). |
| I-349A | (3R)-3-((S)-1-(3-chlorophenyl)-1-hydroxy-5-methoxypentyl)-N-((2R,3S)-3-hydroxy-4-methyl-1-(methylamino)pentan-2-yl)piperidine-1-carboxamide | 117 | 1.3 | 485 | 1.90 (3H, d), 1.00 (1H, d), 2.55 (1H, m), 2.70 (3H, s), 3.20 (3H, s), 3.90 (1H, d), 4.10 (1H, m), 4.35 (1H, d), 7.25 (3H, m), 7.40 (1H, m). |
| I-350A | (3R)-3-((S)-1-(benzofuran-7-yl)-1-hydroxy-5-methoxypentyl)-N-((S)-4,4-dimethyl-1-(methylamino)pentan-2-yl)piperidine-1-carboxamide | 33 | 1.4 | 488 | 1.04 (s, 9H), 2.72 (s, 3H), 3.19 (s, 3H), 3.99 (br d, 1H), 4.21 (m, 1H), 4.39 (br d, 1H), 6.82 (d, 1H), 7.20 (m, 1H), 7.41 (d, 1H), 7.52 (d, 1H), 7.68 (d, 1H) |
| I-351A | (3R)-3-((S)-1-(2-tert-butylbenzofuran-7-yl)-1-hydroxy-5-methoxypentyl)-N-((S)-1-(methylamino)propan-2-yl)piperidine-1-carboxamide | 121 | | 488 | 0.84 (m, 1H), 1.37 (s, 9H), 2.22 (m, 1H), 2.52 (m, 2H), 2.71 (s, 3H), 3.03 (m, 2H), 3.29 (s, 3H), 3.92 (m, 1H), 4.01 (m, 1H), 4.43 (m, 1H), 6.42 (s, 1H), 7.16 (m, 1H), 7.48 (m, 2H) |
| I-352A | (3R)—N-((2S,3S)-3-amino-1-cyclohexylbutan-2-yl)-3-((S)-1-(2-fluorophenyl)-1-hydroxy-5-methoxypentyl)piperidine-1-carboxamide | 121 | | 492 | 2.62 (m, 1H), 2.80 (m, 1H), 3.24 (s, 3H), 3.80 (m, 1H), 3.96 (m, 1H), 4.34 (m, 1H), 6.96 (m, 1H), 7.15 (m, 1H), 7.26 (m, 1H), 7.56 (m, 1H) |
| I-353A | (3R)—N-((1S,2R)-1-cyclopentyl-1-hydroxy-3-(methylamino)propan-2-yl)-3-((S)-1-(3-fluorophenyl)-1-hydroxy-5-methoxypentyl)piperidine-1-carboxamide | 117 | 1.29 | 494 | 2.60 (1H, m), 2.70 (1H, m), 2.85 (3H, s), 3.24 (3H, s), 4.01 (1H, d), 4.45 (1H, d), 7.10 (1H, m), 7.25 (2H, m), 7.50 (1H, m). |
| I-354A | (3R)—N-((S)-2-amino-3-cyclohexylpropyl)-3-((S)-1-(3-chlorophenyl)-1-hydroxy-5-methoxypentyl)piperidine-1-carboxamide | 126 | 1.52 | 494, 496 | 2.43 (m, 1H), 2.59 (m, 1H), 3.27 (s, 3H), 3.90 (br d, 1H), 4.38 (br d, 1H), 7.20-7.35 (3H), 7.43 (s, 1H) |
| I-356A | (3R)-3-((S)-1-(3-chlorophenyl)-1-hydroxy-5-methoxypentyl)-N-((S)-4-methoxy-4-methyl-1-(methylamino)pentan-2-yl)piperidine-1-carboxamide | 33 | 1.40 | 498 | 1.00 (m), 1.22 (s), 1.24 (s), 1.26-1.98 (m), 2.44 (dd), 2.66 (dd), 2.70 (s), 2.98 (dd), 3.18 (dd), 3.22 (s), 3.26 (s), 3.32 (t), 3.88 (d), 4.18 (m), 4.36 (d), 7.24 (m), 7.42 (s) |
| I-357A | (3R)-3-((S)-1-(3-cyanophenyl)-1-hydroxy-5-methoxypentyl)-N-((S)-1-cyclohexyl-3-(methylamino)propan-2-yl)piperidine-1-carboxamide | 139 | 1.40 | 499 | 0.84-1.10 (m), 1.18-2.06 (m), 2.54 (m), 2.72 (s), 2.94 (dd), 3.06 (dd), 3.24 (s), 3.30 (t), 3.98 (d), 4.14 (m), 4.34 (d), 7.56 (dd), 7.62 (d), 7.68 (d), 7.78 (s) |
| I-358A | (3R)-3-((R)-1-(3-chloro-2-fluorophenyl)-1-hydroxy-5-methoxypentyl)-N-((S)-4,4-dimethyl-1-(methylamino)pentan-2-yl)piperidine-1-carboxamide | 121 | | 500 | 0.83 (m, 1H), 0.98 (s, 9H), 1.95 (m, 2H), 2.22 (m, 1H), 2.70 (s, 3H), 2.91 (m, 1H), 3.03 (m, 1H), 3.27 (s, 3H), 3.82 (d, 1H), 4.21 (m, 1H), 4.52 (d, 1H), 7.14 (m, 1H), 7.38 (m, 1H), 7.54 (m, 1H) |
| I-359A | (3R)-3-((S)-1-(2-chloro-3-fluorophenyl)-1-hydroxy-5-methoxypentyl)-N-((S)-4,4-dimethyl-1-(methylamino)pentan-2-yl)piperidine-1-carboxamide | 119 | | 500 | 0.74 (m, 1H), 1.00 (s, 9H), 1.92 (m, 1H), 2.46 (m, 1H), 2.71 (s, 3H), 2.92 (m, 2H), 3.04 (m, 1H), 3.25 (s, 3H), 4.02 (d, 2H), 4.18 (m, 1H), 4.32 (d, 1H), 7.14 (m, 1H), 7.28 (m, 1H), 7.58 (m, 1H) |
| I-360A | (3R)-3-((S)-1-(3-chloro-2-fluorophenyl)-1-hydroxy-5-methoxypentyl)-N-((2R,3S)-3-hydroxy-4-methyl-1-(methylamino)pentan-2-yl)piperidine-1-carboxamide | 117 | 1.32 | 503 | 1.90 (3H, d), 1.00 (1H, d), 2.55 (1H, m), 2.70 (3H, s), 3.25 (3H, s), 3.90 (1H, d), 4.10 (1H, m), 4.30 (1H, d), 7.10 (1H, m), 7.35 (1H, m), 7.55 (1H, m). |
| I-361A | (3R)-3-((S)-1-(benzo[b]thiophen-4-yl)-1-hydroxy-5-methoxypentyl)-N-((S)-4,4-dimethyl-1-(methylamino)pentan-2-yl)piperidine-1-carboxamide | 33 | 1.52 | 504 | 0.92 (s, 9H), 2.85 (s, 3H), 3.15 (s, 3H), 3.90 (br d, 1H), 4.12 (s, 1H), 4.30 (br d, 1H), 7.24 (t, 1H), 7.40 (m, 1H), 7.48 (d, 1H), 7.75 (m, 2H) |
| I-362A | (3R)-3-((S)-4-acetamido-1-(2-fluorophenyl)-1-hydroxybutyl)-N-((S)-1-cyclohexyl-3- | 121 | | 505 | 0.88 (m, 1H), 1.02 (m, 2H), 1.82 (m, 1H), 1.87 (s, 3H), 1.96 (m, 2H), 2.16 (m, 1H), 2.64 (m, 1H), 2.71 (d, 3H), 2.80 (m, 1H), |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | (methylamino)propan-2-yl)piperidine-1-carboxamide | | | | 2.95 (m, 1H), 3.08 (m, 3H), 4.00 (d, 1H), 4.14 (m, 1H), 4.32 (d, 1H), 7.00 (m, 1H), 7.16 (m, 1H), 7.26 (m, 1H), 7.58 (m, 1H) |
| I-363A | (3R)—N-((S)-1-cyclohexyl-3-(methylamino)propan-2-yl)-3-((S)-1-(3-fluoro-2-methylphenyl)-1-hydroxy-5-methoxypentyl)piperidine-1-carboxamide | 121 | | 506 | 0.88 (m, 1H), 1.96 (m, 2H), 2.32 (s, 3H), 2.69 (s, 3H), 3.02 (m, 1H), 3.25 (s, 3H), 3.99 (d, 1H), 4.14 (m, 1H), 4.27 (d, 1H), 4.64 (s, 1H), 6.92 (m, 1H), 7.14 (m, 1H), 7.34 (m, 1H) |
| I-363B | (3R)—N-((S)-1-cyclohexyl-3-(methylamino)propan-2-yl)-3-((R)-1-(3-fluoro-2-methylphenyl)-1-hydroxy-5-methoxypentyl)piperidine-1-carboxamide | 121 | | 506 | 0.88 (m, 1H), 2.01 (m, 1H), 2.32 (s, 3H), 2.73 (s, 3H), 2.89 (m, 1H), 3.06 (m, 1H), 3.26 (s, 3H), 3.82 (d, 1H), 4.15 (m, 1H), 4.49 (d, 1H), 6.93 (m, 1H), 7.12 (m, 1H), 7.34 (m, 1H) |
| I-364A | (3R)—N-((S)-1-cyclohexyl-3-(methylamino)propan-2-yl)-3-((S)-1-(3-fluoro-4-methylphenyl)-1-hydroxy-5-methoxypentyl)piperidine-1-carboxamide | 121 | | 506 | 2.24 (s, 3H), 2.50 (m, 2H), 2.69 (s, 3H), 2.92 (m, 1H), 3.05 (m, 1H), 3.27 (s, 3H), 3.97 (d, 1H), 4.12 (m, 1H), 4.36 (d, 1H), 7.05 (m, 2H), 7.17 (m, 1H) |
| I-364B | (3R)—N-((S)-1-cyclohexyl-3-(methylamino)propan-2-yl)-3-((R)-1-(3-fluoro-4-methylphenyl)-1-hydroxy-5-methoxypentyl)piperidine-1-carboxamide | 121 | | 506 | 2.23 (s, 3H), 2.50 (m, 2H), 2.69 (s, 3H), 2.88 (m, 1H), 3.06 (m, 1H), 3.27 (s, 3H), 3.96 (d, 1H), 4.12 (m, 1H), 4.27 (d, 1H), 7.04 (m, 2H), 7.18 (m, 1H) |
| I-366A | (3R)—N-((S)-1-cyclohexyl-3-(methylamino)propan-2-yl)-3-((S)-1-(3-fluoro-2-hydroxyphenyl)-1-hydroxy-5-methoxypentyl)piperidine-1-carboxamide | 121 | | 508 | 0.88 (m, 1H), 2.22 (m, 1H), 2.70 (s, 3H), 2.94 (m, 1H), 3.06 (m, 1H), 3.26 (s, 3H), 3.94 (d, 1H), 4.14 (m, 1H), 4.34 (d, 1H), 6.76 (m, 1H), 6.95 (m, 2H) |
| I-367A | (3R)—N-((1S,2R)-1-cyclohexyl-1-hydroxy-3-(methylamino)propan-2-yl)-3-((S)-1-(2-fluorophenyl)-1-hydroxy-5-methoxypentyl)piperidine-1-carboxamide | 121 | | 508 | 0.86 (m, 1H), 2.17 (m, 1H), 2.64 (m, 1H), 2.71 (s, 3H), 2.78 (m, 1H), 3.04 (m, 1H), 3.24 (s, 3H), 3.46 (m, 1H), 3.96 (m, 1H), 4.10 (m, 1H), 4.34 (m, 1H), 7.01 (m, 1H), 7.16 (m, 1H), 7.27 (m, 1H), 7.56 (m, 1H) |
| I-368A | (3R)—N-((2S,3R)-3-amino-1-cyclohexylbutan-2-yl)-3-((S)-1-(3-chlorophenyl)-1-hydroxy-5-methoxypentyl)piperidine-1-carboxamide | 119 | | 508 | 1.24 (s, 3H), 2.54 (m, 2H), 3.26 (s, 3H), 3.96 (d, 1H), 4.08 (m, 1H), 4.34 (d, 1H), 7.24 (m, 3H), 7.43 (s, 1H) |
| I-369A | (3R)-3-((S)-1-(3-chlorophenyl)-1-hydroxy-5-methoxypentyl)-N-((S)-3-cyclohexyl-2-(methylamino)propyl)piperidine-1-carboxamide | 33 | 1.53 | 508 | 7.43 (s, 1H), 7.32-7.25 (m, 2H), 7.21 (d, 1H), 4.37 (d, 1H), 3.89 (d, 1H), 3.51 (d, 1H), 2.72 (s, 3H), 2.59 (t, 1H), 2.45 (t, 1H), 1.93 (t, 1H), 0.99 (m, 1H). |
| I-370A | (3R)—N-((S)-1-(cis-4-fluorocyclohexyl)-3-(methylamino)propan-2-yl)-3-((S)-1-(2-fluorophenyl)-1-hydroxy-5-methoxypentyl)piperidine-1-carboxamide | 119 | | 510 | 0.85 (m, 1H), 2.15 (m, 1H), 2.77 (s, 1H), 2.81 (m, 1H), 2.93 (m, 1H), 3.07 (m, 1H), 3.24 (s, 3H), 3.98 (d, 1H), 4.15 (m, 1H), 4.33 (d, 1H), 6.99 (m, 1H), 7.16 (m, 1H), 7.28 (m, 1H), 7.60 (m, 1H) |
| I-370B | (3R)—N-((S)-1-(trans-4-fluorocyclohexyl)-3-(methylamino)propan-2-yl)-3-((S)-1-(2-fluorophenyl)-1-hydroxy-5-methoxypentyl)piperidine-1-carboxamide | 119 | | 510 | 0.88 (m, 1H), 2.62 (m, 1H), 2.70 (s, 3H), 2.84 (m, 2H), 3.06 (m, 1H), 3.25 (s, 3H), 3.98 (m, 1H), 4.10 (m, 1H), 4.34 (m, 1H), 7.00 (m, 1H), 7.17 (m, 1H), 7.38 (m, 1H), 7.59 (m, 1H) |
| I-370C | (3R)—N-((S)-1-(trans-4-fluorocyclohexyl)-3-(methylamino)propan-2-yl)-3-((R)-1-(2-fluorophenyl)-1-hydroxy-5-methoxypentyl)piperidine-1-carboxamide | 119 | | 510 | 0.86 (m, 1H), 2.64 (m, 1H), 2.7 (s, 3H), 2.85 (m, 2H), 3.06 (m, 1H), 3.26 (s, 3H), 4.04 (m, 2H), 4.42 (m, 2H), 7.02 (m, 1H), 7.15 (m, 2H), 7.26 (m, 2H), 7.56 (m, 1H) |
| I-371A | (3R)—N-((1S,2R)-1-cyclopentyl-1-hydroxy-3-(methylamino)propan-2-yl)-3-((S)-1-(2,3-difluorophenyl)-1-hydroxy-5-methoxypentyl)piperidine-1-carboxamide | 117 | 1.3 | 512 | 3.05 (3H, s), 3.75 (3H, s), 4.35 (1H, m), 4.75 (1H, m), 7.50 (2H, m), 7.75 (1H, m). |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-372A | (3R)-3-((S)-1-(2-chloro-3-fluorophenyl)-1-hydroxy-5-methoxypentyl)-N-((S)-1-cyclopentyl-3-(methylamino)propan-2-yl)piperidine-1-carboxamide | 121 | | 512 | 0.74 (m, 1H), 1.00 (m, 1H), 2.46 (m, 1H), 2.71 (s, 3H), 2.93 (m, 2H), 3.12 (m, 1H), 3.25 (s, 3H), 4.04 (m, 2H), 4.33 (m, 1H), 7.12 (m, 1H), 7.26 (m, 1H), 7.59 (m, 1H), |
| I-373A | (3R)—N-((S)-2-amino-3-cyclohexylpropyl)-3-((S)-1-(3-chloro-2-fluorophenyl)-1-hydroxy-5-methoxypentyl)piperidine-1-carboxamide | 127 | 1.53 | 512, 514 | 2.68 (m, 2H), 3.88 (br d, 1H), 4.41 (br d, 1H), 7.13 (t, 1H), 7.37 (m, 1H), 7.53 (m, 1H) |
| I-374A | (3R)-3-((S)-1-(benzofuran-4-yl)-1-hydroxy-5-methoxypentyl)-N-((S)-1-cyclohexyl-3-(methylamino)propan-2-yl)piperidine-1-carboxamide | 33 | 1.53 | 514 | 2.69 (s, 3H), 3.92 (br d, 1H), 4.12 (m, 1H), 4.39 (br d, 1H), 7.10 (s, 1H), 7.24 (m, 2H), 7.39 (m, 1H), 7.72 (s, 1H) |
| I-375A | (3R)-3-((S)-4-acetamido-1-(3,5-dimethylphenyl)-1-hydroxybutyl)-N-((S)-1-cyclohexyl-3-(methylamino)propan-2-yl)piperidine-1-carboxamide | 121 | | 515 | 0.90 (m, 1H), 1.02 (m, 1H), 2.30 (s, 6H), 2.55 (m, 2H), 2.71 (s, 3H), 3.98 (d, 1H), 4.13 (m, 1H), 4.22 (d, 1H), 6.86 (s, 1H), 6.97 (s, 2H) |
| I-376A | (3R)-3-((R)-1-cyclohexyl-1-hydroxy-5-methoxypentyl)-N-((S)-1-(4,4-difluorocyclohexyl)-3-(methylamino)propan-2-yl)piperidine-1-carboxamide | 121 | | 516 | 2.04 (m, 2H), 2.72 (s, 3H), 3.32 (s, 3H), 4.14 (m, 3H) |
| I-377A | (3R)—N-((S)-2-amino-3-cyclohexylpropyl)-3-((S)-1-(benzo[b]thiophen-4-yl)-1-hydroxy-5-methoxypentyl)piperidine-1-carboxamide | 127 | 1.53 | 516 | 3.18 (s, 3H), 3.83 (br d, 1H), 4.48 (br d, 1H), 7.30 (t, 1H), 7.45 (m, 1H), 7.55 (d, 1H), 7.80 (m, 2H) |
| I-378A | (3R)-3-((S)-1-(3-chloro-2-fluorophenyl)-1-hydroxy-5-methoxypentyl)-N-((S)-4-methoxy-4-methyl-1-(methylamino)pentan-2-yl)piperidine-1-carboxamide | 33 | 1.43 | 516 | 0.82 (m), 1.22 (s), 1.24 (s), 1.26-2.04 (m), 2.18 (m), 2.62 (m), 2.72 (s), 2.98 (dd), 3.18 (dd), 3.22 (s), 3.24 (s), 3.30 (t), 3.86 (d), 4.18 (m), 4.38 (d), 7.16 (dd), 7.38 (dd), 7.54 (dd) |
| I-379A | (3R)-3-((S)-1-(2-cyano-5-fluorophenyl)-1-hydroxy-5-methoxypentyl)-N-((S)-1-cyclohexyl-3-(methylamino)propan-2-yl)piperidine-1-carboxamide | 140 | 1.09 | 517 | 0.83-1.10 (m), 1.14-1.82 (m), 2.24 (m), 2.32 (m), 2.44 (m), 2.72 (s), 2.98 (dd), 3.06 (d), 3.24 (s), 3.32 (t), 3.96 (d), 4.14 (m), 4.40 (d), 7.62 (m), 8.32 (m) |
| I-380A | (3R)-3-((S)-1-(3-carbamoylphenyl)-1-hydroxy-5-methoxypentyl)-N-((S)-1-cyclohexyl-3-(methylamino)propan-2-yl)piperidine-1-carboxamide | 33 | 1.20 | 517 | 0.82-2.06 (m), 2.50 (m), 2.70 (s), 2.96 (dd), 3.04 (d), 3.24 (s), 3.32 (t), 3.98 (d), 4.12 (m), 4.32 (d), 7.42 (m), 7.58 (d), 7.74 (d), 7.94 (s) |
| I-381A | (RS)—N-((S)-2-amino-3-cyclohexylpropyl)-2-((RS)-1-(benzo[b]thiophen-7-yl)-1-hydroxy-5-methoxypentyl)morpholine-4-carboxamide | 127 | 1.47 | 518 | 2.60 (t, 1H), 2.82 (m, 1H), 3.22 (s, 3H), 4.09 (d, 1H), 7.28-7.56 (4H), 7.72 (d, 1H) |
| I-382A | (3R)-3-((S)-4-acetamido-1-(3-fluoro-5-methylphenyl)-1-hydroxybutyl)-N-((S)-1-cyclohexyl-3-(methylamino)propan-2-yl)piperidine-1-carboxamide | 121 | | 519 | 0.88 (m, 1H), 1.04 (m, 1H), 1.89 (s, 3H), 2.34 (s, 3H), 2.54 (m, 2H), 2.70 (s, 3H), 2.92 (m, 1H), 3.96 (m, 1H), 4.14 (m, 1H), 4.36 (d, 1H), 6.76 (d, 1H), 6.94 (d, 1H), 6.98 (s, 1H) |
| I-383A | (3R)-3-((S)-4-acetamido-1-(2-fluoro-5-methylphenyl)-1-hydroxybutyl)-N-((S)-1-cyclohexyl-3-(methylamino)propan-2-yl)piperidine-1-carboxamide | 121 | | 519 | 1.12 (m, 3H), 1.97 (s, 3H), 2.41 (s, 3H), 2.72 (s, 3H), 2.80 (s, 3H), 2.94 (m, 2H), 3.17 (m, 3H), 4.10 (d, 1H), 4.13 (m, 1H), 4.36 (d, 1H), 6.97 (m, 1H), 7.15 (m, 1H), 7.48 (m, 1H) |
| I-385A | (3R)-3-(1-(2-(cyclopropylmethoxy)-3-fluorophenyl)-1-hydroxy-5-methoxypentyl)-N-((S)-4-methyl-1-(methylamino)pentan-2-yl)piperidine-1-carboxamide | 121 | | 522 | 0.78 (m, 1H), 0.94 (d, 3H), 0.98 (d, 3H), 1.14 (m, 1H), 1.86 (m, 1H), 2.62 (m, 3H), 2.71 (s, 3H), 2.90 (m, 2H), 3.08 (m, 1H), 3.26 (s, 3H), 4.04 (m, 2H), 4.28 (m, 1H), 4.46 (m, 1H), 6.95 (m, 2H), 7.28 (m, 1H), |
| I-386A | (3R)-3-((S)-1-(3-chloro-2-methylphenyl)-1-hydroxy-5-methoxypentyl)-N-((S)-1-cyclohexyl-3-(methylamino)propan-2-yl)piperidine-1-carboxamide | 121 | | 522 | 0.86 (m, 1H), 2.24 (m, 1H), 2.47 (s, 3H), 2.65 (s, 3H), 2.92 (m, 3H), 3.05 (m, 1H), 3.25 (s, 3H), 3.96 (d, 1H), 4.12 (m, 1H), 4.29 (d, 1H), 7.11 (m, 1H), 7.28 (m, 1H), 7.54 (m, 1H) |
| I-386B | (3R)-3-((R)-1-(3-chloro-2-methylphenyl)-1-hydroxy-5-methoxypentyl)-N-((S)-1-cyclohexyl- | 121 | | 522 | 0.88 (m, 1H), 2.06 (m, 1H), 2.32 (m, 1H), 2.47 (s, 3H), 2.72 (s, 3H), 2.90 (m, 1H), 3.06 (m, 1H), 3.25 (s, 3H), 3.84 (d, 1H), |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | 3-(methylamino)propan-2-yl)piperidine-1-carboxamide | | | | 4.16 (m, 1H), 4.48 (d, 1H), 7.12 (m, 1H), 7.26 (m, 1H), 7.55 (m, 1H) |
| I-387A | (3R)-3-((S)-1-(3-chlorophenyl)-1,5-dimethoxypentyl)-N-((S)-1-cyclohexyl-3-(methylamino)propan-2-yl)piperidine-1-carboxamide | 33 | 1.68 | 522, 524 | 7.27-7.15 (m, 4H), 4.18 (d, J = 13.2 Hz, 1H), 4.02-3.95 (m, 1H), 3.86 (d, J = 12.6 Hz, 1H), 3.30 (t, J = 6.3 Hz, 2H), 3.19 (s, 3H), 3.07 (s, 3H), 2.93 (dd, J = 12.6, 2.6 Hz, 1H), 2.80 (dd, J = 12.3, 10.2 Hz, 1H), 2.57 (s, 3H), 2.23-0.72 (m, 26H). |
| I-388A | (3R)-3-((S)-4-acetamido-1-(2,3-difluorophenyl)-1-hydroxybutyl)-N-((S)-1-cyclohexyl-3-(methylamino)propan-2-yl)piperidine-1-carboxamide | 33 | 1.3 | 523 | 7.30-7.25 (m, 1H), 7.10-7.00 (m, 2H), 4.23 (d, J = 12.3 Hz, 1H), 4.08-4.01 (m, 1H), 3.90 (d, J = 12.6 Hz, 1H), 3.02-2.95 (m, 3H), 2.84 (dd, J = 12.6, 10.2 Hz, 1H), 2.71 (t, J = 12.3 Hz, 1H), 2.61 (s, 3H), 2.56-2.50 (m, 1H), 1.79 (s, 3H), 2.08-0.76 (m, 22H). |
| I-389A | (3R)-3-((S)-4-acetamido-1-(3,5-difluorophenyl)-1-hydroxybutyl)-N-((S)-1-cyclohexyl-3-(methylamino)propan-2-yl)piperidine-1-carboxamide | 121 | | 523 | 0.90 (m, 2H), 1.90 (s, 3H), 2.56 (m, 1H), 2.70 (s, 3H), 2.92 (m, 2H), 3.96 (d, 1H), 4.14 (m, 1H), 4.29 (d, 1H), 6.82 (m, 1H), 6.98 (m, 2H), |
| I-390A | (3R)-3-((S)-1-(2,3-difluorophenyl)-1-hydroxy-5-methoxypentyl)-N-((S)-1-(methylamino)-3-(4-methylcyclohexyl)propan-2-yl)piperidine-1-carboxamide | 33 | 1.59 | 524 | 7.33 (t), 7.11 (m), 4.31 (d), 4.06 (m), 3.95 (d), 3.27 (m), 3.26 (s), 3.05 (t), 2.90 (t), 2.78 (t), 2.69 (s), 2.60 (t), 0.92 (d), 0.88 (d) |
| I-391A | (3R)-3-((S)-1-(3-chlorophenyl)-1-hydroxy-5-methoxypentyl)-N-((S)-1-(cis-4-hydroxycyclohexyl)-3-(methylamino)propan-2-yl)piperidine-1-carboxamide | 121 | | 524 | 1.02 (m, 3H), 2.52 (m, 2H), 2.70 (s, 3H), 2.92 (m, 1H), 3.04 (m, 1H), 3.29 (s, 3H), 3.46 (m, 1H), 3.96 (d, 1H), 4.11 (m, 1H), 4.32 (d, 1H), 7.36 (m, 3H), 7.45 (m, 1H) |
| I-391A | (3R)-3-((S)-1-(3-chlorophenyl)-1-hydroxy-5-methoxypentyl)-N-((S)-1-(trans-4-hydroxycyclohexyl)-3-(methylamino)propan-2-yl)piperidine-1-carboxamide | 121 | | 524 | 1.02 (m, 1H), 2.50 (m, 2H), 2.70 (s, 3H), 2.94 (m, 1H), 3.06 (m, 1H), 3.26 (s, 3H), 3.94 (m, 2H), 4.12 (m, 1H), 4.30 (m, 1H), 7.28 (m, 3H), 7.44 (m, 1H) |
| I-392A | (3R)-3-((S)-4-acetamido-1-(2,3-difluorophenyl)-1-hydroxybutyl)-N-((2R)-1-cyclopentyl-1-hydroxy-3-(methylamino)propan-2-yl)piperidine-1-carboxamide | 117 | 1.16 | 525 | 1.89 (3H, s), 2.73 (3H, s), 3.95 (1H, d) 4.00 (1H, m), 4.36 (1H, d), 7.14 (2H, m), 7.36 (1H, m). |
| I-393A | (3R)-3-((S)-(2-acetamidoethoxy)(3-chloro-2-fluorophenyl)methyl)-N-((S)-1-cyclohexyl-3-(methylamino)propan-2-yl)piperidine-1-carboxamide | 121 | | 525 | 0.86 (m, 1H), 0.96 (m, 1H), 1.94 (s, 3H), 2.68 (s, 3H), 3.04 (m, 1H), 3.82 (d, 1H), 3.94 (d, 1H), 4.06 (m, 1H), 4.56 (m, 1H), 7.22 (m, 1H), 7.48 (m, 2H) |
| I-393B | (3R)-3-((R)-(2-acetamidoethoxy)(3-chloro-2-fluorophenyl)methyl)-N-((S)-1-cyclohexyl-3-(methylamino)propan-2-yl)piperidine-1-carboxamide | 121 | | 525 | 0.88 (m, 1H), 1.04 (m, 1H), 1.94 (s, 3H), 2.70 (s, 3H), 2.95 (m, 2H), 3.12 (m, 2H), 3.78 (d, 1H), 4.06 (d, 1H), 4.14 (m, 1H), 4.45 (m, 1H), 7.22 (m, 1H), 7.34 (m, 1H), 7.44 (m, 1H) |
| I-394A | (3R)—N-((R)-2-amino-3-tert-butoxypropyl)-3-((S)-1-(3-chloro-2-fluorophenyl)-1-hydroxy-5-methoxypentyl)piperidine-1-carboxamide | 127 | 1.43 | 502 | 7.53 (t, 1H), 7.36 (t, 1H), 7.13 (t, 1H), 4.40 (d, 1H), 3.86 (d, 1H), 3.61 (dd, 1H), 3.49 (m, 1H), 3.40 (s, 3H), 3.25 (s, 3H), 2.69 (q, 2H), 2.19 (tt, 1H), 1.61 (d, 1H), 1.24 (s, 9H), 0.83 (m, 1H). |
| I-395A | (3R)—N-((1S,2R)-1-cyclohexyl-1-hydroxy-3-(methylamino)propan-2-yl)-3-((S)-1-(2,3-difluorophenyl)-1-hydroxy-5-methoxypentyl)piperidine-1-carboxamide | 117 | 1.40 | 526 | 0.86 (m), 1.04-2.04 (m), 2.18 (m), 2.64 (m), 2.72 (s), 2.78 (m), 3.04 (dd), 3.24 (s), 3.32 (t), 3.42 (m), 3.84, 3.98 (d), 4.12 (m), 4.36, 4.48 (d), 7.16 (m), 7.38 (m) |
| I-396A | (3R)-3-((S)-1-(2,3-difluorophenyl)-1-hydroxy-5-methoxypentyl)-N-((S)-1-(cis-4-hydroxycyclohexyl)-3-(methylamino)propan-2-yl)piperidine-1-carboxamide | 121 | | 526 | 1.75 (m, 1H), 2.16 (m, 1H), 2.70 (s, 3H), 2.95 (m, 1H), 3.06 (m, 1H), 3.48 (m, 1H), 3.96 (d, 1H), 4.12 (m, 1H), 4.35 (d, 1H), 7.15 (m, 2H), 7.36 (m, 1H) |
| I-396B | (3R)-3-((S)-1-(2,3-difluorophenyl)-1-hydroxy-5-methoxypentyl)-N-((S)-1-(trans-4-hydroxycyclohexyl)-3-(methylamino)propan-2-yl)piperidine-1-carboxamide | 121 | | 526 | 0.86 (m, 1H), 2.15 (m, 1H), 2.64 (m, 1H), 2.70 (s, 3H), 2.78 (m, 1H), 2.94 (m, 1H), 3.06 (m, 1H), 3.25 (s, 3H), 3.96 (m, 2H), 4.14 (m, 1H), 4.34 (m, 1H), 7.15 (m, 2H), 7.36 (m, 1H) |
| I397A | (3R)—N-((1S,2R)-1-cyclohexyl-1-hydroxy-3-(methylamino)propan-2- | 121 | | 526 | 0.88 (m, 1H), 1.96 (m, 2H), 2.15 (m, 1H), 2.64 (m, 1H), 2.71 (s, 3H), 2.78 (m, 1H), |

-continued

Table of Compounds

| Cpd. No. | Cpd. Name | Method of Synthesis Example No. | LC-MS (3 min) tR (min) | Mass observed | Selected 1H NMR$^a$ |
|---|---|---|---|---|---|
| | yl)-3-((S)-1-(2,5-difluorophenyl)-1-hydroxy-5-methoxypentyl)piperidine-1-carboxamide | | | | 3.05 (m, 1H), 3.26 (m, 3H), 3.44 (m, 1H), 3.96 (d, 1H), 4.08 (m, 1H), 4.32 (d, 1H), 7.00 (m, 2H), 7.32 (m, 1H) |
| I-398A | (3R)-3-((S)-1-(2-chloro-3-fluorophenyl)-1-hydroxy-5-methoxypentyl)-N-((S)-1-cyclohexyl-3-(methylamino)propan-2-yl)piperidine-1-carboxamide | 121 | | 526 | 0.75 (m, 1H), 2.46 (m, 1H), 2.64 (m, 2H), 2.71 (s, 3H), 2.95 (m, 2H), 3.04 (m, 1H), 3.24 (s, 3H), 4.00 (d, 1H), 4.12 (m, 1H), 4.32 (d, 1H), 7.14 (m, 1H), 7.29 (m, 1H), 7.59 (m, 1H) |
| I-399A | (3R)—N-((2S,3R)-3-amino-1-cyclohexylbutan-2-yl)-3-((S)-1-(3-chloro-2-fluorophenyl)-1-hydroxy-5-methoxypentyl)piperidine-1-carboxamide | 119 | | 526 | 0.84 (m, 1H), 1.98 (m, 2H), 2.16 (m, 1H), 2.64 (m, 1H), 2.34 (m, 1H), 3.26 (s, 3H), 4.00 (d, 1H), 4.08 (m, 1H), 4.36 (d, 1H), 7.15 (m, 1H), 7.38 (m, 1H), 7.53 (m, 1H) |
| I-400A | (3R)—N-((S)-1-cyclohexyl-3-(methylamino)propan-2-yl)-3-((S)-1-hydroxy-5-methoxy-1-(2,3,4-trifluorophenyl)pentyl)piperidine-1-carboxamide | 121 | | 528 | 0.88 (m, 1H), 1.04 (m, 1H), 1.94 (m, 2H), 2.12 (m, 1H), 2.64 (m, 1H), 2.71 (s, 3H), 2.78 (m, 1H), 2.94 (m, 1H), 3.06 (m, 1H), 3.29 (s, 3H), 3.97 (d, 1H), 4.14 (m, 1H), 4.34 (m, 1H), 7.08 (m, 1H), 7.37 (m, 1H) |
| I-401A | (3R)—N-((S)-1-(4,4-difluorocyclohexyl)-3-(methylamino)propan-2-yl)-3-((S)-1-(2-fluorophenyl)-1-hydroxy-5-methoxypentyl)piperidine-1-carboxamide | 121 | | 528 | 2.71 (s, 3H), 2.80 (m, 1H), 2.94 (m, 1H), 3.06 (m, 1H), 3.27 (s, 3H), 3.96 (d, 1H), 4.14 (m, 1H), 4.32 (d, 1H), 7.00 (m, 1H), 7.16 (m, 1H), 7.28 (m, 1H), 7.60 (m, 1H) |
| I-402A | (3R)-3-((S)-1-(2,5-difluorophenyl)-1-hydroxy-5-methoxypentyl)-N-((S)-1-(cis-4-fluorocyclohexyl)-3-(methylamino)propan-2-yl)piperidine-1-carboxamide | 119 | | 528 | 0.86 (m, 1H), 2.72 (s, 3H), 3.06 (m, 1H), 3.23 (s, 3H), 3.96 (d, 1H), 4,14 (m, 1H), 4.32 (d, 1H), 7.01 (m, 2H), 7.32 (m, 1H) |
| I-402B | (3R)-3-((S)-1-(2,5-difluorophenyl)-1-hydroxy-5-methoxypentyl)-N-((S)-1-(trans-4-fluorocyclohexyl)-3-(methylamino)propan-2-yl)piperidine-1-carboxamide | 119 | | 528 | 0.86 (m, 1H), 1.80 (m, 1H), 2.62 (m, 1H), 2.71 (s, 3H), 2.84 (m, 2H), 3.25 (s, 3H), 3.96 (m, 1H), 4.12 (m, 1H), 4.34 (m, 1H), 4.94 (m, 1H), 7.02 (m, 2H), 7.30 (m, 1H) |
| I-403A | (3R)-3-((S)-1-(2,3-difluorophenyl)-1-hydroxy-5-methoxypentyl)-N-((S)-1-(trans-4-fluorocyclohexyl)-3-(methylamino)propan-2-yl)piperidine-1-carboxamide | 119 | | 528 | 2.64 (m, 1H), 2.71 (s, 3H), 2.78 (m, 1H), 2.94 (m, 1H), 3.06 (m, 1H), 3.25 (s, 3H), 3.96 (m, 1H), 4.12 (m, 1H), 4.40 (m, 2H), 7.15 (m, 2H), 7.36 (m, 1H) |
| I-403B | (3R)-3-((R)-1-(2,3-difluorophenyl)-1-hydroxy-5-methoxypentyl)-N-((S)-1-(trans-4-fluorocyclohexyl)-3-(methylamino)propan-2-yl)piperidine-1-carboxamide | 119 | | 528 | 2.64 (m, 1H), 2.70 (s, 3H), 2.86 (m, 2H), 3.05 (m, 1H), 3.25 (m, 3H), 3.96 (m, 1H), 4.10 (m, 1H), 4.35 (m, 1H), 4.50 (m, 1H), 7.14 (m, 2H), 7.36 (m, 1H) |
| I-404A | 2-((R)-1-(3-chloro-2-fluorophenyl)-1-hydroxy-5-methoxypentyl)-N-((S)-1-cyclohexyl-3-(methylamino)propan-2-yl)morpholine-4-carboxamide | 33 | 1.47 | 528 | 7.53 (t, 1H), 7.36 (t, 1H), 7.13 (t, 1H), 3.82 (q, 3H), 3.71 (d, 1H), 3.42 (q, 2H), 3.27 (s, 3H), 2.71 (s, 3H), 2.10 (q, 1H) 1.03 (m, 1H). |
| I-405A | (3R)-3-((S)-1-(3-chloro-2-fluorophenyl)-1-hydroxy-5-methoxypentyl)-N-((1S,2R)-1-cyclopentyl-1-hydroxy-3-(methylamino)propan-2-yl)piperidine-1-carboxamide | 117 | 1.36 | 528 | 3.00 (3H, s), 3.55 (3H, s), 4.25 (1H, d), 4.37 (1H, m), 4.70 (1H, d), 7.40 (1H, m), 7.70 (1H, m), 7.85 (1H, m). |
| I-406A | (3R)-3-((S)-1-(3-chloro-2-fluorophenyl)-1-hydroxy-5-methoxypentyl)-N-((S)-1-(methylamino)-3-(tetrahydro-2H-pyran-4-yl)propan-2-yl)piperidine-1-carboxamide | 33 | 1.26 | 528 | 2.72 (3H, s), 3.25 (3H, s), 3.40 (4H, m), 4.84 (1H, d), 7.14 (1H, m), 7.38 (1H, m), 7.53 (1H, m). |
| I-406B | (3R)-3-((S)-1-(3-chloro-2-fluorophenyl)-1-hydroxy-5-methoxypentyl)-N-((R)-1-(methylamino)-3-(tetrahydro-2H-pyran-4-yl)propan-2-yl)piperidine-1-carboxamide | 33 | 1.26 | 526 | 2.71 (3H, s), 3.20 (3H, s), 3.40 (4H, m), 4.50 (1H, d), 7.14 (1H, m), 7.37 (1H, m), 7.53 (1H, m). |
| I-408A | (3R)-3-((S)-1-(benzo[b]thiophen-4-yl)-1-hydroxy-5-methoxypentyl)-N-((S)-1-cyclohexyl-3-(methylamino)propan-2-yl)piperidine-1-carboxamide | 33 | 1.64 | 530 | 2.64 (s, 3H), 3.13 (s, 3H), 3.90 (br d, 1H), 4.34 (br d, 1H), 7.24 (t, 1H), 7.40 (m, 1H), 7.47 (d, 1H), 7.75 (m, 2H) |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-410A | (3R)-3-((S)-1-(benzofuran-7-yl)-1-hydroxy-5-methoxypentyl)-N-((S)-1-(cis-4-fluorocyclohexyl)-3-(methylamino)propan-2-yl)piperidine-1-carboxamide | 119 | | 532 | 0.74 (m, 1H), 2.26 (m, 1H), 2.46 (m, 1H), 2.72 (s, 3H), 2.78 (m, 1H), 2.93 (m, 1H), 3.07 (m, 1H), 3.21 (s, 3H), 3.96 (m, 1H), 4.15 (m, 1H), 4.42 (m, 1H), 4.75 (m, 1H), 6.84 (m, 1H), 7.24 (m, 1H), 7.41-7.53 (m, 2H), 7.72 (m, 1H) |
| I-411A | (3R)—N-((S)-1-cyclohexyl-3-(methylamino)propan-2-yl)-3-((S)-1-(2-fluorobenzofuran-7-yl)-1-hydroxy-5-methoxypentyl)piperidine-1-carboxamide | 33 | 1.6 | 532 | 2.71 (s, 3H), 3.20 (s, 3H), 3.24 (t, 2H), 4.00 (br d, 1H), 4.15 (m, 1H), 4.40 (br d, 1H), 6.03 (d, 1H), 7.22 (m, 1H), 7.41 (m, 2H) |
| I-412A | methyl 3-((S)-1-((R)-1-((S)-1-cyclohexyl-3-(methylamino)propan-2-ylcarbamoyl)piperidin-3-yl)-1-hydroxy-5-methoxypentyl)benzoate | 141 | 1.44 | 532 | 0.84-1.14 (m), 1.18-2.06 (m), 2.54 (m), 2.70 (s), 2.93 (dd), 3.04 (dd), 3.24 (s), 3.30 (t), 3.92 (s), 3.98 (d), 4.14 (m), 4.32 (d), 7.44 (dd), 7.62 (d), 7.90 (d), 8.06 (s) |
| I-413A | (RS)-2-((RS)-1-(benzo[b]thiophen-7-yl)-1-hydroxy-5-methoxypentyl)-N-((S)-1-cyclohexyl-3-(methylamino)propan-2-yl)morpholine-4-carboxamide | 33 | 1.52 | 532 | 2.65 (s, 3H), 3.21 (s, 3H), 7.28-7.52 (4H), 7.72 (m, 1H) |
| I-416A | (3R)-3-((S)-1-(3-chlorophenyl)-1-hydroxy-4-propionamidobutyl)-N-((S)-1-cyclohexyl-3-(methylamino)propan-2-yl)piperidine-1-carboxamide | 33 | 1.38 | 535, 537 | 7.33-7.32 (m, 1H), 7.22-7.10 (m, 3H), 4.18 (d, J = 13.2 Hz, 1H), 4.06-3.98 (m, 1H), 3.86 (d, J = 12.6 Hz, 1H), 3.02-2.93 (m, 3H), 2.83 (dd, J = 12.6, 10.2 Hz, 1H), 2.59 (s, 3H), 2.47-2.38 (m, 2H), 2.04 (q, J = 7.6 Hz, 2H), 0.98 (t, J = 7.6 Hz, 3H), 1.90-0.77 (m, 22H). |
| I-417A | (3R)-3-(1-(2-(cyclopropylmethoxy)-3-fluorophenyl)-1-hydroxy-5-methoxypentyl)-N-((S)-4,4-dimethyl-1-(methylamino)pentan-2-yl)piperidine-1-carboxamide | 121 | | 536 | 0.82 (m, 1H), 1.10 (s, 9H), 1.86 (m, 1H), 2.58 (m, 1H), 2.70 (s, 3H), 2.84 (m, 1H), 2.96 (m, 2H), 3.26 (s, 3H), 4.05 (m, 1H), 4.24 (m, 2H), 4.89 (m, 1H), 6.96 (m, 2H), 7.27 (m, 1H) |
| I-418A | (3R)-3-((S)-1-(3-chlorophenyl)-1-hydroxy-4-(3-methylureido)butyl)-N-((S)-1-cyclohexyl-3-(methylamino)propan-2-yl)piperidine-1-carboxamide | 33 | 1.36 | 536, 538 | 7.36-7.35 (m, 1H), 7.26-7.15 (m, 3H), 4.21 (d, J = 13.5 Hz, 1H), 4.10-4.03 (m, 1H), 3.92 (d, J = 13.8 Hz, 1H), 3.01-2.97 (m, 3H), 2.86 (dd, J = 12.6, 10.2 Hz, 1H), 2.64 (s, 3H), 2.59 (s, 3H), 2.52-2.44 (m, 2H), 1.94-0.79 (m, 22H). |
| I-421A | (3R)—N-((2S,3S)-3-amino-1-cyclohexylbutan-2-yl)-3-((S)-1-(3 chlorophenyl)-1-hydroxy-5-methoxypentyl)piperidine-1-carboxamide | 119 | | 508 | 1.29 (m, 3H), 2.54 (m, 2H), 3.29 (s, 3H), 3.54 (m, 1H), 3.14 (m, 3H), 3.82 (m, 1H), 3.96 (m, 1H), 4.30 (m, 1H), 7.28 (m, 3H), 7.44 (m, 1H) |
| I-423A | (3R)-3-((S)-4-acetamido-1-(3-chloro-2-fluorophenyl)-1-hydroxybutyl)-N-((S)-1-cyclohexyl-3-(methylamino)propan-2-yl)piperidine-1-carboxamide | 121 | | 539 | 1.88 (s, 3H), 2.16 (m, 1H), 2.64 (m, 1H), 2.71 (s, 3H), 2.88 (m, 2H), 4.02 (d, 1H), 4.15 (m, 1H), 4.32 (d, 1H), 7.16 (m, 1H), 7.48 (m, 1H), 7.54 (m, 1H) |
| I-424A | (3R)-3-((S)-4-acetamido-1-(3-chloro-5-fluorophenyl)-1-hydroxybutyl)-N-((S)-1-cyclohexyl-3-(methylamino)propan-2-yl)piperidine-1-carboxamide | 121 | | 539 | 0.89 (m, 1H), 1.03 (m, 1H), 1.89 (s, 3H), 1.96 (m, 1H), 2.56 (m, 2H), 2.71 (s, 3H), 2.92 (m, 1H), 3.05 (m, 3H), 3.96 (d, 1H), 4.12 (m, 1H), 4.29 (d, 1H), 7.07 (m, 2H), 7.24 (m, 1H) |
| I-425A | (3R)-3-((S)-4-acetamido-1-(2-chloro-3-fluorophenyl)-1-hydroxybutyl)-N-((S)-1-cyclohexyl-3-(methylamino)propan-2-yl)piperidine-1-carboxamide | 121 | | 539 | 0.90 (m, 2H), 1.02 (m, 2H), 1.87 (s, 3H), 1.95 (m, 1H), 2.46 (m, 1H), 2.64 (m, 2H), 2.71 (s, 3H), 2.92 (m, 2H), 3.08 (m, 3H), 4.00 (d, 1H), 4.15 (m, 1H), 4.32 (d, 1H), 7.15 (m, 1H), 7.30 (m, 1H), 7.60 (m, 1H) |
| I-426A | (3R)-3-((S)-1-(3-chloro-2-fluorophenyl)-1,5-dimethoxypentyl)-N-((S)-1-cyclohexyl-3-(methylamino)propan-2-yl)piperidine-1-carboxamide | 33 | 1.72 | 540, 542 | 7.35-7.29 (m, 2H), 7.06 (t, J = 8.0 Hz, 1H), 4.22 (d, J = 12.9 Hz, 1H), 4.04-3.97 (m, 1H), 3.88 (d, J = 12.9 Hz, 1H), 3.31-3.27 (m, 2H), 3.20 (s, 3H), 3.15 (s, 3H), 2.94 (dd, J = 12.7, 3.4 Hz, 1H), 2.83 (dd, J = 12.6, 10 Hz, 1H), 2.59 (s, 3H), 2.36-0.76 (m, 26H). |
| I-427A | (3R)—N-((2R,3S)-3-hydroxy-4-methyl-1-(methylamino)pentan-2-yl)-3-((S)-1-hydroxy-5-methoxy-1-(2-phenoxyphenyl)pentyl)piperidine-1-carboxamide | 117 | 1.42 | 543 | 0.76 (3H, d), 0.88 (3H, d), 1.76 (1H, m), 2.84 (3H, s), 3.26 (3H, s), 3.95 (2H, m), 4.28 (1H, m), 6.72 (1H, 1H), 6.93 (2H, m), 7.14 (3H, m), 7.35 (2H, m), 7.64 (1H, m). |
| I-428A | (3R)-3-((S)-1-(3-chloro-2-fluorophenyl)-1-hydroxy-5- | 117 | 1.45 | 542 | 0.82 (m), 1.04-2.04 (m), 2.18 (m), 2.64 (m), 2.72 (s), 2.78 (m), 3.04 (dd), 3.24 (s), |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | methoxypentyl)-N-((1S,2R)-1-cyclohexyl-1-hydroxy-3-(methylamino)propan-2-yl)piperidine-1-carboxamide | | | | 3.30 (t), 3.42 (m), 3.82, 3.98 (d), 4.12 (m), 4.38, 4.50 (d), 7.16 (dd), 7.38 (dd), 7.56 (dd) |
| I-428A | (3R)-3-((S)-1-(3-chloro-2-fluorophenyl)-1-hydroxy-5-methoxypentyl)-N-((1S,2R)-1-cyclohexyl-1-hydroxy-3-(methylamino)propan-2-yl)piperidine-1-carboxamide | 121 | | 542 | 0.84 (m, 1H), 1.88 (m, 2H), 2.16 (m, 1H), 2.64 (m, 1H), 2.71 (s, 3H), 2.38 (m, 1H), 3.04 (m, 1H), 3.26 (s, 3H), 3.44 (m, 1H), 3.96 (d, 1H), 4.12 (m, 1H), 4.36 (d, 1H), 7.15 (m, 1H), 7.38 (m, 1H), 7.54 (m, 1H) |
| I-429A | (3R)-3-((S)-1-(3-chloro-2-fluorophenyl)-1-hydroxy-5-methoxypentyl)-N-((S)-1-(cis-4-hydroxycyclohexyl)-3-(methylamino)propan-2-yl)piperidine-1-carboxamide | 120 | | 542 | 2.17 (m, 1H), 2.65 (m, 1H), 2.70 (s, 3H), 2.78 (m, 1H), 3.00 (m, 2H), 3.26 (s, 3H), 3.94 (m, 1H), 3.96 (d, 1H), 4.12 (m, 1H), 4.36 (d, 1H), 7.15 (m, 1H), 7.37 (m, 1H), 7.54 (m, 1H) |
| I-429B | (3R)-3-((S)-1-(3-chloro-2-fluorophenyl)-1-hydroxy-5-methoxypentyl)-N-((S)-1-(trans-4-hydroxycyclohexyl)-3-(methylamino)propan-2-yl)piperidine-1-carboxamide | 121 | | 542 | 0.84 (m, 1H), 1.96 (m, 2H), 2.62 (m, 1H), 2.70 (s, 3H), 2.35 (m, 2H), 3.06 (m, 1H), 3.96 (m, 1H), 4.12 (m, 1H), 4.34 (m, 1H), 7.15 (m, 1H), 7.37 (m, 1H), 7.54 (m, 1H) |
| I-430A | (3R)-3-((S)-1-(2-chloro-3-fluorophenyl)-1-hydroxy-5-methoxypentyl)-N-((1S,2R)-1-cyclohexyl-1-hydroxy-3-(methylamino)propan-2-yl)piperidine-1-carboxamide | 121 | | 542 | 0.76 (m, 1H), 2.48 (m, 1H), 2.73 (s, 3H), 2.92 (m, 1H), 3.05 (m, 1H), 3.25 (s, 3H), 3.46 (m, 1H), 3.94 (d, 1H), 4.12 (m, 1H), 4.34 (d, 1H), 7.16 (m, 1H), 7.34 (m, 1H), 7.62 (m, 1H) |
| I-431A | 3-(1-acetamido-1-(3-chlorophenyl)-5-methoxypentyl)-N-((S)-1-cyclohexyl-3-(methylamino)propan-2-yl)benzamide | 133 | 1.47 | 542, 544 | 7.80-7.14 (m, 8H), 4.42 (m, 1H), 3.27 (t, J = 6.2 Hz, 2H), 3.20 (s, 3H), 3.11-2.93 (m), 2.63 (m, 3H), 2.58-2.41 (m), 1.95 (s, 3H), 1.79-0.84 (m). |
| I-432A | (3R)-3-((S)-1-(3-chloro-2-fluorophenyl)-1-hydroxy-5-methoxypentyl)-N-((S)-1-(trans-4-fluorocyclohexyl)-3-(methylamino)propan-2-yl)piperidine-1-carboxamide | 119 | | 544 | 0.82 (m, 1H), 1.80 (m, 1H), 2.71 (s, 3H), 2.80 (m, 1H), 2.92 (m, 1H), 3.05 (m, 1H), 3.25 (s, 3H), 3.96 (d, 1H), 4.11 (m, 1H), 4.34 (m, 1H), 7.12 (m, 1H), 7.39 (m, 1H), 7.55 (m, 1H) |
| I-432B | (3R)-3-((S)-1-(3-chloro-2-fluorophenyl)-1-hydroxy-5-methoxypentyl)-N-((S)-1-(cis-4-fluorocyclohexyl)-3-(methylamino)propan-2-yl)piperidine-1-carboxamide | 119 | | 544 | 0.84 (m, 1H), 2.15 (m, 1H), 2.71 (s, 3H), 2.82 (m, 1H), 2.94 (m, 1H), 3.06 (m, 1H), 3.25 (s, 3H), 3.94 (d, 1H), 4.16 (m, 1H), 4.36 (d, 1H), 7.13 (m, 1H), 7.36 (m, 1H), 7.53 (m, 1H) |
| I-433A | (3R)-3-((S)-1-(3-chloro-2,4-difluorophenyl)-1-hydroxy-5-methoxypentyl)-N-((S)-1-cyclohexyl-3-(methylamino)propan-2-yl)piperidine-1-carboxamide | 121 | | 544 | 0.84 (m, 1H), 2.70 (s, 3H), 3.06 (m, 1H), 3.27 (s, 3H), 3.96 (d, 1H), 4.13 (m, 1H), 4.30 (d, 1H), 7.12 (m, 1H), 7.56 (m, 1H) |
| I-433B | (3R)-3-((R)-1-(3-chloro-2,4-difluorophenyl)-1-hydroxy-5-methoxypentyl)-N-((S)-1-cyclohexyl-3-(methylamino)propan-2-yl)piperidine-1-carboxamide | 121 | | 544 | 0.86 (m, 1H), 2.17 (m, 1H), 2.70 (s, 3H), 2.91 (m, 1H), 3.04 (m, 1H), 3.25 (s, 3H), 3.92 (m, 1H), 4.14 (m, 1H), 4.42 (m, 1H), 7.10 (m, 1H), 7.52 (m, 1H) |
| I-434A | (3R)-3-((S)-1-(3-chloro-2-fluorophenyl)-1-hydroxy-5-methoxypentyl)-N-((S)-1-(1-fluorocyclohexyl)-3-(methylamino)propan-2-yl)piperidine-1-carboxamide | 121 | | 544 | 0.84 (m, 1H), 2.18 (m, 1H), 2.70 (s, 3H), 2.96 (m, 1H), 3.14 (m, 1H), 3.25 (s, 3H), 3.84 (m, 1H), 4.38 (m, 2H), 7.15 (m, 1H), 7.37 (m, 1H), 7.53 (m, 1H) |
| I-435A | (3R)-3-((S)-1-(2-chloro-3-fluorophenyl)-1-hydroxy-5-methoxypentyl)-N-((S)-1-(trans-4-fluorocyclohexyl)-3-(methylamino)propan-2-yl)piperidine-1-carboxamide | 119 | | 544 | 2.06 (m, 2H), 2.46 (m, 1H), 2.71 (s, 3H), 2.94 (m, 2H), 3.06 (m, 1H), 3.26 (s, 3H), 4.04 (m, 2H), 4.42 (m, 2H), 7.15 (m, 1H), 7.32 (m, 1H), 7.60 (m, 1H) |
| I-435B | (3R)-3-((R)-1-(2-chloro-3-fluorophenyl)-1-hydroxy-5-methoxypentyl)-N-((S)-1-(trans-4-fluorocyclohexyl)-3-(methylamino)propan-2-yl)piperidine-1-carboxamide | 119 | | 544 | 2.07 (m, 2H), 2.46 (m, 1H), 2.71 (s, 3H), 2.92 (m, 2H), 3.07 (m, 1H), 3.26 (s, 3H), 3.96 (d, 1H), 4.12 (m, 1H), 4.34 (d, 1H), 7.16 (m, 1H), 7.30 (m, 1H), 7.60 (m, 1H) |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-436A | (3R)—N-((S)-1-(cis-4-fluorocyclohexyl)-3-(methylamino)propan-2-yl)-3-((S)-1-hydroxy-5-methoxy-1-(2,3,5-trifluorophenyl)pentyl)piperidine-1-carboxamide | 119 | | 546 | 1.08 (m, 1H), 2.70 (s, 3H), 3.06 (m, 1H), 3.22 (s, 3H), 4.14 (m, 3H), 6.94 (m, 1H), 7.23 (m, 1H) |
| I-437A | (3R)-2-((R)-1-(3-chloro-2-fluorophenyl)-1-hydroxy-5-methoxypentyl)-N-((S)-1-(trans-4-fluorocyclohexyl)-3-(methylamino)propan-2-yl)morpholine-4-carboxamide | 33 | 1.38 | 546 | 7.53 (t, 1H), 7.36 (t, 1H), 7.12 (t, 1H), 4.48 (m, 1H), 4.36 (m, 1H), 3.43 (t, 2H), 3.24 (s, 3H), 2.70 (s, 3H), 0.85 (m, 1H). |
| I-438A | (3R)-3-((S)-1-(3-chlorophenyl)-4-(cyclopropanecarboxamido)-1-hydroxybutyl)-N-((S)-1-cyclohexyl-3-(methylamino)propan-2-yl)piperidine-1-carboxamide | 33 | 1.41 | 547, 549 | 7.35-7.34 (m, 1H), 7.24-7.12 (m, 3H), 4.19 (d, J = 13.2 Hz, 1H), 4.08-4.01 (m, 1H), 3.88 (d, J = 13.2 Hz, 1H), 3.03 (t, J = 7.0 Hz, 2H), 2.97 (dd, J = 12.6, 3.5 Hz, 1H), 2.85 (dd, J = 12.5, 10.1 Hz, 1H), 2.61 (s, 3H), 2.49-2.40 (m, 2H), 1.92-0.59 (m, 27H). |
| I-439A | (3R)-3-((S)-4-butyramido-1-(3-chlorophenyl)-1-hydroxybutyl)-N-((S)-1-cyclohexyl-3-(methylamino)propan-2-yl)piperidine-1-carboxamide | 33 | 1.43 | 550, 552 | 7.32-7.31 (m, 1H), 7.22-7.10 (m, 3H), 4.18 (d, J = 12.9 Hz, 1H), 4.06-3.99 (m, 1H), 3.85 (d, J = 13.2 Hz, 1H), 3.02-2.93 (m, 3H), 2.83 (dd, J = 12.6, 10.2 Hz, 1H), 2.59 (s, 3H), 2.46-2.37 (m, 2H), 2.00 (q, J = 7.3 Hz, 2H), 0.80 (t, J = 7.3 Hz, 3H), 1.90-0.76 (m, 24H). |
| I-440A | (3R)-3-((S)-1-(3-chlorophenyl)-4-(3,3-dimethylureido)-1-hydroxybutyl)-N-((S)-1-cyclohexyl-3-(methylamino)propan-2-yl)piperidine-1-carboxamide | 33 | 1.38 | 550, 552 | 7.35 (m, 1H), 7.26-7.15 (m, 3H), 4.20 (d, J = 13.5 Hz, 1H), 4.10-4.04 (m, 1H), 3.94 (d, J = 12.9 Hz, 1H), 3.06-2.98 (m, 3H), 2.86 (dd, J = 12.5, 10.4 Hz, 1H), 2.78 (s, 6H), 2.64 (s, 3H), 2.54-2.44 (m, 2H), 1.93-0.79 (m, 22H). |
| I-442A | (3R)-3-((S)-1-(3-bromophenyl)-1-hydroxy-5-methoxypentyl)-N-((S)-1-cyclohexyl-3-(methylamino)propan-2-yl)piperidine-1-carboxamide | 33 | 1.56 | 552 | 0.84-1.12 (m), 1.20-2.04 (m), 2.58 (m), 2.72 (s), 2.94 (dd), 3.06 (m), 3.26 (s), 3.28 (t), 3.98 (d), 4.14 (m), 4.28 (d), 7.24 (m), 7.36 (d), 7.40 (d), 7.60 (s) |
| I-447A | (3R)-3-((S)-1-(3-chloro-2-fluorophenyl)-1-hydroxy-5-methoxypentyl)-N-((1R,2R)-1-cycloheptyl-1-hydroxy-3-(methylamino)propan-2-yl)piperidine-1-carboxamide | 117 | 1.52 | 556 | 2.72 (3H, s), 3.25 (3H, s) 4.07 (1H, m), 3.99 (1H, d), 4.13 (1H, d), 7.14 (1H, m), 7.37 (1H, m), 7.52 (1H, m). |
| I-449A | (3R)-3-((S)-1-(3-chlorophenyl)-1-hydroxy-4-(methylsulfonamido)butyl)-N-((S)-1-cyclohexyl-3-(methylamino)propan-2-yl)piperidine-1-carboxamide | 33 | 1.38 | 558, 560 | 7.34 (m, 1H), 7.23-7.11 (m, 3H), 4.20 (d, J = 12.9 Hz, 1H), 4.06-3.99 (m, 1H), 3.86 (d, J = 12.6 Hz, 1H), 2.97-2.81 (m, 4H), 2.76 (s, 3H), 2.59 (s, 3H), 2.48-2.42 (m, 2H), 1.96-0.75 (m, 22H). |
| I-450A | (3R)-3-((S)-1-(3-chlorophenyl)-1-hydroxy-4-(sulfamoylamino)butyl)-N-((S)-1-cyclohexyl-3-(methylamino)propan-2-yl)piperidine-1-carboxamide | 33 | 1.33 | 559, 561 | 7.33-7.32 (m, 1H), 7.22-7.09 (m, 3H), 4.19 (d, J = 13.2 Hz, 1H), 4.05-3.98 (m, 1H), 3.84 (d, J = 13.2 Hz, 1H), 2.96-2.81 (m, 4H), 2.59 (s, 3H), 2.48-2.40 (m, 2H), 1.95-0.76 (m, 22H). |
| I-451A | (3R)-3-((S)-4-acetamido-1-(2,3-difluorophenyl)-1-hydroxybutyl)-N-((S)-1-(4,4-difluorocyclohexyl)-3-(methylamino)propan-2-yl)piperidine-1-carboxamide | 33 | 1.26 | 559 | 7.31-7.26 (m, 1H), 7.12-7.02 (m, 2H), 4.25 (d, J = 13.8 Hz, 1H), 4.10-4.03 (m, 1H), 3.90 (d, J = 12.3 Hz, 1H), 3.03-2.98 (m, 3H), 2.87 (dd, J = 12.6, 10.2 Hz, 1H), 2.71 (t, J = 12.2 Hz, 1H), 2.63 (s, 3H), 2.59-2.53 (m, 1H), 1.80 (s, 3H), 2.08-0.89 (m, 20H). |
| I-452A | (3R)-3-((S)-1-(3-fluoro-2-phenoxyphenyl)-1-hydroxy-5-methoxypentyl)-N-((2R,3S)-3-hydroxy-4-methyl-1-(methylamino)pentan-2-yl)piperidine-1-carboxamide | 117 | 1.41 | 561 | 0.76 (3H, d), 0.88 (3H, d), 1.80 (1H, m), 2.70 (3H, s), 3.30 (3H, s), 3.90 (1H, d), 3.95 (1H, m), 4.30 (1H, d), 6.80 (2H, m), 7.03 (1H, m), 7.13 (1H, m), 7.25 (3H, m), 7.50 (1H, m). |
| I-454A | | | | | |
| I-455A | (3R)-3-((S)-1-(3-chlorophenyl)-1-hydroxy-4-((R)-2-methoxypropanamido)butyl)-N-((S)-1-cyclohexyl-3-(methylamino)propan-2- | 33 | 1.43 | 565, 567 | 7.32-7.31 (m, 1H), 7.21-7.10 (m, 3H), 4.18 (d, J = 12.9 Hz, 1H), 4.05-3.98 (m, 1H), 3.84 (d, J = 12.9 Hz, 1H), 3.56 (q, J = 6.7 Hz, 1H), 3.21 (s, 3H), 3.11-2.97 (m, 2H), 2.94 (dd, J = 12.6, 3.2 Hz, 1H), |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | yl)piperidine-1-carboxamide | | | | 2.82 (dd, J = 12.5, 10.4 Hz, 1H), 2.58 (s, 3H), 2.46-2.35 (m, 2H), 1.16 (d, J = 6.7 Hz, 3H), 1.89-0.73 (m, 22H). |
| I-455B | (3R)-3-((S)-1-(3-chlorophenyl)-1-hydroxy-4-((S)-2-methoxypropanamido)butyl)-N-((S)-1-cyclohexyl-3-(methylamino)propan-2-yl)piperidine-1-carboxamide | 33 | 1.41 | 565, 567 | 7.31-7.30 (m, 1H), 7.21-7.09 (m, 3H), 4.17 (d, J = 12.9 Hz, 1H), 4.05-3.97 (m, 1H), 3.85 (d, J = 12.3 Hz, 1H), 3.55 (q, J = 6.7 Hz, 1H), 3.20 (s, 3H), 3.06-3.00 (m, 2H), 2.94 (dd, J = 12.7, 3.4 Hz, 1H), 2.82 (dd, J = 12.5, 10.4 Hz, 1H), 2.58 (s, 3H), 2.45-2.34 (m, 2H), 1.16 (d, J = 6.7 Hz, 3H), 1.89-0.73 (m, 22H). |
| I-456A | (3R)-3-((S)-1-(3-chlorophenyl)-1-hydroxy-2-(2-methoxyethoxy)ethyl)-N-((S)-1-cyclohexyl-3-(methylamino)propan-2-yl)piperidine-1-carboxamide | 121 | | 510 | 0.98 (m, 2H), 1.94 (m, 1H), 2.45 (m, 1H), 2.70 (s, 3H), 2.42 (m, 1H), 3.06 (m, 1H), 3.29 (m, 1H), 3.50 (m, 2H), 3.62 (m, 2H), 3.72 (m, 1H), 3.83 (m, 2H), 4.00&4.34 (m, 1H), 4.16 (m, 2H), 7.30 (m, 3H), 7.52 (m, 1H) |
| I-457A | (3R)—N-((1S,2R)-1-cyclopentyl-1-hydroxy-3-(methylamino)propan-2-yl)-3-((S)-1-hydroxy-5-methoxy-1-(2-phenoxyphenyl)pentyl)piperidine-1-carboxamide | 117 | 1.47 | 568 | 2.70 (3H, s), 3.30 (3H, s), 3.95 (2H, m), 4.35 (1H, d), 6.77 (1H, d, 8.4), 6.97 (2H, d, 8.4), 7.15 (2H, m), 7.23 (1H, t, 6.8), 7.40 (2H, t, 7.6), 7.70 (1H, d, 6.4). |
| I-458A | 2-(1-acetamido-1-(3-chloro-2-fluorophenyl)-5-methoxypentyl)-N-((S)-1-cyclohexyl-3-(methylamino)propan-2-yl)morpholine-4-carboxamide | 133 | 1.45 | 569 | 7.41-7.31 (m, 2H), 7.13 (q, 1H), 3.39 (m, 2H), 3.04 (m, 1H), 2.67 (s, 3H), 1.00 (m, 1H), 0.89 (m, 1H). |
| I-459A | (3R)-3-((S)-1-(2-bromo-5-fluorophenyl)-1-hydroxy-5-methoxypentyl)-N-((S)-1-cyclohexyl-3-(methylamino)propan-2-yl)piperidine-1-carboxamide | 33 | 1.59 | 570 | 0.70-1.16 (m), 1.20-1.90 (m), 2.64 (m), 2.70 (s), 2.78 (m), 2.94 (dd), 3.06 (dd), 3.24 (s), 3.30 (t), 4.02 (d), 4.14 (m), 4.30 (d), 6.92 (m), 7.58 (m) |
| I-463A | (3R)-3-((S)-1-(3-fluoro-2-(o-tolyloxy)phenyl)-1-hydroxy-5-methoxypentyl)-N-((2R,3S)-3-hydroxy-4-methyl-1-(methylamino)pentan-2-yl)piperidine-1-carboxamide | 117 | 1.45 | 575 | 0.80 (3H, d), 0.95 (3H, d), 1.70 (1H, m), 2.50 (3H, 2d), 3.20 (3H, s), 3.30 (3H, s), 3.80 (1H, d), 4.00 (1H, m), 4.25 (1H, d), 6.40 (1H, m), 6.90 (1H, m), 7.05 (1H, m), 7.15 (1H, m), 7.30 (2H, m), 7.50 (1H, m). |
| I-464A | (3R)-3-((S)-1-(3-chlorophenyl)-1-hydroxy-4-(2,2,2-trifluoroacetamido)butyl)-N-((S)-1-cyclohexyl-3-(methylamino)propan-2-yl)piperidine-1-carboxamide | 33 | 1.56 | 577575, | not determined |
| I-466A | (3R)—N-((1S,2R)-1-cyclopentyl-1-hydroxy-3-(methylamino)propan-2-yl)-3-((S)-1-(3-fluoro-2-phenoxyphenyl)-1-hydroxy-5-methoxypentyl)piperidine-1-carboxamide | 117 | 1.45 | 586 (M + 1) | 2.75 (3H, s), 3.40 (3H, s), 3.95 (1H, d), 4.00 (1H, m), 4.35 (1H, d), 6.85 (2H, d), 7.10 (1H, t), 7.20 (1H, t), 7.35 (3H, m), 7.60 (1H, d). |
| I-467A | (3R)-3-((S)-1-(3'-chloro-6-fluorobiphenyl-2-yl)-1-hydroxy-5-methoxypentyl)-N-((S)-1-cyclopentyl-3-(methylamino)propan-2-yl)piperidine-1-carboxamide | 119 | | 588 | 1.81 (s, 1H), 2.66 (s, 3H), 3.25 (s, 3H), 3.64 (m, 1H), 4.00 (m, 1H), 4.34 (m, 1H), 4.60 (m, 1H), 7.25 (m, 1H), 7.35-7.47 (m, 5H), 7.62 (m, 1H) |
| I-468A | (3R)—N-(1-(3,3-difluorocyclobutyl)-3-(methylamino)propan-2-yl)-3-((S)-1-(3-fluoro-2-phenoxyphenyl)-1-hydroxy-5-methoxypentyl)piperidine-1-carboxamide | 33 | 1.52 | 592 | 7.49 (d), 7.27-7.19 (m), 7.11 (t), 6.99 (m), 6.78 (d), 4.41 (d), 4.22 (d), 3.95 (m), 3.85 (d), 3.70 (d), 3.27 (m), 3.21 (m), 2.65 (s) |
| I-469A | (3R)-3-((S)-1-butyramido-1-(3-chloro-2-fluorophenyl)-5-methoxypentyl)-N-((S)-1-cyclohexyl-3-(methylamino)propan-2-yl)piperidine-1-carboxamide | 133 | 1.55 | 595 | 8.01 (d, 1H), 7.40 (t, 1H), 7.28 (t, 1H), 7.15 (t, 1H), 4.29 (m, 1H), 4.12 (m, 1H), 3.92 (d, 1H), 3.37 (t, 2H), 3.29 (s, 3H), 2.71 (s, 3H), 2.54 (t, 1H), 1.92 (d, 1H), 1.84 (d, 1H), 0.99 (t, 3H). |
| I-470A | (3S)-3-(1-(3-chloro-2-fluorophenyl)-5-methoxypentyl)-N-((S)-1-cyclohexyl-3-(methylamino)propan-2-yl)piperidine-1-carboxamide | 33 | 1.79 | 510 | 7.34 (t, J = 7.2 Hz, 1H), 7.20 (t, J = 7.2 Hz, 1H), 7.13 (t, J = 7.2 Hz, 1H), 4.12-3.85 (m, 3H), 3.66 (brd, J = 13.2 Hz, 1H), 3.25 (s, 3H), 3.05 and 2.92 (m, 1H), 3.00 (dd, J = 12.4, 3.2 Hz, 1H), 2.83 (t, J = 11.1 Hz, 2H), 2.77-2.73 (m, 1H), 2.65 (s, 3H), 2.47 (t, J = 12.0 Hz, 1H), 2.13-2.09 (m, 1H), 1.84 (m, 1H), |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-471A | (R)-2-((S)-(3-chloro-2-fluorophenyl)(3-methoxypropoxy)methyl)-N-((S)-1-cyclohexyl-3-(methylamino)propan-2-yl)morpholine-4-carboxamide | 33 | 1.56 | 514 | 1.78-1.64 (m, 8H), 1.58-1.17 (m, 9H), 1.13-1.04 (m, 4H), 0.99 (m, 1H). 0.87 (m, 1H). 7.42 (t, 1H), 7.37 (t, 1H), 7.19 (t, 1H), 4.61 ((d, 1H), 4.11 (d, 2H), 3.80 (t, 2H), 3.55 (t, 1H), 3.28 (s, 3H), 3.04 (td, 1H), 2.69 (s, 3H), 1.48 (m, 1H), 1.01 (m, 1H), 0.89 (m, 1H). |
| I-472A | (3R)—N-((S)-2-amino-5-methoxy-4,4-dimethylpentyl)-3-((S)-1-(3-chloro-2-fluorophenyl)-1-hydroxy-5-methoxypentyl)piperidine-1-carboxamide | 127 | 1.45 | 516 | 0.82 (m), 0.98 (s), 1.00 (s), 1.18-1.64 (m), 1.96 (m), 2.20 (m), 2.68 (m), 3.16 (d), 3.24 (sd), 3.30 (m), 3.38 (s), 3.86 (d), 4.42 (d), 7.14 (dd), 7.38 (dd), 7.54 (dd). |
| I-473A | (3R)—N-((S)-1-amino-5-methoxy-4,4-dimethylpentan-2-yl)-3-((S)-1-(3-chloro-2-fluorophenyl)-1-hydroxy-5-methoxypentyl)piperidine-1-carboxamide | 33 | 1.44 | 516 | 0.82 (m), 0.98 (s), 1.12-1.64 (m), 1.98 (m), 2.18 (m), 2.64 (m), 2.78 (dd), 2.84 (dd), 2.98 (m), 3.10 (s), 3.24 (s), 3.30 (m), 3.34 (s), 3.94 (m), 4.12 (m), 4.38 (d), 7.14 (dd), 7.38 (dd), 7.54 (dd). |
| I-474A | (3R)-3-((S)-1-(3-chlorophenyl)-1-hydroxy-5-methoxypentyl)-N-((2S,3R)-1-cyclohexyl-3-(methylamino)butan-2-yl)piperidine-1-carboxamide | 119 | | 522 | 1.12 (d, 3H), 2.54 (m, 2H), 2.72 (s, 3H), 3.14 (m, 1H), 3.26 (s, 3H), 3.93 (m, 2H), 4.17 (m, 1H), 4.32 (m, 1H), 7.26 (m, 3H), 7.43 (m, 1H) |
| I-475A | (3R)-3-((S)-1-(3-chloro-2-fluorophenyl)-1-hydroxy-5-methoxypentyl)-N-((S)-3-cyclohexyl-2-(methylamino)propyl)piperidine-1-carboxamide | 127 | 1.56 | 526 | 7.52 (t, 1H), 7.36 (t, 1H), 7.13 (t, 1H), 4.40 (d, 1H), 3.89 (d, 1H), 3.53 (d, 1H), 3.24 (s, 3H), 2.73 (s, 3H), 2.18 (tt, 1H), 1.00 (m, 1H), 0.83 (m, 1H). |
| I-476A | (3R)-3-((S)-1-(3-chlorophenyl)-1-(methylamino)propan-2-(1-fluorocyclohexyl)-3-(methylamino)propan-2-yl)piperidine-1-carboxamide | 121 | | 526 | 0.98 (m, 1H), 2.38 (m, 1H), 2.71 (s, 3H), 2.96 (m, 1H), 3.13 (m, 1H), 3.23 (s, 3H), 3.81&3.98 (m, 1H), 4.35 (m, 2H), 7.25 (m, 3H), 7.42 (m, 1H) |
| I-476B | (3R)-3-((S)-1-(3-chlorophenyl)-1-hydroxy-5-methoxypentyl)-N-((S)-1-(1-fluorocyclohexyl)-3-(methylamino)propan-2-yl)piperidine-1-carboxamide | 121 | 1.52 | 526 | 7.42 (s), 7.27 (m), 7.22 (m), 4.38 (d), 4.20 (br m), 3.83 (d), 3.26 (s), 2.72 (m), 2.58 (m), 2.46 (s), 2.39 (t). |
| I-476C | (3R)-3-((S)-1-(3-chlorophenyl)-1-hydroxy-5-methoxypentyl)-N-((R)-1-(1-fluorocyclohexyl)-3-(methylamino)propan-2-yl)piperidine-1-carboxamide | 121 | 1.51 | 526 | 7.42 (s), 7.28 (m), 7.22 (m), 4.28 (d), 4.19 (br m), 3.95 (d), 3.27 (s), 2.65 (m), 2.57 (q), 2.42 (s). |
| I-477A | (3R)—N-((2R,3S)-3-amino-4-cyclohexylbutan-2-yl)-3-((S)-1-(3-chloro-2-fluorophenyl)-1-hydroxy-5-methoxypentyl)piperidine-1-carboxamide | 127 | | 526 | 0.80 (m, 1H), 1.30 (s, 3H), 2.18 (m, 2H), 2.68 (m, 2H), 3.25 (s, 3H), 3.88 (m, 1H), 4.04 (m, 1H), 4.44 (m, 1H), 7.15 (m, 1H), 7.36 (m, 1H), 7.54 (m, 1H) |
| I-477B | (3R)—N-((2S,3S)-3-amino-4-cyclohexylbutan-2-yl)-3-((S)-1-(3-chloro-2-fluorophenyl)-1-hydroxy-5-methoxypentyl)piperidine-1-carboxamide | 127 | | 526 | 0.80 (m, 1H), 1.30 (s, 3H), 2.18 (m, 2H), 2.68 (m, 2H), 3.25 (s, 3H), 3.88 (m, 1H), 4.04 (m, 1H), 4.44 (m, 1H), 7.15 (m, 1H), 7.36 (m, 1H), 7.54 (m, 2H) |
| I-478A | (3R)-3-(1-(3-chloro-2-fluorophenyl)-1-fluoro-5-methoxypentyl)-N-((S)-1-cyclohexyl-3-(methylamino)propan-2-yl)piperidine-1-carboxamide | 149 | 1.71 | 528, 530 | 7.41-7.27 (m, 2H), 7.16-7.06 (m, 1H), 4.34-3.63 (m, 3H), 3.23-3.18 (m, 3H), 3.15 (s, 3H), 3.00-2.48 (m, 4H), 2.57 (s, 3H), 2.17-0.72 (m, 24H). |
| I-479A | (3R)-3-((S)-1-(benzo[b]thiophen-7-yl)-1-hydroxy-5-methoxypentyl)-N-(1-(methylamino)-3-(tetrahydro-2H-pyran-4-yl)propan-2-yl)piperidine-1-carboxamide | 33 | 1.32 | 532 | |
| I-480A | (3R)-3-((S)-1-(2,3-dihydrobenzofuran-7-yl)-1-hydroxy-5-methoxypentyl)-N-((S)-1-((1r,4S)-4-fluorocyclohexyl)-3-(methylamino)propan-2-yl)piperidine-1-carboxamide | 151 | | 532 | 2.72 (m, 3H), 2.90 (m, 3H), 3.28 (s, 3H), 4.05 (m, 2H), 4.30 (m, 2H), 7.22 (m, 1H), 7.50 (m, 1H), 7.74 (m, 1H) |
| I-481A | (3R)-3-((S)-1-(3-chlorophenyl)-1-ethoxy-5-methoxypentyl)-N-((S)-1-cyclohexyl-3-(methylamino)propan-2-yl)piperidine-1-carboxamide | 33 | 1.76 | 536, 538 | 7.32-7.17 (m, 4H), 4.24 (d, J = 13.2 Hz, 1H), 4.06-3.99 (m, 1H), 3.88 (d, J = 12.6 Hz, 1H), 3.40-3.31 (m, 3H), 3.23 (s, 3H), 3.19-3.11 (m, 1H), 2.97 (dd, J = 12.7, 3.4 Hz, |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | | | | | 1H), 2.85 (dd, J = 12.6, 10.0 Hz, 1H), 2.62 (s, 3H), 2.30-0.75 (m, 26H), 1.19 (t, J = 7.0 Hz, 3H). |
| I-482A | (3R)-3-((S)-1-(3-chlorophenyl)-1-hydroxy-5-methoxypentyl)-N-((S)-1-((1r,4S)-4-hydroxy-4-methylcyclohexyl)-3-(methylamino)propan-2-yl)piperidine-1-carboxamide | 119 | | 538 | 1.02 (m, 2H), 1.19 (s, 3H), 1.96 (m, 2H), 2.52 (m, 2H), 2.71 (s, 3H), 2.94 (m, 1H), 3.07 (m, 1H), 3.27 (s, 3H), 3.96 (m, 1H), 4.10 (m, 1H), 4.29 (m, 1H), 7.27 (m, 3H), 7.44 (m, 1H) |
| I-483A | (R)-3-((S)-1-(2,3-difluorophenyl)-1-hydroxy-5-methoxypentyl)-N-((S)-1-((1r,4S)-4-hydroxy-4-methylcyclohexyl)-3-(methylamino)propan-2-yl)piperidine-1-carboxamide | 119 | | 540 | 0.89 (m, 1H), 1.19 (s, 3H), 1.98 (m, 2H), 2.15 (m, 1H), 2.70 (s, 3H), 2.94 (m, 1H), 3.06 (m, 1H), 3.28 (s, 3H), 3.96 (m, 1H), 4.12 (m, 1H), 4.34 (m, 1H), 7.13 (m, 2H), 7.37 (m, 1H) |
| I-484A[b] | (3R)-3-((S)-1-(2,3-difluorophenyl)-1-hydroxy-5-methoxypentyl)-N-((S)-1-((1r,4S)-4-methoxycyclohexyl)-3-(methylamino)propan-2-yl)piperidine-1-carboxamide | 121 | | 540 | 1.00 (m, 3H), 2.30 (m, 1H), 2.75 (s, 3H), 2.86 (m, 1H), 3.10 (m, 1H), 3.27 (s, 3H), 3.33 (s, 3H), 3.75 (m, 2H), 4.20 (m, 2H), 6.08 (m, 1H), 7.05 (m, 2H), 7.32 (m, 1H), 8.92 (brs, 1H), 10.00 (brs, 1H) |
| I-484B[b] | (3R)-3-((R)-1-(2,3-difluorophenyl)-1-hydroxy-5-methoxypentyl)-N-((S)-1-((1r,4S)-4-methoxycyclohexyl)-3-(methylamino)propan-2-yl)piperidine-1-carboxamide | 121 | | 540 | 1.00 (m, 3H), 2.32 (m, 1H), 2.76 (s, 3H), 2.92 (m, 1H), 3.08 (m, 1H), 3.27 (s, 3H), 3.29 (m, 3H), 3.75 (m, 1H), 4.20 (m, 1H), 6.05 (m, 1H), 7.05 (m, 2H), 7.34 (m, 1H), 8.90 (brs, 1H), 10.00 (brs, 1H) |
| I-485A | (3R)-3-((S)-1-(3-chloro-2-fluorophenyl)-1-hydroxy-5-methoxypentyl)-N-((2S,3R)-1-cyclohexyl-3-(methylamino)butan-2-yl)piperidine-1-carboxamide | 119 | | 540 | 0.95 (m, 4H), 1.23 (d, 3H), 2.00 (m, 2H), 2.18 (m, 1H), 2.73 (s, 3H), 3.15 (m, 1H), 3.25 (s, 3H), 4.00 (m, 1H), 4.18 (m, 1H), 4.39 (m, 1H), 7.14 (m, 1H), 7.37 (m, 1H), 7.53 (m, 1H) |
| I-485B | (3R)-3-((R)-1-(3-chloro-2-fluorophenyl)-1-hydroxy-5-methoxypentyl)-N-((2S,3R)-1-cyclohexyl-3-(methylamino)butan-2-yl)piperidine-1-carboxamide | 119 | | 540 | 0.95 (m, 4H), 1.28 (m, 3H), 1.99 (m, 2H), 2.20 (m, 1H), 2.74 (s, 3H), 3.25 (s, 3H), 3.64 (m, 1H), 3.90 (m, 1H), 4.05 (m, 1H), 4.43 (m, 1H), 7.15 (m, 1H), 7.37 (m, 1H), 7.53 (m, 1H) |
| I-488A | (3R)—N-((2S,3S)-3-amino-4-cyclohexyl-1-hydroxybutan-2-yl)-3-((S)-1-(3-chloro-2-fluorophenyl)-1-hydroxy-5-methoxypentyl)piperidine-1-carboxamide | 150 | 1.48 | 542 | 0.70-1.02 (m,), 1.06-2.00 (m,), 2.16 (m,), 2.64 (m,), 3.20 (s), 3.24 (t), 3.50 (m,), 3.62 (dd), 3.70 (dd), 3.84 (d), 3.92 (m,), 4.40 (d), 7.06 (dd), 7.34 (dd), 7.46 (dd). |
| I-489A | (3R)—N-((1S,2R)-1-cyclohexyl-1-hydroxy-3-(methylamino)propan-2-yl)-3-((S)-1-hydroxy-5-methoxy-1-(2,3,5-trifluorophenyl)pentyl)piperidine-1-carboxamide | 117 | | 544 | 1.77 (m, 3H), 1.93 (m, 2H), 2.21 (m, 1H), 2.68 (s, 3H), 2.83 (m, 1H), 3.03 (m, 1H), 3.27 (s, 3H), 3.40 (m, 1H), 3.99 (m, 1H), 4.07 (m, 1H), 4.27 (m, 1H), 6.91 (m, 1H), 7.22 (m, 1H) |
| I-490A | (3R)-3-((S)-1-(2-chloro-3-fluorophenyl)-1-hydroxy-5-methoxypentyl)-N-((S)-1-(1-fluorocyclohexyl)-3-(methylamino)propan-2-yl)piperidine-1-carboxamide | 121 | | 544 | 0.75 (m, 1H), 1.02 (m, 1H), 2.50 (m, 1H), 2.71 (s, 3H), 2.95 (m, 2H), 3.15 (m, 1H), 3.27 (s, 3H), 3.82&4.00 (m, 1H), 4.32&4.49 (m, 2H), 7.13 (m, 1H), 7.30 (m, 1H), 7.62 (m, 1H) |
| I-491A | (3R)—N-((S)-1-((1r,4S)-4-fluorocyclohexyl)-3-(methylamino)propan-2-yl)-3-((S)-1-hydroxy-5-methoxy-1-(2,3,5-trifluorophenyl)pentyl)piperidine-1-carboxamide | 119 | | 546 | 2.23 (m, 1H), 2.70 (s, 3H), 2.88 (m, 2H), 3.08 (m, 1H), 3.27 (s, 3H), 4.01 (m, 1H), 4.08 (m, 1H), 4.26 (m, 1H), 4.35&4.47 (m, 1H), 6.92 (m, 1H), 7.22 (m, 1H) |
| I-492A | (3R)—N-((S)-2-amino-3-(4,4-difluorocyclohexyl)propyl)-3-((S)-1-(3-chloro-2-fluorophenyl)-1-hydroxy-5-methoxypentyl)piperidine-1-carboxamide | 127 | | 548 | 0.84 (m, 1H), 2.16 (m, 2H), 2.68 (m, 2H), 3.25 (s, 3H), 3.40 (m, 2H), 3.88 (m, 1H), 4.42 (m, 1H), 7.15 (m, 1H), 7.37 (m, 1H), 7.53 (m, 1H) |
| I-493A | (3R)—N-((1S,2R)-3-amino-1-(noradamant-3-yl)-1-hydroxypropan-2-yl)-3-((S)-1-(3-chlorophenyl)-1-hydroxy-5-methoxypentyl)piperidine-1-carboxamide | 117 | 1.55 | 548 | 7.42 (1H), 7.26 (3H), 4.30 (1H), 4.08 (1H), 3.73 (1H), 2.24 (1H) |
| I-495A | (3R)-3-((S)-1-(3-chloro-2-fluorophenyl)-1-hydroxy-5- | 121 | | 556 | 0.84 (m, 1H), 1.20 (s, 3H), 1.96 (m, 2H), 2.17 (m, 1H), 2.73 (s, 3H), 2.95 (m, 1H), |

-continued

Table of Compounds

| Cpd. No. | Cpd. Name | Method of Synthesis Example No. | LC-MS (3 min) tR (min) | Mass observed | Selected 1H NMR$^a$ |
|---|---|---|---|---|---|
| | methoxypentyl)-N-((S)-1-((1r,4S)-4-hydroxy-4-methylcyclohexyl)-3-(methylamino)propan-2-yl)piperidine-1-carboxamide | | | | 3.08 (m, 1H), 3.28 (s, 3H), 3.96 (m, 1H), 4.12 (m, 1H), 4.37 (m, 1H), 7.14 (m, 1H), 7.37 (m, 1H), 7.54 (m, 1H) |
| I-497A | (3R)-3-((S)-1-(3-chloro-2,4-difluorophenyl)-1-hydroxy-5-methoxypentyl)-N-((1S,2R)-1-cyclohexyl-1-hydroxy-3-(methylamino)propan-2-yl)piperidine-1-carboxamide | 117 | | 560 | 0.82 (m, 1H), 1.95 (m, 2H), 2.12 (m, 1H), 2.74 (s, 3H), 3.04 (m, 1H), 3.26 (s, 3H), 3.42 (m, 1H), 3.96 (m, 1H), 4.10 (m, 1H), 4.32 (m, 1H), 7.09 (m, 1H), 7.55 (m, 1H) |
| I-498A | (3R)-3-((S)-1-(3-chloro-2,4-difluorophenyl)-1-hydroxy-5-methoxypentyl)-N-((S)-1-((1r,4S)-4-fluorocyclohexyl)-3-(methylamino)propan-2-yl)piperidine-1-carboxamide | 119 | | 562 | 2.70 (s, 3H), 2.99 (m, 4H), 3.26 (s, 3H), 4.02 (m, 2H), 4.43 (m, 2H), 7.11 (m, 1H), 7.57 (m, 1H) |
| I-499A | (3R)—N-((1S,2R)-(3-amino-1-(noradamant-3-yl)-1-hydroxy)propan-2-yl)-3-((S)-1-(2-fluoro-3-chlorophenyl)-1-hydroxy-5-methoxypentyl)piperidine-1-carboxamide | 117 | 1.55 | 567 | 7.51 (1H), 7.36 (1H), 7.13 (1H), 4.34 (1H), 4.10 (1H), 23.73 (1H) |
| I-502A | (3R)-3-((R)-(3-chlorophenyl)(2-hydroxyethoxy)methyl)-N-((S)-1-cyclohexyl-3-(methylamino)propan-2-yl)piperidine-1-carboxamide | 33 | 1.52 | 466, 468 | 7.31-7.16 (m, 4H), 4.17-4.12 (m, 1H), 4.09-4.03 (m, 1H), 4.00 (d, J = 9.1 Hz, 1H), 3.82 (d, J = 12.9 Hz, 1H), 3.60-3.57 (m, 2H), 3.31-3.22 (m, 2H), 3.03-2.78 (m, 4H), 2.65 (s, 3H), 1.76-0.80 (m, 18H). |
| I-503A | (3R)—N-(2-amino-3-cyclopentylpropyl)-3-((S)-1-(3-chlorophenyl)-1-hydroxy-5-methoxypentyl)piperidine-1-carboxamide | 127 | 1.47 | 480 | 7.43 ((s, 1H), 7.32-7.20 (m, 3H), 4.36 (d, 1H), 3.89 (d, 1H), 3.44 (t, 1H), 3.27 (s, 3H), 2.59 (t, 1H), 2.44 (t, 1H), 1.76 (tt, 1H), 1.01 (m, 1H). |
| I-504A | (3R)—N-((2S)-2-amino-3-(tetrahydrofuran-2-yl)propyl)-3-((S)-1-(3-chlorophenyl)-1-hydroxy-5-methoxypentyl)piperidine-1-carboxamide | 127 | 1.35 | 482 | 7.43 (s), 7.30-7.22 (m), 4.35 (d), 4.00 (br m), 3.90 (m), 3.76 (m), 3.26 (m), 2.58 (t), 2.44 (t). |
| I-505A | (3R)—N-((2S)-1-amino-3-(tetrahydrofuran-2-yl)propan-2-yl)-3-((S)-1-(3-chlorophenyl)-1-hydroxy-5-methoxypentyl)piperidine-1-carboxamide | 33 | 1.37 | 482 | 7.43 (s), 7.31-7.22 (m), 4.30 (m), 4.03 (br m), 3.91 (m), 3.75 (m), 3.26 (m), 3.12 (m), 2.93 (m). |
| I-507A | (3S)-3-((R)-1-(3-chlorophenyl)-2-(2-methoxyethoxy)ethyl)-N-((S)-1-cyclohexyl-3-(methylamino)propan-2-yl)piperidine-1-carboxamide | 121 | | 494 | 0.99 (m, 1H), 1.06 (m, 2H), 1.53 (m, 3H), 2.71 (s, 3H), 3.08 (m, 1H), 3.52 (m, 4H), 3.66 (m, 2H), 4.15 (m, 2H), 7.15 (m, 1H), 7.27 (m, 3H) |
| I-508A | (3R)—N-(2-amino-3-(tetrahydro-2H-pyran-4-yl)propyl)-3-((S)-1-(3-chlorophenyl)-1-hydroxy-5-methoxypentyl)piperidine-1-carboxamide | 127 | 1.29 | 496 | 7.43 (s), 7.32-7.20 (m, 3H), 4.36 (d, 1H), 3.91 (m, 3H), 3.26 (s, 3H), 2.58 (t, 1H), 2.43 (td, 1H), 1.93 (t, 1H), 1.00 (m, 1H). |
| I-509A | (3R)—N-((2S)-1-amino-3-(tetrahydro-2H-pyran-2-yl)propan-2-yl)-3-((S)-1-(3-chlorophenyl)-1-hydroxy-5-methoxypentyl)piperidine-1-carboxamide | 33 | 1.4 | 496 | 7.43 (s), 7.28-7.23 (m), 4.30 (m), 4.07 (m), 3.94 (m), 3.45 (m), 3.26 (m) |
| I-510A | (3R)—N-((S)-1-amino-3-(3-methoxycyclobutyl)propan-2-yl)-3-((S)-1-(3-chlorophenyl)-1-hydroxy-5-methoxypentyl)piperidine-1-carboxamide | 33 | | 496 | 1.02 (m, 1H), 1.41 (m, 3H), 1.95 (m, 3H), 2.49 (m, 4H), 2.85 (m, 1H), 3.03 (m, 1H), 3.21 (s, 3H), 3.26 (s, 3H), 3.72 (m, 1H), 3.90 (m, 1H), 4.30 (m, 1H), 7.26 (m, 3H), 7.44 (m, 1H) |
| I-511A | (3R)—N-((S)-2-amino-3-(trans-3-methoxycyclobutyl)propyl)-3-((S)-1-(3-chlorophenyl)-1-hydroxy-5-methoxypentyl)piperidine-1-carboxamide | 127 | | 496 | 1.00 (m, 1H), 1.29 (m, 3H), 1.50 (m, 4H), 1.96 (m, 3H), 2.49 (m, 3H), 3.18 (s, 3H), 3.26 (s, 3H), 3.77 (m, 1H), 3.88 (m, 1H), 4.37 (m, 1H), 7.25 (m, 3H), 7.44 (m, 1H) |
| I-511B | (3R)—N-((S)-2-amino-3-(cis-3-methoxycyclobutyl)propyl)-3-((S)-1-(3-chlorophenyl)-1-hydroxy-5-methoxypentyl)piperidine-1-carboxamide | 127 | | 496 | 1.01 (m, 1H), 1.98 (m, 3H), 2.50 (m, 4H), 3.16 (m, 1H), 3.27 (s, 3H), 3.29 (s, 3H), 3.78 (m, 1H), 3.86 (m, 1H), 4.35 (m, 1H), 7.25 (m, 3H), 7.44 (m, 1H) |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-512A | (S)—N-((S)-2-amino-3-cyclohexylpropyl)-3-((S)-1-(3-chloro-2-fluorophenyl)-5-methoxypentyl)piperidine-1-carboxamide | 127 | 1.68 | 496 | 7.32 (t, J = 7.6 Hz, 1H), 7.20 (t, J = 7.6 Hz, 1H), 7.13 (t, J = 7.6 Hz, 1H), 3.73 (brd, J = 13.2 Hz, 2H), 3.34-3.25 (m, 4H), 3.24 (s, 3H), 3.14 (dd, J = 13.6, 6.8 Hz, 1H), 2.83 (m, 2H), 2.38 (d, J = 7.2 Hz, 1H), 2.09 (brd, J = 7.6 Hz, 1H), 1.94 (m, 1H), 1.74-1.66 (m, 8H), 1.54-1.48 (m, 6H), 1.37-1.15 (m, 4H), 1.12-1.03 (m, 2H), 0.99-0.88 (m 2H). |
| I-512B | (S)—N-((S)-2-amino-3-cyclohexylpropyl)-3-((R)-1-(3-chloro-2-fluorophenyl)-5-methoxypentyl)piperidine-1-carboxamide | 127 | 1.68 | 496 | 7.32 (t, J = 7.2 Hz, 1H), 7.1--7.10 (m, 2H), 4.20 (brd, J = 13.6 Hz, 1H), 3.73 (brd, J = 13.6 Hz, 2H), 3.42-3.26 (m, 4H), 3.25 (s, 3H), 2.82 (t, J = 10.0 Hz, 2H). 2.64 (t, J = 10.0 Hz 1H), 1.90 (m, 1H), 1.81-1.67 (m, 6H), 1.64-1.42 (m, 6H), 1.39-1.19 (m, 3H), 1.25-0.90 (m, 3H). |
| I-513A | (3R)—N-((2S)-2-amino-3-(tetrahydrofuran-2-yl)propyl)-3-((S)-1-(3-chloro-2-fluorophenyl)-1-hydroxy-5-methoxypentyl)piperidine-1-carboxamide | 127 | 1.36 | 500 | 7.52 (m), 7.36 (m), 7.13 (m), 4.40 (d), 4.00 (br m), 3.90 (m), 3.76 (m), 3.44-3.35 (m), 3.24 (m), 2.68 (q) |
| I-514A | (3R)—N-((2S)-1-amino-3-(tetrahydrofuran-2-yl)propan-2-yl)-3-((S)-1-(3-chloro-2-fluorophenyl)-1-hydroxy-5-methoxypentyl)piperidine-1-carboxamide | 33 | 1.36 | 500 | 7.52 (m), 7.36 (m), 7.13 (m), 4.34 (m), 4.03 (m), 3.91 (m), 3.76 (m), 3.24 (m), 3.12 (m), 2.95 (m), 2.69 (m). |
| I-515A | (3R)—N-((S)-2-amino-4-phenylbutyl)-3-((S)-1-(3-chlorophenyl)-1-hydroxy-5-methoxypentyl)piperidine-1-carboxamide | 127 | | 502 | 1.00 (m, 2H), 2.50 (m, 2H), 2.76 (m, 2H), 3.28 (s, 3H), 3.47 (m, 1H), 3.89 (m, 1H), 4.36 (m, 1H), 7.16-7.48 (m, 9H) |
| I-520A | (3R)—N-((S)-2-amino-4-cyclohexylbutyl)-3-((S)-1-(3-chlorophenyl)-1-hydroxy-5-methoxypentyl)piperidine-1-carboxamide | 127 | | 508 | 0.98 (m, 3H), 1.94 (m, 2H), 2.50 (m, 2H), 3.17 (s, 3H), 3.88 (m, 1H), 4.35 (m, 1H), 7.26 (m, 3H), 7.44 (m, 1H) |
| I-522A | (S)-3-((R)-1-(3-chloro-2-fluorophenyl)-5-methoxypentyl)-N-((S)-1-cyclohexyl-3-(methylamino)propan-2-yl)piperidine-1-carboxamide | 33 | 1.76 | 510 | 7.33 (t, J = 7.6 Hz, 1H), 7.13 (m, 2H), 3.86 (brd, J = 13.2 Hz, 2H), 3.72 (m, 1H), 3.25 (s, 3H), 3.08 (m, 2H), 2.93-2.75 (m, 4H), 2.70 (s, 3H0, 1.93 (m, 1H), 1.85-1.65 (m, 8H), 1.63-1.02 (m, 15H), 0.91 (m, 1H). |
| I-522B | (S)-3-((S)-1-(3-chloro-2-fluorophenyl)-5-methoxypentyl)-N-((S)-1-cyclohexyl-3-(methylamino)propan-2-yl)piperidine-1-carboxamide | 33 | 1.75 | 510 | 7.34 (t, J = 7.6 Hz, 1H), 7.20 (t, J = 7.6 Hz, 1H), 7.14 (t, J = 7.6 Hz, 1H), 4.02 (m, 1H), 3.79, m, 1H), 3.67 (m, 1H), 3.24 (s, 3H), 2.99 (ss, J = 12.8, 3.2 Hz, 1H), 2.84 (m, 2H), 2.74 (td, J = 12.8, 2.8 Hz, 1H), 2.51 (s, 3H), 2.48 (m, 2H), 2.12 (m, 1H), 1.87 (m, 1H), 1.75-1.66 (m, 8H), 1.59-1.38 (m, 3H), 1.32-1.20 (m, 5H), 1.13-1.08 (m, 2H), 0.98 (m, 1H), 0.85 (m, 1H). |
| I-523A | (3R)-3-((S)-1-(6-fluoro-3'-methylbiphenyl-2-yl)-1-hydroxy-5-methoxypentyl)-N-((S)-piperidin-3-yl)piperidine-1-carboxamide | 154 | 1.4 | 512 | 7.57 (d, J = 8.4 Hz, 1H), 7.36-7.20 (m, 3H), 7.04-7.02 (m, 2H), 6.92 (m, 1H), 4.03 (m, 1H), 3.85-3.75 (m, 2H), 3.39-3.32 (m, 3H), 3.29 (s, 3H), 2.86 (m, 1H), 2.71-2.56 (m, 3H), 2.37, 2.35 (two s, 3H, rotamer), 1.99 (m, 2H), 1.88-1.26 (m, 13H), 0.92 (m, 1H). |
| I-524A | (3R)-3-((R)-(3-chloro-2-fluorophenyl)(3-methoxypropoxy)methyl)-N-((S)-1-cyclohexyl-3-(methylamino)propan-2-yl)piperidine-1-carboxamide | 33 | 1.71 | 512 | 7.43 (t, 1H), 7.33 (t, 1H), 7.21 (t, 1H), 4.41 (d, 1H), 4.22 (d, 1H), 4.09 (m, 1H), 3.89 (d, 1H), 3.27 (s, 3H), 3.05 (dd, 1H), 2.69 (s, 3H), 1.02 (m, 1H), 0.88 (m, 1H). |
| I-525A | (3R)—N-(azetidin-3-ylmethyl)-3-((S)-1-(3-fluoro-2-(o-tolyloxy)phenyl)-1-hydroxy-5-methoxypentyl)piperidine-1-carboxamide | 155 | 1.45 | 514 | 2.38 (s), 2.40 (s), 3.18 (s), 3.26 (s), 3.8-4.1 (m), 6.38 (m), 6.42 (m), 6.9-7.3 (m), 7.52 (m) |
| I-526A | (3R)—N-((2S)-1-amino-3-(tetrahydro-2H-pyran-2-yl)propan-2-yl)-3-((S)-1- | 33 | 1.4 | 514 | 7.53 (m), 7.36 (m), 7.13 (m), 4.35 (m), 4.10 (br m), 3.95 (m), 3.45 (m), 3.24 (m). |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| | (3-chloro-2-fluorophenyl)-1-hydroxy-5-methoxypentyl)piperidine-1-carboxamide | | | | |
| I-527A | (3R)—N-((S)-2-amino-3-(3-methoxycyclobutyl)propyl)-3-((S)-1-(3-chloro-2-fluorophenyl)-1-hydroxy-5-methoxypentyl)piperidine-1-carboxamide | 127 | | 514 | 0.84 (m, 1H), 1.20 (m, 1H), 2.50 (m, 2H), 2.69 (m, 3H), 3.22 (s, 3H), 3.23 (s, 3H), 3.78 (m, 1H), 3.86 (m, 1H), 4.40 (m, 1H), 7.11 (m, 1H), 7.38 (m, 1H), 7.52 (m, 1H) |
| I-528A | (3R)—N-((S)-1-amino-3-(3-methoxycyclobutyl)propan-2-yl)-3-((S)-1-(3-chloro-2-fluorophenyl)-1-hydroxy-5-methoxypentyl)piperidine-1-carboxamide | 33 | | 514 | 0.83 (m, 1H), 1.20 (m, 1H), 1.45 (m, 3H), 1.95 (m, 3H), 2.15 (m, 1H), 2.43 (m, 2H), 2.64 (m, 2H), 2.80 (m, 2H), 3.04 (m, 1H), 3.22 (s, 3H), 3.26 (s, 3H), 3.77 (m, 1H), 3.95 (m, 2H), 4.35 (m, 1H), 7.13 (m, 1H), 7.36 (m, 1H), 7.53 (m, 1H) |
| I-531A | (3R)-3-((R)-(3-chlorophenyl)(2-propionamidoethoxy)methyl)-N-((S)-1-cyclohexyl-3-(methylamino)propan-2-yl)piperidine-1-carboxamide | 121 | | 521 | 0.98 (m, 2H), 1.12 (t, 3H), 2.21 (m, 2H), 2.71 (s, 3H), 3.87 (m, 1H), 4.04 (m, 1H), 4.15 (m, 2H), 7.20 (m, 1H), 7.34 (m, 3H) |
| I-533A | (3R)—N-((3RS,4RS)-4-cyclohexylpiperidin-3-yl)-3-((S)-1-(2,3-difluorophenyl)-1-hydroxy-5-methoxypentyl)piperidine-1-carboxamide | 158 | 1.49 | 522 | 7.36 (t, 1H), 7.19-7.10 (m, 2H), 4.40 (dd, 1H), 3.97 (m, 2H), 3.40 (t, 2H), 3.25 (s, 3H), 2.18 (q, 1H), 1.79 (m, 1H), 1.12 (m, 1H), 0.86 (m, 1H). |
| I-534A | (3R)-3-((1S)-1-(3-chlorophenyl)-1,6-dihydroxyheptyl)-N-((S)-1-cyclohexyl-3-(methylamino)propan-2-yl)piperidine-1-carboxamide | | 1.52 | 522, 524 | 7.37-7.36 (m, 1H), 7.26-7.14 (m, 3H), 4.23 (d, J = 13.5 Hz, 1H), 4.10-4.02 (m, 1H), 3.91 (d, J = 12.9 Hz, 1H), 3.60-3.55 (m, 1H), 3.00 (dd, J = 12.7, 3.4 Hz, 1H), 2.87 (dd, J = 12.6, 10.0 Hz, 1H), 2.64 (s, 3H), 2.52-2.44 (m, 2H), 1.03 (d, J = 6.15 Hz, 3H), 1.97-0.79 (m, 26H). |
| I-536A | (3R)—N-((2S)-1-cyclohexyl-3-(methylamino)propan-2-yl)-3-((R)-(2,3-difluorophenyl)(2-propionamidoethoxy)methyl)piperidine-1-carboxamide | 121 | | 523 | 0.90 (m, 1H), 1.03 (m, 1H), 1.12 (t, 3H), 1.51 (m, 1H), 2.21 (m, 2H), 2.71 (s, 3H), 2.95 (m, 2H), 3.10 (m, 2H), 3.79 (m, 1H), 4.10 (m, 2H), 4.46 (m, 1H0, 7.19 (m, 3H) |
| I-537A | (3R)-3-((S)-1-(3-chlorophenyl)-1-hydroxy-2-(2-methoxyacetamido)ethyl)-N-((S)-1-cyclohexyl-3-(methylamino)propan-2-yl)piperidine-1-carboxamide | 121 | | 523 | 1.00 (m, 2H), 2.60 (m, 2H), 2.71 (s, 3H), 2.95 (m, 1H), 3.08 (m, 1H), 3.24 (s, 3H), 4.15 (m, 1H), 7.31 (m, 3H), 7.50 (m, 1H) |
| I-541A | (3R)—N-((2S,3S)-3-amino-1-cyclohexylbutan-2-yl)-3-((S)-1-(3-chloro-2-fluorophenyl)-1-hydroxy-5-methoxypentyl)piperidine-1-carboxamide | 121 | | 526 | 0.86 (m, 2H), 1.28 (m, 3H), 2.00 (m, 2H), 2.18 (s, 2H), 2.65 (m, 1H), 2.72 (m, 1H), 3.29 (s, 3H), 3.82 (m, 1H), 3.98 (m, 1H), 4.36 (m, 1H), 7.13 (m, 1H), 7.38 (m, 1H), 7.53 (m, 1H) |
| I-544A | (3R)-3-((S)-1-(3-chloro-2-fluorophenyl)-1-hydroxy-5-methoxypentyl)-N-((3RS,4RS)-4-cyclohexylpiperidin-3-yl)piperidine-1-carboxamide | 157 | 1.58 | 538 | 7.48 (td, 1H), 7.32 (tt, 1H), 7.09 (td, 1H), 4.37 (dd, 1H), 3.69 (m, 1H), 3.21 (s, 3H), 2.15 (m, 1H), 0.98 (m, 1H), 0.79 (m, 1H). |
| I-545A | (3R)-3-((S)-1-(3-chlorophenyl)-1-hydroxy-5-methoxypentyl)-N-((S)-1-(cis-4-methoxycyclohexyl)-3-(methylamino)propan-2-yl)piperidine-1-carboxamide | 121 | | 538 | 1.02 (m, 1H), 2.50 (m, 2H), 2.69 (s, 3H), 2.94 (m, 1H), 3.07 (m, 1H), 3.27 (s, 3H), 3.44 (m, 1H), 3.95 (m, 1H), 4.10 (m, 1H), 4.28 (m, 1H), 7.27 (m, 3H), 7.43 (m, 1H) |
| I-545B | (3R)-3-((S)-1-(3-chlorophenyl)-1-hydroxy-5-methoxypentyl)-N-((S)-1-(cis-4-methoxycyclohexyl)-3-(methylamino)propan-2-yl)piperidine-1-carboxamide | 121 | | 538 | 2.09 (m, 3H), 2.52 (m, 3H), 2.70 (s, 3H), 3.10 (m, 2H), 3.27 (s, 3H), 3.96 (m, 1H), 4.10 (m, 2H), 4.27 (m, 1H), 7.26 (m, 3H), 7.44 (m, 1H) |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-546A | (3R)-3-((S)-4-acetamido-1-(3-chloro-2-fluorophenyl)-1-hydroxybutyl)-N-((2S,3R)-3-amino-1-cyclohexylbutan-2-yl)piperidine-1-carboxamide | 121 | | 539 | 0.95 (m, 4H), 1.23 (m, 3H), 1.60 (m, 3H), 1.85 (s, 3H), 1.99 (m, 3H), 2.64 (m, 1H), 2.72 (m, 1H), 3.08 (m, 2H), 4.05 (m, 2H), 4.36 (m, 1H), 7.13 (m, 1H), 7.36 (m, 1H), 7.53 (m, 1H) |
| I-546B | (3R)-3-((R)-4-acetamido-1-(3-chloro-2-fluorophenyl)-1-hydroxybutyl)-N-((2S,3R)-3-amino-1-cyclohexylbutan-2-yl)piperidine-1-carboxamide | 121 | | 539 | 0.95 (m, 4H), 1.22 (m, 3H), 1.88 (s, 3H), 1.99 (m, 2H), 2.19 (m, 1H), 3.10 (m, 2H), 7.14 (m, 1H), 7.36 (m, 1H), 7.52 (m, 1H) |
| I-547A | (3R)-3-((R)-(3-chloro-2-fluorophenyl)(2-propionamidoethoxy)methyl)-N-((2S)-1-cyclohexyl-3-(methylamino)propan-2-yl)piperidine-1-carboxamide | 121 | | 539 | 0.95 (m, 2H), 1.11 (t, 3H), 2.21 (m, 2H), 2.70 (s, 3H), 2.95 (m, 2H), 3.09 (m, 2H), 3.79 (m, 1H), 4.10 (m, 2H), 4.45 (m, 1H), 7.20 (m, 1H), 7.35 (m, 1H), 7.44 (m, 1H) |
| I-548A | (3R)-3-((S)-1-(2,3-difluorophenyl)-1-hydroxy-5-methoxypentyl)-N-((S)-1-(cis-4-methoxycyclohexyl)-3-(methylamino)propan-2-yl)piperidine-1-carboxamide | 121 | | 540 | 0.88 (m, 2H), 1.86 (m, 2H), 1.97 (m, 2H), 2.14 (m, 2H), 2.69 (s, 3H), 2.70 (m, 1H), 2.80 (m, 1H), 3.07 (m, 1H), 3.26 (s, 3H), 3.64 (s, 3H), 3.96 (m, 1H), 4.13 (m, 1H), 4.34 (m, 1H), 7.15 (m, 2H), 7.36 (m, 1H) |
| I-549A | (3R)-3-((S)-1-(3-chloro-2-fluorophenyl)-1-hydroxy-5-methoxypentyl)-N-((3RS,4RS)-4-(pentan-3-yloxy)piperidin-3-yl)piperidine-1-carboxamide | 158 | 1.55 | 542 | 7.52 (t, 1H), 7.37 (t, 1H), 7.13 (t, 1H), 4.43 (t, 1H), 3.89 (m, 2H), 3.62 (m, 1H), 3.29 (s, 3H), 3.02 (t, 2H), 2.68 (m, 2H), 1.97 (m, 2H), 0.82 (m, 1H). |
| I-551A | (3R)—N-((1S,2R)-3-amino-1-(trans-4-fluorocyclohexyl)-1-hydroxypropan-2-yl)-3-((S)-1-(3-chloro-2-fluorophenyl)-1-hydroxy-5-methoxypentyl)piperidine-1-carboxamide | 117 | 1.35 | 546 | 7.53 (1H), 7.37 (1H), 7.14 (1H), 4.36 (1H), 4.10 (1H), 3.94 (1H), 3.25 (3H). 19F:−116 (1F), −171 (1F) |
| I-552A | (3R)-3-((S)-1-(3-chlorophenyl)-1-hydroxy-5-methoxypentyl)-N-((2S)-1-(3-noradamantyl)-3-(methylamino)propan-2-yl)piperidine-1-carboxamide | 164 | 1.69 | 546 | 7.24 (2H), 7.30 (1H), 7.42 (1H), 2.68 (3H) |
| I-553A | (3R)-3-((S)-1-acetamido-5-ethoxy-1-(3-fluorophenyl)pentyl)-N-((S)-1-cyclohexyl-3-(methylamino)propan-2-yl)piperidine-1-carboxamide | 133 | | 547 | 0.85 (m, 2H), 1.11 (m, 1H), 1.16 (t, 3H), 1.83 (m, 1H), 1.90 (m, 1H), 2.07 (s, 3H), 2.18 (m, 1H), 2.35 (m, 4H), 2.71 (s, 3H), 2.98 (m, 1H), 3.05 (m, 1H), 3.45 (m, 4H), 3.88 (m, 1H), 4.10 (m, 1H), 4.19 (m, 1H), 7.01 (m, 2H), 7.14 (m, 1H), 7.34 (m, 1H) |
| I-554A | (R)-3-((S)-1-(3-chloro-2-fluorophenyl)-1-hydroxy-5-methoxypenty)-N-((S)-1-((1r,3R,4S)-3,4-difluorocyclopentyl)-3-(methylamino)propan-2-yl)piperidine-1-carboxamide | 165 | 1.42 | 547 | 753 (1H), 7.37 (1H), 7.14 (1H), 4.88 (1H), 4.35 (1H), 4.07 (1H), 3.95 (1H) 2.74 (3H) 19F:−117 (1F), −198 (2F) |
| I-556A | (3R)-3-((S)-1-(3-chloro-2-fluorophenyl)-1-hydroxy-5-methoxypentyl)-N-((S)-1-(cis-4-methoxycyclohexyl)-3-(methylamino)propan-2-yl)piperidine-1-carboxamide | 121 | | 556 | 0.83 (m, 1H), 1.18 (m, 1H), 1.87 (m, 2H), 1.98 (m, 2H), 2.15 (m, 1H), 2.71 (s, 3H), 2.72 (m, 1H), 2.94 (m, 1H), 3.07 (m, 1H), 3.25 (s, 3H), 3.45 (m, 1H), 3.97 (m, 1H), 4.13 (m, 1H), 4.33 (m, 1H), 7.13 (m, 1H), 7.36 (m, 1H), 7.53 (m, 1H) |
| I-556B | (3R)-3-((S)-1-(3-chloro-2-fluorophenyl)-1-hydroxy-5-methoxypentyl)-N-((S)-1-(trans-4-methoxycyclohexyl)-3-(methylamino)propan-2-yl)piperidine-1-carboxamide | 121 | | 556 | 0.83 (m, 1H), 1.46 (m, 5H), 1.51 (m, 4H), 1.79 (m, 1H), 1.90 (m, 1H), 1.99 (m, 2H), 271 (s, 3H), 2.68 (m, 1H), 2.95 (m, 1H), 3.06 (m, 1H), 3.15 (m, 1H), 3.25 (s, 3H), 3.98 (m, 1H), 4.13 (m, 1H), 3.35 (m, 1H), 7.13 (m, 1H), 7.36 (m, 1H), 7.53 (m, 1H) |
| I-558A | (3R)-3-((S)-1-acetamido-1-(3-chlorophenyl)-5-ethoxypentyl)-N-((S)-1-cyclohexyl-3-(methylamino)propan-2-yl)piperidine-1-carboxamide | 133 | | 563 | 0.90 (m, 4H), 1.16 (t, 3H), 1.30 (m, 7H), 1.55 (m, 9H), 2.07 (s, 3H), 2.15 (m, 1H), 2.71 (m, 3H), 3.00 (m, 2H), 3.45 (m, 3H), 3.89 (m, 1H), 4.09 (m, 1H), 4.19 (m, 1H), 7.26 (m, 2H), 7.32 (m, 2H) |

-continued

Table of Compounds

| Cpd. No. | Cpd. Name | Method of Synthesis Example No. | LC-MS (3 min) tR (min) | Mass observed | Selected 1H NMR[a] |
|---|---|---|---|---|---|
| I-559A | (3R)—N-((2R,3S)-2-amino-3-(3-noradamantyl)-3-hydroxypropyl)-3-((S)-1-(3-chloro-2-fluorophenyl)-1-hydroxy-5-methoxypentyl)piperidine-1-carboxamide | 165 | 1.57 | 566 | 7.53 (t, 1H), 7.36 (t, 1H), 7.13 (t, 1H), 4.43 (d, 1H), 3.87 (d, 1H), 3.83 (s, 1H), 3.63 (d, 1H), 3.24 (s, 3H), 2.68 (t, 2H), 1.21 (br s, 1H), 0.83 (m, 1H). |

Footnotes

[a] 1H NMR spectra were acquired in MeOH-$d_4$ unless otherwise noted.
[b] 1H NMR spectrum acquired in CDCl$_3$.
[c] Prepared from the less polar diastereomer of tert-butyl 2-((3-methoxypropoxy)(phenyl)methyl)-morpholine-4-carboxylate.
[d] Mixture of 4 diastereomers all with cis relative stereochemistry around cyclohexane ring.
[e] Mixture of 2 isomers of 3-((S)-1-amino-3-cyclohexylpropan-2-ylamino)-4-(3-((3-methoxypropoxy)(phenyl)methyl)piperidin-1-yl)cyclobut-3-ene-1,2-dione separated by prep HPLC. The stereochemical configurations of the chiral centers on the piperidine ring and at the ether bearing carbon of the other isomer present are unknown.
[f] Mixture of 2 isomers of 3-((S)-1-amino-3-cyclohexylpropan-2-ylamino)-4-(3-((3-methoxypropoxy)(phenyl)methyl)piperidin-1-yl)cyclobut-3-ene-1,2-dione separated by prep HPLC. The stereochemical configurations of the chiral centers on the piperidine ring and at the ether bearing carbon are unknown.
[g] Mixture of 2 isomers prepared from less polar fraction of 2-(trimethylsilyl)ethyl (S)-2-(2-(3-((3-methoxypropoxy)(phenyl)methyl)piperidin-1-yl)-3,4-dioxocyclobut-1-enylamino)-3-cyclohexylpropylcarbamate separated by preparative chiral chromatography. One of the isomers present has the following configuration: 3-((S)-1-amino-3-cyclohexylpropan-2-ylamino)-4-((R)-3-((R)-(3-methoxypropoxy)(phenyl)methyl)piperidin-1-yl)cyclobut-3-ene-1,2-dione.
[h] Stereoisomers were separated by preparative HPLC on a chiral column

What is claimed is:

1. A compound of Formula I

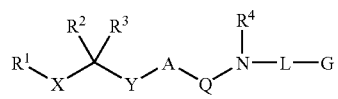

I wherein $R^1$ is a) cyclohexyl or trifluoromethyl; or b) phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl optionally substituted with 1 to 3 substituents independently selected from:

fluorine, chlorine, bromine, cyano, methyl, ethyl, isopropyl, t-butyl, isobutyl, trifluoromethyl, allyl, cyclohexyl, cyclohexen-1-yl, cyclopropylethylynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, hydroxyl aminocarbonyl, methoxycarbonyl, phenyl, phenoxy, benzyloxy, and heteroaryloxy, wherein the phenyl, phenoxy, benzyloxy and heteroaryloxy groups are optionally substituted with 1 to 3 substituents independently selected from fluorine, chlorine, cyano, methyl, ethyl, trifluoromethyl, and aminocarbonyl;

X and Y is each a single bond;

$R^2$ is methyl, ethyl, propyl, butyl, pentyl, hexyl, 5-pentenyloxy, 3,3,3-trifluoropropyl, 4,4-difluoropentyl, 3-(cyclopropyl)propyl, 4-(cyclopropyl)butyl, 3-hydroxypropyl, 4-hydroxybutyl, 4-hydroxypentyl, 4-hydroxyhexyl, 5-hydroxyhexyl, 2-hydroxyethoxy, 3-methoxypropyl, 3-ethoxypropyl, 4-methoxybutyl, 4-ethoxybutyl, 2-(ethoxy)ethoxy, 3-methoxypropoxy, 3-ethoxypropoxy, 3-propoxypropoxy, 2-cyclopropylethoxy, (2-(methoxy)ethoxy)methyl, 3-(acetylamino)propyl, 3-(propionylamino)propyl, 3-(butanoylamino)propyl, 3((2-methoxypropionyl)amino)propyl, 3-(cyclopropanecarbonylamino)propyl, 3-(trifluoroacetylamino)propyl, 3-(methylaminocarbonylamino)propyl, 3-(dimethylaminocarbonylamino)propyl, 2-(acetylamino)ethoxy, 2-(propionylamino)ethoxy, methoxymethylcarbonylaminomethyl, 3-(aminosulfonylamino)propyl or 3-methanesulfonylamino)propyl;

$R^3$ is H, F, OH, methoxy, ethoxy, 3-hydroxypropoxy, acetylamino, propionylamino, (2-methylpropionyl)amino or butanoylamino, provided that when $R^3$ is F or OH, $R^2$ is not 2-(ethoxy)ethoxy, 3-methoxypropoxy, 3-ethoxypropoxy, 3-propoxypropoxy, 2-cyclopropylethoxy, 2-(acetylamino)ethoxy or 2-(propionylamino)ethoxy;

A is 2,4-disubstituted morpholine with $R^1XCR^2R^3Y$ attached at the 2-position and Q attached at the 4-position, 1,3-disubstituted piperidine with $R^1XCR^2R^3Y$ attached at the 3-position and Q attached at the 1-position, or 1,3-disubstituted-3-methylpiperidine with $R^1XCR^2R^3Y$ attached at the 3-position and Q attached at the 1-position;

Q is Q1, Q2, Q4, Q5, Q9, or Q10

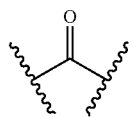

Q1

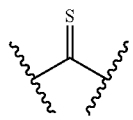

Q2

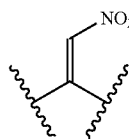

Q4

-continued

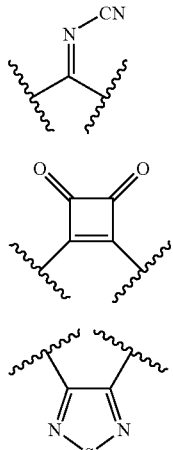

wherein A and N are attached to the truncated bonds

R⁴ is H or methyl;
L is a C₂ alkyl chain in which one hydrogen atom is optionally replaced with a group selected from R⁵;
L is optionally substituted with R⁶,
R⁶ is methyl or hydroxymethyl;
R⁵ is methyl, isobutyl, t-butylmethyl, 2,2,2-trifluoroethyl, 2-(trifluoromethyl)propyl, cyclopropylmethyl, cyclopentylmethyl, cyclohexylmethyl, 2-(cyclohexyl)ethyl, (3-noradamantyl)methyl, (3,3-difluorocyclobutyl)methyl, (3,4-difluorocyclopentyl)methyl, 4,4-difluorocyclohexylmethyl, (4-methylcyclohexyl)methyl, tert-butoxymethyl, (2-tetrahydrofuranyl)methyl, (2-tetrahydropyranyl)methyl, (4-tetrahydropyranyl)methyl, (3-methoxycyclobutyl)methyl, (4-methoxycyclohexyl)methyl, benzyl, phenethyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (4-fluorocyclohexyl)(hydroxy)methyl, (cycloheptyl)(hydroxy)methyl, (1-hydroxycyclohexyl)methyl, (4-hydroxycyclohexyl)methyl, (4-hydroxy-4-methylcyclohexyl)methyl, (3-noradamantyl)(hydroxy)methyl, 2-methoxy-2-methylpropyl or 2,2-dimethyl-3-methoxypropyl;
G is NH₂, NHR⁹, or NR⁹R¹⁰;
R⁹ is methyl, ethyl, propyl, butyl, isobutyl, pentyl, isopentyl, aminocarbonylmethyl; or R⁹ together with R⁵ is —(CH₂)₃—, —(CH₂)₄—, —(CH₂)₂CH(c-hex)-, or —(CH₂)₂CH(OCH(C₂H₅)₂)—;
R¹⁰ is methyl;
provided that when R² is methyl, ethyl, propyl, butyl, pentyl or hexyl and R³ is OH, R⁶ is absent;
or an enantiomer, diastereomer or pharmaceutically acceptable salt thereof.

2. A compound of claim 1 of Formula IIa

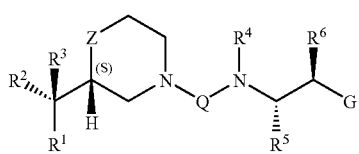

wherein
Z is CH₂ or O;
R¹ is a) cyclohexyl or trifluoromethyl; or b) phenyl 2-thienyl, 3-thienyl, 2-pyridyl, 2-imidazolyl, or 2-thiazolyl, optionally substituted with 1 to 3 substituents independently selected from: fluorine, chlorine, bromine, cyano, methyl, ethyl, isopropyl, trifluoromethyl, allyl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and 3-pyridyloxy, wherein the phenyl and phenoxy, benzyloxy and pyridyloxy groups are optionally substituted with 1 to 3 substituents independently selected from fluorine, chlorine, cyano, methyl, ethyl, and trifluoromethyl; or c) 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl, optionally substituted with 1 to 3 substituents independently selected from fluorine, methyl, isobutyl, and t-butyl;
R² is methyl, ethyl, propyl, butyl, hexyl, 3,3,3-trifluoropropyl, 4,4-difluoropentyl, 3-(cyclopropyl)propyl, 4-(cyclopropyl)butyl, 3-hydroxypropyl, 4-hydroxybutyl, 4-hydroxypentyl, 4-hydroxyhexyl, 5-hydroxyhexyl, 2-hydroxyethoxy, 3-ethoxypropyl, 4-methoxybutyl, 4-ethoxybutyl, 2-(ethoxy)-ethoxy, 3-methoxypropoxy, 3-propoxypropoxy, 2-cyclopropylethoxy, (2-(methoxy)ethoxy)methyl, 3-(acetylamino)propyl, 3-(propionylamino)propyl, 3-(butanoylamino)propyl, 3-((2-methoxypropionyl)amino)propyl, 3(cyclopropanecarbonylamino)propyl, 3-(trifluoroacetylamino)propyl, 3-(methylaminocarbonylamino)propyl, 3-(dimethylaminocarbonylamino)propyl, methoxymethylcarbonylaminomethyl, or 3-(aminosulfonylamino)propyl;
R³ is H, F, OH, methoxy, 3-hydroxypropoxy, acetylamino, propionylamino, (2-methylpropionyl)amino, or butanoylamino;
provided that when R³ is F or OH, R² is not 3-methoxypropoxy, 3-ethoxypropoxy, 3-propoxypropoxy, or 2-cyclopropylethoxy;
R⁵ is methyl, isobutyl, t-butylmethyl, 2,2,2-trifluoroethyl, 2-(trifluoromethyl)propyl, cyclopropylmethyl, cyclopentylmethyl, cyclohexylmethyl, 2-(cyclohexyl)ethyl, (3-noradamantyl)methyl, (3,3-difluorocyclobutyl)methyl, (3,4-difluorocyclopentyl)methyl, (4,4-difluorocyclohexyl)methyl, (4-methylcyclohexyl)methyl, tert-butoxymethyl, (2-tetrahydrofuranyl)methyl, (2-tetrahydropyranyl)methyl, (4-tetrahydro-pyranyl)methyl, (3-methoxycyclobutyl)methyl, (4-methoxycyclohexyl)methyl, benzyl, phenethyl, (1-fluorocyclohexyl)methyl, (4-fluorocyclohexyl)methyl, 1-hydroxy-2-methylpropyl, (cyclopentyl)(hydroxy)methyl, (cyclohexyl)(hydroxy)methyl, (4-fluorocyclohexyl)(hydroxy)methyl, (cycloheptyl)(hydroxy)methyl, (1-hydroxycyclohexyl)methyl, (4-hydroxycyclohexyl)methyl, (3-noradamantyl)(hydroxy)methyl, or 2-methoxy-2-methylpropyl;
or a pharmaceutically acceptable salt thereof.

3. A compound of claim 1 selected from the group consisting of:
I-1 N-(1-amino-3-cyclohexylpropan-2-yl)-3-(1-hydroxy-1-phenylpentyl)piperidine-1-carboxamide I-3 3-((2-cyclopropylethoxy)(phenyl)methyl)-N-(1-amino-3-cyclohexylpropan-2-yl)piperidine-1-carboxamide I-4 N-(1-amino-3-cyclohexylpropan-2-yl)-3-(5-methoxy-1-phenylpentyl)piperidine-1-carboxamide I-5 3-((3-methoxypropoxy)(phenyl)methyl)-N-(1-amino-3-cyclohexylpropan-2-yl)piperidine-1-carboxamide I-6 3-((3-methoxypropoxy)(phenyl)methyl)-N-(2-amino-3-cyclohexylpropyl)piperidine-1-carboxamide I-7 N-(1-amino-3-cyclopentylpropan-2-yl)-3-(1-hydroxy-5-methoxy-1-phenylpentyl)piperidine-1-carboxamide I-8 2-((3-methoxypropoxy)(phenyl)methyl)-N-(1-amino-3-cyclohexylpropan-2-yl)morpholine-4-carboxamide I-9 N-(3-tert-butoxy-1-aminopropan-2-yl)-3-(1-hydroxy-5-methoxy-1-phenylpentyl)piperidine-1-carboxamide I-10 3-(1-(3-fluorophenyl)-1-hydroxy-5-methoxypentyl)-N-(4-methyl-1-(methylamino)pentan-2-yl)piperidine-1-carboxamide I-12 N-(1-amino-3-phenylpropan-2-yl)-3-(1-hydroxy-5-methoxy-1-phenylpentyl)piperidine-1-carboxamide I-13 N-(1-amino-3-cyclohexylpropan-2-yl)-3-(1-hydroxy-1-phenylheptyl)piperidine-1-carboxamide I-14 N-(3-cyclohexyl-1-(methylamino)propan-2-yl)-3-(5-methoxy-1-phenylpentyl)piperidine-1-carboxamide I-15 N-(1-amino-3-cyclohexylpropan-2-yl)-3-(5-ethoxy-1-phenylpentyl)piperidine-1-carboxamide I-16 3-((3-methoxypropoxy)(phenyl)methyl)-N-(3-cyclohexyl-1-(methylamino)propan-2-yl)piperidine-1-carboxamide I-17 3-((3-ethoxypropoxy)(phenyl)methyl)-N-(1-amino-3-cyclohexylpropan-2-yl)piperidine-1-carboxamide I-19 N-(1-amino-3-cyclohexylpropan-2-yl)-3-(1-hydroxy-5-methoxy-1-phenylpentyl)piperidine-1-carboxamide I-21 N-(3-cyclohexyl-1-(methylamino)propan-2-yl)-3-(1-hydroxy-4-methoxy-1-phenylbutyl)piperidine-1-carboxamide I-22 3-((3-methoxypropoxy)(4-fluorophenyl)methyl)-N-(1-amino-3-cyclohexylpropan-2-yl)piperidine-1-carboxamide I-23 3-((3-methoxypropoxy)(2-fluorophenyl)methyl)-N-(1-amino-3-cyclohexylpropan-2-yl)piperidine-1-carboxamide I-24 N-(3-cyclohexyl-1-(methylamino)propan-2-yl)-3-(1-cyclohexyl-5-methoxypentyl)piperidine-1-carboxamide I-25 N-(3-cyclohexyl-1-(methylamino)propan-2-yl)-3-(4-cyclopropyl-1-hydroxy-1-phenylbutyl)piperidine-1-carboxamide I-26 3-((3-methoxypropoxy)(3-cyanophenyl)methyl)-N-(1-amino-3-cyclohexylpropan-2-yl)piperidine-1-carboxamide I-27 N-(3-cyclohexyl-1-(methylamino)propan-2-yl)-3-(5-ethoxy-1-phenylpentyl)piperidine-1-carboxamide I-28 N-(3-cyclohexyl-1-(methylamino)propan-2-yl)-3-(1-hydroxy-5-methoxy-1-phenylpentyl)cyclohexanecarboxamide I-29 N-(1-amino-4-(trifluoromethyl)pentan-2-yl)-3-(1-hydroxy-5-methoxy-1-phenylpentyl)piperidine-1-carboxamide I-30 3-((3-methoxypropoxy)(phenyl)methyl)-N-(3-cyclohexyl-1-(ethylamino)propan-2-yl)piperidine-1-carboxamide I-31 N-(1-cyclohexyl-3-(methylamino)propan-2-yl)-3-((3-ethoxypropoxy)(phenyl)methyl)piperidine-1-carboxamide I-32 N-(1-amino-3-cyclohexylpropan-2-yl)-3-(5-ethoxy-1-hydroxy-1-phenylpentyl)piperidine-1-carboxamide I-33 N-(3-cyclohexyl-1-(methylamino)propan-2-yl)-3-(1-hydroxy-5-methoxy-1-phenylpentyl)piperidine-1-carboxamide I-34 3-((3-ethoxypropoxy)(phenyl)methyl)-N-(1-amino-3-cyclohexylpropan-2-yl)-3-methylpiperidine-1-carboxamide I-36 N-(2-amino-5-methoxy-4,4-dimethylpentyl)-3-(1-(3-chlorophenyl)-1-hydroxy-5-methoxypentyl)piperidine-1-carboxamide I-37 N-(3-cyclohexyl-1-(methylamino)propan-2-yl)-3-(1-(3-fluorophenyl)-5-methoxypentyl)piperidine-1-carboxamide I-38 N-(1-cyclohexyl-3-(methylamino)propan-2-yl)-3-(1-fluoro-5-methoxy-1-phenylpentyl)piperidine-1-carboxamide I-39 3-((3-methoxypropoxy)(3-fluorophenyl)methyl)-N-(3-cyclohexyl-1-(methylamino)propan-2-yl)piperidine-1-carboxamide I-40 N-(1-amino-3-cyclohexylpropan-2-yl)-3-(1-(3-fluorophenyl)-1-hydroxy-5-methoxypentyl)piperidine-1-carboxamide I-41 N-(3-cyclohexyl-1-(methylamino)propan-2-yl)-3-(1-cyclohexyl-1-hydroxy-5-methoxypentyl)piperidine-1-carboxamide I-42 3-((3-methoxypropoxy)(2,4-difluorophenyl)methyl)-N-(1-amino-3-cyclohexylpropan-2-yl)piperidine-1-carboxamide I-43 3-((3-methoxypropoxy)(3,4-difluorophenyl)methyl)-N-(1-amino-3-cyclohexylpropan-2-yl)piperidine-1-carboxamide I-44 3-(1-hydroxy-5-methoxy-1-(2-phenoxyphenyl)pentyl)-N-(1-(methylamino)propan-2-yl)piperidine-1-carboxamide I-45 3-((3-methoxypropoxy)(3-cyanophenyl)methyl)-N-(3-cyclohexyl-1-(methylamino)propan-2-yl)piperidine-1-carboxamide I-46 3-((3-methoxypropoxy)(2-allylphenyl)methyl)-N-(1-amino-3-cyclohexylpropan-2-yl)piperidine-1-carboxamide I-47 3-((3-methoxypropoxy)(phenyl)methyl)-N-(3-cyclohexyl-1-(propylamino)propan-2-yl)piperidine-1-carboxamide I-48 N-(3-cyclohexyl-1-(methylamino)propan-2-yl)-3-(5-ethoxy-1-hydroxy-1-phenylpentyl)piperidine-1-carboxamide I-49 3-((3-propoxypropoxy)(phenyl)methyl)-N-(3-cyclohexyl-1-(methylamino)propan-2-yl)piperidine-1-carboxamide I-50 N-(3-cyclohexyl-1-(methylamino)propan-2-yl)-3-(1-hydroxy-5-methoxy-1-m-tolylpentyl)piperidine-1-carboxamide I-51 N-(1-amino-5-methoxy-4,4-dimethylpentan-2-yl)-3-(1-(3-chlorophenyl)-1-hydroxy-5-methoxypentyl)piperidine-1-carboxamide I-52 N2-((Z)-1-(3-((3-methoxypropoxy)(phenyl)methyl)piperidin-1-yl)-2-nitrovinyl)-3-cyclohexylpropane-1,2-diamine I-53 N-(3-cyclohexyl-1-(methylamino)propan-2-yl)-3-(1-(3-fluorophenyl)-1-hydroxy-5-methoxypentyl)piperidine-1-carboxamide I-54 N-(2-amino-5-methoxy-4,4-dimethylpentyl)-3-(1-(2,3-difluorophenyl)-1-hydroxy-5-methoxypentyl)piperidine-1-carboxamide I-55 3-(1-amino-3-cyclohexylpropan-2-ylamino)-4-(3-((2-cyclopropylethoxy)(phenyl)methyl)piperidin-1-yl)cyclobut-3-ene-1,2-dione I-56 3-(1-hydroxy-5-methoxy-1-(2-phenoxyphenyl)pentyl)-N-(piperidin-3-yl)piperidine-1-carboxamide I-57 N-(3-cyclohexyl-1-(methylamino)propan-2-yl)-3-(4,4,4-trifluoro-1-hydroxy-1-m-tolylbutyl)piperidine-1-carboxamide I-58 3-(1-amino-3-cyclohexylpropan-2-ylamino)-4-(3-((3-methoxypropoxy)(phenyl)methyl)piperidin-1-yl)cyclobut-3-ene-1,2-dione I-59 3-(1-amino-3-cyclohexylpropan-2-ylamino)-4-(2-((3-methoxypropoxy)(phenyl)methyl)morpholino)cyclobut-3-ene-1,2-dione I-60 4-(3-((3-methoxypropoxy)(phenyl)methyl)piperidin-1-yl)-N-(1-amino-3-cyclohexylpropan-2-yl)-1,2,5-thiadiazol-3-amine I-61 3-((3-methoxypropoxy)(phenyl)methyl)-N-(1-(butylamino)-3-cyclohexylpropan-2-yl)piperidine-1-carboxamide I-62 3-((3-methoxypropoxy)(phenyl)methyl)-N-(3-cyclohexyl-1-(isobutylamino)propan-2-yl)piperidine-1-carboxamide I-63 N-(3-cyclohexyl-1-(dimethylamino)propan-2-yl)-3-(5-ethoxy-1-hydroxy-1-phenylpentyl)piperidine-1-carboxamide I-64 3-(1-(3-chlorophenyl)-1-hydroxy-5-methoxypentyl)-N-(3-cyclohexyl-1-(methylamino)propan-2-yl)piperidine-1-carboxamide I-65 3-((3-ethoxypropoxy)(3,4-difluorophenyl)methyl)-N-(3-cyclohexyl-1-(methylamino)propan-2-yl)piperidine-1-carboxamide I-66 N-(3-cyclohexyl-1-(methylamino)propan-2-yl)-3-(1-(2,5-difluorophenyl)-1-hydroxy-5-methoxypentyl)piperidine-1-carboxamide I-67 N-(3-(4,4-difluorocyclohexyl)-1-(methylamino)propan-2-yl)-3-(1-hydroxy-5-methoxy-1-phenylpentyl)piperidine-1-carboxamide I-68 N-(3-cyclohexyl-1-(methylamino)propan-2-yl)-3-(1-(3,4-difluorophenyl)-1-hydroxy-5-methoxypentyl)piperidine-1-carboxamide I-69 3-(1-amino-3-cyclohexylpropan-2-ylamino)-4-(3-(1-hydroxy-1-phenylheptyl)piperidin-1-yl)cyclobut-3-ene-1,2-dione I-70 3-(3-amino-1-cyclohexylbutan-2-ylamino)-4-(3-((3-methoxypropoxy)(phenyl)methyl)piperidin-1-yl)cyclobut-3-ene-1,2-dione I-71 3-(3-cyclohexyl-1-(methylamino)propan-2-ylamino)-4-(3-((3-methoxypropoxy)(phenyl)methyl)piperidin-1-yl)cyclobut-3-ene-1,2-dione I-72 3-(1-(2-(p-tolyloxy)-5-methylphenyl)-1-hydroxy-5-methoxypentyl)-N-(1-(methylamino)propan-2-yl)piperidine-1-carboxamide I-73 3-(3-((3-methoxypropoxy)(phenyl)methyl)piperidin-1-yl)-4-(N-(1-amino-3-cyclohexylpropan-2-yl)-N-methylamino)cyclobut-3-ene-1,2-dione I-74 3-((3-methoxypropoxy)(2-(trifluoromethyl)phenyl)methyl)-N-(1-amino-3-cyclohexylpropan-2-yl)piperidine-1-carboxamide I-75 3-(1-amino-3-cyclohexylpropan-2-ylamino)-4-(3-((3-methoxypropoxy)(4-fluorophenyl)methyl)piperidin-1-yl)cyclobut-3-ene-1,2-dione I-76 3-(1-amino-3-cyclohexylpropan-2-ylamino)-4-(3-((3-methoxypropoxy)(2-fluorophenyl)methyl)piperidin-1-yl)cyclobut-3-ene-1,2-dione I-77 3-((3-methoxypropoxy)(phenyl)methyl)-N-(3-cyclohexyl-1-(isopentylamino)propan-2-yl)piperidine-1-carboxamide I-78 3-((3-methoxypropoxy)(phenyl)methyl)-N-(3-cyclohexyl-1-(pentylamino)propan-2-yl)piperidine-1-carboxamide I-79 N-(3-cyclohexyl-1-(methylamino)propan-2-yl)-3-(1-hydroxy-1-(3-isopropylphenyl)-5-methoxypentyl)piperidine-1-carboxamide I-80 3-(1-(3-chlorophenyl)-4,4,4-trifluoro-1-hydroxybutyl)-N-(3-cyclohexyl-1-(methylamino)propan-2-yl)piperidine-1-carboxamide I-81 3-(1-(5-chloro-2-phenoxyphenyl)-1-hydroxy-5-methoxypentyl)-N-(1-(methylamino)propan-2-yl)piperidine-1-carboxamide I-82 3-(1-(3-chlorophenyl)-5-cyclopropyl-1-hydroxypentyl)-N-(3-cyclohexyl-1-(methylamino)propan-2-yl)piperidine-1-carboxamide I-83 3-((3-methoxypropoxy)(2-phenylphenyl)methyl)-N-(2-amino-3-cyclohexylpropyl)piperidine-1-carboxamide I-84 3-((3-methoxypropoxy)(2-(2-cyclopropylethynyl)phenyl)methyl)-N-(3-cyclohexyl-1-(methylamino)propan-2-yl)piperidine-1-carboxamide I-85 3-(3-cyclohexyl-1-(ethylamino)propan-2-ylamino)-4-(3-((3-methoxypropoxy)(phenyl)methyl)piperidin-1-yl)cyclobut-3-ene-1,2-dione I-86 3-(1-hydroxy-5-methoxy-1-(2-phenoxyphenyl)pentyl)-N-(4-methyl-1-(methylamino)pentan-2-yl)piperidine-1-carboxamide I-87 N-(1-amino-5-methoxy-4,4-dimethylpentan-2-yl)-3-(1-(2,3-difluorophenyl)-1-hydroxy-5-methoxypentyl)piperidine-1-carboxamide I-88 N-(3-(4,4-difluorocyclohexyl)-1-(methylamino)propan-2-yl)-3-(1-(3-fluorophenyl)-1-hydroxy-5-methoxypentyl)piperidine-1-carboxamide I-89 3-(1-amino-3-cyclohexylpropan-2-ylamino)-4-(3-((3-methoxypropoxy)(2,4-difluorophenyl)methyl)piperidin-1-yl)cyclobut-3-ene-1,2-dione I-90 3-(1-amino-3-cyclohexylpropan-2-ylamino)-4-(3-((3-methoxypropoxy)(3,4-difluorophenyl)methyl)piperidin-1-yl)cyclobut-3-ene-1,2-dione I-91 N-(1-(carbamoylmethylamino)-3-cyclohexylpropan-2-yl)-3-(1-(3-fluorophenyl)-1-hydroxy-5-methoxypentyl)piperidine-1-carboxamide I-92 3-(3-cyclohexyl-1-(propylamino)propan-2-ylamino)-4-(3-((3-methoxypropoxy)(phenyl)methyl)piperidin-1-yl)cyclobut-3-ene-1,2-dione I-93 N-(3-cyclohexyl-1-(methylamino)propan-2-yl)-3-(1-(3-(trifluoromethyl)phenyl)-1-hydroxy-5-methoxypentyl)piperidine-1-carboxamide I-94 3-(3-cyclohexyl-1-(isobutylamino)propan-2-ylamino)-4-(3-((3-methoxypropoxy)(phenyl)methyl)piperidin-1-yl)cyclobut-3-ene-1,2-dione I-95 3-(3-(butylamino)-1-cyclohexylpropan-2-ylamino)-4-(3-((3-methoxypropoxy)(phenyl)methyl)piperidin-1-yl)cyclobut-3-ene-1,2-dione I-96 3-(1-(2-(p-tolyloxy)-5-methylphenyl)-1-hydroxy-5-methoxypentyl)-N-(4-methyl-1-(methylamino)pentan-2-yl)piperidine-1-carboxamide I-97 3-(1-(5-chloro-2-phenoxyphenyl)-1-hydroxy-5-methoxypentyl)-N-(4-methyl-1-(methylamino)pentan-2-yl)piperidine-1-carboxamide I-98 3-(3-cyclohexyl-1-(methylamino)propan-2-ylamino)-4-(3-((3-ethoxypropoxy)(3,4-difluorophenyl)methyl)piperidin-1-yl)cyclobut-3-ene-1,2-dione I-99 3-(1-amino-3-cyclohexylpropan-2-ylamino)-4-(3-((3-methoxypropoxy)(2-(trifluoromethyl)phenyl)methyl)piperidin-1-yl)cyclobut-3-ene-1,2-dione I-100 N-(3-cyclohexyl-1-(methylamino)propan-2-yl)-3-(1-hydroxy-5-methoxy-1-(2-phenoxyphenyl)pentyl)piperidine-1-carboxamide I-101 3-(1-cyclohexyl-3-(pentylamino)propan-2-ylamino)-4-(3-((3-methoxypropoxy)(phenyl)methyl)piperidin-1-yl)cyclobut-3-ene-1,2-dione I-102 3-(1-cyclohexyl-3-(isopentylamino)propan-2-ylamino)-4-(3-((3-methoxypropoxy)(phenyl)methyl)piperidin-1-yl)cyclobut-3-ene-1,2-dione I-103 3-(1-(2-(p-tolyloxy)-5-methylphenyl)-1-hydroxy-5-methoxypentyl)-N-(3-cyclohexyl-1-(methylamino)propan-2-yl)piperidine-1-carboxamide I-104 3-(1-(5-chloro-2-phenoxyphenyl)-1-hydroxy-5-methoxypentyl)-N-(3-cyclohexyl-1-(methylamino)propan-2-yl)piperidine-1-carboxamide I-108 3-(1-(2-(cyclopropylmethoxy)phenyl)-1-hydroxy-5-methoxypentyl)-N-(1-(methylamino)propan-2-yl)piperidine-1-carboxamide I-109 3-((S)-1-hydroxy-5-methoxy-1-m-tolylpentyl)-N-(4,4-dimethyl-1-(methylamino)pentan-2-yl)piperidine-1-carboxamide I-110 N-(3-cyclohexyl-1-(methylamino)propan-2-yl)-3-(5-methoxy-1-(thiophen-2-yl)pentyl)piperidine-1-carboxamide I-111 N-(3-cyclohexyl-1-(methylamino)propan-2-yl)-3-(1,1,1-trifluoro-2-hydroxy-6-methoxyhexan-2-yl)piperidine-1-carboxamide I-113 3-(1-(3-fluorophenyl)-1-hydroxy-5-methoxypentyl)-N-(4,4-dimethyl-1-(methylamino)pentan-2-yl)piperidine-1-carboxamide I-116 3-(1-(3-chlorophenyl)-1-hydroxy-5-methoxypentyl)-N-(4-methyl-1-(methylamino)pentan-2-yl)piperidine-1-carboxamide I-117 3-(1-(2,3-difluorophenyl)-1-hydroxy-5-methoxypentyl)-N-(4-methyl-1-(methylamino)pentan-2-yl)piperidine-1-carboxamide I-118 3-(1-(benzofuran-7-yl)-1-hydroxy-5-methoxypentyl)-N-(4-methyl-1-(methylamino)pentan-2-yl)piperidine-1-carboxamide I-119 N-(3-cyclohexyl-1-(methylamino)propan-2-yl)-3-(1-hydroxy-5-methoxy-1-(pyridin-2-yl)pentyl)piperidine-1-carboxamide I-120 3-(1-(2-(2-cyclopropylethoxy)phenyl)-1-hydroxy-5-methoxypentyl)-N-(1-(methylamino)propan-2-yl)piperidine-1-carboxamide I-121 3-(1-(2-(cyclopentyloxy)phenyl)-1-hydroxy-5-methoxypentyl)-N-(1-(methylamino)propan-2-yl)piperidine-1-carboxamide I-122 3-((3-methoxypropoxy)(phenyl)methyl)-N-(3-cyclohexyl-1-(methylamino)propan-2-yl)piperidine-1-carbothioamide I-123 N-(1-amino-3-cyclohexylpropan-2-yl)-3-(1-(3-fluorophenyl)-1-hydroxy-5-methoxypentyl)piperidine-1-carboxamide I-124 3-(1-hydroxy-5-methoxy-1-(2-(neopentyloxy)phenyl)pentyl)-N-(1-(methylamino)propan-2-yl)piperidine-1-carboxamide I-125 N-(3-cyclohexyl-1-(methylamino)propan-2-yl)-3-(1-hydroxy-5-methoxy-1-(1-methyl-1H-imidazol-2-yl)pentyl)piperidine-1-carboxamide I-126 N-(3-cyclohexyl-1-(methylamino)propan-2-yl)-3-(1-hydroxy-5-methoxy-1-(thiophen-2-yl)pentyl)piperidine-1-carboxamide I-127 N-(3-cyclohexyl-1-(methylamino)propan-2-yl)-3-(1-hydroxy-5-methoxy-1-(thiophen-3-yl)pentyl)piperidine-1-carboxamide I-130 N-(3-cyclohexyl-1-(methylamino)propan-2-yl)-3-(1-hydroxy-5-methoxy-1-(thiazol-2-yl)pentyl)piperidine-1-carboxamide I-131 3-(1-(2-(3-methylphenyl)phenyl)-1-hydroxy-5-methoxypentyl)-N-(1-(methylamino)propan-2-yl)piperidine-1-carboxamide I-132 3-(1-(2-(4-methylphenyl)phenyl)-1-hydroxy-5-methoxypentyl)-N-(1-(methylamino)propan-2-yl)piperidine-1-carboxamide I-133 3-(1-(2-(2-methylphenyl)phenyl)-1-hydroxy-5-methoxypentyl)-N-(1-(methylamino)propan-2-yl)piperidine-1-carboxamide I-134 3-(1-(3-chlorophenyl)-1-hydroxy-5-methoxypentyl)-N-(4,4-dimethyl-1-(methylamino)pentan-2-yl)piperidine-1-carboxamide I-135 3-(1-(2,3-difluorophenyl)-1-hydroxy-5-methoxypentyl)-N-(4,4-dimethyl-1-(methylamino)pentan-2-yl)piperidine-1-carboxamide I-136 3-(1-(2-(o-tolyloxy)phenyl)-1-hydroxy-5-methoxypentyl)-N-(2-aminoethyl)-N-methylpiperidine-1-carboxamide I-139 3-(1-hydroxy-5-methoxy-1-(quinolin-8-yl)pentyl)-N-(4-methyl-1-(methylamino)pentan-2-yl)piperidine-1-carboxamide I-140 3-(1-(2-(2-fluorophenyl)phenyl)-1-hydroxy-5-methoxypentyl)-N-(1-(methylamino)propan-2-yl)piperidine-1-carboxamide I-141 3-(1-(2-phenyl-3-fluorophenyl)-1-hydroxy-5-methoxypentyl)-N-(1-(methylamino)propan-2-yl)piperidine-1-carboxamide I-142 3-(1-(2-(3-fluorophenyl)phenyl)-1-hydroxy-5-methoxypentyl)-N-(1-(methylamino)propan-2-yl)piperidine-1-carboxamide I-143 3-((S)-1-(2-(4-fluorophenyl)phenyl)-1-hydroxy-5-methoxypentyl)-N-(1-(methylamino)propan-2-yl)piperidine-1-carboxamide I-144 3-(1-hydroxy-5-methoxy-1-(2-methylbenzofuran-7-yl)pentyl)-N-(4-methyl-1-(methylamino)pentan-2-yl)piperidine-1-carboxamide I-145 3-(1-hydroxy-1-(2-isobutylbenzofuran-7-yl)-5-methoxypentyl)-N-(1-(methylamino)propan-2-yl)piperidine-1-carboxamide I-146 N-(3-cyclohexyl-1-(methylamino)propan-2-yl)-3-(1-hydroxy-5-methoxy-1-phenylpentyl)-3-methylpiperidine-1-carboxamide I-147 3-(1-(2-(cyclopentylmethoxy)phenyl)-1-hydroxy-5-methoxypentyl)-N-(1-(methylamino)propan-2-yl)piperidine-1-carboxamide I-148 N-(3-cyclohexyl-1-(methylamino)propan-2-yl)-3-(1-(2-fluoro-5-methylphenyl)-5-methoxypentyl)piperidine-1-carboxamide I-149 3-(1-(benzo[b]thiophen-7-yl)-1-hydroxy-5-methoxypentyl)-N-(4-methyl-1-(methylamino)pentan-2-yl)piperidine-1-carboxamide I-151 N-(3-cyclohexyl-1-(methylamino)propan-2-yl)-3-(1-(2-fluorophenyl)-1-hydroxy-5-methoxypentyl)piperidine-1-carboxamide I-152 3-((3-ethoxypropoxy)(3-fluorophenyl)methyl)-N-(3-cyclohexyl-1-(methylamino)propan-2-yl)piperidine-1-carboxamide I-153 N-(1-amino-3-cyclohexylpropan-2-yl)-3-(1-(3-chlorophenyl)-1-hydroxy-5-methoxypentyl)piperidine-1-carboxamide I-154 3-((3-ethoxypropoxy)(3-chlorophenyl)methyl)-N-(1-amino-3-cyclohexylpropan-2-yl)piperidine-1-carboxamide I-155 3-(1-(3-chlorophenyl)-1,5-dihydroxypentyl)-N-(3-cyclohexyl-1-(methylamino)propan-2-yl)piperidine-1-carboxamide I-156 3-(1-(3-chlorophenyl)-1-hydroxy-5-methoxypentyl)-N-(3-cyclopentyl-1-(methylamino)propan-2-yl)piperidine-1-carboxamide I-157 N-(3-cyclohexyl-1-(methylamino)propan-2-yl)-3-(1-hydroxy-5-methoxy-1-(5-methylthiazol-2-yl)pentyl)piperidine-1-carboxamide I-159 3-((3-methoxypropoxy)(4-chloropyridin-2-yl)methyl)-N-(3-cyclohexyl-1-(methylamino)propan-2-yl)piperidine-1-carboxamide I-160 3-(1-hydroxy-5-methoxy-1-(2-phenoxyphenyl)pentyl)-N-(2-methyl-1-(methylamino)propan-2-yl)piperidine-1-carboxamide I-161 3-(1-(2-(o-tolyloxy)phenyl)-1-hydroxy-5-methoxypentyl)-N-(1-(methylamino)propan-2-yl)piperidine-1-carboxamide I-162 3-(1-(2-(m-tolyloxy)phenyl)-1-hydroxy-5-methoxypentyl)-N-(1-(methylamino)propan-2-yl)piperidine-1-carboxamide I-163 N-(3-(3,3-difluorocyclobutyl)-1-(methylamino)propan-2-yl)-3-(1-(3-fluorophenyl)-1-hydroxy-5-methoxypentyl)piperidine-1-carboxamide I-165 3-((S)-1-(benzofuran-7-yl)-1-hydroxy-5-methoxypentyl)-N-(3-cyclopentyl-1-(methylamino)propan-2-yl)piperidine-1-carboxamide I-166 3-(1-(3-chloro-2-fluorophenyl)-1-hydroxy-5-methoxypentyl)-N-(4,4-dimethyl-1-(methylamino)pentan-2-yl)piperidine-1-carboxamide I-168 3-(1-(2-(4-fluorophenoxy)phenyl)-1-hydroxy-5-methoxypentyl)-N-(1-(methylamino)propan-2-yl)piperidine-1-carboxamide I-169 3-(1-(5-fluoro-2-phenoxyphenyl)-1-hydroxy-5-methoxypentyl)-N-(1-(methylamino)propan-2-yl)piperidine-1-carboxamide I-170 3-(1-(2-(3-fluorophenoxy)phenyl)-1-hydroxy-5-methoxypentyl)-N-(1-(methylamino)propan-2-yl)piperidine-1-carboxamide I-171 3-(1-(2-(2-fluorophenoxy)phenyl)-1-hydroxy-5-methoxypentyl)-N-(1-(methylamino)propan-2-yl)piperidine-1-carboxamide I-172 N-(3-cyclopentyl-1-(methylamino)propan-2-yl)-3-((S)-1-(2,3-dihydrobenzofuran-7-yl)-1-hydroxy-5-methoxypentyl)piperidine-1-carboxamide I-173 N-(3-cyclohexyl-1-(methylamino)propan-2-yl)-3-(1-hydroxy-5-methoxy-1-(2,5-dimethylphenyl)pentyl)piperidine-1-carboxamide I-174 N-(3-cyclohexyl-1-(methylamino)propan-2-yl)-3-(1-(3-ethylphenyl)-1-hydroxy-5-methoxypentyl)piperidine-1-carboxamide I-175 N-(3-cyclohexyl-1-(methylamino)propan-2-yl)-3-(1-hydroxy-5-methoxy-1-(2,3-dimethylphenyl)pentyl)piperidine-1-carboxamide I-176 N-(3-cyclohexyl-1-(methylamino)propan-2-yl)-3-(1-hydroxy-5-methoxy-1-(3,5-dimethylphenyl)pentyl)piperidine-1-carboxamide I-177 3-(1-(2-(2-chlorophenyl)phenyl)-1-hydroxy-5-methoxypentyl)-N-(1-(methylamino)propan-2-yl)piperidine-1-carboxamide I-178 3-(1-(2-phenylphenyl)-1-hydroxy-5-methoxypentyl)-N-(1-(methylamino)propan-2-yl)piperidine-1-carboxamide I-179 N-(3-cyclohexyl-1-(methylamino)propan-2-yl)-3-(1-hydroxy-5-methoxy-1-(3-methoxyphenyl)pentyl)piperidine-1-carboxamide I-180 3-(1-(2-(cyclopropylmethoxy)phenyl)-1-hydroxy-5-methoxypentyl)-N-(4-methyl-1-(methylamino)pentan-2-yl)piperidine-1-carboxamide I-181 3-(1-(3-chlorophenyl)-4-cyclopropyl-1-hydroxybutyl)-N-(3-cyclohexyl-1-(methylamino)propan-2-yl)piperidine-1-carboxamide I-182 N-(3-cyclohexyl-1-(methylamino)propan-2-yl)-3-(1-(3-fluoro-5-methylphenyl)-1-hydroxy-5-methoxypentyl)piperidine-1-carboxamide I-183 N-(3-cyclohexyl-1-(methylamino)propan-2-yl)-3-((S)-1-(2-fluoro-5-methylphenyl)-1-hydroxy-5-methoxypentyl)piperidine-1-carboxamide I-184 N-(3-cyclohexyl-1-(methylamino)propan-2-yl)-3-(1-(5-fluoro-2-methylphenyl)-1-hydroxy-5-methoxypentyl)piperidine-1-carboxamide I-185 N-(3-cyclohexyl-1-(methylamino)propan-2-yl)-3-(1-(2-fluoro-3-methylphenyl)-1-hydroxy-5-methoxypentyl)piperidine-1-carboxamide I-186 N-(1-cyclohexyl-1-hydroxy-3-(methylamino)propan-2-yl)-3-(1-(3-fluorophenyl)-1-hydroxy-5-methoxypentyl)piperidine-1-carboxamide I-187 3-((S)-1-(3-fluorophenyl)-1-hydroxy-5-methoxypentyl)-N-(3-(1-hydroxycyclohexyl)-1-(methylamino)propan-2-yl)piperidine-1-carboxamide I-188 3-(1-(3-fluorophenyl)-1-hydroxy-5-methoxypentyl)-N-(3-(1-hydroxycyclohexyl)-2-(methylamino)propyl)piperidine-1-carboxamide I-190 3-((3-ethoxypropoxy)(3-chlorophenyl)methyl)-N-(3-cyclohexyl-1-(methylamino)propan-2-yl)piperidine-1-carboxamide I-191 3-(1-(3-chlorophenyl)-1,5-dihydroxyhexyl)-N-(3-cyclohexyl-1-(methylamino)propan-2-yl)piperidine-1-carboxamide I-192 3-(1-(2-chlorophenyl)-1-hydroxy-5-methoxypentyl)-N-(3-cyclohexyl-1-(methylamino)propan-2-yl)piperidine-1-carboxamide I-193 3-(1-(4-chloropyridin-2-yl)-1-hydroxy-5-methoxypentyl)-N-(3-cyclohexyl-1-(methylamino)propan-2-yl)piperidine-1-carboxamide I-194 3-((3-ethoxypropoxy)(phenyl)methyl)-N-(3-(4,4-difluorocyclohexyl)-1-(methylamino)propan-2-yl)piperidine-1-carboxamide I-195 N-(3-cyclohexyl-1-(methylamino)propan-2-yl)-3-(1-(3,5-difluorophenyl)-1-hydroxy-5-methoxypentyl)piperidine-1-carboxamide I-196 N-(3-cyclohexyl-1-(methylamino)propan-2-yl)-3-(1-(2,3-difluorophenyl)-1-hydroxy-5-methoxypentyl)piperidine-1-carboxamide I-197 N-(3-cyclopentyl-1-(methylamino)propan-2-yl)-3-(5-ethoxy-1-(2,3-difluorophenyl)-1-hydroxypentyl)piperidine-1-carboxamide I-198 N-(3-cyclohexyl-1-(methylamino)propan-2-yl)-3-(1-(2,3-difluorophenyl)-1-hydroxy-5-methoxypentyl)piperidine-1-carboxamide I-199 3-(1-(2-phenylphenyl)-1-hydroxy-5-methoxypentyl)-N-(4-methyl-1-(methylamino)pentan-2-yl)piperidine-1-carboxamide I-200 3-(1-(3-chlorophenyl)-1-hydroxy-5-methoxypentyl)-N-(3-(tetrahydro-2H-pyran-4-yl)-1-(methylamino)propan-2-yl)piperidine-1-carboxamide I-201 2-(1-(3-chlorophenyl)-1-hydroxy-5-methoxypentyl)-N-(3-cyclohexyl-1-(methylamino)propan-2-yl)morpholine-4-carboxamide I-202 N-(3-amino-1-cyclohexyl-1-hydroxypropan-2-yl)-3-(1-(3-chlorophenyl)-1-hydroxy-5-methoxypentyl)piperidine-1-carboxamide I-203 3-(1-(3-chlorophenyl)-1-hydroxy-5-methoxypentyl)-N-(1-cyclopentyl-1-hydroxy-3-(methylamino)propan-2-yl)piperidine-1-carboxamide I-204 3-(1-(2-(o-tolyloxy)phenyl)-1-hydroxy-5-methoxypentyl)-N-(2-methyl-1-(methylamino)propan-2-yl)piperidine-1-carboxamide I-205 3-(1-(2-(2-ethylphenoxy)phenyl)-1-hydroxy-5-methoxypentyl)-N-(1-(methylamino)propan-2-yl)piperidine-1-carboxamide I-206 3-(1-(3-chloro-2-fluorophenyl)-1-hydroxy-5-methoxypentyl)-N-(3-cyclopentyl-1-(methylamino)propan-2-yl)piperidine-1-carboxamide I-207 3-(1-(5-chloro-1-methyl-1H-imidazol-2-yl)-1-hydroxy-5-methoxypentyl)-N-(3-cyclohexyl-1-(methylamino)propan-2-yl)piperidine-1-carboxamide I-208 3-(1-(2,2-difluorobenzo[d][1,3]dioxol-4-yl)-1-hydroxy-5-methoxypentyl)-N-(4-methyl-1-(methylamino)pentan-2-yl)piperidine-1-carboxamide I-209 3-(1-(3-chlorophenyl)-1-hydroxyethyl)-N-(1-cyclohexyl-3-(methylamino)propan-2-yl)piperidine-1-carboxamide I-210 3-(1-(benzofuran-7-yl)-1-hydroxy-5-methoxypentyl)-N-(3-cyclohexyl-1-(methylamino)propan-2-yl)piperidine-1-carboxamide I-211 N-(3-cyclohexyl-1-(methylamino)propan-2-yl)-3-(1-hydroxy-1-(1H-indazol-7-yl)-5-methoxypentyl)piperidine-1-carboxamide I-212 N-(3-cyclohexyl-1-(methylamino)propan-2-yl)-3-(1-hydroxy-1-(1H-indazol-7-yl)-5-methoxypentyl)piperidine-1-carboxamide I-213 3-(1-(2-(4-fluorophenoxy)phenyl)-1-hydroxy-5-methoxypentyl)-N-(2-methyl-1-(methylamino)propan-2-yl)piperidine-1-carboxamide I-214 3-(1-(2-(3-fluorophenoxy)phenyl)-1-hydroxy-5-methoxypentyl)-N-(2-methyl-1-(methylamino)propan-2-yl)piperidine-1-carboxamide I-215 3-(1-(3-(o-tolyloxy)-2-fluorophenyl)-1-hydroxy-5-methoxypentyl)-N-(1-(methylamino)propan-2-yl)piperidine-1-carboxamide I-216 3-(1-(2-(o-tolyloxy)-3-fluorophenyl)-1-hydroxy-5-methoxypentyl)-N-(1-(methylamino)propan-2-yl)piperidine-1-carboxamide I-217 3-(1-(2-(5-fluoro-2-methylphenoxy)phenyl)-1-hydroxy-5-methoxypentyl)-N-(1-(methylamino)propan-2-yl)piperidine-1-carboxamide I-218 3-(1-(2-(4-fluoro-2-methylphenoxy)phenyl)-1-hydroxy-5-methoxypentyl)-N-(1-(methylamino)propan-2-yl)piperidine-1-carboxamide I-219 N-(3-cyclohexyl-1-(methylamino)propan-2-yl)-3-(1-(2,3-dihydrobenzofuran-7-yl)-1-hydroxy-5-methoxypentyl)piperidine-1-carboxamide I-220 3-(1-(3-chlorophenyl)-1-hydroxy-5-methoxypentyl)-N-(3-(3,3-difluorocyclobutyl)-1-(methylamino)propan-2-yl)piperidine-1-carboxamide I-221 N-(3-(3,3-difluorocyclobutyl)-1-(methylamino)propan-2-yl)-3-(1-(2,3-difluorophenyl)-1-hydroxy-5-methoxypentyl)piperidine-1-carboxamide I-222 3-(1-(2-(cyclopentyloxy)phenyl)-1-hydroxy-5-methoxypentyl)-N-(4-methyl-1-(methylamino)pentan-2-yl)piperidine-1-carboxamide I-223 3-(1-(2-(2-cyclopropylethoxy)phenyl)-1-hydroxy-5-methoxypentyl)-N-(4-methyl-1-(methylamino)pentan-2-yl)piperidine-1-carboxamide I-224 3-(1-(2-(2-chlorophenoxy)phenyl)-1-hydroxy-5-methoxypentyl)-N-(1-(methylamino)propan-2-yl)piperidine-1-carboxamide I-225 3-(1-hydroxy-5-methoxy-1-(2-(neopentyloxy)phenyl)pentyl)-N-(4-methyl-1-(methylamino)pentan-2-yl)piperidine-1-carboxamide I-226 N-(3-cyclohexyl-1-(methylamino)propan-2-yl)-3-(1-hydroxy-5-methoxy-1-(3-(methylthio)phenyl)pentyl)piperidine-1-carboxamide I-227 3-(4-(acetylamino)-1-(3-chlorophenyl)-1-hydroxybutyl)-N-(3-cyclohexyl-1-(methylamino)propan-2-yl)piperidine-1-carboxamide I-228 3-(1-(2-(allyloxy)-5-fluorophenyl)-5-ethoxy-1-hydroxypentyl)-N-(4-methyl-1-(methylamino)pentan-2-yl)piperidine-1-carboxamide I-229 N-(3-cyclohexyl-1-(methylamino)propan-2-yl)-3-(1-(5-fluoro-2-methoxyphenyl)-1-hydroxy-5-methoxypentyl)piperidine-1-carboxamide I-230 N-(3-cyclohexyl-1-(methylamino)propan-2-yl)-3-(1-(2-fluoro-6-methoxyphenyl)-1-hydroxy-5-methoxypentyl)piperidine-1-carboxamide I-231 3-(4-cyclopropyl-1-hydroxy-1-(2-phenoxyphenyl)butyl)-N-(4-methyl-1-(methylamino)pentan-2-yl)piperidine-1-carboxamide I-232 3-(1-(3-chlorophenyl)-1-hydroxy-5-methoxypentyl)-N-(5,5,5-trifluoro-4-methyl-1-(methylamino)pentan-2-yl)piperidine-1-carboxamide I-233 3-(1-(3-chlorophenyl)-1,5-dimethoxypentyl)-N-(3-cyclohexyl-1-(methylamino)propan-2-yl)piperidine-1-carboxamide I-234 3-(1-(3-chlorophenyl)-1-hydroxy-5-methoxypentyl)-N-(3-cyclohexyl-1-(ethylamino)propan-2-yl)piperidine-1-carboxamide I-235 3-(1-(3-chlorophenyl)-1,5-dihydroxyheptyl)-N-(3-cyclohexyl-1-(methylamino)propan-2-yl)piperidine-1-carboxamide I-236 3-(4-cyclopropyl-1-(3-fluorophenyl)-1-hydroxybutyl)-N-(3-(4,4-difluorocyclohexyl)-1-(methylamino)propan-2-yl)piperidine-1-carboxamide I-237 N-(3-(4,4-difluorocyclohexyl)-1-(methylamino)propan-2-yl)-3-(1-hydroxy-5-methoxy-1-m-tolylpentyl)piperidine-1-carboxamide I-238 3-((3-ethoxypropoxy)(m-tolyl)methyl)-N-(3-(4,4-difluorocyclohexyl)-1-(methylamino)propan-2-yl)piperidine-1-carboxamide I-239 N-(3-cyclohexyl-1-(methylamino)propan-2-yl)-3-(5-ethoxy-1-(2,3-difluorophenyl)-1-hydroxypentyl)piperidine-1-carboxamide I-240 3-(1-(2-fluoro-3-methylphenyl)-1-hydroxy-5-methoxypentyl)-N-(3-(4-fluorocyclohexyl)-1-(methylamino)propan-2-yl)piperidine-1-carboxamide I-241 N-(3-cyclopropyl-1-(methylamino)propan-2-yl)-3-(1-hydroxy-5-methoxy-1-(2-phenoxyphenyl)pentyl)piperidine-1-carboxamide I-242 3-(1-(2-(3-methylphenyl)phenyl)-1-hydroxy-5-methoxypentyl)-N-(4-methyl-1-(methylamino)pentan-2-yl)piperidine-1-carboxamide I-243 3-(1-(2-(4-methylphenyl)phenyl)-1-hydroxy-5-methoxypentyl)-N-(4-methyl-1-(methylamino)pentan-2-yl)piperidine-1-carboxamide I-244 3-(1-(3-chlorophenyl)-1-hydroxy-5-methoxypentyl)-N-(1-cyclohexyl-1-hydroxy-3-(methylamino)propan-2-yl)piperidine-1-carboxamide I-245 3-(1-(3-chlorophenyl)-1-hydroxy-5-methoxypentyl)-N-(3-(1-hydroxycyclohexyl)-1-(methylamino)propan-2-yl)piperidine-1-carboxamide I-246 3-(1-(3-chlorophenyl)-1-hydroxy-5-methoxypentyl)-N-(3-(1-hydroxycyclohexyl)-2-(methylamino)propyl)piperidine-1-carboxamide I-247 3-(1-(3-chlorophenyl)-1-hydroxy-5-methoxypentyl)-N-(3-cyclohexyl-1-(methylamino)propan-2-yl)piperidine-1-carbothioamide I-248 N-(3-cyclohexyl-1-(methylamino)propan-2-yl)-3-(1-hydroxy-5-methoxy-1-(quinolin-8-yl)pentyl)piperidine-1-carboxamide I-249 3-(1-(2-(p-tolyloxy)-5-methylphenyl)-1-hydroxy-5-methoxypentyl)-N-(2-methyl-1-(methylamino)propan-2-yl)piperidine-1-carboxamide I-250 3-(1-(3-chloro-5-fluorophenyl)-1-hydroxy-5-methoxypentyl)-N-(3-cyclohexyl-1-(methylamino)propan-2-yl)piperidine-1-carboxamide I-251 3-(1-(3-chloro-2-fluorophenyl)-1-hydroxy-5-methoxypentyl)-N-(3-cyclohexyl-1-(methylamino)propan-2-yl)piperidine-1-carboxamide I-252 3-(1-(3-chloro-2-fluorophenyl)-5-ethoxy-1-hydroxypentyl)-N-(3-cyclopentyl-1-(methylamino)propan-2-yl)piperidine-1-carboxamide I-253 3-(1-(3-chlorophenyl)-1-hydroxy-5-methoxypentyl)-N-(3-(4-fluorocyclohexyl)-1-(methylamino)propan-2-yl)piperidine-1-carboxamide I-254 3-(1-hydroxy-5-methoxy-1-(2-(pyridin-3-yloxy)phenyl)pentyl)-N-(4-methyl-1-(methylamino)pentan-2-yl)piperidine-1-carboxamide I-255 3-((3-ethoxypropoxy)(3-fluorophenyl)methyl)-N-(3-(4,4-difluorocyclohexyl)-1-(methylamino)propan-2-yl)piperidine-1-carboxamide I-256 N-(3-cyclohexyl-1-(methylamino)propan-2-yl)-3-(1-(2,3,5-trifluorophenyl)-1-hydroxy-5-methoxypentyl)piperidine-1-carboxamide I-257 N-(3-cyclopentyl-1-(methylamino)propan-2-yl)-3-(5-ethoxy-1-(2,3,5-trifluorophenyl)-1-hydroxypentyl)piperidine-1-carboxamide I-258 3-(1-(2-(2-ethylphenoxy)phenyl)-1-hydroxy-5-methoxypentyl)-N-(3-hydroxy-1-(methylamino)propan-2-yl)piperidine-1-carboxamide I-259 3-(1-(3-fluoro-2-phenylphenyl)-1-hydroxy-5-methoxypentyl)-N-(4-methyl-1-(methylamino)pentan-2-yl)piperidine-1-carboxamide I-260 3-(1-(2-(2-fluorophenyl)phenyl)-1-hydroxy-5-methoxypentyl)-N-(4-methyl-1-(methylamino)pentan-2-yl)piperidine-1-carboxamide I-261 3-(1-(2-(3-fluorophenyl)phenyl)-1-hydroxy-5-methoxypentyl)-N-(4-methyl-1-(methylamino)pentan-2-yl)piperidine-1-carboxamide I-262 3-(1-(2-(4-fluorophenyl)phenyl)-1-hydroxy-5-methoxypentyl)-N-(4-methyl-1-(methylamino)pentan-2-yl)piperidine-1-carboxamide I-263 3-(1-(3-chlorophenyl)-5,5-difluoro-1-hydroxyhexyl)-N-(3-cyclohexyl-1-(methylamino)propan-2-yl)piperidine-1-carboxamide I-264 3-((3-methoxypropoxy)(2,3-dichlorophenyl)methyl)-N-(3-cyclohexyl-1-(methylamino)propan-2-yl)piperidine-1-carboxamide I-265 3-(1-(2,3-dichlorophenyl)-1-hydroxy-5-methoxypentyl)-N-(3-cyclopentyl-1-(methylamino)propan-2-yl)piperidine-1-carboxamide I-266 3-((3-ethoxypropoxy)(2,3-dichlorophenyl)methyl)-N-(3-cyclopentyl-1-(methylamino)propan-2-yl)piperidine-1-carboxamide I-267 3-(1-(benzo[b]thiophen-7-yl)-1-hydroxy-5-methoxypentyl)-N-(3-cyclohexyl-1-(methylamino)propan-2-yl)piperidine-1-carboxamide I-268 3-(1-(benzo[b]thiophen-2-yl)-1-hydroxy-5-methoxypentyl)-N-(3-cyclohexyl-1-(methylamino)propan-2-yl)piperidine-1-carboxamide I-269 3-(1-hydroxy-5-methoxy-1-(3-(trifluoromethoxy)phenyl)pentyl)-N-(4,4-dimethyl-1-(methylamino)pentan-2-yl)piperidine-1-carboxamide I-270 N-(3-cyclohexyl-1-(methylamino)propan-2-yl)-3-(1-(5-fluorobenzofuran-7-yl)-1-hydroxy-5-methoxypentyl)piperidine-1-carboxamide I-271 3-(1-(3-chlorophenyl)-1-hydroxy-5-methoxypentyl)-N'-cyano-N-(3-cyclohexyl-1-(methylamino)propan-2-yl)piperidine-1-carboxamidine I-272 3-(1-acetamido-1-(3-fluorophenyl)-5-methoxypentyl)-N-(3-cyclohexyl-1-(methylamino)propan-2-yl)piperidine-1-carboxamide I-273 3-(1-(3-chloro-2-fluorophenyl)-1-hydroxy-5-methoxypentyl)-N-(3-(3,3-difluorocyclobutyl)-1-(methylamino)propan-2-yl)piperidine-1-carboxamide I-275 3-(1-(2-(o-tolyloxy)phenyl)-1-hydroxy-5-methoxypentyl)-N-(4-methyl-1-(methylamino)pentan-2-yl)piperidine-1-carboxamide I-276 3-(1-hydroxy-5-methoxy-1-(2-phenoxyphenyl)pentyl)-N-(4,4-dimethyl-1-(methylamino)pentan-2-yl)piperidine-1-carboxamide I-277 3-(1-(2-(benzyloxy)phenyl)-1-hydroxy-5-methoxypentyl)-N-(4-methyl-1-(methylamino)pentan-2-yl)piperidine-1-carboxamide I-278 3-(1-(2-(m-tolyloxy)phenyl)-1-hydroxy-5-methoxypentyl)-N-(4-methyl-1-(methylamino)pentan-2-yl)piperidine-1-carboxamide I-279 3-(1-(3-chloro-2-fluorophenyl)-5-ethoxy-1-hydroxypentyl)-N-(3-cyclohexyl-1-(methylamino)propan-2-yl)piperidine-1-carboxamide I-280 3-(1-(3-chloro-2-fluorophenyl)-1-hydroxy-5-methoxypentyl)-N-(1-(methylamino)-3-(4-methylcyclohexyl)propan-2-yl)piperidine-1-carboxamide I-281 N-(3-cyclohexyl-1-(methylamino)propan-2-yl)-3-(1-(2-(trifluoromethyl)phenyl)-1-hydroxy-5-methoxypentyl)piperidine-1-carboxamide I-282 N-(3-cyclohexyl-1-(methylamino)propan-2-yl)-3-(5-ethoxy-1-(2,3,5-trifluorophenyl)-1-hydroxypentyl)piperidine-1-carboxamide I-283 3-(1-(2-fluoro-3-methylphenyl)-1-hydroxy-5-methoxypentyl)-N-(3-(4,4-difluorocyclohexyl)-1-(methylamino)propan-2-yl)piperidine-1-carboxamide I-284 3-(1-(2,3-dichlorophenyl)-1-hydroxy-5-methoxypentyl)-N-(3-cyclohexyl-1-(methylamino)propan-2-yl)piperidine-1-carboxamide I-285 3-((3-ethoxypropoxy)(2,3-dichlorophenyl)methyl)-N-(3-cyclohexyl-1-(methylamino)propan-2-yl)piperidine-1-carboxamide I-286 3-(1-(2,3-dichlorophenyl)-5-ethoxy-1-hydroxypentyl)-N-(3-cyclopentyl-1-(methylamino)propan-2-yl)piperidine-1-carboxamide I-287 3-(1-(2-(4-fluorophenoxy)phenyl)-1-hydroxy-5-methoxypentyl)-N-(4-methyl-1-(methylamino)pentan-2-yl)piperidine-1-carboxamide I-288 3-(1-(5-fluoro-2-phenoxyphenyl)-1-hydroxy-5-methoxypentyl)-N-(4-methyl-1-(methylamino)pentan-2-yl)piperidine-1-carboxamide I-289 3-(1-(2-(3-fluorophenoxy)phenyl)-1-hydroxy-5-methoxypentyl)-N-(4-methyl-1-(methylamino)pentan-2-yl)piperidine-1-carboxamide I-290 3-(1-(2-(2-fluorophenoxy)phenyl)-1-hydroxy-5-methoxypentyl)-N-(4-methyl-1-(methylamino)pentan-2-yl)piperidine-1-carboxamide I-291  3-(1-(3-fluoro-2-phenoxyphenyl)-1-hydroxy-5-methoxypentyl)-N-(4-methyl-1-(methylamino)pentan-2-yl)piperidine-1-carboxamide I-292  3-(1-(3-(4-fluorophenoxy)phenyl)-1-hydroxy-5-methoxypentyl)-N-(4-methyl-1-(methylamino)pentan-2-yl)piperidine-1-carboxamide I-293  3-(1-(3-chlorophenyl)-1-hydroxy-5-methoxypentyl)-N-(3-(4,4-difluorocyclohexyl)-1-(methylamino)propan-2-yl)piperidine-1-carboxamide I-294  3-((3-ethoxypropoxy)(3-chlorophenyl)methyl)-N-(3-(4,4-difluorocyclohexyl)-1-(methylamino)propan-2-yl)piperidine-1-carboxamide I-295  3-(1-(3-chloro-2-fluorophenyl)-1-hydroxy-5-methoxypentyl)-N-(3-(4-fluorocyclohexyl)-1-(methylamino)propan-2-yl)piperidine-1-carboxamide I-296  3-(1-(2-(2-chlorophenyl)phenyl)-1-hydroxy-5-methoxypentyl)-N-(4-methyl-1-(methylamino)pentan-2-yl)piperidine-1-carboxamide I-297  3-(1-(2-(4-chlorophenyl)phenyl)-1-hydroxy-5-methoxypentyl)-N-(4-methyl-1-(methylamino)pentan-2-yl)piperidine-1-carboxamide I-298  3-(1-(2-(3-chlorophenyl)phenyl)-1-hydroxy-5-methoxypentyl)-N-(4-methyl-1-(methylamino)pentan-2-yl)piperidine-1-carboxamide I-299  N-(3-(4,4-difluorocyclohexyl)-1-(methylamino)propan-2-yl)-3-(1-(2,3-difluorophenyl)-1-hydroxy-5-methoxypentyl)piperidine-1-carboxamide I-300  2-(1-(3-chlorophenyl)-1-hydroxy-5-methoxypentyl)-N-(3-(4,4-difluorocyclohexyl)-1-(methylamino)propan-2-yl)morpholine-4-carboxamide I-301  3-(1-acetamido-1-(3-chlorophenyl)-5-methoxypentyl)-N-(3-cyclohexyl-1-(methylamino)propan-2-yl)piperidine-1-carboxamide I-302  3-(1-(benzofuran-7-yl)-1-hydroxy-5-methoxypentyl)-N-(3-(4,4-difluorocyclohexyl)-1-(methylamino)propan-2-yl)piperidine-1-carboxamide I-303  N-(4,4,4-trifluoro-1-(methylamino)butan-2-yl)-3-(1-hydroxy-5-methoxy-1-(2-phenoxyphenyl)pentyl)piperidine-1-carboxamide I-304  3-(1-(2-(2-(trifluoromethyl)phenoxy)phenyl)-1-hydroxy-5-methoxypentyl)-N-(1-(methylamino)propan-2-yl)piperidine-1-carboxamide I-306  N-(3-cyclohexyl-1-(methylamino)propan-2-yl)-3-(1-(2,2-difluorobenzo[d][1,3]dioxol-4-yl)-1-hydroxy-5-methoxypentyl)piperidine-1-carboxamide I-307  3-(1-(2-(o-tolyloxy)-3-methylphenyl)-1-hydroxy-5-methoxypentyl)-N-(4-methyl-1-(methylamino)pentan-2-yl)piperidine-1-carboxamide I-308  3-(1-(2,3-dichlorophenyl)-5-ethoxy-1-hydroxypentyl)-N-(3-cyclohexyl-1-(methylamino)propan-2-yl)piperidine-1-carboxamide I-309  N-(3-cyclohexyl-1-(methylamino)propan-2-yl)-3-(1-hydroxy-5-methoxy-1-(3-(trifluoromethoxy)phenyl)pentyl)piperidine-1-carboxamide I-310  N-(3-cyclohexyl-1-(methylamino)propan-2-yl)-3-(1-hydroxy-5-methoxy-1-(2-(trifluoromethoxy)phenyl)pentyl)piperidine-1-carboxamide I-311  3-(1-(2-(p-tolyloxy)-3-fluorophenyl)-1-hydroxy-5-methoxypentyl)-N-(4-methyl-1-(methylamino)pentan-2-yl)piperidine-1-carboxamide I-312  3-(1-(2-(o-tolyloxy)-3-fluorophenyl)-1-hydroxy-5-methoxypentyl)-N-(4-methyl-1-(methylamino)pentan-2-yl)piperidine-1-carboxamide I-313  3-(1-(2-(5-fluoro-2-methylphenoxy)phenyl)-1-hydroxy-5-methoxypentyl)-N-(4-methyl-1-(methylamino)pentan-2-yl)piperidine-1-carboxamide I-314  3-(1-(2-(4-fluoro-2-methylphenoxy)phenyl)-1-hydroxy-5-methoxypentyl)-N-(4-methyl-1-(methylamino)pentan-2-yl)piperidine-1-carboxamide I-315  N-(3-cyclohexyl-1-(methylamino)propan-2-yl)-3-(1-(2-(cyclopentyloxy)phenyl)-1-hydroxy-5-methoxypentyl)piperidine-1-carboxamide I-316  3-(1-(2-(2-cyclopropylethoxy)phenyl)-1-hydroxy-5-methoxypentyl)-N-(3-cyclohexyl-1-(methylamino)propan-2-yl)piperidine-1-carboxamide I-317  3-(5-ethoxy-1-(2,3-difluorophenyl)-1-hydroxypentyl)-N-(3-(4,4-difluorocyclohexyl)-1-(methylamino)propan-2-yl)piperidine-1-carboxamide I-318  3-(1-(2-(4-fluorophenoxy)-5-fluorophenyl)-1-hydroxy-5-methoxypentyl)-N-(4-methyl-1-(methylamino)pentan-2-yl)piperidine-1-carboxamide I-319  3-(1-(3,5-difluoro-2-phenoxyphenyl)-1-hydroxy-5-methoxypentyl)-N-(4-methyl-1-(methylamino)pentan-2-yl)piperidine-1-carboxamide I-320  3-(1-(3-chloro-2-fluorophenyl)-1-hydroxy-5-methoxypentyl)-N-(3-(4,4-difluorocyclohexyl)-1-(methylamino)propan-2-yl)piperidine-1-carboxamide I-321  3-((3-ethoxypropoxy)(3-chloro-2-fluorophenyl)methyl)-N-(3-(4,4-difluorocyclohexyl)-1-(methylamino)propan-2-yl)piperidine-1-carboxamide I-322  3-(1-(3-chlorophenyl)-5-methoxy-1-(propionamido)pentyl)-N-(3-cyclohexyl-1-(methylamino)propan-2-yl)piperidine-1-carboxamide I-323  N-(3-(4,4-difluorocyclohexyl)-1-(methylamino)propan-2-yl)-3-(1-(2,3,5-trifluorophenyl)-1-hydroxy-5-methoxypentyl)piperidine-1-carboxamide I-324  3-((3-ethoxypropoxy)(2,3,5-trifluorophenyl)methyl)-N-(3-(4,4-difluorocyclohexyl)-1-(methylamino)propan-2-yl)piperidine-1-carboxamide I-325  N-(3-(3,3-difluorocyclobutyl)-1-(methylamino)propan-2-yl)-3-(1-hydroxy-5-methoxy-1-(3-(trifluoromethoxy)phenyl)pentyl)piperidine-1-carboxamide I-326  3-(1-(3-hydroxypropoxy)-1-(3-chlorophenyl)-5-methoxypentyl)-N-(3-cyclohexyl-1-(methylamino)propan-2-yl)piperidine-1-carboxamide I-328  N-(3-cyclohexyl-1-(methylamino)propan-2-yl)-3-(1-hydroxy-5-methoxy-1-(2-(pyridin-3-yloxy)phenyl)pentyl)piperidine-1-carboxamide I-329  3-(1-acetamido-1-(3-chloro-2-fluorophenyl)-5-methoxypentyl)-N-(3-cyclohexyl-1-(methylamino)propan-2-yl)piperidine-1-carboxamide I-330  3-(1-(2-(allyloxy)-3-bromophenyl)-1-hydroxy-5-methoxypentyl)-N-(4-methyl-1-(methylamino)pentan-2-yl)piperidine-1-carboxamide I-332  3-(1-(3-chlorophenyl)-1-(isobutyramido)-5-methoxypentyl)-N-(3-cyclohexyl-1-(methylamino)propan-2-yl)piperidine-1-carboxamide I-333  3-(5-ethoxy-1-(2,3,5-trifluorophenyl)-1-hydroxypentyl)-N-(3-(4,4-difluorocyclohexyl)-1-(methylamino)propan-2-yl)piperidine-1-carboxamide I-334  N-(5,5,5-trifluoro-4-methyl-1-(methylamino)pentan-2-yl)-3-(1-hydroxy-5-methoxy-1-(2-phenoxyphenyl)pentyl)piperidine-1-carboxamide I-335  3-(1-(2-(benzyloxy)phenyl)-1-hydroxy-5-methoxypentyl)-N-(3-cyclohexyl-1-(methylamino)propan-2-yl)piperidine-1-carboxamide I-336  3-(1-(3-chloro-2-fluorophenyl)-5-methoxy-1-(propionamido)pentyl)-N-(3-cyclohexyl-1-(methylamino)propan-2-yl)piperidine-1-carboxamide I-337  3-(1-(2-(4-fluorophenoxy)phenyl)-1-hydroxy-5-methoxypentyl)-N-(3-cyclohexyl-1-(methylamino)propan-2-yl)piperidine-1-carboxamide I-338 N-(3-cyclohexyl-1-(methylamino)propan-2-yl)-3-(1-(5-fluoro-2-phenoxyphenyl)-1-hydroxy-5-methoxypentyl)piperidine-1-carboxamide I-339 3-(1-(2-(2-(trifluoromethyl)phenoxy)phenyl)-1-hydroxy-5-methoxypentyl)-N-(4-methyl-1-(methylamino)pentan-2-yl)piperidine-1-carboxamide I-340 3-(1-(3-chloro-2-fluorophenyl)-1-(isobutyramido)-5-methoxypentyl)-N-(3-cyclohexyl-1-(methylamino)propan-2-yl)piperidine-1-carboxamide I-341 3-(1-(3-chlorophenyl)-1-hydroxypropyl)-N-(1-cyclohexyl-3-(methylamino)propan-2-yl)piperidine-1-carboxamide I-342 N-(1-cyclohexyl-3-(methylamino)propan-2-yl)-2-(5-methoxy-1-phenylpentyl)morpholine-4-carboxamide I-343 3-(1-(3-chlorophenyl)-1-hydroxybutyl)-N-(1-cyclohexyl-3-(methylamino)propan-2-yl)piperidine-1-carboxamide I-346 3-(1-(3-chlorophenyl)-1-hydroxypentyl)-N-(1-cyclohexyl-3-(methylamino)propan-2-yl)piperidine-1-carboxamide I-347 3-(1-cyclohexyl-1-hydroxy-5-methoxypentyl)-N-(1-cyclohexyl-3-(methylamino)propan-2-yl)piperidine-1-carboxamide I-348 3-(1-(3-chlorophenyl)-1,4-dihydroxybutyl)-N-(1-cyclohexyl-3-(methylamino)propan-2-yl)piperidine-1-carboxamide I-349 3-(1-(3-chlorophenyl)-1-hydroxy-5-methoxypentyl)-N-(3-hydroxy-4-methyl-1-(methylamino)pentan-2-yl)piperidine-1-carboxamide I-350 3-(1-(benzofuran-7-yl)-1-hydroxy-5-methoxypentyl)-N-(4,4-dimethyl-1-(methylamino)pentan-2-yl)piperidine-1-carboxamide I-351 3-(1-(2-tert-butylbenzofuran-7-yl)-1-hydroxy-5-methoxypentyl)-N-(1-(methylamino)propan-2-yl)piperidine-1-carboxamide I-352 N-(3-amino-1-cyclohexylbutan-2-yl)-3-(1-(2-fluorophenyl)-1-hydroxy-5-methoxypentyl)piperidine-1-carboxamide I-353 N-(1-cyclopentyl-1-hydroxy-3-(methylamino)propan-2-yl)-3-(1-(3-fluorophenyl)-1-hydroxy-5-methoxypentyl)piperidine-1-carboxamide I-354 N-(2-amino-3-cyclohexylpropyl)-3-(1-(3-chlorophenyl)-1-hydroxy-5-methoxypentyl)piperidine-1-carboxamide I-356 3-(1-(3-chlorophenyl)-1-hydroxy-5-methoxypentyl)-N-(4-methoxy-4-methyl-1-(methylamino)pentan-2-yl)piperidine-1-carboxamide I-357 3-(1-(3-cyanophenyl)-1-hydroxy-5-methoxypentyl)-N-(1-cyclohexyl-3-(methylamino)propan-2-yl)piperidine-1-carboxamide I-358 3-(1-(3-chloro-2-fluorophenyl)-1-hydroxy-5-methoxypentyl)-N-(4,4-dimethyl-1-(methylamino)pentan-2-yl)piperidine-1-carboxamide I-359 3-(1-(2-chloro-3-fluorophenyl)-1-hydroxy-5-methoxypentyl)-N-(4,4-dimethyl-1-(methylamino)pentan-2-yl)piperidine-1-carboxamide I-360 3-(1-(3-chloro-2-fluorophenyl)-1-hydroxy-5-methoxypentyl)-N-(3-hydroxy-4-methyl-1-(methylamino)pentan-2-yl)piperidine-1-carboxamide I-361 3-(1-(benzo[b]thiophen-4-yl)-1-hydroxy-5-methoxypentyl)-N-(4,4-dimethyl-1-(methylamino)pentan-2-yl)piperidine-1-carboxamide I-362 3-(4-acetamido-1-(2-fluorophenyl)-1-hydroxybutyl)-N-(1-cyclohexyl-3-(methylamino)propan-2-yl)piperidine-1-carboxamide I-363 N-(1-cyclohexyl-3-(methylamino)propan-2-yl)-3-(1-(3-fluoro-2-methylphenyl)-1-hydroxy-5-methoxypentyl)piperidine-1-carboxamide I-364 N-(1-cyclohexyl-3-(methylamino)propan-2-yl)-3-(1-(3-fluoro-4-methylphenyl) 1-hydroxy-5-methoxypentyl)piperidine-1-carboxamide I-366 N-(1-cyclohexyl-3-(methylamino)propan-2-yl)-3-(1-(3-fluoro-2-hydroxyphenyl)-1-hydroxy-5-methoxypentyl)piperidine-1-carboxamide I-367 N-(1-cyclohexyl-1-hydroxy-3-(methylamino)propan-2-yl)-3-(1-(2-fluorophenyl)-1-hydroxy-5-methoxypentyl)piperidine-1-carboxamide I-368 N-(3-amino-1-cyclohexylbutan-2-yl)-3-(1-(3-chlorophenyl)-1-hydroxy-5-methoxypentyl)piperidine-1-carboxamide I-369 3-(1-(3-chlorophenyl)-1-hydroxy-5-methoxypentyl)-N-(3-cyclohexyl-2-(methylamino)propyl)piperidine-1-carboxamide I-370 N-(1-(4-fluorocyclohexyl)-3-(methylamino)propan-2-yl)-3-(1-(2-fluorophenyl)-1-hydroxy-5-methoxypentyl)piperidine-1-carboxamide I-371 N-(1-cyclopentyl-1-hydroxy-3-(methylamino)propan-2-yl)-3-(1-(2,3-difluorophenyl)-1-hydroxy-5-methoxypentyl)piperidine-1-carboxamide I-372 3-(1-(2-chloro-3-fluorophenyl)-1-hydroxy-5-methoxypentyl)-N-(1-cyclopentyl-3-(methylamino)propan-2-yl)piperidine-1-carboxamide I-373 N-(2-amino-3-cyclohexylpropyl)-3-(1-(3-chloro-2-fluorophenyl)-1-hydroxy-5-methoxypentyl)piperidine-1-carboxamide I-374 3-(1-(benzofuran-4-yl)-1-hydroxy-5-methoxypentyl)-N-(1-cyclohexyl-3-(methylamino)propan-2-yl)piperidine-1-carboxamide I-375 3-(4-acetamido-1-(3,5-dimethylphenyl)-1-hydroxybutyl)-N-(1-cyclohexyl-3-(methylamino)propan-2-yl)piperidine-1-carboxamide I-376 3-(1-cyclohexyl-1-hydroxy-5-methoxypentyl)-N-(1-(4,4-difluorocyclohexyl)-3-(methylamino)propan-2-yl)piperidine-1-carboxamide I-377 N-(2-amino-3-cyclohexylpropyl)-3-(1-(benzo[b]thiophen-4-yl)-1-hydroxy-5-methoxypentyl)piperidine-1-carboxamide I-378 3-(1-(3-chloro-2-fluorophenyl)-1-hydroxy-5-methoxypentyl)-N-(4-methoxy-4-methyl-1-(methylamino)pentan-2-yl)piperidine-1-carboxamide I-379 3-(1-(2-cyano-5-fluorophenyl)-1-hydroxy-5-methoxypentyl)-N-(1-cyclohexyl-3-(methylamino)propan-2-yl)piperidine-1-carboxamide I-380 3-(1-(3-carbamoylphenyl)-1-hydroxy-5-methoxypentyl)-N-(1-cyclohexyl-3-(methylamino)propan-2-yl)piperidine-1-carboxamide I-381 N-(2-amino-3-cyclohexylpropyl)-2-(1-(benzo[b]thiophen-7-yl)-1-hydroxy-5-methoxypentyl)morpholine-4-carboxamide I-382 3-(4-acetamido-1-(3-fluoro-5-methylphenyl)-1-hydroxybutyl)-N-(1-cyclohexyl-3-(methylamino)propan-2-yl)piperidine-1-carboxamide I-383 3-(4-acetamido-1-(2-fluoro-5-methylphenyl)-1-hydroxybutyl)-N-(1-cyclohexyl-3-(methylamino)propan-2-yl)piperidine-1-carboxamide I-385 3-(1-(2-(cyclopropylmethoxy)-3-fluorophenyl)-1-hydroxy-5-methoxypentyl)-N-(4-methyl-1-(methylamino)pentan-2-yl)piperidine-1-carboxamide I-386 3-(1-(3-chloro-2-methylphenyl)-1-hydroxy-5-methoxypentyl)-N-(1-cyclohexyl-3-(methylamino)propan-2-yl)piperidine-1-carboxamide I-387 3-(1-(3-chlorophenyl)-1,5-dimethoxypentyl)-N-(1-cyclohexyl-3-(methylamino)propan-2-yl)piperidine-1-carboxamide I-388 3-(4-acetamido-1-(2,3-difluorophenyl)-1-hydroxybutyl)-N-(1-cyclohexyl-3-(methylamino)propan-2-yl)piperidine-1-carboxamide I-389 3-(4-acetamido-1-(3,5-difluorophenyl)-1-hydroxybutyl)-N-(1-cyclohexyl-3-(methylamino)propan-2-yl)piperidine-1-carboxamide I-390 3-(1-(2,3-difluorophenyl)-1-hydroxy-5-methoxypentyl)-N-(1-(methylamino)-3-(4-methylcyclohexyl)propan-2-yl)piperidine-1-carboxamide I-391 3-(1-(3-chlorophenyl)-1-hydroxy-5-methoxypentyl)-N-(1-(4-hydroxycyclohexyl)-3-(methylamino)propan-2-yl)piperidine-1-carboxamide I-392 3-(4-acetamido-1-(2,3-difluorophenyl)-1-hydroxybutyl)-N-(1-cyclopentyl-1-hydroxy-3-(methylamino)propan-2-yl)piperidine-1-carboxamide I-393 3-((2-acetamidoethoxy)(3-chloro-2-fluorophenyl)methyl)-N-(1-cyclohexyl-3-(methylamino)propan-2-yl)piperidine-1-carboxamide I-394 N-(2-amino-3-tert-butoxypropyl)-3-(1-(3-chloro-2-fluorophenyl)-1-hydroxy-5-methoxypentyl)piperidine-1-carboxamide I-395 N-(1-cyclohexyl-1-hydroxy-3-(methylamino)propan-2-yl)-3-(1-(2,3-difluorophenyl)-1-hydroxy-5-methoxypentyl)piperidine-1-carboxamide I-396 3-(1-(2,3-difluorophenyl)-1-hydroxy-5-methoxypentyl)-N-(1-(4-hydroxycyclohexyl)-3-(methylamino)propan-2-yl)piperidine-1-carboxamide I-397 N-(1-cyclohexyl-1-hydroxy-3-(methylamino)propan-2-yl)-3-(1-(2,5-difluorophenyl)-1-hydroxy-5-methoxypentyl)piperidine-1-carboxamide I-398 3-(1-(2-chloro-3-fluorophenyl)-1-hydroxy-5-methoxypentyl)-N-(1-cyclohexyl-3-(methylamino)propan-2-yl)piperidine-1-carboxamide I-399 N-(3-amino-1-cyclohexylbutan-2-yl)-3-(1-(3-chloro-2-fluorophenyl)-1-hydroxy-5-methoxypentyl)piperidine-1-carboxamide I-400 N-(1-cyclohexyl-3-(methylamino)propan-2-yl)-3-(1-hydroxy-5-methoxy-1-(2,3,4-trifluorophenyl)pentyl)piperidine-1-carboxamide I-401 N-(1-(4,4-difluorocyclohexyl)-3-(methylamino)propan-2-yl)-3-(1-(2-fluorophenyl)-1-hydroxy-5-methoxypentyl)piperidine-1-carboxamide I-402 3-(1-(2,5-difluorophenyl)-1-hydroxy-5-methoxypentyl)-N-(1-(4-fluorocyclohexyl)-3-(methylamino)propan-2-yl)piperidine-1-carboxamide I-403 3-(1-(2,3-difluorophenyl)-1-hydroxy-5-methoxypentyl)-N-(1-(4-fluorocyclohexyl)-3-(methylamino)propan-2-yl)piperidine-1-carboxamide I-404 2-(1-(3-chloro-2-fluorophenyl)-1-hydroxy-5-methoxypentyl)-N-(1-cyclohexyl-3-(methylamino)propan-2-yl)morpholine-4-carboxamide I-405 3-(1-(3-chloro-2-fluorophenyl)-1-hydroxy-5-methoxypentyl)-N-(1-cyclopentyl-1-hydroxy-3-(methylamino)propan-2-yl)piperidine-1-carboxamide I-406 3-(1-(3-chloro-2-fluorophenyl)-1-hydroxy-5-methoxypentyl)-N-(1-(methylamino)-3-(tetrahydro-2H-pyran-4-yl)propan-2-yl)piperidine-1-carboxamide I-408 3-(1-(benzo[b]thiophen-4-yl)-1-hydroxy-5-methoxypentyl)-N-(1-cyclohexyl-3-(methylamino)propan-2-yl)piperidine-1-carboxamide I-410 3-(1-(benzofuran-7-yl)-1-hydroxy-5-methoxypentyl)-N-(1-(4-fluorocyclohexyl)-3-(methylamino)propan-2-yl)piperidine-1-carboxamide I-411 N-(1-cyclohexyl-3-(methylamino)propan-2-yl)-3-(1-(2-fluorobenzofuran-7-yl)-1-hydroxy-5-methoxypentyl)piperidine-1-carboxamide I-412 methyl 3-(1-(1-(1-cyclohexyl-3-(methylamino)propan-2-ylcarbamoyl)piperidin-3-yl)-1-hydroxy-5-methoxypentyl)benzoate I-413 2-(1-(benzo[b]thiophen-7-yl)-1-hydroxy-5-methoxypentyl)-N-(1-cyclohexyl-3-(methylamino)propan-2-yl)morpholine-4-carboxamide I-416 3-(1-(3-chlorophenyl)-1-hydroxy-4-propionamidobutyl)-N-(1-cyclohexyl-3-(methylamino)propan-2-yl)piperidine-1-carboxamide I-417 3-(1-(2-(cyclopropylmethoxy)-3-fluorophenyl)-1-hydroxy-5-methoxypentyl)-N-(4,4-dimethyl-1-(methylamino)pentan-2-yl)piperidine-1-carboxamide I-418 3-(1-(3-chlorophenyl)-1-hydroxy-4-(3-methylureido)butyl)-N-(1-cyclohexyl-3-(methylamino)propan-2-yl)piperidine-1-carboxamide I-421 N-(3-amino-1-cyclohexylbutan-2-yl)-3-(1-(3-chlorophenyl)-1-hydroxy-5-methoxypentyl)piperidine-1-carboxamide I-423 3-(4-acetamido-1-(3-chloro-2-fluorophenyl)-1-hydroxybutyl)-N-(1-cyclohexyl-3-(methylamino)propan-2-yl)piperidine-1-carboxamide I-424 3-(4-acetamido-1-(3-chloro-5-fluorophenyl)-1-hydroxybutyl)-N-(1-cyclohexyl-3-(methylamino)propan-2-yl)piperidine-1-carboxamide I-425 3-(4-acetamido-1-(2-chloro-3-fluorophenyl)-1-hydroxybutyl)-N-(1-cyclohexyl-3-(methylamino)propan-2-yl)piperidine-1-carboxamide I-426 3-(1-(3-chloro-2-fluorophenyl)-1,5-dimethoxypentyl)-N-(1-cyclohexyl-3-(methylamino)propan-2-yl)piperidine-1-carboxamide I-427 N-(3-hydroxy-4-methyl-1-(methylamino)pentan-2-yl)-3-(1-hydroxy-5-methoxy-1-(2-phenoxyphenyl)pentyl)piperidine-1-carboxamide I-428 3-(1-(3-chloro-2-fluorophenyl)-1-hydroxy-5-methoxypentyl)-N-(1-cyclohexyl-1-hydroxy-3-(methylamino)propan-2-yl)piperidine-1-carboxamide I-429 3-(1-(3-chloro-2-fluorophenyl)-1-hydroxy-5-methoxypentyl)-N-(1-(4-hydroxycyclohexyl)-3-(methylamino)propan-2-yl)piperidine-1-carboxamide I-430 3-(1-(2-chloro-3-fluorophenyl)-1-hydroxy-5-methoxypentyl)-N-(1-cyclohexyl-1-hydroxy-3-(methylamino)propan-2-yl)piperidine-1-carboxamide I-432 3-(1-(3-chloro-2-fluorophenyl)-1-hydroxy-5-methoxypentyl)-N-(1-(4-fluorocyclohexyl)-3-(methylamino)propan-2-yl)piperidine-1-carboxamide I-433 3-(1-(3-chloro-2,4-difluorophenyl)-1-hydroxy-5-methoxypentyl)-N-(1-cyclohexyl-3-(methylamino)propan-2-yl)piperidine-1-carboxamide I-434 3-(1-(3-chloro-2-fluorophenyl)-1-hydroxy-5-methoxypentyl)-N-(1-(1-fluorocyclohexyl)-3-(methylamino)propan-2-yl)piperidine-1-carboxamide I-435 3-(1-(2-chloro-3-fluorophenyl)-1-hydroxy-5-methoxypentyl)-N-(1-(4-fluorocyclohexyl)-3-(methylamino)propan-2-yl)piperidine-1-carboxamide I-436 N-(1-(4-fluorocyclohexyl)-3-(methylamino)propan-2-yl)-3-(1-hydroxy-5-methoxy-1-(2,3,5-trifluorophenyl)pentyl)piperidine-1-carboxamide I-437 2-(1-(3-chloro-2-fluorophenyl)-1-hydroxy-5-methoxypentyl)-N-(1-(4-fluorocyclohexyl)-3-(methylamino)propan-2-yl)morpholine-4-carboxamide I-438 3-(1-(3-chlorophenyl)-4-(cyclopropanecarboxamido)-1-hydroxybutyl)-N-(1-cyclohexyl-3-(methylamino)propan-2-yl)piperidine-1-carboxamide I-439 3-(4-butyramido-1-(3-chlorophenyl)-1-hydroxybutyl)-N-(1-cyclohexyl-3-(methylamino)propan-2-yl)piperidine-1-carboxamide I-440 3-(1-(3-chlorophenyl)-4-(3,3-dimethylureido)-1-hydroxybutyl)-N-(1-cyclohexyl-3-(methylamino)propan-2-yl)piperidine-1-carboxamide I-442 3-(1-(3-bromophenyl)-1-hydroxy-5-methoxypentyl)-N-(1-cyclohexyl-3-(methylamino)propan-2-yl)piperidine-1-carboxamide I-447 3-(1-(3-chloro-2-fluorophenyl)-1-hydroxy-5-methoxypentyl)-N-(1-cycloheptyl-1-hydroxy-3-(methylamino)propan-2-yl)piperidine-1-carboxamide I-449 3-(1-(3-chlorophenyl)-1-hydroxy-4-(methylsulfonamido)butyl)-N-(1-cyclohexyl-3-(methylamino)propan-2-yl)piperidine-1-carboxamide I-450 3-(1-(3-chlorophenyl)-1-hydroxy-4-(sulfamoylamino)butyl)-N-(1-cyclohexyl-3-(methylamino)propan-2-yl)piperidine-1-carboxamide I-451 3-(4-acetamido-1-(2,3-difluorophenyl)-1-hydroxybutyl)-N-(1-(4,4-difluorocyclohexyl)-3-(methylamino)propan-2-yl)piperidine-1-carboxamide I-452 3-(1-(3-fluoro-2-phenoxyphenyl)-1-hydroxy-5-methoxypentyl)-N-(3-hydroxy-4-methyl-1-(methylamino)pentan-2-yl)piperidine-1-carboxamide I-454 N-(1-cyclohexyl-3-(methylamino)propan-2-yl)-3-(1-(2,3-difluorophenyl)-5-methoxy-1-propionamidopentyl)piperidine-1-carboxamide I-455 3-(1-(3-chlorophenyl)-1-hydroxy-4-(2-methoxypropanamido)butyl)-N-(1-cyclohexyl-3-(methylamino)propan-2-yl)piperidine-1-carboxamide I-456 3-(1-(3-chlorophenyl)-1-hydroxy-2-(2-methoxyethoxy)ethyl)-N-(1-cyclohexyl-3-(methylamino)propan-2-yl)piperidine-1-carboxamide I-457 N-(1-cyclopentyl-1-hydroxy-3-(methylamino)propan-2-yl)-3-(1-hydroxy-5-methoxy-1-(2-phenoxyphenyl)pentyl)piperidine-1-carboxamide I-458 2-(1-acetamido-1-(3-chloro-2-fluorophenyl)-5-methoxypentyl)-N-(1-cyclohexyl-3-(methylamino)propan-2-yl)morpholine-4-carboxamide I-459 3-(1-(2-bromo-5-fluorophenyl)-1-hydroxy-5-methoxypentyl)-N-(1-cyclohexyl-3-(methylamino)propan-2-yl)piperidine-1-carboxamide I-463 3-(1-(3-fluoro-2-(o-tolyloxy)phenyl)-1-hydroxy-5-methoxypentyl)-N-(3-hydroxy-4-methyl-1-(methylamino)pentan-2-yl)piperidine-1-carboxamide I-464 3-(1-(3-chlorophenyl)-1-hydroxy-4-(2,2,2-trifluoroacetamido)butyl)-N-(1-cyclohexyl-3-(methylamino)propan-2-yl)piperidine-1-carboxamide I-466 N-(1-cyclopentyl-1-hydroxy-3-(methylamino)propan-2-yl)-3-(1-(3-fluoro-2-phenoxyphenyl)-1-hydroxy-5-methoxypentyl)piperidine-1-carboxamide I-467 3-(1-(3'-chloro-6-fluorobiphenyl-2-yl)-1-hydroxy-5-methoxypentyl)-N-(1-cyclopentyl-3-(methylamino)propan-2-yl)piperidine-1-carboxamide I-468 N-(1-(3,3-difluorocyclobutyl)-3-(methylamino)propan-2-yl)-3-(1-(3-fluoro-2-phenoxyphenyl)-1-hydroxy-5-methoxypentyl)piperidine-1-carboxamide I-469 3-(1-butyramido-1-(3-chloro-2-fluorophenyl)-5-methoxypentyl)-N-(1-cyclohexyl-3-(methylamino)propan-2-yl)piperidine-1-carboxamide I-470 3-(1-(3-chloro-2-fluorophenyl)-5-methoxypentyl)-N-(1-cyclohexyl-3-(methylamino)propan-2-yl)piperidine-1-carboxamide I-471 2-((3-chloro-2-fluorophenyl)(3-methoxypropoxy)methyl)-N-(1-cyclohexyl-3-(methylamino)propan-2-yl)morpholine-4-carboxamide I-472 N-(2-amino-5-methoxy-4,4-dimethylpentyl)-3-(1-(3-chloro-2-fluorophenyl)-1-hydroxy-5-methoxypentyl)piperidine-1-carboxamide I-473 N-(1-amino-5-methoxy-4,4-dimethylpentan-2-yl)-3-(1-(3-chloro-2-fluorophenyl)-1-hydroxy-5-methoxypentyl)piperidine-1-carboxamide I-474 3-(1-(3-chlorophenyl)-1-hydroxy-5-methoxypentyl)-N-(1-cyclohexyl-3-(methylamino)butan-2-yl)piperidine-1-carboxamide I-475 3-(1-(3-chloro-2-fluorophenyl)-1-hydroxy-5-methoxypentyl)-N-(3-cyclohexyl-2-(methylamino)propyl)piperidine-1-carboxamide I-476 3-(1-(3-chlorophenyl)-1-hydroxy-5-methoxypentyl)-N-(1-(1-fluorocyclohexyl)-3-(methylamino)propan-2-yl)piperidine-1-carboxamide I-477 N-(3-amino-4-cyclohexylbutan-2-yl)-3-(1-(3-chloro-2-fluorophenyl)-1-hydroxy-5-methoxypentyl)piperidine-1-carboxamide I-478 3-(1-(3-chloro-2-fluorophenyl)-1-fluoro-5-methoxypentyl)-N-(1-cyclohexyl-3-(methylamino)propan-2-yl)piperidine-1-carboxamide I-479 3-(1-(benzo[b]thiophen-7-yl)-1-hydroxy-5-methoxypentyl)-N-(1-(methylamino)-3-(tetrahydro-2H-pyran-4-yl)propan-2-yl)piperidine-1-carboxamide I-480 3-(1-(2,3-dihydrobenzofuran-7-yl)-1-hydroxy-5-methoxypentyl)-N-(1-(4-fluorocyclohexyl)-3-(methylamino)propan-2-yl)piperidine-1-carboxamide I-481 3-(1-(3-chlorophenyl)-1-ethoxy-5-methoxypentyl)-N-(1-cyclohexyl-3-(methylamino)propan-2-yl)piperidine-1-carboxamide I-482 3-(1-(3-chlorophenyl)-1-hydroxy-5-methoxypentyl)-N-(1-(4-hydroxy-4-methylcyclohexyl)-3-(methylamino)propan-2-yl)piperidine-1-carboxamide I-483 3-(1-(2,3-difluorophenyl)-1-hydroxy-5-methoxypentyl)-N-(1-(4-hydroxy-4-methylcyclohexyl)-3-(methylamino)propan-2-yl)piperidine-1-carboxamide I-484 3-(1-(2,3-difluorophenyl)-1-hydroxy-5-methoxypentyl)-N-(1-(4-methoxycyclohexyl)-3-(methylamino)propan-2-yl)piperidine-1-carboxamide I-485 3-(1-(3-chloro-2-fluorophenyl)-1-hydroxy-5-methoxypentyl)-N-(1-cyclohexyl-3-(methylamino)butan-2-yl)piperidine-1-carboxamide I-488 N-(3-amino-4-cyclohexyl-1-hydroxybutan-2-yl)-3-(1-(3-chloro-2-fluorophenyl)-1-hydroxy-5-methoxypentyl)piperidine-1-carboxamide I-489 N-(1-cyclohexyl-1-hydroxy-3-(methylamino)propan-2-yl)-3-(1-hydroxy-5-methoxy-1-(2,3,5-trifluorophenyl)pentyl)piperidine-1-carboxamide I-490 3-(1-(2-chloro-3-fluorophenyl)-1-hydroxy-5-methoxypentyl)-N-(1-(1-fluorocyclohexyl)-3-(methylamino)propan-2-yl)piperidine-1-carboxamide I-491 N-(1-(4-fluorocyclohexyl)-3-(methylamino)propan-2-yl)-3-(1-hydroxy-5-methoxy-1-(2,3,5-trifluorophenyl)pentyl)piperidine-1-carboxamide I-492 N-(2-amino-3-(4,4-difluorocyclohexyl)propyl)-3-(1-(3-chloro-2-fluorophenyl)-1-hydroxy-5-methoxypentyl)piperidine-1-carboxamide I-493 N-(3-amino-1-(3-noradamantyl)-1-hydroxypropan-2-yl)-3-(1-(3-chlorophenyl)-1-hydroxy-5-methoxypentyl)piperidine-1-carboxamide I-495 3-(1-(3-chloro-2-fluorophenyl)-1-hydroxy-5-methoxypentyl)-N-(1-(4-hydroxy-4-methylcyclohexyl)-3-(methylamino)propan-2-yl)piperidine-1-carboxamide I-497 3-(1-(3-chloro-2,4-difluorophenyl)-1-hydroxy-5-methoxypentyl)-N-(1-cyclohexyl-1-hydroxy-3-(methylamino)propan-2-yl)piperidine-1-carboxamide I-498 3-(1-(3-chloro-2,4-difluorophenyl)-1-hydroxy-5-methoxypentyl)-N-(1-(4-fluorocyclohexyl)-3-(methylamino)propan-2-yl)piperidine-1-carboxamide I-499 N-(3-amino-1-(3-noradamantyl)-1-hydroxypropan-2-yl)-3-(1-(3-chloro-2-fluorophenyl)-1-hydroxy-5-methoxypentyl)piperidine-1-carboxamide I-502 3-((3-chlorophenyl)(2-hydroxyethoxy)methyl)-N-(1-cyclohexyl-3-(methylamino)propan-2-yl)piperidine-1-carboxamide I-503 N-(2-amino-3-cyclopentylpropyl)-3-(1-(3-chlorophenyl)-1-hydroxy-5-methoxypentyl)piperidine-1-carboxamide I-504 N-(2-amino-3-(tetrahydrofuran-2-yl)propyl)-3-(1-(3-chlorophenyl)-1-hydroxy-5-methoxypentyl)piperidine-1-carboxamide I-505 N-(1-amino-3-(tetrahydrofuran-2-yl)propan-2-yl)-3-(1-(3-chlorophenyl)-1-hydroxy-5-methoxypentyl)piperidine-1-carboxamide I-507 3-(1-(3-chlorophenyl)-2-(2-methoxyethoxy)ethyl)-N-(1-cyclohexyl-3-(methylamino)propan-2-yl)piperidine-1-carboxamide I-508 N-(2-amino-3-(tetrahydro-2H-pyran-4-yl)propyl)-3-(1-(3-chlorophenyl)-1-hydroxy-5-methoxypentyl)piperidine-1-carboxamide I-509 N-(1-amino-3-(tetrahydro-2H-pyran-2-yl)propan-2-yl)-3-(1-(3-chlorophenyl)-1-hydroxy-5-methoxypentyl)piperidine-1-carboxamide I-510 N-(1-amino-3-(3-methoxycyclobutyl)propan-2-yl)-3-(1-(3-chlorophenyl)-1-hydroxy-5-methoxypentyl)piperidine-1-carboxamide I-511 N-(2-amino-3-(3-methoxycyclobutyl)propyl)-3-(1-(3-chlorophenyl)-1-hydroxy-5-methoxypentyl)piperidine-1-carboxamide I-512 N-(2-amino-3-cyclohexylpropyl)-3-(1-(3-chloro-2-fluorophenyl)-5-methoxypentyl)piperidine-1-carboxamide I-513 N-(2-amino-3-(tetrahydrofuran-2-yl)propyl)-3-(1-(3-chloro-2-fluorophenyl)-1-hydroxy-5-methoxypentyl)piperidine-1-carboxamide I-514 N-(1-amino-3-(tetrahydrofuran-2-yl)propan-2-yl)-3-(1-(3-chloro-2-fluorophenyl)-1-hydroxy-5-methoxypentyl)piperidine-1-carboxamide I-515 N-(2-amino-4-phenylbutyl)-3-(1-(3-chlorophenyl)-1-hydroxy-5-methoxypentyl)piperidine-1-carboxamide I-520 N-(2-amino-4-cyclohexylbutyl)-3-(1-(3-chlorophenyl)-1-hydroxy-5-methoxypentyl)piperidine-1-carboxamide I-522 3-(1-(3-chloro-2-fluorophenyl)-5-methoxypentyl)-N-(1-cyclohexyl-3-(methylamino)propan-2-yl)piperidine-1-carboxamide I-523 3-(1-(6-fluoro-3'-methylbiphenyl-2-yl)-1-hydroxy-5-methoxypentyl)-N-(piperidin-3-yl)piperidine-1-carboxamide I-524 3-((3-chloro-2-fluorophenyl)(3-methoxypropoxy)methyl)-N-(1-cyclohexyl-3-(methylamino)propan-2-yl)piperidine-1-carboxamide I-526 N-(1-amino-3-(tetrahydro-2H-pyran-2-yl)propan-2-yl)-3-(1-(3-chloro-2-fluorophenyl)-1-hydroxy-5-methoxypentyl)piperidine-1-carboxamide I-527 N-(2-amino-3-(3-methoxycyclobutyl)propyl)-3-(1-(3-chloro-2-fluorophenyl)-1-hydroxy-5-methoxypentyl)piperidine-1-carboxamide I-528 N-(1-amino-3-(3-methoxycyclobutyl)propan-2-yl)-3-(1-(3-chloro-2-fluorophenyl)-1-hydroxy-5-methoxypentyl)piperidine-1-carboxamide I-531 3-((3-chlorophenyl)(2-propionamidoethoxy)methyl)-N-(1-cyclohexyl-3-(methylamino)propan-2-yl)piperidine-1-carboxamide I-533 N-(4-cyclohexylpiperidin-3-yl)-3-(1-(2,3-difluorophenyl)-1-hydroxy-5-methoxypentyl)piperidine-1-carboxamide I-534 3-(1-(3-chlorophenyl)-1,6-dihydroxyheptyl)-N-(1-cyclohexyl-3-(methylamino)propan-2-yl)piperidine-1-carboxamide I-536 N-(1-cyclohexyl-3-(methylamino)propan-2-yl)-3-((2,3-difluorophenyl)(2-propionamidoethoxy)methyl)piperidine-1-carboxamide I-537 3-(1-(3-chlorophenyl)-1-hydroxy-2-(2-methoxyacetamido)ethyl)-N-(1-cyclohexyl-3-(methylamino)propan-2-yl)piperidine-1-carboxamide I-541 N-(3-amino-1-cyclohexylbutan-2-yl)-3-(1-(3-chloro-2-fluorophenyl)-1-hydroxy-5-methoxypentyl)piperidine-1-carboxamide I-544 3-(1-(3-chloro-2-fluorophenyl)-1-hydroxy-5-methoxypentyl)-N-(4-cyclohexylpiperidin-3-yl)piperidine-1-carboxamide I-545 3-(1-(3-chlorophenyl)-1-hydroxy-5-methoxypentyl)-N-(1-(4-methoxycyclohexyl)-3-(methylamino)propan-2-yl)piperidine-1-carboxamide I-546 3-(4-acetamido-1-(3-chloro-2-fluorophenyl)-1-hydroxybutyl)-N-(3-amino-1-cyclohexylbutan-2-yl)piperidine-1-carboxamide I-547 3-((3-chloro-2-fluorophenyl)(2-propionamidoethoxy)methyl)-N-(1-cyclohexyl-3-(methylamino)propan-2-yl)piperidine-1-carboxamide I-548 3-(1-(2,3-difluorophenyl)-1-hydroxy-5-methoxypentyl)-N-(1-(4-methoxycyclohexyl)-3-(methylamino)propan-2-yl)piperidine-1-carboxamide I-549 3-(1-(3-chloro-2-fluorophenyl)-1-hydroxy-5-methoxypentyl)-N-(4-(pentan-3-yloxy)piperidin-3-yl)piperidine-1-carboxamide I-551 N-(3-amino-1-(4-fluorocyclohexyl)-1-hydroxypropan-2-yl)-3-(1-(3-chloro-2-fluorophenyl)-1-hydroxy-5-methoxypentyl)piperidine-1-carboxamide I-552 3-(1-(3-chlorophenyl)-1-hydroxy-5-methoxypentyl)-N-(1-(3-noradamantyl)-3-(methylamino)propan-2-yl)piperidine-1-carboxamide I-553 3-(1-acetamido-5-ethoxy-1-(3-fluorophenyl)pentyl)-N-(1-cyclohexyl-3-(methylamino)propan-2-yl)piperidine-1-carboxamide I-554 3-(1-(3-chloro-2-fluorophenyl)-1-hydroxy-5-methoxypentyl)-N-(1-(3,4-difluorocyclopentyl)-3-(methylamino)propan-2-yl)piperidine-1-carboxamide I-556 3-(1-(3-chloro-2-fluorophenyl)-1-hydroxy-5-methoxypentyl)-N-(1-(4-methoxycyclohexyl)-3-(methylamino)propan-2-yl)piperidine-1-carboxamide I-558 3-(1-acetamido-1-(3-chlorophenyl)-5-ethoxypentyl)-N-(1-cyclohexyl-3-(methylamino)propan-2-yl)piperidine-1-carboxamide and I-559 N-(2-amino-3-(3-noradamantyl)-3-hydroxypropyl)-3-(1-(3-chloro-2-fluorophenyl)-1-hydroxy-5-methoxypentyl)piperidine-1-carboxamide or an enantiomer, diastereomer or pharmaceutically acceptable salt thereof.

4. A composition comprising a compound of claim 1 or 2, or an enantiomer, diastereomer, or pharmaceutically acceptable salt thereof and a pharmaceutically acceptable carrier.

5. A composition of claim 4 further comprising α-blockers, β-blockers, calcium channel blockers, diuretics, natriuretics, saluretics, centrally acting antihypertensives, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonists.

6. A compound of Formula

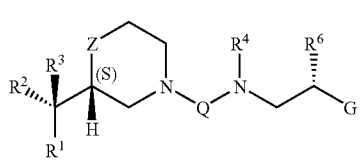

IIb wherein
Z is $CH_2$ or O;
$R^1$ is a) cyclohexyl or trifluoromethyl; or b) phenyl, 2-thienyl, 3-thienyl, 2-pyridyl, 2-imidazolyl, or 2-thiazolyl, optionally substituted with 1 to 3 substituents independently selected from: fluorine, chlorine, bromine, cyano, methyl, ethyl, isopropyl, trifluoromethyl, allyl, cyclopropylethynyl, methoxy, trifluoromethoxy, neopentyloxy, methylthio, allyloxy, cyclopropylmethoxy, (cyclopropyl)ethoxy, cyclopentyloxy, cyclopentylmethoxy, benzyloxy, hydroxyl, aminocarbonyl, methoxycarbonyl, phenyl, phenoxy, benzyloxy, and 3-pyridyloxy, wherein the phenyl and phenoxy, benzyloxy and pyridyloxy groups are optionally substituted with 1 to 3 substituents independently selected from fluorine, chlorine, cyano, methyl, ethyl, and trifluoromethyl; or c) 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl, optionally substituted with 1 to 3 substituents independently selected from fluorine, methyl, isobutyl, and t-butyl;
$R^2$ is $(C_1-C_8)$alkyl, $(C_4-C_8)$cycloalkylalkyl, fluoro$(C_1-C_8)$alkyl, fluoro$(C_4-C_8)$cycloalkylalkyl, $(C_1-C_8)$alkoxy, $(C_4-C_8)$cycloalkylalkoxy, fluoro$(C_1-C_8)$alkoxy, hydroxy$(C_1-C_8)$alkyl, $(C_1-C_5)$alkoxy$(C_1-C_5)$alkyl, $(C_1-C_5)$alkoxy$(C_1-C_5)$hydroxyalkyl, $(C_3-C_4)$cycloalkoxy$(C_1-C_5)$alkyl, fluoro$(C_1-C_5)$alkoxy$(C_1-C_5)$alkyl, fluoro$(C_3-C_4)$cycloalkoxy$(C_1-C_5)$alkyl, $(C_1-C_5)$alkylthio$(C_1-C_5)$alkyl, $(C_1-C_5)$alkoxy$(C_1-C_5)$alkoxy, hydroxy$(C_1-C_8)$alkoxy, $(C_3-C_4)$cycloalkoxy$(C_1-C_5)$alkoxy, fluoro$(C_1-C_5)$alkoxy$(C_1-C_5)$alkoxy, fluoro$(C_3-C_4)$cycloalkoxy$(C_1-C_5)$alkoxy, $(C_1-C_3)$alkoxy$(C_1-C_3)$alkoxy$(C_1-C_3)$alkyl, fluoro$(C_1-C_3)$alkoxy$(C_1-C_3)$alkoxy$(C_1-C_3)$alkyl, aminocarbonylamino$(C_1-C_8)$alkyl, aminocarbonylamino$(C_1-C_8)$alkoxy, $(C_1-C_5)$alkanoylamino$(C_1-C_5)$alkyl, $(C_1-C_5)$alkanoylamino$(C_1-C_5)$alkoxy, fluoro$(C_1-C_5)$alkanoylamino$(C_1-C_5)$alkyl, fluoro$(C_1-C_5)$alkanoylamino$(C_1-C_5)$alkoxy, $(C_1-C_3)$alkoxy$(C_1-C_5)$alkanoylamino$(C_1-C_5)$alkyl, $(C_1-C_3)$alkoxy$(C_1-C_5)$alkanoylamino$(C_1-C_5)$alkoxy, $(C_3-C_4)$cycloalkanecarbonylamino$(C_1-C_5)$alkyl, $(C_3-C_4)$cycloalkanecarbonylamino$(C_1-C_5)$alkoxy, aminosulfonylamino$(C_1-C_8)$alkyl, aminosulfonylamino$(C_1-C_8)$alkoxy, $(C_1-C_5)$alkanesulfonylamino$(C_1-C_5)$alkyl, $(C_1-C_5)$alkanesulfonylamino$(C_1-C_5)$alkoxy, $(C_1-C_5)$alkylaminocarbonylamino$(C_1-C_5)$alkyl, di$(C_1-C_5)$alkylaminocarbonylamino$(C_1-C_5)$alkyl, $(C_1-C_5)$alkylaminocarbonylamino$(C_1-C_5)$alkoxy, di$(C_1-C_5)$alkylaminocarbonylamino$(C_1-C_5)$alkoxy;
$R^3$ is H, F, OH, $(C_1-C_4)$alkanoylamino, or $(C_1-C_3)$alkoxy; provided that when $R^3$ is OH or F, $R^2$ is not $(C_2-C_{10})$alkoxy, $(C_4-C_{10})$cycloalkylalkoxy, halo$(C_2-C_{10})$alkoxy, $(C_2-C_{10})$alkylthio, halo$(C_2-C_{15})$alkylthio, $(C_1-C_5)$alkoxy$(C_1-C_5)$alkoxy, hydroxy$(C_2-C_{10})$alkoxy, $(C_3-C_6)$cycloalkoxy$(C_1-C_5)$alkoxy, halo$(C_1-C_5)$alkoxy$(C_1-C_5)$alkoxy, halo$(C_3-C_6)$-cycloalkoxy$(C_1-C_5)$alkoxy, hydroxy$(C_2-C_{10})$alkylthio, $(C_2-C_5)$alkoxy$(C_1-C_5)$alkylthio, $(C_1-C_5)$alkylthio$(C_1-C_5)$alkoxy, or $(C_1-C_5)$alkylthio$(C_1-C_5)$alkylthio, $(C_3-C_4)$cycloalkane-carbonylamino$(C_1-C_5)$alkoxy, $(C_3-C_4)$cycloalkanecarbonylamino$(C_1-C_5)$alkylthio, $(C_1-C_5)$alkyl-aminocarbonylamino$(C_1-C_5)$alkoxy, $(C_1-C_5)$alkylaminocarbonylamino$(C_1-C_5)$alkylthio, di$(C_1-C_5)$alkylaminocarbonylamino$(C_1-C_5)$alkoxy or di$(C_1-C_5)$alkylaminocarbonylamino$(C_1-C_5)$alkylthio;

Q is Q1, Q2, Q4, Q5, Q9, or Q10

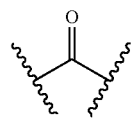

Q1

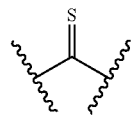

Q2

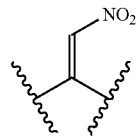

Q4

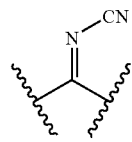

Q5

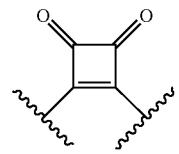

Q9

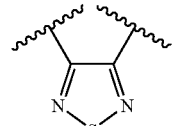

Q10 wherein N and N are attached to the truncated bonds $R^4$ is H or $(C_1-C_3)$alkyl;
$R^6$ is a) $(C_1-C_{10})$alkyl, $(C_4-C_{10})$cycloalkylalkyl, halo$(C_1-C_{10})$alkyl, hydroxy$(C_1-C_{10})$alkyl, halo$(C_4-C_{10})$cycloalkylalkyl, hydroxylated $(C_4-C_{10})$cycloalkylalkyl, $(C_1-C_2)$alkyl$(C_4-C_{10})$cycloalkylalkyl, di$(C_1-C_2)$alkyl$(C_4-C_{10})$cycloalkylalkyl, hydroxylated $(C_1-C_2)$alkyl$(C_4-C_{10})$cycloalkylalkyl, hydroxylated di$(C_1-C_2)$alkyl$(C_4-C_{10})$cycloalkylalkyl, $(C_4-C_{10})$bicycloalkyl$(C_1-C_2)$alkyl, $(C_8-C_{12})$tricycloalkyl$(C_1-C_2)$alkyl, $(C_1-C_5)$alkoxy$(C_1-C_5)$alkyl, halo$(C_1-C_5)$alkoxy$(C_1-C_5)$alkyl, $(C_1-C_5)$alkylthio$(C_1-C_5)$alkyl, halo$(C_1-C_5)$alkylthio$(C_1-C_5)$alkyl, or saturated heterocyclyl$(C_1-C_3)$alkyl; or b) phenyl$(C_1-C_2)$alkyl or heteroaryl$(C_1-C_2)$alkyl, each optionally substituted with 1 to 3 groups independently selected from fluorine, chlorine, cyano, $(C_1-C_3)$alkyl, halo$(C_1-C_3)$alkyl, $(C_1-C_3)$alkoxy, and halo$(C_1-C_3)$alkoxy;

G is OH, $NH_2$, $NHR^9$, or $NR^9R^{10}$;

$R^9$ is a) $(C_1-C_6)$alkyl, halo$(C_1-C_6)$alkyl, $(C_4-C_{10})$cycloalkylalkyl, $(C_1-C_5)$alkoxy$(C_1-C_5)$alkyl, or aminocarbonyl$(C_1-C_6)$alkyl; or b) phenyl$(C_1-C_2)$alkyl optionally substituted with 1 to 3 groups independently selected from:

fluorine, chlorine, cyano, $(C_1-C_3)$alkyl, halo$(C_1-C_3)$alkyl, $(C_1-C_3)$alkoxy, and halo$(C_1-C_3)$alkoxy; or c) $R^6$ and $R^9$ together are $-(CH_2)_2-$, $-(CH_2)_3-$, or $-(CH_2)_4-$ and form a 4-, 5-, 6-, or 7-membered ring with the atoms through which they are connected that is optionally substituted with 1 or 2 groups independently selected from fluorine, $(C_1-C_8)$alkyl, halo$(C_1-C_8)$alkyl, $(C_3-C_8)$cycloalkyl, halo$(C_3-C_8)$cycloalkyl, hydroxy$(C_3-C_8)$cycloalkyl, $(C_3-C_8)$cycloalkyl$(C_1-C_3)$alkyl, halo$(C_3-C_8)$cycloalkyl$(C_1-C_3)$alkyl, and hydroxylated $(C_3-C_8)$cycloalkyl$(C_1-C_3)$alkyl, $(C_1-C_8)$alkoxy, halo$(C_1-C_8)$alkoxy, $(C_3-C_8)$cycloalkoxy, halo$(C_3-C_8)$cycloalkoxy, hydroxy$(C_3-C_8)$cycloalkoxy, $(C_1-C_8)$alkoxy$(C_1-C_3)$alkyl, halo$(C_1-C_1)$alkoxy$(C_1-C_3)$alkyl, $(C_3-C_8)$cycloalkoxy$(C_1-C_3)$alkyl, halo$(C_3-C_8)$cycloalkoxy$(C_1-C_3)$alkyl, hydroxy$(C_3-C_8)$cycloalkoxy$(C_1-C_3)$alkyl, $(C_3-C_8)$cycloalkyl$(C_1-C_3)$alkoxy$(C_1-C_3)$alkyl, halo$(C_3-C_8)$cycloalkyl$(C_1-C_3)$alkoxy$(C_1-C_3)$alkyl, hydroxylated$(C_3-C_8)$cycloalkyl$(C_1-C_3)$alkoxy$(C_1-C_3)$alkyl, $(C_1-C_8)$alkylthio, halo$(C_1-C_8)$alkylthio, $(C_3-C_8)$cycloalkylthio, halo$(C_3-C_8)$cycloalkylthio, hydroxy$(C_3-C_8)$cycloalkylthio, $(C_3-C_8)$cycloalkyl$(C_1-C_3)$alkylthio, halo$(C_3-C_8)$cycloalkyl$(C_1-C_3)$alkylthio, hydroxylated$(C_3-C_8)$cycloalkyl$(C_1-C_3)$alkylthio, $(C_1-C_8)$alkylthio$(C_1-C_3)$alkyl, halo$(C_1-C_8)$alkylthio$(C_1-C_3)$alkyl, $(C_3-C_8)$cycloalkylthio$(C_1-C_3)$alkyl, halo$(C_3-C_8)$cycloalkylthio$(C_1-C_3)$alkyl, hydroxy$(C_3-C_8)$cycloalkylthio$(C_1-C_3)$alkyl, $(C_3-C_8)$cycloalkyl$(C_1-C_3)$alkylthio$(C_1-C_3)$alkyl, halo$(C_3-C_8)$cycloalkyl$(C_1-C_3)$alkylthio$(C_1-C_3)$alkyl, and hydroxylated$(C_3-C_8)$cycloalkyl$(C_1-C_3)$alkylthio$(C_1-C_3)$alkyl;

$R^{10}$ is $(C_1-C_3)$alkyl or halo$(C_1-C_3)$alkyl;

or a pharmaceutically acceptable salt thereof.

7. The compound of claim 6, wherein $R^9$ is $(C_1-C_6)$alkyl, $(C_1-C_5)$alkoxy$(C_1-C_5)$alkyl, or aminocarbonyl$(C_1-C_6)$alkyl.

8. The compound of claim 6, wherein $R^6$ is $(C_1-C_{10})$alkyl or hydroxy$(C_1-C_{10})$alkyl.

9. A composition comprising a compound of any one of claims 6 to 8, or an enantiomer, diastereomer, or pharmaceutically acceptable salt thereof and a pharmaceutically acceptable carrier.

10. A composition of claim 9 further comprising α-blockers, β-blockers, calcium channel blockers, diuretics, natriuretics, saluretics, centrally acting antihypertensives, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonists.

* * * * *